(12) United States Patent
Masse et al.

(10) Patent No.: US 12,221,453 B2
(45) Date of Patent: Feb. 11, 2025

(54) SUBSTITUTED PYRAZOLO[5',1':2,3]PYRIMIDO[5,4-B][1,4] OXAZINES AS TYK2 INHIBITORS

(71) Applicant: TAKEDA PHARMACEUTICAL COMPANY LIMITED, Osaka (JP)

(72) Inventors: Craig E. Masse, Cambridge, MA (US); Jeremy Robert Greenwood, Brooklyn, NY (US); Sayan Mondal, New York, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 17/806,893

(22) Filed: Jun. 14, 2022

(65) Prior Publication Data
US 2023/0110996 A1   Apr. 13, 2023

Related U.S. Application Data

(63) Continuation of application No. 16/602,000, filed on Oct. 15, 2019, now Pat. No. 11,414,431.

(60) Provisional application No. 62/820,509, filed on Mar. 19, 2019, provisional application No. 62/795,869, filed on Jan. 23, 2019, provisional application No. 62/745,642, filed on Oct. 15, 2018.

(51) Int. Cl.
| A61K 31/5383 | (2006.01) |
| C07D 413/14 | (2006.01) |
| C07D 487/04 | (2006.01) |
| C07D 519/00 | (2006.01) |

(52) U.S. Cl.
CPC ......... *C07D 519/00* (2013.01); *C07D 487/04* (2013.01)

(58) Field of Classification Search
CPC .......................... A61K 31/5383; C07D 413/14
USPC ....................................... 514/230.2; 544/101
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 6,552,065 B2 | 4/2003 | Remiszewski et al. |
| 7,390,799 B2 | 6/2008 | Bruncko et al. |
| 8,138,347 B2 | 3/2012 | Knight et al. |
| 9,340,540 B2 | 5/2016 | Masse et al. |
| 9,630,970 B2 | 4/2017 | Masse et al. |
| 10,023,571 B2 | 7/2018 | Masse |
| 10,196,390 B2 | 2/2019 | Masse et al. |
| 10,253,046 B2 | 4/2019 | Dahlgren et al. |
| 10,323,036 B2 | 6/2019 | Greenwood et al. |
| 10,336,752 B2 | 7/2019 | Greenwood et al. |
| 10,508,120 B2 | 12/2019 | Masse et al. |
| 10,562,906 B2 | 2/2020 | Masse et al. |
| 10,562,907 B2 | 2/2020 | Masse et al. |
| 10,570,145 B2 | 2/2020 | Masse et al. |
| 10,577,373 B2 | 3/2020 | Masse et al. |
| 10,647,713 B2 | 5/2020 | Greenwood et al. |
| 10,781,204 B2 | 9/2020 | Masse et al. |
| 10,793,574 B2 | 10/2020 | Greenwood et al. |
| 10,968,236 B2 | 4/2021 | Masse et al. |
| 11,040,967 B2 | 6/2021 | Greenwood et al. |
| 11,046,698 B2 | 6/2021 | Masse et al. |
| 11,053,241 B2 | 7/2021 | Greenwood et al. |
| 11,174,264 B2 | 11/2021 | Masse |
| 11,220,508 B2 | 1/2022 | Greenwood et al. |
| 2006/0128725 A1 | 6/2006 | Guzi et al. |
| 2007/0054925 A1 | 3/2007 | Guzi et al. |
| 2007/0072881 A1 | 3/2007 | Guzi et al. |
| 2007/0072882 A1 | 3/2007 | Guzi et al. |
| 2012/0022043 A1 | 1/2012 | Blaney et al. |
| 2014/0107099 A1 | 4/2014 | Blaney et al. |
| 2016/0251376 A1 | 9/2016 | Dahlgren et al. |
| 2019/0031664 A1 | 1/2019 | Masse |
| 2020/0131201 A1 | 4/2020 | Masse et al. |
| 2021/0047319 A1 | 2/2021 | Masse et al. |

(Continued)

FOREIGN PATENT DOCUMENTS

| CN | 102271515 A | 12/2011 |
| CN | 102627645 A | 8/2012 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Honigman LLP; Lucy X. Yang; Jonahan P. O'Brien

(57) ABSTRACT

The present invention provides compounds of Formula I':

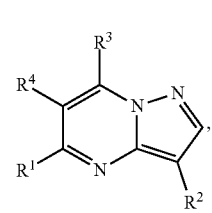

compositions thereof, and methods of using the same for the inhibition of TYK2, and the treatment of TYK2-mediated disorders.

3 Claims, No Drawings

(56) References Cited

U.S. PATENT DOCUMENTS

| | | |
|---|---|---|
| 2021/0094948 A1 | 4/2021 | Greenwood et al. |
| 2021/0238198 A1 | 8/2021 | Dahlgren et al. |

FOREIGN PATENT DOCUMENTS

| | | |
|---|---|---|
| CN | 106661039 A | 5/2017 |
| EP | 1956009 A1 | 8/2008 |
| JP | 2006-519226 A | 8/2006 |
| JP | 2008503510 A | 2/2008 |
| JP | 2008527011 A | 7/2008 |
| JP | 2012-507569 A | 3/2012 |
| JP | 2017-533968 A | 11/2017 |
| JP | 2017-538766 A | 12/2017 |
| WO | 2001042246 A2 | 6/2001 |
| WO | 2002088112 A1 | 11/2002 |
| WO | 2003063794 A2 | 8/2003 |
| WO | 2004019973 A1 | 3/2004 |
| WO | 2004076458 A1 | 9/2004 |
| WO | 2004089925 A1 | 10/2004 |
| WO | 2004106328 A1 | 12/2004 |
| WO | 2005007623 A2 | 1/2005 |
| WO | 2005113554 A2 | 12/2005 |
| WO | 2005123738 A1 | 12/2005 |
| WO | 2006078846 A1 | 7/2006 |
| WO | 2006122806 A2 | 11/2006 |
| WO | 2007016176 A2 | 2/2007 |
| WO | 2007044449 A2 | 4/2007 |
| WO | 2007044729 A2 | 4/2007 |
| WO | 2007053452 A1 | 5/2007 |
| WO | 2007063935 A1 | 6/2007 |
| WO | 2007070514 A1 | 6/2007 |
| WO | 2007084786 A1 | 7/2007 |
| WO | 2007129161 A2 | 11/2007 |
| WO | 2008039218 A2 | 4/2008 |
| WO | 2008109943 A1 | 9/2008 |
| WO | 2008118802 A1 | 10/2008 |
| WO | 2009114512 A1 | 9/2009 |
| WO | 2010051549 A1 | 5/2010 |
| WO | 2011006074 A1 | 1/2011 |
| WO | 2011090760 A1 | 7/2011 |
| WO | 2011090935 A1 | 7/2011 |
| WO | 2014074660 A1 | 5/2014 |
| WO | 2014074661 A1 | 5/2014 |
| WO | 2015089143 A1 | 6/2015 |
| WO | 2015131080 A1 | 9/2015 |
| WO | 2016073895 A1 | 5/2016 |
| WO | 2016079869 A1 | 6/2016 |
| WO | 2016138352 A1 | 9/2016 |
| WO | 2017040757 A1 | 3/2017 |
| WO | 2018071794 A1 | 4/2018 |
| WO | 2018075937 A1 | 4/2018 |
| WO | 2018089695 A1 | 5/2018 |
| WO | 2018165240 A1 | 9/2018 |
| WO | 2019023468 A1 | 1/2019 |
| WO | 2020081508 A1 | 4/2020 |
| WO | 2020112937 A1 | 6/2020 |
| WO | 2020154474 A1 | 7/2020 |

OTHER PUBLICATIONS

Dorwald, F. Zaragoza. Side Reactions in Organic Synthesis: A Guide to Successful Synthesis Design, Weinheim: WILEY-VCH Verlag GmbH & Co. KGaA, 2005, Preface.*

Bacon et al., "Interleukin 12 (IL-12) induces tyrosine phosphorylation of Jak2 and Tyk2: differential use of Janus family kinases by IL-2 and IL-12," The Journal of Experimental Medicine. 1995; 181(1):399-04.

Ban et al., "Replication analysis identifies TYK2 as a multiple sclerosis susceptibility factor," European Journal of Human Genetics. 2009; 17(10):1309-13.

Berge et al., "Pharmaceutical salts," Journal Pharmaceutical Sciences. 1977; 66(1):1-19.

Bronner et al., "A Unique Approach to Design Potent and Selective Cyclic Adenosine Monophosphate Response Element Binding Protein, Binding Protein (CBP) Inhibitors," J. Med. Chem. 2017; 60(24):10151-71.

Cho et al., "Genomics and the multifactorial nature of human auto-immune disease," The New England Journal Medicine. 2011; 365(17):1612-23.

Cortes et al., "Identification of multiple risk variants for ankylosing spondylitis through high-density genotyping of immune-related loci," Nature Genetics. 2013; 45(7):730-38.

Duerr et al., "A Genome-Wide Association Study Identifies IL23R as an Inflammatory Bowel Disease Gene," Science. 2006; 314(5804):1461-63.

Finbloom et al., "IL-10 induces the tyrosine phosphorylation of Tyk2 and Jak1 and the differential assembly of Stat1 and Stat3 complexes in human T cells and monocytes," Journal immunology. 1995; 155(3):1079-90.

Fontan et al. "Discovering What Makes STAT Signaling TYK in T-ALL," Cancer Discovery. 2013; 3(5):494-96.

Graham et al., "Association of NCF2, IKZF1, IRF8, IFIH1, and TYK2 with Systemic Lupus Erythematosus," PLoS Genetics. 2011;7(10): 9 pages.

Harel et al., "Pharmacologic inhibition of JAK-STAT signaling promotes hair growth," Science Advances. 2015; 1(9): 12 pages.

International Search Report and Written Opinion from PCT/US2019/056230 dated Feb. 14, 2020.

Ishizaki et al., "Tyk2 deficiency protects joints against destruction in anti-type II collagen antibody-induced arthritis in mice," International Immunology. 2011; 23(9):575-82.

Ishizaki et al., "Tyk2 is a therapeutic target for psoriasis-like skin inflammation," International Immunology. 2013; 26(5):257-67.

Oyamada et al., "Tyrosine Kinase 2 Plays Critical Roles in the Pathogenic CD4 T Cell Responses for the Development of Experimental Autoimmune Encephalomyelitis," Journal of Immunology. 2009; 183(11):7539-46.

Parham et al., "A receptor for the heterodimeric cytokine IL-23 is composed of IL-12RB1 and a novel cytokine receptor subunit, IL-23R," Journal of Immunology. 2002; 168(11):5699-08.

Ramirez et al., "Defining causative factors contributing in the activation of hedgehog signaling in diffuse large B-cell lymphoma," Leukemia Research. 2012; 36(10):1267-73.

Remmers et al., "Genome-wide association study identifies variants in the MHC class I, IL10, and IL23R-IL12RB2 regions associated with Behçet's disease," Nature Genetics. 2010; 42(8):698-702.

Rostovtsev et al., "A Stepwise Huisgen Cycloaddition Process: Copper(I)-Catalyzed Regioselective "Ligation" of Azides and Terminal Alkynes," Angew. Chem. Int. Ed. 2002; 41(14):2596-99.

Sanda et al. "TYK2-STAT1-BCL2 Pathway Dependence in T-Cell Acute Lymphoblastic Leukemia," Cancer Discovery. 2013; 3(5):564-77.

Sigurdsson et al., "Polymorphisms in the Tyrosine Kinase 2 and Interferon Regulatory Factor 5 Genes Are Associated with Systemic Lupis Erythematosus," American Journal of Human Genetics. 2005; 76(3):528-37.

Simma et al., "Identification of an Indispensable Role for Tyrosine Kinase 2 in CTL-Mediated Tumor Surveillance," Cancer Research. 2009; 69(1):203-11.

Stahl et al., "Association and activation of Jak-Tyk kinases by CNTF-LIF-OSM-IL-6ß receptor components," Science. 1994; 263(5143):92-95.

Strange et al., "A genome-wide association study identifies new psoriasis susceptibility loci and an interaction between HLA-C and ERAP1," Nature Genetics. 2010; 42(11):985-90.

Sun et al., "Carbohydrate and protein immobilization onto solid surfaces by sequential Diels-Alder and azide-alkyne cycloadditions," Bioconjugate Chemistry. 2006; 17(1):52-57.

Velasquez et al., "A protein kinase in the interferon a/ß signaling pathway," Cell. 1992;70(2):313-22.

Wan et al. "Tyk/STAT3 Signaling Mediates ß-Amyloid-Induced Neuronal Cell Death: Implications in Alzheimer's Disease," Journal of Neuroscience. 2010; 30(20):6873-81.

(56) References Cited

OTHER PUBLICATIONS

Welham et al., "Interleukin-13 signal transduction in lymphohemopoietic cells: similarities and differences in signal transduction with interleukin-4 and insulin," The Journal of Biological chemistry. 1995; 270(20):12286-96.

Xing et al., "Alopecia areata is driven by cytotoxic T lymphocytes and is reversed by JAK inhibition," Nature Medicine. 2014; 20(9):1043-49.

Zhang et al., "Docking protein Gab2 regulates mucin expression and goblet cell hyperplasia through TYK2/STAT6 pathway," The FASEB Journal. 2012; 26(11):4603-13.

Dwyer et al., ""Discovery of pyrazolo[1,5-a]pyrimidine-based CHK1 inhibitors: A template-based approach-Part 1"", Bioorganic & Medicinal Chemistry Letters, 2011, 21(1), pp. 467-470.

\* cited by examiner

SUBSTITUTED PYRAZOLO[5',1':2,3]PYRIMIDO[5,4-B][1,4] OXAZINES AS TYK2 INHIBITORS

CROSS-REFERENCE TO RELATED APPLICATIONS

The present application is a continuation of U.S. application Ser. No. 16/602,000, filed Oct. 15, 2019, which claims priority to U.S. provisional application Ser. No. 62/745,642, filed Oct. 15, 2018, U.S. provisional application Ser. No. 62/795,869, filed Jan. 23, 2019, and U.S. provisional application Ser. No. 62/820,509, filed Mar. 19, 2019, the entirety of each of which is hereby incorporated by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The pseudokinase binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket oTYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of Formula I.

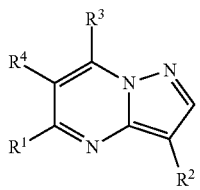

or a pharmaceutically acceptable salt thereof, wherein each of $R^1$, $R^2$, $R^3$, and $R^4$ is as defined below and described in embodiments herein, both singly and in combination.

In some embodiments, the present invention provides a pharmaceutical composition comprising a compound of Formula I, and a pharmaceutically acceptable carrier, adjuvant, or diluent.

In some embodiments, the present invention provides a method of treating a TYK2-mediated disease, disorder, or condition comprising administering to a patient in need thereof, a compound of Formula I or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

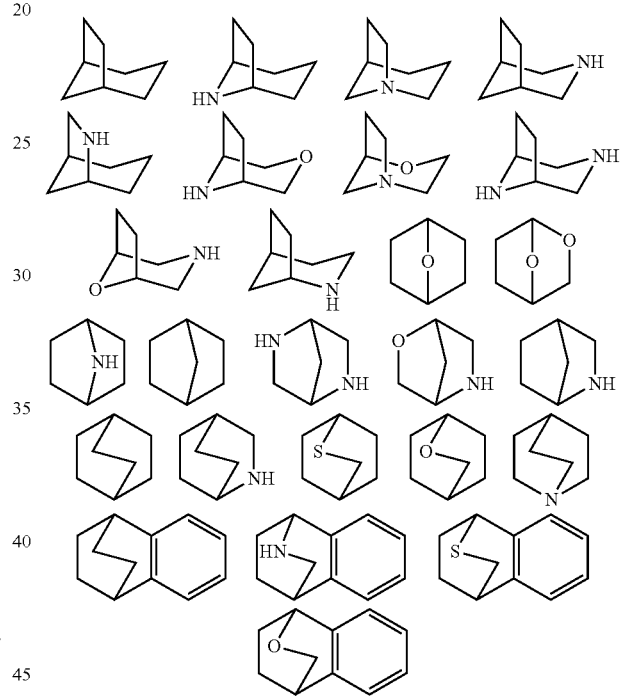

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°;

—N(R°)N(R°)C(O)NR°$_2$; —N(R°)N(R°)C(O)OR°; —N(R°)C(NR°)N(R°)$_2$; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_1$-4 aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^\bullet$ include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of Formula I.

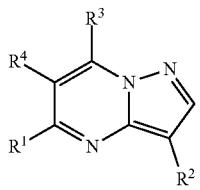

I $R^1$ is -$L^1$-$R^{1A}$;

$L^1$ is a covalent bond; or a $C_{1-6}$ bivalent saturated or unsaturated, straight or branched hydrocarbon chain, wherein one or two methylene units of the chain are optionally and independently replaced by —C(R)$_2$—; —N(R)—; —N(R)C(O)—; —C(O)N(R)—; —N(R)S(O)$_2$—; —S(O)$_2$N(R)—; —O—; —C(O)—; —OC(O)—; —C(O)O—; —S—; —S(O)—; —S(O)$_2$—; or -Cy-;

Cy is an optionally substituted bivalent 5-6 membered monocyclic heteroaryl ring having 1-4 heteroatoms independently selected from nitrogen, oxygen, and sulfur; an optionally substituted bivalent 8-10 membered bicyclic heteroaryl ring having 1-4 heteroatoms independently selected from nitrogen, oxygen, and sulfur; an optionally substituted bivalent 3-7 membered saturated or partially unsaturated carbocyclic ring; or an optionally substituted bivalent 7-12 membered saturated or partially unsaturated bicyclic heterocyclic ring having 1-4 heteroatoms independently selected from nitrogen, oxygen, and sulfur;

$R^{1A}$ is oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; an optionally substituted $C_{1-6}$ aliphatic group; phenyl; an optionally substituted 5-6 membered monocyclic heteroaryl ring having 1-4 heteroatoms independently selected from nitrogen, oxygen, and sulfur; an optionally substituted 8-10 membered bicyclic heteroaryl ring having 1-4 heteroatoms independently selected from nitrogen, oxygen, and sulfur; an optionally substituted 3-7 membered saturated or partially unsaturated carbocyclic ring; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

$R^2$ is —C(O)NH$_2$; —C(O)NR$^{2A}$; —C(O)N(R$^{2A}$)$_2$; or a 5-6 membered monocyclic heteroaryl ring having 1-4 heteroatoms independently selected from nitrogen, oxygen, and sulfur, wherein said heteroaryl ring is substituted with m instances of $R^{2B}$;

$R^{2A}$ is a $C_{1-6}$ aliphatic group; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

wherein $R^{2A}$ is substituted by n instances of $R^{2C}$, wherein two $R^{2C}$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^{2C}$ substituents on adjacent carbons are optionally taken together to form a 3-6 membered saturated or partially unsaturated fused heterocyclic ring having 1-4 heteroatoms independently selected from nitrogen, oxygen, and sulfur;

$R^{2B}$ is oxo; halogen; —CN; —NO$_2$; —R; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; or —N(R)S(O)$_2$R;

each instance of $R^{2C}$ is independently oxo; halogen, —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)NR$_2$; —N(R)C(NR)NR$_2$; —N(R)S(O)$_2$NR$_2$; —N(R)S(O)$_2$R; or an optionally substituted group selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

$R^3$ is hydrogen; halogen; —NH$_2$; —NHR$^{3A}$; or —NHC(O)R$^{3A}$;

$R^{3A}$ is a $C_{1-6}$ aliphatic group; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

wherein $R^{3A}$ is substituted by p instances of $R^{3B}$, wherein two $R^{3B}$ substituents on the same carbon are optionally taken together to form a 3-6 membered saturated or partially unsaturated spiro-fused heterocyclic ring having 1-4 heteroatoms independently selected from nitrogen, oxygen, and sulfur; or wherein two $R^{3B}$ substituents on adjacent carbons are optionally taken together to form a 3-6 membered saturated or partially unsaturated fused heterocyclic ring having 1-4 heteroatoms independently selected from nitrogen, oxygen, and sulfur;

each instance of $R^{3B}$ is independently oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; or an optionally substituted group selected from C$_{1-6}$ aliphatic; phenyl, a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur; or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

$R^4$ is R, or $R^1$ and $R^4$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{1A}$;

each R is independently hydrogen; or an optionally substituted group selected from C$_{1-6}$ aliphatic; phenyl; a 3-7 membered saturated or partially unsaturated heterocyclic having 1-2 heteroatoms independently selected from nitrogen, oxygen, and sulfur; and a 5-6 membered heteroaryl ring having 1-4 heteroatoms independently selected from nitrogen, oxygen, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium;

m is 0, 1, or 2;

n is 0, 1, or 2; and p is 0, 1, or 2.

As described above, in certain embodiments, the present invention provides a compound of Formula I':

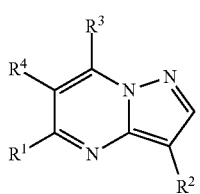

I'

$R^1$ is -L$^1$-R$^{1A}$;

L$^1$ is a covalent bond; or a C$_{1-6}$ bivalent saturated or unsaturated, straight or branched hydrocarbon chain, wherein one or two methylene units of the chain are optionally and independently replaced by —C(R)$_2$—; —N(R)—; —N(R)C(O)—; —C(O)N(R)—; —N(R)S(O)$_2$—; —S(O)$_2$N(R)—; —O—; —C(O)—; —OC(O)—; —C(O)O—; —S—; —S(O)—; —S(O)$_2$—; or -Cy-;

Cy is an optionally substituted bivalent 5-6 membered monocyclic heteroaryl ring having 1-4 heteroatoms independently selected from nitrogen, oxygen, and sulfur; an optionally substituted bivalent 8-10 membered bicyclic heteroaryl ring having 1-4 heteroatoms independently selected from nitrogen, oxygen, and sulfur; an optionally substituted bivalent 3-7 membered saturated or partially unsaturated carbocyclic ring; or an optionally substituted bivalent 7-12 membered saturated or partially unsaturated bicyclic heterocyclic ring having 1-4 heteroatoms independently selected from nitrogen, oxygen, and sulfur;

$R^{1A}$ is oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; an optionally substituted C$_{1-6}$ aliphatic group; phenyl; an optionally substituted 5-6 membered monocyclic heteroaryl ring having 1-4 heteroatoms independently selected from nitrogen, oxygen, and sulfur; an optionally substituted 8-10 membered bicyclic heteroaryl ring having 1-4 heteroatoms independently selected from nitrogen, oxygen, and sulfur; an optionally substituted 3-7 membered saturated or partially unsaturated carbocyclic ring; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

$R^2$ is —C(O)OH; —C(O)NH$_2$; —C(O)NHR$^{2A}$; —C(O)N(R$^{2A}$)$_2$; or a 5-6 membered monocyclic heteroaryl ring having 1-4 heteroatoms independently selected from nitrogen, oxygen, and sulfur, wherein said heteroaryl ring is substituted with m instances of $R^{2B}$;

$R^{2A}$ is a C$_{1-6}$ aliphatic group; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

wherein $R^{2A}$ is substituted by n instances of $R^{2C}$, wherein two $R^{2C}$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two $R^{2C}$ substituents on adjacent carbons are optionally taken together to form a 3-6 membered saturated or partially unsaturated fused heterocyclic ring having 1-4 heteroatoms independently selected from nitrogen, oxygen, and sulfur;

$R^{2B}$ is oxo; halogen; —CN; —NO$_2$; —R; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; or —N(R)S(O)$_2$R;

each instance of $R^{2C}$ is independently oxo; halogen, —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; or an optionally substituted group selected from C$_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

$R^3$ is hydrogen; halogen; —NH$_2$; —NHR$^{3A}$; —NHC(O)R$^{3A}$, or —NR$^{3A}$Boc;

$R^{3A}$ is a C$_{1-6}$ aliphatic group; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

wherein $R^{3A}$ is substituted by p instances of $R^{3B}$ wherein two $R^{3B}$ substituents on the same carbon are optionally taken together to form a 3-6 membered saturated or partially unsaturated spiro-fused heterocyclic ring having 1-4 heteroatoms independently selected from nitrogen, oxygen, and sulfur; or wherein two $R^{3B}$ substituents on adjacent carbons are optionally taken together to form a 3-6 membered saturated or partially unsaturated fused heterocyclic ring having 1-4 heteroatoms independently selected from nitrogen, oxygen, and sulfur;

each instance of $R^{3B}$ is independently oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; or an optionally substituted group selected from C$_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur; or wherein two optional substituents on adjacent carbons are optionally taken together to form a 3-6 membered saturated or partially unsaturated fused heterocyclic ring having 1-4 heteroatoms independently selected from nitrogen, oxygen, and sulfur;

$R^4$ is R or —OR, or $R^1$ and $R^4$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{1A}$;

or $R^3$ and $R^4$ are taken together with their intervening atoms to form a 4-7 membered partially unsaturated, or heteroaryl ring having 0-3 heteroatoms independently selected from nitrogen, oxygen, and sulfur;

each R is independently hydrogen; or an optionally substituted group selected from C$_{1-6}$ aliphatic; phenyl; a 3-7 membered saturated or partially unsaturated heterocyclic having 1-2 heteroatoms independently selected from nitrogen, oxygen, and sulfur; and a 5-6 membered heteroaryl ring having 1-4 heteroatoms independently selected from nitrogen, oxygen, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

wherein each hydrogen bound to carbon can be optionally and independently replaced by deuterium;

m is 0, 1, or 2;

n is 0, 1, or 2; and p is 0, 1, or 2.

As defined generally above, $R^1$ is -L$^1$-R$^{1A}$.

In some embodiments, $R^1$ is selected from those depicted in Table 1, below.

As defined generally above, L$^1$ is a covalent bond; or a C$_{1-6}$ bivalent saturated or unsaturated, straight or branched hydrocarbon chain, wherein one or two methylene units of the chain are optionally and independently replaced by —C(R)$_2$—; —N(R)—; —N(R)C(O)—; —C(O)N(R)—; —N(R)S(O)$_2$—; —S(O)$_2$N(R)—; —O—; —C(O)—; —OC(O)—; —C(O)O—; —S—; —S(O)—; —S(O)$_2$—; or -Cy-.

In some embodiments, L$^1$ is a covalent bond. In some embodiments, L$^1$ is a C$_{1-6}$ bivalent saturated straight hydrocarbon chain, wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-.

In some embodiments, $L^1$ is a $C_{1-6}$ bivalent unsaturated straight hydrocarbon chain, wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-.

In some embodiments, $L^1$ is a $C_{1-6}$ bivalent saturated branched hydrocarbon chain, wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-.

In some embodiments, $L^1$ is a $C_{1-6}$ bivalent unsaturated branched hydrocarbon chain, wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-.

In some embodiments, $L^1$ is —N(R)—. In some embodiments, $L^1$ is —N(H)—. In some embodiments, $L^1$ is -Cy-. In some embodiments, $L^1$ is -Cy-N(R)—. In some embodiments, $L^1$ is -Cy-NH—.

In some embodiments, $L^1$ is

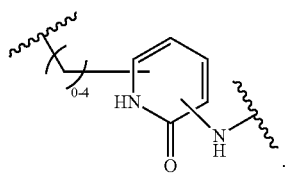

In some embodiments, $L^1$ is

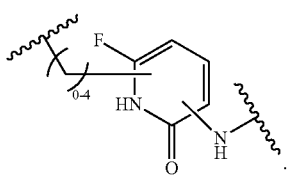

In some embodiments, $L^1$ is

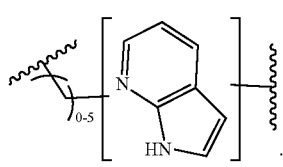

In some embodiments, $L^1$ is

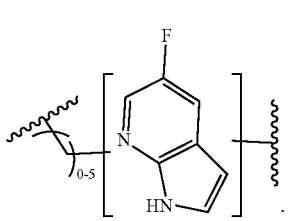

In some embodiments, $L^1$ is

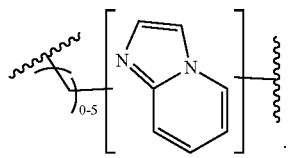

In some embodiments, $L^1$ is

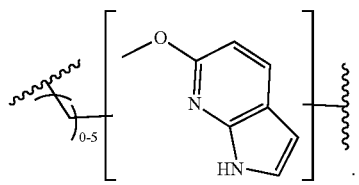

In some embodiments, $L^1$ is

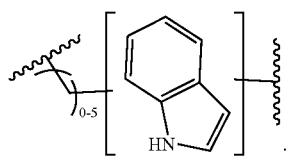

In some embodiments, $L^1$ is

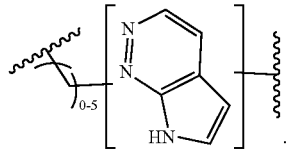

In some embodiments, $L^1$ is

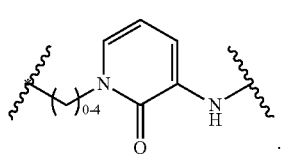

In some embodiments, $L^1$ is

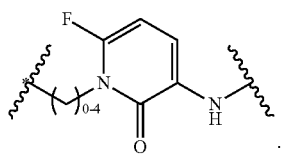

In some embodiments, L¹ is

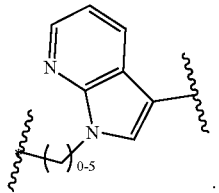

In some embodiments, L¹ is

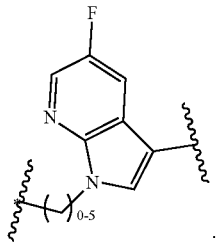

In some embodiments, L¹ is

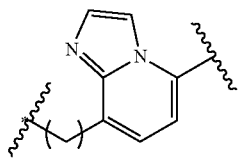

In some embodiments, L¹ is

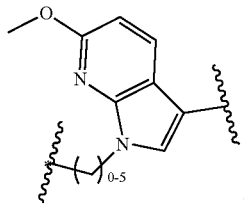

In some embodiments, L¹ is

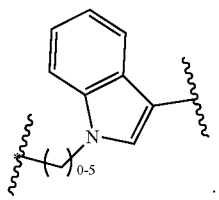

In some embodiments, L¹ is

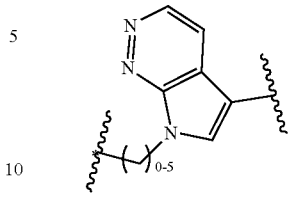

In some embodiments, L¹ is

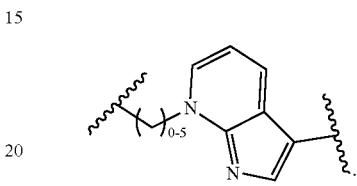

In some embodiments, L¹ is

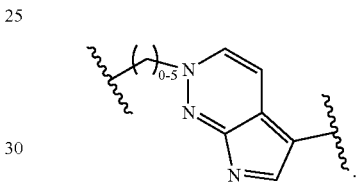

In some embodiments, L¹ is selected from those depicted in Table 1, below.

As defined generally above, Cy is an optionally substituted bivalent 5-6 membered monocyclic heteroaryl ring having 1-4 heteroatoms independently selected from nitrogen, oxygen, and sulfur; an optionally substituted bivalent 8-10 membered bicyclic heteroaryl ring having 1-4 heteroatoms independently selected from nitrogen, oxygen, and sulfur; an optionally substituted bivalent 3-7 membered saturated or partially unsaturated carbocyclic ring; or an optionally substituted bivalent 7-12 membered saturated or partially unsaturated bicyclic heterocyclic ring having 1-4 heteroatoms independently selected from nitrogen, oxygen, and sulfur.

In some embodiments, Cy is an optionally substituted bivalent 5-6 membered monocyclic heteroaryl ring having 1-4 heteroatoms independently selected from nitrogen, oxygen, and sulfur. In some embodiments, Cy is an optionally substituted bivalent 8-10 membered bicyclic heteroaryl ring having 1-4 heteroatoms independently selected from nitrogen, oxygen, and sulfur. In some embodiments, Cy is an optionally substituted bivalent 3-7 membered saturated carbocyclic ring. In some embodiments, Cy is an optionally substituted bivalent 3-7 membered partially unsaturated carbocyclic ring. In some embodiments, Cy is an optionally substituted bivalent 7-12 membered saturated bicyclic heterocyclic ring having 1-4 heteroatoms independently selected from nitrogen, oxygen, and sulfur. In some embodiments, Cy is an optionally substituted bivalent 7-12 membered partially unsaturated bicyclic heterocyclic ring having 1-4 heteroatoms independently selected from nitrogen, oxygen, and sulfur.

In some embodiments, Cy is
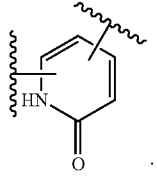
In some embodiments, Cy is
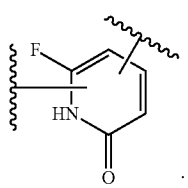
In some embodiments, Cy is
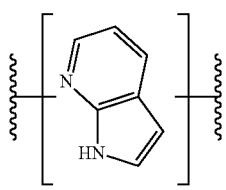
In some embodiments, Cy is
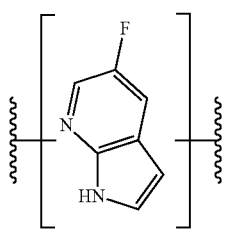
In some embodiments, Cy is
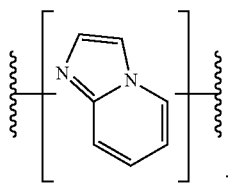
In some embodiments, Cy is

In some embodiments, Cy is
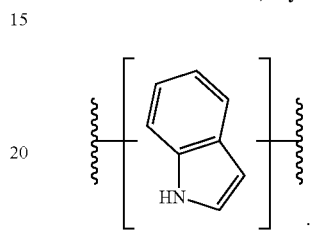
In some embodiments, Cy is
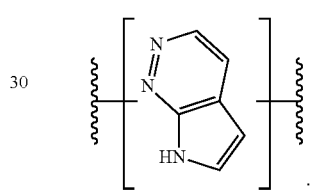
In some embodiments, Cy is
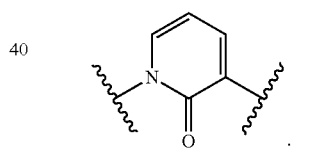
In some embodiments, Cy is
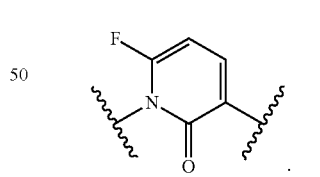
In some embodiments, Cy is
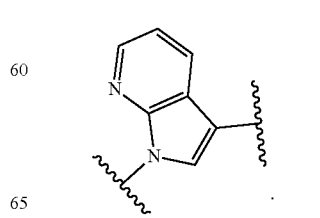

In some embodiments, Cy is

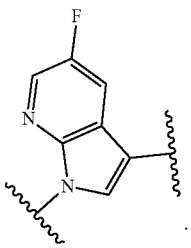 [SMILES: *c1cn(*)c2ncc(F)cc12]

In some embodiments, Cy is

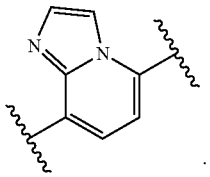 [SMILES: *c1ccc(*)n2ccnc12]

In some embodiments, Cy is

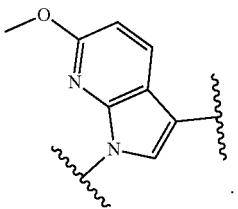 [SMILES: *c1cn(*)c2nc(OC)ccc12]

In some embodiments, Cy is

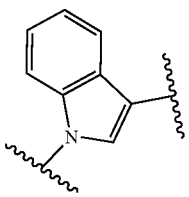

In some embodiments, Cy is

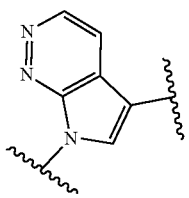

In some embodiments, Cy is

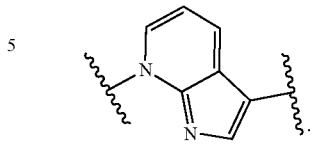

In some embodiments, Cy is

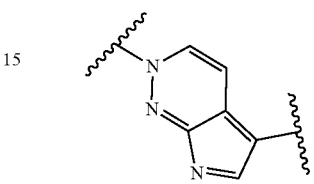

In some embodiments, Cy is selected from those depicted in Table 1, below.

As defined generally above, $R^{14}$ is oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; an optionally substituted C$_{1-6}$ aliphatic group; phenyl; an optionally substituted 5-6 membered monocyclic heteroaryl ring having 1-4 heteroatoms independently selected from nitrogen, oxygen, and sulfur; an optionally substituted 8-10 membered bicyclic heteroaryl ring having 1-4 heteroatoms independently selected from nitrogen, oxygen, and sulfur; an optionally substituted 3-7 membered saturated or partially unsaturated carbocyclic ring; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur.

In some embodiments, $R^{14}$ is oxo. In some embodiments, $R^{14}$ is halogen. In some embodiments, $R^{14}$ is —CN. In some embodiments, $R^{14}$ is —NO$_2$. In some embodiments, $R^{14}$ is —OR. In some embodiments, $R^{14}$ is —SR. In some embodiments, $R^{14}$ is —NR$_2$. In some embodiments, $R^{14}$ is —S(O)$_2$R. In some embodiments, $R^{14}$ is —S(O)$_2$NR$_2$. In some embodiments, $R^{14}$ is —S(O)R. In some embodiments, $R^{14}$ is —S(O)NR$_2$. In some embodiments, $R^{14}$ is —C(O)R. In some embodiments, $R^{14}$ is —C(O)OR. In some embodiments, $R^{14}$ is —C(O)NR$_2$. In some embodiments, $R^{14}$ is —C(O)N(R)OR. In some embodiments, $R^{14}$ is —OC(O)R. In some embodiments, $R^{14}$ is —OC(O)NR$_2$. In some embodiments, $R^{14}$ is —N(R)C(O)OR. In some embodiments, $R^{14}$ is —N(R)C(O)R. In some embodiments, $R^{14}$ is —N(R)C(O)NR$_2$. In some embodiments, $R^{14}$ is —N(R)C(NR)NR$_2$. In some embodiments, $R^{14}$ is —N(R)S(O)$_2$NR$_2$. In some embodiments, $R^{14}$ is —N(R)S(O)$_2$R.

In some embodiments, $R^{14}$ is an optionally substituted C$_{1-6}$ aliphatic group. In some embodiments, $R^{14}$ is phenyl. In some embodiments, $R^{14}$ is an optionally substituted 5-6 membered monocyclic heteroaryl ring having 1-4 heteroatoms independently selected from nitrogen, oxygen, and sulfur. In some embodiments, $R^{14}$ is an optionally substituted 8-10 membered bicyclic heteroaryl ring having 1-4 heteroatoms independently selected from nitrogen, oxygen, and sulfur. In some embodiments, $R^{14}$ is an optionally substituted 3-7 membered saturated carbocyclic ring. In some embodiments, $R^{1A}$ is an optionally substituted 3-7 membered partially unsaturated carbocyclic ring. In some embodiments, $R^{1A}$ is an optionally substituted 3-7 membered saturated monocyclic heterocyclic ring having 1-2 heteroatoms independently selected from nitrogen, oxygen, and sulfur. In some embodiments, $R^{1A}$ is an optionally substituted 3-7 membered partially unsaturated monocyclic heterocyclic ring having 1-2 heteroatoms independently selected from nitrogen, oxygen, and sulfur. In some embodiments, $R^{1A}$ is an optionally substituted 7-12 membered saturated bicyclic heterocyclic ring having 1-4 heteroatoms independently selected from nitrogen, oxygen, and sulfur. In some embodiments, $R^{1A}$ is an optionally substituted 7-12 membered partially unsaturated bicyclic heterocyclic ring having 1-4 heteroatoms independently selected from nitrogen, oxygen, and sulfur.

In some embodiments, $R^{1A}$ is selected from:

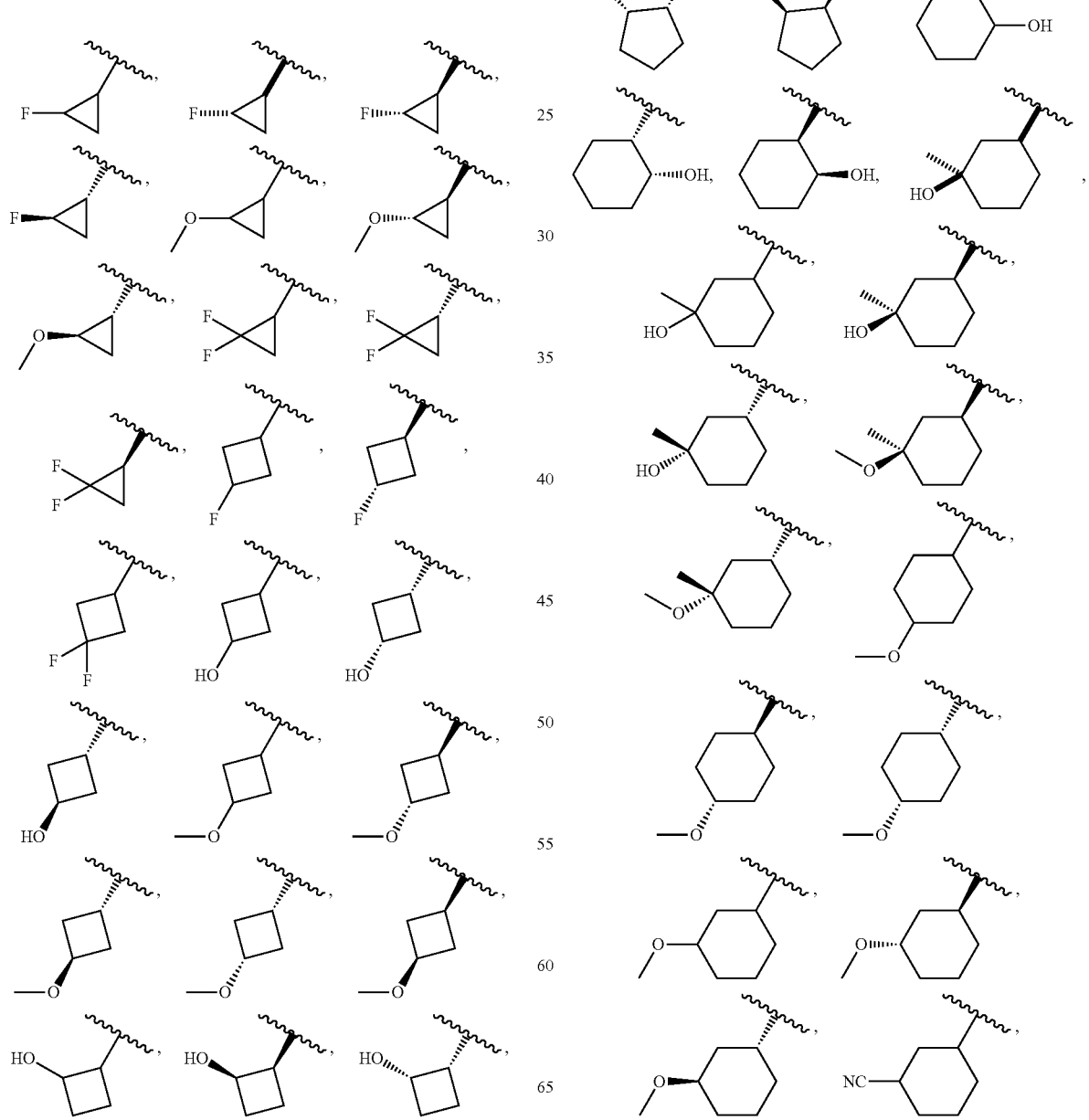

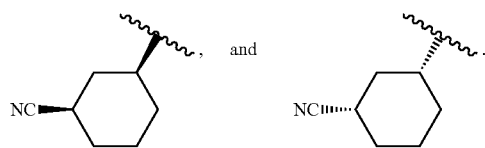, and
In some embodiments, $R^{14}$ is selected from:
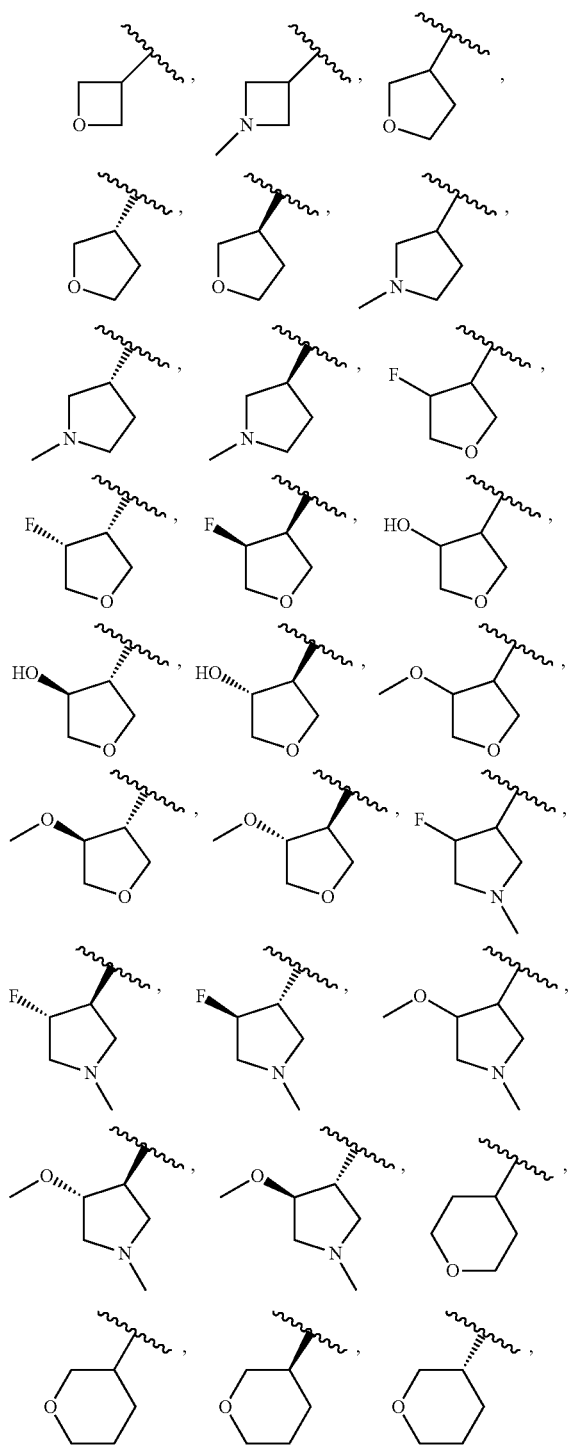
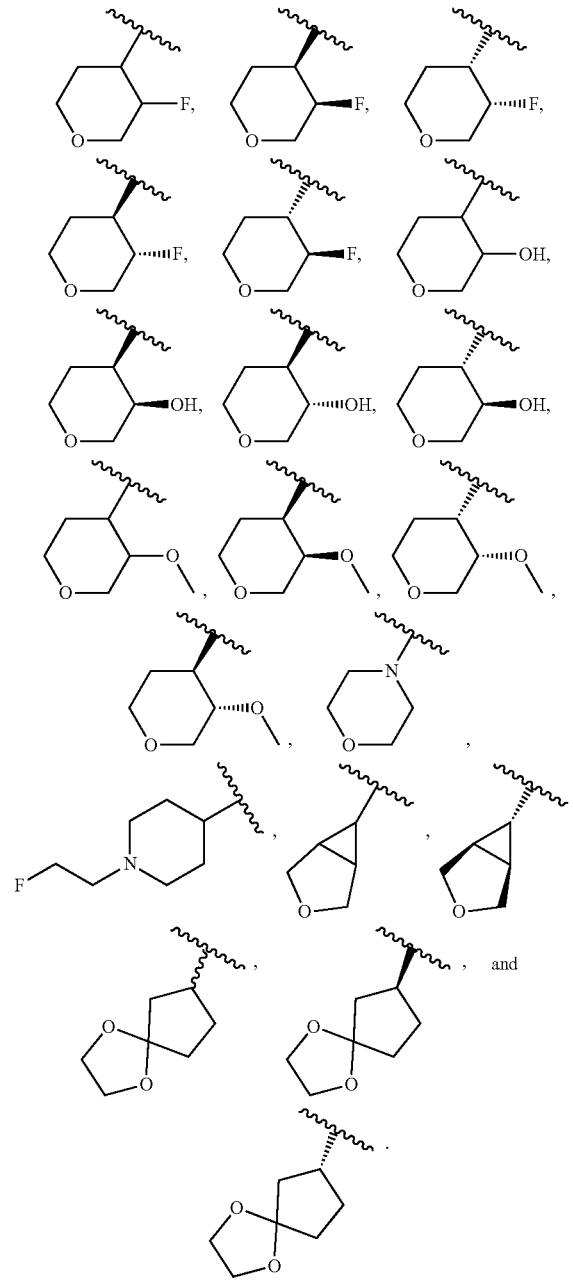
In some embodiments, $R^{14}$ is selected from:
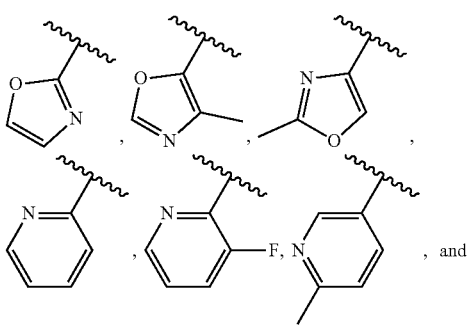

-continued

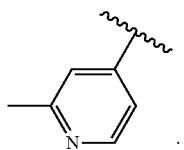

In some embodiments, $R^{1A}$ is selected from:

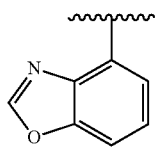

In some embodiments, $R^{1A}$ is

In some embodiments, $R^{1A}$ is selected from

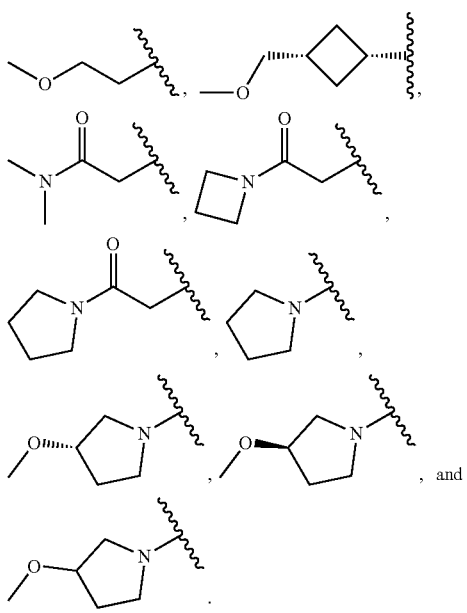

, and

In some embodiments, $R^{1A}$ is selected from:

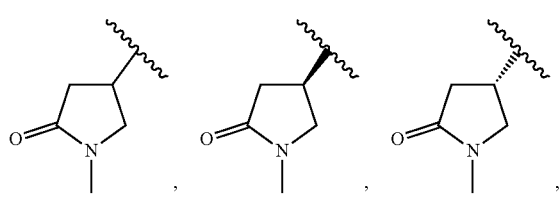

-continued

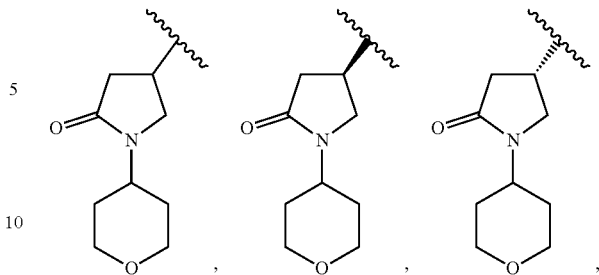

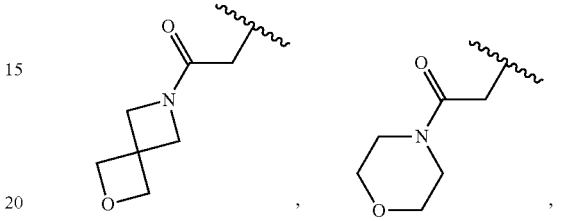

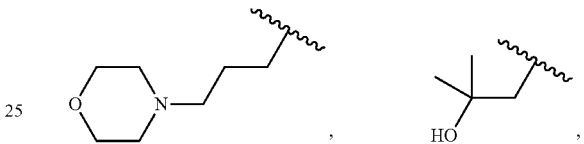

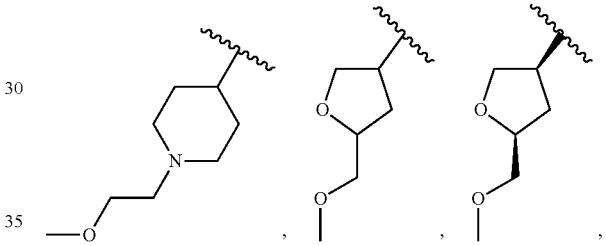

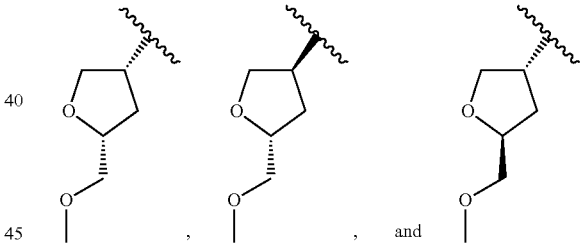

and

In some embodiments, $R^{1A}$ is —NR$_2$. In some embodiments, $R^{1A}$ is —N(H)Me.

In some embodiments, $R^{1A}$ is selected from those depicted in Table 1, below.

As defined generally above, $R^2$ is —C(O)OH, —C(O)NH$_2$; —C(O)NHR$^{2A}$; —C(O)N(R$^{2A}$)$_2$; or a 5-6 membered monocyclic heteroaryl ring having 1-4 heteroatoms independently selected from nitrogen, oxygen, and sulfur, wherein said heteroaryl ring is substituted with m instances of R$^{2B}$.

In some embodiments, $R^2$ is —C(O)OH. In some embodiments, $R^2$ is —C(O)NH$_2$. In some embodiments, $R^2$ is —C(O)NHR$^{2A}$. In some embodiments, $R^2$ is —C(O)N(R$^{2A}$)$_2$.

In some embodiments, $R^2$ is a 5-6 membered monocyclic heteroaryl ring having 1-4 heteroatoms independently selected from nitrogen, oxygen, and sulfur, wherein said heteroaryl ring is substituted with m instances of R$^{2B}$.

In some embodiments, $R^2$ is

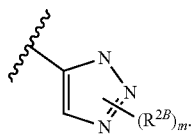

In some embodiments, $R^2$ is

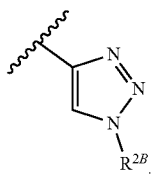

In some embodiments, $R^2$ is selected from those depicted in Table 1, below.

As defined generally above, $R^{2A}$ is a $C_{1-6}$ aliphatic group; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{2A}$ is substituted by n instances of $R^{2C}$; wherein two $R^{2C}$ substituents on the same carbon are optionally taken together to form a 3-6 membered saturated or partially unsaturated spiro-fused heterocyclic ring having 1-4 heteroatoms independently selected from nitrogen, oxygen, and sulfur; or wherein two $R^{2C}$ substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{2A}$ is a $C_{1-6}$ aliphatic group. In some embodiments, $R^{2A}$ is phenyl. In some embodiments, $R^{2A}$ is a 5-6 membered monocyclic heteroaryl ring having 1-4 heteroatoms independently selected from nitrogen, oxygen, and sulfur. In some embodiments, $R^{2A}$ is an 8-10 membered bicyclic heteroaryl ring having 1-4 heteroatoms independently selected from nitrogen, oxygen, and sulfur. In some embodiments, $R^{2A}$ is a 3-7 membered saturated carbocyclic ring. In some embodiments, $R^{2A}$ is a 3-7 membered partially unsaturated carbocyclic ring. In some embodiments, $R^{2A}$ is a 7-12 membered saturated bicyclic heterocyclic ring having 1-4 heteroatoms independently selected from nitrogen, oxygen, and sulfur. In some embodiments, $R^{2A}$ is a 7-12 membered partially unsaturated bicyclic heterocyclic ring having 1-4 heteroatoms independently selected from nitrogen, oxygen, and sulfur.

In some embodiments, $R^{2A}$ is substituted by n instances of $R^{2C}$.

In some embodiments, two $R^{2C}$ substituents on the same carbon are optionally taken together to form a 3-6 membered saturated spiro-fused heterocyclic ring having 1-4 heteroatoms independently selected from nitrogen, oxygen, and sulfur. In some embodiments, two $R^{2C}$ substituents on the same carbon are optionally taken together to form a 3-6 membered partially unsaturated spiro-fused heterocyclic ring having 1-4 heteroatoms independently selected from nitrogen, oxygen, and sulfur.

In some embodiments, two $R^{2C}$ substituents on adjacent carbons are optionally taken together to form a 3-6 membered saturated fused heterocyclic ring having 1-4 heteroatoms independently selected from nitrogen, oxygen, and sulfur. In some embodiments, two $R^{2C}$ substituents on adjacent carbons are optionally taken together to form a 3-6 membered partially unsaturated fused heterocyclic ring having 1-4 heteroatoms independently selected from nitrogen, oxygen, and sulfur.

In some embodiments, $R^{2A}$ selected from the following:

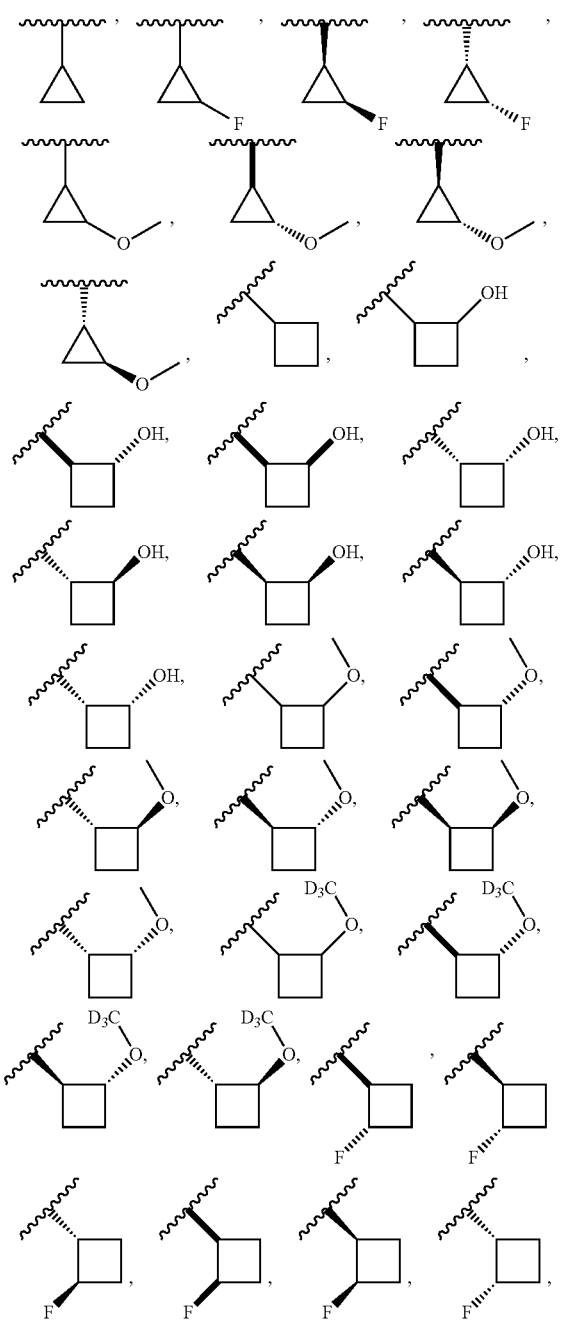

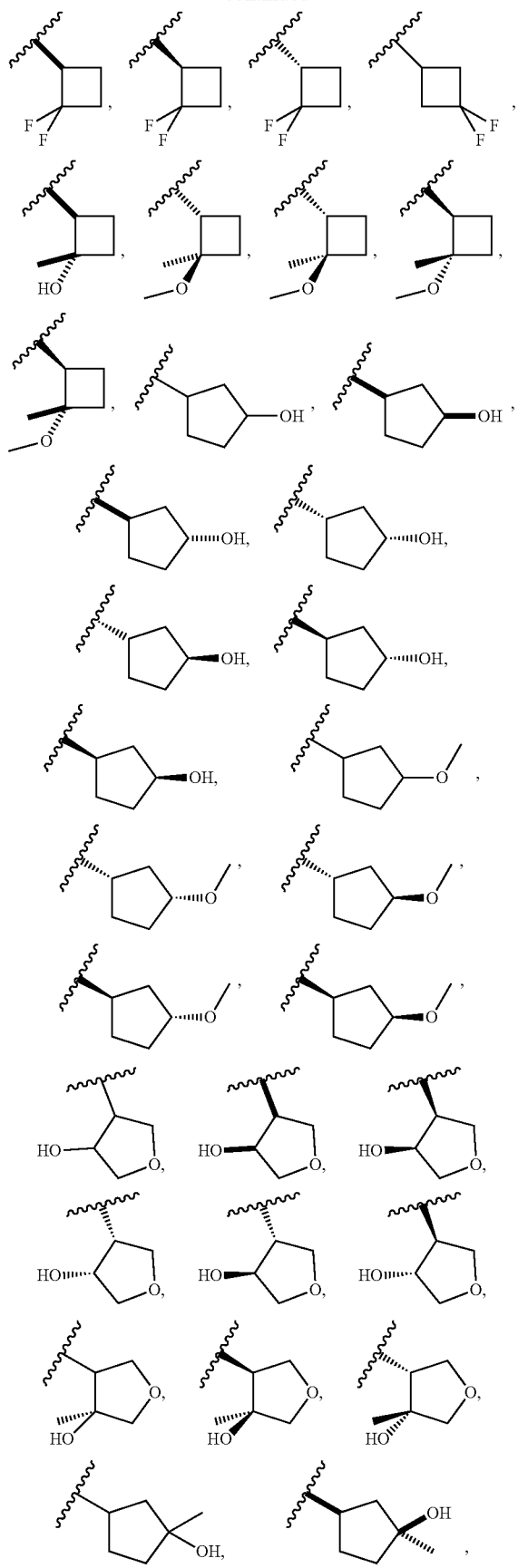
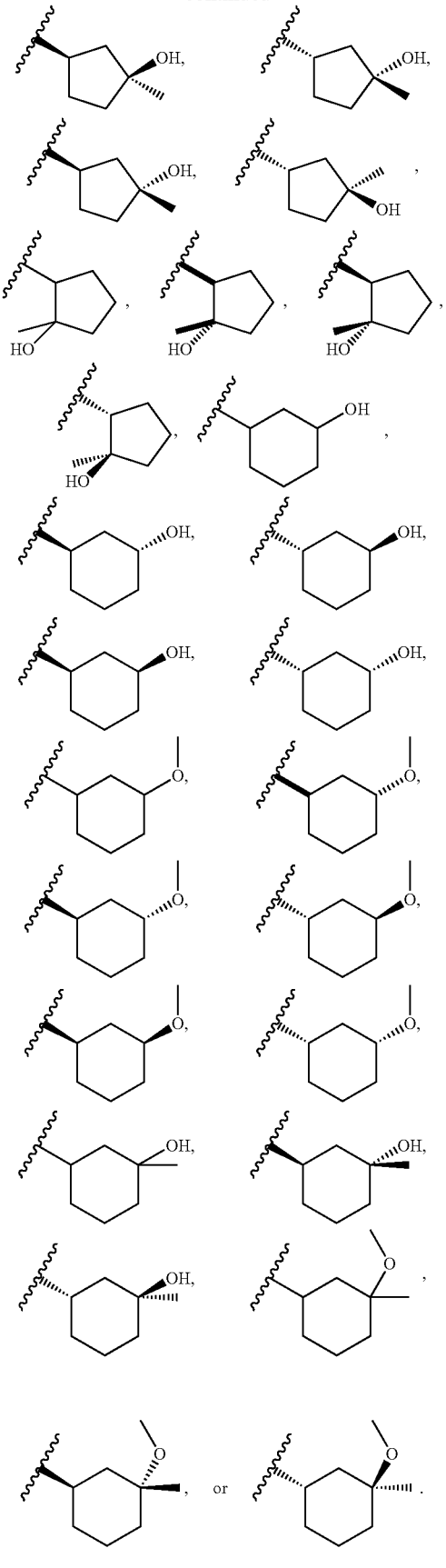

In some embodiments, $R^{2A}$ selected from the following:

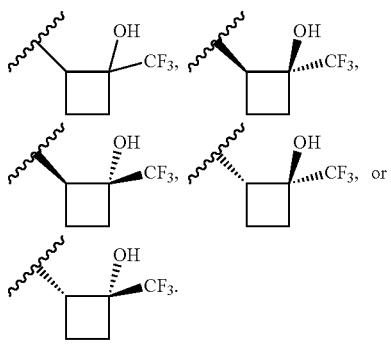

In some embodiments, $R^{2A}$ is selected from those depicted in Table 1, below.

As defined generally above, $R^{2B}$ is oxo, halogen; —CN; —NO$_2$; —R; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; or —N(R)S(O)$_2$R.

In some embodiments, $R^{2B}$ is oxo. In some embodiments, $R^{2B}$ is —CN. In some embodiments, $R^{2B}$ is —NO$_2$. In some embodiments, $R^{2B}$ is —R. In some embodiments, $R^{2B}$ is —OR. In some embodiments, $R^{2B}$ is —SR. In some embodiments, $R^{2B}$ is —NR$_2$. In some embodiments, $R^{2B}$ is —S(O)$_2$R. In some embodiments, $R^{2B}$ is —S(O)$_2$NR$_2$. In some embodiments, $R^{2B}$ is —S(O)R. In some embodiments, $R^{2B}$ is —S(O)NR$_2$. In some embodiments, $R^{2B}$ is —C(O)R. In some embodiments, $R^{2B}$ is —C(O)OR. In some embodiments, $R^{2B}$ is —C(O)NR$_2$. In some embodiments, $R^{2B}$ is —C(O)N(R)OR. In some embodiments, $R^{2B}$ is —OC(O)R. In some embodiments, $R^{2B}$ is —OC(O)NR$_2$. In some embodiments, $R^{2B}$ is —N(R)C(O)OR. In some embodiments, $R^{2B}$ is —N(R)C(O)R. In some embodiments, $R^{2B}$ is —N(R)C(NR)NR$_2$. In some embodiments, $R^{2B}$ is —N(R)S(O)$_2$NR$_2$. In some embodiments, $R^{2B}$ is —N(R)S(O)$_2$R.

In some embodiments, $R^{2B}$ is isopropyl.

In some embodiments, $R^{2B}$ is selected from those depicted in Table 1, below.

As generally defined above, $R^{2C}$ is oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; or an optionally substituted group selected from C$_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{2C}$ is oxo. In some embodiments, $R^{2C}$ is —CN. In some embodiments, $R^{2C}$ is —NO$_2$. In some embodiments, $R^{2C}$ is —R. In some embodiments, $R^{2C}$ is —OR. In some embodiments, $R^{2C}$ is —SR. In some embodiments, $R^{2C}$ is —NR$_2$. In some embodiments, $R^{2C}$ is —S(O)$_2$R. In some embodiments, $R^{2C}$ is —S(O)$_2$NR$_2$. In some embodiments, $R^{2C}$ is —S(O)R. In some embodiments, $R^{2C}$ is —S(O)NR$_2$. In some embodiments, $R^{2C}$ is —C(O)R. In some embodiments, $R^{2C}$ is —C(O)OR. In some embodiments, $R^{2C}$ is —C(O)NR$_2$. In some embodiments, $R^{2C}$ is —C(O)N(R)OR. In some embodiments, $R^{2C}$ is —OC(O)R. In some embodiments, $R^{2C}$ is —OC(O)NR$_2$. In some embodiments, $R^{2C}$ is —N(R)C(O)OR. In some embodiments, $R^{2C}$ is —N(R)C(O)R. In some embodiments, $R^{2C}$ is —N(R)C(NR)NR$_2$. In some embodiments, $R^{2C}$ is —N(R)S(O)$_2$NR$_2$. In some embodiments, $R^{2C}$ is —N(R)S(O)$_2$R.

In some embodiments, $R^{2C}$ is an optionally substituted C$_{1-6}$ aliphatic group. In some embodiments, $R^{2C}$ is an optionally substituted phenyl group. In some embodiments, $R^{2C}$ is an optionally substituted 3-7 membered saturated heterocyclic ring having 1-2 heteroatoms independently selected from nitrogen, oxygen, and sulfur. In some embodiments, $R^{2C}$ is an optionally substituted 3-7 membered partially unsaturated heterocyclic ring having 1-2 heteroatoms independently selected from nitrogen, oxygen, and sulfur. In some embodiments, $R^{2C}$ is an optionally substituted 5-6 membered heteroaryl ring having 1-4 heteroatoms independently selected from nitrogen, oxygen, and sulfur.

In some embodiments, two optional substituents on the same carbon are optionally taken together to form a 3-6 membered saturated or partially unsaturated spiro-fused heterocyclic ring having 1-4 heteroatoms independently selected from nitrogen, oxygen, and sulfur. In some embodiments, two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{2C}$ is selected from those depicted in Table 1, below.

As generally defined above, $R^3$ is hydrogen, halogen, —NH$_2$, —NHR$^{3A}$, —NHC(O)R$^{3A}$ or —NR$^{3A}$Boc.

In some embodiments, $R^3$ is hydrogen. In some embodiments, $R^3$ is halogen. In some embodiments, $R^3$ is —NH$_2$. In some embodiments, $R^3$ is —NHR$^{3A}$. In some embodiments, $R^3$ is —NHC(O)R$^{3A}$. In some embodiments, $R^3$ is —NR$^{3A}$Boc.

In some embodiments, $R^3$ is —NHR$^{3A}$.

In some embodiments, $R^3$ is —C(O)NHR$^{3A}$.

In some embodiments, $R^3$ is —N(Me)Boc.

In some embodiments, $R^3$ is selected from those depicted in Table 1, below.

As generally described above, $R^{3A}$ is a C$_{1-6}$ aliphatic group; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein R$^{3A}$ is substituted by p instances of R$^{3B}$, wherein two R$^{3B}$ substituents on the same carbon are optionally taken together to form a 3-6 membered saturated or partially unsaturated spiro-fused heterocyclic ring having 1-4 heteroatoms independently selected from nitrogen, oxygen, and sulfur, or wherein two R$^{3B}$ substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{3A}$ is a $C_{1-6}$ aliphatic group. In some embodiments, $R^{3A}$ is phenyl. In some embodiments, $R^{3A}$ is a 5-6 membered monocyclic heteroaryl ring having 1-4 heteroatoms independently selected from nitrogen, oxygen, and sulfur. In some embodiments, $R^{3A}$ is an 8-10 membered bicyclic heteroaryl ring having 1-4 heteroatoms independently selected from nitrogen, oxygen, and sulfur. In some embodiments, $R^{3A}$ is a 3-7 membered saturated carbocyclic ring. In some embodiments, $R^{3A}$ is a 3-7 membered partially unsaturated carbocyclic ring. In some embodiments, $R^{3A}$ is a 3-7 membered saturated monocyclic heterocyclic ring having 1-2 heteroatoms independently selected from nitrogen, oxygen, and sulfur. In some embodiments, $R^{3A}$ is a 3-7 membered partially unsaturated monocyclic heterocyclic ring having 1-2 heteroatoms independently selected from nitrogen, oxygen, and sulfur. In some embodiments, $R^{3A}$ is a 7-12 membered saturated bicyclic heterocyclic ring having 1-4 heteroatoms independently selected from nitrogen, oxygen, and sulfur. In some embodiments, $R^{3A}$ is a 7-12 membered partially unsaturated bicyclic heterocyclic ring having 1-4 heteroatoms independently selected from nitrogen, oxygen, and sulfur.

In some embodiments, $R^{3A}$ is substituted by p instances of $R^{3B}$.

In some embodiments, two $R^{3B}$ substituents on the same carbon are optionally taken together to form a 3-6 membered saturated spiro-fused heterocyclic ring having 1-4 heteroatoms independently selected from nitrogen, oxygen, and sulfur. In some embodiments, two $R^{3B}$ substituents on the same carbon are optionally taken together to form a 3-6 membered partially unsaturated spiro-fused heterocyclic ring having 1-4 heteroatoms independently selected from nitrogen, oxygen, and sulfur. In some embodiments, two $R^{3B}$ substituents on adjacent carbons are optionally taken together to form a 3-6 membered saturated fused heterocyclic ring having 1-4 heteroatoms independently selected from nitrogen, oxygen, and sulfur. In some embodiments, two $R^{3B}$ substituents on adjacent carbons are optionally taken together to form a 3-6 membered partially unsaturated fused heterocyclic ring having 1-4 heteroatoms independently selected from nitrogen, oxygen, and sulfur.

In some embodiments, $R^{3A}$ is methyl. In some embodiments, $R^{3A}$ is ethyl.

In some embodiments, $R^{3A}$ is selected from those depicted in Table 1, below.

As generally described above, $R^{3B}$ is oxo; halogen; —CN; —NO$_2$; —OR; —SR; —NR$_2$; —S(O)$_2$R; —S(O)$_2$NR$_2$; —S(O)R; —S(O)NR$_2$; —C(O)R; —C(O)OR; —C(O)NR$_2$; —C(O)N(R)OR; —OC(O)R; —OC(O)NR$_2$; —N(R)C(O)OR; —N(R)C(O)R; —N(R)C(O)NR$_2$; —N(R)C(NR)NR$_2$; —N(R)S(O)$_2$NR$_2$; —N(R)S(O)$_2$R; or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, wherein two optional substituents on the same carbon are optionally taken together to form a 3-6 membered saturated or partially unsaturated spiro-fused heterocyclic ring having 1-4 heteroatoms independently selected from nitrogen, oxygen, and sulfur; or wherein two optional substituents on adjacent carbons are optionally taken together to form a 3-6 membered saturated or partially unsaturated fused heterocyclic ring having 1-4 heteroatoms independently selected from nitrogen, oxygen, and sulfur.

In some embodiments, $R^{3B}$ is oxo. In some embodiments, $R^{3B}$ is halogen. In some embodiments, $R^{3B}$ is —CN. In some embodiments, $R^{3B}$ is —NO$_2$. In some embodiments, $R^{3B}$ is —OR. In some embodiments, $R^{3B}$ is —SR. In some embodiments, $R^{3B}$ is —NR$_2$. In some embodiments, $R^{3B}$ is —S(O)$_2$R. In some embodiments, $R^{3B}$ is —S(O)$_2$NR$_2$. In some embodiments, $R^{3B}$ is —S(O)R. In some embodiments, $R^{3B}$ is —S(O)NR$_2$. In some embodiments, $R^{3B}$ is —C(O)R. In some embodiments, $R^{3B}$ is —C(O)OR. In some embodiments, $R^{3B}$ is —C(O)NR$_2$. In some embodiments, $R^{3B}$ is —C(O)N(R)OR. In some embodiments, $R^{3B}$ is —OC(O)R. In some embodiments, $R^{3B}$ is —OC(O)NR$_2$. In some embodiments, $R^{3B}$ is —N(R)C(O)OR. In some embodiments, $R^{3B}$ is —N(R)C(O)R. In some embodiments, $R^{3B}$ is —N(R)C(O)NR$_2$. In some embodiments, $R^{3B}$ is —N(R)C(NR)NR$_2$. In some embodiments, $R^{3B}$ is —N(R)S(O)$_2$NR$_2$. In some embodiments, $R^{3B}$ is —N(R)S(O)$_2$R.

In some embodiments, $R^{3B}$ is —OR.

In some embodiments, $R^{3B}$ is an optionally substituted $C_{1-6}$ aliphatic group. In some embodiments, $R^{3B}$ is an optionally substituted phenyl group. In some embodiments, $R^{3B}$ is a 3-7 membered saturated heterocyclic ring having 1-2 heteroatoms independently selected from nitrogen, oxygen, and sulfur. In some embodiments, $R^{3B}$ is a 3-7 membered partially unsaturated heterocyclic ring having 1-2 heteroatoms independently selected from nitrogen, oxygen, and sulfur. In some embodiments, $R^{3B}$ is an optionally substituted 5-6 membered heteroaryl ring having 1-4 heteroatoms independently selected from nitrogen, oxygen, and sulfur.

In some embodiments, two optional substituents on the same carbon are optionally taken together to form a 3-6 membered saturated spiro-fused heterocyclic ring having 1-4 heteroatoms independently selected from nitrogen, oxygen, and sulfur. In some embodiments, two optional substituents on the same carbon are optionally taken together to form a 3-6 membered partially unsaturated spiro-fused heterocyclic ring having 1-4 heteroatoms independently selected from nitrogen, oxygen, and sulfur. In some embodiments, two optional substituents on adjacent carbons are optionally taken together to form a 3-6 membered saturated fused heterocyclic ring having 1-4 heteroatoms independently selected from nitrogen, oxygen, and sulfur. In some embodiments, two optional substituents on adjacent carbons are optionally taken together to form a 3-6 membered partially unsaturated fused heterocyclic ring having 1-4 heteroatoms independently selected from nitrogen, oxygen, and sulfur.

As generally defined above, $R^4$ is R or —OR; or $R^1$ and $R^4$ are taken together with their intervening atoms to form a 4-7 membered partially unsaturated, or heteroaryl ring having 0-3 heteroatoms independently selected from nitrogen, oxygen, and sulfur, wherein said ring is substituted by $R^{1A}$; or $R^3$ and $R^4$ are taken together with their intervening atoms to form a 4-7 membered partially unsaturated, or heteroaryl ring having 0-3 heteroatoms independently selected from nitrogen, oxygen, and sulfur.

In some embodiments, $R^4$ is R. In some embodiments, $R^4$ is —OR.

In some embodiments, $R^1$ and $R^4$ are taken together with their intervening atoms to form a 4-7 membered partially unsaturated ring having 0-3 heteroatoms independently selected from nitrogen, oxygen, and sulfur, wherein said ring is substituted by $R^{1A}$. In some embodiments, $R^1$ and $R^4$ are taken together with their intervening atoms to form a 4-7 membered heteroaryl ring having 0-3 heteroatoms independently selected from nitrogen, oxygen, and sulfur, wherein said ring is substituted by $R^{14}$.

In some embodiments, $R^3$ and $R^4$ are taken together with their intervening atoms to form a 4-7 membered partially unsaturated ring having 0-3 heteroatoms selected from nitrogen, oxygen, and sulfur. In some embodiments, $R^3$ and $R^4$ are taken together with their intervening atoms to form a 4-7 membered heteroaryl ring having 0-3 heteroatoms independently selected from nitrogen, oxygen, and sulfur.

In some embodiments, $R^4$ is H.

In some embodiments, $R^4$ is selected from those depicted in Table 1, below.

As generally defined above, each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is an optionally substituted $C_{1-6}$ aliphatic group. In some embodiments, R is an optionally substituted phenyl group. In some embodiments, R is an optionally substituted 3-7 membered saturated heterocyclic having 1-2 heteroatoms independently selected from nitrogen, oxygen, and sulfur. In some embodiments, R is an optionally substituted 3-7 membered partially unsaturated heterocyclic having 1-2 heteroatoms independently selected from nitrogen, oxygen, and sulfur. In some embodiments, R is an optionally substituted 5-6 membered heteroaryl ring having 1-4 heteroatoms independently selected from nitrogen, oxygen, and sulfur.

In some embodiments, two R groups on the same nitrogen are taken together with their intervening atoms to form a 4-7 membered saturated ring having 0-3 heteroatoms, in addition to the nitrogen, independently selected from nitrogen, oxygen, and sulfur. In some embodiments, two R groups on the same nitrogen are taken together with their intervening atoms to form a 4-7 membered partially unsaturated ring having 0-3 heteroatoms, in addition to the nitrogen, independently selected from nitrogen, oxygen, and sulfur. In some embodiments, two R groups on the same nitrogen are taken together with their intervening atoms to form a 4-7 membered heteroaryl ring having 0-3 heteroatoms, in addition to the nitrogen, independently selected from nitrogen, oxygen, and sulfur.

In some embodiments, R is selected from those depicted in Table 1, below.

As generally defined above, each hydrogen bound to carbon can be optionally and independently replaced by deuterium.

As generally defined above, m is 0, 1, or 2. In some embodiments, m is 0. In some embodiments, m is 1. In some embodiments, m is 2.

In some embodiments, m is selected from those depicted in Table 1, below.

As generally defined above, n is 0, 1, or 2. In some embodiments, n is 0. In some embodiments, n is 1. In some embodiments, m is 2.

In some embodiments, n is selected from those depicted in Table 1, below.

As generally defined above, p is 0, 1, or 2. In some embodiments, p is 0. In some embodiments, p is 1. In some embodiments, p is 2.

In some embodiments, p is selected from those depicted in Table 1, below.

In some embodiments, the present invention provides a compound of Formula II:

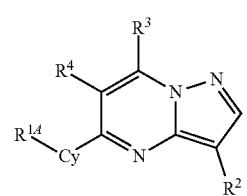

II or a pharmaceutically acceptable salt thereof, wherein each of $R^{14}$, Cy, $R^2$, $R^3$, and $R^4$, is as defined above and described in embodiments herein, both singly and in combination.

In some embodiments, the present invention provides a compound of Formula III:

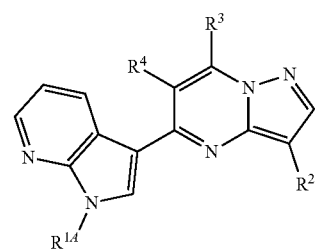

III or a pharmaceutically acceptable salt thereof, wherein each of $R^{14}$, $R^2$, and $R^3$ is as defined above and described in embodiments herein, both singly and in combination.

In some embodiments, the present invention provides a compound of Formula IV:

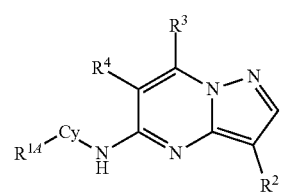

IV or a pharmaceutically acceptable salt thereof, wherein each of $R^{14}$, Cy, $R^2$, $R^3$, and $R^4$ is as defined above and described in embodiments herein, both singly and in combination.

In some embodiments, the present invention provides a compound of Formula V:

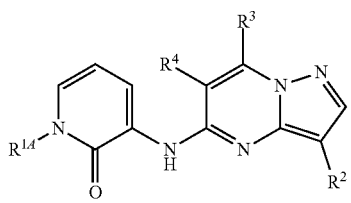

V or a pharmaceutically acceptable salt thereof, wherein each of $R^{1A}$, $R^2$, $R^3$, and $R^4$ is as defined above and described in embodiments herein, both singly and in combination.

In some embodiments, the present invention provides a compound of Formula VI:

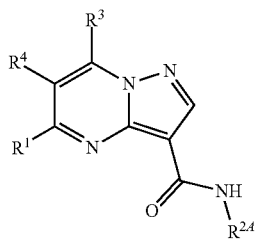

VI or a pharmaceutically acceptable salt thereof, wherein each of $R^1$, $R^{2A}$, $R^3$, and $R^4$ is as defined above and described in embodiments herein, both singly and in combination.

In some embodiments, the present invention provides a compound of Formula VII:

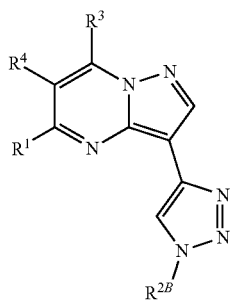

VII or a pharmaceutically acceptable salt thereof, wherein each of $R^1$, $R^{2B}$, $R^3$, and $R^4$ is as defined above and described in embodiments herein, both singly and in combination.

In some embodiments, the present invention provides a compound of Formula VIII:

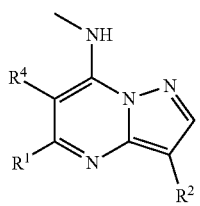

VIII or a pharmaceutically acceptable salt thereof, wherein each of $R^1$, $R^2$, and $R^4$ is as defined above and described in embodiments herein, both singly and in combination.

In some embodiments, the present invention provides a compound of Formula IX:

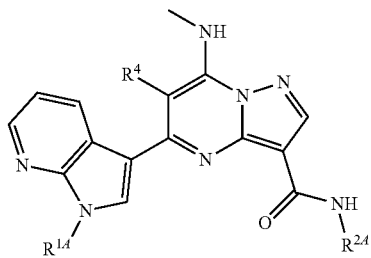

IX or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula X:

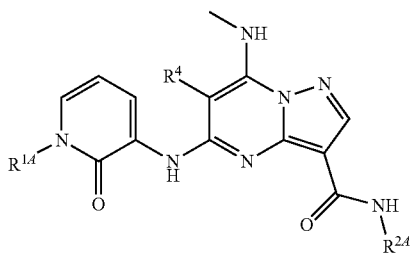

X or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XI:

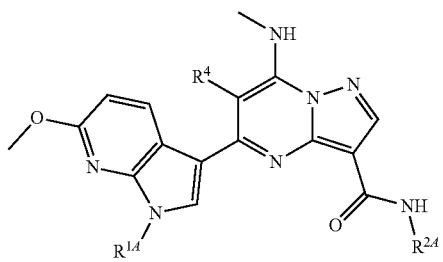

XI or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XII:

XII

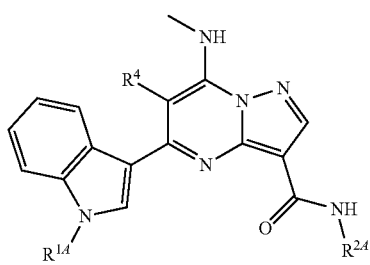

or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XIII:

XIII

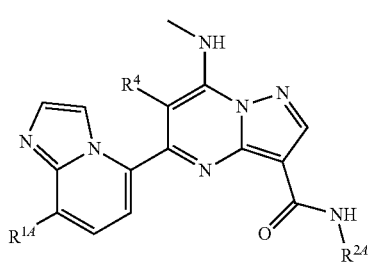

or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XIV:

XIV

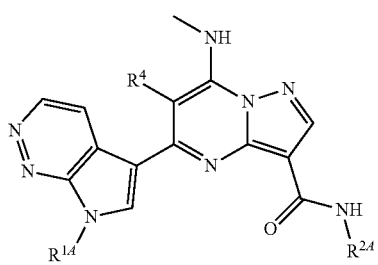

or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XV:

XV

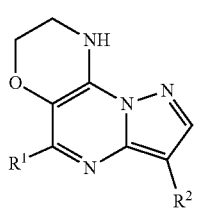

or a pharmaceutically acceptable salt thereof, wherein each of $R^1$ and $R^2$, is as defined above and described in embodiments herein, both singly and in combination.

In some embodiments, the present invention provides a compound of Formula XVI:

XVI

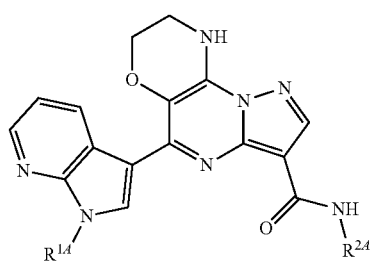

or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XVII:

XVII

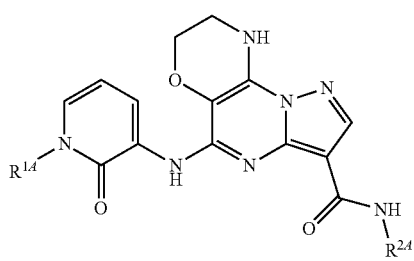

or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XVIII:

XVIII

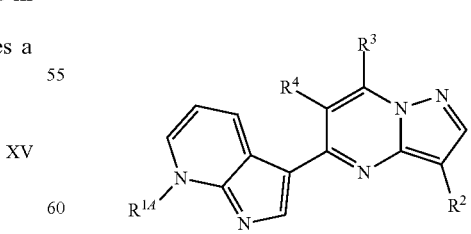

or a pharmaceutically acceptable salt thereof, wherein each of $R^{1A}$, $R^2$, $R^3$, and $R^4$ is as defined above and described in embodiments herein, both singly and in combination.

In some embodiments, the present invention provides a compound of Formula XIX:

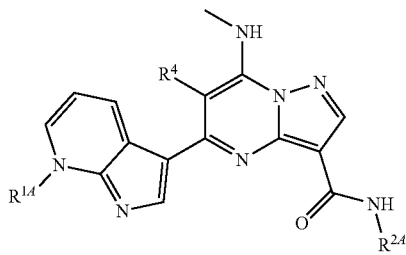

XIX

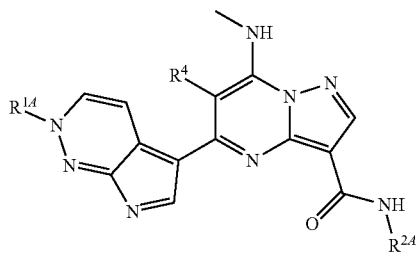

XX or a pharmaceutically acceptable salt thereof, wherein each of $R^{1A}$, $R^{2A}$, and $R^4$ is as defined above and described in embodiments herein, both singly and in combination.

In some embodiments, the present invention provides a compound of Formula XX:

or a pharmaceutically acceptable salt thereof, wherein each of $R^{1A}$, $R^{2A}$, and $R^4$ is as defined above and described in embodiments herein, both singly and in combination.

Exemplary compounds of the invention are set forth in Table 1, below

TABLE 1

Selected Compounds

| Number | Structure |
|---|---|
| I-1 | 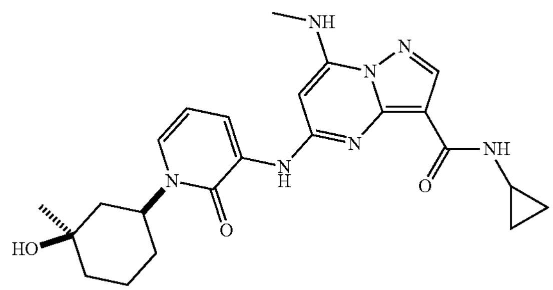 |
| I-2 | 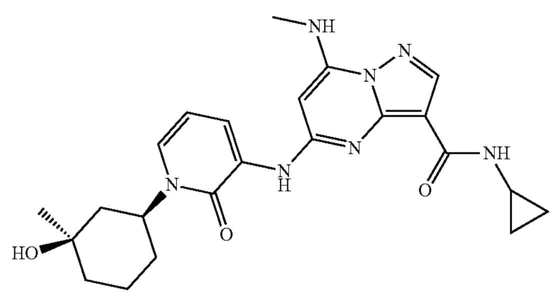 [SMILES: CNc1cc(Nc2cccn([C@H]3CCC[C@@](C)(O)C3)c2=O)nc2c(C(=O)NC3CC3)cnn12] |
| I-3 | 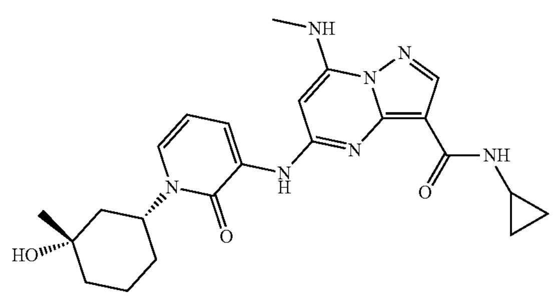 [SMILES: CNc1cc(Nc2cccn([C@@H]3CCC[C@](C)(O)C3)c2=O)nc2c(C(=O)NC3CC3)cnn12] |

TABLE 1-continued

| Selected Compounds | |
|---|---|
| Number | Structure |
| I-4 | *(chemical structure)* |
| I-5 | *(chemical structure)* |
| I-6 | *(chemical structure)* |
| I-7 | *(chemical structure)* |
| I-8 | *(chemical structure)* |

TABLE 1-continued

| Selected Compounds | |
|---|---|
| Number | Structure |
| I-9 | |
| I-10 | |
| I-11 | |
| I-12 | |
| I-13 | |

TABLE 1-continued

| Selected Compounds | |
|---|---|
| Number | Structure |
| I-14 | |
| I-15 | |
| I-16 | |
| I-17 | |

TABLE 1-continued
Selected Compounds
| Number | Structure |
|---|---|
| I-18 | 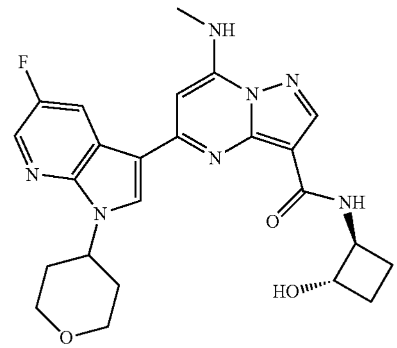 [SMILES: CNc1cc(-c2cn(C3CCOCC3)c3ncc(F)cc23)nc2c(C(=O)N[C@H]3CC[C@@H]3O)cnn12] |
| I-19 | 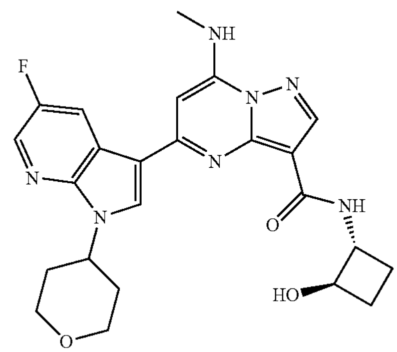 [SMILES: CNc1cc(-c2cn(C3CCOCC3)c3ncc(F)cc23)nc2c(C(=O)N[C@@H]3CC[C@H]3O)cnn12] |
| I-20 | 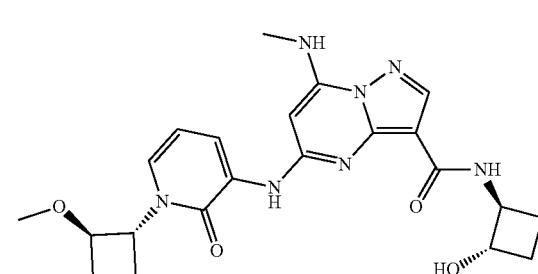 |
| I-21 | 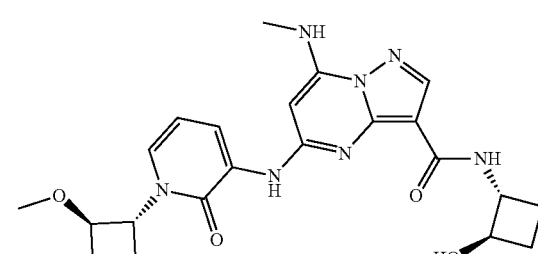 |
| I-22 | 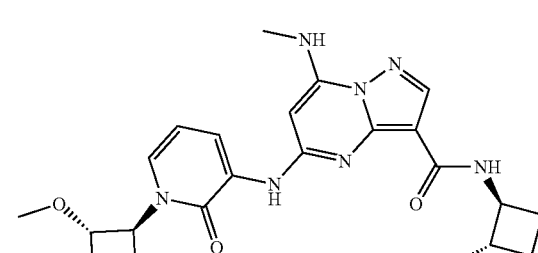 |

TABLE 1-continued

Selected Compounds

| Number | Structure |
|---|---|
| I-23 | 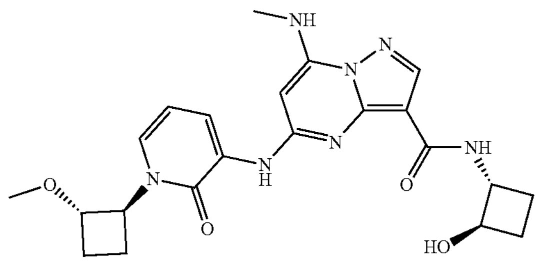 [SMILES: CNc1cc(Nc2cccn([C@H]3CC[C@@H]3OC)c2=O)nc2c(C(=O)N[C@@H]3CC[C@H]3O)cnn12] |
| I-24 | 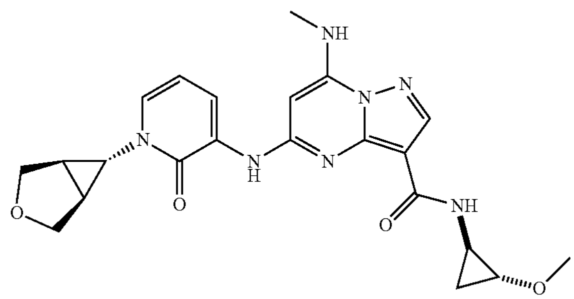 |
| I-25 | 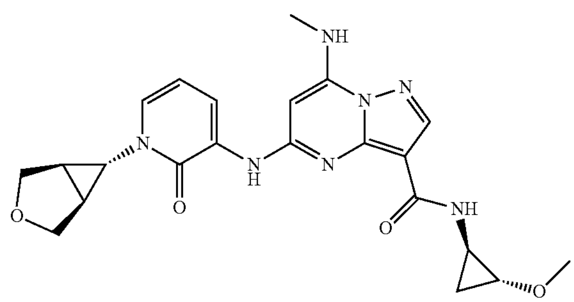 [SMILES: CNc1cc(Nc2cccn([C@H]3[C@@H]4COC[C@@H]43)c2=O)nc2c(C(=O)N[C@@H]3C[C@H]3OC)cnn12] |
| I-26 | 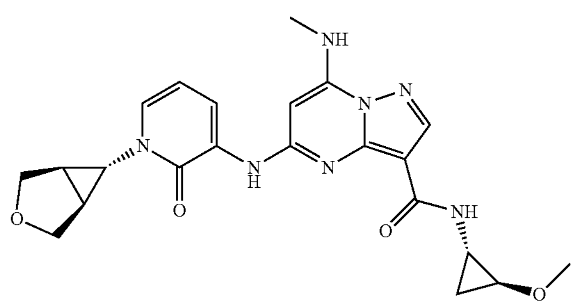 [SMILES: CNc1cc(Nc2cccn([C@H]3[C@@H]4COC[C@@H]43)c2=O)nc2c(C(=O)N[C@H]3C[C@@H]3OC)cnn12] |
| I-27 | 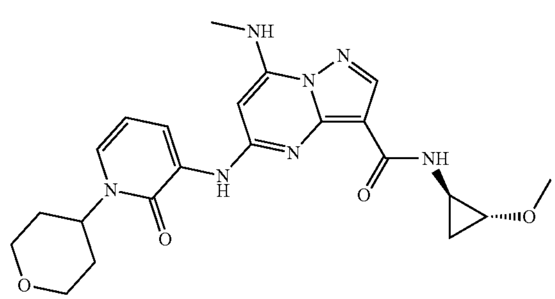 [SMILES: CNc1cc(Nc2cccn(C3CCOCC3)c2=O)nc2c(C(=O)N[C@@H]3C[C@H]3OC)cnn12] |

TABLE 1-continued
Selected Compounds
| Number | Structure |
|---|---|
| I-28 | 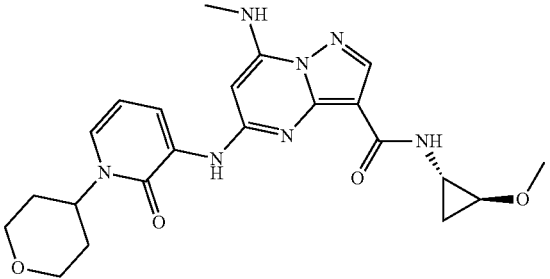 [SMILES: CNc1cc(Nc2cccn(C3CCOCC3)c2=O)nc2c(C(=O)N[C@H]3C[C@@H]3OC)cnn12] |
| I-29 | 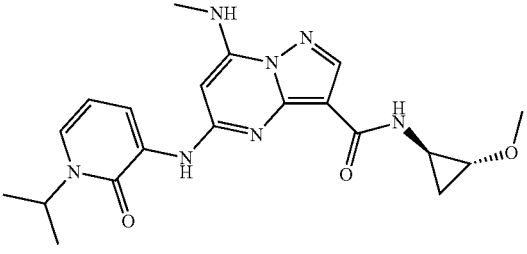 [SMILES: CNc1cc(Nc2cccn(C(C)C)c2=O)nc2c(C(=O)N[C@@H]3C[C@H]3OC)cnn12] |
| I-30 | 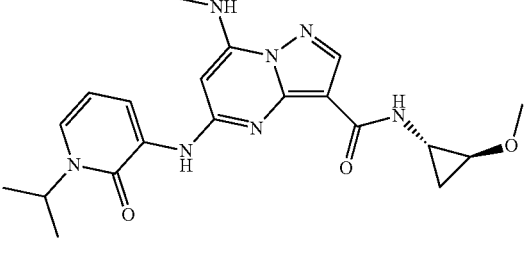 |
| I-31 | 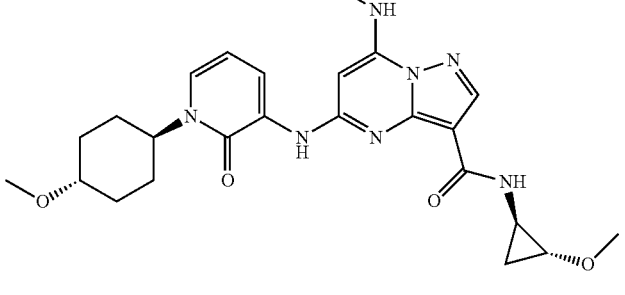 |
| I-32 | 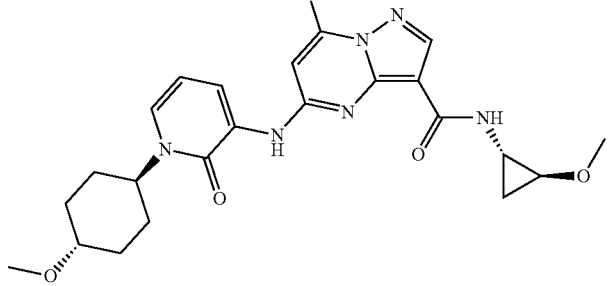 |

TABLE 1-continued
Selected Compounds
| Number | Structure |
|---|---|
| I-33 | 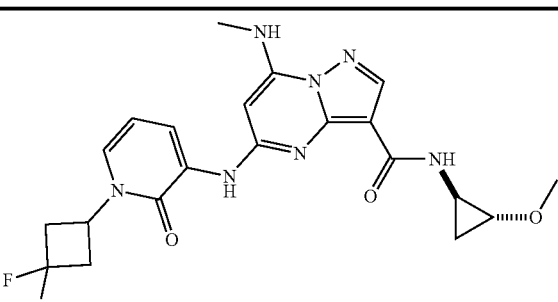 |
| I-34 | 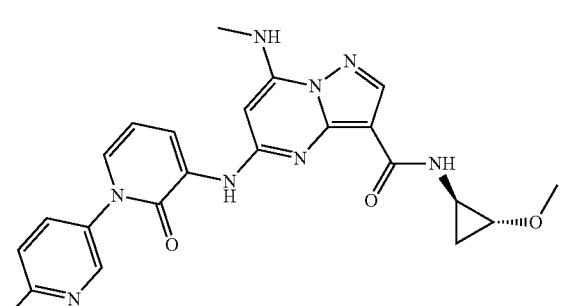 |
| I-35 | 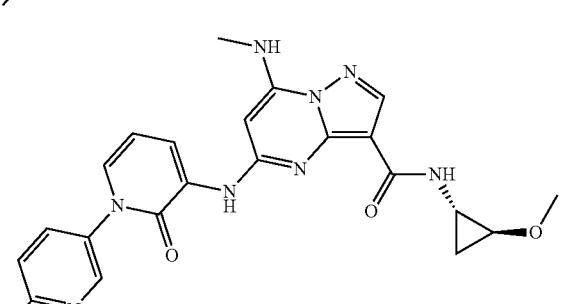 |
| I-36 | 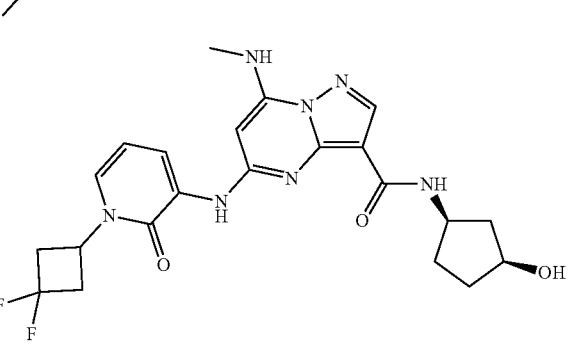 |
| I-37 | 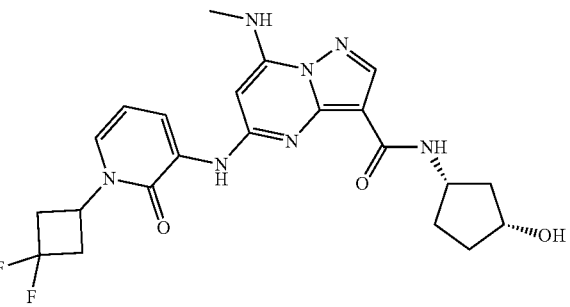 |

TABLE 1-continued
| Selected Compounds | |
|---|---|
| Number | Structure |
| I-38 | 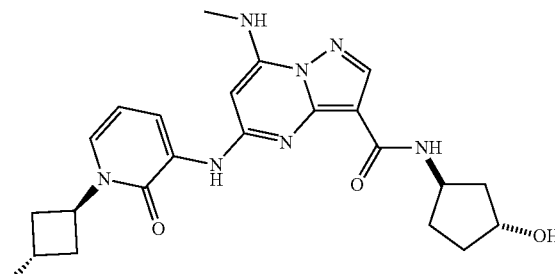 |
| I-39 | 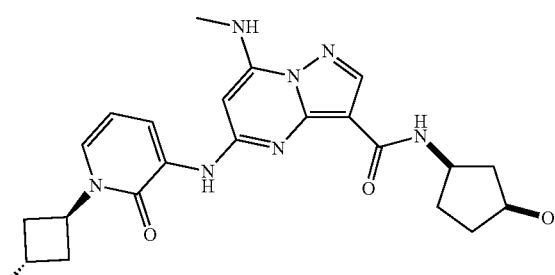 |
| I-40 | 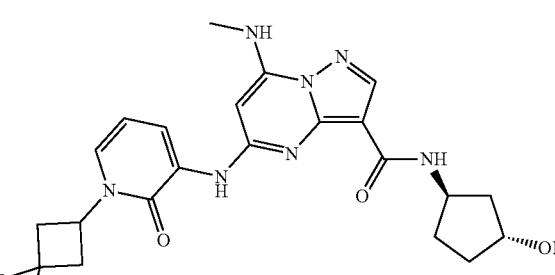 |
| I-41 | 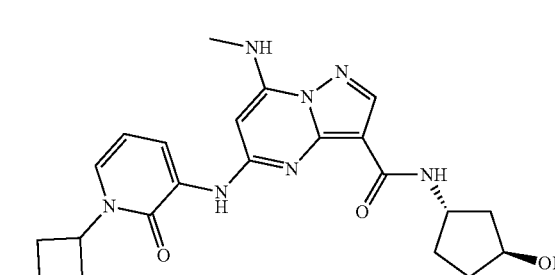 |
| I-42 | 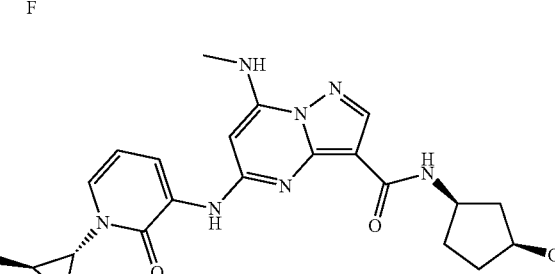 |

TABLE 1-continued
| Selected Compounds | |
|---|---|
| Number | Structure |
| I-43 | 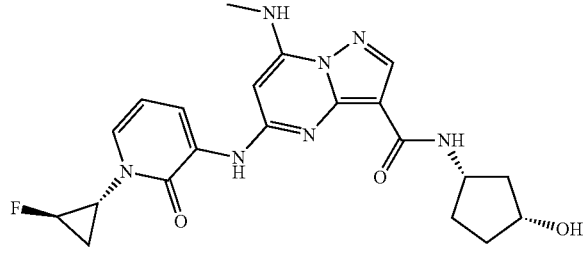 [SMILES: CNc1cc(Nc2cccn([C@@H]3C[C@H]3F)c2=O)nc2c(C(=O)N[C@H]3CC[C@@H](O)C3)cnn12] |
| I-44 | 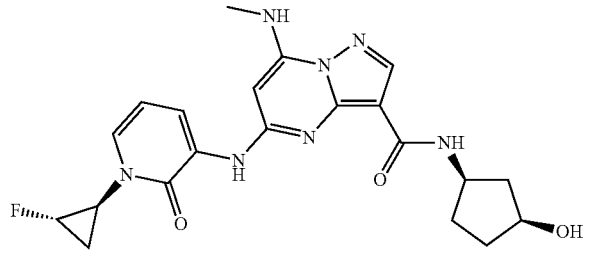 [SMILES: CNc1cc(Nc2cccn([C@H]3C[C@@H]3F)c2=O)nc2c(C(=O)N[C@@H]3CC[C@H](O)C3)cnn12] |
| I-45 | 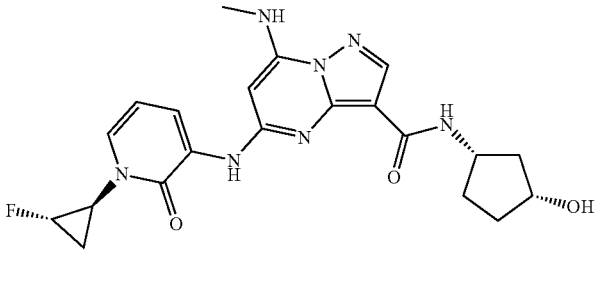 [SMILES: CNc1cc(Nc2cccn([C@H]3C[C@@H]3F)c2=O)nc2c(C(=O)N[C@H]3CC[C@@H](O)C3)cnn12] |
| I-46 | 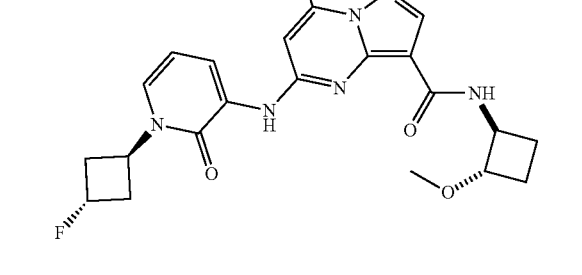 |
| I-47 | 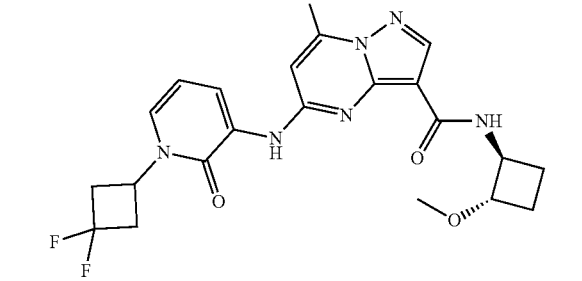 |

TABLE 1-continued

| Selected Compounds | |
|---|---|
| Number | Structure |
| I-48 | |
| I-49 | |
| I-50 | |
| I-51 | |
| I-52 | |

TABLE 1-continued

Selected Compounds

| Number | Structure |
|---|---|
| I-53 | 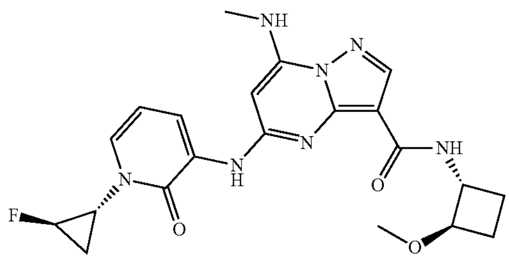 [SMILES: CNc1cc(Nc2cccn([C@@H]3C[C@H]3F)c2=O)nc2c(C(=O)N[C@@H]3CC[C@H]3OC)cnn12] |
| I-54 | 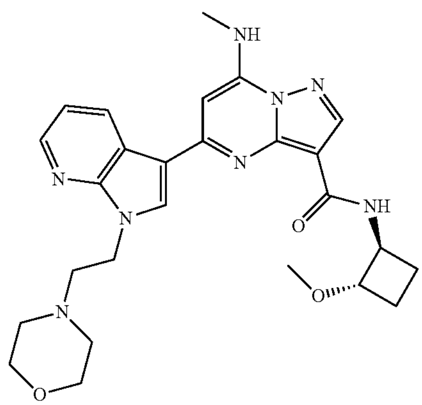 [SMILES: CNc1cc(-c2cn(CCN3CCOCC3)c3ncccc23)nc2c(C(=O)N[C@H]3CC[C@@H]3OC)cnn12] |
| I-55 | 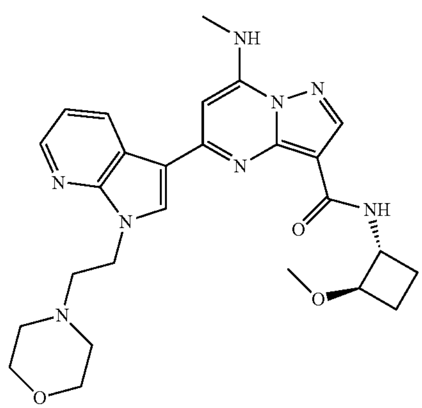 [SMILES: CNc1cc(-c2cn(CCN3CCOCC3)c3ncccc23)nc2c(C(=O)N[C@@H]3CC[C@H]3OC)cnn12] |
| I-56 | 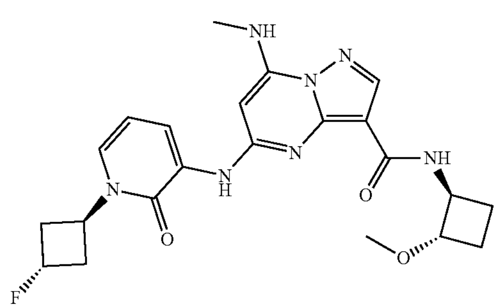 [SMILES: CNc1cc(Nc2cccn([C@H]3C[C@H](F)C3)c2=O)nc2c(C(=O)N[C@H]3CC[C@@H]3OC)cnn12] |

TABLE 1-continued
| Selected Compounds | |
|---|---|
| Number | Structure |
| I-57 | 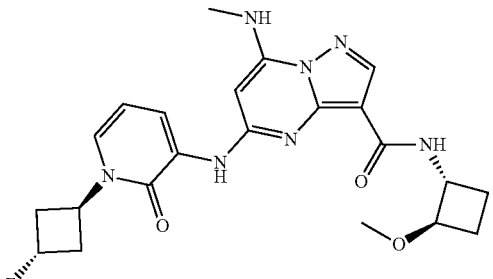 |
| I-58 | 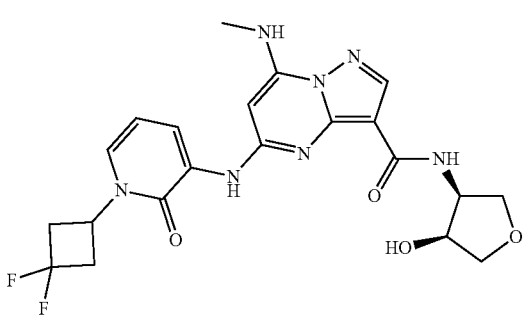 [SMILES: CNc1cc(Nc2cccn(C3CC(F)(F)C3)c2=O)nc2c(C(=O)N[C@H]3COC[C@H]3O)cnn12] |
| I-59 | 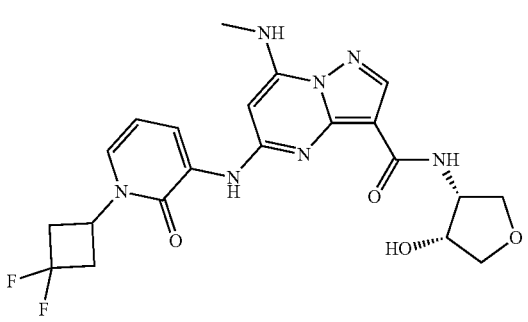 [SMILES: CNc1cc(Nc2cccn(C3CC(F)(F)C3)c2=O)nc2c(C(=O)N[C@@H]3COC[C@@H]3O)cnn12] |
| I-60 | 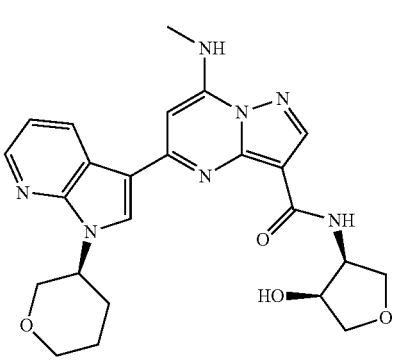 [SMILES: CNc1cc(-c2cn([C@H]3CCCOC3)c3ncccc23)nc2c(C(=O)N[C@H]3COC[C@H]3O)cnn12] |

TABLE 1-continued

Selected Compounds

| Number | Structure |
|---|---|
| I-61 | 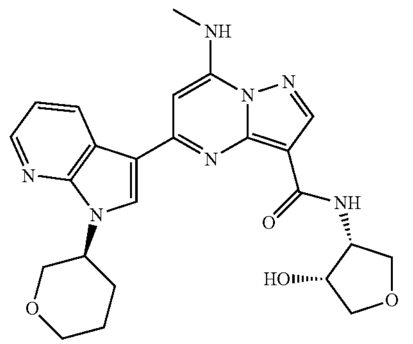 [SMILES: CNc1cc(-c2cn([C@H]3CCCOC3)c3ncccc23)nc2c(C(=O)N[C@@H]3COC[C@@H]3O)cnn12] |
| I-62 | 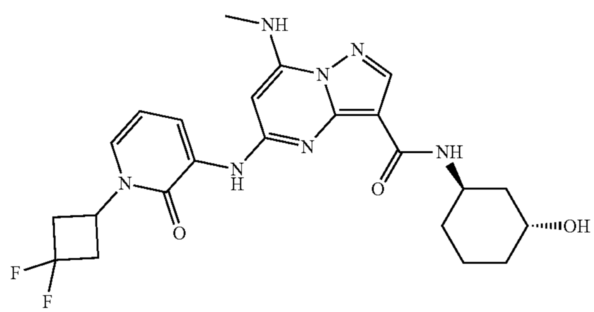 [SMILES: CNc1cc(Nc2cccn(C3CC(F)(F)C3)c2=O)nc2c(C(=O)N[C@@H]3CCC[C@@H](O)C3)cnn12] |
| I-63 | 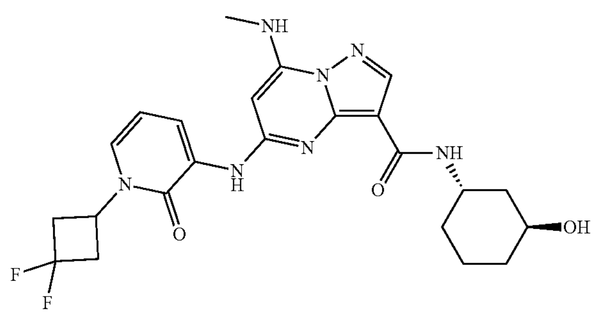 [SMILES: CNc1cc(Nc2cccn(C3CC(F)(F)C3)c2=O)nc2c(C(=O)N[C@H]3CCC[C@H](O)C3)cnn12] |
| I-64 | 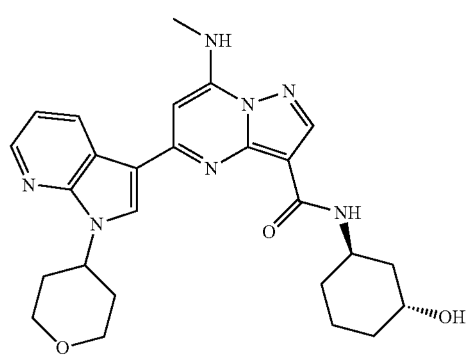 [SMILES: CNc1cc(-c2cn(C3CCOCC3)c3ncccc23)nc2c(C(=O)N[C@@H]3CCC[C@@H](O)C3)cnn12] |

TABLE 1-continued

Selected Compounds

| Number | Structure |
|---|---|
| I-65 | 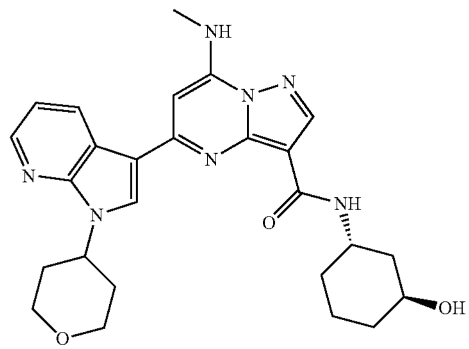 [SMILES: CNc1cc(-c2cn(C3CCOCC3)c3ncccc23)nc2c(C(=O)N[C@H]3CCC[C@H](O)C3)cnn12] |
| I-66 | 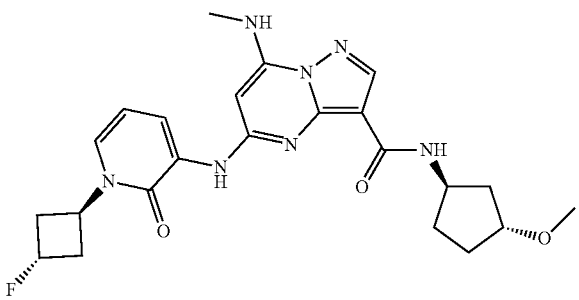 [SMILES: CNc1cc(Nc2cccn([C@H]3C[C@H](F)C3)c2=O)nc2c(C(=O)N[C@@H]3CC[C@@H](OC)C3)cnn12] |
| I-67 | 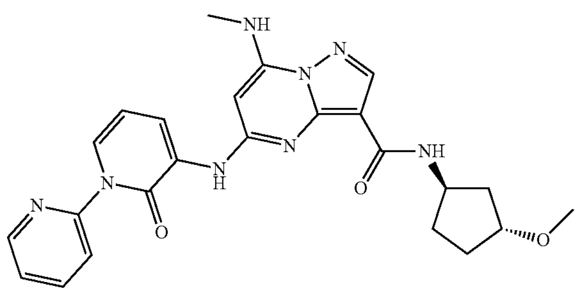 [SMILES: CNc1cc(Nc2cccn(-c3ccccn3)c2=O)nc2c(C(=O)N[C@@H]3CC[C@@H](OC)C3)cnn12] |
| I-68 | 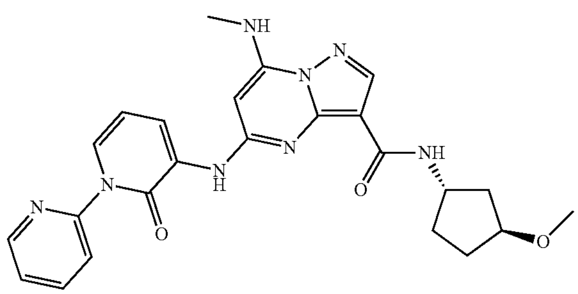 [SMILES: CNc1cc(Nc2cccn(-c3ccccn3)c2=O)nc2c(C(=O)N[C@H]3CC[C@H](OC)C3)cnn12] |
| I-69 | 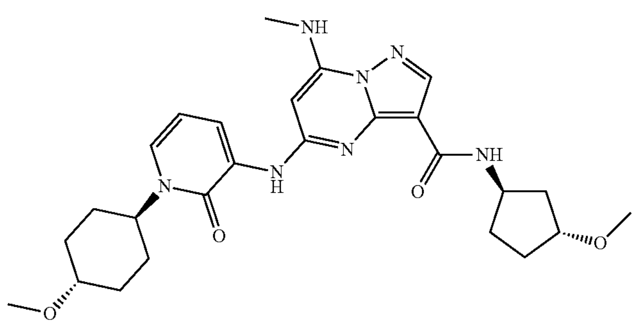 |

TABLE 1-continued

Selected Compounds

| Number | Structure |
|---|---|
| I-70 | 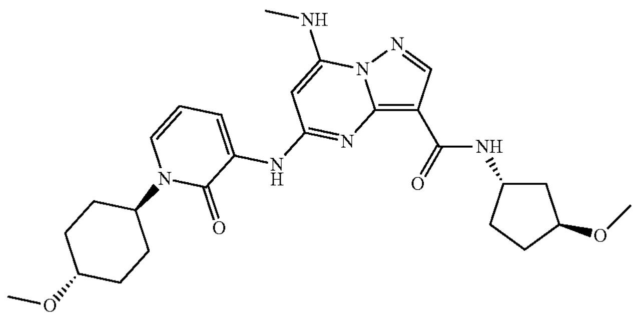 |
| I-71 | 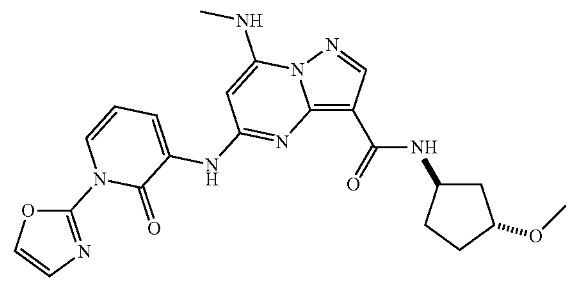 |
| I-72 | 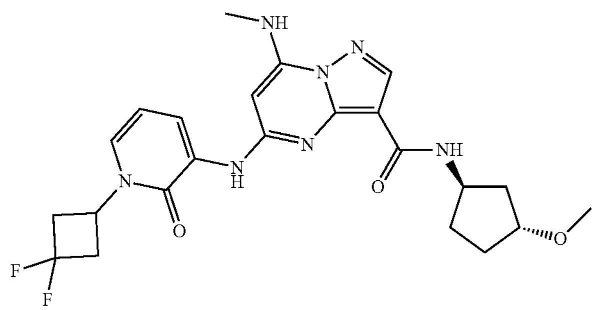 [SMILES: CNc1cc(Nc2cccn(C3CC(F)(F)C3)c2=O)nc2c(C(=O)N[C@@H]3CC[C@@H](OC)C3)cnn12] |
| I-73 | 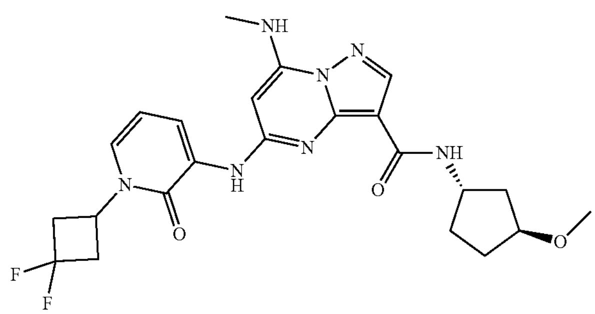 [SMILES: CNc1cc(Nc2cccn(C3CC(F)(F)C3)c2=O)nc2c(C(=O)N[C@H]3CC[C@H](OC)C3)cnn12] |
| I-74 | 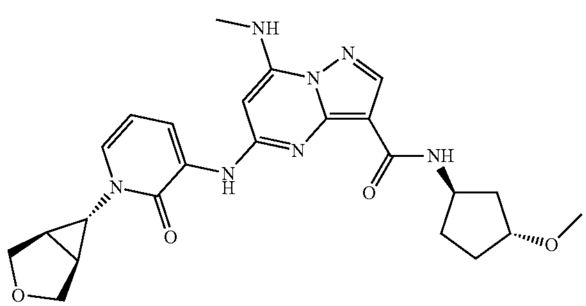 [SMILES: CNc1cc(Nc2cccn([C@H]3[C@@H]4COC[C@@H]43)c2=O)nc2c(C(=O)N[C@@H]3CC[C@@H](OC)C3)cnn12] |

TABLE 1-continued
Selected Compounds
| Number | Structure |
|---|---|
| I-75 | 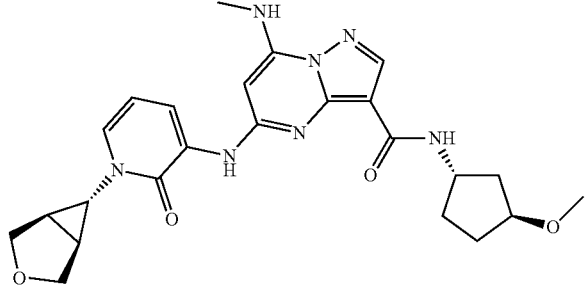 [SMILES: CNc1cc(Nc2cccn([C@H]3[C@@H]4COC[C@@H]43)c2=O)nc2c(C(=O)N[C@H]3CC[C@H](OC)C3)cnn12] |
| I-76 | 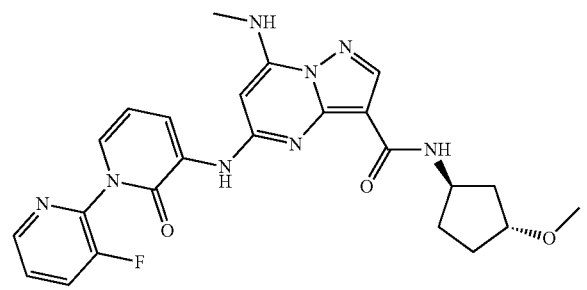 [SMILES: CNc1cc(Nc2cccn(-c3ncccc3F)c2=O)nc2c(C(=O)N[C@@H]3CC[C@@H](OC)C3)cnn12] |
| I-77 | 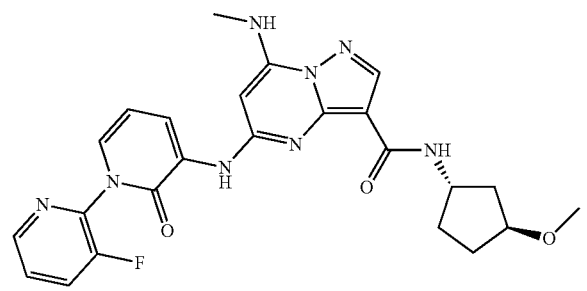 [SMILES: CNc1cc(Nc2cccn(-c3ncccc3F)c2=O)nc2c(C(=O)N[C@H]3CC[C@H](OC)C3)cnn12] |
| I-78 | 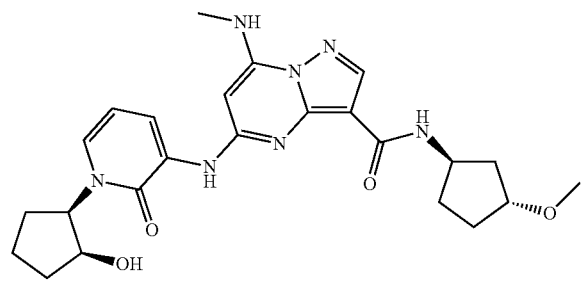 [SMILES: CNc1cc(Nc2cccn([C@@H]3CCC[C@@H]3O)c2=O)nc2c(C(=O)N[C@@H]3CC[C@@H](OC)C3)cnn12] |
| I-79 | 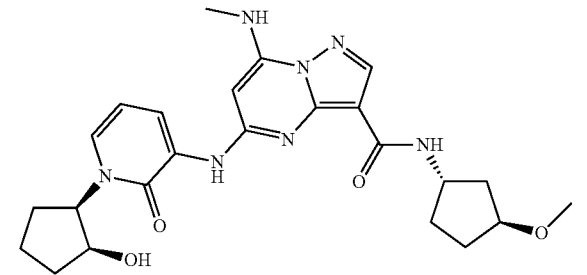 [SMILES: CNc1cc(Nc2cccn([C@@H]3CCC[C@@H]3O)c2=O)nc2c(C(=O)N[C@H]3CC[C@H](OC)C3)cnn12] |

TABLE 1-continued
Selected Compounds
| Number | Structure |
|---|---|
| I-80 | 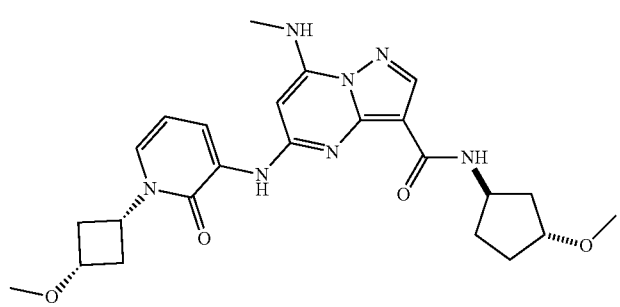 |
| I-81 | 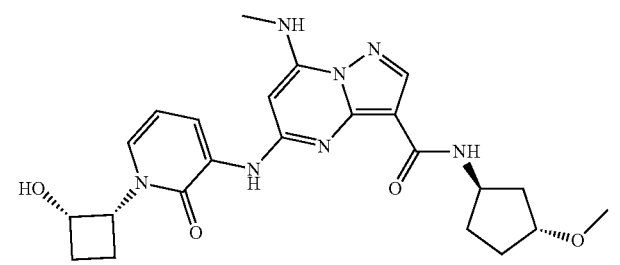 [SMILES: CNc1cc(Nc2cccn([C@@H]3CC[C@@H]3O)c2=O)nc2c(C(=O)N[C@@H]3CC[C@@H](OC)C3)cnn12] |
| I-82 | 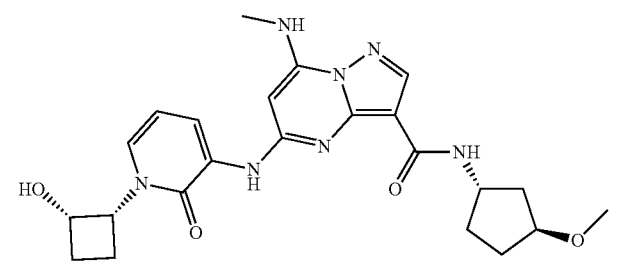 [SMILES: CNc1cc(Nc2cccn([C@@H]3CC[C@@H]3O)c2=O)nc2c(C(=O)N[C@H]3CC[C@H](OC)C3)cnn12] |
| I-83 | 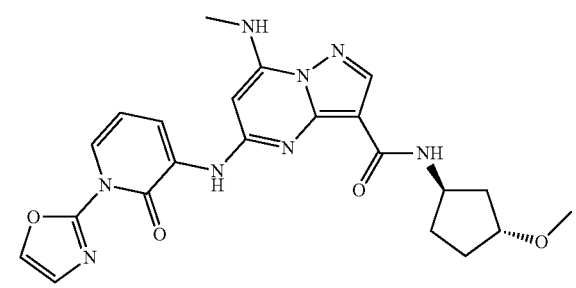 [SMILES: CNc1cc(Nc2cccn(-c3ncco3)c2=O)nc2c(C(=O)N[C@@H]3CC[C@@H](OC)C3)cnn12] |
| I-84 | 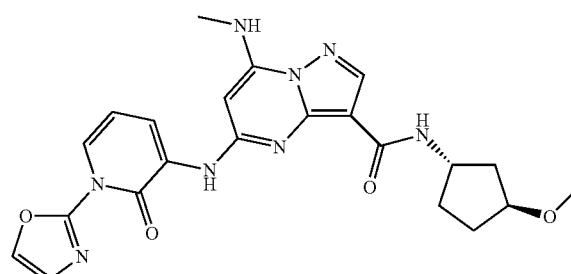 |

TABLE 1-continued

| Number | Structure |
|---|---|
| I-85 | 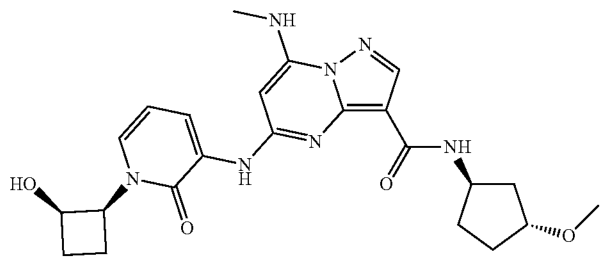 [SMILES: CNc1cc(Nc2cccn([C@H]3CC[C@H]3O)c2=O)nc2c(C(=O)N[C@@H]3CC[C@@H](OC)C3)cnn12] |
| I-86 | 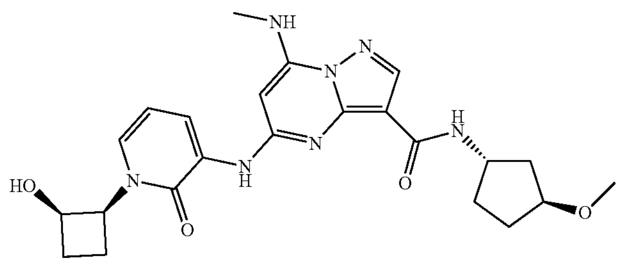 [SMILES: CNc1cc(Nc2cccn([C@H]3CC[C@H]3O)c2=O)nc2c(C(=O)N[C@H]3CC[C@H](OC)C3)cnn12] |
| I-87 | 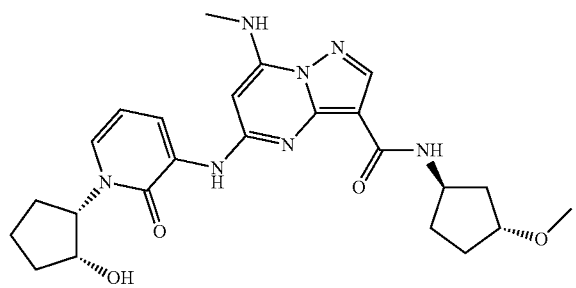 [SMILES: CNc1cc(Nc2cccn([C@H]3CCC[C@H]3O)c2=O)nc2c(C(=O)N[C@@H]3CC[C@@H](OC)C3)cnn12] |
| I-88 | 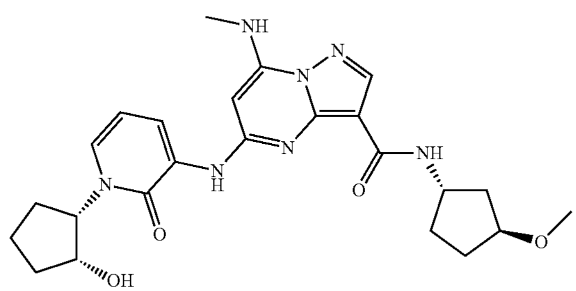 [SMILES: CNc1cc(Nc2cccn([C@H]3CCC[C@H]3O)c2=O)nc2c(C(=O)N[C@H]3CC[C@H](OC)C3)cnn12] |
| I-89 | 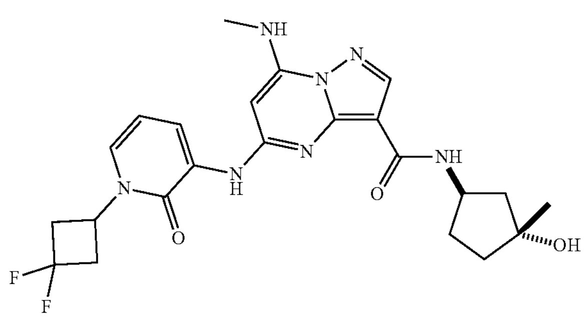 |

TABLE 1-continued
Selected Compounds
| Number | Structure |
|---|---|
| I-90 | 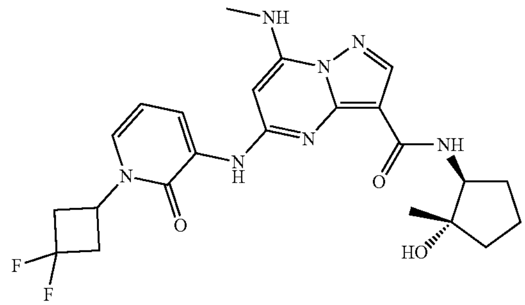 [SMILES: CNc1cc(Nc2cccn(C3CC(F)(F)C3)c2=O)nc2c(C(=O)N[C@H]3CCC[C@]3(C)O)cnn12] |
| I-91 | 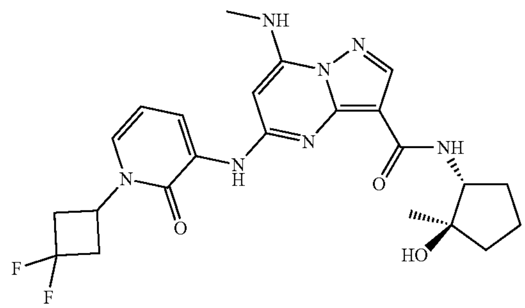 [SMILES: CNc1cc(Nc2cccn(C3CC(F)(F)C3)c2=O)nc2c(C(=O)N[C@@H]3CCC[C@@]3(C)O)cnn12] |
| I-92 | 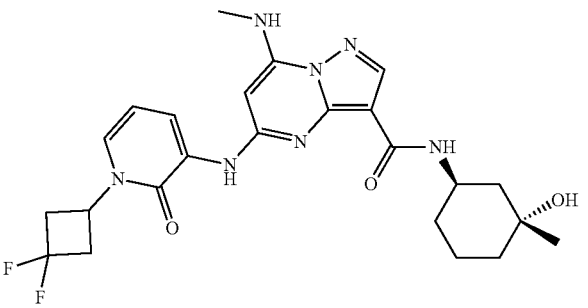 [SMILES: CNc1cc(Nc2cccn(C3CC(F)(F)C3)c2=O)nc2c(C(=O)N[C@@H]3CCC[C@@](C)(O)C3)cnn12] |
| I-93 | 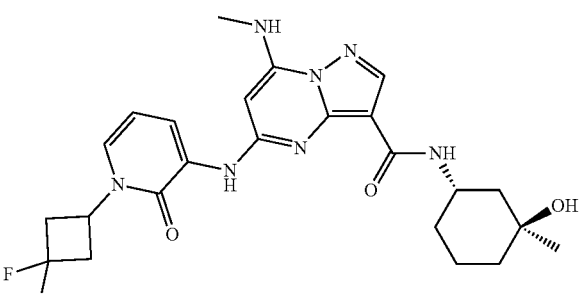 |
| I-94 | 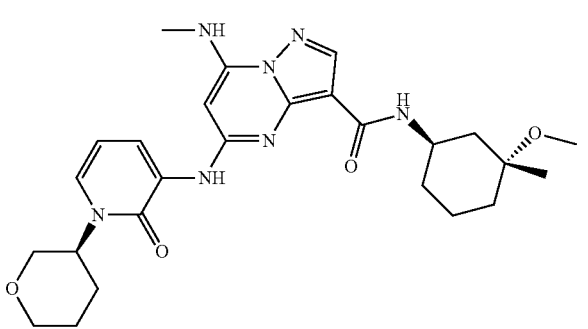 [SMILES: CNc1cc(Nc2cccn([C@H]3CCCOC3)c2=O)nc2c(C(=O)N[C@@H]3CCC[C@@](C)(OC)C3)cnn12] |

TABLE 1-continued

| Number | Structure |
|---|---|
| I-95 | 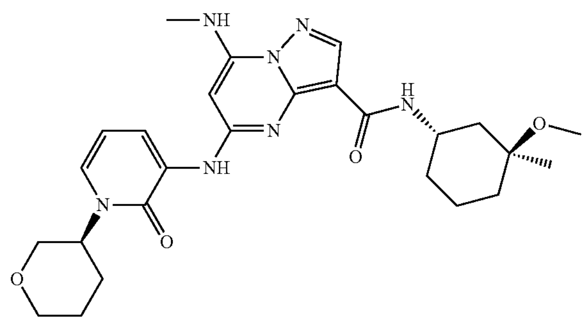 [SMILES: CNc1cc(Nc2cccn([C@H]3CCCOC3)c2=O)nc2c(C(=O)N[C@H]3CCC[C@](C)(OC)C3)cnn12] |
| I-96 | 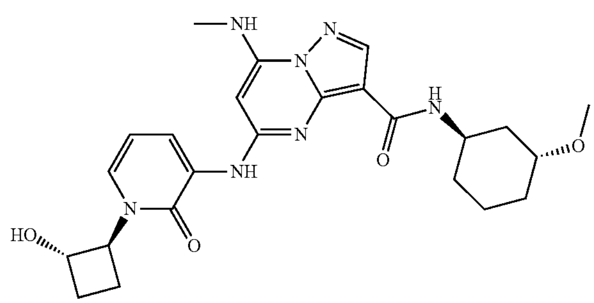 [SMILES: CNc1cc(Nc2cccn([C@H]3CC[C@@H]3O)c2=O)nc2c(C(=O)N[C@@H]3CCC[C@@H](OC)C3)cnn12] |
| I-97 | 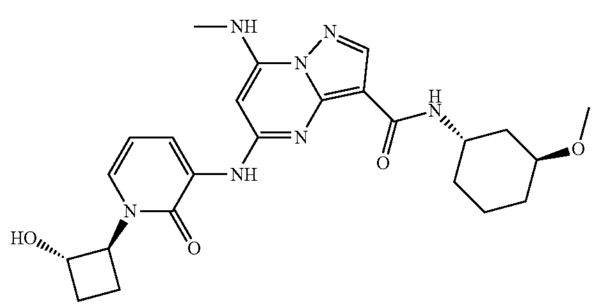 [SMILES: CNc1cc(Nc2cccn([C@H]3CC[C@@H]3O)c2=O)nc2c(C(=O)N[C@H]3CCC[C@H](OC)C3)cnn12] |
| I-98 | 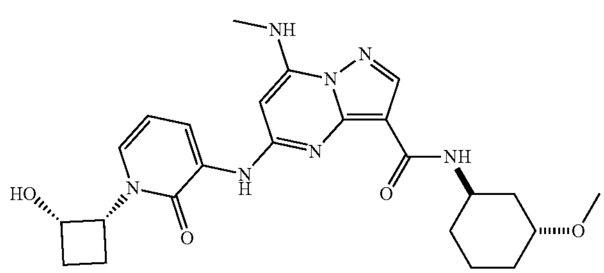 |
| I-99 | 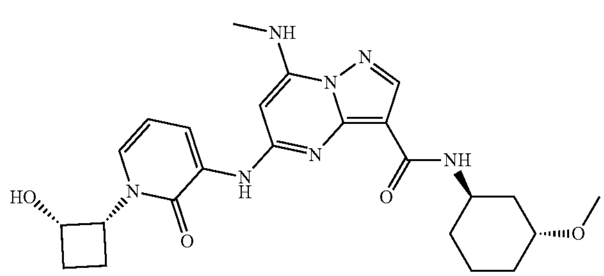 [SMILES: CNc1cc(Nc2cccn([C@@H]3CC[C@@H]3O)c2=O)nc2c(C(=O)N[C@@H]3CCC[C@@H](OC)C3)cnn12] |

TABLE 1-continued

Selected Compounds

| Number | Structure |
| --- | --- |
| I-100 | 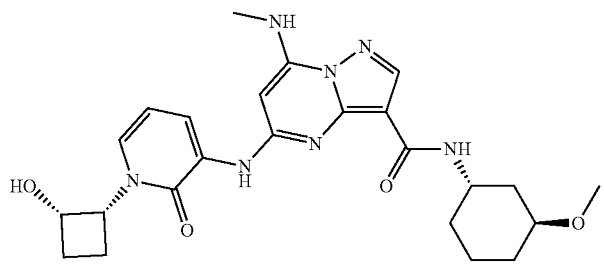 [SMILES: CNc1cc(Nc2cccn([C@@H]3CC[C@@H]3O)c2=O)nc2c(C(=O)N[C@H]3CCC[C@H](OC)C3)cnn12] |
| I-101 | 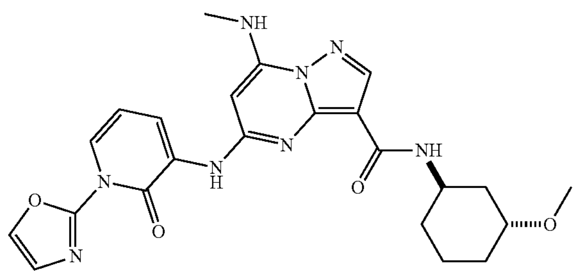 |
| I-102 | 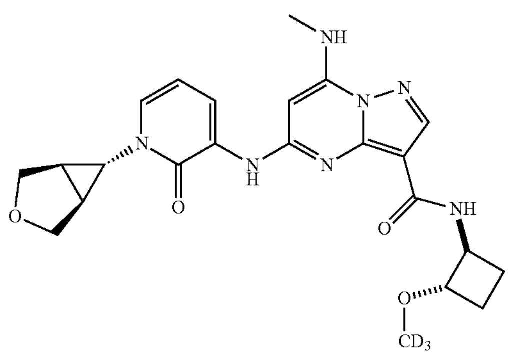 |
| I-103 | 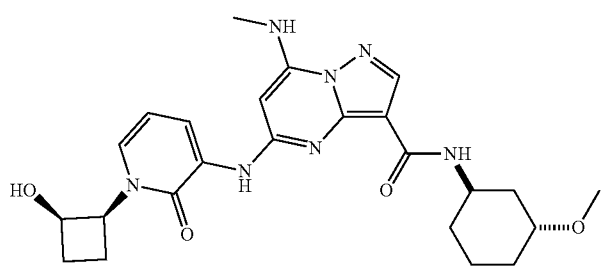 |
| I-104 | 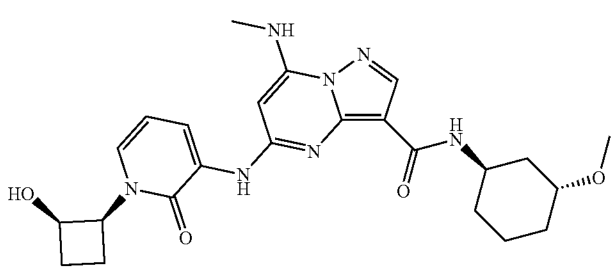 [SMILES: CNc1cc(Nc2cccn([C@H]3CC[C@H]3O)c2=O)nc2c(C(=O)N[C@@H]3CCC[C@@H](OC)C3)cnn12] |

TABLE 1-continued

Selected Compounds

| Number | Structure |
|---|---|
| I-105 | 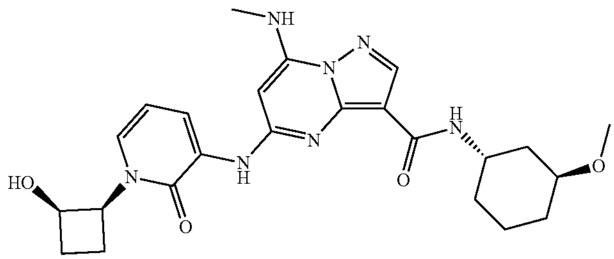 [SMILES: CNc1cc(Nc2cccn([C@H]3CC[C@H]3O)c2=O)nc2c(C(=O)N[C@H]3CCC[C@H](OC)C3)cnn12] |
| I-106 | 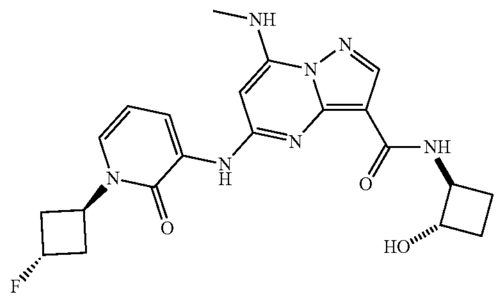 |
| I-107 | 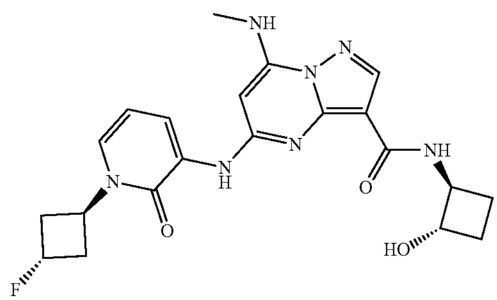 [SMILES: CNc1cc(Nc2cccn([C@H]3C[C@H](F)C3)c2=O)nc2c(C(=O)N[C@H]3CC[C@@H]3O)cnn12] |
| I-108 | 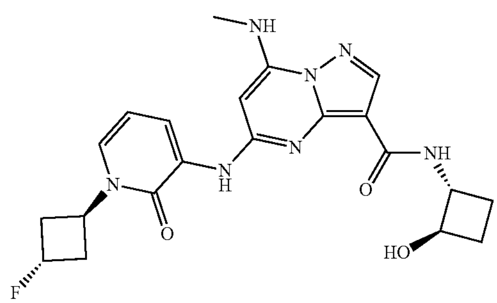 |
| I-109 | 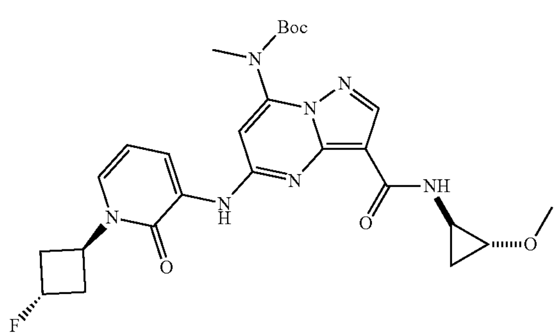 |

TABLE 1-continued

Selected Compounds

| Number | Structure |
|---|---|
| I-110 | 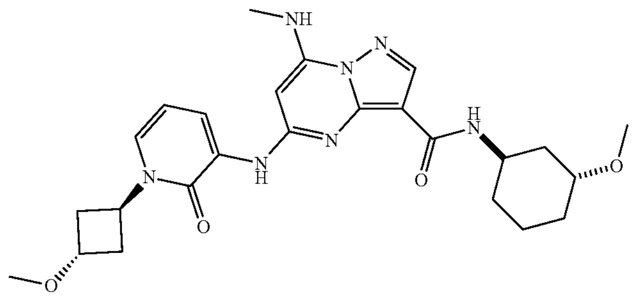 |
| I-111 | 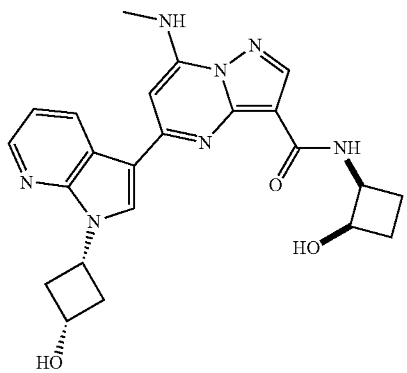 |
| I-112 | 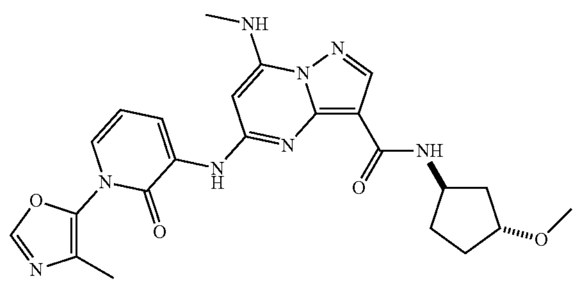 |
| I-113 | 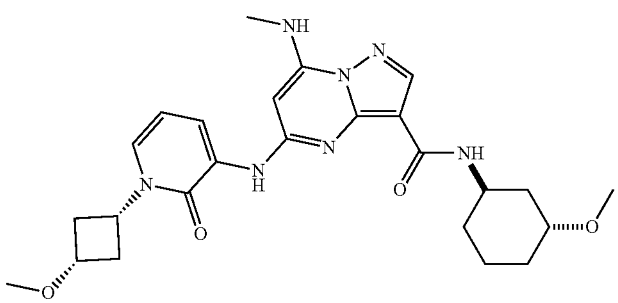 |
| I-114 | 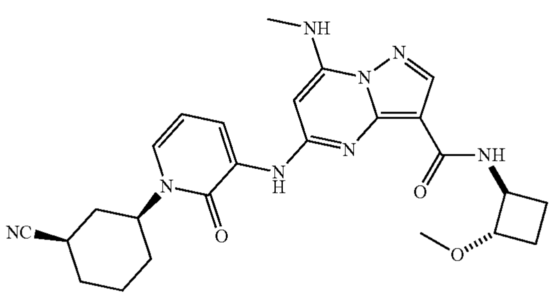 |

TABLE 1-continued

| Number | Structure |
|---|---|
| I-115 | 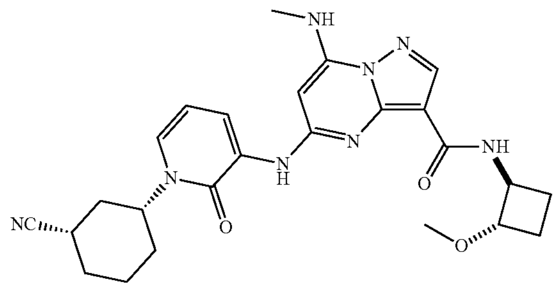 |
| I-116 | 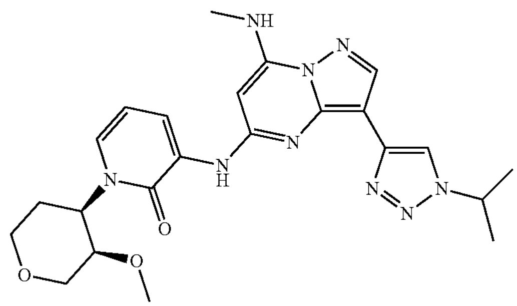 [SMILES: CNc1cc(Nc2cccn([C@@H]3CCOC[C@@H]3OC)c2=O)nc2c(-c3cn(C(C)C)nn3)cnn12] |
| I-117 | 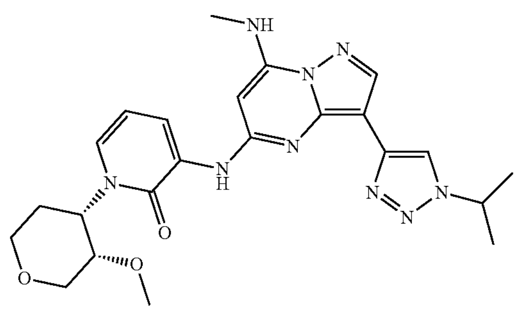 [SMILES: CNc1cc(Nc2cccn([C@H]3CCOC[C@H]3OC)c2=O)nc2c(-c3cn(C(C)C)nn3)cnn12] |
| I-118 | 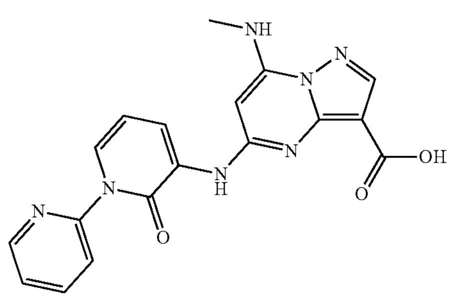 [SMILES: CNc1cc(Nc2cccn(-c3ccccn3)c2=O)nc2c(C(=O)O)cnn12] |
| I-119 | 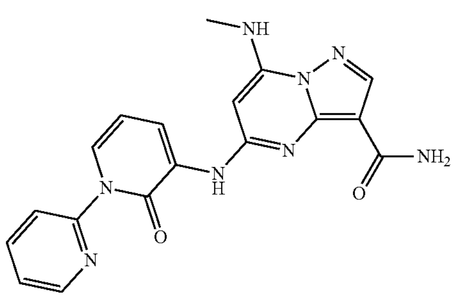 [SMILES: CNc1cc(Nc2cccn(-c3ccccn3)c2=O)nc2c(C(N)=O)cnn12] |

TABLE 1-continued
Selected Compounds
| Number | Structure |
|---|---|
| I-120 | 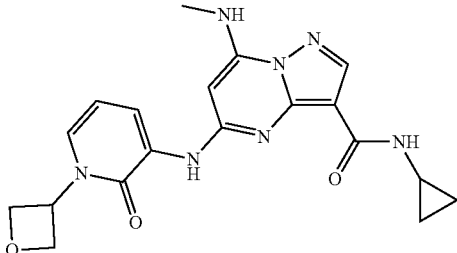 [SMILES: CNc1cc(Nc2cccn(C3COC3)c2=O)nc2c(C(=O)NC3CC3)cnn12] |
| I-121 | 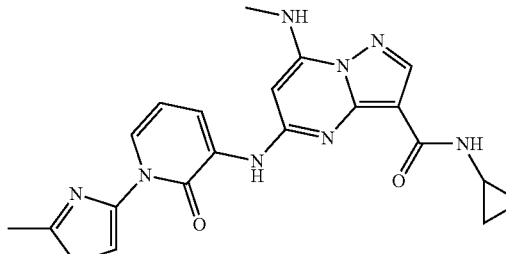 |
| I-122 | 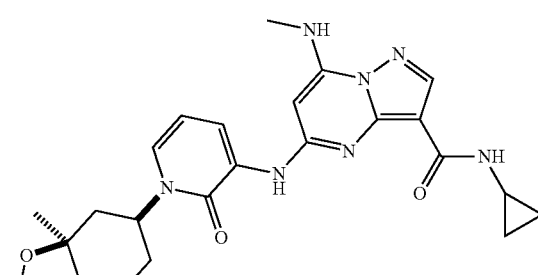 |
| I-123 | 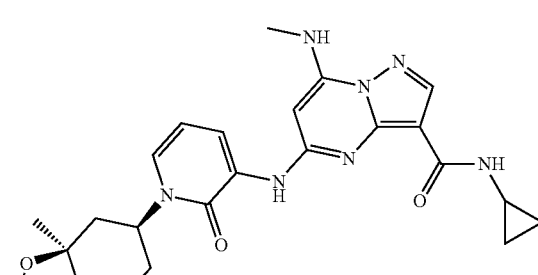 |
| I-124 | 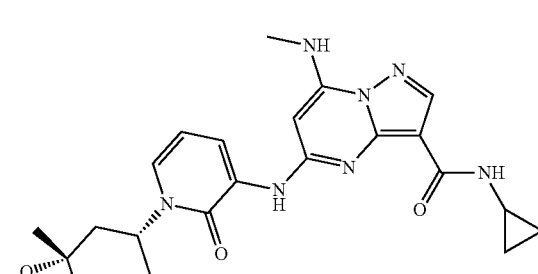 |

TABLE 1-continued
| Selected Compounds | |
|---|---|
| Number | Structure |
| I-125 | 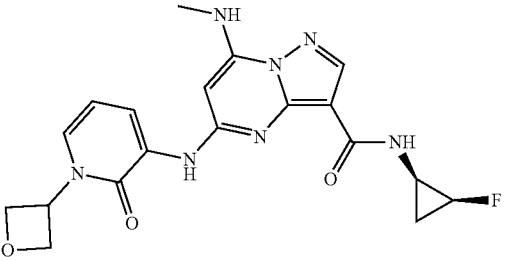 [SMILES: CNc1cc(Nc2cccn(C3COC3)c2=O)nc2c(C(=O)N[C@@H]3C[C@@H]3F)cnn12] |
| I-126 | 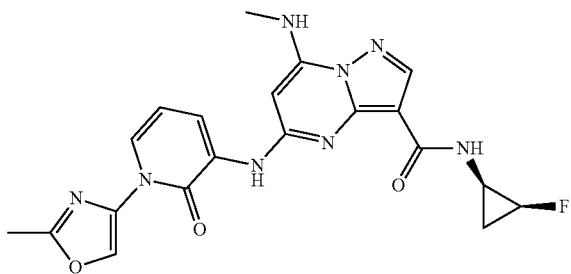 [SMILES: CNc1cc(Nc2cccn(-c3coc(C)n3)c2=O)nc2c(C(=O)N[C@@H]3C[C@@H]3F)cnn12] |
| I-127 | 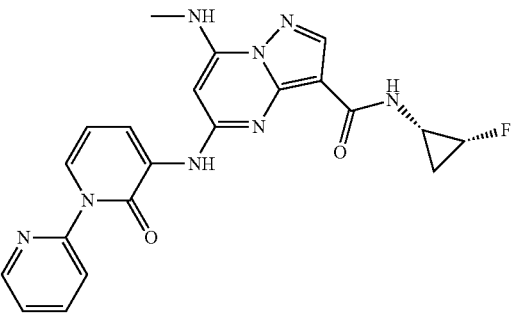 [SMILES: CNc1cc(Nc2cccn(-c3ccccn3)c2=O)nc2c(C(=O)N[C@H]3C[C@H]3F)cnn12] |
| I-128 | 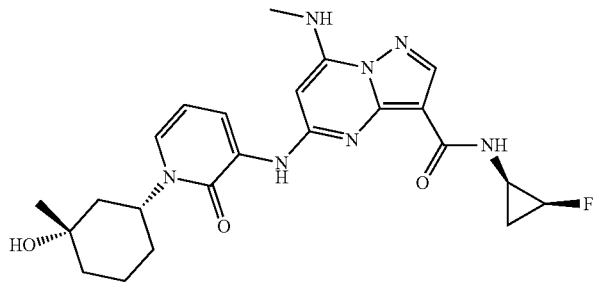 [SMILES: CNc1cc(Nc2cccn([C@@H]3CCC[C@](C)(O)C3)c2=O)nc2c(C(=O)N[C@@H]3C[C@@H]3F)cnn12] |
| I-129 | 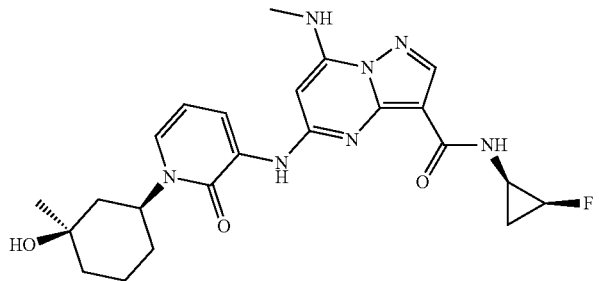 [SMILES: CNc1cc(Nc2cccn([C@H]3CCC[C@@](C)(O)C3)c2=O)nc2c(C(=O)N[C@@H]3C[C@@H]3F)cnn12] |

TABLE 1-continued
| Selected Compounds | |
|---|---|
| Number | Structure |
| I-130 | 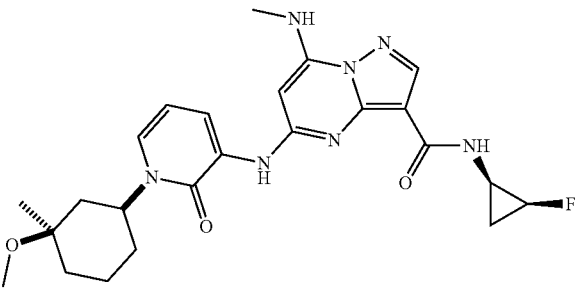 |
| I-131 | 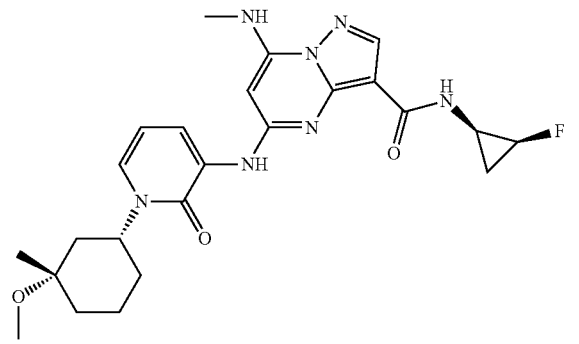 [SMILES: CNc1cc(Nc2cccn([C@@H]3CCC[C@](C)(OC)C3)c2=O)nc2c(C(=O)N[C@@H]3C[C@@H]3F)cnn12] |
| I-132 | 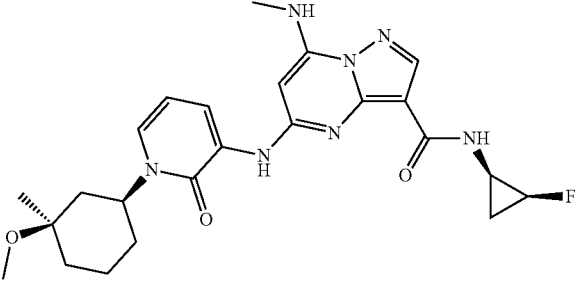 [SMILES: CNc1cc(Nc2cccn([C@H]3CCC[C@@](C)(OC)C3)c2=O)nc2c(C(=O)N[C@@H]3C[C@@H]3F)cnn12] |
| I-133 | 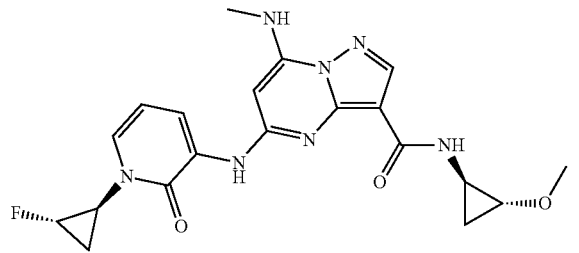 [SMILES: CNc1cc(Nc2cccn([C@H]3C[C@@H]3F)c2=O)nc2c(C(=O)N[C@@H]3C[C@H]3OC)cnn12] |
| I-134 | 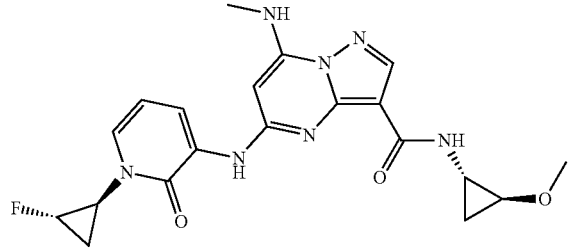 [SMILES: CNc1cc(Nc2cccn([C@H]3C[C@@H]3F)c2=O)nc2c(C(=O)N[C@H]3C[C@@H]3OC)cnn12] |

TABLE 1-continued

Selected Compounds

| Number | Structure |
|---|---|
| I-135 | 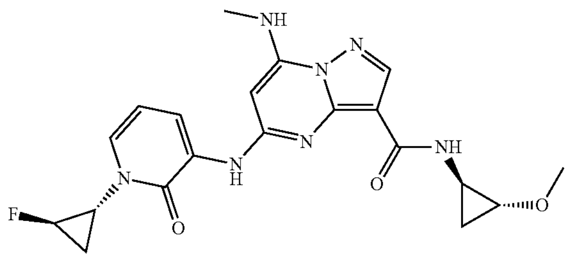 [SMILES: CNc1cc(Nc2cccn([C@@H]3C[C@H]3F)c2=O)nc2c(C(=O)N[C@@H]3C[C@H]3OC)cnn12] |
| I-136 | 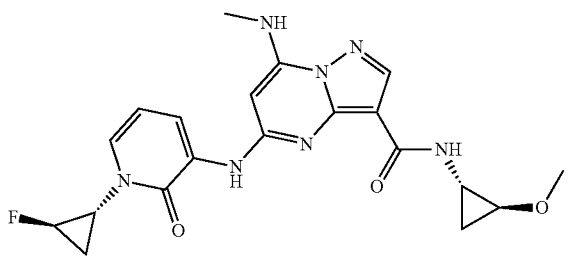 [SMILES: CNc1cc(Nc2cccn([C@@H]3C[C@H]3F)c2=O)nc2c(C(=O)N[C@H]3C[C@@H]3OC)cnn12] |
| I-137 | 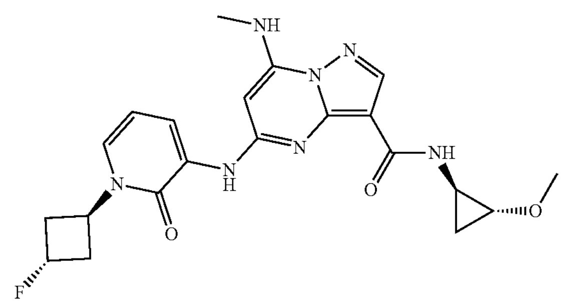 [SMILES: CNc1cc(Nc2cccn([C@H]3C[C@H](F)C3)c2=O)nc2c(C(=O)N[C@@H]3C[C@H]3OC)cnn12] |
| I-138 | 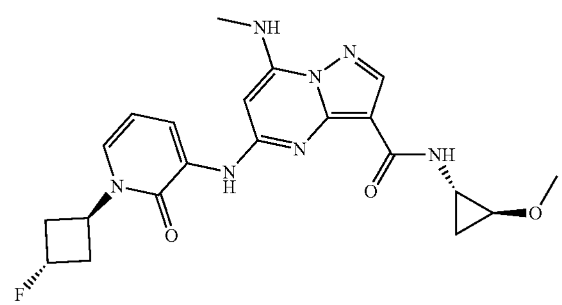 [SMILES: CNc1cc(Nc2cccn([C@H]3C[C@H](F)C3)c2=O)nc2c(C(=O)N[C@H]3C[C@@H]3OC)cnn12] |
| I-139 | 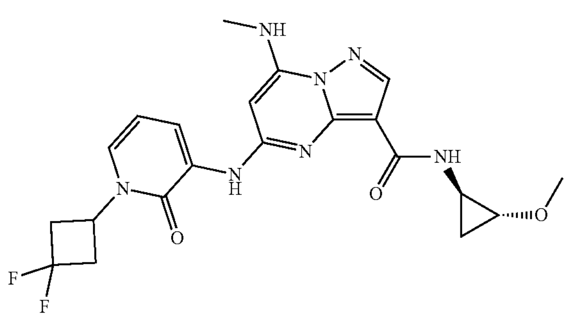 [SMILES: CNc1cc(Nc2cccn(C3CC(F)(F)C3)c2=O)nc2c(C(=O)N[C@@H]3C[C@H]3OC)cnn12] |

TABLE 1-continued

Selected Compounds

| Number | Structure |
|---|---|
| I-140 | 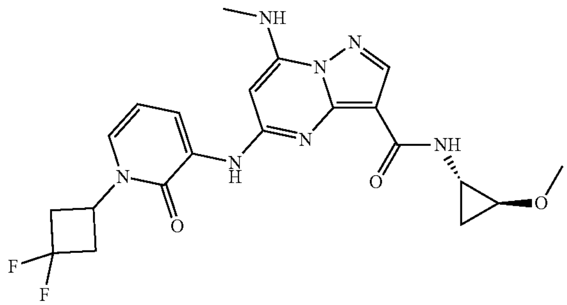 [SMILES: CNc1cc(Nc2cccn(C3CC(F)(F)C3)c2=O)nc2c(C(=O)N[C@H]3C[C@@H]3OC)cnn12] |
| I-141 | 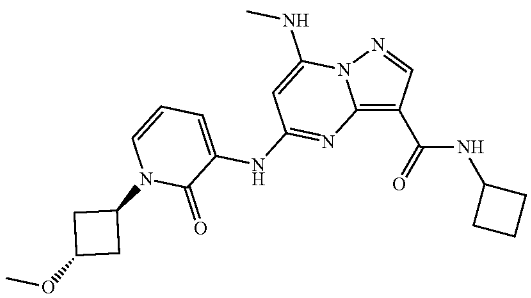 [SMILES: CNc1cc(Nc2cccn([C@H]3C[C@H](OC)C3)c2=O)nc2c(C(=O)NC3CCC3)cnn12] |
| I-142 | 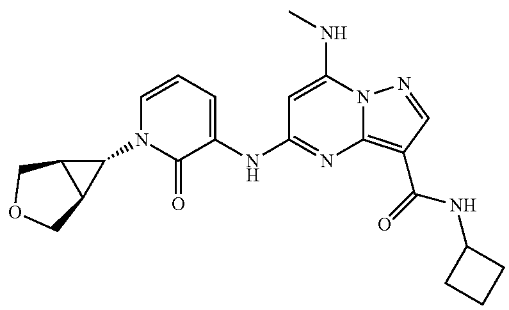 [SMILES: CNc1cc(Nc2cccn([C@H]3[C@@H]4COC[C@@H]43)c2=O)nc2c(C(=O)NC3CCC3)cnn12] |
| I-143 | 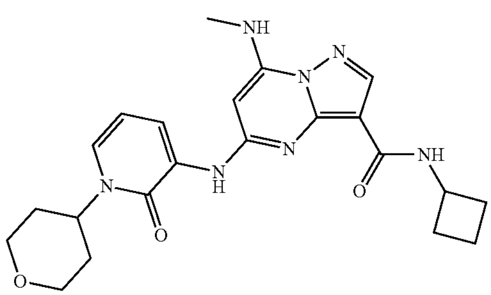 [SMILES: CNc1cc(Nc2cccn(C3CCOCC3)c2=O)nc2c(C(=O)NC3CCC3)cnn12] |
| I-144 | 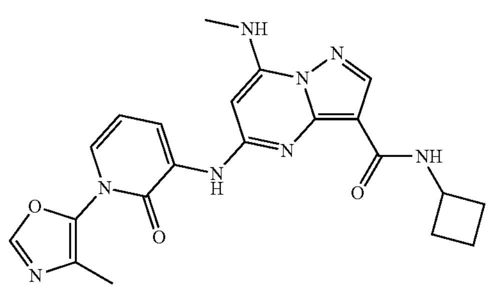 [SMILES: CNc1cc(Nc2cccn(-c3ocnc3C)c2=O)nc2c(C(=O)NC3CCC3)cnn12] |

TABLE 1-continued

Selected Compounds

| Number | Structure |
|---|---|
| I-145 | 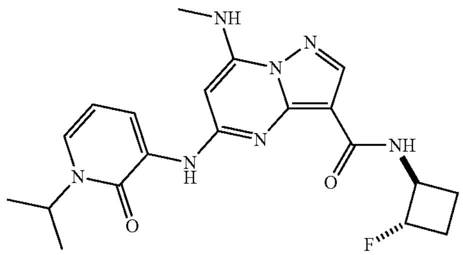 |
| I-146 | 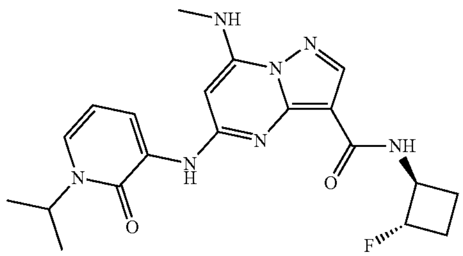 [SMILES: CNc1cc(Nc2cccn(C(C)C)c2=O)nc2c(C(=O)N[C@H]3CC[C@@H]3F)cnn12] |
| I-147 | 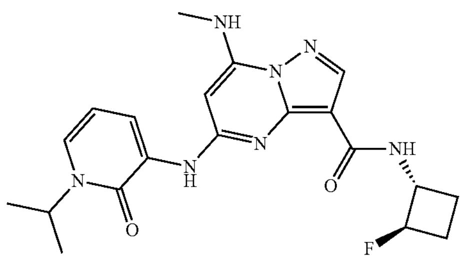 [SMILES: CNc1cc(Nc2cccn(C(C)C)c2=O)nc2c(C(=O)N[C@@H]3CC[C@H]3F)cnn12] |
| I-148 | 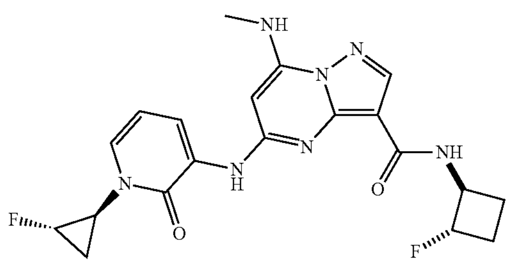 |
| I-149 | 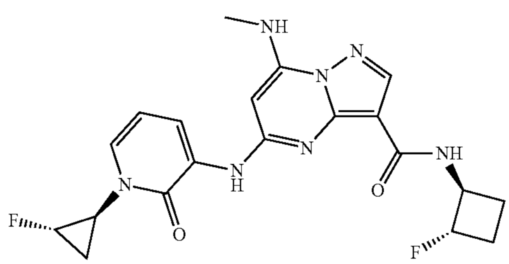 [SMILES: CNc1cc(Nc2cccn([C@H]3C[C@@H]3F)c2=O)nc2c(C(=O)N[C@H]3CC[C@@H]3F)cnn12] |
| I-150 | 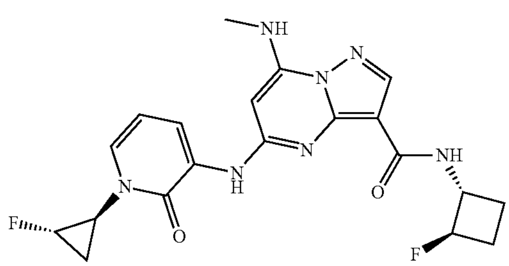 [SMILES: CNc1cc(Nc2cccn([C@H]3C[C@@H]3F)c2=O)nc2c(C(=O)N[C@@H]3CC[C@H]3F)cnn12] |

TABLE 1-continued

| Number | Structure |
|---|---|
| I-151 | (structure) |
| I-152 | (structure) |
| I-153 | (structure) |
| I-154 | (structure) |
| I-155 | (structure) |

TABLE 1-continued
| Number | Structure |
|---|---|
| I-156 | 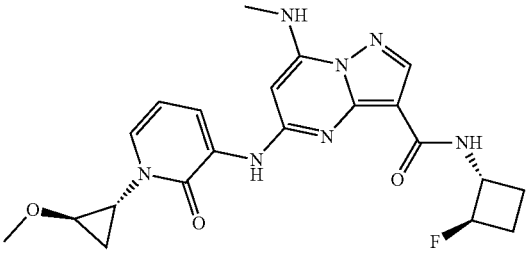 [SMILES: CNc1cc(Nc2cccn([C@@H]3C[C@H]3OC)c2=O)nc2c(C(=O)N[C@@H]3CC[C@H]3F)cnn12] |
| I-157 | 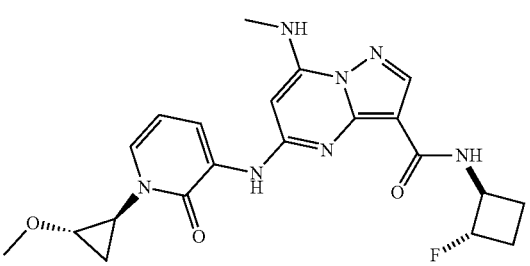 |
| I-158 | 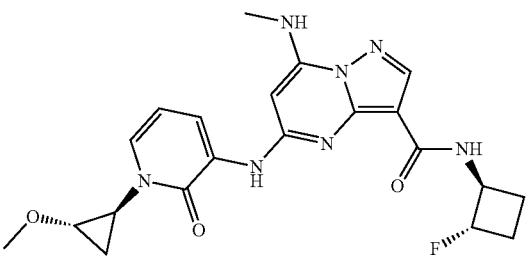 [SMILES: CNc1cc(Nc2cccn([C@H]3C[C@@H]3OC)c2=O)nc2c(C(=O)N[C@H]3CC[C@@H]3F)cnn12] |
| I-159 | 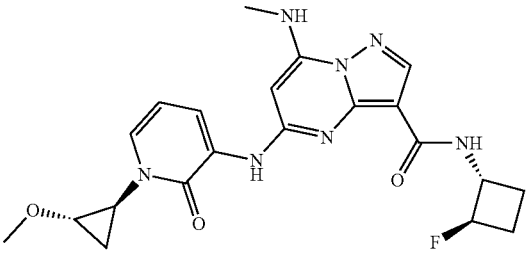 [SMILES: CNc1cc(Nc2cccn([C@H]3C[C@@H]3OC)c2=O)nc2c(C(=O)N[C@@H]3CC[C@H]3F)cnn12] |
| I-160 | 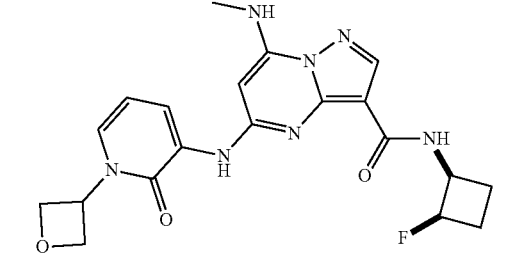 |

TABLE 1-continued
Selected Compounds
| Number | Structure |
|---|---|
| I-161 | 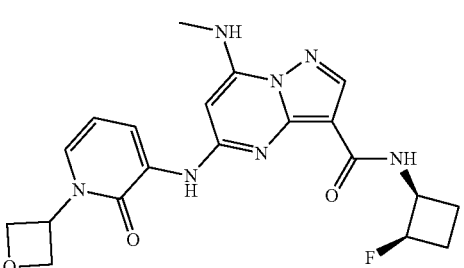 |
| I-162 | 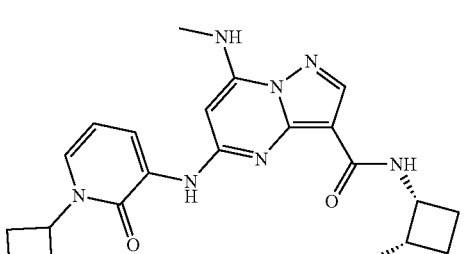 |
| I-163 | 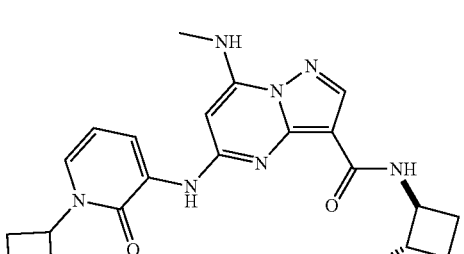 |
| I-164 | 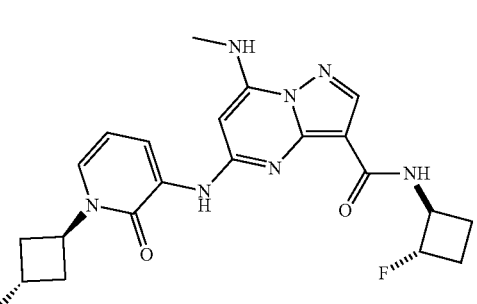 |
| I-165 | 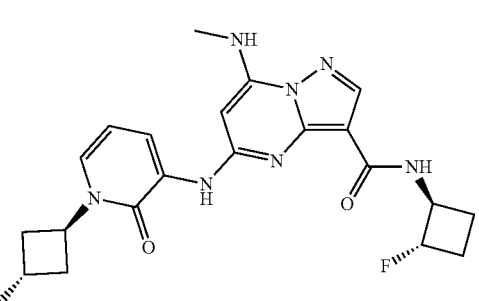 |

TABLE 1-continued
| Selected Compounds | |
|---|---|
| Number | Structure |
| I-166 | 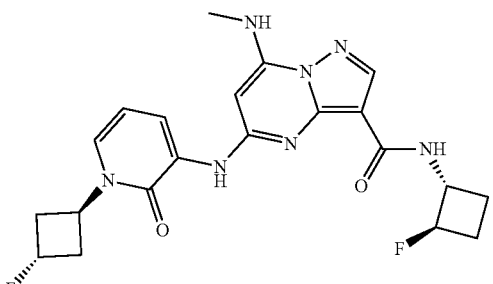 |
| I-167 | 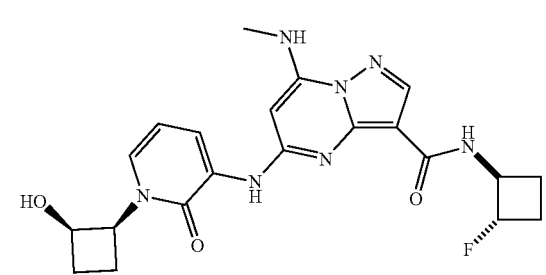 |
| I-168 | 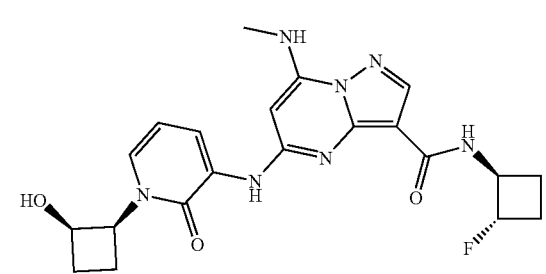 [SMILES: CNc1cc(Nc2cccn([C@H]3CC[C@H]3O)c2=O)nc2c(C(=O)N[C@H]3CC[C@@H]3F)cnn12] |
| I-169 | 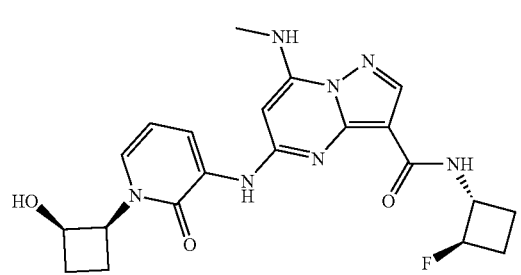 [SMILES: CNc1cc(Nc2cccn([C@H]3CC[C@H]3O)c2=O)nc2c(C(=O)N[C@@H]3CC[C@H]3F)cnn12] |
| I-170 | 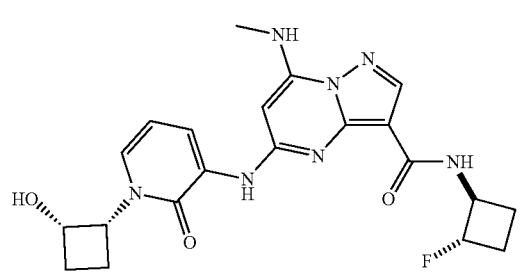 |

TABLE 1-continued

| Number | Structure |
|---|---|
| I-171 | 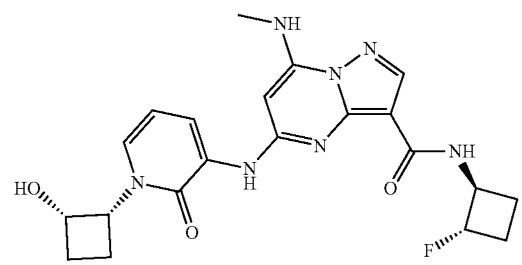 [SMILES: CNc1cc(Nc2cccn([C@@H]3CC[C@@H]3O)c2=O)nc2c(C(=O)N[C@H]3CC[C@@H]3F)cnn12] |
| I-172 | 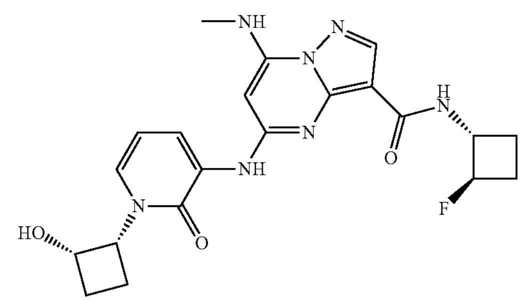 [SMILES: CNc1cc(Nc2cccn([C@@H]3CC[C@@H]3O)c2=O)nc2c(C(=O)N[C@@H]3CC[C@H]3F)cnn12] |
| I-173 | 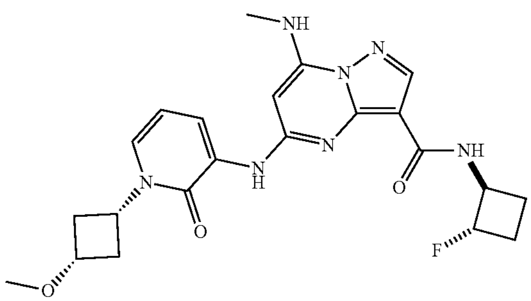 |
| I-174 | 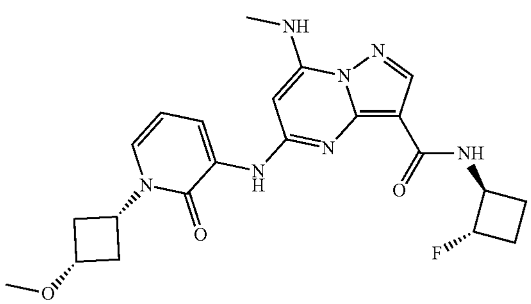 [SMILES: CNc1cc(Nc2cccn([C@H]3C[C@@H](OC)C3)c2=O)nc2c(C(=O)N[C@H]3CC[C@@H]3F)cnn12] |
| I-175 | 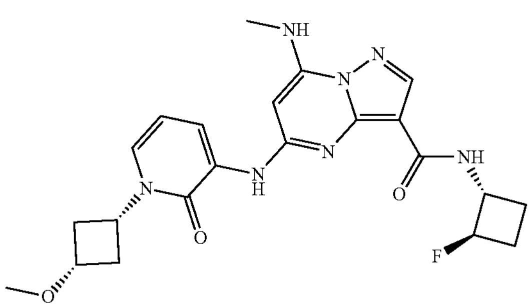 [SMILES: CNc1cc(Nc2cccn([C@H]3C[C@@H](OC)C3)c2=O)nc2c(C(=O)N[C@@H]3CC[C@H]3F)cnn12] |

TABLE 1-continued
| Selected Compounds | |
|---|---|
| Number | Structure |
| I-176 | 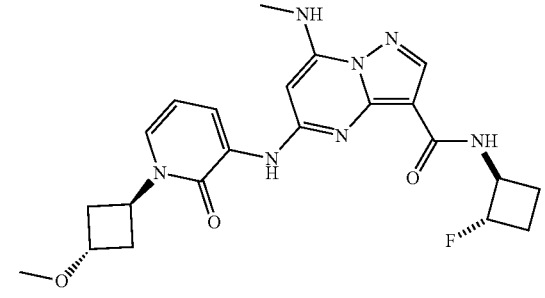 |
| I-177 | 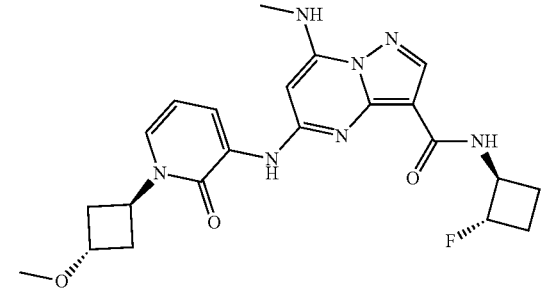 [SMILES: CNc1cc(Nc2cccn([C@H]3C[C@H](OC)C3)c2=O)nc2c(C(=O)N[C@H]3CC[C@@H]3F)cnn12] |
| I-178 | 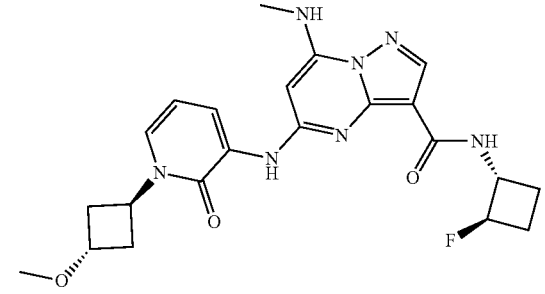 [SMILES: CNc1cc(Nc2cccn([C@H]3C[C@H](OC)C3)c2=O)nc2c(C(=O)N[C@@H]3CC[C@H]3F)cnn12] |
| I-179 | 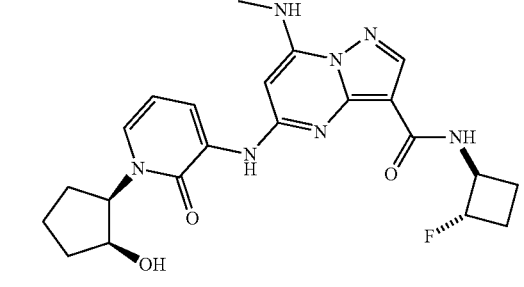 |
| I-180 | 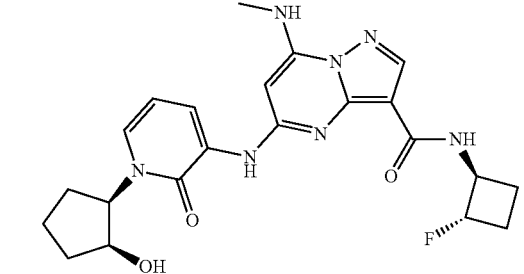 [SMILES: CNc1cc(Nc2cccn([C@@H]3CCC[C@@H]3O)c2=O)nc2c(C(=O)N[C@H]3CC[C@@H]3F)cnn12] |

TABLE 1-continued

| Number | Structure |
|---|---|
| I-181 | 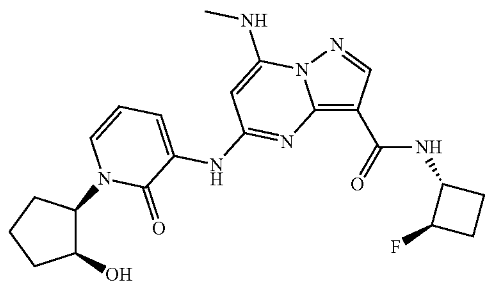 [SMILES: CNc1cc(Nc2cccn([C@@H]3CCC[C@@H]3O)c2=O)nc2c(C(=O)N[C@@H]3CC[C@H]3F)cnn12] |
| I-182 | 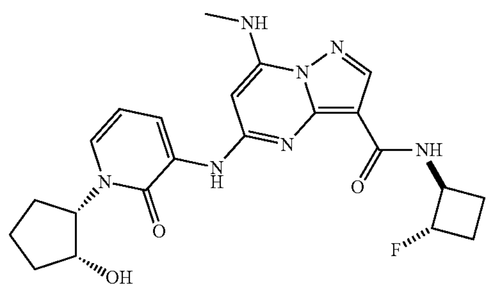 |
| I-183 | 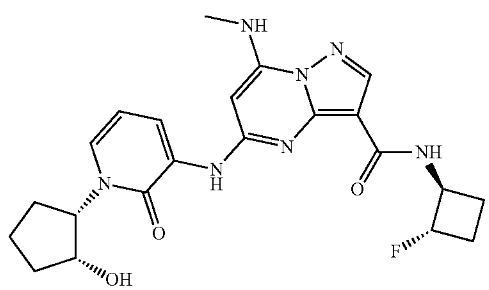 [SMILES: CNc1cc(Nc2cccn([C@H]3CCC[C@H]3O)c2=O)nc2c(C(=O)N[C@H]3CC[C@@H]3F)cnn12] |
| I-184 | 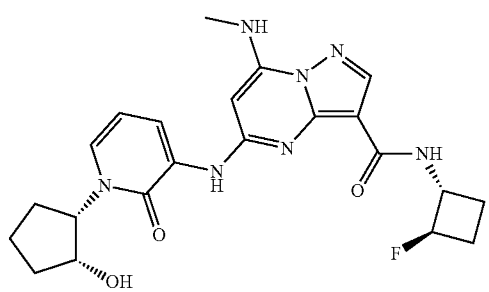 [SMILES: CNc1cc(Nc2cccn([C@H]3CCC[C@H]3O)c2=O)nc2c(C(=O)N[C@@H]3CC[C@H]3F)cnn12] |
| I-185 | 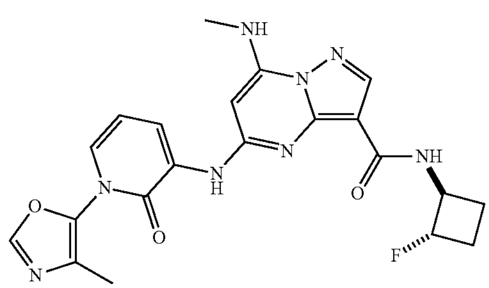 |

TABLE 1-continued

| Number | Structure |
|---|---|
| I-186 | 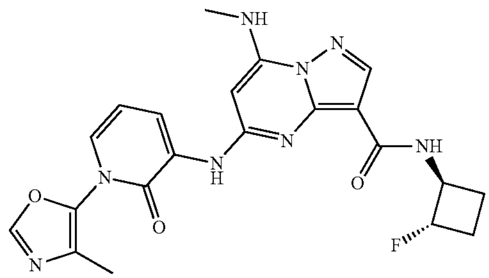 [SMILES: CNc1cc(Nc2cccn(-c3ocnc3C)c2=O)nc2c(C(=O)N[C@H]3CC[C@@H]3F)cnn12] |
| I-187 | 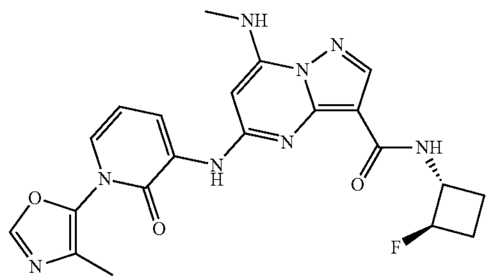 [SMILES: CNc1cc(Nc2cccn(-c3ocnc3C)c2=O)nc2c(C(=O)N[C@@H]3CC[C@H]3F)cnn12] |
| I-188 | 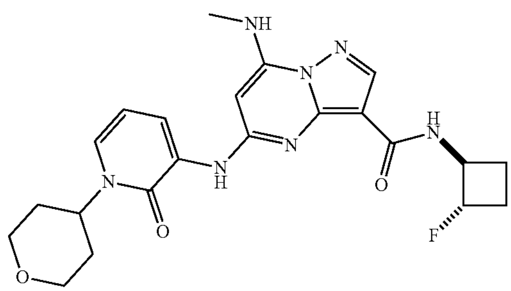 |
| I-189 | 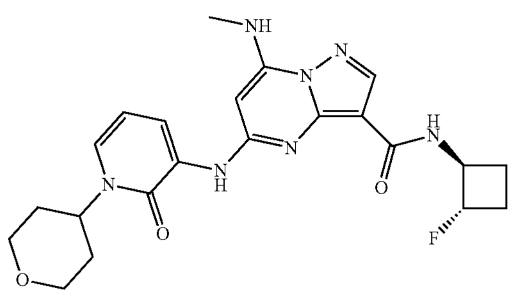 [SMILES: CNc1cc(Nc2cccn(C3CCOCC3)c2=O)nc2c(C(=O)N[C@H]3CC[C@@H]3F)cnn12] |
| I-190 | 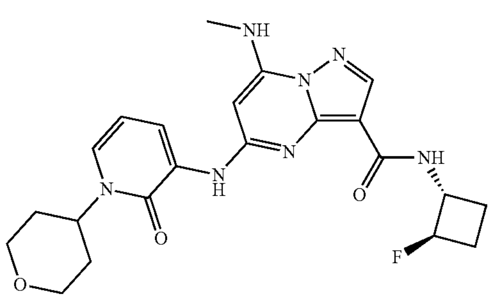 [SMILES: CNc1cc(Nc2cccn(C3CCOCC3)c2=O)nc2c(C(=O)N[C@@H]3CC[C@H]3F)cnn12] |

123
124
TABLE 1-continued
Selected Compounds
| Number | Structure |
|---|---|
| I-191 | 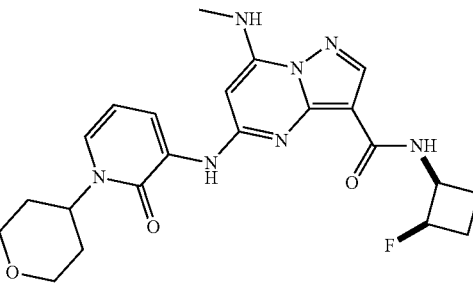 |
| I-192 | 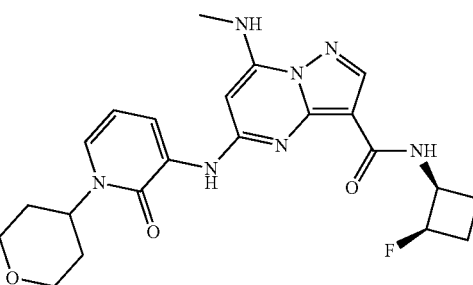 |
| I-193 | 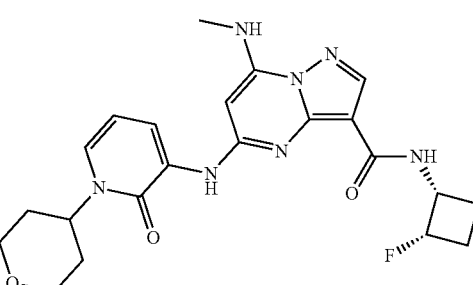 |
| I-194 | 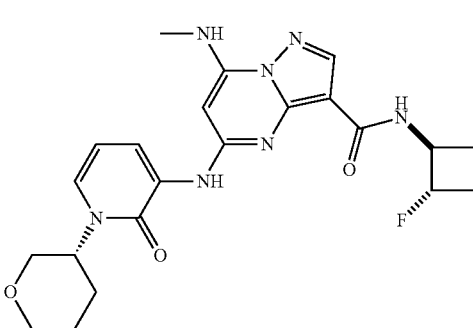 |
| I-195 | 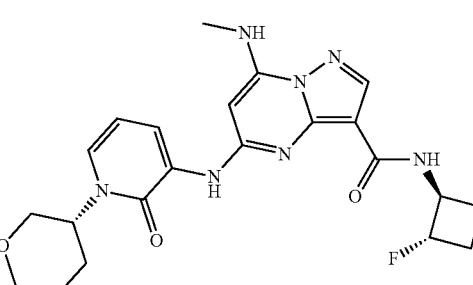 |

TABLE 1-continued
| Selected Compounds | |
|---|---|
| Number | Structure |
| I-196 | 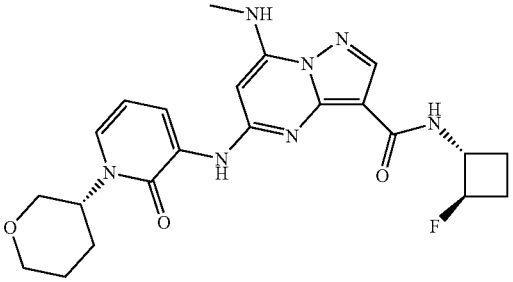 [SMILES: CNc1cc(Nc2cccn([C@@H]3CCCOC3)c2=O)nc2c(C(=O)N[C@@H]3CC[C@H]3F)cnn12] |
| I-197 | 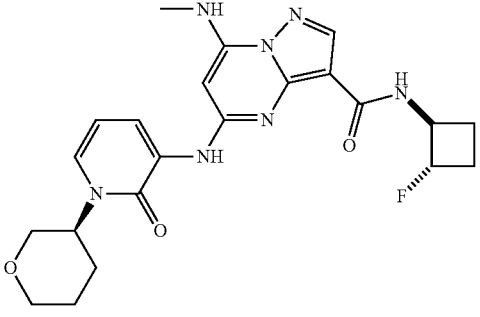 |
| I-198 | 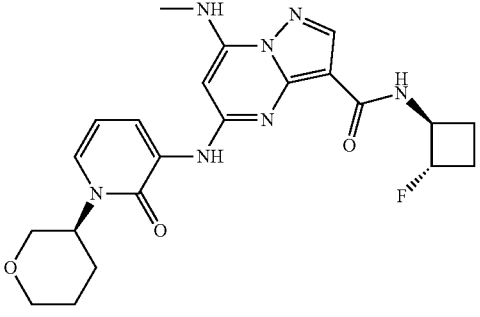 [SMILES: CNc1cc(Nc2cccn([C@H]3CCCOC3)c2=O)nc2c(C(=O)N[C@H]3CC[C@@H]3F)cnn12] |
| I-199 | 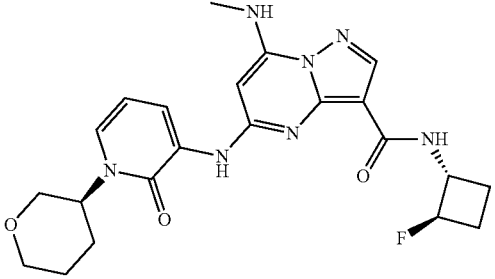 [SMILES: CNc1cc(Nc2cccn([C@H]3CCCOC3)c2=O)nc2c(C(=O)N[C@@H]3CC[C@H]3F)cnn12] |
| I-200 | 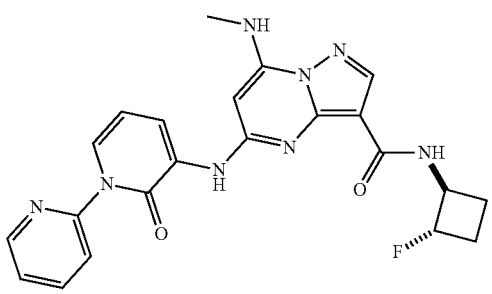 |

TABLE 1-continued

| Number | Structure |
|---|---|
| I-201 | 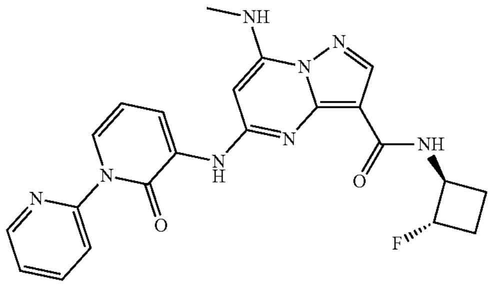 [SMILES: CNc1cc(Nc2cccn(-c3ccccn3)c2=O)nc2c(C(=O)N[C@H]3CC[C@@H]3F)cnn12] |
| I-202 | 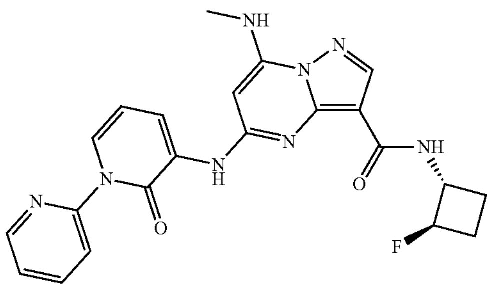 [SMILES: CNc1cc(Nc2cccn(-c3ccccn3)c2=O)nc2c(C(=O)N[C@@H]3CC[C@H]3F)cnn12] |
| I-203 | 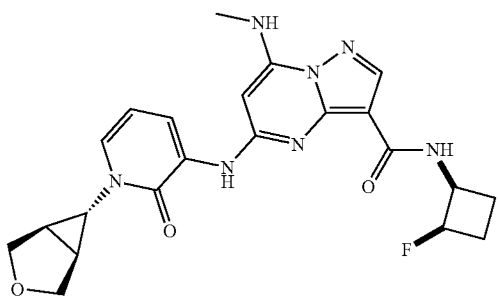 |
| I-204 | 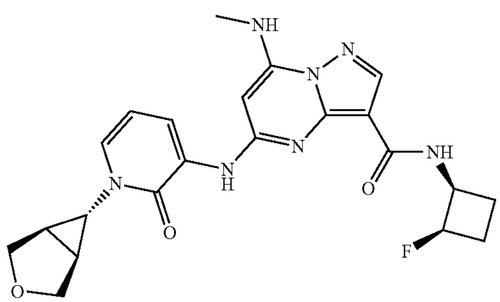 [SMILES: CNc1cc(Nc2cccn([C@H]3[C@@H]4COC[C@@H]43)c2=O)nc2c(C(=O)N[C@H]3CC[C@H]3F)cnn12] |
| I-205 | 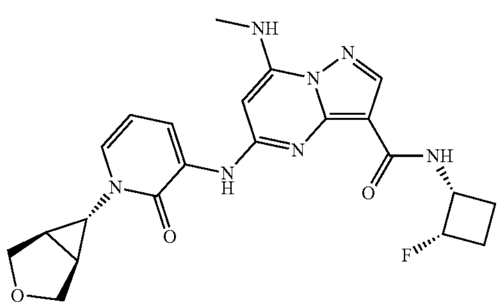 [SMILES: CNc1cc(Nc2cccn([C@H]3[C@@H]4COC[C@@H]43)c2=O)nc2c(C(=O)N[C@@H]3CC[C@@H]3F)cnn12] |

TABLE 1-continued
| Selected Compounds | |
|---|---|
| Number | Structure |
| I-206 | 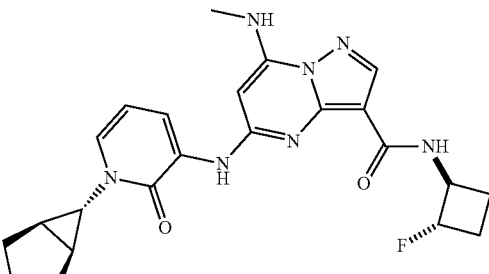 |
| I-207 | 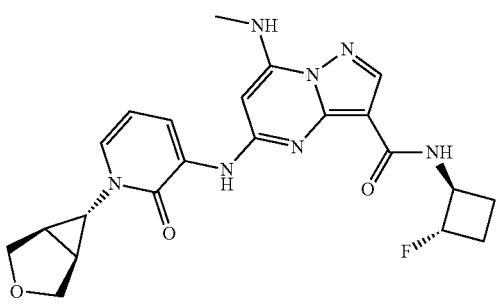 [SMILES: CNc1cc(Nc2cccn([C@H]3[C@@H]4COC[C@@H]43)c2=O)nc2c(C(=O)N[C@H]3CC[C@@H]3F)cnn12] |
| I-208 | 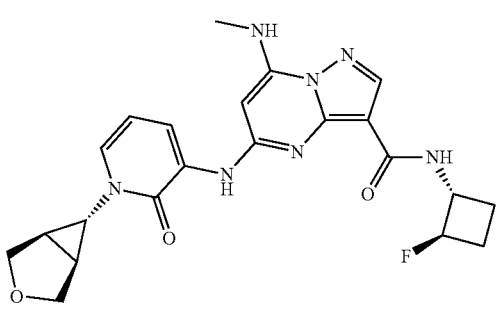 [SMILES: CNc1cc(Nc2cccn([C@H]3[C@@H]4COC[C@@H]43)c2=O)nc2c(C(=O)N[C@@H]3CC[C@H]3F)cnn12] |
| I-209 | 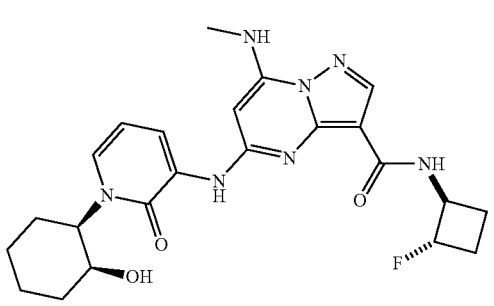 |
| I-210 | 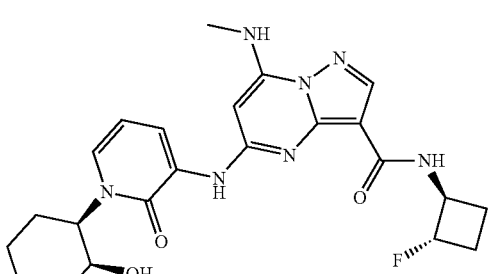 |

TABLE 1-continued

| Number | Structure |
|---|---|
| I-211 | 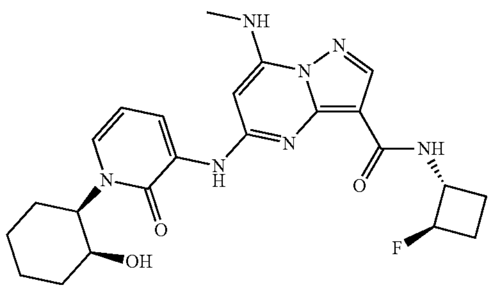 [SMILES: CNc1cc(Nc2cccn([C@@H]3CCCC[C@@H]3O)c2=O)nc2c(C(=O)N[C@@H]3CC[C@H]3F)cnn12] |
| I-212 | 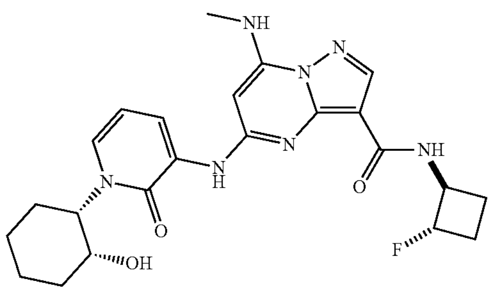 |
| I-213 | 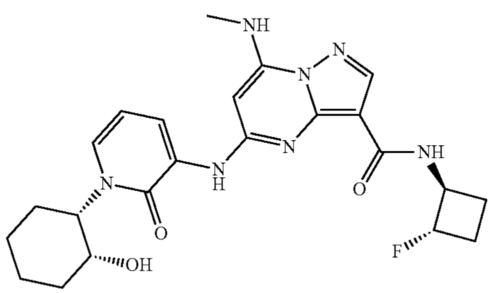 [SMILES: CNc1cc(Nc2cccn([C@H]3CCCC[C@H]3O)c2=O)nc2c(C(=O)N[C@H]3CC[C@@H]3F)cnn12] |
| I-214 | 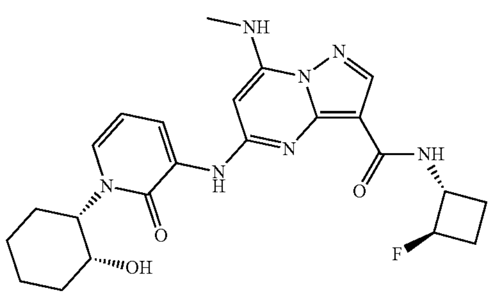 [SMILES: CNc1cc(Nc2cccn([C@H]3CCCC[C@H]3O)c2=O)nc2c(C(=O)N[C@@H]3CC[C@H]3F)cnn12] |
| I-215 | 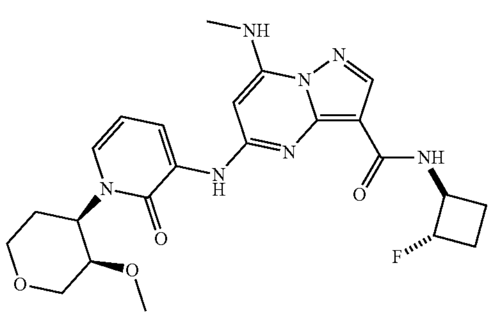 |

TABLE 1-continued
Selected Compounds
| Number | Structure |
|---|---|
| I-216 | 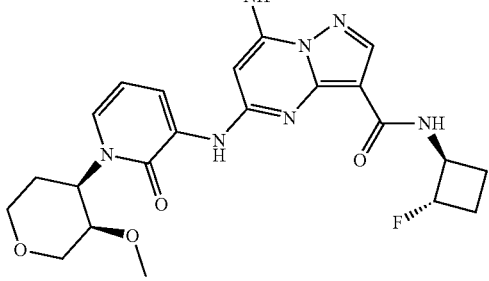 |
| I-217 | 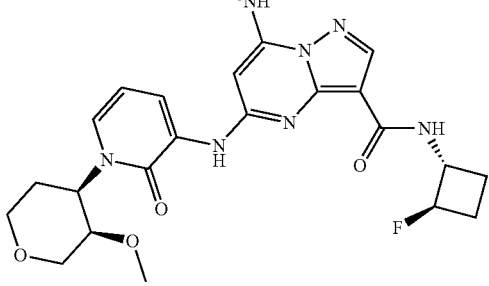 |
| I-218 | 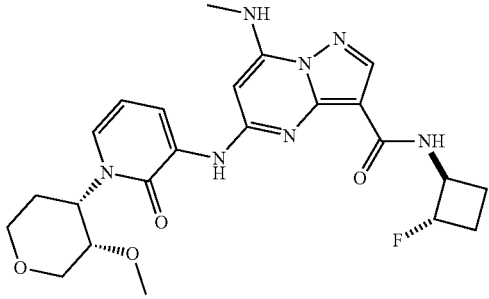 |
| I-219 | 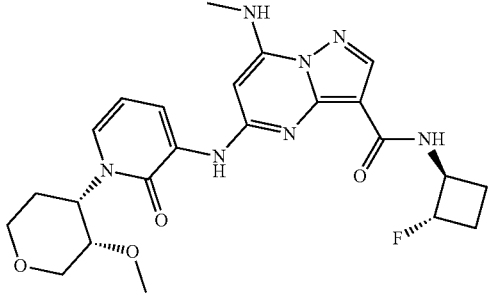 [SMILES: CNc1cc(Nc2cccn([C@H]3CCOC[C@H]3OC)c2=O)nc2c(C(=O)N[C@H]3CC[C@@H]3F)cnn12] |
| I-220 | 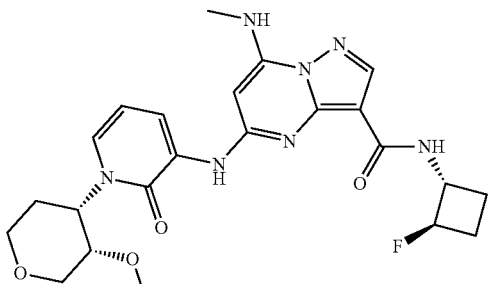 |

TABLE 1-continued

Selected Compounds

| Number | Structure |
|---|---|
| I-221 | 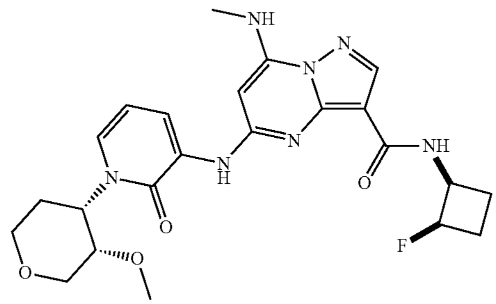 |
| I-222 | 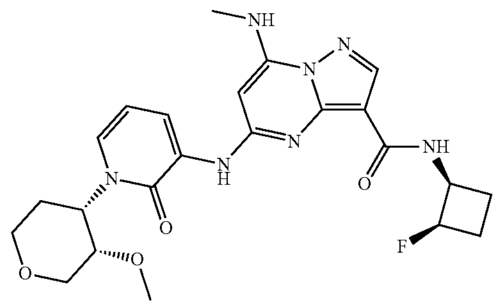 [SMILES: CNc1cc(Nc2cccn([C@H]3CCOC[C@H]3OC)c2=O)nc2c(C(=O)N[C@H]3CC[C@H]3F)cnn12] |
| I-223 | 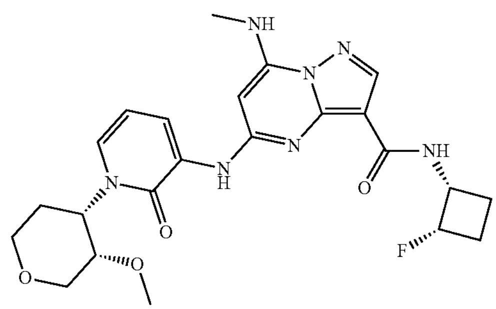 [SMILES: CNc1cc(Nc2cccn([C@H]3CCOC[C@H]3OC)c2=O)nc2c(C(=O)N[C@@H]3CC[C@@H]3F)cnn12] |
| I-224 | 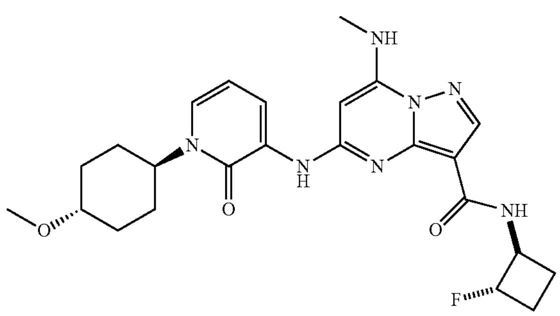 |
| I-225 | 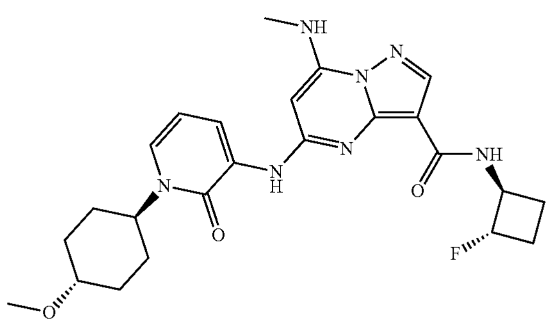 [SMILES: CNc1cc(Nc2cccn([C@H]3CC[C@H](OC)CC3)c2=O)nc2c(C(=O)N[C@H]3CC[C@@H]3F)cnn12] |

TABLE 1-continued
Selected Compounds
| Number | Structure |
|---|---|
| I-226 | 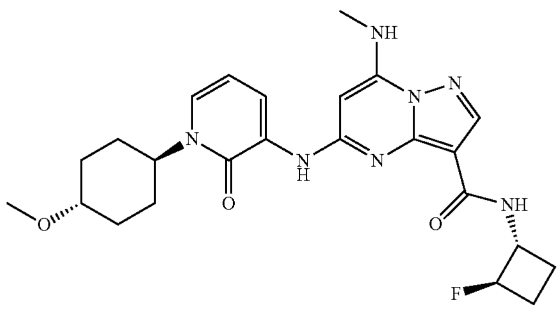 [SMILES: CNc1cc(Nc2cccn([C@H]3CC[C@H](OC)CC3)c2=O)nc2c(C(=O)N[C@@H]3CC[C@H]3F)cnn12] |
| I-227 | 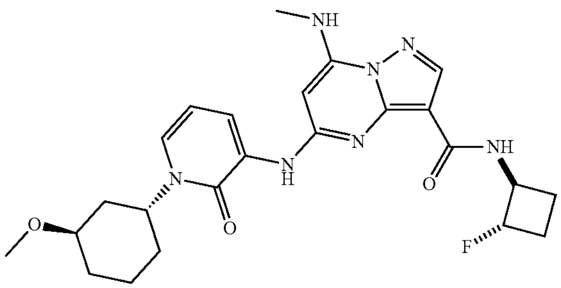 |
| I-228 | 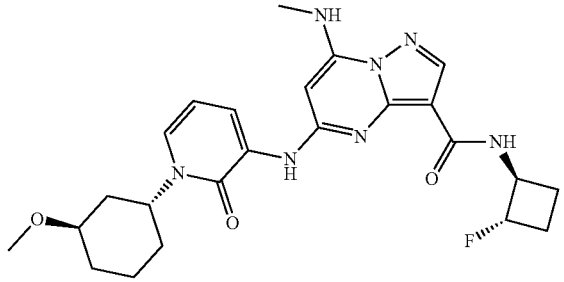 [SMILES: CNc1cc(Nc2cccn([C@@H]3CCC[C@@H](OC)C3)c2=O)nc2c(C(=O)N[C@H]3CC[C@@H]3F)cnn12] |
| I-229 | 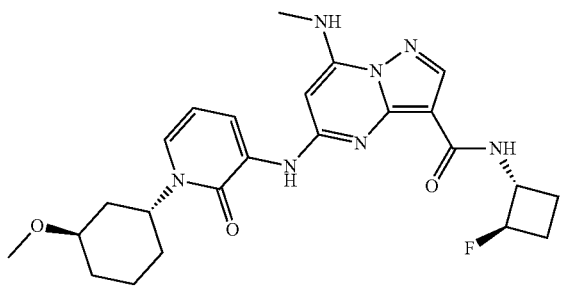 [SMILES: CNc1cc(Nc2cccn([C@@H]3CCC[C@@H](OC)C3)c2=O)nc2c(C(=O)N[C@@H]3CC[C@H]3F)cnn12] |
| I-230 | 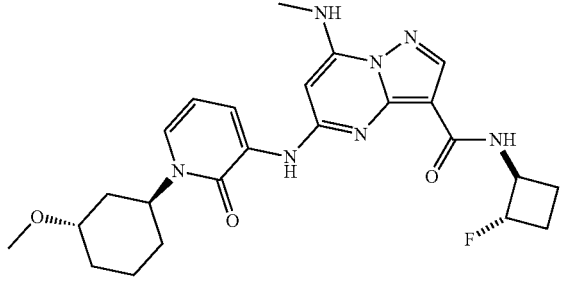 |

TABLE 1-continued

Selected Compounds

| Number | Structure |
|---|---|
| I-231 | 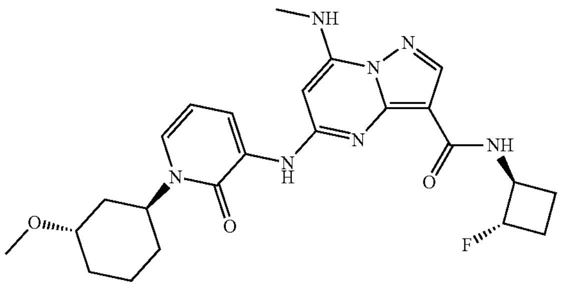 [SMILES: CNc1cc(Nc2cccn([C@H]3CCC[C@H](OC)C3)c2=O)nc2c(C(=O)N[C@H]3CC[C@@H]3F)cnn12] |
| I-232 | 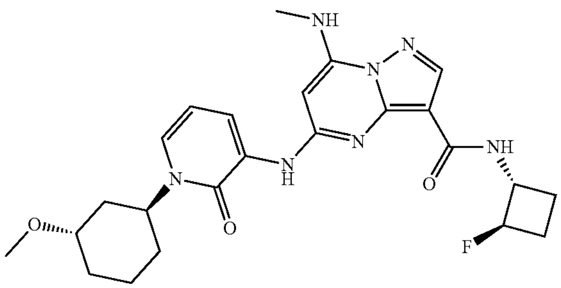 [SMILES: CNc1cc(Nc2cccn([C@H]3CCC[C@H](OC)C3)c2=O)nc2c(C(=O)N[C@@H]3CC[C@H]3F)cnn12] |
| I-233 | 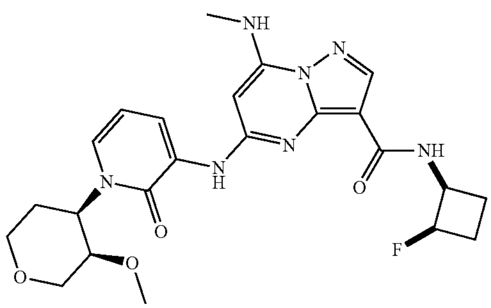 |
| I-234 | 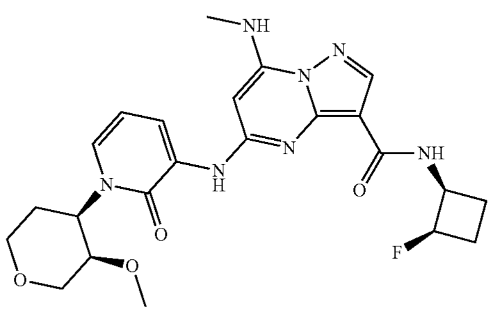 [SMILES: CNc1cc(Nc2cccn([C@@H]3CCOC[C@@H]3OC)c2=O)nc2c(C(=O)N[C@H]3CC[C@H]3F)cnn12] |
| I-235 | 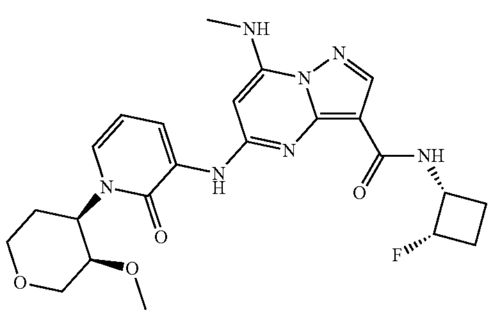 [SMILES: CNc1cc(Nc2cccn([C@@H]3CCOC[C@@H]3OC)c2=O)nc2c(C(=O)N[C@@H]3CC[C@@H]3F)cnn12] |

TABLE 1-continued
Selected Compounds
| Number | Structure |
|---|---|
| I-236 | 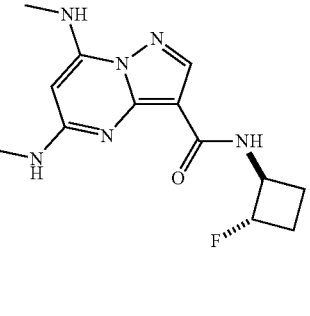 |
| I-237 | 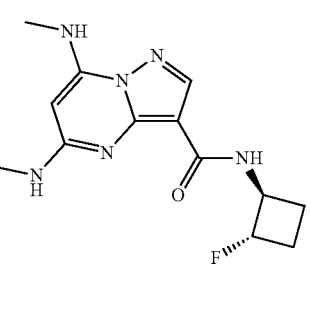 |
| I-238 | 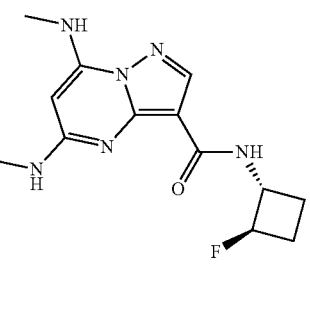 |
| I-239 | 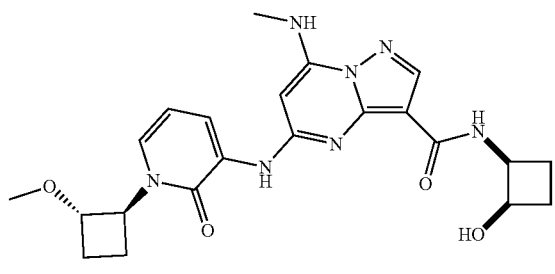 |
| I-240 | 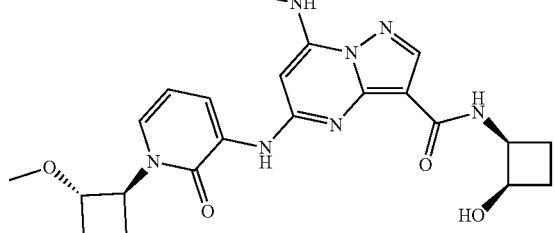 |

TABLE 1-continued

| Number | Structure |
|---|---|
| I-241 | 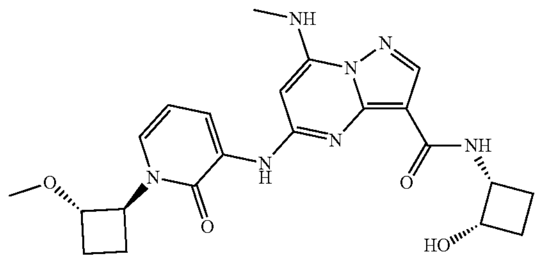 [SMILES: CNc1cc(Nc2cccn([C@H]3CC[C@@H]3OC)c2=O)nc2c(C(=O)N[C@@H]3CC[C@@H]3O)cnn12] |
| I-242 | 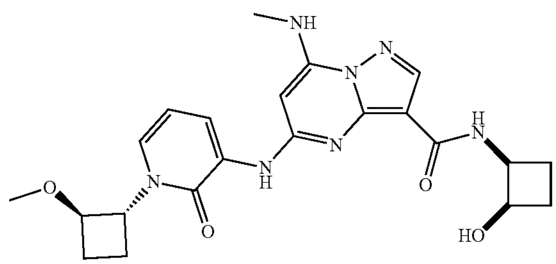 |
| I-243 | 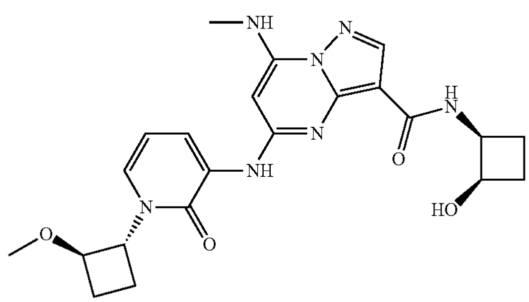 [SMILES: CNc1cc(Nc2cccn([C@@H]3CC[C@H]3OC)c2=O)nc2c(C(=O)N[C@H]3CC[C@H]3O)cnn12] |
| I-244 | 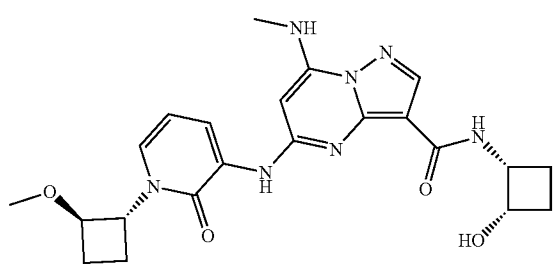 [SMILES: CNc1cc(Nc2cccn([C@@H]3CC[C@H]3OC)c2=O)nc2c(C(=O)N[C@@H]3CC[C@@H]3O)cnn12] |
| I-245 | 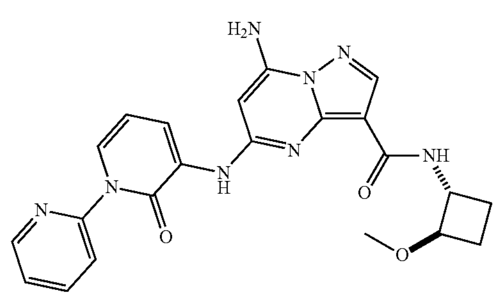 |

TABLE 1-continued

Selected Compounds

| Number | Structure |
|---|---|
| I-246 | (chemical structure) |
| I-247 | (chemical structure) |
| I-248 | (chemical structure) |
| I-249 | (chemical structure) |
| I-250 | (chemical structure) |

TABLE 1-continued

| Selected Compounds | |
|---|---|
| Number | Structure |

I-251

I-252

I-253

I-254

I-255

149
TABLE 1-continued
| Selected Compounds | |
|---|---|
| Number | Structure |
| I-256 | 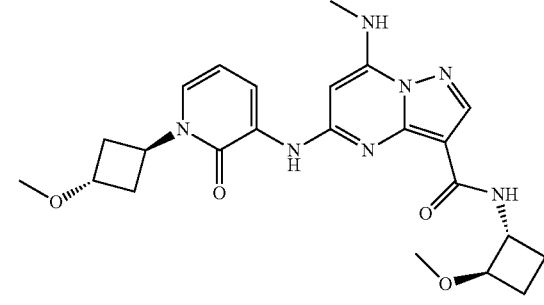 [SMILES: CNc1cc(Nc2cccn([C@H]3C[C@H](OC)C3)c2=O)nc2c(C(=O)N[C@@H]3CC[C@H]3OC)cnn12] |
| I-257 | 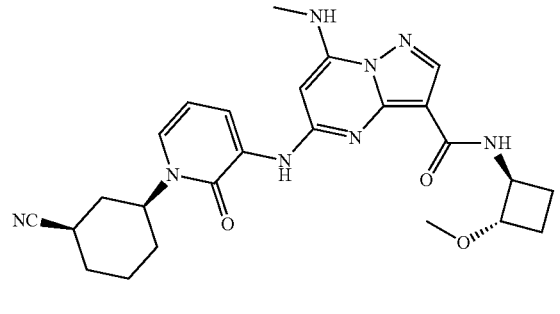 [SMILES: CNc1cc(Nc2cccn([C@H]3CCC[C@@H](C#N)C3)c2=O)nc2c(C(=O)N[C@H]3CC[C@@H]3OC)cnn12] |
| I-258 | 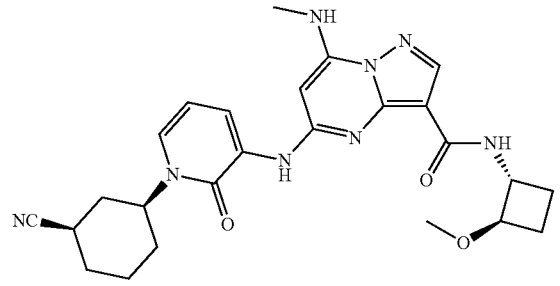 [SMILES: CNc1cc(Nc2cccn([C@H]3CCC[C@@H](C#N)C3)c2=O)nc2c(C(=O)N[C@@H]3CC[C@H]3OC)cnn12] |
| I-259 | 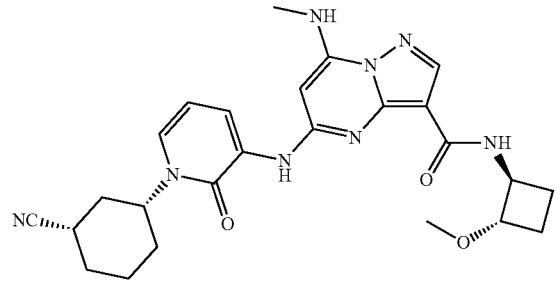 [SMILES: CNc1cc(Nc2cccn([C@@H]3CCC[C@H](C#N)C3)c2=O)nc2c(C(=O)N[C@H]3CC[C@@H]3OC)cnn12] |
| I-260 | 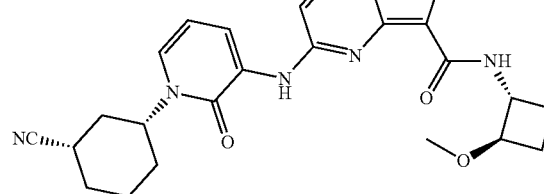 |

TABLE 1-continued

Selected Compounds

| Number | Structure |
|---|---|
| I-261 | 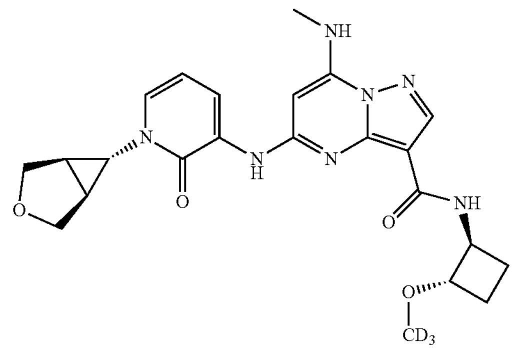 [SMILES: [2H]C([2H])([2H])O[C@H]1CC[C@@H]1NC(=O)c1cnn2c(NC)cc(Nc3cccn([C@H]4[C@@H]5COC[C@@H]54)c3=O)nc12] |
| I-262 | 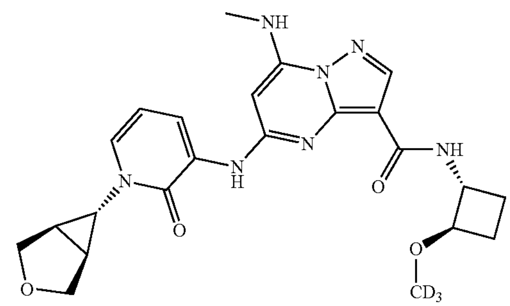 [SMILES: [2H]C([2H])([2H])O[C@@H]1CC[C@H]1NC(=O)c1cnn2c(NC)cc(Nc3cccn([C@H]4[C@@H]5COC[C@@H]54)c3=O)nc12] |
| I-263 | 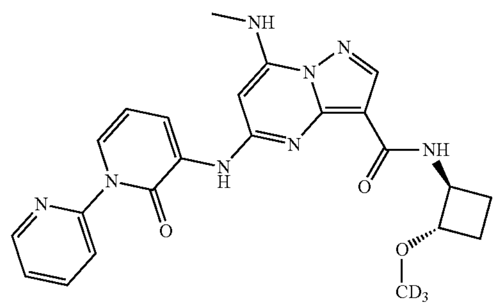 [SMILES: [2H]C([2H])([2H])O[C@H]1CC[C@@H]1NC(=O)c1cnn2c(NC)cc(Nc3cccn(-c4ccccn4)c3=O)nc12] |
| I-264 | 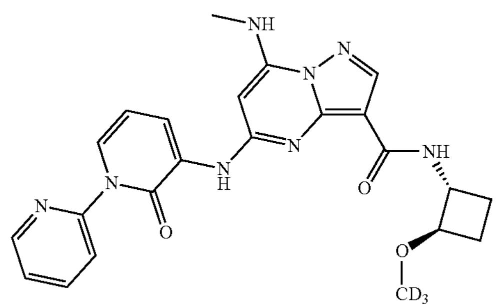 [SMILES: [2H]C([2H])([2H])O[C@@H]1CC[C@H]1NC(=O)c1cnn2c(NC)cc(Nc3cccn(-c4ccccn4)c3=O)nc12] |
| I-265 | 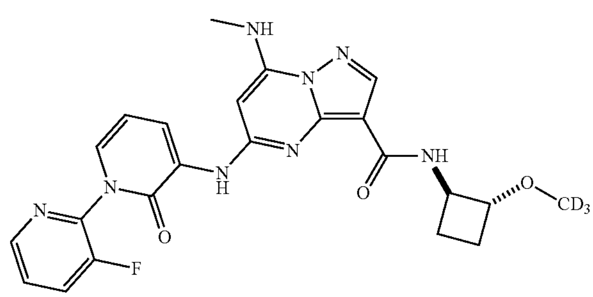 |

TABLE 1-continued

| Number | Structure |
|---|---|
| I-266 | (structure) |
| I-267 | (structure) |
| I-268 | (structure) |
| I-269 | (structure) |
| I-270 | (structure) |

TABLE 1-continued
Selected Compounds
| Number | Structure |
|---|---|
| I-271 | 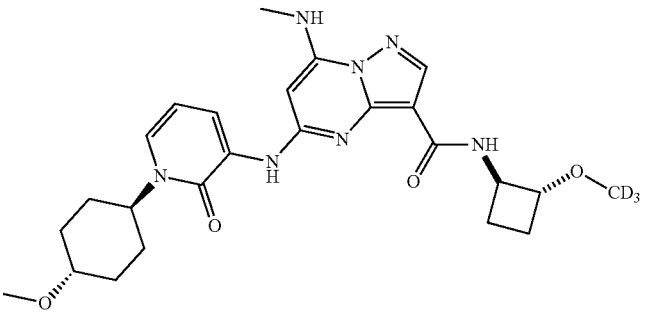 |
| I-272 | 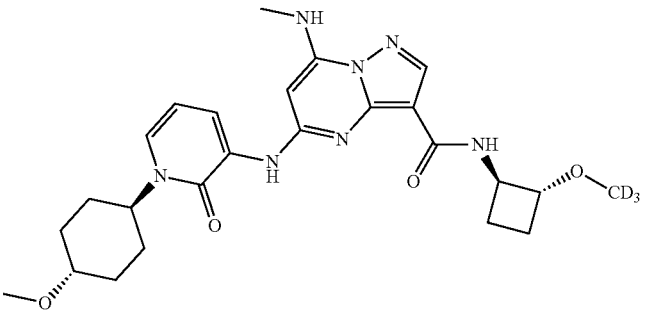 [SMILES: [2H]C([2H])([2H])O[C@@H]1CC[C@H]1NC(=O)c1cnn2c(NC)cc(Nc3cccn([C@H]4CC[C@H](OC)CC4)c3=O)nc12] |
| I-273 | 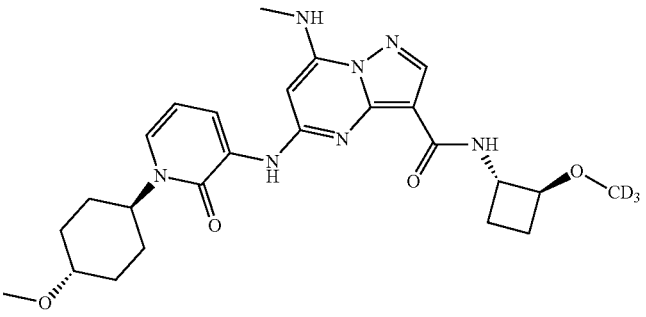 [SMILES: [2H]C([2H])([2H])O[C@H]1CC[C@@H]1NC(=O)c1cnn2c(NC)cc(Nc3cccn([C@H]4CC[C@H](OC)CC4)c3=O)nc12] |
| I-274 | 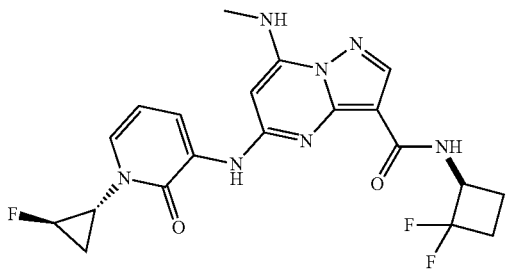 |
| I-275 | 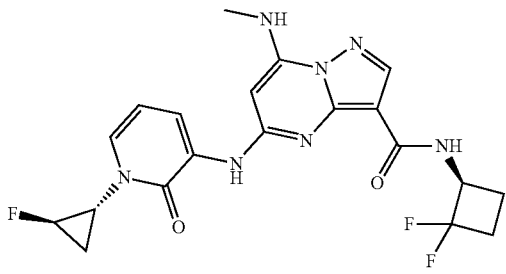 [SMILES: CNc1cc(Nc2cccn([C@@H]3C[C@H]3F)c2=O)nc2c(C(=O)N[C@H]3CCC3(F)F)cnn12] |

TABLE 1-continued
| Selected Compounds | |
|---|---|
| Number | Structure |
| I-276 | 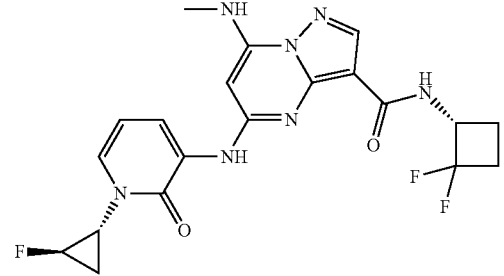 [SMILES: CNc1cc(Nc2cccn([C@@H]3C[C@H]3F)c2=O)nc2c(C(=O)N[C@@H]3CCC3(F)F)cnn12] |
| I-277 | 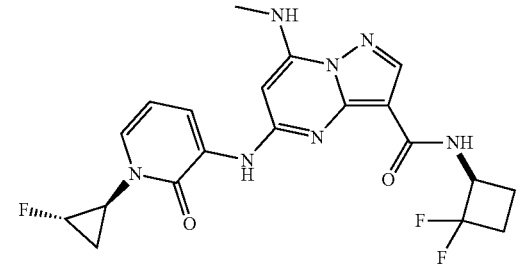 [SMILES: CNc1cc(Nc2cccn([C@H]3C[C@@H]3F)c2=O)nc2c(C(=O)N[C@H]3CCC3(F)F)cnn12] |
| I-278 | 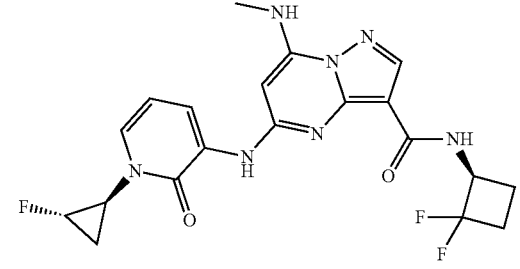 |
| I-279 | 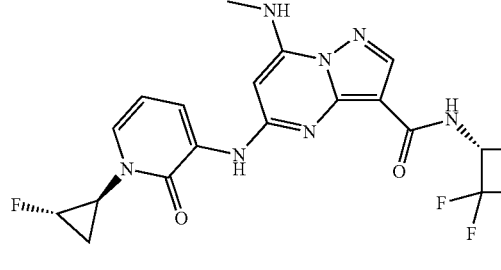 |
| I-280 | 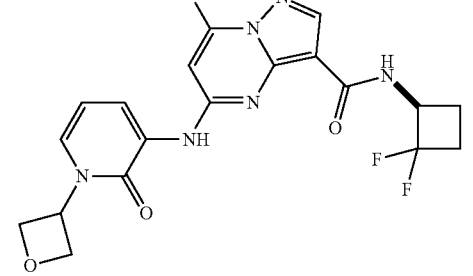 |

TABLE 1-continued

| Number | Structure |
|---|---|
| I-281 | 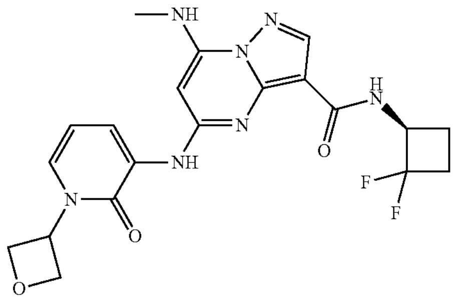 [SMILES: CNc1cc(Nc2cccn(C3COC3)c2=O)nc2c(C(=O)N[C@H]3CCC3(F)F)cnn12] |
| I-282 | 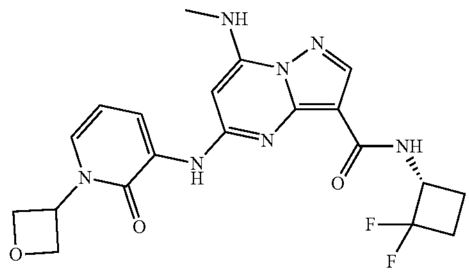 [SMILES: CNc1cc(Nc2cccn(C3COC3)c2=O)nc2c(C(=O)N[C@@H]3CCC3(F)F)cnn12] |
| I-283 | 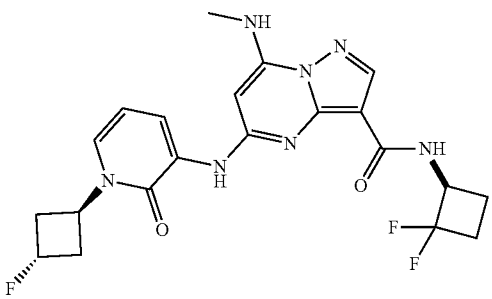 |
| I-284 | 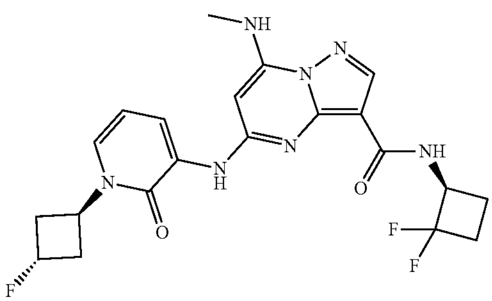 [SMILES: CNc1cc(Nc2cccn([C@H]3C[C@H](F)C3)c2=O)nc2c(C(=O)N[C@H]3CCC3(F)F)cnn12] |
| I-285 | 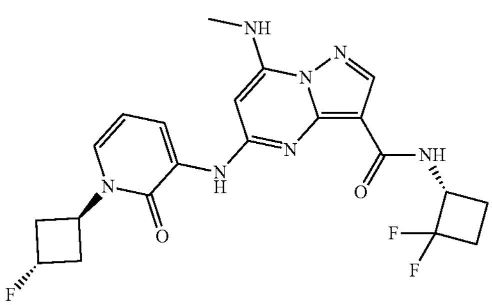 [SMILES: CNc1cc(Nc2cccn([C@H]3C[C@H](F)C3)c2=O)nc2c(C(=O)N[C@@H]3CCC3(F)F)cnn12] |

TABLE 1-continued
Selected Compounds
| Number | Structure |
|---|---|
| I-286 | 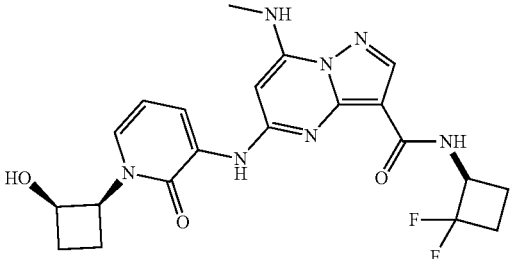 |
| I-287 | 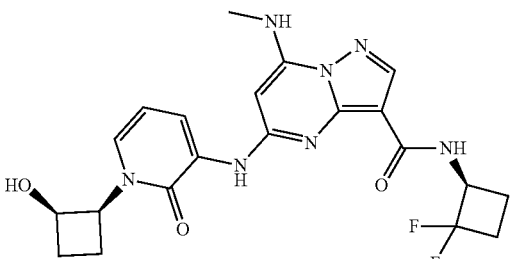 |
| I-288 | 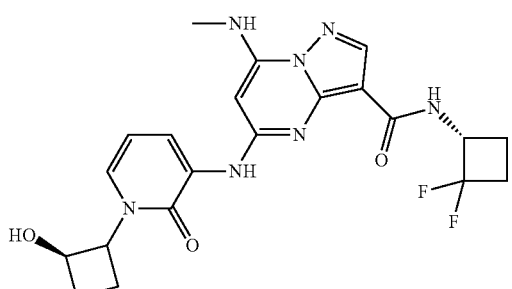 |
| I-289 | 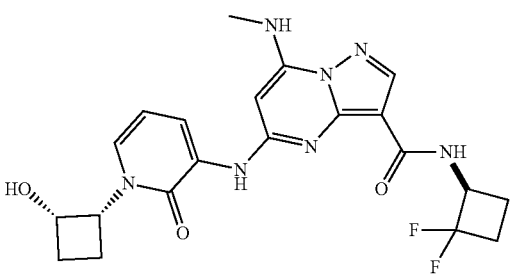 |
| I-290 | 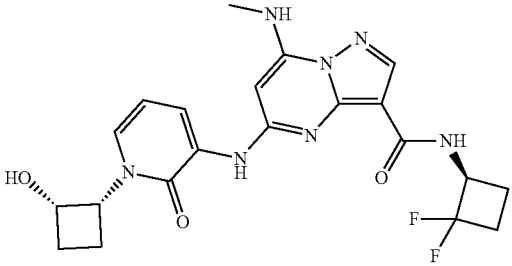 [SMILES: CNc1cc(Nc2cccn([C@@H]3CC[C@@H]3O)c2=O)nc2c(C(=O)N[C@H]3CCC3(F)F)cnn12] |

TABLE 1-continued

| Selected Compounds | |
|---|---|
| Number | Structure |ിറ

I-291

I-292

I-293

I-294

I-295

TABLE 1-continued
| Selected Compounds | |
|---|---|
| Number | Structure |
| I-296 | 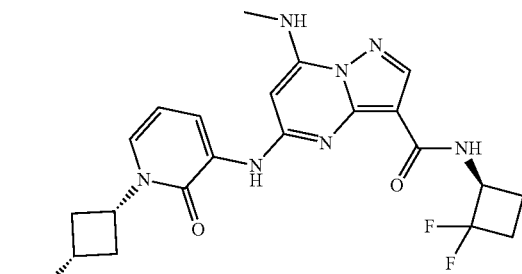 |
| I-297 | 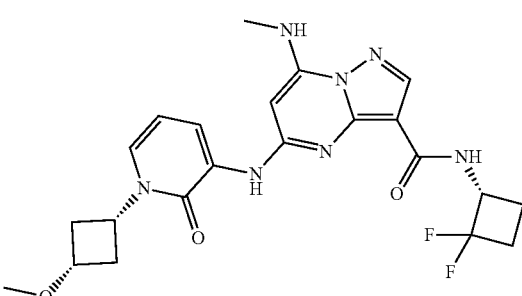 |
| I-298 | 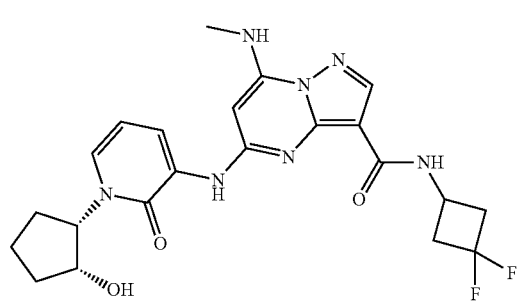 [SMILES: CNc1cc(Nc2cccn([C@H]3CCC[C@H]3O)c2=O)nc2c(C(=O)NC3CC(F)(F)C3)cnn12] |
| I-299 | 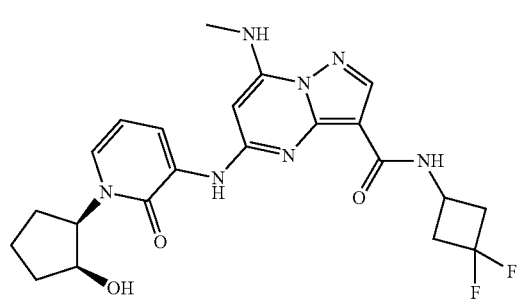 [SMILES: CNc1cc(Nc2cccn([C@@H]3CCC[C@@H]3O)c2=O)nc2c(C(=O)NC3CC(F)(F)C3)cnn12] |
| I-300 | 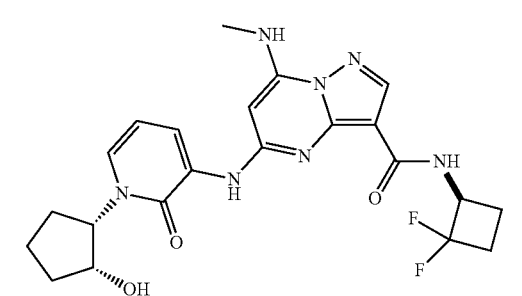 |

TABLE 1-continued

| Number | Structure |
|---|---|
| I-301 | 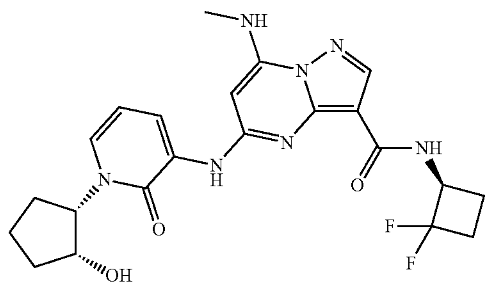 [SMILES: CNc1cc(Nc2cccn([C@H]3CCC[C@H]3O)c2=O)nc2c(C(=O)N[C@H]3CCC3(F)F)cnn12] |
| I-302 | 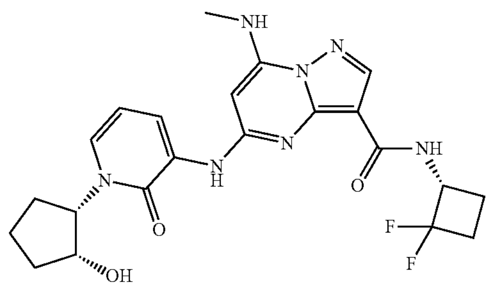 [SMILES: CNc1cc(Nc2cccn([C@H]3CCC[C@H]3O)c2=O)nc2c(C(=O)N[C@@H]3CCC3(F)F)cnn12] |
| I-303 | 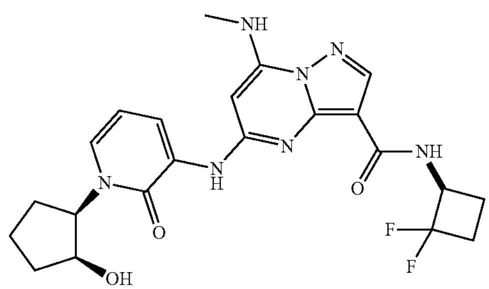 |
| I-304 | 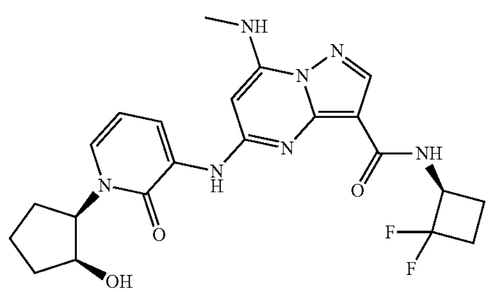 [SMILES: CNc1cc(Nc2cccn([C@@H]3CCC[C@@H]3O)c2=O)nc2c(C(=O)N[C@H]3CCC3(F)F)cnn12] |
| I-305 | 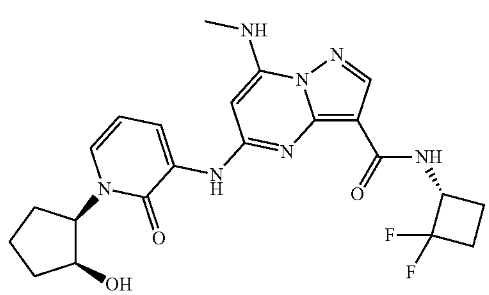 [SMILES: CNc1cc(Nc2cccn([C@@H]3CCC[C@@H]3O)c2=O)nc2c(C(=O)N[C@@H]3CCC3(F)F)cnn12] |

TABLE 1-continued

| Selected Compounds | |
|---|---|
| Number | Structure |
| I-306 | |
| I-307 | |
| I-308 | |
| I-309 | |
| I-310 | |

TABLE 1-continued
| Selected Compounds | |
|---|---|
| Number | Structure |
| I-311 | 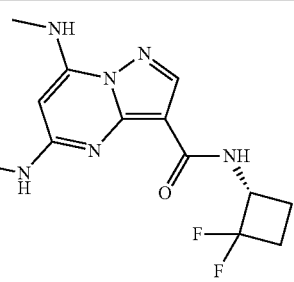 |
| I-312 | 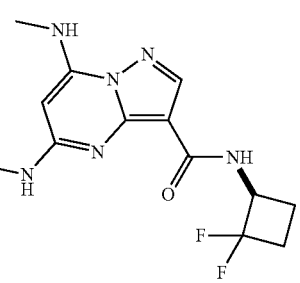 |
| I-313 | 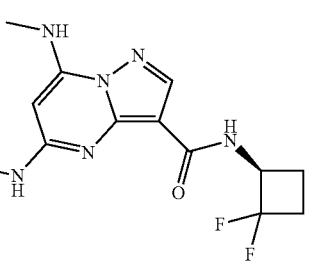 |
| I-314 | 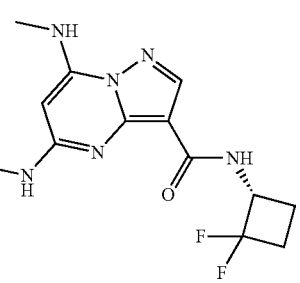 |
| I-315 | 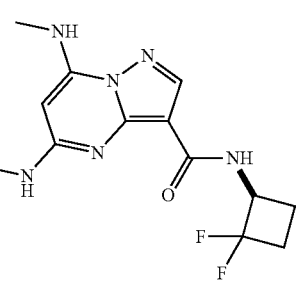 |

TABLE 1-continued

| Number | Structure |
|---|---|
| I-316 | 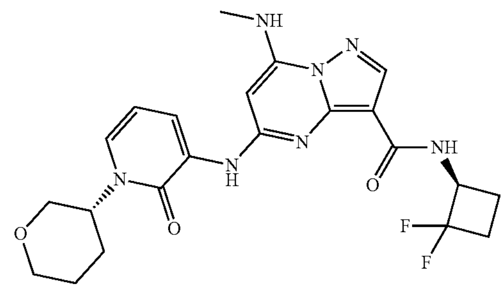 [SMILES: CNc1cc(Nc2cccn([C@@H]3CCCOC3)c2=O)nc2c(C(=O)N[C@H]3CCC3(F)F)cnn12] |
| I-317 | 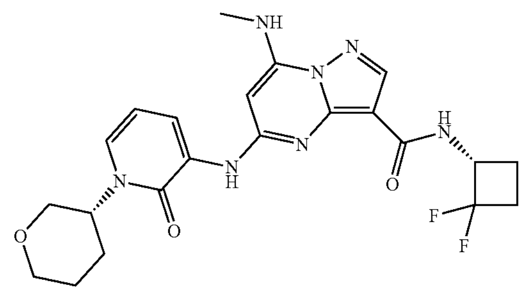 [SMILES: CNc1cc(Nc2cccn([C@@H]3CCCOC3)c2=O)nc2c(C(=O)N[C@@H]3CCC3(F)F)cnn12] |
| I-318 | 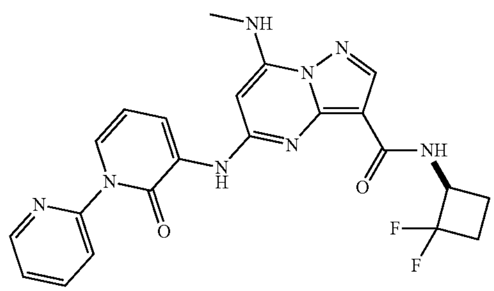 |
| I-319 | 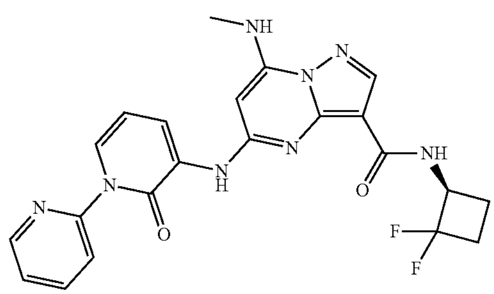 [SMILES: CNc1cc(Nc2cccn(-c3ccccn3)c2=O)nc2c(C(=O)N[C@H]3CCC3(F)F)cnn12] |
| I-320 | 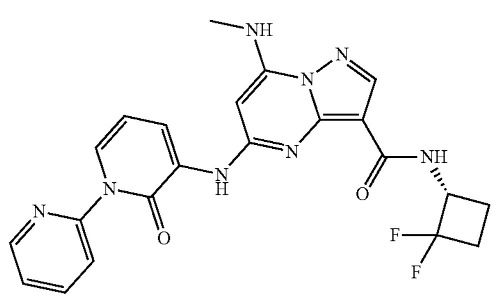 [SMILES: CNc1cc(Nc2cccn(-c3ccccn3)c2=O)nc2c(C(=O)N[C@@H]3CCC3(F)F)cnn12] |

TABLE 1-continued

| Selected Compounds | |
|---|---|
| Number | Structure |
| I-321 | |
| I-322 | |
| I-323 | |
| I-324 | |
| I-325 | |

TABLE 1-continued

| Selected Compounds | |
|---|---|
| Number | Structure |

I-326

I-327

I-328

I-329

I-330

TABLE 1-continued

| Selected Compounds | |
|---|---|
| Number | Structure |
| I-331 | |
| I-332 | |
| I-333 | |
| I-334 | |
| I-335 | |

TABLE 1-continued

Selected Compounds

| Number | Structure |
|---|---|
| I-336 | 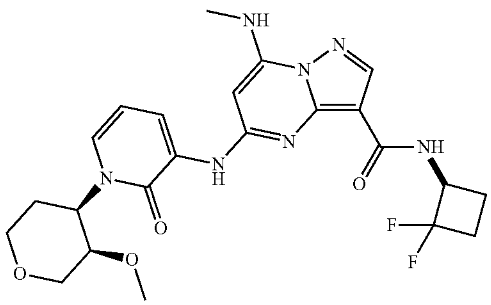 |
| I-337 | 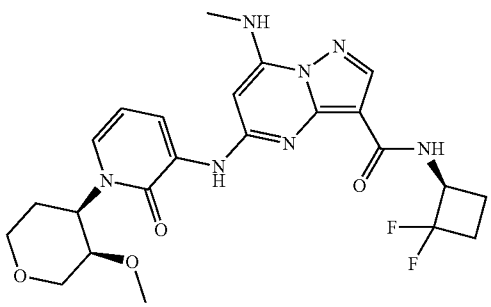 [SMILES: CNc1cc(Nc2cccn([C@@H]3CCOC[C@@H]3OC)c2=O)nc2c(C(=O)N[C@H]3CCC3(F)F)cnn12] |
| I-338 | 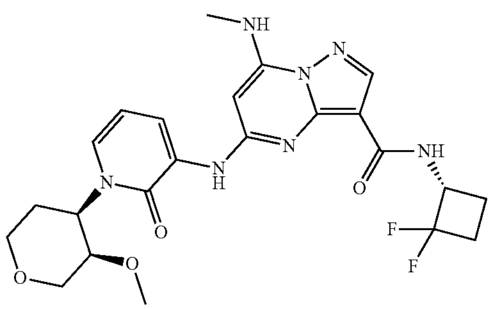 [SMILES: CNc1cc(Nc2cccn([C@@H]3CCOC[C@@H]3OC)c2=O)nc2c(C(=O)N[C@@H]3CCC3(F)F)cnn12] |
| I-339 | 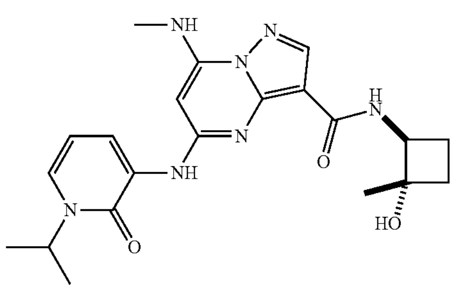 |
| I-340 | 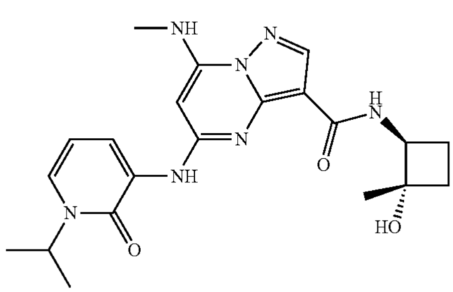 [SMILES: CNc1cc(Nc2cccn(C(C)C)c2=O)nc2c(C(=O)N[C@H]3CC[C@]3(C)O)cnn12] |

TABLE 1-continued

| Selected Compounds | |
|---|---|
| Number | Structure |
| I-341 | |
| I-342 | |
| I-343 | |
| I-344 | |
| I-345 | |

TABLE 1-continued
| Number | Structure |
|---|---|
| I-346 | 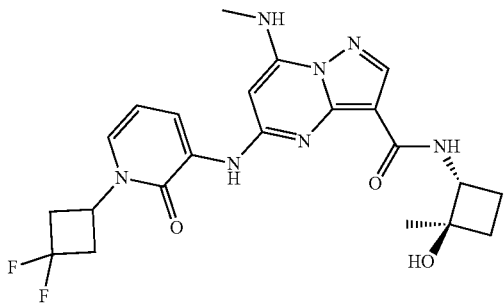 [SMILES: CNc1cc(Nc2cccn(C3CC(F)(F)C3)c2=O)nc2c(C(=O)N[C@@H]3CC[C@@]3(C)O)cnn12] |
| I-347 | 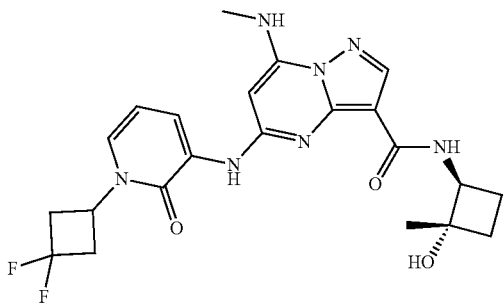 [SMILES: CNc1cc(Nc2cccn(C3CC(F)(F)C3)c2=O)nc2c(C(=O)N[C@H]3CC[C@]3(C)O)cnn12] |
| I-348 | 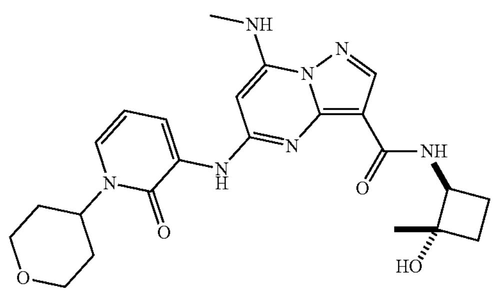 |
| I-349 | 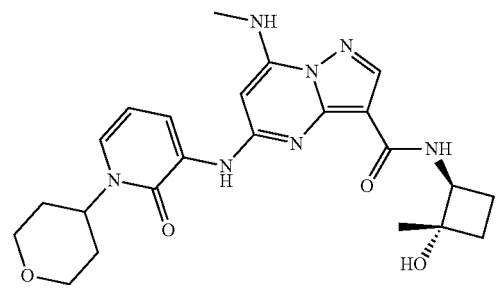 [SMILES: CNc1cc(Nc2cccn(C3CCOCC3)c2=O)nc2c(C(=O)N[C@H]3CC[C@]3(C)O)cnn12] |
| I-350 | 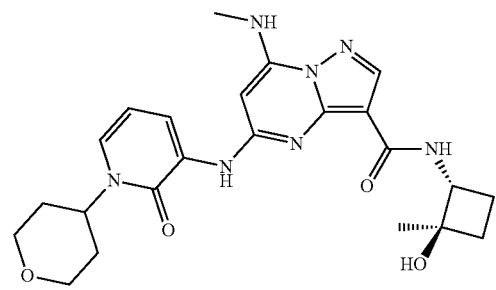 [SMILES: CNc1cc(Nc2cccn(C3CCOCC3)c2=O)nc2c(C(=O)N[C@@H]3CC[C@@]3(C)O)cnn12] |

TABLE 1-continued

| Selected Compounds | |
|---|---|
| Number | Structure |
| I-351 | |
| I-352 | |
| I-353 | |
| I-354 | |
| I-355 | |

TABLE 1-continued

Selected Compounds

| Number | Structure |
|---|---|
| I-356 | 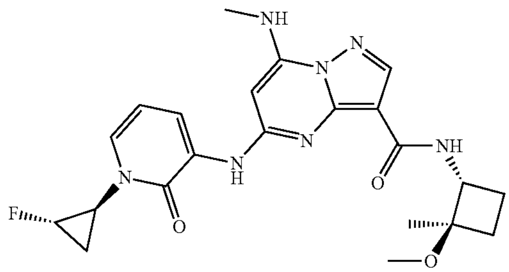 [SMILES: CNc1cc(Nc2cccn([C@H]3C[C@@H]3F)c2=O)nc2c(C(=O)N[C@@H]3CC[C@@]3(C)OC)cnn12] |
| I-357 | 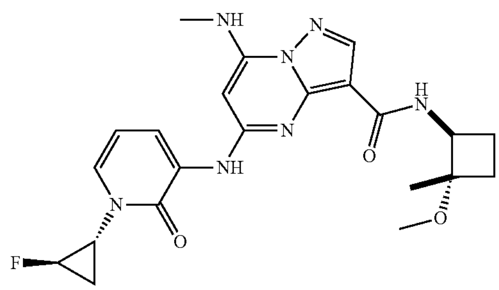 |
| I-358 | 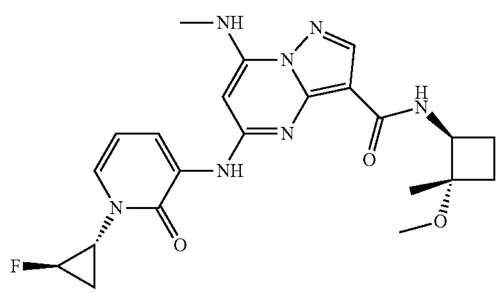 [SMILES: CNc1cc(Nc2cccn([C@@H]3C[C@H]3F)c2=O)nc2c(C(=O)N[C@H]3CC[C@]3(C)OC)cnn12] |
| I-359 | 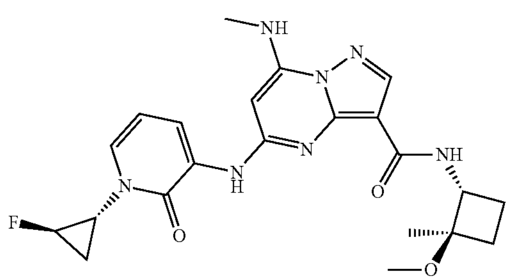 [SMILES: CNc1cc(Nc2cccn([C@@H]3C[C@H]3F)c2=O)nc2c(C(=O)N[C@@H]3CC[C@@]3(C)OC)cnn12] |
| I-360 | 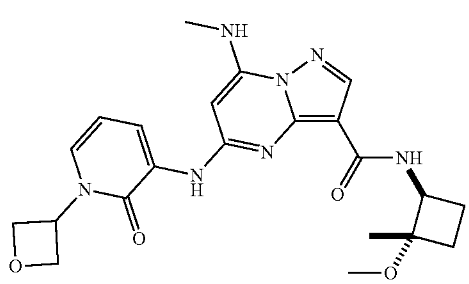 |

TABLE 1-continued
| Number | Structure |
|---|---|
| I-361 | 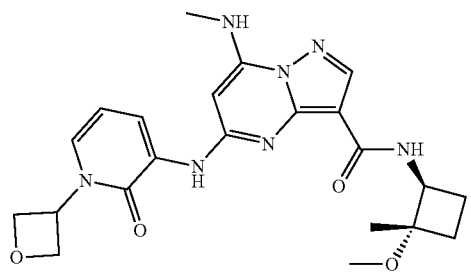 [SMILES: CNc1cc(Nc2cccn(C3COC3)c2=O)nc2c(C(=O)N[C@H]3CC[C@]3(C)OC)cnn12] |
| I-362 | 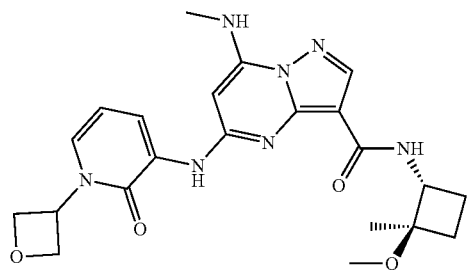 [SMILES: CNc1cc(Nc2cccn(C3COC3)c2=O)nc2c(C(=O)N[C@@H]3CC[C@@]3(C)OC)cnn12] |
| I-363 | 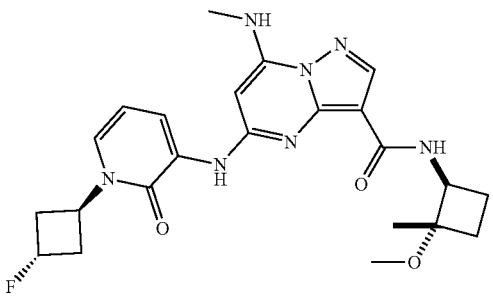 |
| I-364 | 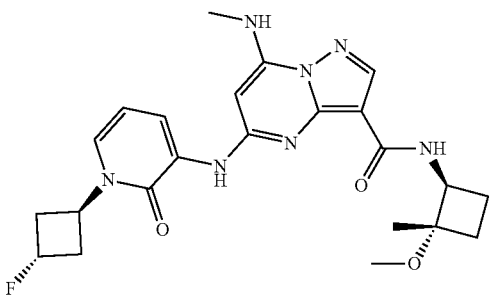 |
| I-365 | 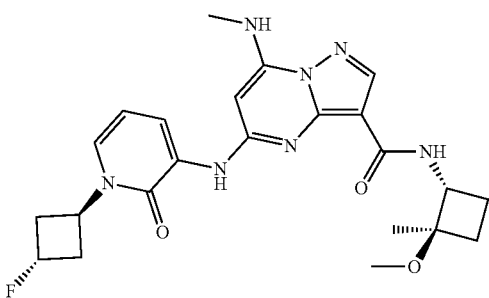 [SMILES: CNc1cc(Nc2cccn([C@H]3C[C@H](F)C3)c2=O)nc2c(C(=O)N[C@@H]3CC[C@@]3(C)OC)cnn12] |

TABLE 1-continued
| Selected Compounds | |
|---|---|
| Number | Structure |
| I-366 | 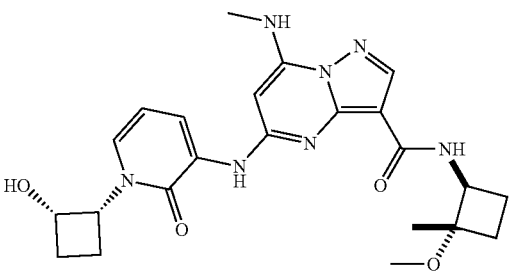 |
| I-367 |  |
| I-368 | 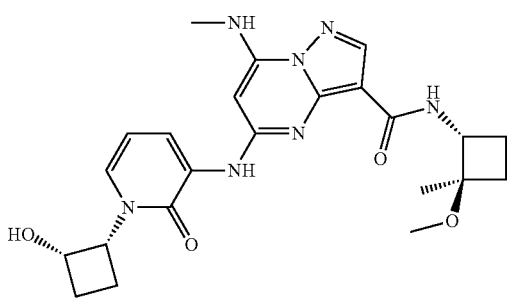 [SMILES: CNc1cc(Nc2cccn([C@@H]3CC[C@@H]3O)c2=O)nc2c(C(=O)N[C@@H]3CC[C@@]3(C)OC)cnn12] |
| I-369 | 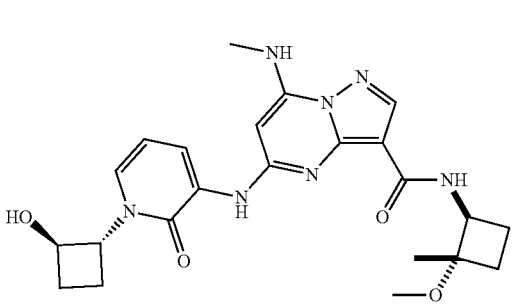 |
| I-370 | 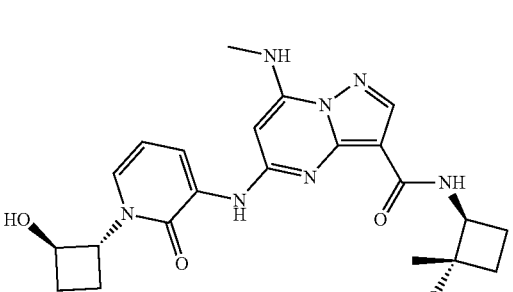 |

TABLE 1-continued

| Selected Compounds | |
|---|---|
| Number | Structure |
| I-371 | |
| I-372 | |
| I-373 | |
| I-374 | |
| I-375 | |

TABLE 1-continued

Selected Compounds

| Number | Structure |
|---|---|
| I-376 | 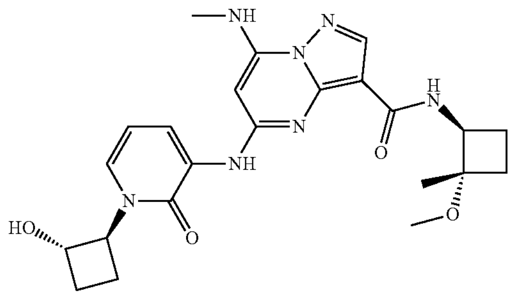 [SMILES: CNc1cc(Nc2cccn([C@H]3CC[C@@H]3O)c2=O)nc2c(C(=O)N[C@H]3CC[C@]3(C)OC)cnn12] |
| I-377 | 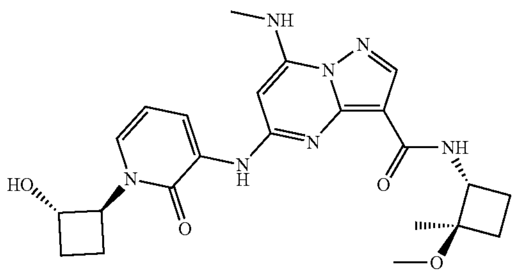 [SMILES: CNc1cc(Nc2cccn([C@H]3CC[C@@H]3O)c2=O)nc2c(C(=O)N[C@@H]3CC[C@@]3(C)OC)cnn12] |
| I-378 | 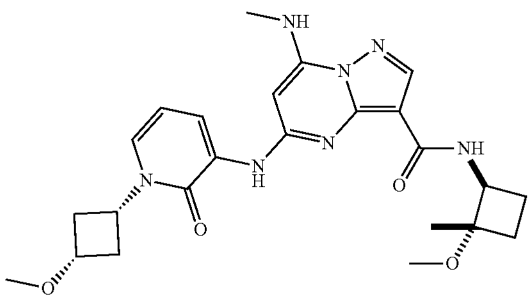 |
| I-379 | 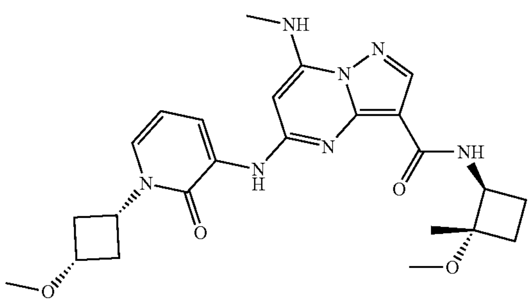 [SMILES: CNc1cc(Nc2cccn([C@H]3C[C@@H](OC)C3)c2=O)nc2c(C(=O)N[C@H]3CC[C@]3(C)OC)cnn12] |
| I-380 | 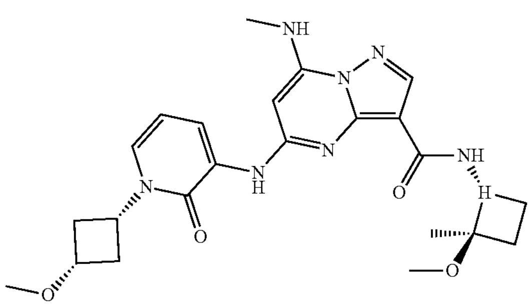 |

TABLE 1-continued

| Number | Structure |
|---|---|
| I-381 | 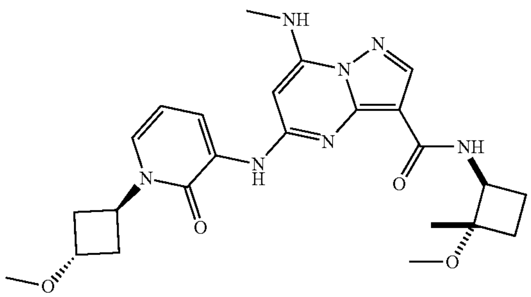 |
| I-382 | 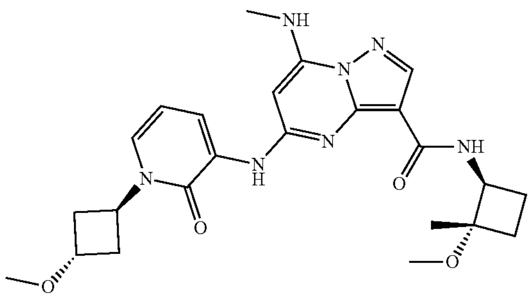 [SMILES: CNc1cc(Nc2cccn([C@H]3C[C@H](OC)C3)c2=O)nc2c(C(=O)N[C@H]3CC[C@]3(C)OC)cnn12] |
| I-383 | 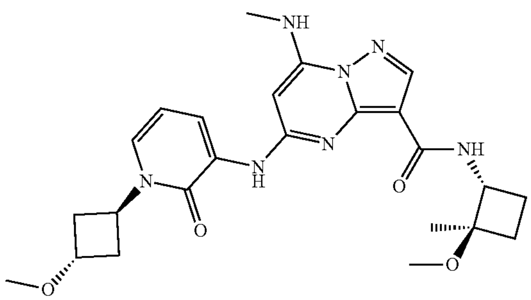 [SMILES: CNc1cc(Nc2cccn([C@H]3C[C@H](OC)C3)c2=O)nc2c(C(=O)N[C@@H]3CC[C@@]3(C)OC)cnn12] |
| I-384 | 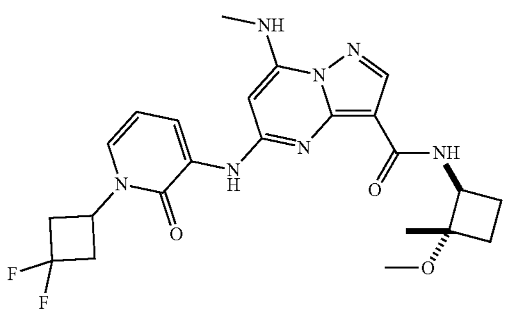 |
| I-385 | 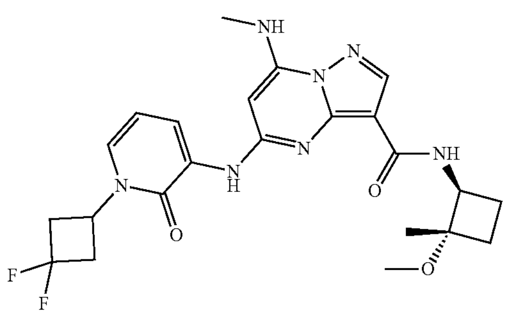 [SMILES: CNc1cc(Nc2cccn(C3CC(F)(F)C3)c2=O)nc2c(C(=O)N[C@H]3CC[C@]3(C)OC)cnn12] |

TABLE 1-continued
| Selected Compounds | |
|---|---|
| Number | Structure |
| I-386 | 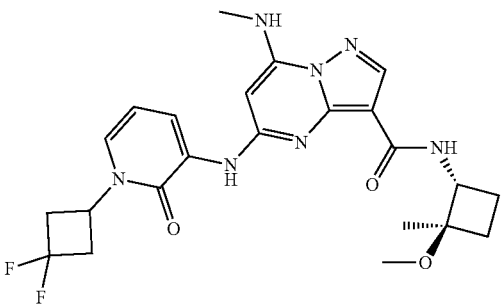 [SMILES: CNc1cc(Nc2cccn(C3CC(F)(F)C3)c2=O)nc2c(C(=O)N[C@@H]3CC[C@@]3(C)OC)cnn12] |
| I-387 | 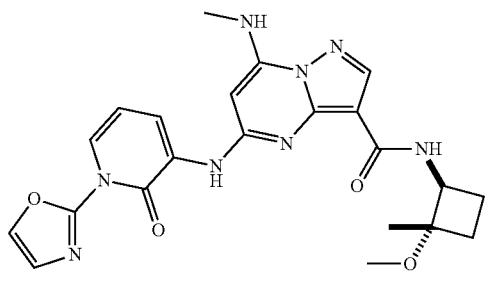 |
| I-388 | 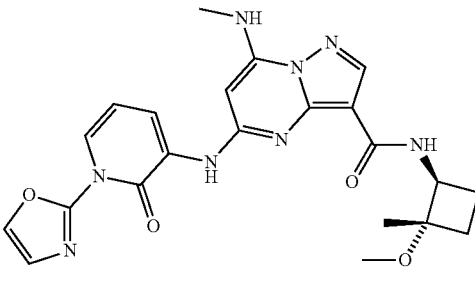 |
| I-389 | 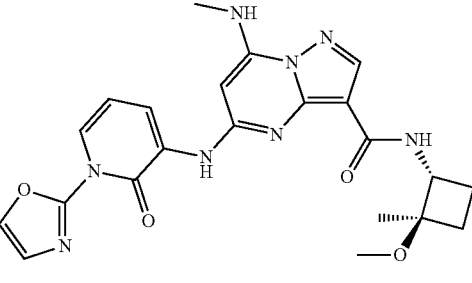 [SMILES: CNc1cc(Nc2cccn(-c3ncco3)c2=O)nc2c(C(=O)N[C@@H]3CC[C@@]3(C)OC)cnn12] |
| I-390 | 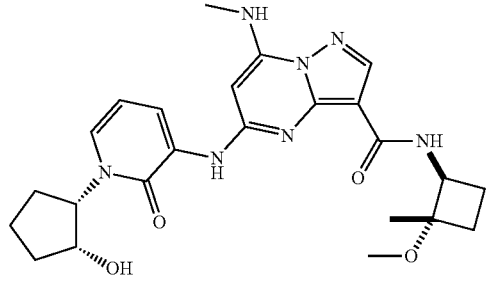 |

TABLE 1-continued

| Selected Compounds | |
|---|---|
| Number | Structure |
| I-391 | |
| I-392 | |
| I-393 | |
| I-394 | |
| I-395 | |

TABLE 1-continued
Selected Compounds
| Number | Structure |
|---|---|
| I-396 | 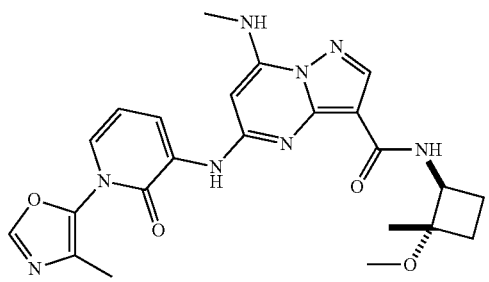 |
| I-397 | 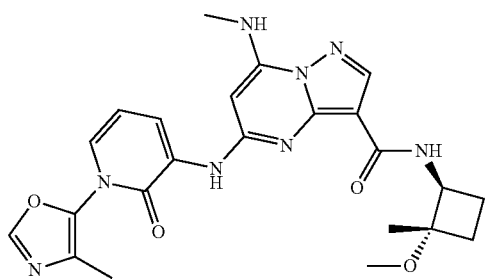 [SMILES: CNc1cc(Nc2cccn(-c3ocnc3C)c2=O)nc2c(C(=O)N[C@H]3CC[C@]3(C)OC)cnn12] |
| I-398 | 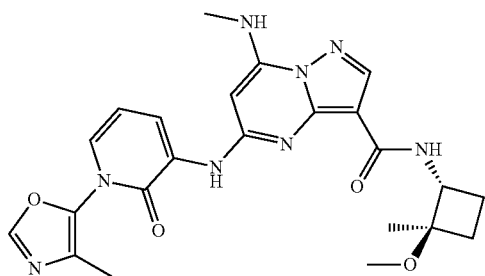 [SMILES: CNc1cc(Nc2cccn(-c3ocnc3C)c2=O)nc2c(C(=O)N[C@@H]3CC[C@@]3(C)OC)cnn12] |
| I-399 | 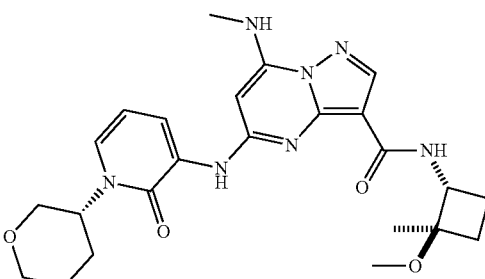 |
| I-400 | 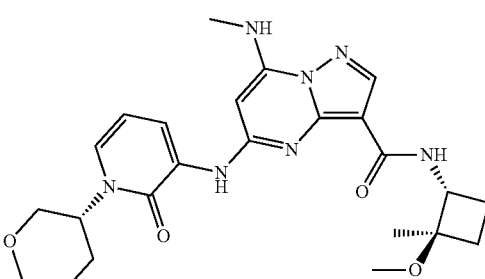 |

TABLE 1-continued

| Selected Compounds | |
|---|---|
| Number | Structure |
| I-401 | |
| I-402 | |
| I-403 | |
| I-404 | |
| I-405 | |

TABLE 1-continued
| Selected Compounds | |
|---|---|
| Number | Structure |
| I-406 | 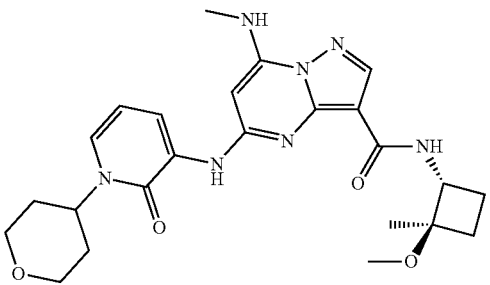 [SMILES: CNc1cc(Nc2cccn(C3CCOCC3)c2=O)nc2c(C(=O)N[C@@H]3CC[C@@]3(C)OC)cnn12] |
| I-407 | 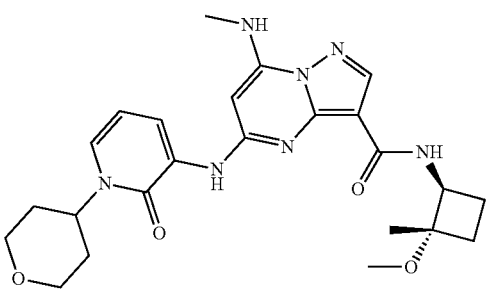 [SMILES: CNc1cc(Nc2cccn(C3CCOCC3)c2=O)nc2c(C(=O)N[C@H]3CC[C@]3(C)OC)cnn12] |
| I-408 | 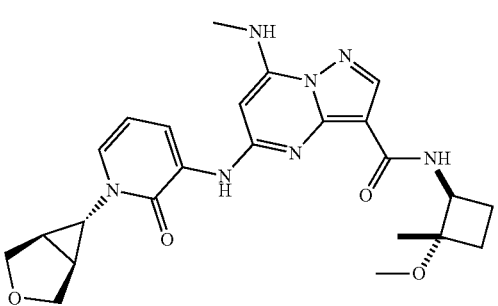 |
| I-409 | 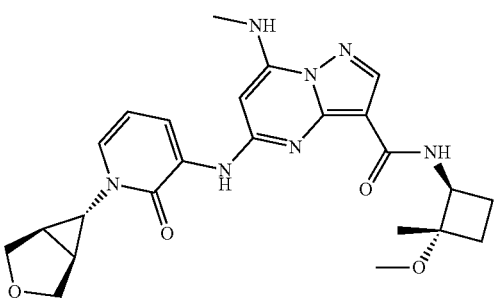 [SMILES: CNc1cc(Nc2cccn([C@H]3[C@@H]4COC[C@@H]43)c2=O)nc2c(C(=O)N[C@H]3CC[C@]3(C)OC)cnn12] |
| I-410 | 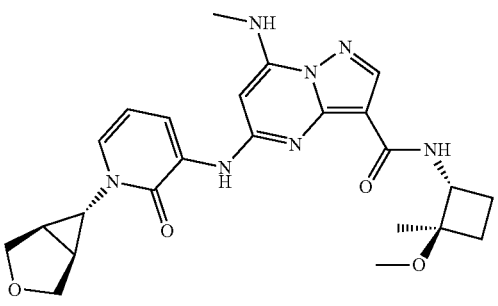 [SMILES: CNc1cc(Nc2cccn([C@H]3[C@@H]4COC[C@@H]43)c2=O)nc2c(C(=O)N[C@@H]3CC[C@@]3(C)OC)cnn12] |

TABLE 1-continued
| Selected Compounds | |
|---|---|
| Number | Structure |
| I-411 | 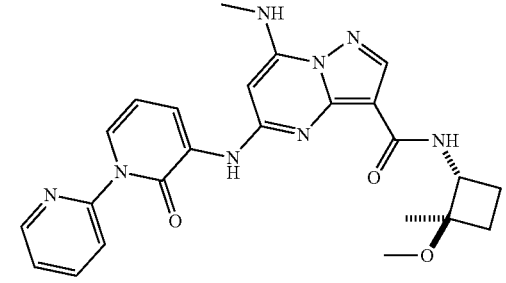 |
| I-412 | 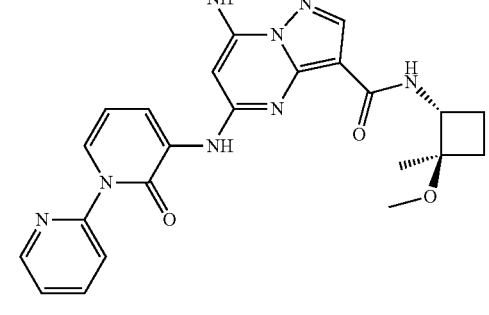 |
| I-413 | 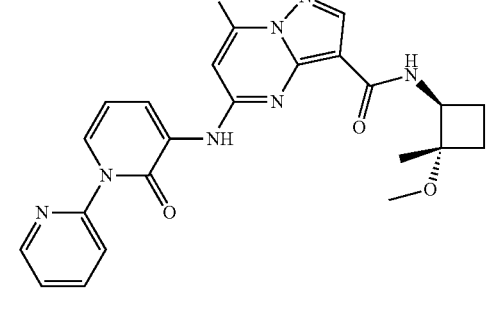 |
| I-414 | 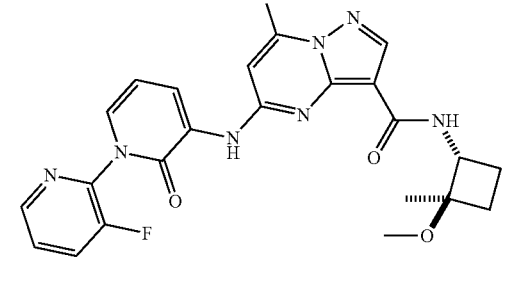 |
| I-415 | 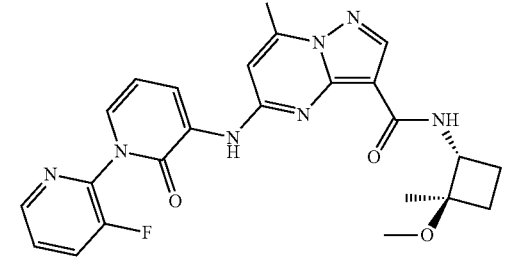 |

TABLE 1-continued

Selected Compounds

| Number | Structure |
|---|---|
| I-416 | 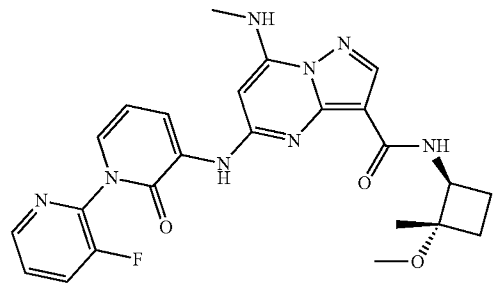 [SMILES: CNc1cc(Nc2cccn(-c3ncccc3F)c2=O)nc2c(C(=O)N[C@H]3CC[C@]3(C)OC)cnn12] |
| I-417 | 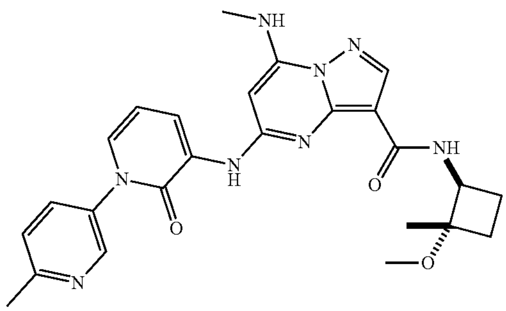 |
| I-418 | 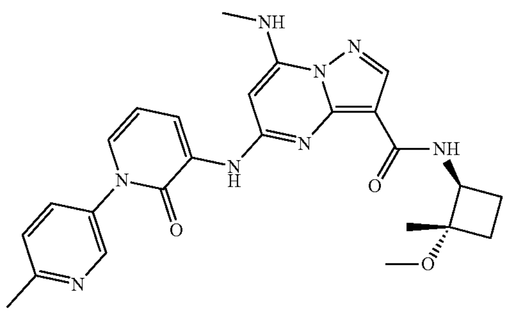 [SMILES: CNc1cc(Nc2cccn(-c3ccc(C)nc3)c2=O)nc2c(C(=O)N[C@H]3CC[C@]3(C)OC)cnn12] |
| I-419 | 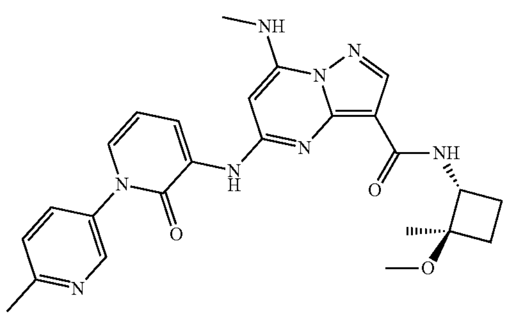 [SMILES: CNc1cc(Nc2cccn(-c3ccc(C)nc3)c2=O)nc2c(C(=O)N[C@@H]3CC[C@@]3(C)OC)cnn12] |
| I-420 | 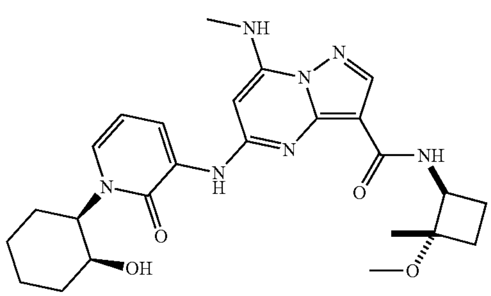 |

TABLE 1-continued
| Selected Compounds | |
|---|---|
| Number | Structure |
| I-421 | 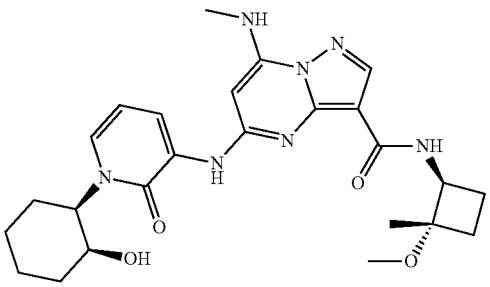 [SMILES: CNc1cc(Nc2cccn([C@@H]3CCCC[C@@H]3O)c2=O)nc2c(C(=O)N[C@H]3CC[C@]3(C)OC)cnn12] |
| I-422 | 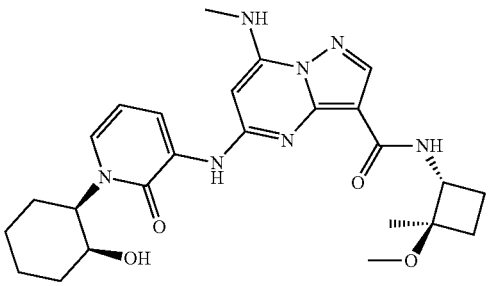 [SMILES: CNc1cc(Nc2cccn([C@@H]3CCCC[C@@H]3O)c2=O)nc2c(C(=O)N[C@@H]3CC[C@@]3(C)OC)cnn12] |
| I-423 | 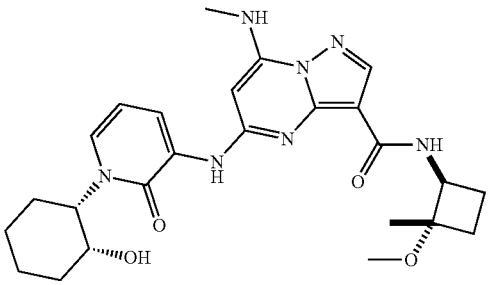 |
| I-424 | 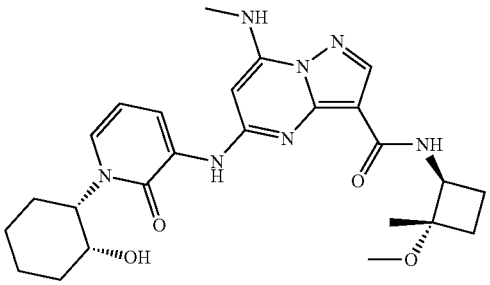 [SMILES: CNc1cc(Nc2cccn([C@H]3CCCC[C@H]3O)c2=O)nc2c(C(=O)N[C@H]3CC[C@]3(C)OC)cnn12] |
| I-425 | 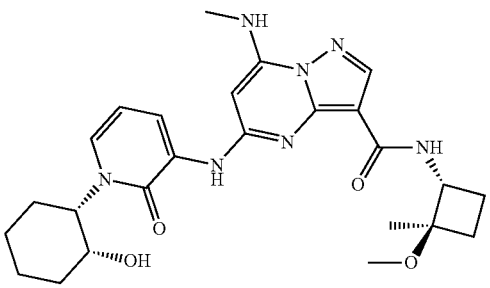 [SMILES: CNc1cc(Nc2cccn([C@H]3CCCC[C@H]3O)c2=O)nc2c(C(=O)N[C@@H]3CC[C@@]3(C)OC)cnn12] |

TABLE 1-continued
Selected Compounds
| Number | Structure |
|---|---|
| I-426 | 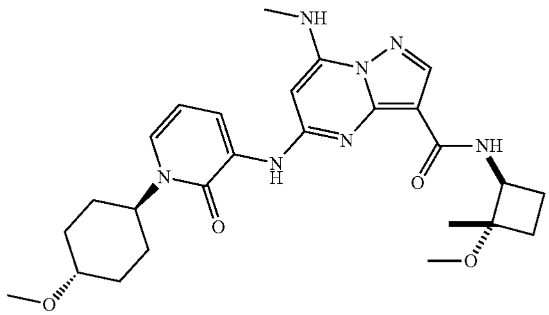 |
| I-427 | 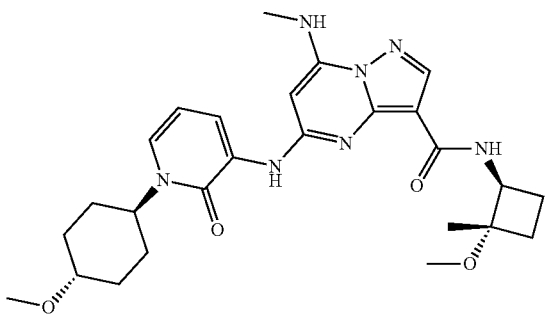 [SMILES: CNc1cc(Nc2cccn([C@H]3CC[C@H](OC)CC3)c2=O)nc2c(C(=O)N[C@H]3CC[C@]3(C)OC)cnn12] |
| I-428 | 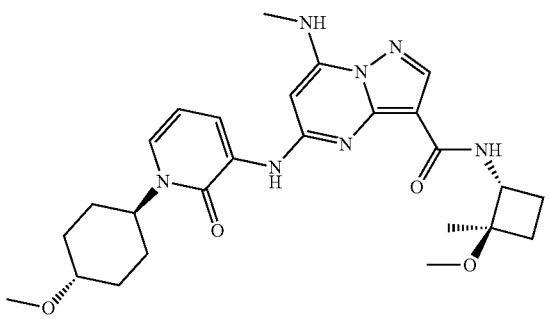 [SMILES: CNc1cc(Nc2cccn([C@H]3CC[C@H](OC)CC3)c2=O)nc2c(C(=O)N[C@@H]3CC[C@@]3(C)OC)cnn12] |
| I-429 | 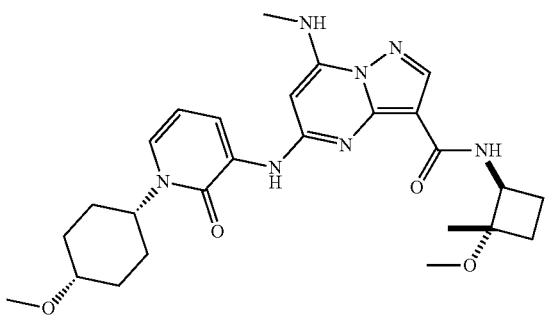 |

TABLE 1-continued

| Selected Compounds | |
|---|---|
| Number | Structure |
| I-430 | |
| I-431 | |
| I-432 | |
| I-433 | |
| I-434 | |

TABLE 1-continued
| Selected Compounds | |
|---|---|
| Number | Structure |
| I-435 | 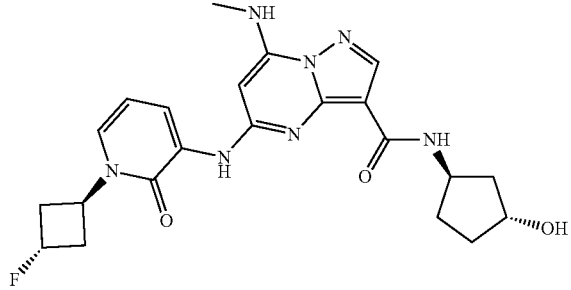 [SMILES: CNc1cc(Nc2cccn([C@H]3C[C@H](F)C3)c2=O)nc2c(C(=O)N[C@@H]3CC[C@@H](O)C3)cnn12] |
| I-436 | 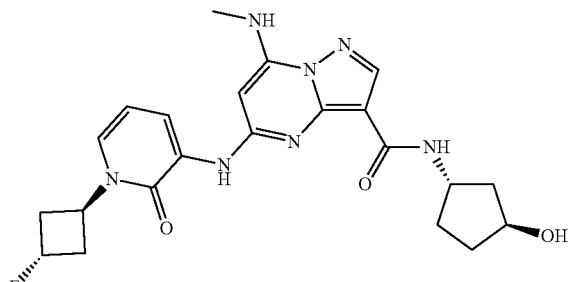 |
| I-437 | 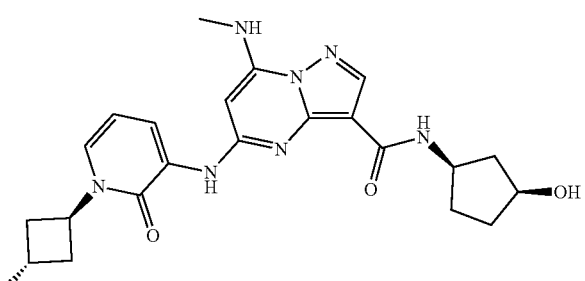 |
| I-438 | 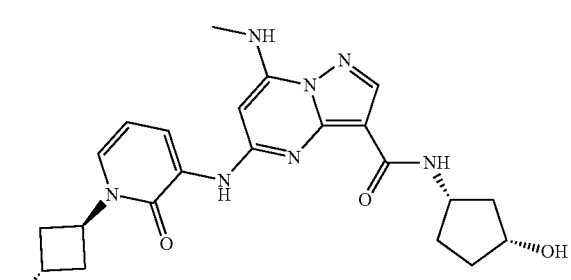 |
| I-439 | 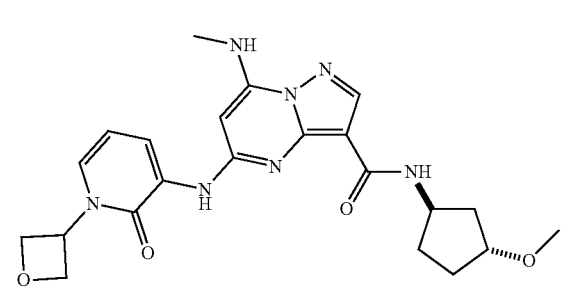 |

TABLE 1-continued

| Number | Structure |
|---|---|
| I-440 | 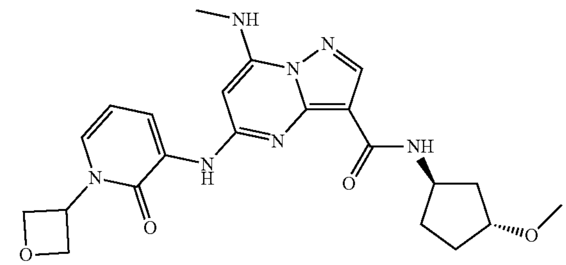 [SMILES: CNc1cc(Nc2cccn(C3COC3)c2=O)nc2c(C(=O)N[C@@H]3CC[C@@H](OC)C3)cnn12] |
| I-441 | 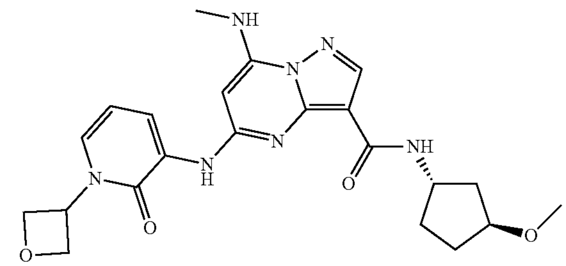 [SMILES: CNc1cc(Nc2cccn(C3COC3)c2=O)nc2c(C(=O)N[C@H]3CC[C@H](OC)C3)cnn12] |
| I-442 | 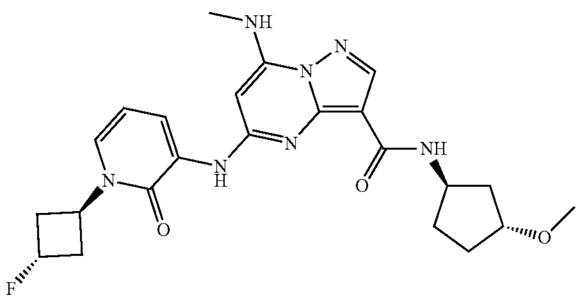 [SMILES: CNc1cc(Nc2cccn([C@H]3C[C@H](F)C3)c2=O)nc2c(C(=O)N[C@@H]3CC[C@@H](OC)C3)cnn12] |
| I-443 | 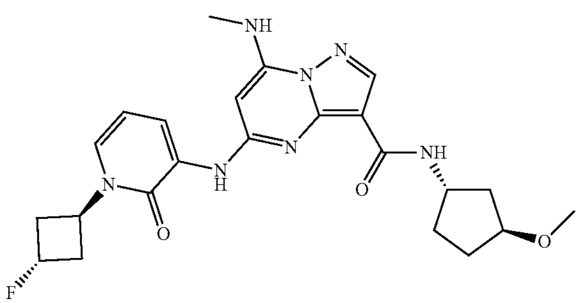 [SMILES: CNc1cc(Nc2cccn([C@H]3C[C@H](F)C3)c2=O)nc2c(C(=O)N[C@H]3CC[C@H](OC)C3)cnn12] |
| I-444 | 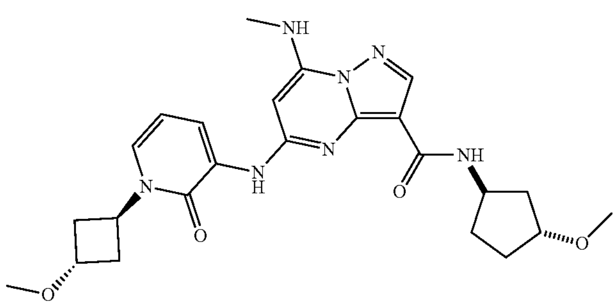 |

TABLE 1-continued

| Number | Structure |
|---|---|
| I-445 | 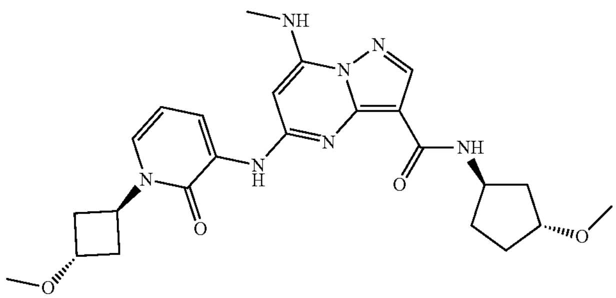 |
| I-446 | 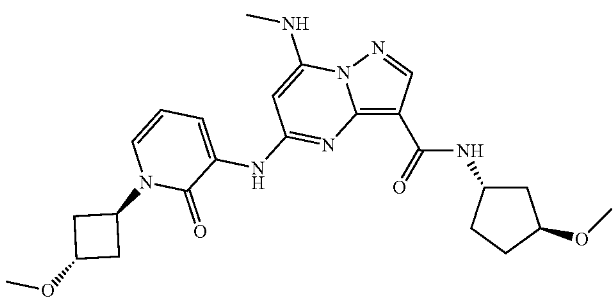 |
| I-447 | 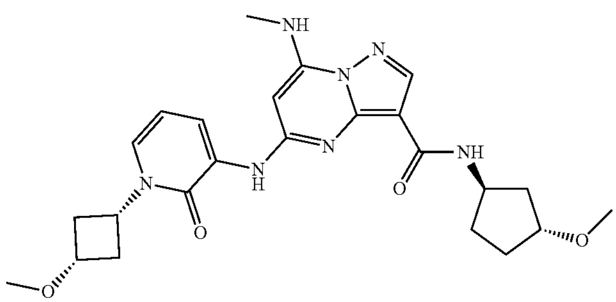 |
| I-448 | 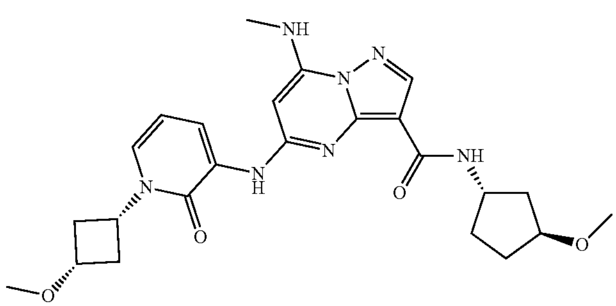 |
| I-449 | 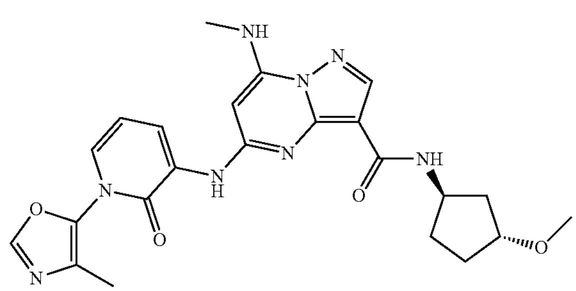 [SMILES: CNc1cc(Nc2cccn(-c3ocnc3C)c2=O)nc2c(C(=O)N[C@@H]3CC[C@@H](OC)C3)cnn12] |

TABLE 1-continued

| Number | Structure |
|---|---|
| I-450 | 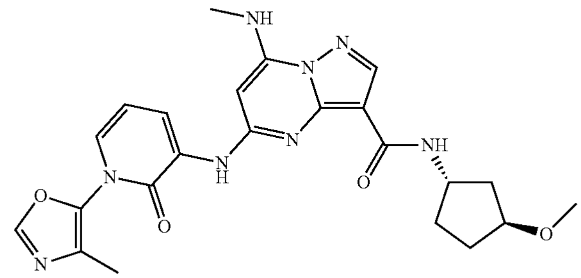 [SMILES: CNc1cc(Nc2cccn(-c3ocnc3C)c2=O)nc2c(C(=O)N[C@H]3CC[C@H](OC)C3)cnn12] |
| I-451 | 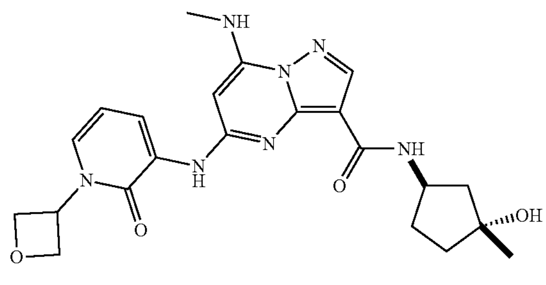 |
| I-452 | 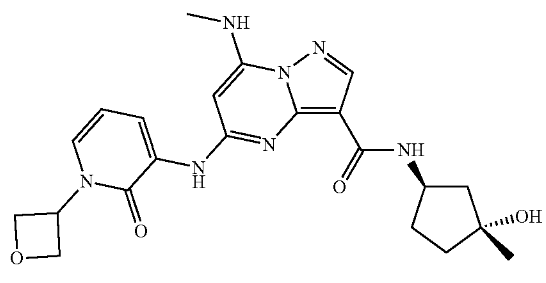 [SMILES: CNc1cc(Nc2cccn(C3COC3)c2=O)nc2c(C(=O)N[C@@H]3CC[C@@](C)(O)C3)cnn12] |
| I-453 | 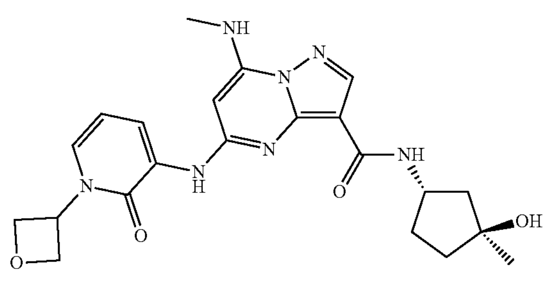 [SMILES: CNc1cc(Nc2cccn(C3COC3)c2=O)nc2c(C(=O)N[C@H]3CC[C@](C)(O)C3)cnn12] |
| I-454 | 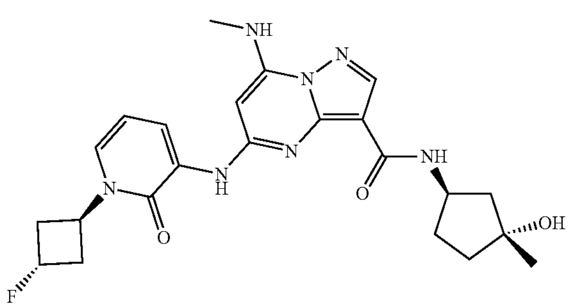 [SMILES: CNc1cc(Nc2cccn([C@H]3C[C@H](F)C3)c2=O)nc2c(C(=O)N[C@@H]3CC[C@@](C)(O)C3)cnn12] |

TABLE 1-continued
| Number | Structure |
|---|---|
| I-455 | 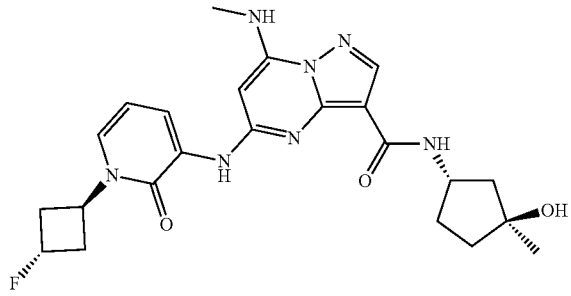 [SMILES: CNc1cc(Nc2cccn([C@H]3C[C@H](F)C3)c2=O)nc2c(C(=O)N[C@H]3CC[C@](C)(O)C3)cnn12] |
| I-456 | 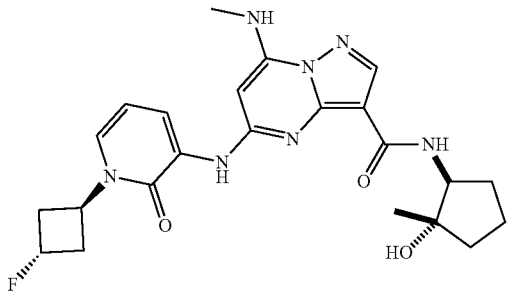 |
| I-457 | 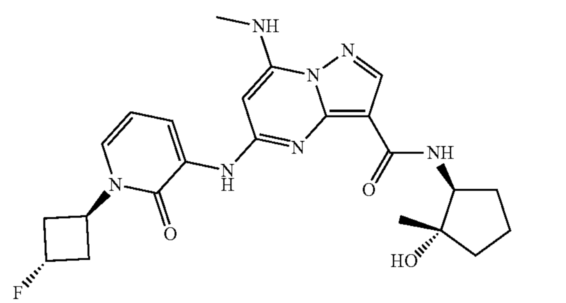 [SMILES: CNc1cc(Nc2cccn([C@H]3C[C@H](F)C3)c2=O)nc2c(C(=O)N[C@H]3CCC[C@]3(C)O)cnn12] |
| I-458 | 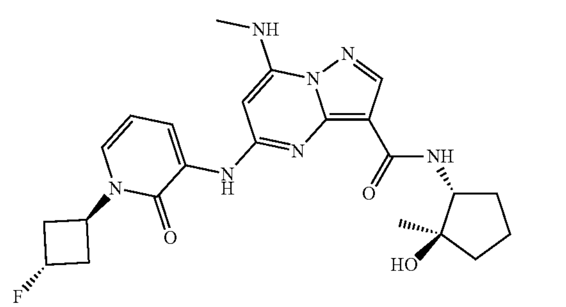 [SMILES: CNc1cc(Nc2cccn([C@H]3C[C@H](F)C3)c2=O)nc2c(C(=O)N[C@@H]3CCC[C@@]3(C)O)cnn12] |
| I-459 | 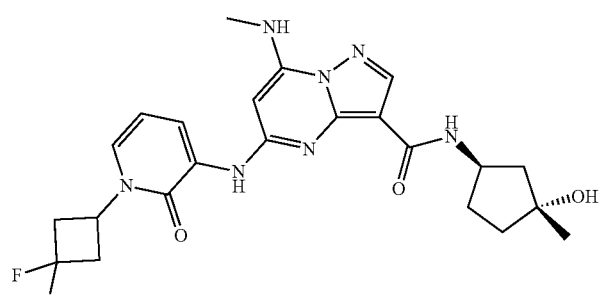 |

TABLE 1-continued
Selected Compounds
| Number | Structure |
|---|---|
| I-460 | 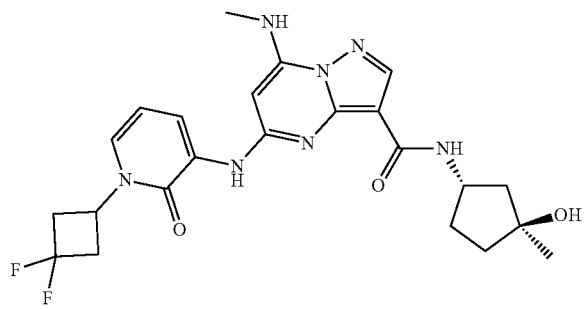 [SMILES: CNc1cc(Nc2cccn(C3CC(F)(F)C3)c2=O)nc2c(C(=O)N[C@H]3CC[C@](C)(O)C3)cnn12] |
| I-461 | 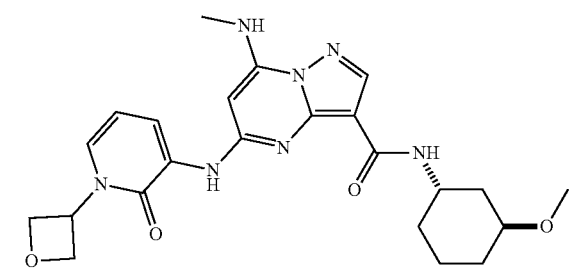 |
| I-462 | 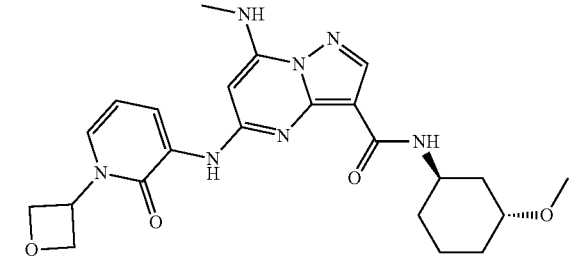 [SMILES: CNc1cc(Nc2cccn(C3COC3)c2=O)nc2c(C(=O)N[C@@H]3CCC[C@@H](OC)C3)cnn12] |
| I-463 | 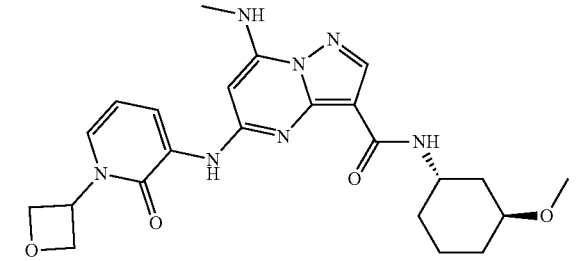 [SMILES: CNc1cc(Nc2cccn(C3COC3)c2=O)nc2c(C(=O)N[C@H]3CCC[C@H](OC)C3)cnn12] |
| I-464 | 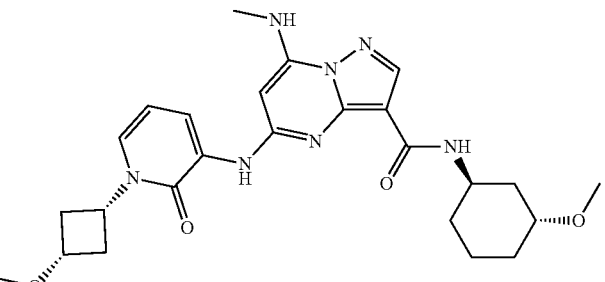 |

TABLE 1-continued

| Number | Structure |
|---|---|
| I-465 | 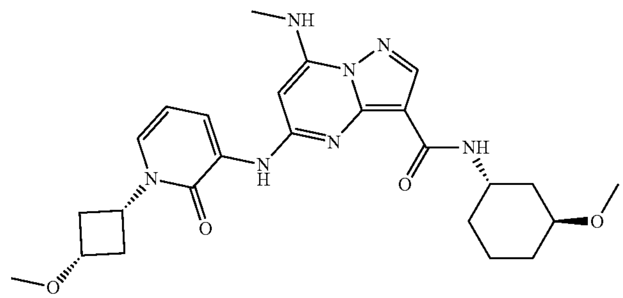 |
| I-466 | 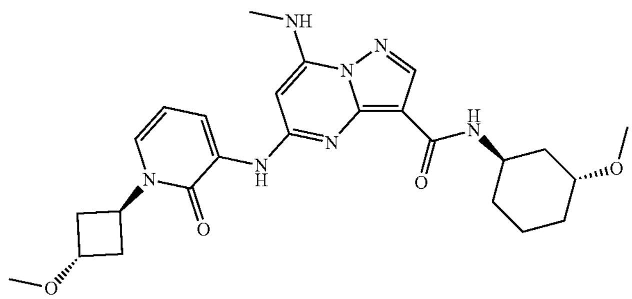 |
| I-467 | 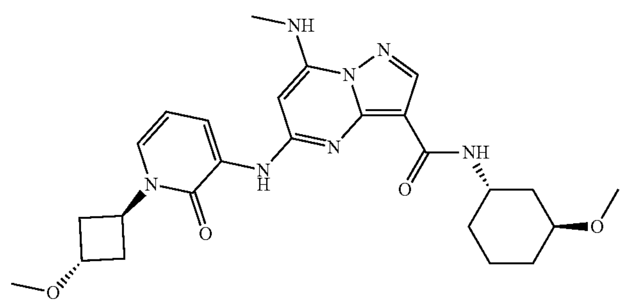 |
| I-468 | 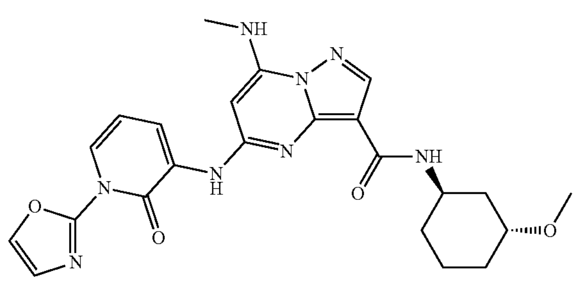 [SMILES: CNc1cc(Nc2cccn(-c3ncco3)c2=O)nc2c(C(=O)N[C@@H]3CCC[C@@H](OC)C3)cnn12] |
| I-469 | 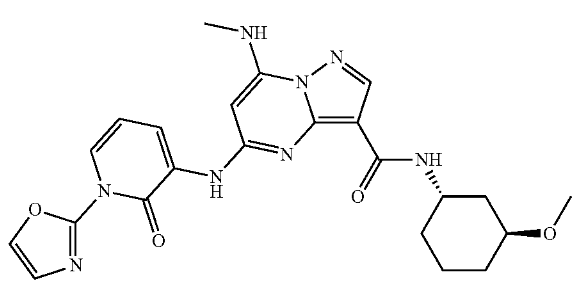 [SMILES: CNc1cc(Nc2cccn(-c3ncco3)c2=O)nc2c(C(=O)N[C@H]3CCC[C@H](OC)C3)cnn12] |

TABLE 1-continued
Selected Compounds
| Number | Structure |
|---|---|
| I-470 | 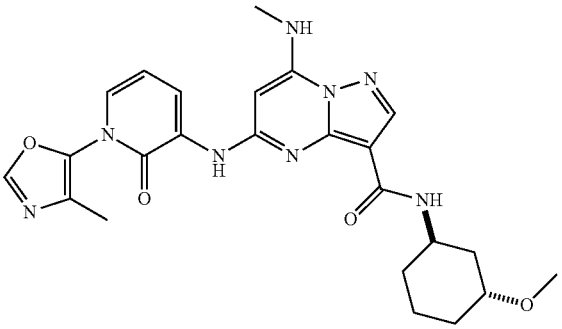 |
| I-471 | 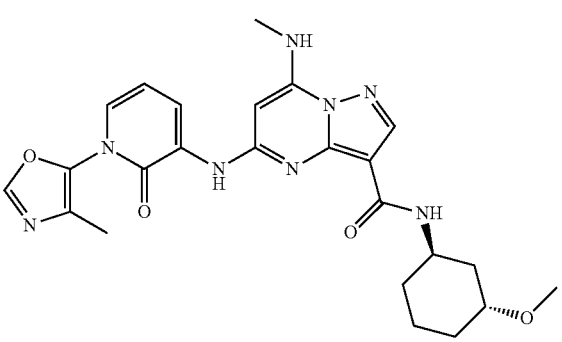 [SMILES: CNc1cc(Nc2cccn(-c3ocnc3C)c2=O)nc2c(C(=O)N[C@@H]3CCC[C@@H](OC)C3)cnn12] |
| I-472 | 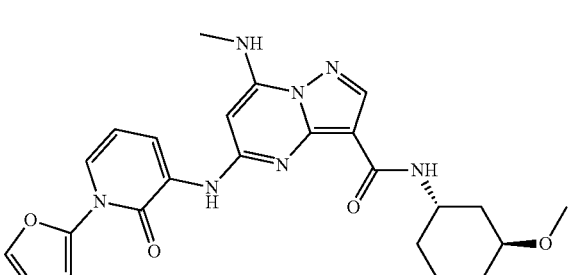 |
| I-473 | 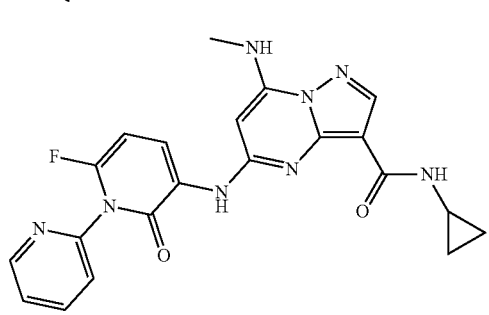 |
| I-474 | 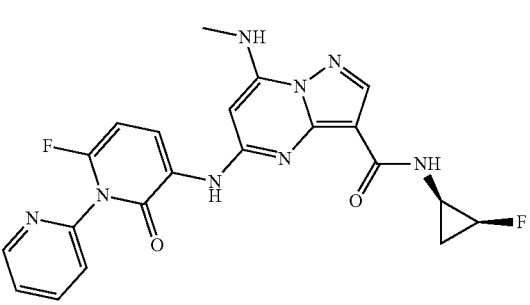 [SMILES: CNc1cc(Nc2ccc(F)n(-c3ccccn3)c2=O)nc2c(C(=O)N[C@@H]3C[C@@H]3F)cnn12] |

237
238
TABLE 1-continued
| Selected Compounds | |
|---|---|
| Number | Structure |
| I-475 | 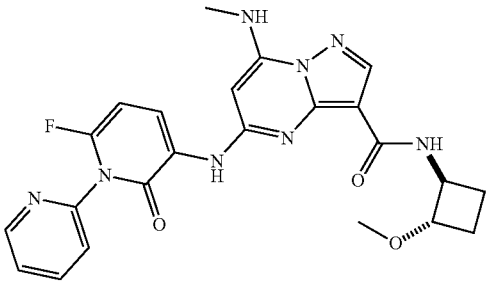 |
| I-476 | 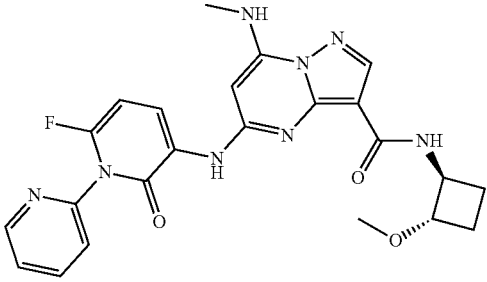 [SMILES: CNc1cc(Nc2ccc(F)n(-c3ccccn3)c2=O)nc2c(C(=O)N[C@H]3CC[C@@H]3OC)cnn12] |
| I-477 | 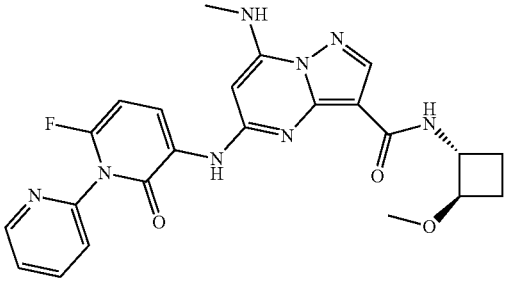 [SMILES: CNc1cc(Nc2ccc(F)n(-c3ccccn3)c2=O)nc2c(C(=O)N[C@@H]3CC[C@H]3OC)cnn12] |
| I-478 | 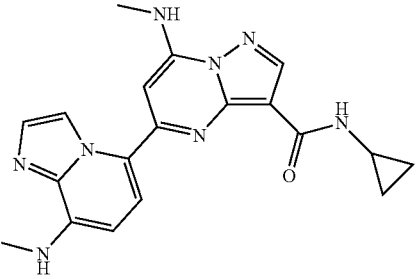 [SMILES: CNc1ccc(-c2cc(NC)n3ncc(C(=O)NC4CC4)c3n2)n2ccnc12] |
| I-479 | 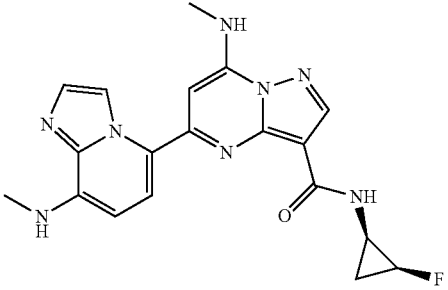 [SMILES: CNc1ccc(-c2cc(NC)n3ncc(C(=O)N[C@@H]4C[C@@H]4F)c3n2)n2ccnc12] |

TABLE 1-continued
| Selected Compounds | |
|---|---|
| Number | Structure |
| I-480 | 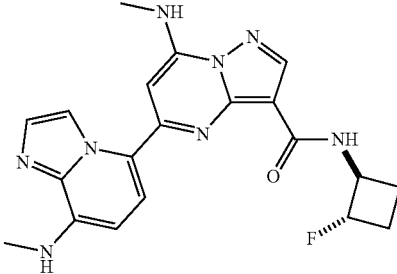 |
| I-481 | 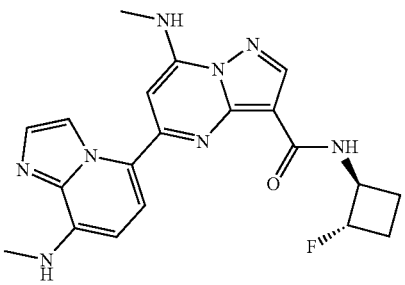 [SMILES: CNc1ccc(-c2cc(NC)n3ncc(C(=O)N[C@H]4CC[C@@H]4F)c3n2)n2ccnc12] |
| I-482 | 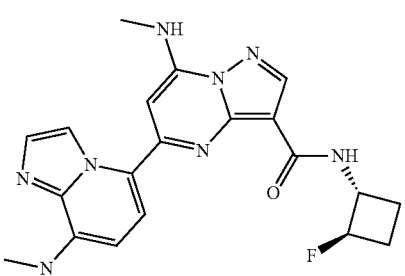 |
| I-483 | 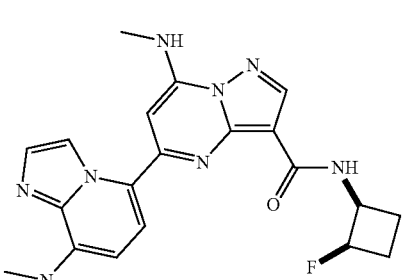 |
| I-484 | 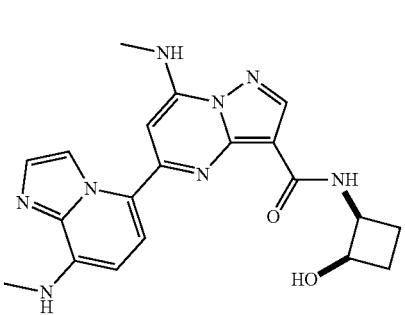 |

241
242
TABLE 1-continued
| Selected Compounds | |
|---|---|
| Number | Structure |
| I-485 | 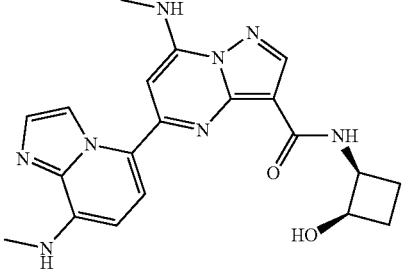 [SMILES: CNc1ccc(-c2cc(NC)n3ncc(C(=O)N[C@H]4CC[C@H]4O)c3n2)n2ccnc12] |
| I-486 | 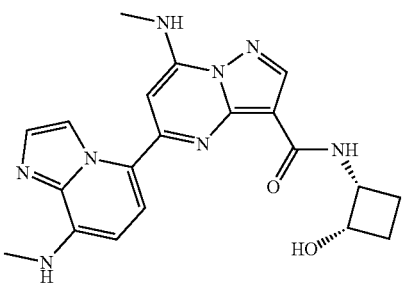 [SMILES: CNc1ccc(-c2cc(NC)n3ncc(C(=O)N[C@@H]4CC[C@@H]4O)c3n2)n2ccnc12] |
| I-487 | 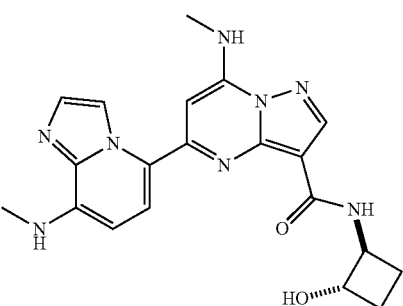 |
| I-488 | 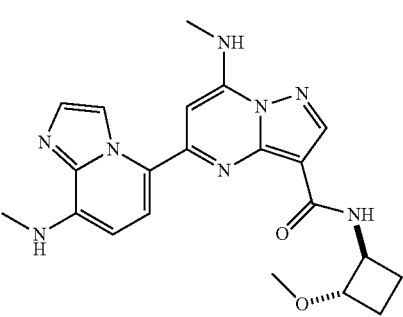 |
| I-489 | 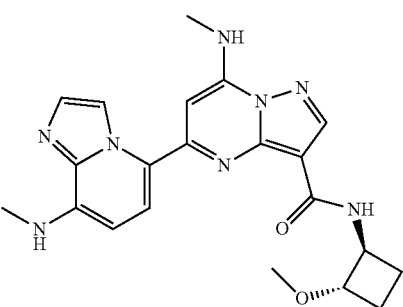 |

TABLE 1-continued

| Number | Structure |
|---|---|
| I-490 | 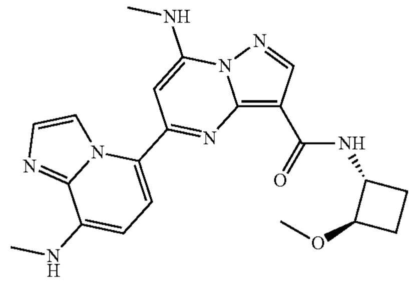 [SMILES: CNc1ccc(-c2cc(NC)n3ncc(C(=O)N[C@@H]4CC[C@H]4OC)c3n2)n2ccnc12] |
| I-491 | 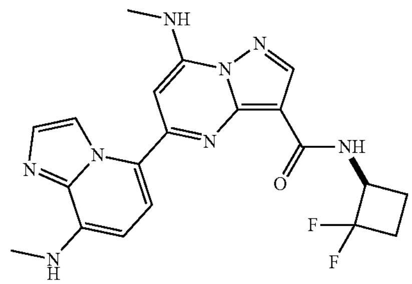 |
| I-492 | 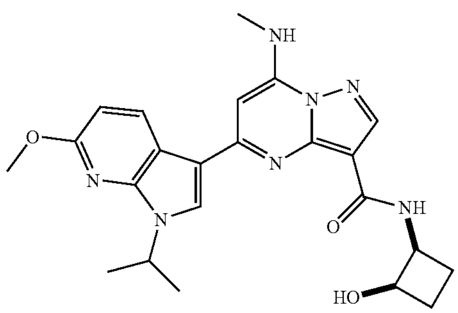 |
| I-493 | 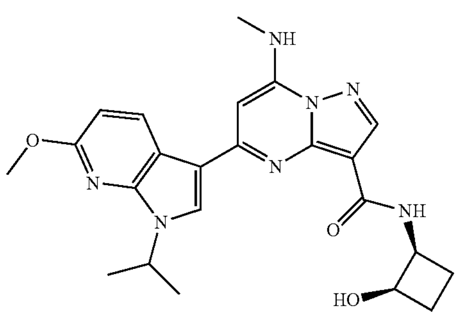 [SMILES: CNc1cc(-c2cn(C(C)C)c3nc(OC)ccc23)nc2c(C(=O)N[C@H]3CC[C@H]3O)cnn12] |
| I-494 | 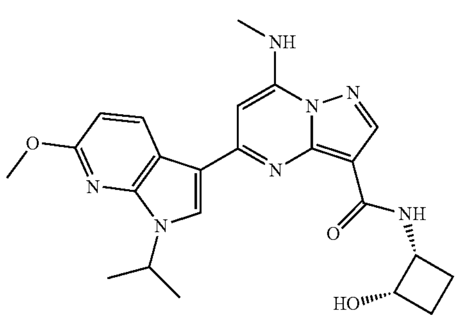 [SMILES: CNc1cc(-c2cn(C(C)C)c3nc(OC)ccc23)nc2c(C(=O)N[C@@H]3CC[C@@H]3O)cnn12] |

TABLE 1-continued

Selected Compounds

| Number | Structure |
|---|---|
| I-495 | 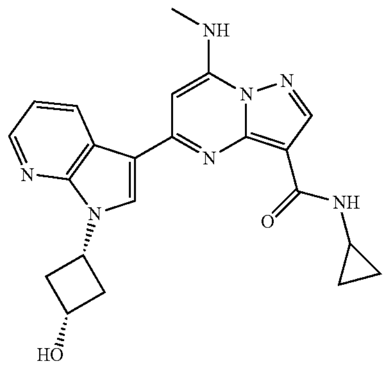 [SMILES: CNc1cc(-c2cn([C@H]3C[C@@H](O)C3)c3ncccc23)nc2c(C(=O)NC3CC3)cnn12] |
| I-496 | 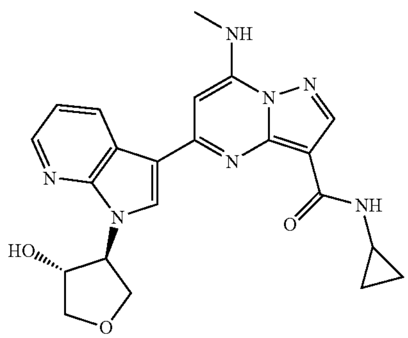 [SMILES: CNc1cc(-c2cn([C@H]3COC[C@@H]3O)c3ncccc23)nc2c(C(=O)NC3CC3)cnn12] |
| I-497 | 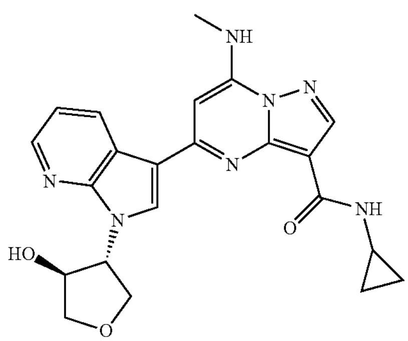 [SMILES: CNc1cc(-c2cn([C@@H]3COC[C@H]3O)c3ncccc23)nc2c(C(=O)NC3CC3)cnn12] |
| I-498 | 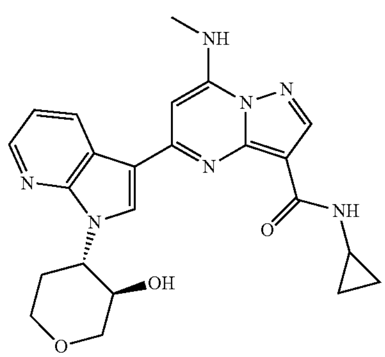 [SMILES: CNc1cc(-c2cn([C@H]3CCOC[C@@H]3O)c3ncccc23)nc2c(C(=O)NC3CC3)cnn12] |

TABLE 1-continued
Selected Compounds
| Number | Structure |
|---|---|
| I-499 | 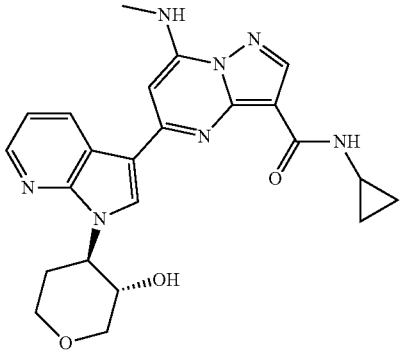 [SMILES: CNc1cc(-c2cn([C@@H]3CCOC[C@H]3O)c3ncccc23)nc2c(C(=O)NC3CC3)cnn12] |
| I-500 | 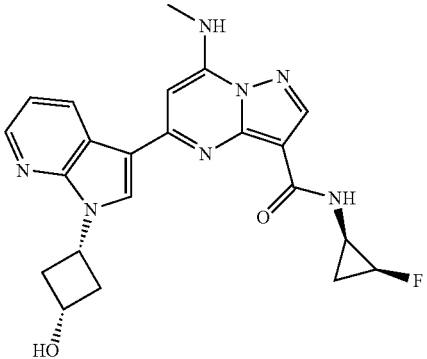 [SMILES: CNc1cc(-c2cn([C@H]3C[C@@H](O)C3)c3ncccc23)nc2c(C(=O)N[C@@H]3C[C@@H]3F)cnn12] |
| I-501 | 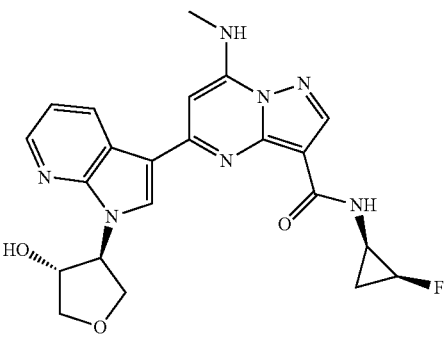 [SMILES: CNc1cc(-c2cn([C@H]3COC[C@@H]3O)c3ncccc23)nc2c(C(=O)N[C@@H]3C[C@@H]3F)cnn12] |
| I-502 | 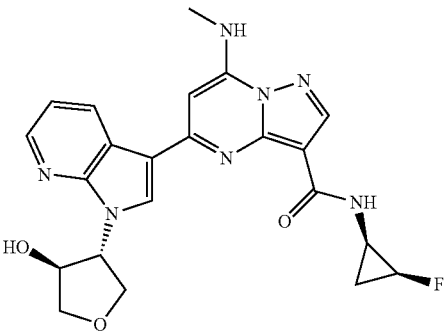 [SMILES: CNc1cc(-c2cn([C@@H]3COC[C@H]3O)c3ncccc23)nc2c(C(=O)N[C@@H]3C[C@@H]3F)cnn12] |

TABLE 1-continued
Selected Compounds
| Number | Structure |
|---|---|
| I-503 | 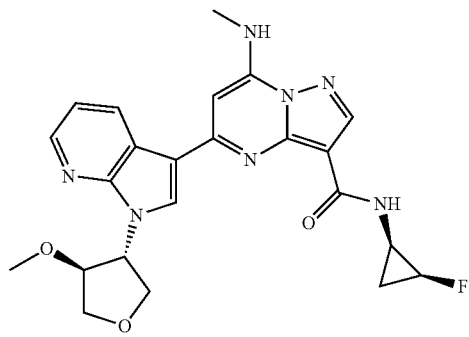 [SMILES: CNc1cc(-c2cn([C@@H]3COC[C@H]3OC)c3ncccc23)nc2c(C(=O)N[C@@H]3C[C@@H]3F)cnn12] |
| I-504 | 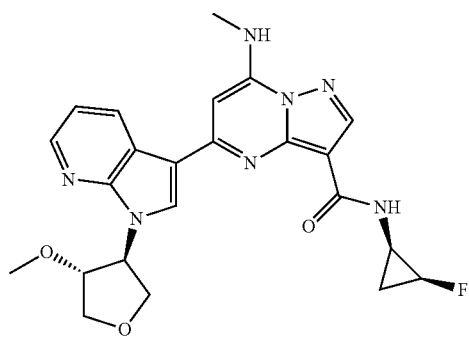 [SMILES: CNc1cc(-c2cn([C@H]3COC[C@@H]3OC)c3ncccc23)nc2c(C(=O)N[C@@H]3C[C@@H]3F)cnn12] |
| I-505 | 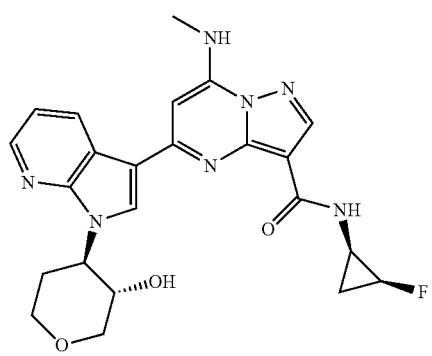 [SMILES: CNc1cc(-c2cn([C@@H]3CCOC[C@H]3O)c3ncccc23)nc2c(C(=O)N[C@@H]3C[C@@H]3F)cnn12] |
| I-506 | 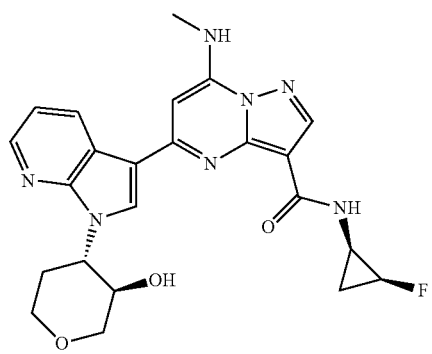 [SMILES: CNc1cc(-c2cn([C@H]3CCOC[C@@H]3O)c3ncccc23)nc2c(C(=O)N[C@@H]3C[C@@H]3F)cnn12] |

TABLE 1-continued
| Selected Compounds | |
|---|---|
| Number | Structure |
| I-507 | 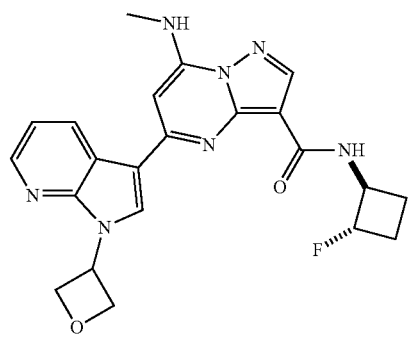 |
| I-508 | 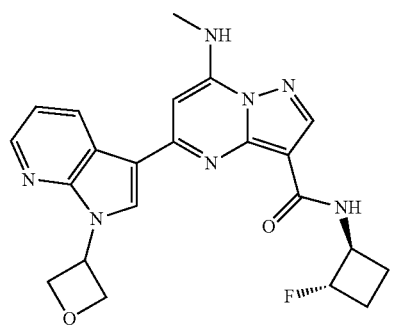 [SMILES: CNc1cc(-c2cn(C3COC3)c3ncccc23)nc2c(C(=O)N[C@H]3CC[C@@H]3F)cnn12] |
| I-509 | 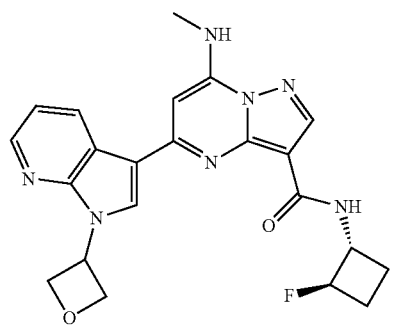 [SMILES: CNc1cc(-c2cn(C3COC3)c3ncccc23)nc2c(C(=O)N[C@@H]3CC[C@H]3F)cnn12] |
| I-510 | 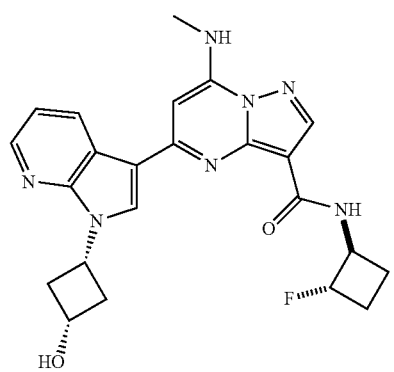 |

TABLE 1-continued
| Selected Compounds | |
|---|---|
| Number | Structure |
| I-511 | 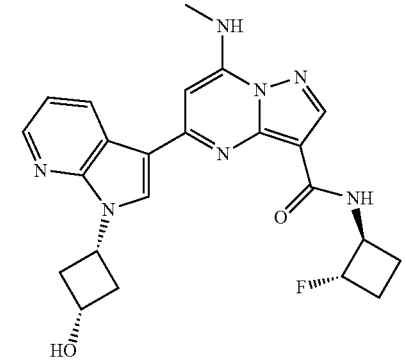 [SMILES: CNc1cc(-c2cn([C@H]3C[C@@H](O)C3)c3ncccc23)nc2c(C(=O)N[C@H]3CC[C@@H]3F)cnn12] |
| I-512 | 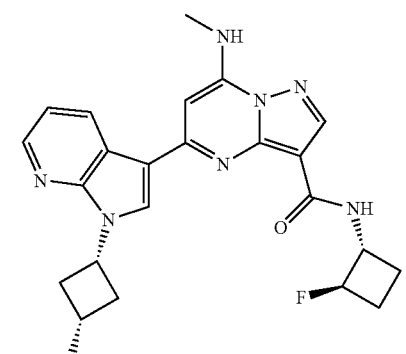 |
| I-513 | 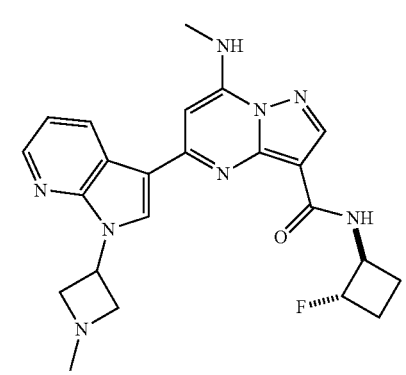 |
| I-514 | 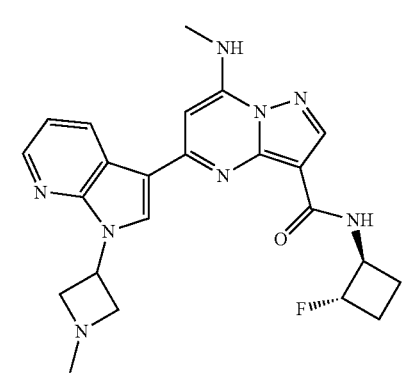 [SMILES: CNc1cc(-c2cn(C3CN(C)C3)c3ncccc23)nc2c(C(=O)N[C@H]3CC[C@@H]3F)cnn12] |

TABLE 1-continued
Selected Compounds
| Number | Structure |
|---|---|
| I-515 | 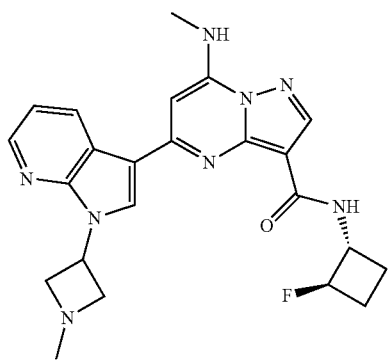 [SMILES: CNc1cc(-c2cn(C3CN(C)C3)c3ncccc23)nc2c(C(=O)N[C@@H]3CC[C@H]3F)cnn12] |
| I-516 | 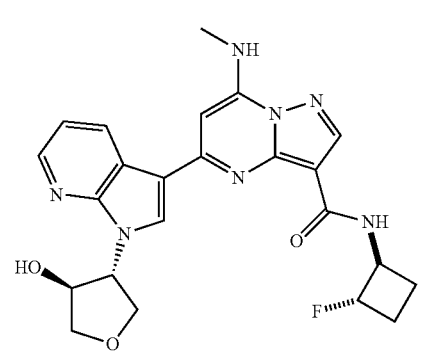 |
| I-517 | 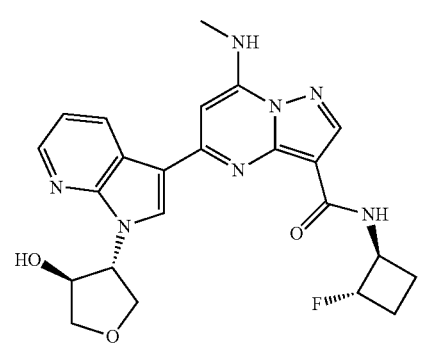 [SMILES: CNc1cc(-c2cn([C@@H]3COC[C@H]3O)c3ncccc23)nc2c(C(=O)N[C@H]3CC[C@@H]3F)cnn12] |
| I-518 | 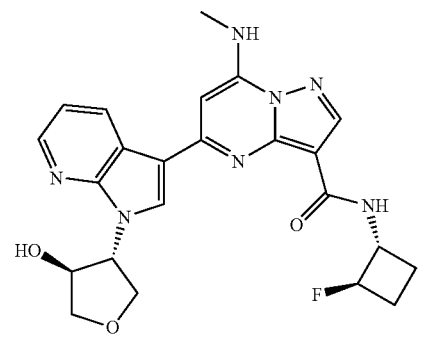 [SMILES: CNc1cc(-c2cn([C@@H]3COC[C@H]3O)c3ncccc23)nc2c(C(=O)N[C@@H]3CC[C@H]3F)cnn12] |

TABLE 1-continued
| Selected Compounds | |
|---|---|
| Number | Structure |
| I-519 | 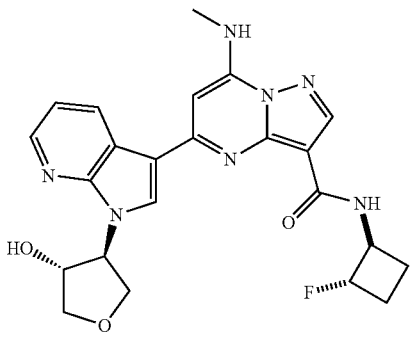 |
| I-520 | 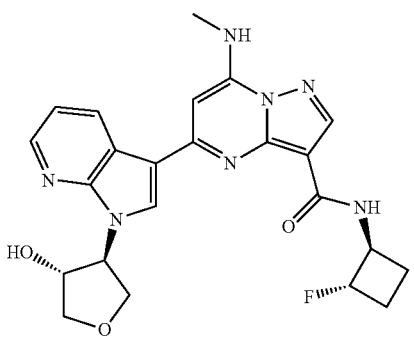 [SMILES: CNc1cc(-c2cn([C@H]3COC[C@@H]3O)c3ncccc23)nc2c(C(=O)N[C@H]3CC[C@@H]3F)cnn12] |
| I-521 | 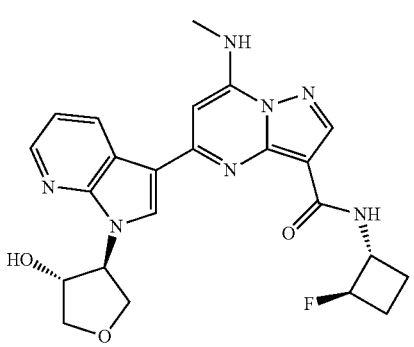 [SMILES: CNc1cc(-c2cn([C@H]3COC[C@@H]3O)c3ncccc23)nc2c(C(=O)N[C@@H]3CC[C@H]3F)cnn12] |
| I-522 | 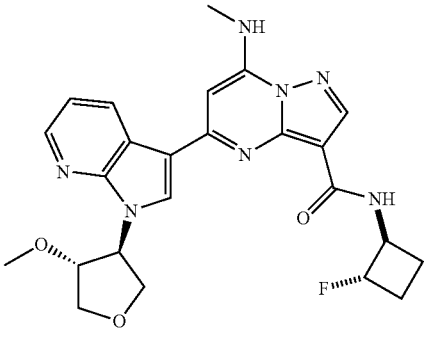 |

TABLE 1-continued
| Selected Compounds | |
|---|---|
| Number | Structure |
| I-523 | 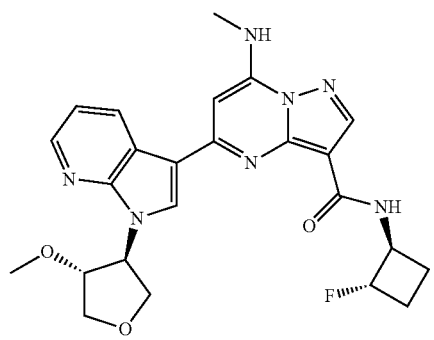 [SMILES: CNc1cc(-c2cn([C@H]3COC[C@@H]3OC)c3ncccc23)nc2c(C(=O)N[C@H]3CC[C@@H]3F)cnn12] |
| I-524 | 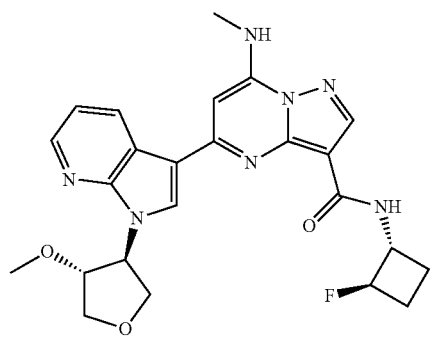 [SMILES: CNc1cc(-c2cn([C@H]3COC[C@@H]3OC)c3ncccc23)nc2c(C(=O)N[C@@H]3CC[C@H]3F)cnn12] |
| I-525 | 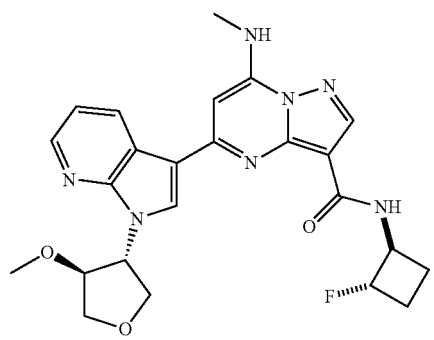 |
| I-526 | 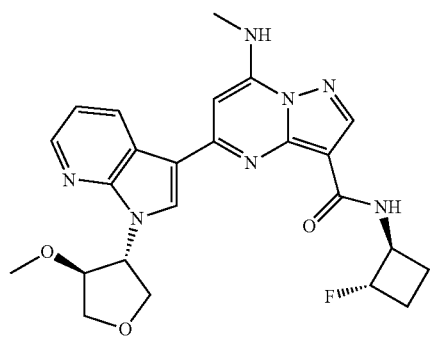 [SMILES: CNc1cc(-c2cn([C@@H]3COC[C@H]3OC)c3ncccc23)nc2c(C(=O)N[C@H]3CC[C@@H]3F)cnn12] |

TABLE 1-continued
Selected Compounds
| Number | Structure |
|---|---|
| I-527 | 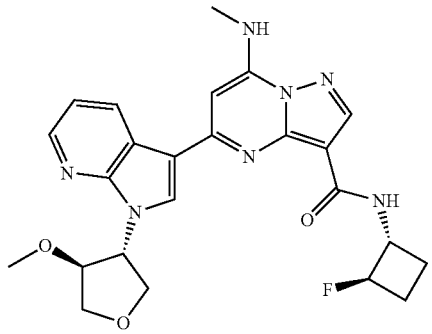 [SMILES: CNc1cc(-c2cn([C@@H]3COC[C@H]3OC)c3ncccc23)nc2c(C(=O)N[C@@H]3CC[C@H]3F)cnn12] |
| I-528 | 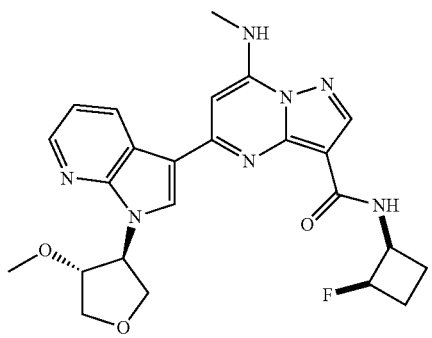 |
| I-529 | 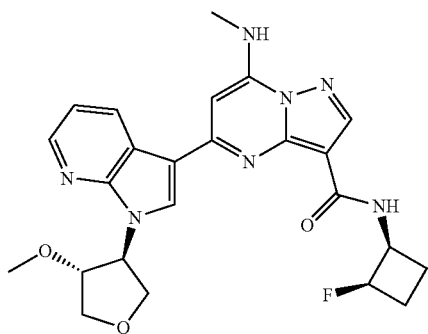 [SMILES: CNc1cc(-c2cn([C@H]3COC[C@@H]3OC)c3ncccc23)nc2c(C(=O)N[C@H]3CC[C@H]3F)cnn12] |
| I-530 | 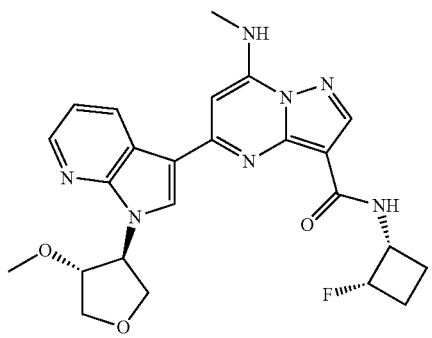 [SMILES: CNc1cc(-c2cn([C@H]3COC[C@@H]3OC)c3ncccc23)nc2c(C(=O)N[C@@H]3CC[C@@H]3F)cnn12] |

TABLE 1-continued

| Number | Structure |
|---|---|
| I-531 | 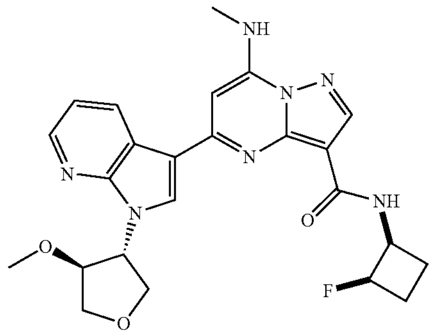 |
| I-532 | 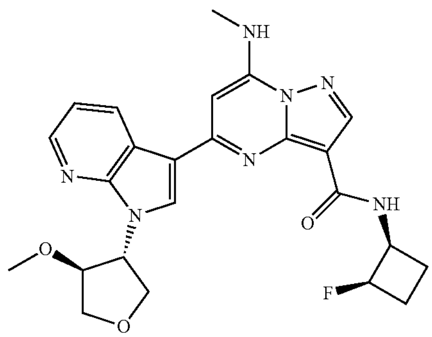 [SMILES: CNc1cc(-c2cn([C@@H]3COC[C@H]3OC)c3ncccc23)nc2c(C(=O)N[C@H]3CC[C@H]3F)cnn12] |
| I-533 | 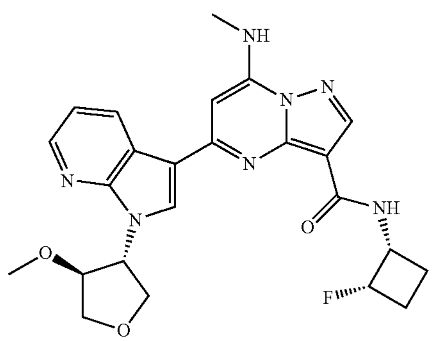 [SMILES: CNc1cc(-c2cn([C@@H]3COC[C@H]3OC)c3ncccc23)nc2c(C(=O)N[C@@H]3CC[C@@H]3F)cnn12] |
| I-534 | 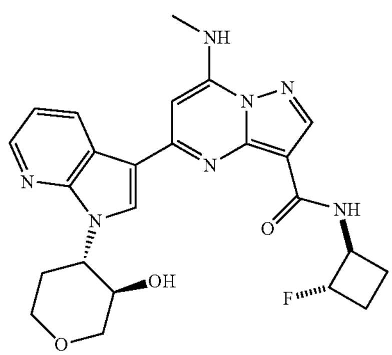 |

TABLE 1-continued
| Selected Compounds | |
|---|---|
| Number | Structure |
| I-535 | 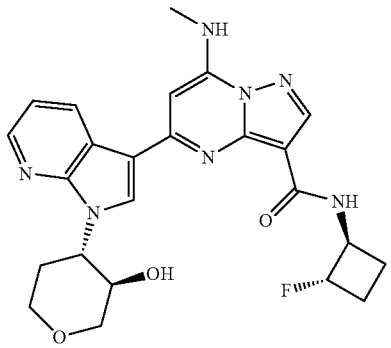 [SMILES: CNc1cc(-c2cn([C@H]3CCOC[C@@H]3O)c3ncccc23)nc2c(C(=O)N[C@H]3CC[C@@H]3F)cnn12] |
| I-536 | 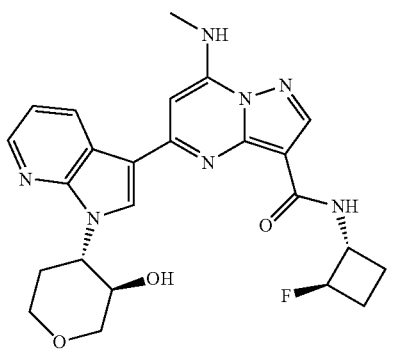 [SMILES: CNc1cc(-c2cn([C@H]3CCOC[C@@H]3O)c3ncccc23)nc2c(C(=O)N[C@@H]3CC[C@H]3F)cnn12] |
| I-537 | 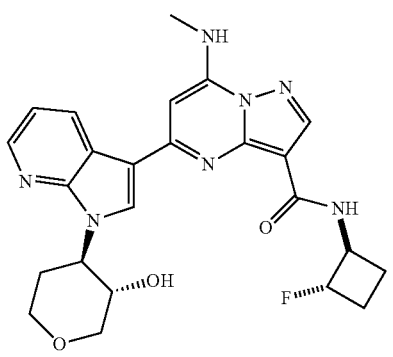 |
| I-538 |  |

TABLE 1-continued
| Selected Compounds | |
|---|---|
| Number | Structure |
| I-539 | 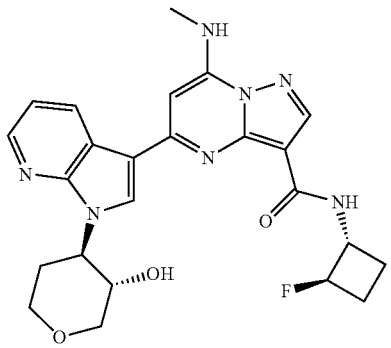 [SMILES: CNc1cc(-c2cn([C@@H]3CCOC[C@H]3O)c3ncccc23)nc2c(C(=O)N[C@@H]3CC[C@H]3F)cnn12] |
| I-540 | 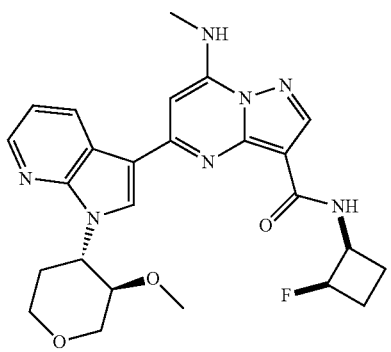 |
| I-541 | 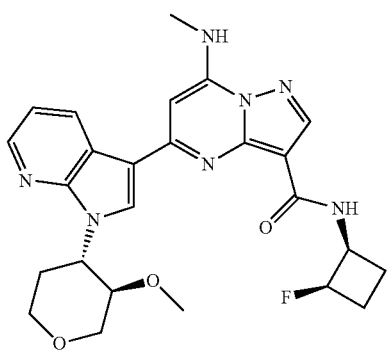 [SMILES: CNc1cc(-c2cn([C@H]3CCOC[C@@H]3OC)c3ncccc23)nc2c(C(=O)N[C@H]3CC[C@H]3F)cnn12] |
| I-542 | 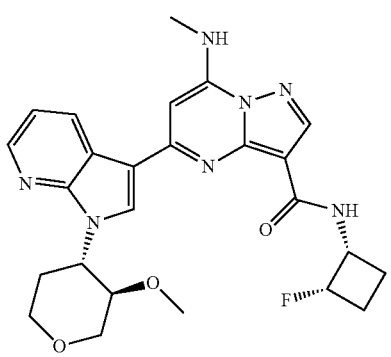 [SMILES: CNc1cc(-c2cn([C@H]3CCOC[C@@H]3OC)c3ncccc23)nc2c(C(=O)N[C@@H]3CC[C@@H]3F)cnn12] |

TABLE 1-continued
| Selected Compounds | |
|---|---|
| Number | Structure |
| I-543 | 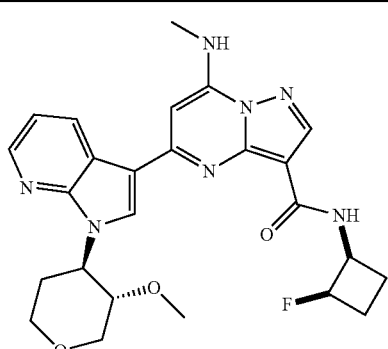 |
| I-544 | 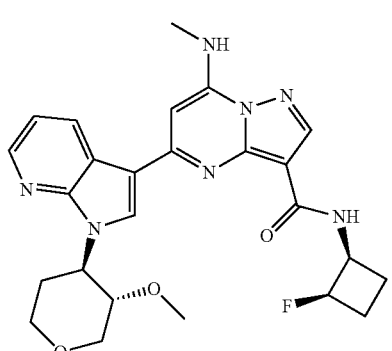 |
| I-545 | 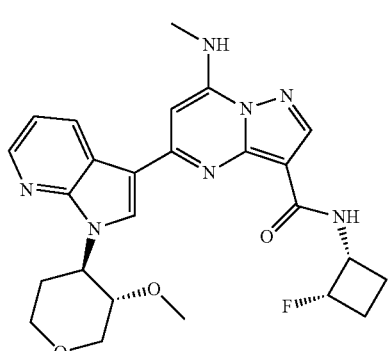 |
| I-546 | 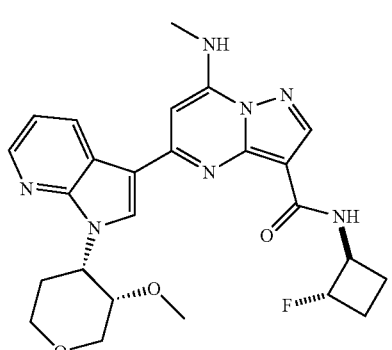 |

TABLE 1-continued
| Number | Structure |
|---|---|
| I-547 | 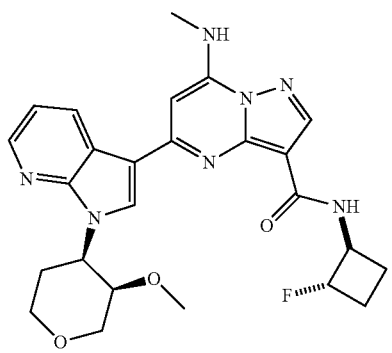 |
| I-548 | 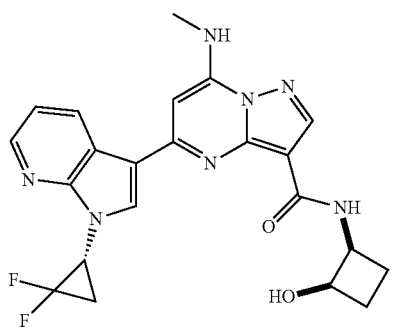 |
| I-549 | 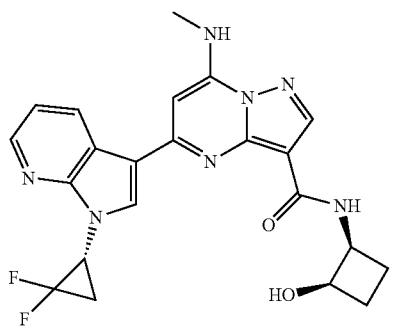 [SMILES: CNc1cc(-c2cn([C@@H]3CC3(F)F)c3ncccc23)nc2c(C(=O)N[C@H]3CC[C@H]3O)cnn12] |
| I-550 | 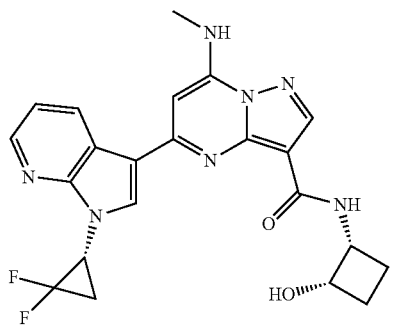 [SMILES: CNc1cc(-c2cn([C@@H]3CC3(F)F)c3ncccc23)nc2c(C(=O)N[C@@H]3CC[C@@H]3O)cnn12] |

TABLE 1-continued
| Selected Compounds | |
|---|---|
| Number | Structure |
| I-551 | 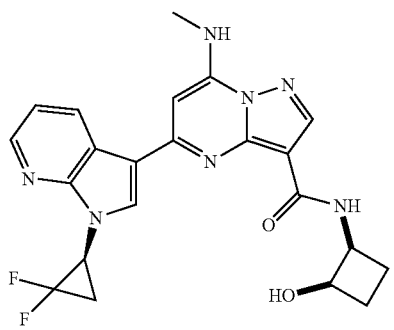 |
| I-552 | 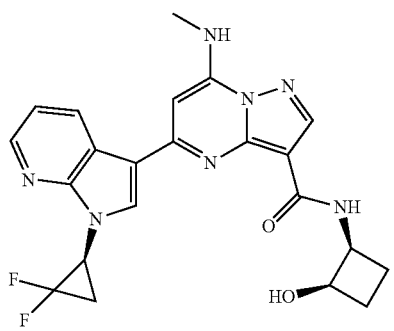 [SMILES: CNc1cc(-c2cn([C@H]3CC3(F)F)c3ncccc23)nc2c(C(=O)N[C@H]3CC[C@H]3O)cnn12] |
| I-553 | 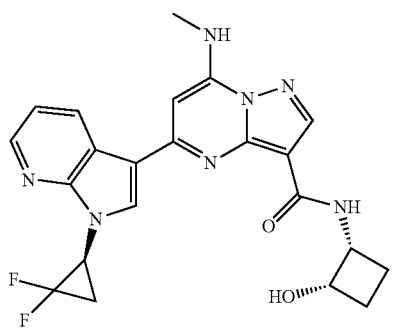 [SMILES: CNc1cc(-c2cn([C@H]3CC3(F)F)c3ncccc23)nc2c(C(=O)N[C@@H]3CC[C@@H]3O)cnn12] |
| I-554 | 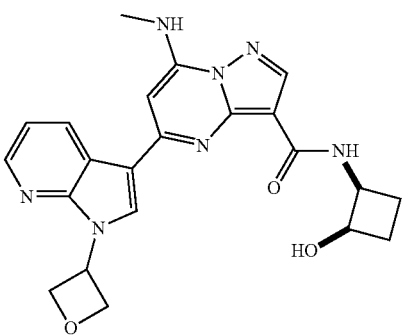 |

TABLE 1-continued
Selected Compounds
| Number | Structure |
|---|---|
| I-555 | 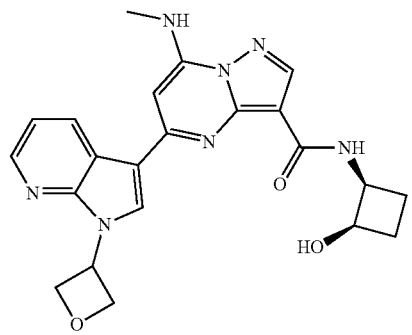 [SMILES: CNc1cc(-c2cn(C3COC3)c3ncccc23)nc2c(C(=O)N[C@H]3CC[C@H]3O)cnn12] |
| I-556 | 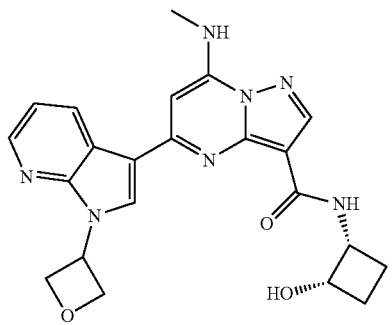 [SMILES: CNc1cc(-c2cn(C3COC3)c3ncccc23)nc2c(C(=O)N[C@@H]3CC[C@@H]3O)cnn12] |
| I-557 | 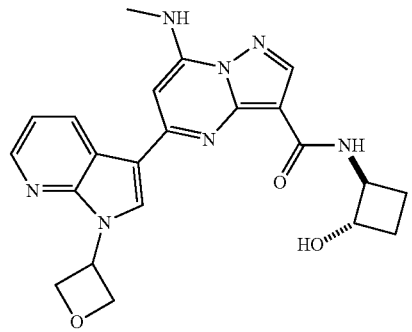 |
| I-558 | 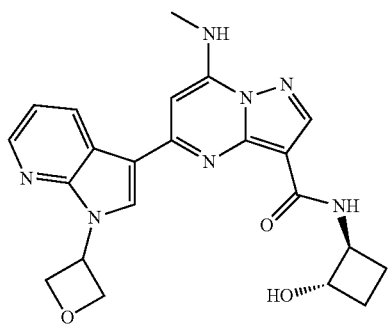 [SMILES: CNc1cc(-c2cn(C3COC3)c3ncccc23)nc2c(C(=O)N[C@H]3CC[C@@H]3O)cnn12] |

TABLE 1-continued

| Selected Compounds | |
| --- | --- |
| Number | Structure |
| I-559 | |
| I-560 | |
| I-561 | |
| I-562 | |

TABLE 1-continued

Selected Compounds

| Number | Structure |
|---|---|
| I-563 | 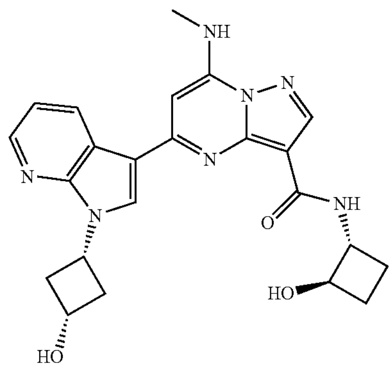 [SMILES: CNc1cc(-c2cn([C@H]3C[C@@H](O)C3)c3ncccc23)nc2c(C(=O)N[C@@H]3CC[C@H]3O)cnn12] |
| I-564 | 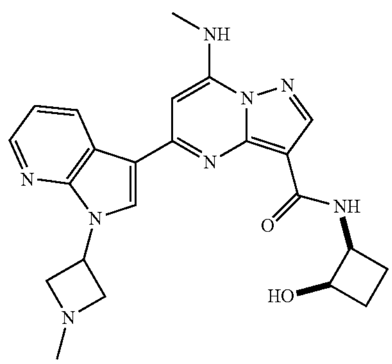 |
| I-565 | 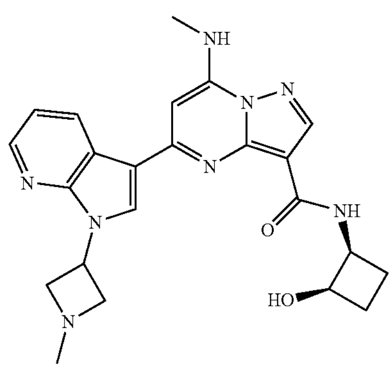 [SMILES: CNc1cc(-c2cn(C3CN(C)C3)c3ncccc23)nc2c(C(=O)N[C@H]3CC[C@H]3O)cnn12] |
| I-566 | 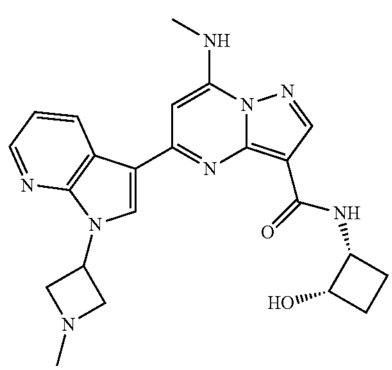 [SMILES: CNc1cc(-c2cn(C3CN(C)C3)c3ncccc23)nc2c(C(=O)N[C@@H]3CC[C@@H]3O)cnn12] |

TABLE 1-continued

| Selected Compounds | |
|---|---|
| Number | Structure |
| I-567 | |
| I-568 | |
| I-569 | |
| I-570 | |

TABLE 1-continued
Selected Compounds
| Number | Structure |
|---|---|
| I-571 | 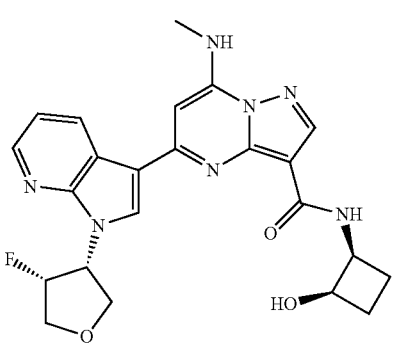 [SMILES: CNc1cc(-c2cn([C@@H]3COC[C@@H]3F)c3ncccc23)nc2c(C(=O)N[C@H]3CC[C@H]3O)cnn12] |
| I-572 | 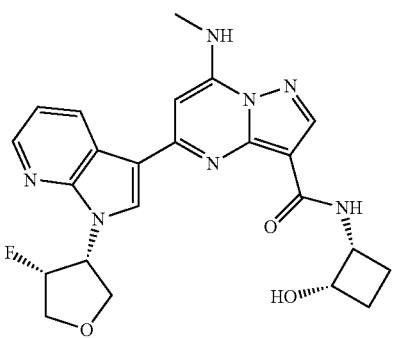 [SMILES: CNc1cc(-c2cn([C@@H]3COC[C@@H]3F)c3ncccc23)nc2c(C(=O)N[C@@H]3CC[C@@H]3O)cnn12] |
| I-573 | 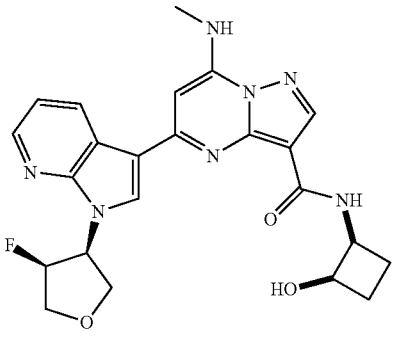 |
| I-574 | 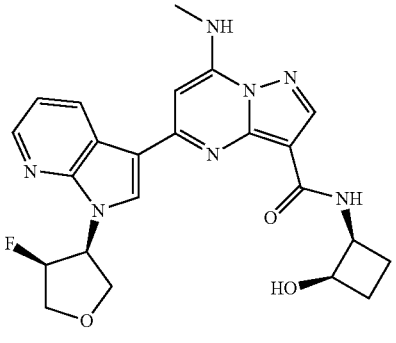 [SMILES: CNc1cc(-c2cn([C@H]3COC[C@H]3F)c3ncccc23)nc2c(C(=O)N[C@H]3CC[C@H]3O)cnn12] |

TABLE 1-continued

| Selected Compounds | |
|---|---|
| Number | Structure |
| I-575 | |
| I-576 | |
| I-577 | |
| I-578 | |

TABLE 1-continued

| Selected Compounds | |
|---|---|
| Number | Structure |
| I-579 | |
| I-580 | |
| I-581 | |
| I-582 | |

TABLE 1-continued
| Number | Structure |
|---|---|
| I-583 | 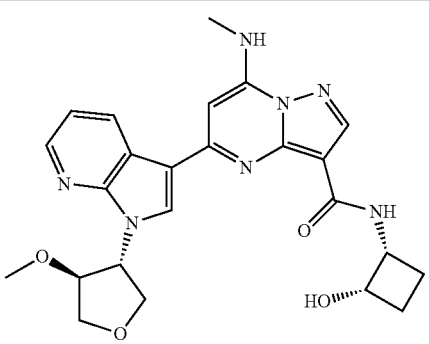 [SMILES: CNc1cc(-c2cn([C@@H]3COC[C@H]3OC)c3ncccc23)nc2c(C(=O)N[C@@H]3CC[C@@H]3O)cnn12] |
| I-584 | 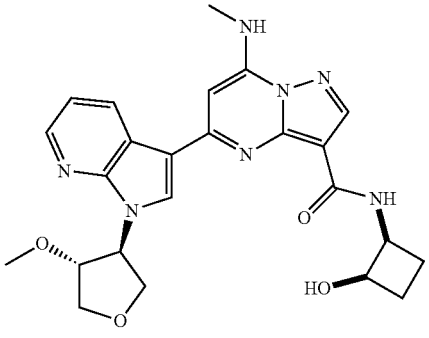 |
| I-585 | 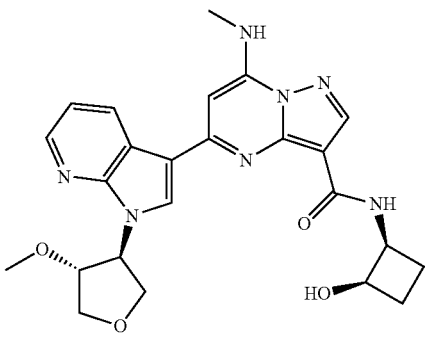 [SMILES: CNc1cc(-c2cn([C@H]3COC[C@@H]3OC)c3ncccc23)nc2c(C(=O)N[C@H]3CC[C@H]3O)cnn12] |
| I-586 | 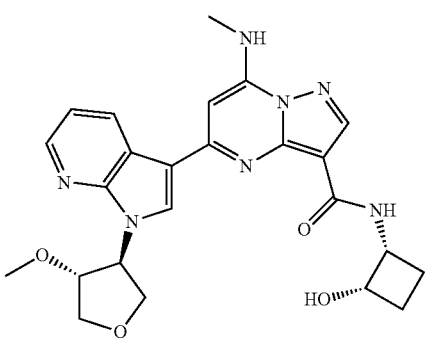 [SMILES: CNc1cc(-c2cn([C@H]3COC[C@@H]3OC)c3ncccc23)nc2c(C(=O)N[C@@H]3CC[C@@H]3O)cnn12] |

TABLE 1-continued
Selected Compounds
| Number | Structure |
|---|---|
| I-587 | 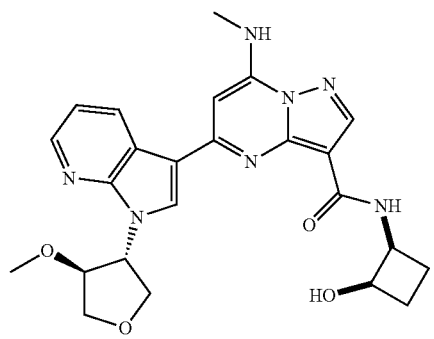 |
| I-588 | 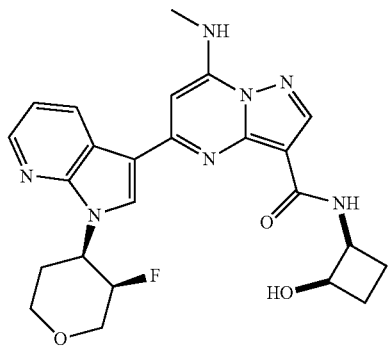 |
| I-589 | 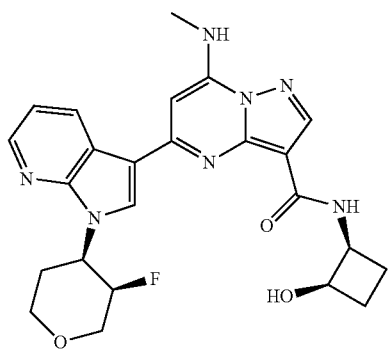 [SMILES: CNc1cc(-c2cn([C@@H]3CCOC[C@@H]3F)c3ncccc23)nc2c(C(=O)N[C@H]3CC[C@H]3O)cnn12] |
| I-590 | 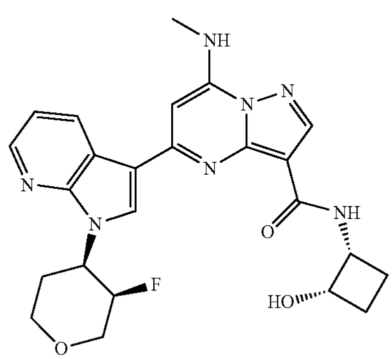 [SMILES: CNc1cc(-c2cn([C@@H]3CCOC[C@@H]3F)c3ncccc23)nc2c(C(=O)N[C@@H]3CC[C@@H]3O)cnn12] |

TABLE 1-continued
| Number | Structure |
|---|---|
| I-591 | 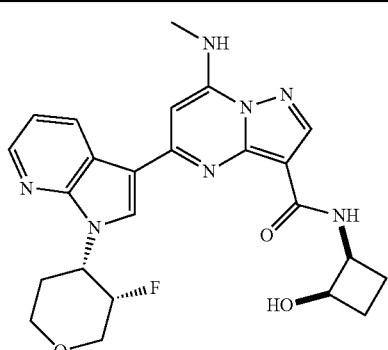 |
| I-592 | 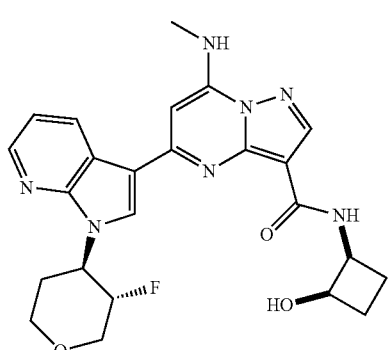 |
| I-593 | 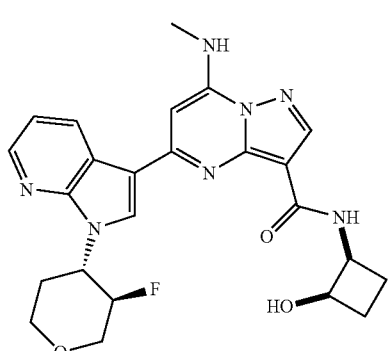 |
| I-594 | 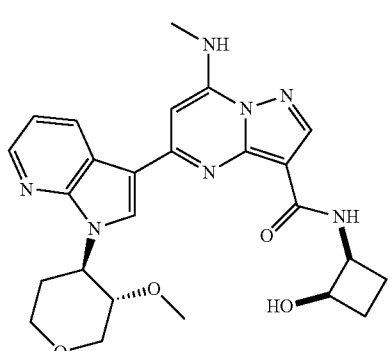 |

TABLE 1-continued

Selected Compounds

| Number | Structure |
|--------|-----------|
| I-595 | 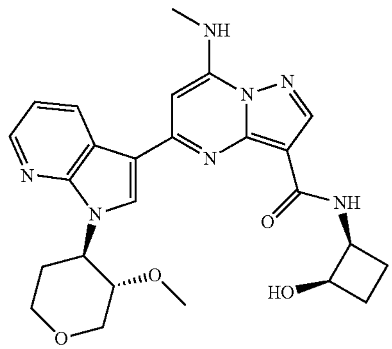 [SMILES: CNc1cc(-c2cn([C@@H]3CCOC[C@H]3OC)c3ncccc23)nc2c(C(=O)N[C@H]3CC[C@H]3O)cnn12] |
| I-596 | 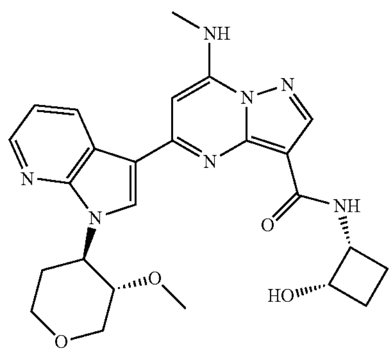 [SMILES: CNc1cc(-c2cn([C@@H]3CCOC[C@H]3OC)c3ncccc23)nc2c(C(=O)N[C@@H]3CC[C@@H]3O)cnn12] |
| I-597 | 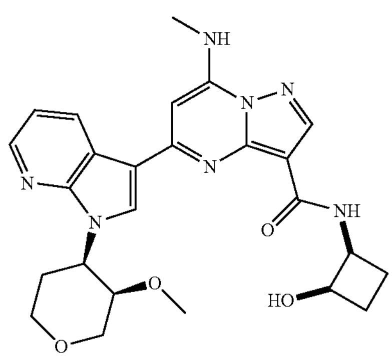 |
| I-598 | 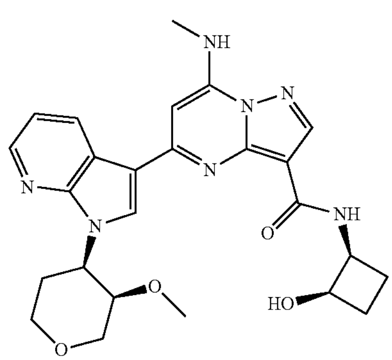 [SMILES: CNc1cc(-c2cn([C@@H]3CCOC[C@@H]3OC)c3ncccc23)nc2c(C(=O)N[C@H]3CC[C@H]3O)cnn12] |

TABLE 1-continued
| Selected Compounds | |
|---|---|
| Number | Structure |
| I-599 | 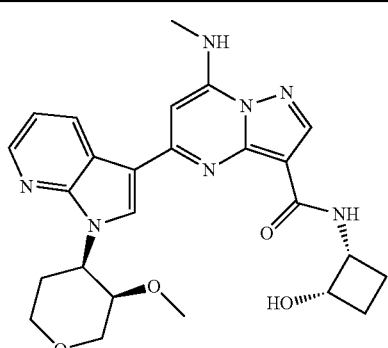 |
| I-600 | 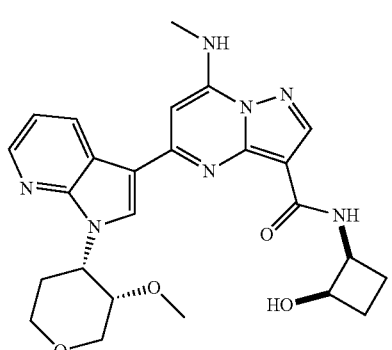 |
| I-601 | 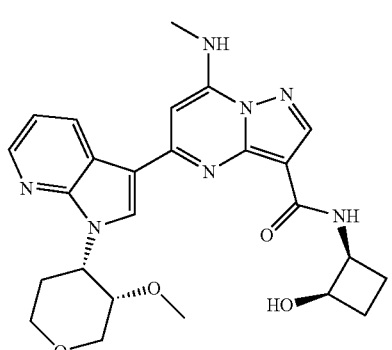 |
| I-602 | 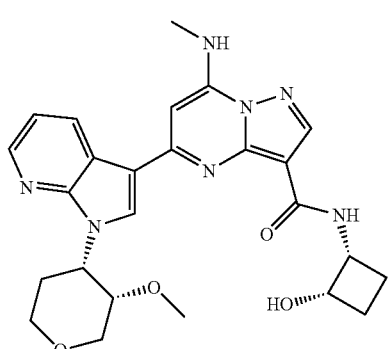 |

TABLE 1-continued

| Selected Compounds | |
|---|---|
| Number | Structure |
| I-603 | |
| I-604 | |
| I-605 | |
| I-606 | |

TABLE 1-continued

Selected Compounds

| Number | Structure |
|---|---|
| I-607 | 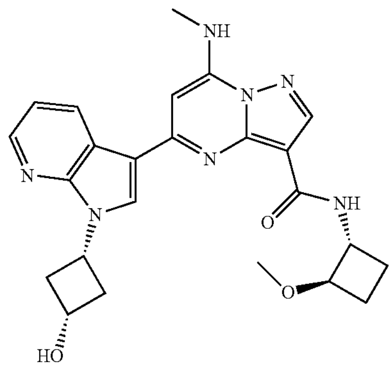 [SMILES: CNc1cc(-c2cn([C@H]3C[C@@H](O)C3)c3ncccc23)nc2c(C(=O)N[C@@H]3CC[C@H]3OC)cnn12] |
| I-608 | 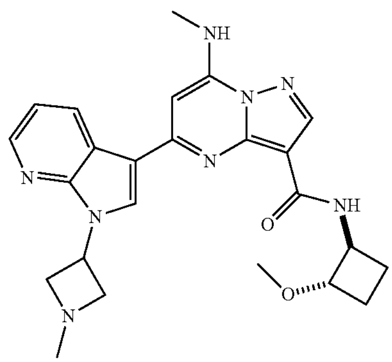 |
| I-609 | 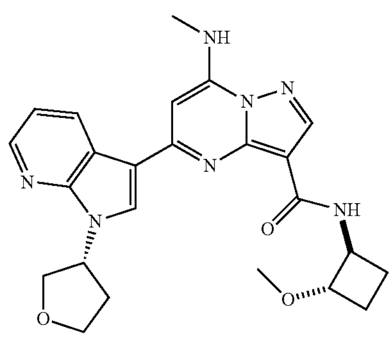 |
| I-610 | 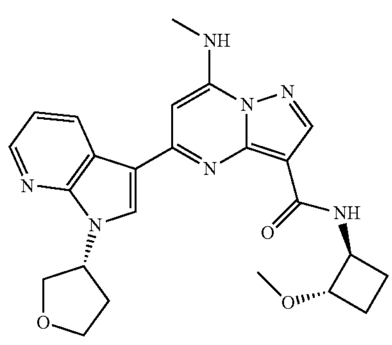 [SMILES: CNc1cc(-c2cn([C@@H]3CCOC3)c3ncccc23)nc2c(C(=O)N[C@H]3CC[C@@H]3OC)cnn12] |

TABLE 1-continued
| Selected Compounds | |
|---|---|
| Number | Structure |
I-611
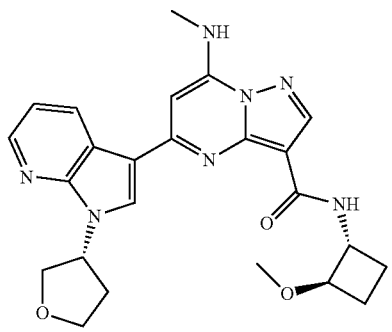 [SMILES: CNc1cc(-c2cn([C@@H]3CCOC3)c3ncccc23)nc2c(C(=O)N[C@@H]3CC[C@H]3OC)cnn12]
I-612
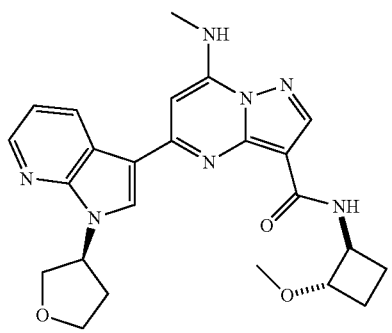
I-613
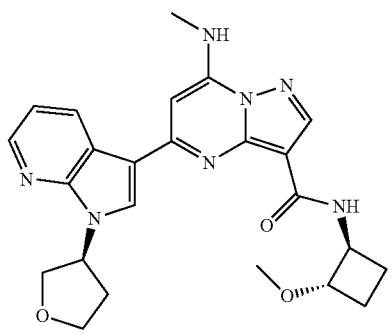 [SMILES: CNc1cc(-c2cn([C@H]3CCOC3)c3ncccc23)nc2c(C(=O)N[C@H]3CC[C@@H]3OC)cnn12]
I-614
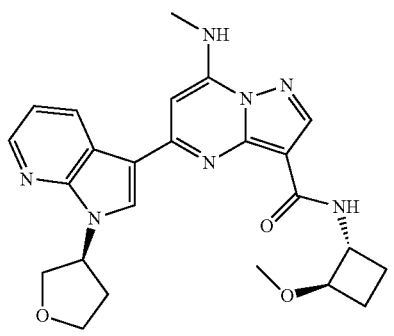 [SMILES: CNc1cc(-c2cn([C@H]3CCOC3)c3ncccc23)nc2c(C(=O)N[C@@H]3CC[C@H]3OC)cnn12]

TABLE 1-continued

| Selected Compounds | |
|---|---|
| Number | Structure |
| I-615 | |
| I-616 | |
| I-617 | |
| I-618 | |

TABLE 1-continued
Selected Compounds
| Number | Structure |
|---|---|
| I-619 | 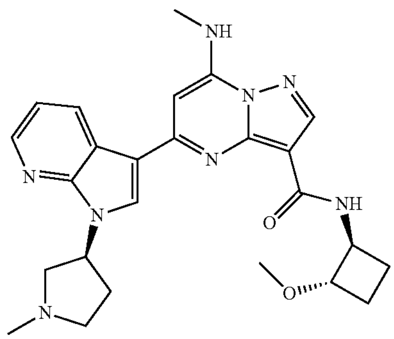 [SMILES: CNc1cc(-c2cn([C@H]3CCN(C)C3)c3ncccc23)nc2c(C(=O)N[C@H]3CC[C@@H]3OC)cnn12] |
| I-620 | 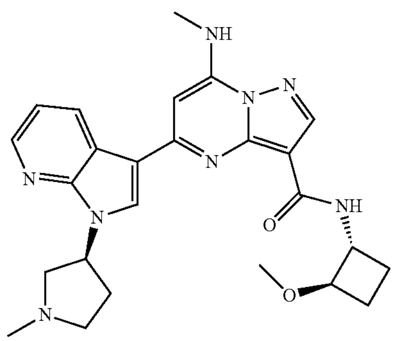 [SMILES: CNc1cc(-c2cn([C@H]3CCN(C)C3)c3ncccc23)nc2c(C(=O)N[C@@H]3CC[C@H]3OC)cnn12] |
| I-621 | 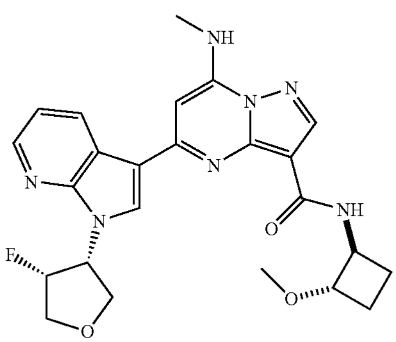 |
| I-622 | 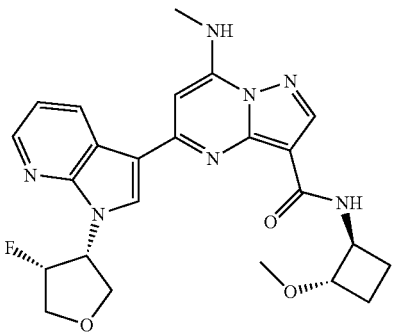 [SMILES: CNc1cc(-c2cn([C@@H]3COC[C@@H]3F)c3ncccc23)nc2c(C(=O)N[C@H]3CC[C@@H]3OC)cnn12] |

TABLE 1-continued

| Number | Structure |
|---|---|
| I-623 | 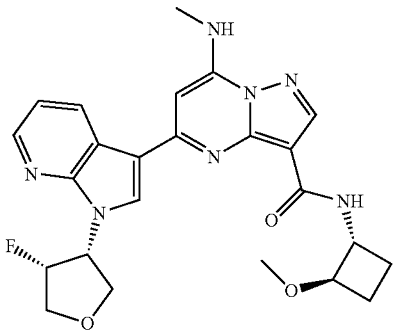 [SMILES: CNc1cc(-c2cn([C@@H]3COC[C@@H]3F)c3ncccc23)nc2c(C(=O)N[C@@H]3CC[C@H]3OC)cnn12] |
| I-624 | 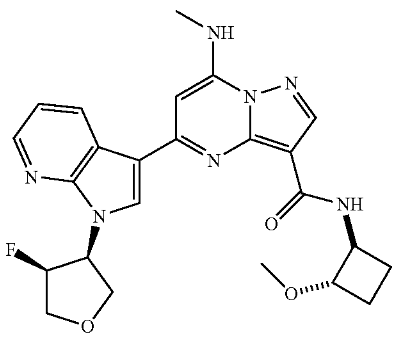 |
| I-625 | 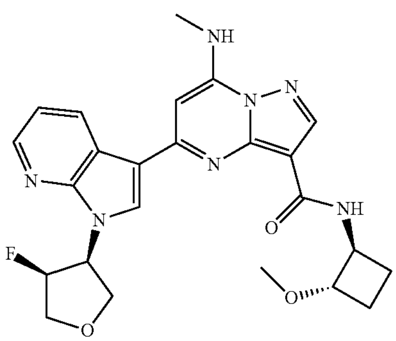 [SMILES: CNc1cc(-c2cn([C@H]3COC[C@H]3F)c3ncccc23)nc2c(C(=O)N[C@H]3CC[C@@H]3OC)cnn12] |
| I-626 | 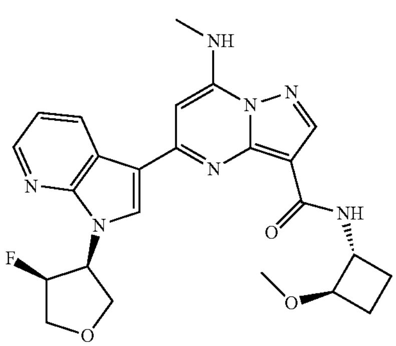 [SMILES: CNc1cc(-c2cn([C@H]3COC[C@H]3F)c3ncccc23)nc2c(C(=O)N[C@@H]3CC[C@H]3OC)cnn12] |

TABLE 1-continued

Selected Compounds

| Number | Structure |
|--------|-----------|
| I-627 | 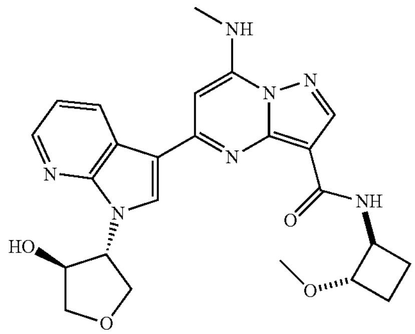 |
| I-628 | 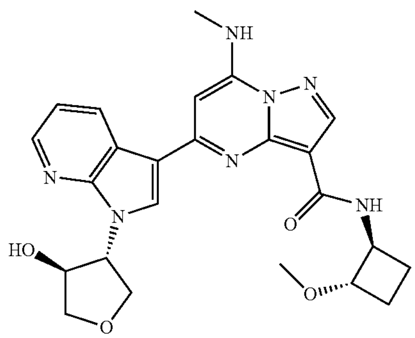 [SMILES: CNc1cc(-c2cn([C@@H]3COC[C@H]3O)c3ncccc23)nc2c(C(=O)N[C@H]3CC[C@@H]3OC)cnn12] |
| I-629 | 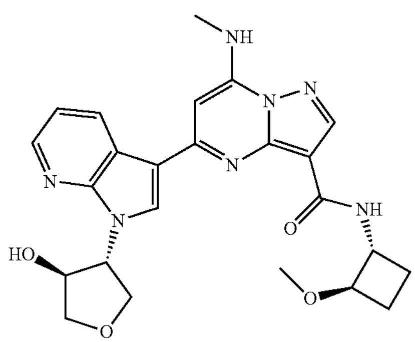 [SMILES: CNc1cc(-c2cn([C@@H]3COC[C@H]3O)c3ncccc23)nc2c(C(=O)N[C@@H]3CC[C@H]3OC)cnn12] |
| I-630 | 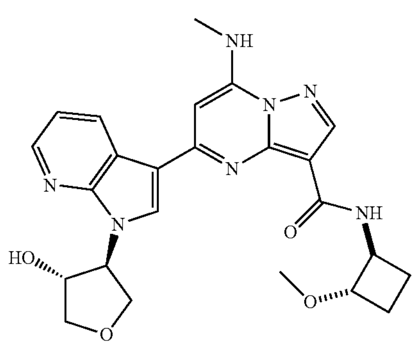 |

TABLE 1-continued
Selected Compounds
| Number | Structure |
|---|---|
| I-631 | 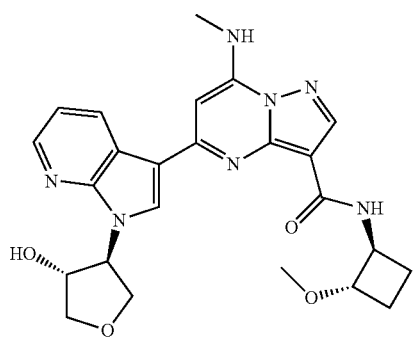 [SMILES: CNc1cc(-c2cn([C@H]3COC[C@@H]3O)c3ncccc23)nc2c(C(=O)N[C@H]3CC[C@@H]3OC)cnn12] |
| I-632 | 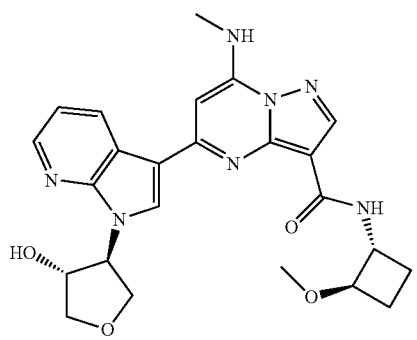 [SMILES: CNc1cc(-c2cn([C@H]3COC[C@@H]3O)c3ncccc23)nc2c(C(=O)N[C@@H]3CC[C@H]3OC)cnn12] |
| I-633 | 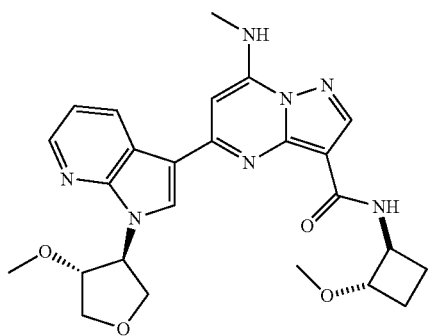 |
| I-634 | 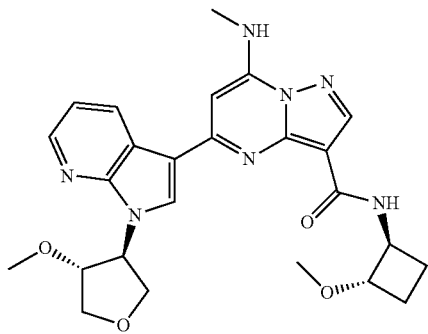 [SMILES: CNc1cc(-c2cn([C@H]3COC[C@@H]3OC)c3ncccc23)nc2c(C(=O)N[C@H]3CC[C@@H]3OC)cnn12] |

TABLE 1-continued

| Selected Compounds | |
|---|---|
| Number | Structure |
| I-635 | |
| I-636 | |
| I-637 | |
| I-638 | |

317 318
TABLE 1-continued
| Selected Compounds | |
|---|---|
| Number | Structure |
| I-639 | 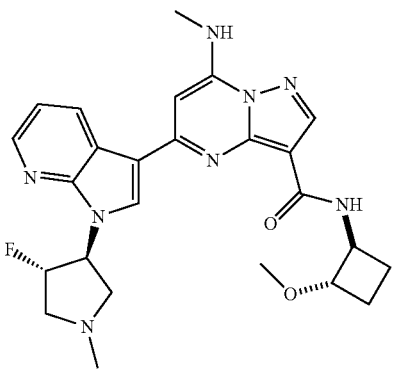 |
| I-640 | 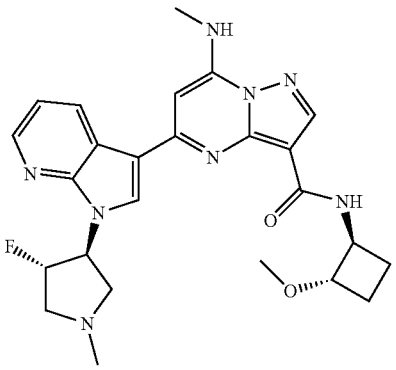 [SMILES: CNc1cc(-c2cn([C@H]3CN(C)C[C@@H]3F)c3ncccc23)nc2c(C(=O)N[C@H]3CC[C@@H]3OC)cnn12] |
| I-641 | 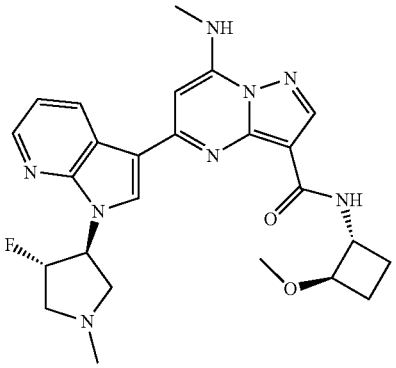 [SMILES: CNc1cc(-c2cn([C@H]3CN(C)C[C@@H]3F)c3ncccc23)nc2c(C(=O)N[C@@H]3CC[C@H]3OC)cnn12] |
| I-642 | 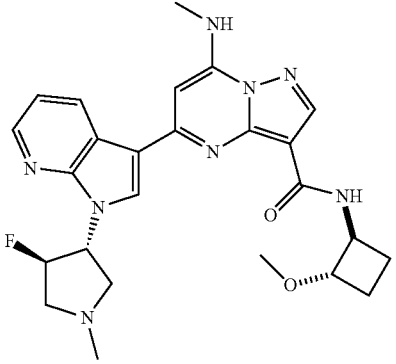 |

TABLE 1-continued

| Number | Structure |
|---|---|
| I-643 | 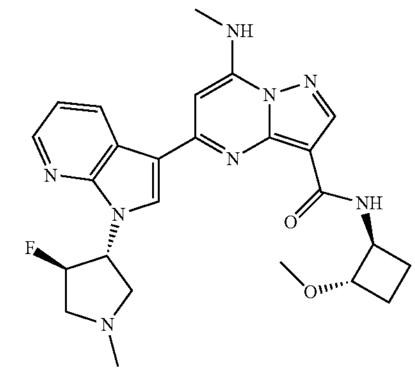 |
| I-644 | 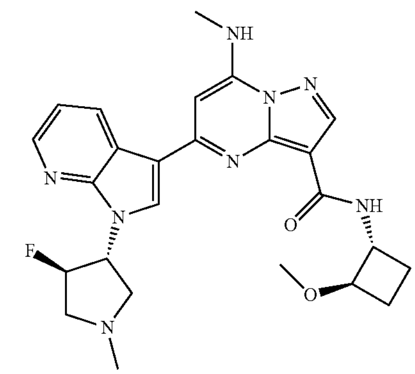 [SMILES: CNc1cc(-c2cn([C@@H]3CN(C)C[C@H]3F)c3ncccc23)nc2c(C(=O)N[C@@H]3CC[C@H]3OC)cnn12] |
| I-645 | 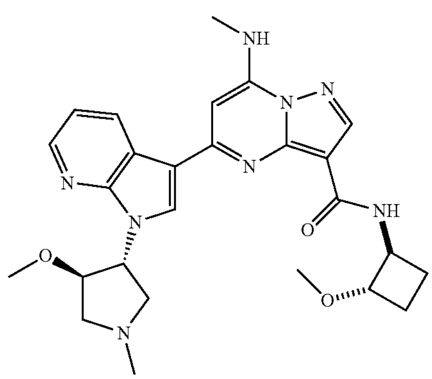 |
| I-646 | 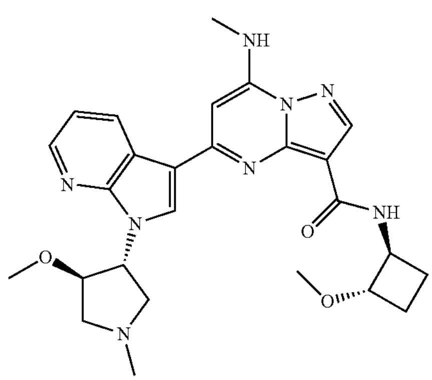 [SMILES: CNc1cc(-c2cn([C@@H]3CN(C)C[C@H]3OC)c3ncccc23)nc2c(C(=O)N[C@H]3CC[C@@H]3OC)cnn12] |

TABLE 1-continued

| Number | Structure |
|---|---|
| I-647 | 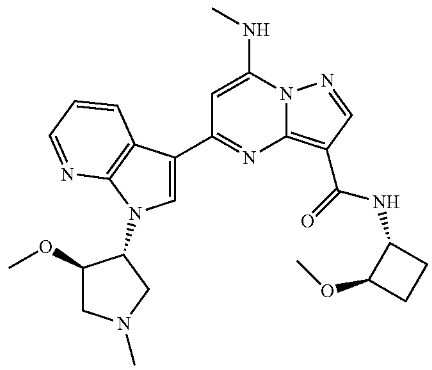 [SMILES: CNc1cc(-c2cn([C@@H]3CN(C)C[C@H]3OC)c3ncccc23)nc2c(C(=O)N[C@@H]3CC[C@H]3OC)cnn12] |
| I-648 | 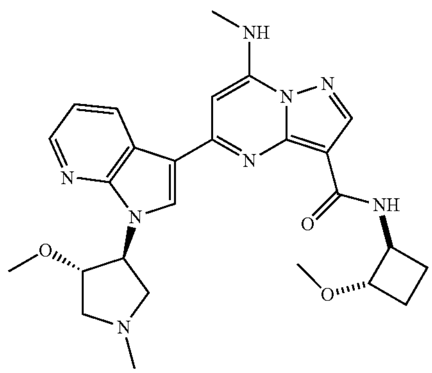 |
| I-649 | 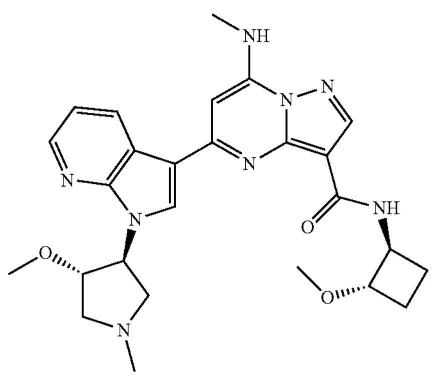 [SMILES: CNc1cc(-c2cn([C@H]3CN(C)C[C@@H]3OC)c3ncccc23)nc2c(C(=O)N[C@H]3CC[C@@H]3OC)cnn12] |
| I-650 | 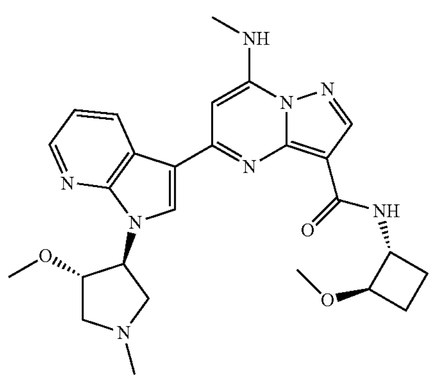 [SMILES: CNc1cc(-c2cn([C@H]3CN(C)C[C@@H]3OC)c3ncccc23)nc2c(C(=O)N[C@@H]3CC[C@H]3OC)cnn12] |

TABLE 1-continued

| Selected Compounds | |
|---|---|
| Number | Structure |
| I-651 | |
| I-652 | |
| I-653 | |
| I-654 | |

325

TABLE 1-continued

Selected Compounds

| Number | Structure |
|---|---|
| I-655 | 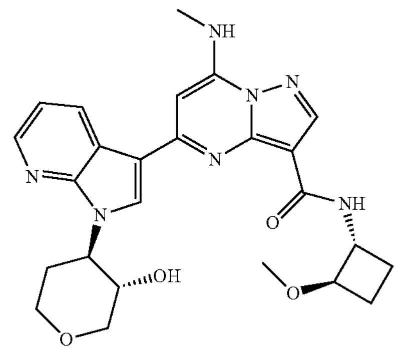 [SMILES: CNc1cc(-c2cn([C@@H]3CCOC[C@H]3O)c3ncccc23)nc2c(C(=O)N[C@@H]3CC[C@H]3OC)cnn12] |
| I-656 | 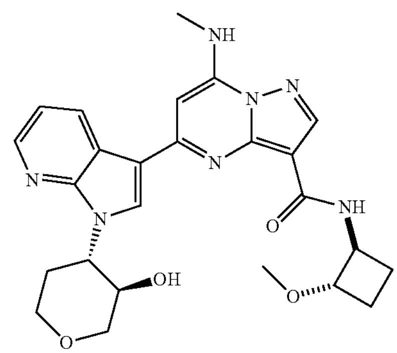 |
| I-657 | 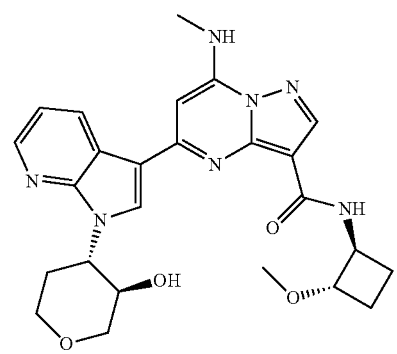 [SMILES: CNc1cc(-c2cn([C@H]3CCOC[C@@H]3O)c3ncccc23)nc2c(C(=O)N[C@H]3CC[C@@H]3OC)cnn12] |
| I-658 | 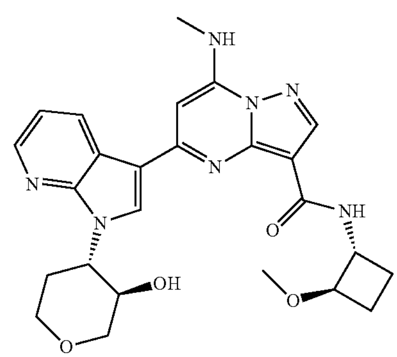 [SMILES: CNc1cc(-c2cn([C@H]3CCOC[C@@H]3O)c3ncccc23)nc2c(C(=O)N[C@@H]3CC[C@H]3OC)cnn12] |

326

TABLE 1-continued

| Selected Compounds | |
|---|---|
| Number | Structure |
| I-659 | |
| I-660 | |
| I-661 | |
| I-662 | |

TABLE 1-continued
| Selected Compounds | |
|---|---|
| Number | Structure |
| I-663 | 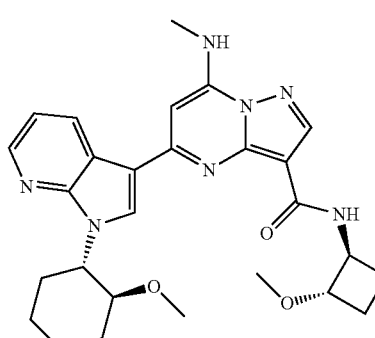 |
| I-664 | 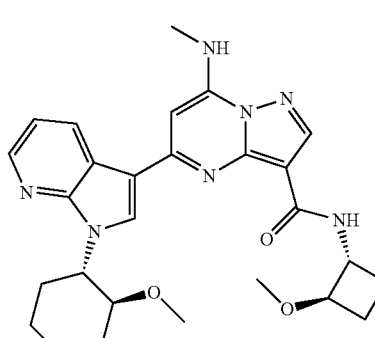 |
| I-665 | 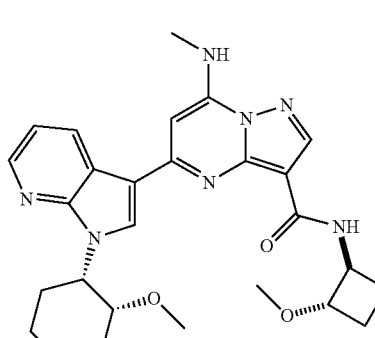 |
| I-666 | 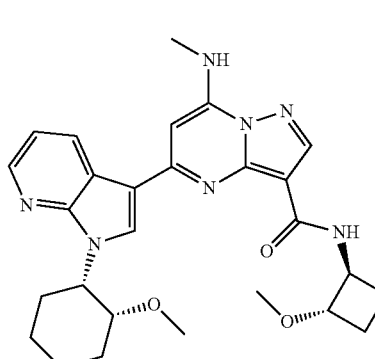 |

TABLE 1-continued

Selected Compounds

| Number | Structure |
|---|---|
| I-667 | 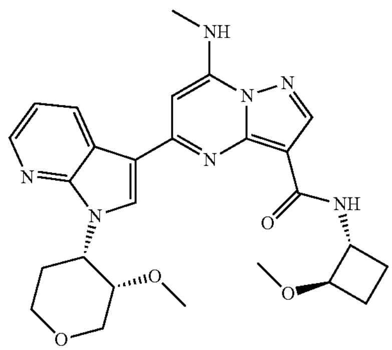 [SMILES: CNc1cc(-c2cn([C@H]3CCOC[C@H]3OC)c3ncccc23)nc2c(C(=O)N[C@@H]3CC[C@H]3OC)cnn12] |
| I-668 | 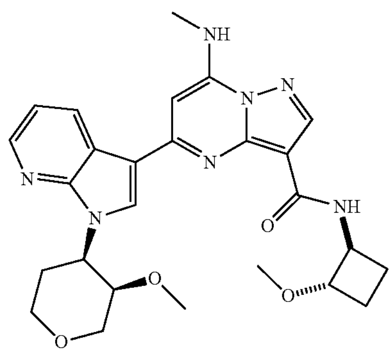 |
| I-669 | 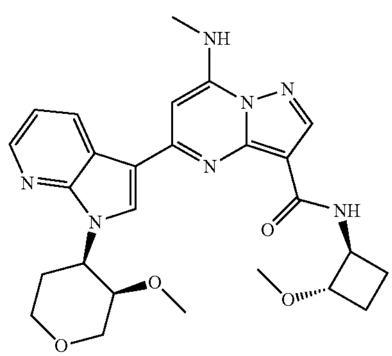 [SMILES: CNc1cc(-c2cn([C@@H]3CCOC[C@@H]3OC)c3ncccc23)nc2c(C(=O)N[C@H]3CC[C@@H]3OC)cnn12] |
| I-670 | 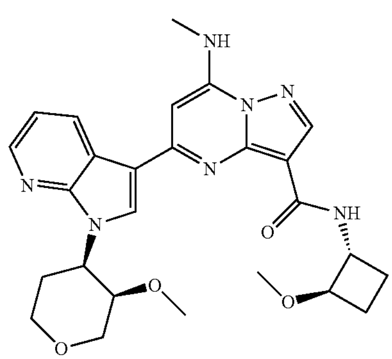 [SMILES: CNc1cc(-c2cn([C@@H]3CCOC[C@@H]3OC)c3ncccc23)nc2c(C(=O)N[C@@H]3CC[C@H]3OC)cnn12] |

TABLE 1-continued

| Selected Compounds | |
|---|---|
| Number | Structure |
| I-671 | |
| I-672 | |
| I-673 | |
| I-674 | |

TABLE 1-continued
Selected Compounds
| Number | Structure |
|---|---|
| I-675 | 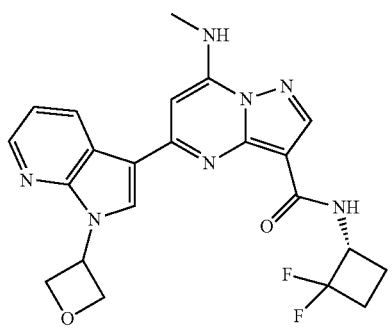 [SMILES: CNc1cc(-c2cn(C3COC3)c3ncccc23)nc2c(C(=O)N[C@@H]3CCC3(F)F)cnn12] |
| I-676 | 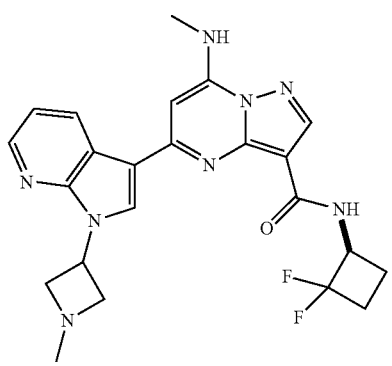 |
| I-677 | 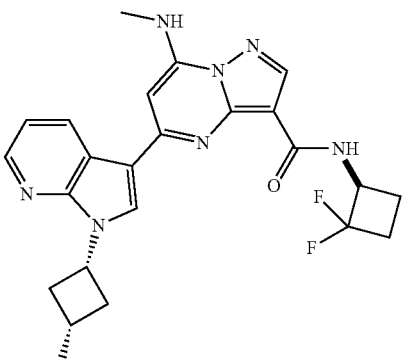 |
| I-678 | 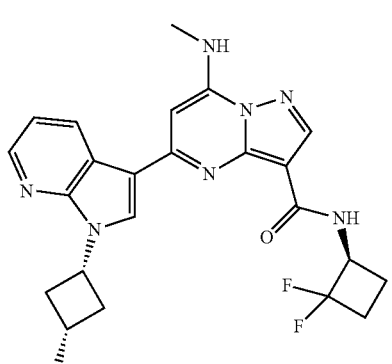 |

US 12,221,453 B2
337                                                                 338
TABLE 1-continued
| Selected Compounds | |
|---|---|
| Number | Structure |
| I-679 | 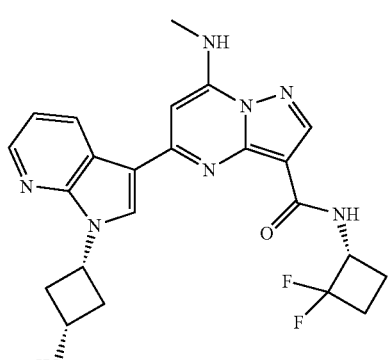 |
| I-680 | 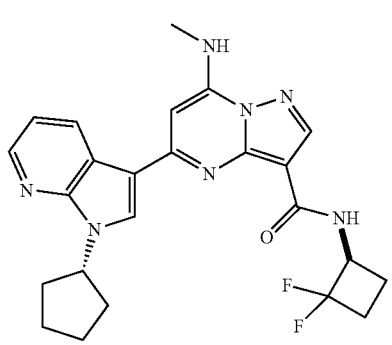 |
| I-681 | 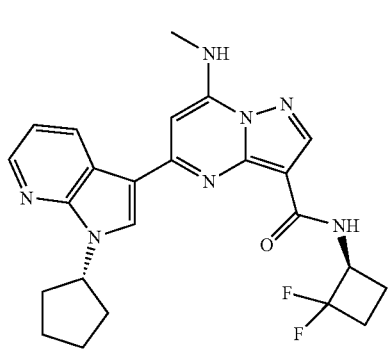 |
| I-682 | 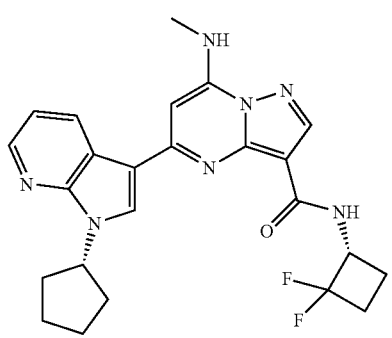 |

TABLE 1-continued

| Selected Compounds | |
|---|---|
| Number | Structure |

I-683

I-684

I-685

I-686

341
342
TABLE 1-continued
| Selected Compounds | |
|---|---|
| Number | Structure |
| I-687 | 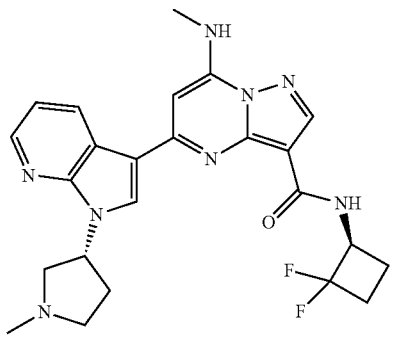 [SMILES: CNc1cc(-c2cn([C@@H]3CCN(C)C3)c3ncccc23)nc2c(C(=O)N[C@H]3CCC3(F)F)cnn12] |
| I-688 | 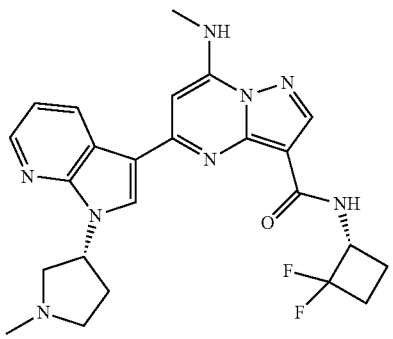 [SMILES: CNc1cc(-c2cn([C@@H]3CCN(C)C3)c3ncccc23)nc2c(C(=O)N[C@@H]3CCC3(F)F)cnn12] |
| I-689 | 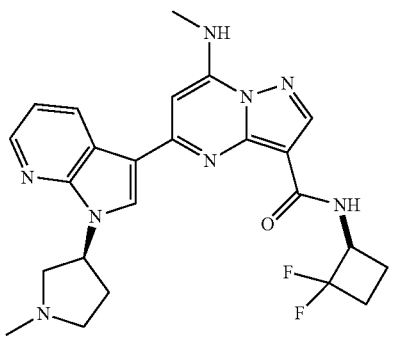 |
| I-690 | 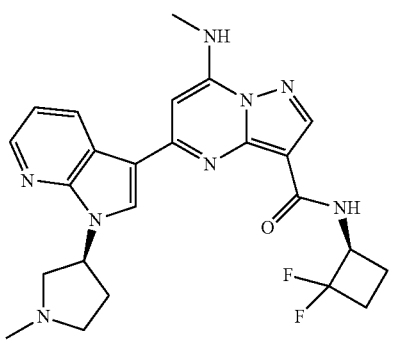 [SMILES: CNc1cc(-c2cn([C@H]3CCN(C)C3)c3ncccc23)nc2c(C(=O)N[C@H]3CCC3(F)F)cnn12] |

TABLE 1-continued

Selected Compounds

| Number | Structure |
|---|---|
| I-691 | 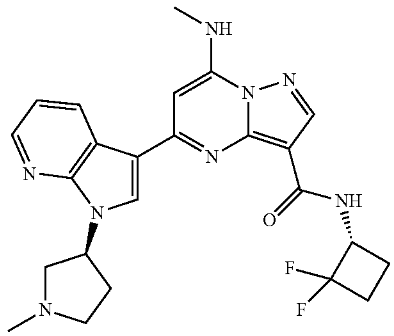 [SMILES: CNc1cc(-c2cn([C@H]3CCN(C)C3)c3ncccc23)nc2c(C(=O)N[C@@H]3CCC3(F)F)cnn12] |
| I-692 | 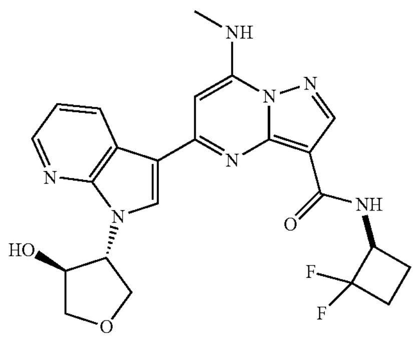 |
| I-693 | 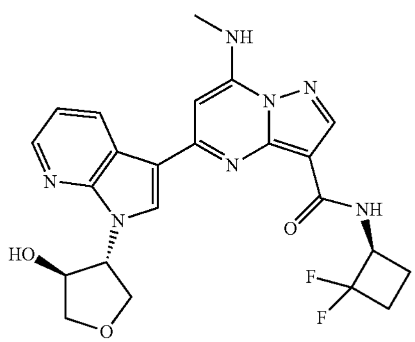 [SMILES: CNc1cc(-c2cn([C@@H]3COC[C@H]3O)c3ncccc23)nc2c(C(=O)N[C@H]3CCC3(F)F)cnn12] |
| I-694 | 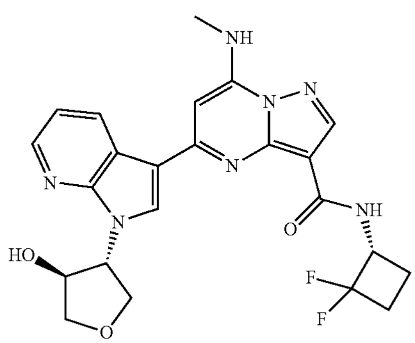 [SMILES: CNc1cc(-c2cn([C@@H]3COC[C@H]3O)c3ncccc23)nc2c(C(=O)N[C@@H]3CCC3(F)F)cnn12] |

TABLE 1-continued

| Number | Structure |
|---|---|
| I-695 | 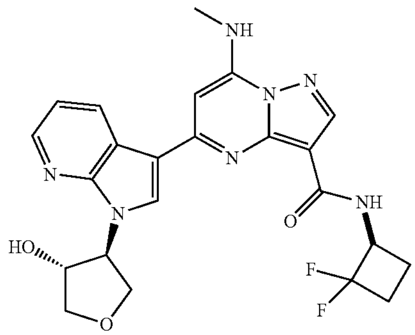 |
| I-696 | 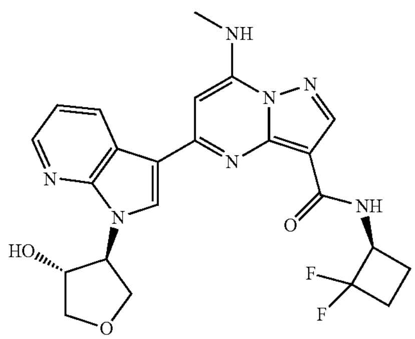 [SMILES: CNc1cc(-c2cn([C@H]3COC[C@@H]3O)c3ncccc23)nc2c(C(=O)N[C@H]3CCC3(F)F)cnn12] |
| I-697 | 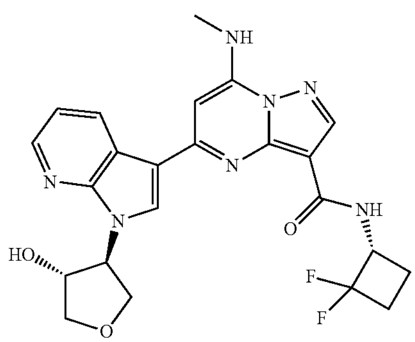 [SMILES: CNc1cc(-c2cn([C@H]3COC[C@@H]3O)c3ncccc23)nc2c(C(=O)N[C@@H]3CCC3(F)F)cnn12] |
| I-698 | 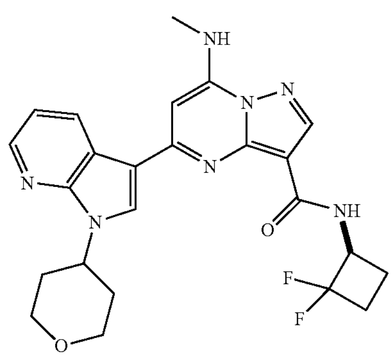 |

TABLE 1-continued
Selected Compounds
| Number | Structure |
|--------|-----------|
| I-699 | 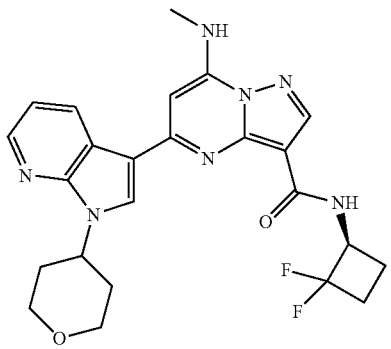 [SMILES: CNc1cc(-c2cn(C3CCOCC3)c3ncccc23)nc2c(C(=O)N[C@H]3CCC3(F)F)cnn12] |
| I-700 | 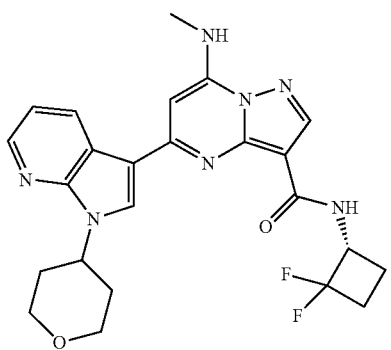 [SMILES: CNc1cc(-c2cn(C3CCOCC3)c3ncccc23)nc2c(C(=O)N[C@@H]3CCC3(F)F)cnn12] |
| I-701 | 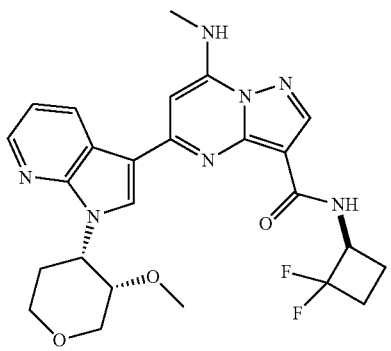 |
| I-702 | 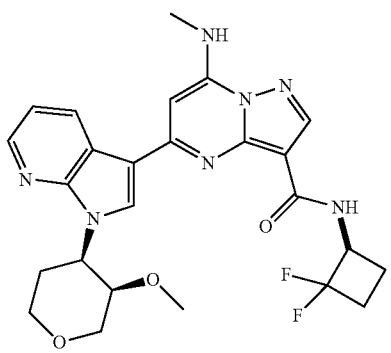 |

TABLE 1-continued
Selected Compounds
| Number | Structure |
|---|---|
| I-703 | 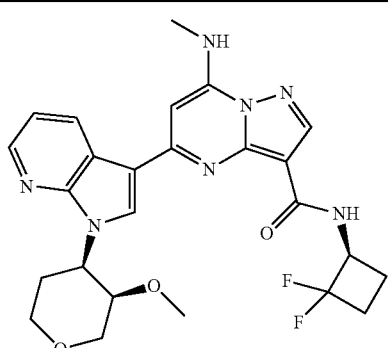 |
| I-704 | 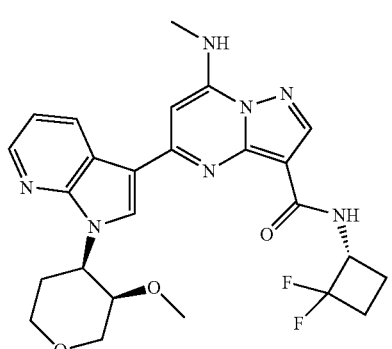 |
| I-705 | 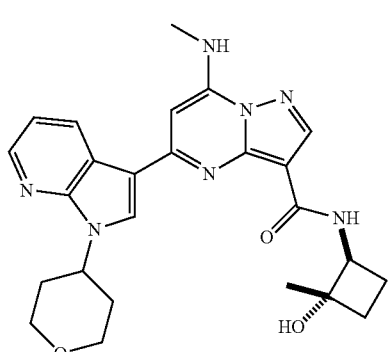 |
| I-706 | 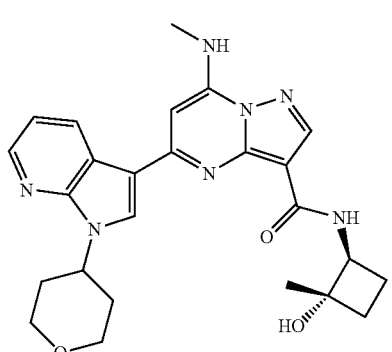 |

TABLE 1-continued

| Selected Compounds | |
|---|---|
| Number | Structure |

I-707

I-708

I-709

I-710

TABLE 1-continued
| Number | Structure |
|---|---|
| I-711 | 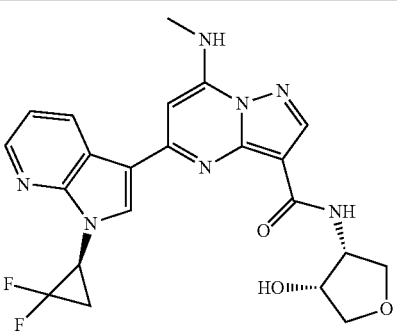 [SMILES: CNc1cc(-c2cn([C@H]3CC3(F)F)c3ncccc23)nc2c(C(=O)N[C@@H]3COC[C@@H]3O)cnn12] |
| I-712 | 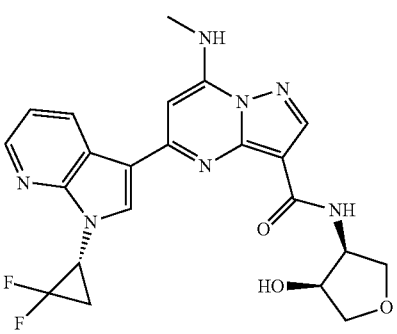 [SMILES: CNc1cc(-c2cn([C@@H]3CC3(F)F)c3ncccc23)nc2c(C(=O)N[C@H]3COC[C@H]3O)cnn12] |
| I-713 | 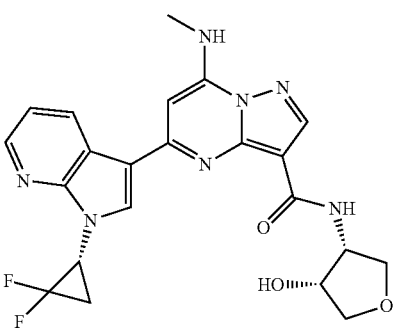 [SMILES: CNc1cc(-c2cn([C@@H]3CC3(F)F)c3ncccc23)nc2c(C(=O)N[C@@H]3COC[C@@H]3O)cnn12] |
| I-714 | 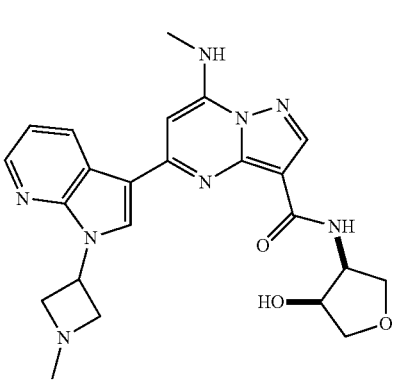 |

TABLE 1-continued
Selected Compounds
| Number | Structure |
|---|---|
| I-715 | 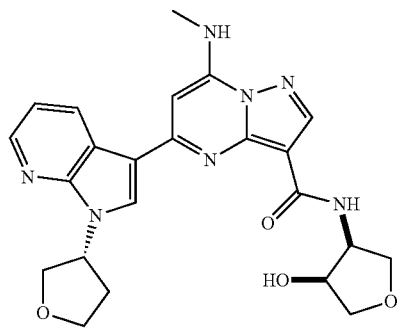 |
| I-716 | 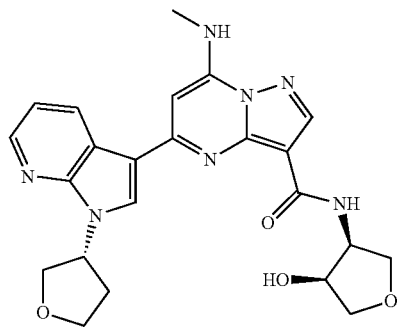 [SMILES: CNc1cc(-c2cn([C@@H]3CCOC3)c3ncccc23)nc2c(C(=O)N[C@H]3COC[C@H]3O)cnn12] |
| I-717 | 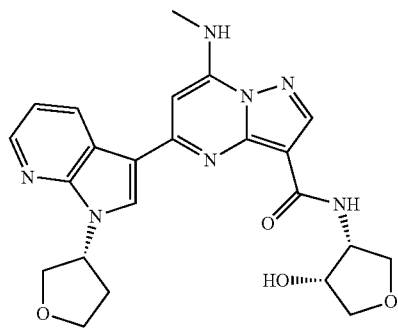 [SMILES: CNc1cc(-c2cn([C@@H]3CCOC3)c3ncccc23)nc2c(C(=O)N[C@@H]3COC[C@@H]3O)cnn12] |
| I-718 | 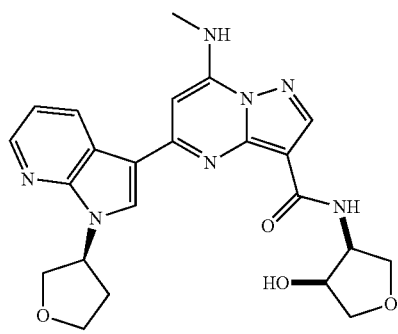 |

TABLE 1-continued
| Selected Compounds | |
|---|---|
| Number | Structure |
| I-719 | 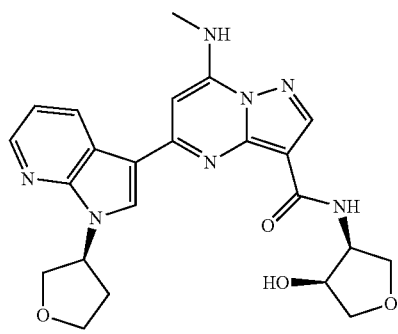 [SMILES: CNc1cc(-c2cn([C@H]3CCOC3)c3ncccc23)nc2c(C(=O)N[C@H]3COC[C@H]3O)cnn12] |
| I-720 | 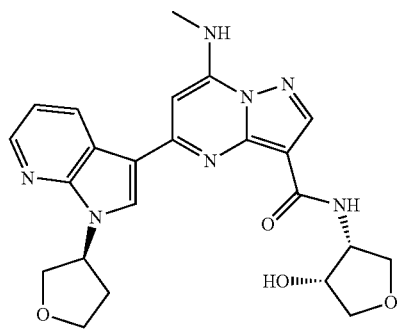 [SMILES: CNc1cc(-c2cn([C@H]3CCOC3)c3ncccc23)nc2c(C(=O)N[C@@H]3COC[C@@H]3O)cnn12] |
| I-721 | 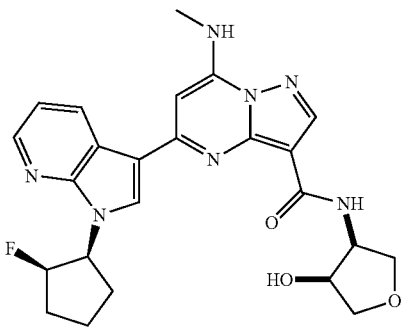 |
| I-722 | 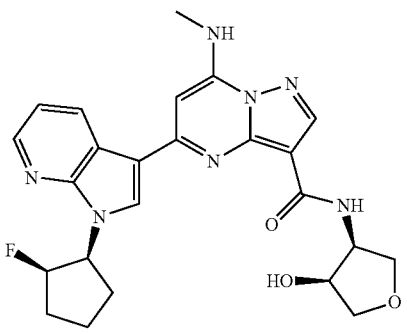 [SMILES: CNc1cc(-c2cn([C@H]3CCC[C@H]3F)c3ncccc23)nc2c(C(=O)N[C@H]3COC[C@H]3O)cnn12] |

TABLE 1-continued

| Selected Compounds | |
|---|---|
| Number | Structure |
| I-723 | |
| I-724 | |
| I-725 | |
| I-726 | |

TABLE 1-continued
| Number | Structure |
|---|---|
| I-727 | 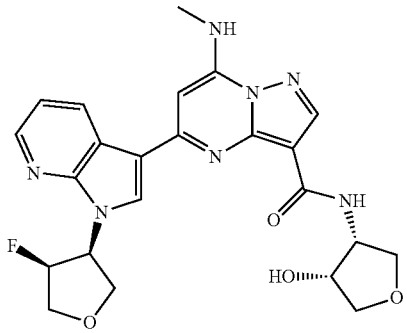 [SMILES: CNc1cc(-c2cn([C@H]3COC[C@H]3F)c3ncccc23)nc2c(C(=O)N[C@@H]3COC[C@@H]3O)cnn12] |
| I-728 | 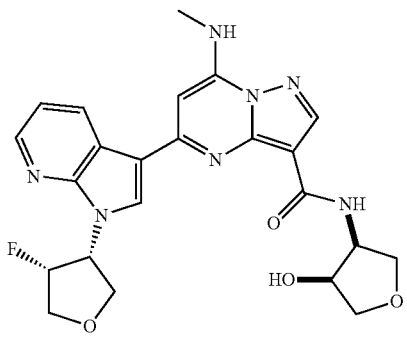 |
| I-729 | 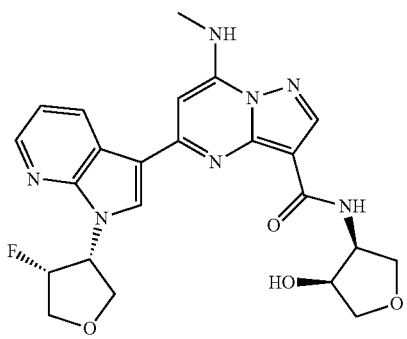 [SMILES: CNc1cc(-c2cn([C@@H]3COC[C@@H]3F)c3ncccc23)nc2c(C(=O)N[C@H]3COC[C@H]3O)cnn12] |
| I-730 | 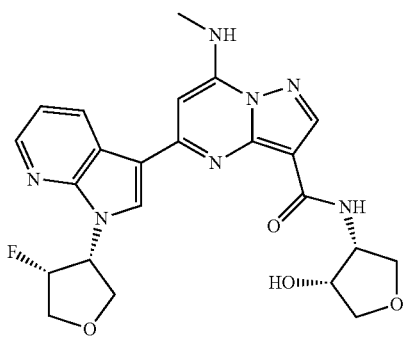 [SMILES: CNc1cc(-c2cn([C@@H]3COC[C@@H]3F)c3ncccc23)nc2c(C(=O)N[C@@H]3COC[C@@H]3O)cnn12] |

TABLE 1-continued
| Selected Compounds | |
|---|---|
| Number | Structure |
| I-731 | 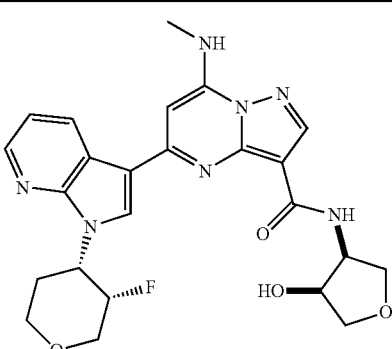 |
| I-732 | 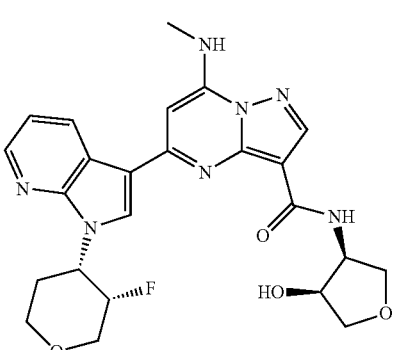 |
| I-733 | 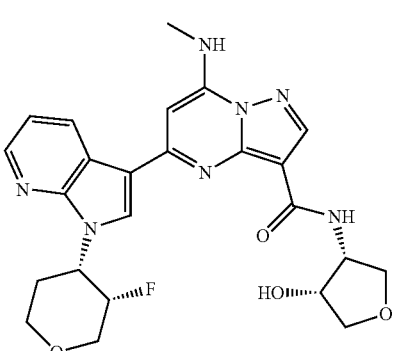 |
| I-734 | 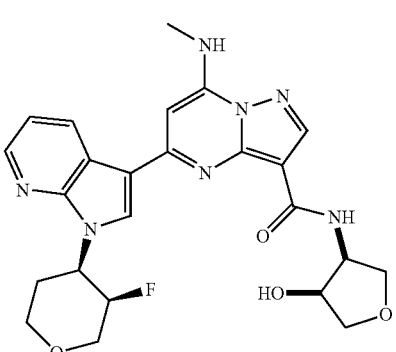 |

TABLE 1-continued
Selected Compounds
| Number | Structure |
|---|---|
| I-735 | 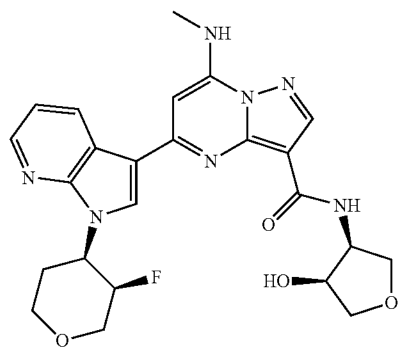 [SMILES: CNc1cc(-c2cn([C@@H]3CCOC[C@@H]3F)c3ncccc23)nc2c(C(=O)N[C@H]3COC[C@H]3O)cnn12] |
| I-736 | 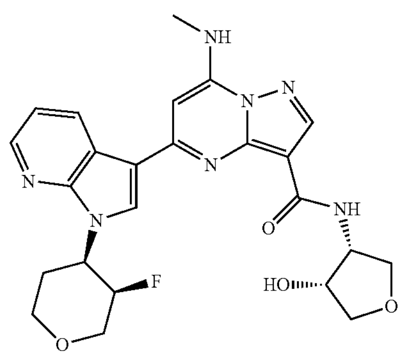 [SMILES: CNc1cc(-c2cn([C@@H]3CCOC[C@@H]3F)c3ncccc23)nc2c(C(=O)N[C@@H]3COC[C@@H]3O)cnn12] |
| I-737 | 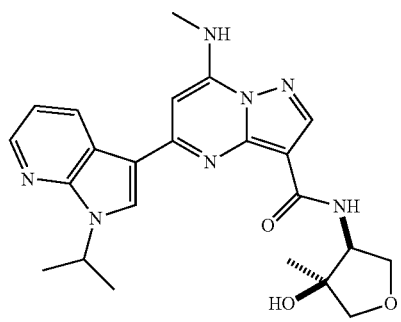 |
| I-738 | 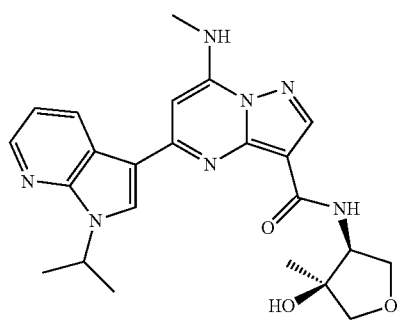 [SMILES: CNc1cc(-c2cn(C(C)C)c3ncccc23)nc2c(C(=O)N[C@H]3COC[C@@]3(C)O)cnn12] |

TABLE 1-continued

Selected Compounds

| Number | Structure |
|---|---|
| I-739 | 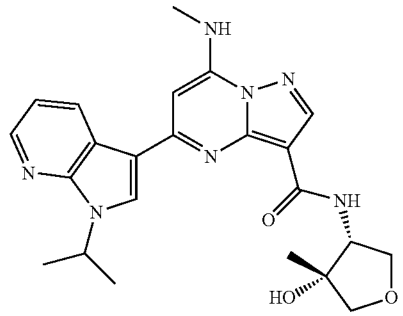 [SMILES: CNc1cc(-c2cn(C(C)C)c3ncccc23)nc2c(C(=O)N[C@@H]3COC[C@]3(C)O)cnn12] |
| I-740 | 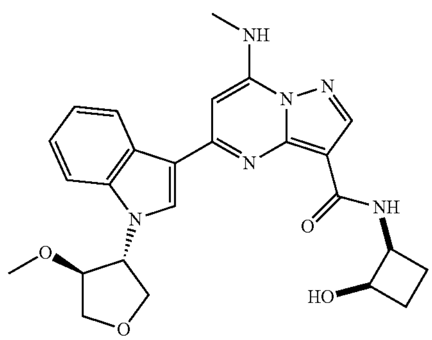 |
| I-741 | 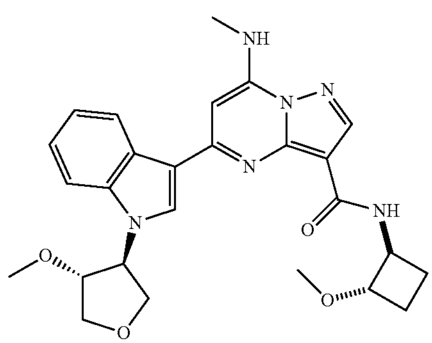 |
| I-742 | 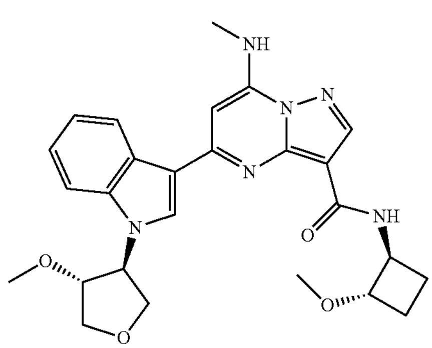 [SMILES: CNc1cc(-c2cn([C@H]3COC[C@@H]3OC)c3ccccc23)nc2c(C(=O)N[C@H]3CC[C@@H]3OC)cnn12] |

TABLE 1-continued

| Number | Structure |
|---|---|
| I-743 | 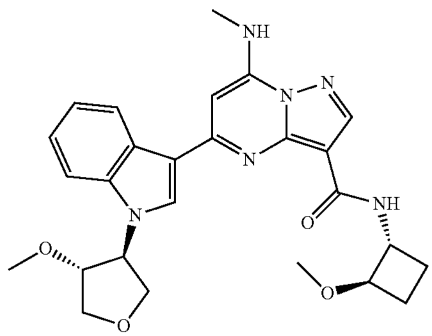 [SMILES: CNc1cc(-c2cn([C@H]3COC[C@@H]3OC)c3ccccc23)nc2c(C(=O)N[C@@H]3CC[C@H]3OC)cnn12] |
| I-744 | 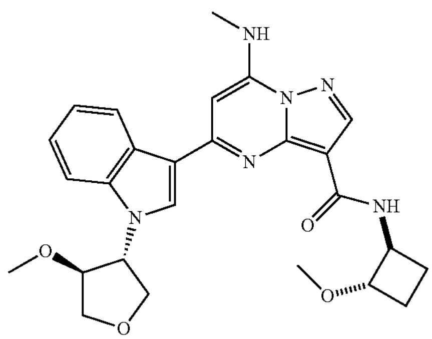 |
| I-745 | 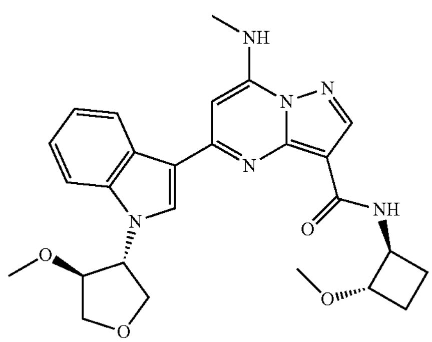 [SMILES: CNc1cc(-c2cn([C@@H]3COC[C@H]3OC)c3ccccc23)nc2c(C(=O)N[C@H]3CC[C@@H]3OC)cnn12] |
| I-746 | 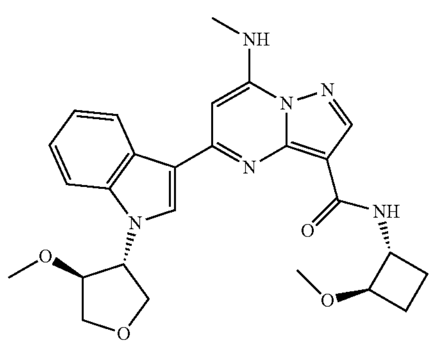 [SMILES: CNc1cc(-c2cn([C@@H]3COC[C@H]3OC)c3ccccc23)nc2c(C(=O)N[C@@H]3CC[C@H]3OC)cnn12] |

TABLE 1-continued
Selected Compounds
| Number | Structure |
|---|---|
| I-747 | 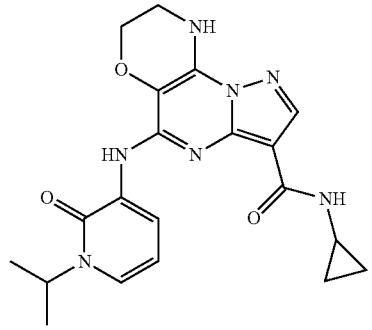 [SMILES: CC(C)n1cccc(Nc2nc3c(C(=O)NC4CC4)cnn3c3c2OCCN3)c1=O] |
| I-748 | 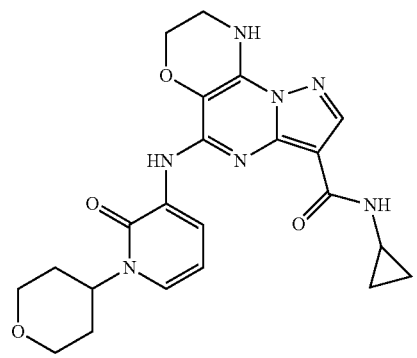 [SMILES: O=C(NC1CC1)c1cnn2c3c(c(Nc4cccn(C5CCOCC5)c4=O)nc12)OCCN3] |
| I-749 | 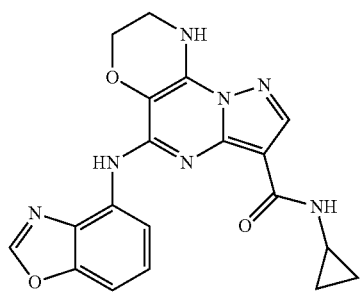 [SMILES: O=C(NC1CC1)c1cnn2c3c(c(Nc4cccc5ocnc45)nc12)OCCN3] |
| I-750 | 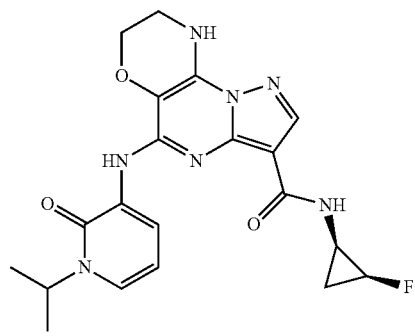 [SMILES: CC(C)n1cccc(Nc2nc3c(C(=O)N[C@@H]4C[C@@H]4F)cnn3c3c2OCCN3)c1=O] |

TABLE 1-continued
Selected Compounds
| Number | Structure |
|---|---|
| I-751 | 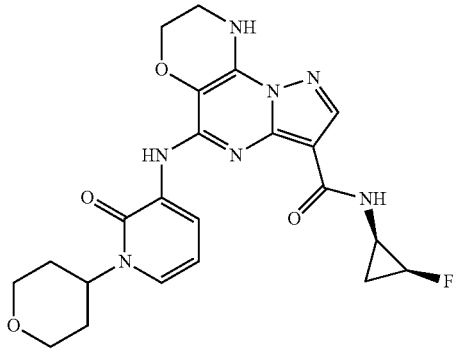 [SMILES: O=C(N[C@@H]1C[C@@H]1F)c1cnn2c3c(c(Nc4cccn(C5CCOCC5)c4=O)nc12)OCCN3] |
| I-752 | 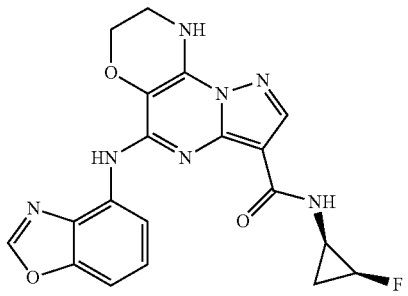 [SMILES: O=C(N[C@@H]1C[C@@H]1F)c1cnn2c3c(c(Nc4cccc5ocnc45)nc12)OCCN3] |
| I-753 | 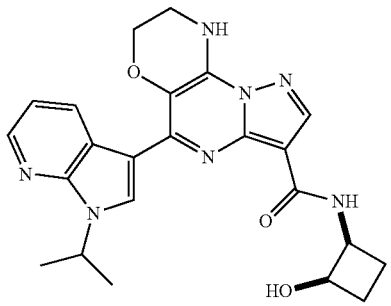 |
| I-754 | 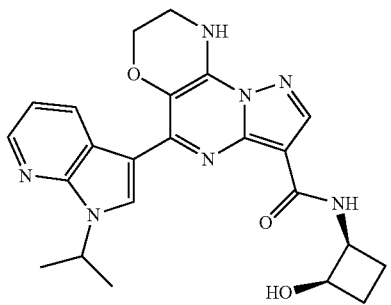 [SMILES: CC(C)n1cc(-c2nc3c(C(=O)N[C@H]4CC[C@H]4O)cnn3c3c2OCCN3)c2cccnc21] |

TABLE 1-continued

| Selected Compounds | |
|---|---|
| Number | Structure |
| I-755 | |
| I-756 | |
| I-757 | |
| I-758 | |

TABLE 1-continued

| Number | Structure |
|---|---|
| I-759 | 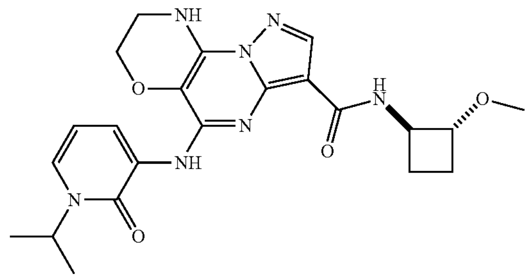 |
| I-760 | 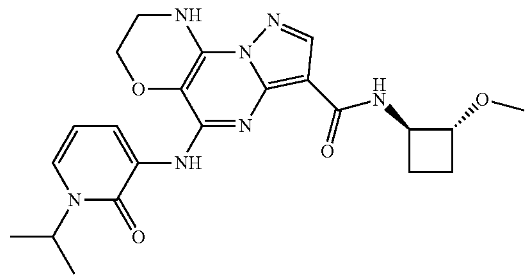 [SMILES: CO[C@@H]1CC[C@H]1NC(=O)c1cnn2c3c(c(Nc4cccn(C(C)C)c4=O)nc12)OCCN3] |
| I-761 | 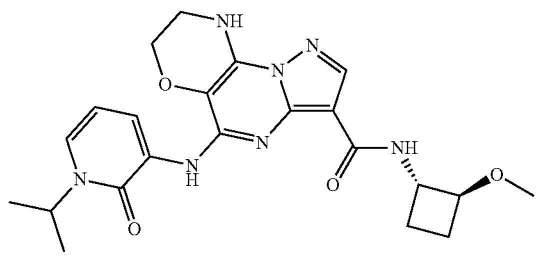 [SMILES: CO[C@H]1CC[C@@H]1NC(=O)c1cnn2c3c(c(Nc4cccn(C(C)C)c4=O)nc12)OCCN3] |
| I-762 | 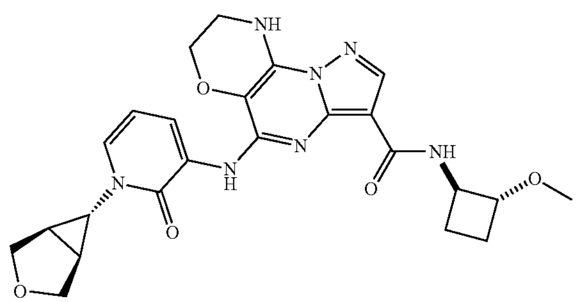 |
| I-763 | 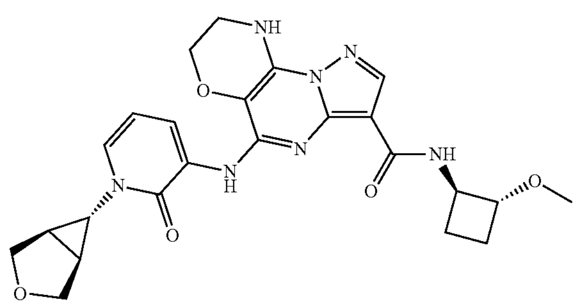 [SMILES: CO[C@@H]1CC[C@H]1NC(=O)c1cnn2c3c(c(Nc4cccn([C@H]5[C@@H]6COC[C@@H]65)c4=O)nc12)OCCN3] |

TABLE 1-continued

| Number | Structure |
|---|---|
| I-764 | 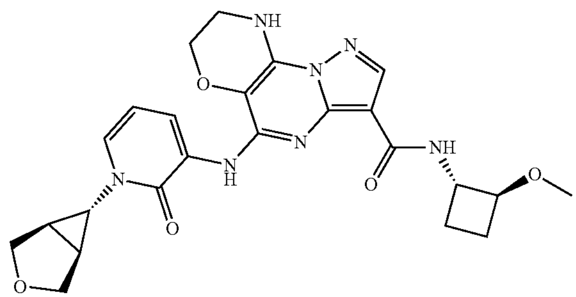 [SMILES: CO[C@H]1CC[C@@H]1NC(=O)c1cnn2c3c(c(Nc4cccn([C@H]5[C@@H]6COC[C@@H]65)c4=O)nc12)OCCN3] |
| I-765 | 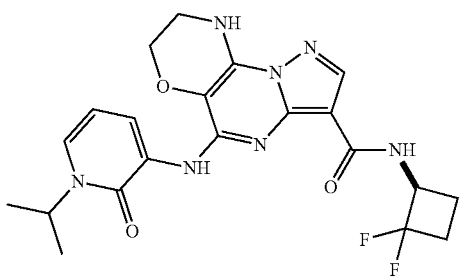 |
| I-766 | 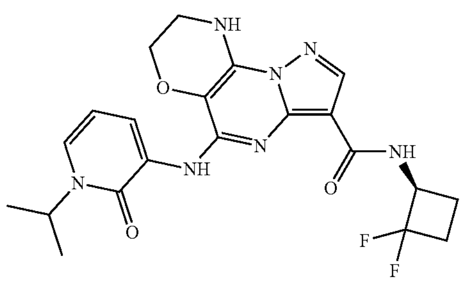 [SMILES: CC(C)n1cccc(Nc2nc3c(C(=O)N[C@H]4CCC4(F)F)cnn3c3c2OCCN3)c1=O] |
| I-767 | 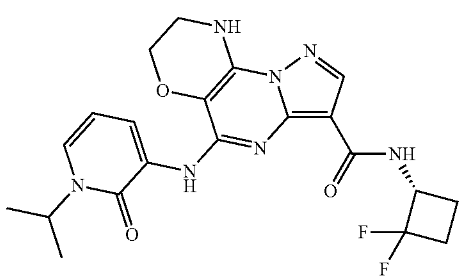 [SMILES: CC(C)n1cccc(Nc2nc3c(C(=O)N[C@@H]4CCC4(F)F)cnn3c3c2OCCN3)c1=O] |
| I-768 | 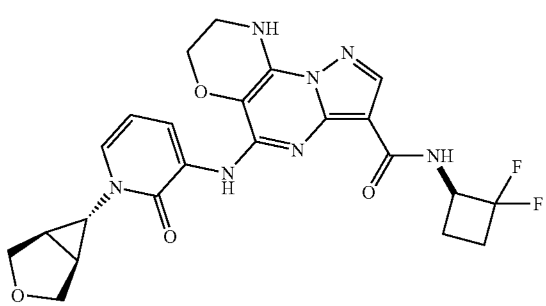 |

TABLE 1-continued

Selected Compounds

| Number | Structure |
|---|---|
| I-769 | 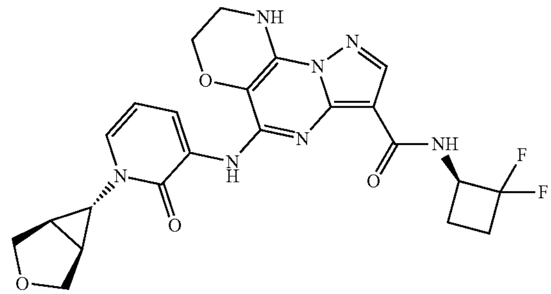 [SMILES: O=C(N[C@@H]1CCC1(F)F)c1cnn2c3c(c(Nc4cccn([C@H]5[C@@H]6COC[C@@H]65)c4=O)nc12)OCCN3] |
| I-770 | 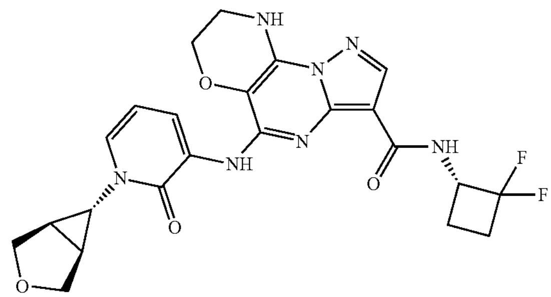 [SMILES: O=C(N[C@H]1CCC1(F)F)c1cnn2c3c(c(Nc4cccn([C@H]5[C@@H]6COC[C@@H]65)c4=O)nc12)OCCN3] |
| I-771 | 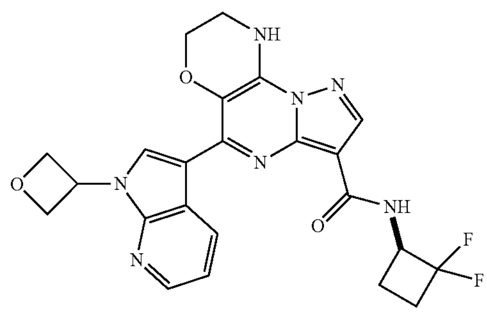 |
| I-772 | 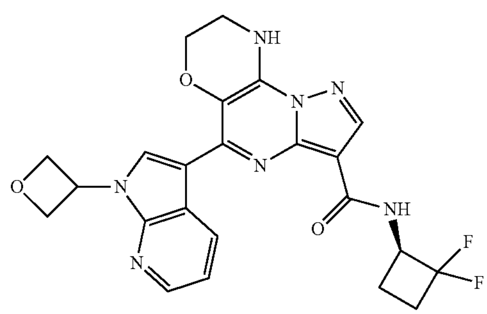 [SMILES: O=C(N[C@@H]1CCC1(F)F)c1cnn2c3c(c(-c4cn(C5COC5)c5ncccc45)nc12)OCCN3] |
| I-773 | 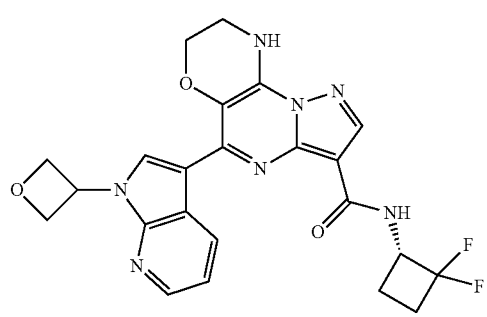 [SMILES: O=C(N[C@H]1CCC1(F)F)c1cnn2c3c(c(-c4cn(C5COC5)c5ncccc45)nc12)OCCN3] |

TABLE 1-continued
Selected Compounds
| Number | Structure |
|---|---|
| I-774 | 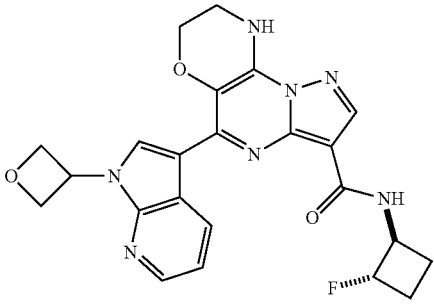 |
| I-775 | 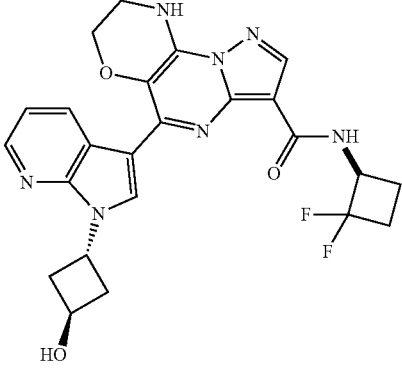 |
| I-776 | 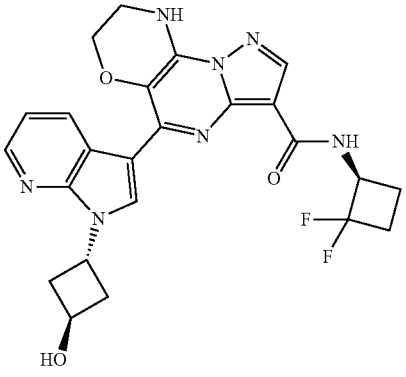 [SMILES: O=C(N[C@H]1CCC1(F)F)c1cnn2c3c(c(-c4cn([C@H]5C[C@H](O)C5)c5ncccc45)nc12)OCCN3] |
| I-777 | 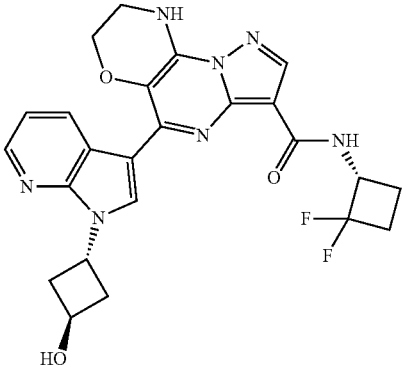 [SMILES: O=C(N[C@@H]1CCC1(F)F)c1cnn2c3c(c(-c4cn([C@H]5C[C@H](O)C5)c5ncccc45)nc12)OCCN3] |

TABLE 1-continued
Selected Compounds
| Number | Structure |
|---|---|
| I-778 | 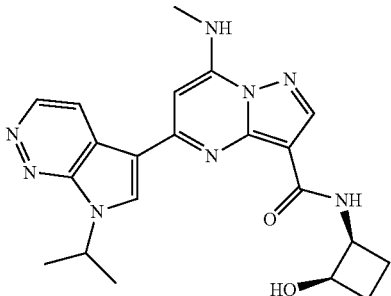 |
| I-779 | 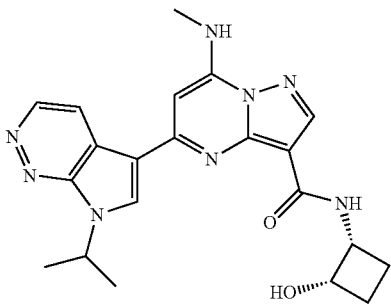 [SMILES: CNc1cc(-c2cn(C(C)C)c3nnccc23)nc2c(C(=O)N[C@@H]3CC[C@@H]3O)cnn12] |
| I-780 | 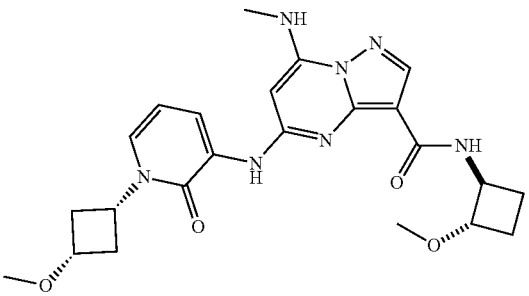 |
| I-781 | 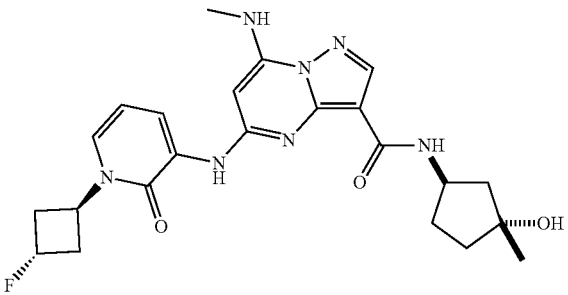 |
| I-782 | 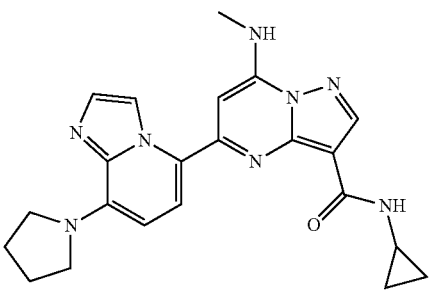 [SMILES: CNc1cc(-c2ccc(N3CCCC3)c3nccn23)nc2c(C(=O)NC3CC3)cnn12] |

TABLE 1-continued

| Number | Structure |
|---|---|
| I-783 | 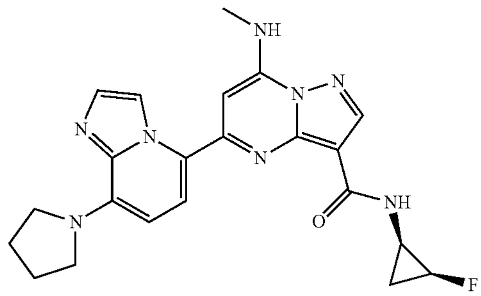 [SMILES: CNc1cc(-c2ccc(N3CCCC3)c3nccn23)nc2c(C(=O)N[C@@H]3C[C@@H]3F)cnn12] |
| I-784 | 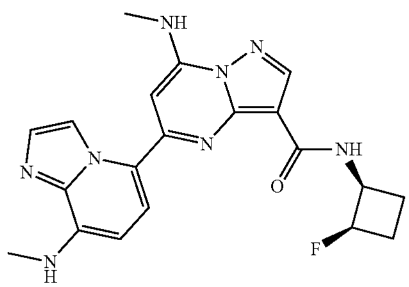 [SMILES: CNc1ccc(-c2cc(NC)n3ncc(C(=O)N[C@H]4CC[C@H]4F)c3n2)n2ccnc12] |
| I-785 | 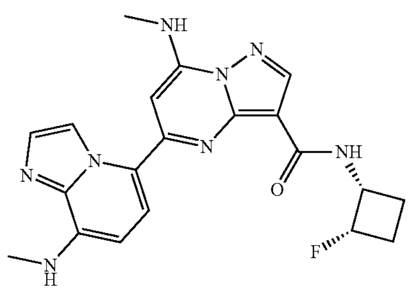 [SMILES: CNc1ccc(-c2cc(NC)n3ncc(C(=O)N[C@@H]4CC[C@@H]4F)c3n2)n2ccnc12] |
| I-786 | 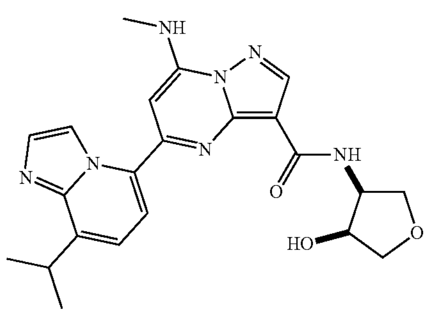 |
| I-787 | 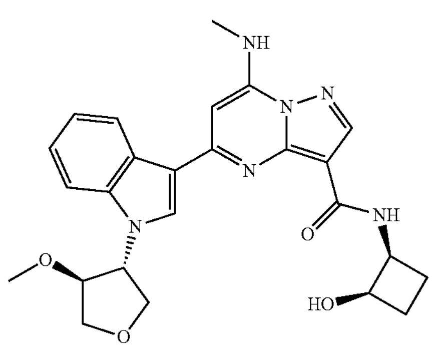 |

TABLE 1-continued
| Selected Compounds | |
|---|---|
| Number | Structure |
| I-788 | 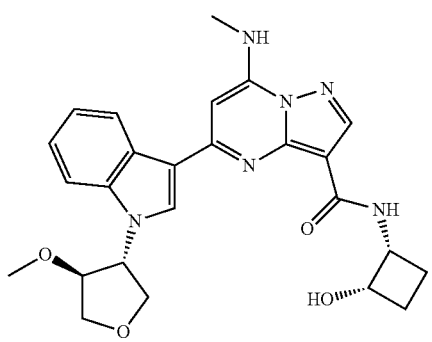 [SMILES: CNc1cc(-c2cn([C@@H]3COC[C@H]3OC)c3ccccc23)nc2c(C(=O)N[C@@H]3CC[C@@H]3O)cnn12] |
| I-789 | 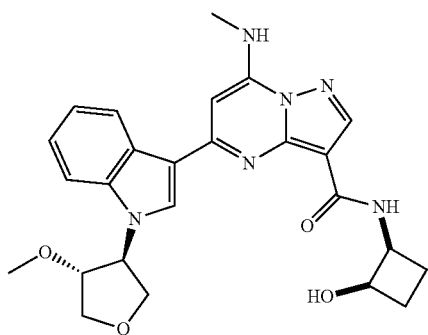 |
| I-790 | 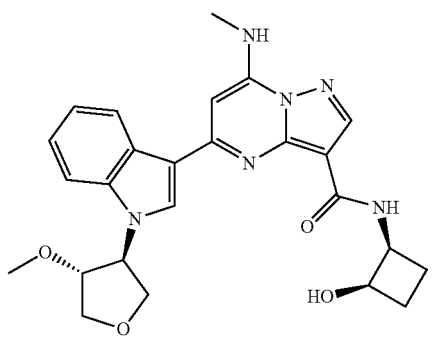 [SMILES: CNc1cc(-c2cn([C@H]3COC[C@@H]3OC)c3ccccc23)nc2c(C(=O)N[C@H]3CC[C@H]3O)cnn12] |
| I-791 | 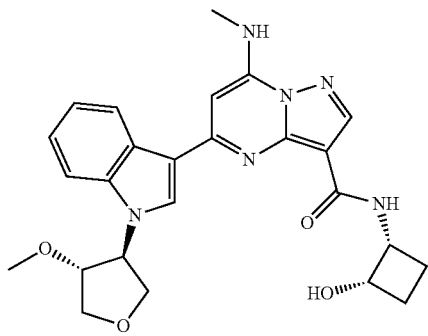 [SMILES: CNc1cc(-c2cn([C@H]3COC[C@@H]3OC)c3ccccc23)nc2c(C(=O)N[C@@H]3CC[C@@H]3O)cnn12] |

TABLE 1-continued

Selected Compounds

| Number | Structure |
|---|---|
| I-792 | 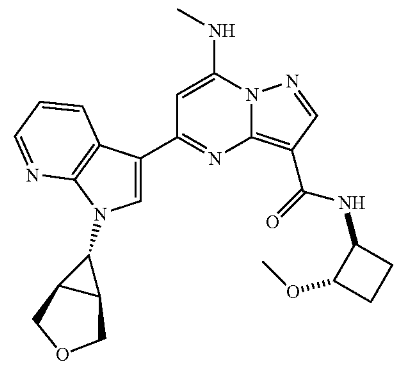 |
| I-793 | 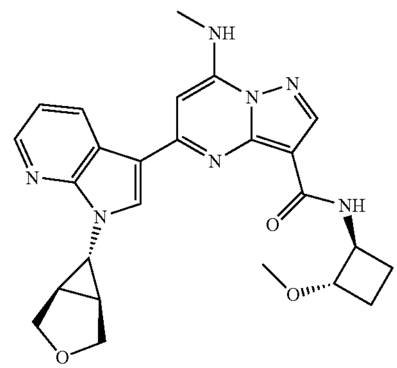 [SMILES: CNc1cc(-c2cn([C@H]3[C@@H]4COC[C@@H]43)c3ncccc23)nc2c(C(=O)N[C@H]3CC[C@@H]3OC)cnn12] |
| I-794 | 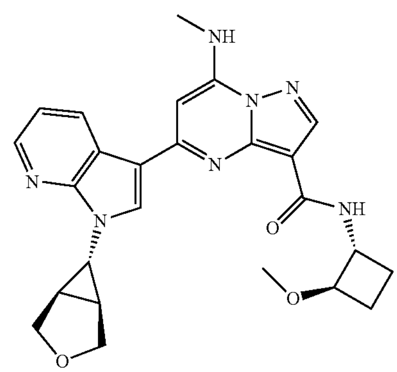 [SMILES: CNc1cc(-c2cn([C@H]3[C@@H]4COC[C@@H]43)c3ncccc23)nc2c(C(=O)N[C@@H]3CC[C@H]3OC)cnn12] |
| I-795 | 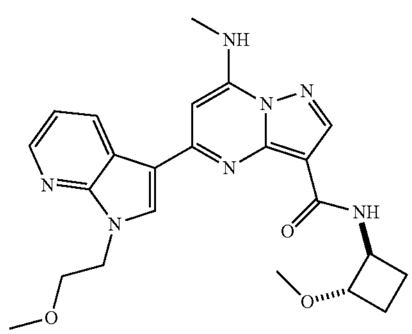 |

TABLE 1-continued
| Number | Structure |
|---|---|
| I-796 | 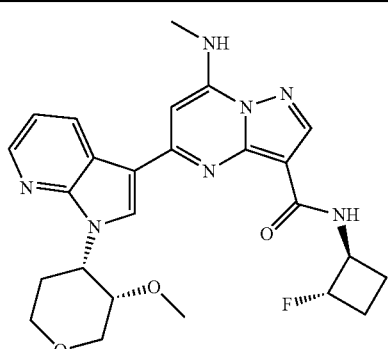 |
| I-797 | 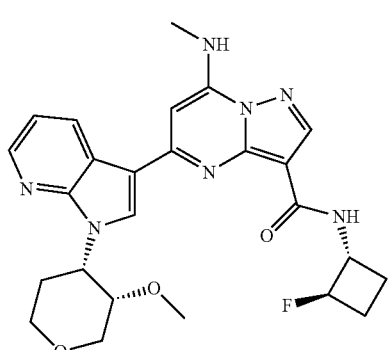 |
| I-798 | 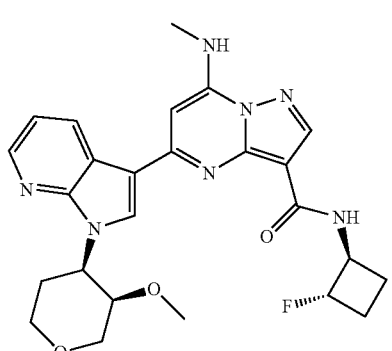 |
| I-799 | 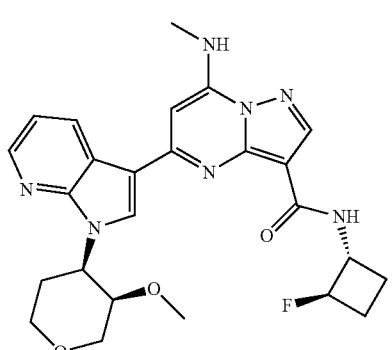 |

TABLE 1-continued

Selected Compounds

| Number | Structure |
|--------|-----------|
| I-800  | 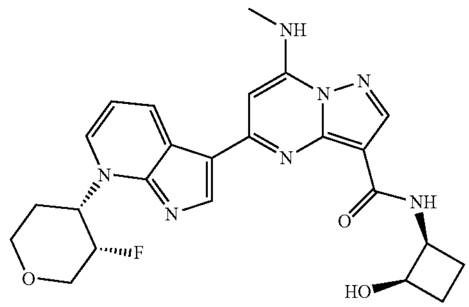 [SMILES: CNc1cc(-c2cnc3n([C@H]4CCOC[C@H]4F)cccc2-3)nc2c(C(=O)N[C@H]3CC[C@H]3O)cnn12]          |
| I-801  | 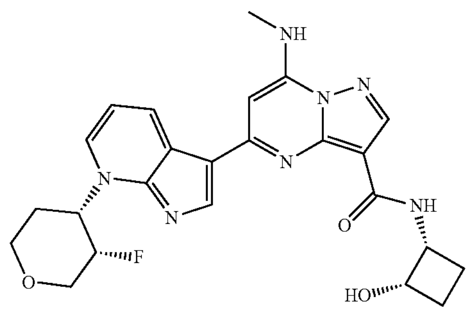 [SMILES: CNc1cc(-c2cnc3n([C@H]4CCOC[C@H]4F)cccc2-3)nc2c(C(=O)N[C@@H]3CC[C@@H]3O)cnn12]          |
| I-802  | 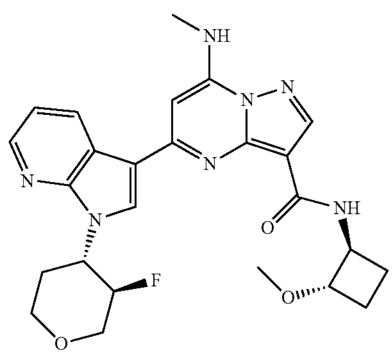 [SMILES: CNc1cc(-c2cn([C@H]3CCOC[C@@H]3F)c3ncccc23)nc2c(C(=O)N[C@H]3CC[C@@H]3OC)cnn12]          |
| I-803  | 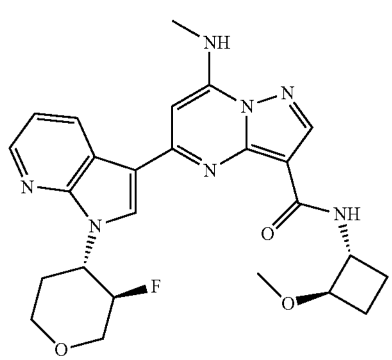 [SMILES: CNc1cc(-c2cn([C@H]3CCOC[C@@H]3F)c3ncccc23)nc2c(C(=O)N[C@@H]3CC[C@H]3OC)cnn12]          |

TABLE 1-continued
Selected Compounds
| Number | Structure |
|---|---|
| I-804 | 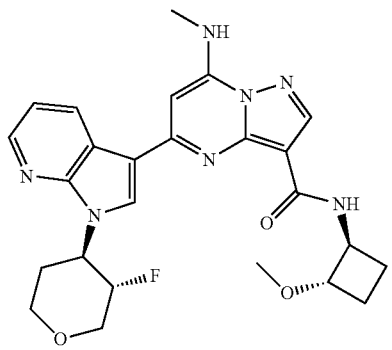 [SMILES: CNc1cc(-c2cn([C@@H]3CCOC[C@H]3F)c3ncccc23)nc2c(C(=O)N[C@H]3CC[C@@H]3OC)cnn12] |
| I-805 | 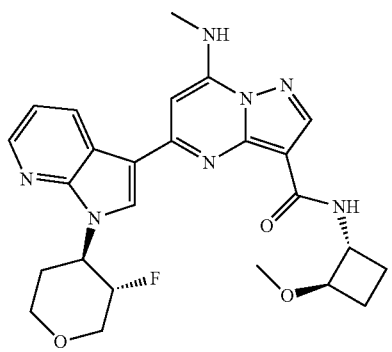 [SMILES: CNc1cc(-c2cn([C@@H]3CCOC[C@H]3F)c3ncccc23)nc2c(C(=O)N[C@@H]3CC[C@H]3OC)cnn12] |
| I-806 | 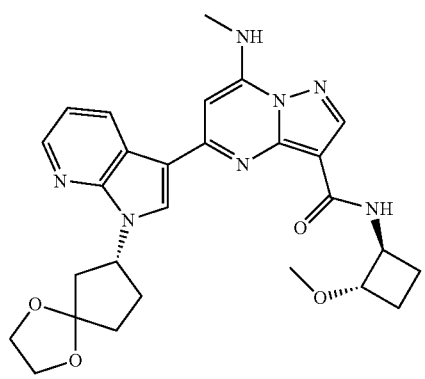 [SMILES: CNc1cc(-c2cn([C@@H]3CCC4(C3)OCCO4)c3ncccc23)nc2c(C(=O)N[C@H]3CC[C@@H]3OC)cnn12] |
| I-807 | 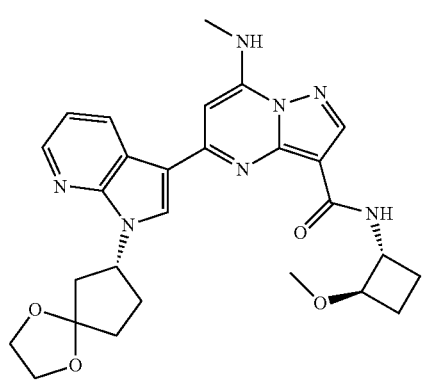 [SMILES: CNc1cc(-c2cn([C@@H]3CCC4(C3)OCCO4)c3ncccc23)nc2c(C(=O)N[C@@H]3CC[C@H]3OC)cnn12] |

TABLE 1-continued

Selected Compounds

| Number | Structure |
|---|---|
| I-808 | 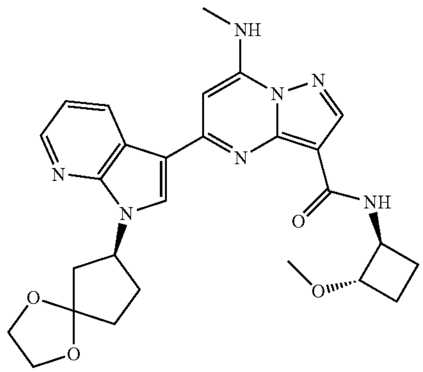 [SMILES: CNc1cc(-c2cn([C@H]3CCC4(C3)OCCO4)c3ncccc23)nc2c(C(=O)N[C@H]3CC[C@@H]3OC)cnn12] |
| I-809 | 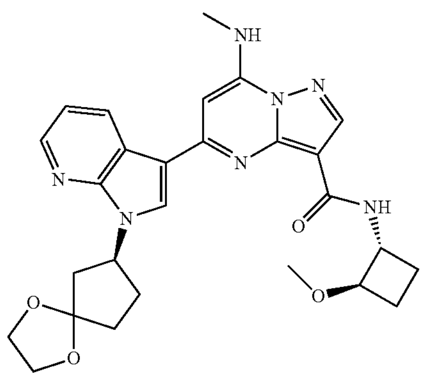 [SMILES: CNc1cc(-c2cn([C@H]3CCC4(C3)OCCO4)c3ncccc23)nc2c(C(=O)N[C@@H]3CC[C@H]3OC)cnn12] |
| I-810 | 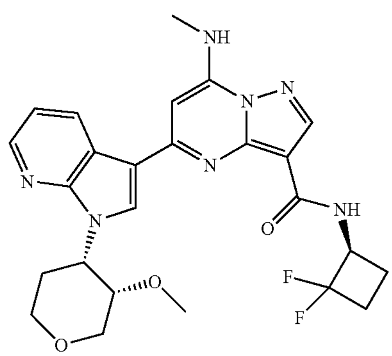 [SMILES: CNc1cc(-c2cn([C@H]3CCOC[C@H]3OC)c3ncccc23)nc2c(C(=O)N[C@H]3CCC3(F)F)cnn12] |
| I-811 | 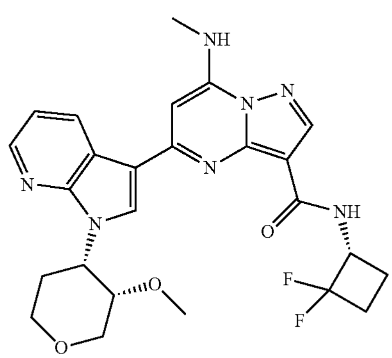 [SMILES: CNc1cc(-c2cn([C@H]3CCOC[C@H]3OC)c3ncccc23)nc2c(C(=O)N[C@@H]3CCC3(F)F)cnn12] |

TABLE 1-continued

Selected Compounds

| Number | Structure |
|---|---|
| I-812 | 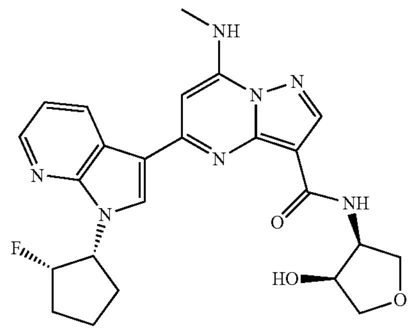 [SMILES: CNc1cc(-c2cn([C@@H]3CCC[C@@H]3F)c3ncccc23)nc2c(C(=O)N[C@H]3COC[C@H]3O)cnn12] |
| I-813 | 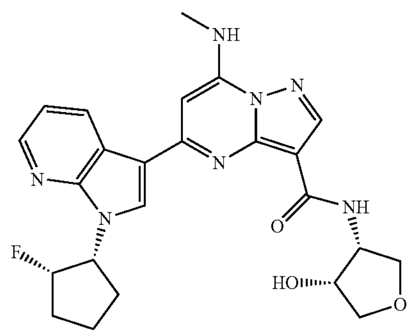 [SMILES: CNc1cc(-c2cn([C@@H]3CCC[C@@H]3F)c3ncccc23)nc2c(C(=O)N[C@@H]3COC[C@@H]3O)cnn12] |
| I-814 | 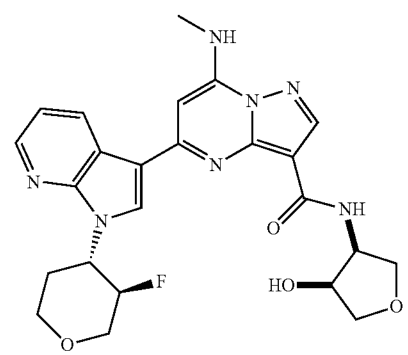 |
| I-815 | 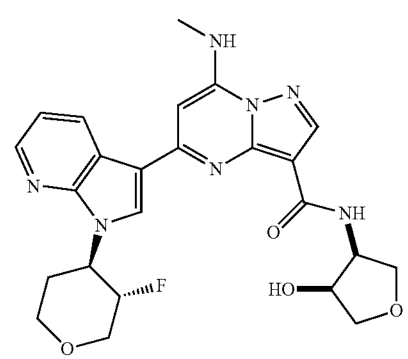 |

TABLE 1-continued

| Number | Structure |
|---|---|
| I-816 | 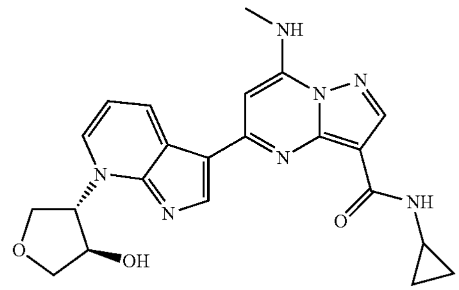 [SMILES: CNc1cc(-c2cnc3n([C@H]4COC[C@@H]4O)cccc2-3)nc2c(C(=O)NC3CC3)cnn12] |
| I-817 | 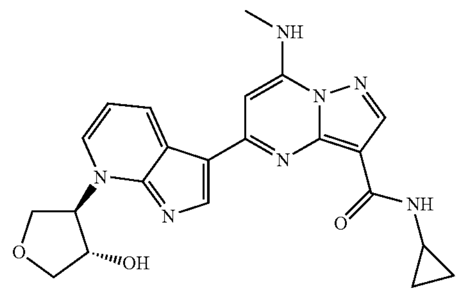 [SMILES: CNc1cc(-c2cnc3n([C@@H]4COC[C@H]4O)cccc2-3)nc2c(C(=O)NC3CC3)cnn12] |
| I-818 | 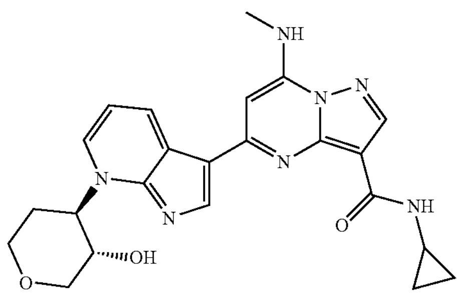 [SMILES: CNc1cc(-c2cnc3n([C@@H]4CCOC[C@H]4O)cccc2-3)nc2c(C(=O)NC3CC3)cnn12] |
| I-819 | 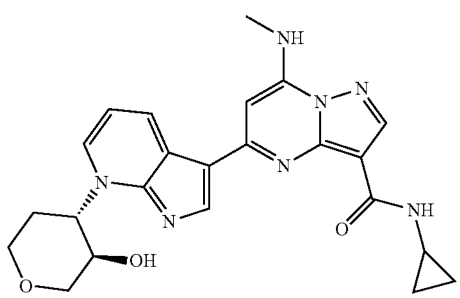 [SMILES: CNc1cc(-c2cnc3n([C@H]4CCOC[C@@H]4O)cccc2-3)nc2c(C(=O)NC3CC3)cnn12] |
| I-820 | 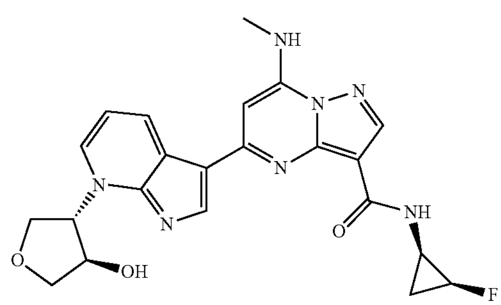 [SMILES: CNc1cc(-c2cnc3n([C@H]4COC[C@@H]4O)cccc2-3)nc2c(C(=O)N[C@@H]3C[C@@H]3F)cnn12] |

TABLE 1-continued
| Selected Compounds | |
|---|---|
| Number | Structure |
| I-821 | 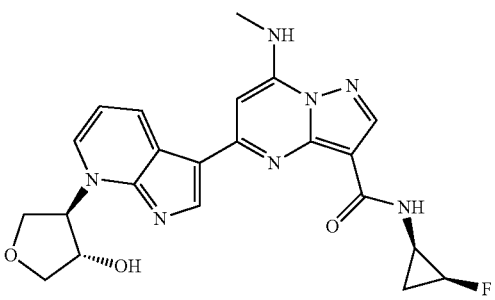 [SMILES: CNc1cc(-c2cnc3n([C@@H]4COC[C@H]4O)cccc2-3)nc2c(C(=O)N[C@@H]3C[C@@H]3F)cnn12] |
| I-822 | 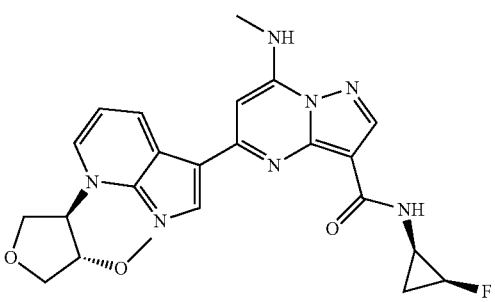 [SMILES: CNc1cc(-c2cnc3n([C@@H]4COC[C@H]4OC)cccc2-3)nc2c(C(=O)N[C@@H]3C[C@@H]3F)cnn12] |
| I-823 | 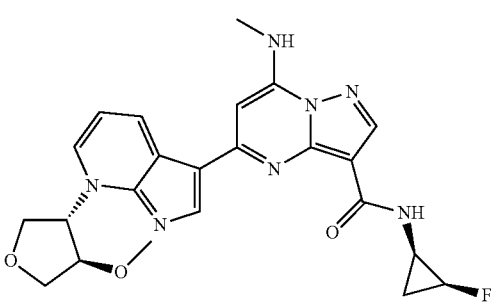 [SMILES: CNc1cc(-c2cnc3n([C@H]4COC[C@@H]4OC)cccc2-3)nc2c(C(=O)N[C@@H]3C[C@@H]3F)cnn12] |
| I-824 | 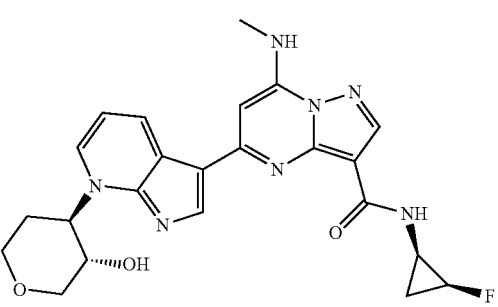 [SMILES: CNc1cc(-c2cnc3n([C@@H]4CCOC[C@H]4O)cccc2-3)nc2c(C(=O)N[C@@H]3C[C@@H]3F)cnn12] |
| I-825 | 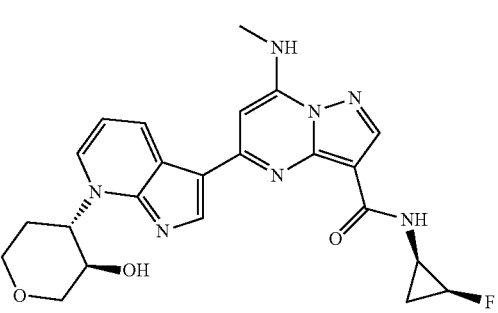 [SMILES: CNc1cc(-c2cnc3n([C@H]4CCOC[C@@H]4O)cccc2-3)nc2c(C(=O)N[C@@H]3C[C@@H]3F)cnn12] |

TABLE 1-continued
Selected Compounds
| Number | Structure |
|---|---|
| I-826 | 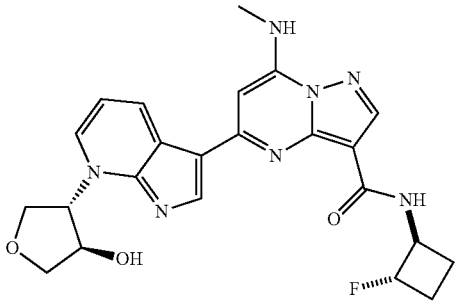 |
| I-827 | 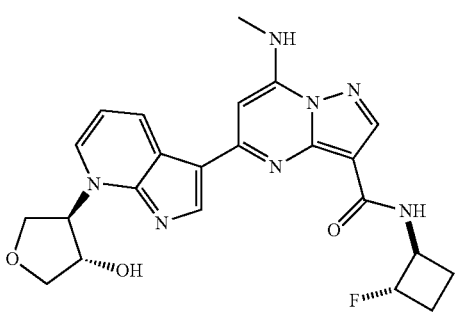 |
| I-828 | 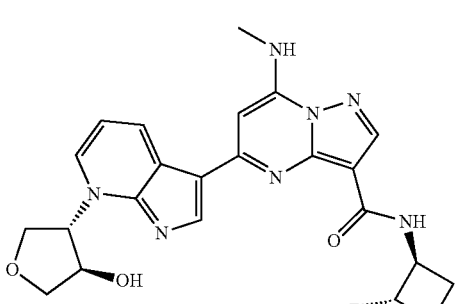 |
| I-829 | 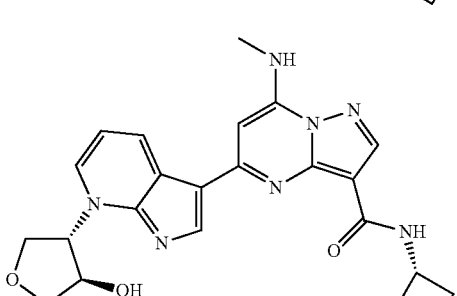 |
| I-830 | 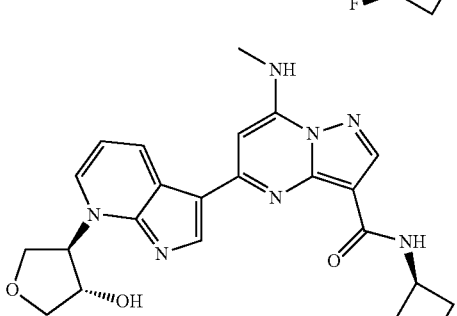 |

TABLE 1-continued

Selected Compounds

| Number | Structure |
|---|---|
| I-831 | 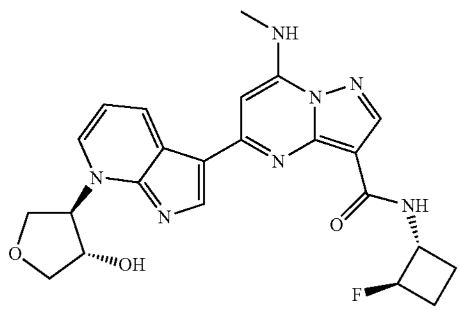 [SMILES: CNc1cc(-c2cnc3n([C@@H]4COC[C@H]4O)cccc2-3)nc2c(C(=O)N[C@@H]3CC[C@H]3F)cnn12] |
| I-832 | 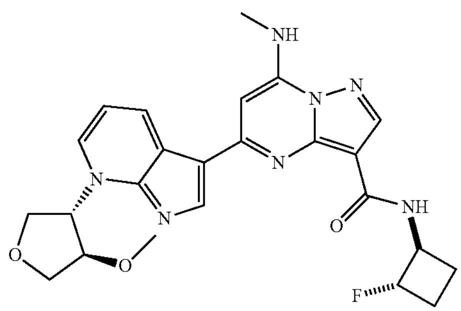 |
| I-833 | 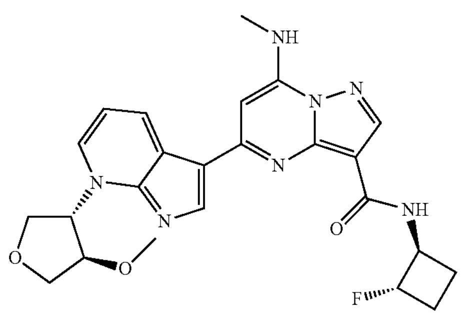 [SMILES: CNc1cc(-c2cnc3n([C@H]4COC[C@@H]4OC)cccc2-3)nc2c(C(=O)N[C@H]3CC[C@@H]3F)cnn12] |
| I-834 | 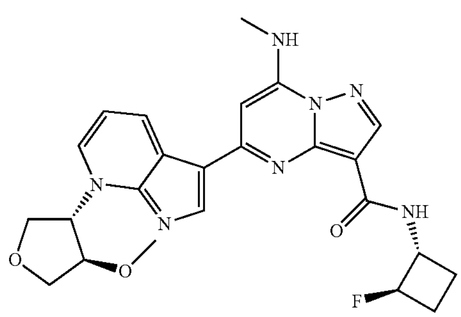 [SMILES: CNc1cc(-c2cnc3n([C@H]4COC[C@@H]4OC)cccc2-3)nc2c(C(=O)N[C@@H]3CC[C@H]3F)cnn12] |
| I-835 | 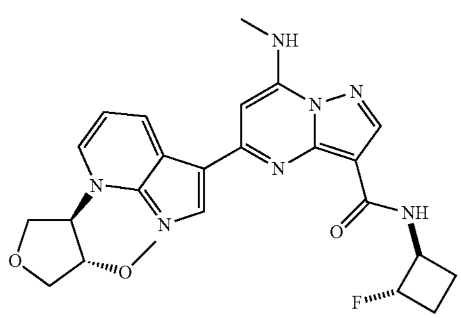 |

TABLE 1-continued

Selected Compounds

| Number | Structure |
|---|---|
| I-836 | 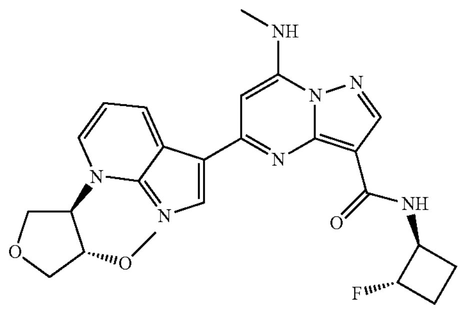 [SMILES: CNc1cc(-c2cnc3n([C@@H]4COC[C@H]4OC)cccc2-3)nc2c(C(=O)N[C@H]3CC[C@@H]3F)cnn12] |
| I-837 | 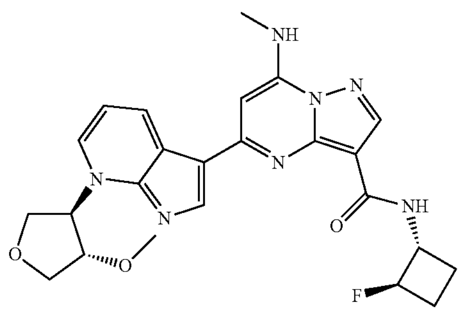 [SMILES: CNc1cc(-c2cnc3n([C@@H]4COC[C@H]4OC)cccc2-3)nc2c(C(=O)N[C@@H]3CC[C@H]3F)cnn12] |
| I-838 | 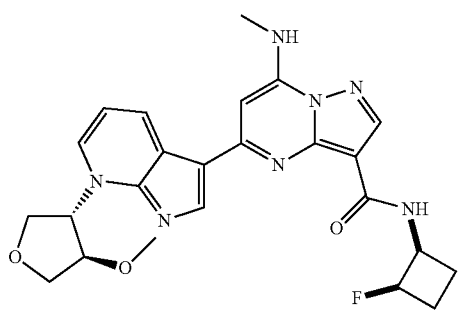 |
| I-839 | 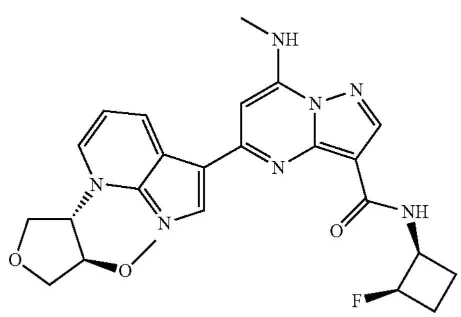 [SMILES: CNc1cc(-c2cnc3n([C@H]4COC[C@@H]4OC)cccc2-3)nc2c(C(=O)N[C@H]3CC[C@H]3F)cnn12] |
| I-840 | 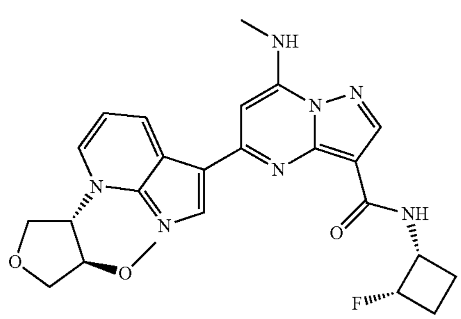 [SMILES: CNc1cc(-c2cnc3n([C@H]4COC[C@@H]4OC)cccc2-3)nc2c(C(=O)N[C@@H]3CC[C@@H]3F)cnn12] |

TABLE 1-continued

Selected Compounds

| Number | Structure |
|---|---|
| I-841 | 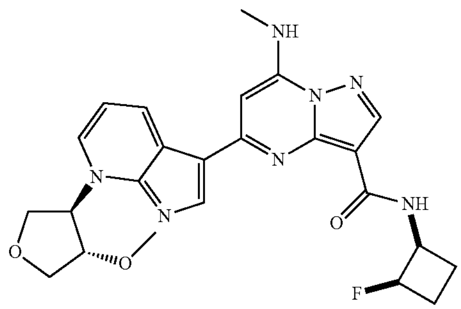 |
| I-842 | 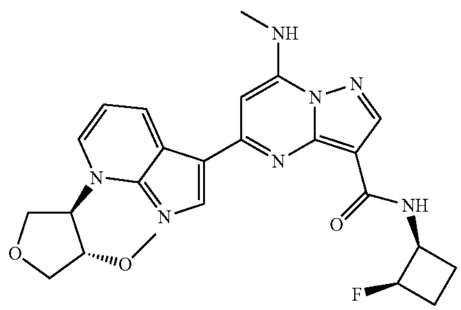 [SMILES: CNc1cc(-c2cnc3n([C@@H]4COC[C@H]4OC)cccc2-3)nc2c(C(=O)N[C@H]3CC[C@H]3F)cnn12] |
| I-843 | 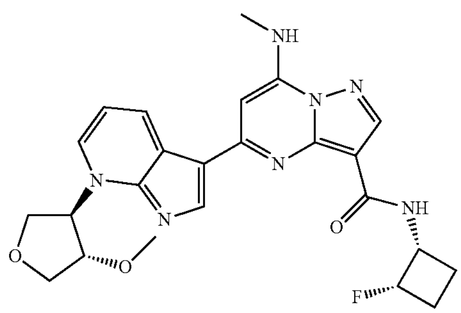 [SMILES: CNc1cc(-c2cnc3n([C@@H]4COC[C@H]4OC)cccc2-3)nc2c(C(=O)N[C@@H]3CC[C@@H]3F)cnn12] |
| I-844 | 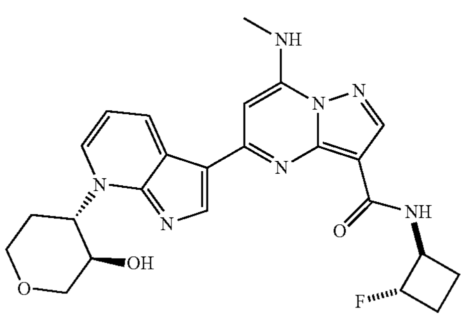 |
| I-845 | 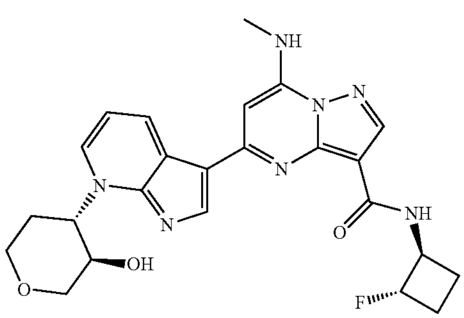 [SMILES: CNc1cc(-c2cnc3n([C@H]4CCOC[C@@H]4O)cccc2-3)nc2c(C(=O)N[C@H]3CC[C@@H]3F)cnn12] |

415
416
TABLE 1-continued
Selected Compounds
| Number | Structure |
|---|---|
| I-846 | 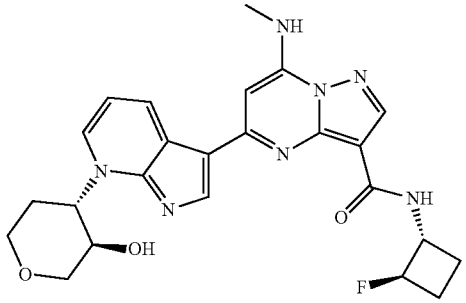 [SMILES: CNc1cc(-c2cnc3n([C@H]4CCOC[C@@H]4O)cccc2-3)nc2c(C(=O)N[C@@H]3CC[C@H]3F)cnn12] |
| I-847 | 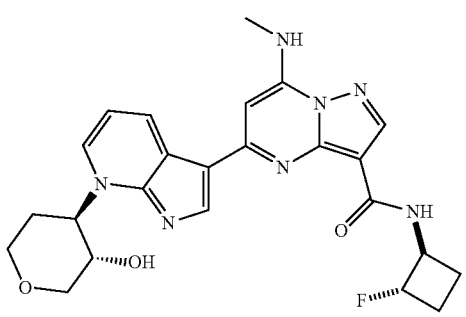 |
| I-848 | 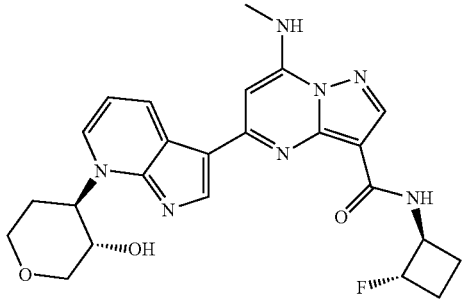 [SMILES: CNc1cc(-c2cnc3n([C@@H]4CCOC[C@H]4O)cccc2-3)nc2c(C(=O)N[C@H]3CC[C@@H]3F)cnn12] |
| I-849 | 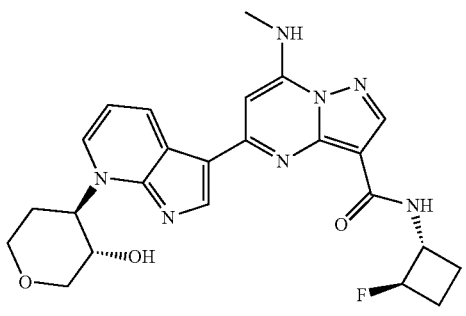 [SMILES: CNc1cc(-c2cnc3n([C@@H]4CCOC[C@H]4O)cccc2-3)nc2c(C(=O)N[C@@H]3CC[C@H]3F)cnn12] |
| I-850 | 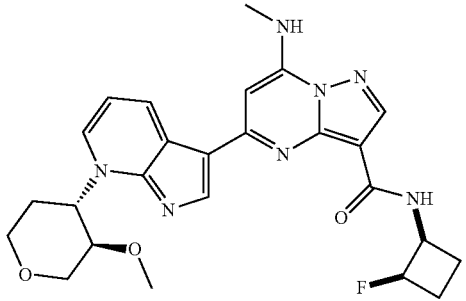 |

TABLE 1-continued

Selected Compounds

| Number | Structure |
|---|---|
| I-851 | 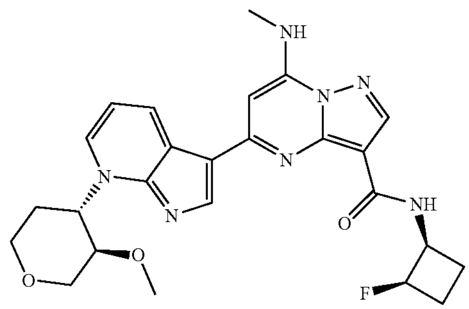 [SMILES: CNc1cc(-c2cnc3n([C@H]4CCOC[C@@H]4OC)cccc2-3)nc2c(C(=O)N[C@H]3CC[C@H]3F)cnn12] |
| I-852 | 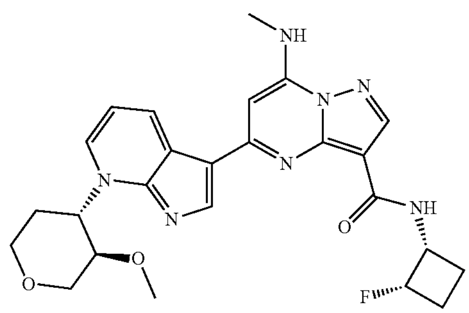 [SMILES: CNc1cc(-c2cnc3n([C@H]4CCOC[C@@H]4OC)cccc2-3)nc2c(C(=O)N[C@@H]3CC[C@@H]3F)cnn12] |
| I-853 | 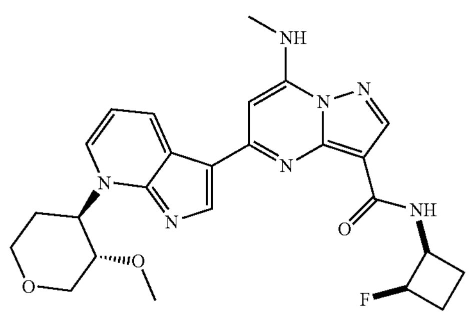 |
| I-854 | 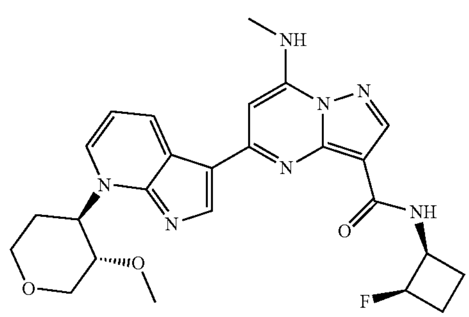 [SMILES: CNc1cc(-c2cnc3n([C@@H]4CCOC[C@H]4OC)cccc2-3)nc2c(C(=O)N[C@H]3CC[C@H]3F)cnn12] |
| I-855 | 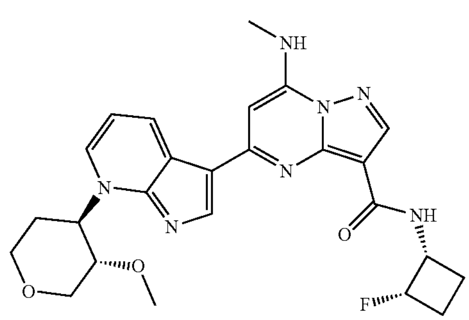 [SMILES: CNc1cc(-c2cnc3n([C@@H]4CCOC[C@H]4OC)cccc2-3)nc2c(C(=O)N[C@@H]3CC[C@@H]3F)cnn12] |

TABLE 1-continued

Selected Compounds

| Number | Structure |
|---|---|
| I-856 | 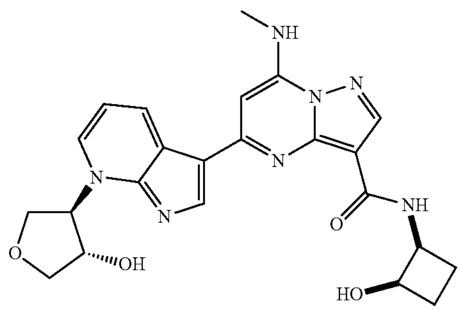 |
| I-857 | 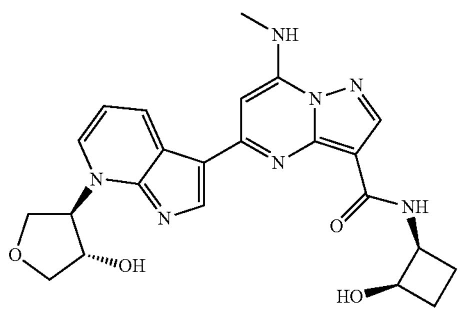 [SMILES: CNc1cc(-c2cnc3n([C@@H]4COC[C@H]4O)cccc2-3)nc2c(C(=O)N[C@H]3CC[C@H]3O)cnn12] |
| I-858 | 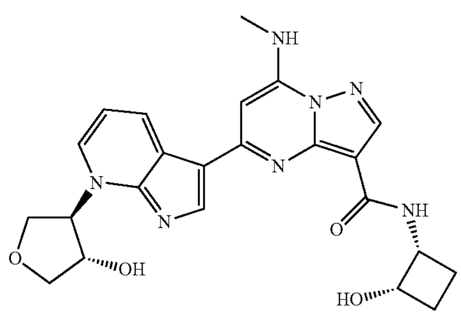 [SMILES: CNc1cc(-c2cnc3n([C@@H]4COC[C@H]4O)cccc2-3)nc2c(C(=O)N[C@@H]3CC[C@@H]3O)cnn12] |
| I-859 | 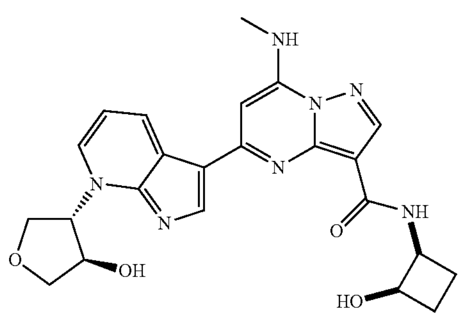 |
| I-860 | 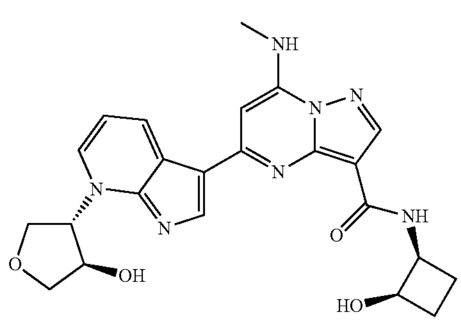 [SMILES: CNc1cc(-c2cnc3n([C@H]4COC[C@@H]4O)cccc2-3)nc2c(C(=O)N[C@H]3CC[C@H]3O)cnn12] |

TABLE 1-continued

Selected Compounds

| Number | Structure |
|---|---|
| I-861 | 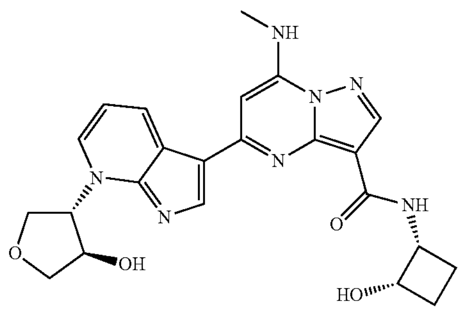 [SMILES: CNc1cc(-c2cnc3n([C@H]4COC[C@@H]4O)cccc2-3)nc2c(C(=O)N[C@@H]3CC[C@@H]3O)cnn12] |
| I-862 | 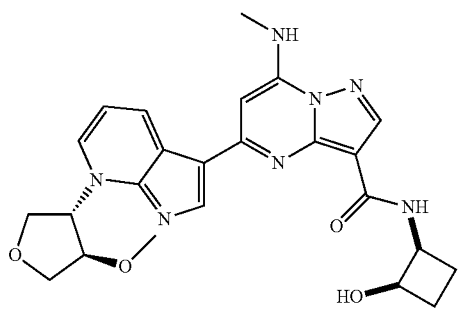 |
| I-863 | 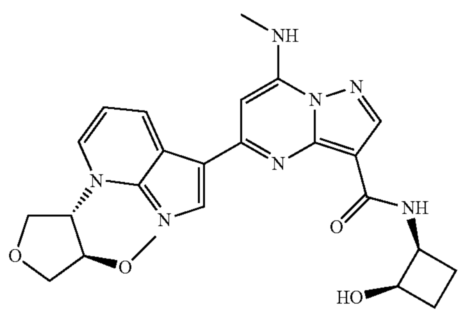 [SMILES: CNc1cc(-c2cnc3n([C@H]4COC[C@@H]4OC)cccc2-3)nc2c(C(=O)N[C@H]3CC[C@H]3O)cnn12] |
| I-864 | 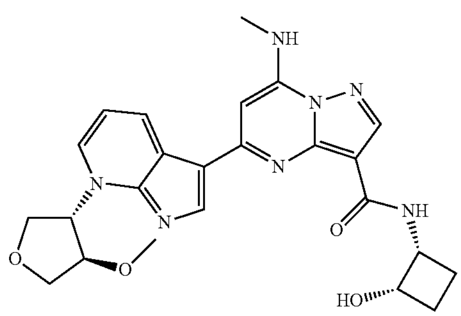 [SMILES: CNc1cc(-c2cnc3n([C@H]4COC[C@@H]4OC)cccc2-3)nc2c(C(=O)N[C@@H]3CC[C@@H]3O)cnn12] |
| I-865 | 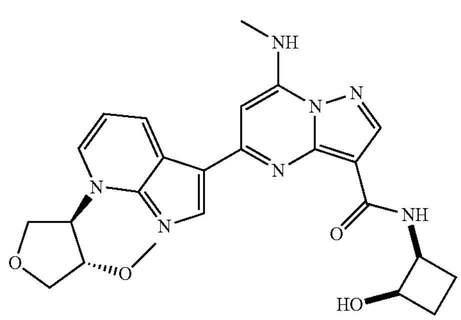 |

TABLE 1-continued

Selected Compounds

| Number | Structure |
|---|---|
| I-866 | 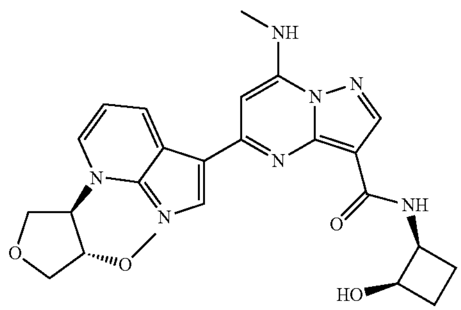 [SMILES: CNc1cc(-c2cnc3n([C@@H]4COC[C@H]4OC)cccc2-3)nc2c(C(=O)N[C@H]3CC[C@H]3O)cnn12] |
| I-867 | 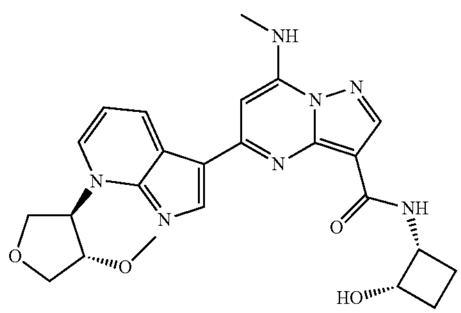 [SMILES: CNc1cc(-c2cnc3n([C@@H]4COC[C@H]4OC)cccc2-3)nc2c(C(=O)N[C@@H]3CC[C@@H]3O)cnn12] |
| I-868 | 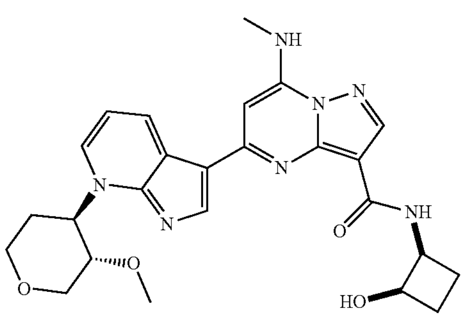 |
| I-869 | 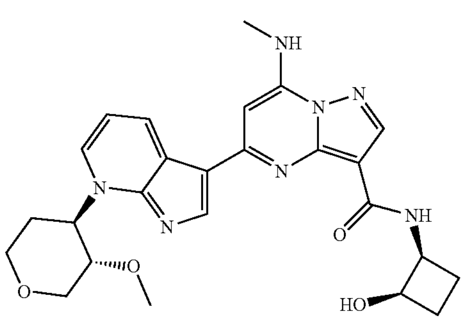 [SMILES: CNc1cc(-c2cnc3n([C@@H]4CCOC[C@H]4OC)cccc2-3)nc2c(C(=O)N[C@H]3CC[C@H]3O)cnn12] |
| I-870 | 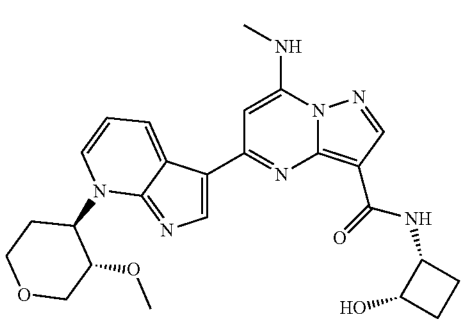 [SMILES: CNc1cc(-c2cnc3n([C@@H]4CCOC[C@H]4OC)cccc2-3)nc2c(C(=O)N[C@@H]3CC[C@@H]3O)cnn12] |

TABLE 1-continued

Selected Compounds

| Number | Structure |
|---|---|
| I-871 | 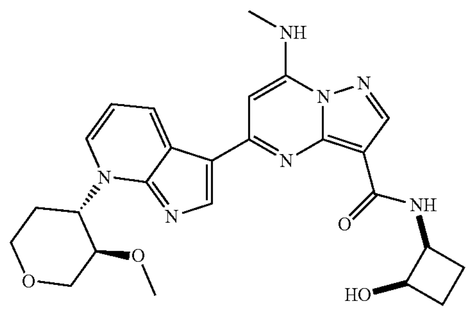 |
| I-872 | 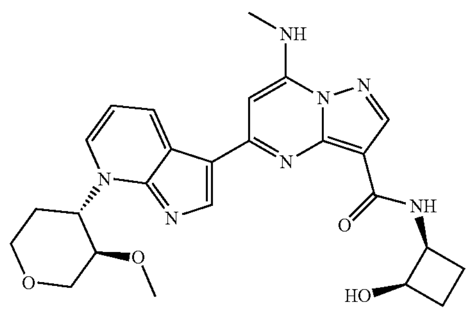 [SMILES: CNc1cc(-c2cnc3n([C@H]4CCOC[C@@H]4OC)cccc2-3)nc2c(C(=O)N[C@H]3CC[C@H]3O)cnn12] |
| I-873 | 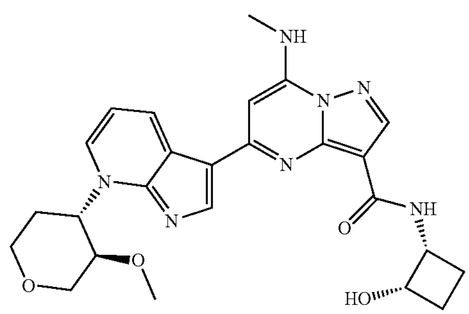 [SMILES: CNc1cc(-c2cnc3n([C@H]4CCOC[C@@H]4OC)cccc2-3)nc2c(C(=O)N[C@@H]3CC[C@@H]3O)cnn12] |
| I-874 | 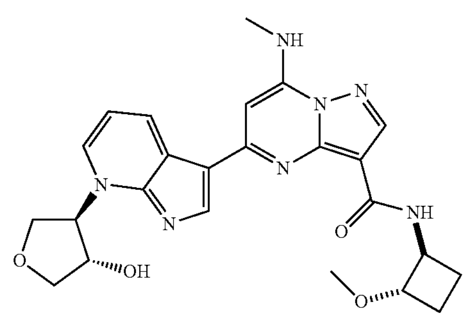 |
| I-875 | 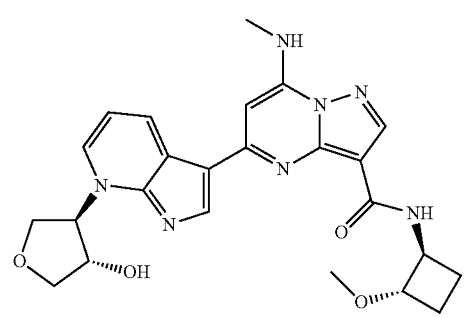 [SMILES: CNc1cc(-c2cnc3n([C@@H]4COC[C@H]4O)cccc2-3)nc2c(C(=O)N[C@H]3CC[C@@H]3OC)cnn12] |

TABLE 1-continued

Selected Compounds

| Number | Structure |
|---|---|
| I-876 | 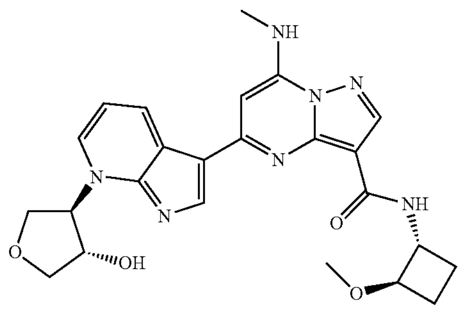 [SMILES: CNc1cc(-c2cnc3n([C@@H]4COC[C@H]4O)cccc2-3)nc2c(C(=O)N[C@@H]3CC[C@H]3OC)cnn12] |
| I-877 | 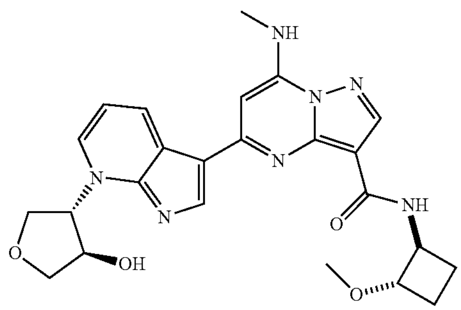 |
| I-878 | 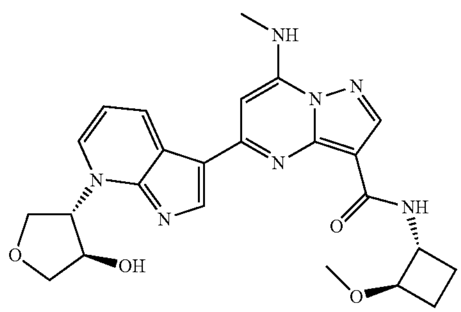 [SMILES: CNc1cc(-c2cnc3n([C@H]4COC[C@@H]4O)cccc2-3)nc2c(C(=O)N[C@@H]3CC[C@H]3OC)cnn12] |
| I-879 | 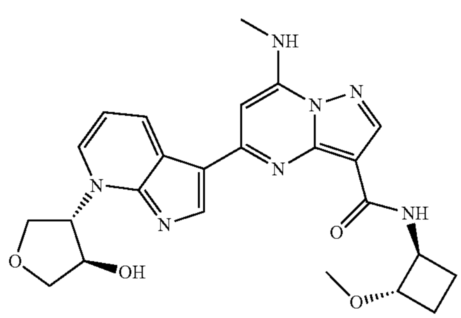 [SMILES: CNc1cc(-c2cnc3n([C@H]4COC[C@@H]4O)cccc2-3)nc2c(C(=O)N[C@H]3CC[C@@H]3OC)cnn12] |
| I-880 | 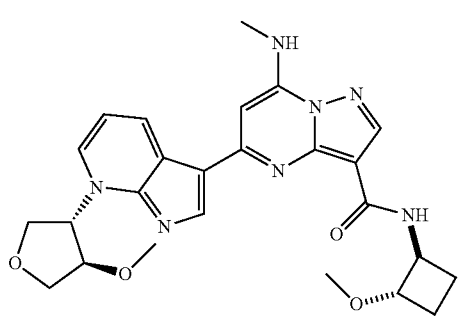 |

429
430
TABLE 1-continued
Selected Compounds
| Number | Structure |
|---|---|
| I-881 | 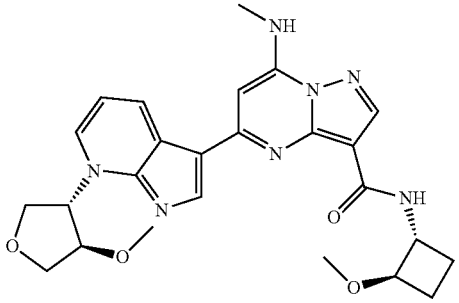 [SMILES: CNc1cc(-c2cnc3n([C@H]4COC[C@@H]4OC)cccc2-3)nc2c(C(=O)N[C@@H]3CC[C@H]3OC)cnn12] |
| I-882 | 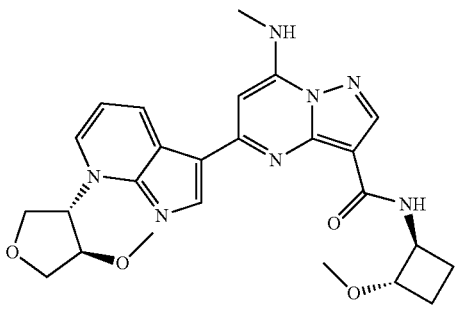 [SMILES: CNc1cc(-c2cnc3n([C@H]4COC[C@@H]4OC)cccc2-3)nc2c(C(=O)N[C@H]3CC[C@@H]3OC)cnn12] |
| I-883 | 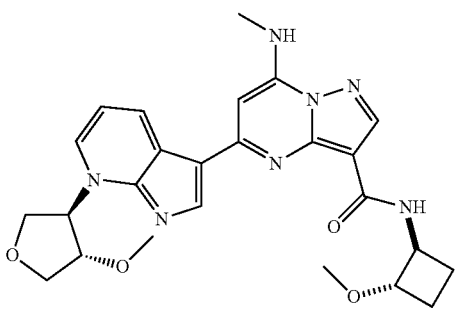 |
| I-884 | 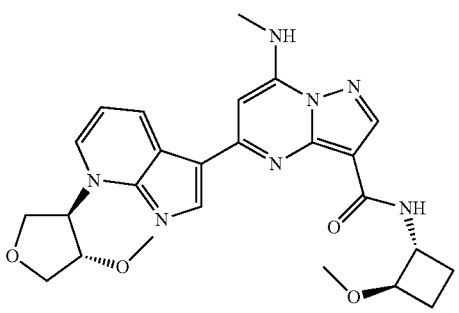 [SMILES: CNc1cc(-c2cnc3n([C@@H]4COC[C@H]4OC)cccc2-3)nc2c(C(=O)N[C@@H]3CC[C@H]3OC)cnn12] |
| I-885 | 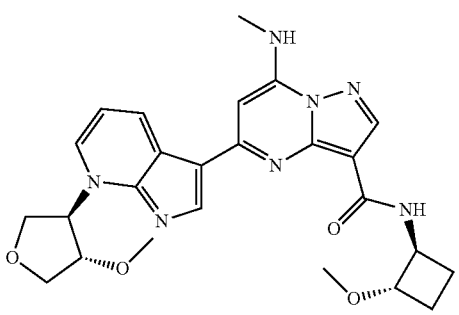 [SMILES: CNc1cc(-c2cnc3n([C@@H]4COC[C@H]4OC)cccc2-3)nc2c(C(=O)N[C@H]3CC[C@@H]3OC)cnn12] |

TABLE 1-continued

Selected Compounds

| Number | Structure |
|---|---|
| I-886 | 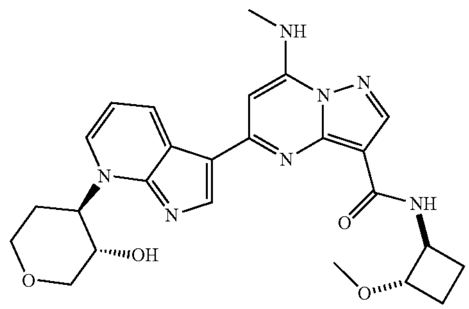 |
| I-887 | 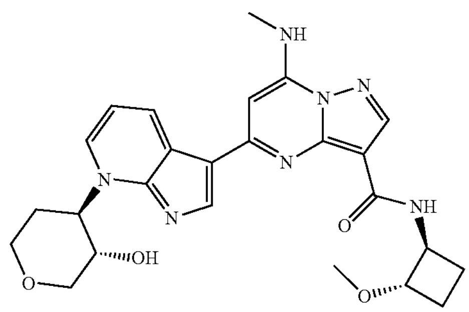 [SMILES: CNc1cc(-c2cnc3n([C@@H]4CCOC[C@H]4O)cccc2-3)nc2c(C(=O)N[C@H]3CC[C@@H]3OC)cnn12] |
| I-888 | 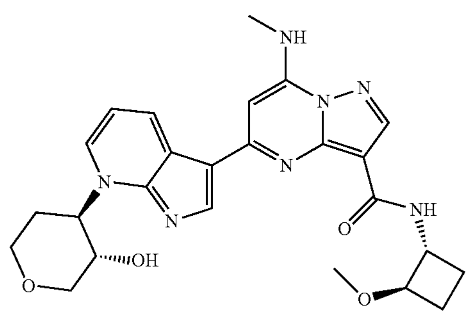 [SMILES: CNc1cc(-c2cnc3n([C@@H]4CCOC[C@H]4O)cccc2-3)nc2c(C(=O)N[C@@H]3CC[C@H]3OC)cnn12] |
| I-889 | 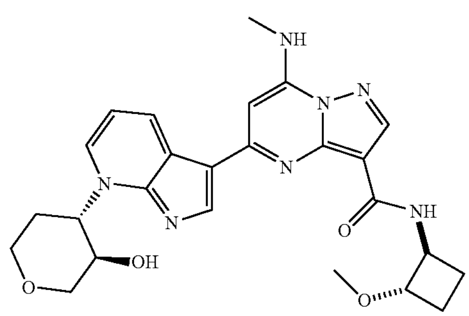 |
| I-890 | 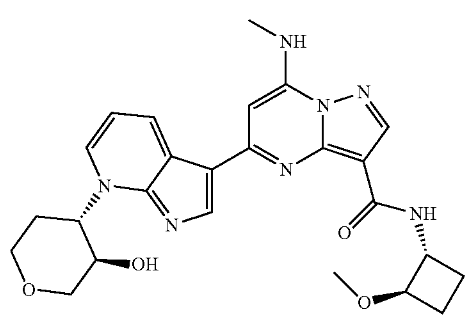 [SMILES: CNc1cc(-c2cnc3n([C@H]4CCOC[C@@H]4O)cccc2-3)nc2c(C(=O)N[C@@H]3CC[C@H]3OC)cnn12] |

TABLE 1-continued

Selected Compounds

| Number | Structure |
|---|---|
| I-891 | 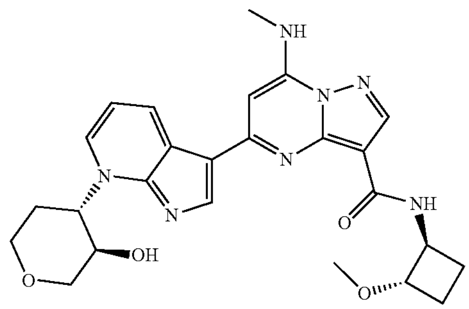 [SMILES: CNc1cc(-c2cnc3n([C@H]4CCOC[C@@H]4O)cccc2-3)nc2c(C(=O)N[C@H]3CC[C@@H]3OC)cnn12] |
| I-892 | 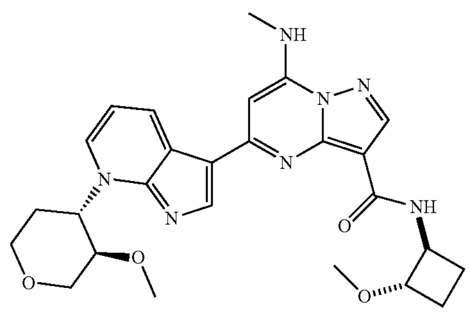 |
| I-893 | 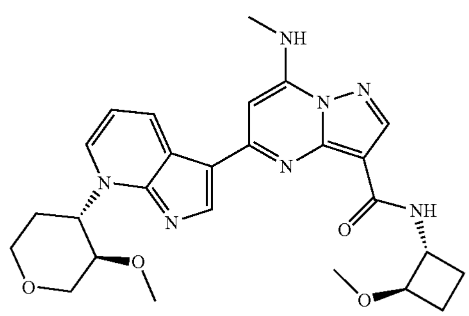 [SMILES: CNc1cc(-c2cnc3n([C@H]4CCOC[C@@H]4OC)cccc2-3)nc2c(C(=O)N[C@@H]3CC[C@H]3OC)cnn12] |
| I-894 | 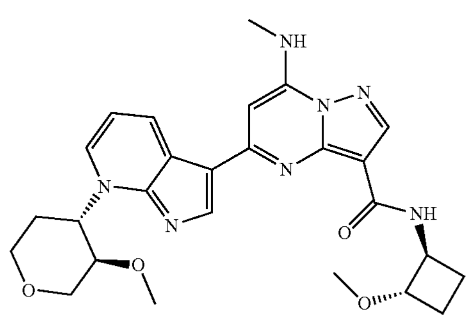 [SMILES: CNc1cc(-c2cnc3n([C@H]4CCOC[C@@H]4OC)cccc2-3)nc2c(C(=O)N[C@H]3CC[C@@H]3OC)cnn12] |
| I-895 | 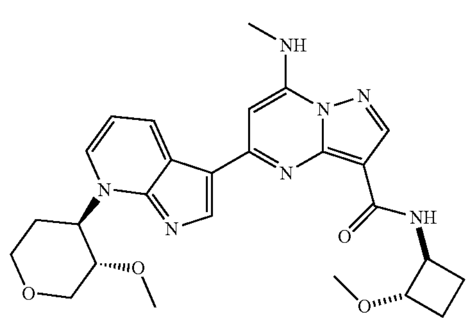 |

TABLE 1-continued
| Selected Compounds | |
|---|---|
| Number | Structure |
I-896
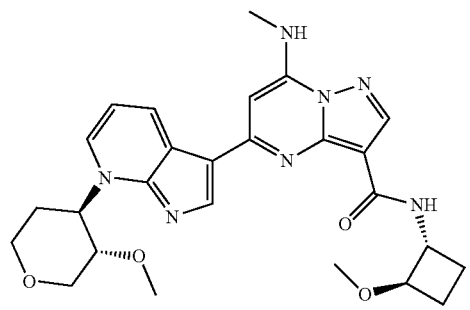 [SMILES: CNc1cc(-c2cnc3n([C@@H]4CCOC[C@H]4OC)cccc2-3)nc2c(C(=O)N[C@@H]3CC[C@H]3OC)cnn12]
I-897
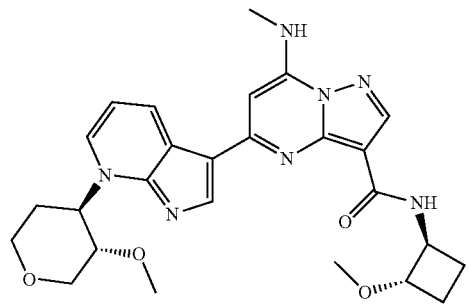 [SMILES: CNc1cc(-c2cnc3n([C@@H]4CCOC[C@H]4OC)cccc2-3)nc2c(C(=O)N[C@H]3CC[C@@H]3OC)cnn12]
I-898
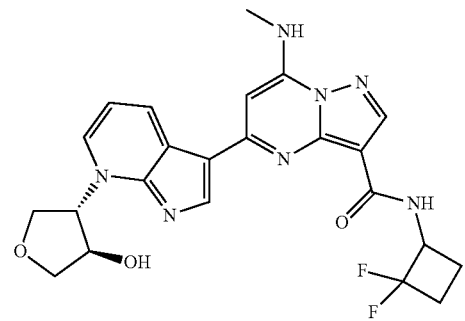 [SMILES: CNc1cc(-c2cnc3n([C@H]4COC[C@@H]4O)cccc2-3)nc2c(C(=O)NC3CCC3(F)F)cnn12]
I-899
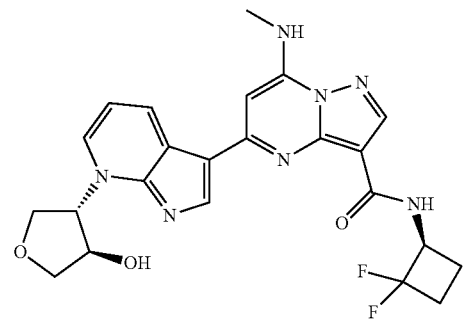 [SMILES: CNc1cc(-c2cnc3n([C@H]4COC[C@@H]4O)cccc2-3)nc2c(C(=O)N[C@H]3CCC3(F)F)cnn12]

TABLE 1-continued

| Number | Structure |
|---|---|
| I-900 | 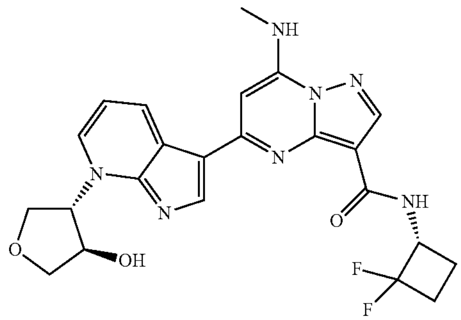 [SMILES: CNc1cc(-c2cnc3n([C@H]4COC[C@@H]4O)cccc2-3)nc2c(C(=O)N[C@@H]3CCC3(F)F)cnn12] |
| I-901 | 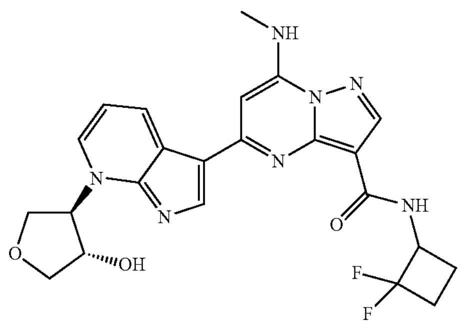 [SMILES: CNc1cc(-c2cnc3n([C@@H]4COC[C@H]4O)cccc2-3)nc2c(C(=O)NC3CCC3(F)F)cnn12] |
| I-902 | 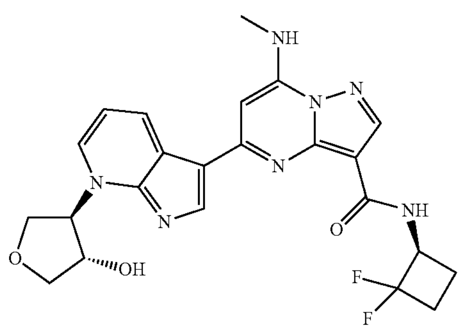 [SMILES: CNc1cc(-c2cnc3n([C@@H]4COC[C@H]4O)cccc2-3)nc2c(C(=O)N[C@H]3CCC3(F)F)cnn12] |
| I-903 | 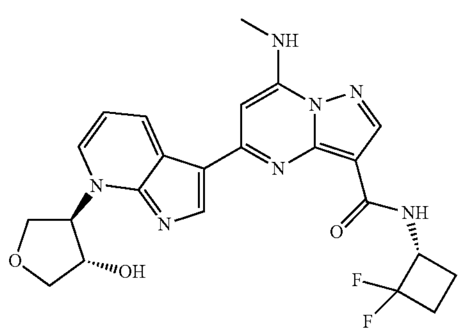 [SMILES: CNc1cc(-c2cnc3n([C@@H]4COC[C@H]4O)cccc2-3)nc2c(C(=O)N[C@@H]3CCC3(F)F)cnn12] |

TABLE 1-continued

Selected Compounds

| Number | Structure |
|---|---|
| I-904 | 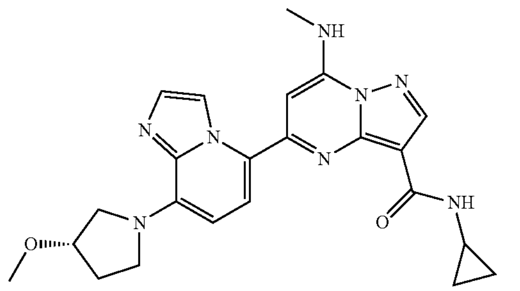 [SMILES: CNc1cc(-c2ccc(N3CC[C@H](OC)C3)c3nccn23)nc2c(C(=O)NC3CC3)cnn12] |
| I-905 | 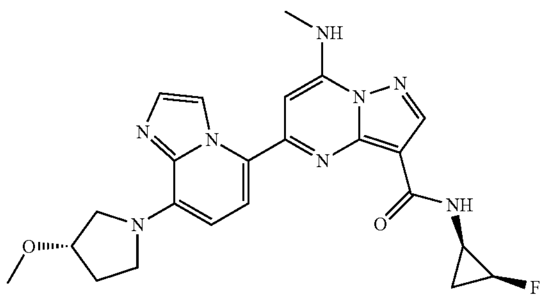 [SMILES: CNc1cc(-c2ccc(N3CC[C@H](OC)C3)c3nccn23)nc2c(C(=O)N[C@@H]3C[C@@H]3F)cnn12] |
| I-906 | 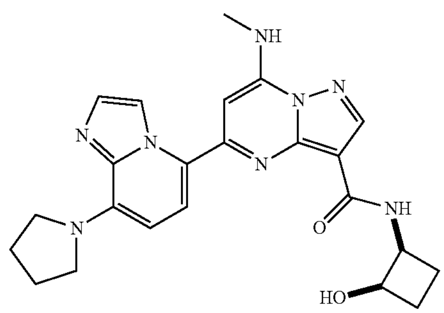 |
| I-907 | 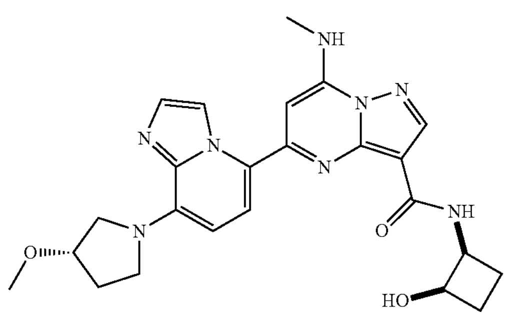 |
| I-908 | 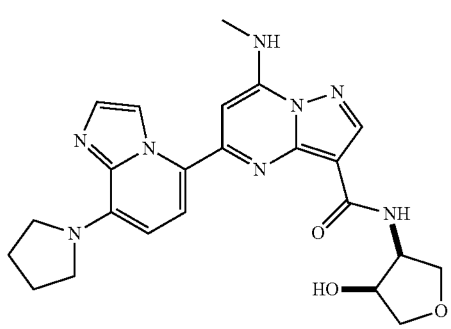 |

TABLE 1-continued

| Number | Structure |
|---|---|
| I-909 | 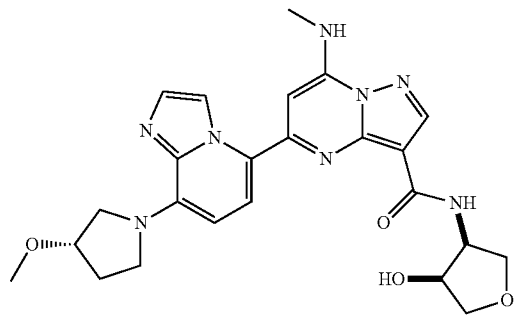 |
| I-910 | 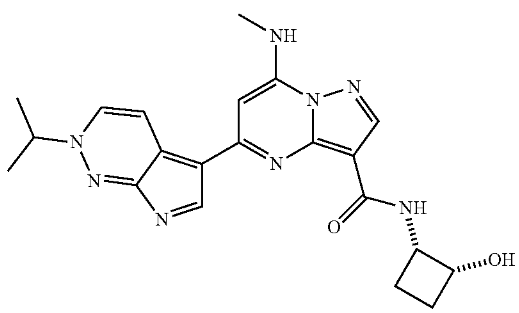 |
| I-911 | 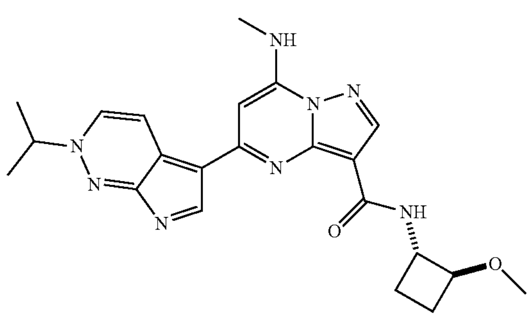 |
| I-912 | 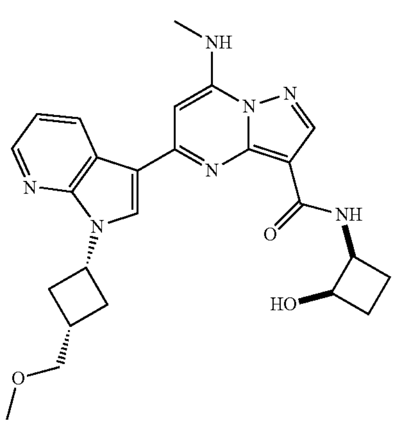 |

TABLE 1-continued
Selected Compounds
| Number | Structure |
|---|---|
| I-913 | 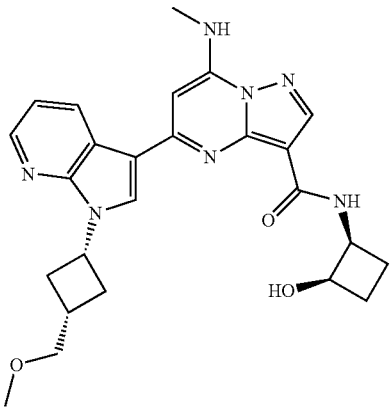 [SMILES: CNc1cc(-c2cn([C@H]3C[C@@H](COC)C3)c3ncccc23)nc2c(C(=O)N[C@H]3CC[C@H]3O)cnn12] |
| I-914 | 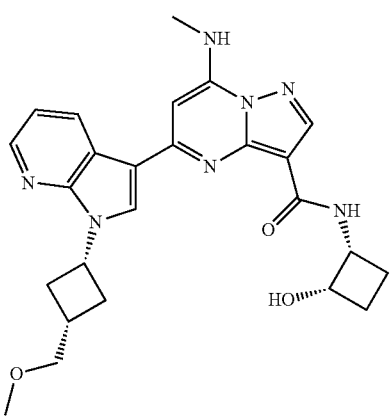 [SMILES: CNc1cc(-c2cn([C@H]3C[C@@H](COC)C3)c3ncccc23)nc2c(C(=O)N[C@@H]3CC[C@@H]3O)cnn12] |
| I-915 | 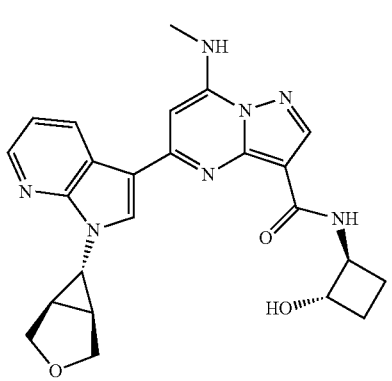 [SMILES: CNc1cc(-c2cn([C@H]3[C@@H]4COC[C@@H]43)c3ncccc23)nc2c(C(=O)N[C@H]3CC[C@@H]3O)cnn12] |
| I-916 | 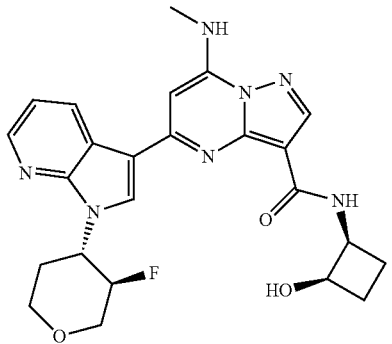 [SMILES: CNc1cc(-c2cn([C@H]3CCOC[C@@H]3F)c3ncccc23)nc2c(C(=O)N[C@H]3CC[C@H]3O)cnn12] |

TABLE 1-continued

| Selected Compounds | |
|---|---|
| Number | Structure |

I-917

I-918

I-919

I-920

TABLE 1-continued
Selected Compounds
| Number | Structure |
|---|---|
| I-921 | 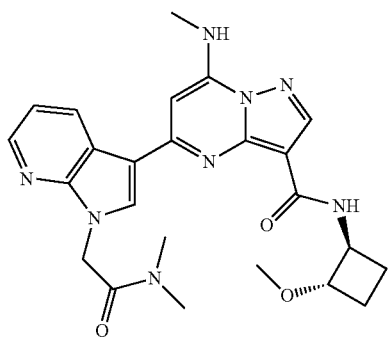 [SMILES: CNc1cc(-c2cn(CC(=O)N(C)C)c3ncccc23)nc2c(C(=O)N[C@H]3CC[C@@H]3OC)cnn12] |
| I-922 | 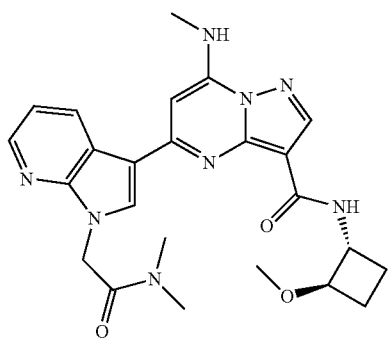 [SMILES: CNc1cc(-c2cn(CC(=O)N(C)C)c3ncccc23)nc2c(C(=O)N[C@@H]3CC[C@H]3OC)cnn12] |
| I-923 | 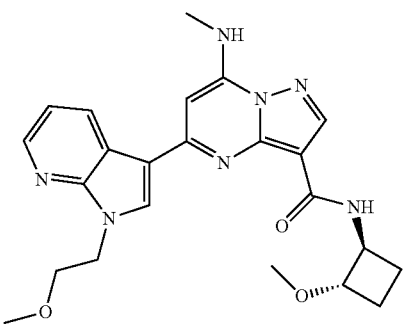 [SMILES: CNc1cc(-c2cn(CCOC)c3ncccc23)nc2c(C(=O)N[C@H]3CC[C@@H]3OC)cnn12] |
| I-924 | 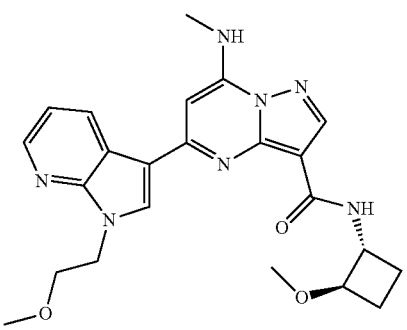 [SMILES: CNc1cc(-c2cn(CCOC)c3ncccc23)nc2c(C(=O)N[C@@H]3CC[C@H]3OC)cnn12] |

TABLE 1-continued

Selected Compounds

| Number | Structure |
|--------|-----------|
| I-925 | 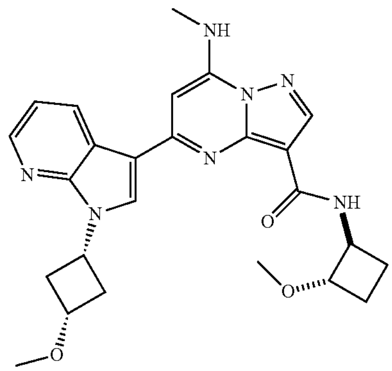 |
| I-926 | 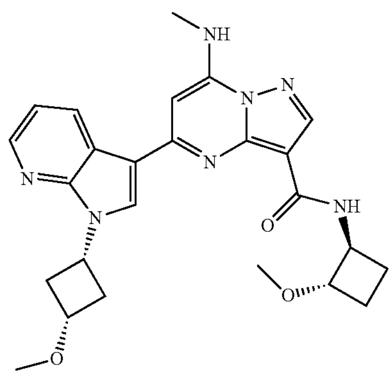 [SMILES: CNc1cc(-c2cn([C@H]3C[C@@H](OC)C3)c3ncccc23)nc2c(C(=O)N[C@H]3CC[C@@H]3OC)cnn12] |
| I-927 | 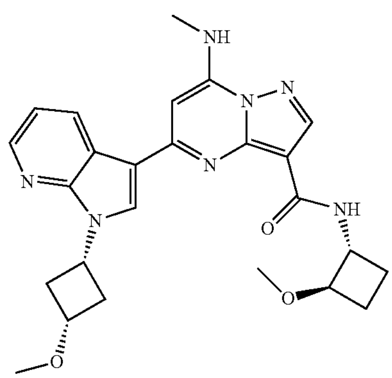 [SMILES: CNc1cc(-c2cn([C@H]3C[C@@H](OC)C3)c3ncccc23)nc2c(C(=O)N[C@@H]3CC[C@H]3OC)cnn12] |
| I-928 | 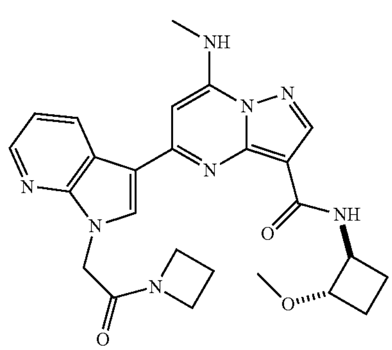 |

451
TABLE 1-continued
| Selected Compounds | |
|---|---|
| Number | Structure |
| I-929 | 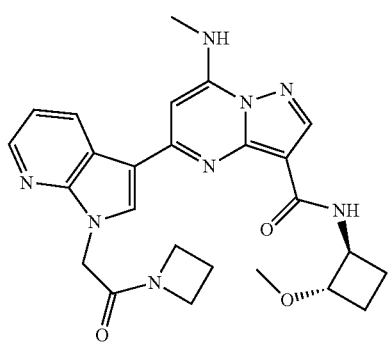 [SMILES: CNc1cc(-c2cn(CC(=O)N3CCC3)c3ncccc23)nc2c(C(=O)N[C@H]3CC[C@@H]3OC)cnn12] |
| I-930 | 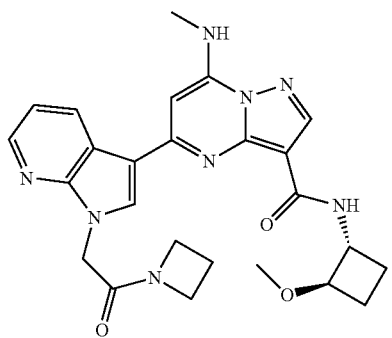 [SMILES: CNc1cc(-c2cn(CC(=O)N3CCC3)c3ncccc23)nc2c(C(=O)N[C@@H]3CC[C@H]3OC)cnn12] |
| I-931 | 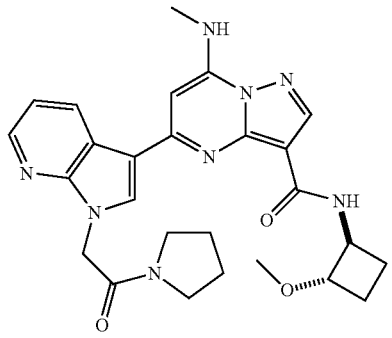 |
| I-932 | 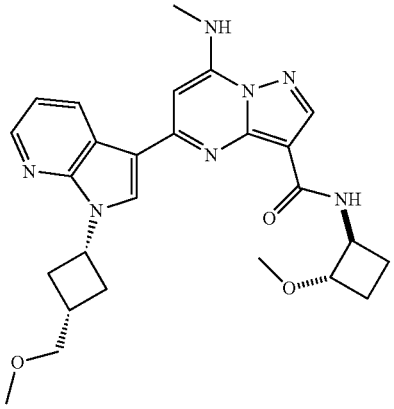 |

TABLE 1-continued

Selected Compounds

| Number | Structure |
|---|---|
| I-933 | 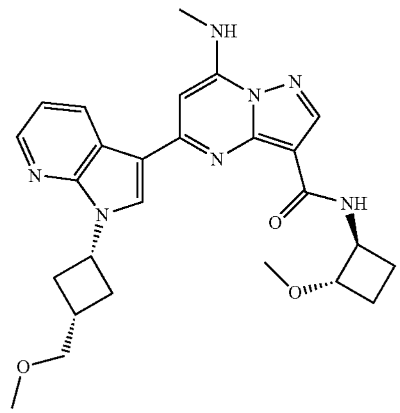 [SMILES: CNc1cc(-c2cn([C@H]3C[C@@H](COC)C3)c3ncccc23)nc2c(C(=O)N[C@H]3CC[C@@H]3OC)cnn12] |
| I-934 | 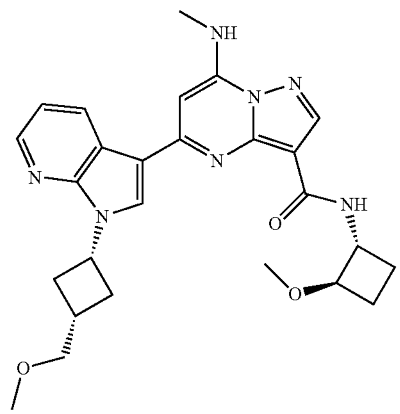 [SMILES: CNc1cc(-c2cn([C@H]3C[C@@H](COC)C3)c3ncccc23)nc2c(C(=O)N[C@@H]3CC[C@H]3OC)cnn12] |
| I-935 | 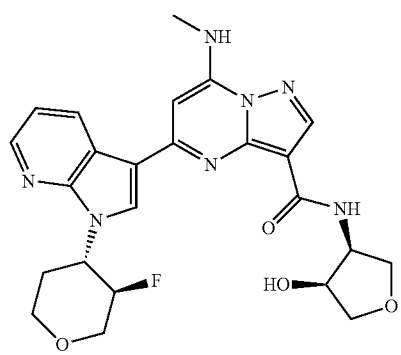 [SMILES: CNc1cc(-c2cn([C@H]3CCOC[C@@H]3F)c3ncccc23)nc2c(C(=O)N[C@H]3COC[C@H]3O)cnn12] |
| I-936 | 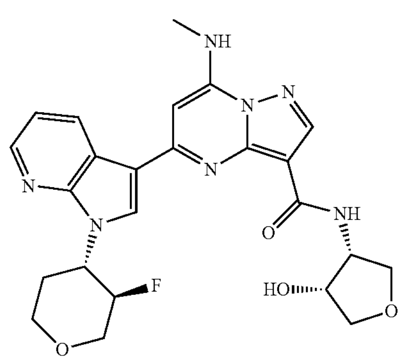 [SMILES: CNc1cc(-c2cn([C@H]3CCOC[C@@H]3F)c3ncccc23)nc2c(C(=O)N[C@@H]3COC[C@@H]3O)cnn12] |

TABLE 1-continued
| Selected Compounds | |
|---|---|
| Number | Structure |
I-937
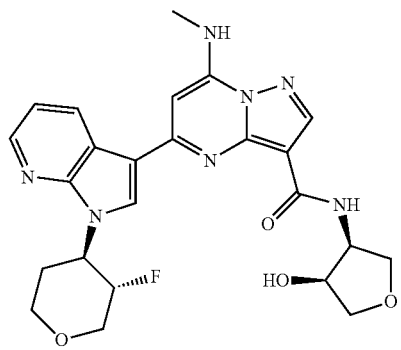 [SMILES: CNc1cc(-c2cn([C@@H]3CCOC[C@H]3F)c3ncccc23)nc2c(C(=O)N[C@H]3COC[C@H]3O)cnn12]
I-938
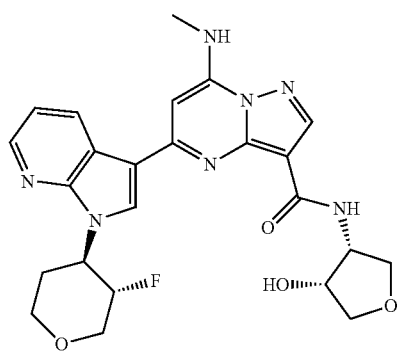 [SMILES: CNc1cc(-c2cn([C@@H]3CCOC[C@H]3F)c3ncccc23)nc2c(C(=O)N[C@@H]3COC[C@@H]3O)cnn12]
I-939
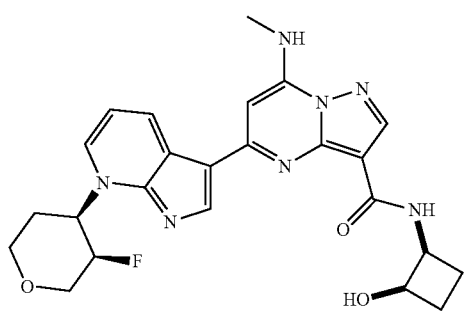
I-940
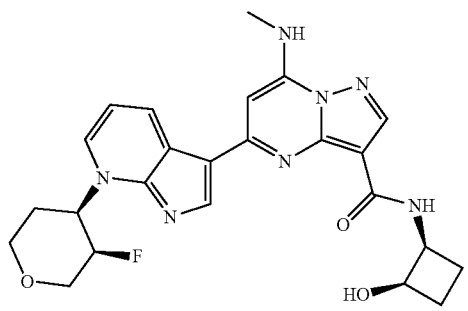 [SMILES: CNc1cc(-c2cnc3n([C@@H]4CCOC[C@@H]4F)cccc2-3)nc2c(C(=O)N[C@H]3CC[C@H]3O)cnn12]

TABLE 1-continued

Selected Compounds

| Number | Structure |
|---|---|
| I-941 | 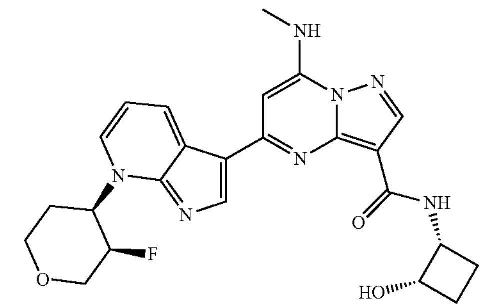 [SMILES: CNc1cc(-c2cnc3n([C@@H]4CCOC[C@@H]4F)cccc2-3)nc2c(C(=O)N[C@@H]3CC[C@@H]3O)cnn12] |
| I-942 | 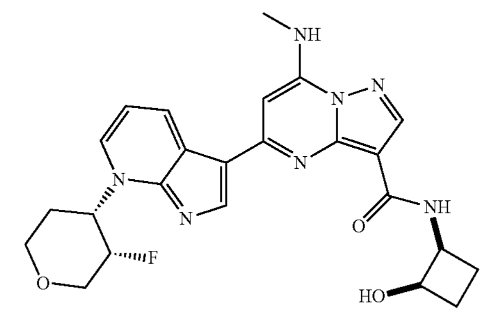 |
| I-943 | 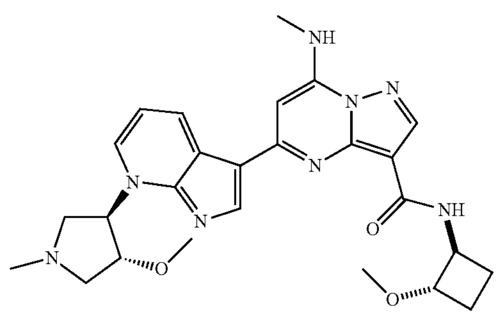 |
| I-944 | 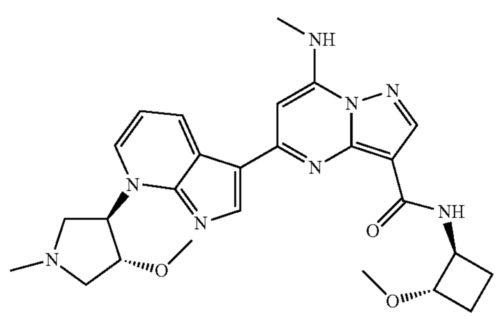 [SMILES: CNc1cc(-c2cnc3n([C@@H]4CN(C)C[C@H]4OC)cccc2-3)nc2c(C(=O)N[C@H]3CC[C@@H]3OC)cnn12] |
| I-945 | 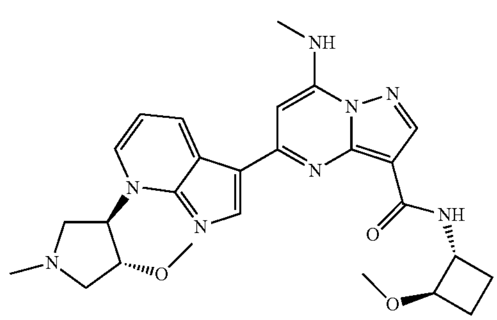 [SMILES: CNc1cc(-c2cnc3n([C@@H]4CN(C)C[C@H]4OC)cccc2-3)nc2c(C(=O)N[C@@H]3CC[C@H]3OC)cnn12] |

TABLE 1-continued

Selected Compounds

| Number | Structure |
|---|---|
| I-946 | 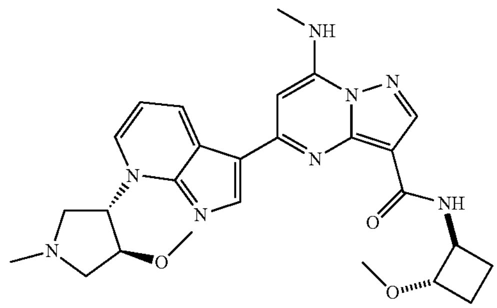 |
| I-947 | 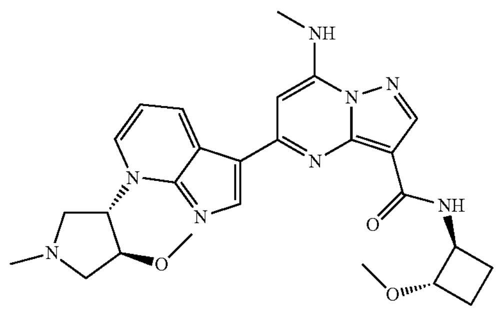 [SMILES: CNc1cc(-c2cnc3n([C@H]4CN(C)C[C@@H]4OC)cccc2-3)nc2c(C(=O)N[C@H]3CC[C@@H]3OC)cnn12] |
| I-948 | 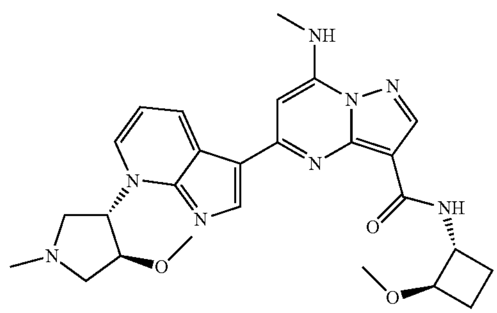 [SMILES: CNc1cc(-c2cnc3n([C@H]4CN(C)C[C@@H]4OC)cccc2-3)nc2c(C(=O)N[C@@H]3CC[C@H]3OC)cnn12] |
| I-949 | 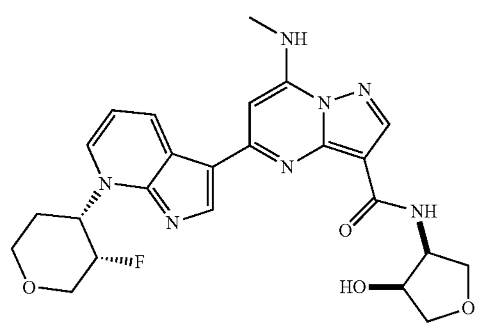 |
| I-950 | 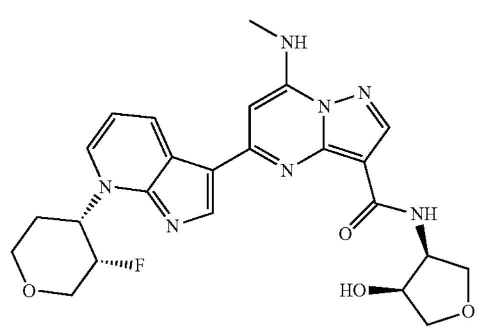 [SMILES: CNc1cc(-c2cnc3n([C@H]4CCOC[C@H]4F)cccc2-3)nc2c(C(=O)N[C@H]3COC[C@H]3O)cnn12] |

461
462
TABLE 1-continued
| Selected Compounds | |
|---|---|
| Number | Structure |
I-951
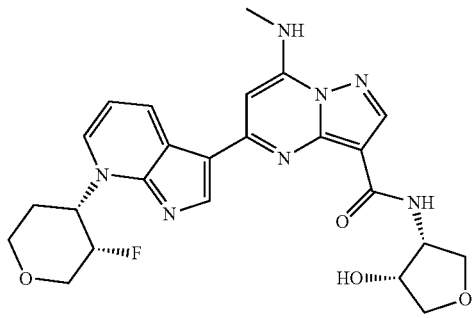 [SMILES: CNc1cc(-c2cnc3n([C@H]4CCOC[C@H]4F)cccc2-3)nc2c(C(=O)N[C@@H]3COC[C@@H]3O)cnn12]
I-952
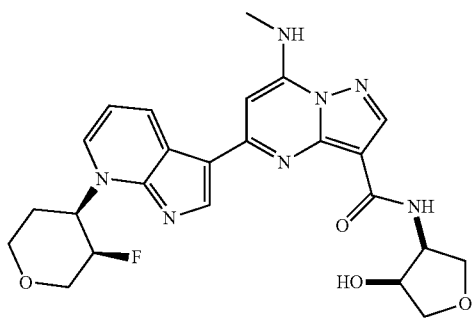
I-953
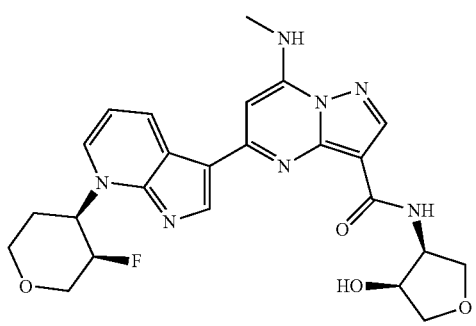 [SMILES: CNc1cc(-c2cnc3n([C@@H]4CCOC[C@@H]4F)cccc2-3)nc2c(C(=O)N[C@H]3COC[C@H]3O)cnn12]
I-954
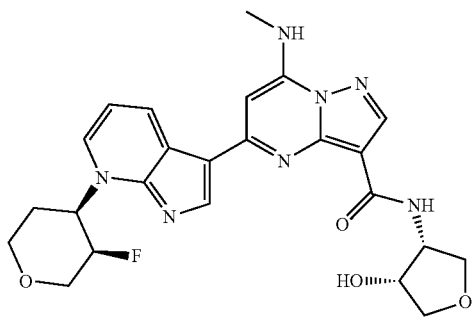 [SMILES: CNc1cc(-c2cnc3n([C@@H]4CCOC[C@@H]4F)cccc2-3)nc2c(C(=O)N[C@@H]3COC[C@@H]3O)cnn12]

TABLE 1-continued
| Selected Compounds | |
|---|---|
| Number | Structure |
| I-955 | 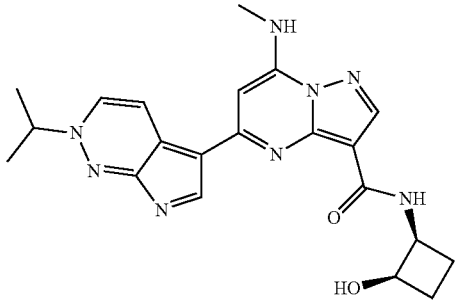 [SMILES: CNc1cc(-c2cnc3nn(C(C)C)ccc2-3)nc2c(C(=O)N[C@H]3CC[C@H]3O)cnn12] |
| I-956 | 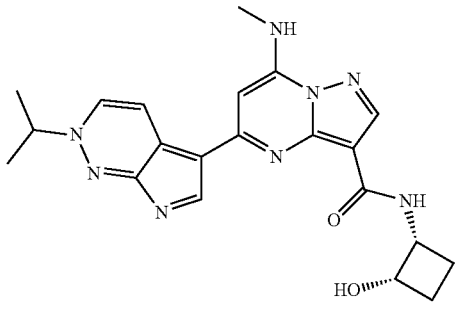 [SMILES: CNc1cc(-c2cnc3nn(C(C)C)ccc2-3)nc2c(C(=O)N[C@@H]3CC[C@@H]3O)cnn12] |
| I-957 | 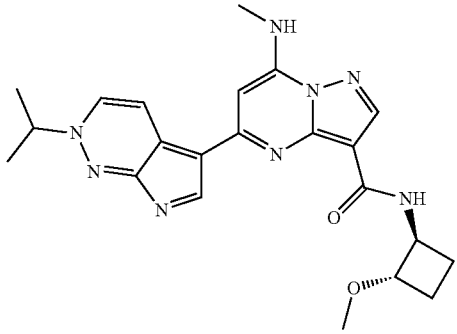 [SMILES: CNc1cc(-c2cnc3nn(C(C)C)ccc2-3)nc2c(C(=O)N[C@H]3CC[C@@H]3OC)cnn12] |
| I-958 | 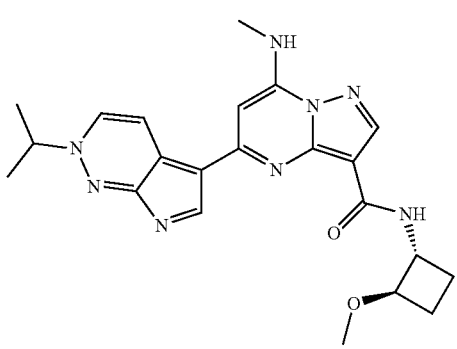 [SMILES: CNc1cc(-c2cnc3nn(C(C)C)ccc2-3)nc2c(C(=O)N[C@@H]3CC[C@H]3OC)cnn12] |

TABLE 1-continued
| Selected Compounds | |
|---|---|
| Number | Structure |
I-959
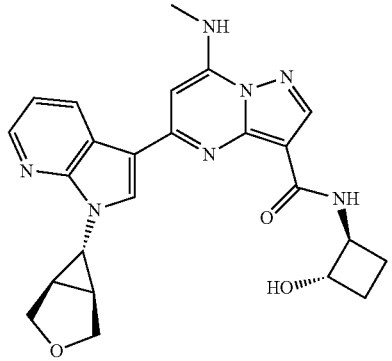 [SMILES: CNc1cc(-c2cn([C@H]3[C@@H]4COC[C@@H]43)c3ncccc23)nc2c(C(=O)N[C@H]3CC[C@@H]3O)cnn12]
I-960
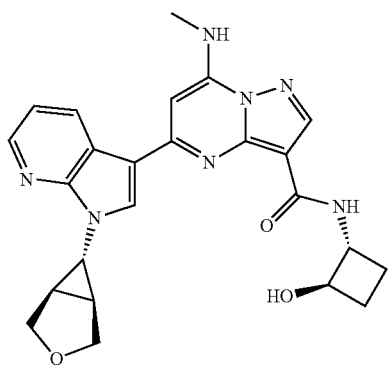 [SMILES: CNc1cc(-c2cn([C@H]3[C@@H]4COC[C@@H]43)c3ncccc23)nc2c(C(=O)N[C@@H]3CC[C@H]3O)cnn12]
I-961
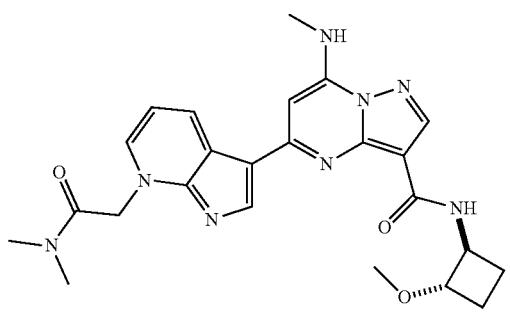
I-962
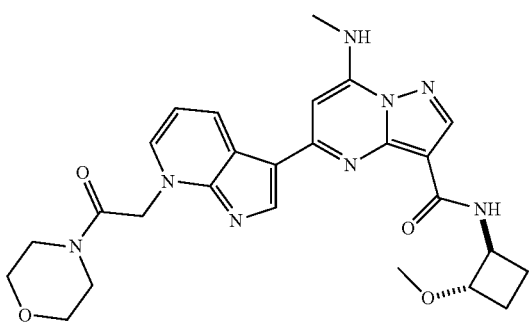

TABLE 1-continued

Selected Compounds

| Number | Structure |
|---|---|
| I-963 | (structure) |
| I-964 | (structure) |
| I-965 | (structure) |
| I-966 | (structure) |

TABLE 1-continued

| Number | Structure |
|---|---|
| I-967 | 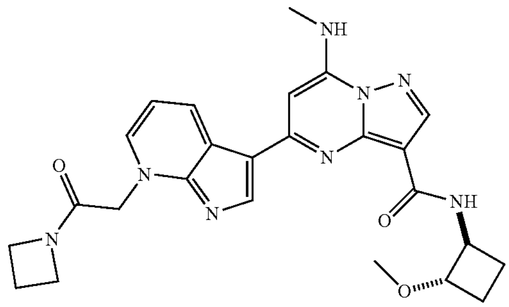 |
| I-968 | 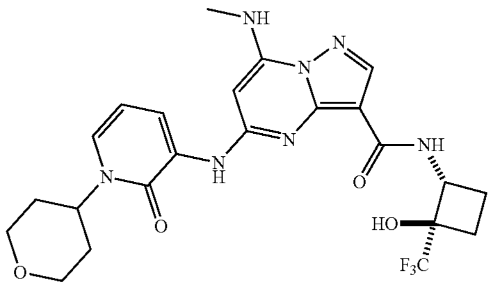 |
| I-969 | 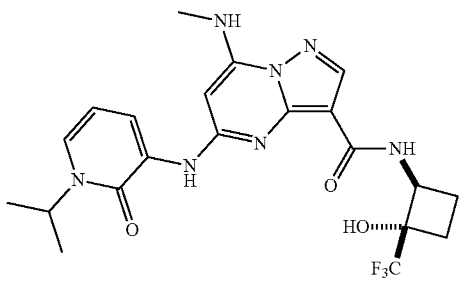 |
| I-970 | 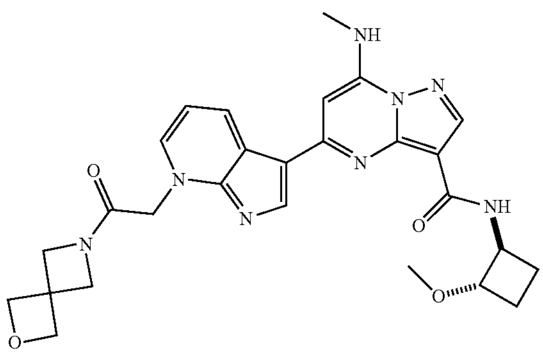 |
| I-971 | 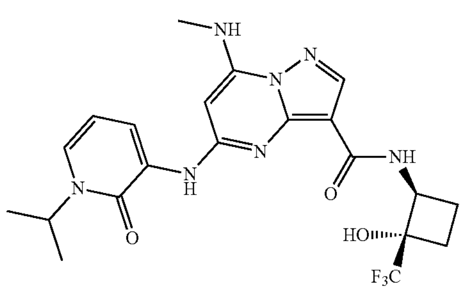 [SMILES: CNc1cc(Nc2cccn(C(C)C)c2=O)nc2c(C(=O)N[C@H]3CC[C@@]3(O)C(F)(F)F)cnn12] |

TABLE 1-continued

| Number | Structure |
|---|---|
| I-972 | 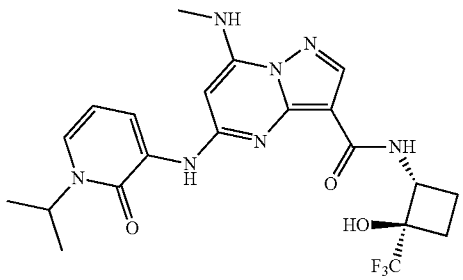 [SMILES: CNc1cc(Nc2cccn(C(C)C)c2=O)nc2c(C(=O)N[C@@H]3CC[C@]3(O)C(F)(F)F)cnn12] |
| I-973 | 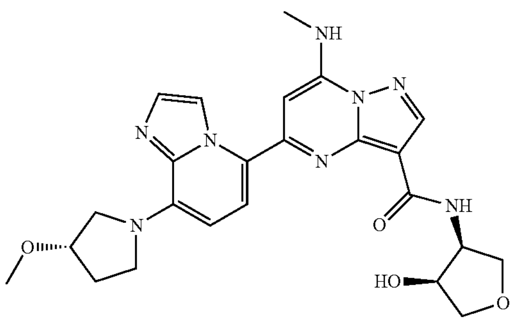 [SMILES: CNc1cc(-c2ccc(N3CC[C@H](OC)C3)c3nccn23)nc2c(C(=O)N[C@H]3COC[C@H]3O)cnn12] |
| I-974 | 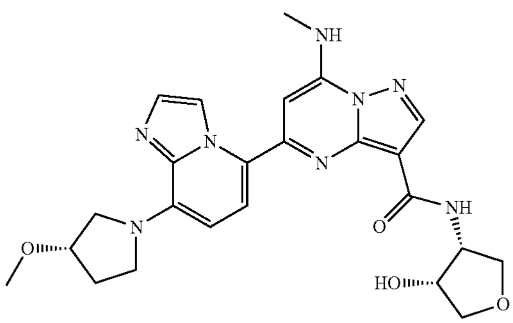 [SMILES: CNc1cc(-c2ccc(N3CC[C@H](OC)C3)c3nccn23)nc2c(C(=O)N[C@@H]3COC[C@@H]3O)cnn12] |
| I-975 | 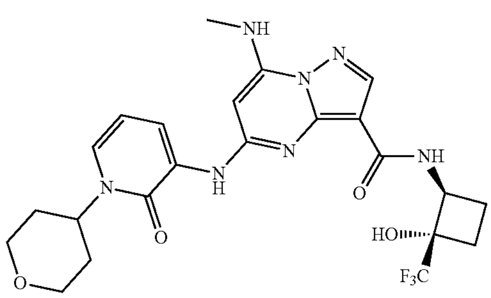 [SMILES: CNc1cc(Nc2cccn(C3CCOCC3)c2=O)nc2c(C(=O)N[C@H]3CC[C@@]3(O)C(F)(F)F)cnn12] |
| I-976 | 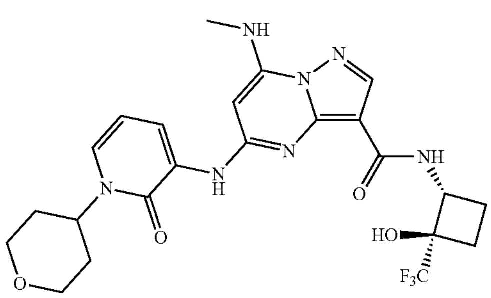 [SMILES: CNc1cc(Nc2cccn(C3CCOCC3)c2=O)nc2c(C(=O)N[C@@H]3CC[C@]3(O)C(F)(F)F)cnn12] |

TABLE 1-continued

Selected Compounds

| Number | Structure |
|---|---|
| I-977 | 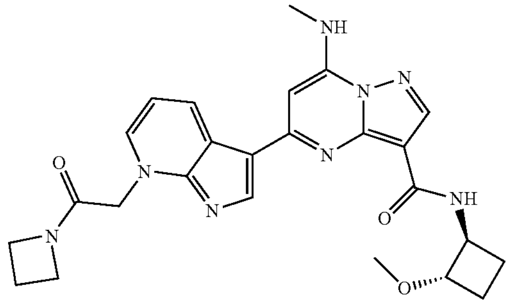 [SMILES: CNc1cc(-c2cnc3n(CC(=O)N4CCC4)cccc2-3)nc2c(C(=O)N[C@H]3CC[C@@H]3OC)cnn12] |
| I-978 | 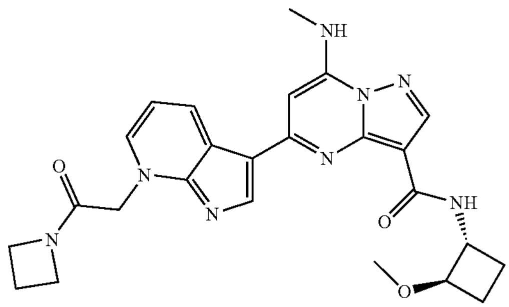 [SMILES: CNc1cc(-c2cnc3n(CC(=O)N4CCC4)cccc2-3)nc2c(C(=O)N[C@@H]3CC[C@H]3OC)cnn12] |
| I-979 | 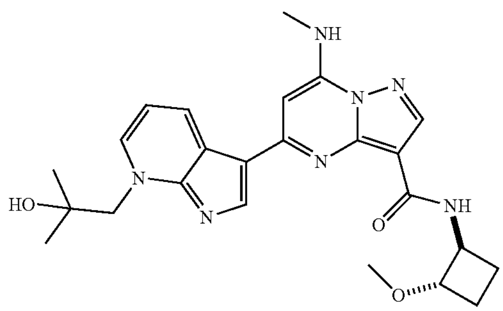 |
| I-980 | 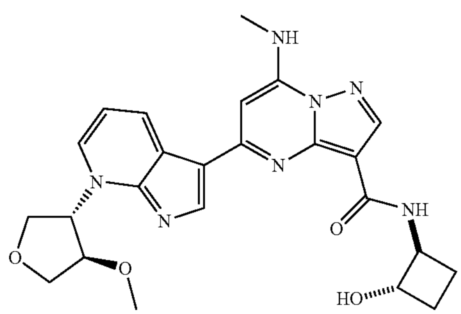 |
| I-981 | 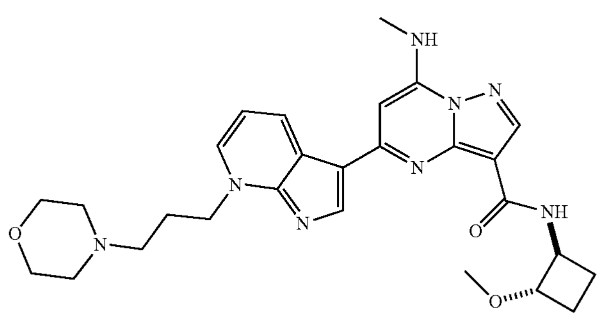 |

TABLE 1-continued
Selected Compounds
| Number | Structure |
|---|---|
| I-982 | 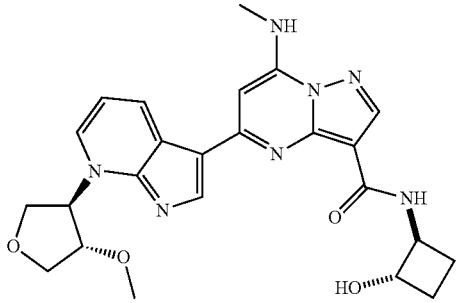 |
| I-983 | 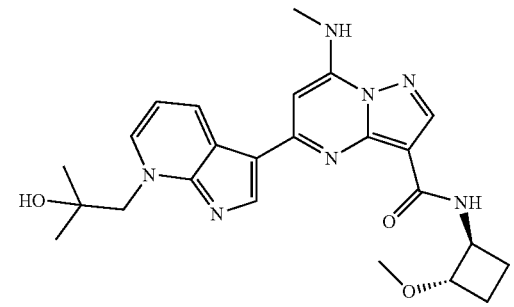 [SMILES: CNc1cc(-c2cnc3n(CC(C)(C)O)cccc2-3)nc2c(C(=O)N[C@H]3CC[C@@H]3OC)cnn12] |
| I-984 | 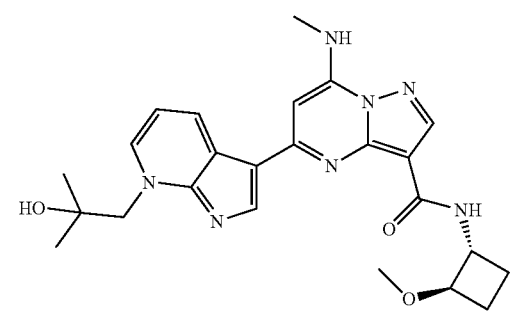 [SMILES: CNc1cc(-c2cnc3n(CC(C)(C)O)cccc2-3)nc2c(C(=O)N[C@@H]3CC[C@H]3OC)cnn12] |
| I-985 | 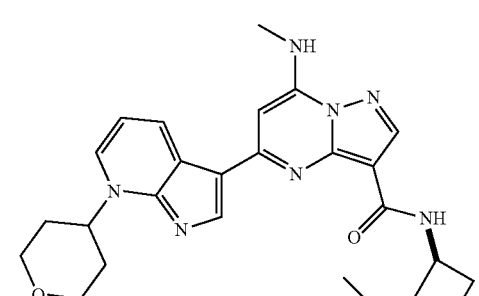 |
| I-986 | 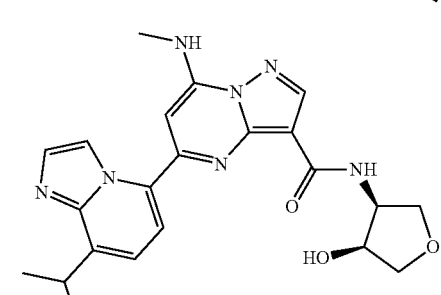 |

TABLE 1-continued

Selected Compounds

| Number | Structure |
|---|---|
| I-987 | 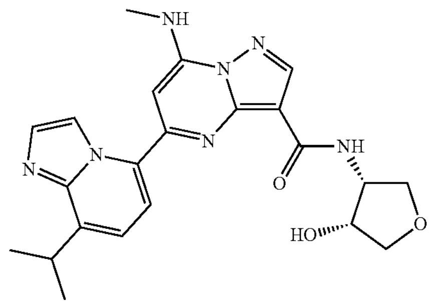 [SMILES: CNc1cc(-c2ccc(C(C)C)c3nccn23)nc2c(C(=O)N[C@@H]3COC[C@@H]3O)cnn12] |
| I-988 | 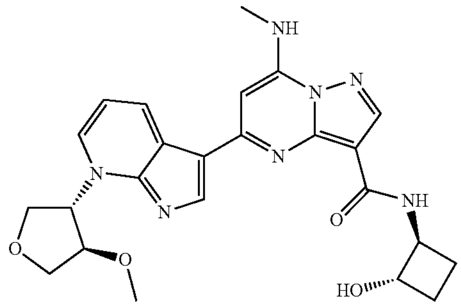 [SMILES: CNc1cc(-c2cnc3n([C@H]4COC[C@@H]4OC)cccc2-3)nc2c(C(=O)N[C@H]3CC[C@@H]3O)cnn12] |
| I-989 | 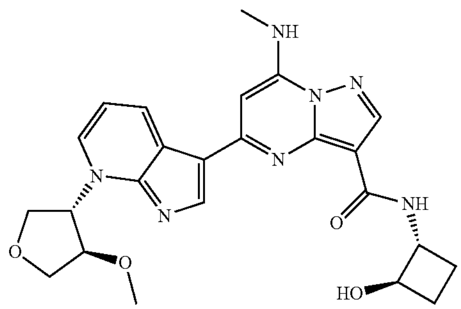 [SMILES: CNc1cc(-c2cnc3n([C@H]4COC[C@@H]4OC)cccc2-3)nc2c(C(=O)N[C@@H]3CC[C@H]3O)cnn12] |
| I-990 | 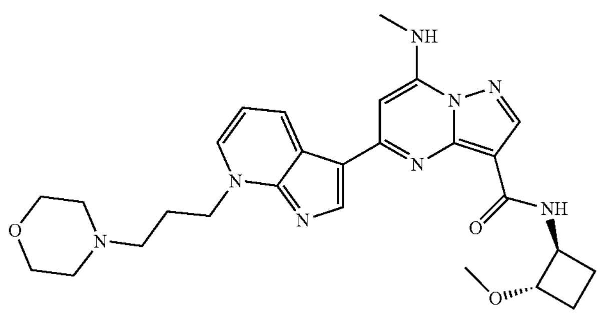 [SMILES: CNc1cc(-c2cnc3n(CCCN4CCOCC4)cccc2-3)nc2c(C(=O)N[C@H]3CC[C@@H]3OC)cnn12] |
| I-991 | 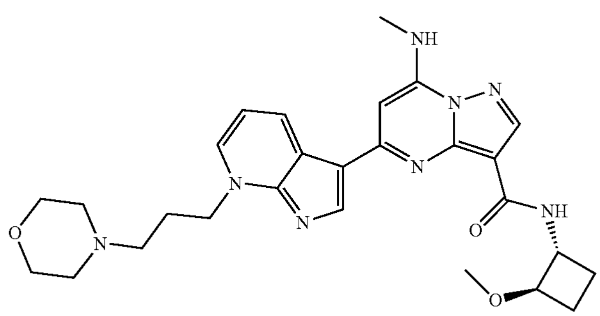 [SMILES: CNc1cc(-c2cnc3n(CCCN4CCOCC4)cccc2-3)nc2c(C(=O)N[C@@H]3CC[C@H]3OC)cnn12] |

TABLE 1-continued
| Number | Structure |
|---|---|
| I-992 | 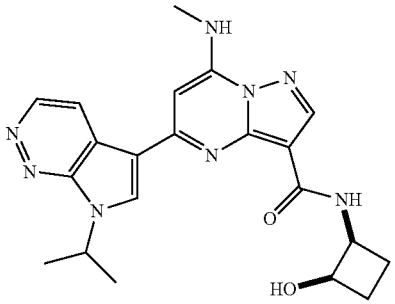 |
| I-993 | 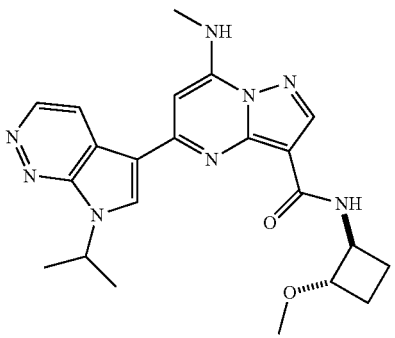 |
| I-994 | 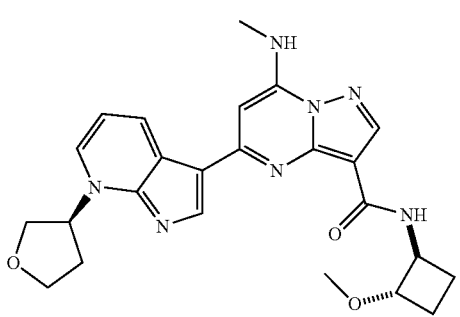 |
| I-995 | 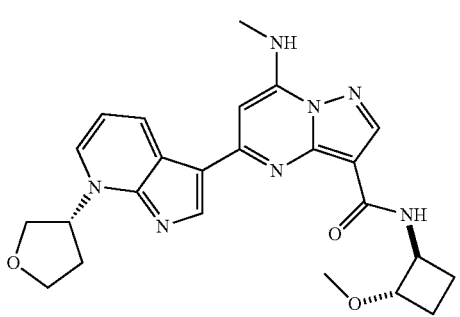 |

TABLE 1-continued
Selected Compounds
| Number | Structure |
|---|---|
| I-996 | 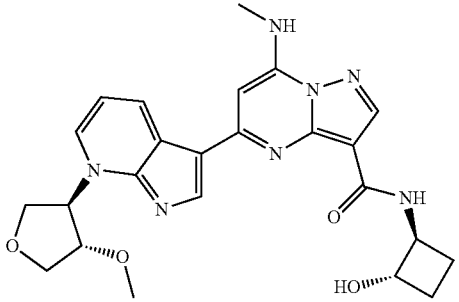 [SMILES: CNc1cc(-c2cnc3n([C@@H]4COC[C@H]4OC)cccc2-3)nc2c(C(=O)N[C@H]3CC[C@@H]3O)cnn12] |
| I-997 | 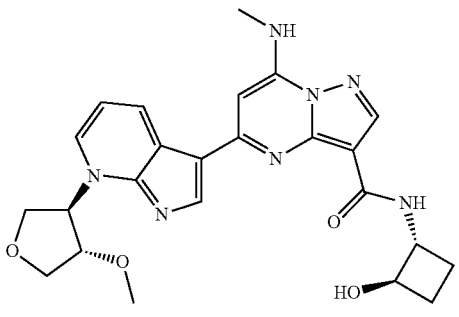 [SMILES: CNc1cc(-c2cnc3n([C@@H]4COC[C@H]4OC)cccc2-3)nc2c(C(=O)N[C@@H]3CC[C@H]3O)cnn12] |
| I-998 | 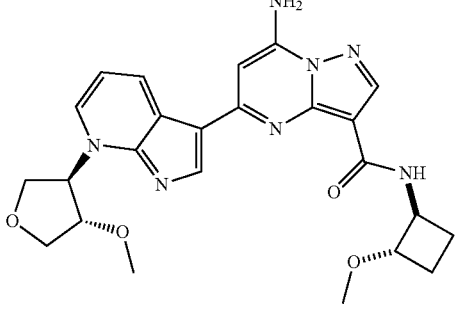 |
| I-999 | 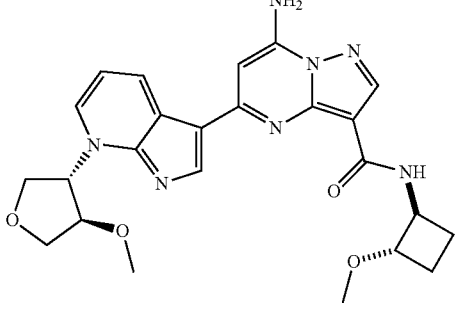 |
| I-1000 | 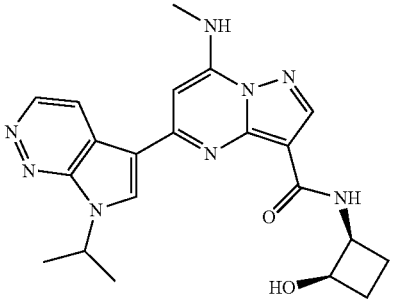 [SMILES: CNc1cc(-c2cn(C(C)C)c3nnccc23)nc2c(C(=O)N[C@H]3CC[C@H]3O)cnn12] |

TABLE 1-continued

Selected Compounds

| Number | Structure |
|--------|-----------|
| I-1001 | 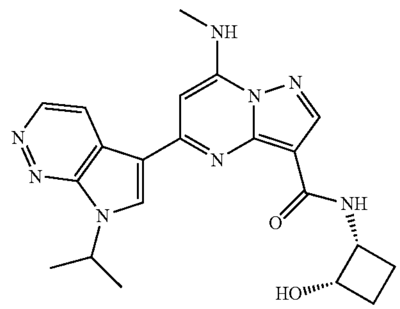 [SMILES: CNc1cc(-c2cn(C(C)C)c3nnccc23)nc2c(C(=O)N[C@@H]3CC[C@@H]3O)cnn12] |
| I-1002 | 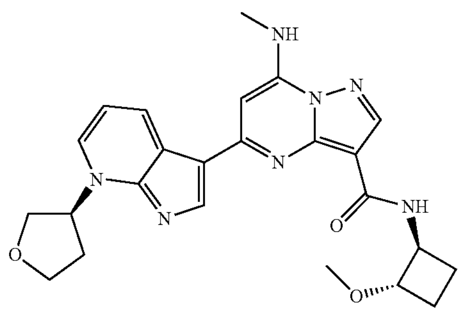 [SMILES: CNc1cc(-c2cnc3n([C@H]4CCOC4)cccc2-3)nc2c(C(=O)N[C@H]3CC[C@@H]3OC)cnn12] |
| I-1003 | 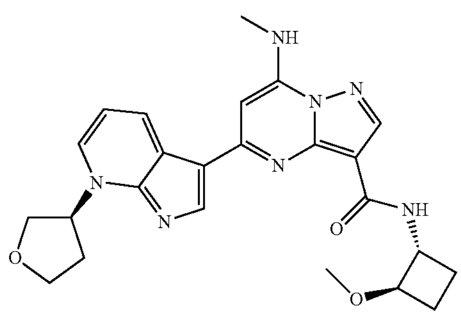 [SMILES: CNc1cc(-c2cnc3n([C@H]4CCOC4)cccc2-3)nc2c(C(=O)N[C@@H]3CC[C@H]3OC)cnn12] |
| I-1004 | 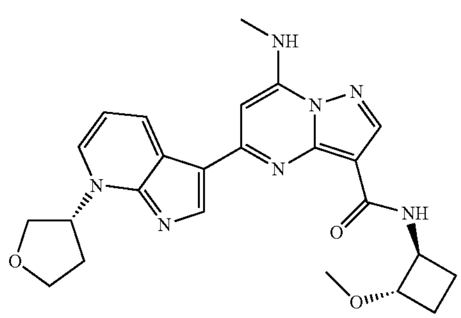 [SMILES: CNc1cc(-c2cnc3n([C@@H]4CCOC4)cccc2-3)nc2c(C(=O)N[C@H]3CC[C@@H]3OC)cnn12] |
| I-1005 | 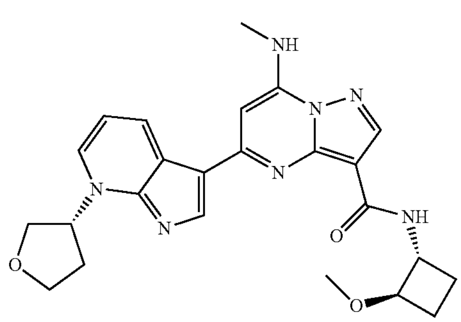 [SMILES: CNc1cc(-c2cnc3n([C@@H]4CCOC4)cccc2-3)nc2c(C(=O)N[C@@H]3CC[C@H]3OC)cnn12] |

TABLE 1-continued
| Selected Compounds | |
|---|---|
| Number | Structure |
I-1006
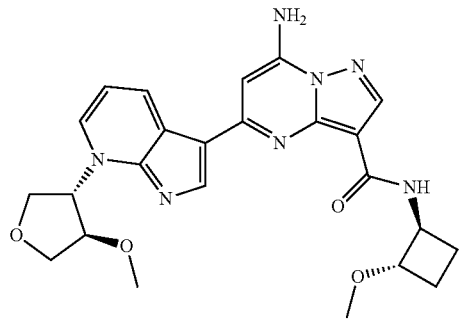 [SMILES: CO[C@H]1CC[C@@H]1NC(=O)c1cnn2c(N)cc(-c3cnc4n([C@H]5COC[C@@H]5OC)cccc3-4)nc12]
I-1007
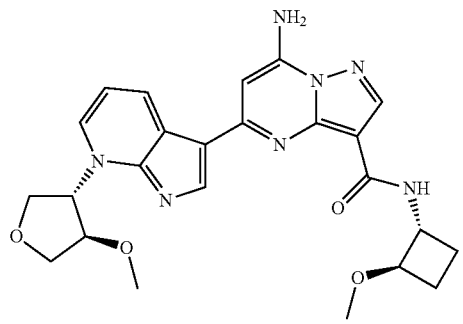 [SMILES: CO[C@H]1COC[C@@H]1n1cccc2c(-c3cc(N)n4ncc(C(=O)N[C@@H]5CC[C@H]5OC)c4n3)cnc1-2]
I-1008
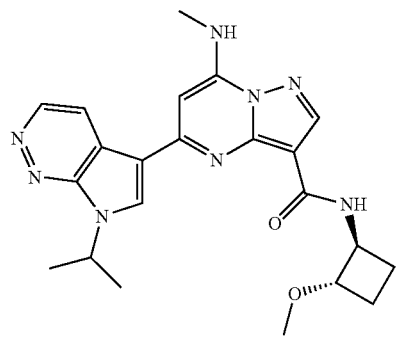 [SMILES: CNc1cc(-c2cn(C(C)C)c3nnccc23)nc2c(C(=O)N[C@H]3CC[C@@H]3OC)cnn12]
I-1009
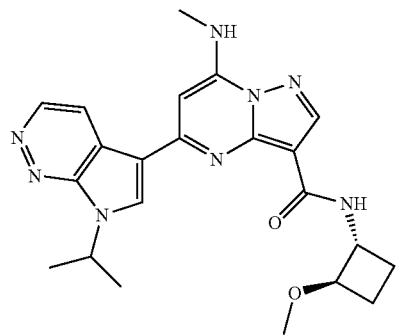 [SMILES: CNc1cc(-c2cn(C(C)C)c3nnccc23)nc2c(C(=O)N[C@@H]3CC[C@H]3OC)cnn12]

TABLE 1-continued

| Selected Compounds | |
|---|---|
| Number | Structure |
| I-1010 | |
| I-1011 | |
| I-1012 | |
| I-1013 | |

TABLE 1-continued

| Selected Compounds | |
|---|---|
| Number | Structure |
| I-1014 | |
| I-1015 | |
| I-1016 | |
| I-1017 | |

TABLE 1-continued

Selected Compounds

| Number | Structure |
|---|---|
| I-1018 | 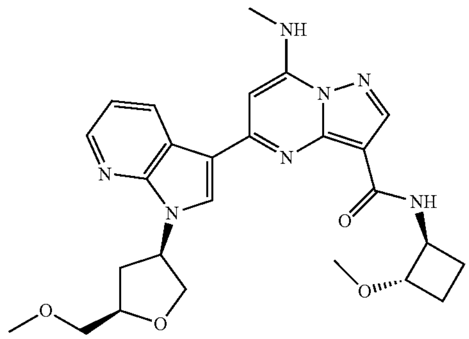 [SMILES: CNc1cc(-c2cn([C@H]3CO[C@@H](COC)C3)c3ncccc23)nc2c(C(=O)N[C@H]3CC[C@@H]3OC)cnn12] |
| I-1019 | 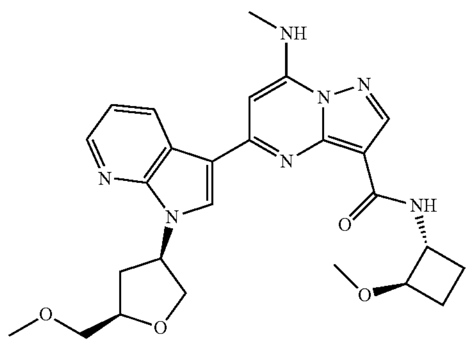 [SMILES: CNc1cc(-c2cn([C@H]3CO[C@@H](COC)C3)c3ncccc23)nc2c(C(=O)N[C@@H]3CC[C@H]3OC)cnn12] |
| I-1020 | 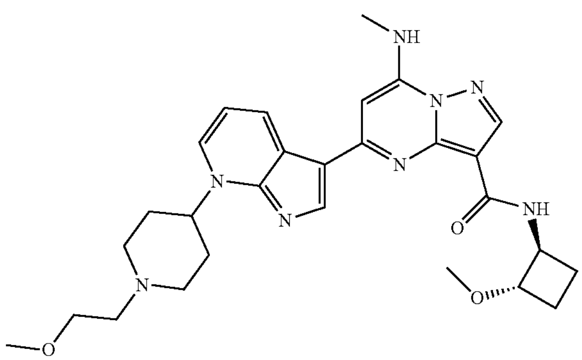 [SMILES: CNc1cc(-c2cnc3n(C4CCN(CCOC)CC4)cccc2-3)nc2c(C(=O)N[C@H]3CC[C@@H]3OC)cnn12] |
| I-1021 | 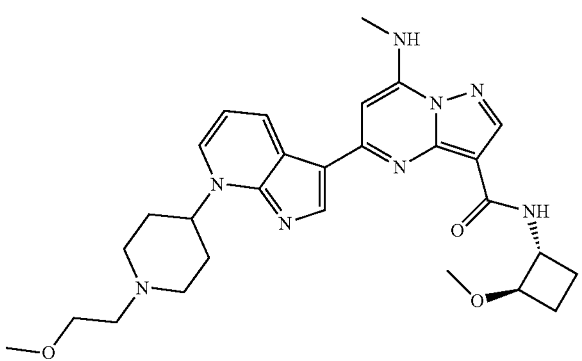 [SMILES: CNc1cc(-c2cnc3n(C4CCN(CCOC)CC4)cccc2-3)nc2c(C(=O)N[C@@H]3CC[C@H]3OC)cnn12] |

TABLE 1-continued

| Number | Structure |
|--------|-----------|
| I-1022 | 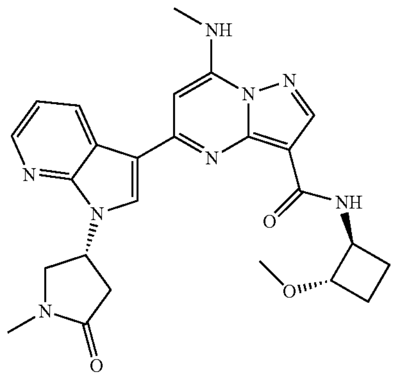 [SMILES: CNc1cc(-c2cn([C@@H]3CC(=O)N(C)C3)c3ncccc23)nc2c(C(=O)N[C@H]3CC[C@@H]3OC)cnn12] |
| I-1023 | 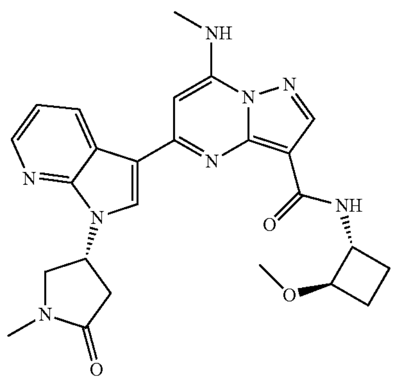 [SMILES: CNc1cc(-c2cn([C@@H]3CC(=O)N(C)C3)c3ncccc23)nc2c(C(=O)N[C@@H]3CC[C@H]3OC)cnn12] |
| I-1024 | 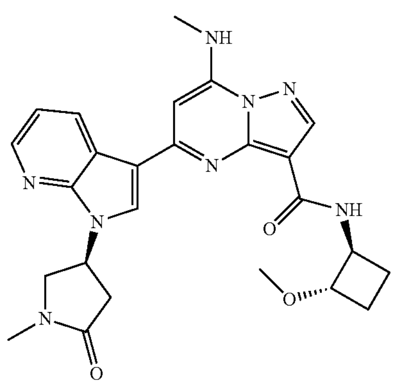 [SMILES: CNc1cc(-c2cn([C@H]3CC(=O)N(C)C3)c3ncccc23)nc2c(C(=O)N[C@H]3CC[C@@H]3OC)cnn12] |
| I-1025 | 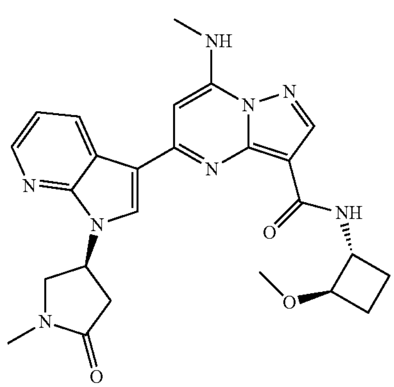 [SMILES: CNc1cc(-c2cn([C@H]3CC(=O)N(C)C3)c3ncccc23)nc2c(C(=O)N[C@@H]3CC[C@H]3OC)cnn12] |

TABLE 1-continued
Selected Compounds
| Number | Structure |
|---|---|
| I-1026 | 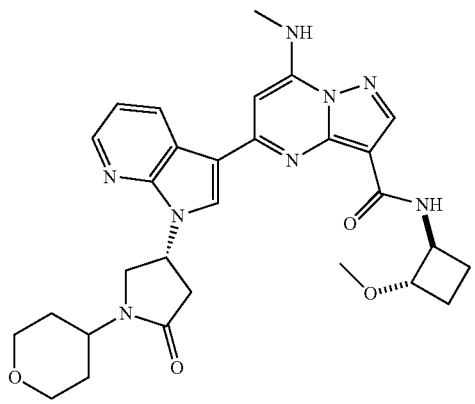 |
| I-1027 | 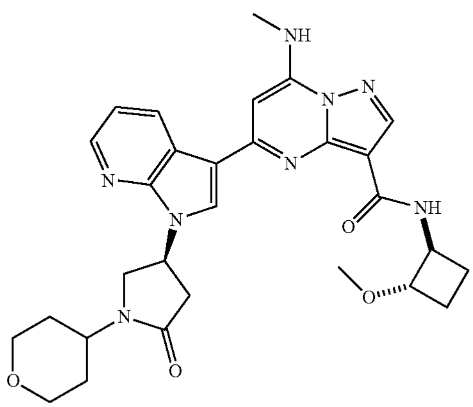 |
| I-1028 | 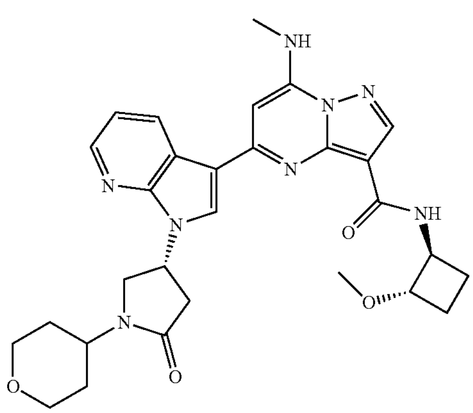 [SMILES: CNc1cc(-c2cn([C@@H]3CC(=O)N(C4CCOCC4)C3)c3ncccc23)nc2c(C(=O)N[C@H]3CC[C@@H]3OC)cnn12] |

TABLE 1-continued

Selected Compounds

| Number | Structure |
|---|---|
| I-1029 | 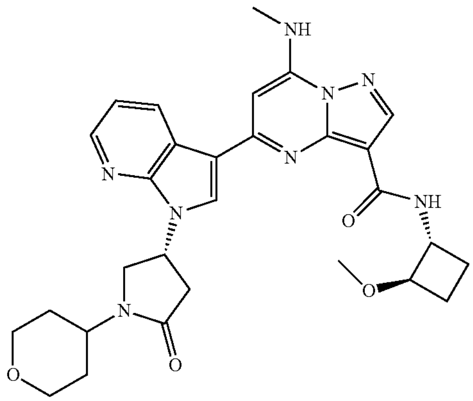 [SMILES: CNc1cc(-c2cn([C@@H]3CC(=O)N(C4CCOCC4)C3)c3ncccc23)nc2c(C(=O)N[C@@H]3CC[C@H]3OC)cnn12] |
| I-1030 | 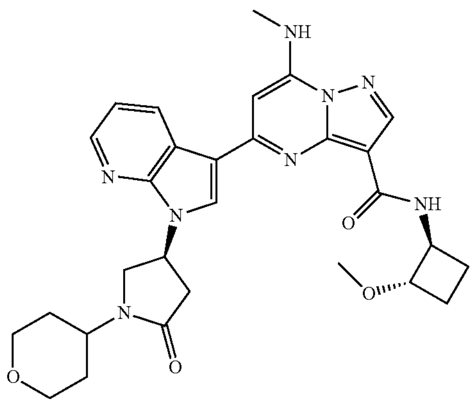 [SMILES: CNc1cc(-c2cn([C@H]3CC(=O)N(C4CCOCC4)C3)c3ncccc23)nc2c(C(=O)N[C@H]3CC[C@@H]3OC)cnn12] |
| I-1031 | 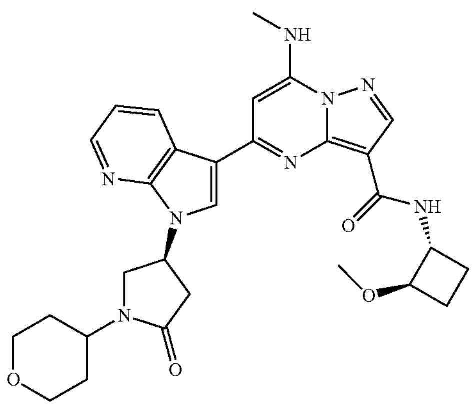 [SMILES: CNc1cc(-c2cn([C@H]3CC(=O)N(C4CCOCC4)C3)c3ncccc23)nc2c(C(=O)N[C@@H]3CC[C@H]3OC)cnn12] |

In some embodiments, the method employs a compound set forth in Table 1, above, or a pharmaceutically acceptable salt thereof. In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2.

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g., IFN-α, IFN-β, IFN-κ, IFN-δ, IFN-ε, IFN-τ, IFN-ω, and IFN-ζ (also known as limiting), and interleukins (e.g., IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12Rβ1 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and IL23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4- mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al., "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al., "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al., "Discovering What Makes STAT Signaling TYK in T-ALL," Cancer Disc. (2013) 3:494-496.

TYK2 mediated STAT3 signaling has also been shown to mediate neuronal cell death caused by amyloid-$\beta$ (A$\beta$) peptide. Decreased TYK2 phosphorylation of STAT3 following A$\beta$ administration lead to decreased neuronal cell death, and increased phosphorylation of STAT3 has been observed in postmortem brains of Alzheimer's patients. Wan et al., "Tyk/STAT3 Signaling Mediates $\beta$-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, cutaneous lupus erythematosus, systemic lupus erythematosus, multiple sclerosis, psoriasis, Behçet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, cutaneous lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g., hemolytic anemia, aplastic anemia, pure red cell anemia and idiopathic thrombocytopenia), cutaneous lupus erythematosus, systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g., including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from cutaneous lupus erythematosus, Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of Formula I and one or more additional therapeutic agents. The therapeutic agent may be administered together with a compound of Formula I, or may be administered prior to or following administration of a compound of Formula I. Suitable therapeutic agents are described in further detail below. In certain embodiments, a compound of Formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of Formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of Formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of Formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of Formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of Formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of Formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of Formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of Formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of Formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of Formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of Formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of Formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of Formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of Formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g., hemolytic anemia, aplastic anemia, pure red cell anemia and idiopathic thrombocytopenia), cutaneous lupus erythematosus, systemic lupus erythematosus, rheumatoid arthritis, polychondritis, scleredoma, Wegener granulamatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g., including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of Formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of Formula I. Other suitable JH2 domain binding compounds include those described in WO 2014/074660A1, WO 2014/074661A1, WO 2015/089143A1, the entirety of each of which is incorporated herein by reference. Suitable JH1 domain binding compounds include those described in WO 2015/131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal©); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™ Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g., under the trademark Carboplat™. Oxaliplatin can be administered, e.g., in the form as it is marketed, e.g., under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3K$\alpha$, PI3K$\gamma$, PI3K$\delta$, PI3K$\beta$, PI3K-C$_2$a, PI3K-C2$\alpha$, PI3K-C2$\gamma$, Vps34, p110-$\alpha$, p110-$\beta$, p110-$\gamma$, p110-$\delta$, p85-$\alpha$, p85-$\beta$, p55-$\gamma$, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO 2008/118802), navitoclax (and analogs thereof, see U.S. Pat. No. 7,390,799), NH-1 (Shenayng Pharmaceutical University), obatoclax (and analogs thereof, see WO 2004/106328), 5-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO2004019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g., unrelated to protein or lipid kinase inhibition, e.g., thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are, e.g., inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MM1270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and $2C_4$ Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g., midostaurin or lestaurtinib), sorafenib, tandutinib, LY-2401401, LS-104, EB-10, famitinib, NOV-110302, NMS-P948, AST-487, G-749, SB-1317, 5-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone, and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g., Patents International (e.g., IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

The present invention is now further described by means of non-limiting embodiments 1 through 31.

Embodiment 1

A compound of Formula I:

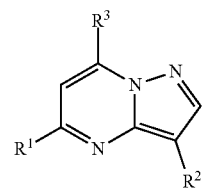

or a pharmaceutically acceptable salt thereof, wherein:
$R^1$ is $-L^1-R^{1A}$;
$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-;
Cy is an optionally substituted 5-6 membered monocyclic heteroaryl ring having 1-4 heteroatoms independently selected from nitrogen, oxygen, and sulfur; an optionally substituted 8-10 membered bicyclic heteroaryl ring having 1-4 heteroatoms independently selected from nitrogen, oxygen, and sulfur; an optionally substituted 3-7 membered saturated or partially unsaturated carbocyclic ring; or an optionally substituted 7-12 membered saturated or partially unsaturated bicyclic heterocyclic ring having 1-4 heteroatoms independently selected from nitrogen, oxygen, and sulfur;

$R^{1A}$ is an optionally substituted $C_{1-6}$ aliphatic; an optionally substituted 3-7 member saturated or partially unsaturated monocyclic carbocyclic ring; an optionally substituted 3-7 membered monocyclic heterocyclic ring having 1-4 heteroatoms independently selected from nitrogen, oxygen, and sulfur; or an optionally substituted 6-10 member bridged heterocyclic ring having 1-2 heteroatoms independently selected from nitrogen, oxygen, and sulfur; or an optionally substituted 5-10 member heteroaryl monocyclic or bicyclic ring having 1-4 heteroatoms independently selected from nitrogen, oxygen, and sulfur;

$R^2$ is —C(O)NH$_2$; —C(O)NHR$^{2A}$; —C(O)N(R$^{2A}$)$_2$; or a 5-6 membered monocyclic heteroaryl ring having 1-4 heteroatoms independently selected from nitrogen, oxygen, and sulfur, wherein said heteroaryl ring is substituted with m instances of $R^{2B}$;

$R^{2A}$ is an optionally substituted 3-6-member saturated or partially unsaturated carbocyclic ring or an optionally substituted 3-6 member heterocyclic ring containing 1-2 heteroatoms independently selected from nitrogen, oxygen, and sulfur;

$R^{2B}$ is an optionally substituted $C_1$-$C_6$ aliphatic;

$R^3$ is —NHR$^{3A}$;

$R^{3A}$ is Me;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur:

wherein each hydrogen bound to carbon can be optionally and independently replaced by deuterium; and m is 0, 1, or 2.

Embodiment 2

The compound of embodiment 1 of Formulae II or IV:

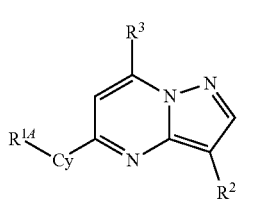

II

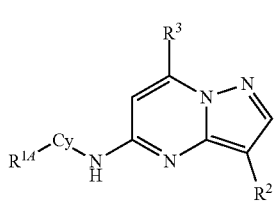

IV or a pharmaceutically acceptable salt thereof.

Embodiment 3

The compound of embodiments 1 or 2 of Formulae III or V:

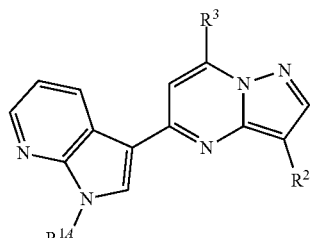

III

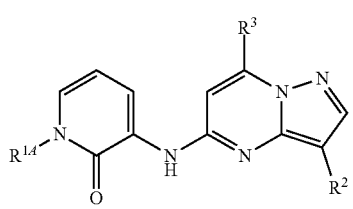

V or a pharmaceutically acceptable salt thereof.

Embodiment 4

The compound of any one of embodiments 1 through 3 of Formula VI:

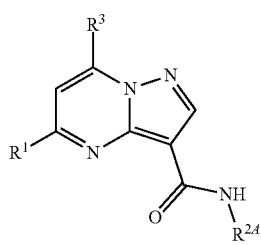

VI or a pharmaceutically acceptable salt thereof.

Embodiment 5

The compound of any one of embodiments 1 through 3 of Formula VII:

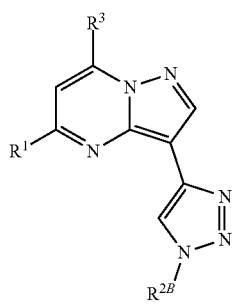

VII or a pharmaceutically acceptable salt thereof.

Embodiment 6

The compound of any one of embodiments 1 through 5 of Formula VIII:

VIII or a pharmaceutically acceptable salt thereof.

Embodiment 7

The compound of any one of embodiments 1 through 6, wherein $R^{1A}$ is selected from:

Embodiment 8

The compound of any one of embodiments 1 through 4, 6, and 7, wherein $R^{2A}$ is selected from:

533

-continued

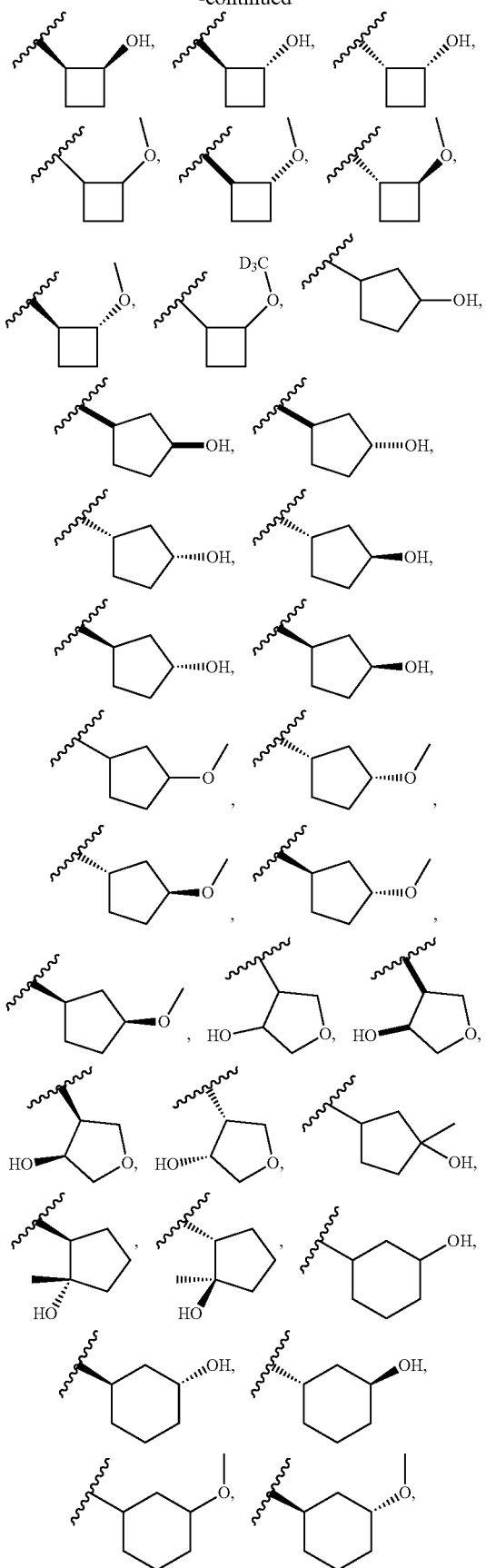

534

-continued

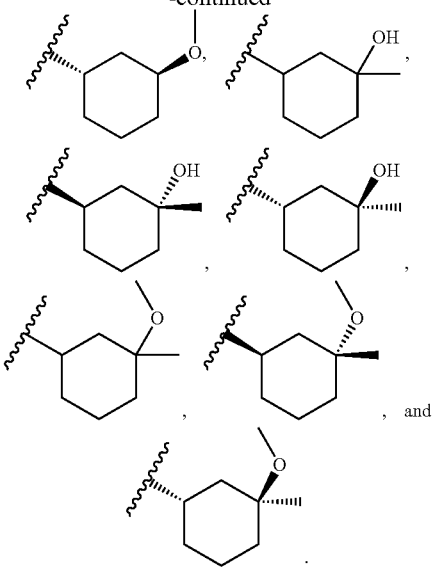

Embodiment 9

The compound of any one of embodiments 1 through 8, selected from those depicted in Table 1, or a pharmaceutically acceptable salt thereof.

Embodiment 10

A pharmaceutical composition comprising a compound according to any one of embodiments 1 through 9, or a pharmaceutically acceptable salt thereof, and a pharmaceutically acceptable carrier, adjuvant, or vehicle.

Embodiment 11

The compound of any one of embodiments 1 through 9, or the pharmaceutical composition of embodiment 10, for use in the manufacture of a medicament for the treatment of a TYK2 mediated disorder, disease, or condition in a patient.

Embodiment 12

A method of inhibiting TYK2 in a biological sample comprising contacting the sample with the compound of any one of embodiments 1 through 9, or a pharmaceutically acceptable salt thereof, or the pharmaceutical composition of embodiment 10.

Embodiment 13

A method of treating a TYK2-mediated disorder, disease, or condition in a patient comprising administering to said patient the compound of any one of embodiments 1 through 9, or a pharmaceutically acceptable salt thereof, or the pharmaceutical composition of embodiment 10.

Embodiment 14

The method of embodiment 13, wherein the disorder is selected from an autoimmune disorder, an inflammatory

535 disorder, a proliferative disorder, an endocrine disorder, a neurological disorder, or a disorder associated with transplantation.

Embodiment 15

The method of embodiment 14, wherein the disorder is an autoimmune disorder.

Embodiment 16

The method of embodiment 15, wherein the autoimmune disorder is selected from type 1 diabetes, ankylosing spondylitis, cutaneous lupus erythematosus, systemic lupus erythematosus, multiple sclerosis, systemic sclerosis, psoriasis, Crohn's disease, ulcerative colitis, and inflammatory bowel disease.

Embodiment 17

The method of embodiment 14, wherein the disorder is an inflammatory disorder.

Embodiment 18

The method of embodiment 17, wherein the inflammatory disorder is selected from rheumatoid arthritis, asthma, chronic obstructive pulmonary disease, psoriasis, Crohn's disease, ulcerative colitis, and inflammatory bowel disease.

Embodiment 19

The method of embodiment 14, wherein the disorder is a proliferative disorder.

Embodiment 20

The method of embodiment 19, wherein the proliferative disorder is a hematological cancer.

Embodiment 21

The method of embodiment 19, wherein the proliferative disorder is a leukemia.

Embodiment 22

The method of embodiment 21, wherein the leukemia is a T-cell leukemia.

Embodiment 23

The method of embodiment 22, wherein the T-cell leukemia is T-cell acute lymphoblastic leukemia (T-ALL).

Embodiment 24

The method of embodiment 20, wherein the proliferative disorder is associated with one or more activating mutations in TYK2.

Embodiment 25

The method of embodiment 14, wherein the disorder is associated with transplantation.

536

Embodiment 26

The method of embodiment 25, wherein the disorder is transplant rejection or graft versus host disease.

Embodiment 27

The method of embodiment 14, wherein the disorder is an endocrine disorder.

Embodiment 28

The method of embodiment 27, wherein the endocrine disorder is polycystic ovary syndrome, Crouzon's syndrome, or type 1 diabetes.

Embodiment 29

The method of embodiment 14, wherein the disorder is a neurological disorder.

Embodiment 30

The method of embodiment 29, wherein the neurological disorder is Alzheimer's disease.

Embodiment 31

The method of embodiment 14, wherein the disorder is associated with type I interferon, IL-10, IL-12, or IL-23 signaling.

Exemplification

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation of Core A: 7-((Tert-butoxycarbonyl)(methyl)amino)-5-chloropyrazolo[1,5-a]pyrimidine-3-carboxylic acid

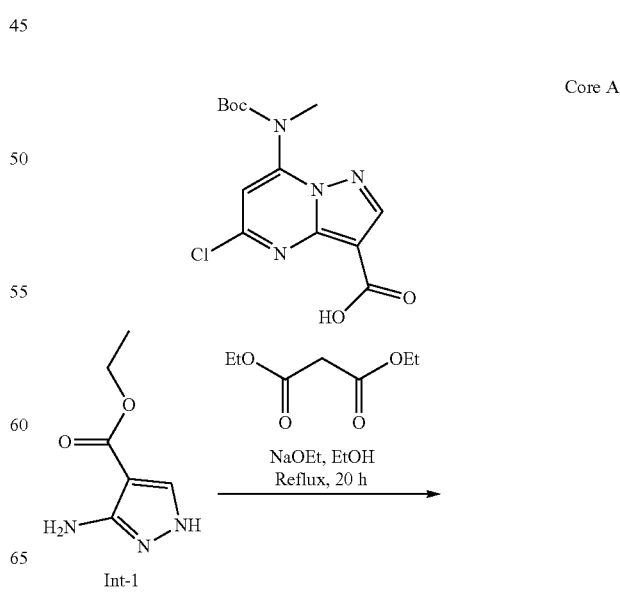

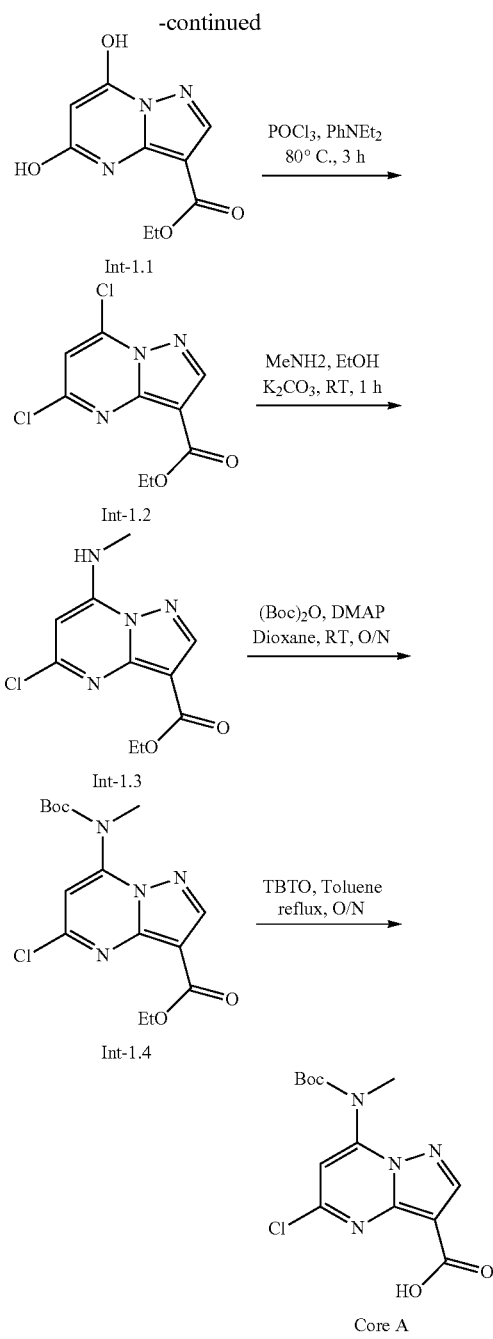

Step 1—Synthesis of Int-1.1: To a solution of Int-1 (50 g, 322.25 mmol, 1.0 eq) in ethanol (250 mL) was added diethyl malonate (103.2 g, 644.51 mmol, 2.0 eq) followed by dropwise addition of sodium ethoxide (75 mL, 21% ethanol solution, 3.0 eq). Reaction mixture was stirred with heating under reflux for 20 h. After completion of reaction, reaction mixture was concentrated under reduced pressure to obtain residue which was dissolved in water, acidified with concentrated hydrochloric acid to pH~3-4. Precipitated solid was filtered, washed with water, diethyl ether and dried well to obtain pure Int-1.1 (43 g, Yield: 59.79%; MS (ES): m/z 224.2 [M+H]$^+$).

Step 2—Synthesis of Int-1.2: To a mixture of Int-1.1 (43 g, 192.6 mmol, 1.0 eq) in phosphorous oxychloride (191 g, 1251 mmol, 6.5 eq) was added diethyl aniline (43 g, 288.9 mmol, 1.5 eq). Reaction mixture stirred at 80° C. for 3 h. After completion of reaction; reaction mixture was concentrated under reduced pressure to obtained residue which was transferred into ice cold water and extracted with dichloromethane. Organic layer was combined, washed with saturated sodium bicarbonate solution followed by brine solution, dried over sodium sulphate and concentrated under reduced pressure to pressure to obtain crude material. This was further purified by column chromatography and the compound was eluted in 20% ethyl acetate in hexane to obtain pure Int 1.2 (35 g, Yield: 69.85%; MS (ES): m/z 261 [M+H]$^+$).

Step 3—Synthesis of Int-1.3: To a solution of Int-1.2 (35 g, 134.58 mmol, 1.0 eq) in ethanol (350 mL) was added potassium carbonate (18.57 g, 134.58 mmol, 1.0 eq) at 0° C. followed by methylamine (40% in water)(10.95 mL, 141.3 mmol, 1.05 eq) and reaction mixture stirred at room temperature for 1 h. After completion of reaction; reaction mixture was concentrated under reduced pressure to obtained residue which was transferred into ice cold water. Precipitated solid was filtered, washed with water and dried well under vacuum to obtain Int-1.3 (30 g, Yield: 87.53%; MS (ES): m/z 255.6 [M+H]$^+$).

Step 4—Synthesis of Int-1.4: To a solution of Int-1.3 (30 g, 117.8 mmol, 1.0 eq) in 1,4-dioxane (300 mL) was added N,N-dimethylaminopyridine (1.43 g, 11.78 mmol, 0.1 eq) followed by Di-tert-butyl dicarbonate (51.36 g, 235.6 mmol, 2.0 eq) and reaction mixture was stirred at room temperature for 12 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 12% ethyl acetate in hexane to obtain Int-1.4 (26 g, 62.21%; MS (ES): m/z 355 [M+H]$^+$).

Step 5—Synthesis of Core A: To a suspension of Int-1.4 (20 g, 56.37 mmol, 1.0 eq) in toluene (200 mL) was added Tributyltin oxide (67.19 g, 112.73 mmol, 2.0 eq) and reaction mixture was heated at 120° C. for 12 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulphate and concentrated under reduced pressure to obtain solid which was triturated with hexane to obtain pure Core A (13.2 g, Yield: 71.67%; $^1$H NMR (DMSO-d6, 400 MHZ): 12.63 (s, 1H), 8.63 (s, 1H), 7.55 (s, 1H), 3.31 (s, 3H), 1.29 (s, 9H)).

Preparation of Core B: 7-(Benzyl(methyl)amino)-5-chloropyrazolo[1,5-a]pyrimidine-3-carboxamide

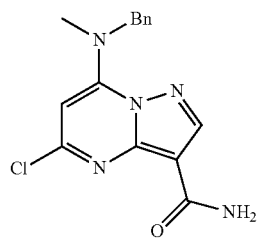

Core B

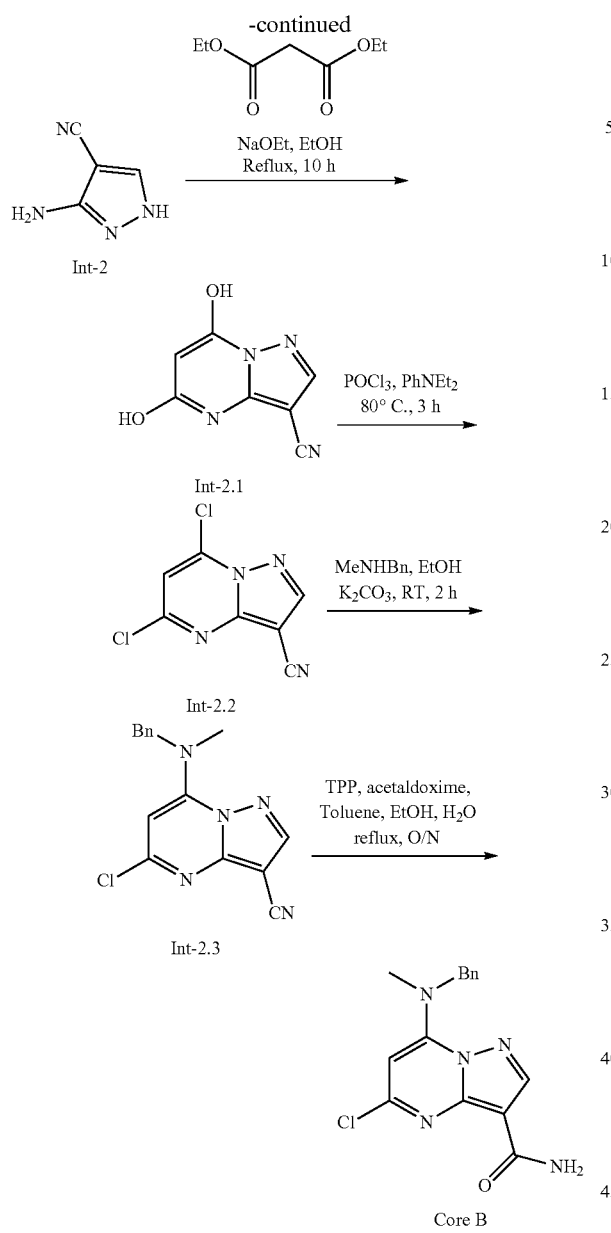

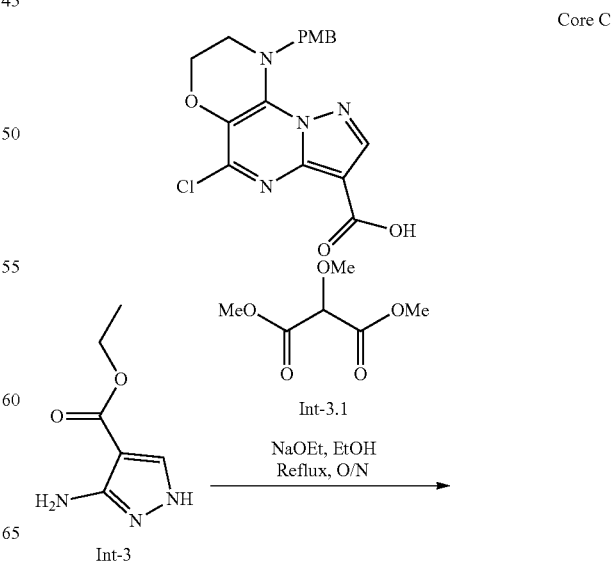

Core C dichloromethane. Organic layer was combined, washed with saturated sodium bicarbonate solution followed by brine solution, dried over sodium sulphate and concentrated under reduced pressure to pressure to obtain crude material. This was further purified by column chromatography and the compound was eluted in 20% ethyl acetate in hexane to obtain pure Int-2.2 (45 g, Yield: 74.42%; MS (ES): m/z 214.02 [M+H]$^+$).

Step 3—Synthesis of Int-2.3: To a solution of Int-2.2 (10 g, 46.94 mmol, 1.0 eq) in ethanol (315 mL) was added potassium carbonate (7.12 g, 51.63 mmol, 1.1 eq) at 0° C. followed by benzyl amine (5.64 mL, 51.63 mmol, 1.1 eq) and reaction mixture was stirred at room temperature for 2 h. After completion of reaction, reaction mixture was concentrated under reduced pressure to obtained residue which was transferred into ice cold water. Precipitated solid was filtered, washed with water and dried well under vacuum to obtain Int 2.3 (10 g, Yield: 71.54%; MS (ES): m/z 298.75 [M+H]$^+$).

Step 4—Synthesis of Core B: To a solution of Int-2.3 (10 g, 33.59 mmol, 1.0 eq) in mixture of toluene:ethanol:water (160 mL, 1.0:0.5:0.25) was added triphenylphosphine (1.76 g, 6.72 mmol, 0.2 eq) at 0° C. followed by acetaldoxime (3.96 g, 67.18 mmol, 2.0 eq) and reaction mixture was stirred at 110° C. for 5 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 25% ethyl acetate in hexane to obtain Core B (4.7 g, Yield: 44.32%; MS (ES): m/z 315.76 [M+H]$^+$; $^1$H NMR (DMSO-d$_6$, 400 MHZ): 8.44 (s, 1H), 7.52-7.50 (d, J=8 Hz, 1H), 7.44 (s, 1H), 7.38-7.29 (m, 5H), 6.50 (s, 1H), 5.41 (s, 2H), 3.23 (s, 3H)).

Preparation of Core C: 5-chloro-1-(4-methoxybenzyl)-2,3-dihydro-1H-pyrazolo[5',1':2,3]pyrimido[5,4-b][1,4]oxazine-7-carboxylic acid Step 1—Synthesis of Int-2.1: To a solution of Int-2 (50 g, 462.5 mmol, 1.0 eq) in methanol (400 mL) was added diethyl malonate (141 mL, 925.06 mmol, 2.0 eq) followed by dropwise addition of sodium ethoxide (21% in ethanol; 108 mL, 1387.5 mmol, 3.0 eq). Reaction mixture was stirred with heating under reflux for 10 h. After completion of reaction, reaction mixture was concentrated under reduced pressure to obtain residue which was dissolved in water, acidified with concentrated hydrochloric acid to pH~3-4. Precipitated solid was filtered, washed with water, diethyl ether and dried well to obtain pure Int-2.1 (50 g, Yield: 61.38%; MS (ES): m/z 177.14 [M+H]$^+$).

Step 2—Synthesis of Int-2.2: To a mixture of Int-2.1 (50 g, 283.87 mmol, 1.0 eq) and phosphorous oxychloride (163 mL, 1704.54 mmol, 6.0 eq) was added diethyl aniline (68.26 mL, 426.13 mmol, 1.5 eq). Reaction mixture stirred at 90° C. for 3 h. After completion of reaction; reaction mixture was concentrated under reduced pressure to obtained residue which was transferred into ice cold water and extracted with

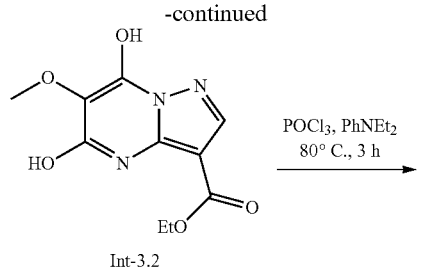

Int-3.2

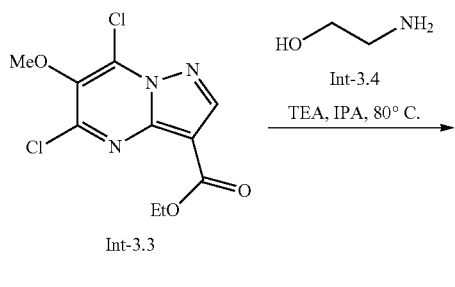

Int-3.3

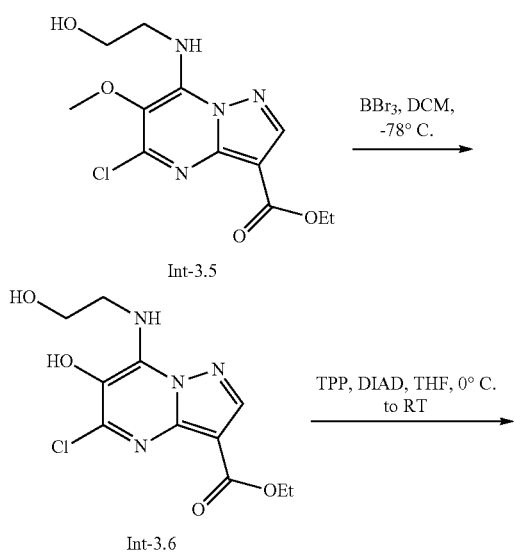

Int-3.5

Int-3.6

Int-3.7

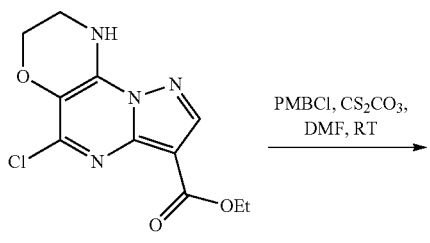

Int-3.8

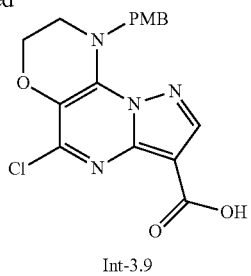

Int-3.9

Step 1—Synthesis of Compound Int-3.2: To a solution of Int-3 (50 g, 322.58 mmol, 1.0 eq) in ethanol (250 mL) was added Int-3.1 (104.5 g, 645.16 mmol, 2.0 eq) followed by drop wise addition of sodium ethoxide (75 mL, 21% ethanol solution, 3.0 eq). Reaction mixture was stirred with heating under reflux for 20 h. After completion of reaction, reaction mixture was concentrated under reduced pressure to obtain residue which was dissolved in water, acidified with concentrated hydrochloric acid to pH~3-4. Precipitated solid was filtered, washed with water, diethyl ether and dried well to obtain pure Int-3.1 (43 g, Yield: 52.70%; MS (ES): m/z 254.07 [M+H]$^+$).

Step 2—Synthesis of Compound Int-3.3: To a mixture of Int-3.2 (43 g, 169.29 mmol, 1.0 eq) and phosphorous oxychloride (168.3 g, 1100.38 mmol, 6.5 eq) was added diethyl aniline (75.7 g, 507.87 mmol, 3.0 eq). Reaction mixture stirred at 80° C. for 3 h. After completion of reaction; reaction mixture was concentrated under reduced pressure to obtained residue which was transferred into ice cold water and extracted with dichloromethane. Organic layer was combined, washed with saturated sodium bicarbonate solution followed by brine solution, dried over sodium sulphate and concentrated under reduced pressure to pressure to obtain crude material. This was further purified by column chromatography and the compound was eluted in 20% ethyl acetate in hexane to obtain pure Int-3.2 (35 g, Yield: 71.05%; MS (ES): m/z 291.00 [M+H]$^+$).

Step 3—Synthesis of Compound Int-3.5: To a solution of Int-3.3 (20 g, 68.96 mmol, 1.0 eq) in Isopropyl alcohol (200 mL) was added Int-3.4 (4.2 g, 68.96 mmol, 1.0 eq) and Triethylamine (13.9 g, 137.92 mmol, 2.0 eq). Reaction mixture stirred at 80° C. for 6 h. After completion of reaction, reaction mixture was concentrated under reduced pressure to obtain crude material which was purified by column chromatography and the compound was eluted in 3% methanol in dichloromethane to obtain pure Int-3.5 (10.0 g, Yield: 46.09%; MS (ES): m/z 315.08 [M+H]$^+$).

Step 4—Synthesis of Compound Int-3.6: To a mixture of Int-3.5 (10.0 g, 31.84 mmol, 1.0 eq) in dichloromethane (100 mL) was added drop wise boron tri-bromide (39.8 g, 159.2 mmol, 5.0 eq) at −78° C. Reaction mixture stirred at room temperature for 2 h. After completion of reaction, reaction mixture was transferred into sodium bicarbonate and product was extracted with ethyl acetate. Organic layer was combined, dried over sodium sulphate and concentrated under reduced pressure to obtain crude material. This was further purified by column chromatography and the compound was eluted in 10% methanol in dichloromethane to obtain pure Int-3.6 (6.0 g, Yield: 62.80%; MS (ES): m/z 302.06 [M+H]$^+$).

Step 5—Synthesis of Compound Int-3.7: To a solution of Int-3.6 (6.0 g 16.62 mmol, 1.0 eq) in dichloromethane (80 mL) was added triphenylphosphine (13.06 g, 49.86 mmol, 3.0 eq) and diisopropyl azodicarboxylate (10.07 g, 49.86 mmol, 3.0 eq) at 0° C. Reaction mixture stirred at room temperature for 12 h. After completion of reaction, reaction mixture was transferred into water and product was extracted with ethyl acetate. Organic layer was combined, dried over sodium sulphate and concentrated under reduced pressure to obtain Int-3.7 (3.9 g, Yield: 83.60%; MS (ES): m/z 283.06 [M+H]⁺).

Step 6—Synthesis of Compound Int-3.8: To a solution of Int-3.7 (3.9 g 13.82 mmol, 1.0 eq) in N,N-dimethylformamide (40 mL) was added 4-methoxybenzyl chloride (2.3 g, 15.20 mmol, 1.1 eq) and cesium carbonate (8.9 g, 27.84 mmol, 2.0 eq) at 0° C. Reaction mixture stirred at room temperature for 2 h. After completion of reaction, reaction mixture was transferred into water and product was extracted with ethyl acetate. Organic layer was combined, dried over sodium sulphate and concentrated under reduced pressure to obtain crude material. This was further purified by column chromatography and the compound was eluted in 20% ethyl acetate in hexane to obtain pure Int-3.8 (3.0 g, Yield: 53.98%; MS (ES): m/z 403.11 [M+H]⁺).

Step 7—Synthesis of Core C: To a suspension of Int-3.8 (3.0 g, 7.46 mmol, 1.0 eq) in toluene (30 mL) was added tributyltin oxide (8.8 g, 14.92 mmol, 2.0 eq) and reaction mixture was refluxed for 12 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulphate and concentrated under reduced pressure to obtain solid which was triturated with hexane to obtain pure Core C (1.9 g, Yield: 68.79%), MS (ES): m/z 375.08 [M+H]⁺).

Preparation of Core D: ethyl 7-(benzyl(methyl)amino)-5-(1H-pyrrolo[2,3-b]pyridin-3-yl)pyrazolo[1,5-a]pyrimidine-3-carboxylate

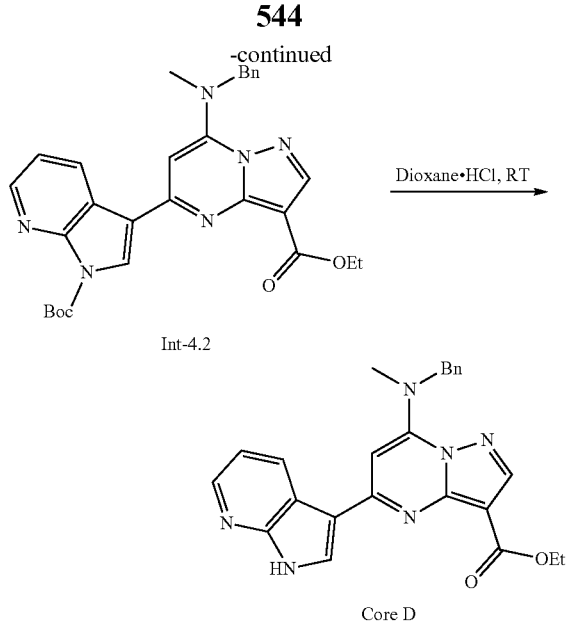

Synthesis of compound Int-4. Compound was synthesized using the general procedure of Core A synthesis to obtain Int-4. (Yield: 45%), MS (ES): m/z 345.10 [M+H]⁺.

Synthesis of compound Int-4.2. Argon was purged for 15 min through a stirring solution of 1 (3.5 g, 10.15 mmol, 1.0 eq), Int-4.1 (4.5 g, 13.19 mmol, 1.3 eq) and Sodium carbonate (2.6 g, 25.37 mmol, 2.5 eq) in 1,4 dioxane:water (140 mL, 9:1) [1,1'-Bis(diphenylphosphino)ferrocene]palladium (II) dichloride (0.738 mg, 1.01 mmol, 0.1 eq) was added to it and further purging done for 10 min. Reaction was allowed to stirred at 110° C. for 6 h. After completion of reaction, reaction mixture was poured over water and product was extracted with ethyl acetate. Organic layer was combined, washed with brine solution, dried over sodium sulphate and concentrated under reduced pressure to obtain Int-4.2. (3.1 g, 57.99%). MS (ES): m/z 527.24[M+H]⁺

Synthesis of compound Core D. To Int-4.2 (3.1 g, 5.88 mmol, 1.0 eq) was added 4M hydrochloric acid in 1,4 Dioxane (60 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain Core D. (2.1 g, 83.64%). MS (ES): m/z 427.18 [M+H]⁺

General Procedure A (Acid-Amine Coupling):

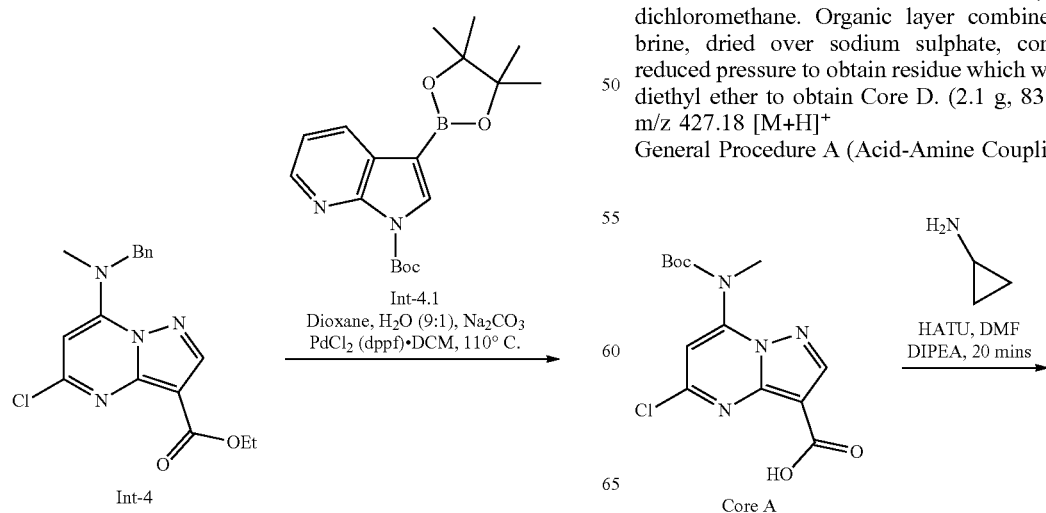

-continued

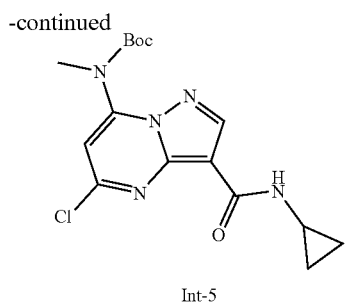

Int-5

Synthesis of Int-5: To a solution of Core A (4 g, 12.26 mmol, 1.0 eq), in N,N-dimethylformamide (40 mL) was added 1-[Bis(dimethylamino)methylene]-1H-1,2,3-triazolo[4,5-b]pyridinium 3-oxid hexafluorophosphate (9.32 g, 24.53 mmol, 2.0 eq) and stirred at room temperature for 15 min. To this added diisopropylethylamine (6.40 mL, 36.78 mmol, 3.0 eq) followed by addition of cyclopropanamine (0.699 g, 12.26 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 40% ethyl acetate in hexane to obtain Int-5 (2.4 g, Yield: 53.69%; MS (ES): m/z 366.13 [M+H]$^+$).

General Procedure B (Buchwald Amination)

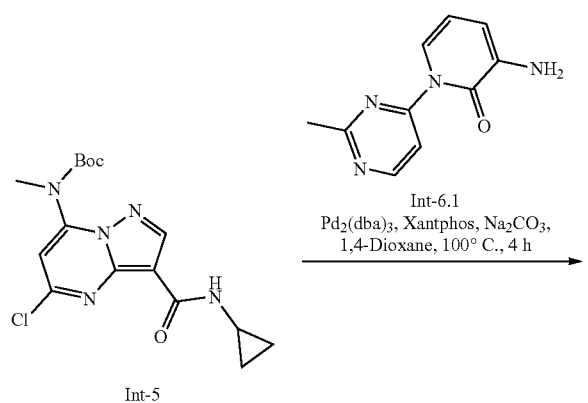

Int-5

Int-6.1
Pd$_2$(dba)$_3$, Xantphos, Na$_2$CO$_3$,
1,4-Dioxane, 100° C., 4 h

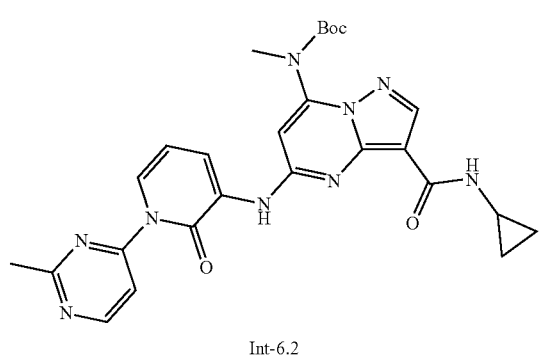

Int-6.2

Synthesis of Int-6.2: To a solution of Int-5 (0.125 g, 0.342 mmol, 1.0 eq) in 1,4-dioxane (5 mL) was added Int-6.1 (0.082 g, 0.410 mmol, 1.2 eq), sodium carbonate (0.072 g, 0.684 mmol, 2.0 eq). The reaction mixture was degassed for 10 min. under argon atmosphere, then tris(dibenzylideneacetone)dipalladium(0) (0.015 g, 0.017 mmol, 0.05 eq) and 4,5-Bis(diphenylphosphino)-9,9-dimethylxanthene (0.019 g, 0.034 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure Int-6.2 (0.070 g, Yield: 38.6%; MS (ES): m/z 532.23 [M+H]$^+$).

General Procedure C (BOC-Deprotection):

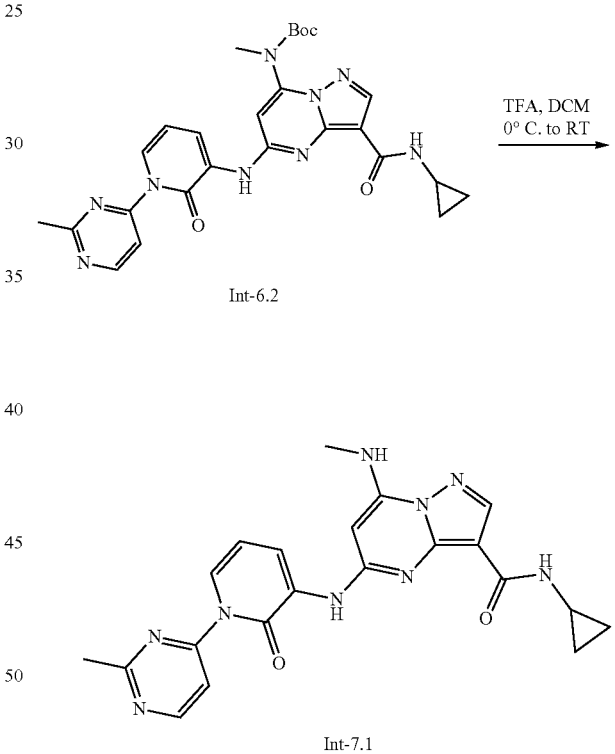

Synthesis of Int-7.1: Int-6.2 (0.070 g, 0.131 mmol, 1.0 eq) was dissolved in dichloromethane (2 mL) and trifluoroacetic acid (0.1 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure Int-7.1 (0.040 g, Yield: 70.17%; MS (ES): m/z 432.24 [M+H]$^+$).

547

Preparation of Intermediate A: 3-amino-1-(tetrahydro-2H-pyran-4-yl)pyridin-2(1H)-one

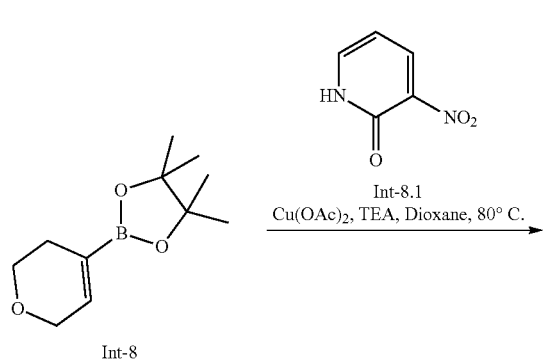

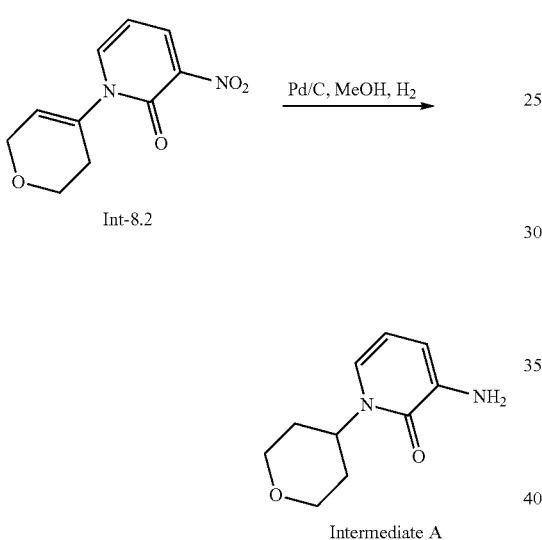

Synthesis of compound Int-8.2. To a solution of Int-8 (3 g, 14.28 mmol, 1.0 eq) and Int-8.1 (2.4 g, 17.14 mmol, 1.2 eq) in dioxane (30 mL) was added copper acetate (2.60 g, 14.28 mmol, 1.0 eq) and triethylamine (5.00 mL, 35.7 mmol, 2.5 eq) under nitrogen. The reaction was stirred at 80° C. for 5 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 10% ethyl acetate in hexane to obtain pure Int-8.2 (0.380 g, 11.98%), MS (ES): m/z 222.20 [M+H]$^+$.

Synthesis of Intermediate A. To a solution of Int-8.1 (0.380 g, 1.71 mmol, 1.0 eq) in methanol (4 ml), palladium on charcoal (0.100 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 1.4% methanol in dichloromethane to obtain pure Intermediate A (0.120 g, 36.13%). MS (ES): m/z 195.23 [M+H]$^+$.

548

Example 1: N-Cyclopropyl-5-((1-(3-hydroxy-3-methylcyclohexyl)-2-oxo-1,2-dihydropyridin-3-yl)amino)-7-(methylamino)pyrazolo[1,5-a]pyrimidine-3-carboxamide (I-1)

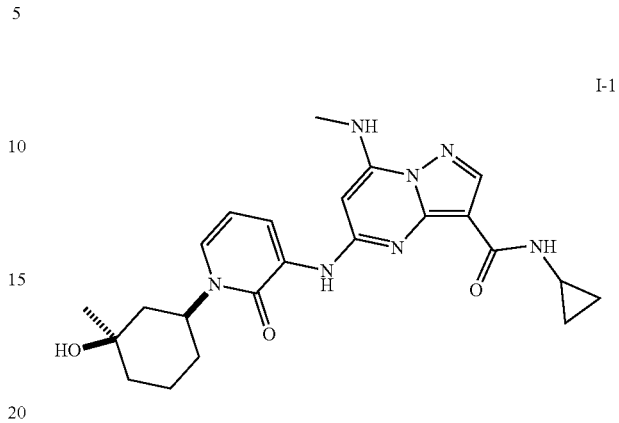

Scheme 1

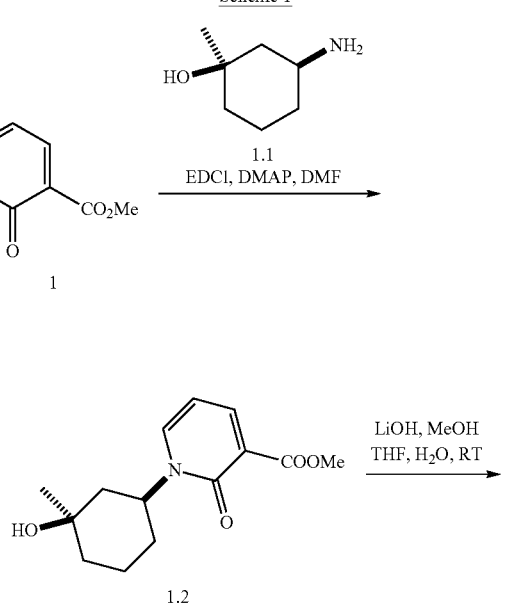

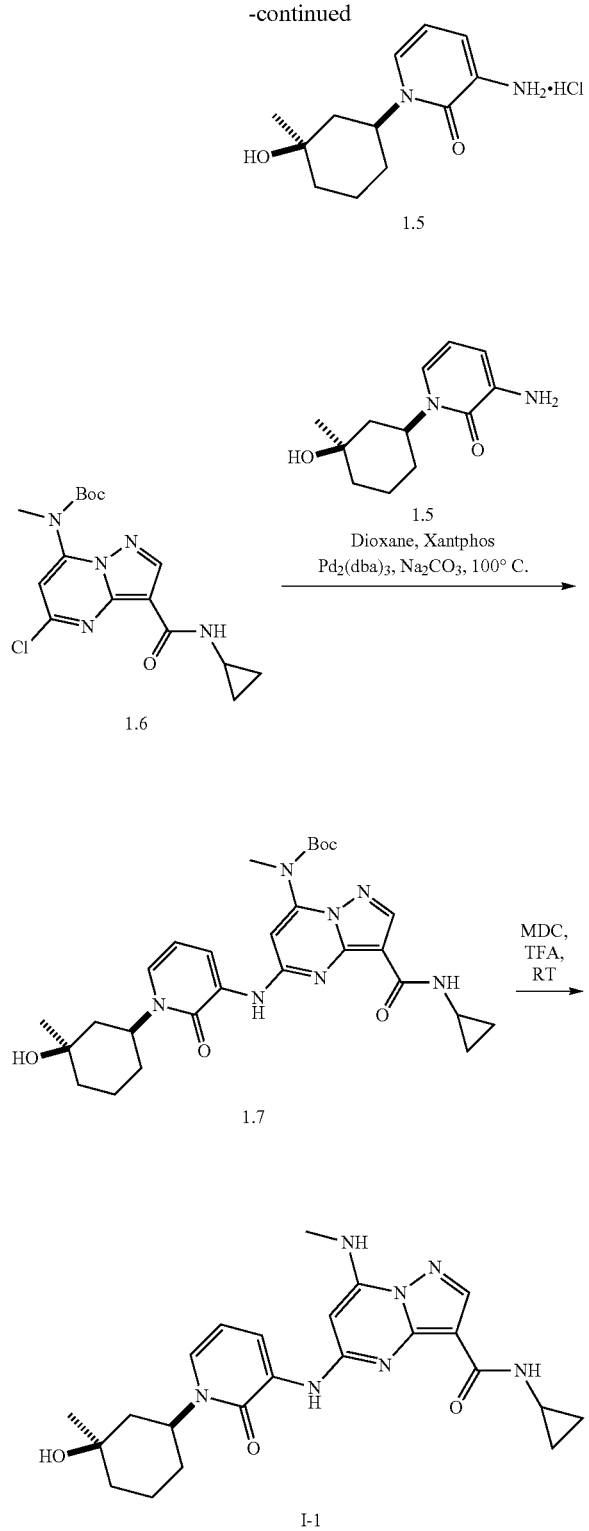

Step 1—Synthesis of Compound 1.2: To a cooled solution of 1 (0.260 g, 1.68 mmol, 1.0 eq), in N,N-dimethylformamide (4 mL) was added 1.1 (0.217 g, 1.68 mmol, 1.0 eq). The reaction mixture was stirred at 0° C. for 30 min and further stirred at room temperature for 15 min. N-Ethyl-N′-(3-dimethylaminopropyl)carbodiimide hydrochloride (0.338 g, 2.18 mmol, 1.3 eq) and 4-Dimethylaminopyridine (0.040 g, 0.33 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 1.2. (0.154 g, Yield 34.41%; MS (ES): m/z 266.13 [M+H]$^+$).

Step 2—Synthesis of Compound 1.3: To a solution of 1.2 (0.140 g, 0.52 mmol, 1.0 eq), in tetrahydrofuran:water (4 mL, 2:1) was added lithium hydroxide (0.124 g, 5.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 1.3 (0.130 g, Yield: 89.13%; MS (ES): m/z 252.12 [M+H]$^+$).

Step 3—Synthesis of Compound 1.4: To a solution of 1.3 (0.130 g, 0.51 mmol, 1.0 eq) in tert-butanol (3 mL) was added triethylamine (0.087 g, 0.86 mmol, 1.7 eq) and diphenyl phosphoryl azide (0.182 g, 0.66 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4 (0.210 g, Yield: 95.93%; MS (ES): m/z 323.19 [M+H]$^+$).

Step 4—Synthesis of Compound 1.5: A cooled solution of 1.4 (0.210 g, 0.65 mmol, 1 eq) in dioxane (4 mL) was added 4N hydrochloric acid in dioxane (6 mL) as a dropwise. The reaction mixture was stirred at room temperature for 2 h. After completion of reaction, reaction mixture was concentrated under reduced pressure to obtain pure 1.5 (0.170 g, Yield: 97.90%; MS (ES): m/z 223.14 [M+H]$^+$).

Step 5—Synthesis of Compound 1.6: Compound was synthesized using the procedure for the preparation of Core A to obtain 1.6 (Yield: 57.16%; MS (ES): m/z 366.82 [M+H]$^+$).

Step 6—Synthesis of Compound 1.7: Compound was synthesized using general procedure B to obtain 1.7 (0.130 g, Yield: 61.58%; MS (ES): 552.29 [M+H]$^+$).

Step 7—Synthesis of Compound I-1: Compound was synthesized using general procedure C to obtain I-1 (0.025 g, Yield: 87.27%; MS (ES): 452.42 [M+H]$^+$; LCMS purity: 96.18%; HPLC purity: 96.68%; CHIRAL HPLC: 47.64%, 48.76%; $^1$H NMR (DMSO-d$_6$, 400 MHZ): 8.92 (s, 1H), 8.20 (s, 1H), 8.12-8.10 (d, J=8 Hz, 1H), 7.93-7.92 (d, J=4.8 Hz, 1H), 7.84-7.83 (d, J=4 Hz, 1H), 7.47-7.45 (d, J=6.4 Hz, 1H), 7.40 (s, 1H), 6.35-6.31 (t, J=7.2 Hz, 1H), 6.20 (s, 1H), 4.92 (bs, 1H), 4.69 (bs, 1H), 2.91-2.90 (d, J=4.8 Hz, 3H), 1.78 (bs, 3H), 1.67 (bs, 2H), 1.45-1.48 (m, 2H), 1.24 (bs, 4H), 0.80-0.79 (d, J=5.6 Hz, 2H), 0.51 (bs, 2H)).

Example 2: N-Cyclopropyl-5-((1-((1S,3R)-3-hydroxy-3-methylcyclohexyl)-2-oxo-1,2-dihydropyridin-3-yl)amino)-7-(methylamino)pyrazolo[1,5-a]pyrimidine-3-carboxamide (I-2)
And
N-cyclopropyl-5-((1-((1R,3S)-3-hydroxy-3-methylcyclohexyl)-2-oxo-1,2-dihydropyridin-3-yl)amino)-7-(methylamino)pyrazolo[1,5-a]pyrimidine-3-carboxamide (I-3)
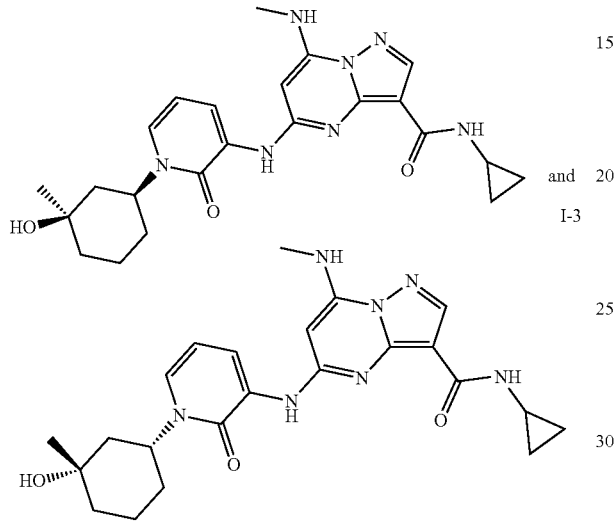
Scheme 2
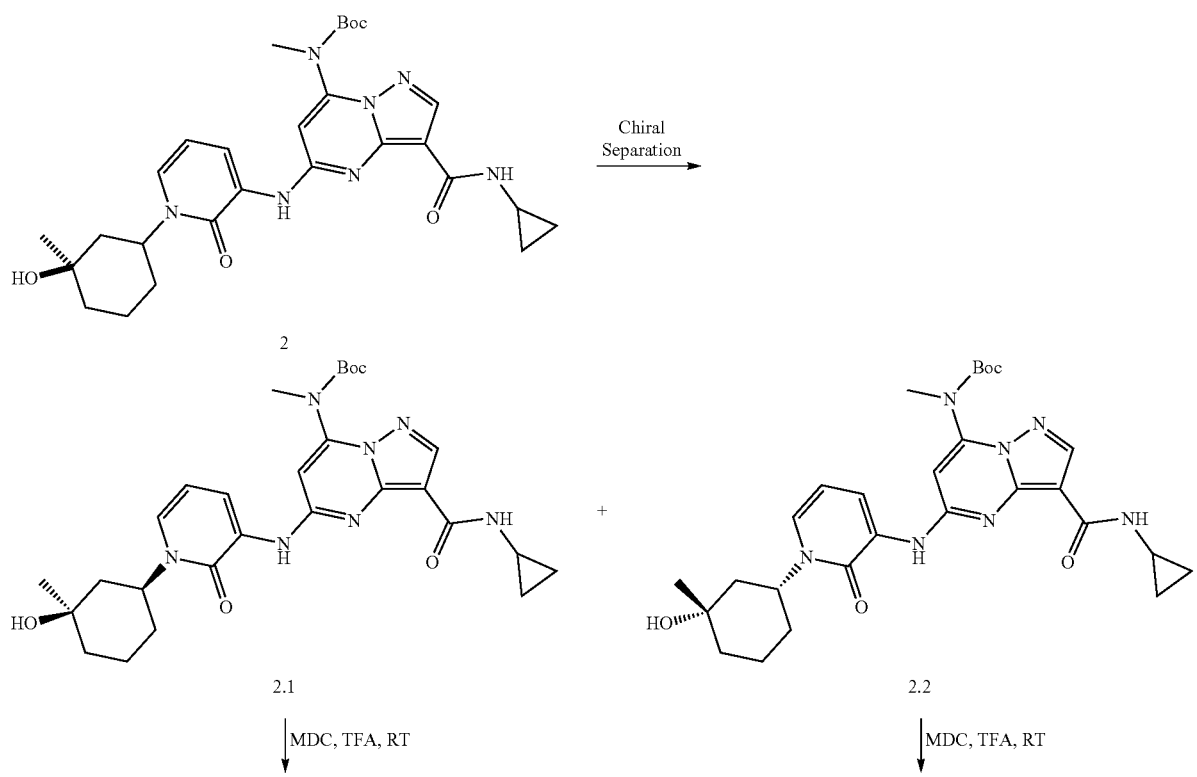

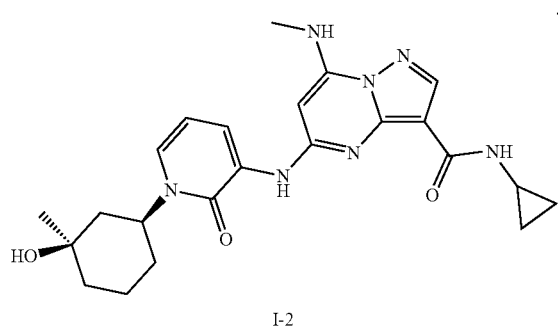

I-2

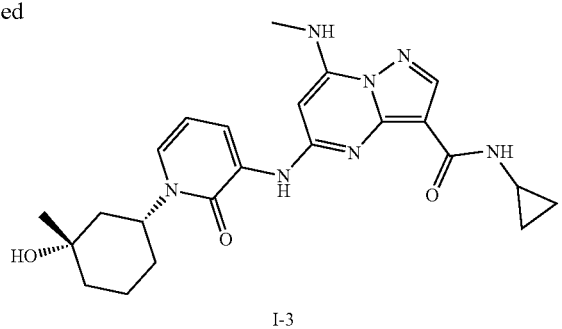

I-3

Step 1—Synthesis of Compound 2: Compound was synthesized as per experimental protocol of I-1 (Example 1) to obtain 2 (Yield: 61.58%; MS (ES): m/z 552.29 [M+H]$^+$).

Step 2—Synthesis of Compound 2.1 and 2.2: Isomers of 2 (0.105 g) were separated out using column CHIRALCEL OJ-H (250 mm*4.6 mm, 5 μm) and 0.1% DEA in methanol as co-solvent with flow rate of 4 mL/min to get pure fraction-1 (FR-a) and fraction-2 (FR-b).

FR-a was concentrated under reduced pressure at 30° C. to afford pure 2.1 (0.040 g; MS (ES): m/z 552.29 [M+H]$^+$).

FR-b was concentrated under reduced pressure at 30° C. to afford pure 2.2 (0.042 g; MS (ES): m/z 552.29 [M+H]$^+$.

Step 3—Synthesis of Compound I-2: Compound was synthesized using general procedure C to obtain I-2 (0.032 g, Yield: 97.74%; MS (ES): m/z 452.2 [M+H]$^+$; LCMS purity: 99.00%; HPLC purity: 99.58%; CHIRAL HPLC purity: 100%; $^1$H NMR (DMSO-d$_6$, 400 MHZ): 8.89 (s, 1H), 8.18 (s, 1H), 8.10-8.08 (d, J=6.8 Hz, 1H), 7.91-7.89 (d, J=4.8 Hz, 1H), 7.82-7.81 (d, J=3.6 Hz, 1H), 7.45-7.43 (d, J=6.8 Hz, 1H), 6.33-6.29 (t, J=7.2 Hz, 1H), 6.16 (s, 1H), 4.67 (s, 1H), 2.89-2.88 (d, J=4.4 Hz, 3H), 2.86-2.82 (m, 1H), 1.76 (bs, 2H), 1.59 (bs, 2H), 1.46-1.40 (m, 2H), 1.23 (s, 6H), 0.78-0.77 (d, J=5.2 Hz, 2H), 0.49 (bs, 2H)).

Step 4—Synthesis of Compound I-3: Compound was synthesized using general procedure C to obtain I-3 (0.032 g, Yield: 93.08%; MS (ES): m/z 452.2 [M+H]$^+$; LCMS purity: 100%; HPLC purity: 98.97%, CHIRAL HPLC purity: 98.25%; $^1$H NMR (DMSO-d$_6$, 400 MHZ): 8.90 (s, 1H), 8.18 (s, 1H), 8.10-8.08 (d, J=6.8 Hz, 1H), 7.90-7.89 (d, J=4.8 Hz, 1H), 7.82-7.81 (d, J=3.6 Hz, 1H), 7.45-7.43 (d, J=6.8 Hz, 1H), 6.33-6.29 (t, J=7.2 Hz, 1H), 6.16 (s, 1H), 4.67 (s, 1H), 2.89-2.88 (d, J=4.4 Hz, 3H), 2.86-2.82 (m, 1H), 1.76 (bs, 2H), 1.59 (bs, 2H), 1.46-1.40 (m, 2H), 1.22 (s, 6H), 0.78-0.77 (d, J=5.2 Hz, 2H), 0.49 (bs, 2H)).

Example 3: N-Cyclopropyl-5-((1-((1r,3r)-3-methoxycyclobutyl)-2-oxo-1,2-dihydropyridin-3-yl)amino)-7-(methylamino)pyrazolo[1,5-a]pyrimidine-3-carboxamide (I-4)

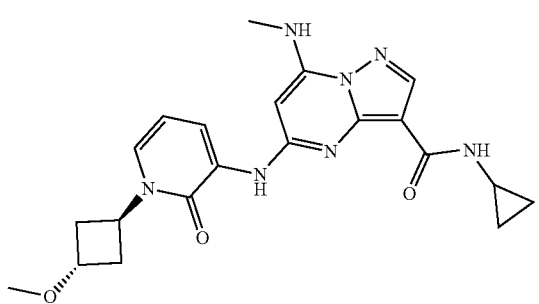

I-4

Scheme 3

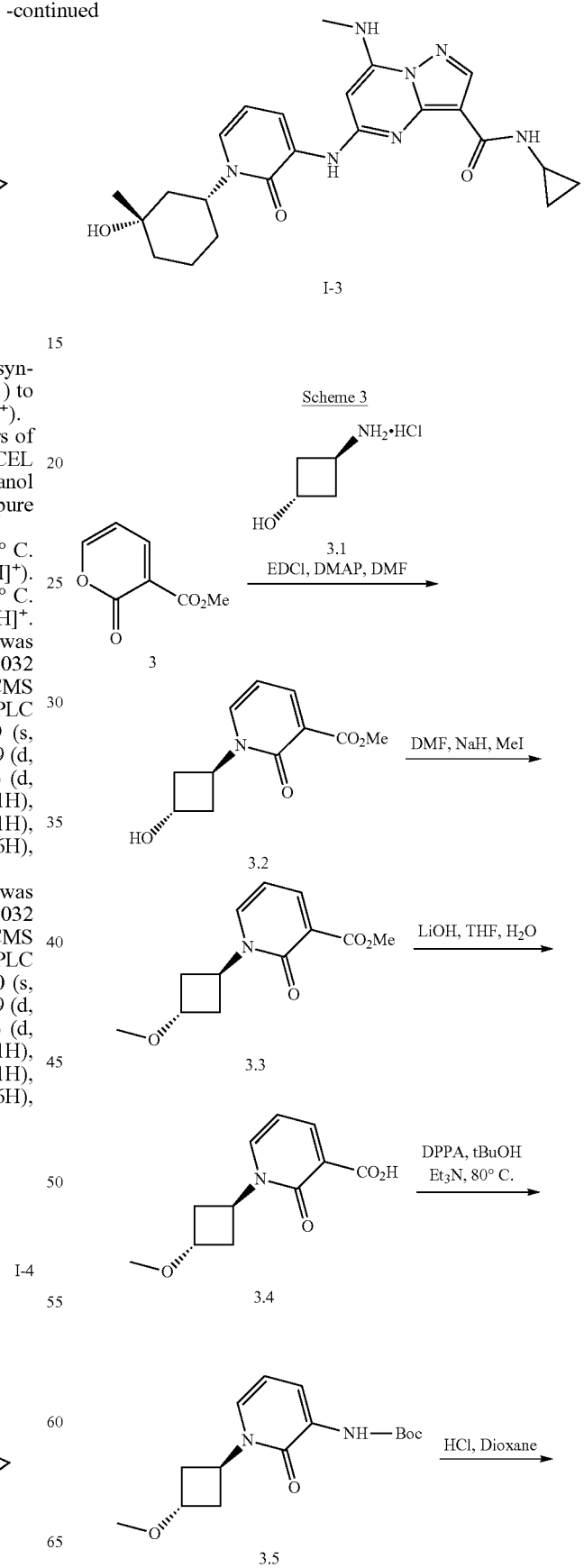

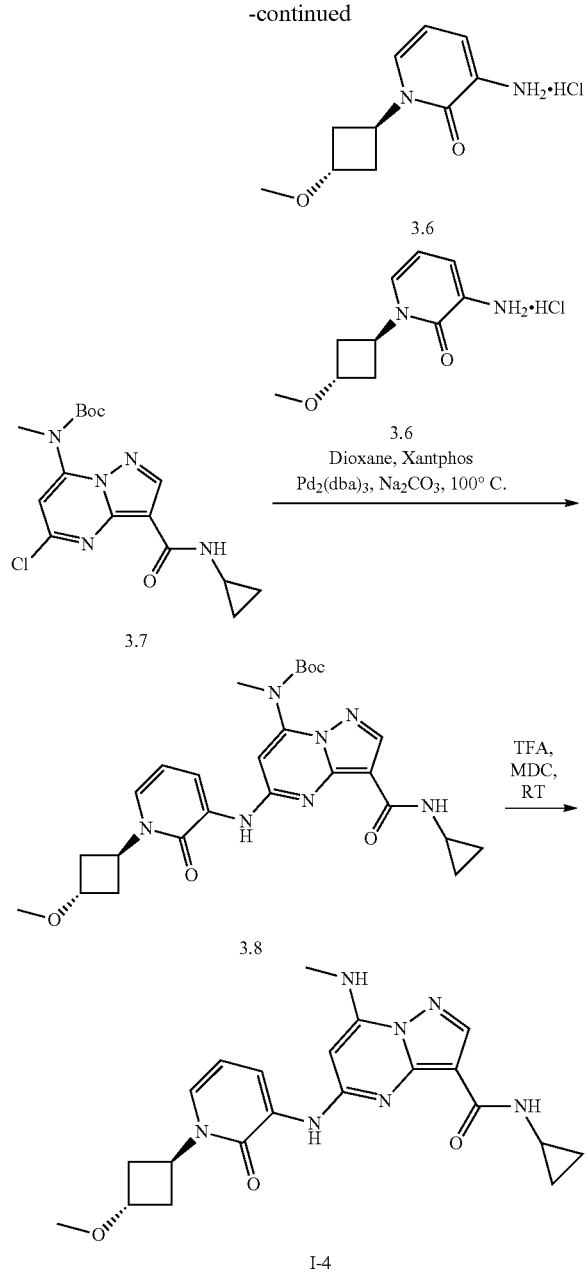

Step 1—Synthesis of Compound 3.2: To a cooled solution of 3 (5.0 g, 32.44 mmol, 1.0 eq), in N,N-dimethylformamide (50 mL) was added 3.1 (3.99 g, 32.44 mmol, 1.0 eq). The reaction mixture was stirred at 0° C. for 30 min and further stirred at room temperature for 15 min N-Ethyl-N'-(3-dimethylaminopropyl)carbodiimide hydrochloride (6.5 g, 42.17 mmol, 1.3 eq) and 4-Dimethylaminopyridine (0.790 g, 6.48 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 3.2 (3.35 g, Yield: 46.26%; MS (ES): m/z 224.09 [M+H]⁺).

Step 2—Synthesis of Compound 3.3: To a cooled solution of 3.2 (3.35 g, 15.02 mmol, 1.0 eq) in N,N-dimethylformamide (35 mL) was added sodium hydride (1.44 g, 6.08 mmol, 4.0 eq) at 0° C. portion wise and allowed to stir for 30 min followed by dropwise addition of methyl iodide (2.7 g, 19.52 mmol, 1.3 eq). Reaction mixture was stirred at same temperature for 20 min and mixture was allowed to stir at room temperature for 6 h. After completion of reaction, reaction mixture transferred into ice water and product was extracted with ethyl acetate. Organic layer was combined, washed with brine solution, dried over sodium sulphate and concentrated under reduced pressure to obtain crude product which was purified by column chromatography eluting pure compound in 2-2.5% methanol in dichloromethane to obtain pure 3.3 (2.85 g, Yield: 80.04%; MS (ES): m/z 238.10 [M+H]⁺).

Step 3—Synthesis of Compound 3.4: To a solution of 3.3 (2.85 g, 12.02 mmol, 1.0 eq), in tetrahydrofuran:water (30 mL, 2:1) was added lithium hydroxide (2.88 g, 120.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 3.4 (2.4 g, Yield: 89.50%; MS (ES): m/z 224.09 [M+H]⁺).

Step 4—Synthesis of Compound 3.5: To a solution of 3.4 (2.4 g, 10.76 mmol, 1.0 eq) in tert-butanol (25 mL) was added triethylamine (1.84 g, 18.29 mmol, 1.7 eq) and diphenyl phosphoryl azide (3.84 g, 13.98 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 3.5 (2.0 g, Yield: 63.20%; MS (ES): m/z 295.16 [M+H]⁺).

Step 5—Synthesis of Compound 3.6: A cooled solution of 3.5 (2.0 g, 6.80 mmol, 1 eq) in dioxane (20 mL) was added 4N hydrochloric acid in dioxane (22 mL) as a dropwise. The reaction mixture was stirred at room temperature for 2 h. After completion of reaction, reaction mixture was concentrated under reduced pressure to obtain pure 3.6 (1.4 g, Yield: 89.32%; MS (ES): m/z 195.11 [M+H]⁺).

Step 6—Synthesis of Compound 3.7: Compound was synthesized from Core A utilizing general method A to obtain 3.7 (Yield: 57.16%; MS (ES): m/z 366.82 [M+H]⁺).

Step 7—Synthesis of Compound 3.8: Compound was synthesized using general procedure B to obtain 3.8 (0.085 g, Yield: 59.39%; MS (ES): m/z 524.26 [M+H]⁺).

Step 7—Synthesis of Compound I-4: Compound was synthesized using general procedure C to obtain I-4 (0.060 g, Yield: 87.28%; MS (ES): m/z 424.82 [M+H]⁺; LCMS purity: 100%; HPLC purity: 99.28%; CHIRAL HPLC: 96.77%; ¹H NMR (DMSO-d₆, 400 MHZ): 8.92 (s, 1H), 8.20 (s, 1H), 8.14-8.12 (d, J=7.2 Hz, 1H), 7.92-7.91 (d, J=4 Hz, 1H), 7.83 (bs, 1H), 7.54-7.53 (d, J=6.8 Hz, 1H), 6.37-6.33 (t, J=7.6 Hz, 1H), 6.20 (s, 1H), 4.07 (bs, 1H), 3.21 (s, 3H), 2.90-2.89 (d, J=4.8 Hz, 3H), 2.51 (bs, 4H), 1.24 (bs, 2H), 0.80-0.78 (d, J=6.8 Hz, 2H), 0.50 (bs, 2H)).

Example 4: N-Cyclopropyl-5-((1-((1s,3s)-3-methoxycyclobutyl)-2-oxo-1,2-dihydropyridin-3-yl)amino)-7-(methylamino)pyrazolo[1,5-a]pyrimidine-3-carboxamide (I-5)

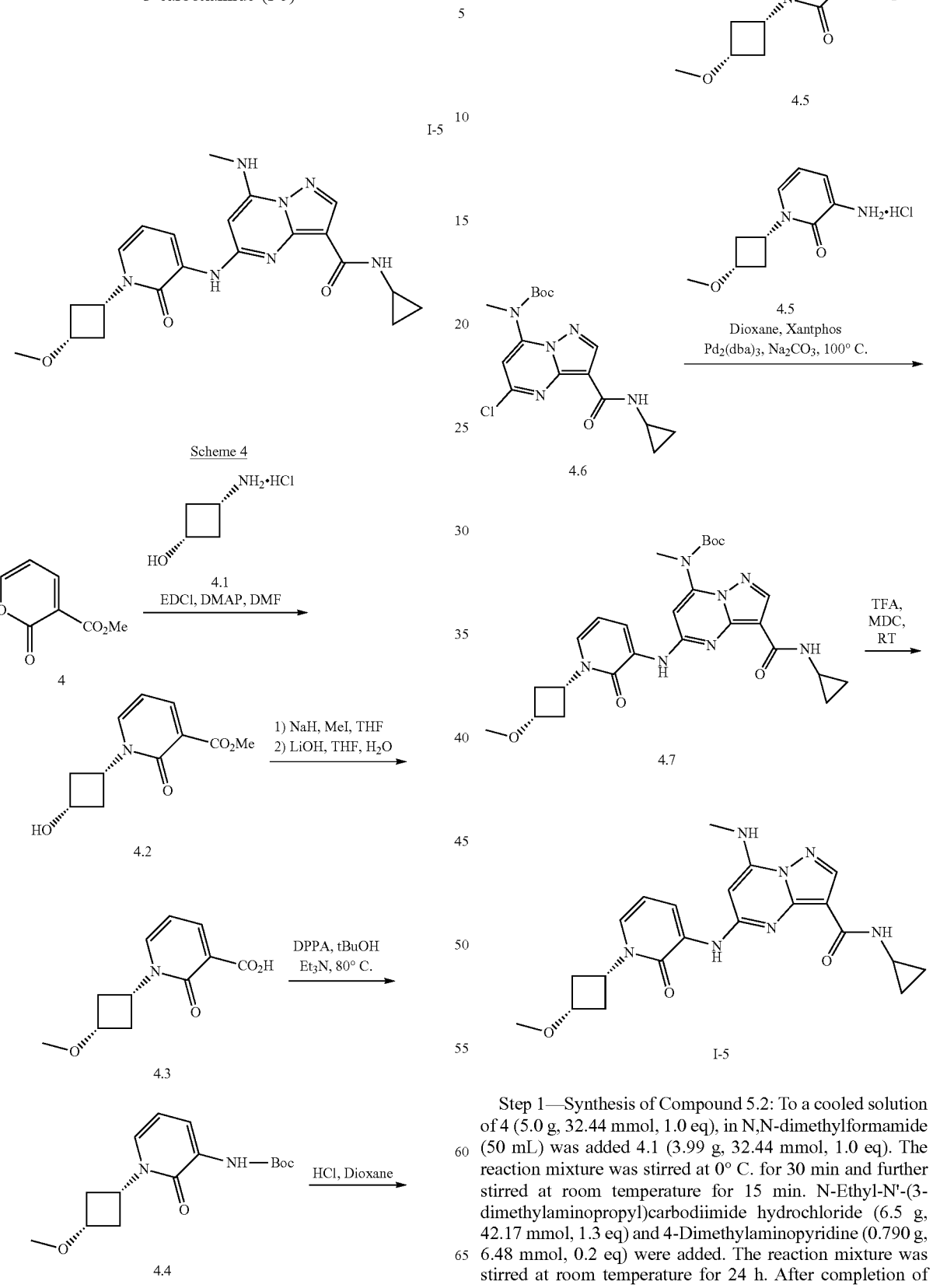

Step 1—Synthesis of Compound 5.2: To a cooled solution of 4 (5.0 g, 32.44 mmol, 1.0 eq), in N,N-dimethylformamide (50 mL) was added 4.1 (3.99 g, 32.44 mmol, 1.0 eq). The reaction mixture was stirred at 0° C. for 30 min and further stirred at room temperature for 15 min. N-Ethyl-N'-(3-dimethylaminopropyl)carbodiimide hydrochloride (6.5 g, 42.17 mmol, 1.3 eq) and 4-Dimethylaminopyridine (0.790 g, 6.48 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 4.2 (3.35 g, Yield: 46.26%; MS (ES): m/z 224.09 [M+H]$^+$).

Step 2—Synthesis of Compound 4.3: To a solution of 4.2 (2.85 g, 12.02 mmol, 1.0 eq), in tetrahydrofuran:water (30 mL, 2:1) was added lithium hydroxide (2.88 g, 120.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 4.3 (2.4 g, Yield: 89.50%; MS (ES): m/z 224.09 [M+H]$^+$).

Step 3—Synthesis of Compound 4.4: To a solution of 4.3 (2.4 g, 10.76 mmol, 1.0 eq) in tert.butanol (25 mL) was added triethylamine (1.84 g, 18.29 mmol, 1.7 eq) and diphenyl phosphoryl azide (3.84 g, 13.98 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 4.4 (2.0 g, Yield: 63.20%; MS (ES): m/z 295.16 [M+H]$^+$).

Step 4—Synthesis of Compound 4.5: A cooled solution of 4.4 (2.0 g, 6.80 mmol, 1 eq) in dioxane (20 mL) was added 4N hydrochloric acid in dioxane (22 mL) as a dropwise. The reaction mixture was stirred at room temperature for 2 h. After completion of reaction, reaction mixture was concentrated under reduced pressure to obtain pure 4.5. (1.4 g, Yield: 89.32%); MS (ES): m/z 195.11 [M+H]$^+$).

Step 5—Synthesis of Compound 4.6: Compound was synthesized from core A utilizing general procedure A to obtain 4.6 (Yield: 57.16%; MS (ES): m/z 366.82 [M+H]$^+$).

Step 6—Synthesis of Compound 4.7: Compound was synthesized using general procedure B to obtain 4.7 (0.061 g, Yield: 35.52%; MS (ES): 524.26 [M+H]$^+$).

Step 7—Synthesis of Compound I-5: Compound was synthesized using general procedure C to obtain I-5 (0.038 g, Yield: 77.02%; MS (ES): m/z 424.37 [M+H]$^+$; LCMS purity: 100%; HPLC purity: 100%; CHIRAL HPLC: 95.00%; $^1$H NMR (DMSO-d$_6$, 400 MHZ): 8.91 (s, 1H), 8.20 (s, 1H), 8.14-8.12 (d, J=6.4 Hz, 1H), 7.91 (bs, 1H), 7.83 (bs, 1H), 7.49-7.47 (d, J=6 Hz, 1H), 6.35-6.33 (t, J=6.4 Hz, 1H), 6.20 (s, 1H), 4.73-4.69 (m, 1H), 3.79 (bs, 1H), 3.21 (s, 3H), 2.90-2.89 (d, J=4.8 Hz, 3H), 2.83 (bs, 3H), 2.14-2.12 (d, J=7.6 Hz, 2H), 0.89-0.79 (d, J=5.6 Hz, 2H), 0.50 (bs, 2H)).

Example 5: N-((1R,2S)-2-Fluorocyclopropyl)-5-((1-(3-hydroxy-3-methylcyclohexyl)-2-oxo-1,2-dihydropyridin-3-yl)amino)-7-(methylamino)pyrazolo[1,5-a]pyrimidine-3-carboxamide (I-6)

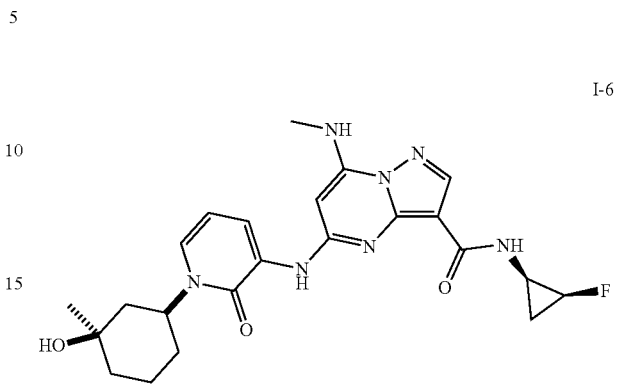

Scheme 5

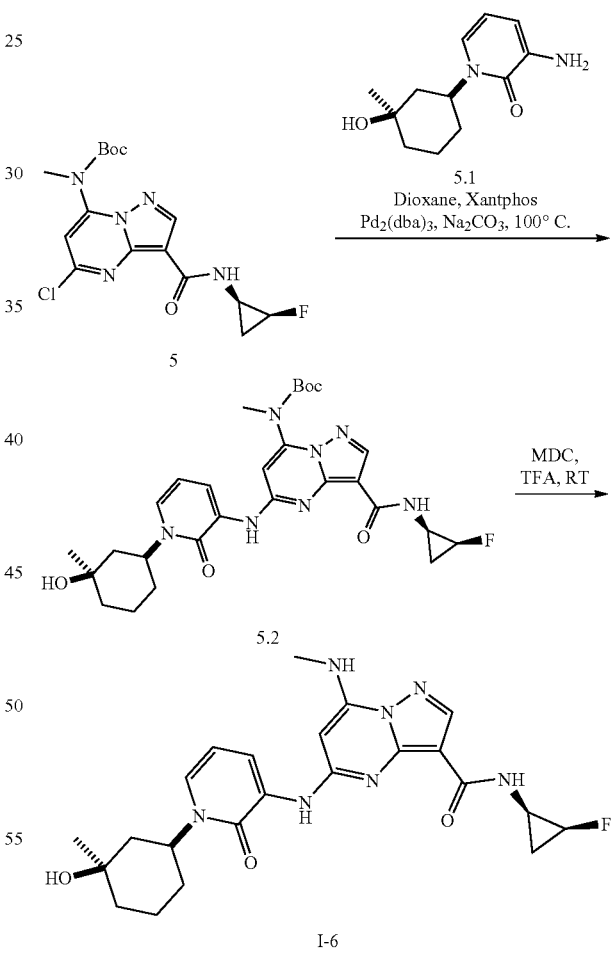

Step 1—Synthesis of Compound 5: Compound was synthesized from Core A utilizing general method A to obtain 5 (Yield: 51.08%; MS (ES): m/z 384.81 [M+H]$^+$).

Step 2—Synthesis of Compound 5.1: Compound was synthesized as per experimental protocol of I-1 (Example 1) to obtain 5.1 (Yield: 97.90%; MS (ES): m/z 223.14 [M+H]$^+$).

Step 3—Synthesis of Compound 5.2: Compound was synthesized using general procedure B to obtain 5.2 (0.130 g, Yield: 62.56%; MS (ES): 570.28 [M+H]$^+$).

Step 4—Synthesis of Compound I-6: Compound was synthesized using general procedure C to obtain I-6 (0.034 g, Yield: 83.19%; MS (ES): m/z 470.87 [M+H]$^+$; LCMS purity: 96.10%; HPLC purity: 94.95%; CHIRAL HPLC: 46.44%, 47.34%; $^1$H NMR (DMSO-$d_6$, 400 MHZ): 8.88 (s, 1H), 8.23 (s, 1H), 8.11-8.10 (d, J=8 Hz, 1H), 7.93-7.92 (d, J=4.8 Hz, 1H), 7.81-7.79 (d, J=4.4 Hz, 1H), 7.42-7.40 (d, J=6.8 Hz, 1H), 6.29-6.25 (t, J=7.2 Hz, 1H), 6.20 (s, 1H), 4.80 (bs, 2H), 4.68 (bs, 1H), 2.98 (bs, 1H), 2.90-2.89 (d, J=4.8 Hz, 3H), 1.76 (bs, 2H), 1.65 (bs, 1H), 1.47 (bs, 3H), 1.24 (bs, 5H), 0.85-0.84 (d, J=6.4 Hz, 2H)).

Example 6: 5-((1-((1r,3R)-3-Fluorocyclobutyl)-2-oxo-1,2-dihydropyridin-3-yl)amino)-N-((1R,2S)-2-fluorocyclopropyl)-7-(methylamino)pyrazolo[1,5-a]pyrimidine-3-carboxamide (I-7)

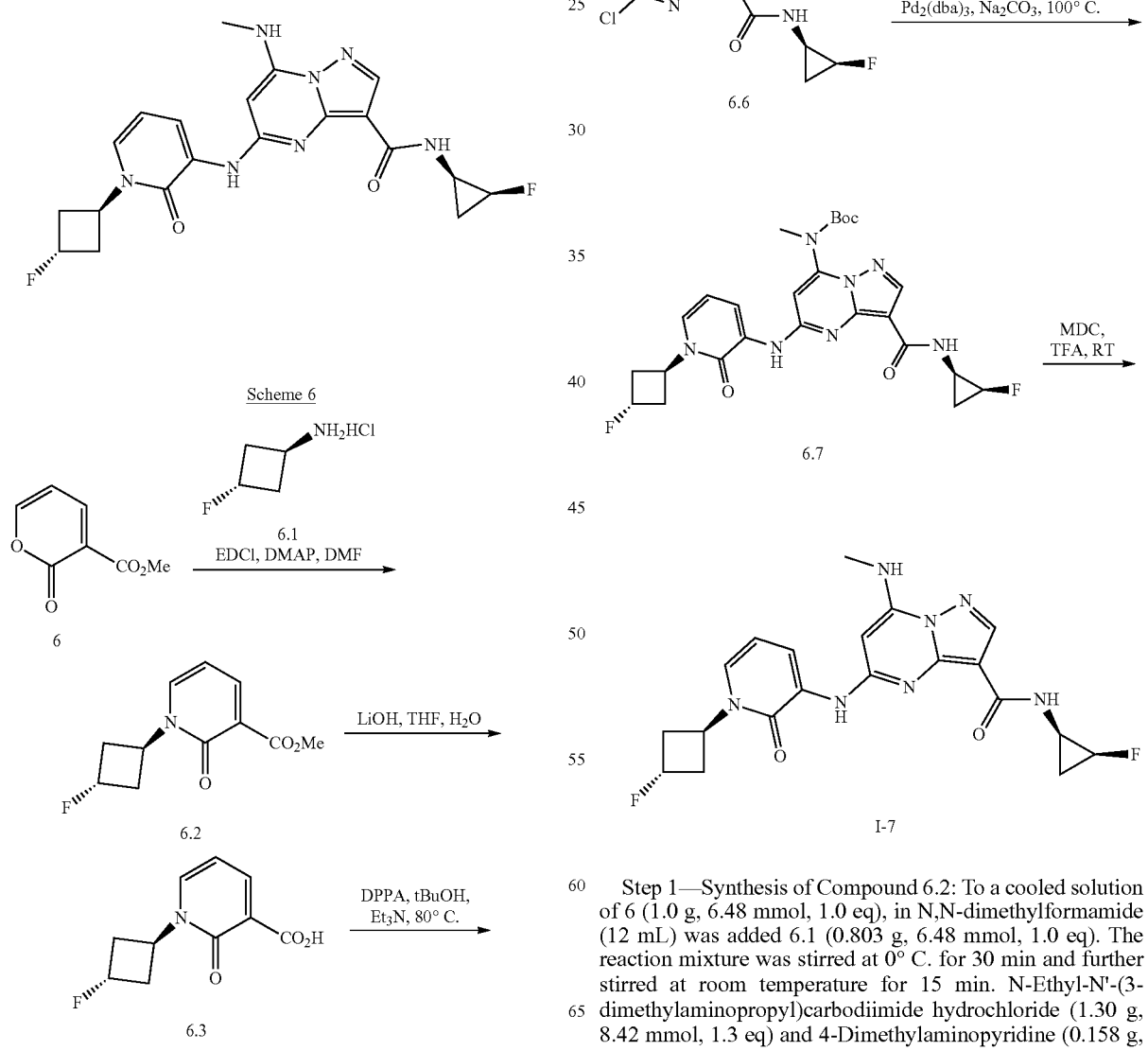

Scheme 6

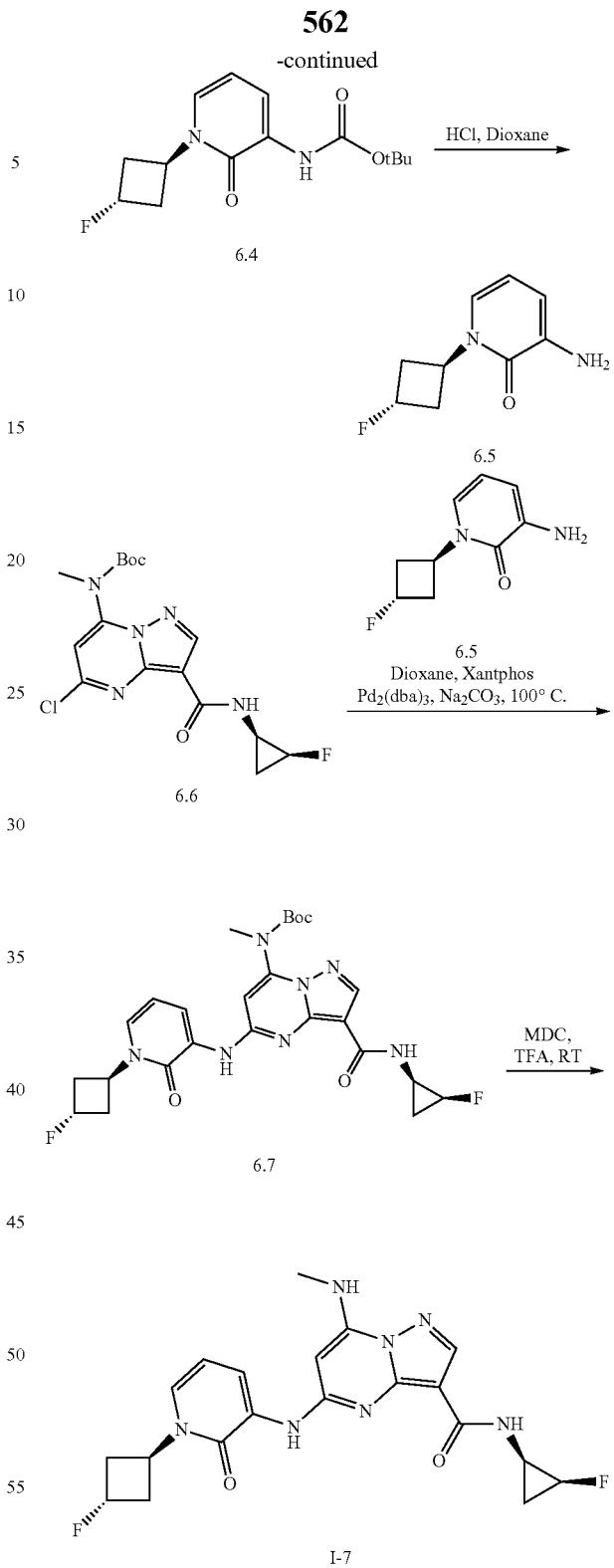

Step 1—Synthesis of Compound 6.2: To a cooled solution of 6 (1.0 g, 6.48 mmol, 1.0 eq), in N,N-dimethylformamide (12 mL) was added 6.1 (0.803 g, 6.48 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.30 g, 8.42 mmol, 1.3 eq) and 4-Dimethylaminopyridine (0.158 g, 1.29 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 6.2 (0.7 g, Yield: 47.90%; MS (ES): m/z 226.08 [M+H]$^+$).

Step 2—Synthesis of Compound 6.3: To a solution of 6.2 (0.7 g, 3.11 mmol, 1.0 eq) in tetrahydrofuran:water (10 mL, 2:1) was added lithium hydroxide (0.746 g, 31.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 6.3 (0.610 g, Yield: 92.93%; MS (ES): m/z 212.07 [M+H]$^+$).

Step 3—Synthesis of Compound 6.4: To a solution of 6.3 (0.610 g, 2.89 mmol, 1.0 eq) in tert-butanol (8 mL) was added triethylamine (0.496 g, 4.91 mmol, 1.7 eq) and diphenyl phosphoryl azide (1.0 g, 3.75 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 6.4 (0.480 g, Yield: 58.86%; MS (ES): m/z 283.14 [M+H]$^+$).

Step 4—Synthesis of Compound 6.5: A cooled solution of 6.4 (0.480 g, 1.70 mmol, 1 eq) in dioxane (6 mL) was added 4N hydrochloric acid in dioxane (8 mL) as a dropwise. The reaction mixture was stirred at room temperature for 2 h. After completion of reaction, reaction mixture was concentrated under reduced pressure to obtain pure 6.5 (0.310 g, Yield: 98.46%: MS (ES): m/z 183.09 [M+H]$^+$).

Step 5—Synthesis of Compound 6.6: Compound was synthesized from Core A utilizing general method A to obtain 6.6 (Yield: 51.08%; MS (ES): m/z 384.81 [M+H]$^+$).

Step 6—Synthesis of Compound 6.7: Compound was synthesized using general procedure B to obtain 6.7 (0.054 g, Yield: 39.14%; MS (ES): m/z 530.23 [M+H]$^+$).

Step 7—Synthesis of Compound I-7: Compound was synthesized using general procedure C to obtain I-7 (0.038 g, Yield: 86.78%; MS (ES): m/z 430.82 [M+H]$^+$; LCMS purity: 100%; HPLC purity: 98.21%; CHIRAL HPLC: 100%; $^1$H NMR (DMSO-d$_6$, 400 MHZ): 8.90 (s, 1H), 8.23 (s, 1H), 8.15-8.13 (d, J=6.8 Hz, 1H), 7.93-7.92 (d, J=4.8 Hz, 1H), 7.80-7.79 (d, J=4 Hz, 1H), 7.45-7.43 (d, J=6.8 Hz, 1H), 6.31-6.27 (t, J=7.2 Hz, 1H), 6.23 (s, 1H), 5.44-5.38 (m, 2H), 4.97 (bs, 1H), 4.80 (bs, 1H), 2.98 (bs, 1H), 2.90-2.89 (d, J=4.8 Hz, 3H), 2.72-2.67 (m, 3H), 1.27-1.16 (m, 1H), 0.83 (bs, 1H)).

Example 7: N-((1R,2S)-2-Fluorocyclopropyl)-5-((1-((1r,3R)-3-methoxycyclobutyl)-2-oxo-1,2-dihydropyridin-3-yl)amino)-7-(methylamino)pyrazolo[1,5-a]pyrimidine-3-carboxamide (I-8)

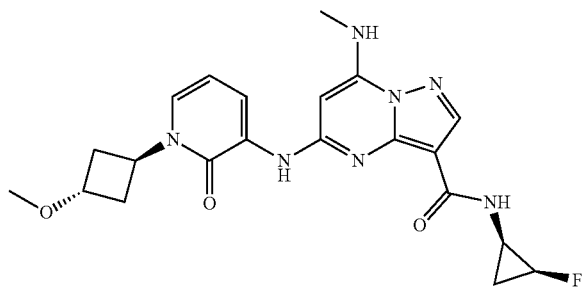

I-8

Scheme 7

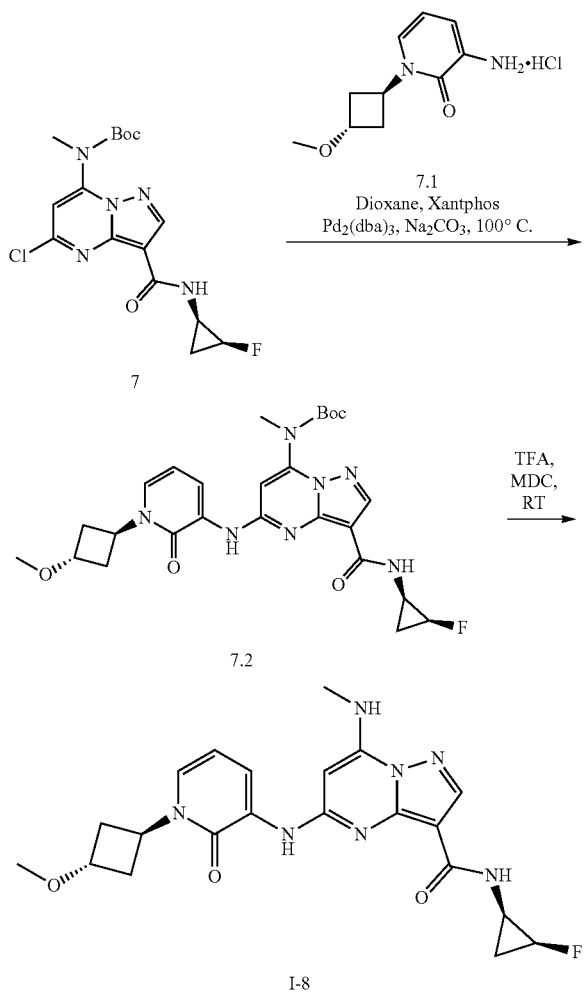

Step 1—Synthesis of Compound 7: Compound was synthesized from Core A utilizing general method A to obtain 8 (Yield: 51.08% MS (ES): m/z 384.81 [M+H]$^+$).

Step 2—Synthesis of Compound 7.1: Compound was synthesized as per experimental protocol of I-4 (Example 3) to obtain 8.1 (Yield: 89.32%; MS (ES): m/z 195.11 [M+H]⁺).

Step 3—Synthesis of Compound 7.2: Compound was synthesized using general procedure B to obtain 7.2 (0.085 g, Yield: 60.24%; MS (ES): m/z 542.25[M+H]⁺).

Step 4—Synthesis of compound I-8: Compound was synthesized using general procedure C to obtain I-8 (0.060 g, Yield: 86.60%; MS (ES): m/z 442.82 [M+H]⁺; LCMS purity: 100%; HPLC purity: 99.41%; CHIRAL HPLC: 96.29%; ¹H NMR (DMSO-d₆, 400 MHZ): 8.89 (s, 1H), 8.24 (s, 1H), 8.15-8.13 (d, J=6.4 Hz, 1H), 7.94-7.93 (d, J=4.4 Hz, 1H), 7.81 (bs, 1H), 7.50-7.49 (d, J=6 Hz, 1H), 6.32-6.29 (t, J=7.2 Hz, 1H), 6.24 (s, 1H), 5.31-5.27 (m, 1H), 4.97 (bs, 1H), 4.06 (bs, 1H), 3.23 (s, 3H), 2.99 (s, 1H), 2.91-2.90 (d, J=4.8 Hz, 3H), 2.51 (bs, 4H), 1.12-1.09 (t, J=7.2 Hz, 1H), 0.86 (bs, 1H)).

Example 8: N-((1R,2S)-2-Fluorocyclopropyl)-5-((1-((1s,3S)-3-methoxycyclobutyl)-2-oxo-1,2-dihydro-pyridin-3-yl)amino)-7-(methylamino)pyrazolo[1,5-a]pyrimidine-3-carboxamide (I-9)

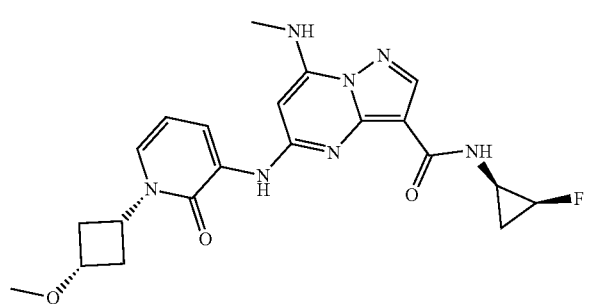

I-9

Scheme 8

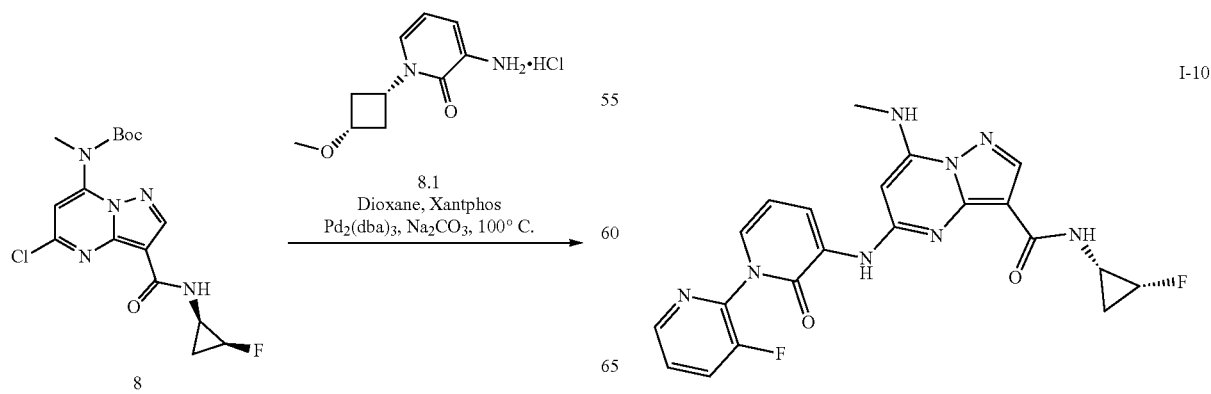

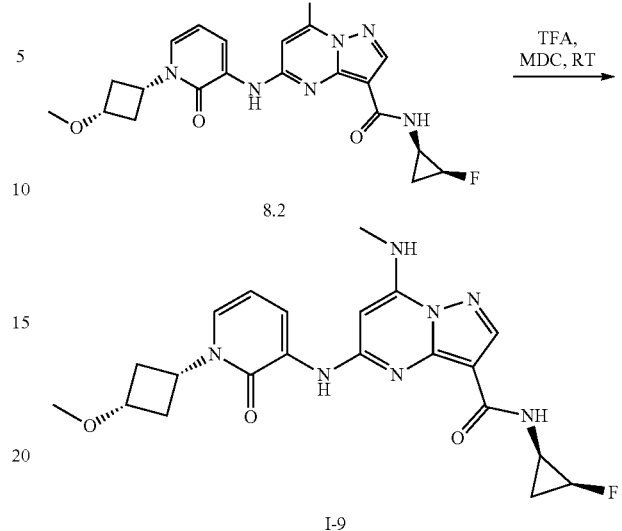

I-9

Step 1—Synthesis of Compound 8: Compound was synthesized from Core A utilizing general method A to obtain 8 (Yield: 51.08%; MS (ES): m/z 384.81 [M+H]⁺).

Step 2—Synthesis of Compound 8.1: Compound was synthesized as per experimental protocol of I-5 (Example 4) to obtain 8.1 (Yield: 89.32%; MS (ES): m/z 195.11 [M+H]⁺).

Step 3—Synthesis of Compound 8.2: Compound was synthesized using general procedure B to obtain 8.2 (0.054 g, Yield: 31.89%; MS (ES): 542.25 [M+H]⁺).

Step 4—Synthesis of Compound I-9: Compound was synthesized using general procedure C to obtain I-9 (0.036 g, Yield: 81.79%; MS (ES): m/z 442.37 [M+H]⁺; LCMS purity: 100%; HPLC purity: 100%; CHIRAL HPLC: 95.00%; ¹H NMR (DMSO-d₆, 400 MHZ): 8.89 (s, 1H), 8.24 (s, 1H), 8.14-8.13 (d, J=6.4 Hz, 1H), 7.93 (bs, 1H), 7.81 (bs, 1H), 7.49-7.45 (d, J=6 Hz, 1H), 6.35-6.30 (t, J=6.4 Hz, 1H), 6.23 (s, 1H), 4.71 (bs, 1H), 3.80 (bs, 1H), 3.20 (s, 3H), 3.00 (bs, 1H), 2.90-2.89 (d, J=4.8 Hz, 3H), 2.68 (bs, 3H), 2.13-2.11 (d, J=7.6 Hz, 3H), 1.24 (bs, 1H)).

Example 9: 5-((3'-Fluoro-2-oxo-2H-[1,2'-bipyridin]-3-yl)amino)-N-((1S,2R)-2-fluorocyclopropyl)-7-(methylamino)pyrazolo[1,5-a]pyrimidine-3-carboxamide (I-10)

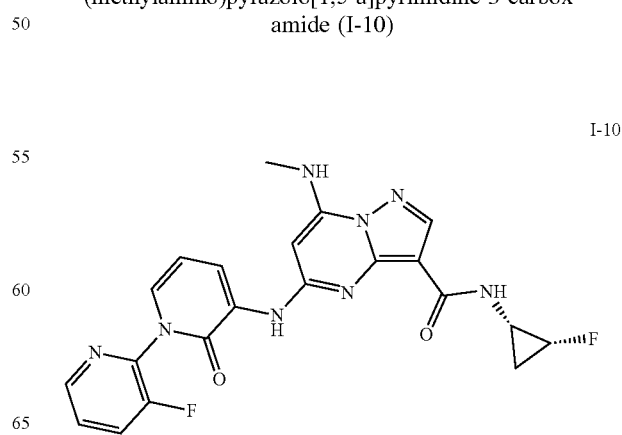

I-10

Scheme 9

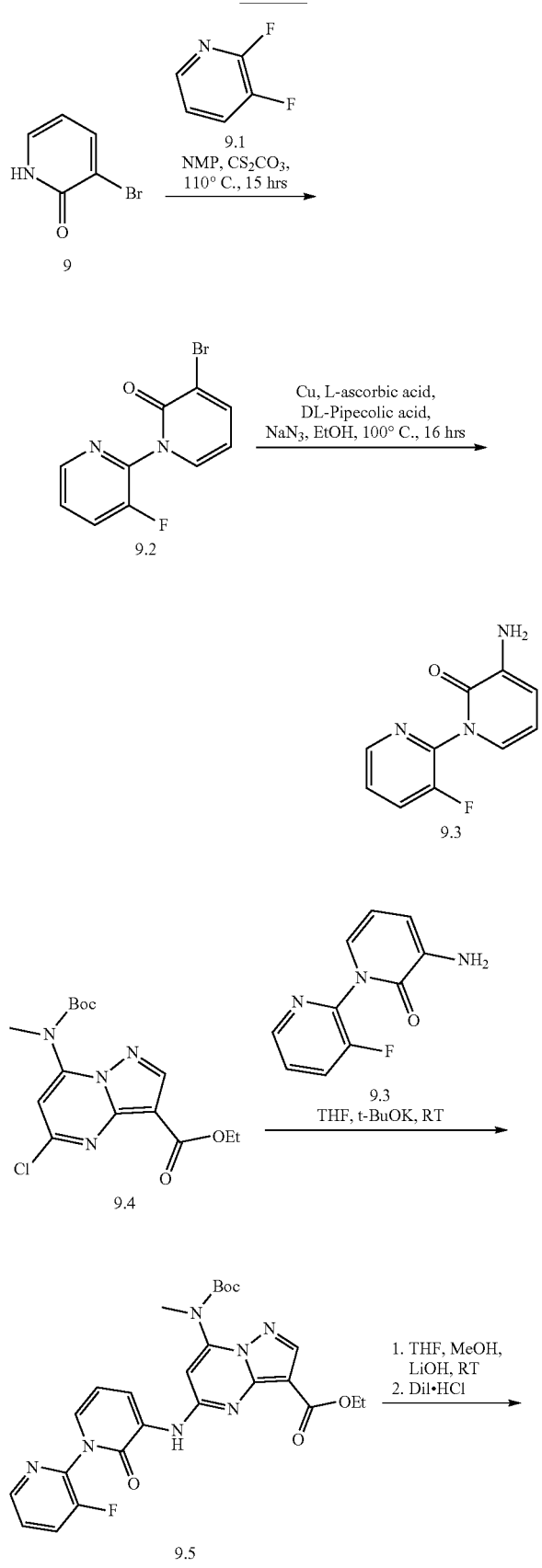

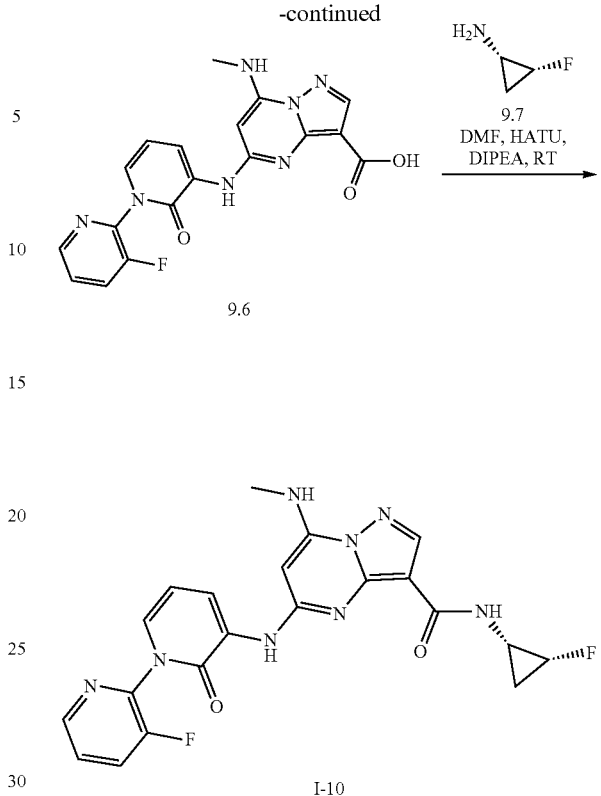

Step 1—Synthesis of Compound 9.2: To a solution of 9 (10 g, 57.47 mmol, 1.0 eq) in 1-methylpyrrolidin-2-one (240 mL) 9.1 (7.34 g, 63.79 mmol, 1.1 eq) was added followed by addition of cesium carbonate (46.81 g, 143.67 mmol, 2.5 eq). The reaction mixture was heated at 110° C. for 15 h. After completion of reaction, reaction mixture was cooled to room temperature, transferred into cold water and product was extracted with ethyl acetate. Organic layer was combined, washed with brine solution, dried over sodium sulphate and concentrated under reduced pressure to obtain crude material. This was further purified by column chromatography using 50% ethyl acetate in hexane as eluant to obtain 19.2 (2.6 g, Yield: 16.81%; MS (ES): m/z 269.04 [M]$^+$).

Step 2—Synthesis of compound 9.3: To a solution of 9.2 (2.6 g, 9.66 mmol, 1.0 eq) in ethanol (26 mL) was added copper powder (0.073 g, 1.15 mmol, 0.12 eq), L-ascorbic acid (0.34 g, 1.93 mmol, 0.2 eq), DL-Pipecolic acid (0.37 g, 2.89 mmol, 0.3 eq) and sodium azide (2.26 g, 34.77 mmol, 3.6 eq). The reaction mixture was heated at 100° C. for 16 h. After completion of reaction, reaction mixture was cooled to room temperature, transferred into cold water and product was extracted with ethyl acetate. Organic layer was combined, washed with brine solution, dried over sodium sulphate and concentrated under reduced pressure to obtain crude material. This was further purified column chromatography using 55-60% ethyl acetate in hexane as eluant to obtain 9.3 (1.6 g, Yield: 80.70%; MS (ES): m/z 206.29 [M+H]$^+$).

Step 3—Synthesis of Compound 9.4: Compound was synthesized using the procedure for the preparation of Core A to obtain 9.4 (MS (ES): m/z 355.11 [M+H]$^+$).

Step 4—Synthesis of Compound 9.2: To a cooled solution of 9.4 (0.2 g, 0.56 mmol, 1.0 eq), and 9.3 (0.114 g, 0.67 mmol, 1.2 eq) in tetrahydrofuran (4 mL) at 0° C. was added potassium tert-butoxide (1M in tetrahydrofuran; 1.12 mL, 1.12 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 9.5 (0.120 g, Yield: 42.11%; MS (ES): m/z 524.20 [M+H]$^+$).

Step 6—Synthesis of Compound 9.6: To a solution of 9.5 (0.120 g, 0.22 mmol, 1.0 eq) in methanol:tetrahydrofuran:water (4 mL, 2:1:1) was added lithium hydroxide (0.055 g, 2.3 mmol, 10 eq). The reaction was stirred at 60° C. for 16 h. After completion of reaction, reaction mixture was concentrated under reduced pressure to obtain residue. To this added water followed by hydrochloric acid to adjust pH~1-2, stirred for 1 h at 10° C. and neutralised by saturated sodium bicarbonate. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 9.6 (0.065 g, Yield: 72.56%; MS (ES): m/z 396.12 [M+H]$^+$).

Step 7—Synthesis of Compound I-10: Compound was synthesized using general procedure A to obtain I-10 (0.032 g, 27.96%; MS (ES): m/z 453.37 [M+H]$^+$; LCMS purity: 95.20%; HPLC purity: 95.01%; CHIRAL HPLC: 96.00%; $^1$H NMR (DMSO-$d_6$, 400 MHZ): 9.02 (s, 1H), 8.53-8.52 (d, J=4.8 Hz, 1H), 8.30-8.28 (d, J=8 Hz, 1H), 8.27 (s, 1H), 8.10-8.05 (d, J=9.2 Hz 1H), 7.99-7.98 (d, J=4.8 Hz, 1H), 7.84-7.83 (d, J=4.4 Hz, 1H), 7.76-7.72 (m, 1H), 7.45-7.43 (d, J=6.8 Hz, 1H), 6.45-6.41 (t, J=6.8 Hz, 1H), 6.26 (s, 1H), 4.83-4.81 (m, 1H), 3.18-3.17 (d, J=5.2 Hz, 1H), 3.03-3.01 (m, 1H), 2.91-2.90 (d, J=4.8 Hz, 3H), 1.30-1.21 (m, 1H)).

Example 10: 5-((1-((1r,3S)-3-Fluorocyclobutyl)-2-oxo-1,2-dihydropyridin-3-yl)amino)-N-(2-hydroxycyclobutyl)-7-(methylamino)pyrazolo[1,5-a]pyrimidine-3-carboxamide (I-11)

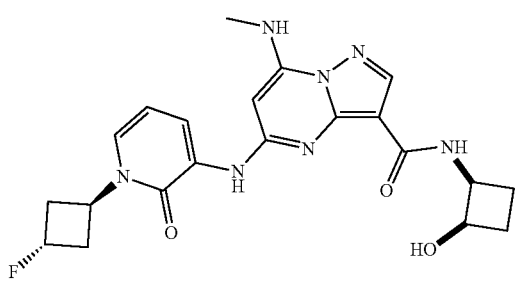

Scheme 10

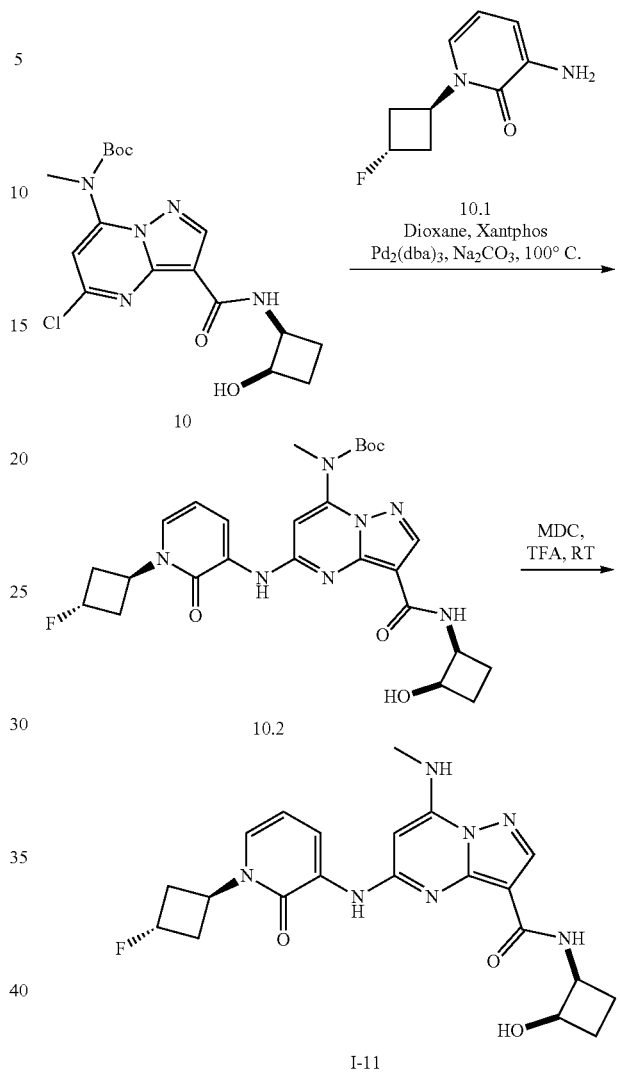

Step 1—Synthesis of Compound 10: Compound was synthesized from Core A utilizing general method A to obtain 10 (Yield: 50.51%; MS (ES): m/z 396.84 [M+H]$^+$).

Step 2—Synthesis of Compound 10.1: Compound was synthesized as per experimental protocol of I-7 (Example 6) to obtain 10.1 (Yield: 98.46%; MS (ES): m/z 183.09 [M+H]$^+$).

Step 2—Synthesis of Compound 10.2: Compound was synthesized using general procedure B to obtain 10.2 (0.145 g, Yield: 70.65%; MS (ES): m/z 542.25 [M+H]$^+$).

Step 3—Synthesis of Compound I-1: Compound was synthesized using general procedure C to obtain I-11 (0.028 g, Yield: 85.87%; MS (ES): m/z 442.27 [M+H]$^+$; LCMS purity: 97.66%; HPLC purity: 97.71%; CHIRAL HPLC: 48.80%, 49.46%; $^1$H NMR (DMSO-$d_6$, 400 MHZ): 8.86 (s, 1H), 8.54-8.52 (d, J=7.2 Hz, 1H), 8.19 (s, 1H), 8.05-8.02 (d, J=8.8 Hz, 1H), 7.89-7.87 (d, J=4.8 Hz, 1H), 7.44-7.42 (d, J=6 Hz, 1H), 6.43-6.40 (t, J=7.2 Hz, 1H), 6.27 (s, 1H), 5.44-5.37 (m, 2H), 4.58-4.55 (m, 2H), 4.35 (bs, 1H), 2.90-2.89 (d, J=4.8 Hz, 3H), 2.83-2.79 (m, 1H), 2.73-2.68 (m, 3H), 2.19 (bs, 1H), 2.07-2.02 (m, 1H), 1.99-1.95 (m, 1H), 1.65 (bs, 1H)).

Example 11: 5-((1-((1S,2S)-2-Fluorocyclopropyl)-2-oxo-1,2-dihydropyridin-3-yl)amino)-N-((1S,2R)-2-hydroxycyclobutyl)-7-(methylamino)pyrazolo[1,5-a]pyrimidine-3-carboxamide (I-12)
And
5-((1-((1S,2S)-2-Fluorocyclopropyl)-2-oxo-1,2-dihydropyridin-3-yl)amino)-N-((1R,2S)-2-hydroxycyclobutyl)-7-(methylamino)pyrazolo[1,5-a]pyrimidine-3-carboxamide (I-13)
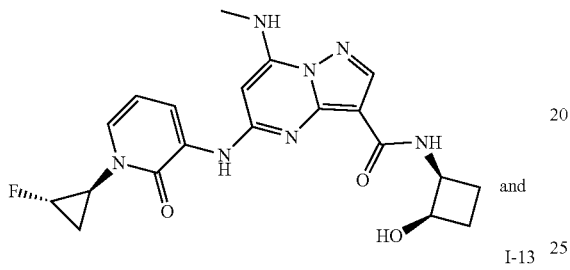
and
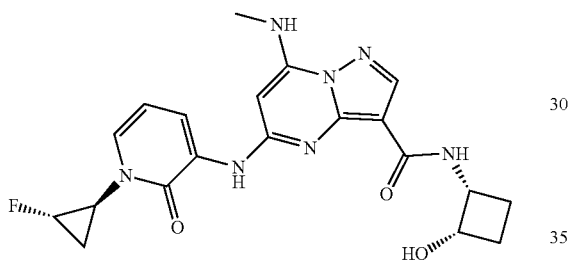
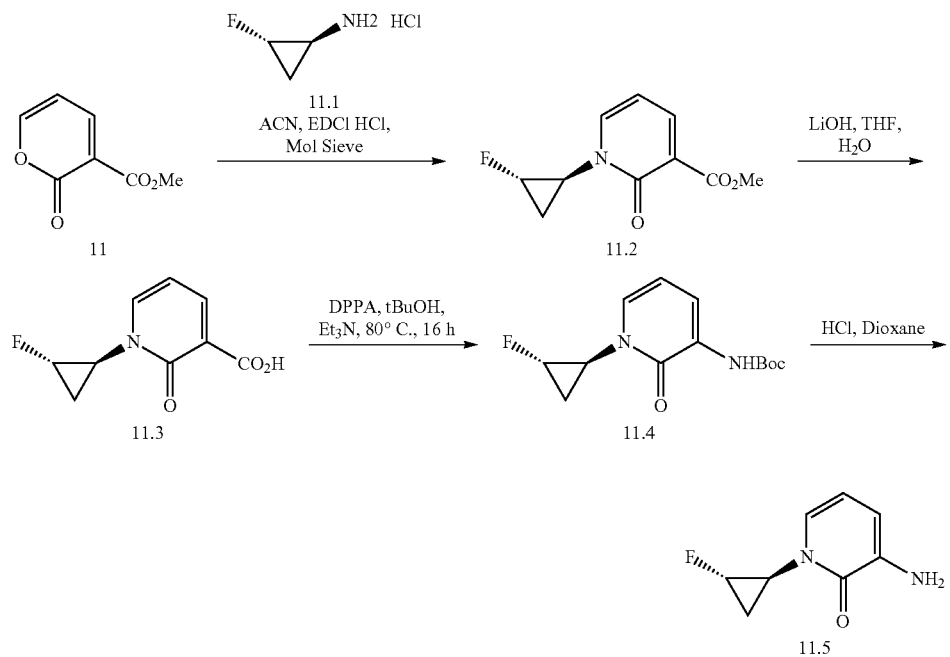

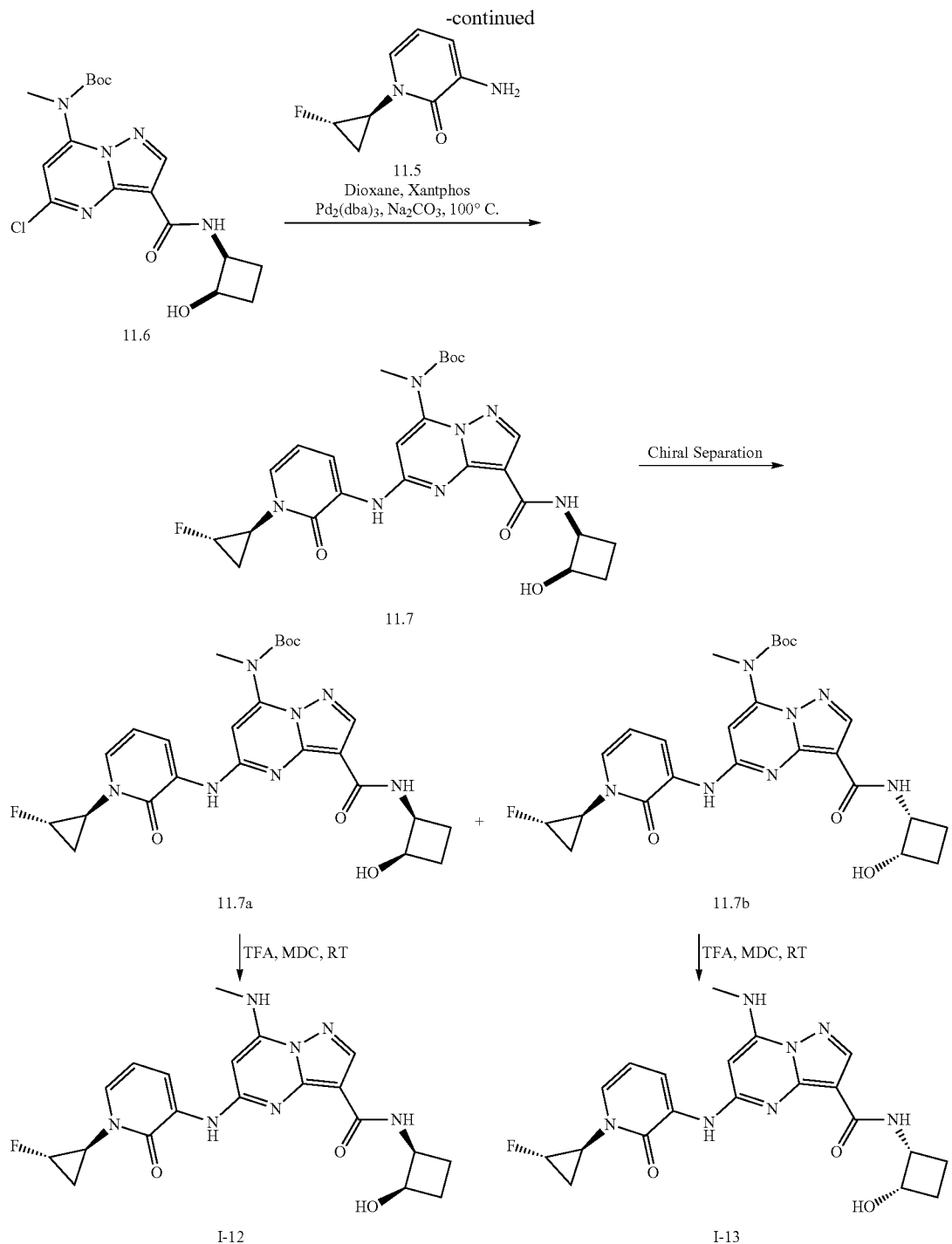

Step 1—Synthesis of Compound 11.2: To a cooled solution of 11 (0.5 g, 3.24 mmol, 1.0 eq), in Acetonitrile (10 mL) was added 11.1 (0.395 g, 3.56 mmol, 1.1 eq). The reaction mixture was stirred at 0° C. for 30 min and further stirred at room temperature for 15 min. N-Ethyl-N'-(3-dimethylaminopropyl)carbodiimide hydrochloride (0.652 g, 4.21 mmol, 1.3 eq) and molecular sieves were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 11.2 (0.320 g, Yield: 46.71%; MS (ES): m/z 212.07 [M+H]$^+$).

Step 2—Synthesis of Compound 11.3: To a solution of 11.2 (0.320 g, 1.51 mmol, 1.0 eq), in tetrahydrofuran:water (8 mL, 2:1) was added lithium hydroxide (0.362 g, 15.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 11.3 (0.265 g, Yield: 88.70%; MS (ES): m/z 198.05 [M+H]$^+$).

Step 3—Synthesis of Compound 11.4: To a solution of 11.3 (0.265 g, 1.34 mmol, 1.0 eq) in tert-butanol (6 mL) was added triethylamine (0.230 g, 2.27 mmol, 1.7 eq) and diphenyl phosphoryl azide (0.478 g, 1.74 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 11.4 (0.160 g, Yield: 44.37%; MS (ES): m/z 269.13 [M+H]$^+$).

Step 4—Synthesis of Compound 11.5: A cooled solution of 11.4 (0.160 g, 0.59 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 11.5 (0.125 g, Yield: 98.33%; MS (ES): m/z 205.05 [M+HCl]$^+$).

Step 5—Synthesis of Compound 11.6: Compound was synthesized from Core A utilizing general method A to obtain 11.6 (Yield: 50.51%; MS (ES): m/z 396.84 [M+H]$^+$).

Step 6—Synthesis of Compound 11.7: Compound was synthesized per general method B to obtain 11.7 (0.135 g, Yield: 67.53%; MS (ES): m/z 527.5 [M+H]$^+$).

Step 7—Synthesis of Compounds 11.7a and 11.7b: Isomers of 11.7 (0.1 g) were separated out using column CHIRALPAK OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 11.7a (0.040 g; MS (ES): m/z 527.5 [M+H]$^+$). FR-b was concentrated under reduced pressure at 30° C. to afford pure 11.7b (0.045 g; MS (ES): m/z 527.5 [M+H]$^+$).

Step 8—Synthesis of Compound I-12: Compound was synthesized using general procedure C to obtain I-12 (0.027 g, Yield: 83.31%; MS (ES): m/z 428.18 [M+H]$^+$; LCMS purity: 100%; HPLC purity: 100%; CHIRAL HPLC purity: 96.10%; $^1$H NMR (DMSO-d$_6$, 400 MHZ): 8.87 (s, 1H), 8.51-8.50 (d, J=6 Hz, 1H), 8.19 (s, 1H), 8.03-8.01 (d, J=9.2 Hz, 1H), 7.89-7.88 (d, J=4.8 Hz, 1H), 7.14-7.12 (d, J=5.6 Hz, 1H), 6.35-6.31 (t, J=7.2 Hz, 1H), 6.27 (bs, 1H), 5.40-5.39 (d, J=4 Hz, 1H), 4.57-4.54 (m, 1H), 4.34 (bs, 1H), 3.89-3.81 (m, 1H), 2.91-2.89 (d, J=4.8 Hz, 3H), 2.50 (s, 3H), 1.23 (bs, 4H)).

Step 9—Synthesis of Compound I-13: Compound was synthesized using general procedure C to obtain I-13 (0.032 g, 87.77%; MS (ES): m/z 428.18 [M+H]$^+$; LCMS purity: 100%; HPLC purity: 98.81%; CHIRAL HPLC purity: 99.25%; H NMR (DMSO-d$_6$, 400 MHZ): 8.88 (s, 1H), 8.51-8.50 (d, J=6 Hz, 1H), 8.19 (s, 1H), 8.03-8.01 (d, J=9.2 Hz, 1H), 7.89-7.88 (d, J=4.8 Hz, 1H), 7.13-7.11 (d, J=5.6 Hz, 1H), 6.35-6.31 (t, J=7.2 Hz, 1H), 6.27 (bs, 1H), 5.40-5.39 (d, J=4 Hz, 1H), 4.57-4.54 (m, 1H), 4.34 (bs, 1H), 3.89-3.81 (m, 1H), 2.91-2.89 (d, J=4.8 Hz, 3H), 2.50 (s, 3H), 1.24 (bs, 4H)).

Example 12: N-((1R,2S)-2-Hydroxycyclobutyl)-7-(methylamino)-5-(1-((S)-tetrahydro-2H-pyran-3-yl)-1H-pyrrolo[2,3-b]pyridin-3-yl)pyrazolo[1,5-a]pyrimidine-3-carboxamide (I-14)

And

N-((1S,2R)-2-Hydroxycyclobutyl)-7-(methylamino)-5-(1-((S)-tetrahydro-2H-pyran-3-yl)-1H-pyrrolo[2,3-b]pyridin-3-yl)pyrazolo[1,5-a]pyrimidine-3-carboxamide (I-15)

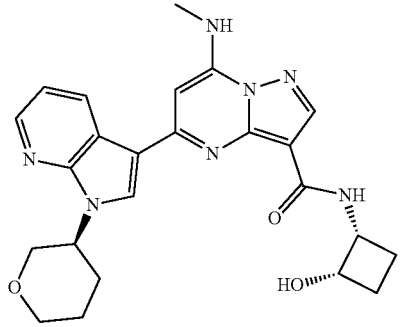

I-14 and

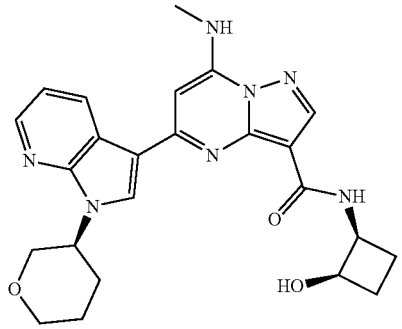

I-15

Scheme 12

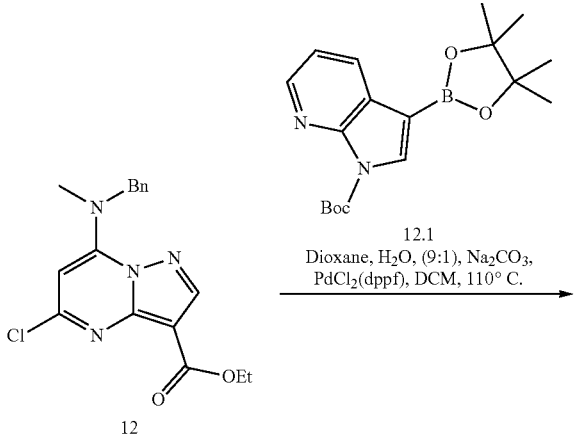

12.1
Dioxane, H$_2$O, (9:1), Na$_2$CO$_3$, PdCl$_2$(dppf), DCM, 110° C.

577
-continued
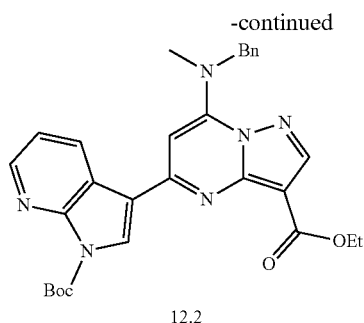
12.2
Dioxane HCl, RT →
578
-continued
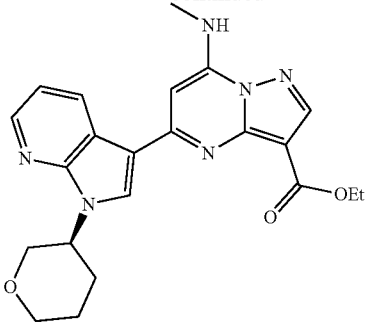
12.6a
+
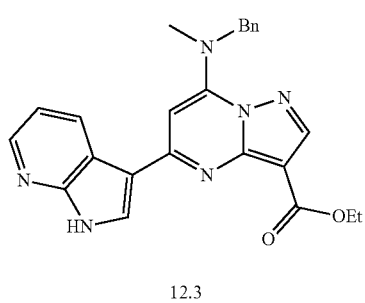
12.3
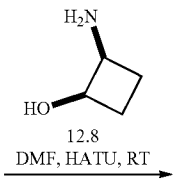
12.4
Dioxane: DMF, CuI, DMEDA, K₂CO₃, 80° C., O/N →
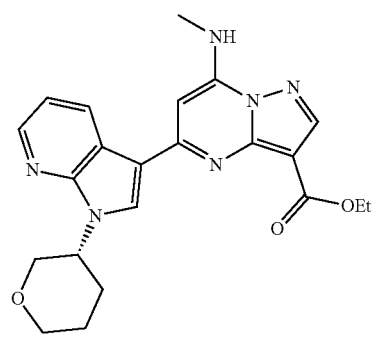
12.6b
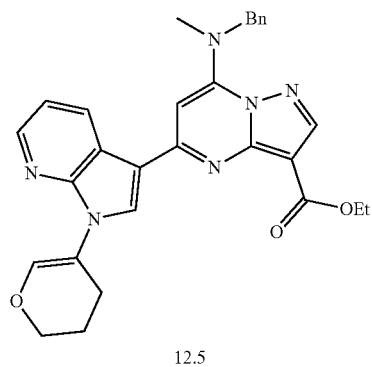
12.5
MeOH, Pd—C, H₂ RT, 48 h →
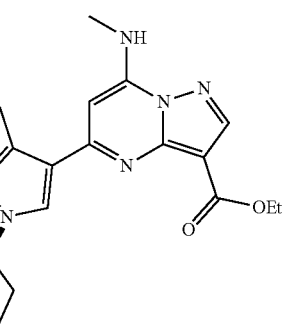
12.6a
LiOH, MeOH, Water, RT →
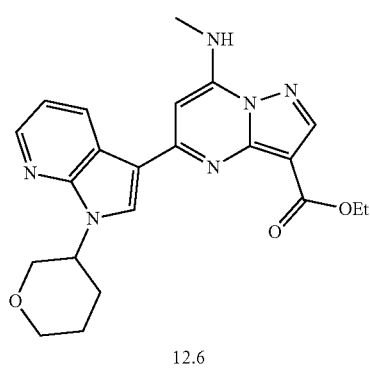
12.6
Chiral Separation →
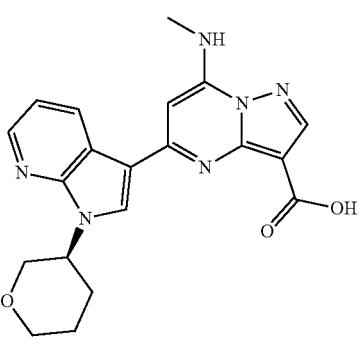
12.7
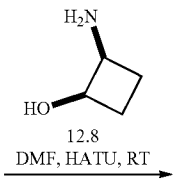
12.8
DMF, HATU, RT →

-continued

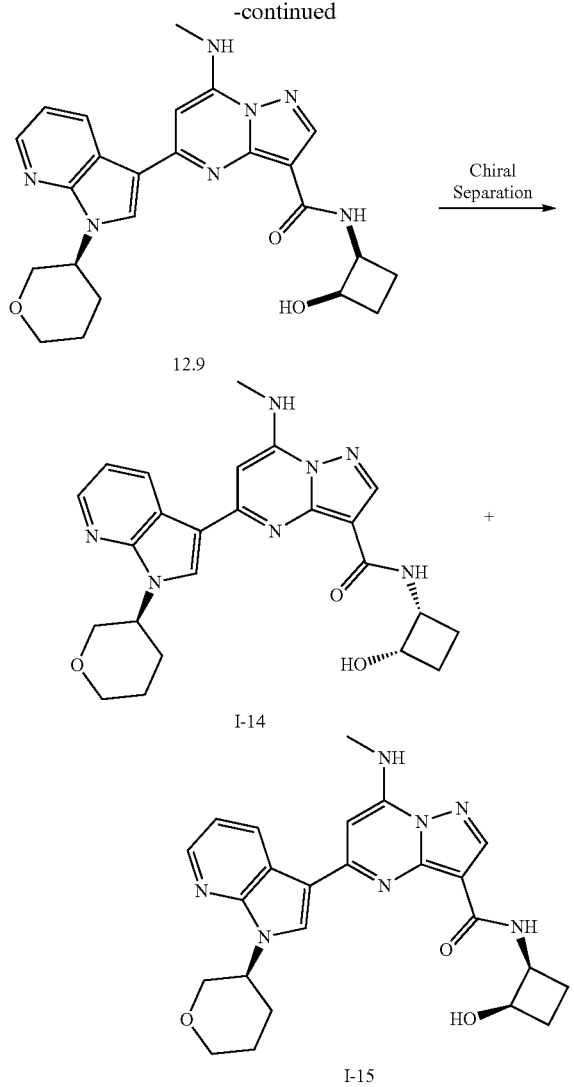

Step 1—Synthesis of Compound 12: Compound was synthesized using the procedure for the preparation of Core B to obtain 12.

Step 2—Synthesis of Compound 12.2: Argon was purged for 15 min through a stirring solution of 12 (3.5 g, 10.15 mmol, 1.0 eq), 12.1 (4.5 g, 13.19 mmol, 1.3 eq), and sodium carbonate (2.6 g, 25.37 mmol, 2.5 eq) in 1,4 dioxane:water (140 mL, 9:1) [1,1'-bis(diphenylphospino)ferrocence]palladium(II) dichloride (0.738 mg, 1.01 mmol, 0.1 eq) was added to it and further purging done for 10 min. Reaction was allowed to stir at 110° C. for 6 h. After completion of reaction, reaction mixture was poured over water and product was extracted with ethyl acetate. Organic layer was combined, washed with brine solution, dried over sodium sulphate, and concentrated under reduced pressure to obtain 12.2 (3.1 g, Yield: 57.99%; MS (ES): m/z 527.24 [M+H]$^+$).

Step 3—Synthesis of Compound 12.3: To 12.2 (3.1 g, 5.88 mmol, 1.0 eq) was added 4M hydrochloric acid in 1,4 Dioxane (60 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain 12.3 (2.1 g, Yield: 83.64%; MS (ES): m/z 427.18 [M+H]$^+$).

Step 4—Synthesis of Compound 12.5: To a solution of 12.3 (2.0 g, 4.68 mmol, 1 eq) and 12.4 (0.915 g, 5.61 mmol, 1.2 eq) in 1,4-dioxane (60 mL) was added potassium carbonate (1.29 g, 9.36 mmol, 2.0 eq) and degassed with argon for 15 min. Copper iodide (0.178 g, 0.93 mmol, 0.2 eq) and 1,2-dimethylethylenediamine (0.165 g, 1.87 mmol, 0.4 eq) were added and reaction mixture again degassed with argon for 5 min followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 12.5 (1.0 g, Yield: 41.93%; MS (ES): m/z 509.23 [M+H]$^+$).

Step 5—Synthesis of Compound 12.6: To a solution of 12.5 (1.0 g, 1.96 mmol, 1.0 eq) in methanol (12 mL), palladium on charcoal (0.4 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with pantane to obtain pure 12.6 (0.610 g, Yield: 73.78%; MS (ES): m/z 421.19 [M+H]$^+$).

Step 6—Synthesis of Compounds 12.6a and 12.6b: Isomers of 12.6 (0.610 g) were separated out using column CHIRALPAK OX-H (250 mm×4.6 mm, 5 μm) and 0.1% DEA_HEX_IPA-CAN (70-30) as co-solvent with flow rate of 4 mL/min. to get pure fraction-1 (FR-a) and fraction-2 (FR-b). FR-a was concentrated under reduced pressure at 30° C. to afford pure 12.6a (0.190 g; MS (ES): m/z 421.19 [M+H]$^+$). FR-b was concentrated under reduced pressure at 30° C. to afford pure 12.6b (0.180 g; MS (ES): m/z 421.19 [M+H]$^+$).

Step 7—Synthesis of Compound 12.7: To a solution of 12.6a (0.4 g, 0.956 mmol, 1.0 eq), in methanol:water (8 mL, 2:1) was added lithium hydroxide (0.219 g, 9.56 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 12.7 (0.350 g, Yield: 93.76%; MS (ES): m/z 393.16 [M+H]$^+$).

Step 8—Synthesis of Compound 12.9: Compound was synthesized using general procedure A to obtain 12.9 (0.125 g, Yield: 70.86%; MS (ES): m/z 462.61 [M+H]$^+$; LCMS purity: 97.36%; HPLC purity: 97.32%; CHIRAL HPLC: 48.06%, 48.35%; $^1$H NMR (DMSO-$d_6$, 400 MHZ): 9.04-9.02 (d, J=8.4 Hz, 1H), 8.82-8.81 (d, J=3.6 Hz, 1H), 8.68-8.64 (t, J=7.6 Hz, 1H), 8.41-8.40 (d, J=4 Hz, 1H), 8.37 (s, 1H), 7.27-7.26 (d, J=4.4 Hz, 1H), 7.34-7.31 (m, 1H), 6.75 (s, 1H), 5.78 (s, 1H), 5.53 (bs, 1H), 4.97 (bs, 1H), 4.60 (bs, 1H), 4.44 (bs, 1H), 4.04 (bs, 1H), 3.98 (bs, 1H), 3.75-3.72 (m, 1H), 3.52 (s, 1H), 3.15-3.14 (d, J=4.4 Hz, 3H), 2.22 (bs, 3H), 1.86 (bs, 3H), 1.28-1.25 (m, 1H)).

Step 9: Synthesis of Compounds I-14 and I-15: Isomers of 12.9 (0.105 g) were separated out using column CHIRAL PAK OX-H (250 mm×4.6 mm, 5 μm) 0.1% DEA_HEX_IPA-ACN (70-30) to get pure fraction-1 (FR-a) and fraction-2 (FR-b).

FR-a was concentrated under reduced pressure at 30° C. to afford pure I-14 (0.035 g; MS (ES): m/z 462.57 [M+H]$^+$; LCMS purity: 100%; HPLC purity: 97.32%; CHIRAL HPLC purity: 100%; H NMR (DMSO-d$_6$, 400 MHZ): 9.03-9.01 (d, J=8 Hz, 1H), 8.81 (s, 1H), 8.67-8.65 (d, J=8 Hz, 1H), 8.40-8.39 (d, J=4.4 Hz, 1H), 8.37 (s, 1H), 8.27-8.26 (d, J=4.4 Hz, 1H), 7.33-7.30 (m, 1H), 6.74 (s, 1H), 5.54-5.53 (d, J=3.2 Hz, 1H), 4.97 (bs, 1H), 4.60 (bs, 1H), 4.44 (bs, 1H), 4.05-4.03 (d, J=8.8 Hz, 1H), 3.98-3.95 (d, J=12 Hz, 1H), 3.74-3.69 (t, J=10.4 Hz, 1H), 3.53-3.51 (t, J=7.6 Hz, 1H), 3.14-3.13 (d, J=4 Hz, 3H), 2.34 (bs, 3H), 2.06-2.02 (m, 2H), 1.86 (bs, 3H)).

FR-b was concentrated under reduced pressure at 30° C. to afford pure I-15 (0.035 g; MS (ES): m/z 462.66 [M+H]$^+$; LCMS purity: 100%; HPLC purity: 99.87%; CHIRAL HPLC purity: 93.05%; $^1$H NMR (DMSO-d$_6$, 400 MHZ): 9.04-9.03 (d, J=8 Hz, 1H), 8.80 (s, 1H), 8.65-8.63 (d, J=8 Hz, 1H), 8.40-8.39 (d, J=4.4 Hz, 1H), 8.37 (s, 1H), 8.27-8.26 (d, J=4.4 Hz, 1H), 7.33-7.30 (m, 1H), 6.74 (s, 1H), 5.53-5.52 (d, J=3.2 Hz, 1H), 4.97 (bs, 1H), 4.60 (bs, 1H), 4.44 (bs, 1H), 4.05-4.03 (d, J=8.8 Hz, 1H), 3.98-3.95 (d, J=12 Hz, 1H), 3.74-3.69 (t, J=10.4 Hz, 1H), 3.53-3.51 (t, J=7.6 Hz, 1H), 3.14-3.13 (d, J=4 Hz, 3H), 2.34 (bs, 3H), 2.06-2.02 (m, 2H), 1.86 (bs, 3H)).

Example 13: 5-((1-((1r,3S)-3-Fluorocyclobutyl)-2-oxo-1,2-dihydropyridin-3-yl)amino)-N-((1S,2R)-2-hydroxycyclobutyl)-7-(methylamino)pyrazolo[1,5-a]pyrimidine-3-carboxamide (I-16)

And 5-((1-((1r,3R)-3-Fluorocyclobutyl)-2-oxo-1,2-dihydropyridin-3-yl)amino)-N-((1R,2S)-2-hydroxycyclobutyl)-7-(methylamino)pyrazolo[1,5-a]pyrimidine-3-carboxamide (I-17)

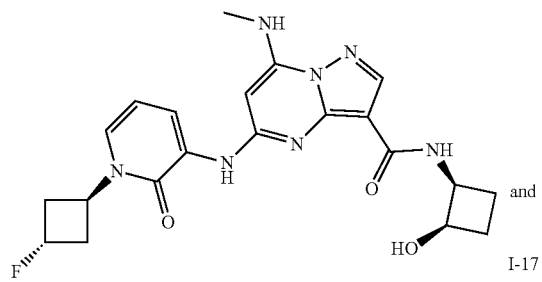

I-16 and

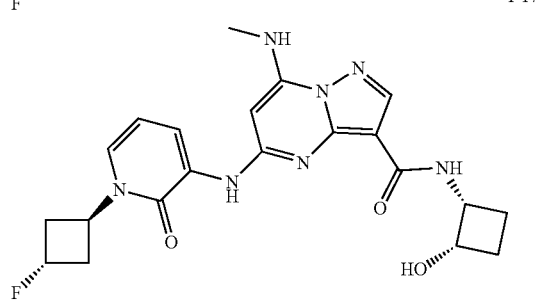

I-17

Scheme 13

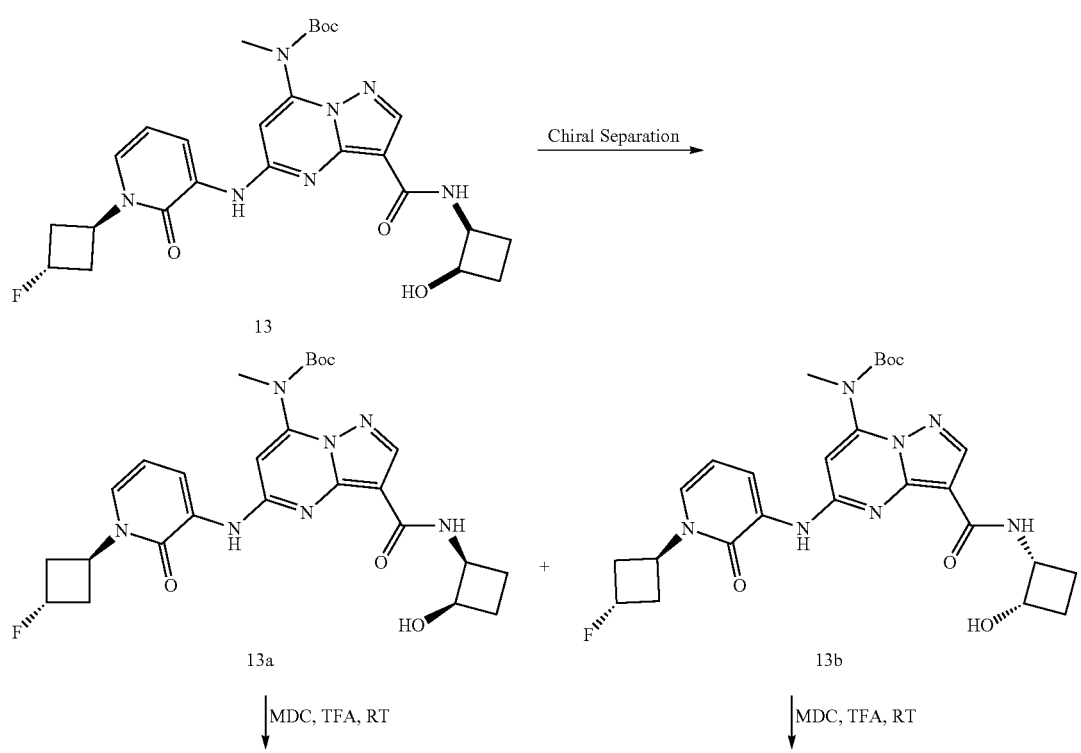

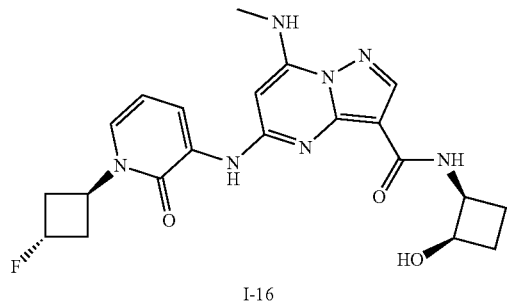

I-16

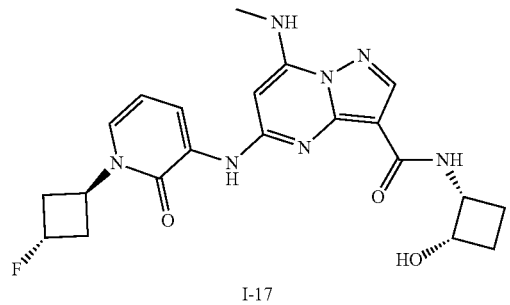

I-17

Step 1—Synthesis of Compound 13: Compound was synthesized as per experimental protocol of I-11 (Example 10) to obtain 13 (Yield: 70.65%; MS (ES): 542.25 [M+H]$^+$).

Step 2—Synthesis of Compound 13a and 13b: Isomers of 13 (0.105 g) were separated out using column CHIRALPAK OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 13a (0.042 g; MS (ES): m/z 542.25 [M+H]$^+$). FR-b was concentrated under reduced pressure at 30° C. to afford pure 13b (0.042 g; MS (ES): m/z 542.25 [M+H]$^+$).

Step 3—Synthesis of Compound I-16: Compound was synthesized using general procedure C to obtain I-16 (0.030 g, 87.63%; MS (ES): m/z 442.52 [M+H]$^+$; LCMS purity: 100%; HPLC purity: 97.05%; CHIRAL HPLC purity: 97.29%; $^1$H NMR (DMSO-d$_6$, 400 MHZ): 8.87 (s, 1H), 8.55-8.53 (d, J=7.2 Hz, 1H), 8.21 (s, 1H), 8.06-8.04 (d, J=8.8 Hz, 1H), 7.90-7.88 (d, J=4.8 Hz, 1H), 7.45-7.43 (d, J=6.8 Hz, 1H), 6.43-6.41 (t, J=7.2 Hz, 1H), 6.28 (s, 1H), 5.45-5.37 (m, 2H), 5.31 (bs, 1H), 4.59-4.58 (m, 1H), 4.36 (bs, 1H), 2.92-2.91 (d, J=4.8 Hz, 3H), 2.74-2.69 (m, 3H), 2.34 (bs, 1H), 2.21 (bs, 1H), 2.01-1.96 (m, 2H), 1.74 (bs, 1H)).

Step 4—Synthesis of Compound I-17: Compound was synthesized using general procedure C to obtain I-17 (0.030 g, Yield: 87.63%; MS (ES): m/z 442.56 [M+H]$^+$; LCMS purity: 98.00%; HPLC purity: 98.07%; CHIRAL HPLC purity: 98.29%; $^1$H NMR (DMSO-d$_6$, 400 MHZ): 8.87 (s, 1H), 8.55-8.53 (d, J=7.2 Hz, 1H), 8.21 (s, 1H), 8.06-8.04 (d, J=8.8 Hz, 1H), 7.90-7.88 (d, J=4.8 Hz, 1H), 7.45-7.43 (d, J=6.8 Hz, 1H), 6.44-6.41 (t, J=7.2 Hz, 1H), 6.28 (s, 1H), 5.45-5.39 (m, 2H), 5.29 (bs, 1H), 4.60-4.56 (m, 1H), 4.36 (bs, 1H), 2.92-2.91 (d, J=4.8 Hz, 3H), 2.74-2.69 (m, 3H), 2.34 (bs, 1H), 2.21 (bs, 1H), 2.01-1.96 (m, 2H), 1.74 (bs, 1H)).

Example 14: 5-(5-Fluoro-1-(tetrahydro-2H-pyran-4-yl)-1H-pyrrolo[2,3-b]pyridin-3-yl)-N-((1S,2S)-2-hydroxycyclobutyl)-7-(methylamino)pyrazolo[1,5-a]pyrimidine-3-carboxamide (I-18

And 5-(5-Fluoro-1-(tetrahydro-2H-pyran-4-yl)-1H-pyrrolo[2,3-b]pyridin-3-yl)-N-((1R,2R)-2-hydroxycyclobutyl)-7-(methylamino)pyrazolo[1,5-a]pyrimidine-3-carboxamide (I-19)

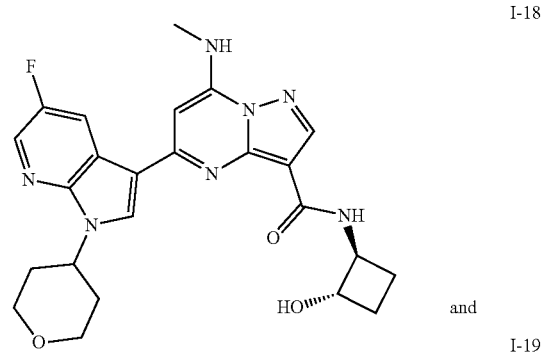

I-18 and

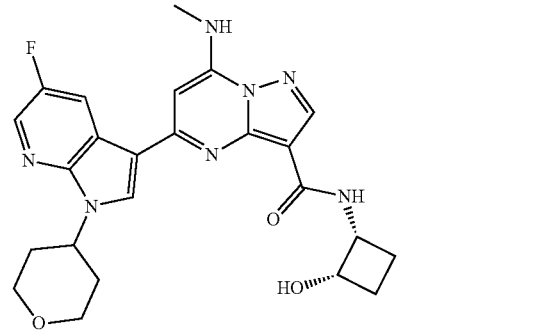

I-19

Scheme 14
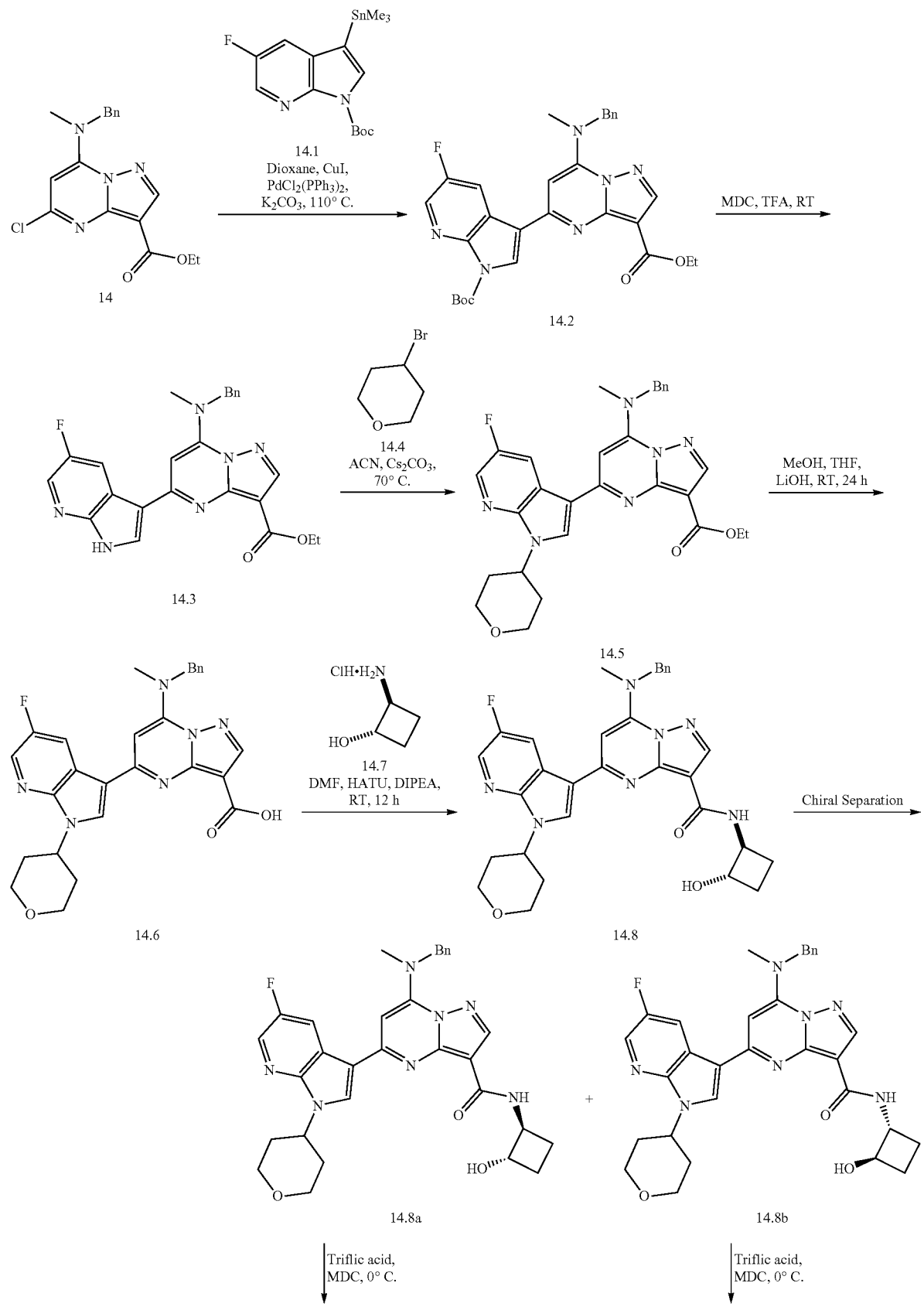

-continued

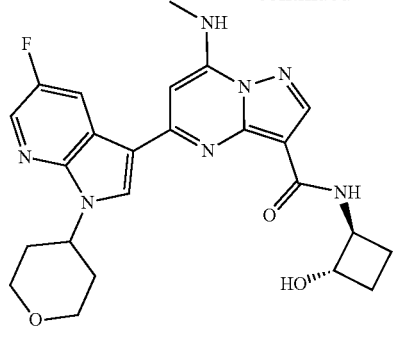

I-18

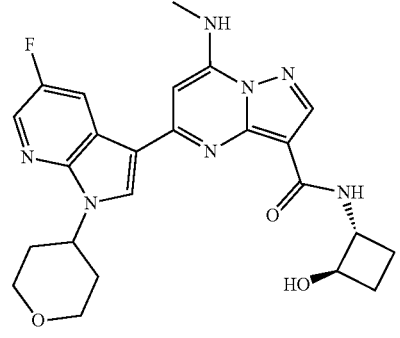

I-19

Step 1—Synthesis of Compound 14: Compound was synthesized using general procedure of core B synthesis to obtain 14 (Yield: 45%; MS (ES): m/z 345.10 [M+H]$^+$)

Step 2—Synthesis of Compound 14.2: Argon was purged for 15 min through a stirring solution of 14 (3.5 g, 1.16 mmol, 1.0 eq), 14.1 (0.696 g, 1.74 mmol, 1.5 eq) and potassium carbonate (0.4 g, 2.9 mmol, 2.5 eq) in 1,4-dioxane (8 mL). Copper(I) iodide (0.043 g, 0.23 mmol, 0.2 eq) and Bis(triphenylphosphine)palladium(II) dichloride (0.077 mg, 0.11 mmol, 0.1 eq) was added to it and further purging done for 10 min. Reaction was allowed to stirred at 110° C. for 6 h. After completion of reaction, reaction mixture was poured over water and product was extracted with ethyl acetate. Organic layer was combined, washed with brine solution, dried over sodium sulphate and concentrated under reduced pressure to obtain 14.2 (0.4 g, Yield: 63.31%; MS (ES): m/z 545.23 [M+H]$^+$).

Step 3—Synthesis of Compound 14.3: Compound was synthesized using general procedure C to obtain 14.3 (0.310 g, Yield: 94.96%; MS (ES): 445.17 [M+H]$^+$).

Step 4—Synthesis of Compound 14.5: To a cooled solution of 14.3 (0.350 g, 0.78 mmol, 1.0 eq), and 14.4 (0.153 g, 0.93 mmol, 1.2 eq) in Acetonitrile (10 mL) at 0° C. was added Cesium carbonate (0.635 g, 1.95 mmol, 2.5 eq). The reaction was stirred at 70° C. for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 14.5 (0.3 g, Yield: 72.07%; MS (ES): m/z 529.23 [M+H]$^+$).

Step 5—Synthesis of Compound 14.6: To a solution of 14.5 (0.3 g, 0.56 mmol, 1.0 eq), in methanol:tetrahydrofuran (8 mL, 2:1) was added lithium hydroxide (0.134 g, 5.6 mmol, 10 eq). The reaction was stirred at 60° C. for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 14.6 (0.250 g, Yield: 88.00%; MS (ES): m/z 501.20 [M+H]$^+$).

Step 6—Synthesis of Compound 14.8: Compound was synthesized using general procedure A to obtain 14.8 (0.150 g, Yield: 52.72%; MS (ES): 570.26 [M+H]$^+$).

Step 5—Synthesis of Compounds 14.8a and 14.8b: Isomers of 14.8 (0.120 g) were separated out using column CHIRALPAK AD-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 14.8a (0.032 g; MS (ES): m/z 570.26 [M+H]$^+$). FR-b was concentrated under reduced pressure at 30° C. to afford pure 14.8b (0.033 g; MS (ES): m/z 570.26 [M+H]$^+$).

Step 6—Synthesis of Compound 1I-18: To a solution of 14.8a (0.032 g, 0.056 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-18 (0.021 g, Yield: 77.96%; MS (ES): m/z 480.51 [M+H]$^+$; LCMS purity: 99.20%; HPLC purity: 97.20%; CHIRAL HPLC: 99.08%; $^1$H NMR (DMSO-d$_6$, 400 MHZ): 8.97 (s, 1H), 8.51 (s, 1H), 8.42 (s, 1H), 8.37-8.36 (d, J=6.8 Hz, 1H), 8.33 (s, 1H), 8.27 (bs, 1H), 6.82 (s, 1H), 5.44 (bs, 1H), 5.05-5.02 (m, 1H), 4.38-4.34 (t, J=8.4 Hz, 1H), 4.08-4.06 (m, 4H), 3.64-3.58 (t, J=11.6 Hz, 3H), 3.11-3.10 (d, J=3.6 Hz, 4H), 2.11-2.07 (m, 3H), 1.53-1.49 (m, 1H), 1.43-1.38 (m, 1H)).

Step 7—Synthesis of Compound 1I-19: To a solution of 14.8b (0.033 g, 0.056 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-19 (0.021 g, Yield: 75.60%; MS (ES): m/z 480.51 [M+H]$^+$; LCMS purity: 93.46%; HPLC purity: 96.00%; CHIRAL HPLC: 95.92%; $^1$H NMR (DMSO-d$_6$, 400 MHZ): 8.99 (s, 1H), 8.53-8.51 (d, J=8.8 Hz, 1H), 8.44 (s, 1H), 8.39-8. $^1$H 37 (d, J=6.8 Hz, 1H), 8.35 (s, 1H), 8.29 (bs, 1H), 6.83 (s, 1H), 5.45 (bs, 1H), 5.06 (bs, 1H), 4.39-4.35 (t, J=8.4 Hz, 1H), 4.09-4.07 (m, 4H), 3.65-3.59 (t, J=11.6 Hz, 3H), 3.12-3.11 (d, J=3.6 Hz, 4H), 2.18 (bs, 3H), 2.10 (bs, 1H), 1.52-1.42 (m, 1H)).

Example 15: N-((1S,2S)-2-Hydroxycyclobutyl)-5-((1-((1R,2R)-2-methoxycyclobutyl)-2-oxo-1,2-dihydropyridin-3-yl)amino)-7-(methylamino)pyrazolo[1,5-a]pyrimidine-3-carboxamide (I-20)
And
N-((1R,2R)-2-Hydroxycyclobutyl)-5-((1-((1R,2R)-2-methoxycyclobutyl)-2-oxo-1,2-dihydropyridin-3-yl)amino)-7-(methylamino)pyrazolo[1,5-a]pyrimidine-3-carboxamide (I-21)
I-20
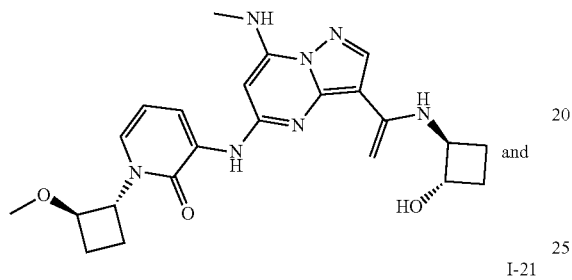
and
I-21
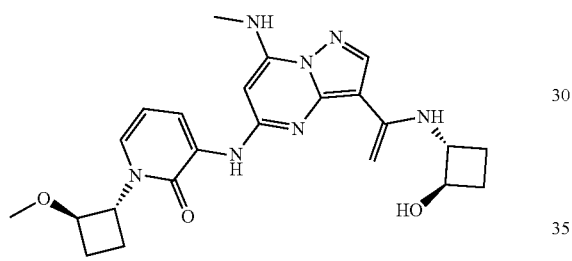
Scheme 15
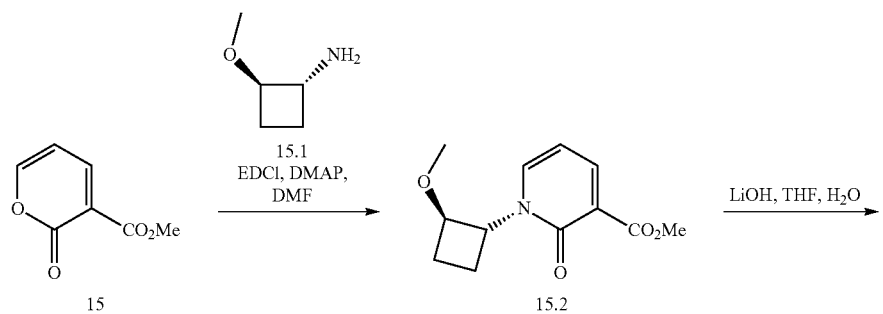
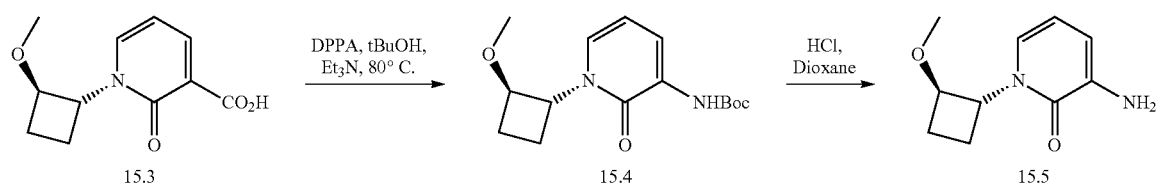

-continued

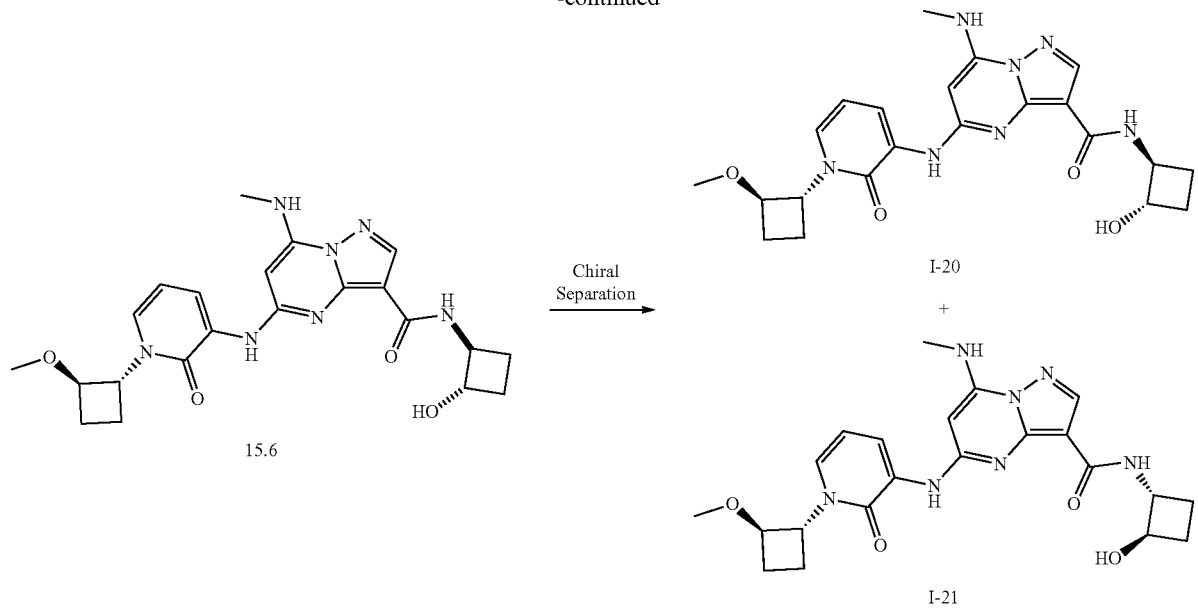

Step 1—Synthesis of Compound 15.2: To a cooled solution of 15 (0.5 g, 3.24 mmol, 1.0 eq), in N,N-dimethylformamide (8 mL) was added 15.1 (0.327 g, 3.24 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.653 g, 4.21 mmol, 1.3 eq) and 4-Dimethylaminopyridine (0.078 g, 0.64 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 15.2 (0.390 g, Yield: 50.67%; MS (ES): m/z 238.10 [M+H]$^+$).

Step 2—Synthesis of Compound 15.3: To a solution of 15.2 (0.390 g, 1.64 mmol, 1.0 eq), in tetrahydrofuran: water (5 mL, 2:1) was added lithium hydroxide (0.393 g, 16.4 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 15.3. (0.3 g, Yield: 81.76%; MS (ES): m/z 224.09 [M+H]$^+$).

Step 3—Synthesis of Compound 15.4: To a solution of 15.3 (0.3 g, 1.34 mmol, 1.0 eq) in tert-butanol (5 mL) was added triethylamine (0.229 g, 2.27 mmol, 1.7 eq) and diphenyl phosphoryl azide (0.478 g, 1.74 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 15.4 (0.275 g, Yield: 69.52%; MS (ES): m/z 295.16 [M+H]$^+$).

Step 4—Synthesis of Compound 15.5: To a cooled solution of 15.4 (0.275 g, 0.93 mmol, 1 eq) in dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain pure 15.5 (0.2 g, 92.80%; MS (ES): m/z 231.09 [M+HCl]$^+$).

Step 5—Synthesis of Compound 15.6: Compound was synthesized from Core A utilizing 15.5 in a manner similar to I-11 (Example 10).

Step 6—Synthesis of Compound I-20 and I-21: Isomers of 15.6 (0.1 g) were separated out using column CHIRAL PAK IC-H (250 mm×4.6 mm, 5 μm) 0.1% DEA_HEX_IPA-ACN (70-30) to get pure fraction-1 (FR-a) and fraction-2 (FR-b).

FR-a was concentrated under reduced pressure at 30° C. to afford pure I-20 (0.026 g; MS (ES): m/z 454.2 [M+H]$^+$; LCMS purity: 100%; HPLC purity: 99.00%; CHIRAL HPLC purity: 99.00%; $^1$H NMR (DMSO-d$_6$, 400 MHZ): 8.96 (s, 1H), 8.26-8.24 (d, J=7.2 Hz, 1H), 8.20 (s, 1H), 8.03-8.01 (d, J=8.8 Hz, 1H), 7.94-7.93 (d, J=4.4 Hz, 1H), 7.60-7.58 (d, J=6.8 Hz, 1H), 6.40-6.37 (t, J=6.8 Hz, 1H), 6.24 (s, 1H), 5.46-5.44 (m, 1H), 5.21-5.14 (m, 1H), 4.25-4.18 (m, 2H), 3.86 (bs, 1H), 3.17 (s, 3H), 2.92-2.90 (d, J=4.8 Hz, 3H), 1.69-1.62 (m, 2H), 1.24 (bs, 6H)).

FR-b was concentrated under reduced pressure at 30° C. to afford pure I-21 (0.030 g; MS (ES): m/z 454.2 [M+H]$^+$; LCMS purity: 100%; HPLC purity: 99.00%; CHIRAL HPLC purity: 99.00%; $^1$H NMR (DMSO-d$_6$, 400 MHZ): 8.97 (s, 1H), 8.26-8.24 (d, J=7.2 Hz, 1H), 8.20 (s, 1H), 8.04-8.02 (d, J=8.8 Hz, 1H), 7.94-7.93 (d, J=4.4 Hz, 1H), 7.60-7.58 (d, J=6.8 Hz, 1H), 6.41-6.38 (t, J=6.8 Hz, 1H), 6.24 (s, 1H), 5.46-5.44 (m, 1H), 5.21-5.14 (m, 1H), 4.25-4.18 (m, 2H), 3.86 (bs, 1H), 3.17 (s, 3H), 2.92-2.90 (d, J=4.8 Hz, 3H), 1.69-1.62 (m, 2H), 1.23 (bs, 6H)).

Example 16: N-((1S,2S)-2-Hydroxycyclobutyl)-5-((1-((1S,2S)-2-methoxycyclobutyl)-2-oxo-1,2-dihydropyridin-3-yl)amino)-7-(methylamino)pyrazolo[1,5-a]pyrimidine-3-carboxamide (I-22)

And

N-((1R,2R)-2-Hydroxycyclobutyl)-5-((1-((1S,2S)-2-methoxycyclobutyl)-2-oxo-1,2-dihydropyridin-3-yl)amino)-7-(methylamino)pyrazolo[1,5-a]pyrimidine-3-carboxamide (I-23)

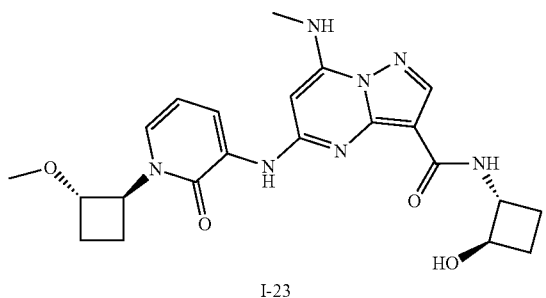

I-23

Step 1—Synthesis of Compound 16: Compound was synthesized as per experimental protocol of I-20 (Example 15).

Step 2—Synthesis of Compound I-22 and I-23: Isomers of 16 (0.095 g) were separated out using column CHIRALPAK OX-H (250 mm×4.6 mm, 5 μm) 0.1% DEA_HEX_IPA-ACN (70-30) to get pure fraction-1 (FR-a) and fraction-2 (FR-b).

FR-a was concentrated under reduced pressure at 30° C. to afford pure I-22 (0.028 g; MS (ES): m/z 454.2 [M+H]$^+$; LCMS purity: 100%; HPLC purity: 98.77%; CHIRAL HPLC purity: 99.00%; $^1$H NMR (DMSO-d6, 400 MHZ): 8.96 (s, 1H), 8.26-8.24 (d, J=7.2 Hz, 1H), 8.20 (s, 1H), 8.03-8.01 (d, J=8.8 Hz, 1H), 7.94-7.93 (d, J=4.4 Hz, 1H), 7.60-7.58 (d, J=6.8 Hz, 1H), 6.40-6.37 (t, J=6.8 Hz, 1H), 6.24 (s, 1H), 5.46-5.44 (m, 1H), 5.21-5.14 (m, 1H), 4.25-4.18 (m, 2H), 3.86 (bs, 1H), 3.17 (s, 3H), 2.92-2.90 (d, J=4.8 Hz, 3H), 1.69-1.62 (m, 2H), 1.24 (bs, 6H)).

FR-b was concentrated under reduced pressure at 30° C. to afford pure I-23 (0.032 g; MS (ES): m/z 454.2 [M+H]$^+$; LCMS purity: 99.00%; HPLC purity: 96.20%; CHIRAL HPLC purity: 99.00%; $^1$H NMR (DMSO-d$_6$, 400 MHZ) 8.95 (s, 1H), 8.25-8.23 (d, J=7.2 Hz, 1H), 8.20 (s, 1H), 8.03-8.01 (d, J=8.8 Hz, 1H), 7.94-7.93 (d, J=4.4 Hz, 1H), 7.60-7.58 (d, J=6.8 Hz, 1H), 6.40-6.37 (t, J=6.8 Hz, 1H), 6.24 (s, 1H), 5.46-5.44 (m, 1H), 5.21-5.14 (m, 1H), 4.25-4.18 (m, 2H), 3.86 (bs, 1H), 3.17 (s, 3H), 2.92-2.90 (d, J=4.8 Hz, 3H), 1.69-1.62 (m, 2H), 1.23 s (bs, 6H)).

Example 17: 5-((1-((1R,5S,6r)-3-Oxabicyclo[3.1.0]hexan-6-yl)-2-oxo-1,2-dihydropyridin-3-yl)amino)-N-(2-methoxycyclopropyl)-7-(methylamino)pyrazolo[1,5-a]pyrimidine-3-carboxamide (I-24)

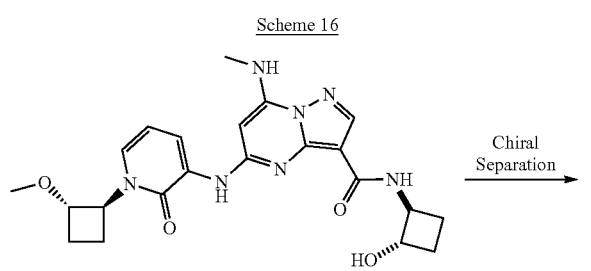

I-22

Scheme 16

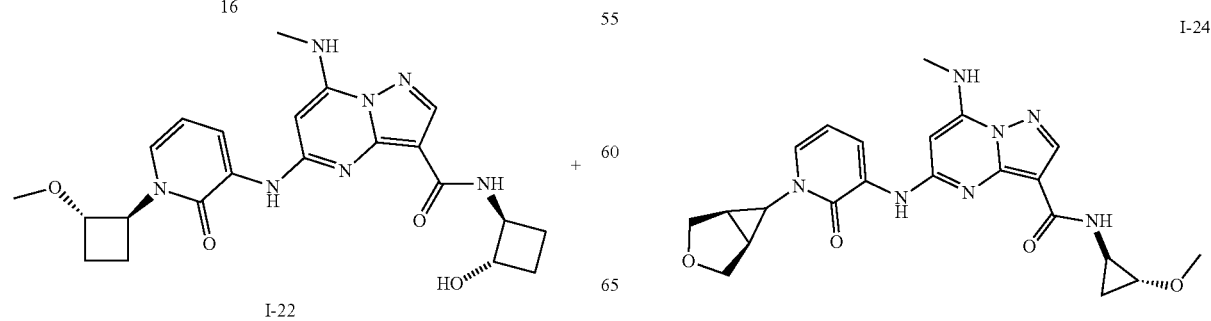

Scheme 17

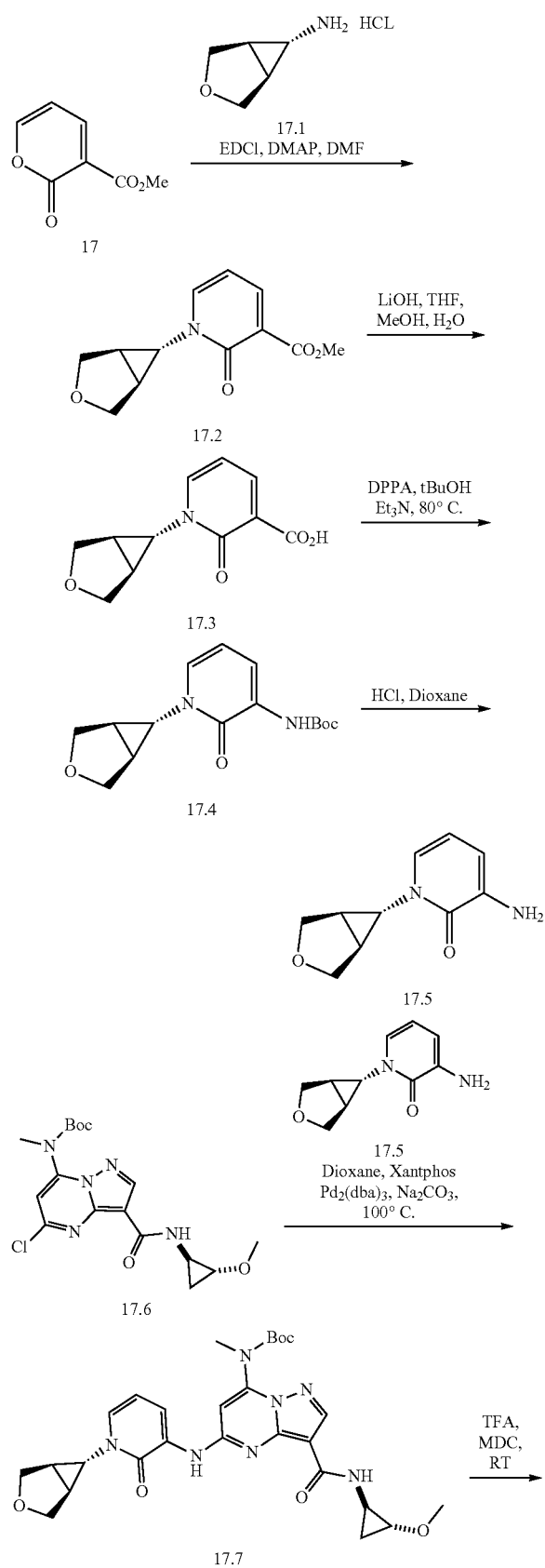

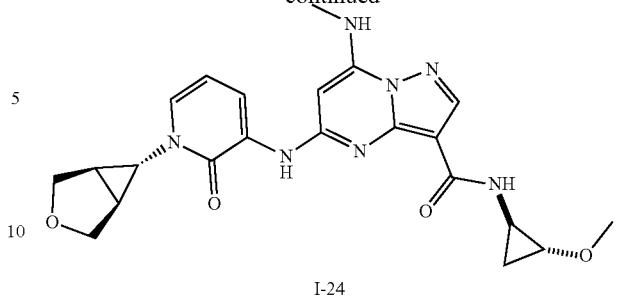

I-24

Step 1—Synthesis of Compound 17.2: To a solution of 17 (0.250 g, 1.62 mmol, 1.0 eq) in N,N-dimethylformamide (12 mL) was added 17.1 (0.218 g, 1.62 mmol, 1.0 eq). The reaction mixture was stirred at room temperature for 1 h followed by addition of N-Ethyl-N'-(3-dimethylaminopropyl) carbodiimide hydrochloride (0.402 g, 2.10 mmol, 1.3 eq) and 4-dimethylaminopryidine (0.049 g, 0.405 mmol, 0.25 eq). The reaction was stirred at room temperature for 16 h. After completion of reaction, reaction mixture was transferred into ice cold water and product was extracted with ethyl acetate. Organic layer was combined, washed with brine solution, dried over sodium sulphate and concentrated under reduced pressure to obtain crude material. This was further purified by combi flash using 30% ethyl acetate in hexane as eluant to 17.2 (0.180 g, Yield: 47.17%; MS (ES): m/z 236.24 [M+H]$^+$).

Step 2—Synthesis of Compound 17.3: To a solution of 17.2 (0.180 g, 0.765 mmol, 1.0 eq), in tetrahydrofuran:methanol:water (5 mL, 1:1:1) was added lithium hydroxide (0.160 g, 3.82 mmol, 5.0 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 17.3 (0.140 g, Yield: 82.71%; MS (ES): m/z 222.07 [M+H]$^+$).

Step 3—Synthesis of Compound 17.4. To a solution of 17.3 (0.140 g, 0.632 mmol, 1.0 eq) in tert-Butyl alcohol was added diphenylphosphorylazide (0.226 g, 0.821 mmol, 1.3 eq), triethylamine (0.108 g, 1.074 mmol, 1.7 eq). The reaction was stirred at 90° C. for 16 h. After completion of reaction, reaction mixture was concentrated under reduced pressure to obtain crude material. This was further purified by combi flash using 1.0% MeOH in Dichloromethane as eluent to 17.4 (0.150 g, Yield: 81.08%; MS (ES): m/z 293.34 [M+H]$^+$).

Step 4—Synthesis of Compound 17.5: To 17.4 (0.150 g, 0.513 mmol, 1.0 eq) was added 4M hydrochloric acid in 1,4-Dioxane (7 mL) and stirred at room temperature for 4 h. After completion of reaction, reaction mixture was concentrated under reduced pressure, residue was triturated with diethyl ether to obtain 17.5 (0.090 g, Yield: 76.70%; MS (ES): m/z 229.68 [M+H]$^+$).

Step 5—Synthesis of Compound 17.6: Compound was synthesized from Core A utilizing general method A to obtain 17 (Yield: 56.13%; MS (ES): m/z 396.14 [M+H]$^+$).

Step 6—Synthesis of Compound 17.7: Compound was synthesized using general procedure B to obtain 17.7 (0.119 g, Yield: 56.93%; MS (ES): m/z 552.25 [M+H]$^+$).

Step 7—Synthesis of Compound I-24: Compound was synthesized using general procedure C to obtain I-24 (0.017 g, Yield: 69.23%; MS (ES): m/z 452.52 [M+H]$^+$; LCMS purity: 98.79%; HPLC purity: 99.36%; CHIRAL HPLC: 49.51%, 49.74%; $^1$H NMR (DMSO-d$_6$, 400 MHZ): 8.89 (s, 1H), 8.22 (s, 1H), 8.15-8.13 (d, J=7.2 Hz, 1H), 7.92-7.91 (d, J=4.8 Hz, 1H), 7.67-7.65 (d, J=6 Hz, 1H), 7.28-7.27 (d, J=6.8 Hz, 1H), 6.26-6.23 (t, J=7.2 Hz, 1H), 6.10 (s, 1H), 3.98 (s, 2H), 3.74-3.72 (d, J=8 Hz, 2H), 3.24 (bs, 3H), 3.14 (bs, 1H), 3.08-3.04 (m, 1H), 2.90-2.89 (d, J=4.8 Hz, 3H), 2.27 (bs, 2H). 2.22 (bs, 2H), 1.08-1.03 (m, 1H)).
Example 18: 5-((1-((1R,5S,6r)-3-Oxabicyclo[3.1.0]hexan-6-yl)-2-oxo-1,2-dihydropyridin-3-yl)amino)-N-((1R,2R)-2-methoxycyclopropyl)-7-(methylamino)pyrazolo[1,5-a]pyrimidine-3-carboxamide (I-25)
And
5-((1-((1R,5S,6r)-3-Oxabicyclo[3.1.0]hexan-6-yl)-2-oxo-1,2-dihydropyridin-3-yl)amino)-N-((1S,2S)-2-methoxycyclopropyl)-7-(methylamino)pyrazolo[1,5-a]pyrimidine-3-carboxamide
I-25
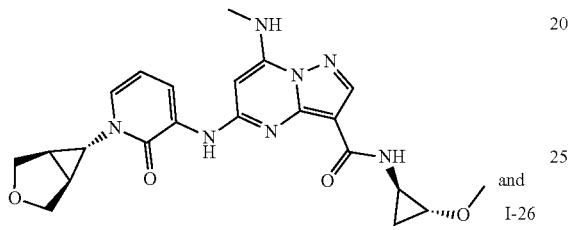
and
I-26
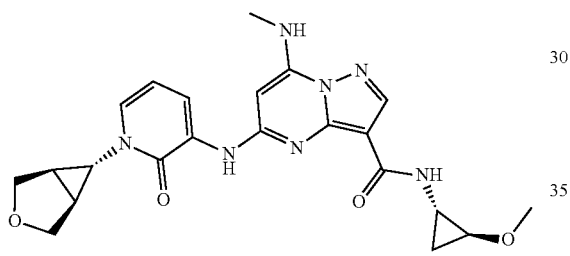
Scheme 18
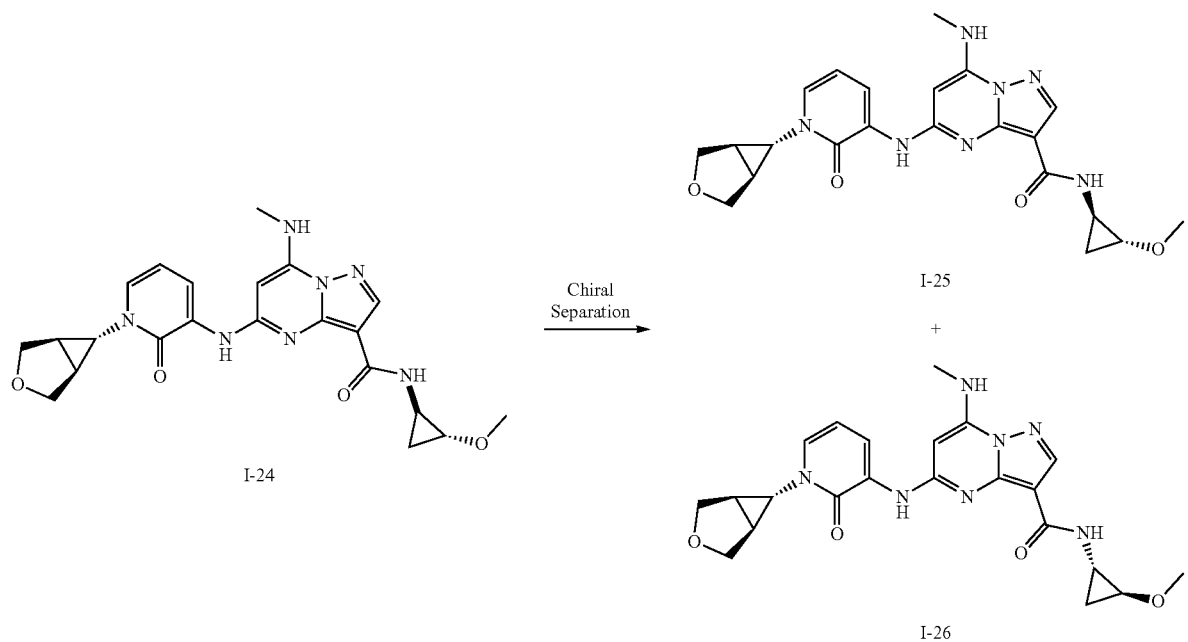

Synthesis of Compound I-25 and I-26: Isomers of I-24 (Example 17) (0.070 g) were separated out using column CHIRAL PAK OJ-H (250 mm×4.6 mm, 5 μm) 0.1% DEA in methanol to get pure fraction-1 (FR-a) and fraction-2 (FR-b).

FR-a was concentrated under reduced pressure at 30° C. to afford pure I-25 (0.025 g; MS (ES): m/z 452.87 [M+H]$^+$; LCMS purity: 96.75%; HPLC purity: 95.00%; CHIRAL HPLC purity: 95.02%; $^1$H NMR (DMSO-d$_6$, 400 MHZ): 8.89 (bs, 1H), 8.22 (s, 1H), 8.13-8.12 (d, J=7.2 Hz, 1H), 7.72-7.71 (d, J=6 Hz, 1H), 7.29-7.27 (d, J=6.8 Hz, 1H), 6.27-6.23 (t, J=7.2 Hz, 1H), 6.13 (s, 1H), 3.99 (s, 2H), 3.73-3.71 (d, J=8 Hz, 2H), 3.32 (bs, 1H), 3.23 (s, 3H), 3.11 (bs, 1H), 3.06-3.03 (m, 1H), 2.90-2.89 (d, J=4.8 Hz, 3H), 2.24 (bs, 2H), 2.22 (bs, 2H), 1.08-1.03 (m, 1H)).

FR-b was concentrated under reduced pressure at 30° C. to afford pure I-26 (0.025 g; MS (ES): m/z 452.87 [M+H]$^+$; LCMS purity: 97.55%; HPLC purity: 96.10%; CHIRAL HPLC purity: 99.65%; $^1$H NMR (DMSO-d$_6$, 400 MHZ): 8.89 (bs, 1H), 8.22 (s, 1H), 8.14-8.13 (d, J=7.2 Hz, 1H), 7.71-7.69 (d, J=6 Hz, 1H), 7.29-7.27 (d, J=6.8 Hz, 1H), 6.26-6.23 (t, J=7.2 Hz, 1H), 6.16 (s, 1H), 3.99 (s, 2H), 3.74-3.72 (d, J=8 Hz, 2H), 3.32 (bs, 1H), 3.24 (s, 3H), 3.12 (bs, 1H), 3.06-3.03 (m, 1H), 2.84-2.82 (d, J=8.4 Hz, 3H), 2.25 (bs, 2H), 2.22 (bs, 2H), 1.07-1.05 (m, 1H)).

Example 19: N-((1R,2R)-2-Methoxycyclopropyl)-7-(methylamino)-5-((2-oxo-1-(tetrahydro-2H-pyran-4-yl)-1,2-dihydropyridin-3-yl)amino)pyrazolo[1,5-a]pyrimidine-3-carboxamide (I-27)

And

N-((1S,2S)-2-Methoxycyclopropyl)-7-(methylamino)-5-((2-oxo-1-(tetrahydro-2H-pyran-4-yl)-1,2-dihydropyridin-3-yl)amino)pyrazolo[1,5-a]pyrimidine-3-carboxamide (I-28)

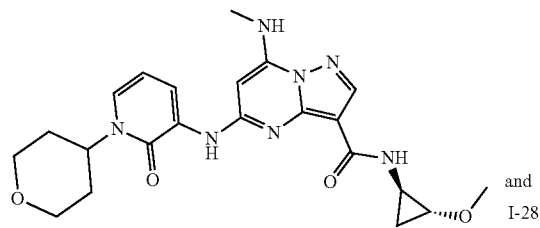

I-27

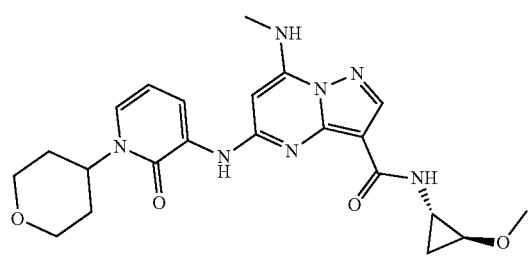

and I-28

Scheme 19

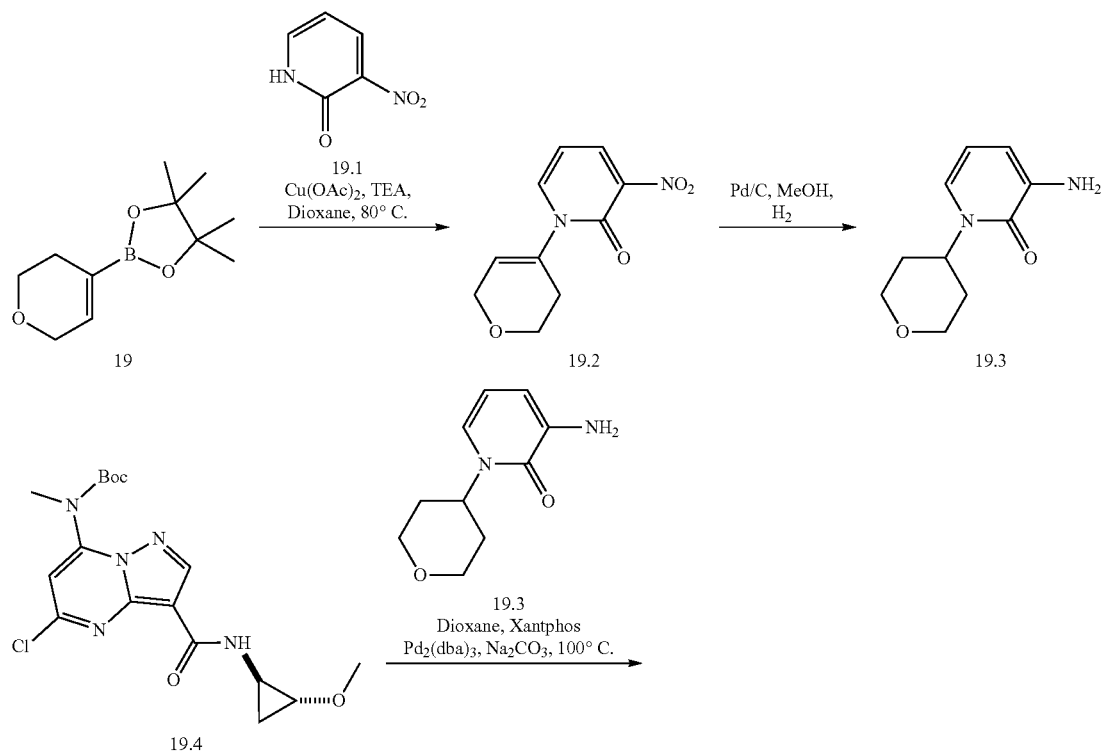

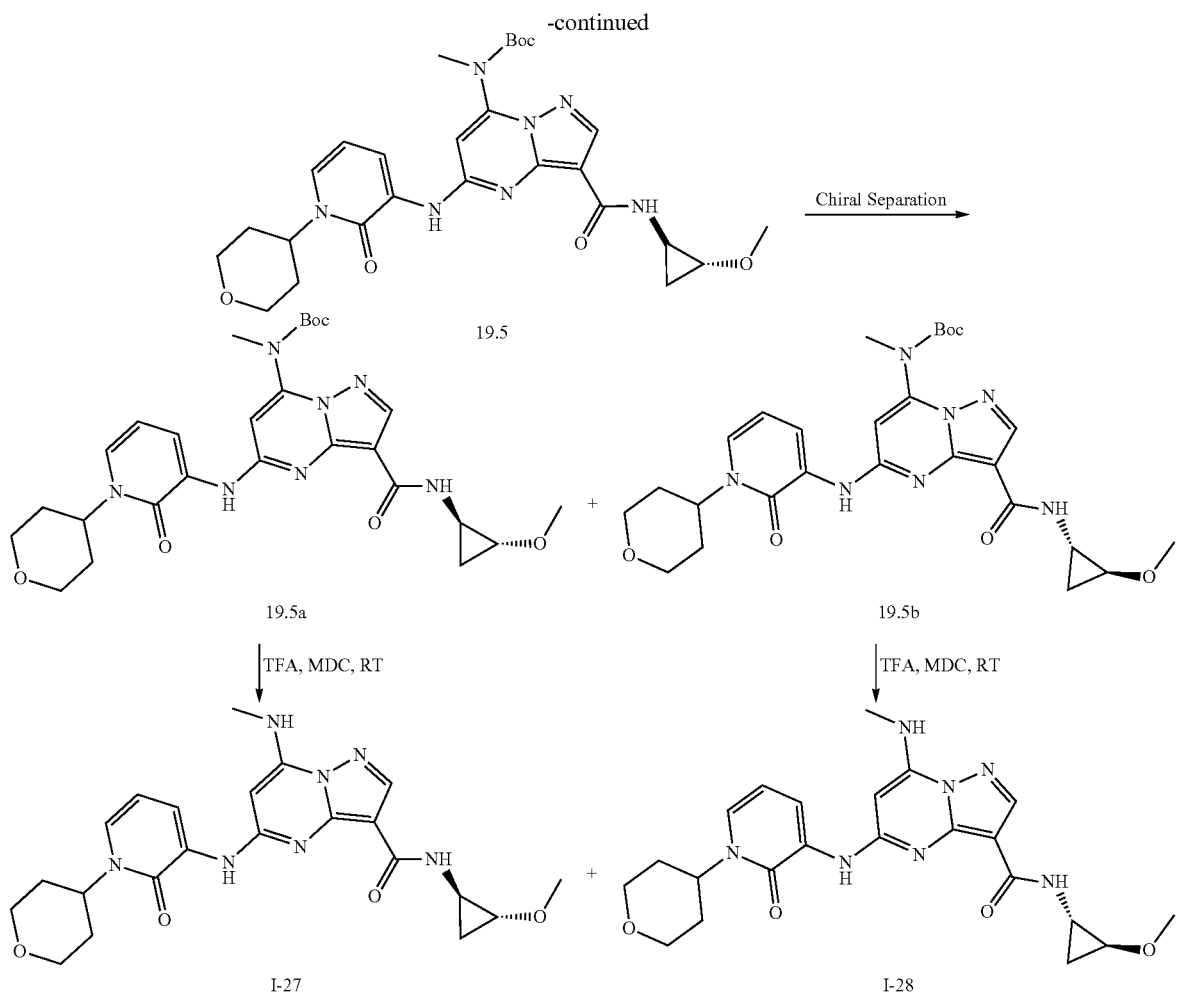

Step 1—Synthesis of Compound 19.2: To a solution of 19 (3 g, 14.28 mmol, 1.0 eq) and 19.1 (2.4 g, 17.14 mmol, 1.2 eq) in dioxane (30 mL) was added copper acetate (2.60 g, 14.28 mmol, 1.0 eq) and triethylamine (5.00 mL, 35.7 mmol, 2.5 eq) under nitrogen. The reaction was stirred at 80° C. for 5 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 10% ethyl acetate in hexane to obtain pure 19.2 (0.380 g, Yield: 11.98%; MS (ES): m/z 222.20 [M+H]$^+$).

Step 2—Synthesis of Compound 19.3: To a solution of 19.2 (0.380 g, 1.71 mmol, 1.0 eq) in methanol (4 ml), palladium on charcoal (0.100 g) was added. Hydrogen was purged through reaction mixture for 3 h at room temperature. After completion of reaction, reaction mixture was filtered through celite-bed and washed with methanol. Filtrate was concentrated under reduced pressure to obtain crude material. This was further purified by column chromatography and compound was eluted in 1.4% methanol in dichloromethane to obtain pure 19.3 (0.120 g, Yield: 36.13%; MS (ES): m/z 195.23 [M+H]$^+$).

Step 3—Synthesis of Compound 19.4: Compound was synthesized from Core A utilizing general method A to obtain 19.4.

Step 4—Synthesis of Compound 19.5: Compound was synthesized using general procedure B to obtain 19.5 (Yield: 64.35%; MS (ES): m/z 554.27 [M+H]$^+$).

Step 5—Synthesis of Compounds 19.5a and 19.5b: Isomers of 19.5 (0.105 g) were separated out using column CHIRALPAK AD-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 19.5a (0.045 g; MS (ES): m/z 554.27 [M+H]$^+$). FR-b was concentrated under reduced pressure at 30° C. to afford pure 19.5b (0.050 g; MS (ES): m/z 554.27 [M+H]$^+$).

Step 5—Synthesis of Compound I-27: Compound was synthesized using general procedure C to obtain I-27 (0.030 g, Yield: 81.38%; MS (ES): m/z 454.86 [M+H]$^+$; LCMS purity: 100%; HPLC purity: 97.87%; CHIRAL HPLC purity: 100%; $^1$H NMR (DMSO-d$_6$, 400 MHZ): 8.83 (s, 1H), 8.21 (bs, 1H), 8.16-8.14 (d, J=6.4 Hz, 1H), 7.91-7.90 (d, J=4.8 Hz, 1H), 7.67-7.66 (d, J=7.2 Hz, 1H), 7.46-7.45 (d, J=6.4 Hz, 1H), 6.31-6.28 (t, J=7.2 Hz, 1H), 6.22 (s, 1H), 5.03 (bs, 1H), 4.02 (bs, 2H), 3.53-3.47 (t, J=11.6 Hz, 2H), 3.24 (s, 3H), 3.07-3.06 (m, 1H), 2.90-2.89 (d, J=4.8 Hz, 3H), 1.97-1.91 (m, 2H), 1.76 (bs, 2H), 1.23 (s, 2H), 1.08-1.02 (m, 1H)).

Step 6—Synthesis of Compound I-28: Compound was synthesized using general procedure C to obtain I-28 (0.030 g, Yield: 73.25%; MS (ES): m/z 454.86 [M+H]$^+$; LCMS purity: 100%; HPLC purity: 98.96%; CHIRAL HPLC purity: 96.00%; $^1$H NMR (DMSO-d$_6$, 400 MHZ): 8.82 (s, 1H), 8.21 (bs, 1H), 8.16-8.14 (d, J=6.4 Hz, 1H), 7.91-7.89 (d, J=4.8 Hz, 1H), 7.67-7.66 (d, J=7.2 Hz, 1H), 7.46-7.44 (d, J=6.4 Hz, 1H), 6.31-6.28 (t, J=7.2 Hz, 1H), 6.22 (s, 1H), 5.03 (bs, 1H), 4.02 (bs, 2H), 3.53-3.47 (t, J=11.6 Hz, 2H), 3.24 (s, 3H), 3.07-3.06 (m, 1H), 2.90-2.89 (d, J=4.8 Hz, 3H), 1.97-1.91 (m, 2H), 1.76 (bs, 2H), 1.23 (s, 2H), 1.08-1.02 (m, 1H)).
Example 20: 5-((1-Isopropyl-2-oxo-1,2-dihydropyridin-3-yl)amino)-N-((1R,2R)-2-methoxycyclopropyl)-7-(methylamino)pyrazolo[1,5-a]pyrimidine-3-carboxamide (I-29)
And
5-((1-Isopropyl-2-oxo-1,2-dihydropyridin-3-yl)amino)-N-((1S,2S)-2-methoxycyclopropyl)-7-(methylamino)pyrazolo[1,5-a]pyrimidine-3-carboxamide (I-30)
I-29
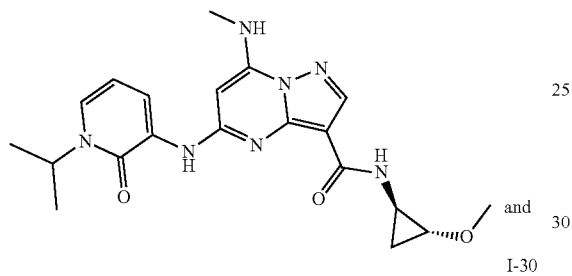
and
I-30
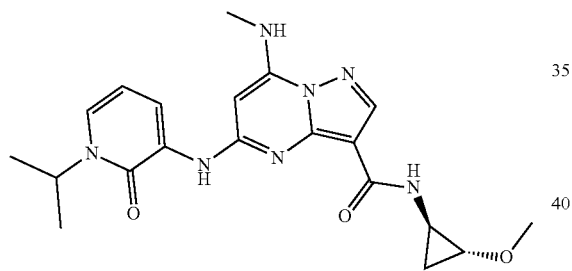
Scheme 20
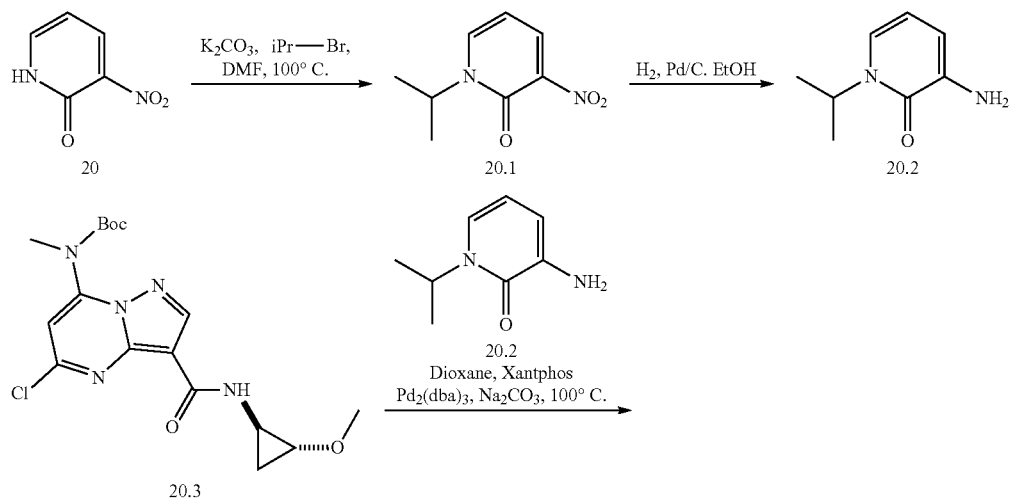

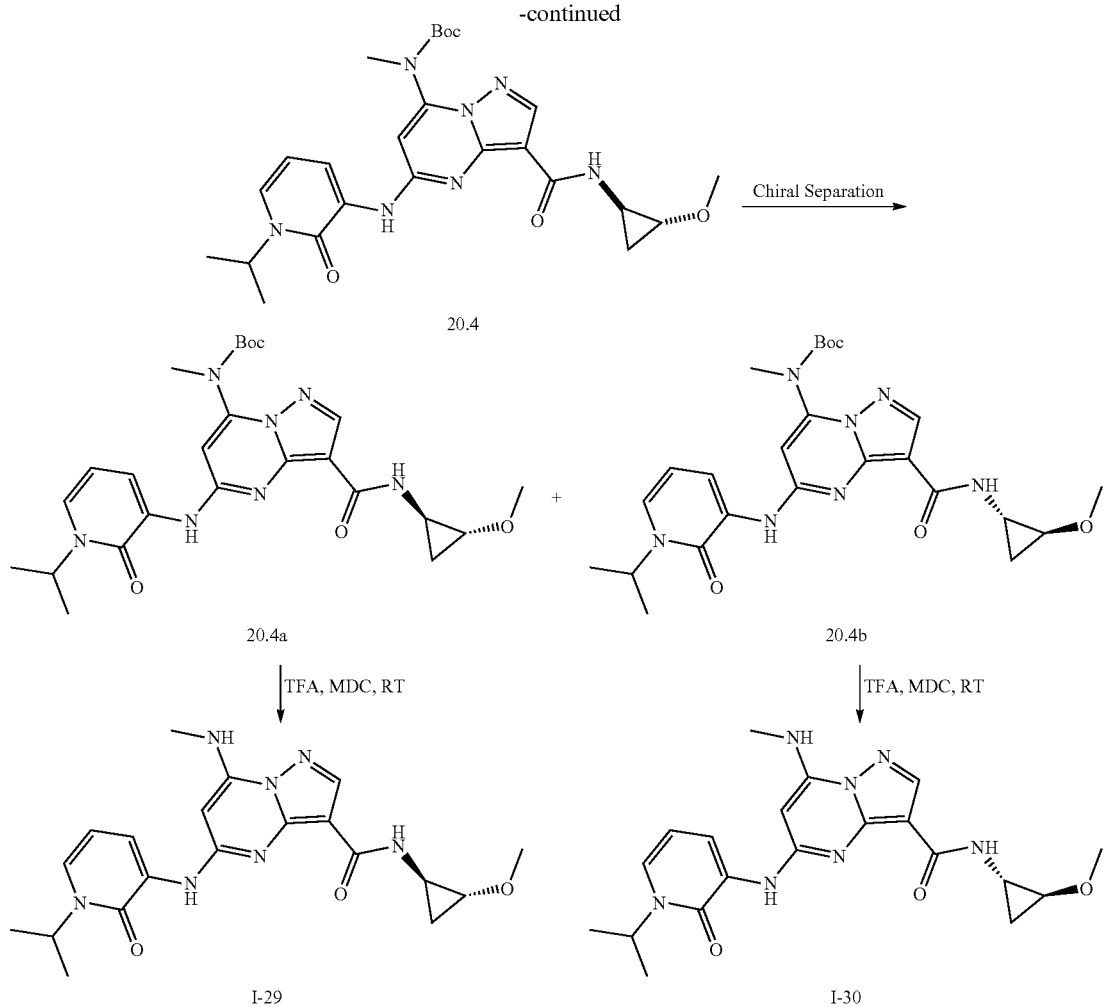

Step 1—Synthesis of Compound 20.1: To a solution of 20 (1 g, 7.14 mmol, 1.0 eq) in dimethylformamide (10 mL), 2-propyl bromide (1.3 g, 10.71 mmol, 1.5 eq) was added. The reaction mixture was degassed for 10 min under argon atmosphere followed by addition of potassium carbonate (2.9 g, 21.42 mmol, 3.0 eq). The reaction mixture was heated at 100° C. for 10 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 20.1 (0.320 g, Yield: 24.61%; MS (ES): m/z 183.07 [M+H]$^+$).

Step 2—Synthesis of Compound 20.2: To a solution of 20.1 (0.32 g, 1.75 mmol, 1.0 eq) in ethanol (7 ml), palladium on charcoal (0.16 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 20.2 (0.220 g, Yield: 82.29%; MS (ES): m/z 153.10 [M+H]$^+$).

Step 3—Synthesis of Compound 20.3: Compound was synthesized from Core A utilizing general method A to obtain 20.3.

Step 4—Synthesis of Compound 20.4: Compound was synthesized using general procedure B to obtain 20.4 (Yield: 72.22%; MS (ES): m/z 512.26 [M+H]$^+$).

Step 5—Synthesis of Compounds 20.4a and 20.4b: Isomers of 20.4 (0.110 g) were separated out using column CHIRALCEL OJ-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 20.4a (0.045 g; MS (ES): m/z 512.26 [M+H]$^+$). FR-b was concentrated under reduced pressure at 30° C. to afford pure 20.4b (0.040 g; MS (ES): m/z 512.26 [M+H]$^+$).

Step 6—Synthesis of Compound I-29: Compound was synthesized using general procedure C to obtain I-29 (0.030 g, Yield: 82.89%; MS (ES): m/z 412.37 [M+H]$^+$; LCMS purity: 100%; HPLC purity: 99.51%; CHIRAL HPLC purity: 100%; $^1$H NMR (DMSO-d$_6$, 400 MHZ): 8.86 (s, 1H), 8.23 (bs, 1H), 8.17-8.15 (d, J=7.2 Hz, 1H), 7.92-7.91 (d, J=4.8 Hz, 1H), 7.70-7.68 (d, J=7.2 Hz, 1H), 7.44-7.42 (d, J=6.4 Hz, 1H), 6.33-6.30 (t, J=7.2 Hz, 1H), 6.24 (s, 1H), 5.22-5.15 (m, 1H), 3.26 (s, 3H), 3.09-3.04 (m, 1H), 2.92-2.91 (d, J=4.8 Hz, 3H), 1.37-1.35 (d, J=6.8 Hz, 6H), 1.10-1.04 (m, 1H), 0.53 (bs, 2H)).

Step 7—Synthesis of Compound I-30: Compound was synthesized using general procedure C to obtain I-30 (0.028 g, 87.03%; MS (ES): m/z 412.42 [M+H]$^+$; LCMS purity:

97.73%; HPLC purity: 98.62%; CHIRAL HPLC purity: 100%; $^1$H NMR (DMSO-$d_6$, 400 MHZ): 8.86 (s, 1H), 8.23 (bs, 1H), 8.16-8.15 (d, J=7.2 Hz, 1H), 7.92-7.91 (d, J=4.8 Hz, 1H), 7.69-7.68 (d, J=7.2 Hz, 1H), 7.44-7.42 (d, J=6.4 Hz, 1H), 6.33-6.30 (t, J=7.2 Hz, 1H), 6.24 (s, 1H), 5.21-5.15 (m, 1H), 3.26 (s, 3H), 3.09-3.04 (m, 1H), 2.92-2.90 (d, J=4.8 Hz, 3H), 1.36-1.35 (d, J=6.8 Hz, 6H), 1.09-1.04 (m, 1H), 0.52 (bs, 2H)).

Example 21: 5-((1-((1r,4R)-4-Methoxycyclohexyl)-2-oxo-1,2-dihydropyridin-3-yl)amino)-N-((1R,2R)-2-methoxycyclopropyl)-7-(methylamino)pyrazolo[1,5-a]pyrimidine-3-carboxamide (I-31)

And 5-((1-((1r,4S)-4-Methoxycyclohexyl)-2-oxo-1,2-dihydropyridin-3-yl)amino)-N-((1S,2S)-2-methoxycyclopropyl)-7-(methylamino)pyrazolo[1,5-a]pyrimidine-3-carboxamide (I-32)

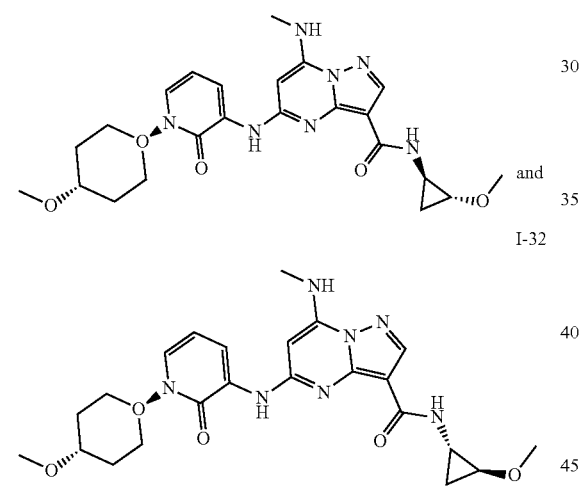

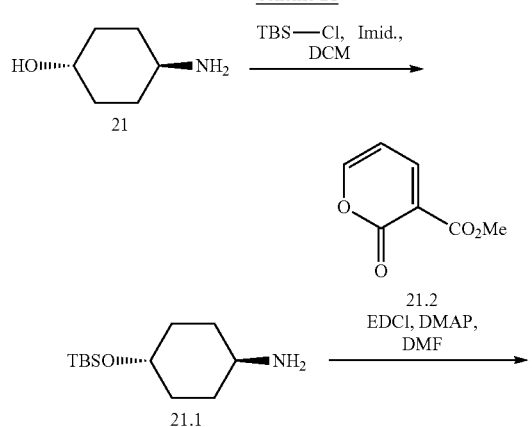

Scheme 21

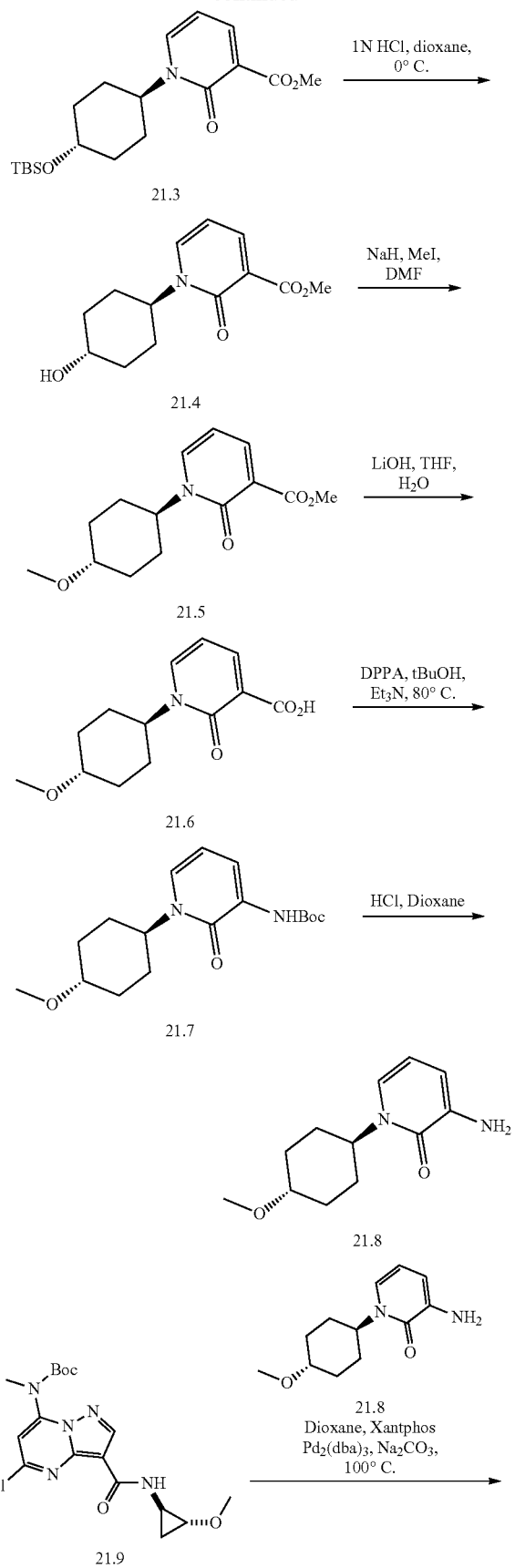

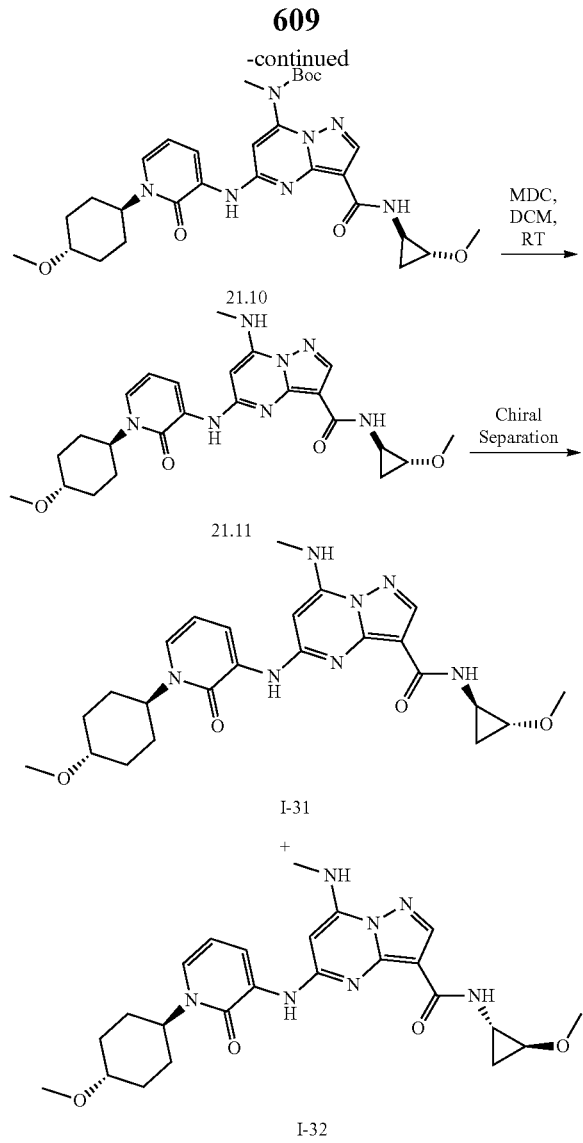

Step 1—Synthesis of Compound 21.1: To a solution of 21 (4 g, 34.73 mmol, 1.0 eq) in dichloromethane (40 mL), imidazole (7 g, 104.19 mmol, 3.0 eq), tert-butyldimethylsilyl chloride (7.8 g, 52.09 mmol, 1.5 eq) was added at 0° C. The reaction mixture was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% methanol in dichloromethane as eluant to 21.1 (5.2 g, Yield: 65.26%; MS (ES): m/z 230.44 [M+H]$^+$).

Step 2—Synthesis of Compound 21.3: To a solution of 21.1 (5.2 g, 22.66 mmol, 1.0 eq) in dimethylformamide (50 mL) was added 21.2 (3.4 g, 22.66 mmol, 1.0 eq). The reaction mixture was stirred at room temperature for 1 h followed by addition of N-Ethyl-N'-(3-dimethylaminopropyl) carbodiimidehydrochloride (6.5 g, 33.99 mol, 1.5 eq) and 4-dimethylaminopryidine (0.69 g, 5.66 mmol, 0.25 eq). The reaction mixture was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 30% ethylacetate in hexane as eluant to 21.3 (1.8 g, Yield: 21.73%; MS (ES): m/z 366.55 [M+H]$^+$).

Step 3—Synthesis of Compound 21.4: To 21.3 (1.8 g, 4.92 mmol, 1.0 eq) added hydrochloric acid in 1,4-dioxane (10 mL). The reaction mixture was stirred at room temperature for 1 h. After completion of reaction, reaction mixture was concentrated under reduced pressure to obtain residue which was stirred with diethyl ether and filtered to obtain pure 21.4 (1.2 g, Yield: 96.98%; MS (ES): m/z 252.28 [M+H]$^+$).

Step 4—Synthesis of Compound 21.5: To a solution of 21.4 (1.2 g, 4.78 mmol, 1.0 eq) in tetrahydrofuran (10 mL), sodium hydride (0.10 g, 7.17 mmol, 1.5 eq), was added 0° C. followed by addition of methyl iodide (0.67 g, 4.78 mmol, 1.0 eq). The reaction mixture was stirred at room temperature for 16 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 1.4% methanol in dichloromethane as eluant to 21.5 (0.78 g, Yield: 61.56%; MS (ES): m/z 266.31 [M+H]$^+$).

Step 5—Synthesis of Compound 21.6: To a solution of 21.5 (0.78 g, 2.94 mmol, 1.0 eq), in tetrahydrofuran:methanol:water (5 mL, 1:1:1) was added lithium hydroxide (1.2 g, 29.4 mmol, 10 eq). The reaction was stirred at 70° C. for 3 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain 21.6 (0.65 g, Yield: 87.99%; MS (ES): m/z: 252.28 [M+H]$^+$).

Step 6—Synthesis of Compound 21.7: To a solution of 21.6 (0.65 g, 2.59 mmol, 1.0 eq) in tert-butanol (6 mL) was added diphenylphosphorylazide (1.1 g, 4.14 mmol, 1.6 eq), trimethylamine (10 mL, 7.7 mmol, 3.0 eq). The reaction mixture was heated at 80° C. for 18 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by combi flash using 5% ethyl acetate in hexane as eluant to 21.7 (0.38 g, Yield: 45.56%; MS (ES): m/z 323.41 [M+H]$^+$).

Step 7—Synthesis of Compound 21.8: To 21.7 (0.38 g, 1.18 mmol, 1.0 eq) added hydrochloric acid in 1,4-dioxane (1 mL). The reaction mixture was stirred at room temperature for 1 h. After completion of reaction, reaction mixture was concentrated under reduced pressure to obtain residue which was stirred with diethyl ether and filtered to obtain pure 21.8 (0.20 g, Yield: 76.34%; MS (ES): m/z 223.29 [M+H]$^+$).

Step 8—Synthesis of Compound 21.9: Compound was synthesized from Core A utilizing general method A to obtain 21.9.

Step 9—Synthesis of Compound 21.10: Compound was synthesized using general procedure B to obtain 21.10.

Step 10—Synthesis of Compound 21.11: Compound was synthesized using general procedure C to obtain 21.11.

Step 11—Synthesis of Compound I-31 and I-32: Isomers of 21.11 (0.1 g) were separated out using column CHIRAL PAK AD-H (250 mm×4.6 mm, 5 μm) and 0.1% DEA in HEX_IPA-MEOH (50-50) as co-solvent with flow rate of 4 mL/min to get pure fraction-1 (FR-a) and fraction-2 (FR-b).

FR-a was concentrated under reduced pressure at 30° C. to afford pure I-31 (0.031 g; MS (ES): m/z 482.92 [M+H]+; LCMS purity: 99.74%; HPLC purity: 97.51%; CHIRAL HPLC purity: 100%; ¹H NMR (DMSO-d₆, 400 MHZ): 8.81 (s, 1H), 8.22 (s, 1H), 8.15-8.13 (d, J=6.4 Hz, 1H), 7.92-7.90 (d, J=4.8 Hz, 1H), 7.68-7.66 (d, J=7.2 Hz, 1H), 7.41-7.39 (d, J=6 Hz, 1H), 6.30-6.26 (t, J=7.2 Hz, 1H), 6.22 (s, 1H), 4.79 (bs, 1H), 3.27 (s, 3H), 3.24 (s, 3H), 3.09-3.03 (m, 1H), 2.91-2.90 (d, J=4.8 Hz, 3H), 2.16 (bs, 2H), 1.80 (bs, 3H), 1.76 (bs, 3H), 1.23 (bs, 3H), 1.09-1.02 (m, 1H)).

FR-b was concentrated under reduced pressure at 30° C. to afford pure I-32 (0.030 g; MS (ES): m/z 482.92 [M+H]+; LCMS purity: 99.49%; HPLC purity: 97.02%; CHIRAL HPLC purity: 100%; H NMR (DMSO-d₆, 400 MHZ): 8.82 (s, 1H), 8.22 (s, 1H), 8.14-8.12 (d, J=6.4 Hz, 1H), 7.92-7.90 (d, J=4.8 Hz, 1H), 7.67-7.65 (d, J=7.2 Hz, 1H), 7.41-7.39 (d, J=6 Hz, 1H), 6.30-6.26 (t, J=7.2 Hz, 1H), 6.23 (s, 1H), 4.79 (bs, 1H), 3.27 (s, 3H), 3.24 (s, 3H), 3.09-3.03 (m, 1H), 2.91-2.90 (d, J=4.8 Hz, 3H), 2.16 (bs, 2H), 1.80 (bs, 3H), 1.76 (bs, 3H), 1.24 (bs, 3H), 1.08-1.02 (m, 1H)).

Example 22: 5-((1-(3,3-Difluorocyclobutyl)-2-oxo-1,2-dihydropyridin-3-yl)amino)-N-((trans-1,2)-2-methoxycyclopropyl)-7-(methylamino)pyrazolo[1,5-a]pyrimidine-3-carboxamide (I-33)

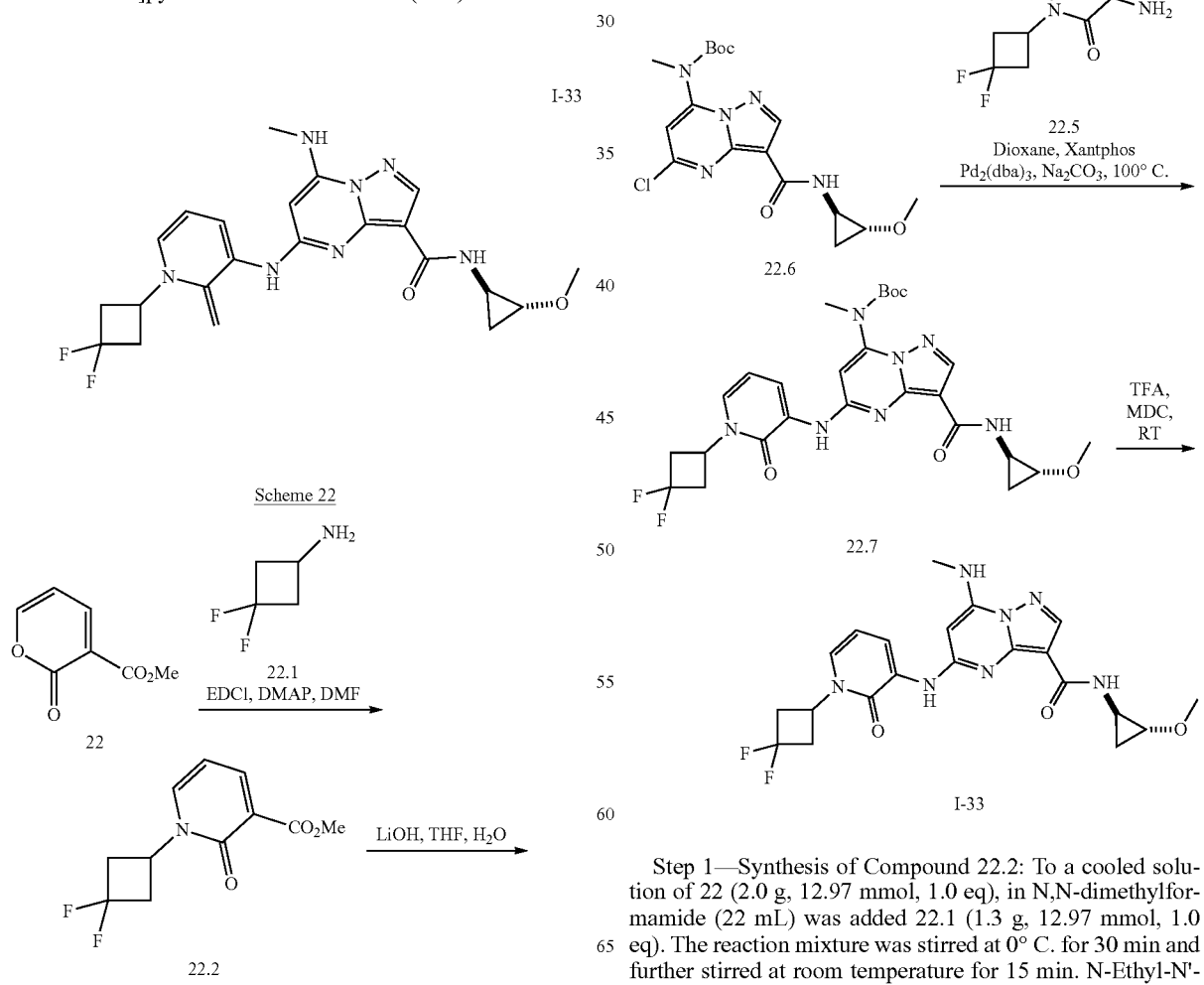

Step 1—Synthesis of Compound 22.2: To a cooled solution of 22 (2.0 g, 12.97 mmol, 1.0 eq), in N,N-dimethylformamide (22 mL) was added 22.1 (1.3 g, 12.97 mmol, 1.0 eq). The reaction mixture was stirred at 0° C. for 30 min and further stirred at room temperature for 15 min. N-Ethyl-N'-(3-dimethylaminopropyl)carbodiimide hydrochloride (2.6 g, 16.86 mmol, 1.3 eq) and 4-Dimethylaminopyridine (0.316 g, 2.59 mmol, 0.2 eq) was added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 22.2 (1.8 g, Yield: 57.03%; MS (ES): m/z 244.07 [M+H]$^+$).

Step 2—Synthesis of Compound 22.3: To a solution of 22.2 (1.8 g, 7.40 mmol, 1.0 eq), in tetrahydrofuran:water (20 mL, 2:1) was added lithium hydroxide (1.7 g, 74.5 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 22.3 (1.4 g, Yield: 82.54%; MS (ES): m/z 230.06 [M+H]$^+$).

Step 3—Synthesis of Compound 22.4: To a solution of 22.3 (1.4 g, 6.10 mmol, 1.0 eq) in tert-butanol (14 mL) was added triethylamine (1.0 g, 10.37 mmol, 1.7 eq) and diphenyl phosphoryl azide (2.1 g, 7.93 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 22.4 (1.1 g, Yield: 59.96%; MS (ES): m/z 301.13 [M+H]$^+$).

Step 4—Synthesis of Compound 22.5: A cooled solution of 22.4 (1.1 g, 3.66 mmol, 1 eq) in dioxane (10 mL) was added 4N hydrochloric acid in dioxane (15 mL) as a dropwise. The reaction mixture was stirred at room temperature for 2 h. After completion of reaction, reaction mixture was concentrated under reduced pressure to obtain pure 22.5 (0.750 g, Yield: 99.55%; MS (ES): m/z 201.08 [M+HCl]).

Step 5—Synthesis of Compound 22.6: Compound was synthesized from Core A utilizing general method A to obtain 22.6 (Yield: 56.13%; MS (ES): m/z 396.14 [M+H]$^+$).

Step 6—Synthesis of Compound 22.7: Compound was synthesized using general procedure B to obtain 22.7 (0.150 g, Yield: 71.74%; MS (ES): 560.24 [M+H]$^+$).

Step 7—Synthesis of Compound I-33: Compound was synthesized using general procedure C to obtain I-33 (0.025 g, Yield: 76.12%; MS (ES): 461.01 [M+H]$^+$; LCMS purity: 100%; HPLC purity: 99.87%; CHIRAL HPLC: 49.24%, 50.75%; $^1$H NMR (DMSO-$d_6$, 400 MHZ): 8.93 (s, 1H), 8.23-8.22 (d, J=5.2 Hz, 1H), 8.20 (s, 1H), 7.94-7.93 (d, J=4.8 Hz, 1H), 7.68-7.66 (d, J=5.6 Hz, 1H), 7.43-7.42 (d, J=6.8 Hz, 1H), 6.35-6.31 (t, J=7.2 Hz, 1H), 6.25 (s, 1H), 4.92 (bs, 1H), 3.22 (bs, 3H), 3.15-3.08 (m, 4H), 2.91-2.90 (d, J=4.8 Hz, 3H), 1.24 (bs, 2H), 1.08-1.06 (d, J=8 Hz, 2H)).

Example 23: N-((1R,2R)-2-Methoxycyclopropyl)-5-((6'-methyl-2-oxo-2H-[1,3'-bipyridin]-3-yl)amino)-7-(methylamino)pyrazolo[1,5-a]pyrimidine-3-carboxamide (I-34)

And

N-((1S,2S)-2-Methoxycyclopropyl)-5-((6'-methyl-2-oxo-2H-[1,3'-bipyridin]-3-yl)amino)-7-(methylamino)pyrazolo[1,5-a]pyrimidine-3-carboxamide (I-35)

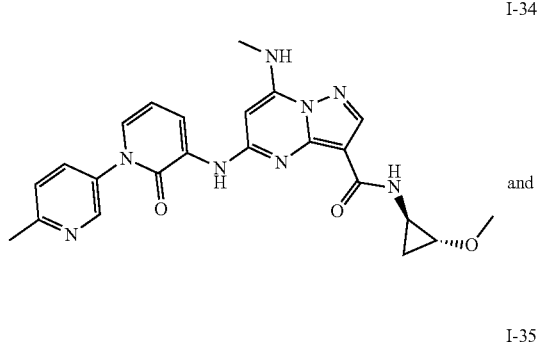

I-34

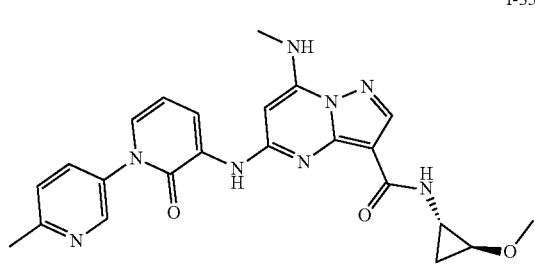

I-35

Scheme 23

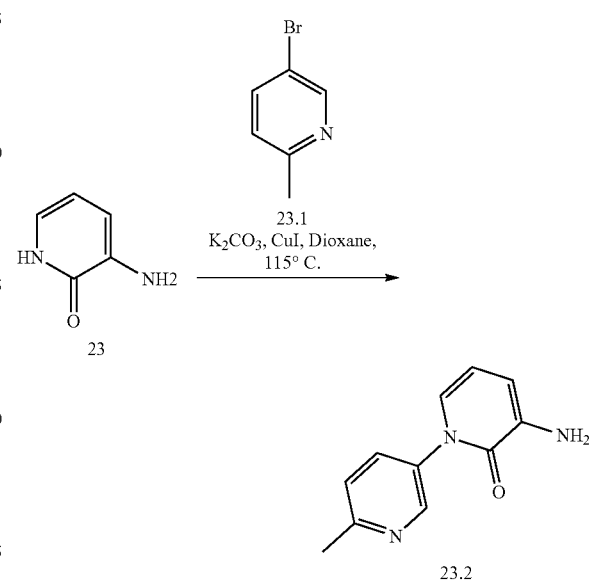

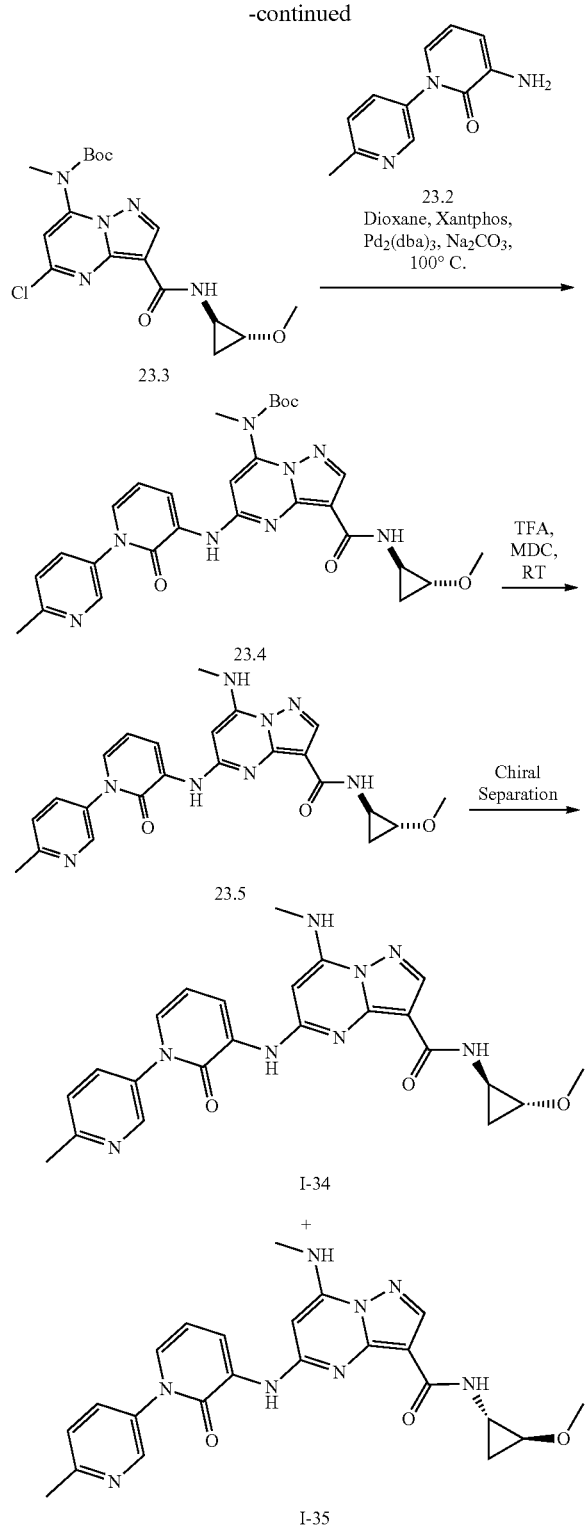

After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 23.2 (1.56 g, Yield: 44.45%; MS (ES): m/z 202.09 [M+H]$^+$).

Step 2—Synthesis of Compound 23.3: Compound was synthesized from Core A utilizing general method A to obtain 23.3.

Step 3—Synthesis of Compound 23.4: Compound was synthesized using general procedure B to obtain 23.4.

Step 4—Synthesis of Compound 23.5: Compound was synthesized using general procedure C to obtain 23.5.

Step 5—Synthesis of Compounds I-34 and I-35: Isomers of 23.5 (0.1 g) were separated out using column CHIRAL PAK AD-H (250 mm×4.6 mm, 5 μm) and 0.1% DEA in HEX_IPA-MEOH (50-50) as co-solvent with flow rate of 4 mL/min to get pure fraction-1 (FR-a) and fraction-2 (FR-b).

FR-a was concentrated under reduced pressure at 30° C. to afford pure I-34 (0.032 g; MS (ES): m/z 461.20 [M+H]$^+$; LCMS purity: 100%; HPLC purity: 99.23% CHIRAL HPLC purity: 98.00%; $^1$H NMR (DMSO-d$_6$, 400 MHZ): 8.95 (s, 1H), 8.58-8.57 (d, J=2.4 Hz, 1H), 8.30-8.28 (d, J=7.2 Hz, 1H), 7.24 (s, 1H), 7.95-7.94 (d, J=4.8 Hz, 1H), 7.88-7.87 (d, J=2.4 Hz, 1H), 7.71-7.69 (d, J=6 Hz, 1H), 7.46-7.44 (d, J=8.4 Hz, 1H), 7.38-7.37 (d, J=6.8 Hz, 1H), 6.40-6.36 (t, J=7.2 Hz, 1H), 6.26 (s, 1H), 3.28 (s, 3H), 3.10-3.07 (m, 1H), 2.90-2.89 (d, J=4.8 Hz, 3H), 2.56 (s, 3H), 2.50 (s, 3H)).

FR-b was concentrated under reduced pressure at 30° C. to afford pure I-35 (0.032 g; MS (ES): m/z 461.20 [M+H]$^+$; LCMS purity: 99.49%; HPLC purity: 98.10%; CHIRAL HPLC purity: 98.00%; $^1$H NMR (DMSO-d$_6$, 400 MHZ): 8.94 (s, 1H), 8.58-8.57 (d, J=2.4 Hz, 1H), 8.30-8.28 (d, J=7.2 Hz, 1H), 7.24 (s, 1H), 7.95-7.94 (d, J=4.8 Hz, 1H), 7.87-7.86 (d, J=2.4 Hz, 1H), 7.70-7.68 (d, J=6 Hz, 1H), 7.46-7.44 (d, J=8.4 Hz, 1H), 7.38-7.37 (d, J=6.8 Hz, 1H), 6.39-6.35 (t, J=7.2 Hz, 1H), 6.26 (s, 1H), 3.28 (s, 3H), 3.10-3.07 (m, 1H), 2.90-2.89 (d, J=4.8 Hz, 3H), 2.57 (s, 3H), 2.50 (s, 3H)).

Example 24: 5-((1-(3,3-Difluorocyclobutyl)-2-oxo-1,2-dihydropyridin-3-yl)amino)-N-((1R,3S)-3-hydroxycyclopentyl)-7-(methylamino)pyrazolo[1,5-a]pyrimidine-3-carboxamide (I-36)

And 5-((1-(3,3-Difluorocyclobutyl)-2-oxo-1,2-dihydropyridin-3-yl)amino)-N-((1S,3R)-3-hydroxycyclopentyl)-7-(methylamino)pyrazolo[1,5-a]pyrimidine-3-carboxamide (I-37)

Step 1—Synthesis of Compound 23.2: To a solution of 23 (3.0 g, 17.44 mmol, 1 eq) in 1,4-dioxane (150 mL), 23.1 (2.30 g, 20.92 mmol, 1.2 eq) was added. The reaction mixture was degassed for 10 min under argon atmosphere followed by addition of potassium carbonate (6.0 g, 43.6 mmol, 2.5 eq), N,N-dimethylethylenediamine (0.384 g, 4.36 mmol, 0.25 eq), and copper iodide (0.497 g, 2.61 mmol, 0.15 eq). The reaction mixture was heated at 115° C. for 12 h.

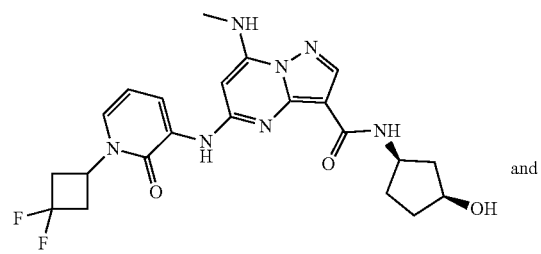

I-36 and

-continued
I-37
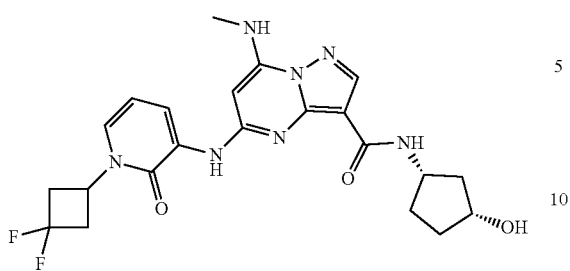
Scheme 24
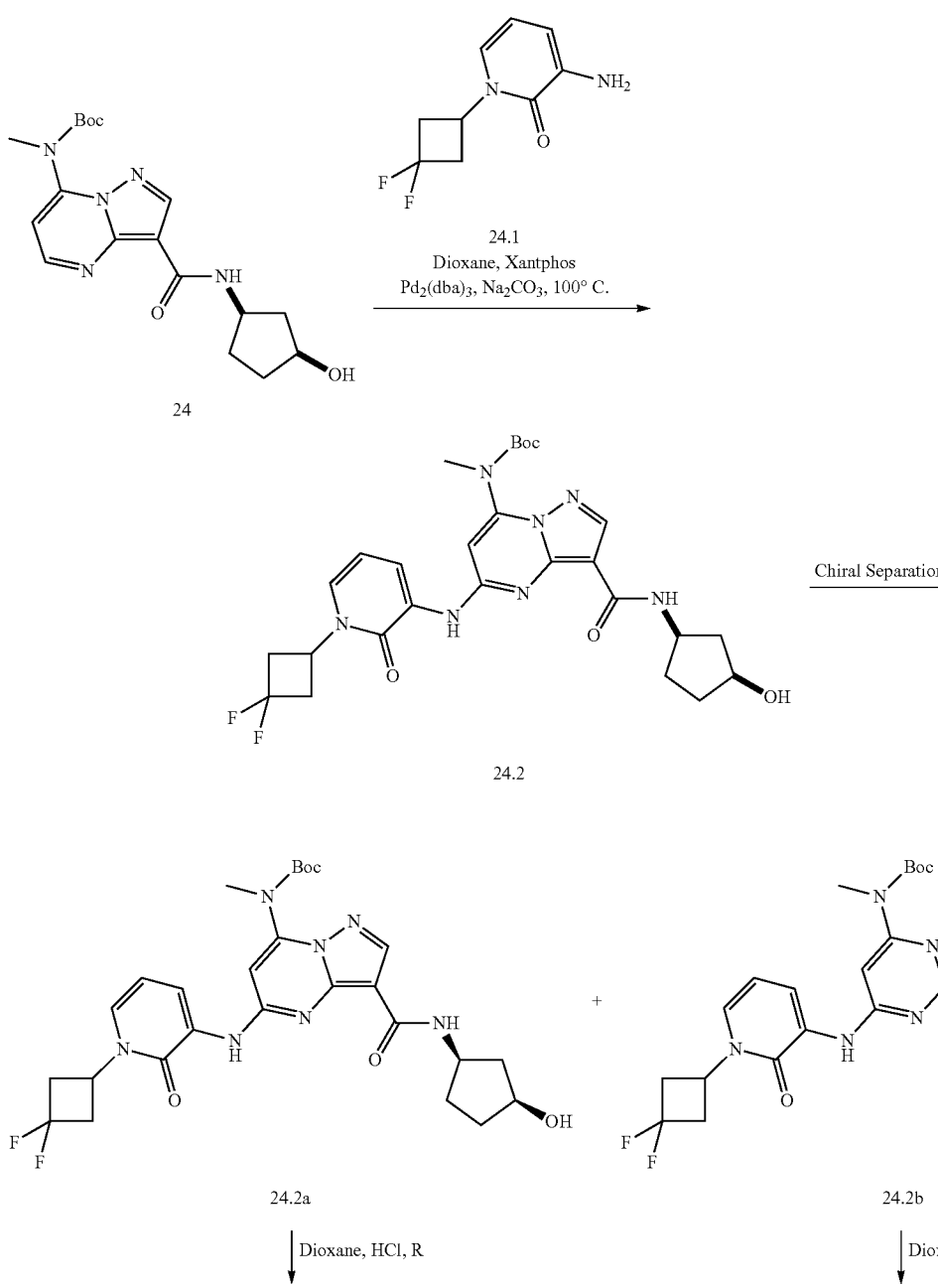

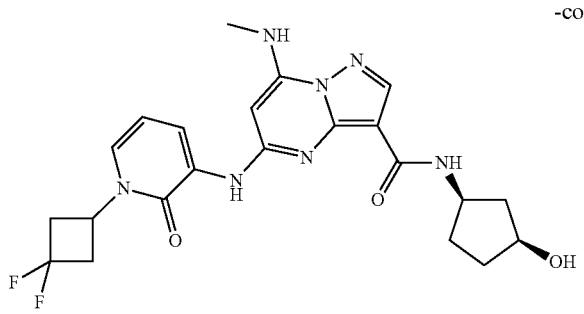

I-36

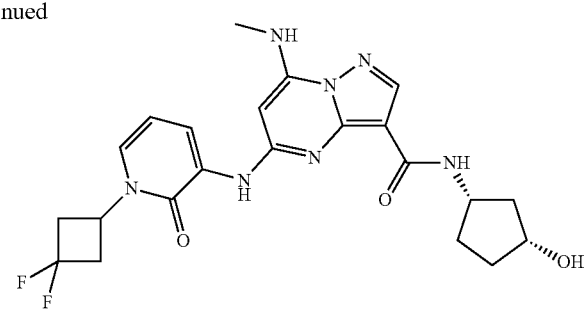

I-37

Step 1—Synthesis of Compound 24: Compound was synthesized from Core A utilizing general method A to obtain 24.

Step 2—Synthesis of Compound 24.1: Compound was synthesized as per experimental protocol of I-33 (Example 22) to obtain 24.1.

Step 3—Synthesis of Compound 24.2: Compound was synthesized using general procedure B to obtain 24.2 (Yield: 66.69%; MS (ES): 574.25 [M+H]$^+$).

Step 4—Synthesis of Compounds 24.2a and 24.2b: Isomers of 24.2 (0.1 g) were separated out using column CHIRALPAK OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 24.2a (0.040 g; MS (ES): m/z 574.25 [M+H]$^+$). FR-b was concentrated under reduced pressure at 30° C. to afford pure 24.2b (0.040 g; MS (ES): m/z 574.25 [M+H]$^+$).

Step 3—Synthesis of Compound I-36: To 24.2a (0.040 g, 0.27 mmol, 1.0 eq) was added 4M hydrochloric acid in 1,4 Dioxane (2 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-36 (0.029 g, Yield: 87.83%; MS (ES): m/z 475.01 [M+H]$^+$; LCMS purity: 100%; HPLC purity: 98.36%; CHIRAL HPLC purity: 100%; $^1$H NMR (DMSO-d$_6$, 400 MHZ): 8.94 (s, 1H), 8.33-8.32 (d, J=6.4 Hz, 1H), 8.20 (s, 1H), 7.92 (bs, 1H), 7.71-7.69 (d, J=7.6 Hz, 1H), 7.43-7.42 (d, J=6.4 Hz, 1H), 6.52 (bs, 1H), 6.27 (bs, 1H), 4.92 (bs, 1H), 4.76 (bs, 1H), 4.29 (bs, 1H), 4.18 (bs, 1H), 3.24 (bs, 3H), 2.91 (s, 3H), 2.26 (bs, 2H), 2.03 (bs, 1H), 1.68 (bs, 3H), 1.25 (bs, 1H)).

Step 4—Synthesis of Compound I-37: To 24.2b (0.040 g, 0.27 mmol, 1.0 eq) was added 4M hydrochloric acid in 1,4 Dioxane (2 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-37 (0.032 g, Yield: 96.92%; MS (ES): m/z 474.91 [M+H]$^+$; LCMS purity: 100% HPLC purity: 95.37%; CHIRAL HPLC purity: 98.53%; $^1$H NMR (DMSO-d$_6$, 400 MHZ): 8.94 (s, 1H), 8.33-8.32 (d, J=6.4 Hz, 1H), 8.21 (s, 1H), 7.92 (bs, 1H), 7.71-7.69 (d, J=7.6 Hz, 1H), 7.43-7.42 (d, J=6.4 Hz, 1H), 6.53 (bs, 1H), 6.28 (bs, 1H), 4.92 (bs, 1H), 4.76 (bs, 1H), 4.29 (bs, 1H), 4.18 (bs, 1H), 3.59 (bs, 3H), 2.81-2.78 (d, J=10 Hz, 3H), 2.27 (bs, 2H), 2.04 (bs, 1H), 1.68 (bs, 3H), 1.25 (bs, 1H)).

Example 25: 5-((1-((1r,3R)-3-Fluorocyclobutyl)-2-oxo-1,2-dihydropyridin-3-yl)amino)-N-((trans-1,3)-3-hydroxycyclopentyl)-7-(methylamino)pyrazolo[1,5-a]pyrimidine-3-carboxamide (I-38)

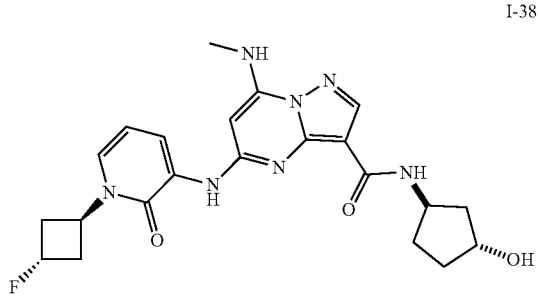

I-38

Scheme 25

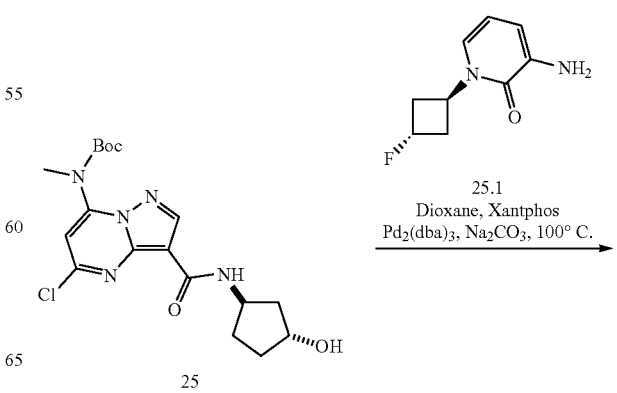

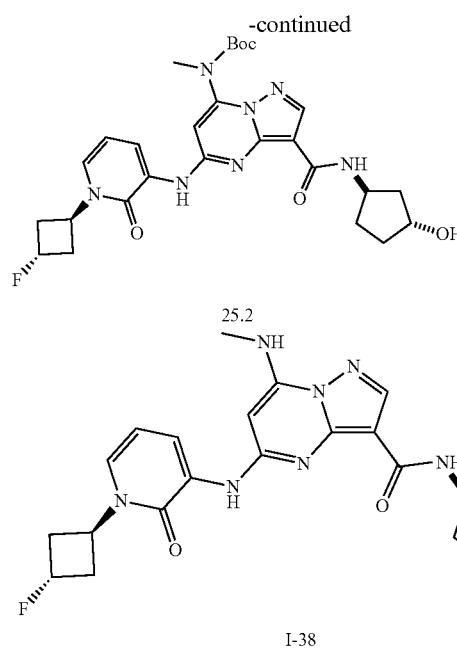

I-38

Step 1—Synthesis of Compound 25: Compound was synthesized from Core A utilizing general method A to obtain 25 (Yield: 47.83%; MS (ES): m/z 410.16 [M+H]$^+$).

Step 2—Synthesis of Compound 25.1: Compound was synthesized as per experimental protocol of 1-7 (Example 6) to obtain 25.1 (Yield: 98.46%; MS (ES): m/z 183.09 [M+H]$^+$).

Step 3—Synthesis of Compound 25.2: Compound was synthesized using general procedure B to obtain 25.2 (0.145 g, Yield: 71.31%; MS (ES): 556.26 [M+H]$^+$).

Step 4—Synthesis of Compound I-38: Compound was synthesized using general procedure C to obtain I-38 (0.027 g, Yield: 94.10%; MS (ES): m/z 456.52 [M+H]$^+$; LCMS purity: 100%; HPLC purity: 95.68%; CHIRAL HPLC: 48.95%, 51.04%; $^1$H NMR (DMSO-d$_6$, 400 MHZ): 8.92 (s, 1H), 8.19 (bs, 2H), 7.91 (bs, 1H), 7.65-7.63 (d, J=8 Hz, 1H), 7.48 (bs, 1H), 7.40 (bs, 1H), 6.30-6.26 (t, J=6.8 Hz, 1H), 6.22 (s, 1H), 5.45-5.30 (m, 2H), 4.62 (bs, 1H), 4.48-4.46 (d, J=6.4 Hz, 1H), 4.23 (bs, 1H), 3.58 (s, 2H), 2.92-2.91 (d, J=4.8 Hz, 3H), 2.17 (bs, 2H), 1.96 (bs, 3H), 1.25 (bs, 2H)).

Example 26: 5-((1-((1r,3R)-3-Fluorocyclobutyl)-2-oxo-1,2-dihydropyridin-3-yl)amino)-N-((cis-1,3)-3-hydroxycyclopentyl)-7-(methylamino)pyrazolo[1,5-a]pyrimidine-3-carboxamide (I-39)

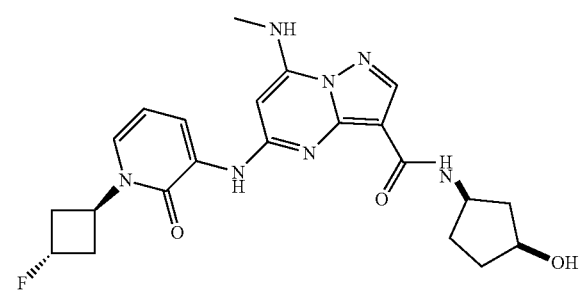

I-39

Scheme 26

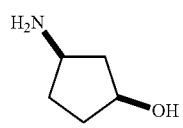

26

HATU, DMF
DIPEA, 5 min

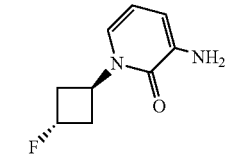

26.2

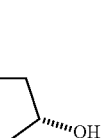

26.3

Dioxane, Xantphos
Pd$_2$(dba)$_3$, Na$_2$CO$_3$, 100° C.

MDC, TFA, RT

I-39

Step 1—Synthesis of Compound 26: Compound was synthesized using the procedure for the preparation of Core A to obtain 26 (Yield: 47.83%; MS (ES): m/z 410.87 [M+H]$^+$).

Step 2—Synthesis of Compound 26.2: Compound was synthesized using general procedure A to obtain 26.2 (0.3 g, 47.83%; MS (ES): m/z 410.87 [M+H]$^+$).

Step 3—Synthesis of Compound 26.3: Compound was synthesized as per experimental protocol of I-7 (Example 6) to obtain 26.3 (Yield: 98.46%; MS (ES): m/z 183.09 [M+H]$^+$).

Step 4—Synthesis of Compound 26.4: Compound was synthesized using general procedure B to obtain 26.2 (0.145 g, 71.31%; MS (ES): m/z 556.26 [M+H]$^+$).

Step 5—Synthesis of Compound I-39: Compound was synthesized using general procedure C to obtain I-39 (0.027 g, 94.10%; MS (ES): m/z 456.21 [M+H]$^+$; LCMS purity: 96.00%; HPLC purity: 96.07%; CHIRAL HPLC: 49.39%, 49.62%; $^1$H NMR (DMSO-d$_6$, 400 MHZ): 8.88 (s, 1H), 8.30-8.29 (d, J=7.2 Hz, 1H), 8.18 (s, 1H), 7.90-7.88 (d, J=4.8 Hz, 1H), 7.70-7.68 (d, J=8 Hz, 1H), 7.46-7.44 (d, J=6.8 Hz, 1H), 6.51-6.47 (t, J=7.2 Hz, 1H), 6.25 (s, 1H), 5.43-5.47 (m, 1H), 5.30 (bs, 1H), 4.75-4.74 (d, J=3.2 Hz, 1H), 4.30-4.24 (m, 1H), 4.17 (bs, 1H), 3.11 (s, 1H), 2.90-2.89 (d, J=4.8 Hz, 3H), 2.64 (bs, 4H), 2.26-2.22 (m, 1H), 2.03-1.99 (m, 1H), 1.72 (bs, 3H)).

Example 27: 5-((1-(3,3-Difluorocyclobutyl)-2-oxo-1,2-dihydropyridin-3-yl)amino)-N-((1R,3R)-3-hydroxycyclopentyl)-7-(methylamino)pyrazolo[1,5-a]pyrimidine-3-carboxamide (I-40)

And 5-((1-(3,3-Difluorocyclobutyl)-2-oxo-1,2-dihydropyridin-3-yl)amino)-N-((1S,3S)-3-hydroxycyclopentyl)-7-(methylamino)pyrazolo[1,5-a]pyrimidine-3-carboxamide (I-41)

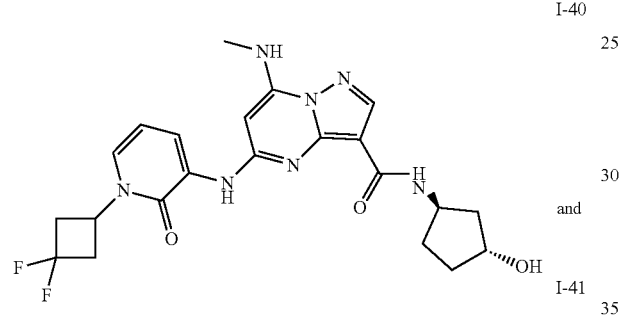

I-40 and

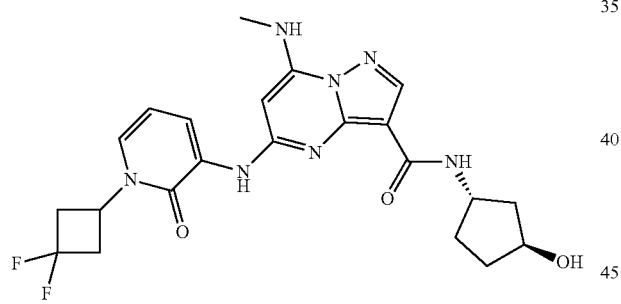

I-41

Scheme 27

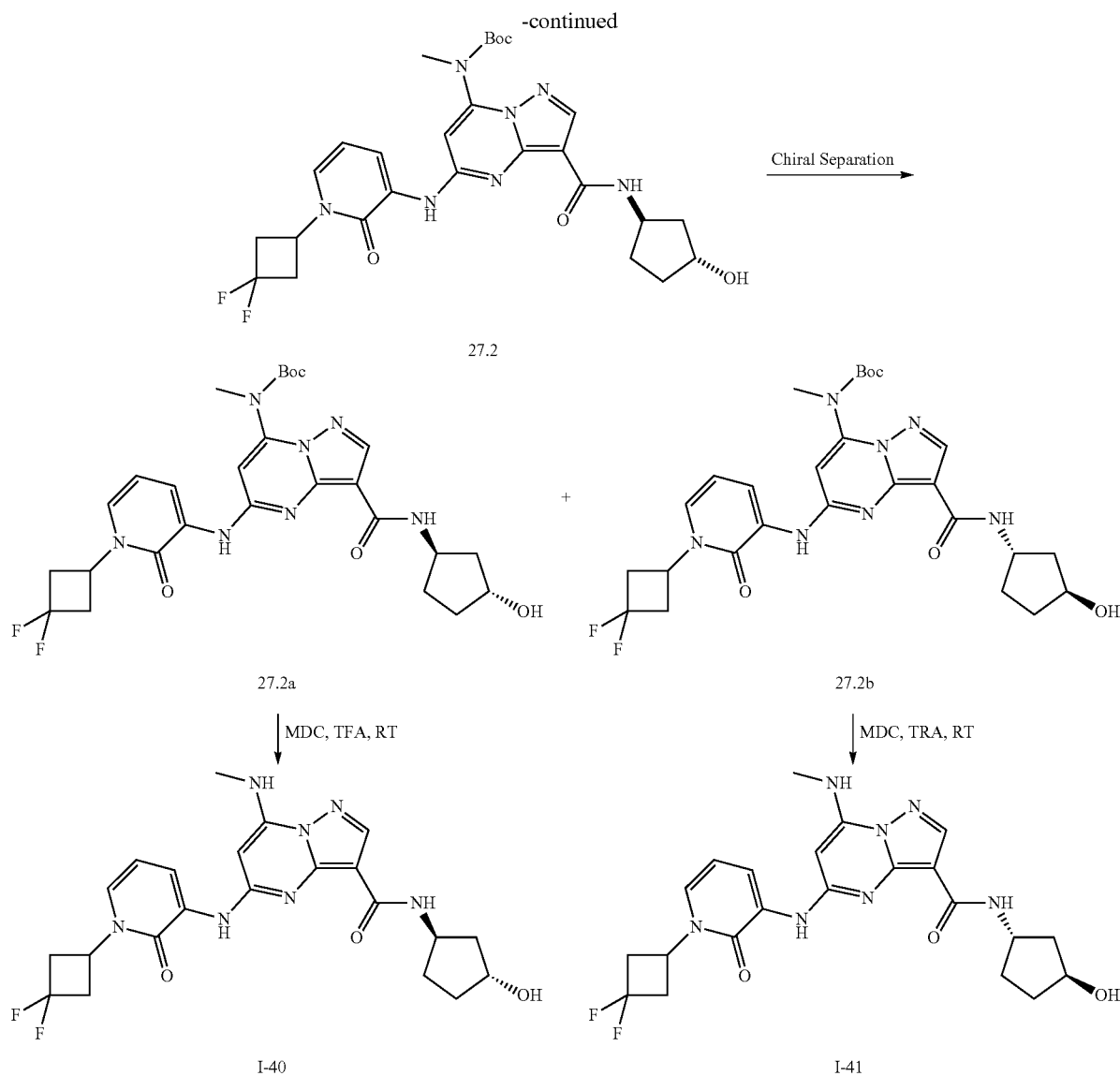

Step 1—Synthesis of Compound 27: Compound was synthesized from Core A utilizing general method A to obtain 27 (MS (ES): m/z 574.25 [M+H]$^+$).

Step 2—Synthesis of Compound 27.1: Compound was synthesized as per experimental protocol of I-33 (Example 22) to obtain 27.1.

Step 3—Synthesis of Compound 27.2: Compound was synthesized using general procedure B to obtain 27.2 (Yield: 64.31%).

Step 3—Synthesis of Compounds 27.2a and 27.2b: Isomers of 27.2 (0.109 g) were separated out using column CHIRALCEL OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 27.2a (0.045 g; MS (ES): m/z 574.25 [M+H]$^+$). FR-b was concentrated under reduced pressure at 30° C. to afford pure 27.2b (0.042 g; MS (ES): m/z 574.25 [M+H]$^+$).

Step 3—Synthesis of Compound I-40: Compound was synthesized using general procedure C to obtain I-40 (0.034 g, Yield: 91.53%; MS (ES): m/z 474.47 [M+H]$^+$; LCMS purity: 98.28%; HPLC purity: 96.37; CHIRAL HPLC: 98.91%; $^1$H NMR (DMSO-$d_6$, 400 MHZ): 8.93 (s, 1H), 8.21-8.20 (d, J=7.2 Hz, 1H), 8.17 (s, 1H), 7.90-7.89 (d, J=4.8 Hz, 1H), 7.62-7.60 (d, J=7.2 Hz, 1H), 7.43-7.42 (d, J=6 Hz, 1H), 6.29-6.25 (t, J=6.8 Hz, 1H), 6.22 (s, 1H), 4.90 (bs, 1H), 4.60 (bs, 1H), 4.48-4.42 (m, 1H), 4.22 (bs, 1H), 3.56 (s, 1H), 2.89-2.88 (d, J=4.8 Hz, 3H), 2.17-2.11 (m, 1H), 1.97-1.90 (m, 2H), 1.55-1.50 (m, 2H), 1.36-1.33 (m, 1H), 1.23 (bs, 3H)).

Step 4—Synthesis of Compound I-41: Compound was synthesized using general procedure C to obtain I-41 (0.032 g, Yield: 92.30%; MS (ES): m/z 474.87 [M+H]$^+$; LCMS purity: 98.74%; HPLC purity: 96.22%; CHIRAL HPLC: 97.23%; $^1$H NMR (DMSO-$d_6$, 400 MHZ): 8.93 (s, 1H), 8.21-8.20 (d, J=7.2 Hz, 1H), 8.17 (s, 1H), 7.90-7.89 (d, J=4.8 Hz, 1H), 7.62-7.60 (d, J=7.2 Hz, 1H), 7.43-7.42 (d, J=6 Hz, 1H), 6.29-6.25 (t, J=6.8 Hz, 1H), 6.22 (s, 1H), 4.90 (bs, 1H), 4.60-4.59 (d, J=6 Hz, 1H), 4.48-4.42 (m, 1H), 4.22 (bs, 1H), 3.56 (s, 1H), 2.89-2.88 (d, J=4.8 Hz, 3H), 2.18-2.11 (m, 1H), 1.96-1.90 (m, 2H), 1.57-1.50 (m, 2H), 1.40-1.33 (m, 1H), 1.23 (bs, 3H)).

Example 28: 5-((1-((1R,2R)-2-Fluorocyclopropyl)-2-oxo-1,2-dihydropyridin-3-yl)amino)-N-((1R,3S)-3-hydroxycyclopentyl)-7-(methylamino)pyrazolo[1,5-a]pyrimidine-3-carboxamide (I-42)

And 5-((1-((1R,2R)-2-Fluorocyclopropyl)-2-oxo-1,2-dihydropyridin-3-yl)amino)-N-((1S,3R)-3-hydroxycyclopentyl)-7-(methylamino)pyrazolo[1,5-a]pyrimidine-3-carboxamide (I-43)

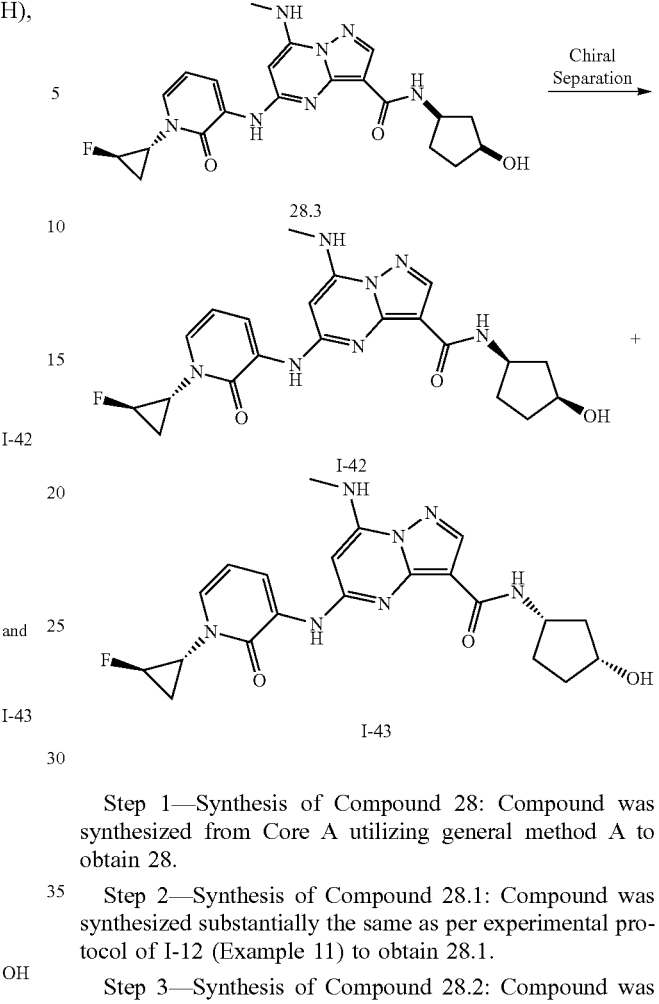

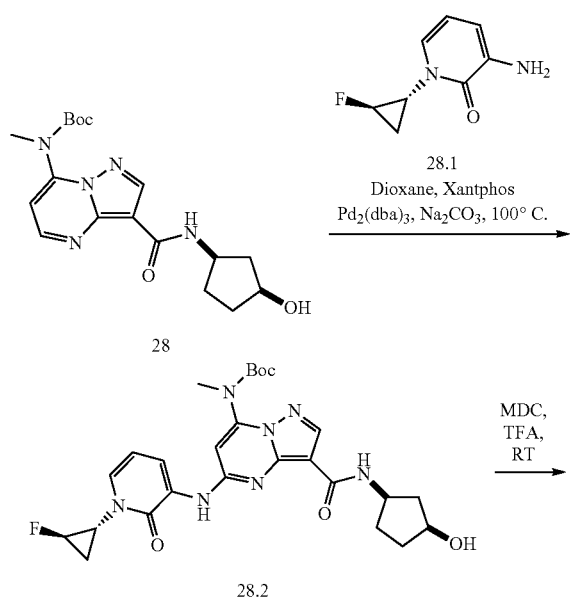

Scheme 28

Step 1—Synthesis of Compound 28: Compound was synthesized from Core A utilizing general method A to obtain 28.

Step 2—Synthesis of Compound 28.1: Compound was synthesized substantially the same as per experimental protocol of I-12 (Example 11) to obtain 28.1.

Step 3—Synthesis of Compound 28.2: Compound was synthesized using general procedure B to obtain 28.2.

Step 4—Synthesis of Compound 28.2: Compound was synthesized using general procedure C to obtain 28.3.

Step 5—Synthesis of Compounds I-42 and I-43: Isomers of 28.3 (0.095 g) were separated out using column CHIRALPAK OX-H (250 mm×4.6 mm, 5 µm) 0.1% DEA_HEX_IPA-ACN (70-30) to get pure fraction-1 (FR-a) and fraction-2 (FR-b).

FR-a was concentrated under reduced pressure at 30° C. to afford pure I-42 (0.027 g; MS (ES): m/z 442.47 [M+H]+; LCMS purity: 100%; HPLC purity: 100%; CHIRAL HPLC purity: 99.17%; $^1$H NMR (DMSO-$d_6$, 400 MHZ): 8.92 (s, 1H), 8.29-8.27 (d, J=6.4 Hz, 1H), 8.19 (s, 1H), 7.92-7.91 (d, J=5.2 Hz, 1H), 7.69-7.67 (d, J=7.6 Hz, 1H), 7.17-7.16 (d, J=7.2 Hz, 1H), 6.44-6.40 (t, J=7.2 Hz, 1H), 6.27 (s, 1H), 5.09 (bs, 1H), 4.93 (bs, 1H), 4.74-4.65 (t, J=2 Hz, 1H), 4.30-4.26 (m, 1H), 4.16 (bs, 1H), 3.91-3.85 (m, 1H), 2.92-2.90 (d, J=4.8 Hz, 3H), 2.28-2.21 (m, 1H), 2.03 (bs, 1H), 1.35 (s, 2H), 1.24 (bs, 3H)).

FR-b was concentrated under reduced pressure at 30° C. to afford pure I-43 (0.028 g; MS (ES): m/z 442.47 [M+H]+; LCMS purity: 100%; HPLC purity: 100%; CHIRAL HPLC purity: 98.62%; $^1$H NMR (DMSO-$d_6$, 400 MHZ): 8.93 (s, 1H), 8.28-8.26 (d, J=6.4 Hz, 1H), 8.20 (s, 1H), 7.92-7.91 (d, J=5.2 Hz, 1H), 7.69-7.67 (d, J=7.6 Hz, 1H), 7.17-7.16 (d, J=7.2 Hz, 1H), 6.44-6.40 (t, J=7.2 Hz, 1H), 6.27 (s, 1H), 5.09 (bs, 1H), 4.93 (bs, 1H), 4.74-4.65 (t, J=2 Hz, 1H), 4.30-4.27 (m, 1H), 4.16 (bs, 1H), 3.91-3.85 (m, 1H), 2.92-2.90 (d, J=4.8 Hz, 3H), 2.28-2.21 (m, 1H), 2.03 (bs, 1H), 1.35 (s, 2H), 1.23 (bs, 3H)).

Example 29: 5-((1-((1S,2S)-2-Fluorocyclopropyl)-2-oxo-1,2-dihydropyridin-3-yl)amino)-N-((1R,3S)-3-hydroxycyclopentyl)-7-(methylamino)pyrazolo[1,5-a]pyrimidine-3-carboxamide (I-44)

And 5-((1-((1S,2S)-2-Fluorocyclopropyl)-2-oxo-1,2-dihydropyridin-3-yl)amino)-N-((1S,3R)-3-hydroxycyclopentyl)-7-(methylamino)pyrazolo[1,5-a]pyrimidine-3-carboxamide (I-45)

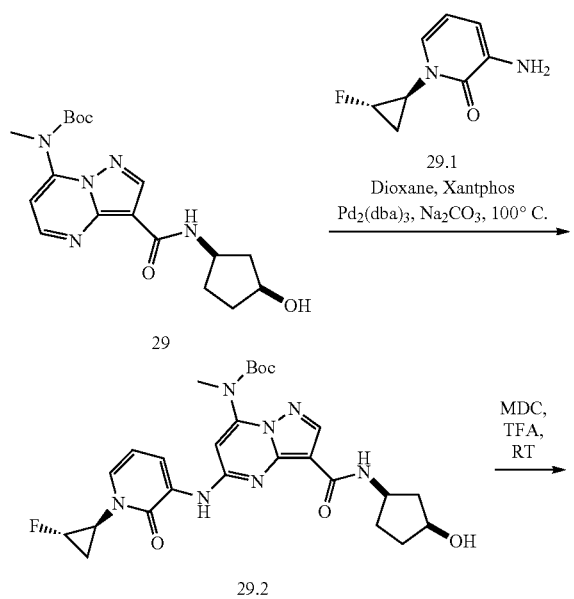

Scheme 29

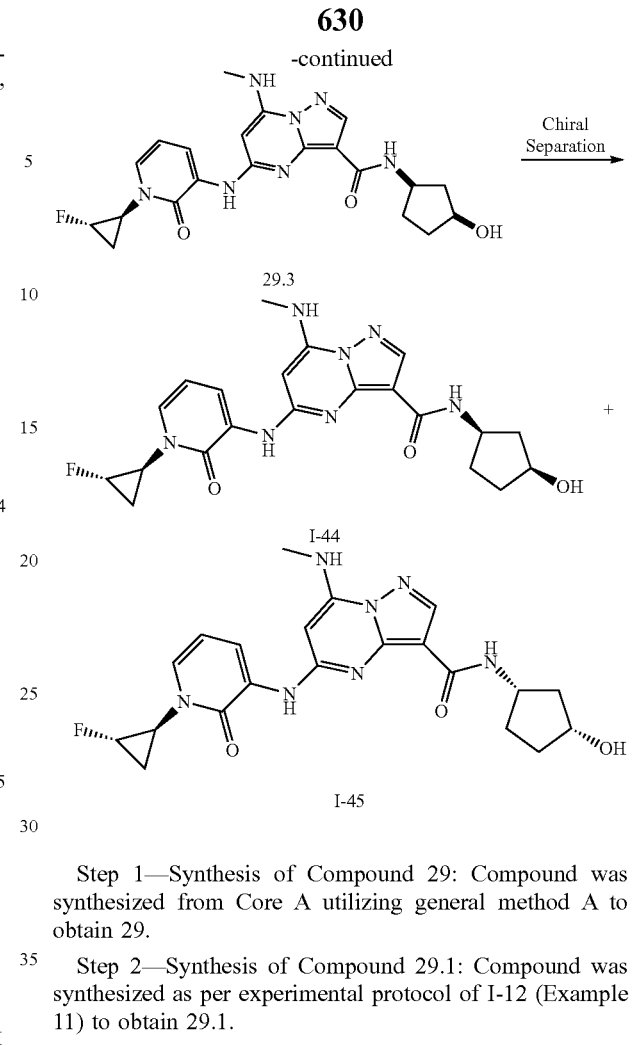

Step 1—Synthesis of Compound 29: Compound was synthesized from Core A utilizing general method A to obtain 29.

Step 2—Synthesis of Compound 29.1: Compound was synthesized as per experimental protocol of I-12 (Example 11) to obtain 29.1.

Step 3—Synthesis of Compound 29.2: Compound was synthesized using general procedure B to obtain 29.2.

Step 4—Synthesis of Compound 29.3: Compound was synthesized using general procedure C to obtain 28.3.

Step 5—Synthesis of Compound I-44 and I-45: Isomers of Compound 29.3 (0.095 g) were separated out using column CHIRALPAK OX-H (250 mm×4.6 mm, 5 µm) 0.1% DEA_HEX_IPA-ACN (70-30) to get pure fraction-1 (FR-a) and fraction-2 (FR-b).

FR-a was concentrated under reduced pressure at 30° C. to afford pure I-44 (0.027 g; MS (ES): m/z 442.20 [M+H]$^+$; LCMS purity: 100%; HPLC purity: 98.77%; CHIRAL HPLC purity: 99.00%; $^1$H NMR (DMSO-d6, 400 MHZ): 8.93 (s, 1H), 8.29-8.27 (d, J=6.8 Hz, 1H), 8.19 (s, 1H), 7.92-7.91 (d, J=5.2 Hz, 1H), 7.69-7.67 (d, J=8 Hz, 1H), 7.18-7.16 (d, J=6.8 Hz, 1H), 6.44-6.40 (t, J=7.2 Hz, 1H), 6.27 (s, 1H), 4.75 (bs, 1H), 4.26 (bs, 1H), 4.16 (bs, 1H), 3.87-3.84 (m, 1H), 2.92-2.91 (d, J=4.8 Hz, 3H), 2.27-2.23 (m, 1H), 2.03-2.01 (m, 1H), 1.69 (bs, 3H), 1.63 (bs, 3H), 1.56 (bs, 1H)).

FR-b was concentrated under reduced pressure at 30° C. to afford pure I-45 (0.027 g; MS (ES): m/z 442.20 [M+H]$^+$; LCMS purity: 100%; HPLC purity: 99.20%; CHIRAL HPLC purity: 99.00%; 1H NMR (DMSO-d$_6$, 400 MHZ): 8.95 (s, 1H), 8.28-8.26 (d, J=6.8 Hz, 1H), 8.18 (s, 1H), 7.92-7.91 (d, J=5.2 Hz, 1H), 7.69-7.67 (d, J=8 Hz, 1H), 7.18-7.16 (d, J=6.8 Hz, 1H), 6.44-6.40 (t, J=7.2 Hz, 1H), 6.28 (s, 1H), 4.75 (bs, 1H), 4.26 (bs, 1H), 4.16 (bs, 1H), 3.87-3.84 (m, 1H), 2.92-2.91 (d, J=4.8 Hz, 3H), 2.27-2.23 (m, 1H), 2.03-2.01 (m, 1H), 1.69 (bs, 3H), 1.63 (bs, 3H), 1.56 (bs, 1H)).

Example 30: 5-((1-((1r,3S)-3-Fluorocyclobutyl)-2-oxo-1,2-dihydropyridin-3-yl)amino)-N-((trans-1,2)-2-methoxycyclobutyl)-7-(methylamino)pyrazolo[1,5-a]pyrimidine-3-carboxamide (I-46)

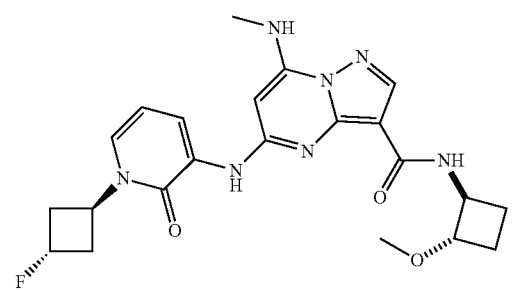

I-46

Scheme 30

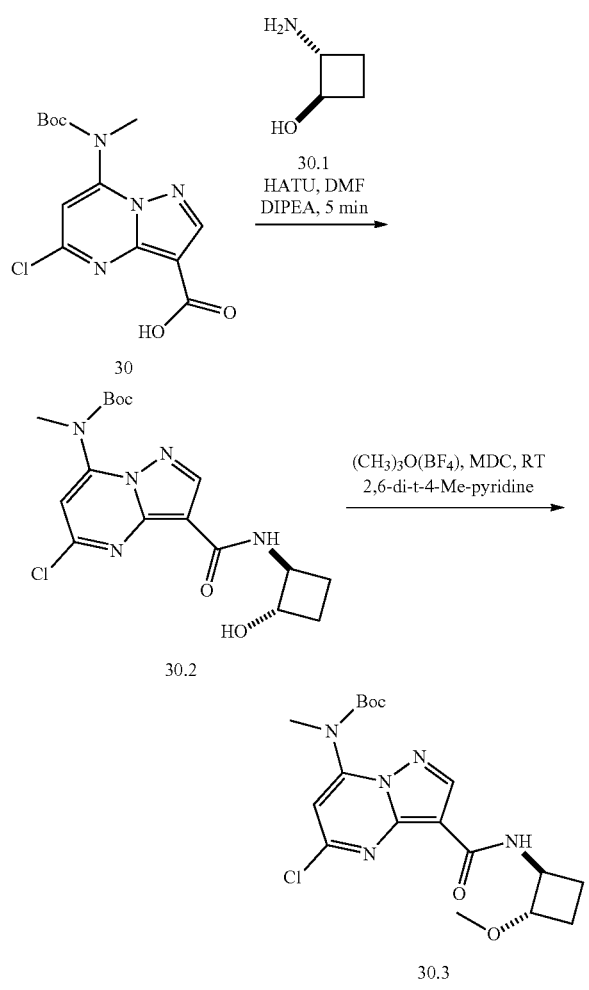

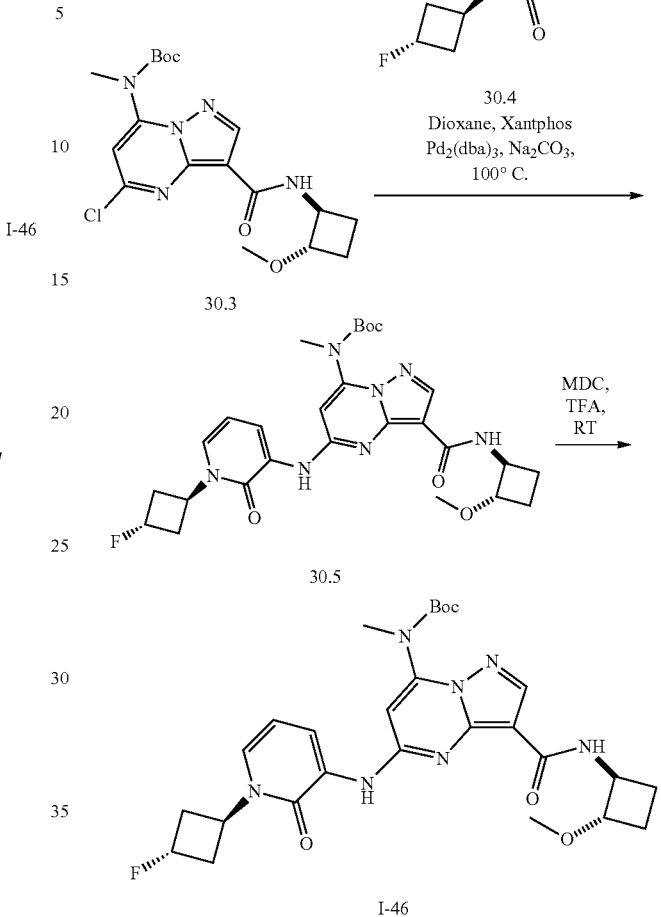

Step 1—Synthesis of Compound 30: Compound was synthesized using the procedure for the preparation of Core A to obtain 30 (Yield: 71.67%; MS (ES): m/z 327.08 [M+H]$^+$).

Step 2—Synthesis of Compound 30.2: Compound was synthesized using general procedure A to obtain 30.2 (0.640 g, Yield: 52.83%; MS (ES): m/z 396.14 [M+H]$^+$).

Step 3—Synthesis of Compound 30.3: To a solution of 30.2 (1.0 g, 2.52 mmol, 1 eq) in dichloromethane (20 mL), Triethyloxonium tetrafluoroborate (0.957 g, 5.04 mmol, 2.0 eq) and 2,6-Di-tert-butyl-4-methylpyridine (1.54 g, 7.56 mmol, 3.0 eq) was added. The reaction mixture was stirred at room temperature for 4 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 30.3 (0.600 g, Yield: 57.95%; MS (ES): m/z 410.16 [M+H]$^+$).

Step 4—Synthesis of Compound 30.4: Compound was synthesized as per experimental protocol of I-7 (Example 6) to obtain 30.4 (Yield: 98.46%; MS (ES): m/z 183.09 [M+H]$^+$).

Step 5—Synthesis of Compound 30.5: Compound was synthesized using general procedure B to obtain 30.5 (0.150 g, Yield: 73.77%; MS (ES): 556.26 [M+H]$^+$).

Step 6—Synthesis of Compound I-46: Compound was synthesized using general procedure C to obtain I-46 (0.025 g, Yield: 76.24%; MS (ES): 456.87 [M+H]+; LCMS purity: 100%; HPLC purity: 99.90%; CHIRAL HPLC: 51.21%, 48.45%; $^1$H NMR (DMSO-$d_6$, 400 MHZ): 8.97 (s, 1H), 8.26-8.24 (d, J=6.8 Hz, 1H), 8.20 (s, 1H), 8.09-8.06 (d, J=9.6 Hz, 1H), 7.95 (bs, 1H), 7.51-7.50 (d, J=6.8 Hz, 1H), 6.35-6.33 (t, J=7.2 Hz, 1H), 6.23 (s, 1H), 5.45-5.40 (m, 2H), 5.31 (m, 1H), 4.30 (bs, 1H), 3.71 (bs, 1H), 3.21 (s, 3H), 2.91-2.90 (d, J=4.8 Hz, 3H), 2.83 (bs, 1H). 2.68 (bs, 2H), 2.14-2.08 (m, 2H), 1.53 (bs, 1H), 1.37-1.35 (m, 1H)).

Example 31: 5-((1-(3,3-Difluorocyclobutyl)-2-oxo-1,2-dihydropyridin-3-yl)amino)-N-((1S,2S)-2-methoxycyclobutyl)-7-(methylamino)pyrazolo[1,5-a]pyrimidine-3-carboxamide (I-47)

And 5-((1-(3,3-Difluorocyclobutyl)-2-oxo-1,2-dihydropyridin-3-yl)amino)-N-((1R,2R)-2-methoxycyclobutyl)-7-(methylamino)pyrazolo[1,5-a]pyrimidine-3-carboxamide (I-48)

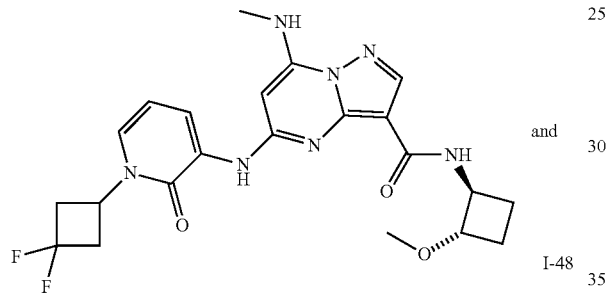

I-47 and

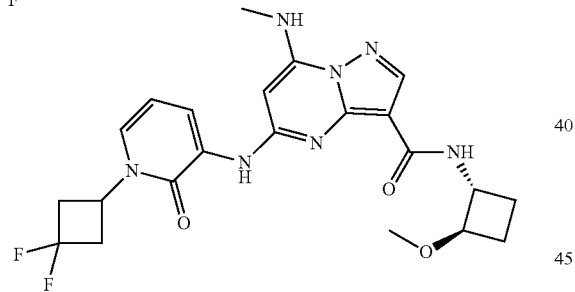

I-48

Scheme 31

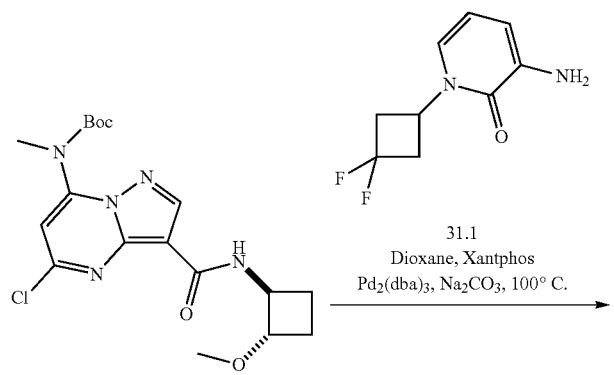

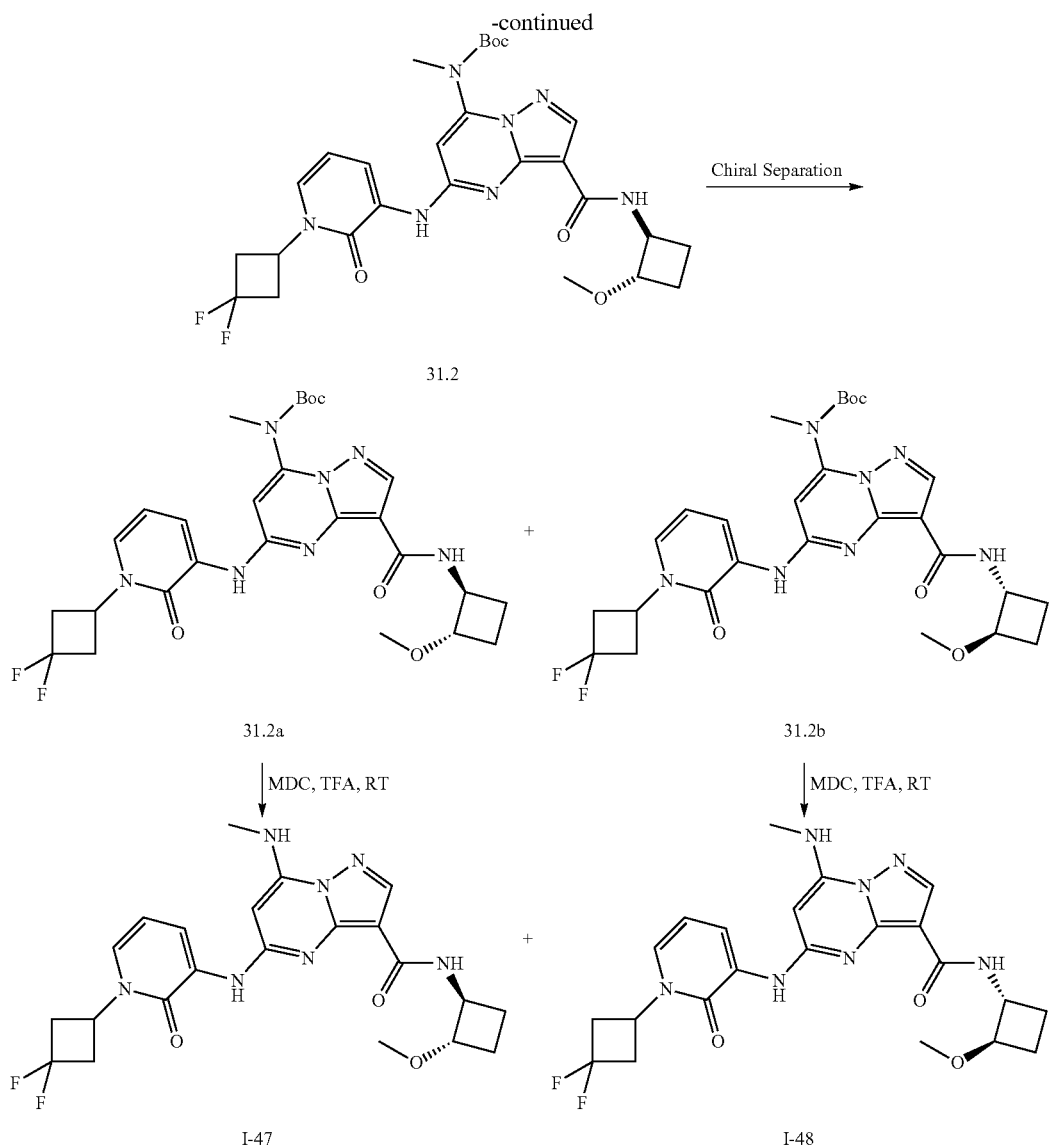

Step 1—Synthesis of Compound 31: Compound was synthesized as per experimental protocol of I-46 (Example 30) to obtain 31 (Yield: 57.95%; MS (ES): m/z 410.16 [M+H]$^+$).

Step 2—Synthesis of Compound 31.1: Compound was synthesized as per experimental protocol of I-33 (Example 22) to obtain 31.1.

Step 3—Synthesis of Compound 31.2: Compound was synthesized using general procedure B to obtain 32.2 (0.140 g, Yield: 66.69%; MS (ES): m/z 574.25 [M+H]$^+$).

Step 4—Synthesis of Compounds 31.2a and 31.2b: Isomers of 31.2 (0.1 g) were separated out using column CHIRALPAK AD-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 31.2a (0.042 g; MS (ES): m/z 574.25 [M+H]$^+$). FR-b was concentrated under reduced pressure at 30° C. to afford pure 31.2b (0.040 g; MS (ES): m/z 574.25 [M+H]$^+$).

Step 5—Synthesis of Compound I-47: Compound was synthesized using general procedure C to obtain I-47 (0.032 g, Yield: 92.30%; MS (ES): 474.82 [M+H]$^+$; LCMS purity: 95.02%; HPLC purity: 95.78%; CHIRAL HPLC: 96.02%; $^1$H NMR (DMSO-d$_6$, 400 MHZ): 8.99 (s, 1H), 8.27-8.26 (d, J=6.4 Hz, 1H), 8.20 (s, 1H), 8.07-8.05 (d, J=9.2 Hz, 1H), 7.94-7.93 (d, J=4.8 Hz, 1H), 7.47-7.45 (d, J=6.4 Hz, 1H), 6.37-6.33 (t, J=7.2 Hz, 1H), 6.22 (s, 1H), 4.92 (bs, 1H), 4.33-4.29 (m, 1H), 3.72-3.67 (m, 1H), 3.20 (s, 4H), 2.90-2.89 (d, J=4.8 Hz, 3H), 2.15-2.05 (m, 2H), 1.57-1.50 (m, 1H), 1.37-1.32 (m, 2H), 1.23 (bs, 2H)).

Step 6—Synthesis of Compound I-48: Compound was synthesized using general procedure C to obtain I-48 (0.034 g, Yield: 99.94%; MS (ES): m/z 474.52 [M+H]$^+$; LCMS purity: 100%; HPLC purity: 97.73%; CHIRAL HPLC: 100%; $^1$H NMR (DMSO-d$_6$, 400 MHZ): 9.00 (s, 1H), 8.27-8.26 (d, J=6.4 Hz, 1H), 8.20 (s, 1H), 8.07-8.05 (d, J=9.2 Hz, 1H), 7.94-7.93 (d, J=4.8 Hz, 1H), 7.47-7.45 (d, J=6.4 Hz, 1H), 6.37-6.33 (t, J=7.2 Hz, 1H), 6.23 (s, 1H), 4.92 (bs, 1H), 4.33-4.29 (m, 1H), 3.72-3.67 (m, 1H), 3.20 (s, 4H), 2.90-2.89 (d, J=4.8 Hz, 3H), 2.15-2.05 (m, 2H), 1.57-1.50 (m, 1H), 1.37-1.32 (m, 2H), 1.23 (bs, 2H)).

Example 32: 5-((1-((1S,2S)-2-Fluorocyclopropyl)-2-oxo-1,2-dihydropyridin-3-yl)amino)-N-((1S,2S)-2-methoxycyclobutyl)-7-(methylamino)pyrazolo[1,5-a]pyrimidine-3-carboxamide (I-49)
And
5-((1-((1S,2S)-2-Fluorocyclopropyl)-2-oxo-1,2-dihydropyridin-3-yl)amino)-N-((1R,2R)-2-methoxycyclobutyl)-7-(methylamino)pyrazolo[1,5-a]pyrimidine-3-carboxamide (I-50)
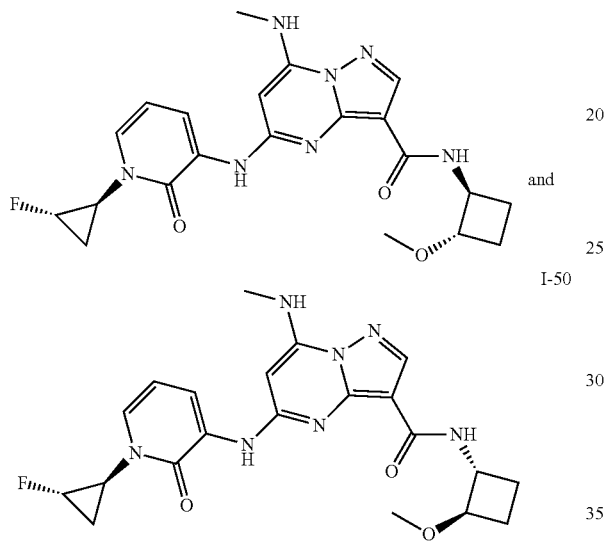
Scheme 32
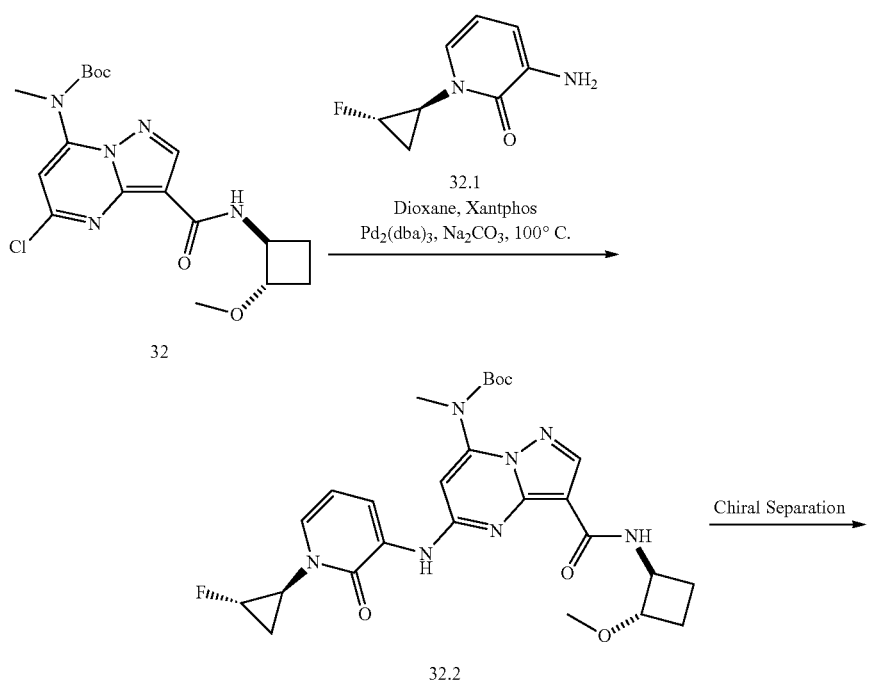

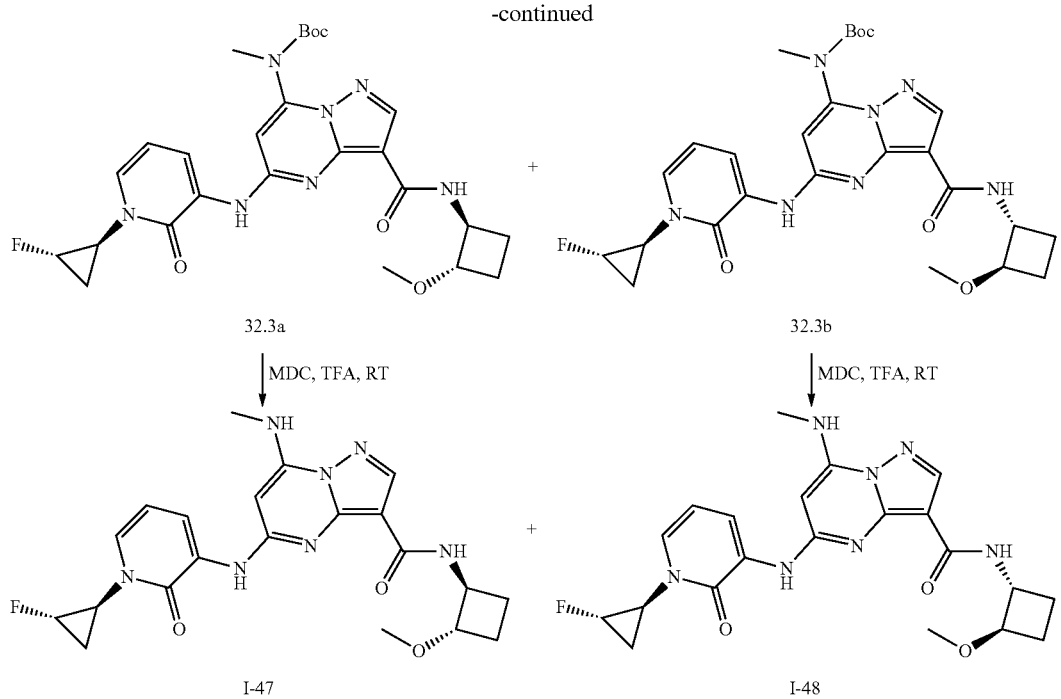

Step 1—Synthesis of Compound 32: Compound was synthesized as per experimental protocol of I-46 (Example 30) to obtain 32.

Step 2—Synthesis of Compound 32.1: Compound was synthesized as per experimental protocol of I-12 (Example 11) to obtain 32.1.

Step 3—Synthesis of Compound 32.2: Compound was synthesized using general procedure B to obtain 32.2 (Yield: 73.16%; MS (ES): m/z 542.25 [M+H]$^+$).

Step 2—Synthesis of Compounds 32.2a and 32.2b: Isomers of 32.2 (0.105 g) were separated out using column CHIRALPAK AD-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 32.2a (0.042 g; MS (ES): m/z 542.25 [M+H]$^+$). FR-b was concentrated under reduced pressure at 30° C. to afford pure 32.2b (0.042 g; MS (ES): m/z 542.25 [M+H]$^+$).

Step 3—Synthesis of Compound I-49: Compound was synthesized using general procedure C to obtain I-49 (0.030 g, Yield: 87.63%; MS (ES): m/z 442.5 [M+H]$^+$; LCMS purity: 100%; HPLC purity: 99.06%; CHIRAL HPLC purity: 100%; $^1$H NMR (DMSO-d$_6$, 400 MHZ): 9.00 (s, 1H), 8.25-8.23 (d, J=6.8 Hz, 1H), 8.21 (s, 1H), 8.07-8.05 (d, J=9.2 Hz, 1H), 7.96-7.95 (d, J=5.2 Hz, 1H), 7.23-7.21 (d, J=6.4 Hz, 1H), 6.28-6.27 (t, J=7.2 Hz, 1H), 6.24 (s, 1H), 5.10 (bs, 1H), 4.96 (bs, 1H), 4.34-4.28 (m, 1H), 3.92-3.84 (m, 1H), 3.71-3.68 (m, 1H), 3.20 (s, 3H), 2.92-2.91 (d, J=4.8 Hz, 3H), 2.16-2.02 (m, 2H), 1.24 (bs, 3H)).

Step 4—Synthesis of Compound I-50: Compound was synthesized using general procedure C to obtain I-50 (0.030 g, 87.63%; MS (ES): m/z 442.5 [M+H]$^+$; LCMS purity: 99.00%; HPLC purity: 99.15%; CHIRAL HPLC purity: 98.70%; H NMR (DMSO-d$_6$, 400 MHZ): 9.00 (s, 1H), 8.24-8.22 (d, J=6.8 Hz, 1H), 8.21 (s, 1H), 8.07-8.05 (d, J=9.2 Hz, 1H), 7.96-7.95 (d, J=5.2 Hz, 1H), 7.23-7.21 (d, J=6.4 Hz, 1H), 6.28-6.27 (t, J=7.2 Hz, 1H), 6.23 (s, 1H), 5.11 (bs, 1H), 4.96 (bs, 1H), 4.34-4.28 (m, 1H), 3.92-3.84 (m, 1H), 3.71-3.68 (m, 1H), 3.20 (s, 3H), 2.92-2.91 (d, J=4.8 Hz, 3H), 2.16-2.02 (m, 2H), 1.23 (bs, 3H)).

Example 33: N-((trans-1,2)-2-Methoxycyclobutyl)-5-((1-((1r,3S)-3-methoxycyclobutyl)-2-oxo-1,2-dihydropyridin-3-yl)amino)-7-(methylamino)pyrazolo[1,5-a]pyrimidine-3-carboxamide (I-51)

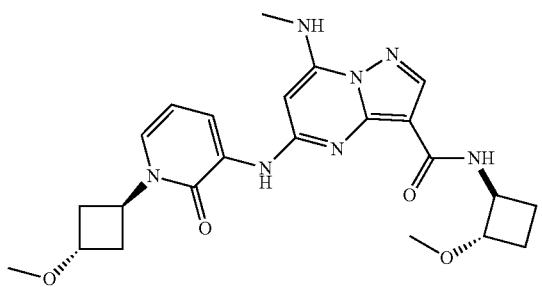

Scheme 33

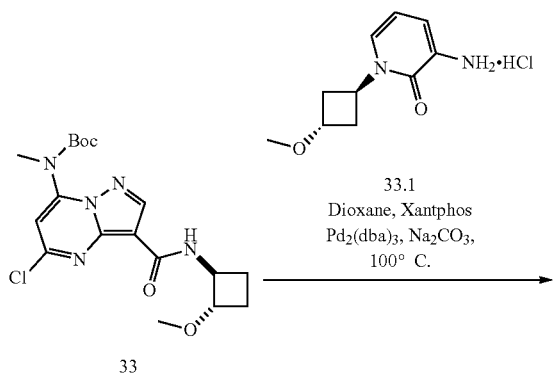

-continued

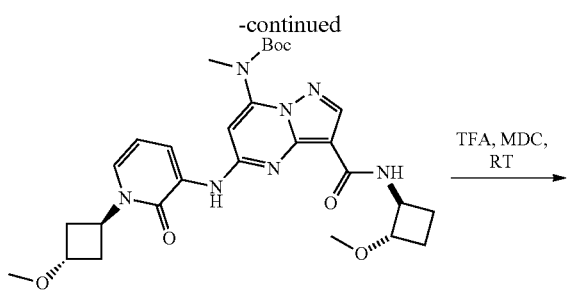

33.2

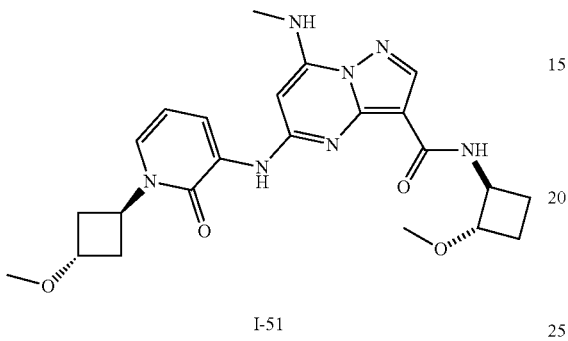

I-51

Step 1—Synthesis of Compound 33: Compound was synthesized as per experimental protocol of I-46 (Example 30) to obtain 33 (Yield: 57.95%; MS (ES): m/z 410.16 [M+H]$^+$).

Step 2—Synthesis of Compound 33.1: Compound was synthesized as per experimental protocol of I-4 (Example 3) to obtain 33.1 (Yield: 89.32%); MS (ES): m/z 195.11 [M+H]$^+$).

Step 3—Synthesis of Compound 33.2: Compound was synthesized using general procedure B to obtain 33.2 (0.145 g, 69.80%; MS (ES): m/z 568.28[M+H]$^+$).

Step 4—Synthesis of Compound I-51: Compound was synthesized using general procedure C to obtain I-51 (0.025 g, 75.88%; MS (ES): m/z 468.52 [M+H]$^+$; LCMS purity: 100%; HPLC purity: 99.20%; CHIRAL HPLC: 50.19%, 49.09%; $^1$H NMR (DMSO-d$_6$, 400 MHZ): 8.95 (s, 1H), 8.25-8.23 (d, J=7.6 Hz, 1H), 8.20 (s, 1H), 8.09-8.07 (d, J=9.2 Hz, 1H), 7.93 (bs, 1H), 7.56-7.54 (d, J=6.8 Hz, 1H), 6.35-6.32 (t, J=7.2 Hz, 1H), 6.22 (s, 1H), 5.30-5.28 (m, 1H), 4.33 (bs, 1H), 4.07 (bs, 1H), 3.71-3.70 (d, J=7.6 Hz, 1H), 3.21 (s, 6H), 2.91-2.90 (d, J=4.8 Hz, 3H), 2.14-2.06 (m, 3H), 1.66 (bs, 1H), 1.40-1.35 (m, 1H), 1.24 (bs, 2H), 1.12-1.10 (m, 1H)).

Example 34: 5-((1-((1R,2R)-2-Fluorocyclopropyl)-2-oxo-1,2-dihydropyridin-3-yl)amino)-N-((1S,2S)-2-methoxycyclobutyl)-7-(methylamino)pyrazolo[1,5-a]pyrimidine-3-carboxamide (I-52)

And 5-((1-((1R,2R)-2-Fluorocyclopropyl)-2-oxo-1,2-dihydropyridin-3-yl)amino)-N-((1R,2R)-2-methoxy-cyclobutyl)-7-(methylamino)pyrazolo[1,5-a]pyrimidine-3-carboxamide (I-53)

I-52

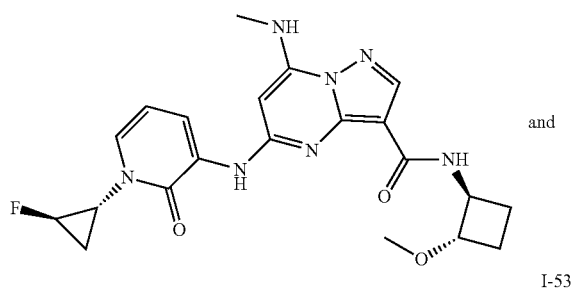

and

I-53

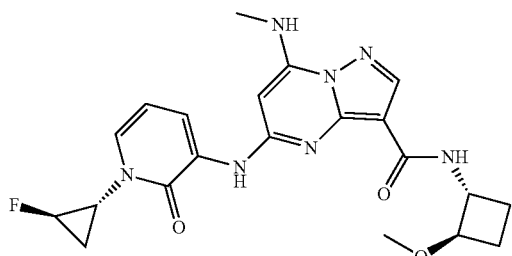

Scheme 34

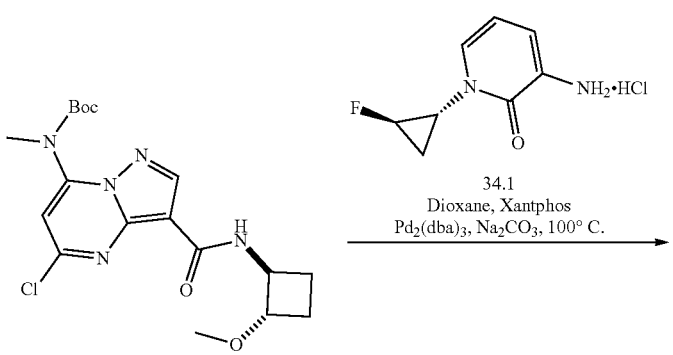

34

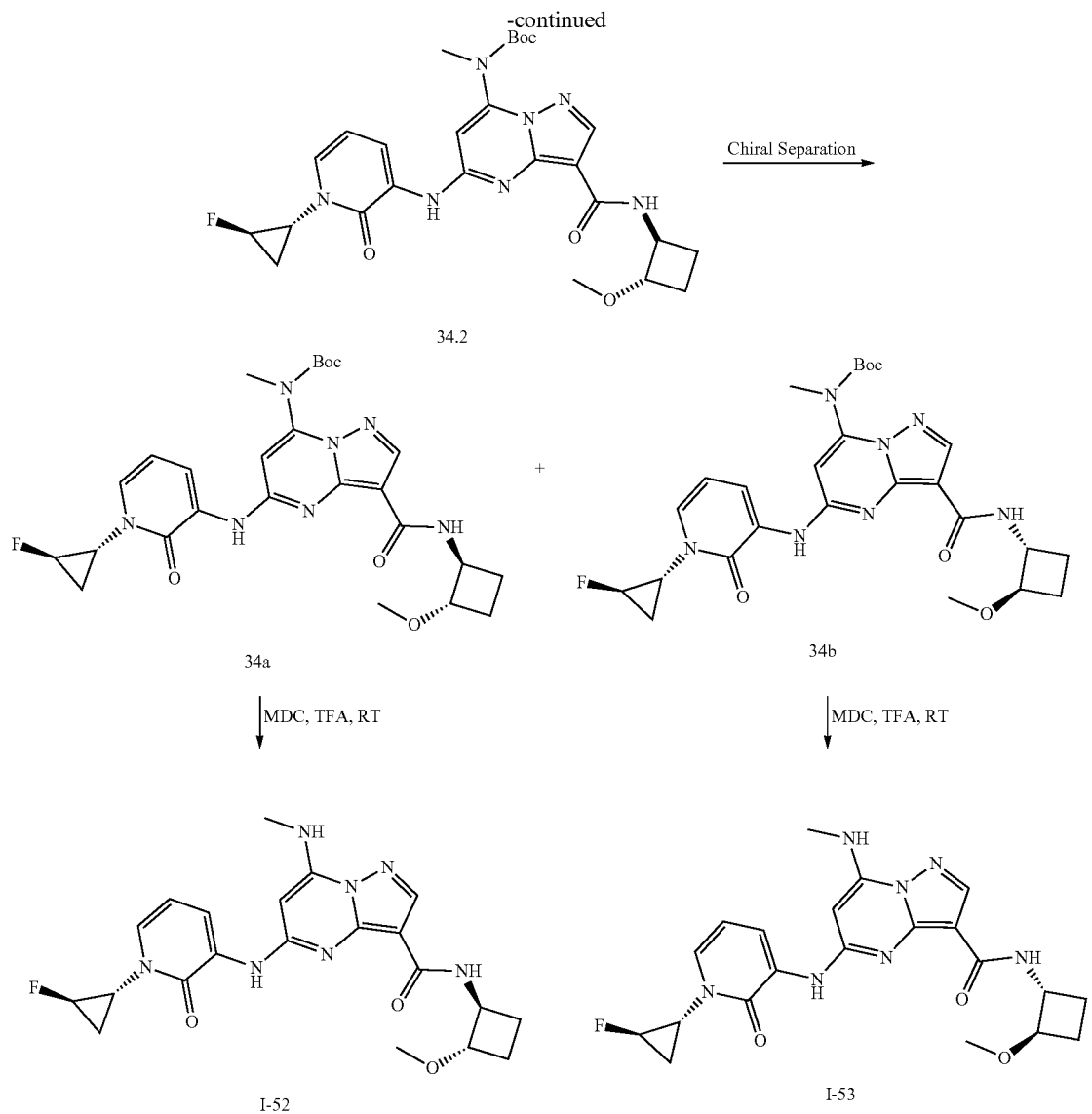

Step 1—Synthesis of Compound 34: Compound was synthesized as per experimental protocol of I-46 (Example 30) to obtain 34.

Step 2—Synthesis of Compound 34.1: Compound was synthesized as per experimental protocol of I-42 (Example 28) to obtain 34.1 (MS (ES): m/z 195.11 [M+H]$^+$).

Step 3—Synthesis of Compound 34.2: Compound was synthesized using general procedure B to obtain 34.2 (Yield: 70.63%; MS (ES): m/z 542.25 [M+H]$^+$).

Step 4—Synthesis of Compounds 34.2a and 34.2b: Isomers of 34.2 (0.1 g) were separated out using column CHIRALCEL OJ-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 34.2a (0.042 g; MS (ES): m/z 542.25 [M+H]$^+$). FR-b was concentrated under reduced pressure at 30° C. to afford pure 34.2b (0.045 g; MS (ES): m/z 542.25 [M+H]$^+$).

Step 5—Synthesis of Compound I-52: Compound was synthesized using general procedure C to obtain I-52 (0.032 g, 93.47%; MS (ES): m/z 442.20 [M+H]$^+$; LCMS purity: 100%; HPLC purity: 99.00%; CHIRAL HPLC purity: 100%; $^1$H NMR (DMSO-d$_6$, 400 MHZ): 9.00 (s, 1H), 8.24-8.23 (d, J=7.2 Hz, 1H), 8.21 (s, 1H), 8.07-8.05 (d, J=9.2 Hz, 1H), 7.96-7.94 (d, J=4.8 Hz, 1H), 7.22-7.21 (d, J=6.4 Hz, 1H), 6.29-6.27 (t, J=7.2 Hz, 1H), 6.24 (s, 1H), 4.93 (bs, 1H), 4.34-4.28 (m, 1H), 3.92-3.84 (m, 1H), 3.73-3.67 (m, 1H), 3.21 (s, 3H), 2.92-2.91 (d, J=4.8 Hz, 3H), 2.16-2.02 (m, 2H), 1.78-1.72 (m, 1H), 1.59-1.53 (m, 2H), 1.38-1.33 (t, J=9.6 Hz, 1H)).

Step 6—Synthesis of Compound I-53: Compound was synthesized using general procedure C to obtain I-53 (0.033 g, Yield: 89.96%; MS (ES): m/z 442.20 [M+H]$^+$; LCMS purity: 100%; HPLC purity: 99.00%; CHIRAL HPLC purity: 100%; $^1$H NMR (DMSO-d$_6$, 400 MHZ): 9.00 (s, 1H), 8.24-8.23 (d, J=7.2 Hz, 1H), 8.21 (s, 1H), 8.07-8.05 (d, J=9.2 Hz, 1H), 7.96-7.95 (d, J=4.8 Hz, 1H), 7.23-7.21 (d, J=6.4 Hz, 1H), 6.28-6.25 (t, J=7.2 Hz, 1H), 6.24 (s, 1H), 4.93 (bs, 1H), 4.34-4.28 (m, 1H), 3.92-3.84 (m, 1H), 3.73-3.67 (m, 1H), 3.21 (s, 3H), 2.92-2.91 (d, J=4.8 Hz, 3H), 2.16-2.02 (m, 2H), 1.78-1.72 (m, 1H), 1.59-1.53 (m, 2H), 1.38-1.33 (t, J=9.6 Hz, 1H)).

Example 35: N-((1S,2S)-2-Methoxycyclobutyl)-7-(methylamino)-5-(1-(2-morpholinoethyl)-1H-pyrrolo[2,3-b]pyridin-3-yl)pyrazolo[1,5-a]pyrimidine-3-carboxamide (I-54)
And
N-((1R,2R)-2-Methoxycyclobutyl)-7-(methylamino)-5-(1-(2-morpholinoethyl)-1H-pyrrolo[2,3-b]pyridin-3-yl)pyrazolo[1,5-a]pyrimidine-3-carboxamide (I-55)
I-54
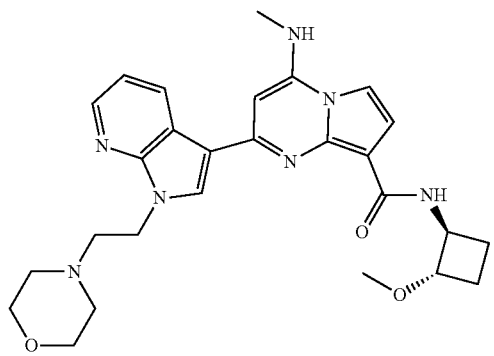
and
I-55
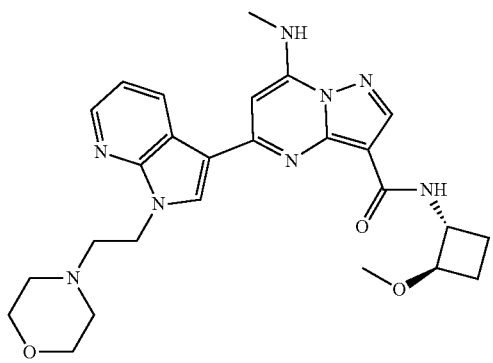
Scheme 35
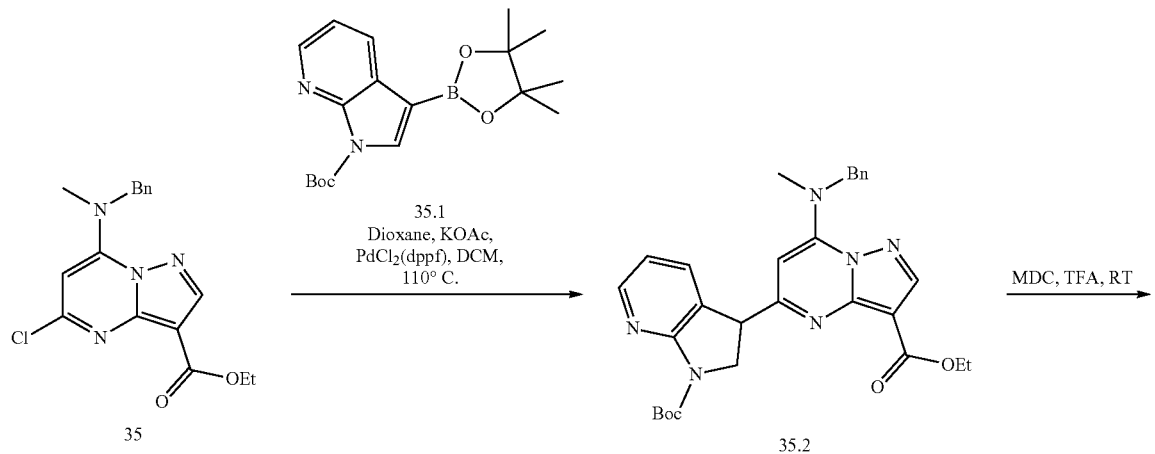

-continued
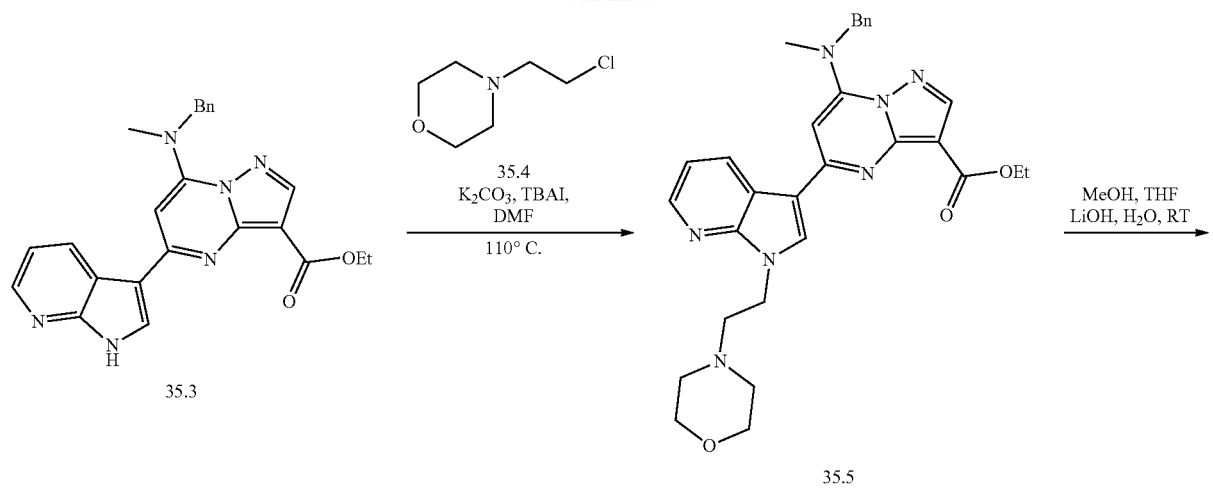
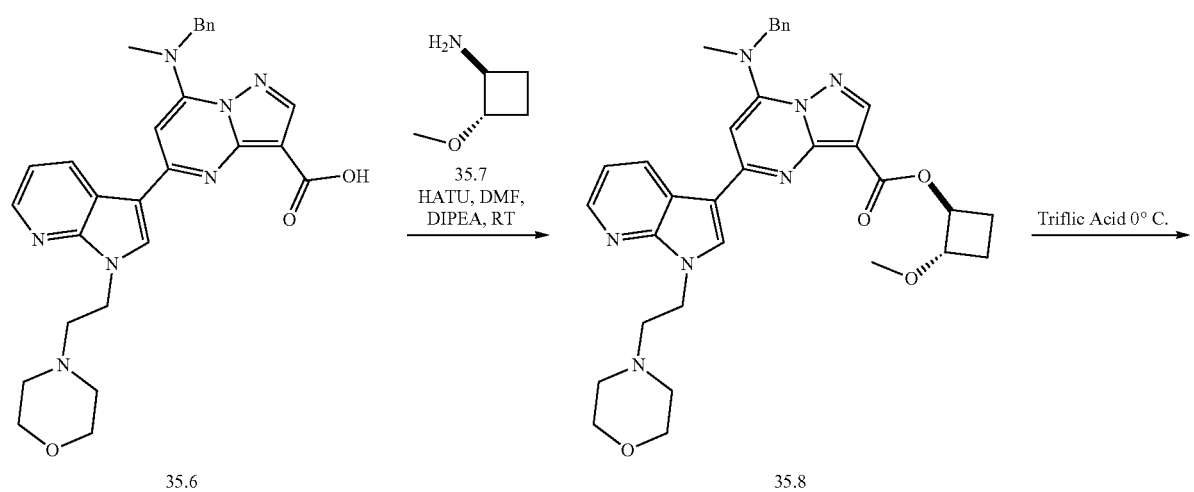
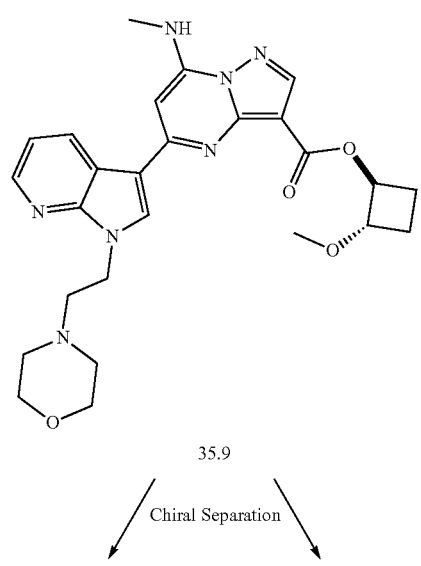
Chiral Separation

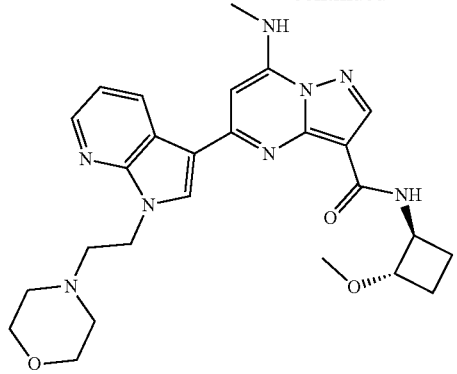

I-54

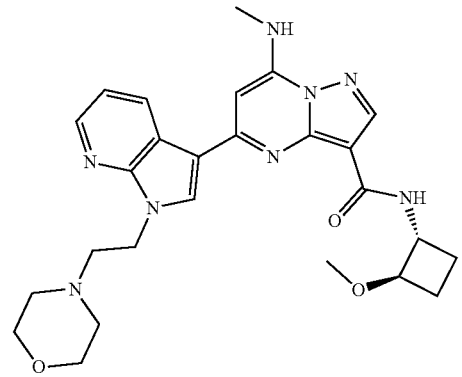

I-55

Step 1—Synthesis of Compound 35: Compound was synthesized using general procedure of Core B synthesis to obtain 35 (26 g, Yield: 62.21%; MS (ES): m/z 355 [M+H]$^+$).

Step 2—Synthesis of Compound 35.2: To a solution of 35 (0.1 g, 0.290 mmol, 1.0 eq), in dioxane (5 mL) were added 35.1 (0.129 g, 0.377 mmol, 1.3 eq) and sodium carbonate (0.076 g, 0.725 mmol 2.5 eq). The reaction mixture was degassed for 10 min under argon atmosphere, then [1,1'-Bis (diphenylphosphino)ferrocene] dichloropalladium (II), complex with dichloromethane (0.028 g, 0.029 mmol 0.1 eq) was added, again degassed for 5 min. The reaction was stirred at 100° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using eluted in 25% ethyl acetate in hexane to obtain pure 35.2 (0.083 g, Yield: 54.35%; MS (ES): m/z 527 [M+H]$^+$).

Step 3—Synthesis of Compound 35.3: Compound was synthesized using general procedure C to obtain 35.3 (0.220 g, Yield: 90.55%; MS (ES): m/z 427 [M+H]$^+$).

Step 4—Synthesis of Compound 35.5: To a solution of 35.3 (0.500 g, 1.17 mmol, 1.0 eq) in N,N-Dimethyl formamide (5 mL) was added 35.2 (2.0 eq), Potassium carbonate (0.485 g, 3.57 mmol, 3.0 eq), followed by addition of Tetrabutylammonium iodide (0.043 g, 0.117 mmol, 0.1 eq). The reaction was stirred at 110° C. for 48 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 52% ethyl acetate in hexane to obtain pure 35.5.

Step 5—Synthesis of Compound 35.6: To a solution of 35.5 (1.0 eq), in tetrahydrofuran:methanol:water (2:2:1) was added lithium hydroxide (5.0 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 35.6.

Step 6—Synthesis of Compound 35.8: Compound was synthesized as per general method A to obtain 35.8.

Step 7—Synthesis of Compound 35.9: The compound 35.8 was dissolved in dichloromethane. Triflic acid was added to cooled reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 35.9 (MS (ES): m/z 505.27[M+H]$^+$; LCMS purity: 97.48%; HPLC purity: 96.18%; CHIRAL HPLC: 48.61%, 49.47%; $^1$H NMR (DMSO-d$_6$, 400 MHZ): 8.77-8.76 (d, J=6.8 Hz, 1H), 8.71 (s, 1H), 8.53-8.51 (d, J=8.8 Hz, 1H), 8.42-8.41 (d, J=3.6 Hz, 1H), 8.38 (s, 1H), 8.30-8.29 (d, J=4.8 Hz, 1H), 7.33-7.30 (m, 1H), 6.70 (s, 1H), 4.53-4.50 (t, J=6.8 Hz, 2H), 4.43-4.39 (t, J=7.6 Hz, 1H), 3.87-3.82 (m, 1H), 3.55 (bs, 4H), 3.24 (s, 3H), 3.11-3.10 (d, J=4.8 Hz, 3H), 2.85-2.81 (t, J=6.4 Hz, 2H), 1.60-1.50 (m, 3H), 1.24 (bs, 3H), 0.87-0.84 (m, 2H)).

Step 8—Synthesis of Compounds I-54 and I-55: Isomers of 35.9 (0.110 g) were separated out using column CHIRAL PAK OX-H (250×4.6 mm, 5 μm) and 0.1% HEX_IPA_MEOH (50-50) as co-solvent with flow rate of 4 mL/min to get pure fraction-1 (FR-a) and fraction-2 (FR-b).

FR-a was concentrated under reduced pressure at 30° C. to afford pure I-54 (0.030 g; MS (ES): m/z 506.02 [M+H]$^+$; LCMS purity: 95.19%; HPLC purity: 95.05%; CHIRAL HPLC purity: 96.64%; $^1$H NMR (DMSO-d$_6$, 400 MHZ): 8.77-8.76 (d, J=6.8 Hz, 1H), 8.71 (s, 1H), 8.53-8.51 (d, J=8.8 Hz, 1H), 8.42-8.41 (d, J=3.6 Hz, 1H), 8.38 (s, 1H), 8.30-8.29 (d, J=4.8 Hz, 1H), 7.33-7.30 (m, 1H), 6.70 (s, 1H), 4.53-4.50 (t, J=6.8 Hz, 2H), 4.43-4.39 (t, J=7.6 Hz, 1H), 3.87-3.81 (m, 1H), 3.55 (bs, 4H), 3.24 (s, 3H), 3.11-3.10 (d, J=4.8 Hz, 3H), 2.85-2.81 (t, J=6.4 Hz, 2H), 1.60-1.48 (m, 3H), 1.24 (bs, 3H), 0.87-0.84 (m, 2H)).

FR-b was concentrated under reduced pressure at 30° C. to afford pure I-55 (0.030 g; MS (ES): m/z 505.51 [M+H]$^+$; LCMS purity: 99.17%; HPLC purity: 97.79%; CHIRAL HPLC purity: 100%; $^1$H NMR (DMSO-d$_6$, 400 MHZ): 8.77-8.76 (d, J=6.8 Hz, 1H), 8.71 (s, 1H), 8.53-8.50 (d, J=8.8 Hz, 1H), 8.42-8.41 (d, J=3.6 Hz, 1H), 8.38 (s, 1H), 8.30-8.29 (d, J=4.8 Hz, 1H), 7.33-7.29 (m, 1H), 6.70 (s, 1H), 4.53-4.50 (t, J=6.8 Hz, 2H), 4.43-4.39 (t, J=7.6 Hz, 1H), 3.87-3.81 (m, 1H), 3.55 (bs, 4H), 3.24 (s, 3H), 3.11-3.10 (d, J=4.8 Hz, 3H), 2.85-2.81 (t, J=6.4 Hz, 2H), 1.60-1.48 (m, 3H), 1.24 (bs, 3H), 0.87-0.84 (m, 2H)).

Example 36: 5-((1-((1r,3S)-3-Fluorocyclobutyl)-2-oxo-1,2-dihydropyridin-3-yl)amino)-N-((1S,2S)-2-methoxycyclobutyl)-7-(methylamino)pyrazolo[1,5-a]pyrimidine-3-carboxamide (I-56)
And
5-((1-((1r,3R)-3-Fluorocyclobutyl)-2-oxo-1,2-dihydropyridin-3-yl)amino)-N-((1R,2R)-2-methoxycyclobutyl)-7-(methylamino)pyrazolo[1,5-a]pyrimidine-3-carboxamide (I-57)
I-56
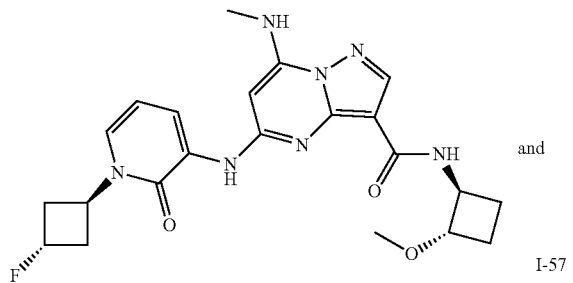
and
I-57
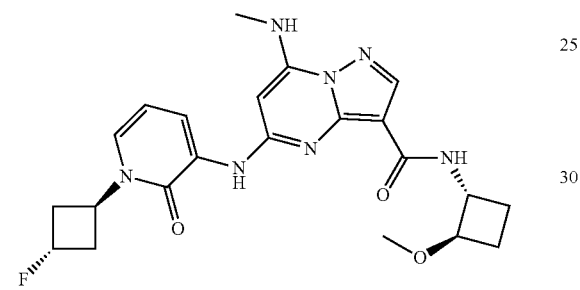
Scheme 36
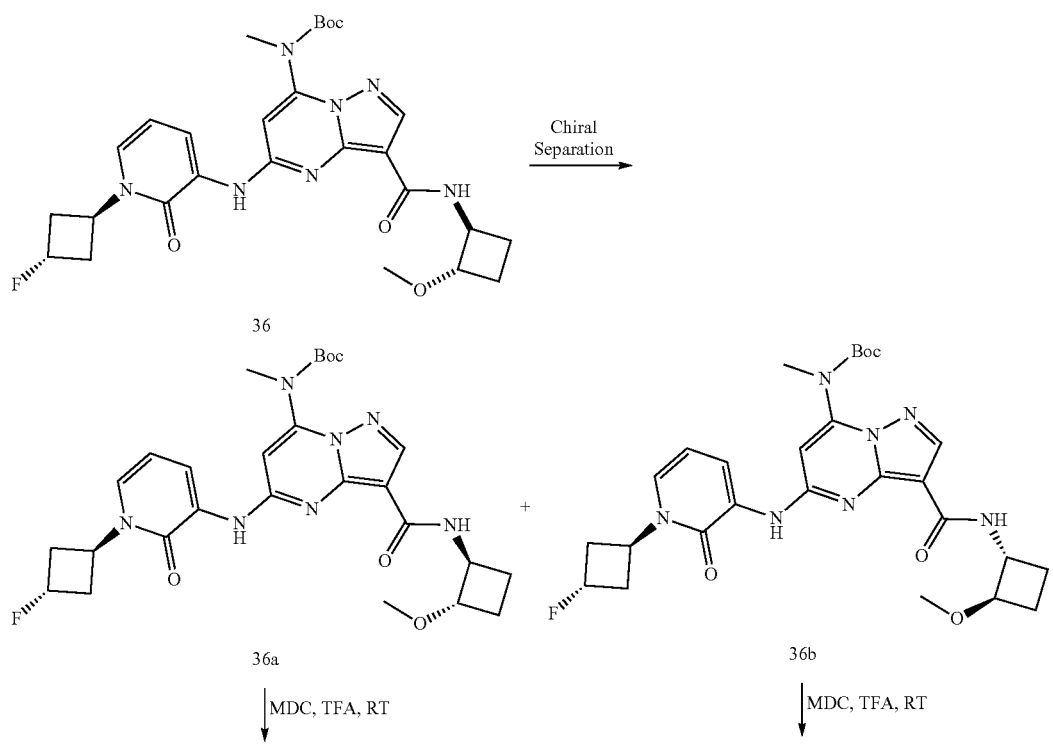

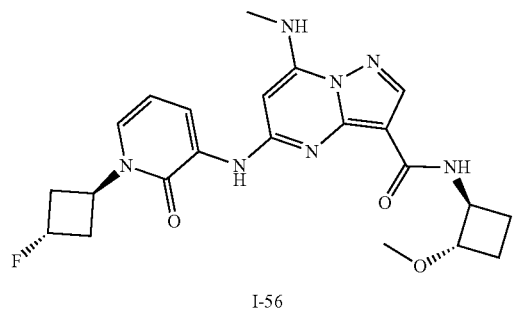

I-56

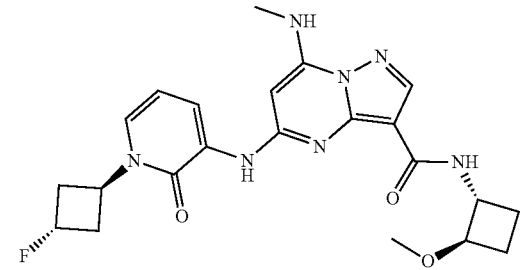

I-57

Step 1—Synthesis of Compound 36: Compound was synthesized as per experimental protocol of I-46 (Example 30) to obtain 36. (Yield: 73.77%; MS (ES): m/z 556.26 [M+H]$^+$).

Step 2—Synthesis of Compounds 36a and 36b: Isomers of 36 (0.110 g) were separated out using column CHIRAL-PAK AD-H (250 mm×4.6 mm, 5 μm) and 0.1% DEA in IPA:ACN (50:50) as co-solvent with flow rate of 4 mL/min to get pure fraction-1 (FR-a) and fraction-2 (FR-b). FR-a was concentrated under reduced pressure at 30° C. to afford pure 36a (0.048 g; MS (ES): m/z 556.26 [M+H]$^+$). FR-b was concentrated under reduced pressure at 30° C. to afford pure 36b (0.045 g; MS (ES): m/z 556.26 [M+H]$^+$).

Step 3—Synthesis of Compound I-56: Compound was synthesized using general procedure C to obtain I-56 (0.025 g, Yield: 63.53%; MS (ES): m/z 456.5 [M+H]$^+$; LCMS purity: 100%; HPLC purity: 99.06%; CHIRAL HPLC purity: 100%; $^1$H NMR (DMSO-d$_6$, 400 MHZ): 8.97 (s, 1H), 8.26-8.24 (d, J=6.8 Hz, 1H), 8.20 (s, 1H), 8.09-8.06 (d, J=9.6 Hz, 1H), 7.95-7.94 (d, J=4.8 Hz, 1H), 7.51-7.50 (d, J=6.8 Hz, 1H), 6.36-6.33 (t, J=7.2 Hz, 1H), 6.22 (s, 1H), 5.45-5.36 (m, 1H), 5.31 (bs, 1H), 4.36-4.30 (m, 1H), 3.73-3.67 (m, 1H), 3.20 (s, 3H), 2.91-2.90 (d, J=4.8 Hz, 3H), 2.83 (bs, 1H), 2.74-2.69 (m, 3H), 2.16-2.03 (m, 2H), 1.55-1.48 (m, 1H), 1.40-1.30 (m, 1H)).

Step 4—Synthesis of Compound I-57: Compound was synthesized using general procedure C to obtain I-57 (0.028 g, Yield: 75.90%; MS (ES): m/z 456.5 [M+H]$^+$; LCMS purity: 100%; HPLC purity: 97.00%; CHIRAL HPLC purity: 98.70%; $^1$H NMR (DMSO-d$_6$, 400 MHZ): 8.96 (s, 1H), 8.25-8.23 (d, J=6.8 Hz, 1H), 8.22 (s, 1H), 8.08-8.05 (d, J=9.6 Hz, 1H), 7.95-7.94 (d, J=4.8 Hz, 1H), 7.51-7.50 (d, J=6.8 Hz, 1H), 6.36-6.33 (t, J=7.2 Hz, 1H), 6.22 (s, 1H), 5.45-5.36 (m, 1H), 5.31 (bs, 1H), 4.36-4.30 (m, 1H), 3.73-3.67 (m, 1H), 3.20 (s, 3H), 2.91-2.90 (d, J=4.8 Hz, 3H), 2.84 (bs, 1H), 2.74-2.69 (m, 3H), 2.16-2.03 (m, 2H), 1.55-1.48 (m, 1H), 1.40-1.30 (m, 1H)).

Example 37: 5-((1-(3,3-Difluorocyclobutyl)-2-oxo-1,2-dihydropyridin-3-yl)amino)-N-((3S,4S)-4-hydroxytetrahydrofuran-3-yl)-7-(methylamino)pyrazolo[1,5-a]pyrimidine-3-carboxamide (I-58)

And 5-((1-(3,3-Difluorocyclobutyl)-2-oxo-1,2-dihydropyridin-3-yl)amino)-N-((3R,4R)-4-hydroxytetrahydrofuran-3-yl)-7-(methylamino)pyrazolo[1,5-a]pyrimidine-3-carboxamide (I-59)

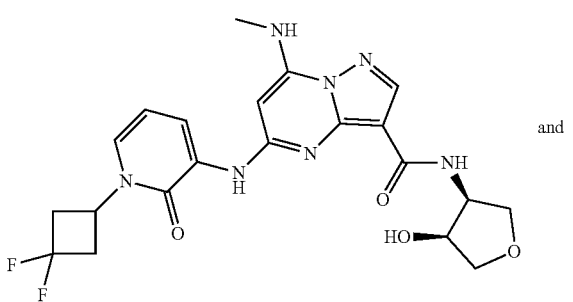

I-58 and

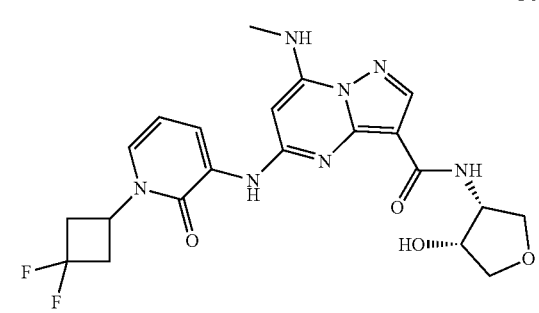

I-59

Scheme 37
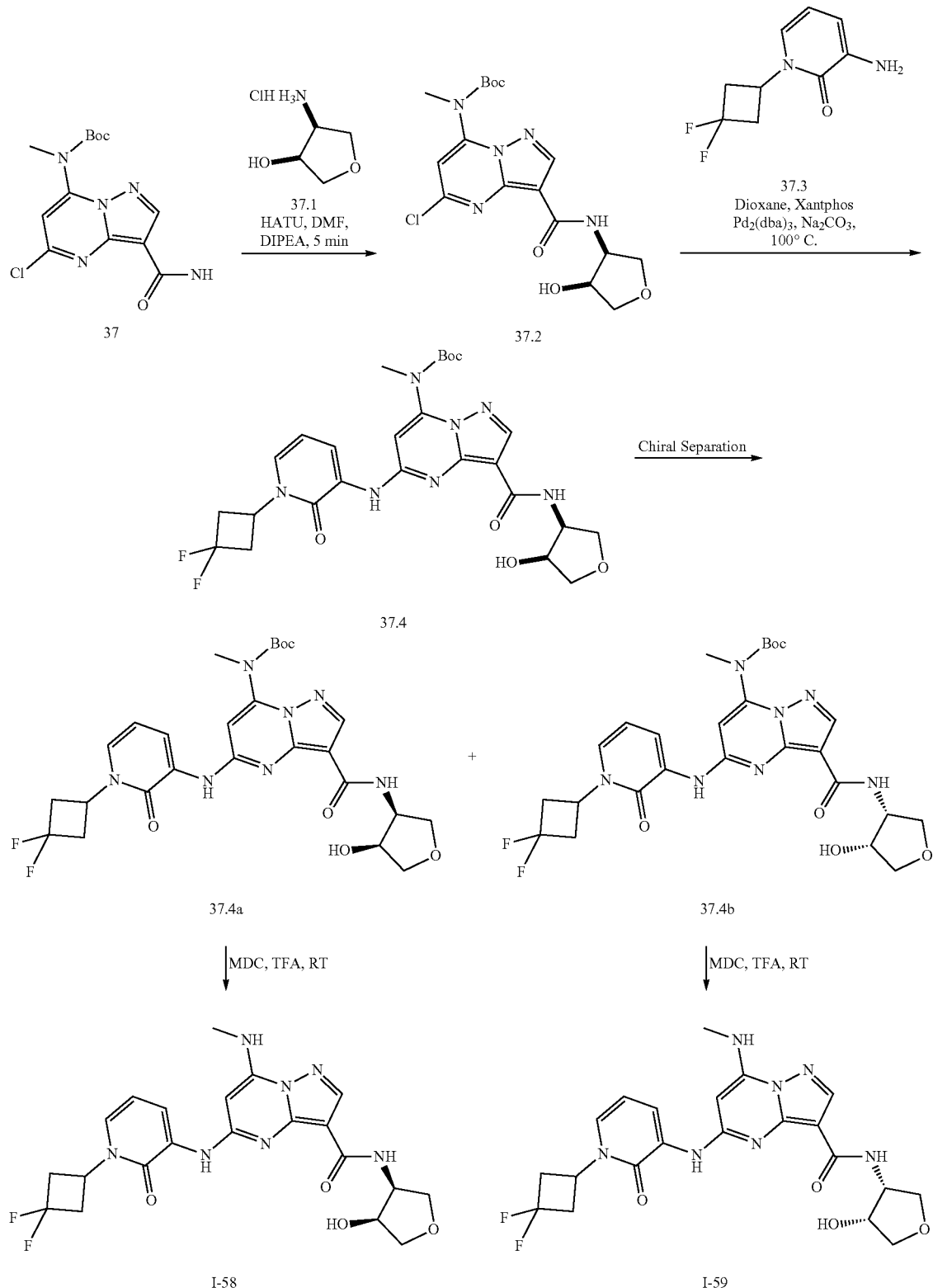
Step 1—Synthesis of Compound 37: Compound was synthesized using general procedure of Core A synthesis to obtain 37 (Yield: 71.67%; MS (ES): m/z 327.08 [M+H]$^+$).
Step 2—Synthesis of Compound 37.2: Compound was synthesized as per general method A to obtain 37.2. (2.1 g, 83.30%; MS (ES): 412.13 [M+H]$^+$).

Step 3—Synthesis of Compound 37.3: Compound was synthesized as per experimental protocol of I-33 (Example 22) to obtain 37.3.

Step 4—Synthesis of Compound 37.4: Compound was synthesized using general procedure B to obtain 37.4 (Yield: 67.74%; MS (ES): 576.23 [M+H]+).

Step 4—Synthesis of Compounds 37.4a and 37.4b: Isomers of 37.4 (0.102 g) were separated out using column CHIRALPAK AD-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 37.4a (0.041 g; MS (ES): m/z 576.23 [M+H]+). FR-b was concentrated under reduced pressure at 30° C. to afford pure 37.4b (0.044 g; MS (ES): m/z 576.23 [M+H]+).

Step 3—Synthesis of Compound I-58: Compound was synthesized using general procedure C to obtain I-58 (0.025 g, Yield: 76.89%; MS (ES): 476.41 [M+H]+; LCMS purity: 100%; HPLC purity: 97.55%; CHIRAL HPLC: 99.17%; $^1$H NMR (DMSO-$d_6$, 400 MHZ): 8.90 (s, 1H), 8.48-8.46 (d, J=7.2 Hz, 1H), 8.23 (s, 1H), 7.92-7.90 (d, J=4.8 Hz, 1H), 7.86-7.84 (d, J=8.8 Hz, 1H), 7.42-7.40 (d, J=6.8 Hz, 1H), 6.40-6.36 (t, J=7.2 Hz, 1H), 6.29 (s, 1H), 5.59 (bs, 1H), 4.94-4.89 (m, 1H), 4.62-4.56 (m, 1H), 4.21 (bs, 1H), 4.02-3.99 (m, 2H), 3.74-3.72 (m, 1H), 3.23-3.18 (m, 3H), 2.91-2.90 (d, J=4.8 Hz, 3H), 2.10 (s, 1H), 1.24 (s, 1H)).

Step 4—Synthesis of Compound I-59: Compound was synthesized using general procedure C to obtain I-59 (0.026 g, Yield: 71.53%; MS (ES): 476.46 [M+H]+; LCMS purity: 98.30%; HPLC purity: 97.54%; CHIRAL HPLC: 97.62%; $^1$H NMR (DMSO-$d_6$, 400 MHZ): 8.90 (s, 1H), 8.48-8.46 (d, J=7.2 Hz, 1H), 8.23 (s, 1H), 7.92-7.90 (d, J=4.8 Hz, 1H), 7.86-7.84 (d, J=8.8 Hz, 1H), 7.41-7.40 (d, J=6.8 Hz, 1H), 6.40-6.36 (t, J=7.2 Hz, 1H), 6.29 (s, 1H), 5.59 (bs, 1H), 4.94-4.89 (m, 1H), 4.62-4.58 (m, 1H), 4.21 (bs, 1H), 4.02-3.99 (m, 2H), 3.74-3.72 (m, 1H), 3.23-3.18 (m, 3H), 2.91-2.90 (d, J=4.8 Hz, 3H), 2.10 (s, 1H), 1.24 (s, 1H)).

Example 38: N-((3S,4S)-4-Hydroxytetrahydrofuran-3-yl)-7-(methylamino)-5-(1-((S)-tetrahydro-2H-pyran-3-yl)-1H-pyrrolo[2,3-b]pyridin-3-yl)pyrazolo[1,5-a]pyrimidine-3-carboxamide (I-60)

And

N-((3R,4R)-4-Hydroxytetrahydrofuran-3-yl)-7-(methylamino)-5-(1-((S)-tetrahydro-2H-pyran-3-yl)-1H-pyrrolo[2,3-b]pyridin-3-yl)pyrazolo[1,5-a]pyrimidine-3-carboxamide (I-61)

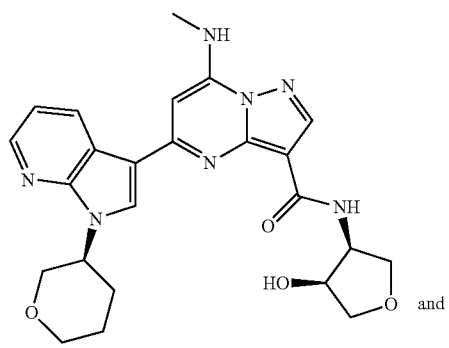

I-60

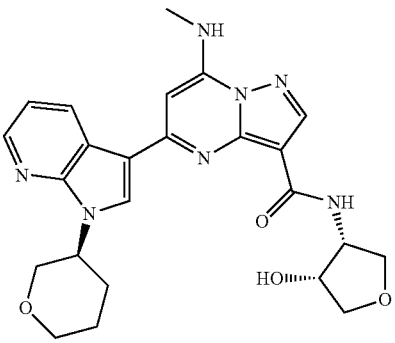

I-61

Scheme 38

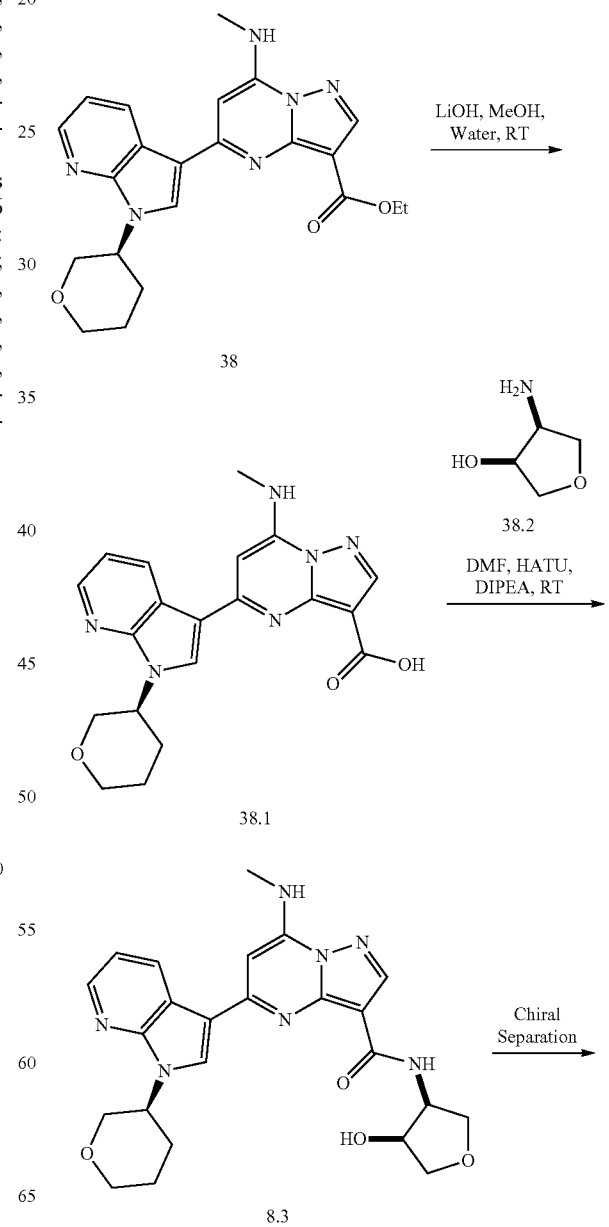

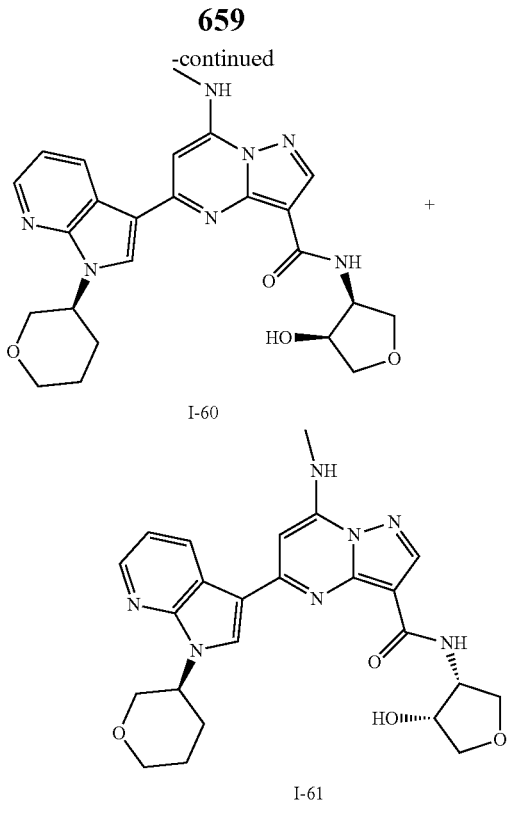

Step 1—Synthesis of Compound 38: Compound was synthesized as per experimental protocol of I-14/15 (Example 12) to obtain 38.

Step 2—Synthesis of Compound 38.1: To a solution of 38 (0.4 g, 0.956 mmol, 1.0 eq) in methanol:water (8 mL, 2:1) was added lithium hydroxide (0.219 g, 9.56 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 38.1 (0.340 g, Yield: 91.08%; MS (ES): m/z 393.16 [M+H]$^+$).

Step 3—Synthesis of Compound 38.3: Compound was synthesized using general procedure A to obtain 38.3 (0.120 g, Yield: 88.72%; MS (ES): m/z 462.77 [M+H]$^+$; LCMS purity: 98.94%; HPLC purity: 98.02%; CHIRAL HPLC: 47.81%, 49.84%; $^1$H NMR (DMSO-d$_6$, 400 MHZ): 9.04-9.02 (d, J=8.4 Hz, 1H), 8.82-8.81 (d, J=3.6 Hz, 1H), 8.68-8.64 (t, J=7.6 Hz, 1H), 8.41-8.40 (d, J=4 Hz, 1H), 8.37 (s, 1H), 8.27-8.26 (d, J=4.4 Hz, 1H), 7.34-7.31 (m, 1H), 6.75 (s, 1H), 4.97 (bs, 1H), 4.60 (bs, 1H), 4.44 (bs, 1H), 4.04 (bs, 1H), 3.98-3.95 (d, J=10.8 Hz, 1H), 3.75-3.72 (d, J=10.4 Hz, 1H), 3.46 (s, 1H), 3.15-3.014 (d, J=4.4 Hz, 4H), 2.22 (bs, 4H), 1.86 (bs, 3H), 1.28-1.25 (m, 1H)).

Step 4—Synthesis of Compounds I-60 and I-61: Isomers of 38.3 (0.110 g) were separated out using column CHIRALPAK AD-H (250 mm×4.6 mm, 5 μm) 0.1% DEA in methanol to get pure fraction-1 (FR-a) and fraction-2 (FR-b).

FR-a was concentrated under reduced pressure at 30° C. to afford pure I-60 (0.035 g; MS (ES): m/z 477.53 [M+H]$^+$; LCMS purity: 100%; HPLC purity: 99.77%; CHIRAL HPLC purity: 100%; $^1$H NMR (DMSO-d6, 400 MHZ): 8.94-8.92 (d, J=7.6 Hz, 1H), 8.78 (s, 1H), 8.49-8.47 (t, J=7.6 Hz, 1H), 8.39 (s, 1H), 8.29-8.28 (d, J=4 Hz, 1H), 7.31-7.28 (m, 1H), 6.74 (s, 1H), 5.72-5.71 (d, J=4.4 Hz, 1H), 5.71-5.68 (m, 1H), 4.96 (bs, 1H), 4.59-4.55 (m, 1H), 4.33 (bs, 1H), 4.06-3.98 (m, 3H), 3.76-3.69 (m, 2H), 3.57-3.54 (m, 2H), 3.15-3.13 (d, J=4.4 Hz, 3H), 3.02 (s, 1H), 2.21 (bs, 1H), 1.86 (bs, 3H)).

FR-b was concentrated under reduced pressure at 30° C. to afford pure I-61 (0.034 g; MS (ES): m/z 478.66 [M+H]$^+$; LCMS purity: 100%; HPLC purity: 95.20%; CHIRAL HPLC purity: 95.00%; $^1$H NMR (DMSO-d$_6$, 400 MHZ): 8.95-8.93 (d, J=7.6 Hz, 1H), 8.77 (s, 1H), 8.48-8.46 (t, J=7.6 Hz, 1H), 8.39 (s, 1H), 8.29-8.28 (d, J=4 Hz, 1H), 7.31-7.27 (m, 1H), 6.74 (s, 1H), 5.72-5.71 (d, J=4.4 Hz, 1H), 5.71-5.68 (m, 1H), 4.96 (bs, 1H), 4.59-4.55 (m, 1H), 4.33 (bs, 1H), 4.06-3.98 (m, 3H), 3.76-3.69 (m, 2H), 3.57-3.54 (m, 2H), 3.15-3.13 (d, J=4.4 Hz, 3H), 3.02 (s, 1H), 2.21 (bs, 1H), 1.86 (bs, 3H)).

Example 39: 5-((1-(3,3-Difluorocyclobutyl)-2-oxo-1,2-dihydropyridin-3-yl)amino)-N-((1R,3R)-3-hydroxycyclohexyl)-7-(methylamino)pyrazolo[1,5-a]pyrimidine-3-carboxamide (I-62)

And 5-((1-(3,3-Difluorocyclobutyl)-2-oxo-1,2-dihydropyridin-3-yl)amino)-N-((1S,3S)-3-hydroxycyclohexyl)-7-(methylamino)pyrazolo[1,5-a]pyrimidine-3-carboxamide (I-63)

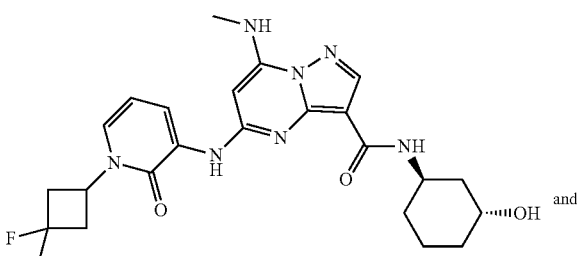

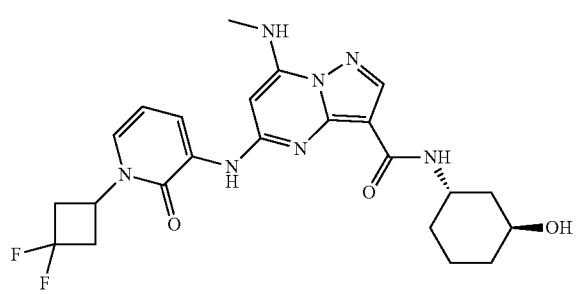

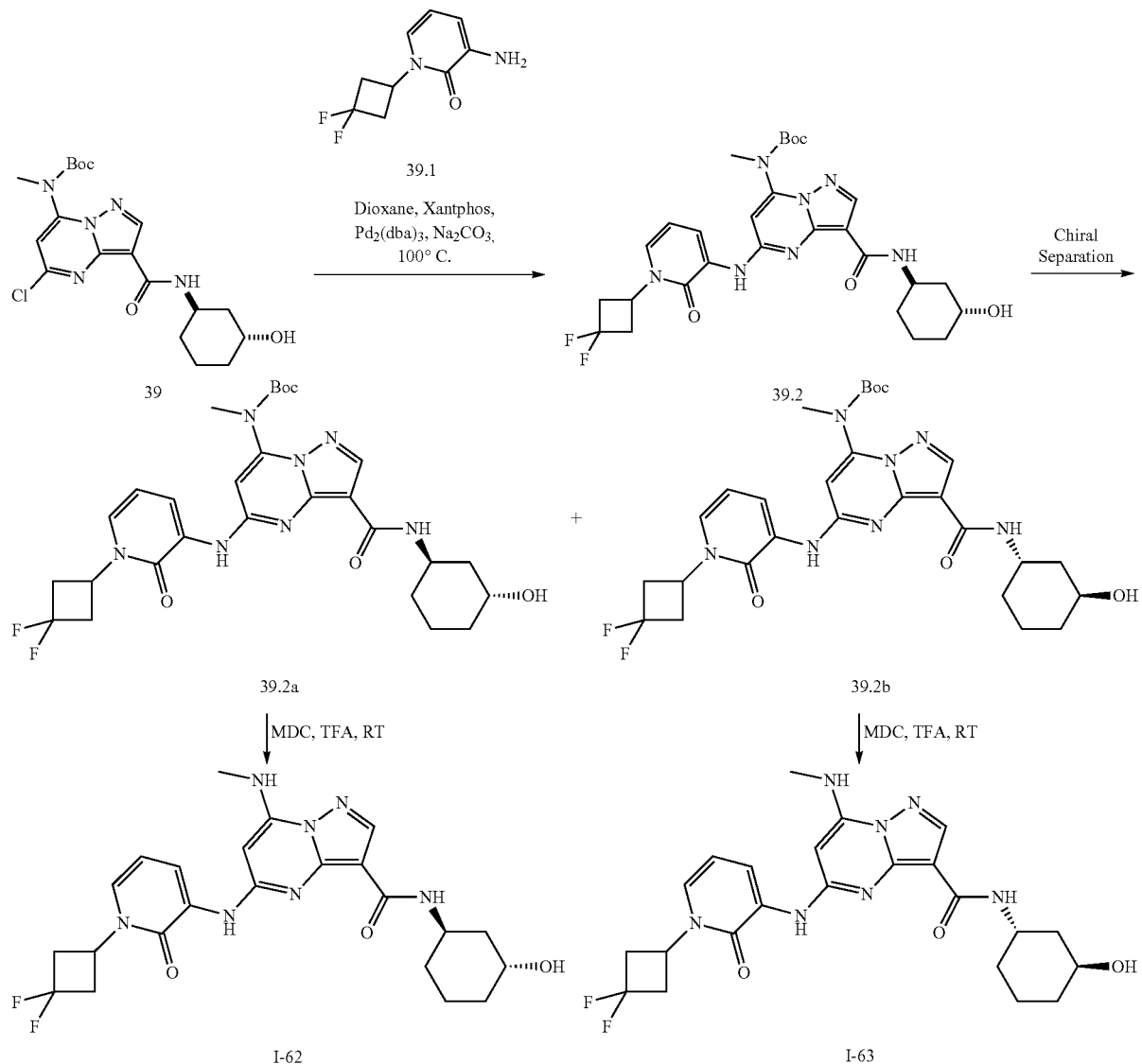

Scheme 39

Step 1—Synthesis of Compound 39: Compound was synthesized from Core A utilizing general method A to obtain 39.

Step 1—Synthesis of Compound 39.1: Compound was synthesized as per experimental protocol of I-33 (Example 22) to obtain 39.1.

Step 1—Synthesis of Compound 39.2: Compound was synthesized using general procedure B to obtain 39.2 (Yield: 75.02%; MS (ES): m/z 588.27 [M+H]$^+$).

Step 2—Synthesis of Compounds 39.2a and 39.2b: Isomers of 39.2 (0.116 g) were separated out using column CHIRALPAK OX-H (250 mm×4.6 mm, 5 µm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 39.2a (0.041 g; MS (ES): m/z 588.27 [M+H]$^+$). FR-b was concentrated under reduced pressure at 30° C. to afford pure 39.2b (0.039 g; MS (ES): m/z 588.27 [M+H]$^+$).

Step 3—Synthesis of Compound I-62: Compound was synthesized using general procedure C to obtain I-62 (0.027 g, 79.38%; MS (ES): 488.87 [M+H]$^+$; LCMS purity: 95.10%; HPLC purity: 98.23%; CHIRAL HPLC purity: 95.00%; $^1$H NMR (DMSO-d$_6$, 400 MHZ): 8.96 (s, 1H), 8.24-8.22 (d, J=6.4 Hz, 1H), 8.19 (s, 1H), 7.93-7.92 (d, J=4.4 Hz, 1H), 7.56-7.53 (d, J=8 Hz, 1H), 7.45-7.44 (d, J=6.8 Hz, 1H), 6.33-6.30 (t, J=7.2 Hz, 1H), 6.24 (s, 1H), 4.90 (bs, 1H), 4.55 (bs, 1H), 4.24 (bs, 1H), 3.98 (bs, 1H), 3.25-3.21 (m, 3H), 2.91-2.89 (d, J=4.8 Hz, 3H), 1.88 (bs, 2H), 1.75 (bs, 1H), 1.57 (bs, 1H), 1.45-1.42 (d, J=12.8 Hz, 3H), 1.24 (bs, 2H)).

Step 4—Synthesis of Compound I-63: Compound was synthesized using general procedure C to obtain I-63 (0.026 g, Yield: 82.36%; MS (ES): m/z 488.87 [M+H]$^+$; LCMS purity: 95.04%; HPLC purity: 96.29%; CHIRAL HPLC purity: 95.33%; $^1$H NMR (DMSO-d$_6$, 400 MHZ): 8.95 (s, 1H), 8.24-8.22 (d, J=6.4 Hz, 1H), 8.19 (s, 1H), 7.93-7.92 (d, J=4.4 Hz, 1H), 7.56-7.53 (d, J=8 Hz, 1H), 7.45-7.44 (d, J=6.8 Hz, 2H), 6.33-6.29 (t, J=7.2 Hz, 1H), 6.24 (s, 1H), 4.92-4.89 (m, 1H), 4.56-4.55 (d, J=3.2 Hz, 1H), 4.24 (bs, 1H), 3.98 (bs, 1H), 3.25-3.21 (m, 3H), 2.91-2.89 (d, J=4.8 Hz, 3H), 1.88 (bs, 2H), 1.75 (bs, 1H), 1.57 (bs, 1H), 1.45-1.42 (d, J=12.8 Hz, 2H), 1.24 (bs, 2H)).

Example 40: N-((1R,3R)-3-Hydroxycyclohexyl)-7-(methylamino)-5-(1-(tetrahydro-2H-pyran-4-yl)-1H-pyrrolo[2,3-b]pyridin-3-yl)pyrazolo[1,5-a]pyrimidine-3-carboxamide (I-64)
And
N-((1S,3S)-3-Hydroxycyclohexyl)-7-(methylamino)-5-(1-(tetrahydro-2H-pyran-4-yl)-1H-pyrrolo[2,3-b]pyridin-3-yl)pyrazolo[1,5-a]pyrimidine-3-carboxamide (I-65)
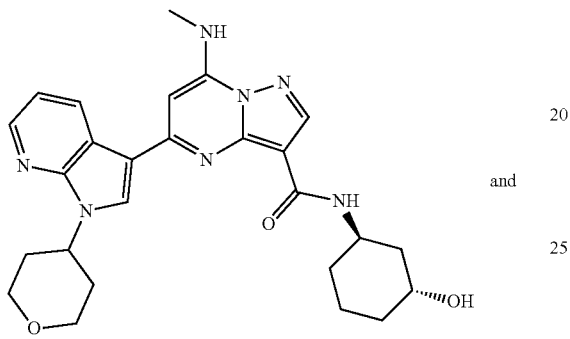
I-64
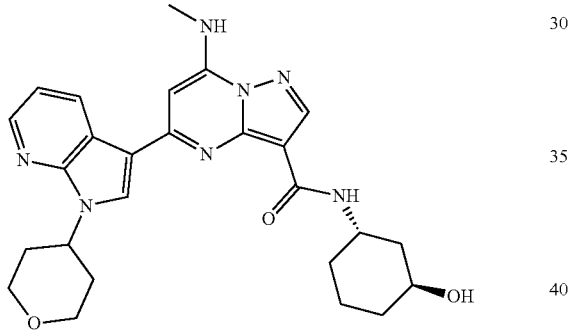
I-65
Scheme 40
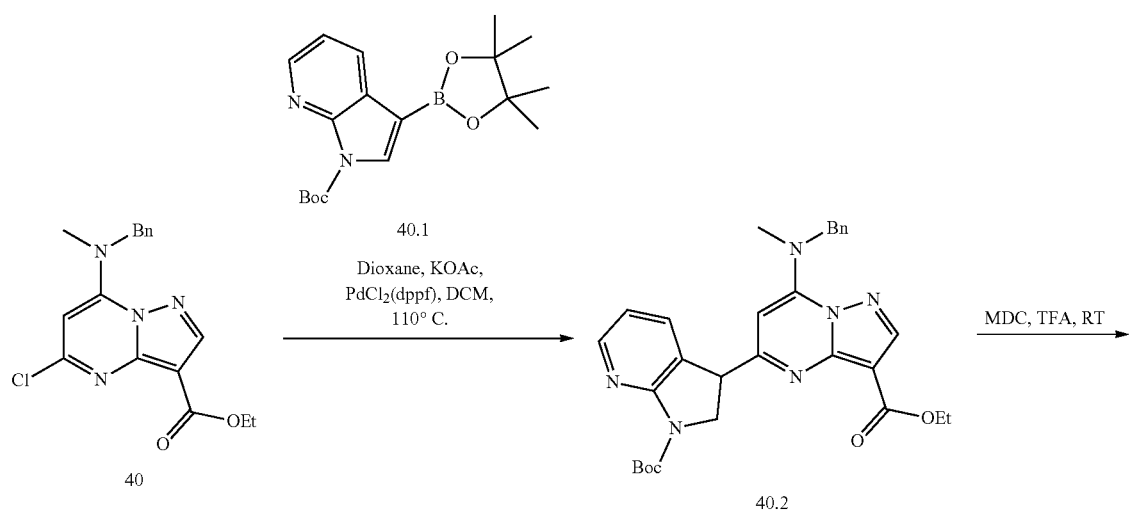

-continued
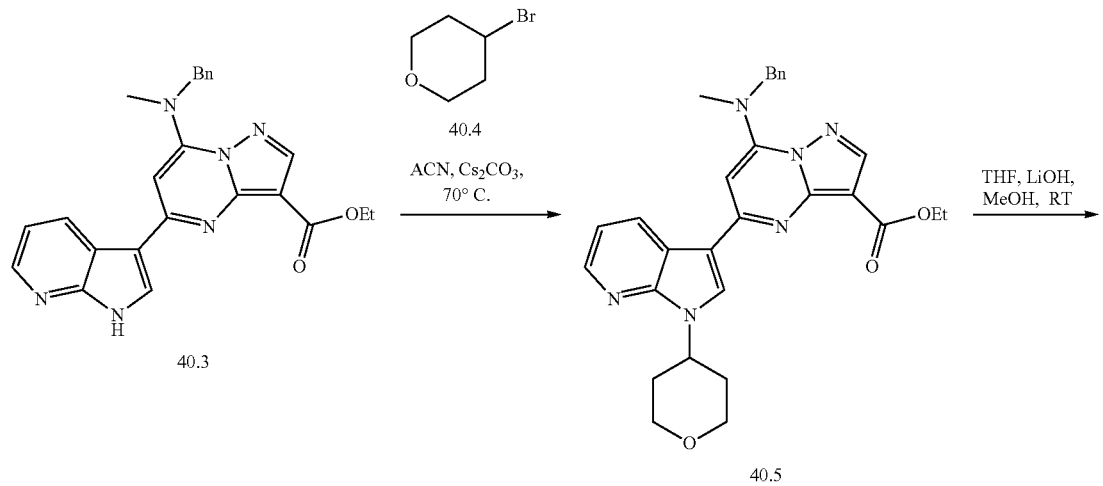
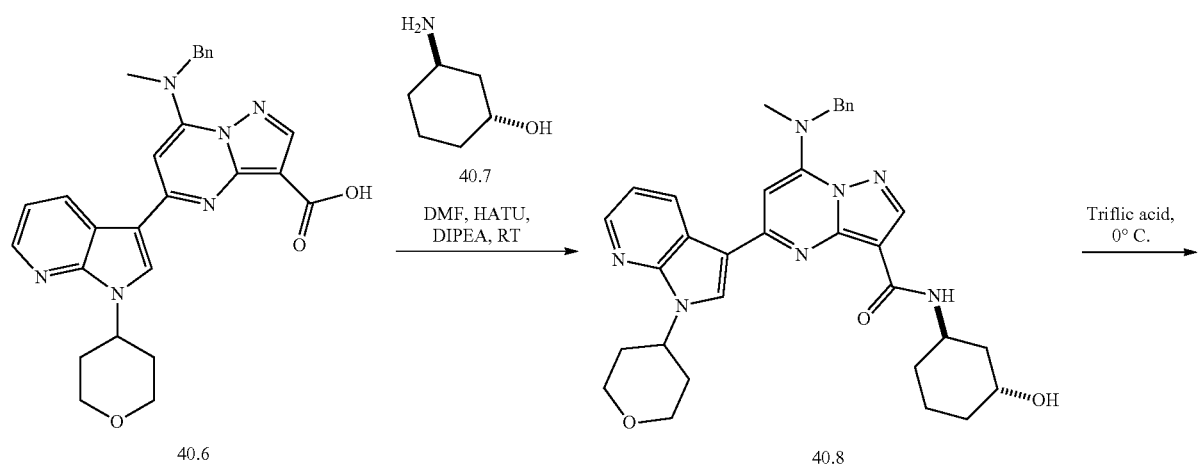
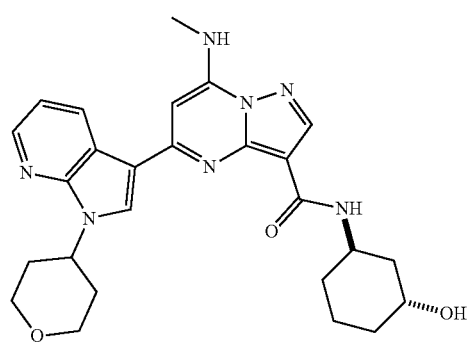
40.9
Chiral Separation

-continued

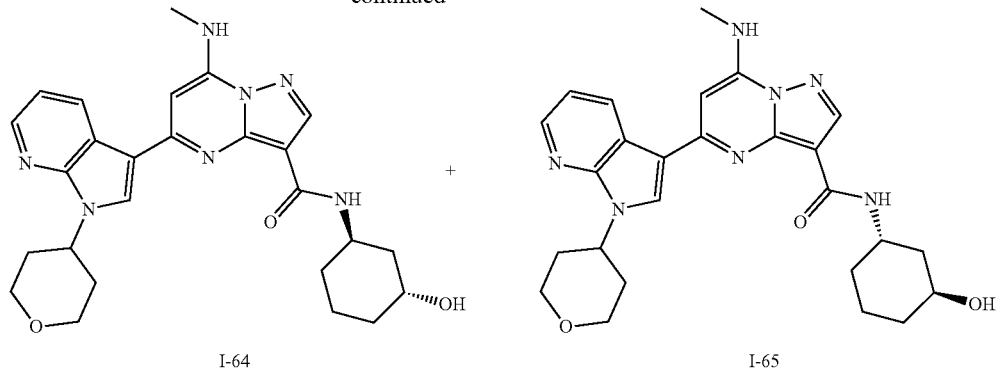

I-64 +

I-65

Step 1—Synthesis of Compound 40: Compound was synthesized using general procedure of core B synthesis to obtain 40 (26 g, Yield: 62.21%; MS (ES): m/z 355 [M+H]$^+$).

Step 2—Synthesis of Compound 40.2: To a solution of 40 (0.1 g, 0.290 mmol, 1.0 eq), in dioxane (5 mL) were added 40.1 (0.129 g, 0.377 mmol, 1.3 eq) and sodium carbonate (0.076 g, 0.725 mmol 2.5 eq). The reaction mixture was degassed for 10 min under argon atmosphere, then [1,1'-Bis (diphenylphosphino)ferrocene] dichloropalladium (II), complex with dichloromethane (0.028 g, 0.029 mmol 0.1 eq) was added, again degassed for 5 min. The reaction was stirred at 100° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using eluted in 25% ethyl acetate in hexane to obtain pure 40.2 (0.083 g, Yield: 54.35%; MS (ES): m/z 527 [M+H]$^+$).

Step 3—Synthesis of Compound 40.3: Compound was synthesized using general procedure C to obtain 40.3 (0.220 g, Yield: 90.55%; MS (ES): m/z 427 [M+H]$^+$).

Step 4—Synthesis of Compound 40.5: To a cooled solution of 40.3 (0.5 g, 1.17 mmol, 1.0 eq), and 40.4 (0.386 g, 2.34 mmol, 1.2 eq) in Acetonitrile (15 mL) at 0° C. was added Cesium carbonate (0.9 g, 2.92 mmol, 2.5 eq). The reaction was stirred at 70° C. for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 40.5 (0.150 g, Yield: 25.06%; MS (ES): m/z 511.24 [M+H]$^+$).

Step 5—Synthesis of Compound 40.6: To a solution of 40.5 (0.150 g, 0.29 mmol, 1.0 eq), in methanol:tetrahydrofuran (4 mL, 2:1) was added lithium hydroxide (0.069 g, 2.9 mmol, 10 eq). The reaction was stirred at 60° C. for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 40.6 (0.140 g, Yield: 98.76%; MS (ES): m/z 483.21 [M+H]$^+$).

Step 6—Synthesis of Compound 40.8: Compound was synthesized using general procedure A to obtain 40.8 (0.15 g, Yield: 62.64%; MS (ES): 590.70 [M+H]$^+$).

Step 7—Synthesis of Compound 40.9: Solution of 40.8 (0.040 g, 0.067 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 40.9 (0.025 g, Yield: 75.28%; MS (ES): m/z 490.18 [M+H]$^+$; LCMS purity: 100%; HPLC purity: 98.65%; CHIRAL HPLC: 50.40%, 47.94%; $^1$H NMR (DMSO-d$_6$, 400 MHz): 8.84 (s, 1H), 8.74-8.72 (d, J=6.8 Hz, 1H), 8.41-8.40 (d, J=3.2 Hz, 1H), 8.35 (s, 1H), 8.25-8.24 (d, J=4.8 Hz, 1H), 8.04-8.01 (d, J=8.4 Hz, 1H), 7.29-7.26 (m, 1H) 6.79 (s, 1H), 5.12-5.06 (t, J=11.6 Hz, 1H), 4.58 (s, 1H), 4.31 (s, 1H), 4.08-4.01 (m, 3H), 3.65-3.59 (t, J=11.6 Hz, 2H), 3.11-3.10 (d, J=4.4 Hz, 3H), 2.21-2.18 (m, 3H), 2.01-1.92 (m, 4H), 1.77-1.74 (m, 2H), 1.39-1.22 (m, 3H)).

Step 8—Synthesis of Compounds I-64 and I-65: Isomers of 40.9 (0.095 g) were separated out using column CHIRAL PAK OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure I-64 (0.030 g; MS (ES): m/z 490.82 [M+H]$^+$; LCMS purity: 100%; HPLC purity: 99.27%; CHIRAL HPLC purity: 99.39%; $^1$H NMR (DMSO-d$_6$, 400 MHZ): 8.82 (s, 1H), 8.73-8.72 (d, J=6.8 Hz, 1H), 8.40-8.39 (d, J=3.2 Hz, 1H), 8.32 (s, 1H), 8.23-8.22 (d, J=4.8 Hz, 1H), 8.02-8.01 (d, J=8.4 Hz, 1H), 7.28-7.25 (m, 1H) 6.78 (s, 1H), 5.11-5.05 (m, 1H), 4.56 (bs, 1H), 4.31 (bs, 1H), 4.07-4.01 (m, 3H), 3.64-3.58 (t, J=11.6 Hz, 2H), 3.10-3.09 (d, J=4.4 Hz, 3H), 2.85-2.80 (m, 1H), 2.24-2.16 (m, 2H), 1.76 (bs, 1H), 1.58 (bs, 5H), 1.22 (bs, 1H), 1.14-1.11 (t, J=7.2 Hz, 2H)).

FR-b was concentrated under reduced pressure at 30° C. to afford pure I-65 (0.030 g; MS (ES): m/z 490.82 [M+H]$^+$; LCMS purity: 99.29%; HPLC purity: 98.90%; CHIRAL HPLC purity: 100%; $^1$H NMR (DMSO-d$_6$, 400 MHZ): 8.82 (s, 1H), 8.74-8.72 (d, J=6.8 Hz, 1H), 8.40-8.39 (d, J=3.2 Hz, 1H), 8.35 (s, 1H), 8.23-8.22 (d, J=4.8 Hz, 1H), 8.02-8.01 (d, J=8.4 Hz, 1H), 7.28-7.25 (m, 1H) 6.78 (s, 1H), 5.11-5.05 (m, 1H), 4.55 (bs, 1H), 4.30 (bs, 1H), 4.07-4.00 (m, 3H), 3.64-3.58 (t, J=11.6 Hz, 2H), 3.10-3.09 (d, J=4.4 Hz, 3H), 2.85-2.80 (m, 1H), 2.24-2.16 (m, 2H), 1.76 (bs, 1H), 1.58 (bs, 5H), 1.22 (bs, 1H), 1.14-1.11 (t, J=7.2 Hz, 2H)).

Example 41: 5-((1-((1r,3R)-3-Fluorocyclobutyl)-2-oxo-1,2-dihydropyridin-3-yl)amino)-N-(3-methoxycyclopentyl)-7-(methylamino)pyrazolo[1,5-a]pyrimidine-3-carboxamide (I-66)

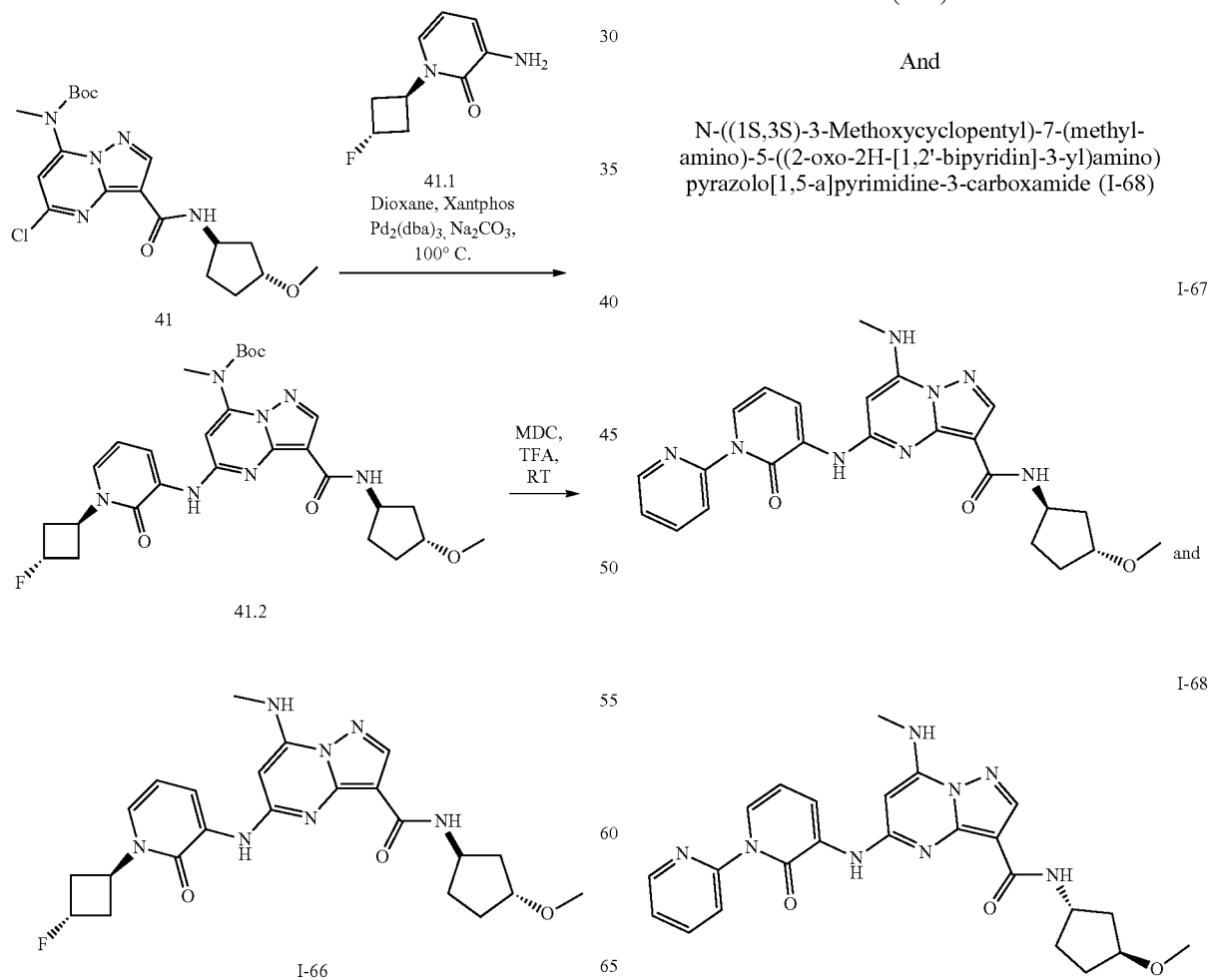

Step 1—Synthesis of Compound 41: Compound was synthesized from Core A utilizing general method A to obtain 41. (Yield: 51.57%; MS (ES): m/z 424.17 [M+H]$^+$).

Step 2—Synthesis of Compound 41.1: Compound was synthesized as per experimental protocol of I-7 (Example 6) to obtain 41.1 (Yield: 98.46%; MS (ES): m/z 183.09 [M+H]$^+$).

Step 3—Synthesis of Compound 41.2: Compound was synthesized using general procedure B to obtain 41.2. (0.135 g, Yield: 66.97%; MS (ES): m/z 570.28 [M+H]$^+$).

Step 4—Synthesis of Compound I-66: Compound was synthesized using general procedure C to obtain I-66 (0.028 g, Yield: 84.93%; MS (ES): 470.23 [M+H]$^+$; LCMS purity: 96.00%; HPLC purity: 97.52%; CHIRAL HPLC: 49.07%, 48.34%; $^1$H NMR (DMSO-d$_6$, 400 MHZ): 8.92 (s, 1H), 8.21 (s, 1H), 8.19 (s, 1H), 7.93-7.92 (d, J=4.4 Hz, 1H), 7.67-7.66 (d, J=6 Hz, 1H), 7.49-7.47 (d, J=6.8 Hz, 1H), 6.31-6.27 (t, J=6.8 Hz, 1H), 6.22 (s, 1H), 5.45-5.37 (m, 1H), 5.31 (bs, 1H), 4.38-4.32 (m, 1H), 3.88 (bs, 1H), 3.20 (s, 3H), 2.91-2.89 (d, J=4.8 Hz, 3H), 2.74-2.68 (m, 4H). 2.12 (bs, 2H), 1.99-1.95 (m, 1H), 1.65 (bs, 2H), 1.45-1.38 (m, 1H)).

Example 42: N-((1R,3R)-3-Methoxycyclopentyl)-7-(methylamino)-5-((2-oxo-2H-[1,2'-bipyridin]-3-yl)amino)pyrazolo[1,5-a]pyrimidine-3-carboxamide (I-67)

And

N-((1S,3S)-3-Methoxycyclopentyl)-7-(methylamino)-5-((2-oxo-2H-[1,2'-bipyridin]-3-yl)amino)pyrazolo[1,5-a]pyrimidine-3-carboxamide (I-68)

Scheme 42
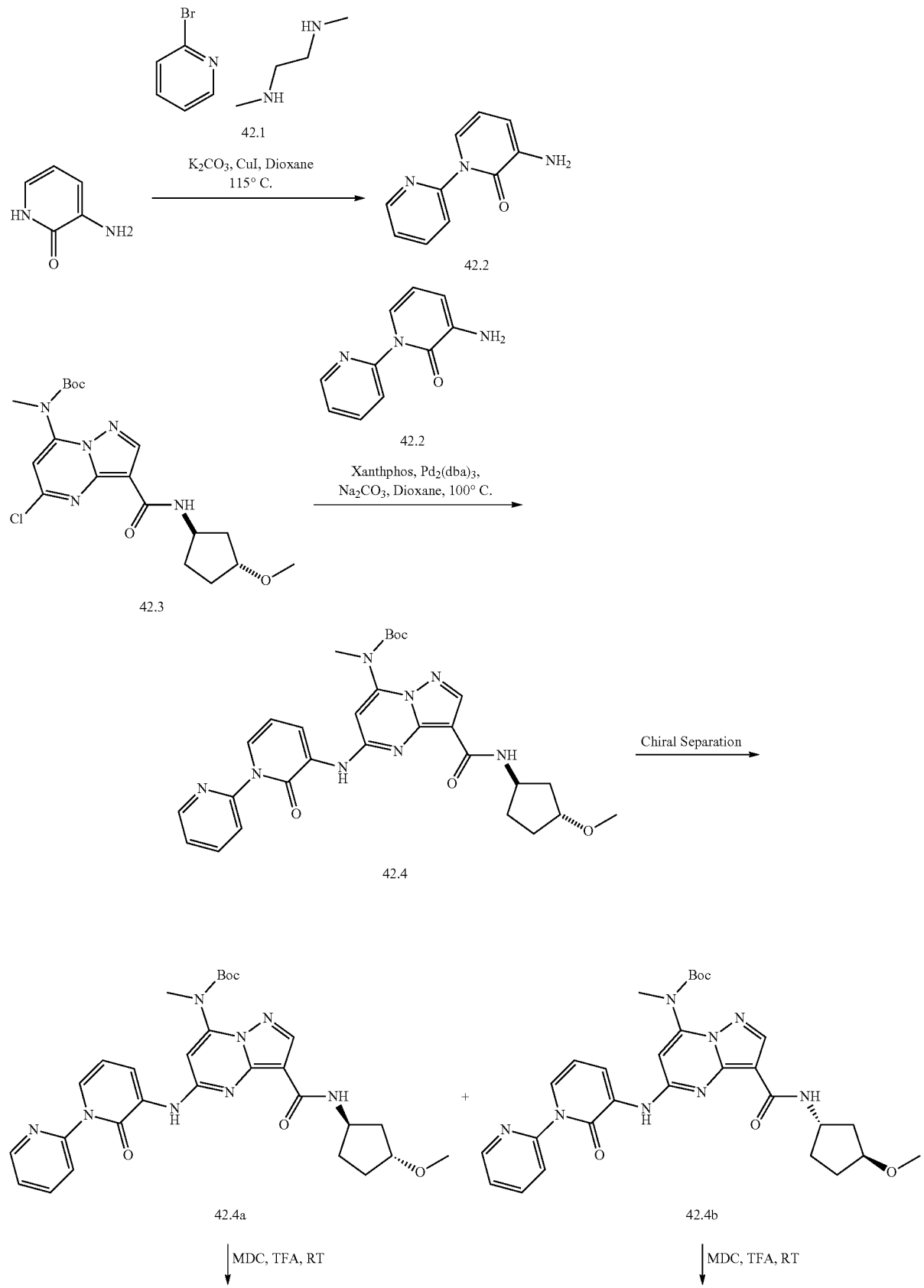

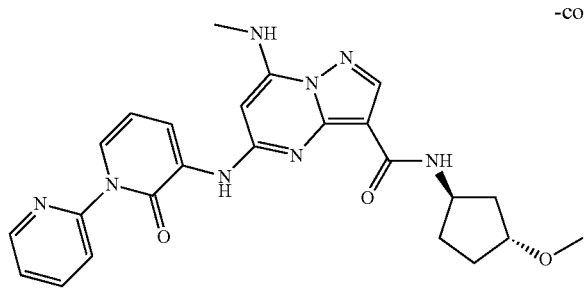

I-67

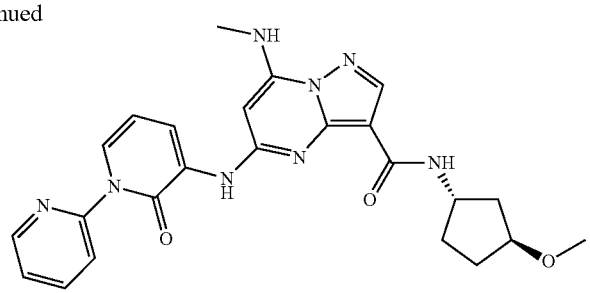

I-68

-continued

Step 1—Synthesis of Compound 42.2: To a solution of 42 (2 g, 18.18 mmol, 1.0 eq) in 1,4-dioxane (40 mL) 42.1 (7.2 g, 45.45 mmol, 2.5 eq) was added. The reaction mixture was degassed for 10 min under argon atmosphere followed by addition of potassium carbonate (7.5 g, 54.54 mmol, 3.0 eq), N,N-dimethylethylenediamine (0.640 g, 7.27 mmol, 0.4 eq), and copper iodide (0.692 g, 3.636 mmol, 0.2 eq). The reaction mixture was heated at 110° C. for 12 h. After completion of reaction, reaction mixture was transferred to ice cold water and product was extracted with ethyl acetate. Organic layer was combined, washed with brine solution, dried over sodium sulphate and concentrated under reduced pressure to obtain crude material. This was further purified by 3% methanol in dichloromethane to obtain 38.2 (2 g, Yield: 58.82%; MS (ES): m/z 188.20 [M+H]$^+$).

Step 2—Synthesis of Compound 42.3: Compound was synthesized from Core A utilizing general method A to obtain 42.3.

Step 3—Synthesis of Compound 42.4: Compound was synthesized using general procedure B to obtain (Yield: 69.83%; MS (ES): m/z 575.27 [M+H]$^+$).

Step 4—Synthesis of Compounds 42.4a and 42.4b: Isomers of 42 (0.105 g) were separated out using column CHIRALCEL OJ-H (250 mm×4.6 mm, 5 µm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 42.4a (0.039 g; MS (ES): m/z 575.27 [M+H]$^+$). FR-b was concentrated under reduced pressure at 30° C. to afford pure 42.4b (0.044 g; MS (ES): m/z 575.27 [M+H]$^+$).

Step 5—Synthesis of Compound I-67: Compound was synthesized using general procedure C to obtain I-67 (0.030 g, Yield: 93.15%; MS (ES): m/z 475.56 [M+H]$^+$; LCMS purity: 100%; HPLC purity: 99.90%; CHIRAL HPLC purity: 99.34%; $^1$H NMR (DMSO-d$_6$, 400 MHZ): 9.00 (s, 1H), 8.66-8.65 (d, J=4 Hz, 1H), 8.31-8.29 (d, J=6.8 Hz, 1H), 8.21 (s, 1H), 8.08-8.04 (t, J=6.8 Hz, 1H), 7.95-7.94 (d, J=4.8 Hz, 1H), 7.87-7.85 (d, J=8 Hz, 1H), 7.71-7.69 (d, J=7.2 Hz, 1H), 7.61-7.60 (d, J=6.8 Hz, 1H), 7.57-7.54 (m, 1H), 6.41-6.38 (d, J=7.2 Hz, 1H), 6.24 (s, 1H), 4.40-4.34 (m, 1H), 3.89 (bs, 1H), 3.20 (s, 3H), 2.92-2.91 (d, J=4.8 Hz, 3H), 2.17-2.09 (m, 2H), 2.03-1.96 (m, 1H), 1.63-1.56 (m, 2H), 1.49-1.44 (m, 1H)).

Step 6—Synthesis of Compound I-68: Compound was synthesized using general procedure C to obtain I-68 (0.032 g, Yield: 88.07%; MS (ES): m/z 475.61 [M+H]$^+$; LCMS purity: 100%; HPLC purity: 99.78%; CHIRAL HPLC purity: 96.73%; $^1$H NMR (DMSO-d$_6$, 400 MHZ): 9.00 (s, 1H), 8.66-8.65 (d, J=4 Hz, 1H), 8.30-8.29 (d, J=6.8 Hz, 1H), 8.21 (s, 1H), 8.08-8.04 (t, J=6.8 Hz, 1H), 7.95-7.94 (d, J=4.8 Hz, 1H), 7.87-7.85 (d, J=8 Hz, 1H), 7.71-7.69 (d, J=7.2 Hz, 1H), 7.61-7.60 (d, J=6.8 Hz, 1H), 7.57-7.54 (m, 1H), 6.41-6.38 (d, J=7.2 Hz, 1H), 6.24 (s, 1H), 4.40-4.34 (m, 1H), 3.89 (bs, 1H), 3.20 (s, 3H), 2.92-2.91 (d, J=4.8 Hz, 3H), 2.17-2.09 (m, 2H), 2.03-1.96 (m, 1H), 1.63-1.56 (m, 2H), 1.49-1.42 (m, 1H)).

Example 43: 5-((1-((1r,4R)-4-Methoxycyclohexyl)-2-oxo-1,2-dihydropyridin-3-yl)amino)-N-((1R,3R)-3-methoxycyclopentyl)-7-(methylamino)pyrazolo[1,5-a]pyrimidine-3-carboxamide (I-69)

And 5-((1-((1r,4S)-4-Methoxycyclohexyl)-2-oxo-1,2-dihydropyridin-3-yl)amino)-N-((1S,3S)-3-methoxycyclopentyl)-7-(methylamino)pyrazolo[1,5-a]pyrimidine-3-carboxamide (I-70)

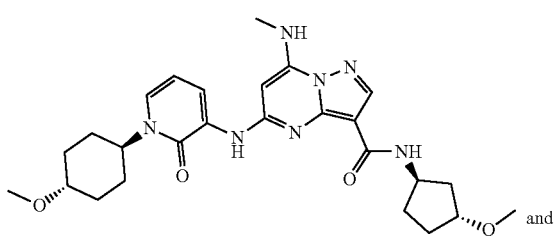

I-69 and

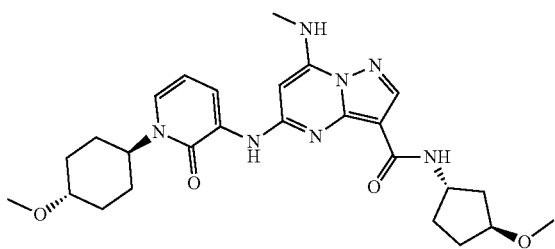

I-70

Scheme 43
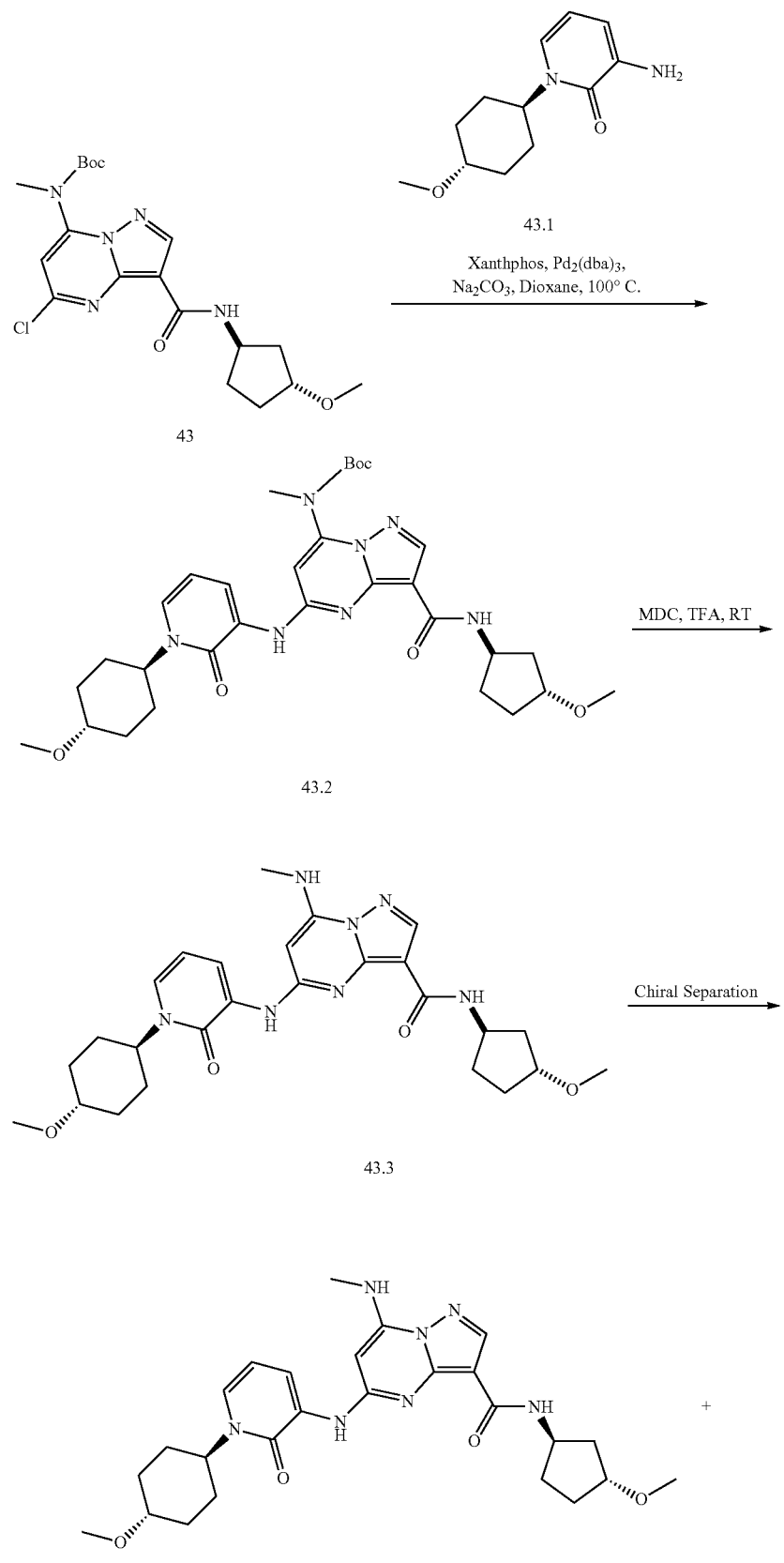

-continued

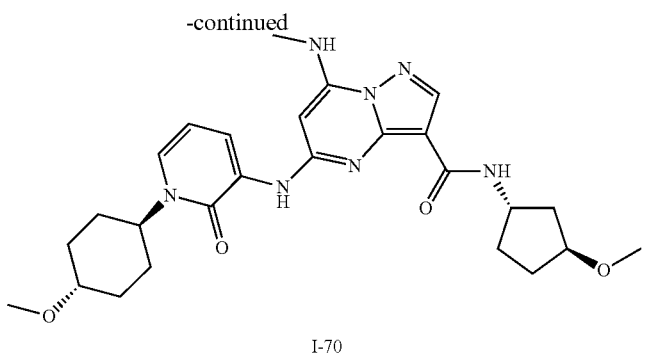

I-70

Step 1—Synthesis of Compound 43: Compound was synthesized from Core A utilizing general method A to obtain 43.

Step 2—Synthesis of Compound 43.1: Compound was synthesized as per experimental protocol of I-31 (Example 21).

Step 3—Synthesis of Compound 43.2: Compound was synthesized using general procedure B to obtain 43.2.

Step 4—Synthesis of Compound 43.2: Compound was synthesized using general procedure C to obtain 43.3.

Step 5—Synthesis of Compounds I-69 and I-70: Isomers of 43.3 (0.1 g) were separated out using column CHIRAL PAK OX-H (250 mm×4.6 mm, 5 μm) 0.1% HEX_IPA-ACN (70-30) to get pure fraction-1 (FR-a) and fraction-2 (FR-b).

FR-a was concentrated under reduced pressure at 30° C. to afford pure I-69 (0.032 g; MS (ES): m/z 510.87 [M+H]$^+$; LCMS purity: 100%; HPLC purity: 98.40%; CHIRAL HPLC purity: 99.65%; $^1$H NMR (DMSO-d$_6$, 400 MHZ): 8.84 (s, 1H), 8.17 (s, 1H), 8.15 (s, 1H), 7.91-7.90 (d, J=4.8 Hz, 1H), 7.66-7.64 (d, J=7.2 Hz, 1H), 7.44-7.42 (d, J=6 Hz, 1H), 6.27-6.24 (t, J=7.2 Hz, 1H), 6.20 (s, 1H), 4.78 (bs, 1H), 4.37-4.31 (m, 1H), 3.87-3.85 (m, 1H), 3.27 (s, 3H), 3.18 (s, 3H), 2.90-2.89 (d, J=4.8 Hz, 3H), 2.33 (bs, 4H), 2.11-2.06 (m, 1H), 1.80 (bs, 2H), 1.77 (bs, 2H), 1.44-1.39 (m, 3H), 1.04-1.03 (m, 3H)).

FR-b was concentrated under reduced pressure at 30° C. to afford pure I-70 (0.035 g; MS (ES): m/z 510.51 [M+H]$^+$; LCMS purity: 100%; HPLC purity: 99.21%; CHIRAL HPLC purity: 100%; $^1$H NMR (DMSO-d$_6$, 400 MHZ): 8.85 (s, 1H), 8.17 (s, 1H), 8.15 (s, 1H), 7.91-7.90 (d, J=4.8 Hz, 1H), 7.66-7.64 (d, J=7.2 Hz, 1H), 7.44-7.42 (d, J=6 Hz, 1H), 6.27-6.24 (t, J=7.2 Hz, 1H), 6.20 (s, 1H), 4.79 (bs, 1H), 4.37-4.31 (m, 1H), 3.86 (bs, 1H), 3.27 (s, 3H), 3.18 (s, 3H), 2.90-2.89 (d, J=4.8 Hz, 3H), 2.33 (bs, 4H), 2.11-2.06 (m, 1H), 1.80 (bs, 2H), 1.77 (bs, 2H), 1.44-1.39 (m, 3H), 1.04-1.03 (m, 3H)).

Example 44: N-((trans-1,3)-3-Methoxycyclopentyl)-7-(methylamino)-5-((1-(oxazol-2-yl)-2-oxo-1,2-dihydropyridin-3-yl)amino)pyrazolo[1,5-a]pyrimidine-3-carboxamide (I-71)

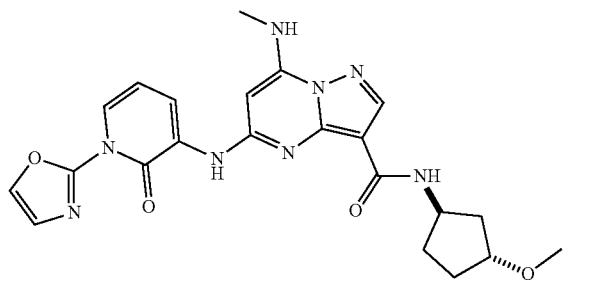

I-71

Scheme 44

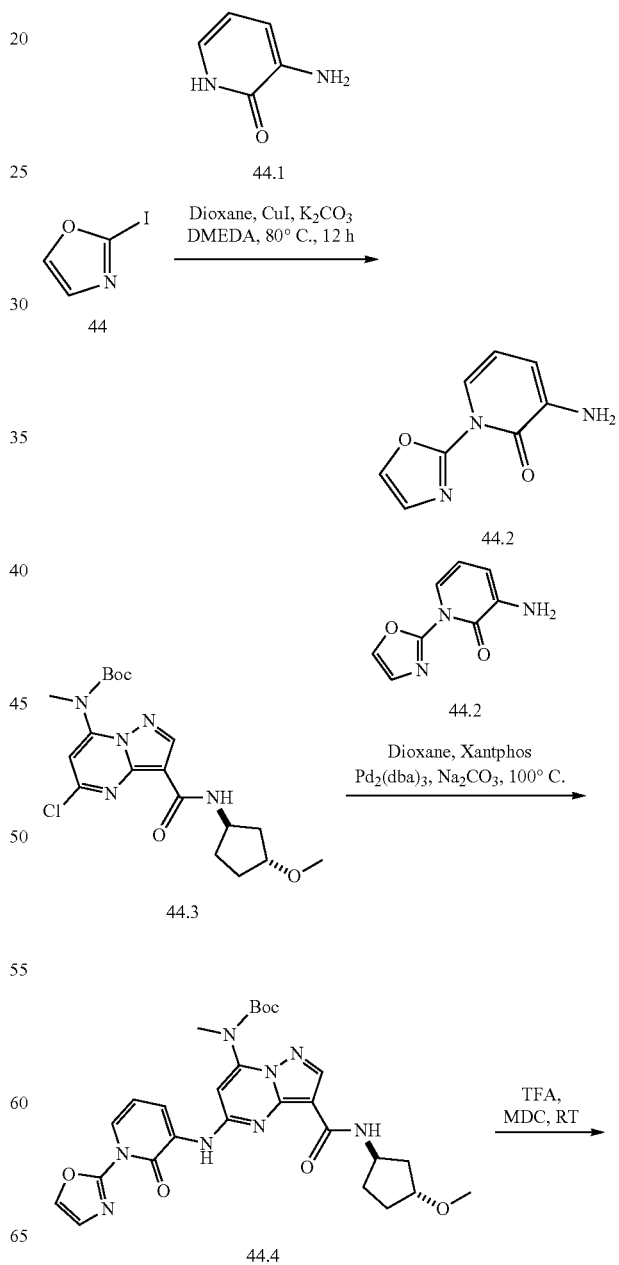

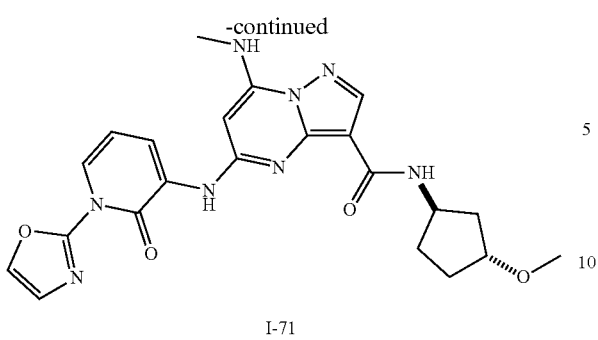

I-71

Step 1—Synthesis of Compound 44.2: To a solution of 44 (0.250 g, 1.28 mmol, 1 eq) in 1,4-dioxane (15 mL) 44.1 (0.169 g, 1.53 mmol, 1.2 eq) was added. The reaction mixture was degassed for 10 min under argon atmosphere followed by addition of potassium carbonate (0.441 g, 3.2 mmol, 2.5 eq), N,N-dimethylethylenediamine (0.028 g, 0.32 mmol, 0.25 eq), and copper iodide (0.036 g, 0.19 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 44.2 (0.060 g, Yield: 26.41%; MS (ES): m/z 178.06 [M+H]$^+$).

Step 2—Synthesis of Compound 44.3: Compound was synthesized from Core A utilizing general method A to obtain 44.3 (Yield: 51.57%; MS (ES): m/z 424.17 [M+H]$^+$).

Step 3—Synthesis of Compound 44.4: Compound was synthesized using general procedure B to obtain 44.4 (0.155 g, Yield: 77.58%; MS (ES): m/z 565.25 [M+H]$^+$).

Step 4—Synthesis of Compound I-71: Compound was synthesized using general procedure C to obtain I-71 (0.028 g, Yield: 85.09%; MS (ES): m/z 465.61 [M+H]$^+$; LCMS purity: 100%; HPLC purity: 99.45%; CHIRAL HPLC: 48.39%, 51.61%; $^1$H NMR (DMSO-d$_6$, 400 MHZ): 9.06 (s, 1H), 8.34 (s, 1H), 8.29-8.27 (d, J=6 Hz, 1H), 8.19 (s, 1H), 7.98-7.97 (d, J=4.8 Hz, 1H), 7.65-7.64 (d, J=7.2 Hz, 1H), 7.48-7.47 (d, J=6.8 Hz, 2H), 6.41-6.38 (t, J=6.8 Hz, 1H), 6.19 (s, 1H), 4.36-4.30 (m, 1H), 3.86 (bs, 1H), 3.17 (s, 3H), 2.90-2.89 (d, J=4.8 Hz, 3H), 2.14-2.09 (m, 2H), 1.97-1.94 (m, 1H), 1.40-1.35 (m, 1H), 1.22 (bs, 2H)).

Example 45: 5-((1-(3,3-Difluorocyclobutyl)-2-oxo-1,2-dihydropyridin-3-yl)amino)-N-((1R,3R)-3-methoxycyclopentyl)-7-(methylamino)pyrazolo[1,5-a]pyrimidine-3-carboxamide (I-72)

And 5-((1-(3,3-Difluorocyclobutyl)-2-oxo-1,2-dihydropyridin-3-yl)amino)-N-((1S,3S)-3-methoxycyclopentyl)-7-(methylamino)pyrazolo[1,5-a]pyrimidine-3-carboxamide (I-73)

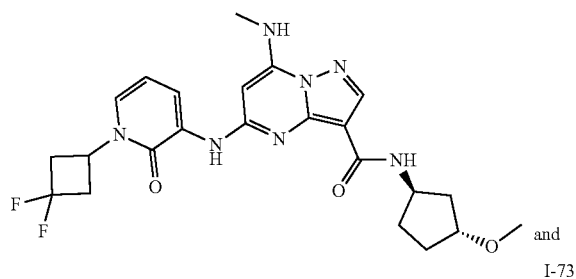

I-72 and

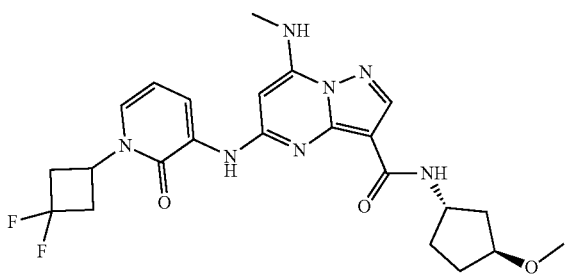

I-73

Scheme 45

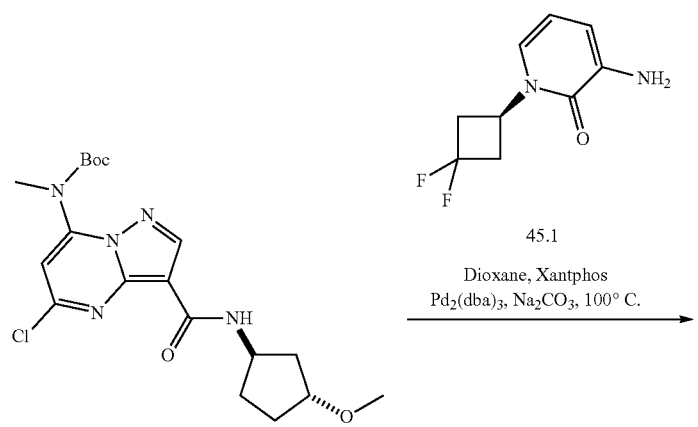

45

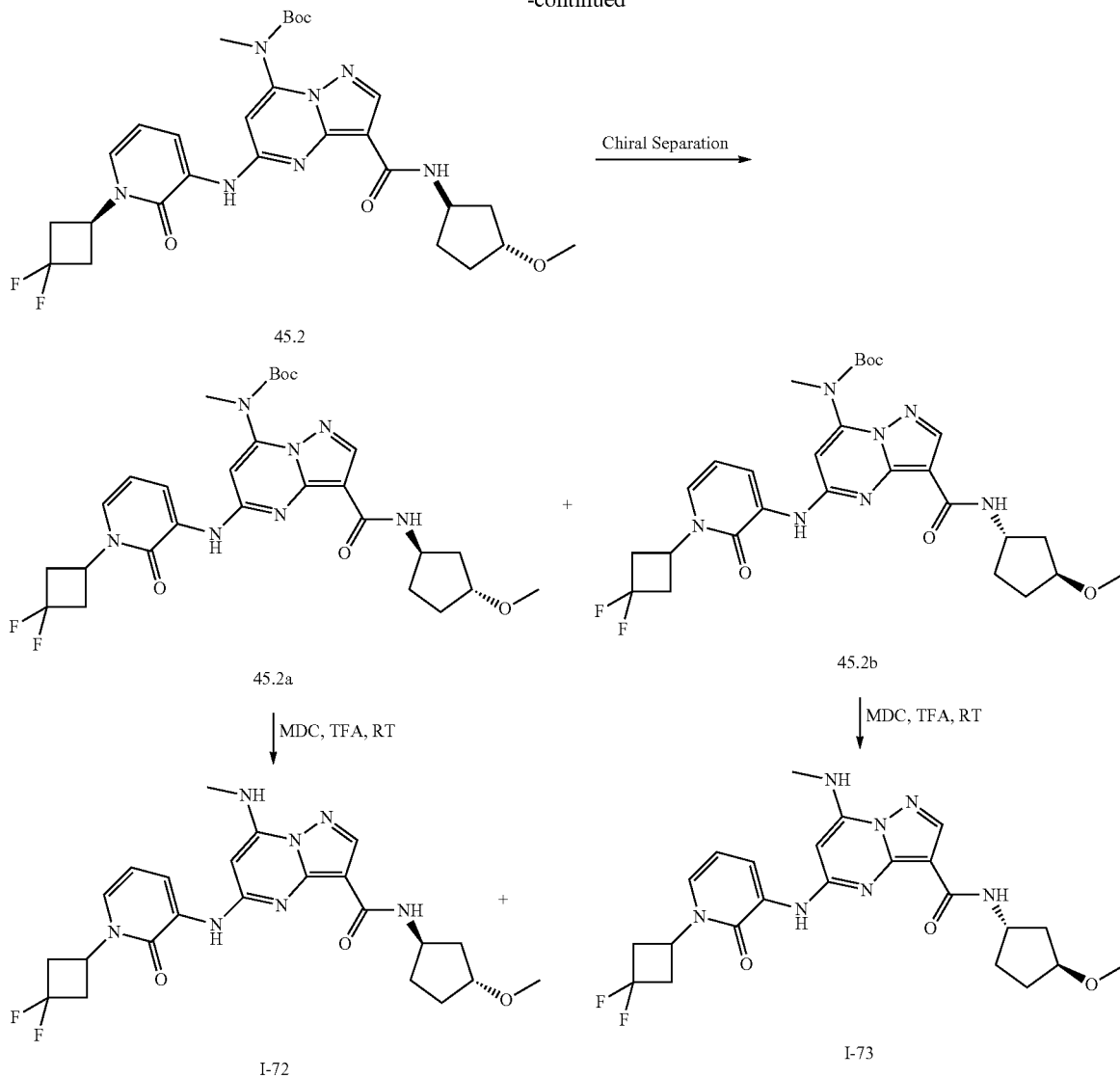

Step 1—Synthesis of Compound 45: Compound was synthesized from Core A utilizing general method A to obtain 45.

Step 2—Synthesis of Compound 45.1: Compound was synthesized as per experimental protocol of I-33 (Example 22) to obtain 45.1.

Step 3—Synthesis of Compound 45.2: Compound was synthesized as per general method A to obtain 45.2 (Yield: 72.14%; MS (ES): m/z 588.27 [M+H]$^+$).

Step 2—Synthesis of Compound 45.2a and 45.2b: Isomers of 45.2 (0.110 g) were separated out using column CHIRALCEL OJ-H (250 mm×4.6 mm, 5 µm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 45.2a (0.041 g; MS (ES): m/z 588.27 [M+H]$^+$). FR-b was concentrated under reduced pressure at 30° C. to afford pure 45.2b (0.042 g; MS (ES): m/z 588.27 [M+H]$^+$).

Step 3—Synthesis of Compound I-72: Compound was synthesized using general procedure C to obtain I-72 (0.031 g, Yield: 91.14%; MS (ES): m/z 488.22 [M+H]$^+$; LCMS purity: 98.00%; HPLC purity: 99.04%; CHIRAL HPLC purity: 100%; $^1$H NMR (DMSO-d$_6$, 400 MHZ): 8.95 (s, 1H), 8.23-8.21 (d, J=6.8 Hz, 1H), 8.18 (s, 1H), 7.92-7.91 (d, J=4.8 Hz, 1H), 7.66-7.64 (d, J=7.6 Hz, 1H), 7.45-7.43 (d, J=6.8 Hz, 1H), 6.31-6.27 (t, J=7.2 Hz, 1H), 6.22 (s, 1H), 5.76 (s, 1H), 4.90 (bs, 1H), 4.37-4.32 (m, 1H), 3.87 (bs, 1H), 3.28 (s, 1H), 3.19 (s, 4H), 2.90-2.88 (d, J=4.8 Hz, 3H), 2.15-2.10 (m, 2H), 2.02-1.94 (m, 1H), 1.64 (bs, 2H), 1.55-1.51 (m, 1H), 1.23 (bs, 1H)).

Step 4—Synthesis of Compound I-73: Compound was synthesized using general procedure C to obtain I-73 (0.030 g, Yield: 86.10%; MS (ES): m/z 427.18 [M+H]$^+$; LCMS purity: 99.00%; HPLC purity: 100%; CHIRAL HPLC purity: 98.06%; $^1$H NMR (DMSO-d$_6$, 400 MHZ): 8.96 (s, 1H), 8.23-8.21 (d, J=6.8 Hz, 1H), 8.18 (s, 1H), 7.93-7.92 (d, J=4.8 Hz, 1H), 7.66-7.64 (d, J=7.6 Hz, 1H), 7.45-7.43 (d, J=6.8 Hz, 1H), 6.31-6.27 (t, J=7.2 Hz, 1H), 6.22 (s, 1H), 5.76 (s, 1H), 4.90 (bs, 1H), 4.37-4.32 (m, 1H), 3.87 (bs, 1H), 3.28 (s, 1H), 3.19 (s, 4H), 2.90-2.88 (d, J=4.8 Hz, 3H), 2.15-2.10 (m, 2H), 2.02-1.94 (m, 1H), 1.64 (bs, 2H), 1.55-1.51 (m, 1H), 1.24 (bs, 1H)).

Example 46: 5-((1-((1R,5S,6r)-3-Oxabicyclo[3.1.0]
hexan-6-yl)-2-oxo-1,2-dihydropyridin-3-yl)amino)-
N-((1R,3R)-3-methoxycyclopentyl)-7-(methyl-
amino)pyrazolo[1,5-a]pyrimidine-3-carboxamide
(I-74)
And
5-((1-((1R,5S,6r)-3-Oxabicyclo[3.1.0]hexan-6-yl)-2-
oxo-1,2-dihydropyridin-3-yl)amino)-N-((1S,3S)-3-
methoxycyclopentyl)-7-(methylamino)pyrazolo[1,5-
a]pyrimidine-3-carboxamide (I-75)
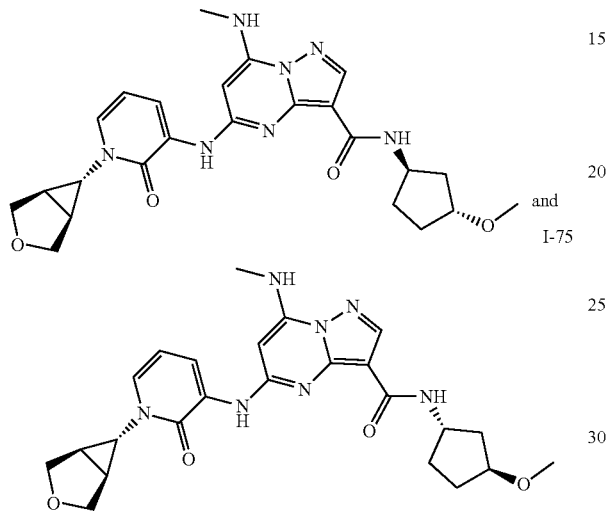
I-74
and
I-75
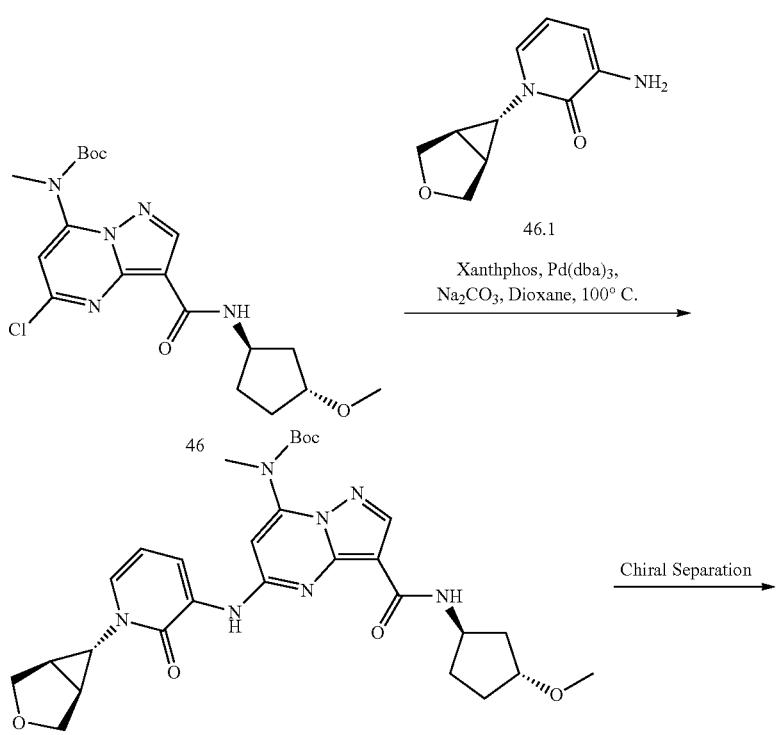
Scheme 46

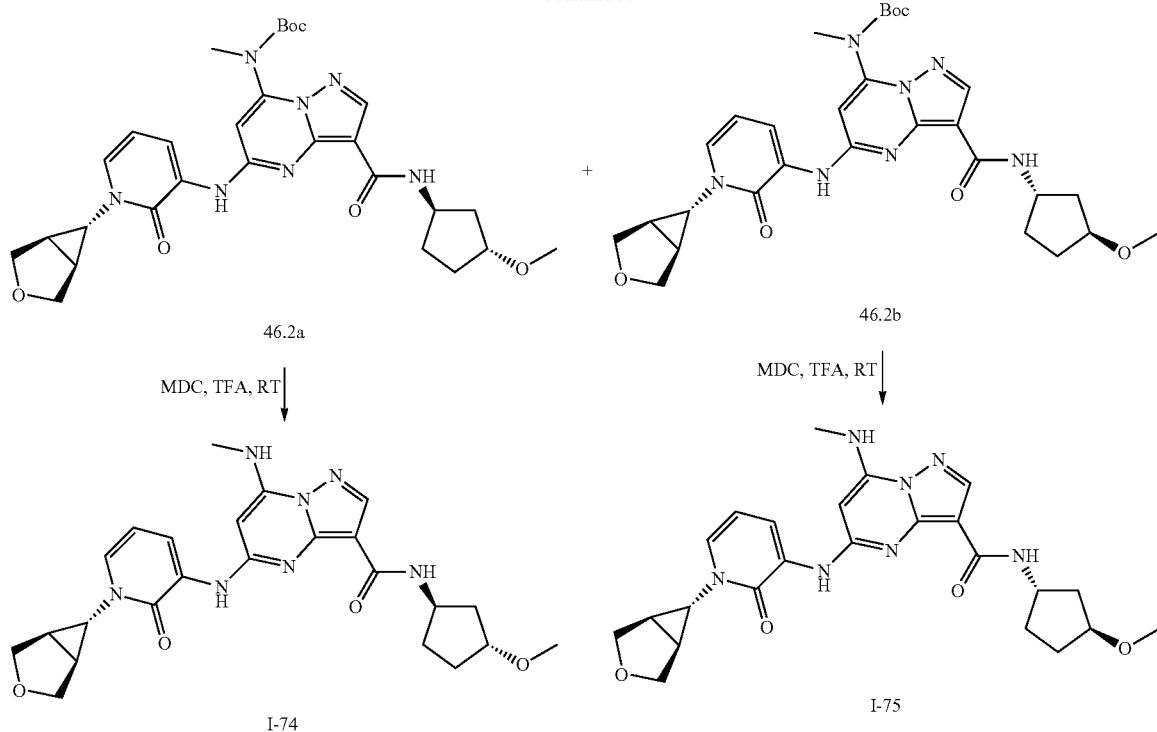

Step 1—Synthesis of Compound 46: Compound was synthesized from Core A utilizing general method A to obtain 46.

Step 2—Synthesis of Compound 46.1: Compound was synthesized as per experimental protocol of I-24 (Example 17) to obtain 46.1

Step 3—Synthesis of Compound 46.2: Compound was synthesized as per general procedure B to obtain 46.2 (Yield: 72.64%; MS (ES): 580.28 [M+H]$^+$).

Step 4—Synthesis of Compounds 46.2a and 46.2b: Isomers of 46.2 (0.109 g) were separated out using column CHIRALCEL OJ-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 46.2a (0.043 g; MS (ES): m/z 580.28 [M+H]$^+$). FR-b was concentrated under reduced pressure at 30° C. to afford pure 46.2b (0.039 g; MS (ES): m/z 580.28 [M+H]$^+$).

Step 5—Synthesis of Compound I-74: Compound was synthesized using general procedure C to obtain I-74 (0.028 g, Yield: 78.71%; MS (ES): m/z 480.92 [M+H]$^+$; LCMS purity: 98.89%; HPLC purity: 98.60%; CHIRAL HPLC: 99.09%; $^1$H NMR (DMSO-d$_6$, 400 MHZ): 8.92 (s, 1H), 8.18 (s, 1H), 8.15 (s, 1H), 7.92-7.91 (d, J=5.2 Hz, 1H), 7.66-7.64 (d, J=7.6 Hz, 1H), 7.31-7.30 (d, J=6.4 Hz, 1H), 6.21-6.19 (t, J=6.8 Hz, 1H), 6.17 (s, 1H), 4.37-4.31 (m, 1H), 3.98 (bs, 2H), 3.86 (bs, 1H), 3.74-3.72 (d, J=8 Hz, 2H), 3.23 (s, 3H), 3.14 (s, 1H), 2.90-2.89 (d, J=4.8 Hz, 3H), 2.33 (bs, 2H), 2.14-2.11 (m, 2H), 1.96-1.91 (m, 1H), 1.63 (bs, 1H), 1.56-1.51 (m, 1H), 1.35 (bs, 1H)).

Step 6—Synthesis of Compound I-75: Compound was synthesized using general procedure C to obtain I-75 (0.026 g, Yield: 80.59%; MS (ES): 480.87 [M+H]$^+$; LCMS purity: 97.88%; HPLC purity: 96.33%; CHIRAL HPLC: 98.99%; $^1$H NMR (DMSO-d$_6$, 400 MHZ): 8.92 (s, 1H), 8.18 (s, 1H), 8.15 (s, 1H), 7.92-7.91 (d, J=5.2 Hz, 1H), 7.66-7.64 (d, J=7.6 Hz, 1H), 7.31-7.30 (d, J=6.4 Hz, 1H), 6.21-6.19 (t, J=6.8 Hz, 1H), 6.17 (s, 1H), 4.37-4.31 (m, 1H), 3.98 (bs, 2H), 3.86 (bs, 1H), 3.74-3.72 (d, J=8 Hz, 2H), 3.18 (s, 3H), 3.14 (s, 1H), 2.90-2.89 (d, J=4.8 Hz, 3H), 2.33 (bs, 2H), 2.14-2.11 (m, 2H), 1.96-1.91 (m, 1H), 1.63 (bs, 1H), 1.56-1.51 (m, 1H), 1.23 (bs, 1H)).

Example 47: 5-((3'-Fluoro-2-oxo-2H-[1,2'-bipyridin]-3-yl)amino)-N-((1R,3R)-3-methoxycyclopentyl)-7-(methylamino)pyrazolo[1,5-a]pyrimidine-3-carboxamide (I-76)

And 5-((3'-Fluoro-2-oxo-2H-[1,2'-bipyridin]-3-yl)amino)-N-((1S,3S)-3-methoxycyclopentyl)-7-(methylamino)pyrazolo[1,5-a]pyrimidine-3-carboxamide (I-77)

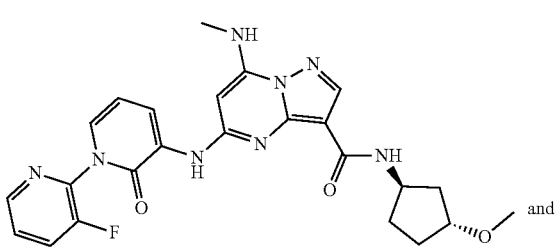

I-76 and

I-77

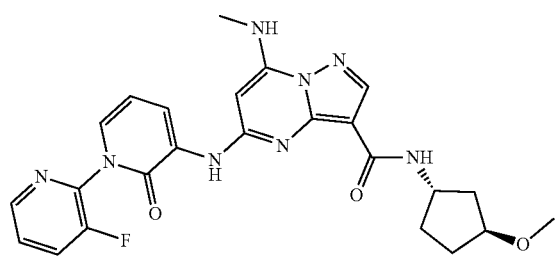

Scheme 47

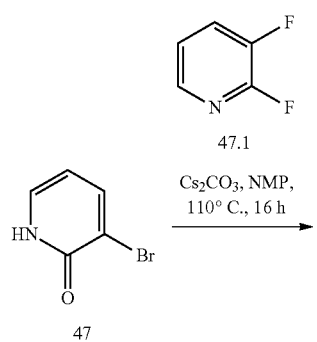

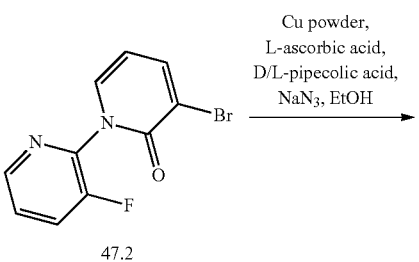

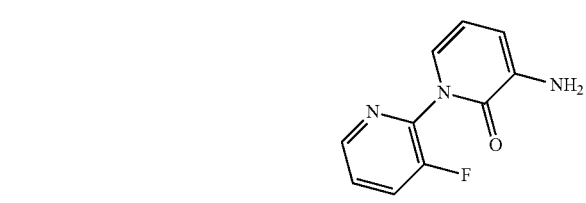

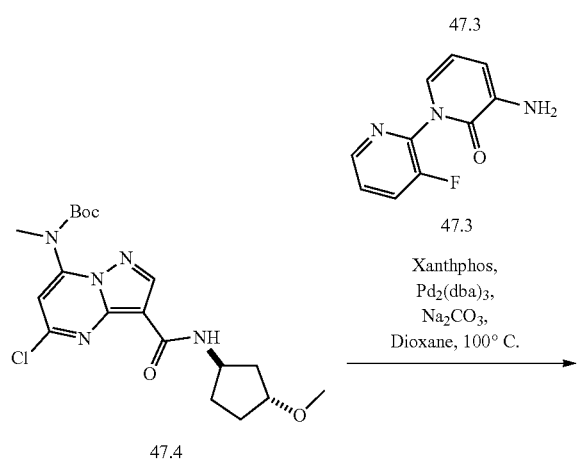

47.4

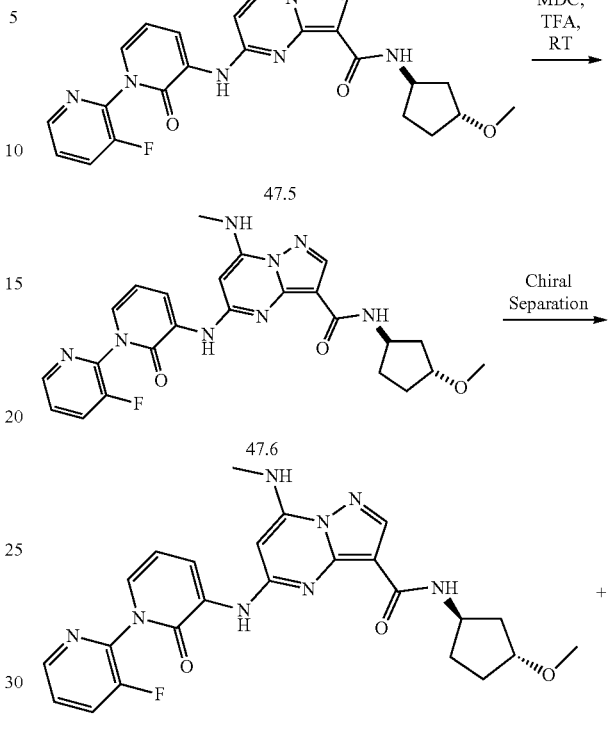

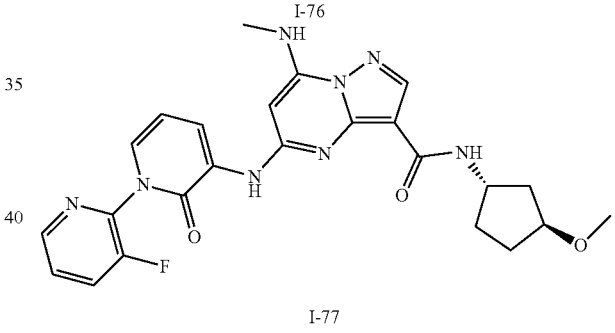

I-77

Step 1—Synthesis of Compound 47.2: To a solution of 47 (3 g, 17.24 mmol, 1.0 eq) in N-methyl-2-pyrrolidone (60 mL) 47.1 (2.4 g, 21.55 mmol, 1.2 eq) and cesium carbonate (1.6 g, 51.72 mmol, 3.0 eq.) were added. The reaction mixture was heated at 110° C. for 16 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 40% ethylacetate in hexane to obtain 47.2 (0.71 g, Yield: 15.30%; MS (ES): m/z 270.07 [M+H]$^+$).

Step 2—Synthesis of Compound 47.3: To a solution of 47.2 (0.70 g, 2.60 mmol, 1.0 eq) in ethanol (9 mL), copper powder (0.01 g, 0.31 mmol, 0.12 eq), L-ascorbic acid (0.09 g, 0.52 mmol, 0.2 eq), and sodium azide (0.33 g, 5.2 mmol, 2.0 eq.) were added. The reaction mixture was heated at 100° C. for 20 h. After completion of reaction, reaction mixture was filtered through celite and product was extracted with ethylacetate. Organic layer was combined, washed with brine solution, dried over sodium sulphate and concentrated under reduced pressure to obtain crude material. This was further purified by 70% ethylacetate in hexane to obtain 47.3 (0.23 g, Yield: 43.09%; MS (ES): m/z 207.19 [M+H]$^+$).

Step 3—Synthesis of Compound 47.4: Compound was synthesized from Core A utilizing general method A to obtain 47.4.

Step 4—Synthesis of Compound 47.5: Compound was synthesized using general procedure B to obtain 47.5.

Step 5—Synthesis of Compound 47.6: Compound was synthesized using general procedure C to obtain 47.6.

Step 2—Synthesis of Compounds I-76 and I-77: Isomers of 47.6 (0.090 g) were separated out using column CHIRALPAK AD-H (250 mm×4.6 mm, 5 μm) 0.1% DEA in methanol to get pure fraction-1 (FR-a) and fraction-2 (FR-b).

FR-a was concentrated under reduced pressure at 30° C. to afford pure I-76 (0.030 g; MS (ES): m/z 493.87 [M+H]$^+$; LCMS purity: 100%; HPLC purity: 100%; CHIRAL HPLC purity: 100%; $^1$H NMR (DMSO-d$_6$, 400 MHZ): 9.02 (s, 1H), 8.51-8.50 (d, J=4.8 Hz, 1H), 8.32-8.30 (d, J=6 Hz, 1H), 8.19 (s, 1H), 8.08-8.04 (t, J=8.4 Hz, 1H), 7.95-7.94 (d, J=5.2 Hz, 1H), 7.74-7.67 (m, 2H), 7.45-7.44 (d, J=5.6 Hz, 1H), 6.43-6.39 (t, J=7.2 Hz, 1H), 6.20 (s, 1H), 4.38-4.32 (m, 1H), 3.87 (bs, 1H), 3.18 (s, 3H), 2.89-2.88 (d, J=4.8 Hz, 3H), 2.14-2.10 (m, 2H), 1.99-1.94 (m, 1H), 1.62-1.54 (m, 2H), 1.46-1.40 (m, 1H)).

FR-b was concentrated under reduced pressure at 30° C. to afford pure I-77 (0.030 g; MS (ES): m/z 493.87 [M+H]$^+$; LCMS purity: 100%; HPLC purity: 100%; CHIRAL HPLC purity: 99.00%; $^1$H NMR (DMSO-d$_6$, 400 MHZ): 9.02 (s, 1H), 8.51-8.50 (d, J=4.8 Hz, 1H), 8.32-8.30 (d, J=6 Hz, 1H), 8.19 (s, 1H), 8.08-8.04 (t, J=8.4 Hz, 1H), 7.95-7.94 (d, J=5.2 Hz, 1H), 7.74-7.67 (m, 2H), 7.45-7.44 (d, J=5.6 Hz, 1H), 6.43-6.39 (t, J=7.2 Hz, 1H), 6.20 (s, 1H), 4.38-4.32 (m, 1H), 3.88 (bs, 1H), 3.18 (s, 3H), 2.89-2.88 (d, J=4.8 Hz, 3H), 2.14-2.10 (m, 2H), 1.99-1.94 (m, 1H), 1.62-1.54 (m, 2H), 1.48-1.40 (m, 1H)).

Example 48: 5-((1-((1R,2S)-2-Hydroxycyclopentyl)-2-oxo-1,2-dihydropyridin-3-yl)amino)-N-((1R,3R)-3-methoxycyclopentyl)-7-(methylamino)pyrazolo[1,5-a]pyrimidine-3-carboxamide (I-78)

And 5-((1-((1R,2S)-2-Hydroxycyclopentyl)-2-oxo-1,2-dihydropyridin-3-yl)amino)-N-((1S,3S)-3-methoxycyclopentyl)-7-(methylamino)pyrazolo[1,5-a]pyrimidine-3-carboxamide (I-79)

I-78

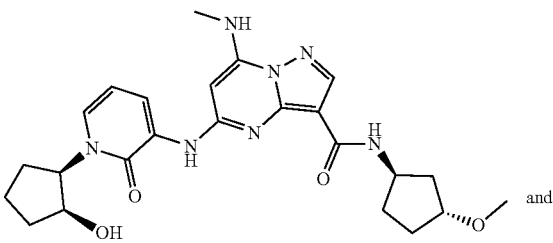

and

I-79

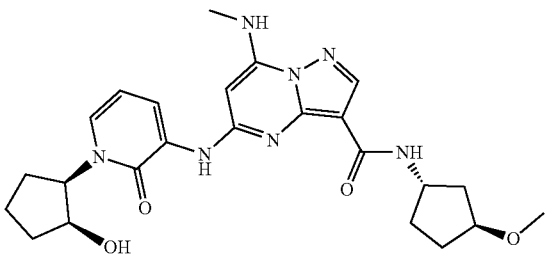

Scheme 48

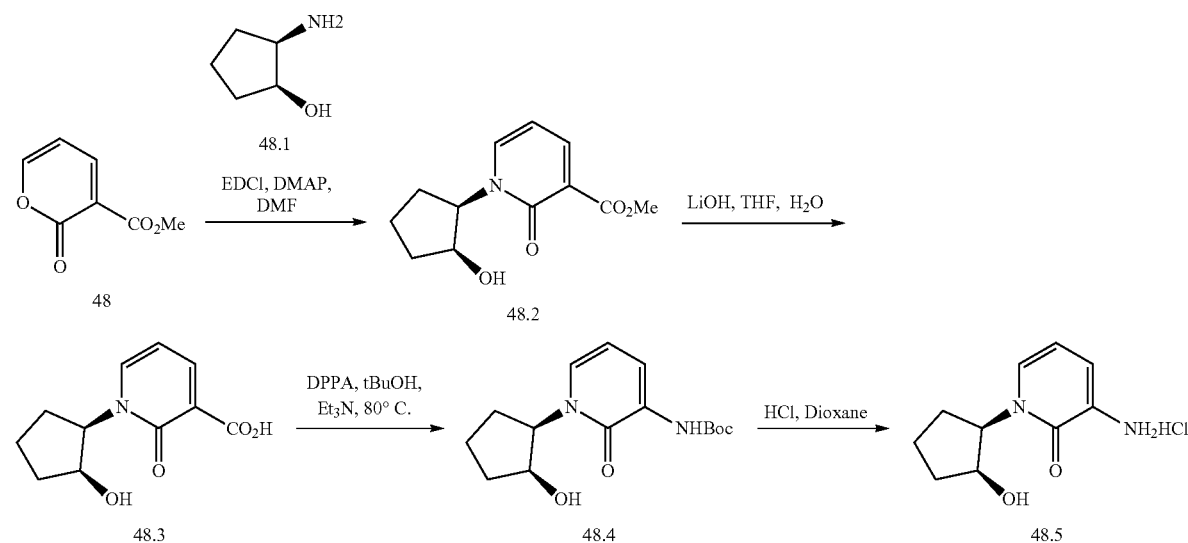

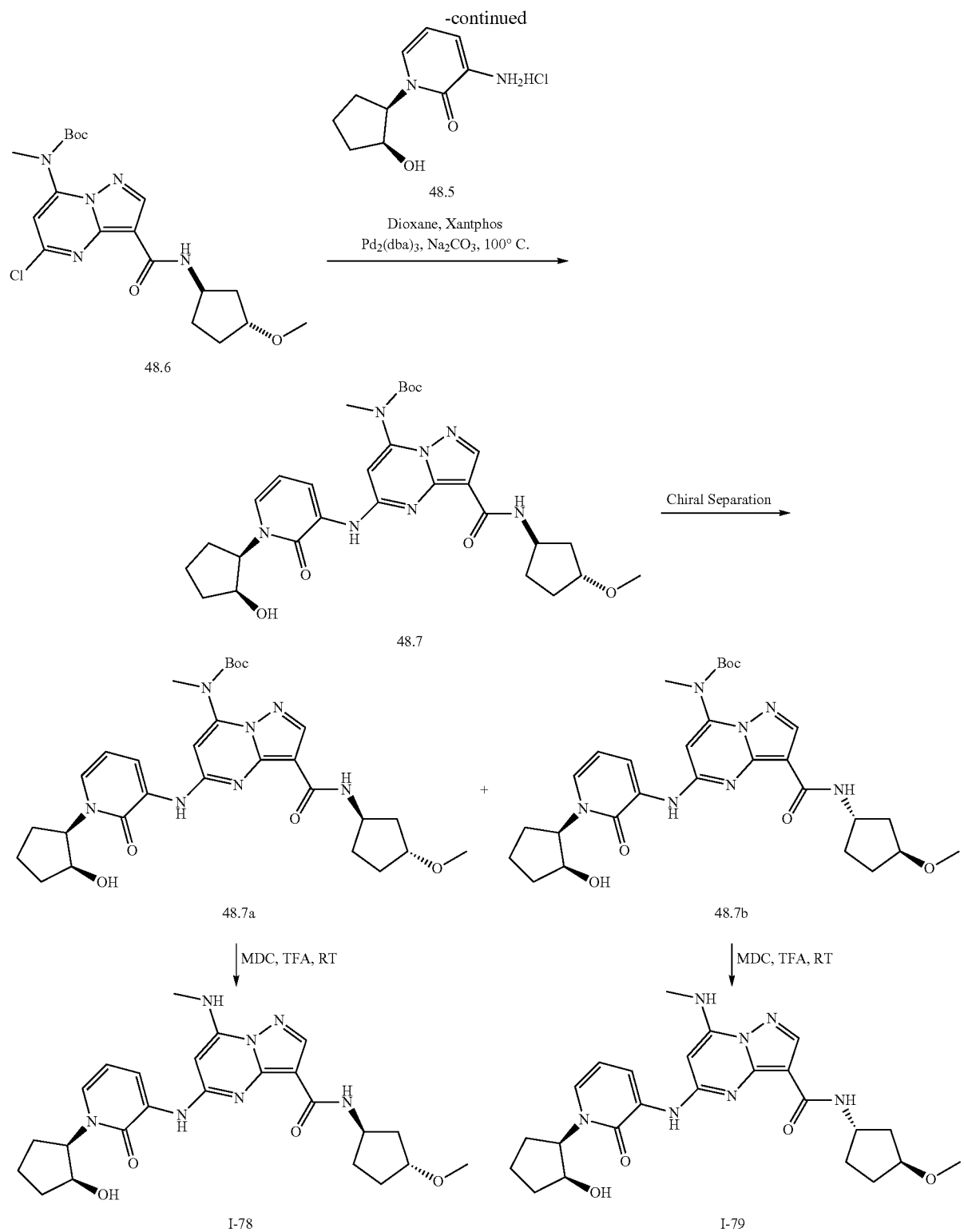

Step 1—Synthesis of Compound 48.2: To a cooled solution of 48 (0.7 g, 4.54 mmol, 1.0 eq), in N,N-dimethylformamide (10 mL) was added 48.1 (0.625 g, 4.54 mmol, 1.0 eq). The reaction mixture was stirred at 0° C. for 6 min and further stirred at room temperature for 15 min. N-Ethyl-N'-(3-dimethylaminopropyl)carbodiimide hydrochloride (1.131 g, 5.90 mmol, 1.3 eq) and 4-Dimethylaminopyridine (0.139 g, 1.135 mmol, 0.25 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 48.2 (0.450 g, Yield: 41.76%; MS (ES): m/z 238.26 [M+H]⁺).

Step 2—Synthesis of Compound 48.3: To a solution of 48.2 (0.45 g, 1.90 mmol, 1.0 eq), in tetrahydrofuran:water (8 mL, 2:1) was added lithium hydroxide (0.362 g, 15.1 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 48.3 (0.36 g, Yield: 85.03%; MS (ES): m/z 224.23 [M+H]⁺).

Step 3—Synthesis of Compound 48.4: To a solution of 48.3 (0.36 g, 1.61 mmol, 1.0 eq) in tert.butanol (6 mL) was added triethylamine (0.277 g, 2.74 mmol, 1.7 eq) and diphenyl phosphoryl azide (0.576 g, 2.093 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 48.4 (0.320 g, Yield: 67.41%; MS (ES): m/z 295.35 [M+H]⁺).

Step 4—Synthesis of Compound 48.5: To a cooled solution of 48.4 (0.320 g, 1.09 mmol, 1 eq) in dioxane (4 mL) was added 4N hydrochloric acid in dioxane (10 mL) as a dropwise. The reaction mixture was stirred at room temperature for 2 h. After completion of reaction, reaction mixture was concentrated under reduced pressure to obtain pure 48.5 (0.24 g, Yield: 95.70%; MS (ES): m/z 231.69 [M+HCl]⁺).

Step 5—Synthesis of Compound 48.6: Compound was synthesized from Core A utilizing general method A to obtain 48.6.

Step 1—Synthesis of Compound 48.7: Compound was synthesized using general procedure B to obtain 48.7 (Yield: 68.02%; MS (ES): m/z 582.30 [M+H]⁺).

Step 2—Synthesis of Compounds 48.7a and 48.7b: Isomers of 48.7 (0.105 g) were separated out using column CHIRALCEL OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 48.7a (0.037 g; MS (ES): m/z 582.30 [M+H]⁺). FR-b was concentrated under reduced pressure at 30° C. to afford pure 48.7b (0.040 g; MS (ES): m/z 582.30 [M+H]⁺).

Step 3—Synthesis of Compound I-78: Compound was synthesized using general procedure C to obtain I-78 (0.028 g, Yield: 91.41%; MS (ES): m/z 482.92 [M+H]⁺; LCMS purity: 100%; HPLC purity: 98.30%; CHIRAL HPLC purity: 98.94%; ¹H NMR (DMSO-d₆, 400 MHZ): 8.84 (bs, 1H), 8.18 (s, 1H), 8.16 (s, 1H), 7.88-7.87 (d, J=5.2 Hz, 1H), 7.68-7.66 (d, J=7.2 Hz, 1H), 7.41-7.40 (d, J=6 Hz, 1H), 6.21-6.19 (d, J=4.4 Hz, 1H), 6.17 (bs, 1H), 4.96-4.90 (m, 1H), 4.86 (bs, 1H), 4.37-4.32 (m, 1H), 4.20 (bs, 1H), 3.86 (bs, 1H), 3.18 (s, 3H), 2.90-2.89 (d, J=4.8 Hz, 3H), 2.10-2.02 (m, 3H), 1.97-1.93 (m, 2H), 1.86 (bs, 2H), 1.63-1.57 (m, 3H), 1.22 (bs, 2H)).

Step 4—Synthesis of Compound I-79: Compound was synthesized using general procedure C to obtain I-79 (0.028 g, Yield: 84.55%; MS (ES): m/z 482.92 [M+H]⁺; LCMS purity: 100%; HPLC purity: 99.04%; CHIRAL HPLC purity: 95.00%; ¹H NMR (DMSO-d₆, 400 MHZ): 8.84 (bs, 1H), 8.18 (s, 1H), 8.16 (s, 1H), 7.88-7.87 (d, J=5.2 Hz, 1H), 7.68-7.66 (d, J=7.2 Hz, 1H), 7.41-7.40 (d, J=6 Hz, 1H), 6.21-6.19 (d, J=4.4 Hz, 1H), 6.17 (bs, 1H), 4.96-4.90 (m, 1H), 4.86 (bs, 1H), 4.37-4.32 (m, 1H), 4.19 (bs, 1H), 3.86 (bs, 1H), 3.18 (s, 3H), 2.90-2.89 (d, J=4.8 Hz, 3H), 2.10-2.02 (m, 3H), 1.97-1.93 (m, 2H), 1.86 (bs, 2H), 1.63-1.57 (m, 3H), 1.22 (bs, 2H)).

Example 49: 5-((1-((1s,3S)-3-Methoxycyclobutyl)-2-oxo-1,2-dihydropyridin-3-yl)amino)-N-((trans-1,3)-3-methoxycyclopentyl)-7-(methylamino)pyrazolo[1,5-a]pyrimidine-3-carboxamide (1-80)

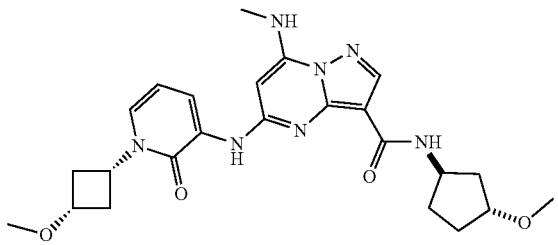

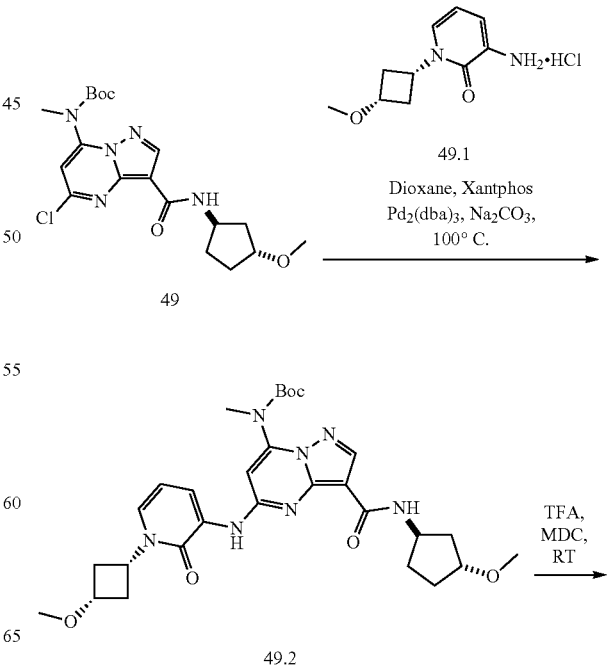

Scheme 49

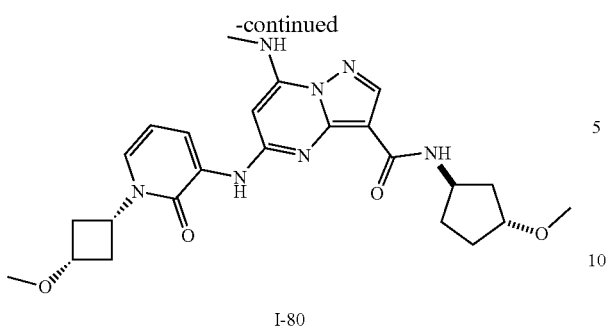

I-80

Step 1—Synthesis of Compound 49: Compound was synthesized from Core A utilizing general procedure A to obtain 49 (Yield: 51.57%; MS (ES): m/z 424.17 [M+H]$^+$).

Step 2—Synthesis of Compound 49.1: Compound was synthesized as per experimental protocol of I-5 (Example 4) to obtain 49.1 (Yield: 89.32%; MS (ES): m/z 195.11 [M+H]$^+$).

Step 3—Synthesis of Compound 49.2: Compound was synthesized using general procedure B to obtain 49.2 (0.161 g, Yield: 78.22%; MS (ES): m/z 582.30 [M+H]$^+$).

Step 4—Synthesis of Compound I-80: Compound was synthesized using general procedure C to obtain I-80 (0.021 g, Yield: 63.41%; MS (ES): m/z 482.46 [M+H]$^+$; LCMS purity: 100%; HPLC purity: 96.40%; CHIRAL HPLC: 47.00%, 52.99%; $^1$H NMR (DMSO-d$_6$, 400 MHZ): 8.89 (s, 1H), 8.19 (s, 1H), 8.18 (s, 1H), 7.91-7.90 (d, J=4.8 Hz, 1H), 7.68-7.66 (d, J=7.6 Hz, 1H), 7.48-7.46 (d, J=6 Hz, 1H), 6.31-6.27 (t, J=7.2 Hz, 1H), 6.20 (s, 1H), 4.75-4.66 (m, 1H), 4.38-4.32 (m, 1H), 3.88 (bs, 1H), 3.80-3.77 (m, 1H), 3.20 (s, 6H), 2.91-2.89 (d, J=4.8 Hz, 3H), 2.83 (bs, 2H), 2.13-2.02 (m, 4H), 1.99-1.95 (m, 1H), 1.58-1.52 (m, 2H), 1.24 (bs, 1H)).

Example 50: 5-((1-((1R,2S)-2-Hydroxycyclobutyl)-2-oxo-1,2-dihydropyridin-3-yl)amino)-N-((1R,3R)-3-methoxycyclopentyl)-7-(methylamino)pyrazolo[1,5-a]pyrimidine-3-carboxamide (I-81)

And 5-((1-((1R,2S)-2-Hydroxycyclobutyl)-2-oxo-1,2-dihydropyridin-3-yl)amino)-N-((1S,3S)-3-methoxycyclopentyl)-7-(methylamino)pyrazolo[1,5-a]pyrimidine-3-carboxamide (I-82)

I-81

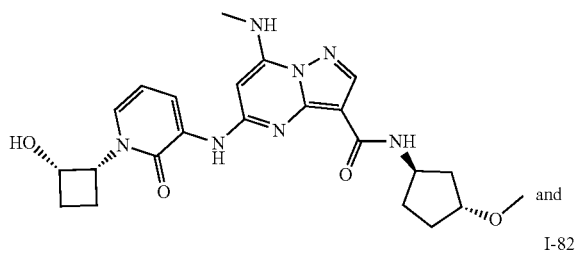

and

I-82

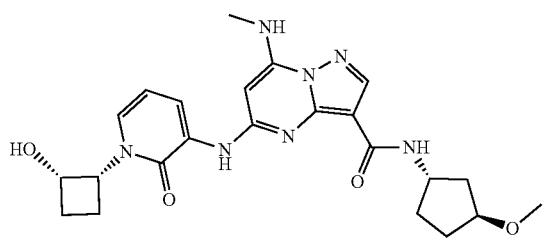

Scheme 50

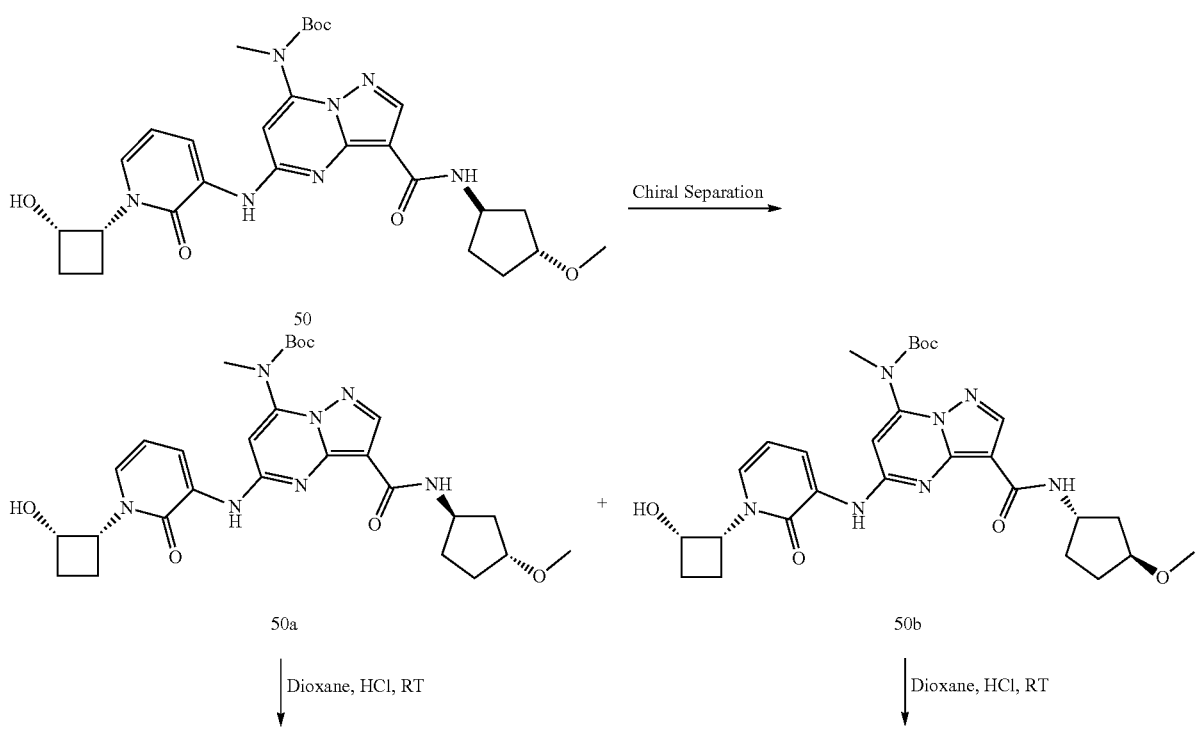

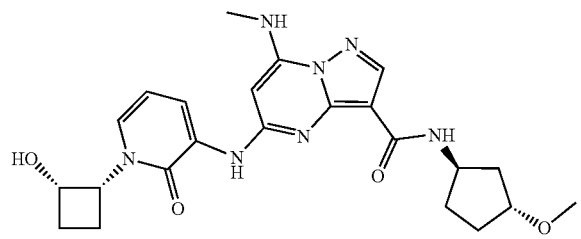

I-81

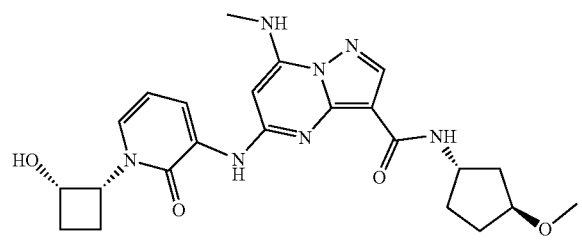

I-82

Step 1—Synthesis of Compound 50: Compound was synthesized from Core A utilizing general methods A and B to obtain 50 (Yield: 72.19%; MS (ES): m/z 568.28 [M+H]$^+$).

Step 2—Synthesis of Compounds 50a and 50b: Isomers of 50 (0.105 g) were separated out using column CHIRALCEL OX-H (250 mm×4.6 mm, 5 μm) and 0.1% DEA in HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 50a (0.040 g; MS (ES): m/z 568.28 [M+H]$^+$). FR-b was concentrated under reduced pressure at 30° C. to afford pure 50b (0.042 g; MS (ES): m/z 568.28 [M+H]$^+$).

Step 3—Synthesis of Compound I-81: To 50a (0.040 g, 0.070 mmol, 1.0 eq) was added 4M hydrochloric acid in 1,4 Dioxane (3 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-81 (0.030 g, Yield: 91.06%; MS (ES): m/z 468.23 [M+H]$^+$; LCMS purity: 100%; HPLC purity: 99.65%; CHIRAL HPLC purity: 99.17%; $^1$H NMR (DMSO-d$_6$, 400 MHZ): 8.85 (s, 1H), 8.20 (bs, 1H), 8.18 (bs, 1H), 7.90-7.89 (d, J=4.4 Hz, 1H), 7.70-7.68 (d, J=7.2 Hz, 1H), 7.48-7.46 (d, J=6.4 Hz, 1H), 6.27-6.23 (d, J=6.8 Hz, 1H), 6.21 (s, 1H), 5.19-5.15 (m, 2H), 4.53 (bs, 1H), 4.39-4.34 (m, 1H), 3.89 (bs, 1H), 3.20 (s, 3H), 2.91-2.90 (d, J=4.8 Hz, 3H), 2.74-2.69 (m, 1H), 2.13-2.04 (m, 4H), 2.03-1.97 (m, 1H), 1.69-1.61 (m, 3H), 1.59-1.54 (m, 1H)).

Step 4—Synthesis of Compound I-82: To 50b (0.042 g, 0.074 mmol, 1.0 eq) was added 4M hydrochloric acid in 1,4 Dioxane (3 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-82 (0.031 g, Yield: 89.62%; MS (ES): m/z 468.23 [M+H]$^+$; LCMS purity: 100%; HPLC purity: 96.81%; CHIRAL HPLC purity: 96.56%; $^1$H NMR (DMSO-d$_6$, 400 MHZ): 8.85 (s, 1H), 8.20 (bs, 1H), 8.18 (bs, 1H), 7.90-7.89 (d, J=4.4 Hz, 1H), 7.70-7.68 (d, J=7.2 Hz, 1H), 7.48-7.46 (d, J=6.4 Hz, 1H), 6.27-6.23 (d, J=6.8 Hz, 1H), 6.21 (s, 1H), 5.19-5.15 (m, 2H), 4.53 (bs, 1H), 4.39-4.34 (m, 1H), 3.90 (bs, 1H), 3.21 s (s, 3H), 2.91-2.90 (d, J=4.8 Hz, 3H), 2.74-2.69 (m, 1H), 2.13-2.04 (m, 4H), 2.03-1.97 (m, 1H), 1.69-1.61 (m, 3H), 1.59-1.54 (m, 1H)).

Example 51: N-((1R,3R)-3-Methoxycyclopentyl)-7-(methylamino)-5-((1-(oxazol-2-yl)-2-oxo-1,2-dihydropyridin-3-yl)amino)pyrazolo[1,5-a]pyrimidine-3-carboxamide (I-83)

And

N-((1S,3S)-3-Methoxycyclopentyl)-7-(methylamino)-5-((1-(oxazol-2-yl)-2-oxo-1,2-dihydropyridin-3-yl)amino)pyrazolo[1,5-a]pyrimidine-3-carboxamide (I-84)

I-83

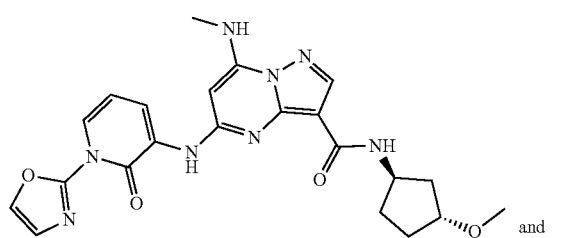

and

I-84

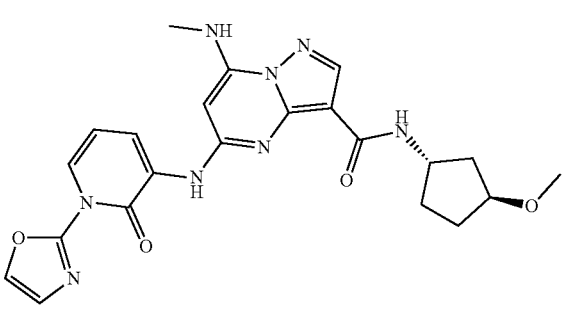

Scheme 51

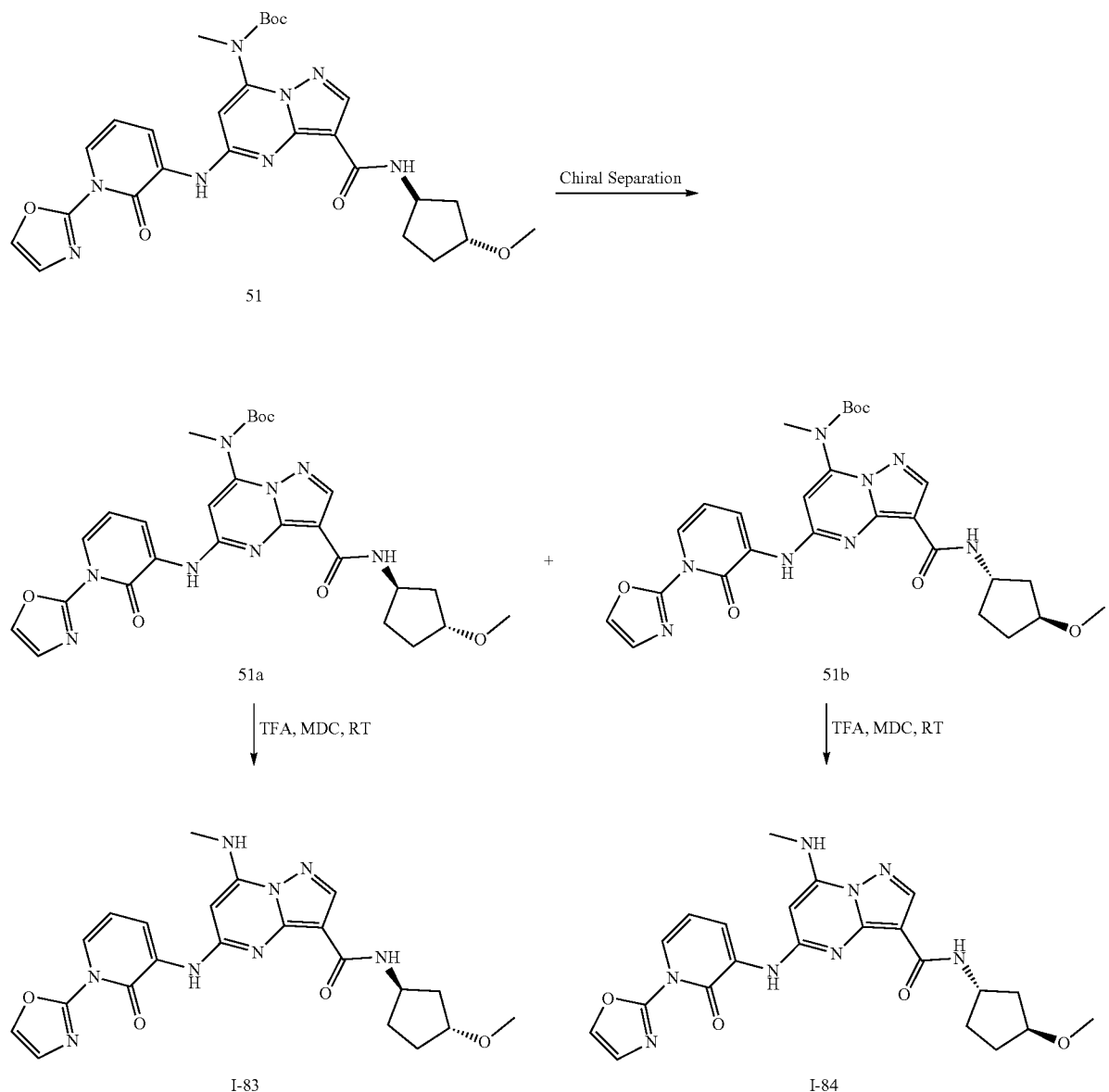

Step 1—Synthesis of Compound 51: Compound was synthesized as per experimental protocol of I-71 (Example 44) to obtain 51 (Yield: 77.58%; MS (ES): m/z 565.25 [M+H]$^+$).

Step 2—Synthesis of Compounds 51a and 51b: Isomers of 51 (0.105 g) were separated out using column CHIRAL-CEL OJ-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 51a (0.045 g; MS (ES): m/z 565.25 [M+H]$^+$). FR-b was concentrated under reduced pressure at 30° C. to afford pure 51b (0.043 g; MS (ES): m/z 565.25 [M+H]$^+$).

Step 3—Synthesis of Compound I-83: Compound was synthesized using general procedure C to obtain I-83 (0.030 g, Yield: 81.04%; MS (ES): m/z 465.87 [M+H]$^+$; LCMS purity: 100%; HPLC purity: 100%; CHIRAL HPLC purity: 100%; $^1$H NMR (DMSO-d$_6$, 400 MHZ): 9.05 (s, 1H), 8.33 (s, 1H), 8.29-8.27 (d, J=6 Hz, 1H), 8.19 (s, 1H), 7.97-7.96 (d, J=4.8 Hz, 1H), 7.65-7.63 (d, J=7.2 Hz, 1H), 7.48-7.47 (d, J=6.8 Hz, 2H), 6.41-6.38 (t, J=6.8 Hz, 1H), 6.19 (s, 1H), 4.36-4.30 (m, 1H), 3.86 (bs, 1H), 3.17 (s, 3H), 2.90-2.89 (d, J=4.8 Hz, 3H), 2.14-2.09 (m, 2H), 1.97-1.94 (m, 1H), 1.40-1.35 (m, 1H), 1.23 (bs, 2H)).

Step 4—Synthesis of Compound I-84: Compound was synthesized using general procedure C to obtain I-84 (0.030 g, Yield: 84.81%; MS (ES): m/z 465.77 [M+H]$^+$; LCMS purity: 100%; HPLC purity: 99.82%; CHIRAL HPLC purity: 97.72%; $^1$H NMR (DMSO-d$_6$, 400 MHZ): 9.07 (s, 1H), 8.35 (s, 1H), 8.30-8.29 (d, J=6 Hz, 1H), 8.21 (s, 1H), 7.98 (bs, 1H), 7.67-7.65 (d, J=7.2 Hz, 1H), 7.50 (bs, 2H), 6.43-6.40 (t, J=6.8 Hz, 1H), 6.21 (s, 1H), 4.36-4.30 (m, 1H), 3.87 (bs, 1H), 3.19 (s, 3H), 2.92-2.91 (d, J=4.8 Hz, 3H), 2.14-2.09 (m, 2H), 1.97-1.94 (m, 1H), 1.40-1.35 (m, 1H), 1.23 (bs, 2H)).

Example 52: 5-((1-((1S,2R)-2-Hydroxycyclobutyl)-2-oxo-1,2-dihydropyridin-3-yl)amino)-N-((1R,3R)-3-methoxycyclopentyl)-7-(methylamino)pyrazolo[1,5-a]pyrimidine-3-carboxamide (I-85)
And
5-((1-((1S,2R)-2-Hydroxycyclobutyl)-2-oxo-1,2-dihydropyridin-3-yl)amino)-N-((1S,3S)-3-methoxycyclopentyl)-7-(methylamino)pyrazolo[1,5-a]pyrimidine-3-carboxamide (I-86)
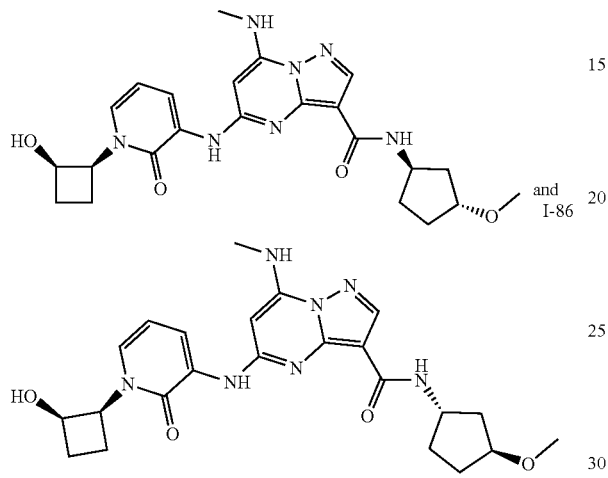
Scheme 52
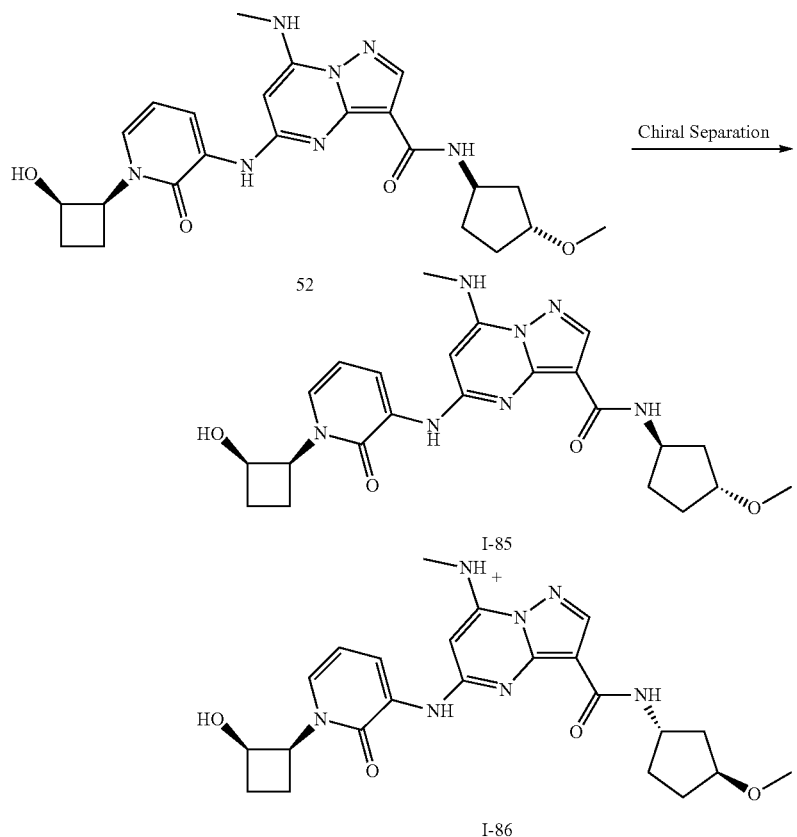

Step 1—Synthesis of Compound 52: Compound was synthesized as per experimental protocol of I-81/82 (Example 50) to obtain 52.

Step 2—Synthesis of Compounds I-85 and I-86: Isomers of 52 (0.098 g) were separated out using column CHIRALPAK AD-H (250 mm×4.6 mm, 5 μm) 0.1% DEA methanol to get pure fraction-1 (FR-a) and fraction-2 (FR-b).

FR-a was concentrated under reduced pressure at 30° C. to afford pure I-85 (0.030 g; MS (ES): m/z 468.91 [M+H]$^+$; LCMS purity: 98.69%; HPLC purity: 97.10%; CHIRAL HPLC purity: 100%; $^1$H NMR (DMSO-d$_6$, 400 MHZ): 8.58 (s, 1H), 8.17 (bs, 1H), 8.15 (bs, 1H), 7.59-7.57 (d, J=7.6 Hz, 1H), 7.52-7.51 (d, J=4.8 Hz, 1H), 7.46-7.44 (d, J=7.2 Hz, 1H), 6.25-6.22 (t, J=7.2 Hz, 1H), 6.10 (s, 1H), 5.19 (bs, 2H), 4.53 (bs, 1H), 4.36 (bs, 1H), 3.89 (bs, 1H), 3.20 (s, 3H), 2.91-2.90 (d, J=4.8 Hz, 3H), 2.74-2.69 (m, 1H), 2.13 (bs, 3H), 1.99 (bs, 1H), 1.61-1.54 (m, 3H), 1.42 (bs, 2H)).

FR-b was concentrated under reduced pressure at 30° C. to afford pure I-86 (0.030 g; MS (ES): m/z 468.64 [M+H]$^+$; LCMS purity: 98.35%; HPLC purity: 95.04%; CHIRAL HPLC purity: 97.47%; $^1$H NMR (DMSO-d$_6$, 400 MHZ): 8.58 (s, 1H), 8.17 (bs, 1H), 8.15 (bs, 1H), 7.59-7.57 (d, J=7.6 Hz, 1H), 7.52-7.51 (d, J=4.8 Hz, 1H), 7.46-7.44 (d, J=7.2 Hz, 1H), 6.25-6.22 (t, J=7.2 Hz, 1H), 6.10 (s, 1H), 4.89 (bs, 2H), 4.58 (bs, 1H), 4.36 (bs, 1H), 3.86 (bs, 1H), 3.20 (s, 3H), 2.91-2.90 (d, J=4.8 Hz, 3H), 2.74-2.69 (m, 1H), 2.13 (bs, 3H), 1.99 (bs, 1H), 1.49-1.44 (m, 3H), 1.42 (bs, 2H)).

Example 53: 5-((1-((1S,2R)-2-Hydroxycyclopentyl)-2-oxo-1,2-dihydropyridin-3-yl)amino)-N-((1R,3R)-3-methoxycyclopentyl)-7-(methylamino)pyrazolo[1,5-a]pyrimidine-3-carboxamide (I-87)

And 5-((1-((1S,2R)-2-Hydroxycyclopentyl)-2-oxo-1,2-dihydropyridin-3-yl)amino)-N-((1S,3S)-3-methoxycyclopentyl)-7-(methylamino)pyrazolo[1,5-a]pyrimidine-3-carboxamide (I-88)

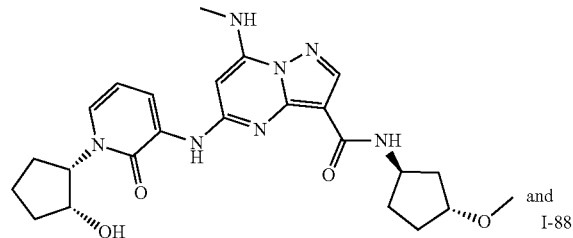

I-87

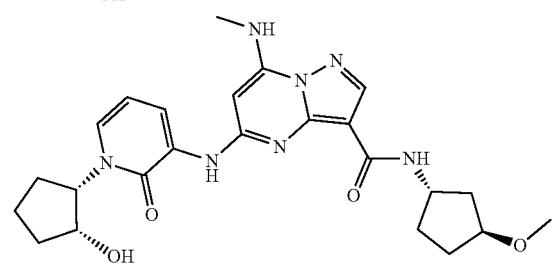

and
I-88

Scheme 53

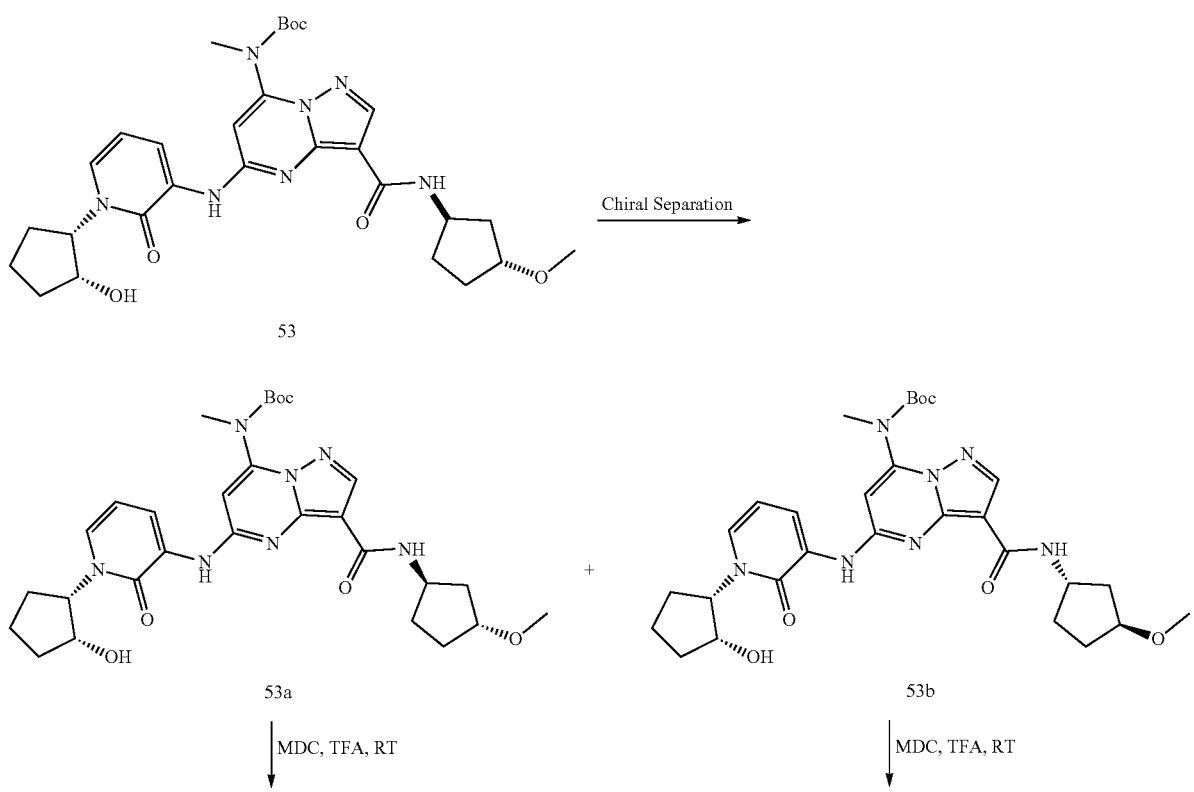

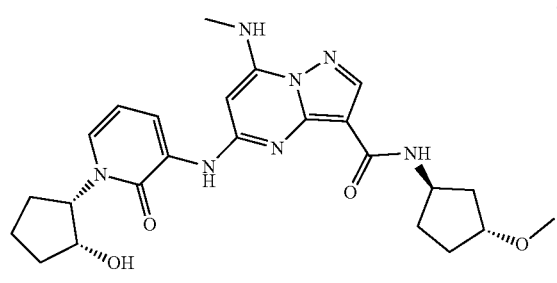

I-87

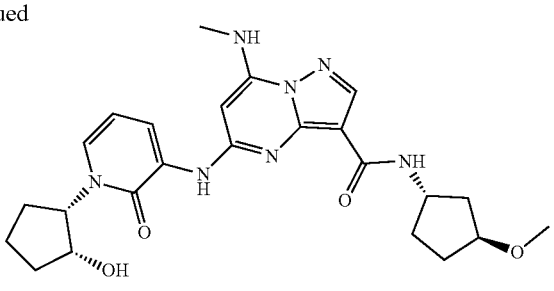

I-88

Step 1—Synthesis of Compound 53: Compound was synthesized from Core A utilizing general methods A and B to obtain 53 (Yield: 65.59%; MS (ES): 582.30 [M+H]$^+$).

Step 2—Synthesis of Compounds 53a and 53b: Isomers of 53 (0.105 g) were separated out using column CHIRALCEL OX-H (250 mm×4.6 mm, 5 μm) and 0.1% DEA_HEX_IPA-ACN (70-30) as co-solvent with flow rate of 4 mL/min to get pure fraction-1 (FR-a) and fraction-2 (FR-b). FR-a was concentrated under reduced pressure at 30° C. to afford pure 53a (0.035 g; MS (ES): m/z 582.30 [M+H]$^+$). FR-b was concentrated under reduced pressure at 30° C. to afford pure 53b (0.037 g; MS (ES): m/z 582.30 [M+H]$^+$).

Step 3—Synthesis of Compound I-87: Compound was synthesized using general procedure C to obtain I-87 (0.025 g, Yield: 86.28%; MS (ES): m/z 482.51 [M+H]$^+$; LCMS purity: 100%; HPLC purity: 98.72%; CHIRAL HPLC purity: 98.50%; $^1$H NMR (DMSO-d$_6$, 400 MHZ): 8.86 (bs, 1H), 8.20 (bs, 1H), 8.18 (s, 1H), 7.90-7.89 (d, J=4.8 Hz, 1H), 7.69-7.68 (d, J=7.2 Hz, 1H), 7.43-7.41 (d, J=6.8 Hz, 1H), 6.22-6.21 (t, J=7.2 Hz, 1H), 6.19 (s, 1H), 4.98-4.95 (m, 1H), 4.88-4.87 (d, J=4.8 Hz, 1H), 4.39-4.33 (m, 1H), 4.21-4.20 (d, J=4.4 Hz, 1H), 3.89 (bs, 1H), 3.20 (s, 3H), 2.91-2.90 (d, J=4.8 Hz, 3H), 2.14-2.11 (m, 3H), 2.01-1.99 (m, 2H), 1.90 (bs, 2H), 1.63 (bs, 2H), 1.57 (bs, 2H), 1.24 (bs, 1H)).

Step 4—Synthesis of Compound I-88: Compound was synthesized using general procedure C to obtain I-88 (0.025 g, Yield: 81.62%; MS (ES): m/z 482.42 [M+H]$^+$; LCMS purity: 99.36%; HPLC purity: 97.83%; CHIRAL HPLC purity: 94.76%; $^1$H NMR (DMSO-d$_6$, 400 MHZ): 8.86 (bs, 1H), 8.20 (bs, 1H), 8.18 (s, 1H), 7.90-7.89 (d, J=4.8 Hz, 1H), 7.69-7.68 (d, J=7.2 Hz, 1H), 7.43-7.41 (d, J=6.8 Hz, 1H), 6.22-6.21 (t, J=7.2 Hz, 1H), 6.19 (s, 1H), 4.98-4.94 (m, 1H), 4.88-4.87 (d, J=4.8 Hz, 1H), 4.39-4.33 (m, 1H), 4.21-4.20 (d, J=4.4 Hz, 1H), 3.89 (bs, 1H), 3.20 (s, 3H), 2.91-2.90 (d, J=4.8 Hz, 3H), 2.14-2.11 (m, 3H), 2.01-1.99 (m, 2H), 1.90 (bs, 2H), 1.63 (bs, 2H), 1.57 (bs, 2H), 1.24 (bs, 1H)).

Example 54: 5-((1-(3,3-Difluorocyclobutyl)-2-oxo-1,2-dihydropyridin-3-yl)amino)-N-(3-hydroxy-3-methylcyclopentyl)-7-(methylamino)pyrazolo[1,5-a]pyrimidine-3-carboxamide (I-89)

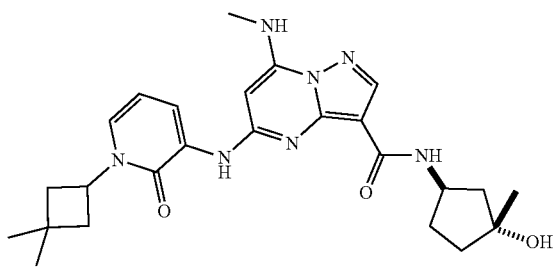

I-89

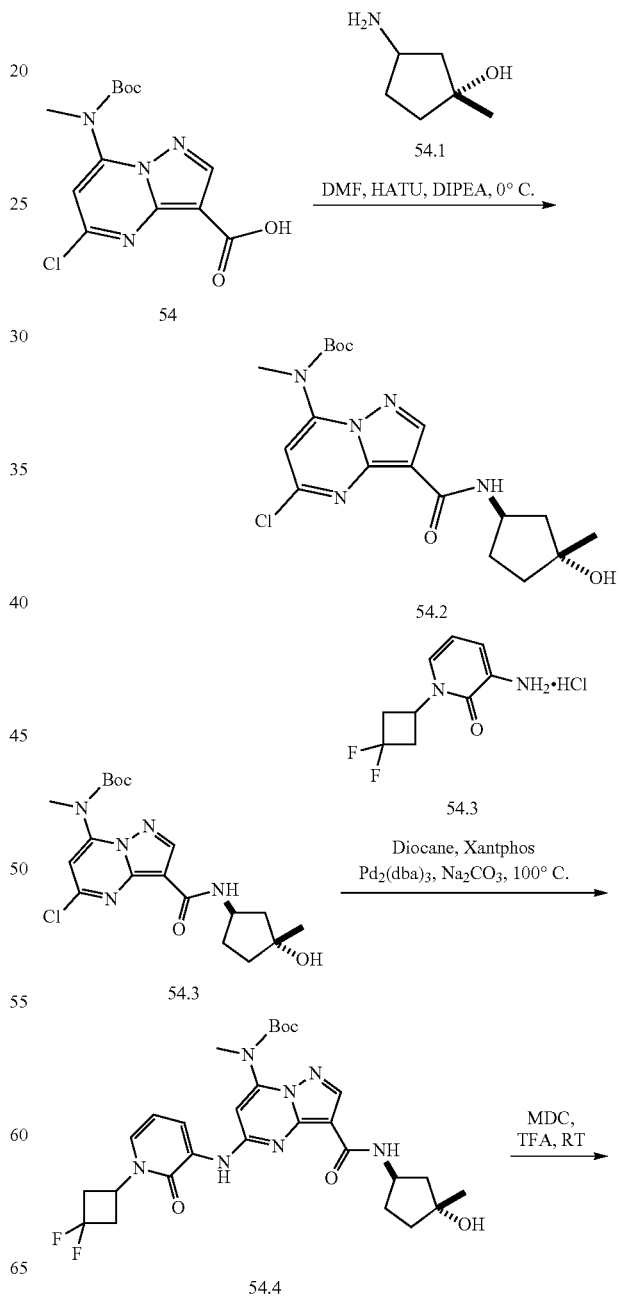

-continued

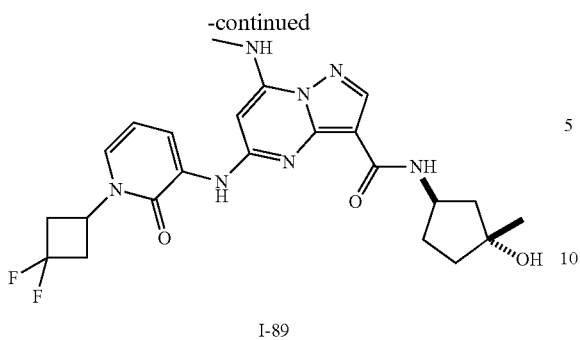

I-89

Step 1—Synthesis of Compound 54: Compound was synthesized using general procedure of Core A synthesis to obtain 54 (Yield: 71.67%; MS (ES): m/z 327.7 [M+H]$^+$).

Step 2—Synthesis of Compound 54.2: Compound was synthesized using general method A to obtain 54.2 (Yield: 47.83%; MS (ES): m/z 424.17 [M+H]$^+$).

Step 3—Synthesis of Compound 54.3: Compound was synthesized as per experimental protocol of I-33 (Example 22) to obtain 54.3.

Step 3—Synthesis of Compound 54.4: Compound was synthesized using general procedure B to obtain 54.4 (0.140 g, Yield: 67.33%; MS (ES): m/z 588.27 [M+H]$^+$).

Step 5—Synthesis of Compound I-89: Compound was synthesized using general procedure C to obtain I-89 (0.025 g, Yield: 86.10%; MS (ES): m/z 488.87 [M+H]$^+$; LCMS purity: 98.22%; HPLC purity: 96.44%; CHIRAL HPLC: 50.85%, 48.99%; $^1$H NMR (DMSO-d$_6$, 400 MHZ): 8.96 (s, 1H), 8.24-8.23 (d, J=6 Hz, 1H), 8.19 (s, 1H), 7.93-7.91 (d, J=4.8 Hz, 1H), 7.67-7.65 (d, J=7.6 Hz, 1H), 7.48-7.47 (d, J=6 Hz, 1H), 6.28-6.26 (t, J=7.2 Hz, 1H), 6.24 (s, 1H), 4.91 (bs, 1H), 4.54 (bs, 1H), 4.44 (s, 1H), 3.22 (bs, 1H), 3.20 (bs, 3H), 2.91-2.90 (d, J=4.8 Hz, 3H), 2.26 (bs, 1H), 2.08-2.06 (m, 1H), 1.73 (bs, 1H), 1.66 (bs, 1H), 1.42-1.36 (m, 2H), 1.25 (bs, 3H)).

Example 55: 5-((1-(3,3-Difluorocyclobutyl)-2-oxo-1,2-dihydropyridin-3-yl)amino)-N-((1S,2S)-2-hydroxy-2-methylcyclopentyl)-7-(methylamino)pyrazolo[1,5-a]pyrimidine-3-carboxamide (I-90)

And 5-((1-(3,3-Difluorocyclobutyl)-2-oxo-1,2-dihydropyridin-3-yl)amino)-N-((1R,2R)-2-hydroxy-2-methylcyclopentyl)-7-(methylamino)pyrazolo[1,5-a]pyrimidine-3-carboxamide (I-91)

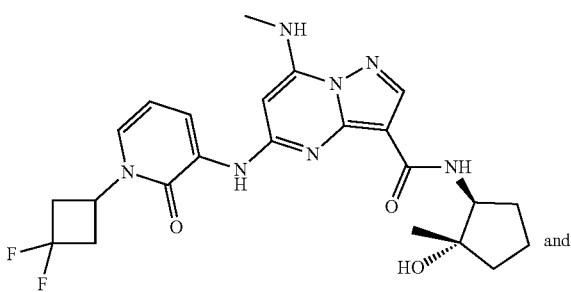

I-90 and

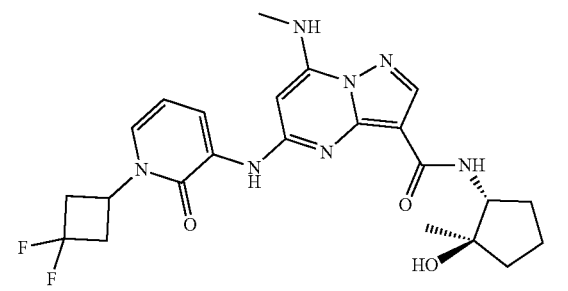

I-91

Scheme 55

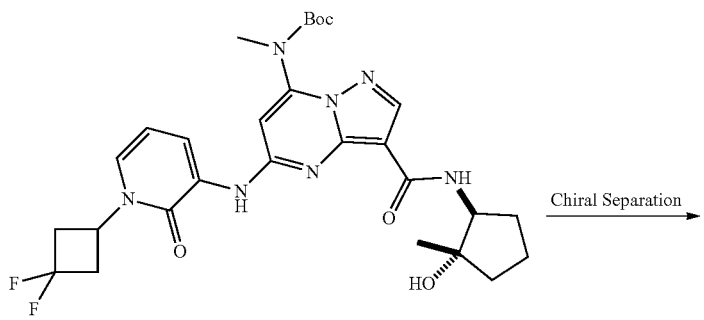

55

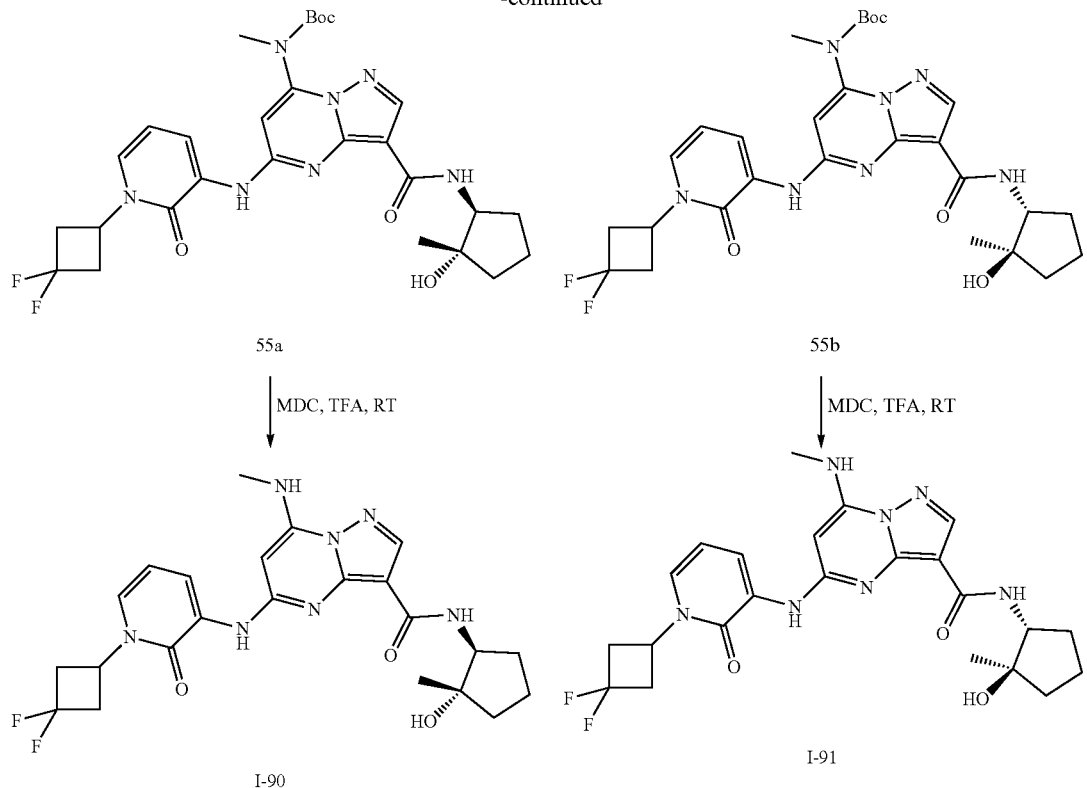

Step 1—Synthesis of Compound 55: Compound was synthesized as per experimental protocol of I-89 (Example 54) to obtain 55 (Yield: 66.37%; MS (ES): m/z 588.27 [M+H]$^+$).

Step 2—Synthesis of Compound 55a and 55b: Isomers of 55 (0.110 g) were separated out using column CHIRALCEL OJ-H (250 mm×4.6 mm, 5 μm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 55a (0.043 g). MS (ES): m/z 588.27 [M+H]$^+$). FR-b was concentrated under reduced pressure at 30° C. to afford pure 55b (0.041 g; MS (ES): m/z 588.27 [M+H]$^+$).

Step 3—Synthesis of Compound I-90: Compound was synthesized using general procedure C to obtain I-90 (0.030 g, Yield: 84.10%; MS (ES): m/z 489.07 [M+H]$^+$; LCMS purity: 100%; HPLC purity: 99.28%; CHIRAL HPLC purity: 100%; $^1$H NMR (DMSO-d$_6$, 400 MHZ): 8.92 (s, 1H), 8.22 (s, 1H), 8.19-8.17 (d, J=6.8 Hz, 1H), 7.94-7.93 (d, J=4.4 Hz, 1H), 7.53-7.51 (d, J=7.6 Hz, 1H), 7.43-7.41 (d, J=5.6 Hz, 1H), 6.29-6.26 (t, J=6.8 Hz, 1H), 6.23 (s, 1H), 4.21-4.15 (m, 2H), 3.19 (bs, 4H), 2.90-2.89 (d, J=4.8 Hz, 3H), 2.21-2.18 (m, 1H), 1.68 (bs, 5H), 1.43-1.39 (m, 1H), 1.05 (s, 3H)).

Step 4—Synthesis of Compound I-91: Compound was synthesized using general procedure C to obtain I-91 (0.031 g, Yield: 91.14%; MS (ES): m/z 489.07 [M+H]$^+$; LCMS purity: 97.70%; HPLC purity: 98.14%; CHIRAL HPLC purity: 95.00%; $^1$H NMR (DMSO-d$_6$, 400 MHZ): 8.92 (s, 1H), 8.22 (s, 1H), 8.18-8.17 (d, J=6.8 Hz, 1H), 7.94-7.93 (d, J=4.4 Hz, 1H), 7.53-7.51 (d, J=7.6 Hz, 1H), 7.43-7.41 (d, J=5.6 Hz, 1H), 6.29-6.26 (t, J=6.8 Hz, 1H), 6.23 (s, 1H), 4.21-4.15 (m, 2H), 3.19 (bs, 4H), 2.90-2.89 (d, J=4.8 Hz, 3H), 2.21-2.18 (m, 1H), 1.68 (bs, 5H), 1.43-1.39 (m, 1H), 1.05 (s, 3H)).

Example 56: 5-((1-(3,3-Difluorocyclobutyl)-2-oxo-1,2-dihydropyridin-3-yl)amino)-N-((1R,3R)-3-hydroxy-3-methylcyclohexyl)-7-(methylamino)pyrazolo[1,5-a]pyrimidine-3-carboxamide (I-92)

And 5-((1-(3,3-Difluorocyclobutyl)-2-oxo-1,2-dihydropyridin-3-yl)amino)-N-((1S,3S)-3-hydroxy-3-methylcyclohexyl)-7-(methylamino)pyrazolo[1,5-a]pyrimidine-3-carboxamide (I-93)

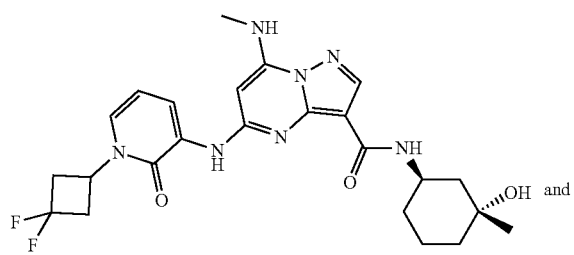

I-92 and

-continued

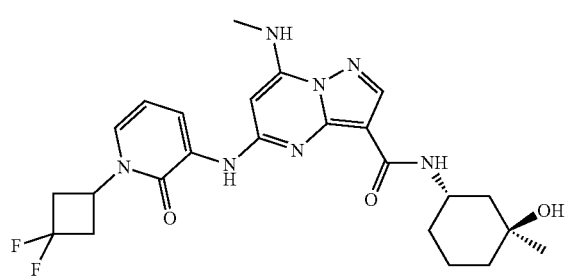

I-93

PAK AD-H (250 mm×4.6 mm, 5 μm) and 0.1% DEA in IPA:MEOH (50:50) as co-solvent with flow rate of 4 mL/min to get pure fraction-1 (FR-a) and fraction-2 (FR-b). FR-a was concentrated under reduced pressure at 30° C. to afford pure 56a (0.042 g). MS (ES): m/z 602.29 [M+H]$^+$). FR-b was concentrated under reduced pressure at 30° C. to afford pure 56b (0.042 g; MS (ES): m/z 602.29 [M+H]$^+$).

Step 3—Synthesis of compound I-92: To 56a (0.040 g, 0.070 mmol, 1.0 eq) was added 4M hydrochloric acid in 1,4 Dioxane (3 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with Scheme 56

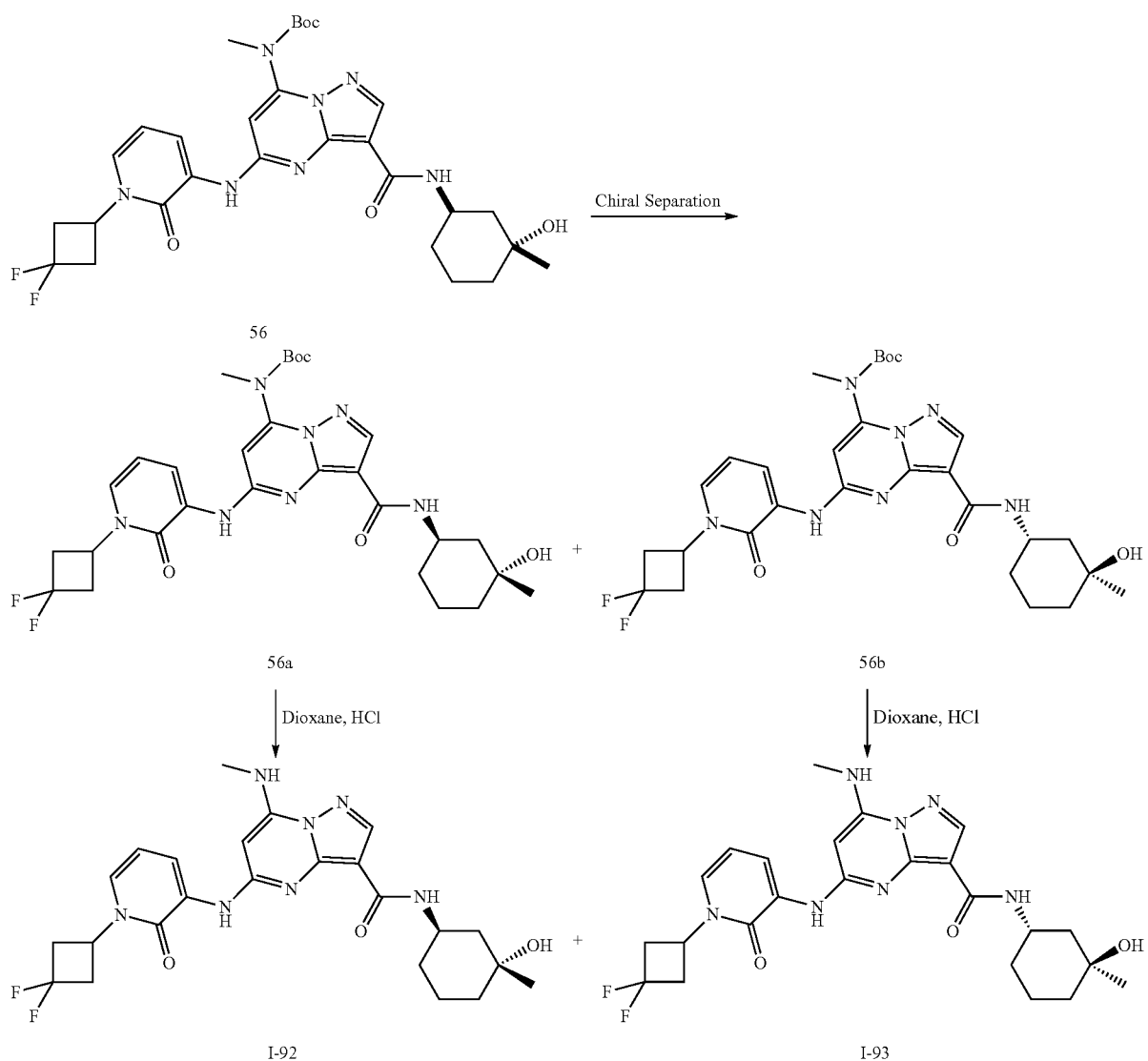

Step 1—Synthesis of Compound 56: Compound was synthesized from Core A utilizing general methods A and B to obtain 56 (Yield: 72.79%; MS (ES): m/z 602.29 [M+H]$^+$).

Step 2—Synthesis of Compounds 56a and 56b: Isomers of 56 (0.110 g) were separated out using column CHIRAL-brine, dried over sodium sulphate, concentrated under reduced pressure to obtain residue which was triturated with diethyl ether to obtain I-92 (0.031 g, Yield: 88.54%; MS (ES): m/z 502.92 [M+H]$^+$; LCMS purity: 95.42%; HPLC purity: 95.19%; CHIRAL HPLC purity: 96.95%; $^1$H NMR (DMSO-d6, 400 MHZ): 8.97 (s, 1H), 8.24-8.22 (d, J=7.2 Hz, 1H), 8.20 (s, 1H), 7.94-7.92 (d, J=4.8 Hz, 1H), 7.55-7.53 (d, J=8 Hz, 1H), 7.49-7.47 (d, J=7.2 Hz, 1H), 6.30-6.26 (t, J=6.8 Hz, 1H), 6.25 (s, 1H), 4.26 (s, 1H), 4.17-4.12 (m, 1H), 2.91-2.90 (d, J=4.8 Hz, 1H), 2.52 (s, 3H), 1.97 (bs, 1H), 1.76 (bs, 1H), 1.66 (bs, 1H), 1.57-1.50 (m, 3H), 1.24 (bs, 3H), 1.18 (bs, 5H), 1.05-1.02 (m, 1H)).

Step 4—Synthesis of Compound I-93: To 56b (0.040 g, 0.070 mmol, 1.0 eq) was added 4M hydrochloric acid in 1,4 Dioxane (3 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulphate, concentrated under reduced pressure to obtain residue which was triturated with diethyl ether to obtain I-93 (0.031 g, Yield: 88.54%; MS (ES): m/z 502.92 [M+H]+; LCMS purity: 96.00%; HPLC purity: 95.00%; CHIRAL HPLC purity: 97.00%; $^1$H NMR (DMSO-d6, 400 MHZ): 8.96 (s, 1H), 8.24-8.22 (d, J=7.2 Hz, 1H), 8.20 (s, 1H), 7.94-7.92 (d, J=4.8 Hz, 1H), 7.55-7.53 (d, J=8 Hz, 1H), 7.50-7.48 (d, J=7.2 Hz, 1H), 6.30-6.26 (t, J=6.8 Hz, 1H), 6.25 (s, 1H), 4.26 (s, 1H), 4.17-4.12 (m, 1H), 2.91-2.90 (d, J=4.8 Hz, 1H), 2.52 (s, 3H), 1.97 (bs, 1H), 1.76 (bs, 1H), 1.66 (bs, 1H), 1.57-1.50 (m, 3H), 1.24 (bs, 3H), 1.18 (bs, 5H), 1.06-1.03 (m, 1H)).

Example 57: N-((1R,3R)-3-Methoxy-3-methylcyclohexyl)-7-(methylamino)-5-((2-oxo-1-((S)-tetrahydro-2H-pyran-3-yl)-1,2-dihydropyridin-3-yl)amino)pyrazolo[1,5-a]pyrimidine-3-carboxamide (I-94)

And

N-((1S,3S)-3-Methoxy-3-methylcyclohexyl)-7-(methylamino)-5-((2-oxo-1-((S)-tetrahydro-2H-pyran-3-yl)-1,2-dihydropyridin-3-yl)amino)pyrazolo[1,5-a]pyrimidine-3-carboxamide (I-95)

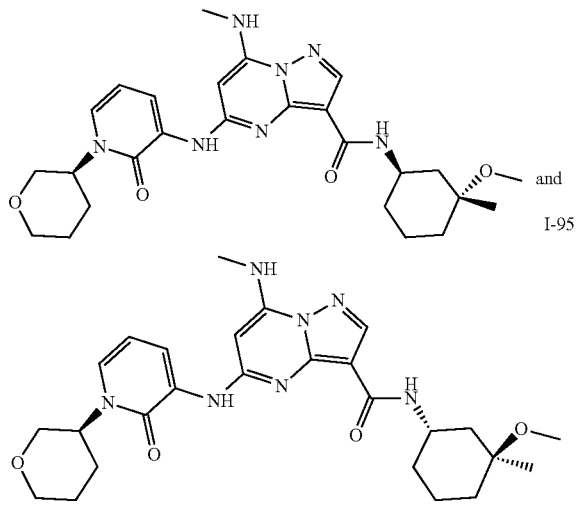

Scheme 57

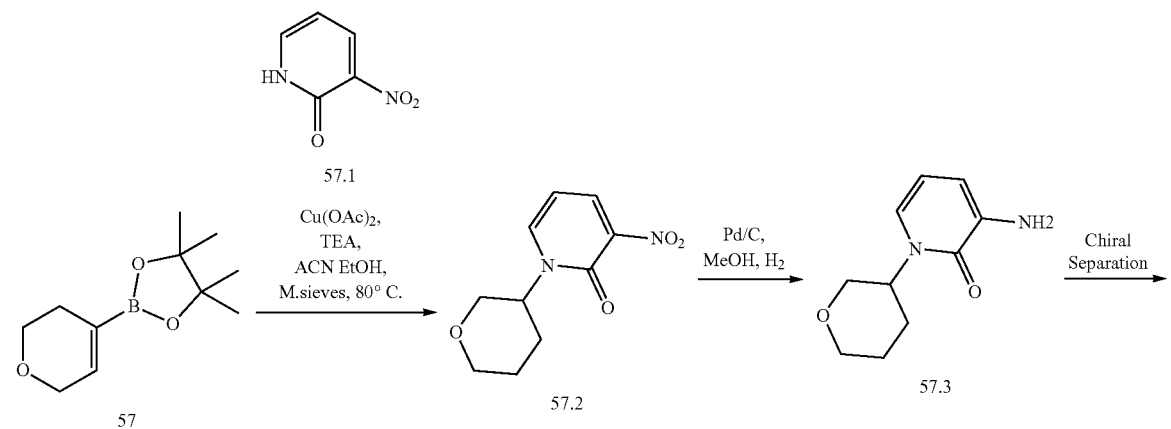

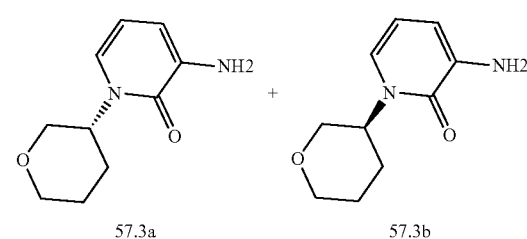

-continued
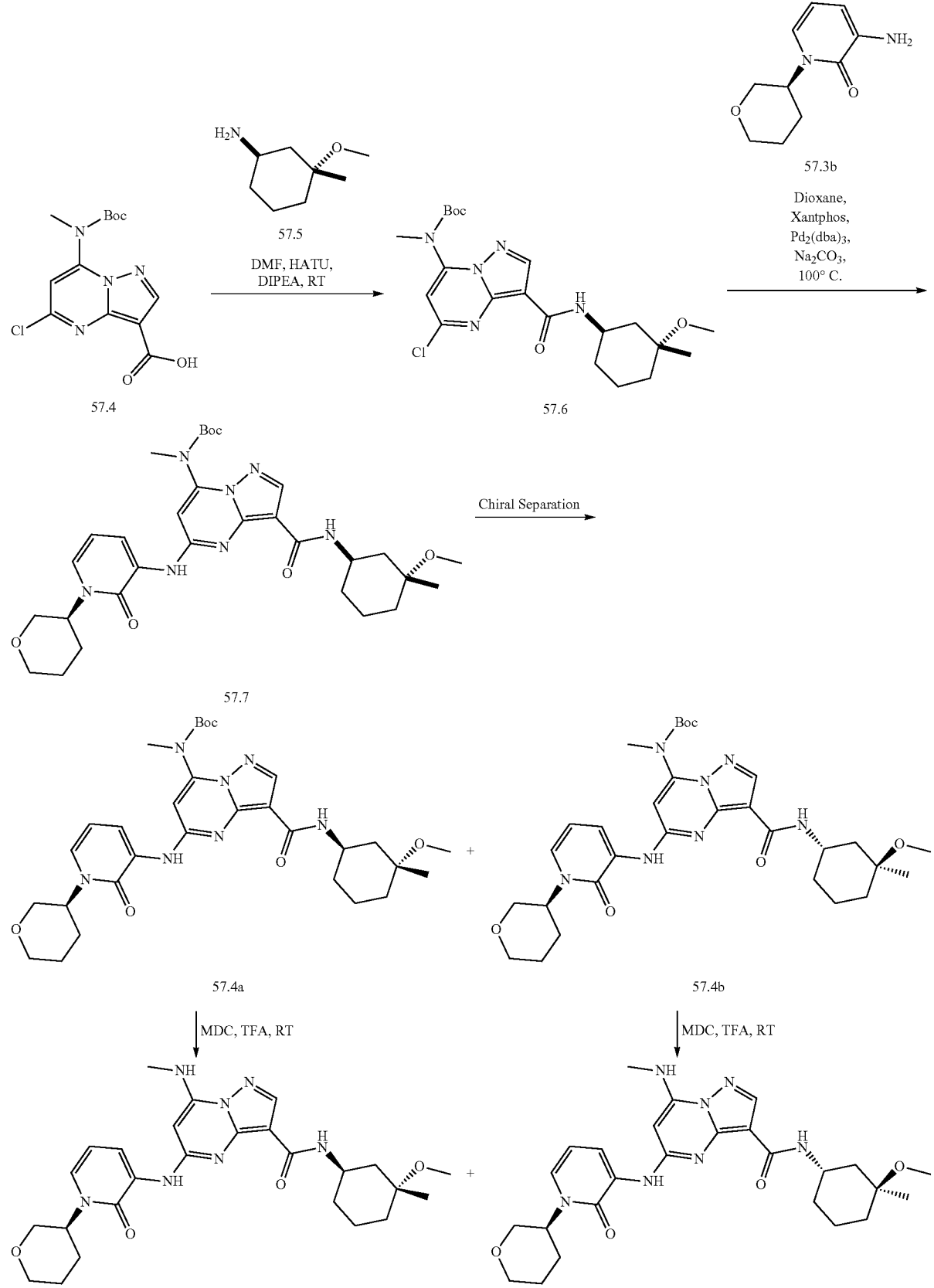

Step 1—Synthesis of Compound 57.2: To a solution of 57 (0.60 g, 2.86 mmol, 1.0 eq) in ethanol:acetonitrile (1:1, 1 mL) was added 57.1 (0.40 g, 2.86 mmol, 1.0 eq) copper acetate (0.51 g, 2.86 mmol, 1.0 eq), molecular sieves (0.40 g, 2.86 mmol, 1.0 eq), and trimethylamine (005 g, 5.72 mmol, 2.0 eq). The reaction mixture was stirred at 80° C. for 3 h. After completion of three reaction, the mixture was filtered through celite and product was washed with methanol. Organic layer was combined, dried over sodium sulphate and concentrated under reduced pressure to obtain crude material. This was further purified by column chromatography to obtain pure 57.2. (0.19 g, Yield: 29.94%; MS (ES) m/z 220.20 [M+H]$^+$).

Step 2—Synthesis of Compound 57.3: To a solution of 57.2 (0.19 g, 0.85 mmol, 1.0 eq) in methanol (3 mL) Pd/C (0.04 g) was added. Hydrogen was purged through the reaction mixture for 24 h at room temperature. After completion of reaction, reaction mixture was filtered through celite-bed and washed with methanol. Filtrate was concentrated under reduced pressure to obtain 57.3 (0.06 g, Yield: 36.13%; MS (ES): m/z 195.23 [M+H]$^+$).

Isomers of 57.3 (0.8 g) were separated using column CHIRAL PAK AD-H (250 mm×4.6 mm, 5 μm) and 0.3% Diethylamine in methanol as co-solvent with flow rate of 4 mL/min to get pure fraction-1 (FR-b) and fraction-2 (FR-b). FR-a was evaporated under reduced pressure at 30° C. to afford pure fraction-1 (0.3 g; MS (ES): m/z 195.11 [M+H]$^+$). FR-b was evaporated under reduced pressure at 30° C. to afford pure fraction-2. (0.3 g; MS (ES): m/z 195.11 [M+H]$^+$).

Step 3—Synthesis of Compound 57.4: Compound was synthesized using the procedure for the preparation of Core A to obtain 57.4 (MS (ES): m/z 327.08 [M+H]$^+$).

Step 4—Synthesis of Compound 57.6: Compound was synthesized using general procedure A to obtain 57.6 (0.510 g, Yield: 55.86%; MS (ES): m/z 452.20 [M+H]$^+$).

Step 5—Synthesis of Compound: Compound was synthesized using general procedure B to obtain 57.7 (Yield: 65.40%; MS (ES): m/z 610.33 [M+H]$^+$).

Step 6—Synthesis of Compounds 57.7a and 57.7b: Isomers of 57.7 (0.150 g) were separated out using column CHIRALPAK AD-H (250 mm×4.6 mm, 5 μm) and 0.1% DEA in IPA:MEOH (50:50) as co-solvent with flow rate of 4 mL/min to get pure fraction-1 (FR-a) and fraction-2 (FR-b). FR-a was concentrated under reduced pressure at 30° C. to afford pure 57a (0.041 g; MS (ES): m/z 610.33 [M+H]$^+$). FR-b was concentrated under reduced pressure at 30° C. to afford pure 57b (0.041 g; MS (ES): m/z 610.33 [M+H]$^+$).

Step 7—Synthesis of Compound I-94: Compound was synthesized using general procedure C to obtain I-94 (0.030 g, Yield: 87.55%; MS (ES): 510.22 [M+H]$^+$; LCMS purity: 95.60%; HPLC purity: 95.16%; CHIRAL HPLC: 100%; $^1$H NMR (DMSO-d$_6$, 400 MHZ): 8.90 (s, 1H), 8.20 (s, 1H), 8.17 (s, 1H), 7.91-7.90 (d, J=4.8 Hz, 1H), 7.56-7.54 (d, J=7.2 Hz, 2H), 6.29-6.25 (t, J=7.2 Hz, 1H), 6.23 (s, 1H), 4.87 (bs, 1H), 3.99 (bs, 1H), 3.84 (bs, 2H), 3.60-3.55 (t, J=9.2 Hz, 1H), 3.13 (s, 3H), 2.90-2.89 (d, J=4.8 Hz, 3H), 1.75 (bs, 3H), 1.54 (bs, 2H), 1.23 (bs, 5H), 1.14 (bs, 6H)).

Step 4—Synthesis of Compound I-95: Compound was synthesized using general procedure C to obtain I-95 (0.030 g, Yield: 87.55%; MS (ES): 510.32 [M+H]$^+$; LCMS purity: 100%; HPLC purity: 100%; CHIRAL HPLC: 96.45%; $^1$H NMR (DMSO-d$_6$, 400 MHZ): 8.92 (s, 1H), 8.21 (s, 1H), 8.18 (s, 1H), 7.92-7.91 (d, J=4.8 Hz, 1H), 7.57-7.55 (d, J=7.2 Hz, 2H), 6.30-6.26 (t, J=7.2 Hz, 1H), 6.24 (s, 1H), 4.91-4.86 (m, 1H), 3.99 (bs, 1H), 3.85 (bs, 2H), 3.61-3.56 (t, J=9.2 Hz, 1H), 3.14 (s, 3H), 2.91-2.90 (d, J=4.8 Hz, 3H), 1.76 (bs, 3H), 1.55 (bs, 2H), 1.23 (bs, 5H), 1.15 (bs, 6H)).

Example 58: 5-((1-((1S,2S)-2-Hydroxycyclobutyl)-2-oxo-1,2-dihydropyridin-3-yl)amino)-N-((1R,3R)-3-methoxycyclohexyl)-7-(methylamino)pyrazolo[1,5-a]pyrimidine-3-carboxamide (I-96)

And 5-((1-((1S,2S)-2-Hydroxycyclobutyl)-2-oxo-1,2-dihydropyridin-3-yl)amino)-N-((1S,3S)-3-methoxycyclohexyl)-7-(methylamino)pyrazolo[1,5-a]pyrimidine-3-carboxamide (I-97)

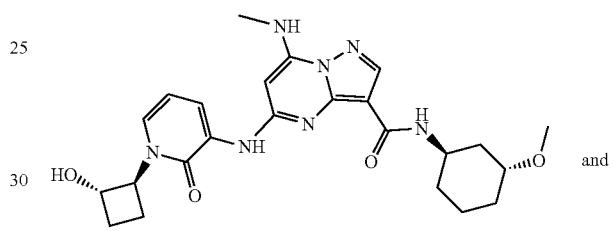

I-96

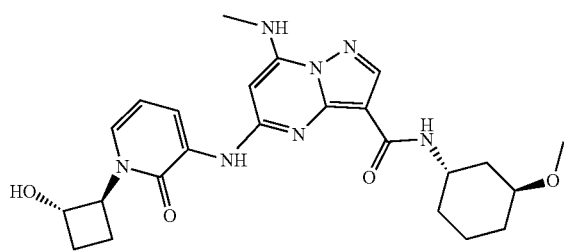

I-97

Scheme 58

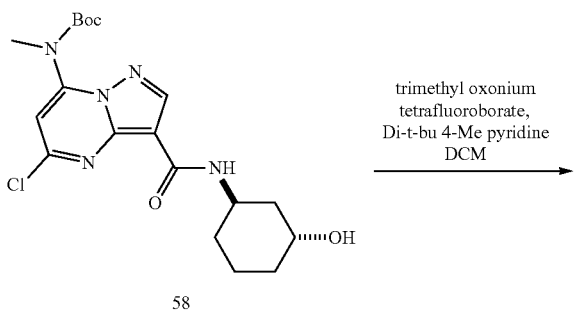

58 trimethyl oxonium tetrafluoroborate,
Di-t-bu 4-Me pyridine
DCM

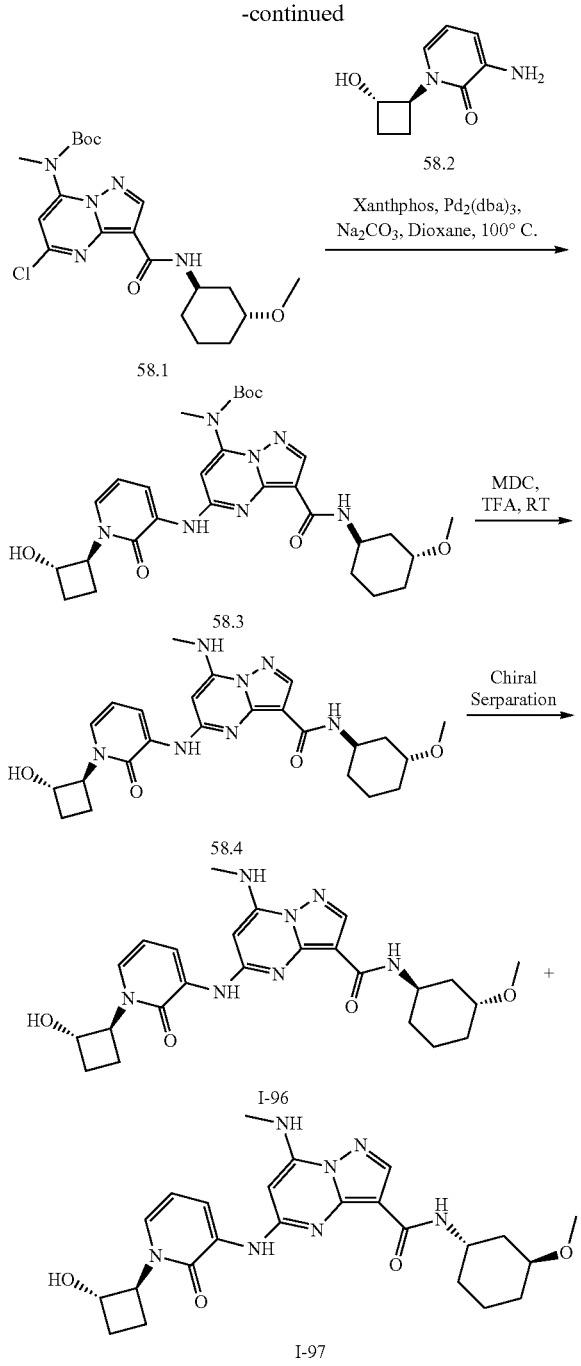

eluted in 2.5% methanol in dichloromethane to obtain pure 58.1 (0.360 g, Yield: 59.06%; MS (ES): m/z 438.19 [M+H]$^+$).

Step 3—Synthesis of Compound 58.3: Compound was synthesized using general procedure B to obtain 58.3 (0.140 g, Yield: 70.27%; MS (ES): m/z 582.30 [M+H]$^+$).

Step 4—Synthesis of Compound 58.4: Compound was synthesized using general procedure C to obtain 58.4 (0.030 g, Yield: 90.59%; MS (ES): m/z 482.41 [M+H]$^+$; LCMS purity: 98.09%; HPLC purity: 98.11%; CHIRAL HPLC: 41.28%, 49.65%; $^1$H NMR (DMSO-d$_6$, 400 MHZ): 8.89 (s, 1H), 8.20 (s, 1H), 8.18 (s, 1H), 7.91-7.90 (d, J=4.8 Hz, 1H), 7.59-7.57 (d, J=8.4 Hz, 1H), 7.50.7.49 (d, J=6.8 Hz, 1H), 7.39 (bs, 2H), 6.33-6.29 (t, J=7.2 Hz, 1H), 6.22 (s, 1H), 5.62 (bs, 1H), 4.93-4.91 (d, J=8.4 Hz, 1H), 4.36 (bs, 1H), 4.07 (bs, 1H), 3.57 (bs, 1H), 3.24 (s, 3H), 2.90-2.89 (d, J=4.8 Hz, 3H), 2.13-2.11 (d, J=7.2 Hz, 3H), 1.77 (bs, 3H), 1.59 (bs, 3H), 0.85 (bs, 1H)).

Step 5—Synthesis of Compounds I-96 and I-97: Isomers of 58.4 (0.102 g) were separated out using column CHIRAL PAK OX-H (250 mm×4.6 mm, 5 μm) 0.1% DEA_HEX_IPA-ACN (70-30) to get pure fraction-1 (FR-a) and fraction-2 (FR-b).

FR-a was concentrated under reduced pressure at 30° C. to afford pure I-96 (0.035 g; MS (ES): m/z 482.2 [M+H]$^+$; LCMS purity: 100%; HPLC purity: 99.59%; CHIRAL HPLC purity: 97.02%; $^1$H NMR (DMSO-d$_6$, 400 MHZ): 8.91 (s, 1H), 8.21 (s, 1H), 8.19 (s, 1H), 7.93-7.92 (d, J=4.8 Hz, 1H), 7.61-7.59 (d, J=8 Hz, 1H), 7.52-7.50 (d, J=6.8 Hz, 1H), 6.34-6.31 (t, J=7.2 Hz, 1H), 6.23 (s, 1H), 5.65-5.63 (d, J=6.8 Hz, 1H), 5.95-5.90 (m, 1H), 4.37 (bs, 1H), 4.10 (bs, 1H), 3.59 (bs, 1H), 2.26 (s, 3H), 2.91-2.90 (d, J=4.8 Hz, 3H), 2.14-2.13 (d, J=7.2 Hz, 3H), 1.90 (bs, 1H), 1.79 (bs, 1H), 1.63 (bs, 3H), 1.24 (bs, 2H), 1.04 (bs, 1H), 0.89-0.85 (t, J=7.2 Hz, 1H)).

FR-b was concentrated under reduced pressure at 30° C. to afford pure I-97 (0.036 g; MS (ES): m/z 482.2 [M+H]$^+$; LCMS purity: 100%; HPLC purity: 99.00%; CHIRAL HPLC purity: 97.70%; $^1$H NMR (DMSO-d$_6$, 400 MHZ): 8.90 (s, 1H), 8.21 (s, 1H), 8.19 (s, 1H), 7.93-7.92 (d, J=4.8 Hz, 1H), 7.61-7.59 (d, J=8 Hz, 1H), 7.52-7.50 (d, J=6.8 Hz, 1H), 6.34-6.31 (t, J=7.2 Hz, 1H), 6.23 (s, 1H), 5.65-5.63 (d, J=6.8 Hz, 1H), 5.95-5.90 (m, 1H), 4.37 (bs, 1H), 4.10 (bs, 1H), 3.59 (bs, 1H), 2.26 (s, 3H), 2.91-2.90 (d, J=4.8 Hz, 3H), 2.14-2.13 (d, J=7.2 Hz, 3H), 1.90 (bs, 1H), 1.79 (bs, 1H), 1.63 (bs, 3H), 1.23 (bs, 2H), 1.04 (bs, 1H), 0.89-0.85 (t, J=7.2 Hz, 1H)).

Example 59: 5-((1-((1R,2S)-2-Hydroxycyclobutyl)-2-oxo-1,2-dihydropyridin-3-yl)amino)-N-((trans-1,3)-3-methoxycyclohexyl)-7-(methylamino)pyrazolo[1,5-a]pyrimidine-3-carboxamide (I-98)

Step 1—Synthesis of Compound 58: Compound was synthesized from Core A utilizing general method A to obtain 58 (Yield: 59.06%; MS (ES): m/z 438.19 [M+H]$^+$).

Step 2—Synthesis of Compound 58.1: To a solution of 58 (0.590 g, 1.39 mmol, 1.0 eq), in dichloromethane (6 mL) was added Trimethyloxonium tetrafluoroborate (0.411 g, 2.78 mmol, 2.0 eq) and Di t-Bu 4-methyl pyridine (0.854 g, 4.17 mmol, 3.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was

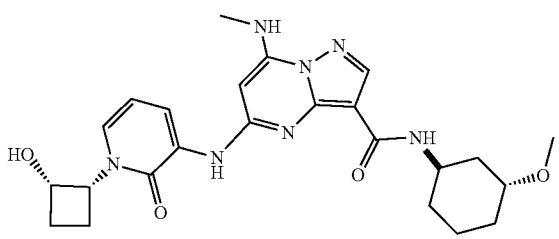

I-98

Scheme 59

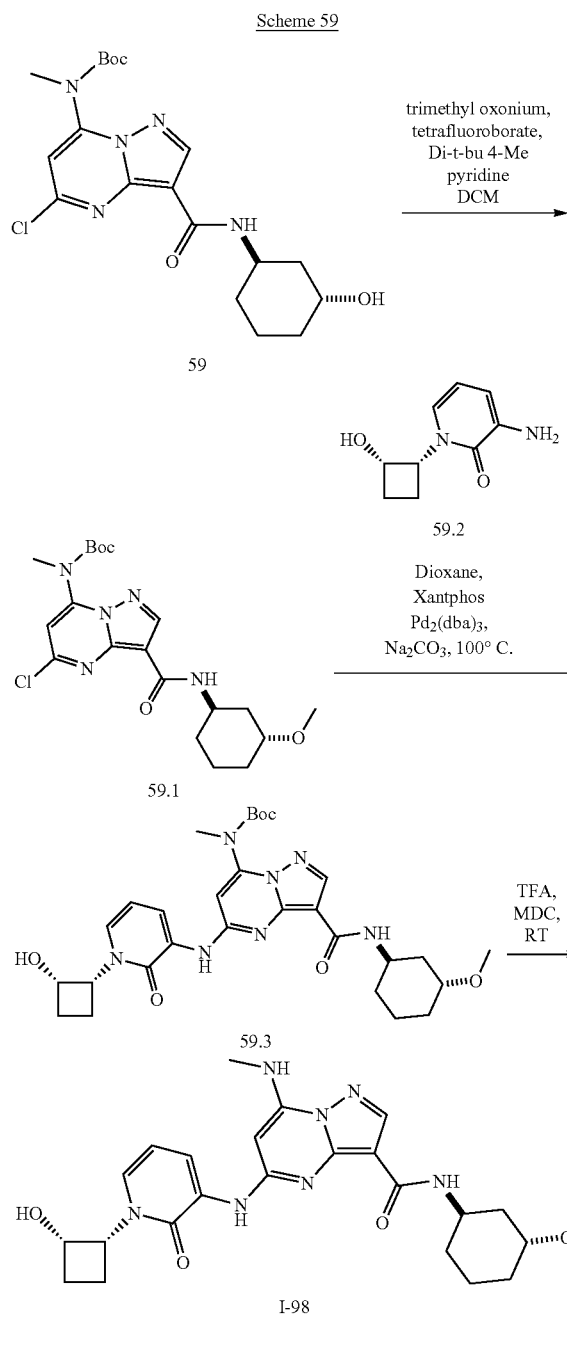

Step 1—Synthesis of Compound 59: Compound was synthesized from Core A utilizing general method A to obtain 59 (Yield: 59.06%; MS (ES): m/z 438.19 [M+H]⁺).

Step 2—Synthesis of Compound 59.1: To a solution of 59 (0.590 g, 1.39 mmol, 1.0 eq), in dichloromethane (6 mL) was added Trimethyloxonium tetrafluoroborate (0.411 g, 2.78 mmol, 2.0 eq) and Di t-Bu 4-methyl pyridine (0.854 g, 4.17 mmol, 3.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 2.5% methanol in dichloromethane to obtain pure 59.1 (0.360 g, Yield: 59.06%; MS (ES): m/z 438.19 [M+H]⁺).

Step 3—Synthesis of Compound 59.3: Compound was synthesized using general procedure B to obtain 59.3 (0.155 g, Yield: 77.80%; MS (ES): m/z 582.30 [M+H]⁺).

Step 4—Synthesis of compound I-98: Compound was synthesized using general procedure C to obtain I-98 (0.125 g, Yield: 97.41%; MS (ES): m/z 482.41 [M+H]⁺; LCMS purity: 99.14%; HPLC purity: 98.55%; CHIRAL HPLC: 51.03%, 48.97%; ¹H NMR (DMSO-d₆, 400 MHZ): 8.86 (s, 1H), 8.22-8.21 (d, J=7.2 Hz, 1H), 8.19 (s, 1H), 7.91-7.90 (d, J=4.4 Hz, 1H), 7.62-7.60 (d, J=8 Hz, 1H), 7.48-7.47 (d, J=6.8 Hz, 1H), 6.30-6.26 (t, J=6.8 Hz, 1H), 6.23 (s, 1H), 5.21-5.20 (d, J=4 Hz, 2H), 4.54 (bs, 1H), 4.01 (bs, 1H), 3.60 (bs, 1H), 3.26 (s, 3H), 2.92-2.91 (d, J=4.8 Hz, 3H), 2.74-2.69 (m, 1H), 2.19-2.13 (m, 3H), 1.93 (bs, 1H), 1.56 (bs, 2H), 1.37 (bs, 2H), 1.25 (s, 2H), 1.13-1.09 (t, J=7.2 Hz, 1H)).

Example 60: 5-((1-((1R,2S)-2-Hydroxycyclobutyl)-2-oxo-1,2-dihydropyridin-3-yl)amino)-N-((1R,3R)-3-methoxycyclohexyl)-7-(methylamino)pyrazolo[1,5-a]pyrimidine-3-carboxamide (I-99)

And 5-((1-((1R,2S)-2-Hydroxycyclobutyl)-2-oxo-1,2-dihydropyridin-3-yl)amino)-N-((1S,3S)-3-methoxy-cyclohexyl)-7-(methylamino)pyrazolo[1,5-a]pyrimidine-3-carboxamide (I-100)

Scheme 60

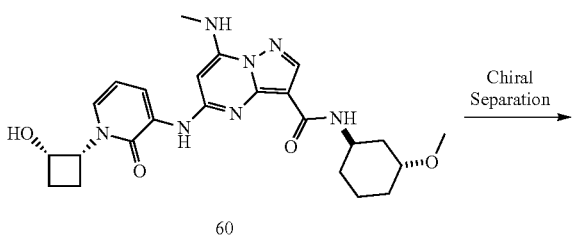

723
-continued

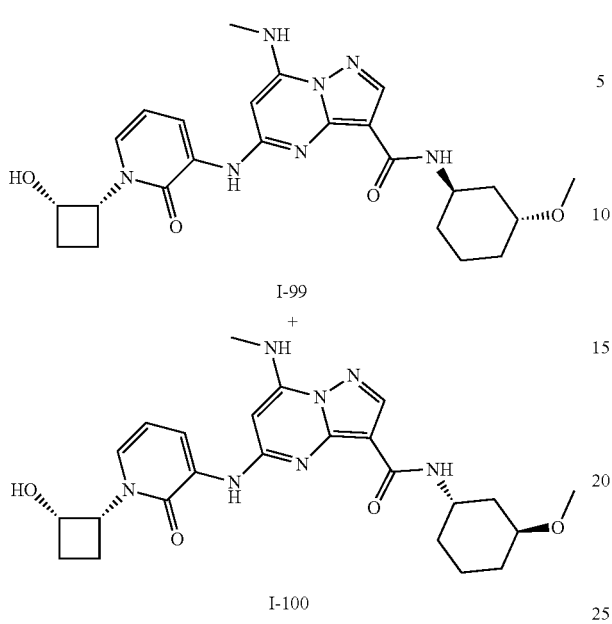

I-99
+
I-100

Step 1—Synthesis of Compound I-98: Compound was synthetized as per experimental protocol of I-98 (Example 59).

Step 2—Synthesis of Compounds I-99 and I-100: Isomers of I-98 (0.105 g) were separated out using column CHIRAL PAK OX-H (250 mm×4.6 mm, 5 µm) 0.1% DEA-_HEX_IPA-ACN (70-30) to get pure fraction-1 (FR-a) and fraction-2 (FR-b).

FR-a was concentrated under reduced pressure at 30° C. to afford pure I-99 (0.030 g; MS (ES): m/z 482.4 [M+H]$^+$; LCMS purity: 100%; HPLC purity: 99.00%; CHIRAL HPLC purity: 98.00%; $^1$H NMR (DMSO-d$_6$, 400 MHZ): 8.86 (s, 1H), 8.22-8.21 (d, J=7.2 Hz, 1H), 8.19 (s, 1H), 7.91-7.90 (d, J=4.4 Hz, 1H), 7.62-7.60 (d, J=8 Hz, 1H), 7.48-7.47 (d, J=6.8 Hz, 1H), 6.30-6.26 (t, J=6.8 Hz, 1H), 6.23 (s, 1H), 5.21-5.20 (d, J=4 Hz, 2H), 4.54 (bs, 1H), 4.01 (bs, 1H), 3.60 (bs, 1H), 3.26 (s, 3H), 2.92-2.91 (d, J=4.8 Hz, 3H), 2.74-2.69 (m, 1H), 2.19-2.13 (m, 3H), 1.93 (bs, 1H), 1.56 (bs, 2H), 1.37 (bs, 2H), 1.25 (s, 2H), 1.13-1.09 (t, J=7.2 Hz, 1H)).

FR-b was concentrated under reduced pressure at 30° C. to afford pure I-100 (0.030 g; MS (ES): m/z 482.4 [M+H]$^+$; LCMS purity: 100%; HPLC purity: 99.00%; CHIRAL HPLC purity: 99.00%; $^1$H NMR (DMSO-d$_6$, 400 MHZ): 8.87 (s, 1H), 8.22-8.21 (d, J=7.2 Hz, 1H), 8.20 (s, 1H), 7.91-7.90 (d, J=4.4 Hz, 1H), 7.62-7.60 (d, J=8 Hz, 1H), 7.48-7.47 (d, J=6.8 Hz, 1H), 6.30-6.26 (t, J=6.8 Hz, 1H), 6.22 (s, 1H), 5.21-5.20 (d, J=4 Hz, 2H), 4.54 (bs, 1H), 4.01 (bs, 1H), 3.60 (bs, 1H), 3.26 (s, 3H), 2.92-2.91 (d, J=4.8 Hz, 3H), 2.74-2.69 (m, 1H), 2.19-2.13 (m, 3H), 1.93 (bs, 1H), 1.56 (bs, 2H), 1.37 (bs, 2H), 1.25 (s, 2H), 1.13-1.09 (t, J=7.2 Hz, 1H)).

724

Example 61: N-((trans-1,3)-3-Methoxycyclohexyl)-7-(methylamino)-5-((1-(oxazol-2-yl)-2-oxo-1,2-dihydropyridin-3-yl)amino)pyrazolo[1,5-a]pyrimidine-3-carboxamide (I-101)

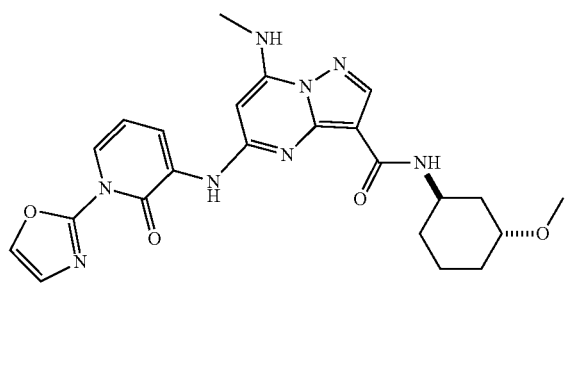

I-101

Scheme 61

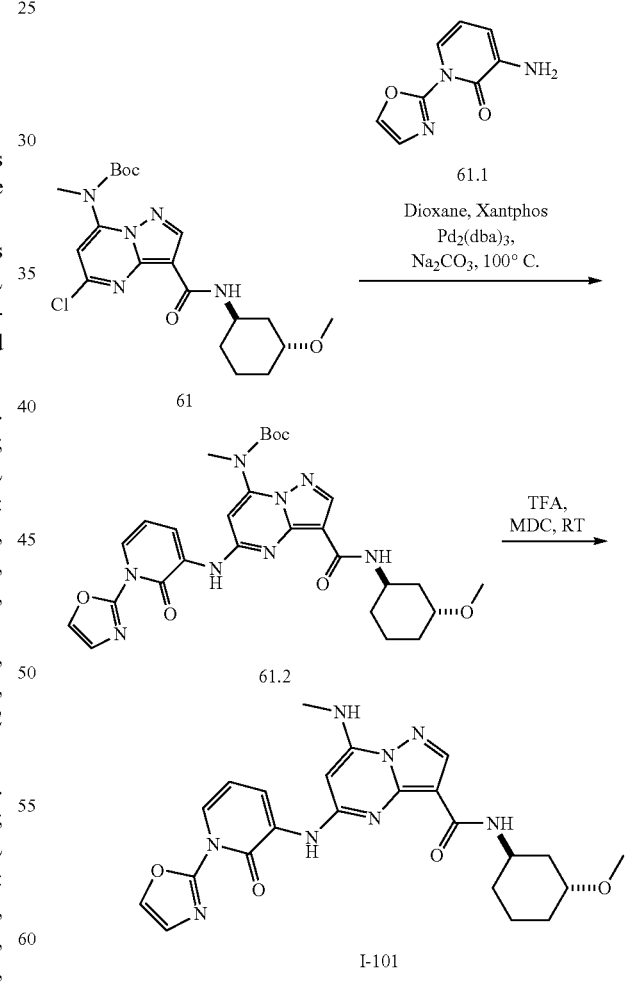

Step 1—Synthesis of Compound 61: Compound was synthesized as per experimental protocol of I-96/97 (Example 58) to obtain 61 (Yield: 59.06%; MS (ES): m/z 438.19 [M+H]$^+$).

Step 2—Synthesis of compound 61.1. Compound was synthesized as per experimental protocol of I-71 (Example 44) to obtain 61.1 (Yield: 26.41%; MS (ES): m/z 178.06 [M+H]⁺).

Step 3—Synthesis of compound 61.2: Compound was synthesized using general procedure B to obtain 61.2 (0.145 g, Yield: 73.16%; MS (ES): m/z 579.26 [M+H]⁺).

Step 4—Synthesis of compound I-102: Compound was synthesized using general procedure C to obtain I-101 (0.028 g, Yield: 84.65%; MS (ES): m/z 479.46 [M+H]⁺; LCMS purity: 100%; HPLC purity: 99.51%; CHIRAL HPLC: 50.12%, 49.88%; ¹H NMR (DMSO-d₆, 400 MHZ): 9.05 (bs, 1H), 8.33 (s, 1H), 8.28 (bs, 1H), 8.20-8.19 (d, J=4 Hz, 1H), 7.98 (bs, 1H), 7.56 (bs, 1H), 7.48 (bs, 2H), 6.43-6.41 (t, J=4.4 Hz, 1H), 6.19 (s, 1H), 4.06 (bs, 2H), 3.56 (bs, 1H), 3.23 (s, 3H), 2.90-2.89 (d, J=4.8 Hz, 3H), 2.09 (bs, 1H), 1.89 (bs, 1H), 1.77 (bs, 1H), 1.58 (bs, 2H), 1.38-1.36 (d, J=10 Hz, 2H)).

Example 62: 5-((1-((1R,5S,6r)-3-Oxabicyclo[3.1.0]hexan-6-yl)-2-oxo-1,2-dihydropyridin-3-yl)amino)-N-((trans-1,2)-2-(methoxy-d3)cyclobutyl)-7-(methylamino)pyrazolo[1,5-a]pyrimidine-3-carboxamide (I-102)

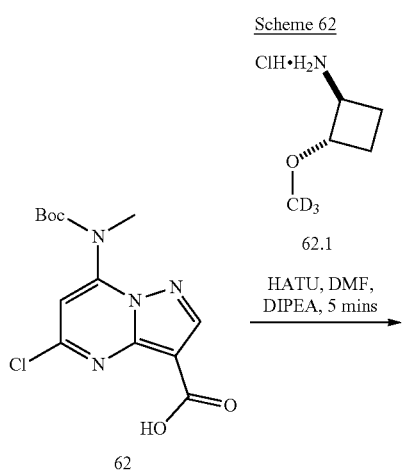

Scheme 62

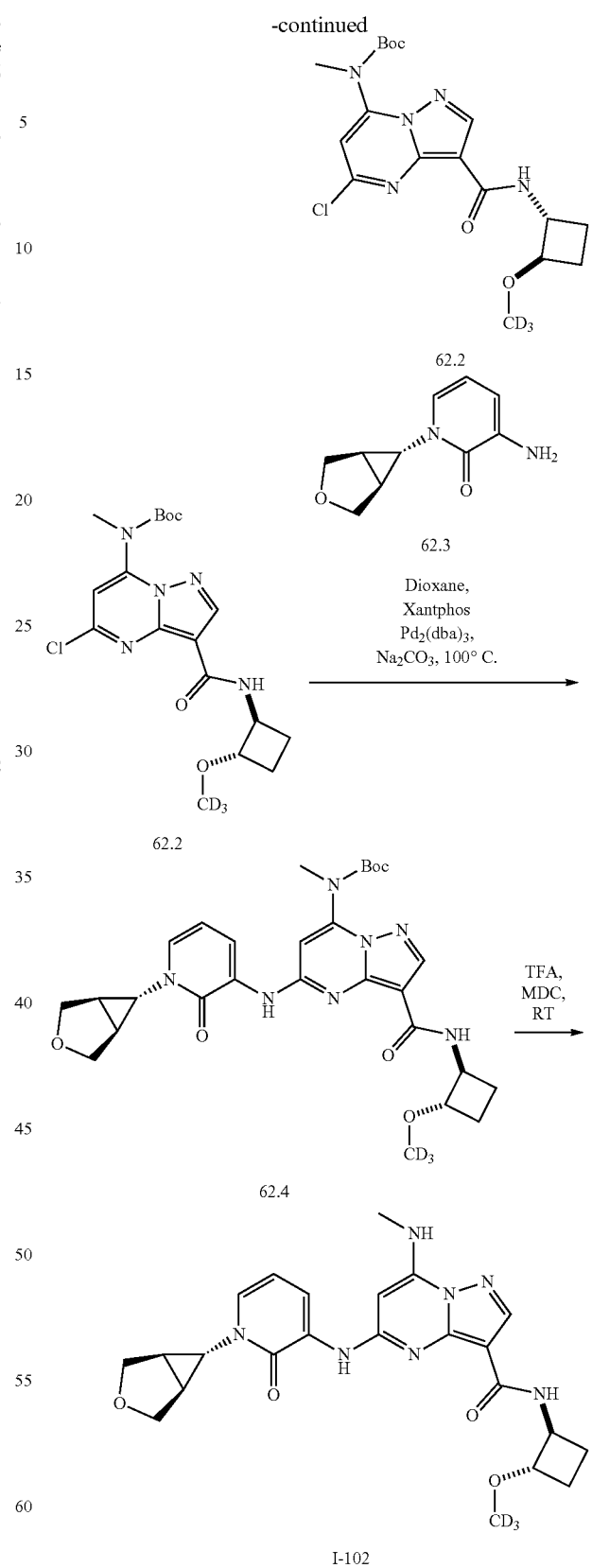

Step 1—Synthesis of Compound 62: Compound was synthesized using general procedure of Core A synthesis to obtain 62 (Yield: 71.67%; MS (ES): m/z 327.7 [M+H]⁺).

Step 2—Synthesis of Compound 62.2: Compound was synthesized using general procedure A to obtain 62.2 (Yield: 47.83%; MS (ES): m/z 413.17 [M+H]$^+$).

Step 3—Synthesis of Compound 62.3: Compound was synthesized using the procedure of I-24 (Example 17).

Step 3—Synthesis of Compound 62.4: Compound was synthesized using general procedure B to obtain 62.4 (0.173 g, Yield: 83.74%; MS (ES): m/z 569.29 [M+H]$^+$).

Step 4—Synthesis of Compound I-102: Compound was synthesized using general procedure C to obtain I-102 (0.021 g, Yield: 63.72%; MS (ES): m/z 469.82 [M+H]$^+$; LCMS purity: 95.16%; HPLC purity: 95.00%; CHIRAL HPLC: 49.50%, 47.12%; $^1$H NMR (DMSO-d$_6$, 400 MHZ): 8.98 (s, 1H), 8.23 (bs, 1H), 8.20 (s, 1H), 8.08-8.05 (d, J=9.2 Hz, 1H), 7.95-7.94 (d, J=4.8 Hz, 1H), 7.34-7.33 (d, J=6.4 Hz, 1H), 6.28-6.24 (t, J=7.2 Hz, 1H), 6.21 (s, 1H), 4.34-4.29 (m, 1H), 3.99 (bs, 2H), 3.75-3.73 (d, J=8.4 Hz, 2H), 3.68 (bs, 1H), 3.16 (bs, 1H), 2.91-2.90 (d, J=4.8 Hz, 3H), 2.29 (bs, 2H), 2.11-2.05 (m, 2H), 1.55-1.48 (m, 1H), 1.39-1.34 (m, 1H)).

Example 63: 5-((1-((1S,2R)-2-Hydroxycyclobutyl)-2-oxo-1,2-dihydropyridin-3-yl)amino)-N-((trans-1,3)-3-methoxycyclohexyl)-7-(methylamino)pyrazolo[1,5-a]pyrimidine-3-carboxamide (I-103)

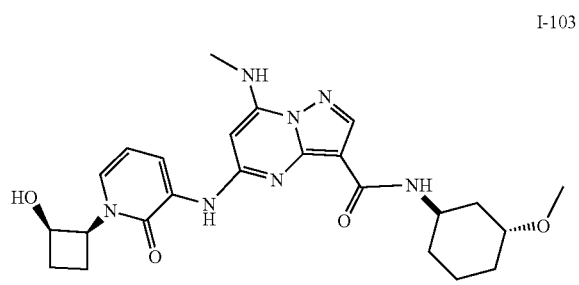

I-103

Scheme 63

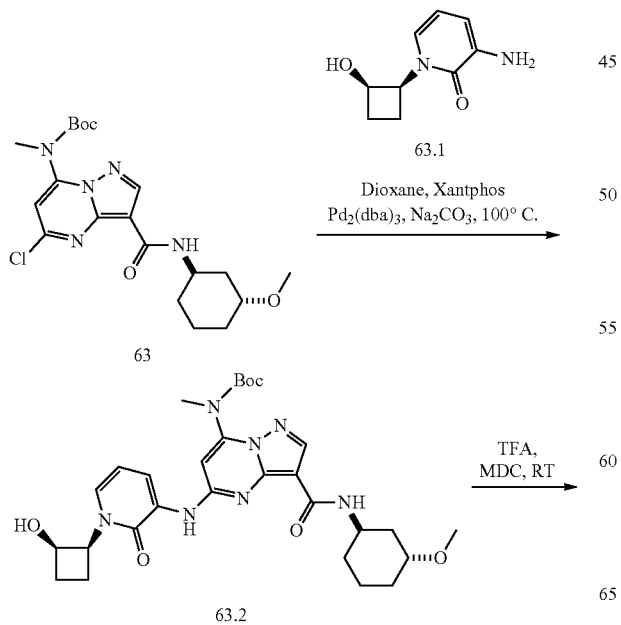

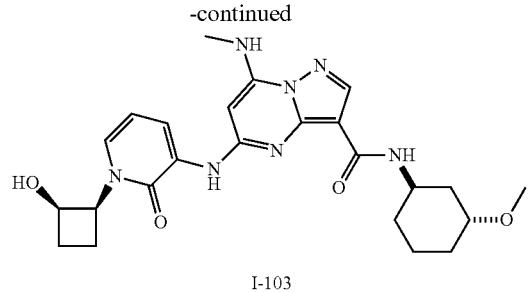

I-103

Step 1—Synthesis of Compound 63: Compound was synthesized as per experimental protocol of I-96/97 (Example 58) to obtain 63 (Yield: 59.06%; MS (ES): m/z 438.19 [M+H]$^+$).

Step 2—Synthesis of Compound 63.2: Compound was synthesized using general procedure B to obtain 63.2 (0.145 g, Yield: 72.78%; MS (ES): m/z 582.30 [M+H]$^+$).

Step 3—Synthesis of Compound I-103: Compound was synthesized using general procedure C to obtain I-103 (0.115 g, Yield: 95.80%; MS (ES): m/z 482.41 [M+H]$^+$; LCMS purity: 100%; HPLC purity: 97.86%; CHIRAL HPLC: 49.29%, 50.57%; $^1$H NMR (DMSO-d$_6$, 400 MHZ): 8.86 (s, 1H), 8.22-8.19 (d, J=7.2 Hz, 1H), 8.16 (s, 1H), 7.91-7.90 (d, J=4.4 Hz, 1H), 7.62-7.60 (d, J=8 Hz, 1H), 7.48-7.47 (d, J=6.8 Hz, 1H), 6.30-6.26 (t, J=6.8 Hz, 1H), 6.23 (s, 1H), 5.20 (bs, 2H), 4.54 (bs, 1H), 4.09 (bs, 1H), 3.60 (bs, 1H), 3.26 (s, 3H), 2.92-2.91 (d, J=4.8 Hz, 3H), 2.74-2.69 (m, 1H), 2.19-2.13 (m, 3H), 1.93 (bs, 1H), 1.56 (bs, 2H), 1.37 (bs, 2H), 1.25 (s, 2H), 1.13-1.09 (t, J=7.2 Hz, 1H)).

Example 64: 5-((1-((1S,2R)-2-Hydroxycyclobutyl)-2-oxo-1,2-dihydropyridin-3-yl)amino)-N-((1R,3R)-3-methoxycyclohexyl)-7-(methylamino)pyrazolo[1,5-a]pyrimidine-3-carboxamide (I-104)

And 5-((1-((1S,2R)-2-Hydroxycyclobutyl)-2-oxo-1,2-dihydropyridin-3-yl)amino)-N-((1S,3S)-3-methoxycyclohexyl)-7-(methylamino)pyrazolo[1,5-a]pyrimidine-3-carboxamide (I-105)

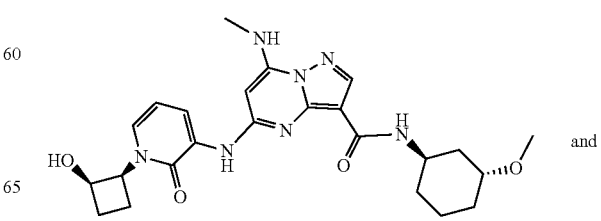

I-104 and

-continued

I-105

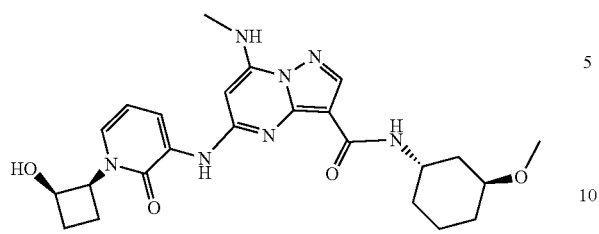

Scheme 61

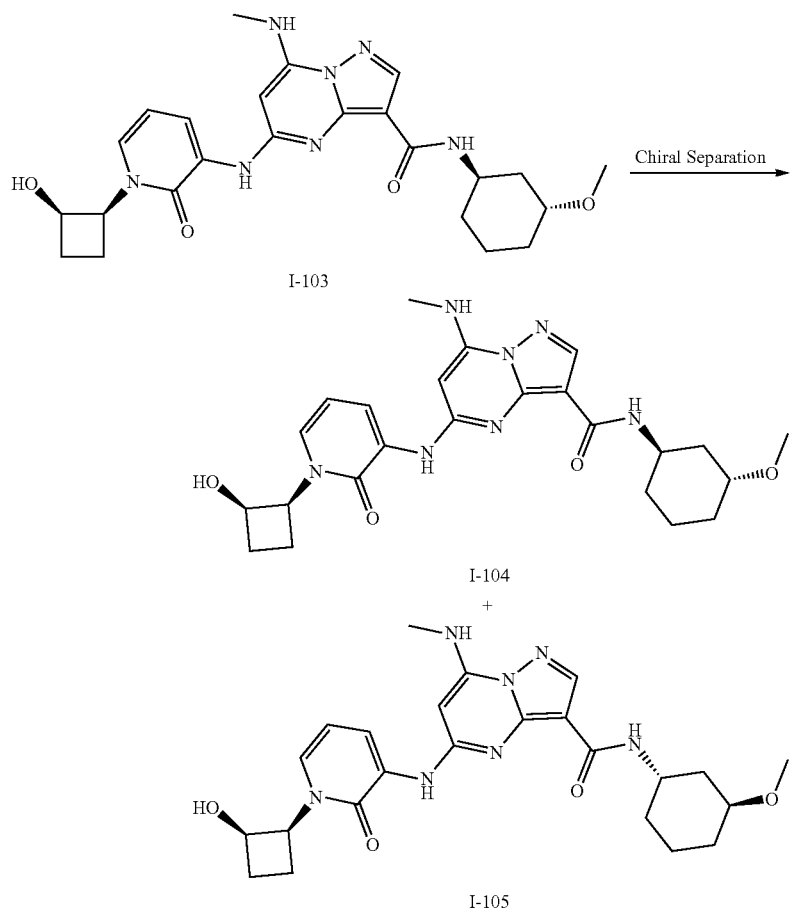

Step 1—Synthesis of Compound I-103: Compound I-103 was synthesized as described in Example 60.

Step 2—Synthesis of Compounds I-104 and I-105: Isomers of I-103 (Example 60) (0.097 g) were separated out using column CHIRAL PAK OX-H (250 mm×4.6 mm, 5 μm) 0.1% DEA_HEX_IPA-ACN (70-30) to get pure fraction-1 (FR-a) and fraction-2 (FR-b).

FR-a was concentrated under reduced pressure at 30° C. to afford pure I-104 (0.025 g; MS (ES): m/z 482.2 [M+H]+; LCMS purity: 100%; HPLC purity: 99.56%; CHIRAL HPLC purity: 100%; $^1$H NMR (DMSO-$d_6$, 400 MHZ): 8.86 (s, 1H), 8.22-8.20 (d, J=7.2 Hz, 1H), 8.18 (s, 1H), 7.90-7.89 (d, J=4.4 Hz, 1H), 7.62-7.60 (d, J=8 Hz, 1H), 7.48-7.46 (d, J=6.8 Hz, 1H), 6.29-6.26 (t, J=6.8 Hz, 1H), 6.23 (s, 1H), 4.11 (bs, 1H), 3.60 (bs, 1H), 4.09 (bs, 1H), 3.60 (bs, 1H), 3.26 (s, 3H), 2.91-2.90 (d, J=4.8 Hz, 3H), 2.74-2.69 (m, 1H), 2.19-2.13 (m, 3H), 1.93 (bs, 1H), 1.56 (bs, 2H), 1.37 (bs, 2H), 1.25 (s, 3H), 1.12-1.09 (t, J=7.2 Hz, 1H)).

FR-b was concentrated under reduced pressure at 30° C. to afford pure I-105 (0.032 g; MS (ES): m/z 482.2 [M+H]+; LCMS purity: 100%; HPLC purity: 99.60%; CHIRAL HPLC purity: 97.70%; $^1$H NMR (DMSO-$d_6$, 400 MHZ): 8.86 (s, 1H), 8.22-8.20 (d, J=7.2 Hz, 1H), 8.18 (s, 1H), 7.90-7.89 (d, J=4.4 Hz, 1H), 7.62-7.60 (d, J=8 Hz, 1H), 7.48-7.46 (d, J=6.8 Hz, 1H), 6.29-6.26 (t, J=6.8 Hz, 1H), 6.23 (s, 1H), 4.11 (bs, 1H), 3.60 (bs, 1H), 4.09 (bs, 1H), 3.60 (bs, 1H), 3.26 (s, 3H), 2.91-2.90 (d, J=4.8 Hz, 3H), 2.74-2.69 (m, 1H), 2.19-2.13 (m, 3H), 1.93 (bs, 1H), 1.56 (bs, 2H), 1.37 (bs, 2H), 1.25 (s, 3H), 1.12-1.09 (t, J=7.2 Hz, 1H)).

Example 65: 5-((1-((1r,3S)-3-Fluorocyclobutyl)-2-oxo-1,2-dihydropyridin-3-yl)amino)-N-((trans-1,2)-2-hydroxycyclobutyl)-7-(methylamino)pyrazolo[1,5-a]pyrimidine-3-carboxamide (I-106)

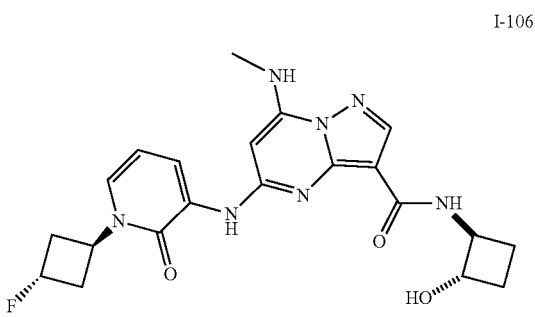

Scheme 65

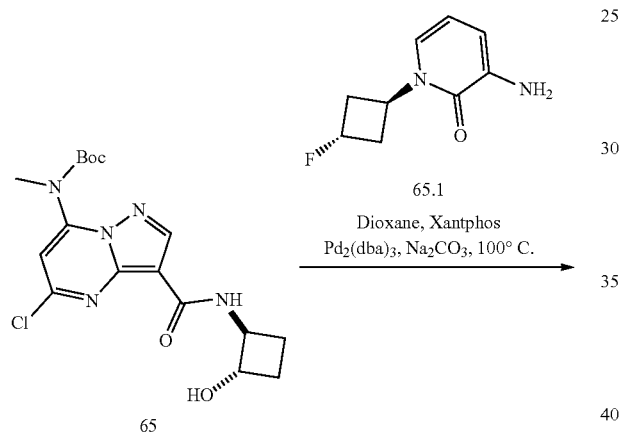

Step 1—Synthesis of Compound 65: Compound was synthesized from Core A utilizing general method A to obtain 65 (Yield: 52.83%; MS (ES): m/z 396.8 [M+H]$^+$).

Step 2—Synthesis of Compound 65.1: Compound was synthesized as per experimental protocol of I-7 (Example 6) to obtain 65.1 (Yield: 98.46%; MS (ES): m/z 183.09 [M+H]$^+$).

Step 3—Synthesis of compound 65.2: Compound was synthesized using general procedure B to obtain 65.2 (0.122 g, Yield: 68.22%; MS (ES): m/z 542.25 [M+H]$^+$).

Step 4—Synthesis of Compound I-106: Compound was synthesized using general procedure C to obtain I-106 (0.020 g, Yield: 70.10%; MS (ES): m/z 442.47 [M+H]$^+$; LCMS purity: 96.66%; HPLC purity: 95.03%; CHIRAL HPLC: 50.18%, 48.90%; $^1$H NMR (DMSO-d$_6$, 400 MHZ): 8.97 (s, 1H), 8.26-8.25 (d, J=6.8 Hz, 1H), 8.20 (s, 1H), 8.04-8.02 (d, J=8.8 Hz, 1H), 7.95-7.93 (d, J=4.8 Hz, 1H), 7.50-7.49 (d, J=6.4 Hz, 1H), 6.38-6.35 (t, J=7.2 Hz, 1H), 6.24 (s, 1H), 5.46-5.38 (m, 2H), 5.31 (bs, 1H), 4.25-4.21 (m, 1H), 3.87-3.83 (m, 1H), 2.90-2.89 (d, J=4.8 Hz, 3H), 2.83 (bs, 1H), 2.71-2.69 (m, 3H), 2.04-2.02 (m, 2H), 1.52-1.47 (m, 1H), 1.24 (bs, 1H)).

Example 66: 5-((1-((1r,3S)-3-Fluorocyclobutyl)-2-oxo-1,2-dihydropyridin-3-yl)amino)-N-((1S,2S)-2-hydroxycyclobutyl)-7-(methylamino)pyrazolo[1,5-a]pyrimidine-3-carboxamide (I-107)

And 5-((1-((1r,3R)-3-Fluorocyclobutyl)-2-oxo-1,2-dihydropyridin-3-yl)amino)-N-((1R,2R)-2-hydroxycyclobutyl)-7-(methylamino)pyrazolo[1,5-a]pyrimidine-3-carboxamide (I-108)

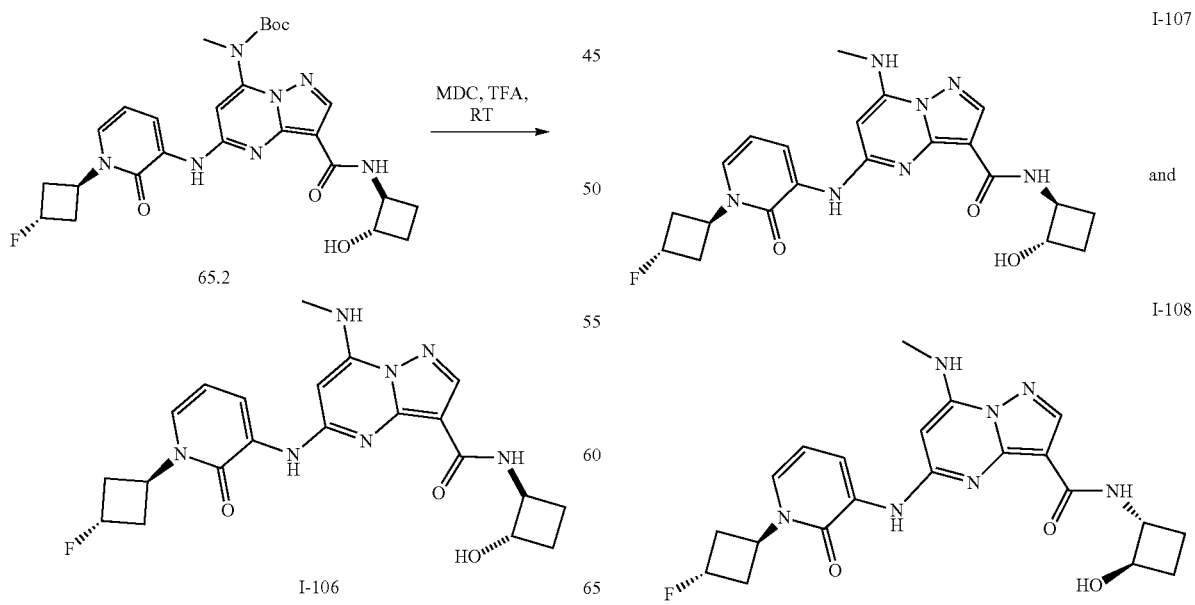

Scheme 66

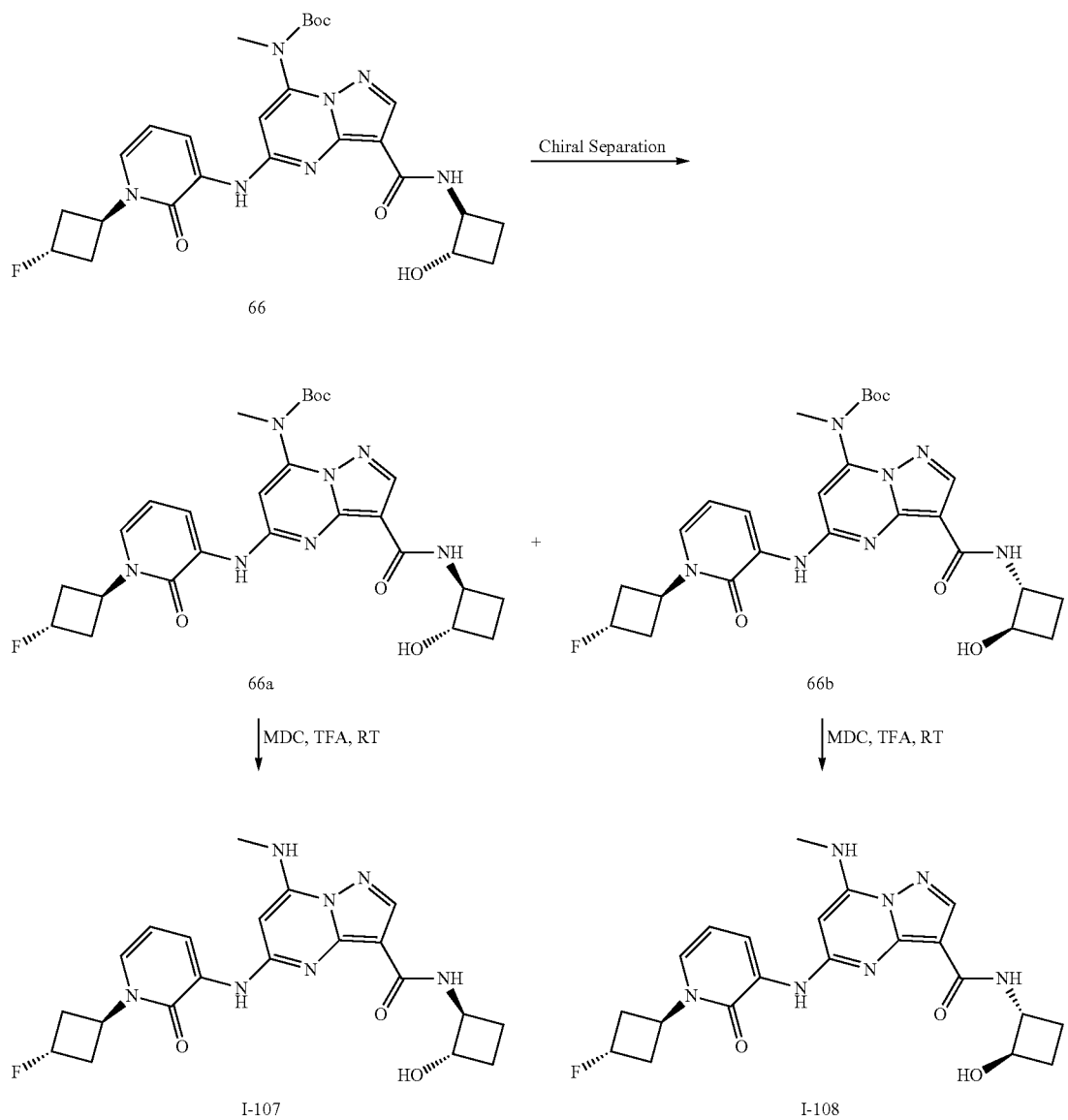

Step 1—Synthesis of Compound 66: Compound was synthesized as per experimental protocol of I-106 (Example 65) to obtain 66 (Yield: 68.22%; MS (ES): 542.25 [M+H]+).

Step 2—Synthesis of Compounds 66a and 66b: Isomers of 66 (0.105 g) were separated out using column CHIRAL-CEL OJ-H (250 mm×4.6 mm, 5 µm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 66a (0.042 g; MS (ES): m/z 542.25 [M+H]+). FR-b was concentrated under reduced pressure at 30° C. to afford pure 66b (0.038 g; MS (ES): m/z 542.25 [M+H]+).

Step 3—Synthesis of Compound I-107: Compound was synthesized using general procedure C to obtain I-107 (0.030 g, Yield: 87.63%; MS (ES): m/z 442.47 [M+H]+; LCMS purity: 96.66%; HPLC purity: 95.03%; CHIRAL HPLC: 50.18%, 48.90%, $^1$H NMR (DMSO-$d_6$, 400 MHZ): 8.97 (s, 1H), 8.26-8.25 (d, J=6.8 Hz, 1H), 8.20 (s, 1H), 8.04-8.02 (d, J=8.8 Hz, 1H), 7.95-7.93 (d, J=4.8 Hz, 1H), 7.50-7.49 (d, J=6.4 Hz, 1H), 6.38-6.35 (t, J=7.2 Hz, 1H), 6.24 (s, 1H), 5.46-5.38 (m, 2H), 5.31 (bs, 1H), 4.25-4.21 (m, 1H), 3.87-3.83 (m, 1H), 2.90-2.89 (d, J=4.8 Hz, 3H), 2.83 (bs, 1H), 2.71-2.69 (m, 3H), 2.04-2.02 (m, 2H), 1.52-1.47 (m, 1H), 1.24 (bs, 1H)).

Step 4—Synthesis of Compound I-108: Compound was synthesized using general procedure C to obtain I-108 (0.030 g, Yield: 87.63%; MS (ES): m/z 442.87 [M+H]+; LCMS purity: 97.66%; HPLC purity: 97.71%; CHIRAL HPLC: 48.80%, 49.46%; $^1$H NMR (DMSO-$d_6$, 400 MHZ): 8.92 (s, 1H), 8.54-8.52 (d, J=7.2 Hz, 1H), 8.19 (s, 1H), 8.05-8.02 (d, J=8.8 Hz, 1H), 7.89-7.87 (d, J=4.8 Hz, 1H), 7.44-7.42 (d, J=6 Hz, 1H), 6.43-6.40 (t, J=7.2 Hz, 1H), 6.27 (s, 1H), 5.44-5.37 (m, 2H), 5.30 (bs, 1H), 4.25-4.21 (m, 1H), 3.87-3.83 (m, 1H), 2.90-2.89 (d, J=4.8 Hz, 3H), 2.83 (bs, 1H), 2.71-2.69 (m, 3H), 2.04-2.02 (m, 2H), 1.52-1.47 (m, 1H), 1.24 (bs, 1H)).

Example 67: 5-((1-((1r,3R)-3-Fluorocyclobutyl)-2-oxo-1,2-dihydropyridin-3-yl)amino)-N-((trans-1,2)-2-methoxycyclopropyl)-7-(methylamino)pyrazolo[1,5-a]pyrimidine-3-carboxamide (I-109)

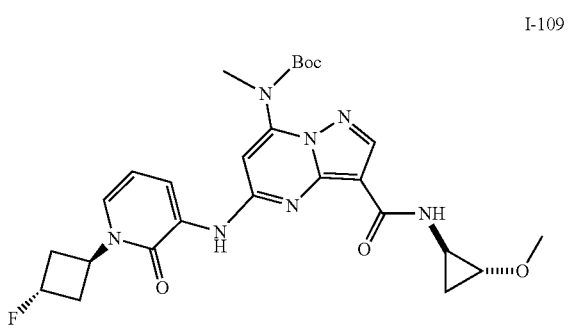

Step 1—Synthesis of Compound 67: Compound was synthesized from Core A utilizing general method A to obtain 67 (Yield: 56.13%; MS (ES): m/z 396.14 [M+H]$^+$).

Step 2—Synthesis of Compound 67.1: Compound was synthesized as per experimental protocol of I-7 (Example 6) to obtain 67.1 (Yield: 98.46%; MS (ES): m/z 183.09 [M+H]$^+$).

Step 3—Synthesis of Compound 67.2: Compound was synthesized using general procedure B to obtain 67.2 (0.140 g, Yield: 68.22%; MS (ES): m/z 542.25 [M+H]$^+$).

Step 4—Synthesis of Compound I-109: Compound was synthesized using general procedure C to obtain I-109 (0.140 g, Yield: 98.14%; MS (ES): m/z 442.20 [M+H]$^+$; LCMS purity: 100%; HPLC purity: 97.86%; CHIRAL HPLC: 48.12%, 47.94%; $^1$H NMR (DMSO-d$_6$, 400 MHZ): 8.88 (s, 1H), 8.22-8.19 (d, J=7.2 Hz, 1H), 8.17 (s, 1H), 7.91-7.90 (d, J=4.4 Hz, 1H), 7.67-7.66 (d, J=8 Hz, 1H), 7.45-7.43 (d, J=6.8 Hz, 1H), 6.32-6.29 (t, J=7.2 Hz, 1H), 6.23 (s, 1H), 5.44-5.40 (m, 1H), 4.38-4.29 (m, 2H), 3.25 (s, 3H), 3.08-3.03 (m, 1H), 2.90-2.89 (d, J=4.8 Hz, 3H), 2.73-2.67 (m, 3H), 1.08-1.03 (m, 2H), 0.54-0.50 (m, 1H)).

Example 68: 5-((1-((1r,3R)-3-Methoxycyclobutyl)-2-oxo-1,2-dihydropyridin-3-yl)amino)-N-((trans-1,3)-3-methoxycyclohexyl)-7-(methylamino)pyrazolo[1,5-a]pyrimidine-3-carboxamide (I-110)

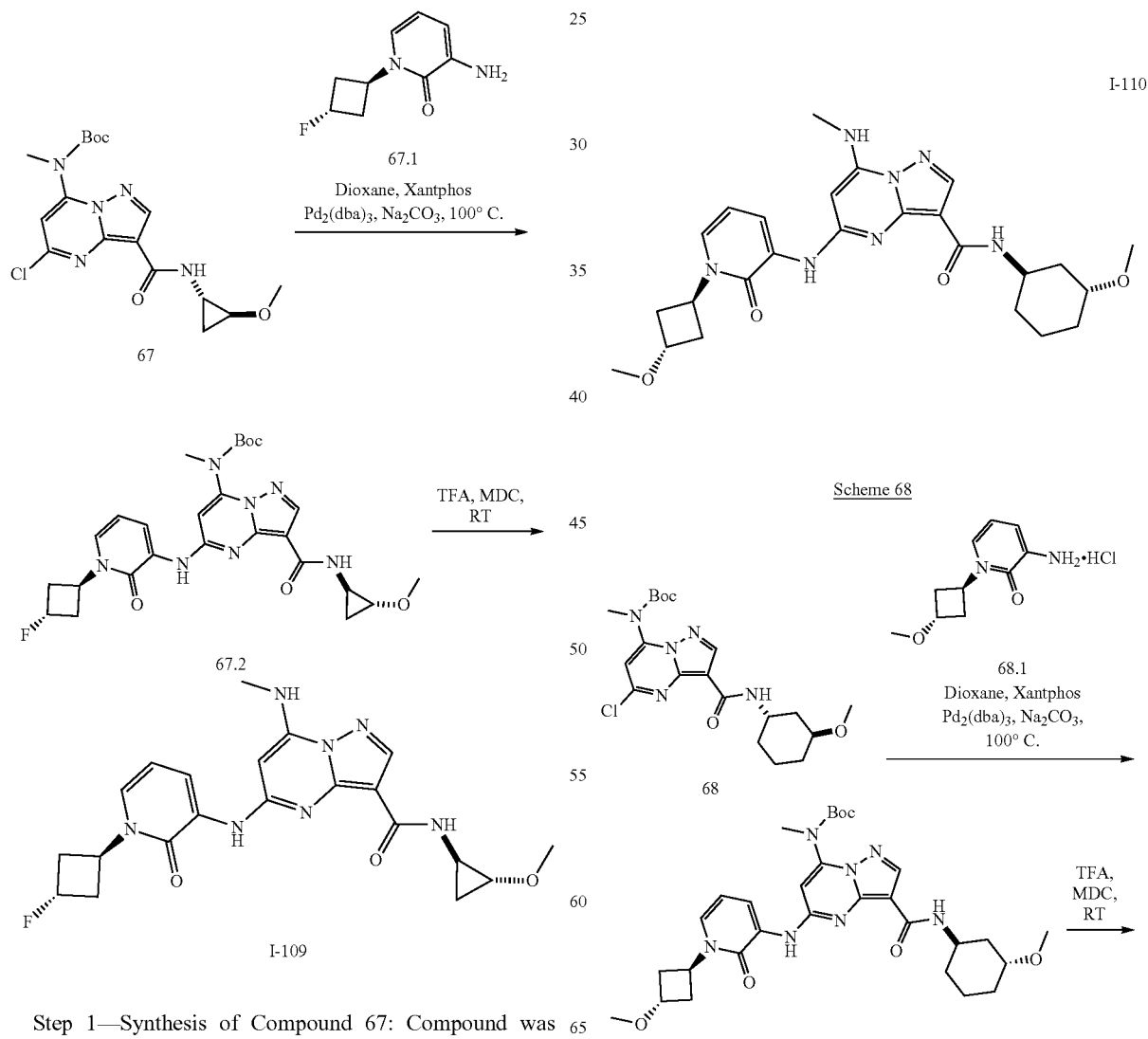

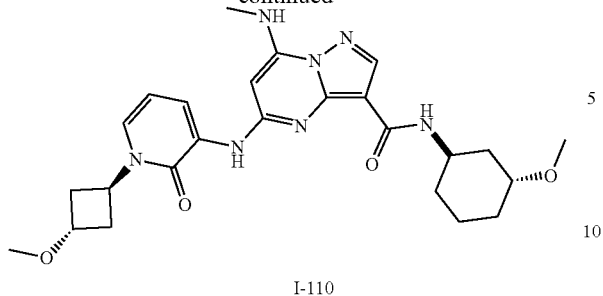

I-110

Step 1—Synthesis of Compound 68: Compound was synthesized as per experimental protocol of I-96/97 (Example 58) to obtain 68 (Yield: 59.06%; MS (ES): m/z 438.19 [M+H]+).

Step 2—Synthesis of Compound 68.1: Compound was synthesized as per experimental protocol of I-4 to obtain 68.1 (Yield: 89.32%; MS (ES): m/z 195.11 [M+H]+).

Step 3—Synthesis of Compound 68.2: Compound was synthesized using general procedure B to obtain 68.2 (0.145 g, Yield: 71.06%; MS (ES): m/z 596.32 [M+H]+).

Step 4—Synthesis of Compound I-110: Compound was synthesized using general procedure C to obtain I-110 (0.025 g, Yield: 75.13%; MS (ES): m/z 496.46 [M+H]+; LCMS purity: 100%; HPLC purity: 99.66%; CHIRAL HPLC: 59.88%, 38.77%; $^1$H NMR (DMSO-$d_6$, 400 MHZ): 8.88 (s, 1H), 8.19 (s, 1H), 8.17 (s, 1H), 7.90-7.87 (d, J=4.8 Hz, 1H), 7.58-7.56 (d, J=8 Hz, 1H), 7.52-7.50 (d, J=7.2 Hz, 1H), 6.31-6.28 (t, J=7.2 Hz, 1H), 6.21 (s, 1H), 4.08-4.05 (m, 3H), 3.56 (bs, 2H), 3.19 (s, 6H), 2.89-2.88 (d, J=4.8 Hz, 3H), 2.09 (bs, 1H), 1.80 (bs, 1H), 1.76 (bs, 2H), 1.62 (bs, 1H), 1.53 (bs, 1H), 1.26 (bs, 3H), 1.23 (bs, 2H)).

Example 69: N-((cis-1,2)-2-Hydroxycyclobutyl)-5-(1-((1s,3R)-3-hydroxycyclobutyl)-1H-pyrrolo[2,3-b]pyridin-3-yl)-7-(methylamino)pyrazolo[1,5-a]pyrimidine-3-carboxamide (I-111)

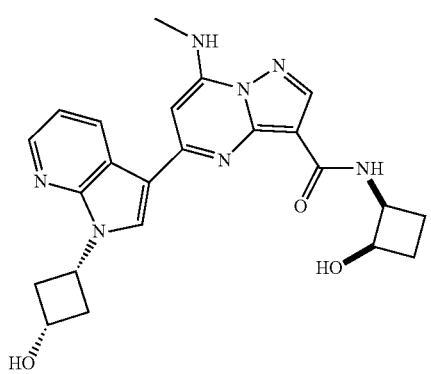

I-111

Scheme 69

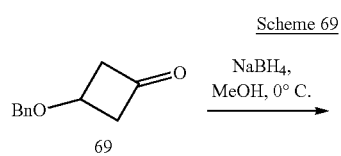

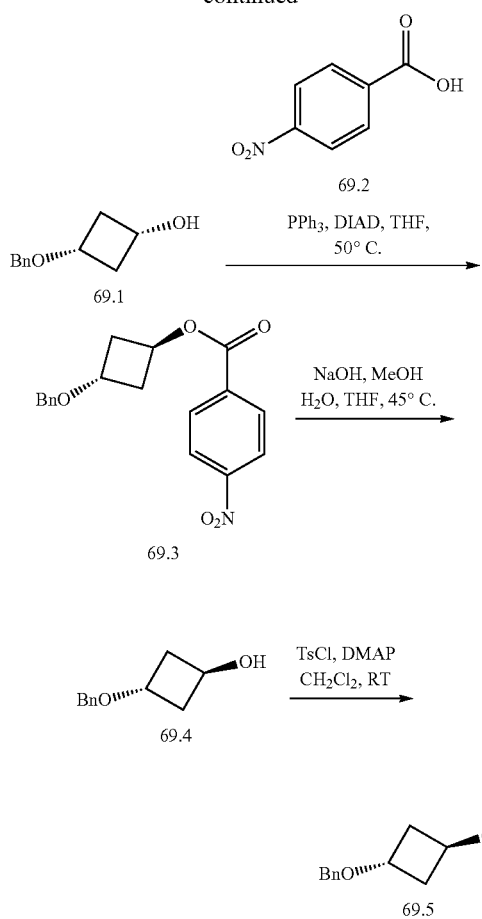

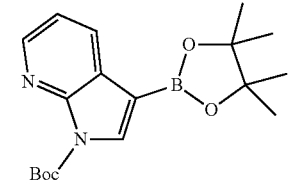

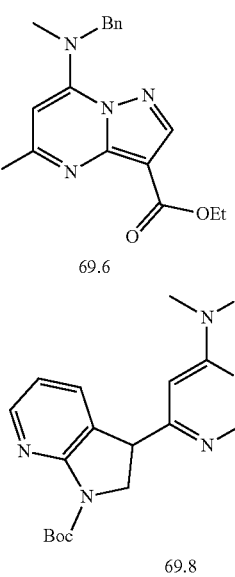

-continued

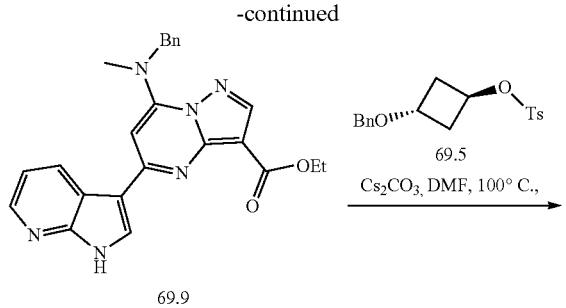

69.9

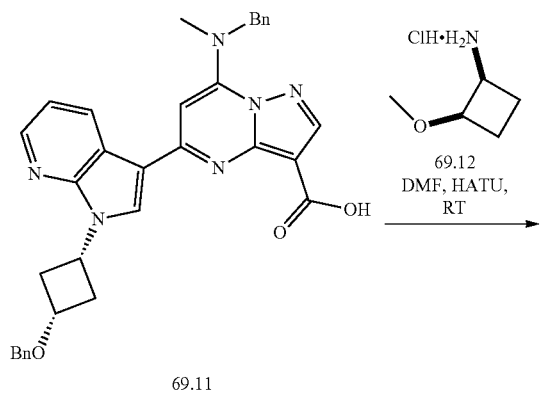

69.10

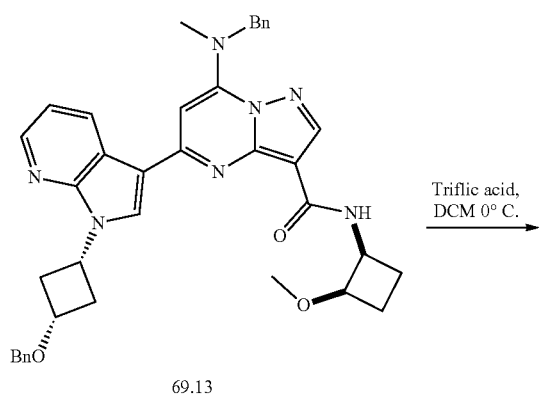

69.11

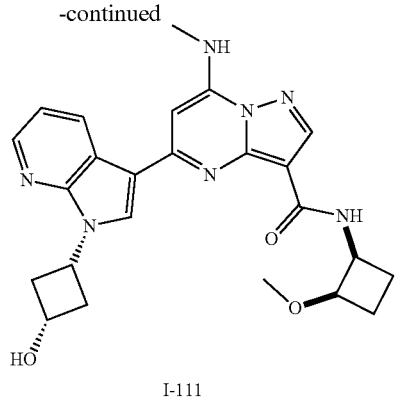

69.13

-continued

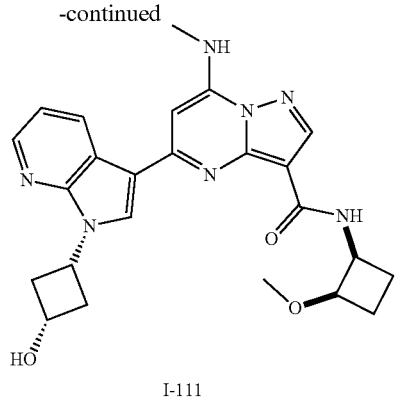

I-111

Step 1—Synthesis of Compound 69.1: To a solution of 69 (2.0 g, 11.35 mmol, 1.0 eq) in methanol (20 mL) was added Sodium borohydride (0.472 g, 12.48 mmol, 1.1 eq) at 0° C. The reaction mixture was stirred at 0° C. for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 69.1 (1.65 g, Yield: 81.57%; MS (ES): m/z 179.10 [M+H]$^+$).

Step 2—Synthesis of Compound 69.3: To a solution of 69.1 (1.65 g, 9.26 mmol, 1.0 eq) and 69.2 (3.0 g, 18.52 mmol, 2.0 eq) in tetrahydrofuran (80 mL) was added triphenylphosphine (7.2 g, 27.78 mmol, 3.0 eq) and Diisopropyl azodicarboxylate (5.6 g, 27.78 mmol, 3.0 eq) at 0° C. The reaction mixture was stirred at 0° C. for 6 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 69.3 (1.0 g, Yield: 33.21%; MS (ES): m/z 328.11 [M+H]$^+$).

Step 3—Synthesis of Compound 69.4: To a solution of 69.3 (0.122 g, 0.37 mmol, 1.0 eq), in tetrahydrofuran:methanol:water (4 mL, 2:2:1) was added sodium hydroxide (0.029 g, 0.74 mmol, 2.0 eq). The reaction was stirred at 45° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 69.4 (0.065 g, Yield: 97.85%; MS (ES): m/z 179.10 [M+H]$^+$).

Step 4—Synthesis of Compound 69.5: To a solution of 69.4 (0.065 g, 0.36 mmol, 1.0 eq), in dichloromethane (3 mL) was added 4-Toluenesulfonyl chloride (0.205 g, 1.08 mmol, 3.0 eq) and 4-Dimethylaminopyridine (0.010 g, 0.072 mmol, 0.2 eq) at 0° C. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 69.5 (0.060 g, Yield: 49.49%; MS (ES): m/z 333.11 [M+H]⁺).

Step 5—Synthesis of Compound 69.6: Compound was synthesized using general procedure of Core B synthesis to obtain 69.6.

Step 6—Synthesis of Compound 69.8: To a solution of 69.6 (0.1 g, 0.290 mmol, 1.0 eq), in dioxane (5 mL) were added 69.7 (0.129 g, 0.377 mmol, 1.3 eq) and sodium carbonate (0.076 g, 0.725 mmol 2.5 eq). The reaction mixture was degassed for 10 min under argon atmosphere, then [1,1'-Bis(diphenylphosphino)ferrocene] dichloropalladium (II), complex with dichloromethane (0.028 g, 0.029 mmol 0.1 eq) was added, again degassed for 5 min. The reaction was stirred at 100° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using eluted in 25% ethyl acetate in hexane to obtain pure 35.2 (0.083 g, Yield: 54.35%; MS (ES): m/z 527 [M+H]⁺).

Step 7—Synthesis of Compound 69.9: Compound was synthesized using general procedure C to obtain 69.9 (0.220 g, Yield: 90.55%; MS (ES): m/z 427 [M+H]⁺).

Step 8—Synthesis of Compound 69.10: To a solution of 69.9 (1.5 g, 3.52 mmol, 1.0 eq), in dimethylformamide (20 mL) was added 69.5 (2.9 g, 8.8 mmol, 2.5 eq) and Cesium carbonate (9.1 g, 28.16 mmol, 8.0 eq). The reaction mixture was stirred at 110° C. for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 69.10 (1.1 g, Yield: 53.31%; MS (ES): m/z 587.27 [M+H]⁺).

Step 9—Synthesis of Compound 69.11: To a solution of 69.10 (1.1 g, 1.87 mmol, 1.0 eq), in tetrahydrofuran:methanol:water (22 mL, 2:1) was added lithium hydroxide (0.224 g, 9.35 mmol, 5.0 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 69.11 (0.9 g, Yield: 85.93%; MS (ES): m/z 559.24 [M+H]⁺).

Step 10—Synthesis of Compound 69.13: Compound was synthesized using general procedure A to obtain 69.13 (0.185 g, Yield: 54.88%; MS (ES): m/z 628.30 [M+H]⁺).

Step 11—Synthesis of Compound I-111: Compound was synthesized using general procedure C to obtain I-111 (0.030 g, Yield: 70.14%; MS (ES): m/z 448.77 [M+H]⁺; LCMS purity: 96.99%; HPLC purity: 98.32%; CHIRAL HPLC: 50.53%, 48.72%; ¹H NMR (DMSO-d₆, 400 MHZ): 9.04-9.02 (d, J=7.2 Hz, 1H), 8.90 (s, 1H), 8.59-8.57 (d, J=8.4 Hz, 1H), 8.35 (s, 2H), 8.22-8.20 (d, J=4.8 Hz, 1H), 7.29-7.26 (m, 1H), 6.83 (s, 1H), 5.48-5.47 (d, J=4 Hz, 1H), 5.44-5.43 (d, J=6 Hz, 1H), 4.97-4.88 (m, 1H), 4.60 (bs, 1H), 4.41 (bs, 1H), 4.16-4.11 (m, 1H), 3.77 (bs, 1H), 3.14-3.12 (d, J=5.2 Hz, 3H), 2.86 (bs, 2H), 2.32 (bs, 1H), 2.10-2.04 (m, 2H), 1.86 (bs, 2H)).

Example 70: N-((trans-1,3)-3-Methoxycyclopentyl)-7-(methylamino)-5-((1-(4-methyloxazol-5-yl)-2-oxo-1,2-dihydropyridin-3-yl)amino)pyrazolo[1,5-a]pyrimidine-3-carboxamide (I-112)

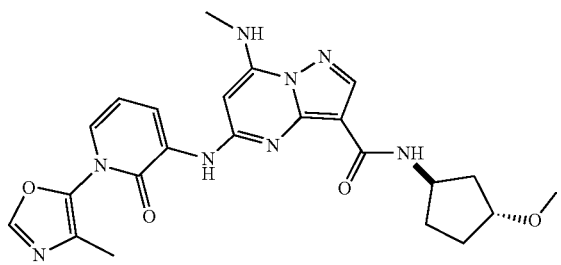

I-112

Scheme 70

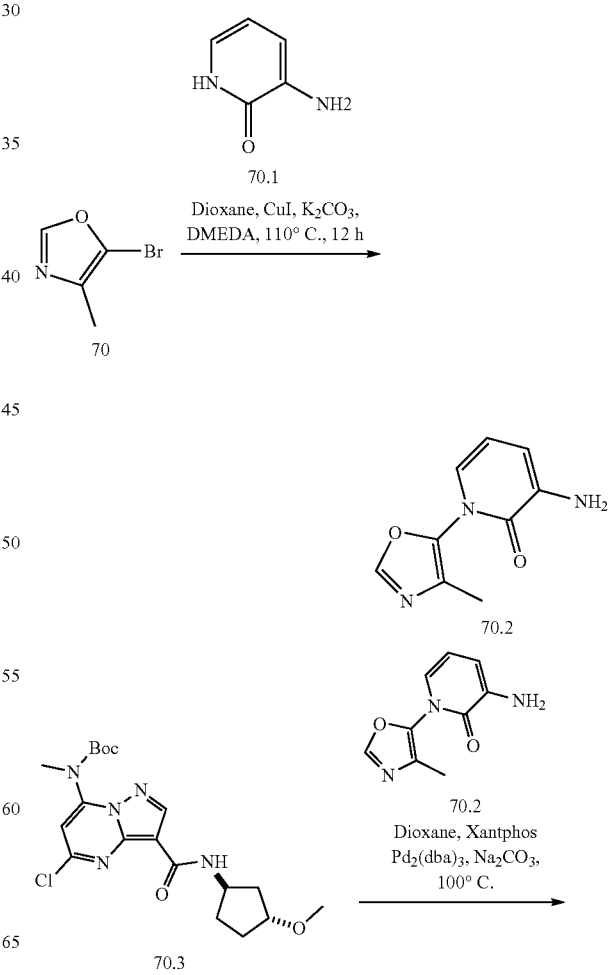

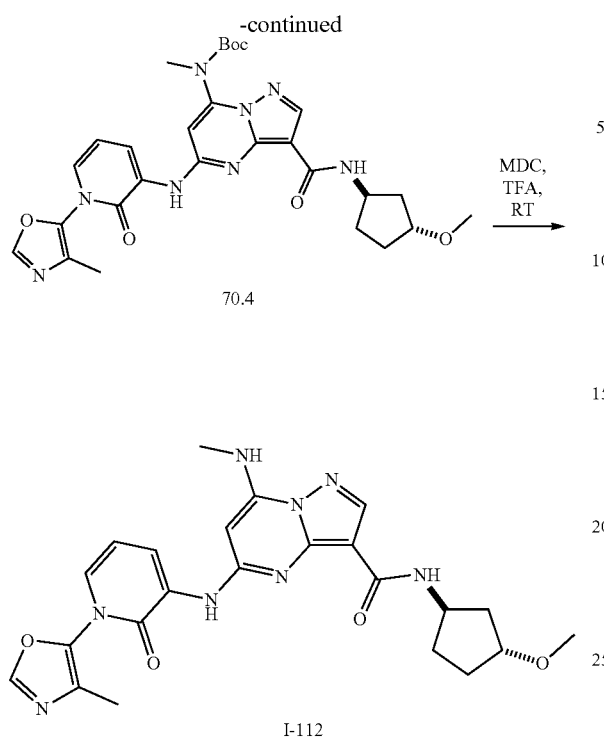

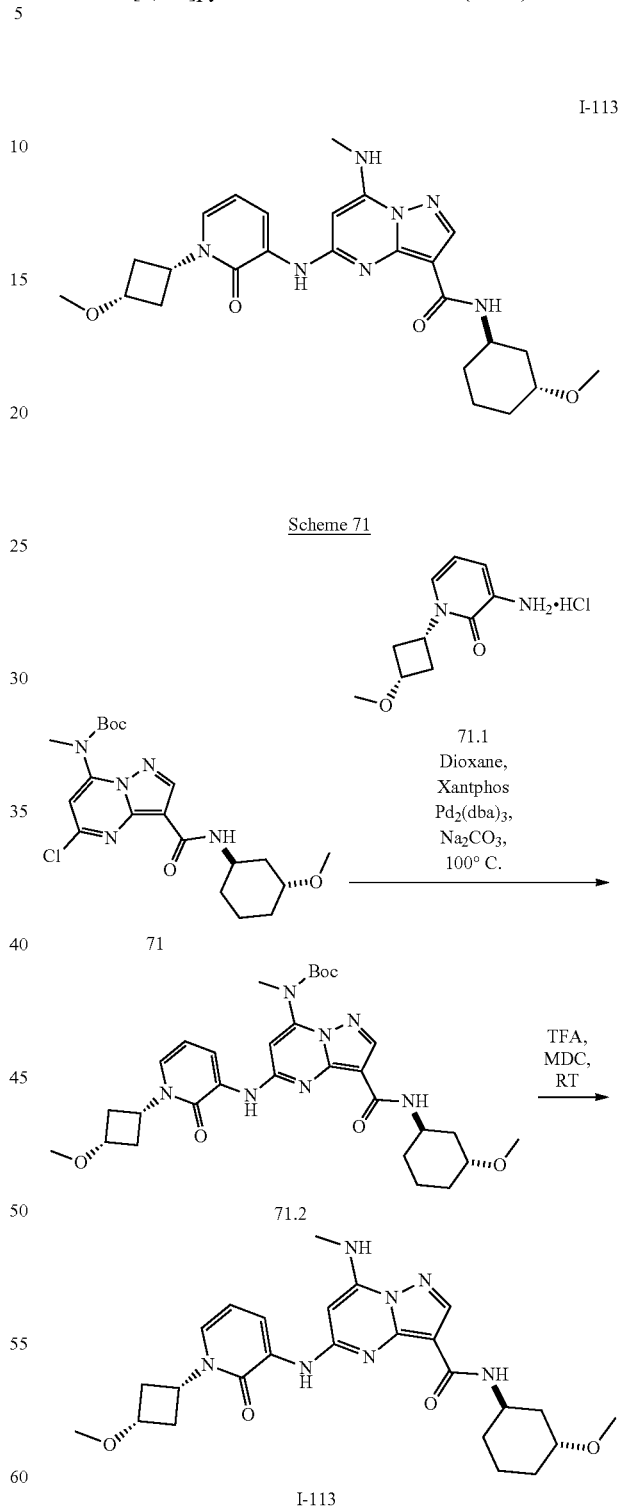

Example 71: 5-((1-((1s,3S)-3-Methoxycyclobutyl)-2-oxo-1,2-dihydropyridin-3-yl)amino)-N-((trans-1,3)-3-methoxycyclohexyl)-7-(methylamino)pyrazolo[1,5-a]pyrimidine-3-carboxamide (I-113)

Step 1—Synthesis of Compound 70.2: To a solution of 70 (0.8 g, 4.93 mmol, 1 eq) in 1,4-dioxane (45 mL), 70.1 (0.650 g, 5.91 mmol, 1.2 eq) was added. The reaction mixture was degassed for 10 min under argon atmosphere followed by addition of potassium carbonate (1.70 g, 12.32 mmol, 2.5 eq), N,N-dimethylethylenediamine (0.108 g, 1.23 mmol, 0.25 eq), and copper iodide (0.139 g, 0.73 mmol, 0.15 eq). The reaction mixture was heated at 110° C. for 12 h. After completion of reaction, reaction mixture was transferred to ice cold water and product was extracted with ethylacetate. Organic layer was combined, washed with brine solution, dried over sodium sulphate and concentrated under reduced pressure to obtain crude material. This was further purified by 5% methanol in dichloromethane to obtain 70.2 (0.37 g, Yield: 39.19%; MS (ES): m/z 192.07 [M+H]$^+$).

Step 2—Synthesis of Compound 70.3: Compound was synthesized from Core A utilizing general method A to obtain 70.3 (Yield: 51.57%; MS (ES): m/z 424.17 [M+H]$^+$).

Step 3—Synthesis of Compound 70.4: Compound was synthesized using general procedure B to obtain 70.2 (0.140 g, Yield: 68.37%).

MS (ES): m/z 579.26 [M+H]$^+$

Step 4—Synthesis of Compound I-112: Compound was synthesized using general procedure C to obtain I-112 (0.028 g, Yield: 84.65%; MS (ES): m/z 479.51 [M+H]$^+$; LCMS purity: 100%; HPLC purity: 95.60%; CHIRAL HPLC: 50.53%, 48.72%; $^1$H NMR (DMSO-$d_6$, 400 MHZ): 9.04 (s, 1H), 8.44 (s, 1H), 8.32-8.30 (d, J=7.6 Hz, 1H), 8.21 (s, 1H), 7.98-7.97 (d, J=5.2 Hz, 1H), 7.67-7.65 (d, J=7.2 Hz, 1H), 7.39-7.38 (d, J=6.8 Hz, 1H), 6.41-6.37 (t, J=7.2 Hz, 1H), 6.23 (s, 1H), 4.39-4.33 (m, 1H), 3.89 (bs, 1H), 3.20 (s, 3H), 2.91-2.90 (d, J=4.8 Hz, 3H), 2.13-2.12 (m, 1H), 2.07 (s, 3H), 1.99 (bs, 1H), 1.62-1.55 (m, 2H), 1.25 (bs, 2H)).

Step 1—Synthesis of Compound 71: Compound was synthesized as per experimental protocol of I-96/97 (Example 58) to obtain 71 (Yield: 59.06%; MS (ES): m/z 438.19 [M+H]$^+$).

Step 2—Synthesis of Compound 71.1: Compound was synthesized as per experimental protocol of I-5 (Example 4) to obtain 71.1 (Yield: 89.32%; MS (ES): m/z 195.11 [M+H]+).

Step 3—Synthesis of Compound 71.2: Compound was synthesized using general procedure B to obtain 71.2 (0.130 g, Yield: 63.71%; MS (ES): m/z 596.32 [M+H]+).

Step 4—Synthesis of Compound I-113: Compound was synthesized using general procedure C to obtain I-113 (0.020 g, Yield: 80.13%; MS (ES): m/z 496.56 [M+H]+; LCMS purity: 100%; HPLC purity: 98.32%; CHIRAL HPLC: 47.14%, 50.87%; ¹H NMR (DMSO-d₆, 400 MHZ): 8.90 (s, 1H), 8.21 (s, 1H), 8.19 (s, 1H), 7.92-7.91 (d, J=4.8 Hz, 1H), 7.60-7.58 (d, J=8.4 Hz, 1H), 7.48-7.46 (d, J=6.8 Hz, 1H), 6.34-6.30 (t, J=7.2 Hz, 1H), 6.22 (s, 1H), 4.72-4.69 (m, 1H), 4.10 (bs, 1H), 3.82-3.79 (t, J=6.8 Hz, 1H), 3.58 (bs, 1H), 3.21 (s, 5H), 2.91-2.90 (d, J=4.8 Hz, 3H), 2.81 (bs, 2H), 2.14-2.11 (m, 3H), 7.90 (bs, 1H), 1.78 (bs, 1H), 1.57 (bs, 1H), 1.39-1.33 (m, 2H), 1.24 (bs, 3H)).

Example 72: 5-((1-((1S,3R)-3-Cyanocyclohexyl)-2-oxo-1,2-dihydropyridin-3-yl)amino)-N-((trans-1,2)-2-methoxycyclobutyl)-7-(methylamino)pyrazolo[1,5-a]pyrimidine-3-carboxamide (I-114)

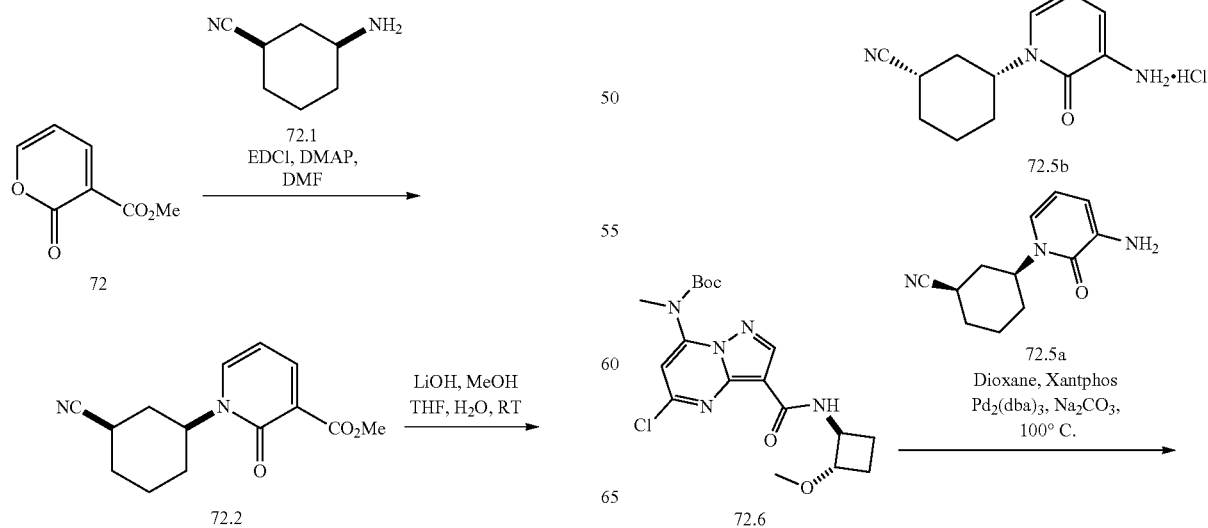

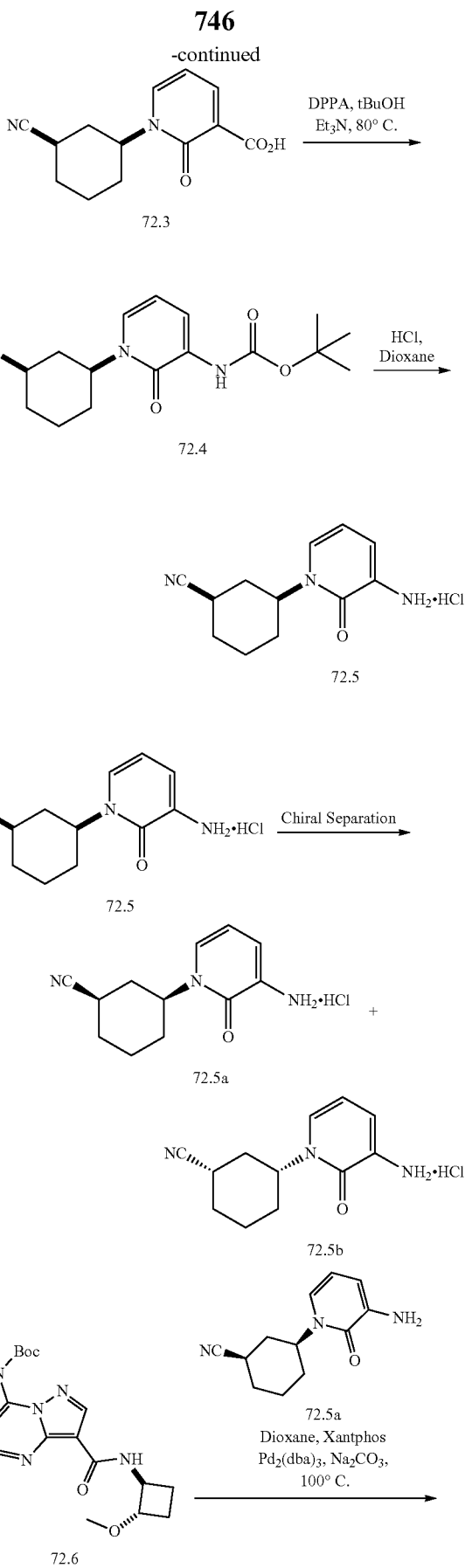

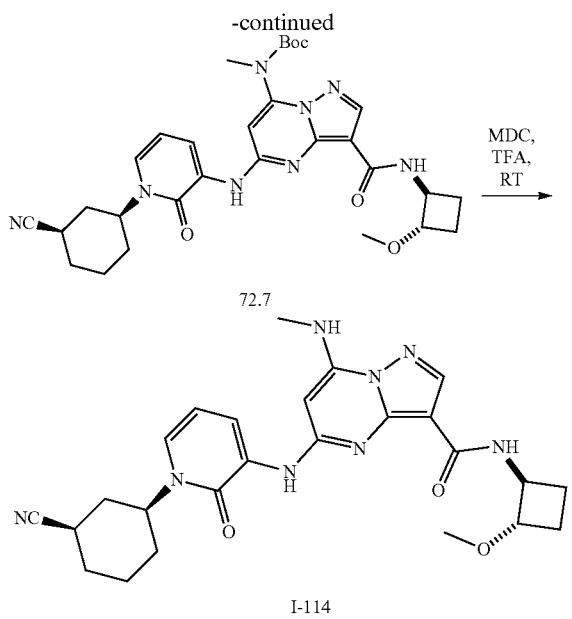

Step 1—Synthesis of compound 72.2: To a cooled solution of 72 (1.0 g, 6.48 mmol, 1.0 eq) in N,N-dimethylformamide (10 mL) was added 72.1 (0.803 g, 6.48 mmol, 1.0 eq). The reaction mixture was stirred at 0° C. for 30 min and further stirred at room temperature for 15 min. N-Ethyl-N'-(3-dimethylaminopropyl)carbodiimide hydrochloride (1.3 g, 8.42 mmol, 1.3 eq) and 4-Dimethylaminopyridine (0.158 g, 1.29 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 72.2 (0.810 g, 40.96%; MS (ES): m/z 261.12 [M+H]$^+$).

Step 2—Synthesis of Compound 72.3: To a solution of 72.2 (0.810 g, 3.11 mmol, 1.0 eq) in tetrahydrofuran:methanol:water (16 mL, 2:2:1) was added lithium hydroxide (0.746 g, 31.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 72.3 (0.650 g, Yield: 84.82%; MS (ES): m/z 247.10 [M+H]$^+$).

Step 3—Synthesis of Compound 72.4: To a solution of 72.3 (0.650 g, 2.64 mmol, 1.0 eq) in tert-butanol (7 mL) was added triethylamine (0.453 g, 4.48 mmol, 1.7 eq) and diphenyl phosphoryl azide (0.943 g, 3.43 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 72.4 (0.5 g, Yield: 59.69%; MS (ES): m/z 318.18 [M+H]$^+$).

Step 4—Synthesis of Compound 72.5: A cooled solution of 72.4 (0.5 g, 1.57 mmol, 1 eq) in dioxane (10 mL) was added 4N hydrochloric acid in dioxane (12 mL) as a dropwise. The reaction mixture was stirred at room temperature for 2 h. After completion of reaction, reaction mixture was concentrated under reduced pressure to obtain pure 72.5 (0.350 g, Yield: 87.56%; MS (ES): m/z 254.10 [M+HCl]).

Step 5—Synthesis of Compounds 72.5a and 72.5b: Isomers of 72.5 (0.250 g) were separated out using column CHIRALPAK AD-H (250 mm×4.6 mm, 5 µm) and 0.1% DEA in methanol as co-solvent with flow rate of 4 mL/min to get pure fraction-1 (FR-a) and fraction-2 (FR-b).

FR-a was concentrated under reduced pressure at 30° C. to afford pure 72.5a (0.090 g; MS (ES): m/z 254.10 [M+H]$^+$).

FR-b was concentrated under reduced pressure at 30° C. to afford pure 72.5b (0.090 g; MS (ES): m/z 254.10 [M+H]$^+$).

Step 6—Synthesis of Compound 72.6: Compound was synthesized as per experimental protocol of I-46 (Example 30) to obtain 72.6 (Yield: 57.95%; MS (ES): m/z 410.16 [M+H]$^+$).

Step 7—Synthesis of Compound 72.7: Compound was synthesized using general procedure B to obtain 72.7 (0.130 g, Yield: 60.14%; MS (ES): 591.30 [M+H]$^+$).

Step 8—Synthesis of Compound I-114: Compound was synthesized using general procedure C to obtain I-114 (0.050 g, Yield: 51.87%; MS (ES): m/z 491.82 [M+H]$^+$; LCMS purity: 100%; HPLC purity: 97.27%; CHIRAL HPLC: 48.54%, 47.99%; $^1$H NMR (DMSO-d$_6$, 400 MHZ): 8.89 (s, 1H), 8.22 (s, 1H), 8.20-8.19 (d, J=4 Hz, 1H), 8.06-8.04 (d, J=8.8 Hz, 1H), 7.93-7.92 (d, J=4.8 Hz, 1H), 7.50-7.48 (d, J=6.8 Hz, 1H), 6.35-6.31 (d, J=7.2 Hz, 1H), 6.20 (bs, 1H), 4.82 (bs, 1H), 4.32-4.28 (t, J=8 Hz, 1H), 3.71-3.65 (m, 1H), 3.19 (s, 3H), 3.06 (bs, 1H), 2.90-2.89 (d, J=4.8 Hz, 3H), 2.12-2.04 (m, 4H), 1.88 (bs, 1H), 1.67 (bs, 2H), 1.49 (bs, 3H), 1.35-1.30 (m, 1H), 0.87-0.83 (t, J=6.8 Hz, 1H)).

Example 73: 5-((1-((1R,3S)-3-Cyanocyclohexyl)-2-oxo-1,2-dihydropyridin-3-yl)amino)-N-((trans-1,2)-2-methoxycyclobutyl)-7-(methylamino)pyrazolo[1,5-a]pyrimidine-3-carboxamide (I-115)

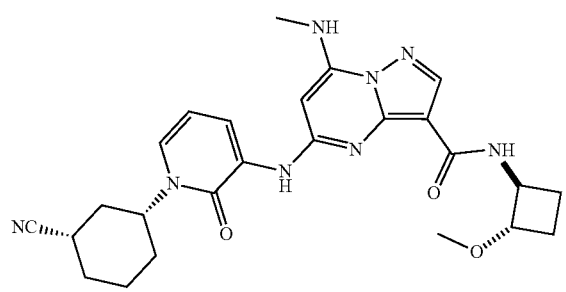

Scheme 73

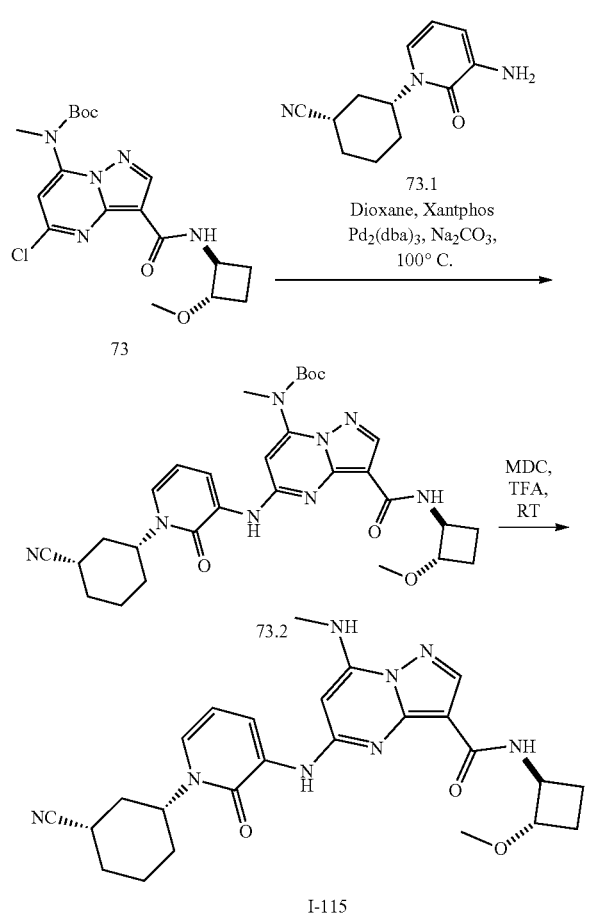

Step 1—Synthesis of Compound 73: Compound was synthesized as per experimental protocol of I-46 (Example 30) to obtain 73 (Yield: 57.95%; MS (ES): m/z 410.16 [M+H]$^+$).

Step 2—Synthesis of Compound 73.1: Compound was synthesized as per experimental protocol of I-114 (Example 72) to obtain 73.1 (MS (ES): m/z 254.10 [M+H]$^+$).

Step 3—Synthesis of Compound 73.2: Compound was synthesized using general procedure B to obtain 73.2 (0.120 g, Yield: 54.88%; MS (ES): m/z 591.30 [M+H]$^+$).

Step 4—Synthesis of Compound I-115: Compound was synthesized using general procedure C to obtain I-115 (0.028 g, Yield: 75.65%; MS (ES): m/z 491.82 [M+H]$^+$; LCMS purity: 100%; HPLC purity: 97.37%; CHIRAL HPLC: 50.39%, 47.73%; $^1$H NMR (DMSO-$d_6$, 400 MHZ): 8.89 (s, 1H), 8.22 (s, 1H), 8.20-8.19 (d, J=4.4 Hz, 1H), 8.06-8.04 (d, J=9.2 Hz, 1H), 7.93-7.92 (d, J=4.8 Hz, 1H), 7.50-7.48 (d, J=6.8 Hz, 1H), 6.35-6.31 (t, J=7.2 Hz, 1H), 6.20 (s, 1H), 4.82 (bs, 1H), 4.32-4.28 (m, 1H), 3.71-3.65 (m, 1H), 3.19 (s, 3H), 3.06 (bs, 1H), 2.90-2.89 (d, J=4.8 Hz, 3H), 2.12-2.04 (m, 4H), 1.88 (bs, 1H), 1.72 (bs, 3H), 1.40-1.33 (m, 3H), 1.18-1.17 (m, 1H)).

Example 74: 3-((3-(1-Isopropyl-1H-1,2,3-triazol-4-yl)-7-(methylamino)pyrazolo[1,5-a]pyrimidin-5-yl)amino)-1-((3R,4R)-3-methoxytetrahydro-2H-pyran-4-yl)pyridin-2(1H)-one (I-116)

And 3-((3-(1-Isopropyl-1H-1,2,3-triazol-4-yl)-7-(methylamino)pyrazolo[1,5-a]pyrimidin-5-yl)amino)-1-((3S,4S)-3-methoxytetrahydro-2H-pyran-4-yl)pyridin-2(1H)-one (I-117)

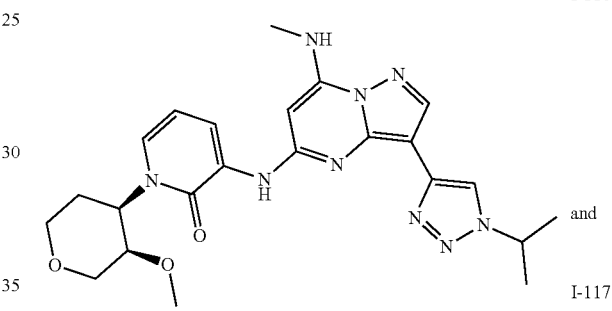

Scheme 74

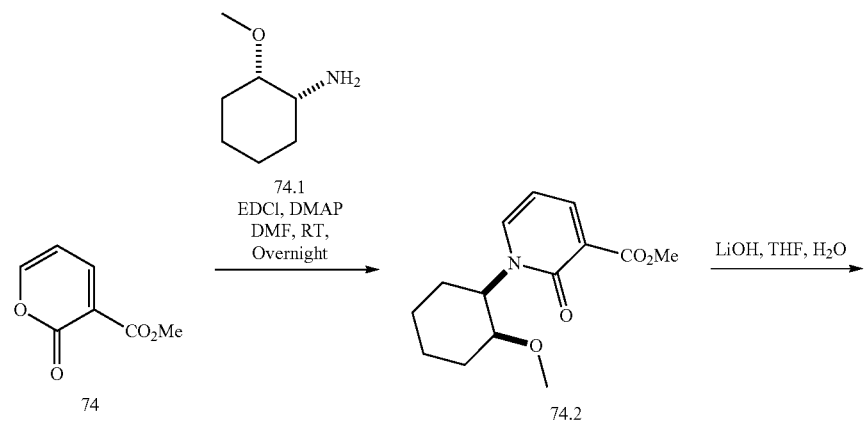

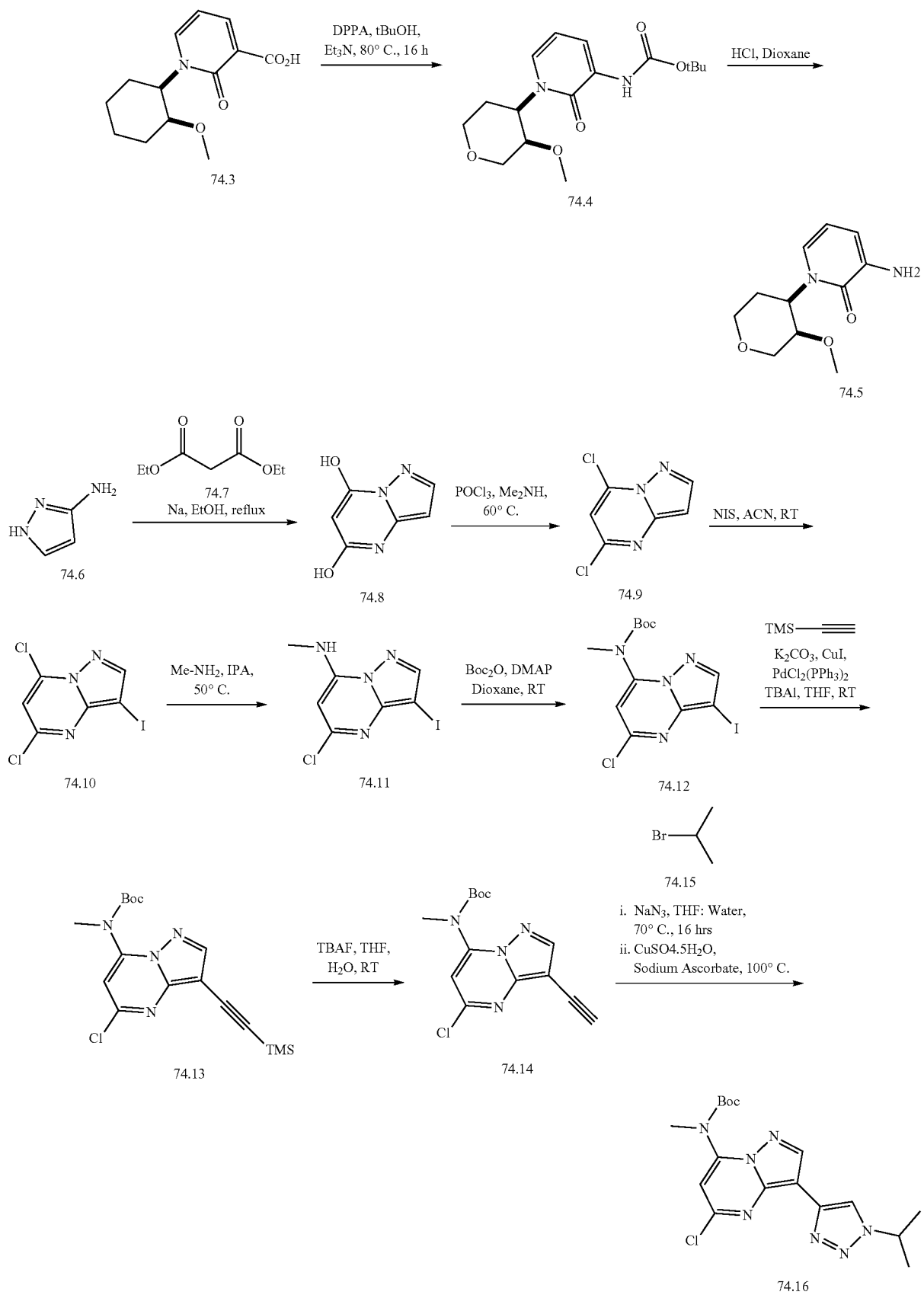

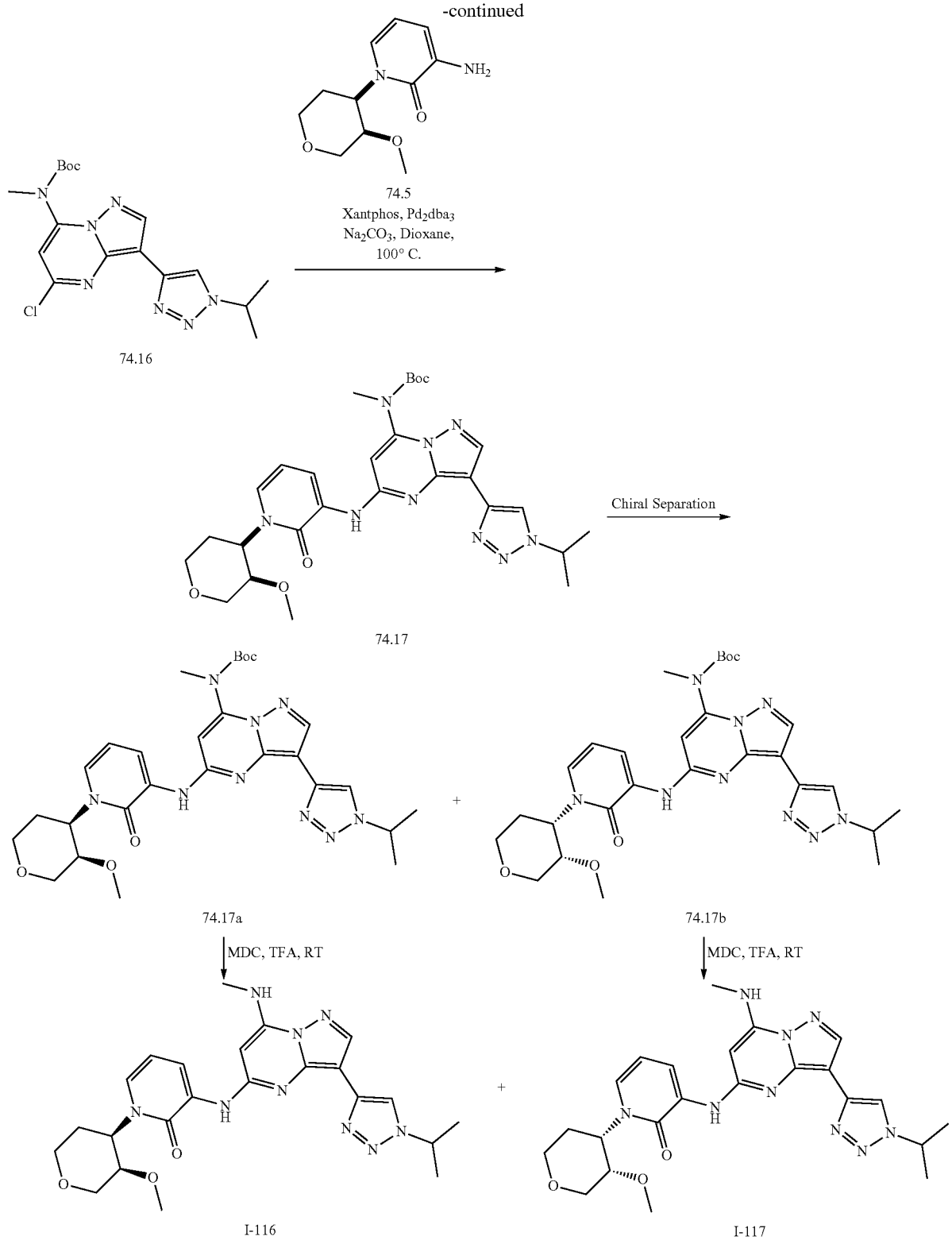

Step 1—Synthesis of Compound 74.2: To a cooled solution of 74 (3.0 g, 19.46 mmol, 1.0 eq) in N,N-dimethylformamide (30 mL) was added 74.1 (2.5 g, 19.46 mmol, 1.0 eq). The reaction mixture was stirred at 0° C. for 30 min and further stirred at room temperature for 15 min. N-Ethyl-N'-(3-dimethylaminopropyl)carbodiimide hydrochloride (3.9 g, 25.29 mmol, 1.3 eq) and 4-Dimethylaminopyridine (0.475 g, 3.89 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 74.2 (1.1 g, Yield: 21.30%; MS (ES): m/z 266.13 [M+H]$^+$).

Step 2—Synthesis of Compound 74.3: To a solution of 74.2 (1.1 g, 4.14 mmol, 1.0 eq), in tetrahydrofuran:water (22 mL, 2:1) was added lithium hydroxide (0.993 g, 41.4 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 74.3 (0.8 g, Yield: 76.79%; MS (ES): m/z 252.12 [M+H]$^+$).

Step 3—Synthesis of Compound 74.4: To a solution of 74.3 (0.8 g, 3.18 mmol, 1.0 eq) in tert-butanol (20 mL) was added triethylamine (0.545 g, 5.40 mmol, 1.7 eq) and diphenyl phosphoryl azide (1.1 g, 4.13 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 74.4 (0.550 g, Yield: 53.58%; MS (ES): m/z 323.19 [M+H]$^+$).

Step 4—Synthesis of Compound 74.5: A cooled solution of 74.4 (0.550 g, 1.70 mmol, 1 eq) in dioxane (12 mL) was added 4N hydrochloric acid in dioxane (24 mL) as a dropwise. The reaction mixture was stirred at room temperature for 2 h. After completion of reaction, reaction mixture was concentrated under reduced pressure to obtain pure 74.5 (0.4 g, Yield: 98.89%; MS (ES): m/z 223.14 [M−HCl]$^+$).

Step 5—Synthesis of Compound 74.8: To a solution of 74.6 (20.0 g, 240.96 mmol, 1.0 eq) and 74.7 (38.5 g, 240.96 mmol, 1.0 eq) in ethanol (200 mL) was added sodium metal (6.6 g, 289.15 mmol, 1.2 eq) and reflux at 80° C. for 5 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 74.8 (15.0 g, Yield: 41.24%; MS (ES): m/z 152.04 [M+H]$^+$).

Step 6—Synthesis of Compound 74.9: To a solution of 74.8 (15.0 g, 99.33 mmol, 1.0 eq) in Dimethylamine (90 mL) was added Phosphoryl chloride (18.23 g, 119.19 mmol, 1.2 eq) and stirred at 60° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 74.9 (11.0 g, Yield: 58.95%; MS (ES): m/z 190.96 [M+H]$^+$).

Step 7—Synthesis of Compound 74.10: To a solution of 74.9 (5.0 g, 26.59 mmol, 1.0 eq) in acetonitrile (50 mL), were added N-Iodo-succinimide (7.17 g, 31.90 mmol, 1.2 eq) at 0° C. The reaction mixture was stirred at room temperature for overnight. After completion of reaction, reaction mixture was transferred to ice cold water and product was extracted with dichloromethane. Organic layer was combined, washed with brine solution, dried over sodium sulphate and concentrated under reduced pressure to obtain crude material. This was further purified by 20% ethyl acetate in hexane to obtain 74.10 (3.7 g, Yield: 44.32%; MS (ES): m/z 314.86 [M+H]$^+$).

Step 8—Synthesis of Compound 74.11: To a solution of 74.10 (3.7 g, 11.78 mmol, 1.0 eq) in Isopropyl alcohol (50 mL) was added Methylamine (0.438 g, 14.13 mmol, 1.2 eq) and stirred at 50° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 74.11 (2.8 g, Yield: 77.00%; MS (ES): m/z 309.93 [M+H]$^+$).

Step 9—Synthesis of Compound 74.12: To a solution of 74.11 (2.8 g, 9.07 mmol, 1.0 eq) in 1,4-dioxane (30 mL) were added di-tert-butyl dicarbonate (3.5 g, 16.32 mmol, 1.8 eq) and 4-Dimethylaminopyridine (0.197 g, 0.90 mmol, 0.1 eq) stirred at room temperature for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 74.16 (2.3 g, Yield: 62.02%; MS (ES): m/z 409.98 [M+H]$^+$).

Step 10 Synthesis of Compound 74.13: To a solution of 74.12 (2.3 g, 5.62 mmol, 1.0 eq) in tetrahydrofuran (25 mL) were added bis(triphenylphosphine)palladium(II)dichloride (0.394 g, 0.56 mmol, 0.1 eq), Potassium carbonate (1.5 g, 11.24 mmol, 2.0 eq), followed by addition of Tetrabutylammonium iodide (0.207 g, 0.56 mmol, 0.1 eq) and Copper(I) iodide (0.213 g, 1.12 mmol, 0.2 eq) at room temperature. The reaction was stirred at room temperature for 3 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 74.13 (1.7 g, Yield: 79.70%; MS (ES): m/z 379.13 [M+H]$^+$).

Step 11—Synthesis of Compound 74.14: To a solution of 74.13 (1.7 g, 4.48 mmol, 1.0 eq) in tetrahydrofuran (20 mL) was added Tetra-n-butylammonium fluoride (2.3 g, 8.96 mmol, 2.0 eq) at room temperature. The reaction was stirred at room temperature for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 50% ethyl acetate in hexane to obtain pure 74.14 (0.9 g, Yield: 65.40%; MS (ES): m/z 307.09 [M+H]$^+$).

Step 12—Synthesis of Compound 74.16: To a solution of 74.14 (1.0 g, 3.25 mmol, 1.0 eq) in tetrahydrofuran:water (20 mL, 1:1) was added Sodium azide (0.274 g, 4.22 mmol, 1.3 eq) and 74.15 (0.399 g, 3.25 mmol, 1.0 eq) followed by addition of Copper(II) sulfate (0.039 g, 0.16 mmol, 0.05 eq) and Sodium Ascorbate, (0.320 g, 1.62 mmol, 0.5 eq) at room temperature. The reaction was stirred at 75° C. for 2 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 3% methanol in dichloromethane to obtain pure 74.16 (0.390 g, Yield: 30.53%; MS (ES): m/z 392.16 [M+H]$^+$).

Step 13—Synthesis of Compound 74.17: Compound was synthesized using general procedure B to obtain 74.17 (Yield: 48.00%; MS (ES): m/z 580.30 [M+H]$^+$).

Step 14—Synthesis of Compounds 74.17a and 74.17b: Isomers of 74.17 (0.105 g) were separated out using column CHIRALCEL OJ-H (250 mm×4.6 mm, 5 µm) and 0.1% DEA in methanol as co-solvent with flow rate of 4 mL/min to get pure fraction-1 (FR-a) and fraction-2 (FR-b). FR-a was concentrated under reduced pressure at 30° C. to afford pure 74.17a (0.044 g; MS (ES): m/z 580.30 [M+H]$^+$). FR-b was concentrated under reduced pressure at 30° C. to afford pure 74.17b (0.044 g; MS (ES): m/z 580.30 [M+H]$^+$).

Step 15—Synthesis of Compound I-116: Compound was synthesized using general procedure C to obtain (0.032 g, Yield: 87.91%; MS (ES): m/z 480.2 [M+H]$^+$; LCMS purity: 100%; HPLC purity: 99.00%; CHIRAL HPLC purity: 100%; $^1$H NMR (DMSO-d$_6$, 400 MHZ): 8.69-8.68 (d, J=7.2 Hz, 1H), 8.47 (s, 1H), 8.27 (s, 1H), 8.17 (s, 1H), 7.37-7.35 (d, J=7.2 Hz, 2H), 6.31-6.27 (t, J=7.6 Hz, 1H), 6.06 (s, 1H), 5.17 (s, 1H), 4.93-4.88 (m, 1H), 4.08-4.02 (m, 2H), 3.83 (bs, 2H), 3.79-3.72 (m, 3H), 3.26 (s, 3H), 1.98 (bs, 2H), 1.84 (bs, 1H), 1.62-1.61 (d, J=6.4 Hz, 6H)).

Step 16—Synthesis of Compound I-117: Compound was synthesized using general procedure C to obtain I-117 (0.032 g, Yield: 87.91%; MS (ES): m/z 480.2 [M+H]$^+$; LCMS purity: 100%; HPLC purity: 99.00%; CHIRAL HPLC purity: 99.10%; $^1$H NMR (DMSO-d$_6$, 400 MHZ): 8.68-8.67 (d, J=7.2 Hz, 1H), 8.47 (s, 1H), 8.27 (s, 1H), 8.17 (s, 1H), 7.37-7.35 (d, J=7.2 Hz, 2H), 6.31-6.27 (t, J=7.6 Hz, 1H), 6.06 (s, 1H), 5.17 (s, 1H), 4.93-4.88 (m, 1H), 4.08-4.02 (m, 2H), 3.83 (bs, 2H), 3.79-3.72 (m, 3H), 3.26 (s, 3H), 1.98 (bs, 2H), 1.84 (bs, 1H), 1.61-1.60 (d, J=6.4 Hz, 6H)

Example 75: N-Cyclopropyl-5-((1-(3-methoxy-3-methylcyclohexyl)-2-oxo-1,2-dihydropyridin-3-yl)amino)-7-(methylamino)pyrazolo[1,5-a]pyrimidine-3-carboxamide (I-122)

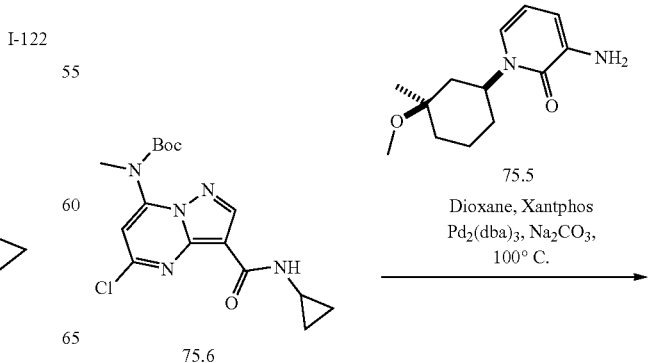

I-122

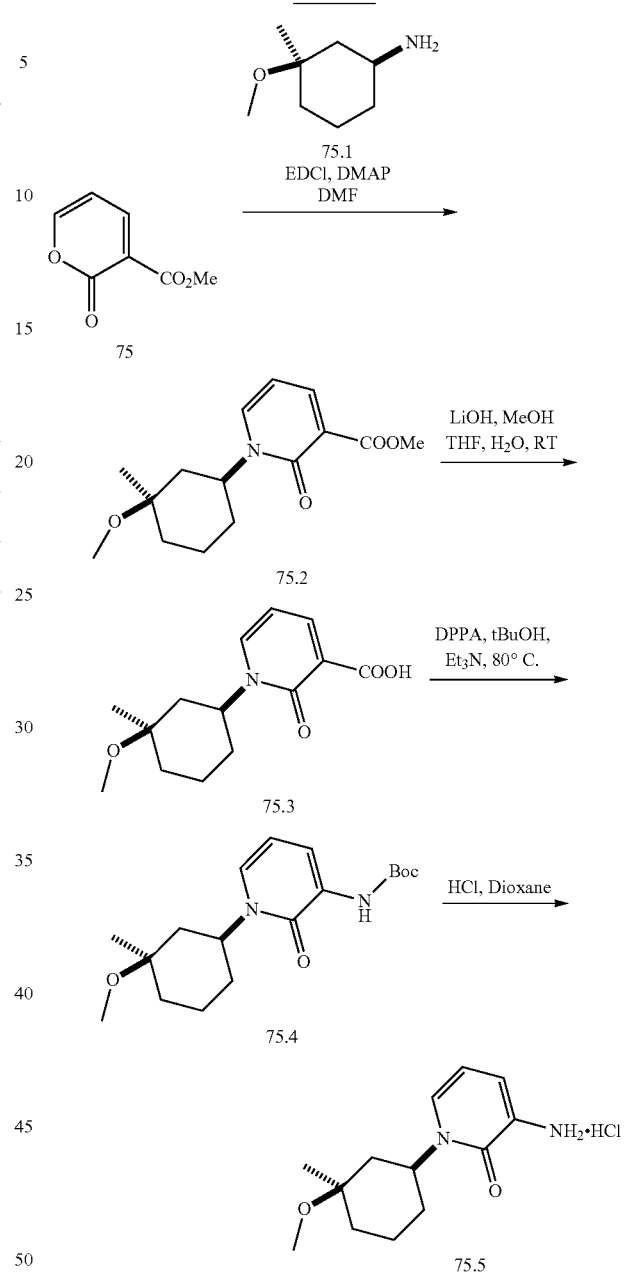

Scheme 75

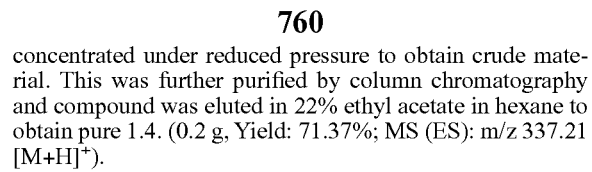

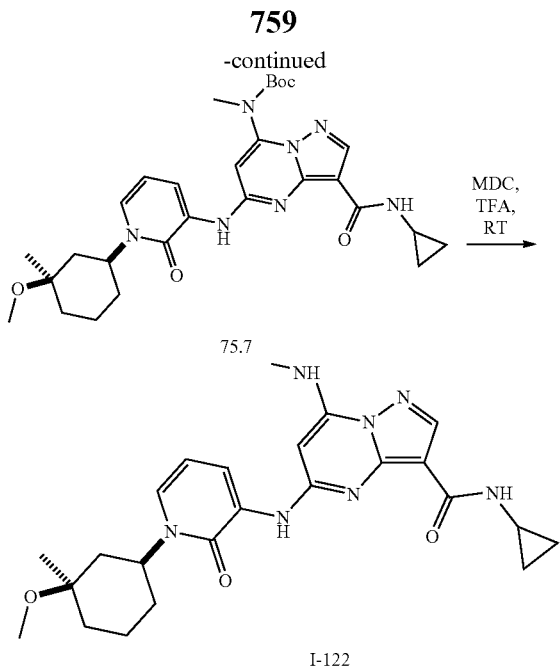

Step 1—Synthesis of Compound 75.2: To a cooled solution of 75 (0.358 g, 2.32 mmol, 1.0 eq), in N,N-dimethylformamide (5 mL) was added 75.1 (0.331 g, 3.24 mmol, 1.0 eq). The reaction mixture was stirred at 0° C. for 30 min and further stirred at room temperature for 15 min. N-Ethyl-N'-(3-dimethylaminopropyl)carbodiimide hydrochloride (0.579 g, 3.01 mmol, 1.3 eq) and 4-Dimethylaminopyridine (0.056 g, 0.46 mmol, 0.2 eq) were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 75.2 (0.280 g, Yield: 43.15%; MS (ES): m/z 280.15 [M+H]+).

Step 2—Synthesis of Compound 75.3: To a solution of 75.2 (0.280 g, 1.0 mmol, 1.0 eq), in methanol:tetrahydrofuran: water (5 mL, 2:1:1) was added lithium hydroxide (0.240 g, 1.0 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 75.3 (0.22 g, Yield: 83.10%). MS (ES): m/z 266.13 [M+H]+.

Step 3—Synthesis of Compound 75.4: To a solution of 75.3 (0.221 g, 0.83 mmol, 1.0 eq) in tert.butanol (3 mL) was added triethylamine (0.142 g, 1.41 mmol, 1.7 eq) and diphenyl phosphoryl azide (0.296 g, 1.07 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 1.4. (0.2 g, Yield: 71.37%; MS (ES): m/z 337.21 [M+H]+).

Step 4—Synthesis of Compound 75.5: To a cooled solution of 75.4 (0.2 g, 0.59 mmol, 1 eq) in dioxane (4 mL) was added 4N hydrochloric acid in dioxane (6 mL) dropwise. The reaction mixture was stirred at room temperature for 2 h. After completion of reaction, reaction mixture was concentrated under reduced pressure to obtain pure 75.5 (0.160 g, Yield: 98.67%; MS (ES): m/z 273.13 [M+HCl]).

Step 5—Synthesis of Compound 75.6: Compound was synthesized from Core A using general procedure A to obtain 75.6 (Yield: 57.16%; MS (ES): m/z 366.82 [M+H]+).

Step 6—Synthesis of Compound 1.7: Compound was synthesized using general procedure B to obtain 75.7 (0.140 g, Yield: 60.36%; MS (ES): m/z 566.30 [M+H]+).

Step 7—Synthesis of Compound I-122: Compound was synthesized using general procedure C to obtain I-122 (0.025 g, Yield: 86.79%; MS (ES): m/z 466.47 [M+H]+; LCMS purity: 95.73%; HPLC purity: 95.00%; CHIRAL HPLC: 51.26%, 48.60%; 1H NMR (DMSO-d6, 400 MHZ): 8.89 (s, 1H), 8.18 (s, 1H), 8.10-8.08 (d, J=7.2 Hz, 1H), 7.91-7.89 (d, J=4.8 Hz, 1H), 7.82-7.81 (d, J=3.6 Hz 1H), 7.50-7.48 (d, J=6.4 Hz, 1H), 6.33-6.29 (t, J=6.8 Hz, 1H), 6.16 (s, 1H), 3.14 (s, 3H), 2.89-2.88 (d, J=4.8 Hz, 3H), 2.86-2.84 (m, 1H), 1.76-1.67 (m, 4H), 1.50 (bs, 1H), 1.26 (bs, 3H), 1.23 (m, 2H), 1.10-1.07 (t, J=6.8 Hz, 1H), 0.85 (bs, 1H), 0.80-0.77 (m, 2H), 0.48 (bs, 2H)).

Example 76: N-((trans-1,2)-2-Fluorocyclobutyl)-5-((1-((1S,2S)-2-fluorocyclopropyl)-2-oxo-1,2-dihydropyridin-3-yl)amino)-7-(methylamino)pyrazolo[1,5-a]pyrimidine-3-carboxamide (I-148)

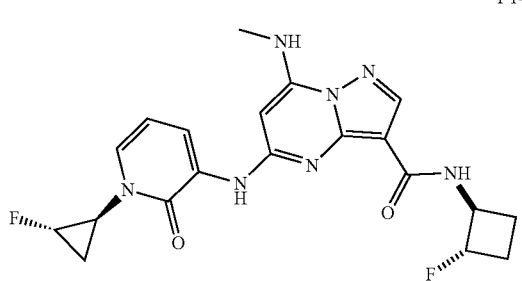

Scheme 76

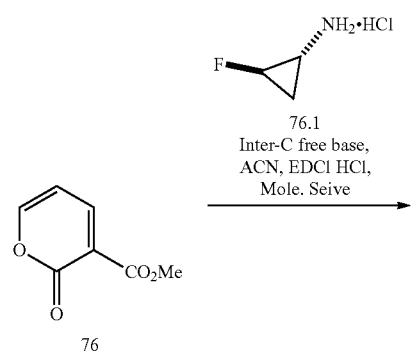

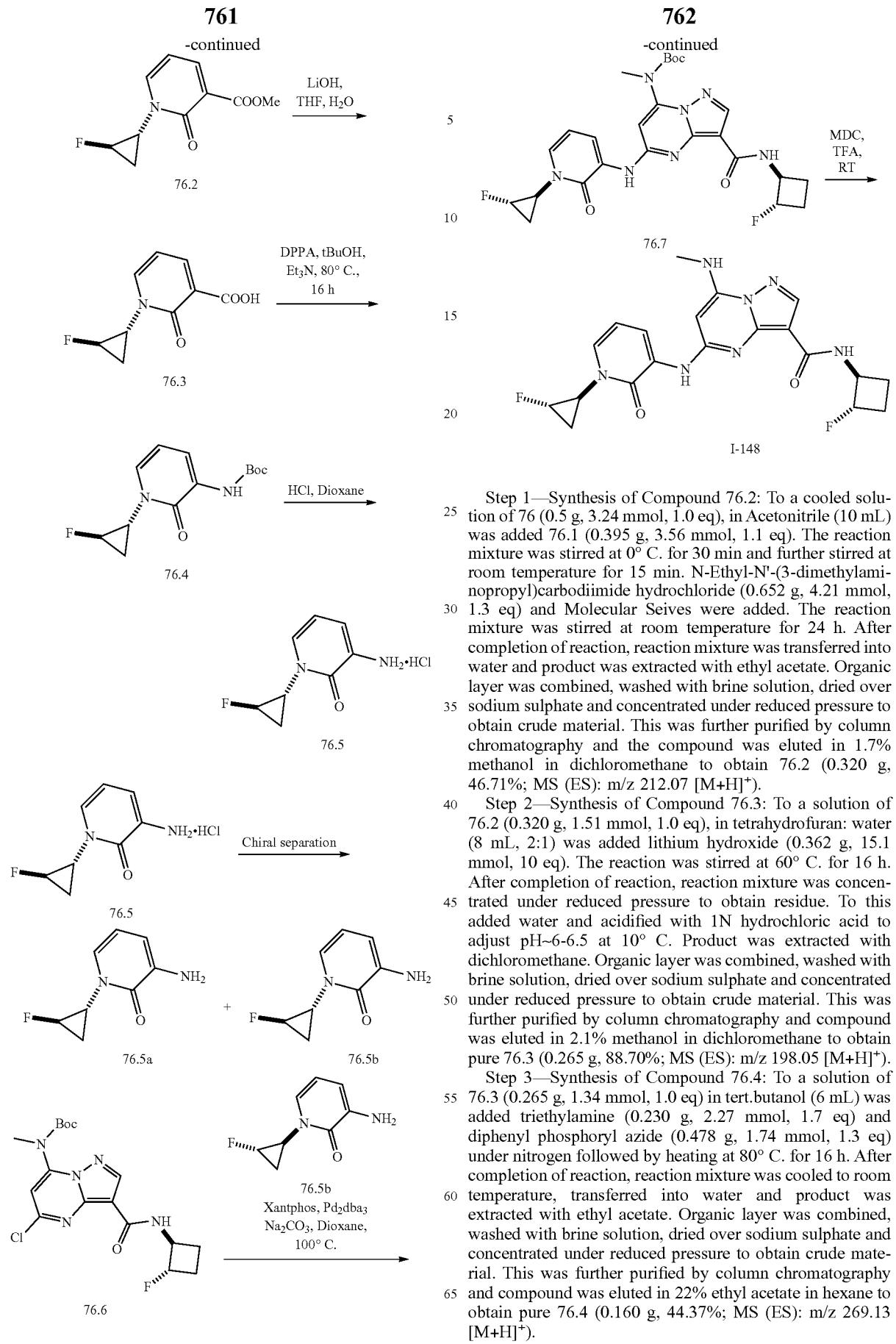

Step 1—Synthesis of Compound 76.2: To a cooled solution of 76 (0.5 g, 3.24 mmol, 1.0 eq), in Acetonitrile (10 mL) was added 76.1 (0.395 g, 3.56 mmol, 1.1 eq). The reaction mixture was stirred at 0° C. for 30 min and further stirred at room temperature for 15 min. N-Ethyl-N'-(3-dimethylaminopropyl)carbodiimide hydrochloride (0.652 g, 4.21 mmol, 1.3 eq) and Molecular Seives were added. The reaction mixture was stirred at room temperature for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.7% methanol in dichloromethane to obtain 76.2 (0.320 g, 46.71%; MS (ES): m/z 212.07 [M+H]$^+$).

Step 2—Synthesis of Compound 76.3: To a solution of 76.2 (0.320 g, 1.51 mmol, 1.0 eq), in tetrahydrofuran: water (8 mL, 2:1) was added lithium hydroxide (0.362 g, 15.1 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 76.3 (0.265 g, 88.70%; MS (ES): m/z 198.05 [M+H]$^+$).

Step 3—Synthesis of Compound 76.4: To a solution of 76.3 (0.265 g, 1.34 mmol, 1.0 eq) in tert.butanol (6 mL) was added triethylamine (0.230 g, 2.27 mmol, 1.7 eq) and diphenyl phosphoryl azide (0.478 g, 1.74 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 76.4 (0.160 g, 44.37%; MS (ES): m/z 269.13 [M+H]$^+$).

Step 4—Synthesis of Compound 76.5: To a cooled solution of 76.4 (0.160 g, 0.59 mmol, 1 eq) in dioxane (4 mL) was added 4N hydrochloric acid in dioxane (10 mL) dropwise. The reaction mixture was stirred at room temperature for 2 h. After completion of reaction, reaction mixture was concentrated under reduced pressure to obtain 76.5 (0.125 g, 98.33%; MS (ES): m/z 205.05 [M+HCl]$^+$).

Step 5—Synthesis of Compound 76.5a and 76.5b: Isomers of 76.5 (0.8 g) were separated out using column (CHIRAL PAK AD-H 250×4.6 mm, 5 μM) and 0.3% Diethylamine in methanol as co-solvent with flow rate of 4 mL/min. to get pure 76.5a fraction-1 and 76.5b fraction-2 (FR-b). FR-a was evaporated under reduced pressure at 30° C. to afford pure 76.5a (0.07 g). MS (ES): m/z 205.05 [M+H]$^+$. FR-b was evaporated under reduced pressure at 30° C. to afford pure 76.5b (0.07 g; MS (ES): m/z 205.05 [M+H]$^+$).

Step 6—Synthesis of Compound 76.6: Compound was synthesized from Core A using general procedure A to obtain 76.6 (Yield: 56.86%; MS (ES): m/z 398.14 [M+H]$^+$).

Step 7—Synthesis of Compound 76.7: Compound was synthesized using general procedure B to obtain 76.7 (0.050 g, 53.66%; MS (ES): m/z 530.55 [M+H]$^+$).

Step 8—Synthesis of Compound I-148: Compound was synthesized using general procedure C to obtain I-148 (0.025 g, 61.66%; MS (ES): m/z 430.55 [M+H]$^+$; LCMS purity: 100%; HPLC purity: 97.71%, CHIRAL HPLC: 49.58%, 50.19%; $^1$H NMR (DMSO-d$_6$, 400 MHZ): 8.97 (s, 1H), 8.23-8.21 (d, J=7.6 Hz, 1H), 8.19 (s, 1H), 8.11-8.09 (d, J=8.4 Hz, 1H), 7.94-7.93 (d, J=4.8 Hz, 1H), 7.19-7.18 (d, J=5.6 Hz, 1H), 6.26-6.24 (d, J=7.6 Hz, 1H), 6.22 (s, 1H), 5.08-4.77 (m, 2H), 4.54-4.46 (m, 1H), 3.90-3.82 (m, 1H), 2.91-2.90 (d, J=4.4 Hz, 3H), 2.18-2.13 (m, 2H), 1.89-1.69 (m, 2H), 1.57-1.49 (m, 1H), 1.36-1.31 (m, 1H)).

Example 77: 7-Amino-N-((trans-1,2)-2-methoxycyclobutyl)-5-((2-oxo-2H-[1,2'-bipyridin]-3-yl)amino)pyrazolo[1,5-a]pyrimidine-3-carboxamide (I-245)

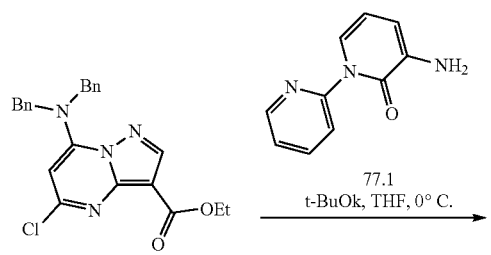

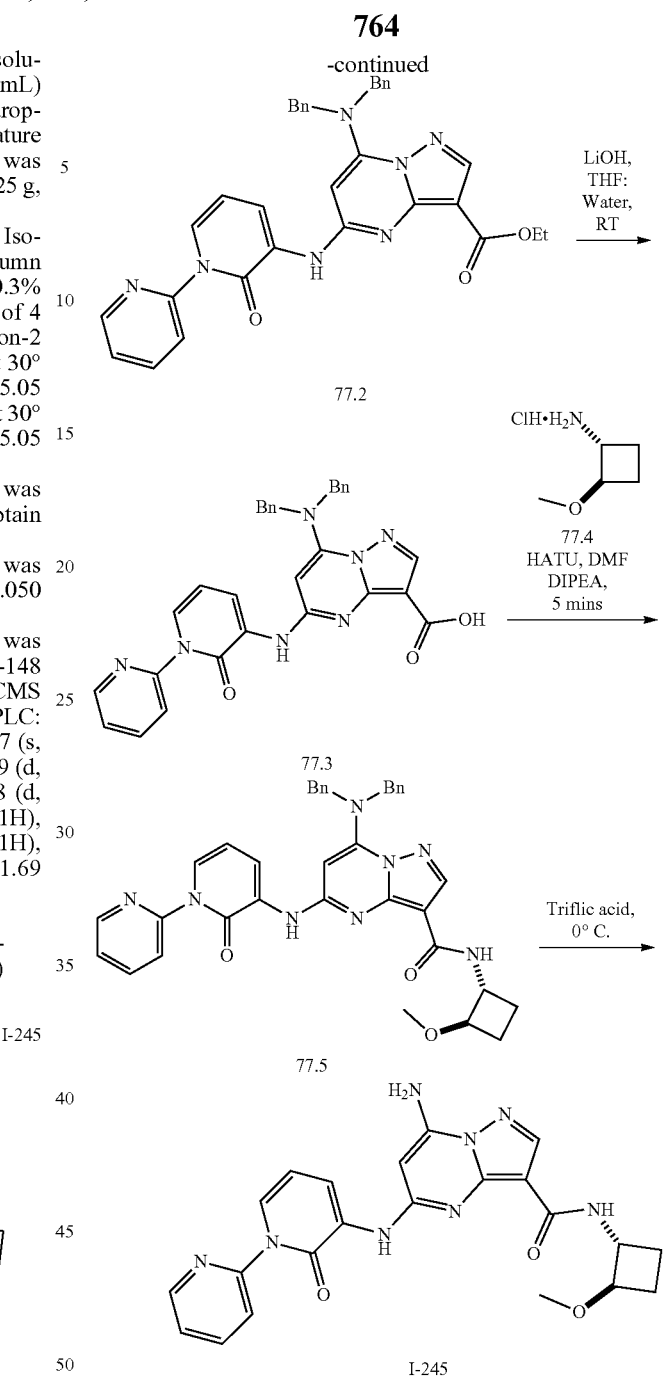

Step—Synthesis of Compound 77: Compound was synthesized using general procedure of core synthesis to obtain 77. (Yield: 62.00%; MS (ES): m/z 421.9 [M+H]$^+$).

Step 2—Synthesis of Compound 77.2: To a cooled solution of 77 (0.5 g, 1.19 mmol, 1.0 eq) and 77.1 (0.267 g, 1.42 mmol, 1.2 eq) in tetrahydrofuran (5 mL) at 0° C. was added potassium tert-butoxide (1M in tetrahydrofuran; 2.38 mL, 2.38 mmol, 2.0 eq). The reaction was stirred at room temperature for 2 h. After completion of reaction, reaction mixture was transferred into water and product was extracted with ethyl acetate. Organic layer was combined and dried over sodium sulphate and concentrated under reduced pressure to obtain crude material. This was further purified by column chromatography and compound was eluted in 25% ethyl acetate in hexane to obtain pure 77.2 (0.482 g, Yield: 70.98%). MS (ES): m/z 572.24 [M+H]$^+$).

Step 3—Synthesis of Compound 77.3: To a solution of 77.2 (0.482 g, 0.84 mmol, 1.0 eq), in tetrahydrofuran: water (6 mL, 2:1) was added lithium hydroxide (0.201 g, 8.4 mmol, 10 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 77.3 (0.370 g, Yield: 80.73%; MS (ES): m/z 544.21 [M+H]$^+$).

Step 4—Synthesis of Compound 77.5: Compound was synthesized using general procedure A to obtain 77.5 (0.250 g, Yield: 58.60%; MS (ES): m/z 627.28 [M+H]$^+$).

Step 5—Synthesis of Compound I-245: A solution of 77.5 (0.060 g, 0.095 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-245 (0.025 g, Yield: 58.49%; MS (ES): m/z 447.62 [M+H]$^+$; LCMS purity: 98.97%; HPLC purity: 96.75%; CHIRAL HPLC: 49.95%, 50.02%; $^1$H NMR (DMSO-d$_6$, 400 MHZ): 9.09 (s, 1H), 8.65 (bs, 1H), 8.28-8.26 (d, J=7.2 Hz, 1H), 8.21 (s, 1H), 8.14-8.12 (d, J=8.8 Hz, 1H), 8.08-8.04 (t, J=6.8 Hz, 1H), 7.87-7.85 (d, J=8.4 Hz, 1H), 7.70 (bs, 1H), 7.65-7.63 (d, J=6.8 Hz, 2H), 7.57-7.54 (d, J=5.6 Hz, 1H), 6.47-6.44 (t, J=6.8 Hz, 1H), 6.13 (s, 1H), 4.35-4.31 (m, 1H), 3.21 (s, 3H), 2.14-2.01 (m, 2H), 1.56 (s, 1H), 1.25 (s, 2H)).

Example 78: N-((S)-2,2-Difluorocyclobutyl)-5-((1-((3S,4S)-3-methoxytetrahydro-2H-pyran-4-yl)-2-oxo-1,2-dihydropyridin-3-yl)amino)-7-(methylamino)pyrazolo[1,5-a]pyrimidine-3-carboxamide (I-333)

I-333

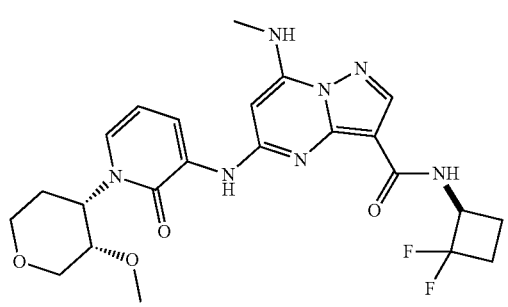

Scheme 78

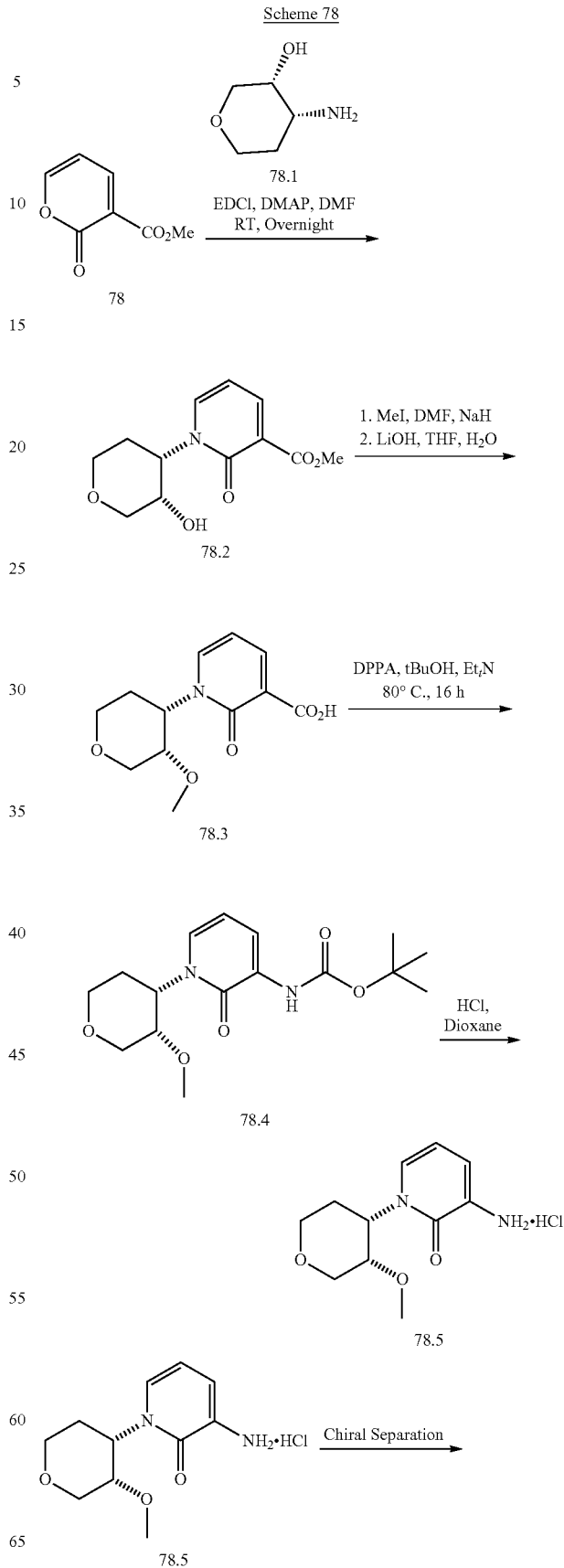

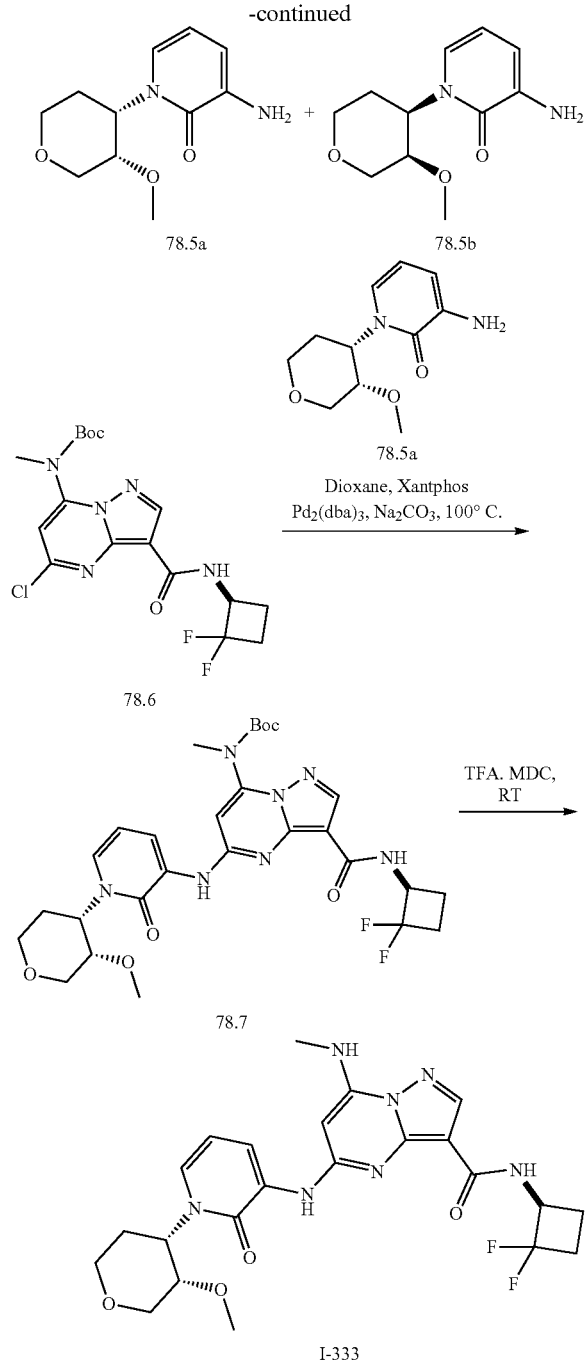

Step 1—Synthesis of Compound 78.2: To a cooled solution of 78 (5.0 g, 32.44 mmol, 1.0 eq), in N,N-dimethylformamide (80 mL) was added 78.1 (3.7 g, 32.44 mmol, 1.0 eq). The reaction mixture was stirred at 0° C. for 30 min and further stirred at room temperature for 15 min. N-Ethyl-N'-(3-dimethylaminopropyl) carbodiimide hydrochloride (8.0 g, 42.17 mmol, 1.3 eq) and 4-Dimethylaminopyridine (0.989 g, 8.11 mmol, 0.25 eq) was added. The reaction mixture was stirred at room temperature for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 78.2 (3.0 g, Yield: 36.51%; MS (ES): m/z 254.10 [M+H]$^+$).

Step 2—Synthesis of Compound 78.3: To a suspension of sodium hydride (0.568 g, 23.7 mmol, 2 eq) in Dimethylformamide (4 mL) at 0° C. was added 78.2 (3.0 g, 11.85 mmol, 1.0 eq) and stirred for 15 min followed by addition of Methyl iodide (1.8 g, 13.03 mmol, 1.1 eq). Reaction mixture was stirred at room temperature for 2 h. After completion of reaction, reaction mixture was diluted with water extracted with diethyl ether. Organic layer was combined, dried over sodium sulphate and concentrated under reduced pressure to obtain crude material (1.5 g). This crude material (1.5 g, 5.61 mmol, 1.0 eq) was taken in tetrahydrofuran: water (15 mL, 2:1) and lithium hydroxide (0.561 g, 56.1 mmol, 10 eq) was added. The reaction mixture was stirred at temperature for 24 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 78.3 (1.2 g, Yield: 80.00%; MS (ES): m/z 254.10 [M+H]$^+$).

Step 3—Synthesis of Compound 78.4: To a solution of 78.3 (1.2 g, 4.74 mmol, 1.0 eq) in tert-butanol (15 mL) was added triethylamine (0.813 g, 8.05 mmol, 1.7 eq) and diphenyl phosphoryl azide (1.6 g, 6.16 mmol, 1.3 eq) under nitrogen followed by heating at 80° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 22% ethyl acetate in hexane to obtain pure 78.4 (1.1 g, Yield: 71.57%; MS (ES): m/z 325.17 [M+H]$^+$).

Step 4—Synthesis of Compound 78.5: To a cooled solution of 78.4 (1.1 g, 3.39 mmol, 1 eq) in dioxane (11 mL) was added 4N hydrochloric acid in dioxane (15 mL) dropwise. The reaction mixture was stirred at room temperature for 2 h. After completion of reaction, reaction mixture was concentrated under reduced pressure to obtain pure 78.5 (0.9 g, Yield: 80.59%; MS (ES): m/z 225.12 [M+H]$^+$).

Step 5—Synthesis of Compounds 78.5a and 78.5b: Isomers of 78.5 (0.1 g) were separated out using column CHIRALCEL OJ-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 78.5a (0.280 g; MS (ES): m/z 225.12 [M+H]$^+$). FR-b was concentrated under reduced pressure at 30° C. to afford pure 78.5b (0.280 g; MS (ES): m/z 225.12 [M+H]$^+$).

Step 6—Synthesis of Compound 78.6: Compound was synthesized from Core A using general procedure A to obtain 78.6 (Yield: 67.72%; MS (ES): m/z 406.12 [M+H]$^+$).

Step 7—Synthesis of Compound 78.7: Compound was synthesized using general procedure B to obtain 78.7 (0.140 g, Yield: 68.89%; MS (ES): m/z 604.27 [M+H]$^+$).

Step 8—Synthesis of Compound I-333: Compound was synthesized using general procedure C to obtain I-333 (0.025 g, Yield: 74.93%; MS (ES): m/z 504.61 [M+H]$^+$; LCMS purity: 95.00%; HPLC purity: 98.98%; CHIRAL HPLC: 47.20%, 49.19%; $^1$H NMR (DMSO-$d_6$, 400 MHZ): 8.92-8.91 (d, J=3.6 Hz, 1H), 8.25 (s, 1H), 8.22-8.20 (d, J=7.2 Hz, 1H), 8.16-8.13 (m, 1H), 7.97-7.96 (d, J=4.8 Hz, 1H), 7.38-7.36 (d, J=6.8 Hz, 1H), 6.31-6.27 (t, J=6.8 Hz, 1H), 6.25 (s, 1H), 5.14 (bs, 1H), 5.08-5.02 (m, 1H), 4.14 (bs, 1H), 4.02 (bs, 1H), 3.63-3.57 (t, J=12 Hz, 1H), 3.46 (s, 2H), 3.15 (bs, 3H), 2.93-2.91 (d, J=4.8 Hz, 3H), 1.56 (bs, 2H), 1.24 (bs, 4H)).

Example 79: 5-(((6-Fluoro-2-oxo-2H-[1,2'-bipyridin]-3-yl)amino)-N-((1R,2S)-2-fluorocyclopropyl)-7-(methylamino)pyrazolo[1,5-a]pyrimidine-3-carboxamide (I-474)

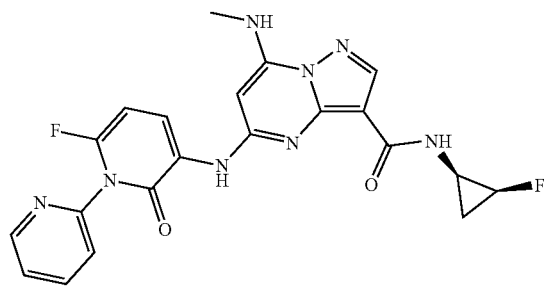

I-474

Scheme 79

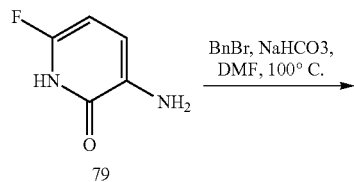

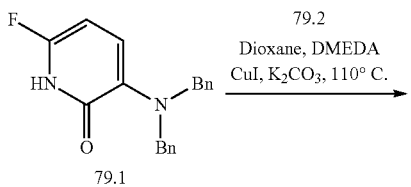

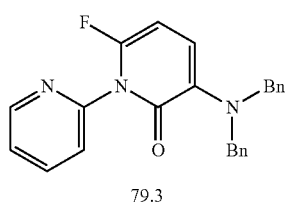

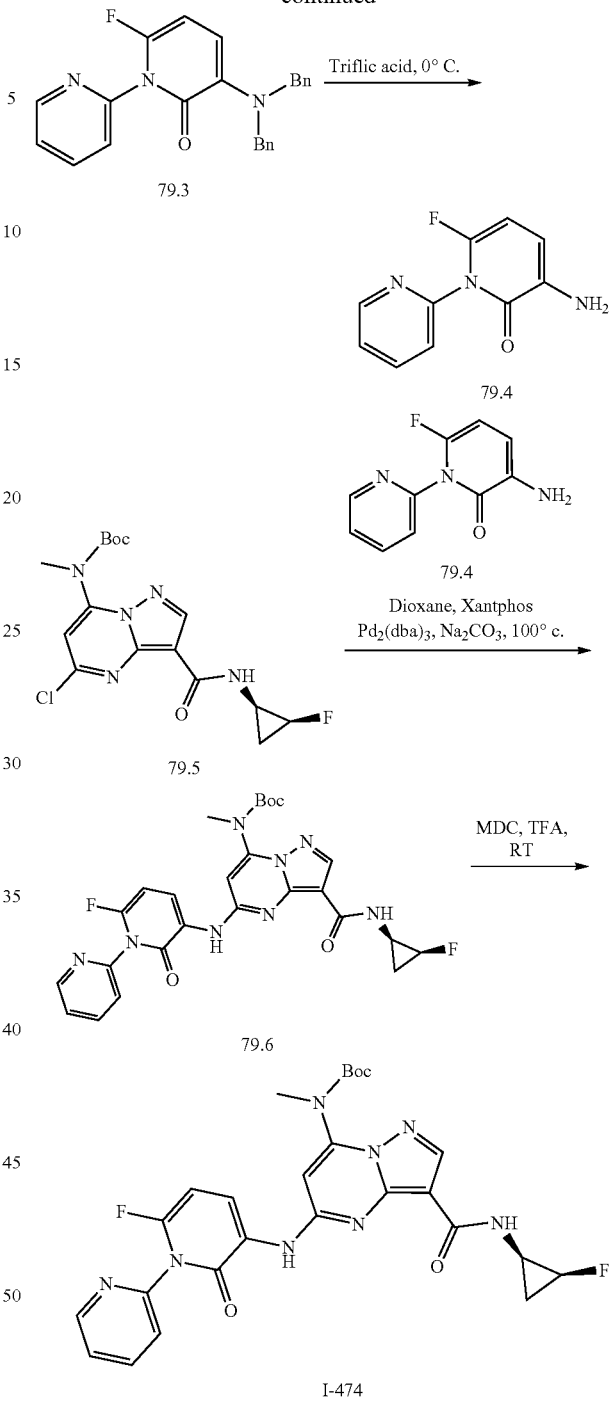

Step 1—Synthesis of Compound 79.1: To a solution of 79 (1.0 g, 7.81 mmol, 1.0 eq) in dimethylformamide (15 mL) was added Sodium bicarbonate (2.6 g, 31.24 mmol, 4.0 eq). benzyl bromide (2.9 g, 17.18 mmol, 2.2 eq) was added to the reaction mixture and reaction mixture was stirred at 100° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 79.1 (0.650 g, Yield: 27.00%; MS (ES): m/z 309.14 [M+H]⁺).

Step 2—Synthesis of Compound 79.3: To a solution of 79.1 (0.2 g, 0.64 mmol, 1.0 eq) and 79.2 (0.121 g, 0.76 mmol, 1.2 eq) in 1,4-dioxane (8 mL) was added potassium carbonate (0.176 g, 1.28 mmol, 2.0 eq) and degassed with argon for 15 min. Copper iodide (0.024 g, 0.12 mmol, 0.2 eq) and 1,2-dimethylethylenediamine (0.022 g, 0.25 mmol, 0.4 eq) was added and reaction mixture again degassed with argon for 5 min followed by heating at 110° C. for 16 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 1.2% methanol in dichloromethane to obtain pure 79.3 (0.162 g, Yield: 64.80%; MS (ES): m/z 386.16 [M+H]⁺).

Step 3—Synthesis of Compound 79.4: To a solution of 79.3 (0.162 g, 0.42 mmol, 1.0 eq) in dichloromethane (2 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 79.4 (0.070 g, Yield: 81.17%; MS (ES): m/z 206.07 [M+H]⁺).

Step 4—Synthesis of Compound 79.5: Compound was synthesized from Core A using general procedure A to obtain 79.5 (Yield: 51.08%; MS (ES): m/z 384.81 [M+H]⁺).

Step 5—Synthesis of Compound 79.6: Compound was synthesized using general procedure B to obtain 79.6 (0.040 g, Yield: 39.69%), MS (ES): m/z 553.21 [M+H]⁺).

Step 6—Synthesis of Compound I-474: Compound was synthesized using general procedure C to obtain I-474 (0.027 g, Yield: 82.44%), MS (ES): m/z 453.32 [M+H]⁺, LCMS purity: 98.02%, HPLC purity: 96.56%, CHIRAL HPLC: 97.82%, ¹H NMR (DMSO-d₆, 400 MHZ): 9.21 (s, 1H), 8.48-8.44 (t, J=8.4 Hz, 1H), 8.26-8.25 (d, J=3.2 Hz, 1H), 8.18 (bs, 1H), 7.94-7.90 (m, 2H), 7.82-7.81 (d, J=4.4 Hz, 1H), 7.28-7.25 (m, 1H), 7.16-7.14 (d, J=8.4 Hz, 1H), 7.00-6.97 (m, 1H), 5.78 (s, 1H), 4.86 (bs, 1H), 2.88-2.87 (d, J=4.8 Hz, 3H), 2.19-2.15 (t, J=8 Hz, 1H), 1.91-1.87 (m, 1H), 1.17-1.08 (m, 1H)).

Example 80: N-Cyclopropyl-7-(methylamino)-5-(8-(methylamino)imidazo[1,2-a]pyridin-5-yl)pyrazolo[1,5-a]pyrimidine-3-carboxamide (I-478)

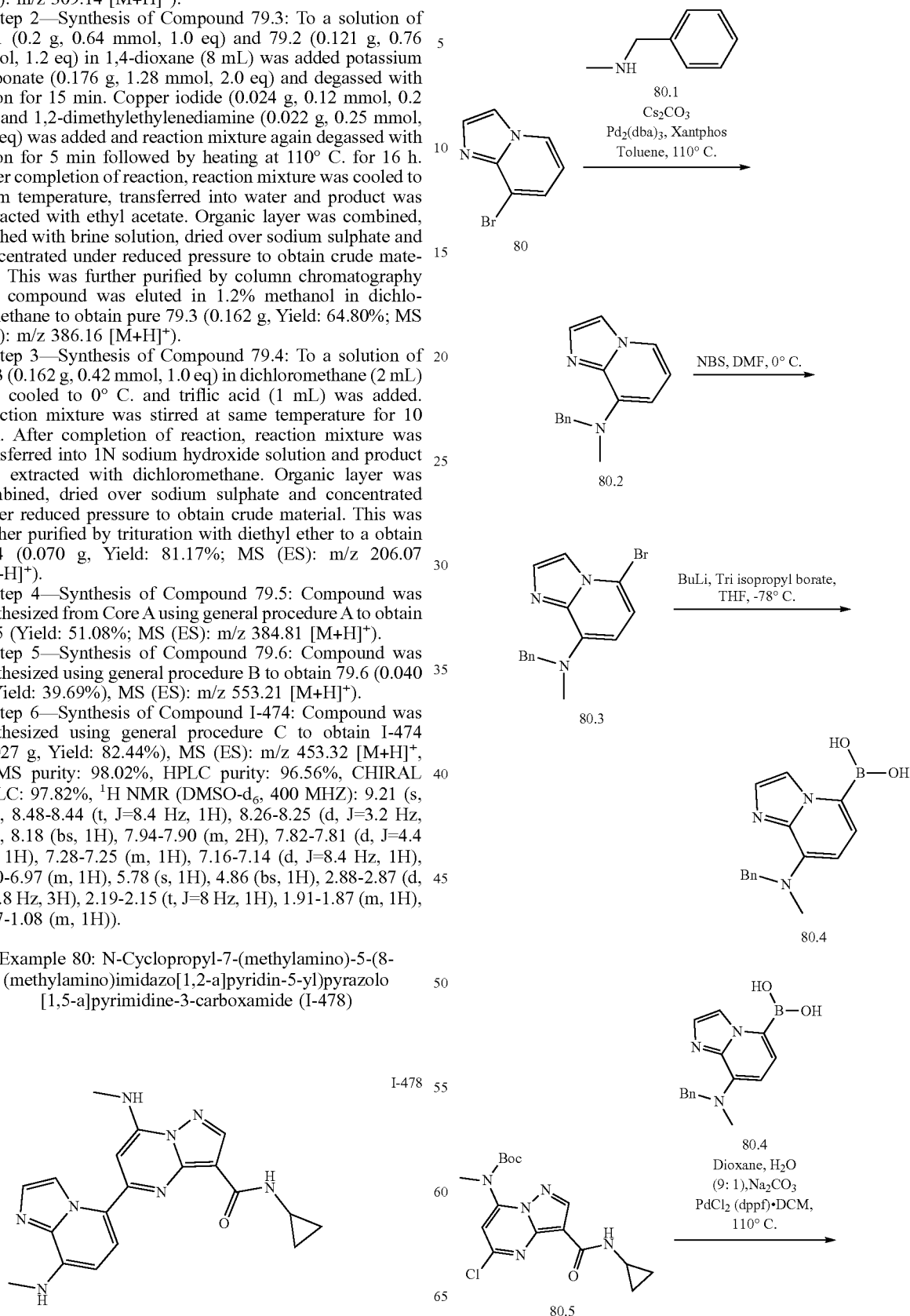

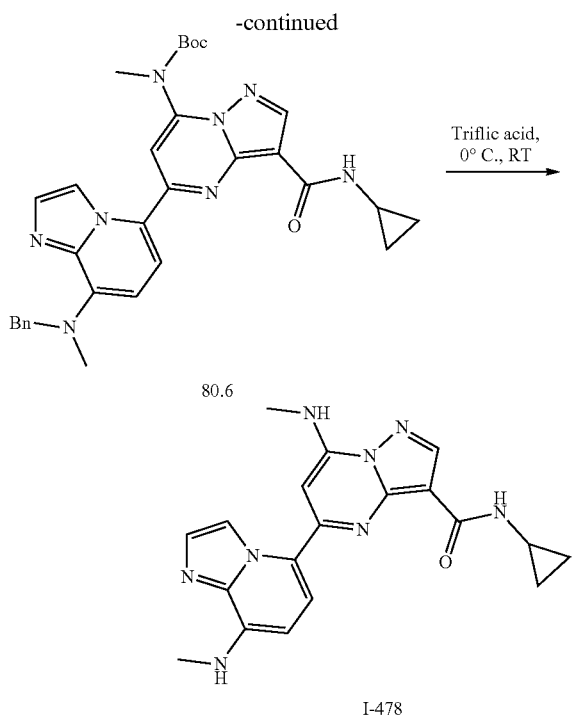

Step 1—Synthesis of Compound 80.2: To a solution of 80 (5.0 g, 25.38 mmol, 1.0 eq) in Toluene (120 mL) was added 80.1 (3.6 g, 30.45 mmol, 1.2 eq), cesium carbonate (12.4 g, 38.07 mmol, 1.5 eq). The reaction mixture was degassed for 10 min. under argon atmosphere, then tris(dibenzylideneacetone)dipalladium(0) (1.1 g, 1.26 mmol, 0.05 eq) and 4,5-bis(diphenylphosphino)-9,9-dimethylxanthene (1.4 g, 2.53 mmol, 0.1 eq) were added, again degassed for 5 min. The reaction mixture was stirred at 110° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 3% methanol in dichloromethane as eluant to obtain pure 80.2 (4.3 g, Yield: 71.41%; MS (ES): m/z 238.13 [M+H]$^+$).

Step 2—Synthesis of Compound 80.3: To a solution of 80.2 (4.3 g, 18.14 mmol, 1.0 eq) in dimethylformamide (43 mL) was added N-Bromosuccinimide (3.2 g, 18.14 mmol, 1.0 eq) at 0° C. The reaction mixture was stirred at 0° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 5% ethyl acetate in hexane to obtain pure 80.3 (2.05 g, 35.78%; MS (ES): m/z 317.04 [M+H]$^+$).

Step 3—Synthesis of Compound 80.4: To a solution of 80.3 (1.0 g, 3.16 mmol, 1.0 eq) in tetrahydrofuran (10 mL) was added n-Butyllithium (3.16 mL, 4.74 mmol, 1.5 eq) at −78° C. and stirred for 15 min. Tri isopropyl borate (1.1 g, 6.32 mmol, 2.0 eq) was added and reaction mixture was stirred at −78° C. for 2 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by column chromatography and compound was eluted in 25% ethyl acetate in hexane to obtain pure 80.4. (0.810 g, 91.11%; MS (ES): m/z 282.14 [M+H]$^+$).

Step 4—Synthesis of Compound 80.5: Compound was synthesized from Core A using general procedure A to obtain 80.5. (Yield: 57.16%; MS (ES): m/z 366.82 [M+H]$^+$).

Step 5—Synthesis of Compound 80.6: Argon was purged for 15 min through a stirred mixture of 80.5 (0.2 g, 0.54 mmol, 1.0 eq), 80.4 (0.197 g, 0.70 mmol, 1.3 eq) and Sodium carbonate (0.143 g, 1.35 mmol, 2.5 eq) in 1,4-dioxane:water (10 mL, 9:1). [1,1'-Bis(diphenylphosphino)ferrocene]palladium(II) dichloride (0.039 g, 0.05 4 mmol, 0.1 eq) was added to it and further purging done for 10 min. Reaction mixture was allowed to stir at 110° C. for 6 h. After completion of reaction, reaction mixture was transferred into water and product was extracted with ethyl acetate. Organic layer was combined, washed with brine solution, dried over sodium sulphate and concentrated under reduced pressure to obtain 80.6 (0.1 g, 32.28%; MS (ES): m/z 567.28 [M+H]$^+$).

Step 6—Synthesis of compound I-478: A solution of 80.6 (0.052 g, 0.091 mmol, 1.0 eq) in dichloromethane (2 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-478 (0.025 g, 72.37%; MS (ES): m/z 377.72 [M+H]$^+$; LCMS purity: 95.00%; HPLC purity: 97.78%; $^1$H NMR (DMSO-d$_6$, 400 MHZ): 8.90 (s, 1H), 8.44-8.42 (d, J=7.6 Hz, 1H), 8.09-8.08 (d, J=4 Hz, 1H), 7.68-7.66 (d, J=8.4 Hz, 1H), 7.59 (s, 1H), 7.08 (bs, 1H), 6.90-6.89 (m, 1H), 6.65 (s, 1H), 6.25-6.23 (d, J=8 Hz, 1H), 3.51 (s, 1H), 3.11-3.10 (d, J=4.8 Hz, 3H), 2.96-2.95 (d, J=4.8 Hz, 3H), 0.77-0.75 (d, J=5.2 Hz, 2H), 0.53 (bs, 2H)).

Example 81: N-((cis-1,2)-2-Hydroxycyclobutyl)-5-(1-isopropyl-6-methoxy-1H-pyrrolo[2,3-b]pyridin-3-yl)-7-(methylamino)pyrazolo[1,5-a]pyrimidine-3-carboxamide (I-492)

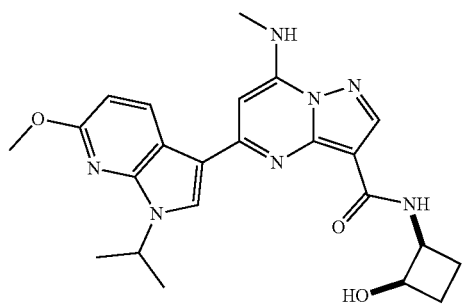

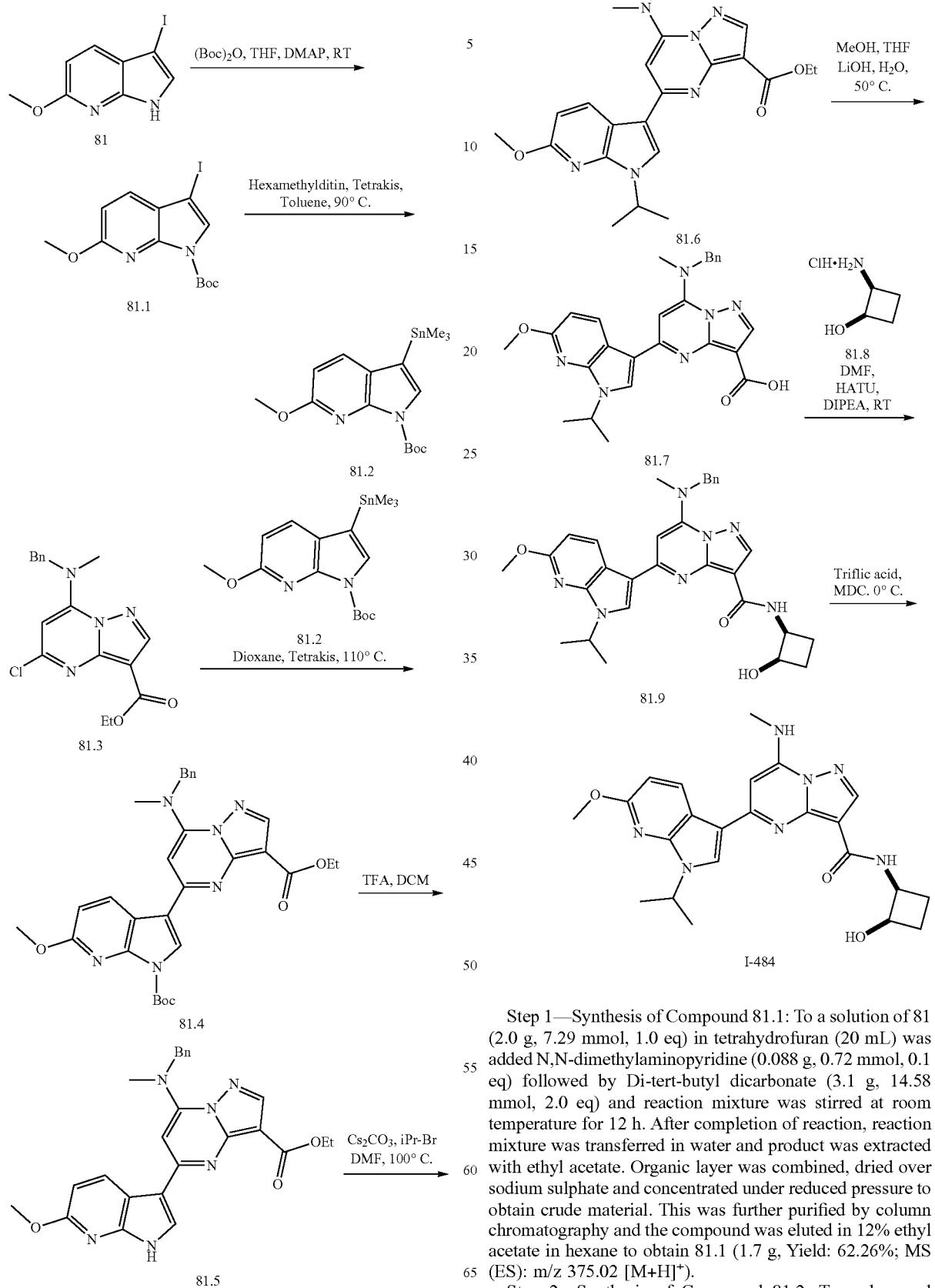

Step 1—Synthesis of Compound 81.1: To a solution of 81 (2.0 g, 7.29 mmol, 1.0 eq) in tetrahydrofuran (20 mL) was added N,N-dimethylaminopyridine (0.088 g, 0.72 mmol, 0.1 eq) followed by Di-tert-butyl dicarbonate (3.1 g, 14.58 mmol, 2.0 eq) and reaction mixture was stirred at room temperature for 12 h. After completion of reaction, reaction mixture was transferred in water and product was extracted with ethyl acetate. Organic layer was combined, dried over sodium sulphate and concentrated under reduced pressure to obtain crude material. This was further purified by column chromatography and the compound was eluted in 12% ethyl acetate in hexane to obtain 81.1 (1.7 g, Yield: 62.26%; MS (ES): m/z 375.02 [M+H]$^+$).

Step 2—Synthesis of Compound 81.2: To a degassed solution of 81.1 (1.5 g, 4.01 mmol, 1.0 eq) and hexamethylditin (5.2 g, 16.04 mmol, 4.0 eq) in toluene (70 mL) was added Tetrakis(triphenylphosphine)palladium(0) (0.463 g, 0.40 mmol, 0.1 eq) and the reaction mixture was heated at 90° C. for 1 h under $N_2$. Reaction mixture was cooled to room temperature purified by column chromography using 5.0% ethyl acetate in hexane as eluent to obtain pure 81.2 (1.62 g, Yield: 98.30%; MS (ES): m/z 412.08 $[M+H]^+$).

Step 3—Synthesis of Compound 81.3: Compound was synthesized using general procedure of Core B synthesis to obtain 81.3 (Yield: 45%; MS (ES): m/z 345.10 $[M+H]^+$).

Step 4—Synthesis of Compound 81.4: To a degassed solution of 81.2 (1.7 g, 4.11 mmol, 2.9 eq) and 81.3 (0.5 g, 1.42 mmol, 1.0 eq) in 1,4-dioxane (25 mL) was added Tetrakis(triphenylphosphine)palladium(0) (0.164 g, 0.142 mmol, 0.1 eq) and the reaction mixture was stirred at 110° C. for 5 h. After completion of reaction, reaction mixture was cooled to room temperature and filtered. The filtrate was concentrated under reduced pressure to obtain crude material. This was further purified by combi flash using 65% ethyl acetate in hexane as eluent to obtain pure 81.4 (0.730 g, Yield: 31.71%; MS (ES): m/z 557.25 $[M+H]^+$).

Step 5—Synthesis of Compound 81.5: Compound was synthesized using general procedure C to obtain 81.5. (0.510 g, Yield: 85.18%; MS (ES): m/z 457.19 $[M+H]^+$).

Step 6—Synthesis of Compound 81.6: To a solution of 81.5 (0.510 g, 1.11 mmol, 1.0 eq), in dimethylformamide (20 mL) was added Isopropyl bromide (0.341 g, 2.77 mmol, 2.5 eq) and Cesium carbonate (1.0 g, 3.33 mmol, 3.0 eq). The reaction mixture was stirred at 100° C. for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 20% ethyl acetate in hexane to obtain 81.6 (0.460 g, Yield: 82.58%; MS (ES): m/z 499.24 $[M+H]^+$).

Step 7—Synthesis of Compound 81.7: To a solution of 81.6 (0.460 g, 0.92 mmol, 1.0 eq), in tetrahydrofuran:methanol:water (6 mL, 2:1:1) was added lithium hydroxide (0.110 g, 4.6 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 81.7 (0.380 g, Yield: 87.53%; MS (ES): m/z 471.21 $[M+H]^+$).

Step 8—Synthesis of Compound 81.9: Compound was synthesized using general procedure A to obtain 81.9 (0.290 g, Yield: 66.54%; MS (ES): m/z 540.27 $[M+H]^+$).

Step 9—Synthesis of Compound I-492: A solution of 81.9 (0.050 g, 0.092 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-492 (0.023 g, Yield: 55.22%; MS (ES): m/z 450.46 $[M+H]^+$; LCMS purity: 100%; HPLC purity: 99.59%; CHI- RAL HPLC: 49.84%, 50.16%; $^1$H NMR (DMSO-$d_6$, 400 MHZ): 8.90-8.87 (d, J=8.4 Hz, 1H), 8.65-8.63 (d, J=6.8 Hz, 1H), 8.56 (bs, 1H), 8.34 (bs, 1H), 8.19-8.18 (d, J=4.8 Hz, 1H), 6.73-7.71 (t, J=8.4 Hz, 1H), 6.69 (bs, 1H), 5.51-5.50 (d, J=3.6 Hz, 1H), 5.08-5.05 (m, 1H), 4.60-4.57 (m, 1H), 4.43 (bs, 1H), 3.96 (s, 3H), 3.13-3.11 (d, J=4.8 Hz, 3H), 2.15-2.06 (m, 3H), 1.86-1.84 (m, 1H), 1.58-1.57 (d, J=6 Hz, 6H)).

Example 82: N-Cyclopropyl-5-(7-((3S,4R)-3-hydroxytetrahydro-2H-pyran-4-yl)-7H-pyrrolo[2,3-b]pyridin-3-yl)-7-(methylamino)pyrazolo[1,5-a]pyrimidine-3-carboxamide (I-818)

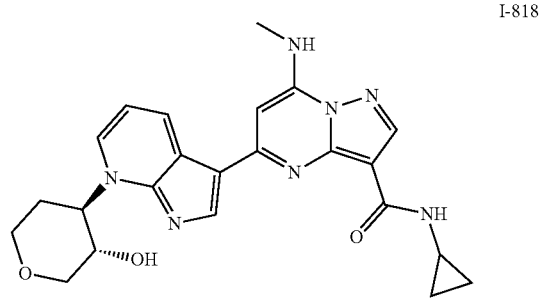 [SMILES: CNc1cc(-c2cnc3n([C@@H]4CCOC[C@H]4O)cccc2-3)nc2c(C(=O)NC3CC3)cnn12]

Scheme 82

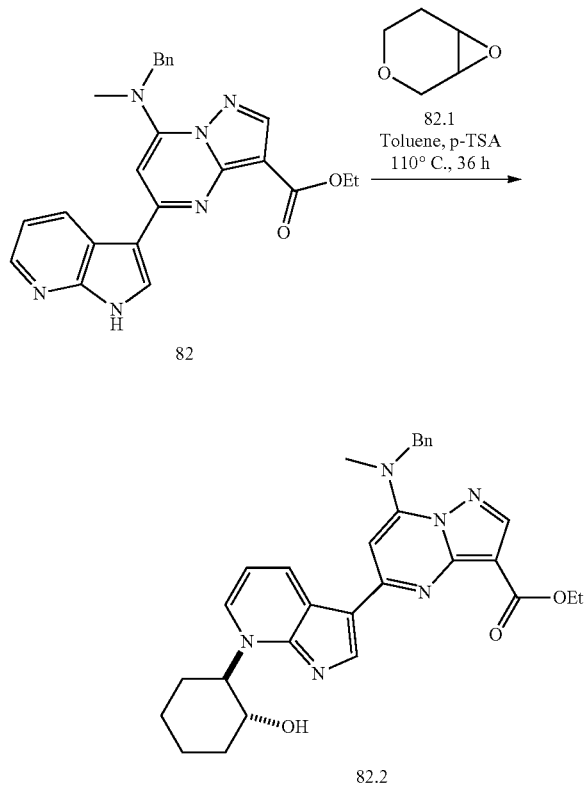

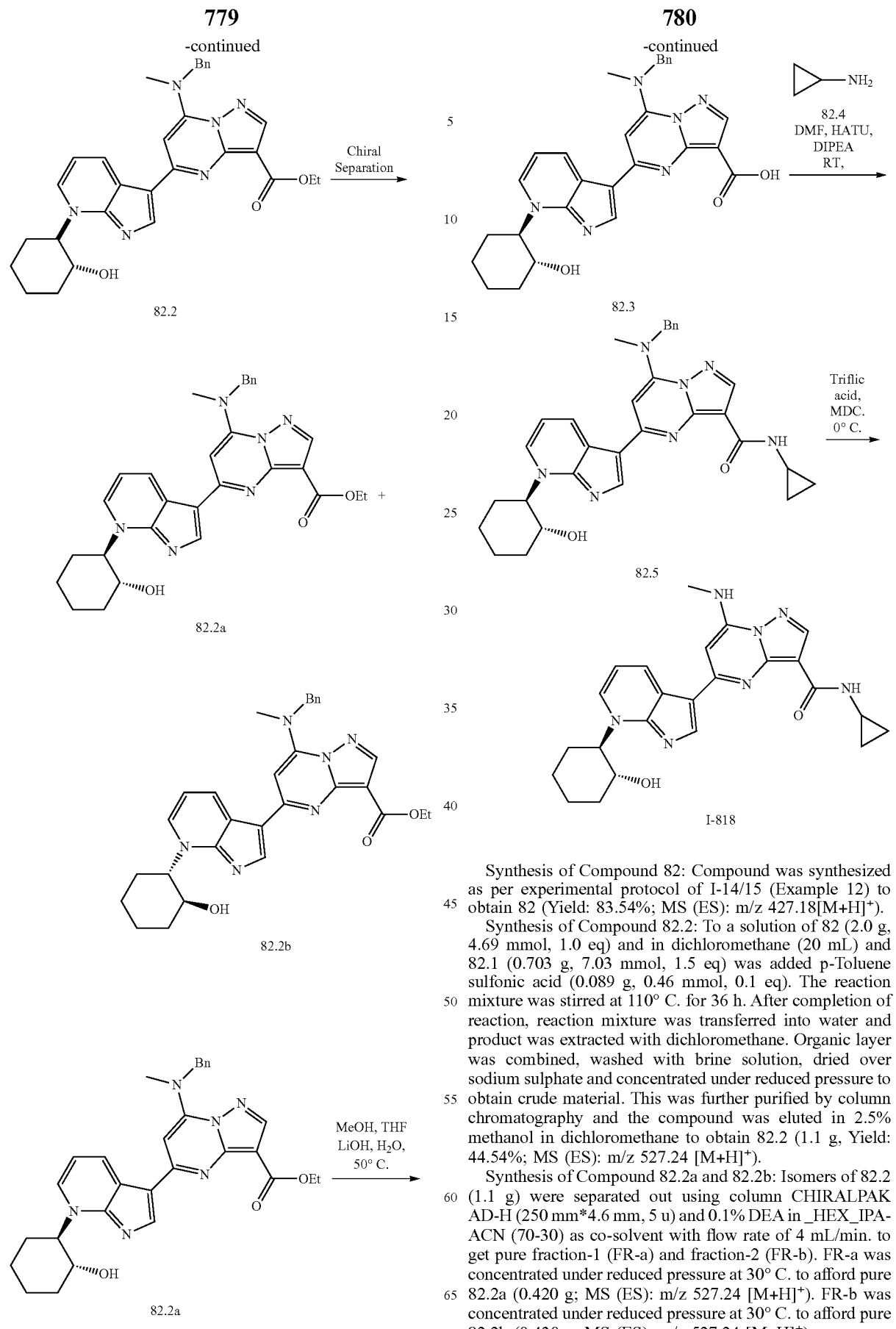

Synthesis of Compound 82: Compound was synthesized as per experimental protocol of I-14/15 (Example 12) to obtain 82 (Yield: 83.54%; MS (ES): m/z 427.18[M+H]$^+$).

Synthesis of Compound 82.2: To a solution of 82 (2.0 g, 4.69 mmol, 1.0 eq) and in dichloromethane (20 mL) and 82.1 (0.703 g, 7.03 mmol, 1.5 eq) was added p-Toluene sulfonic acid (0.089 g, 0.46 mmol, 0.1 eq). The reaction mixture was stirred at 110° C. for 36 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.5% methanol in dichloromethane to obtain 82.2 (1.1 g, Yield: 44.54%; MS (ES): m/z 527.24 [M+H]$^+$).

Synthesis of Compound 82.2a and 82.2b: Isomers of 82.2 (1.1 g) were separated out using column CHIRALPAK AD-H (250 mm*4.6 mm, 5 u) and 0.1% DEA in _HEX_IPA-ACN (70-30) as co-solvent with flow rate of 4 mL/min. to get pure fraction-1 (FR-a) and fraction-2 (FR-b). FR-a was concentrated under reduced pressure at 30° C. to afford pure 82.2a (0.420 g; MS (ES): m/z 527.24 [M+H]$^+$). FR-b was concentrated under reduced pressure at 30° C. to afford pure 82.2b (0.430 g; MS (ES): m/z 527.24 [M+H]$^+$).

Synthesis of Compound 82.3: To a solution of 82.2a (0.420 g, 0.79 mmol, 1.0 eq), in tetrahydrofuran: methanol: water (8 mL, 2:2:1) was added lithium hydroxide (0.094 g, 3.95 mmol, 5.0 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 82.3 (0.360 g, Yield: 90.54%; MS (ES): m/z 499.20 [M+H]$^+$).

Synthesis of Compound 82.5: Compound was synthesized using general procedure A to obtain 82.5 (0.060 g, Yield: 69.55%; MS (ES): m/z 538.25 [M+H]$^+$).

Synthesis of Compound I-818: A solution of 82.5 (0.060 g, 0.11 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-818 (0.035 g, Yield: 70.08%; MS (ES): m/z 448.77 [M+H]$^+$; LCMS purity: 99.17%; HPLC purity: 97.99%; CHIRAL HPLC: 99.57%; $^1$H NMR (DMSO-d$_6$, 400 MHZ): 8.84-8.82 (d, J=7.2 Hz, 1H), 8.63 (s, 1H), 8.47-8.45 (d, J=6 Hz, 1H), 8.40-8.39 (d, J=3.2 Hz, 1H), 8.31 (s, 1H), 8.10-8.09 (d, J=4.8 Hz, 1H), 7.31-7.28 (d, J=6.4 Hz, 1H), 6.66 (s, 1H), 5.34-5.32 (d, J=5.6 Hz, 2H), 4.60 (bs, 1H), 4.06-4.03 (m, 2H), 3.95-3.90 (m, 1H), 3.61-3.52 (t, J=11.6 Hz, 1H), 3.09-3.08 (d, J=4.4 Hz, 3H), 2.90 (bs, 1H), 2.10 (bs, 1H), 1.76 (bs, 1H), 0.88-0.87 (d, J=6.4 Hz, 2H), 0.63 (bs, 2H)).

Example 83: N-((trans-1,2)-2-Fluorocyclobutyl)-5-(7-((3S,4R)-4-hydroxytetrahydrofuran-3-yl)-7H-pyrrolo[2,3-b]pyridin-3-yl)-7-(methylamino)pyrazolo[1,5-a]pyrimidine-3-carboxamide (I-826)

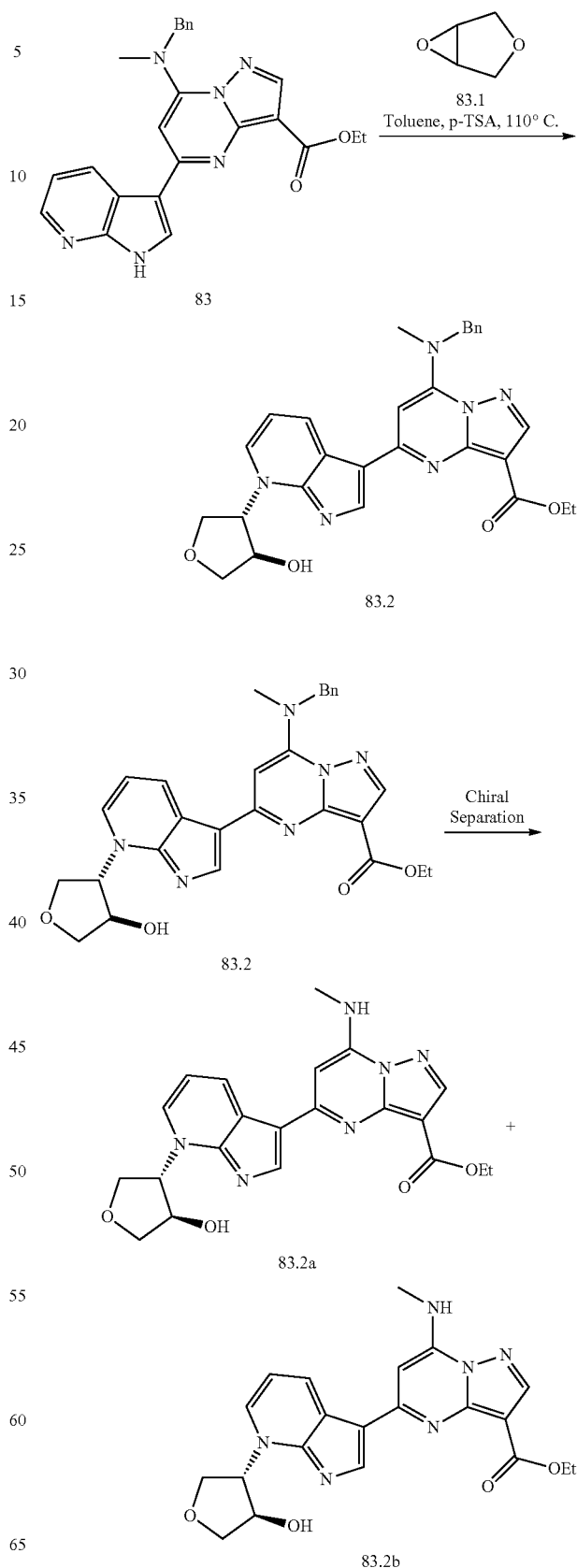

Scheme 83

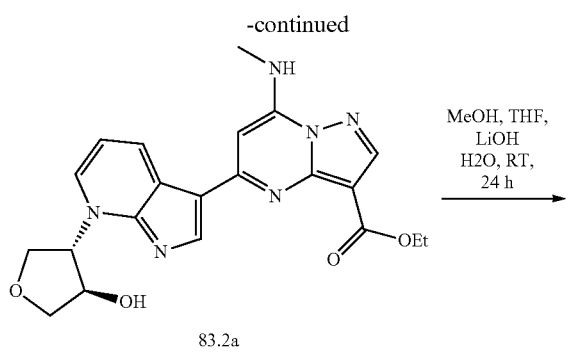

83.2a

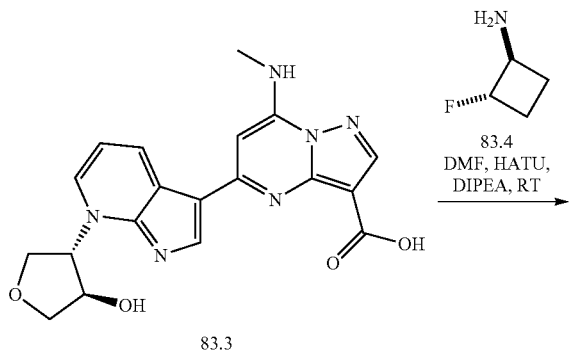

83.3

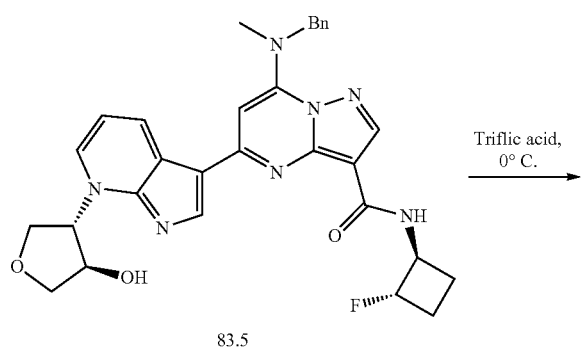

83.5

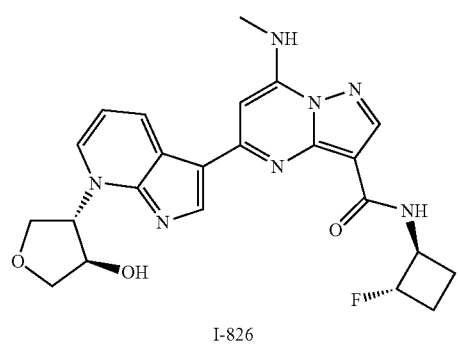

I-826

Step 1—Synthesis of Compound 83: Compound was synthesized as per experimental protocol of I-14/15 (Example 12) to obtain 83 (Yield: 83.54%; MS (ES): m/z 427.18 [M+H]$^+$).

Step 2—Synthesis of Compound 83.2: To a solution of 83 (2.0 g, 4.69 mmol, 1.0 eq) and in dichloromethane (20 mL) and 83.1 (0.604 g, 7.03 mmol, 1.5 eq) was added p-Toluene sulfonic acid (0.089 g, 0.46 mmol, 0.1 eq). The reaction mixture was stirred at 110° C. for 36 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.5% methanol in dichloromethane to obtain 83.2 (0.910 g, Yield: 37.86%; MS (ES): m/z 513.22 [M+H]$^+$).

Step 3—Synthesis of Compound 83.2a and 83.2b: Isomers of 83.2 (0.910 g) were separated out using column CHIRALPAK AD-H (250 mm*4.6 mm, 5 u) and 0.1% DEA in _HEX_IPA-ACN (70-30) as co-solvent with flow rate of 4 mL/min. to get pure fraction-1 (FR-a) and fraction-2 (FR-b). FR-a was concentrated under reduced pressure at 30° C. to afford pure 83.2a (0.330 g; MS (ES): m/z 513.22 [M+H]$^+$). FR-b was concentrated under reduced pressure at 30° C. to afford pure 83.2b (0.320 g; MS (ES): m/z 513.22 [M+H]$^+$).

Step 4—Synthesis of Compound 83.3: To a solution of 83.2a (0.650 g, 1.26 mmol, 1.0 eq), in tetrahydrofuran: methanol: water (12 mL, 2:2:1) was added lithium hydroxide (0.151 g, 6.3 mmol, 5.0 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 83.3 (0.550 g, Yield: 89.51%; MS (ES): m/z 485.19 [M+H]$^+$).

Step 5—Synthesis of Compound 83.5: Compound was synthesized using general procedure A to obtain 83.5 (0.160 g, Yield: 73.60%; MS (ES): m/z 556.24 [M+H]$^+$).

Step 6—Synthesis of Compound I-826: A solution of 83.5 (0.040 g, 0.072 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-826 (0.020 g, Yield: 59.68%; MS (ES): m/z 466.72 [M+H]$^+$; LCMS purity: 100%; HPLC purity: 100%; CHIRAL HPLC: 49.43%, 49.11%; $^1$H NMR (DMSO-d$_6$, 400 MHZ): 8.94-8.92 (d, J=7.6 Hz, 1H), 8.67 (s, 1H), 8.59-8.57 (d, J=8 Hz, 1H), 8.32 (s, 1H), 8.19-8.17 (d, J=6.4 Hz, 1H), 8.12-8.11 (d, J=4.8 Hz, 1H), 7.29-7.25 (t, J=6.8 Hz, 1H), 6.68 (s, 1H), 5.99-5.98 (d, J=4.4 Hz, 1H), 5.89 (bs, 1H), 4.93 (bs, 1H), 4.68 (bs, 1H), 4.61-4.53 (m, 1H), 4.37-4.24 (m, 3H), 3.72-3.69 (m, 1H), 3.09-3.08 (d, J=4.8 Hz, 3H), 2.22 (bs, 2H), 1.90-1.81 (m, 1H), 1.50-1.43 (m, 1H)).

Example 84: 5-(7-((3R,4R)-3-fluorotetrahydro-2H-pyran-4-yl)-7H-pyrrolo[2,3-b]pyridin-3-yl)-N-((cis-1,2)-2-hydroxycyclobutyl)-7-(methylamino)pyrazolo[1,5-a]pyrimidine-3-carboxamide (I-939)
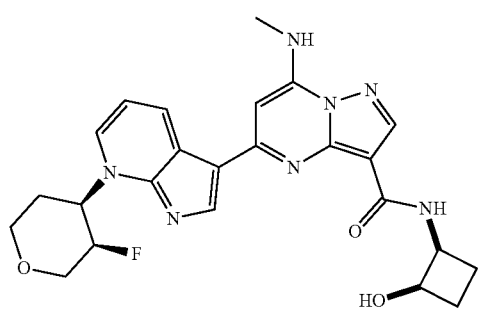
Scheme 84
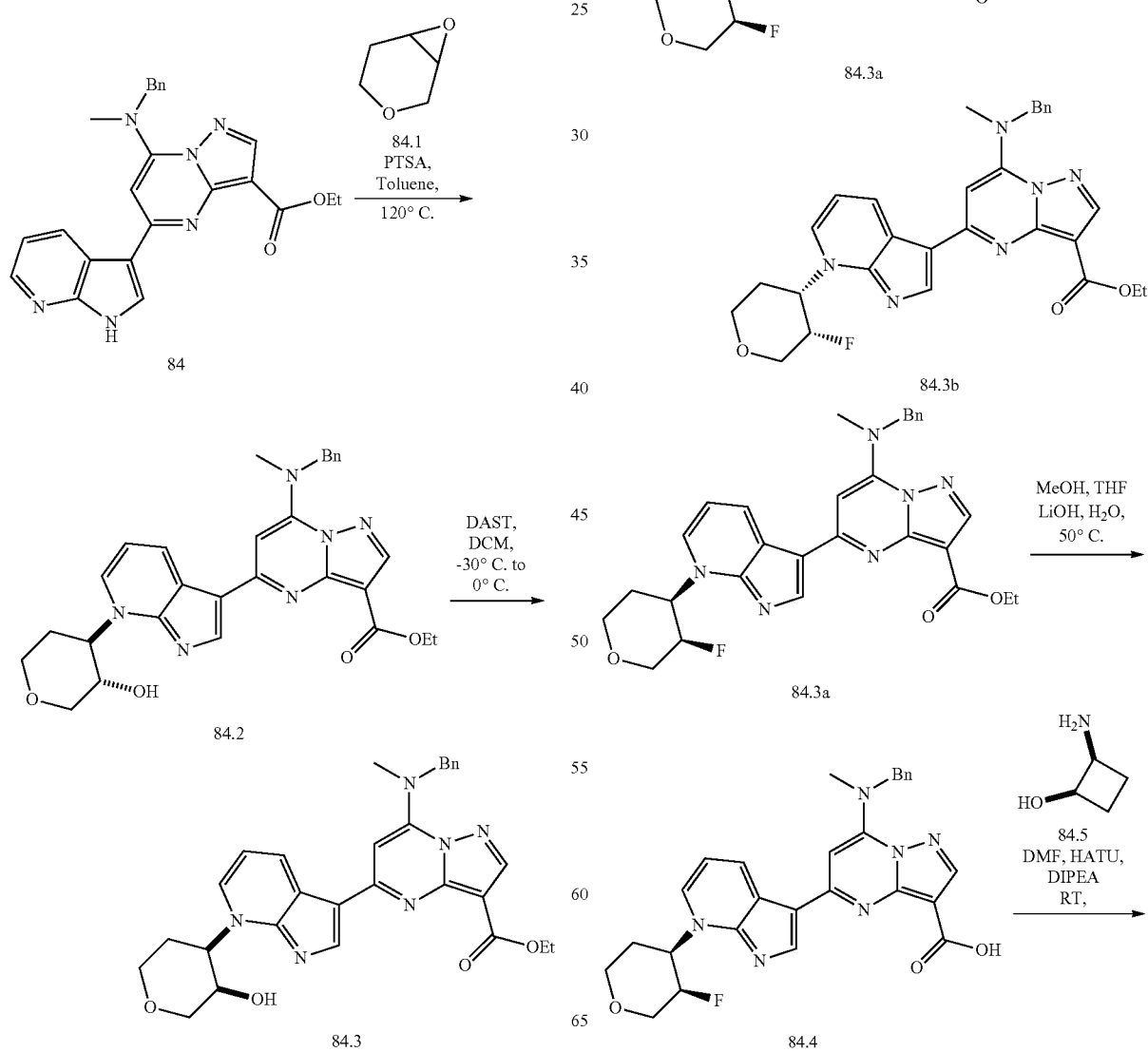

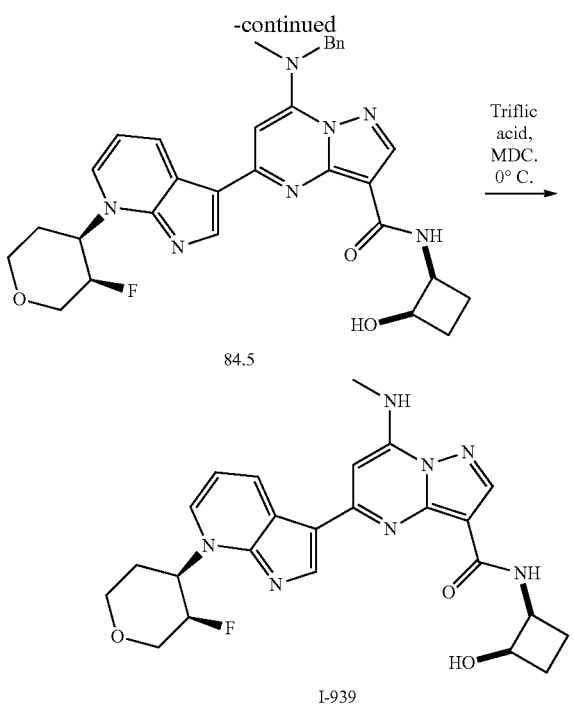

Step 1—Synthesis of Compound 84: Compound was synthesized as per experimental protocol of I-14/15 (Example 12) to obtain 84 (Yield: 83.54.%; MS (ES): m/z 427.18 [M+H]$^+$).

Step 2—Synthesis of Compound 84.2: To a solution of 1 (3.0 g, 7.04 mmol, 1.0 eq) in toluene (35 mL) was added 84.1 (1.05 g, 10.56 mmol, 1.5 eq) and p-Toluene sulfonic acid (0.121 g, 0.70 mmol, 0.1 eq). The reaction mixture was stirred at 120° C. for 48 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.500 methanol in dichloromethane to obtain 84.2 (1.3 g, Yield: 35.09%). MS (ES): m/z 527.24 [M+H]$^+$)

Step 3—Synthesis of Compound 84.3: To a solution of 84.2 (1.3 g, 2.47 mmol, 1.0 eq) in dichloromethane (15 mL) was added Diethylaminosulfur trifluoride (1.62 mL, 12.35 mmol, 5.0 eq) at −30° C. The reaction mixture was stirred for 1 h at same temperature. Then reaction mixture was warmed to 0° C. and stirred for 1 h at 0° C. After completion of reaction, reaction mixture was transferred into water and washed with saturated Sodium bicarbonate. Product was extracted with dichloromethane. Organic layer was combined, washed with brine solution, dried over sodium sulphate and concentrated under reduced pressure to obtain crude material. This was further purified by column chromatography and the compound was eluted in 0.8% methanol in dichloromethane to obtain 84.3 (0.450 g, Yield: 34.48%; MS (ES): m/z 529.23 [M+H]$^+$).

Step 4—Synthesis of Compound 84.3a and 84.3b: Isomers of 84.3 (0.3 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 84.3a (0.093 g; MS (ES): m/z 529.23 [M+H]$^+$). FR-b was concentrated under reduced pressure at 30° C. to afford pure 84.3b (0.100 g; MS (ES): m/z 529.23 [M+H]$^+$).

Step 5—Synthesis of Compound 84.4: To a solution of 84.3a (0.093 g, 0.17 mmol, 1.0 eq), in tetrahydrofuran:methanol:water (4 mL, 2:1:1) was added lithium hydroxide (0.020 g, 0.85 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 84.4 (0.060 g, Yield: 68.13%; MS (ES): m/z 501.20 [M+H]$^+$).

Step 6—Synthesis of Compound 84.6: Compound was synthesized using general procedure A to obtain 84.6 (0.045 g, Yield: 65.90%). MS (ES): m/z 570.26 [M+H]$^+$).

Step 7—Synthesis of Compound I-939: A solution of 84.6 (0.045 g, 0.079 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-939 (0.025 g, Yield: 66.00%; MS (ES): m/z 480.31 [M+H]$^+$; LCMS purity: 98.00%; HPLC purity: 96.72%; CHIRAL HPLC: 47.44%, 49.20%; $^1$H NMR (DMSO-d$_6$, 400 MHZ): 9.32-9.31 (d, J=7.2 Hz, 1H), 8.72 (s, 1H), 8.61-8.59 (d, J=5.6 Hz, 1H), 8.30 (s, 1H), 8.27-8.26 (d, J=5.6 Hz, 1H), 8.08-8.06 (d, J=4.8 Hz, 1H), 7.24-7.20 (t, J=6.8 Hz, 1H), 6.68 (s, 1H), 5.55 (bs, 1H), 5.35 (bs, 1H), 4.59 (bs, 1H), 4.38 (bs, 2H), 3.90 (bs, 2H), 3.82-3.77 (t, J=11.2 Hz, 1H), 3.10-3.08 (t, J=4.8 Hz, 3H), 2.15-2.03 (m, 4H), 1.82 (bs, 1H), 1.24 (bs, 1H), 1.04-1.02 (d, J=6 Hz, 1H)).

Example 85: 5-(1-((3S,4R)-3-Fluorotetrahydro-2H-pyran-4-yl)-1H-pyrrolo[2,3-b]pyridin-3-yl)-N-((cis-1,2)-2-hydroxycyclobutyl)-7-(methylamino)pyrazolo[1,5-a]pyrimidine-3-carboxamide (I-592)

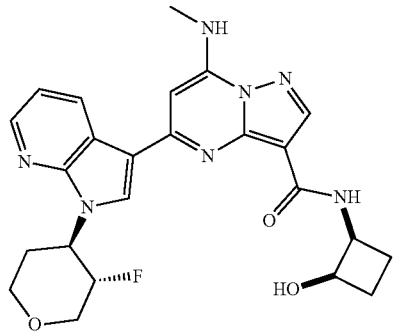

Scheme 85

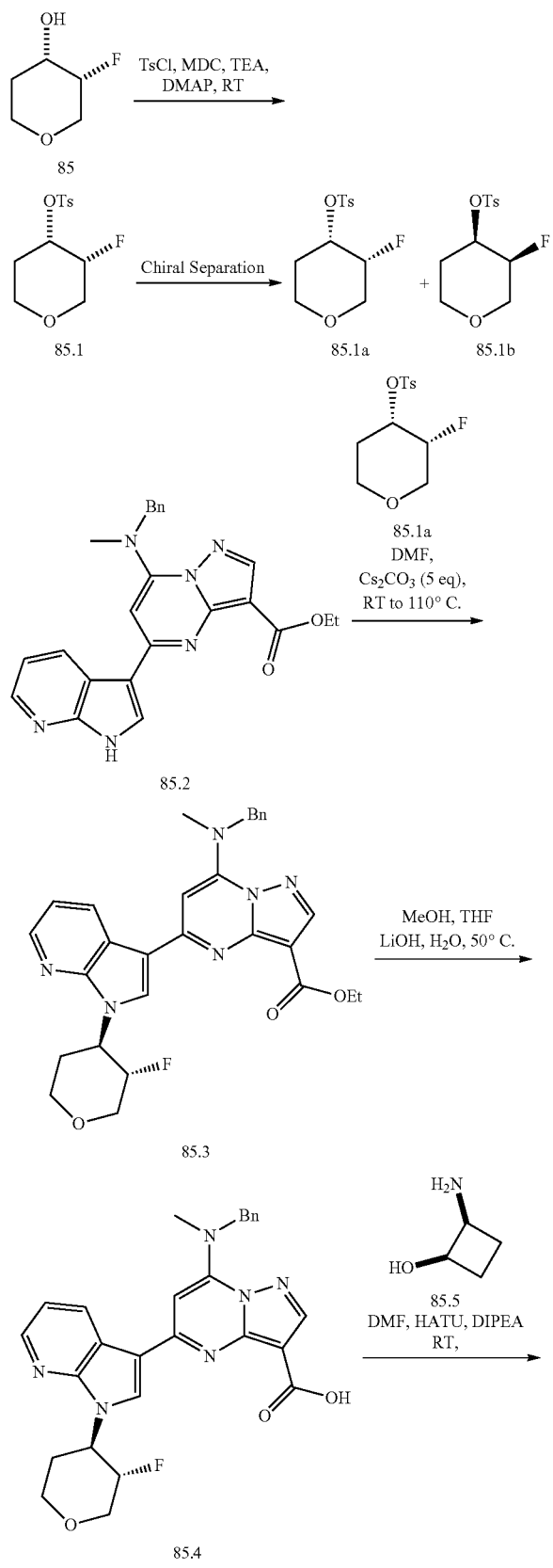

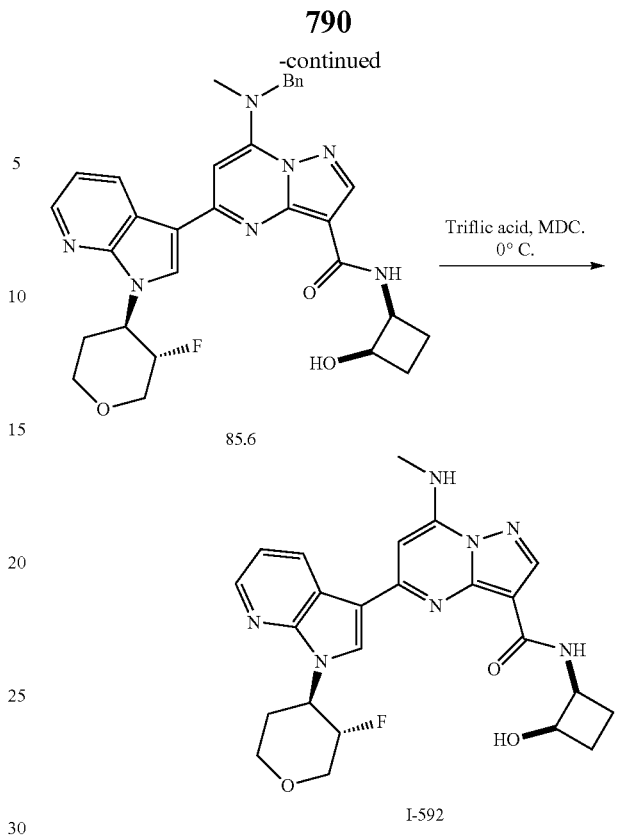

Step 1—Synthesis of Compound 85.1: To the solution of compound 85 (2.0 g, 16.66 mmol, 1.0 eq) in dichloromethane (20 mL) was added triethylamine (3.3 g, 33.32 mmol, 2.0 eq). After 10 min 4-Toluenesulfonyl chloride (3.4 g, 18.32 mmol, 1.1 eq) was added portion wise into reaction mixture at room temperature followed by 4-dimethylaminopyridine (0.203 g, 1.66 mmol, 0.1 eq) and reaction mixture was stirred at same temperature for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 12% ethyl acetate in hexane to obtain 85.1 (2.4 g, Yield: 52.55%; MS (ES): m/z 275.07 M+H]$^+$).

Step 2—Synthesis of Compound 85.1a and 85.1b: Isomers of 85.1 (0.6 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 85.1a (0.240 g; MS (ES): m/z 275.07 [M+H]$^+$). FR-b was concentrated under reduced pressure at 30° C. to afford pure 85.1b (0.252 g; MS (ES): m/z 275.07 [M+H]$^+$).

Step 3—Synthesis of Compound 85.2: Compound was synthesized as per experimental protocol of I-14/15 (Example 12) to obtain 85.2 (Yield: 83.54%; MS (ES): m/z 427.18 [M+H]$^+$).

Step 4—Synthesis of Compound 85.3: To a solution of 85.2 (0.150 g, 0.35 mmol, 1.0 eq), in dimethylformamide (3 mL) was added 85.1a (0.239 g, 0.87 mmol, 2.0 eq) and cesium carbonate (0.341 g, 1.05 mmol, 3.0 eq). The reaction mixture was stirred at 110° C. for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1% methanol in dichloromethane to obtain 85.3 (0.074 g, Yield: 39.80%; MS (ES): m/z 529.23 [M+H]⁺).

Step 5—Synthesis of Compound 85.4: To a solution of 85.3 (0.074 g, 0.14 mmol, 1.0 eq), in tetrahydrofuran:methanol:water (4 mL, 2:1:1) was added lithium hydroxide (0.016 g, 0.7 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 85.4 (0.060 g, Yield: 85.63%; MS (ES): m/z 501.20 [M+H]⁺).

Step 6—Synthesis of Compound 85.6: Compound was synthesized using general procedure A to obtain 85.6 (0.042 g, Yield: 61.51%). MS (ES): m/z 570.26 [M+H]⁺).

Step 7—Synthesis of Compound I-592: A solution of 85.6 (0.042 g, 0.073 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-592 (0.018 g, Yield: 50.91%; MS (ES): m/z 480.52 [M+H]⁺; LCMS purity: 98.21%; HPLC purity: 98.46%; CHIRAL HPLC: 45.33%, 46.62%; ¹H NMR (DMSO-d₆, 400 MHZ): 9.09-9.08 (d, J=6 Hz, 1H), 9.01 (bs, 1H), 8.63 (bs, 1H), 8.40-8.39 (d, J=4.4 Hz, 1H), 8.38 (bs, 1H), 8.29-8.27 (d, J=4.8 Hz, 1H), 7.35-7.32 (m, 1H), 6.77 (s, 1H), 5.54-5.53 (d, J=3.2 Hz, 1H), 4.61 (bs, 1H), 4.44 (bs, 2H), 4.15 (bs, 1H), 3.67-3.59 (t, J=7.6 Hz, 1H), 3.14-3.13 (d, J=4.4 Hz, 3H), 2.13-2.08 (m, 1H), 1.86 (bs, 1H), 1.56 (bs, 1H), 1.24 (bs, 3H), 0.90-0.87 (m, 3H)).

Example 86: N-((cis-1,2)-2-Hydroxycyclobutyl)-5-(7-((3S,4R)-3-methoxytetrahydro-2H-pyran-4-yl)-7H-pyrrolo[2,3-b]pyridin-3-yl)-7-(methylamino)pyrazolo[1,5-a]pyrimidine-3-carboxamide (I-868)

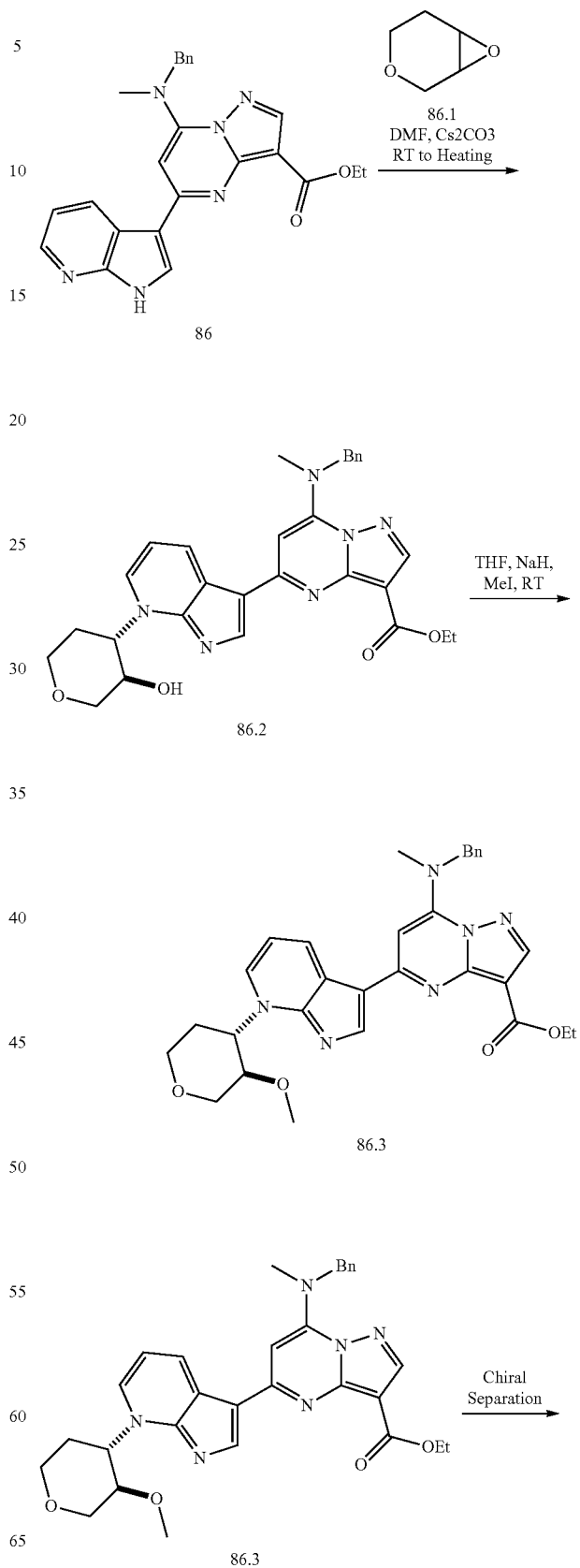

-continued

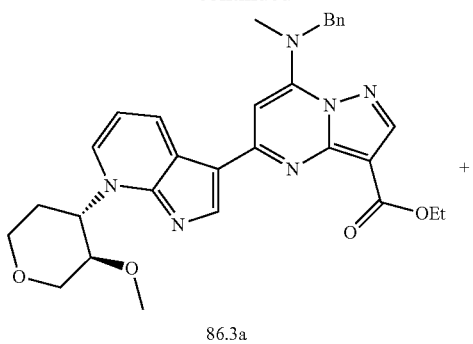
86.3a

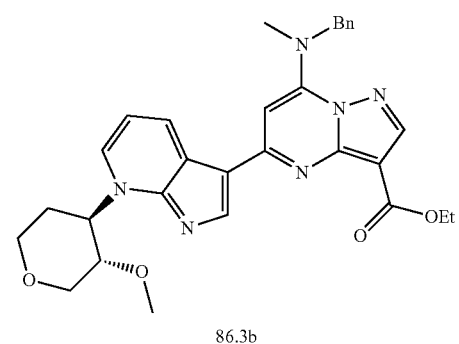
86.3b

MeOH, THF
LiOH, H₂O,
50° C.

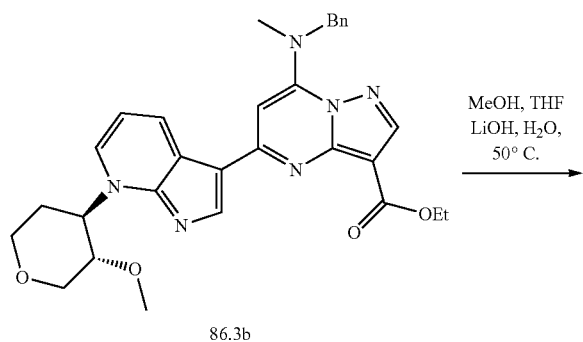
86.3b

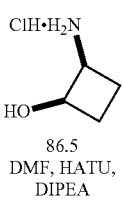
86.5
DMF, HATU,
DIPEA
RT,

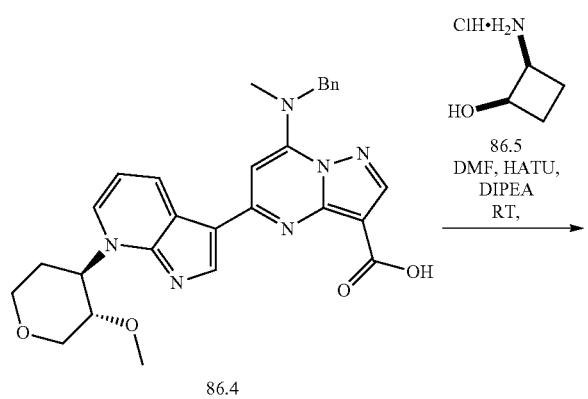
86.4

-continued

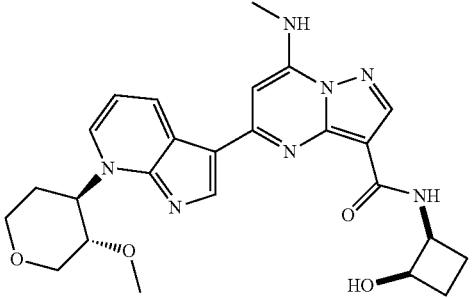
86.6

Triflic acid, MDC. 0° C.

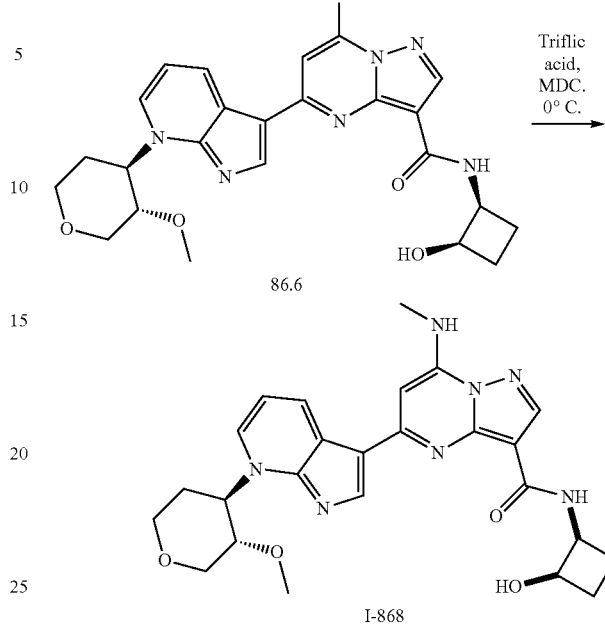
I-868

Step 1—Synthesis of Compound 86: Compound was synthesized as per experimental protocol of I-14/15 (Example 12) to obtain 86 (Yield: 83.54%; MS (ES): m/z 427.18 [M+H]⁺).

Step 2—Synthesis of Compound 86.2: To a solution of 86 (1.37 g, 3.21 mmol, 1.0 eq), in dimethylformamide (15 mL) was added 86.1 (0.481 g, 4.81 mmol, 1.5 eq) and cesium carbonate (3.1 g, 9.63 mmol, 3.0 eq). The reaction mixture was stirred at 110° C. for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1% methanol in dichloromethane to obtain 86.2 (1.05 g, Yield: 62.07%; MS (ES): m/z 527.24[M+H]⁺).

Step 3—Synthesis of Compound 86.3: To a solution of 86.2 (1.05 g, 1.99 mmol, 1.0 eq) in tetrahydrofuran (12 mL), was added sodium hydride (60%; 0.095 g, 3.98 mmol, 2.0 eq) at 0° C. and stirred for 20 min. Methyl iodide (0.310 g, 2.18 mmol, 1.1 eq) was added and reaction mixture was stirred at room temperature for 2 h. After completion of reaction, reaction mixture was transferred into ice, stirred and extracted with ethyl acetate. Organic layer was combined, dried over sodium sulphate and concentrated under reduced pressure to obtain crude material. This was further purified by column chromatography and the compound was eluted in 0.6% methanol in dichloromethane to obtain 86.3 (1.0 g, Yield: 92.77%; MS (ES): m/z 541.25 [M+H]⁺).

Step 4—Synthesis of Compound 86.3a and 86.3b: Isomers of 86.3 (1.0 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 86.3a (0.410 g). MS (ES): m/z 541.25 [M+H]⁺. FR-b was concentrated under reduced pressure at 30° C. to afford pure 86.3b (0.400 g; MS (ES): m/z 541.25 [M+H]⁺).

Step 5—Synthesis of Compound 86.4: To a solution of 86.3b (0.410 g, 0.75 mmol, 1.0 eq), in tetrahydrofuran:methanol:water (6 mL, 2:1:1) was added lithium hydroxide (0.090 g, 3.75 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 86.4 (0.340 g, Yield: 87.47%; MS (ES): m/z 513.22 [M+H]$^+$).

Step 6—Synthesis of Compound 86.6: Compound was synthesized using general procedure A to obtain 86.6. (0.150 g, Yield: 77.75%; MS (ES): m/z 582.28 [M+H]$^+$).

Step 7—Synthesis of Compound I-868: A solution of 86.2 (0.050 g, 0.086 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-868 (0.025 g, Yield: 59.17%; MS (ES): m/z 492.44 [M+H]$^+$; LCMS purity: 97.09%; HPLC purity: 94.95%; CHIRAL HPLC: 50.67%, 47.66%; $^1$H NMR (DMSO-d$_6$, 400 MHZ): 9.31-9.29 (d, J=7.2 Hz, 1H), 8.71 (bs, 1H), 8.61-8.59 (d, J=8.4 Hz, 1H), 8.49-8.48 (d, J=6 Hz, 1H), 8.31 (s, 1H), 8.07-8.06 (d, J=4.8 Hz, 1H), 7.27-7.24 (t, J=6.8 Hz, 1H), 6.68 (s, 1H), 5.57-5.56 (d, J=4 Hz, 1H), 5.46 (bs, 1H), 4.63 (bs, 1H), 4.44 (bs, 2H), 3.97 (bs, 3H), 3.52-3.45 (t, J=12.4 Hz, 1H), 3.10-3.09 (d, J=4.8 Hz, 3H), 2.22 (bs, 1H), 2.15-2.10 (m, 1H), 2.06-2.00 (m, 2H), 1.84 (bs, 1H), 1.56 (bs, 1H), 1.24 (bs, 2H), 0.90-0.87 (m, 1H)).

Example 87: 5-(1-((3S,4S)-4-Fluorotetrahydrofuran-3-yl)-1H-pyrrolo[2,3-b]pyridin-3-yl)-N-((trans-1,2)-2-methoxycyclobutyl)-7-(methylamino)pyrazolo[1,5-a]pyrimidine-3-carboxamide (I-624)

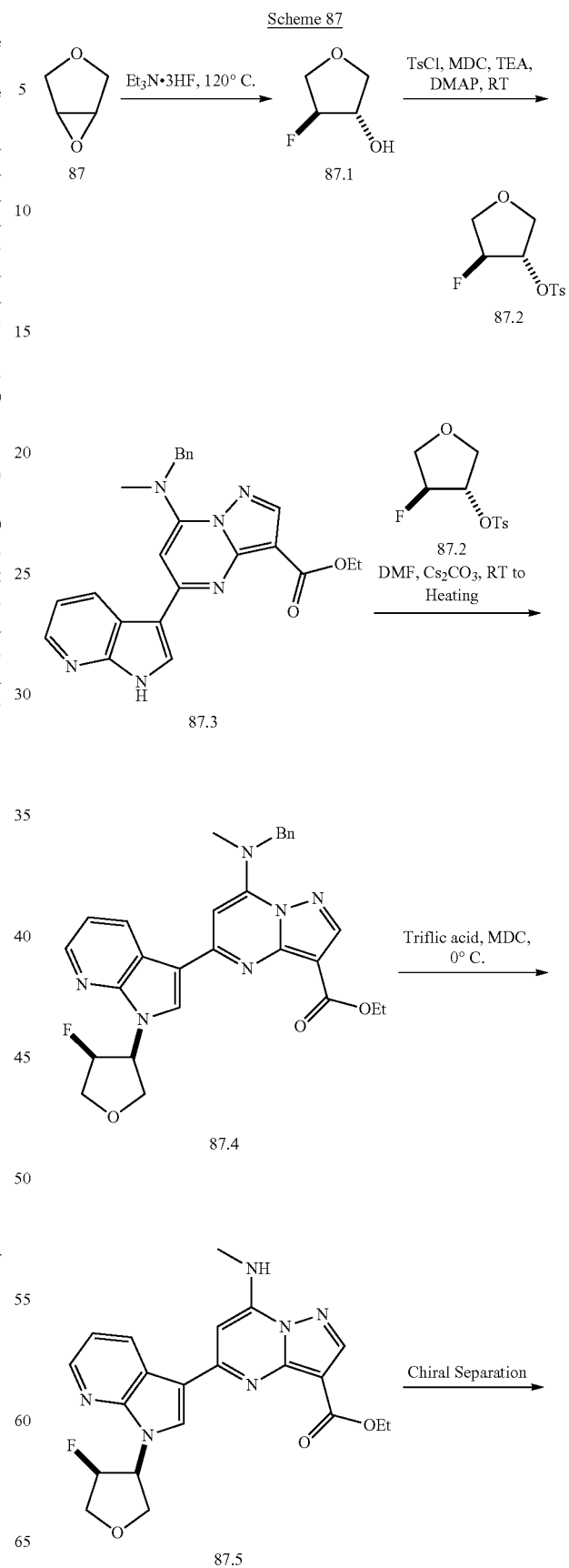

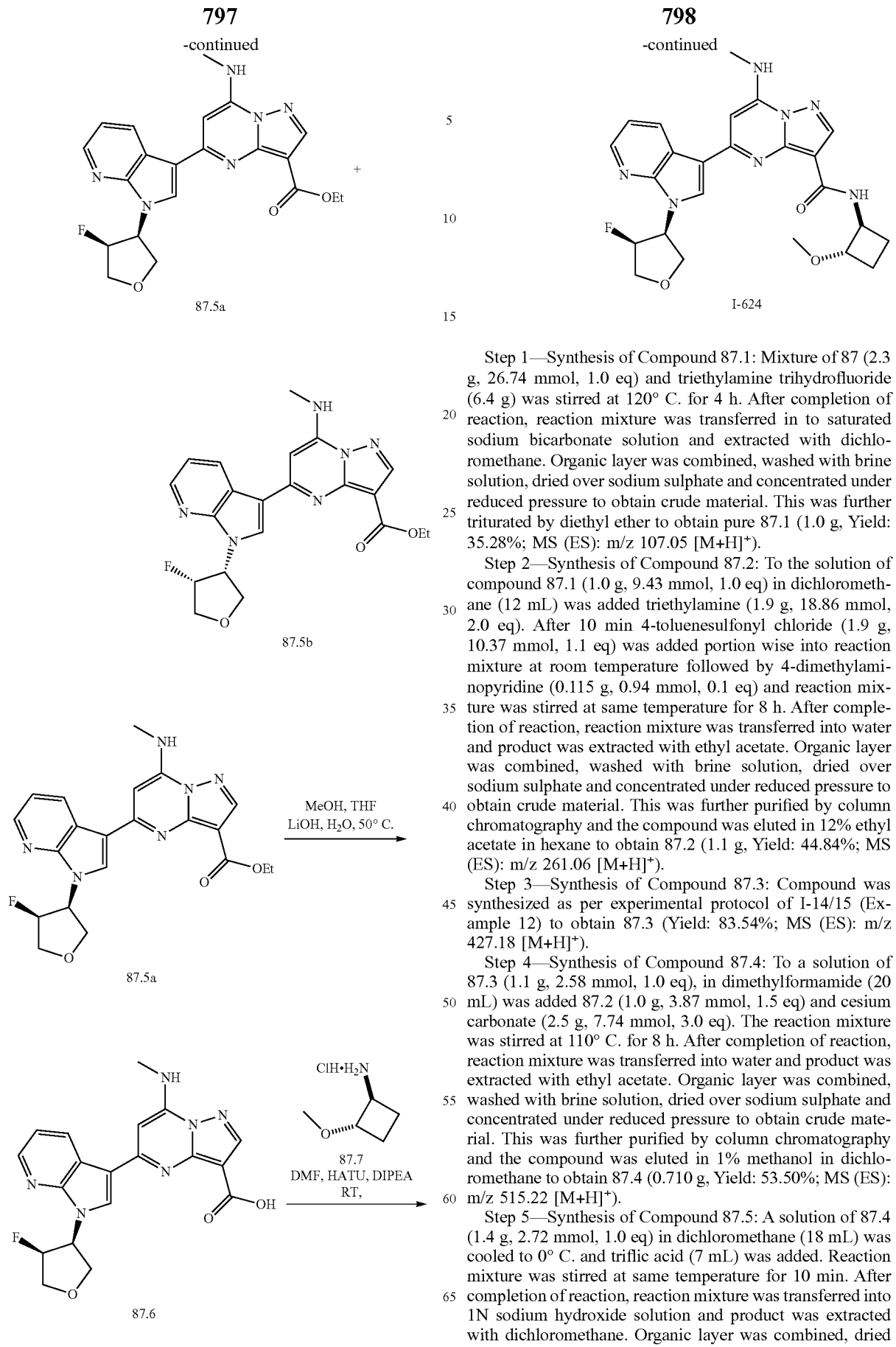

Step 1—Synthesis of Compound 87.1: Mixture of 87 (2.3 g, 26.74 mmol, 1.0 eq) and triethylamine trihydrofluoride (6.4 g) was stirred at 120° C. for 4 h. After completion of reaction, reaction mixture was transferred in to saturated sodium bicarbonate solution and extracted with dichloromethane. Organic layer was combined, washed with brine solution, dried over sodium sulphate and concentrated under reduced pressure to obtain crude material. This was further triturated by diethyl ether to obtain pure 87.1 (1.0 g, Yield: 35.28%; MS (ES): m/z 107.05 [M+H]$^+$).

Step 2—Synthesis of Compound 87.2: To the solution of compound 87.1 (1.0 g, 9.43 mmol, 1.0 eq) in dichloromethane (12 mL) was added triethylamine (1.9 g, 18.86 mmol, 2.0 eq). After 10 min 4-toluenesulfonyl chloride (1.9 g, 10.37 mmol, 1.1 eq) was added portion wise into reaction mixture at room temperature followed by 4-dimethylaminopyridine (0.115 g, 0.94 mmol, 0.1 eq) and reaction mixture was stirred at same temperature for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 12% ethyl acetate in hexane to obtain 87.2 (1.1 g, Yield: 44.84%; MS (ES): m/z 261.06 [M+H]$^+$).

Step 3—Synthesis of Compound 87.3: Compound was synthesized as per experimental protocol of I-14/15 (Example 12) to obtain 87.3 (Yield: 83.54%; MS (ES): m/z 427.18 [M+H]$^+$).

Step 4—Synthesis of Compound 87.4: To a solution of 87.3 (1.1 g, 2.58 mmol, 1.0 eq), in dimethylformamide (20 mL) was added 87.2 (1.0 g, 3.87 mmol, 1.5 eq) and cesium carbonate (2.5 g, 7.74 mmol, 3.0 eq). The reaction mixture was stirred at 110° C. for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1% methanol in dichloromethane to obtain 87.4 (0.710 g, Yield: 53.50%; MS (ES): m/z 515.22 [M+H]$^+$).

Step 5—Synthesis of Compound 87.5: A solution of 87.4 (1.4 g, 2.72 mmol, 1.0 eq) in dichloromethane (18 mL) was cooled to 0° C. and triflic acid (7 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain 87.5 (1.0 g, Yield: 86.60%; MS (ES): m/z 425.17 [M+H]⁺).

Step 6—Synthesis of Compounds 87.5a and 87.5b: Isomers of 87.5 (1.0 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 87.5a (0.280 g; MS (ES): m/z 425.17 [M+H]⁺). FR-b was concentrated under reduced pressure at 30° C. to afford pure 87.5b (0.280 g; MS (ES): m/z 425.17 [M+H]⁺).

Step 7—Synthesis of Compound 87.6: To a solution of 87.5a (0.280 g, 0.66 mmol, 1.0 eq), in tetrahydrofuran:methanol:water (6 mL, 2:1:1) was added lithium hydroxide (0.079 g, 3.3 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 87.6 (0.240 g, Yield: 91.78%; MS (ES): m/z 397.14 [M+H]⁺).

Step 8—Synthesis of Compound I-624: Compound was synthesized using general procedure A to obtain I-624 (0.110 g, Yield: 75.77%; MS (ES): m/z 480.72 [M+H]⁺; LCMS purity: 97.34%; HPLC purity: 98.01%; CHIRAL HPLC: 51.85%, 48.15%; ¹H NMR (DMSO-d₆, 400 MHZ): 8.84-8.82 (d, J=8 Hz, 1H), 8.79 (s, 1H), 8.53-8.50 (dd, J=4 Hz & 8.8 Hz, 1H), 8.47-8.46 (d, J=4 Hz, 1H), 8.39 (s, 1H), 8.30-8.28 (d, J=5.2 Hz, 1H), 7.40-7.37 (t, J=4.8 Hz, 1H), 6.85 (s, 1H), 5.87-5.77 (m, 1H), 5.59-5.45 (m, 1H), 4.51-4.36 (m, 3H), 4.32-4.19 (m, 2H), 3.86-3.80 (m, 1H), 3.25-3.23 (m, 3H), 3.13-3.12 (d, J=4.8 Hz, 3H), 2.22-2.13 (m, 2H), 1.60-1.48 (m, 2H)).

Example 88: 5-(1-((3S,4S)-4-Fluoro-1-methylpyrrolidin-3-yl)-1H-pyrrolo[2,3-b]pyridin-3-yl)-N-((trans-1,2)-2-methoxycyclobutyl)-7-(methylamino)pyrazolo[1,5-a]pyrimidine-3-carboxamide (I-639)

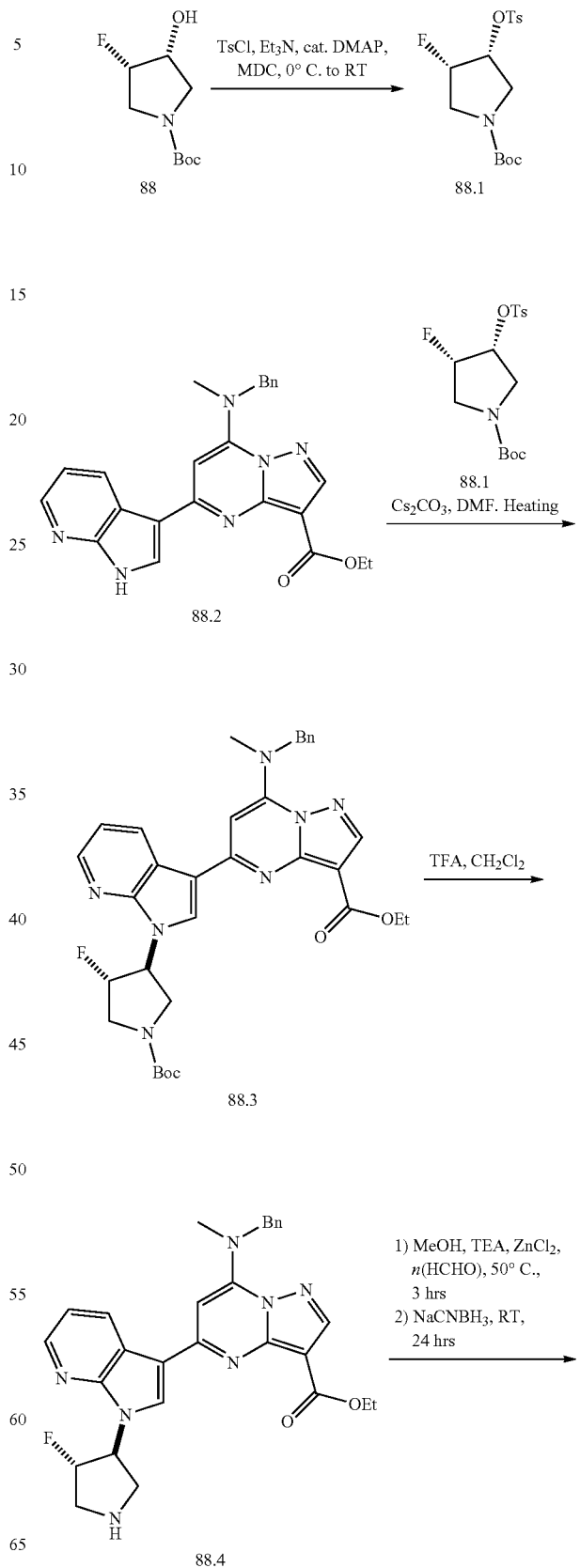

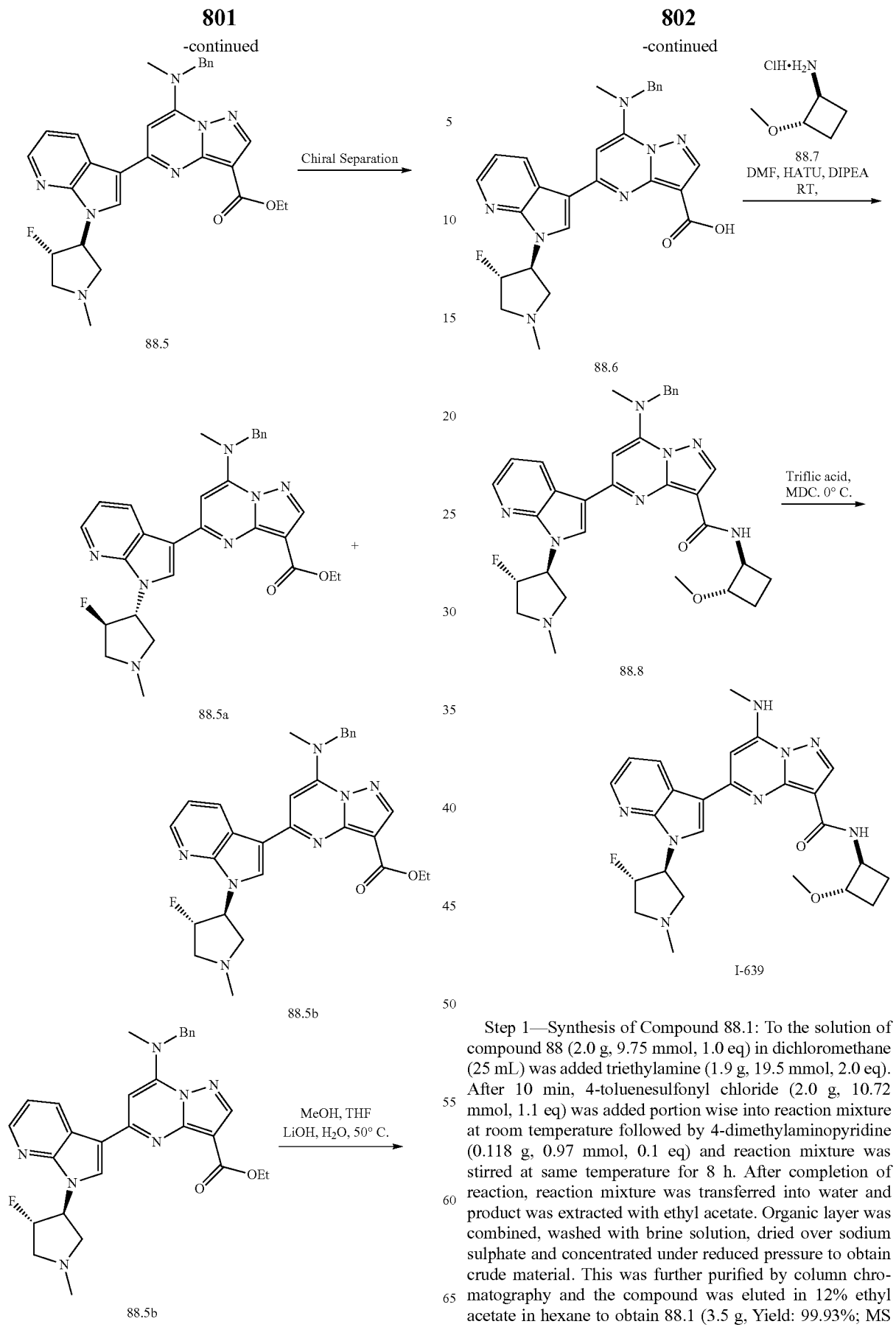

Step 1—Synthesis of Compound 88.1: To the solution of compound 88 (2.0 g, 9.75 mmol, 1.0 eq) in dichloromethane (25 mL) was added triethylamine (1.9 g, 19.5 mmol, 2.0 eq). After 10 min, 4-toluenesulfonyl chloride (2.0 g, 10.72 mmol, 1.1 eq) was added portion wise into reaction mixture at room temperature followed by 4-dimethylaminopyridine (0.118 g, 0.97 mmol, 0.1 eq) and reaction mixture was stirred at same temperature for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 12% ethyl acetate in hexane to obtain 88.1 (3.5 g, Yield: 99.93%; MS (ES): m/z 360.12 [M+H]$^+$).

Step 2—Synthesis of Compound 88.2: Compound was synthesized as per experimental protocol of I-14/15 (Example 12) to obtain 88.2. (Yield: 83.54%; MS (ES): m/z 427.18 [M+H]⁺).

Step 3—Synthesis of Compound 88.3: To a solution of 88.2 (2 g, 4.69 mmol, 1.0 eq), in dimethylformamide (20 mL) was added 88.1 (2.5 g, 7.03 mmol, 1.5 eq) and cesium carbonate (4.5 g, 14.07 mmol, 3.0 eq). The reaction mixture was stirred at 110° C. for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1% methanol in dichloromethane to obtain 88.3 (0.710 g, Yield: 24.67%; MS (ES): m/z 614.28 [M+H]⁺).

Step 4—Synthesis of Compound 88.4: Compound was synthesized using general procedure C to obtain 88.4 (0.488 g, Yield: 98.85%; MS (ES): m/z 514.23 [M+H]⁺).

Step 5—Synthesis of Compound 88.5: To a solution of compound 88.4 (0.548 g, 1.06 mmol, 1.0 eq) in methanol (8 mL), was added paraformaldehyde (0.159 g, 5.3 mmol, 5.0 eq) at room temperature. Triethylamine (0.321 g, 3.18 mmol, 3.0 eq) and anhydrous zinc chloride (0.015 g, 0.10 mmol, 0.1 eq) were added to the reaction mixture and stirred at 50° C. for 2 h. Reaction mixture was cooled to 0° C. then sodium cyanoborohydride (0.2 g, 3.18 mmol, 3.0 eq) was added portion wise to the reaction mixture and stirred reaction mixture at room temperature for 24 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.0% methanol in dichloromethane to obtain 88.5. (0.460 g, Yield: 81.71%; MS (ES): m/z 528.25 [M+H]⁺).

Step 6—Synthesis of Compounds 88.5a and 88.5b: Isomers of 88.5 (0.460 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 87.5a (0.180 g; MS (ES): m/z 528.25 [M+H]⁺). FR-b was concentrated under reduced pressure at 30° C. to afford pure 88.5b (0.180 g; MS (ES): m/z 528.25 [M+H]⁺).

Step 7—Synthesis of Compound 88.6: To a solution of 88.5b (0.180 g, 0.34 mmol, 1.0 eq), in tetrahydrofuran:methanol:water (4 mL, 2:1:1) was added lithium hydroxide (0.040 g, 1.7 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 88.6 (0.160 g, Yield: 93.88%; MS (ES): m/z 500.2 [M+H]⁺).

Step 8—Synthesis of Compound 87.8: Compound was synthesized using general procedure A to obtain 88.8 (0.140 g, Yield: 75.02%; MS (ES): m/z 583.29 [M+H]⁺).

Step 9—Synthesis of Compound I-639: A solution of 88.8 (0.040 g, 0.068 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-639 (0.021 g, Yield: 62.11%; MS (ES): m/z 493.44 [M+H]⁺; LCMS purity: 97.79%; HPLC purity: 96.41%; CHIRAL HPLC: 49.52%; 49.10%; ¹H NMR (DMSO-d₆, 400 MHZ): 8.80-8.78 (d, J=8 Hz, 1H), 8.70 (s, 1H), 8.52-8.50 (d, J=8.8 Hz, 1H), 8.46-8.45 (d, J=3.2 Hz, 1H), 8.39 (s, 1H), 8.34-8.33 (d, J=5.2 Hz, 1H), 7.38-7.35 (m, 1H), 6.74 (s, 1H), 5.51-5.49 (m, 1H), 4.42-4.38 (t, J=8.4 Hz, 1H), 3.82 (bs, 1H), 3.24 (s, 3H), 3.14-3.12 (d, J=4.8 Hz, 3H), 2.43 (bs, 3H), 2.21-2.12 (m, 2H), 1.55 (bs, 4H), 1.24 (bs, 2H), 0.90-0.87 (m, 1H)).

Example 89: N-((trans-1,2)-2-methoxycyclobutyl)-5-(7-((3R,4S)-3-methoxytetrahydro-2H-pyran-4-yl)-7H-pyrrolo[2,3-b]pyridin-3-yl)-7-(methylamino)pyrazolo[1,5-a]pyrimidine-3-carboxamide (I-892)

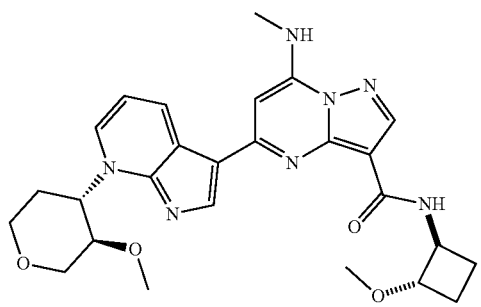

I-892

Scheme 89

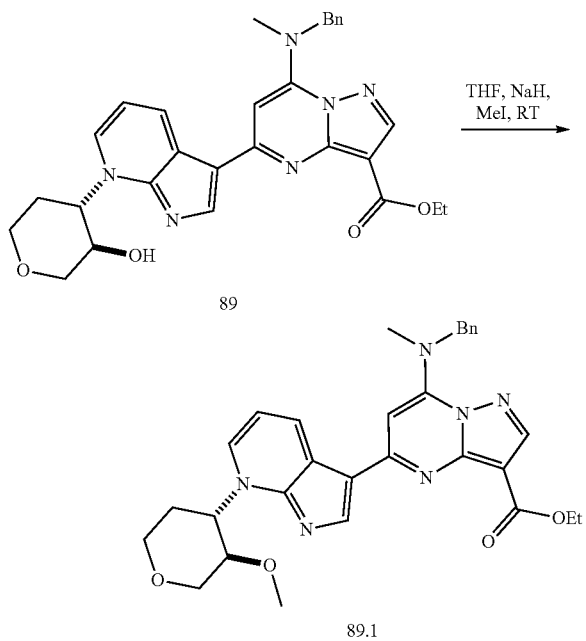

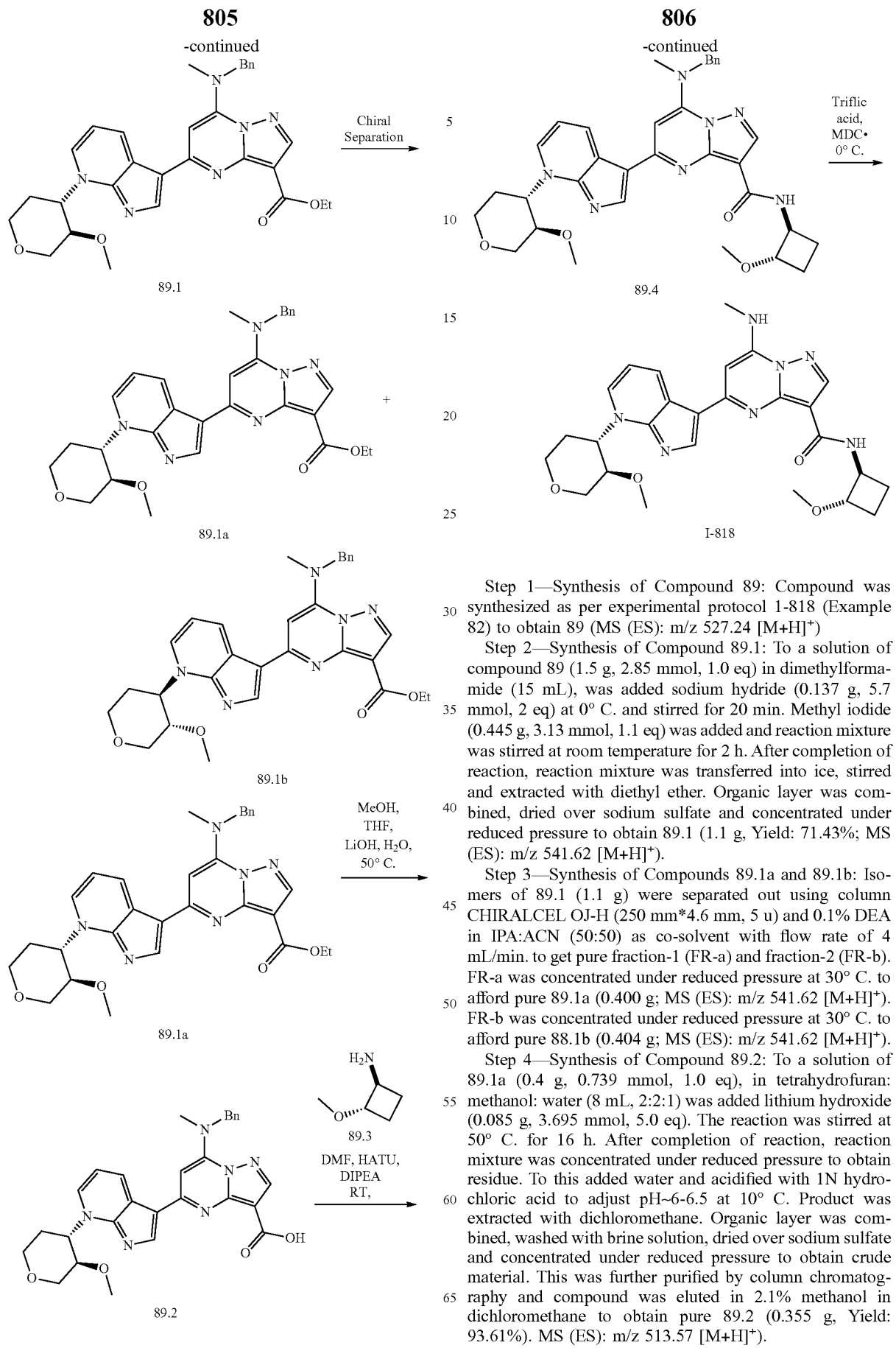

Step 1—Synthesis of Compound 89: Compound was synthesized as per experimental protocol I-818 (Example 82) to obtain 89 (MS (ES): m/z 527.24 [M+H]$^+$)

Step 2—Synthesis of Compound 89.1: To a solution of compound 89 (1.5 g, 2.85 mmol, 1.0 eq) in dimethylformamide (15 mL), was added sodium hydride (0.137 g, 5.7 mmol, 2 eq) at 0° C. and stirred for 20 min. Methyl iodide (0.445 g, 3.13 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain 89.1 (1.1 g, Yield: 71.43%; MS (ES): m/z 541.62 [M+H]$^+$).

Step 3—Synthesis of Compounds 89.1a and 89.1b: Isomers of 89.1 (1.1 g) were separated out using column CHIRALCEL OJ-H (250 mm*4.6 mm, 5 u) and 0.1% DEA in IPA:ACN (50:50) as co-solvent with flow rate of 4 mL/min. to get pure fraction-1 (FR-a) and fraction-2 (FR-b). FR-a was concentrated under reduced pressure at 30° C. to afford pure 89.1a (0.400 g; MS (ES): m/z 541.62 [M+H]$^+$). FR-b was concentrated under reduced pressure at 30° C. to afford pure 88.1b (0.404 g; MS (ES): m/z 541.62 [M+H]$^+$).

Step 4—Synthesis of Compound 89.2: To a solution of 89.1a (0.4 g, 0.739 mmol, 1.0 eq), in tetrahydrofuran: methanol: water (8 mL, 2:2:1) was added lithium hydroxide (0.085 g, 3.695 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 89.2 (0.355 g, Yield: 93.61%). MS (ES): m/z 513.57 [M+H]$^+$).

Step 5—Synthesis of Compound 89.4: Compound was synthesized using general procedure A to obtain 89.4. (0.050 g, Yield: 86.04%; MS (ES): m/z 596.70 [M+H]$^+$)

Step 6—Synthesis of Compound I-892: A solution of 89.4 (0.050 g, 0.084 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain I-892 (0.025 g, Yield: 58.91%; MS (ES): m/z 506.35 [M+H]$^+$; LCMS purity: 98.04%; HPLC purity: 97.69%; CHIRAL HPLC: 48.89%, 47.68%; $^1$H NMR (DMSO-d$_6$, 400 MHZ): 8.97-8.95 (d, J=7.6 Hz, 1H), 8.67 (s, 1H), 8.57-8.52 (m, 2H), 8.34 (s, 1H), 8.14-8.13 (d, J=4.8 Hz, 1H), 7.33-7.29 (t, J=7.2 Hz, 1H), 6.69 (s, 1H), 5.47 (bs, 1H), 4.49-4.39 (m, 2H), 4.09-4.01 (m, 3H), 3.88-3.82 (m, 1H), 3.67-3.61 (t, J=12 Hz, 1H), 3.26 (s, 3H), 3.15 (s, 3H), 3.11-3.10 (d, J=4.8 Hz, 3H), 2.42-2.35 (m, 2H), 2.27-2.15 (m, 2H), 1.67-1.56 (m, 2H)).

Example 90: N-((trans-1,2)-2-Methoxycyclobutyl)-5-(1-((3S,4S)-3-methoxytetrahydro-2H-pyran-4-yl)-1H-pyrrolo[2,3-b]pyridin-3-yl)-7-(methylamino)pyrazolo[1,5-a]pyrimidine-3-carboxamide (I-665)

I-665

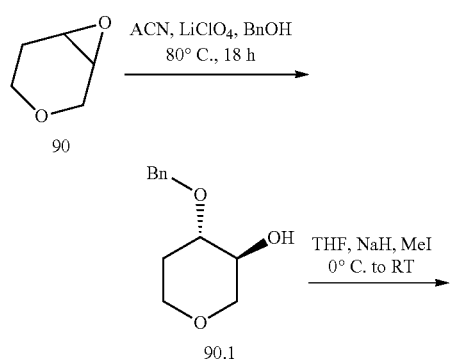

Scheme 90

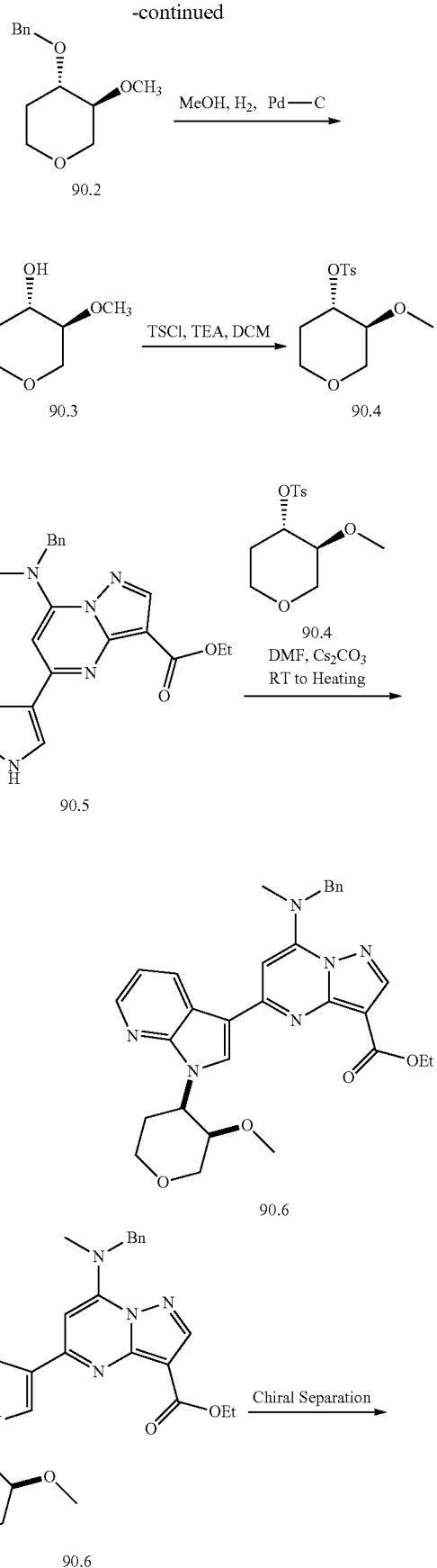

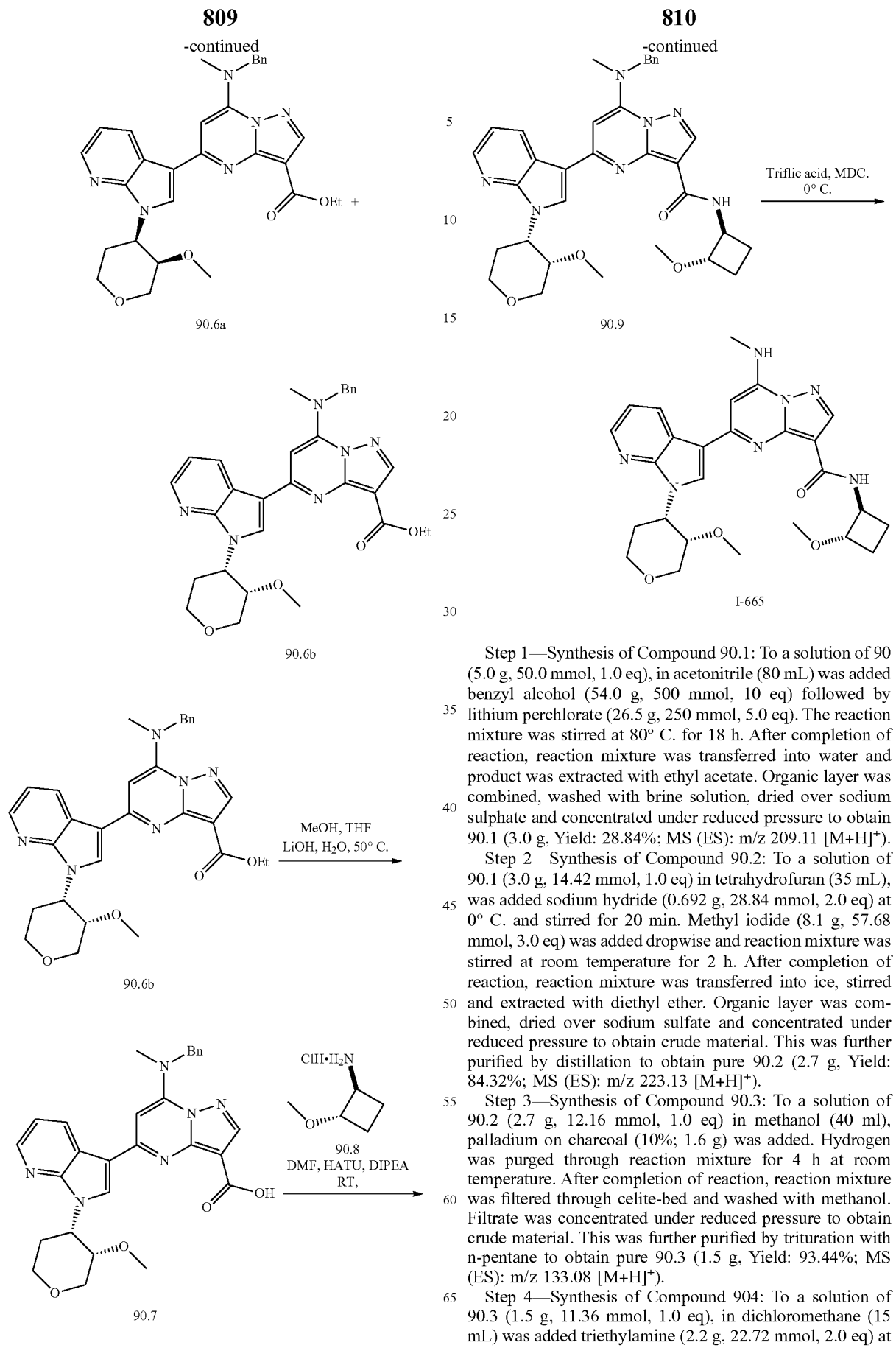

Step 1—Synthesis of Compound 90.1: To a solution of 90 (5.0 g, 50.0 mmol, 1.0 eq), in acetonitrile (80 mL) was added benzyl alcohol (54.0 g, 500 mmol, 10 eq) followed by lithium perchlorate (26.5 g, 250 mmol, 5.0 eq). The reaction mixture was stirred at 80° C. for 18 h. After completion of reaction, reaction mixture was transferred into water and product was extracted with ethyl acetate. Organic layer was combined, washed with brine solution, dried over sodium sulphate and concentrated under reduced pressure to obtain 90.1 (3.0 g, Yield: 28.84%; MS (ES): m/z 209.11 [M+H]$^+$).

Step 2—Synthesis of Compound 90.2: To a solution of 90.1 (3.0 g, 14.42 mmol, 1.0 eq) in tetrahydrofuran (35 mL), was added sodium hydride (0.692 g, 28.84 mmol, 2.0 eq) at 0° C. and stirred for 20 min. Methyl iodide (8.1 g, 57.68 mmol, 3.0 eq) was added dropwise and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 90.2 (2.7 g, Yield: 84.32%; MS (ES): m/z 223.13 [M+H]$^+$).

Step 3—Synthesis of Compound 90.3: To a solution of 90.2 (2.7 g, 12.16 mmol, 1.0 eq) in methanol (40 ml), palladium on charcoal (10%; 1.6 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure 90.3 (1.5 g, Yield: 93.44%; MS (ES): m/z 133.08 [M+H]$^+$).

Step 4—Synthesis of Compound 904: To a solution of 90.3 (1.5 g, 11.36 mmol, 1.0 eq), in dichloromethane (15 mL) was added triethylamine (2.2 g, 22.72 mmol, 2.0 eq) at 0° C. At same temperature 4-Toluenesulfonyl chloride (2.3 g, 12.49 mmol, 1.1 eq) was added portionwise into reaction mixture and stirred at room temperature for 4 h. After completion of reaction, reaction mixture was transferred into water and product was extracted with dichloromethane. Organic layer was combined, washed with brine solution, dried over sodium sulfate and concentrated under reduced pressure to obtain 90.4 (2.1 g, Yield: 64.62%; MS (ES): m/z 287.09 [M+H]$^+$).

Step 5—Synthesis of Compound 90.5: Compound was synthesized as per experimental protocol of I-14/15 (Example 12) to obtain 90.5 (Yield: 83.54%; MS (ES): m/z 427.18 [M+H]$^+$).

Step 6—Synthesis of Compound 90.6: To a solution of 90.5 (1.0 g, 2.34 mmol, 1.0 eq), in dimethylformamide (15 mL) was added 90.4 (1.3 g, 4.68 mmol, 2.0 eq) and cesium carbonate (2.2 g, 7.02 mmol, 3.0 eq). The reaction mixture was stirred at 110° C. for 8 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 1% methanol in dichloromethane to obtain 90.6 (0.850 g, Yield: 67.05%; MS (ES): m/z 541.25 [M+H]$^+$).

Step 7—Synthesis of Compounds 90.6a and 90.6b: Isomers of 90.6 (0.850 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 90.6a (0.380 g; MS (ES): m/z 541.25 [M+H]$^+$). FR-b was concentrated under reduced pressure at 30° C. to afford pure 89.6b (0.380 g; MS (ES): m/z 541.25 [M+H]$^+$).

Step 8—Synthesis of Compound 90.7: To a solution of 90.6b (0.380 g, 0.70 mmol, 1.0 eq), in tetrahydrofuran:methanol:water (5 mL, 2:1:1) was added lithium hydroxide (0.084 g, 3.5 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 90.7 (0.337 g, Yield: 93.54%; MS (ES): m/z 513.22 [M+H]$^+$).

Step 9—Synthesis of Compound 90.9: Compound was synthesized using general procedure A to obtain 90.9. (0.150 g, Yield: 77.75%; MS (ES): m/z 596.29 [M+H]$^+$).

Step 10—Synthesis of Compound I-665: A solution of 90.9 (0.050 g, 0.084 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain I-665 (0.025 g, Yield: 59.17%; MS (ES): m/z 506.52 [M+H]$^+$; LCMS purity: 100%; HPLC purity: 96.21%; CHIRAL HPLC: 49.67%, 48.14%; $^1$H NMR (DMSO-d$_6$, 400 MHZ): 8.80-8.78 (d, J=7.6 Hz, 1H), 8.76 (bs, 1H), 8.53 (bs, 1H), 8.41-8.40 (d, J=4 Hz, 1H), 8.36 (bs, 1H), 8.24-8.22 (d, J=5.2 Hz, 1H), 7.33-7.27 (m, 1H), 6.85 (s, 1H), 5.22 (bs, 1H), 4.42-4.38 (t, J=8.4 Hz, 1H), 4.18-4.08 (m, 1H), 4.06 (bs, 1H), 3.84-3.80 (m, 2H), 3.71-3.66 (t, J=10.8 Hz, 1H), 3.56 (bs, 2H), 3.22 (s, 3H), 3.12-3.11 (d, J=4.4 Hz, 3H), 3.06 (bs, 3H), 2.16-2.12 (m, 2H), 1.78 (bs, 1H), 1.59-1.49 (m, 2H)).

Example 91: 5-(1-((R)-2,2-Difluorocyclopropyl)-1H-pyrrolo[2,3-b]pyridin-3-yl)-N-((cis-3,4)-4-hydroxytetrahydrofuran-3-yl)-7-(methylamino)pyrazolo[1,5-a]pyrimidine-3-carboxamide (I-708)

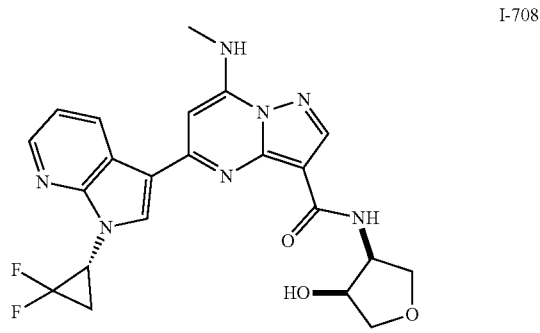

I-708

Scheme 91

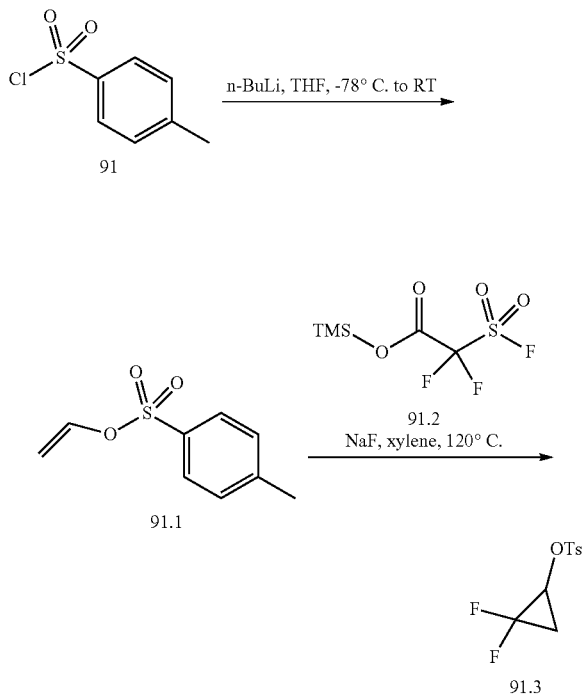

-continued
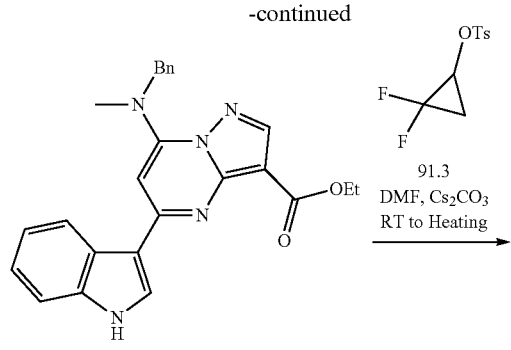
91.4
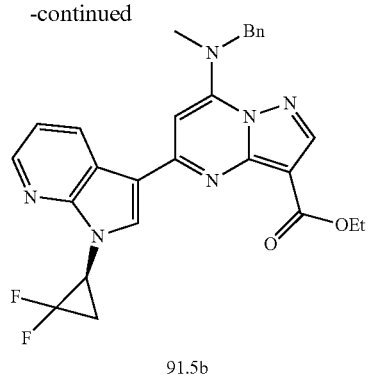
91.5b
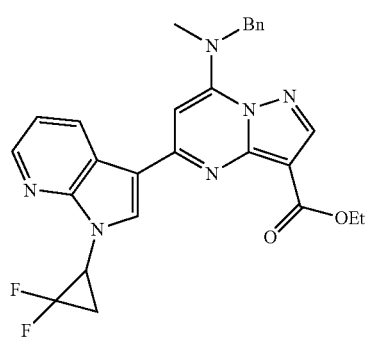
91.5
91.5a
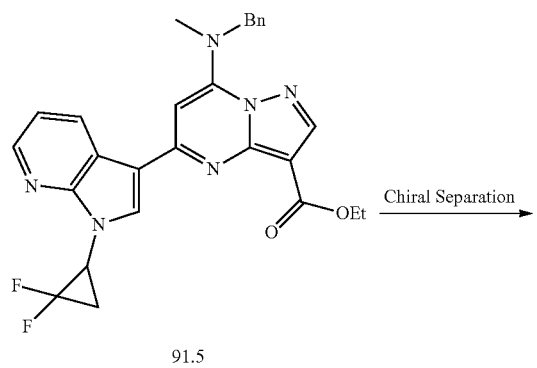
91.5
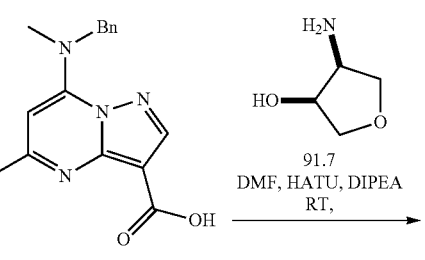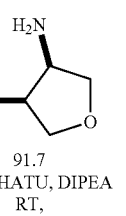
91.6
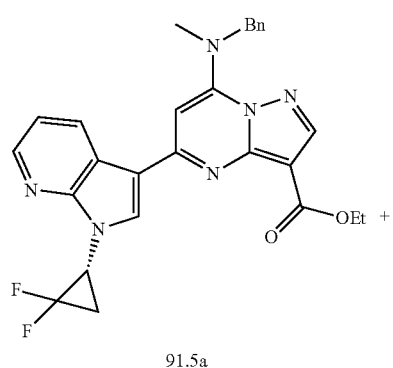
91.5a
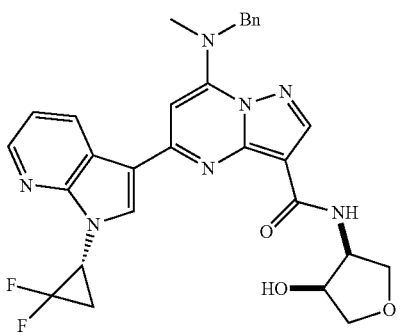
91.8

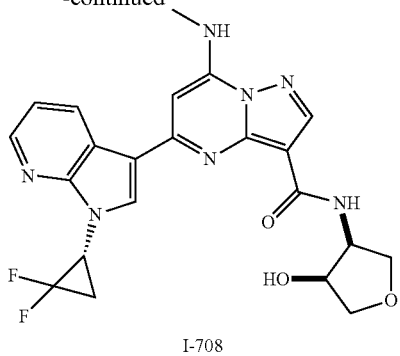

I-708

Step 1—Synthesis of Compound 91.1: To a stirred solution of 91 (20.0 g, 105.26 mmol, 1.0 eq) in dry tetrahydrofuran (160 mL) was added n-butyllithium (127 mL, 2.5M in hexane, 315.78 mmol, 3.0 eq) at −70° C. under argon dropwise over 20 mins. The reaction mixture was allowed to warm to −25° C. over 40 min, stirred for 1 h at room temperature. After completion of reaction, reaction mixture was quenched by slow addition of cold water and the product was extracted with ethyl acetate. The combined organic phase was dried over sodium sulfate and concentrated under reduced pressure to obtain crude material. This was further purified by column chromatography and compound was eluted in 4% ethyl acetate in hexane to obtain pure 91.1 (4.5 g, Yield: 21.64%; MS (ES): m/z 199.04 [M+H]$^+$).

Step 2—Synthesis of Compound 91.3: To a solution of 91.1 (4.5 g, 22.72 mmol, 1.0 eq), in xylene (2.2 mL) was added Sodium fluoride (0.095 g, 2.27 mmol, 0.1 eq) and heated up to 120° C. After 1 h 91.2 (26.8 mL, 136.32 mmol, 6.0 eq) was added dropwise to the reaction mixture and reaction mixture stirred at 120° C. for 16 h. After completion of reaction, reaction mixture was diluted with ethyl acetate and concentrated under reduced pressure to obtain crude material. This was further purified by column chromatography and the compound was eluted in 2% ethyl acetate in hexane to obtain 91.3 (1.92 g, Yield: 34.07%; MS (ES): m/z 248.03 [M+H]$^+$).

Step 3—Synthesis of Compound 91.4: Compound was synthesized as per experimental protocol of I-14/15 (Example 12) to obtain 91.4 (Yield: 83.64%; MS (ES): m/z 427.18 [M+H]$^+$).

Step 4—Synthesis of Compound 91.5: To a solution of 91.4 (1.0 g, 2.34 mmol, 1.0 eq), in dimethylformamide (15 mL) was added 91.3 (0.754 g, 3.04 mmol, 1.5 eq) and cesium carbonate (2.2 g, 7.02 mmol, 3.0 eq). The reaction mixture was stirred at 80° C. for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1% methanol in dichloromethane to obtain 90.5 (0.5 g, Yield: 42.43%; MS (ES): m/z 503.20 [M+H]$^+$).

Step 5—Synthesis of Compounds 91.5a and 91.5b: Isomers of 91.5 (0.5 g) were separated out using column CHIRALCEL OJ-H (250 mm*4.6 mm, 5 u) and 0.1% DEA in methanol as co-solvent with flow rate of 4 mL/min. to get pure fraction-1 (FR-a) and fraction-2 (FR-b). FR-a was concentrated under reduced pressure at 30° C. to afford pure 91.5a (0.160 g; MS (ES): m/z 503.20 [M+H]$^+$). FR-b was concentrated under reduced pressure at 30° C. to afford pure 91.5b (0.140 g; MS (ES): m/z 503.20 [M+H]$^+$).

Step 6—Synthesis of Compound 91.6: To a solution of 91.5a (0.350 g, 0.69 mmol, 1.0 eq), in tetrahydrofuran:methanol:water (6 mL, 2:1:1) was added lithium hydroxide (0.165 g, 6.9 mmol, 10 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 91.6 (0.310 g, Yield: 93.81%; MS (ES): m/z 475.16 [M+H]$^+$).

Step 7—Synthesis of Compound 91.8: Compound was synthesized using general procedure A to obtain 91.8 (0.140 g, Yield: 76.59%; MS (ES): m/z 560.22 [M+H]$^+$).

Step 8—Synthesis of Compound I-708: A solution of 91.8 (0.035 g, 0.062 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain I-708 (0.021 g, Yield: 71.52%; MS (ES): m/z 470.61 [M+H]$^+$; LCMS purity: 98.47%, HPLC purity: 96.61%; CHIRAL HPLC: 50.51%, 49.48%; $^1$H NMR (DMSO-d$_6$, 400 MHZ): 8.99-8.95 (t, J=7.6 Hz, 1H), 8.67 (bs, 1H), 8.43-8.41 (d, J=10.4 Hz, 2H), 8.40 (bs, 1H), 8.31 (bs, 1H), 7.34 (bs, 1H), 6.76 (s, 1H), 5.77 (s, 1H), 5.69 (bs, 1H), 4.31 (bs, 1H), 3.77-3.74 (m, 1H), 3.59-3.51 (m, 1H), 3.12-3.11 (d, J=4.8 Hz, 3H), 1.56 (bs, 1H), 1.24 (bs, 3H), 0.87 (bs, 1H)).

Example 92: 5-(1-((1S,2R)-2-Fluorocyclopentyl)-1H-pyrrolo[2,3-b]pyridin-3-yl)-N-((cis-3,4)-4-hydroxytetrahydrofuran-3-yl)-7-(methylamino)pyrazolo[1,5-a]pyrimidine-3-carboxamide (I-721)

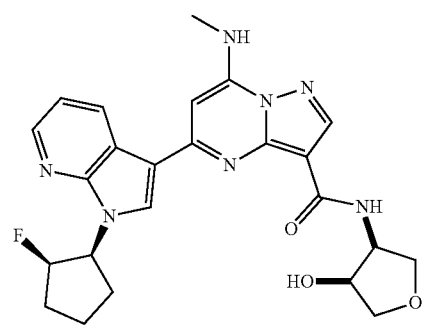

I-721

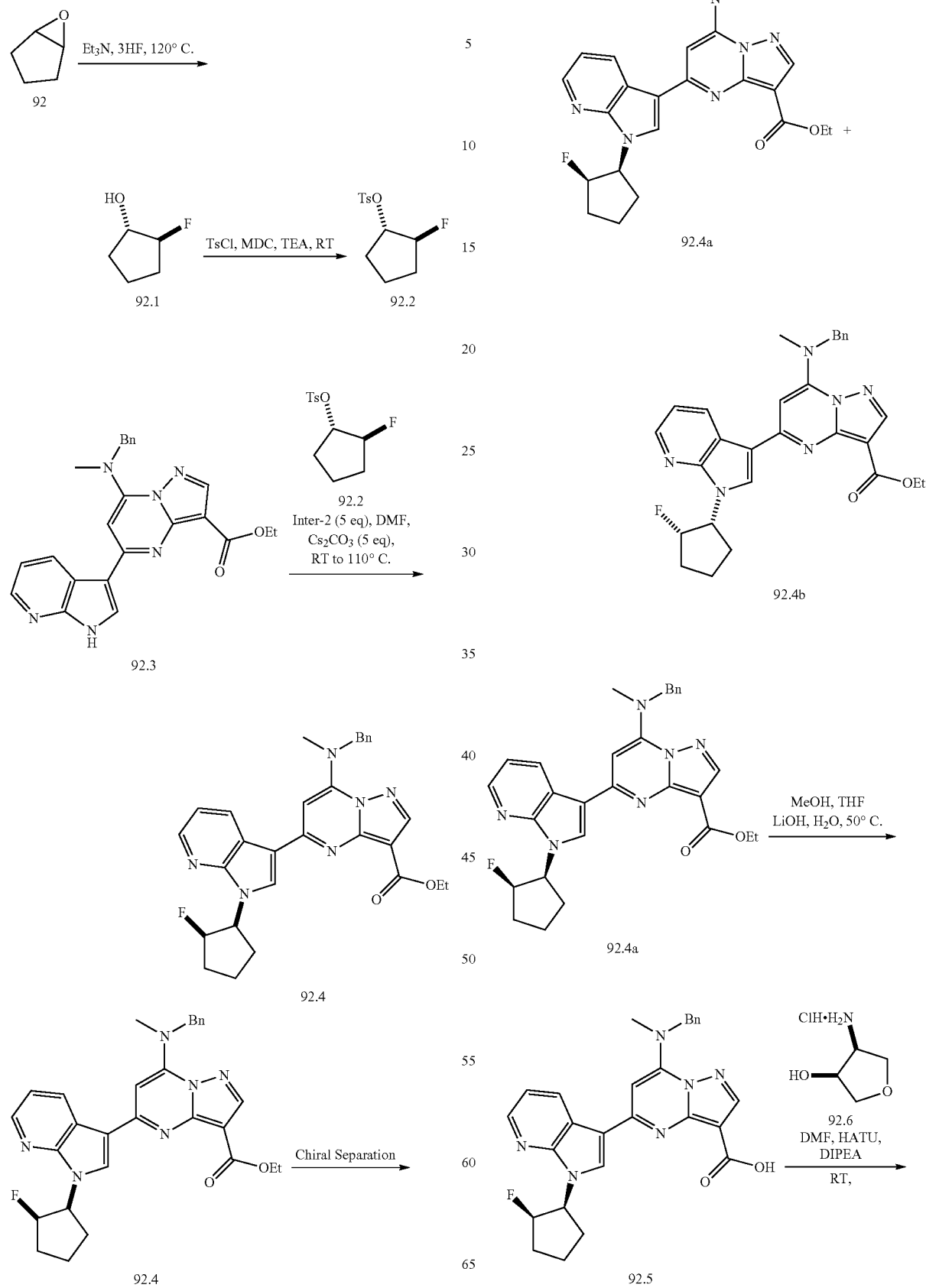

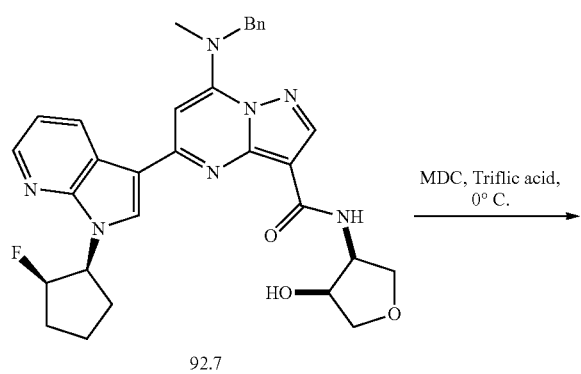

92.7

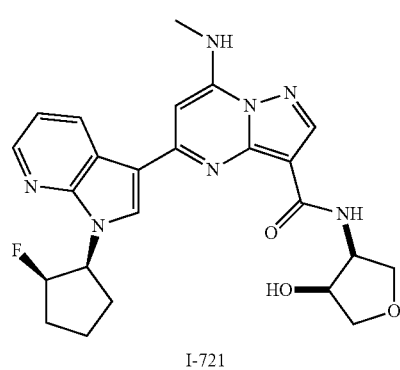

I-721

Step 1—Synthesis of Compound 9231: Mixture of 92 (2.0 g, 23.80 mmol, 1.0 eq) and triethylamine trihydrofluoride (5.0 g) was stirred at 120° C. for 4 h. After completion of reaction, reaction mixture was transferred in to saturated sodium bicarbonate solution and extracted with dichloromethane. Organic layer was combined, washed with brine solution, dried over sodium sulfate and concentrated under reduced pressure to obtain crude material. This was further triturated by diethyl ether to obtain pure 92.1 (1.2 g, Yield: 48.47%; MS (ES): m/z 105.07 [M+H]$^+$).

Step 2—Synthesis of Compound 92.2: To the solution of compound 92.1 (1.2 g, 11.53 mmol, 1.0 eq) in dichloromethane (15 mL) was added triethylamine (2.3 g, 23.06 mmol, 2.0 eq). After 10 min 4-toluenesulfonyl chloride (2.4 g, 12.68 mmol, 1.1 eq) was added portion wise into reaction mixture at room temperature followed by 4-dimethylaminopyridine (0.140 g, 1.15 mmol, 0.1 eq) and reaction mixture was stirred at same temperature for 8 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 12% ethyl acetate in hexane to obtain 92.2 (0.9 g, Yield: 30.23%; MS (ES): m/z 259.08 [M+H]$^+$).

Step 3—Synthesis of Compound 92.3: Compound was synthesized as per experimental protocol of I-14/15 (Example 12) to obtain 92.3 (Yield: 83.54%; MS (ES): m/z 427.18 [M+H]$^+$).

Step 4—Synthesis of Compound 92.4: To a solution of 92.3 (0.5 g, 1.17 mmol, 1.0 eq), in dimethylformamide (10 mL) was added 92.2 (1.5 g, 5.85 mmol, 5.0 eq) and cesium carbonate (1.9 g, 5.85 mmol, 5.0 eq). The reaction mixture was stirred at 110° C. for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1% methanol in dichloromethane to obtain 92.4 (0.410 g, Yield: 68.22%; MS (ES): m/z 513.24 [M+H]$^+$).

Step 5—Synthesis of Compounds 92.4a and 92.4b: Isomers of 92.4 (0.410 g) were separated out using column CHIRALCEL OX-H (250 mm*4.6 mm, 5 u) and 0.1% DEA in IPA-ACN (70-30) as co-solvent with flow rate of 4 mL/min. to get pure fraction-1 (FR-a) and fraction-2 (FR-b). FR-a was concentrated under reduced pressure at 30° C. to afford pure 92.4a (0.170 g; MS (ES): m/z 513.24 [M+H]$^+$). FR-b was concentrated under reduced pressure at 30° C. to afford pure 92.4b (0.170 g; MS (ES): m/z 513.24 [M+H]$^+$).

Step 6—Synthesis of Compound 92.5: To a solution of 92.4a (0.170 g, 0.33 mmol, 1.0 eq), in tetrahydrofuran: methanol:water (6 mL, 2:1:1) was added lithium hydroxide (0.039 g, 1.65 mmol, 5.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 92.5 (0.147 g, Yield: 91.48%; MS (ES): m/z 485.21 [M+H]$^+$).

Step 7—Synthesis of Compound 92.7: Compound was synthesized using general procedure A to obtain 91.7 (0.140 g, Yield: 81.01%), MS (ES): 570.26 [M+H]$^+$).

Step 8—Synthesis of Compound I-721: A solution of 92.7 (0.040 g, 0.070 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain I-721 (0.023 g, Yield: 68.31%; MS (ES): m/z 480.34 [M+H]$^+$; LCMS purity: 96.69%; HPLC purity: 95.00%; CHIRAL HPLC: 49.15%, 49.75%; $^1$H NMR (DMSO-d$_6$, 400 MHZ): 9.01-8.95 (m, 1H), 8.77 (s, 1H), 8.39 (s, 1H), 8.22 (bs, 1H), 7.74-7.70 (m, 2H), 7.31-7.28 (m, 1H), 6.81-6.80 (d, J=4 Hz, 1H), 5.62-5.61 (d, J=4.4 Hz, 1H), 5.16 (bs, 1H), 4.61-4.56 (m, 1H), 4.30 (bs, 1H), 4.04-3.98 (m, 3H), 3.61-3.55 (m, 1H), 3.14-3.13 (d, J=4.8 Hz, 3H), 2.16-2.04 (m, 1H), 1.86 (bs, 1H), 1.56 (bs, 1H), 1.24 (bs, 3H), 0.90-0.87 (m, 1H)).

821

Example 93: N-((1R,2S)-2-Fluorocyclopropyl)-5-((2-oxo-1-(tetrahydro-2H-pyran-4-yl)-1,2-dihydro-pyridin-3-yl)amino)-2,3-dihydro-1H-pyrazolo[5',1': 2,3]pyrimido[5,4-b][1,4]oxazine-7-carboxamide (I-751)

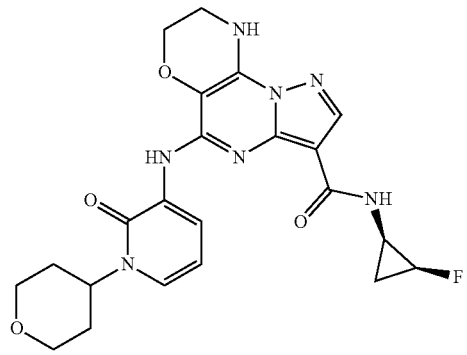

I-751

Scheme 93

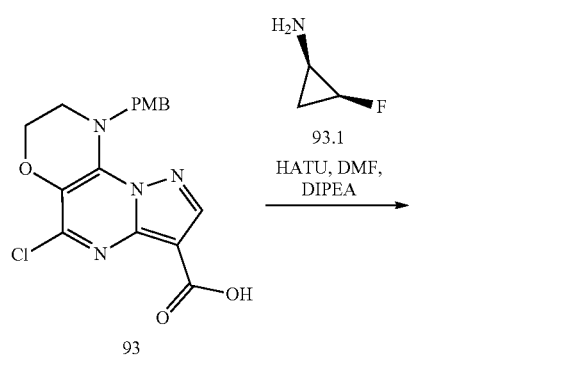

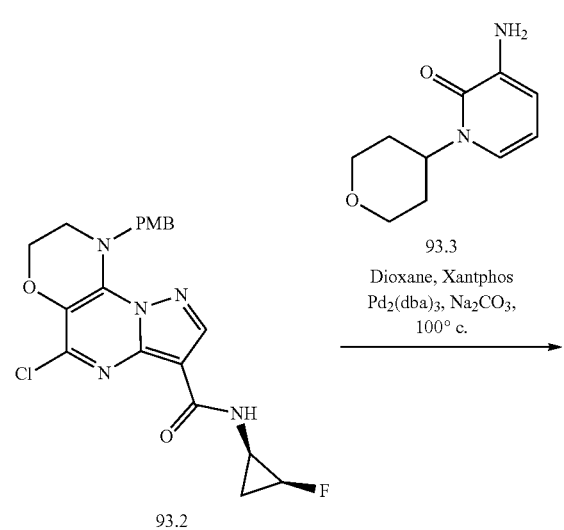

822

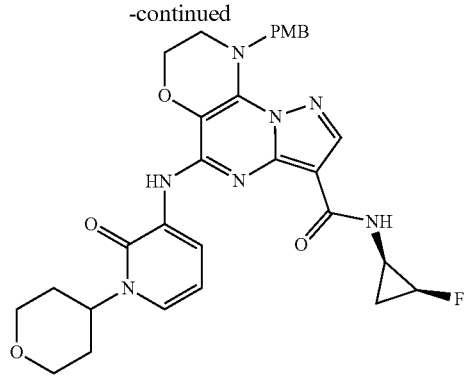

Step 1—Synthesis of Compound 93: Compound was synthesized using the procedure for the preparation of Core C (1.9 g, Yield: 68.79%), MS (ES): m/z 375.08 [M+H]+.

Step 2—Synthesis of Compound 93.2: Compound was synthesized using general Procedure A to obtain 93.2 (0.2 g, Yield: 57.86%; MS (ES): m/z 432.12 [M+H]+).

Step 3—Synthesis of Compound 93.4: Compound was synthesized using general procedure B to obtain 92.4: (0.070 g, Yield: 51.27%), MS (ES): m/z 590.25 [M+H]+).

Step 4—Synthesis of Compound I-751: A solution of 93.4 (0.070 g, 0.11 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain I-751 (0.032 g, Yield: 57.41%; MS (ES): m/z 471.16 [M+H]+; LCMS purity: 100%; HPLC purity: 96.74%; CHIRAL HPLC: 100%; ¹H NMR (DMSO-d₆, 400 MHZ): 8.41 (s, 1H), 8.37 (s, 1H), 8.18-8.26 (s, 1H), 8.18-8.16 (d, J=7.2 Hz, 1H), 7.70-7.69 (d, J=4.4 Hz, 1H), 7.48-7.47 (d, J=6.8 Hz, 1H), 6.33-6.29 (t, J=7.2 Hz, 1H), 5.00 (bs, 2H), 4.84 (bs, 1H), 4.30 (bs, 1H), 3.99 (bs, 2H), 3.65 (bs, 3H), 3.52-3.46 (d, J=11.6 Hz, 3H), 3.02 (bs, 1H), 1.76 (bs, 1H), 1.27-1.21 (m, 2H), 0.85 (bs, 1H)).

Example 94: 5-((1-Isopropyl-2-oxo-1,2-dihydropyridin-3-yl)amino)-N-(2-methoxycyclobutyl)-2,3-dihydro-1H-pyrazolo[5',1':2,3]pyrimido[5,4-b][1,4]oxazine-7-carboxamide (I-759)

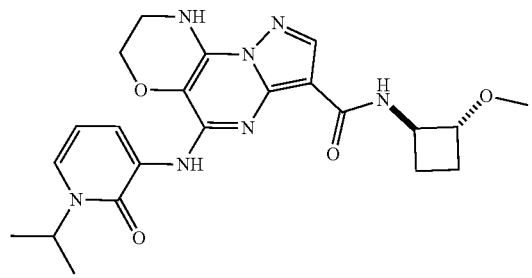

I-759

Scheme 94

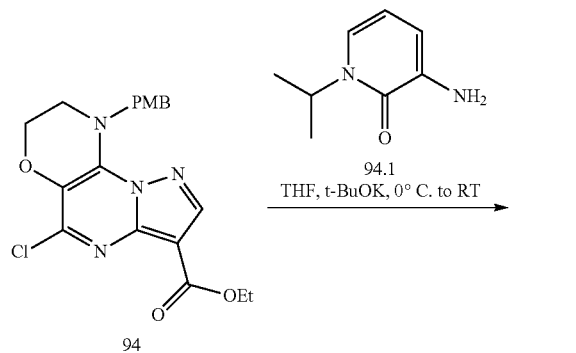

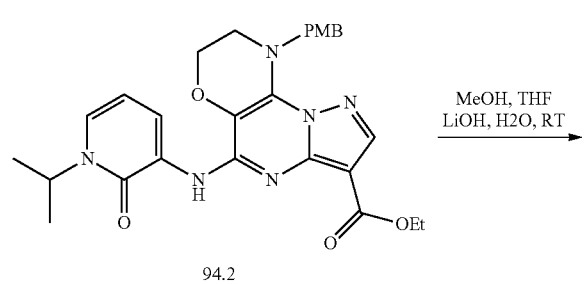

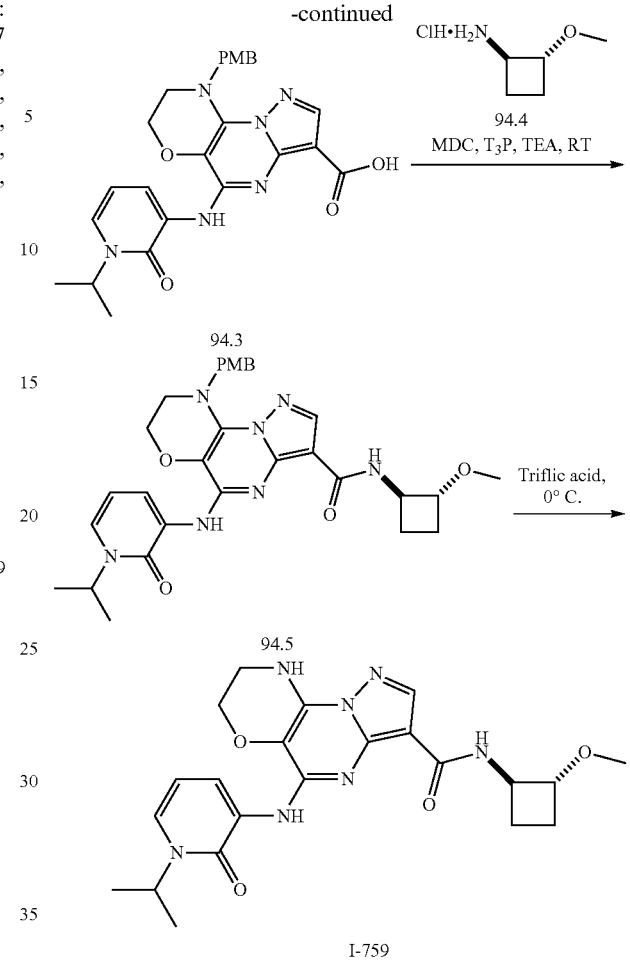

Step 1—Synthesis of Compound 94: Compound was synthesized using the procedure for the preparation of Core C to obtain 94 (Yield: 53.98%; MS (ES): m/z 403.11 [M+H]⁺).

Step 2-Synthesis of Compound 94.2: To a cooled solution of 94 (1.0 g, 2.48 mmol, 1.0 eq), and 94.1 (0.453 g, 2.98 mmol, 1.2 eq) in tetrahydrofuran (15 mL) at 0° C. was added potassium tert-butoxide (1M in tetrahydrofuran; 4.9 mL, 4.9 6 mmol, 2.0 eq). The reaction was stirred at room temperature for 2 h. After completion of reaction, reaction mixture was transferred into water and product was extracted with ethyl acetate. Organic layer was combined and dried over sodium sulfate and concentrated under reduced pressure to obtain crude material. This was further purified by column chromatography and compound was eluted in 25% ethyl acetate in hexane to obtain pure 94.2 (0.682 g, Yield: 52.98%; MS (ES): m/z 519.57 [M+H]⁺).

Step 3—Synthesis of Compound 94.3: To a solution of 94.2 (0.682 g, 1.32 mmol, 1.0 eq), in methanol:tetrahydrofuran: water (8 mL, 2:2:1) was added lithium hydroxide (0.317 g, 13.2 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 94.3 (0.480 g, Yield: 74.41%; MS (ES): m/z 491.52 [M+H]+).

Step 4—Synthesis of Compound 94.5: To a solution of 94.3 (0.2 g, 0.407 mmol, 1.0 eq), in dichloromethane (3 mL) was added propylphosphonicanhydride (0.235 g, 0.814 mmol, 2.0 eq) and stirred at room temperature for 15 min. To this added triethylamine (0.112 g, 1.11 mmol, 3.0 eq) followed by addition of 94.4 (0.067 g, 0.489 mmol, 1.2 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 94.5 (0.168 g, Yield: 71.83%; MS (ES): m/z 574.65 [M+H]+).

Step 5—Synthesis of Compound I-759: A solution of 94.5 (0.050 g, 0.086 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-759 (0.023 g, Yield: 58.19%; MS (ES): m/z 454.52 [M+H]+; LCMS purity: 100%, HPLC purity: 95%; CHIRAL HPLC: 49.55%, 49.45%; $^1$H NMR (DMSO-$d_6$, 400 MHZ): 8.42 (s, 1H), 8.37 (s, 1H), 8.29-8.28 (d, J=6.8 Hz, 1H), 8.23 (s, 1H), 7.97-7.95 (d, J=9.2 Hz, 1H), 7.49-7.47 (d, J=6.8 Hz, 1H), 6.38-6.35 (t, J=7.2 Hz, 1H), 5.16-5.13 (m, 1H), 4.35-4.31 (m, 3H), 3.76-3.70 (m, 3H), 3.21 (s, 3H), 2.18-2.05 (m, 2H), 1.56-1.49 (m, 1H), 1.45-1.41 (m, 1H), 1.36-1.34 (d, J=6.4 Hz, 6H)).

Example 95: N-(2,2-Difluorocyclobutyl)-5-(1-(oxetan-3-yl)-1H-pyrrolo[2,3-b]pyridin-3-yl)-2,3-dihydro-1H-pyrazolo[5',1':2,3]pyrimido[5,4-b][1,4]oxazine-7-carboxamide (I-771)

I-771

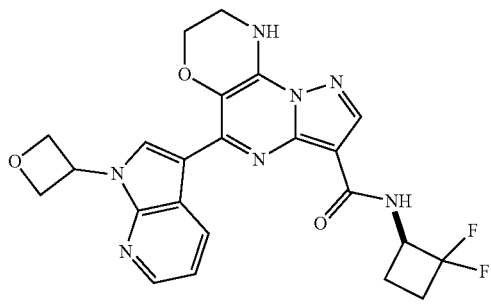

Scheme 95

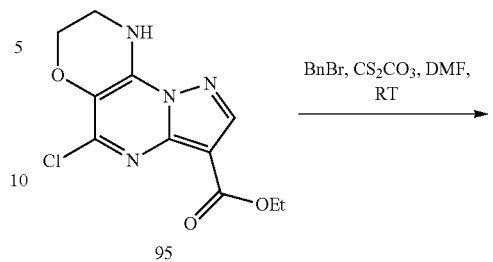

95

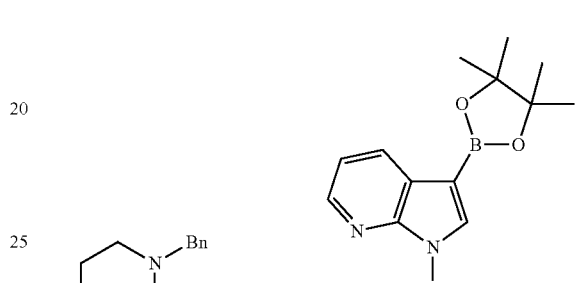

95.1

95.2
Dioxane, H$_2$O (9:1), Na$_2$CO$_3$
PdCl$_2$ (dppf)·DCM, 110° C.

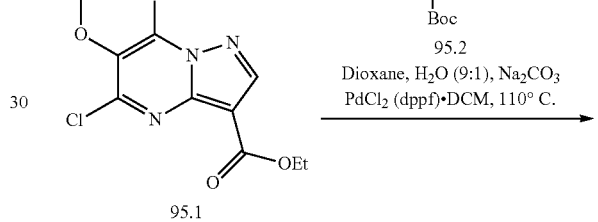

95.3
Dioxane·HCl, RT

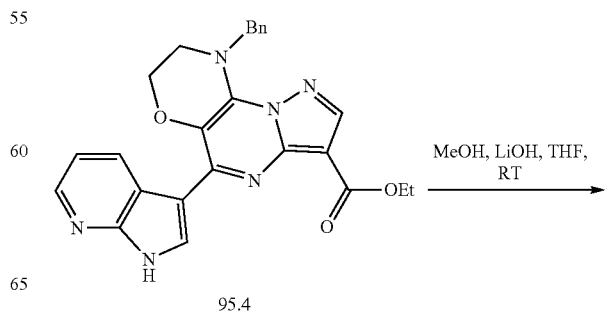

95.4
MeOH, LiOH, THF, RT

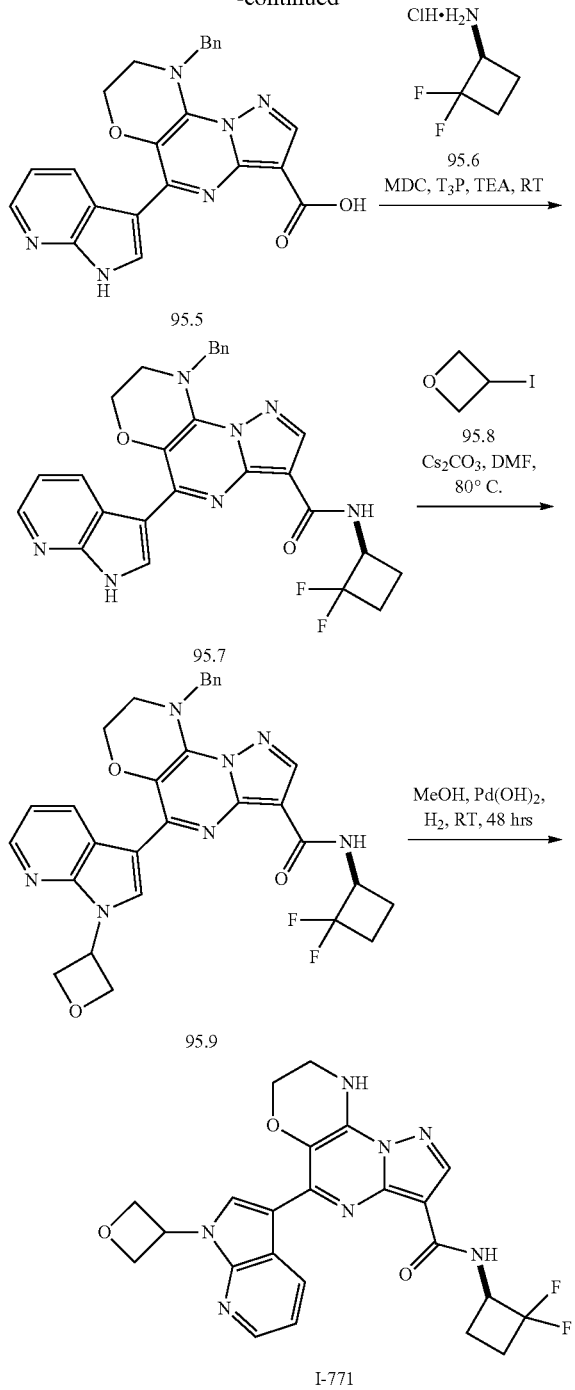

centrated under reduced pressure to obtain crude material. This was further purified by column chromatography and the compound was eluted in 20% ethyl acetate in hexane to obtain pure 95.1 (1.42 g Yield: 53.84%; MS (ES): m/z 373.10 [M+H]$^+$).

Step 3—Synthesis of Compound 95.3: Argon was purged for 15 min through a stirred solution of 95.1 (1.0 g, 2.68 mmol, 1.0 eq), 95.2 (1.1 g, 3.48 mmol, 1.3 eq) and sodium carbonate (0.710 g, 6.7 mmol, 2.5 eq) in 1,4 dioxane:water (20 mL, 9:1) [1,1'-bis(diphenylphosphino)ferrocene]dichloropalladium(II), complex with dichloromethane (0.218 mg, 0.26 mmol, 0.1 eq) was added to it and further purging done for 10 min. Reaction was allowed to stir at 110° C. for 6 h. After completion of reaction, reaction mixture was transferred into water and product was extracted with ethyl acetate. Organic layer was combined, washed with brine solution, dried over sodium sulfate and concentrated under reduced pressure to obtain 95.3 (0.562 g, Yield: 37.78%; MS (ES): m/z 555.23 [M+H]$^+$).

Step 4—Synthesis of Compound 95.4: To the compound 95.3 (0.562 g, 1.01 mmol, 1.0 eq) was added 4M hydrochloric acid in 1,4 dioxane (10 mL) and stirred at room temperature for 4 h. After completion of reaction, reaction mixture was concentrated under reduced pressure, residue was stirred with saturated sodium bicarbonate solution, extracted with dichloromethane. Organic layer combined, washed with brine, dried over sodium sulfate, concentrated under reduced pressure to obtain residue which was triturated with diethyl ether to obtain 95.4 (0.460 g, Yield: 99.88%; MS (ES): m/z 455.18 [M+H]$^+$).

Step 5—Synthesis of Compound 95.5: To a solution of 95.4 (0.481 g, 1.05 mmol, 1.0 eq), in tetrahydrofuran:methanol (8 mL, 2:1) was added lithium hydroxide (0.126 g, 5.25 mmol, 5.0 eq). The reaction was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 95.5 (0.410 g, Yield: 90.85%; MS (ES): m/z 427.15 [M+H]$^+$).

Step 6—Synthesis of Compound 95.7: To a solution of 95.5 (0.205 g, 0.48 mmol, 1.0 eq), in dichloromethane (3 mL) was added propylphosphonicanhydride (0.305 g, 0.96 mmol, 2.0 eq) and stirred at room temperature for 15 min. To this added triethylamine (1.5 g, 15.66 mmol, 3.0 eq) followed by addition of 95.6 (0.082 g, 0.57 mmol, 1.2 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 95.7 (0.149 g, Yield: 60.12%; MS (ES): m/z 516.19 [M+H]$^+$).

Step 7—Synthesis of Compound 95.9: To a solution of 95.7 (0.149 g, 0.28 mmol, 1.0 eq), in dimethylformamide (4 mL) was added 95.8 (0.128 g, 0.7 mmol, 2.5 eq) and cesium carbonate (0.4 g, 1.4 mmol, 5.0 eq). The reaction mixture was stirred at 80° C. for 3 h. After completion of reaction, reaction mixture was transferred into water and product was extracted with ethyl acetate. Organic layer was combined, Step 1—Synthesis of Compound 95: Compound was synthesized using the procedure for the preparation of Core C to obtain 95 (Yield: 83.60%; MS (ES): m/z 283.06 [M+H]$^+$).

Step 2—Synthesis of Compound 95.1: To a solution of 95 (2.0 g 7.09 mmol, 1.0 eq) in N,N-dimethylformamide (25 mL) was added benzyl bromide (1.3 g, 7.79 mmol, 1.1 eq) and cesium carbonate (4.6 g, 14.18 mmol, 2.0 eq) at 0° C. Reaction mixture stirred at room temperature for 2 h. After completion of reaction, reaction mixture was transferred into water and product was extracted with ethyl acetate. Organic layer was combined, dried over sodium sulphate and conwashed with brine solution, dried over sodium sulfate and concentrated under reduced pressure to obtain crude material. This was further purified by column chromatography and the compound was eluted in 20% ethyl acetate in hexane to obtain 95.9 (0.155 g, Yield: 93.82%; MS (ES): m/z 572.22 [M+H]+).

Step 8—Synthesis of Compound I-771: To a solution of 95.9 (0.040 g, 0.070 mmol, 1.0 eq) in methanol (2 mL), palladium hydroxide on carbon (20%, 0.02 g) was added. Hydrogen was purged through reaction mixture for 48 h at room temperature. After completion of reaction, reaction mixture was filtered through celite-bed and washed with methanol. Filtrate was concentrated under reduced pressure to obtain crude material. This was further purified by trituration with n-pentane to obtain pure I-771 (0.019 g, Yield: 56.39%; MS (ES): m/z 482.67 [M+H]+; LCMS purity: 100%, HPLC purity: 98.50%; CHIRAL HPLC: 50.35%, 49.64%; $^1$H NMR (DMSO-$d_6$, 400 MHZ): 8.91 (bs, 1H), 8.82-8.80 (d, J=7.6 Hz, 1H), 8.74 (s, 1H), 8.43 (s, 2H), 8.41-8.40 (d, J=4.4 Hz, 1H), 7.31-7.28 (m, 1H), 6.09-6.05 (t, J=7.2 Hz, 1H), 5.14-5.11 (m, 3H), 5.09-5.05 (m, 3H), 4.42 (bs, 2H), 3.75 (bs, 2H), 3.59 (bs, 2H), 1.71-1.66 (m, 1H)).

Example 96: N-(2,2-Difluorocyclobutyl)-5-(1-((1r,3S)-3-hydroxycyclobutyl)-1H-pyrrolo[2,3-b]pyridin-3-yl)-2,3-dihydro-1H-pyrazolo[5',1':2,3]pyrimido[5,4-b][1,4]oxazine-7-carboxamide (I-775)

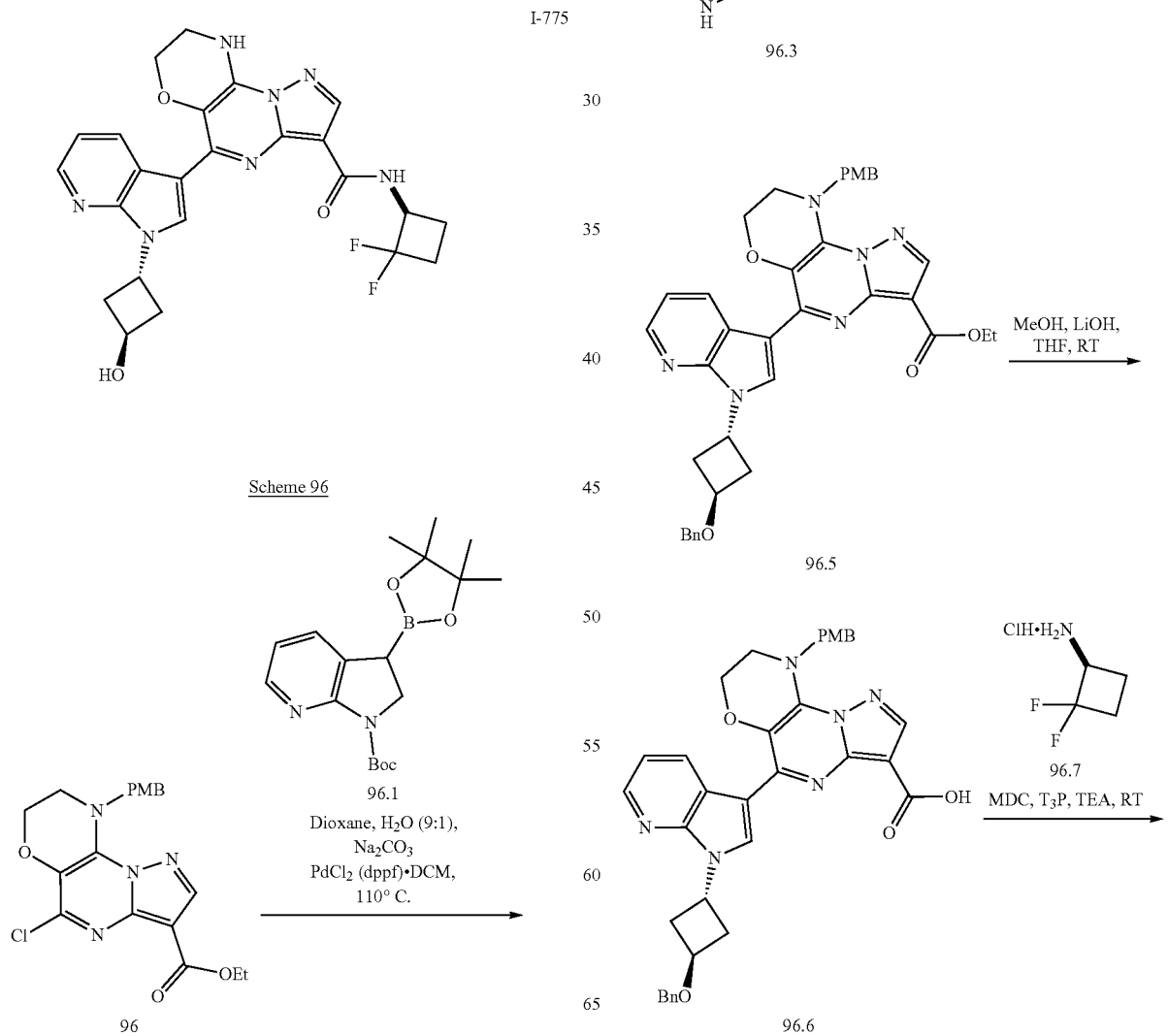

-continued

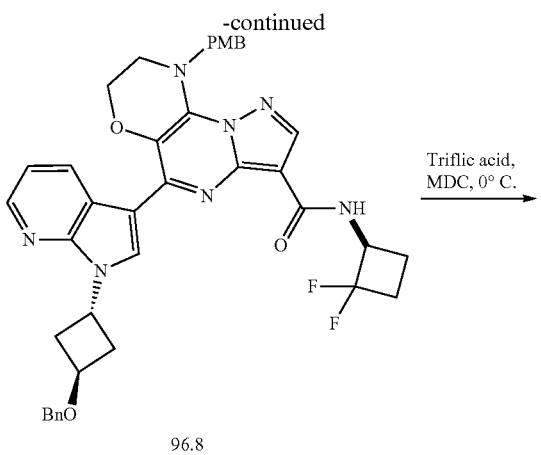

96.8

Triflic acid,
MDC, 0° C.

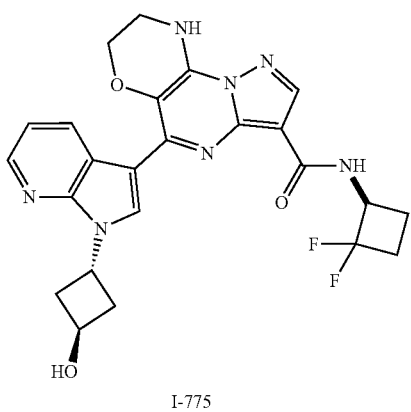

I-775

Step 1—Synthesis of Compound 96: Compound 96 was synthesized using the procedure for the preparation of Core C to obtain 96 (Yield: 53.98%; MS (ES): m/z 403.11 [M+H]$^+$).

Step 2—Synthesis of Compound 96.2: Argon was purged for 15 min through a stirred mixture of 96 (4.5 g, 11.19 mmol, 1.0 eq), 96.1 (5.0 g, 14.54 mmol, 1.3 eq) and Sodium carbonate (2.9 g, 27.97 mmol, 2.5 eq) in 1,4 dioxane:water (60 mL, 9:1). [1,1'-bis(diphenylphosphino)ferrocene]dichloropalladium(II), complex with dichloromethane (0.913 g, 1.11 mmol, 0.1 eq) was added to it and further purging done for 10 min. Reaction mixture was allowed to stir at 110° C. for 5 h. After completion of reaction, reaction mixture was transferred into water and product was extracted with ethyl acetate. Organic layer was combined, washed with brine solution, dried over sodium sulfate and concentrated under reduced pressure to obtain 95.2 (3.5 g, Yield: 53.59%; MS (ES): m/z 585.24 [M+H]$^+$).

Step 3—Synthesis of Compound 96.3: To 96.2 (3.5 g, 5.99 mmol, 1.0 eq) was added 4M hydrochloric acid in 1,4 dioxane (30 mL) and stirred at room temperature for 4 h. After completion of reaction, reaction mixture was concentrated under reduced pressure, residue was stirred with saturated sodium bicarbonate solution, extracted with dichloromethane. Organic layer was combined, washed with brine, dried over sodium sulfate, concentrated under reduced pressure to obtain residue which was triturated with diethyl ether to obtain 96.3 (2.8 g, Yield: 96.53%; MS (ES): m/z 485.19 [M+H]$^+$).

Step 4—Synthesis of Compound 96.5: To a solution of 96.3 (1.2 g, 2.47 mmol, 1.0 eq), in dimethylformamide (25 mL) was added 96.4 (2.0 g, 6.17 mmol, 2.5 eq) and cesium carbonate (4.0 g, 12.35 mmol, 5.0 eq). The reaction mixture was stirred at 110° C. for 3 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 96.5 (0.9 g, Yield: 56.36%; MS (ES): m/z 645.28 [M+H]$^+$).

Step 5—Synthesis of Compound 96.6: To a solution of 96.5 (0.9 g, 1.39 mmol, 1.0 eq), in tetrahydrofuran:methanol:water (12 mL, 2:2:1) was added lithium hydroxide (0.166 g, 6.95 mmol, 5.0 eq). The reaction mixture was stirred at room temperature for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 95.6 (0.805 g, Yield: 93.51%; MS (ES): m/z 617.25 [M+H]$^+$).

Step 6—Synthesis of Compound 96.8: To a solution of 96.6 (0.250 g, 0.40 mmol, 1.0 eq), in dichloromethane (5 mL) was added propylphosphonicanhydride (0.174 g, 0.8 mmol, 2.0 eq) and stirred at room temperature for 15 min. To this added triethylamine (0.12 g, 1.2 mmol, 3.0 eq) followed by addition of 96.7 (0.051 g, 0.48 mmol, 1.2 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 96.8 (0.208 g, Yield: 72.70%; MS (ES): m/z 706.29 [M+H]$^+$).

Step 7—Synthesis of Compound I-775: To a solution of 96.8 (0.070 g, 0.099 mmol, 1.0 eq) in dichloromethane (1 mL) was added triflic acid (1 mL) at 0° C. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain I-775 (0.021 g, Yield: 42.73%; MS (ES): m/z 496.82 [M+H]$^+$; LCMS purity: 98.54%, HPLC purity: 97.70%, CHIRAL HPLC: 48.07%, 49.32%; $^1$H NMR (DMSO-d$_6$, 400 MHZ): 8.88 (bs, 1H), 8.78-8.76 (d, J=8 Hz, 1H), 8.58 (bs, 1H), 8.46 (bs, 1H), 8.42-8.40 (d, J=8.4 Hz, 1H), 7.28-7.25 (m, 1H), 6.82-6.80 (d, J=6.4 Hz 1H), 5.60-5.56 (t, J=6.8 Hz, 1H), 4.53 (bs, 1H), 4.42 (bs, 1H), 4.09 (bs, 1H), 3.74 (bs, 2H), 3.17-3.16 (d, J=4 Hz, 1H), 2.80 (bs, 2H), 1.71-1.66 (t, J=10.4 Hz 1H), 1.54 (bs, 4H), 1.22 (bs, 2H)).

833
Example 97: N-((cis-3,4)-4-hydroxytetrahydrofuran-3-yl)-5-(8-isopropylimidazo[1,2-a]pyridin-5-yl)-7-(methylamino)pyrazolo[1,5-a]pyrimidine-3-carboxamide (I-786)
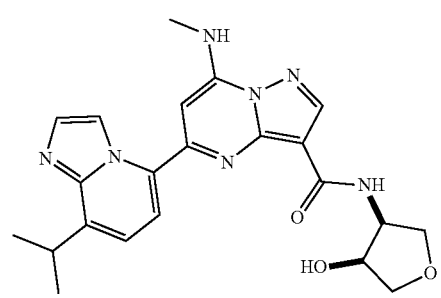
I-786
Scheme 97
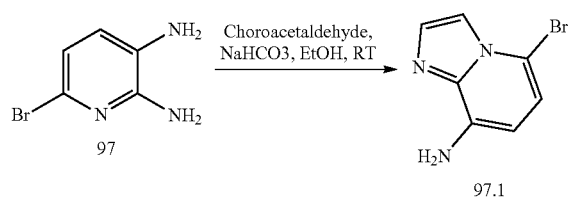
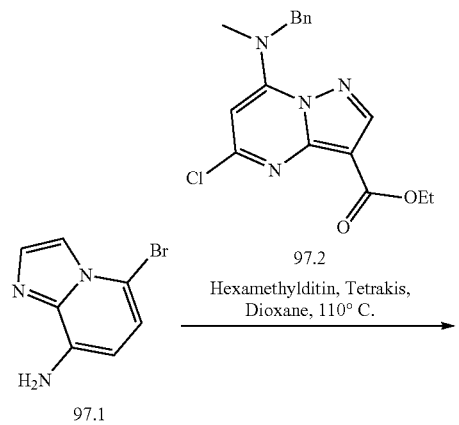
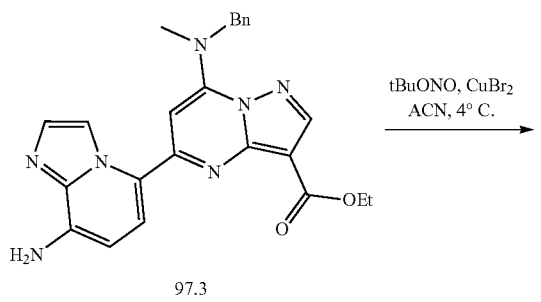
834
-continued
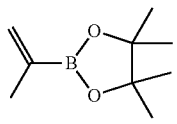
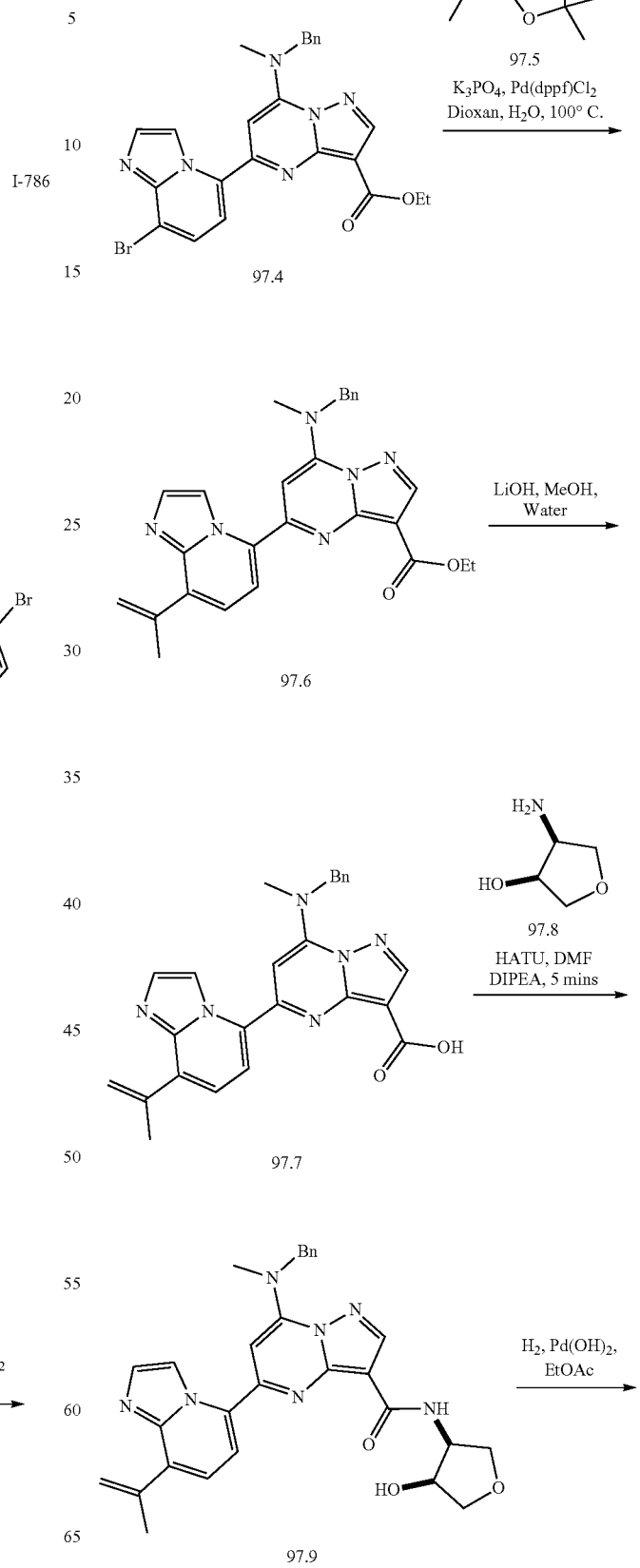

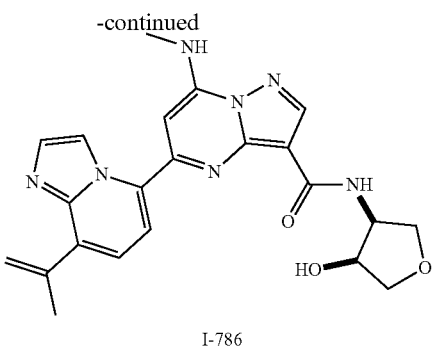

I-786

Step 1—Synthesis of Compound 97.1: To a solution of 97 (10.0 g, 53.19 mmol, 1.0 eq) in ethanol (100 mL) was added Sodium bicarbonate (4.9 g, 58.50 mmol, 1.1 eq) and reaction mixture was stirred at room temperature for 15 min. Then Choroacetaldehyde (4.13 mL, 58.50 mmol, 1.1 eq) was added to the reaction mixture slowly and stirred at room temperature for 18 h. After completion of reaction, reaction mixture was transferred into diluted sodium hydroxide and product was extracted with ethyl acetate. Organic layer was combined, washed with brine solution, dried over sodium sulphate and concentrated under reduced pressure to obtain crude material. This was further purified by combi flash using 20% ethyl acetate in hexane as eluant to obtain pure 97.1 (5.4 g, Yield: 47.88%; MS (ES): m/z 212.9 [M+H]$^+$).

Step 2—Synthesis of Compound 97.2: Compound was synthesized using general procedure of core A synthesis to obtain 97.2 (Yield: 45%; MS (ES): m/z 345.10 [M+H]$^+$).

Step 3—Synthesis of Compound 97.3: To a degassed solution of 97.1 (3.0 g, 14.15 mmol, 1.0 eq) and 97.2 (4.8 g, 14.15 mmol, 1.0 eq) in toluene (40 mL) was added hexamethylditin (5.5 g, 16.98 mmol, 1.2 eq), tetrakis(triphenylphosphine)palladium(0) (0.817 g, 0.70 mmol, 0.05 eq) and the reaction mixture was heated at 110° C. for 16 h under N$_2$. After completion of reaction, reaction mixture was transferred into water and product was extracted with ethyl acetate. Organic layer was combined, washed with brine solution, dried over sodium sulphate and concentrated under reduced pressure to obtain crude material. This was further purified by combi flash using 2% methanol in dichloromethane as eluant to obtain pure 97.3 (0.970 g, Yield: 25.25%; MS (ES): m/z 442.19 [M+H]$^+$).

Step 4—Synthesis of Compound 97.4: To a solution of compound 97.3 (0.4 g, 0.90 mmol, 1.0 eq) in acetonitrile (5 ml) was added tert-butyl nitrite (0.101 g, 0.99 mmol, 1.1 eq) and copper(II) bromide (0.402 g, 1.8 mmol, 2.0 eq) The reaction was stirred at room temperature for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by combi flash using 1.2% methanol in dichloromethane as eluant to obtain pure 97.4 (0.143 g, Yield: 31.23%; MS (ES): m/z 506.09 [M+H]$^+$).

Step 5—Synthesis of Compound 97.6: Argon was purged for 15 min through a stirred mixture of 97.4 (0.143 g, 0.28 mmol, 1.0 eq), 97.5 (0.061 g, 0.36 mmol, 1.3 eq) and tripotassium phosphate (0.148 g, 0.7 mmol, 2.5 eq) in 1,4 dioxane:water (10 mL, 9:1) [1,1'-bis(diphenylphosphino) ferrocene]palladium(II) dichloride (0.020 g, 0.028 mmol, 0.1 eq) was added to it and further purging done for 10 min. Reaction was allowed to stir at 100° C. for 5 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by combi flash using 2.2% methanol in dichloromethane as eluant to obtain pure 97.6 (0.070 g, Yield: 53.03%; MS (ES): m/z 467.2 [M+H]$^+$).

Step 6—Synthesis of Compound 97.7: To a solution of 97.6 (0.070 g, 0.15 mmol, 1.0 eq), in methanol:water (4 mL, 2:1) was added lithium hydroxide (0.036 g, 1.5 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 97.7 (0.052 g, Yield: 79.04%; MS (ES): m/z 439.18 [M+H]$^+$).

Step 7—Synthesis of compound 97.9: Compound was synthesized using general procedure A to obtain 97.9 (0.042 g, 67.64%; MS (ES): m/z 524.24 [M+H]$^+$).

Step 8—Synthesis of Compound I-786: To a solution of 97.9 (0.042 g, 0.080 mmol, 1.0 eq) in methanol (2 mL), palladium hydroxide on carbon (20%, 0.025 g) was added. Hydrogen was purged through reaction mixture for 4 h at room temperature. After completion of reaction, reaction mixture was filtered through celite-bed and washed with methanol. Filtrate was concentrated under reduced pressure to obtain crude material. This was further purified by trituration with n-pentane to obtain pure I-786 (0.030 g, Yield: 85.88%; MS (ES): m/z 436.2 [M+H]$^+$; LCMS purity: 97.25%; HPLC purity: 97.15%; CHIRAL HPLC: 49.91%, 50.09%; $^1$H NMR (DMSO-d$_6$, 400 MHZ): 8.77 (s, 1H), 8.54 (s, 1H), 8.24-8.22 (d, J=8 Hz, 1H), 7.65 (s, 1H), 7.59-7.57 (d, J=7.2 Hz, 1H), 7.26-7.24 (t, J=7.6 Hz, 1H), 7.09-7.07 (d, J=6.8 Hz, 1H), 6.73 (s, 1H), 5.36-5.34 (m, 1H), 4.00-3.93 (m, 3H), 2.90-2.88 (d, J=4.8 Hz, 3H), 1.36-1.34 (d, J=6 Hz, 6H), 1.24 (bs, 2H), 1.08-1.04 (t, J=11.2 Hz, 1H), 0.90-0.87 (m, 1H)).

Example 98: 5-(1-((1R,5S,6r)-3-oxabicyclo[3.1.0] hexan-6-yl)-1H-pyrrolo[2,3-b]pyridin-3-yl)-N-((trans-1,2)-2-methoxycyclobutyl)-7-(methylamino) pyrazolo[1,5-a]pyrimidine-3-carboxamide (I-792)

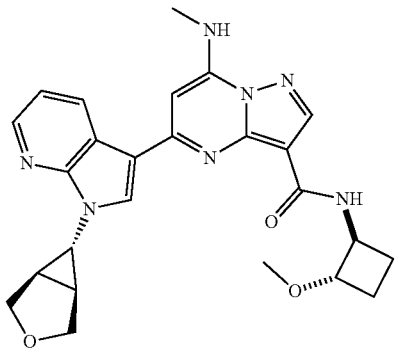

I-792

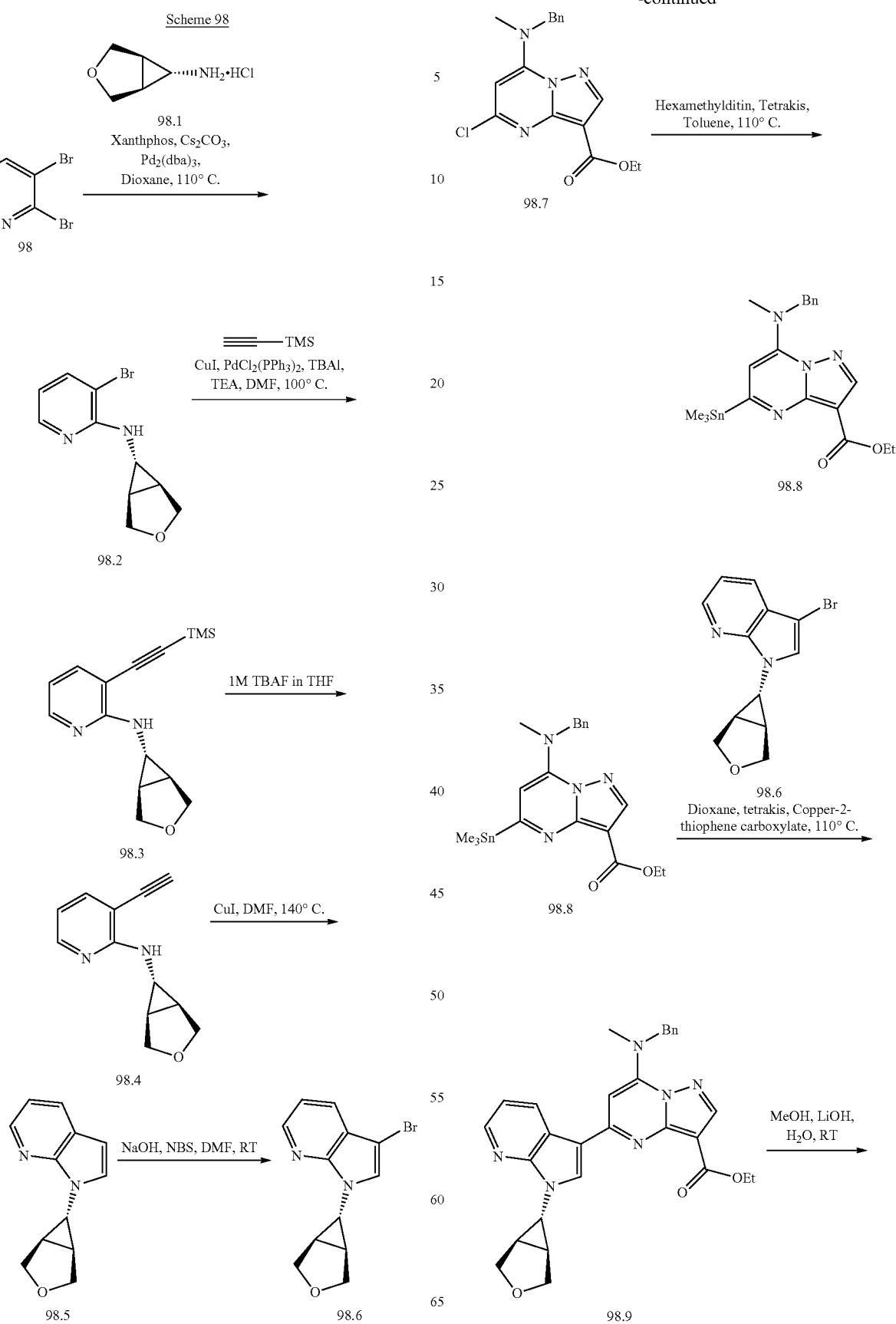

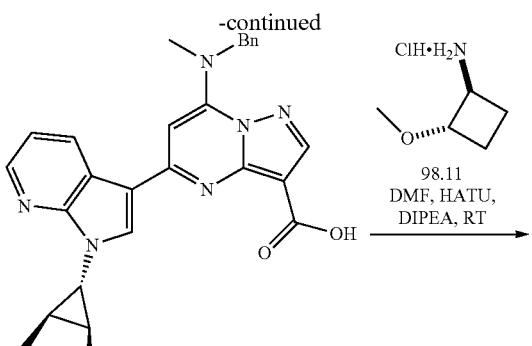

98.10

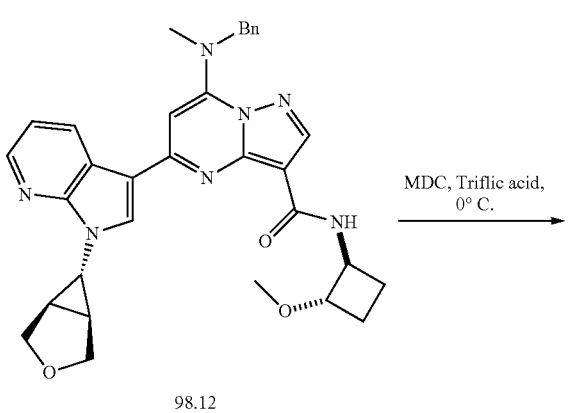

98.12

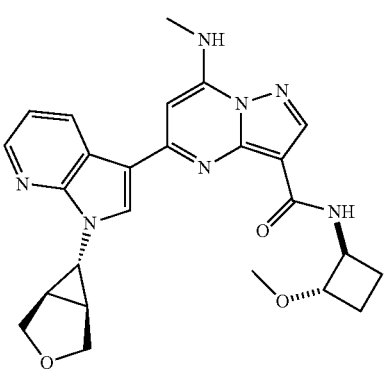

I-792

Step 1—Synthesis of Compound 98.2: To a solution of 98 (0.5 g, 2.11 mmol, 1.0 eq) in 1,4-dioxane (15 mL) were added 98.1 (0.429 g, 3.16 mmol, 1.5 eq), caesium carbonate (2.4 g, 7.38 mmol, 3.5 eq). The reaction mixture was degassed for 10 min. under argon atmosphere, then tris (dibenzylideneacetone)dipalladium(0) (0.193 g, 0.21 mmol, 0.1 eq) and 4,5-bis(diphenylphosphino)-9,9-dimethylxanthene (0.243 g, 0.42 mmol, 0.2 eq) were added, again degassed for 5 min. The reaction mixture was stirred at 110° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 18% ethyl acetate in hexane as eluant to obtain pure 98.2 (0.460 g, Yield: 85.43%; MS (ES): m/z 255.12 [M+H]$^+$).

Step 2—Synthesis of Compound 98.3: To a solution of 98.2 (0.460 g, 1.80 mmol, 1.0 eq) in N,N-dimethylformamide (10 mL) were added copper(I) iodide (0.008 g, 0.045 mmol, 0.025 eq), palladium(II)bis(triphenylphosphine) dichloride (0.063 g, 0.09 mmol, 0.05 eq). The reaction mixture was degassed for 10 min. under argon atmosphere, then tetrabutylammonium iodide (1.3 g, 3.6 mmol, 2.0 eq), triethylamine (4 mL) and ethynyltrimethylsilane (0.352 g, 3.6 mmol, 2.0 eq) were added under argon atmosphere, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 12% ethyl acetate in hexane as eluant to obtain pure 98.3 (0.277 g, Yield: 56.39%; MS (ES): m/z 273.14 [M+H]$^+$).

Step 3—Synthesis of Compound 98.4: To a solution of 98.3 (0.277 g, 1.01 mmol, 1.0 eq) in tetrahydrofuran (10 mL) and water (0.36 mL, 20.2 mmol, 20.0 eq) at 0° C., tetrabutylammonium fluoride solution (1 M in tetrahydrofuran) (0.316 g, 1.21 mmol, 1.2 eq) was added dropwise and stirred reaction mixture at 0° C. for 3 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by combi flash using 14% ethyl acetate in hexane as eluant to obtain pure 98.4 (0.2 g, Yield: 98.23%; MS (ES): m/z 201.09 [M+H]$^+$).

Step 4—Synthesis of Compound 98.5: To a solution of 98.4 (0.2 g, 1.00 mmol, 1.0 eq) in N,N-dimethylformamide (4 mL) was added copper(I) iodide (0.190 g, 1.00 mmol, 1.0 eq) and reaction mixture was heated at 140° C. for 3 h. After completion of reaction, reaction mixture was transferred into cold water and product was extracted with ethyl acetate. Organic layer was combined, washed with brine solution, dried over sodium sulphate and concentrated under reduced pressure to obtain crude material. This was further purified by combi flash using 18% ethyl acetate in hexane as eluant to obtain pure 98.5 (0.180 g, Yield: 90.00%; MS (ES): m/z 201.10 [M+H]$^+$).

Step 5—Synthesis of Compound 98.6: To a solution of 98.5 (0.180 g, 0.9 mmol, 1.0 eq) in N,N-dimethylformamide (3 mL) was added portionwise N-Bromosuccinimide (0.240 g, 1.35 mmol, 1.5 eq) and stirred reaction mixture for 16 h at room temperature. After completion of reaction, reaction mixture was transferred into ice cold water and product was extracted with ethyl acetate. Organic layer was combined and dried over sodium sulphate and concentrated under reduced pressure to obtain 98.6 (0.123 g, Yield: 49.02%; MS (ES): m/z 280.0 [M+H]$^+$).

Step 6—Synthesis of Compound 98.7: Compound was synthesized using general procedure of core synthesis to obtain 98.7 (Yield: 45%; MS (ES): m/z 345.10 [M+H]$^+$).

Step 7—Synthesis of Compound 98.8: To a degassed solution of 98.7 (1.0 g, 2.90 mmol, 1.0 eq) and hexamethylditin (3.7 g, 11.6 mmol, 4.0 eq) in toluene (50 mL) was added tetrakis(triphenylphosphine)palladium(0) (0.334 g, 0.29 mmol, 0.1 eq) and the reaction mixture was heated at 110° C. for 1 h under N₂. After completion of reaction, reaction mixture was concentrated under reduced pressure to obtain crude residue which was purified by column chromatography using 5% ethyl acetate in hexane as eluant to obtain pure 98.8 (0.3 g, Yield: 21.86%; MS (ES): m/z 474.11 [M+H]⁺).

Step 8—Synthesis of Compound 98.9: To a solution of 98.8 (0.2 g, 0.42 mmol, 1.0 eq) in 1,4-dioxane (8 mL) was added 98.6 (0.117 g, 0.42 mmol, 1.0 eq). The reaction mixture was degassed for 10 min. under argon atmosphere, then Tetrakis(triphenylphosphine)palladium(0) (0.024 g, 0.021 mmol, 0.05 eq) and copper(I) thiophene-2-carboxylate (0.008 g, 0.042 mmol, 0.1 eq) were added under argon atmosphere and stirred reaction mixture at 110° C. for 5 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 20% ethyl acetate in hexane to obtain pure 98.9 (0.050 g, Yield: 23.26%; MS (ES): m/z 509.23 [M+H]⁺).

Step 9—Synthesis of Compound 98.10: To a solution of 98.9 (0.070 g, 0.13 mmol, 1.0 eq), in tetrahydrofuran:methanol:water (6 mL; 2:1:1) was added lithium hydroxide (0.031 g, 1.3 mmol, 10.0 eq). The reaction was stirred at 50° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 98.10 (0.064 g, Yield: 96.77%; MS (ES): m/z 481.19 [M+H]⁺).

Step 10—Synthesis of Compound 98.12: Compound was synthesized using general procedure A to obtain 98.12 (0.042 g, Yield: 85.25%; MS (ES): m/z 564.27 [M+H]⁺).

Step 11—Synthesis of Compound I-792: A solution of 98.12 (0.025 g, 0.044 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-792 (0.015 g, Yield: 71.42%; MS (ES): m/z 474.51 [M+H]⁺; LCMS purity: 99.45%; HPLC purity: 98.97%; CHIRAL HPLC: 49.16%, 49.72%; ¹H NMR (DMSO-d₆, 400 MHZ): 8.78-8.76 (d, J=8 Hz, 1H), 8.65 (s, 1H), 8.51-8.48 (d, J=9.2 Hz, 1H), 8.46-8.45 (d, J=4.4 Hz, 1H), 8.38 (s, 1H), 7.28-7.27 (d, J=4.8 Hz, 1H), 7.36-7.32 (m, 1H), 6.78 (s, 1H), 4.42-4.38 (m, 1H), 4.13 (bs, 2H), 3.84-3.82 (d, J=8.4 Hz, 3H), 3.51 (s, 1H), 3.23 (s, 3H), 3.11-3.10 (d, J=4.4 Hz, 3H), 2.20-2.13 (m, 2H), 1.57-1.48 (m, 2H), 1.24 (bs, 2H)).

Example 99: 5-(1-((1R,5S,6r)-3-oxabicyclo[3.1.0]hexan-6-yl)-1H-pyrrolo[2,3-b]pyridin-3-yl)-N-((1S,2S)-2-methoxycyclobutyl)-7-(methylamino)pyrazolo[1,5-a]pyrimidine-3-carboxamide (I-793) & 5-(1-((1R,5S,6r)-3-oxabicyclo[3.1.0]hexan-6-yl)-1H-pyrrolo[2,3-b]pyridin-3-yl)-N-((1R,2R)-2-methoxycyclobutyl)-7-(methylamino)pyrazolo[1,5-a]pyrimidine-3-carboxamide (I-794)

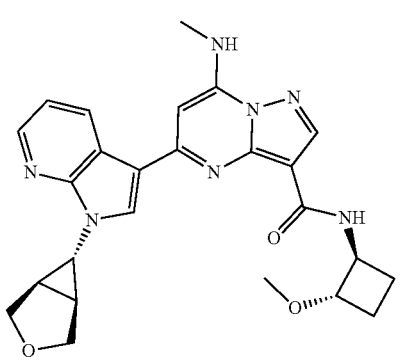

I-793

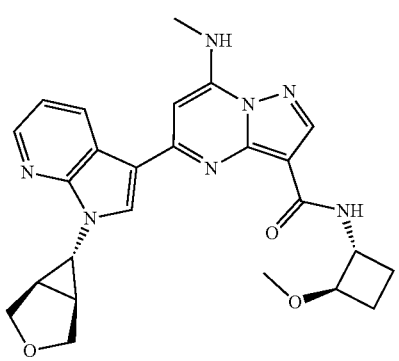

I-794

Scheme 99

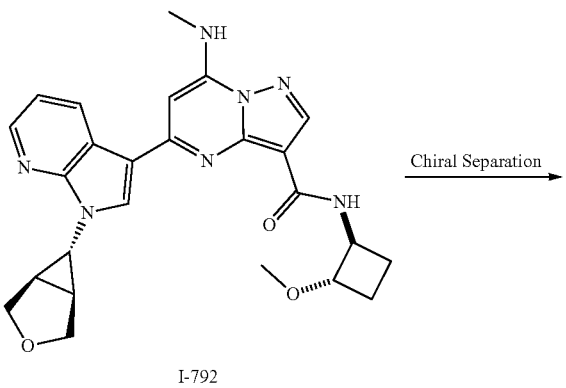

I-792

Chiral Separation →

843
-continued

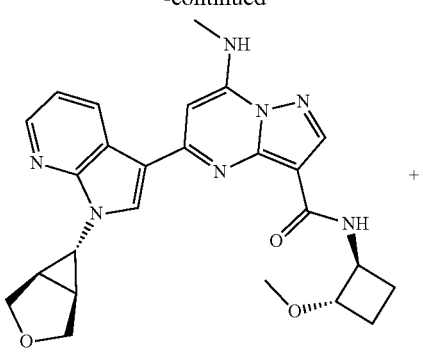

I-793

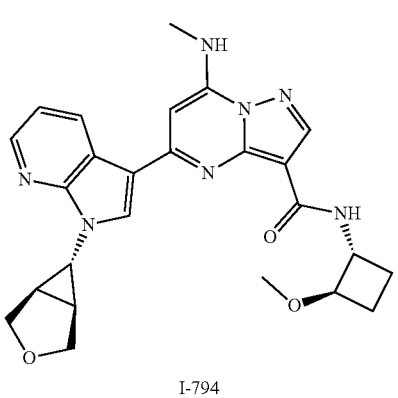

I-794

Step 1—Synthesis of Compounds I-793 & I-794: Isomers of I-792 (0.075 g) were separated out using column CHIRALCEL OJ-H (250 mm*4.6 mm, 5 μm) and 0.1% DEA in methanol as co-solvent with flow rate of 4 mL/min to get pure fraction-1 (FR-a) and fraction-2 (FR-b).

FR-a was concentrated under reduced pressure at 30° C. to afford pure I-793 (0.025 g; MS (ES): m/z 473.7 [M+H]+; LCMS purity: 100%; HPLC purity: 99.44%; CHIRAL HPLC purity: 96.65%; $^1$H NMR (DMSO-d$_6$, 400 MHZ): 8.77-8.75 (d, J=7.6 Hz, 1H), 8.64 (s, 1H), 8.49-8.47 (d, J=8.4 Hz, 1H), 8.45-8.44 (d, J=4 Hz, 1H), 8.37 (s, 1H), 7.27-7.26 (d, J=4.4 Hz, 1H), 7.35-7.31 (m, 1H), 6.77 (s, 1H), 4.14-4.12 (m, 2H), 3.83-3.81 (d, J=8 Hz, 2H), 3.50 (s, 2H), 3.22 (s, 3H), 3.10-3.09 (d, J=4.4 Hz, 3H), 2.20-2.12 (m, 3H), 1.58-1.47 (m, 2H), 1.23 (bs, 2H)).

FR-b was concentrated under reduced pressure at 30° C. to afford pure I-794 (0.027 g; MS (ES): m/z 473.51 [M+H]+; LCMS purity: 100%; HPLC purity: 98.86%; CHIRAL HPLC purity: 97.20%; $^1$H NMR (DMSO-d$_6$, 400 MHZ): 8.77-8.75 (d, J=7.6 Hz, 1H), 8.64 (s, 1H), 8.50-8.47 (d, J=8.4 Hz, 1H), 8.45-8.44 (d, J=4 Hz, 1H), 8.37 (s, 1H), 7.27-7.26 (d, J=4.4 Hz, 1H), 7.35-7.33 (m, 1H), 6.77 (s, 1H), 4.14-4.12 (m, 2H), 3.83-3.81 (d, J=8 Hz, 2H), 3.50 (s, 2H), 3.22 (s, 3H), 3.10-3.09 (d, J=4.4 Hz, 3H), 2.19-2.12 (m, 3H), 1.58-1.47 (m, 2H), 1.23 (bs, 2H)).

844

Example 100: 5-(1-(2-(dimethylamino)-2-oxoethyl)-1H-pyrrolo[2,3-b]pyridin-3-yl)-N-(2-methoxycyclobutyl)-7-(methylamino)pyrazolo[1,5-a]pyrimidine-3-carboxamide (I-920)

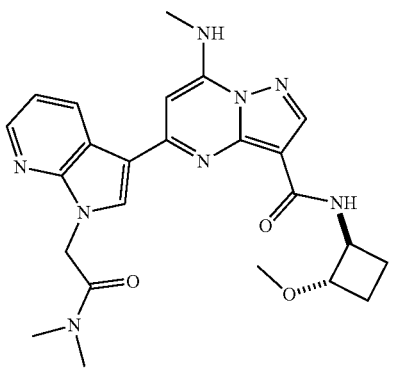

I-920

Scheme 100

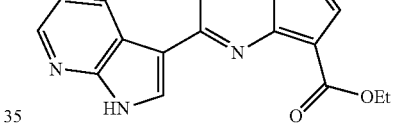

100

MeOH, THF, H$_2$O LiOH, RT

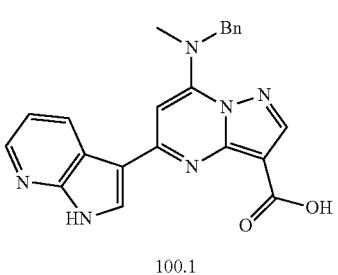

100.1

100.2

DMF, HATU, DIPEA, RT

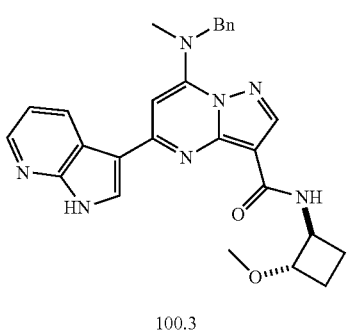

100.3

100.4

DMF, Cs$_2$CO$_3$
80° C., 7 h

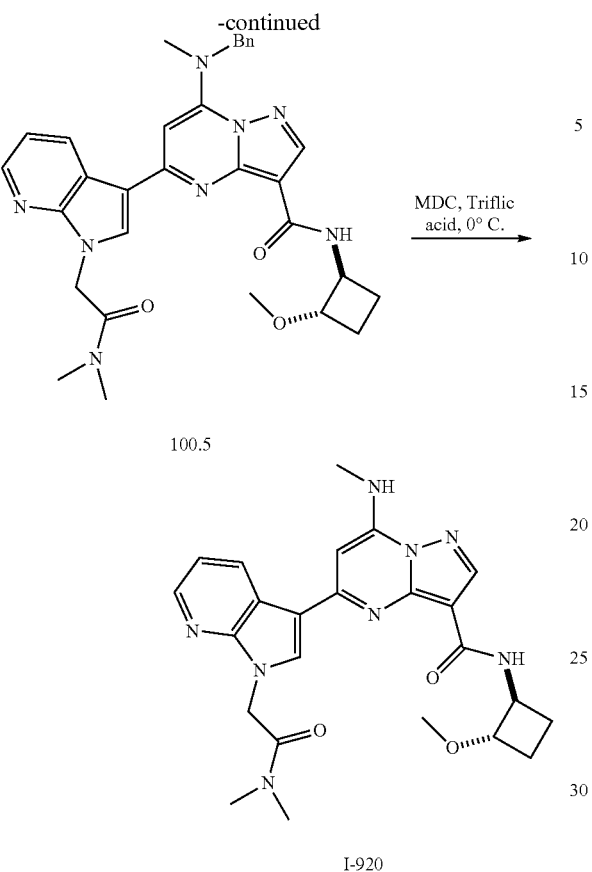

in dichloromethane to obtain 100.5. (0.150 g, Yield: 72.84%). MS (ES): m/z 567.2 [M+H]$^+$ Synthesis of compound I-920: A solution of 100.5 (0.040 g, 0.070 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-920 (0.025 g, Yield: 74.32%). MS (ES): m/z 477.41 [M+H]$^+$ LCMS purity: 100%, HPLC purity: 98.34%, CHIRAL HPLC: 48.72%, 48.75%, $^1$H NMR (DMSO-d$_6$, 400 MHZ): 8.78-8.76 (d, J=7.2 Hz, 1H), 8.57 (s, 1H), 8.55-8.53 (d, J=8.8 Hz, 1H), 8.39 (s, 2H), 8.29-8.28 (d, J=4.8 Hz, 1H), 7.34-7.31 (m, 1H), 6.69 (s, 1H), 5.35 (s, 2H), 4.43-4.39 (m, 1H), 3.24 (s, 6H), 3.10-3.09 (d, J=4.8 Hz, 3H), 2.90 (s, 3H), 2.21-2.13 (m, 2H), 1.56 (bs, 3H).

Example 101: N-(2-methoxycyclobutyl)-5-(1-((1s, 3S)-3-methoxycyclobutyl)-1H-pyrrolo[2,3-b]pyridin-3-yl)-7-(methylamino)pyrazolo[1,5-a]pyrimidine-3-carboxamide (I-925)

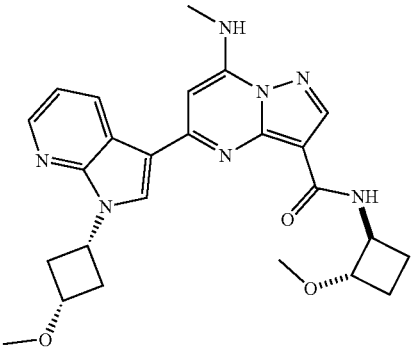

Synthesis of compound 100. Compound 100 was synthesized as per experimental protocol of Core D to obtain 100. (Yield: 83.64%). MS (ES): m/z 427.18 [M+H]$^+$ Synthesis of compound 100.1. To a solution of 100 (0.3 g, 0.70 mmol, 1.0 eq), in tetrahydrofuran:methanol:water (6 mL, 2:1:1) was added lithium hydroxide (0.294 g, 7.0 mmol, 10 eq). The reaction was stirred at room temperature for 24 h. After completion of reaction, reaction mixture was concentrated under reduced pressure to obtain a residue. To this was added water and acidified with 1N hydrochloric acid to adjust pH~6-6.5 at 10° C. The product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 100.1. (0.240 g, Yield: 85.63%). MS (ES): m/z 399.15 [M+H]$^+$ Synthesis of compound 100.3. Compound 100.3 was synthesized using general procedure A to obtain 100.3. (0.175 g, Yield: 60.33%). MS (ES): m/z 482.23 [M+H]$^+$ Synthesis of compound 100.5. To a solution of 100.3 (0.175 g, 0.36 mmol, 1.0 eq), in dimethylformamide (2 mL) was added 100.4 (0.119 g, 0.72 mmol, 2.0 eq) and Cesium carbonate (0.351 g, 1.08 mmol, 3.0 eq). The reaction mixture was stirred at 80° C. for 7 h. After completion of reaction, the reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.8% methanol Scheme 101

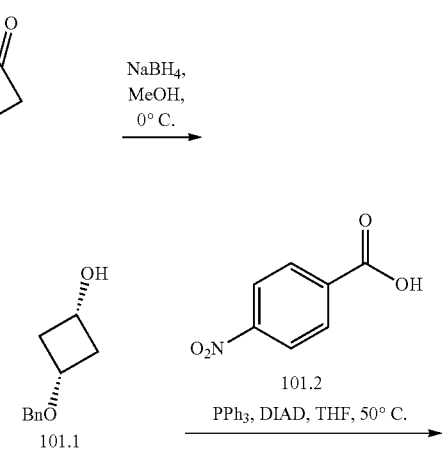

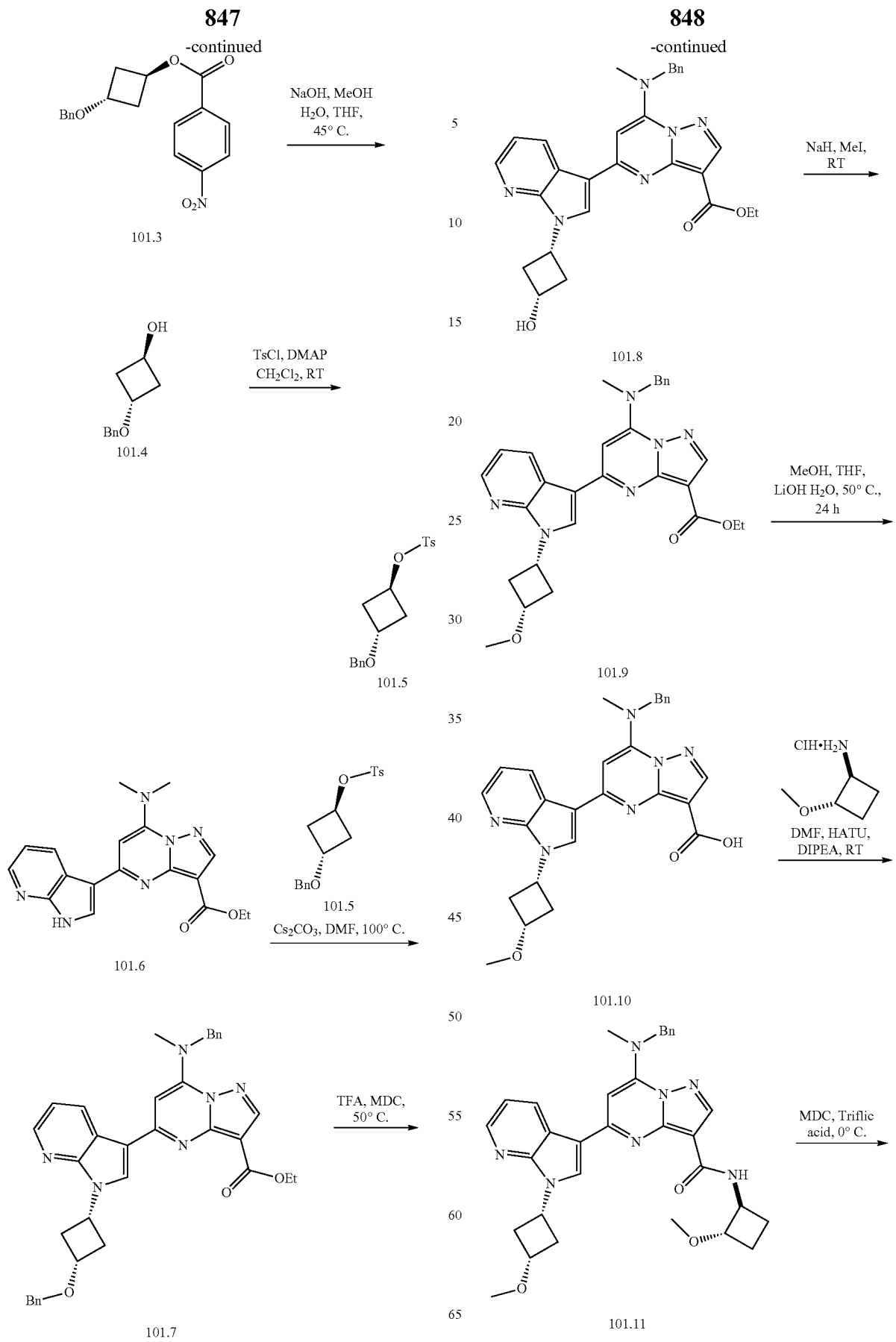

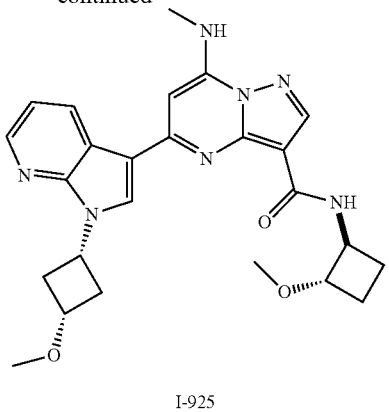

I-925

Synthesis of compound 101.1. The solution of 1 (4.0 g, 22.72 mmol, 1.0 eq) in methanol (40 mL) was cooled to 0° C. and sodium borohydride (0.949 g, 24.99 mmol, 1.1 eq) was added portion wise. Reaction mixture was stirred at room temperature for 1 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and compound was eluted in 20% ethyl acetate in hexane to obtain pure 101.1. (2.78 g, Yield: 68.71%), MS (ES): m/z 178.23 [M+H]$^+$ Synthesis of compound 101.3. To a cooled solution of 101.1 (2.78 g, 15.61 mmol, 1.0 eq) and 101.2 (3.1 g, 18.73 mmol, 1.2 eq) in tetrahydrofuran (30 mL) was added Triphenylphosphine (8.1 g, 31.22 mmol, 2.0 eq) and the reaction mixture was stirred for 5 min. Diisopropyl azodicarboxylate (6.1 mL, 31.22 mmol, 2.0 eq) was added dropwise and reaction mixture stirred at room temperature for 16 h. After completion of reaction, reaction mixture was concentrated under reduced pressure, added 1N Sodium hydroxide solution and extracted with dichloromethane. Organic layer was combined, washed with brine solution, dried over sodium sulphate and concentrated under reduced pressure to obtain crude material. This was further purified by 6% ethyl acetate in hexane to obtain 101.3. (2.8 g, Yield: 54.84%), MS (ES): m/z 328.11 [M+H]$^+$ Synthesis of compound 101.4. To a solution of 101.3 (2.8 g, 8.56 mmol, 1.0 eq), in methanol:tetrahydrofuran:water (4 mL, 2:1) was added sodium hydroxide (1.7 g, 42.8 mmol, 5.0 eq). The reaction was stirred at 45° C. for 16 h. After completion of reaction, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 25% ethyl acetate in hexane to obtain pure 101.4. (1.1 g, Yield: 72.15%). MS (ES): m/z 178.23 [M+H]$^+$ Synthesis of compound 101.5. To the solution of compound 101.4 (1.1 g, 6.1 mmol, 1.0 eq) in dichloromethane (15 mL) was added Triethylamine (1.2 g, 12.2 mmol, 2.0 eq). After 10 min, 4-Toluenesulfonyl chloride (1.2 g, 6.71 mmol, 1.1 eq) was added portion wise into reaction mixture at room temperature followed by 4-Dimethylaminopyridine (0.074 g, 0.61 mmol, 0.1 eq) and reaction mixture was stirred at same temperature for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 12% ethyl acetate in hexane to obtain 101.5. (1.6 g, Yield: 77.99%). MS (ES): m/z 333.1 [M+H]$^+$ Synthesis of compound 101.6. Compound was synthesized as per experimental protocol of Core D to obtain 101.6. (Yield: 83.64%), MS (ES): m/z 427.18 [M+H]$^+$ Synthesis of compound 101.7. To a solution of 101.6 (0.5 g, 1.17 mmol, 1.0 eq) in dimethylformamide (5 mL) was added 101.5 (0.776 g, 2.34 mmol, 2.0 eq) and cesium carbonate (1.14 g, 3.51 mmol, 3.0 eq). The reaction mixture was stirred at 100° C. for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 101.7. (0.295 g, Yield: 42.89%). MS (ES): m/z 587.2 [M+H]$^+$ Synthesis of compound 101.8. The compound 101.7 (0.295 g, 0.50 mmol, 1.0 eq) was dissolved in dichloromethane (8 mL) and trifluoroacetic acid (0.5 mL) was added to the reaction mixture. The reaction was stirred at 50° C. for 2 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 101.8. (0.195 g, Yield: 78.10%). MS (ES): m/z 497.2 [M+H]$^+$ Synthesis of compound 101.9. To a solution of 101.8 (0.195 g, 0.39 mmol, 1.0 eq) in Dimethylformamide (2 mL), was added sodium hydride (0.02 g, 0.78 mmol, 2 eq) at 0° C. and stirred for 20 min. Methyl iodide (0.060 g, 0.42 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulphate and concentrated under reduced pressure to obtain crude material. This was further purified by column chromatography and the compound was eluted in 1.9% methanol in dichloromethane to obtain 101.9. (0.180 g, Yield: 89.77%). MS (ES): m/z 511.24 [M+H]$^+$ Synthesis of compound 101.10. To a solution of 101.9 (0.180 g, 0.35 mmol, 1.0 eq), in tetrahydrofuran:methanol:water (5 mL, 2:1:1) was added lithium hydroxide (0.147 g, 3.5 mmol, 10 eq). The reaction was stirred at 50° C. for 24 h. After completion of reaction, reaction mixture was concentrated under reduced pressure to obtain a residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 101.10. (0.148 g, Yield: 87.00%). MS (ES): m/z 483.2 [M+H]$^+$ Synthesis of compound 101.11. Compound was synthesized using general procedure A to obtain 101.11. (0.145 g, Yield: 83.57%), MS (ES): m/z 566.2 [M+H]+

Synthesis of compound I-925: A solution of 101.11 (0.040 g, 0.070 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-925 (0.025 g, Yield: 74.34%). MS (ES): m/z 476.66 [M+H]+ LCMS purity: 100%, HPLC purity: 98.34%, CHIRAL HPLC: 48.71%, 49.43%, $^1$H NMR (DMSO-$d_6$, 400 MHZ): 8.94 (bs, 1H), 8.80-8.78 (d, J=7.6 Hz, 1H), 8.53-8.50 (d, J=9.2 Hz, 1H), 8.41 (bs, 1H), 8.38 (bs, 1H), 8.27 (bs, 1H), 7.33-7.29 (m, 1H), 6.91 (bs, 1H), 5.10-5.06 (m, 1H), 4.43-4.39 (t, J=8 Hz, 1H), 3.93-3.89 (m, 1H), 3.83 (bs, 1H), 3.28 (bs, 3H), 3.24 (bs, 3H), 3.14-3.13 (t, J=4 Hz, 3H), 2.92 (bs, 2H), 2.21-2.13 (m, 2H), 1.60-1.52 (m, 2H), 1.25 (bs, 2H).

Example 102: 5-(1-(2-(azetidin-1-yl)-2-oxoethyl)-1H-pyrrolo[2,3-b]pyridin-3-yl)-N-(2-methoxycyclobutyl)-7-(methylamino)pyrazolo[1,5-a]pyrimidine-3-carboxamide (I-928)

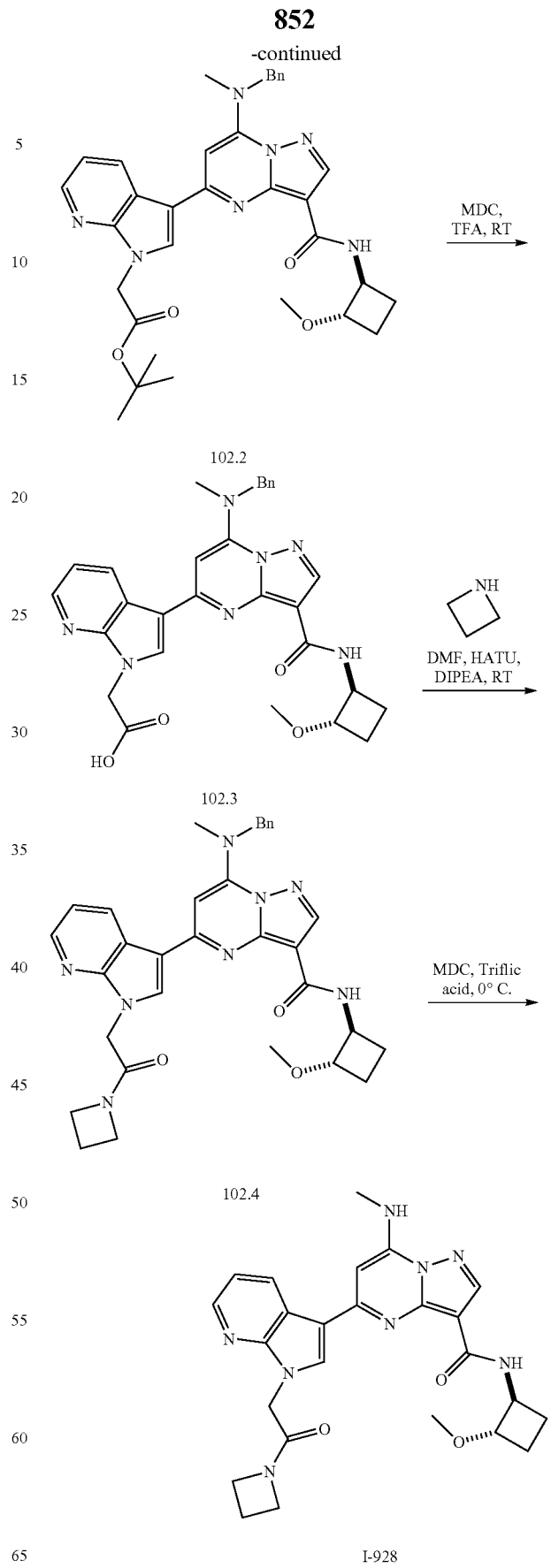

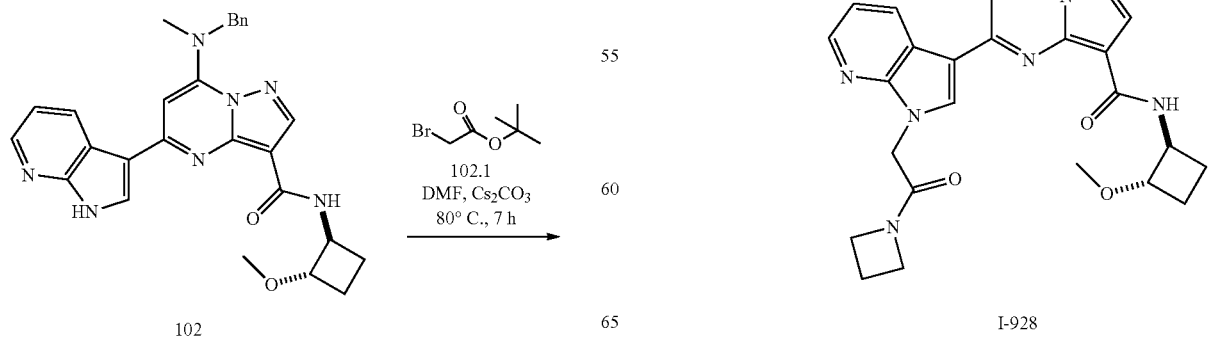

Scheme 102

Synthesis of compound 102. Compound 102 was synthesized as per experimental protocol of 1-920 to obtain 102. (Yield: 60.33%). MS (ES): m/z 482.23 [M+H]+

Synthesis of compound 102.2. To a solution of 102 (0.175 g, 0.64 mmol, 1.0 eq), in dimethylformamide (3 mL) was added 102.1 (0.249 g, 1.28 mmol, 2.0 eq) and Cesium carbonate (0.624 g, 1.92 mmol, 3.0 eq). The reaction mixture was stirred at 80° C. for 7 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 102.2. (0.270 g, Yield: 70.41%). MS (ES): m/z 596.2 [M+H]+

Synthesis of compound 102.3. The compound 102.2 (0.270 g, 0.45 mmol, 1.0 eq) was dissolved in dichloromethane (4 mL) and trifluoroacetic acid (2 mL) was added to the reaction mixture. The reaction was stirred at room temperature for 4 h. After completion of reaction, reaction mixture was transferred into water and product was extracted with ethyl acetate. Organic layer was combined, dried over sodium sulphate and concentrated under reduced pressure to obtain crude material. This was further purified by trituration with diethyl ether to obtain pure 102.3. (0.190 g, Yield: 77.69%). MS (ES): m/z 540.23 [M+H]+

Synthesis of compound 102.4. Compound 102.4 was synthesized using general procedure A to obtain 102.4. (0.140 g, Yield: 68.71%). MS (ES): m/z 579.28 [M+H]+

Synthesis of compound I-928: A solution of 102.4 (0.040 g, 0.069 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-928 (0.023 g, Yield: 68.11%). MS (ES): m/z 489.34 [M+H]+ LCMS purity: 99.16%, HPLC purity: 98.36%, CHIRAL HPLC: 49.56%, 48.30%, 1H NMR (DMSO-$d_6$, 400 MHZ): 8.76-8.75 (d, J=6.8 Hz, 1H), 8.58 (s, 1H), 8.52-8.50 (d, J=8.8 Hz, 1H), 8.39-8.38 (d, J=4.4 Hz, 1H), 8.37 (s, 1H), 8.30-8.29 (d, J=4.8 Hz, 2H), 7.34-7.30 (m, 1H), 6.69 (s, 1H), 5.05 (s, 2H), 4.41-4.37 (t, J=8 Hz, 1H), 4.34-4.30 (t, J=7.6 Hz, 2H), 3.95-3.91 (t, J=7.6 Hz, 2H), 3.85-3.80 (m, 2H), 3.22 (s, 3H), 3.09-3.08 (d, J=4.8 Hz, 3H), 2.34-2.26 (m, 2H), 2.19-2.11 (m, 2H), 1.58-1.49 (m, 1H).

Example 103: N-(2-methoxycyclobutyl)-5-(1-((1s,3R)-3-(methoxymethyl)cyclobutyl)-1H-pyrrolo[2,3-b]pyridin-3-yl)-7-(methylamino)pyrazolo[1,5-a]pyrimidine-3-carboxamide (I-932)

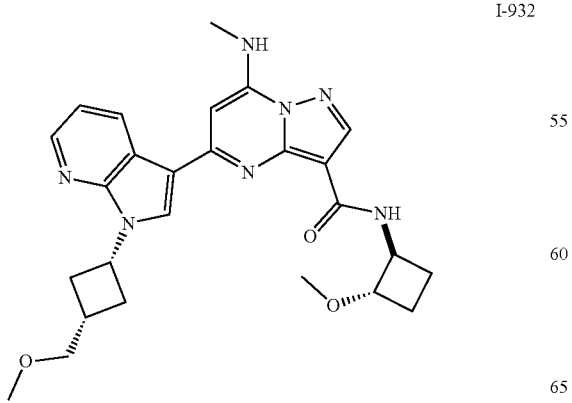

I-932

Scheme 103

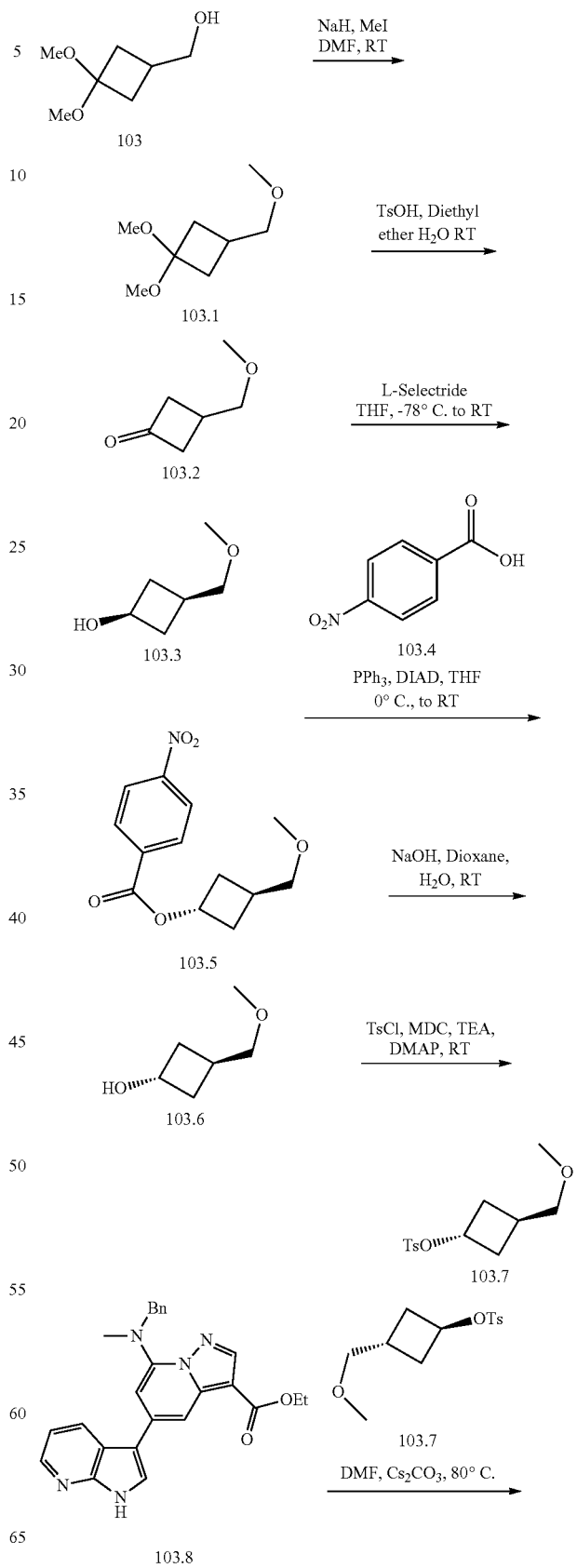

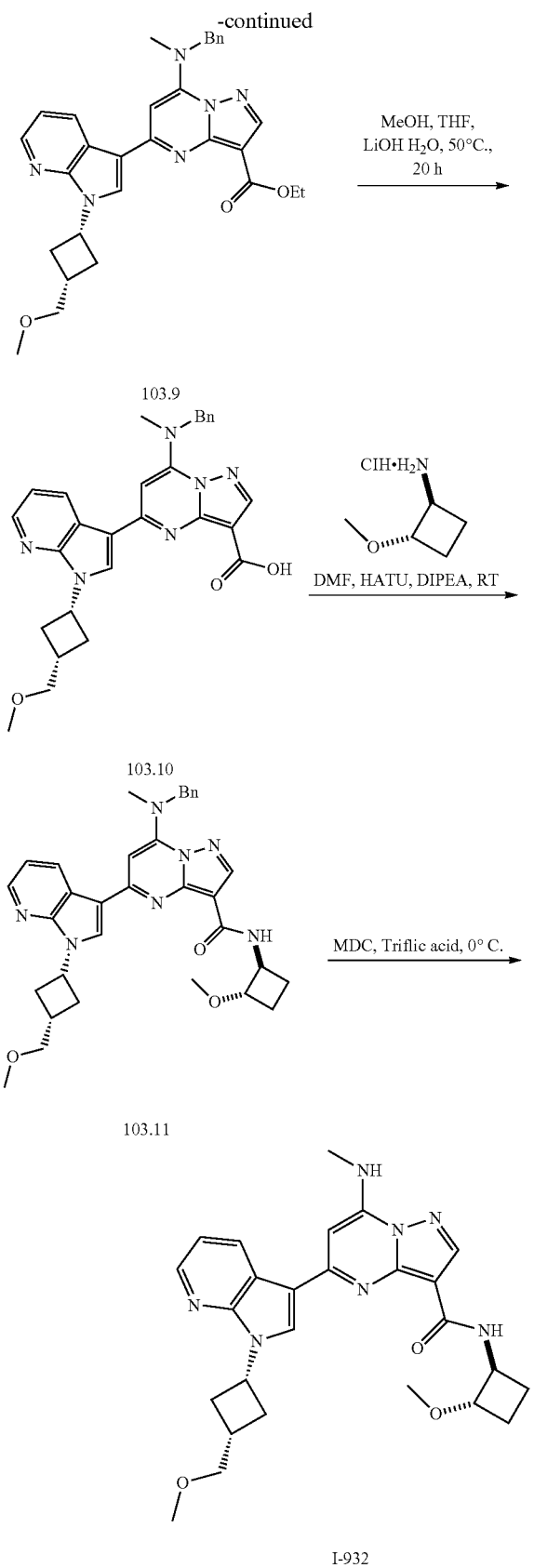

Synthesis of compound 103.1. To a solution of 103 (15.0 g, 102.73 mmol, 1.0 eq) in Dimethylformamide (150 mL), was added sodium hydride (4.9 g, 205.46 mmol, 2.0 eq) at 0° C. and stirred for 20 min. Methyl iodide (16.0 g, 113.0 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulphate and concentrated under reduced pressure to obtain crude material. This was further purified by column chromatography and the compound was eluted in 10% ethyl acetate in hexane to obtain 103.1. (8.7 g, Yield: 52.92%). MS (ES): m/z 161.1 [M+H]$^+$ Synthesis of compound 103.2. To a solution of 103.1 (8.7 g, 54.37 mmol, 1.0 eq) in diethyl ether (170 mL) was added water (10 mL). Then p-Toluenesulfonic acid (1.0 g, 5.43 mmol, 0.1 eq) was added and stirred for 2 h at room temperature. After completion of reaction, sodium sulphate was added to the reaction mixture to remove water then ether layer was concentrated under reduced pressure and triturated with diethyl ether to obtain 103.2. (5.9 g, Yield: 95.19%). MS (ES): m/z 115.0 [M+H]$^+$ Synthesis of compound 103.3. To a solution of 103.2 (5.9 g, 51.75 mmol, 1.0 eq) in tetrahydrofuran (70 mL) was added dropwise L-selectride (1M in tetrahydrofuran) (77.6 mL, 77.62 mmol, 1.5 eq) at −78° C. and stirred for 1 h at same temperature. After completion of reaction, reaction mixture was transferred into aqueous sodium hydroxide solution and extracted with ethyl acetate. Organic layer was combined, dried over sodium sulphate and concentrated under reduced pressure to obtain crude material. This was further purified by column chromatography and the compound was eluted in 20% ethyl acetate in hexane to obtain 103.3. (3.1 g, Yield: 51.63%). MS (ES): m/z 117.0 [M+H]$^+$ Synthesis of compound 103.5. To a cooled solution of 103.3 (3.1 g, 26.72 mmol, 1.0 eq) in tetrahydrofuran (40 mL) was added 103.4 (5.3 g, 32.06 mmol, 1.2 eq) and Triphenylphosphine (14.0 g, 53.44 mmol, 2.0 eq) at 0° C. and stirred for 5 min. Diisopropyl azodicarboxylate (10.5 mL, 53.44 mmol, 2.0 eq) was added dropwise and stirred at room temperature for 16 h. After completion of reaction, reaction mixture was concentrated under reduced pressure, added 1N Sodium hydroxide solution and extracted with dichloromethane. Organic layer was combined, washed with brine solution, dried over sodium sulphate and concentrated under reduced pressure to obtain crude material. This was further purified by 6% ethyl acetate in hexane to obtain 103.5. (1.9 g, Yield: 26.84%), MS (ES): m/z 266.1 [M+H]$^+$ Synthesis of compound 103.6. To a solution of 103.5 (1.9 g, 7.16 mmol, 1.0 eq), in methanol:water (26 mL, 2:1) was added lithium hydroxide (1.5 g, 35.8 mmol, 5.0 eq). The reaction was stirred at 45° C. for 16 h. After completion of reaction, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 25% ethyl acetate in hexane to obtain pure 103.6. (0.460 g, Yield 55.29%). MS (ES): m/z 117.0 [M+H]$^+$ Synthesis of compound 103.7. To the solution of compound 103.6 (0.460 g, 3.96 mmol, 1.0 eq) in dichloromethane (10 mL) was added Triethylamine (1.19 g, 11.88 mmol, 3.0 eq) and 4-Dimethylaminopyridine (0.096 g, 0.79 mmol, 0.2 eq) at 0° C. Then 4-Toluenesulfonyl chloride (1.13 g, 5.94 mmol, 1.5 eq) was added portionwise into reaction mixture at room temperature and reaction mixture was stirred at same temperature for 8 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 5% ethyl acetate in hexane to obtain 103.7. (0.610 g, Yield: 56.98%). MS (ES): m/z 271.1 [M+H]⁺

Synthesis of compound 103.8. Compound 103.8 was synthesized as per experimental protocol of Core D to obtain 103.8. (Yield: 83.64%), MS (ES): m/z 427.18 [M+H]⁺

Synthesis of compound 103.9. To a solution of 103.8 (0.3 g, 0.70 mmol, 1.0 eq) in dimethylformamide (5 mL) was added 103.7 (0.226 g, 0.84 mmol, 1.2 eq) and cesium carbonate (0.455 g, 1.4 mmol, 2.0 eq). The reaction mixture was stirred at 100° C. for 2 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 103.9. (0.190 g, Yield: 51.49%). MS (ES): m/z 525.2 [M+H]⁺

Synthesis of compound 103.10. To a solution of 103.9 (0.190 g, 0.36 mmol, 1.0 eq), in methanol:tetrahydrofuran:water (8 mL, 2:2; 1) was added lithium hydroxide (0.075 g, 1.8 mmol, 5.0 eq). The reaction was stirred at 50° C. for 20 h. After completion of reaction, reaction mixture was concentrated under reduced pressure to obtain a residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 25% ethyl acetate in hexane to obtain pure 103.10. (0.160 g, Yield: 88.97%). MS (ES): m/z 497.2 [M+H]⁺

Synthesis of compound 103.11. Compound 103.11 was synthesized using general procedure A to obtain 103.11. (0.140 g, Yield: 74.95%), MS (ES): m/z 580.3 [M+H]⁺

Synthesis of compound I-932: A solution of 103.11 (0.040 g, 0.069 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-932 (0.021 g, Yield: 62.16%). MS (ES): m/z 490.42 [M+H]⁺ LCMS purity: 100%, HPLC purity: 99.93%, CHIRAL HPLC: 49.86%, 50.13%, ¹H NMR (DMSO-d₆, 400 MHZ): 8.81 (bs, 1H), 8.76-8.75 (d, J=6.8 Hz, 1H), 8.52-8.50 (d, J=9.2 Hz, 1H), 8.40-8.39 (d, J=3.6 Hz, 1H), 8.37 (s, 1H), 8.28-8.27 (d, J=4.8 Hz, 1H), 7.32-7.29 (m, 1H), 6.81 (s, 1H), 5.31-5.27 (t, J=8 Hz, 1H), 4.41-4.37 (m, 1H), 3.80 (bs, 1H), 3.50-3.49 (d, J=6 Hz, 2H), 3.30 (s, 3H), 3.22 (s, 3H), 3.13-3.12 (d, J=4.8 Hz, 3H), 2.37-2.32 (s, 2H), 2.19-2.11 (m, 2H), 1.58-1.47 (m, 2H), 1.56 (bs, 2H), 1.24 (bs, 1H).

Example 104: 5-(7-(2-(azetidin-1-yl)-2-oxoethyl)-7H-pyrrolo[2,3-b]pyridin-3-yl)-N-(2-methoxycyclobutyl)-7-(methylamino)pyrazolo[1,5-a]pyrimidine-3-carboxamide (I-967)

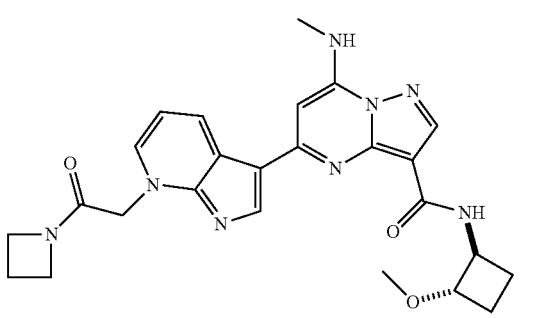

Scheme 104

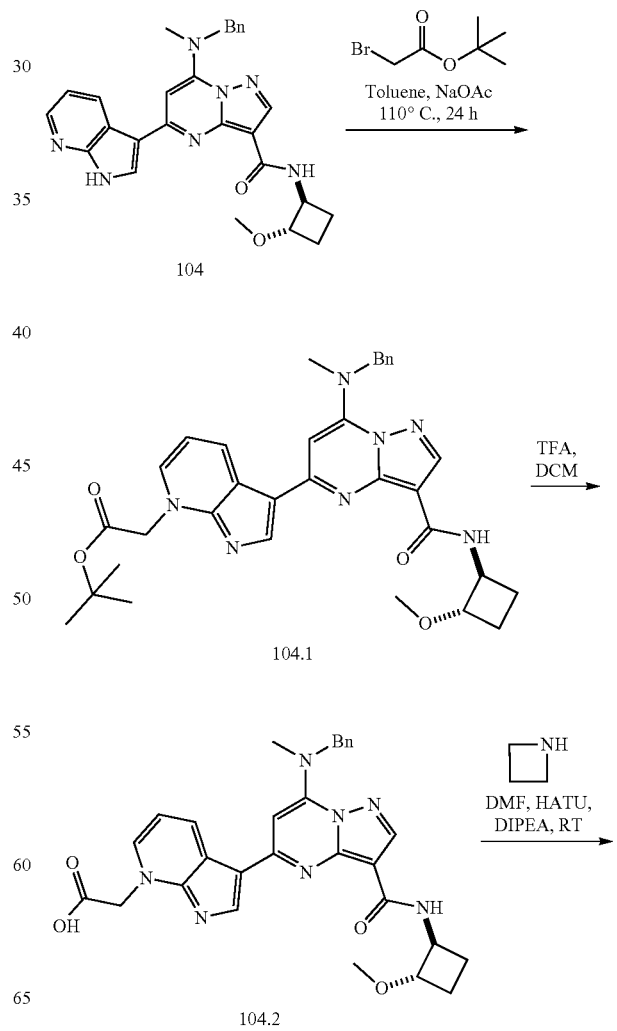

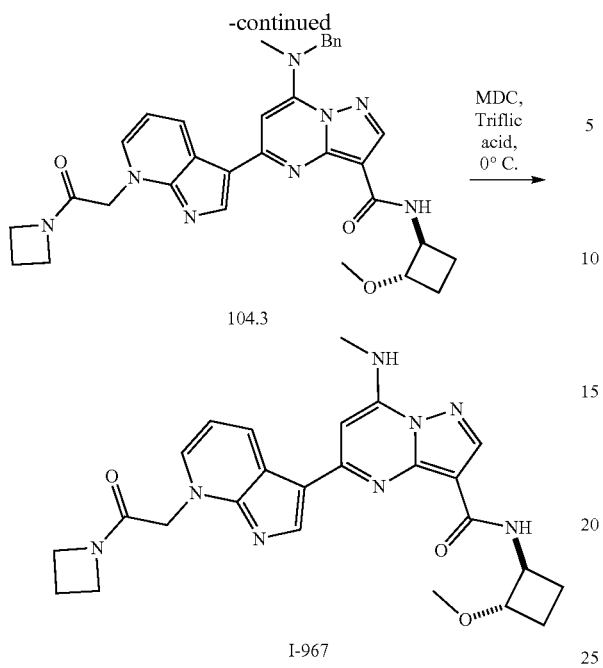

Synthesis of compound 104. Compound 104 was synthesized as per experimental protocol of 1-920 to obtain 104. (Yield: 60.33%). MS (ES): m/z 482.23 [M+H]+

Synthesis of compound 104.1. To a solution of 1 (0.5 g, 1.03 mmol, 1.0 eq) in toluene (15 mL) was added tert-butyl 2-bromoacetate (0.401 g, 2.06 mmol, 2.0 eq) and Sodium acetate (0.253 g, 3.09 mmol, 3.0 eq). The reaction mixture was stirred at 110° C. for 24 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.3% methanol in dichloromethane to obtain 104.1. (0.360 g, Yield: 58.20%). MS (ES): m/z 596.29 [M+H]+

Synthesis of compound 104.2. The compound 104.1 (0.360 g, 0.60 mmol, 1.0 eq) was dissolved in dichloromethane (3 mL) and trifluoroacetic acid (1 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by column chromatography and the compound was eluted in 1.8% methanol in dichloromethane to obtain 104.2. (0.310 g, Yield: 95.07%). MS (ES): m/z 540.23 [M+H]+

Synthesis of compound 104.3. Compound 104.3 was synthesized using general procedure A to obtain 104.3. (0.130 g, Yield: 78.21%). MS (ES): m/z 579.28 [M+H]+

Synthesis of compound I-967: A solution of 104.3 (0.040 g, 0.069 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-967 (0.032 g, Yield: 94.76%). MS (ES): m/z 489.39 [M+H]+ LCMS purity: 100%, HPLC purity: 99.22%, CHIRAL HPLC: 50.27%, 48.81%, $^1$H NMR (DMSO-d$_6$, 400 MHZ): 8.97-8.95 (d, J=7.6 Hz, 1H), 8.63 (s, 1H), 8.59-8.57 (d, J=9.2 Hz, 1H), 8.32 (s, 1H), 8.23-8.22 (d, J=6 Hz, 1H), 8.13-8.12 (d, J=4.8 Hz, 1H), 7.31-7.28 (m, 1H), 6.67 (s, 1H), 5.47 (s, 2H), 4.44-4.38 (m, 2H), 3.98-3.94 (t, J=7.6 Hz, 1H), 3.87-3.82 (m, 1H), 3.25 (s, 3H), 3.10-3.09 (d, J=4.8 Hz, 3H), 2.39-2.31 (m, 2H), 2.22-2.13 (m, 2H), 1.60-1.50 (m, 2H), 1.12-1.08 (m, 2H).

Example 105: N-(2-hydroxy-2-(trifluoromethyl)cyclobutyl)-7-(methylamino)-5-((2-oxo-1-(tetrahydro-2H-pyran-4-yl)-1,2-dihydropyridin-3-yl)amino)pyrazolo[1,5-a]pyrimidine-3-carboxamide (I-968)

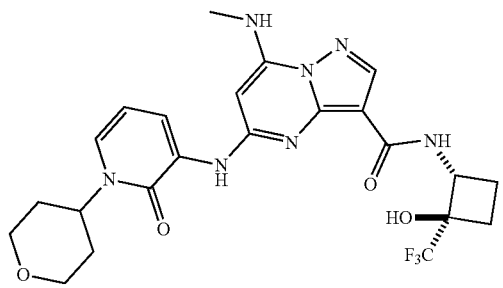

Scheme 105

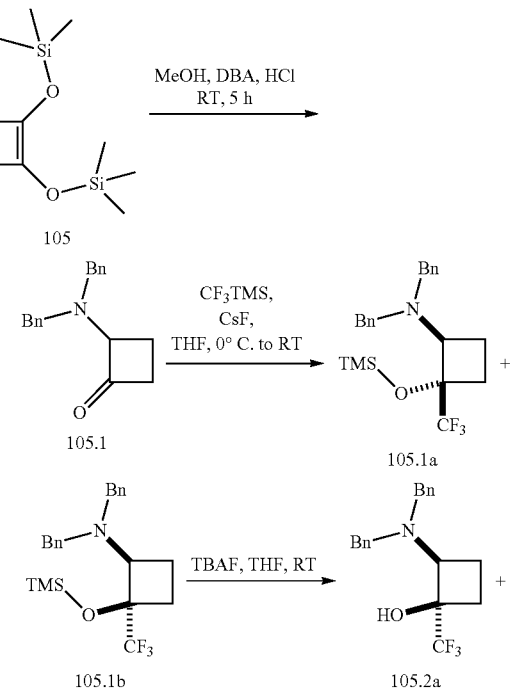

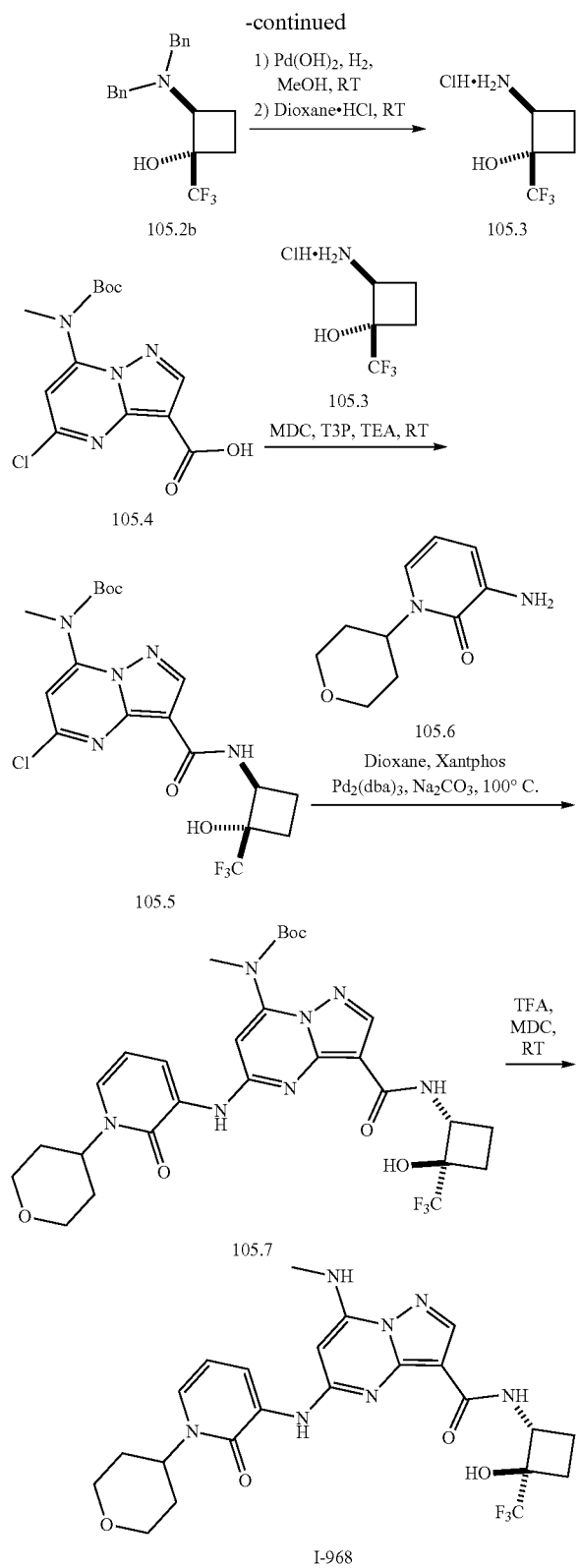

transferred into ice cold water, precipitated solid was filtered, washed with water followed by diethyl ether and dried well to obtain pure 105.1. (14.0 g, Yield: 60.79%). MS (ES): m/z 266.1 [M+H]+

Synthesis of compound 105.1a. and 105.1b. A solution of 105.1 (14 g, 52.83 mmol, 1.0 eq) in tetrahydrofuran (200 mL) was cooled to 0° C., and cesium fluoride (0.8 g, 5.28 mmol, 0.1 eq) and Trimethyl(trifluoromethyl)silane (11.2 g, 79.24 mmol, 1.5 eq) were added and stirred at room temperature for 3 h. To this was added dropwise 105.3 (dissolved in tetrahydrofuran) (0.151 g, 0.79 mmol, 1.3 eq). The reaction mixture was stirred at room temperature for 1 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2% ethyl acetate in hexane to obtain mixture of 105.1a. and 105.1b. (7.3 g, Yield: 33.95%). MS (ES): m/z 408.1[M+H]+

Synthesis of compound 105.2a and 105.2b. A mixture of 105.1a and 105.1b (6.8 g, 16.70 mmol, 1.0 eq) in tetrahydrofuran (2 mL) was cooled to 0° C. and Tetra-n-butylammonium fluoride (1M in tetrahydrofuran) (16.7 mL, 16.70 mmol, 1.0 eq) was added. Reaction mixture was stirred at same temperature for 30 min. After completion of reaction, reaction mixture was transferred into water and product was extracted with ethyl acetate. Organic layer was combined, dried over sodium sulphate and concentrated under reduced pressure to obtain crude material. This was further purified by column chromatography and the compound was eluted in 5% ethyl acetate in hexane to obtain separately 105.2a and 105.2b (Yield: 26.86%). MS (ES): m/z 336.15 [M+H]+

Synthesis of compound 105.3. To a suspension of Palladium hydroxide on carbon (20%) in methanol (12 mL) and tetrahydrofuran (8 mL) was added 105.2b. (0.6 g, 1.79 mmol, 1.0 eq) and reaction mixture was stirred at room temperature under hydrogen atmosphere for 3 h. After completion of reaction, reaction mixture was filtered through celite-bed and washed with methanol. Filtrate was concentrated under reduced pressure to obtain crude material which was stirred under hydrochloride solution 4.0 M in dioxane for 5 min and concentrated under reduced pressure to obtain pure 105.3. (0.2 g, Yield: 58.35%). MS (ES): m/z 192.04[M+H]+

Synthesis of compound 105.4 Compound 105.4 was synthesized as per experimental protocol of core synthesis to obtain 105.4. (Yield: 71.67%) MS (ES): m/z 327.08 [M+H]+

Synthesis of compound 105.5. To a solution of 105.4 (0.2 g, 0.61 mmol, 1.0 eq) in dichloromethane (5 mL) was added Triethylamine (0.308 g, 3.05 mmol, 5.0 eq) and propylphosphonicanhydride (0.290 g, 0.91 mmol, 1.5 eq) and stirred at room temperature for 5 min. To this was added dropwise 105.3 (dissolved in tetrahydrofuran) (0.151 g, 0.79 mmol, 1.3 eq). The reaction mixture was stirred at room temperature for 1 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 35% ethyl acetate in hexane to obtain 105.5. (0.2 g, Yield: 70.44%). MS (ES): m/z 464.1 [M+H]+

Synthesis of compound 105.1. To a solution of 105 (20 g, 86.95 mmol, 1.0 eq) in methanol (200 mL) was added dropwise Dibenzylamine (20.55 g, 104.34 mmol, 1.2 eq) at 0° C. Reaction mixture was stirred at room temperature for 5 h. After completion of reaction, reaction mixture was Synthesis of compound 105.6. Compound 105.6 was synthesized as per experimental protocol Intermediate A to obtain 105.6. (Yield: 36.13%), MS (ES): m/z 195.23 [M+H]$^+$ Synthesis of compound 105.7. Compound 105.7 was synthesized using general procedure B to obtain 105.7. (0.090 g, Yield: 67.16%). MS (ES): m/z 622.2 [M+H]$^+$ Synthesis of compound I-968: Compound I-968 was synthesized using general procedure C to obtain I-968 (0.017 g, Yield: 67.55%). MS (ES): m/z 522.65 [M+H]$^+$ LCMS purity: 98.48%, HPLC purity: 98.71%, CHIRAL HPLC: 52.01%, 44.68%, $^1$H NMR (DMSO-d$_6$, 400 MHZ): 8.86 (s, 1H), 8.23 (s, 1H), 8.16-8.14 (d, J=7.2 Hz, 1H), 7.94-7.93 (d, J=6 Hz, 1H), 7.86-7.84 (d, J=9.2 Hz, 1H), 7.49-7.47 (d, J=6.8 Hz, 1H), 6.71 (s, 1H), 5.77 (s, 1H), 4.90-4.85 (m, 1H), 4.03 (bs, 3H), 3.52-3.48 (d, J=10.8 Hz, 3H), 2.93-2.92 (d, J=4.4 Hz, 3H), 2.34-2.27 (m, 3H), 1.98 (bs, 1H), 1.78 (bs, 1H), 1.57 (s, 1H), 1.24 (bs, 2H).

Example 106: 5-(7-(2-hydroxy-2-methylpropyl)-7H-pyrrolo[2,3-b]pyridin-3-yl)-N-(2-methoxycyclobutyl)-7-(methylamino)pyrazolo[1,5-a]pyrimidine-3-carboxamide (I-979)

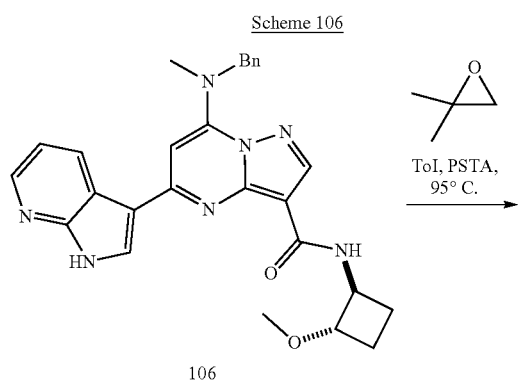

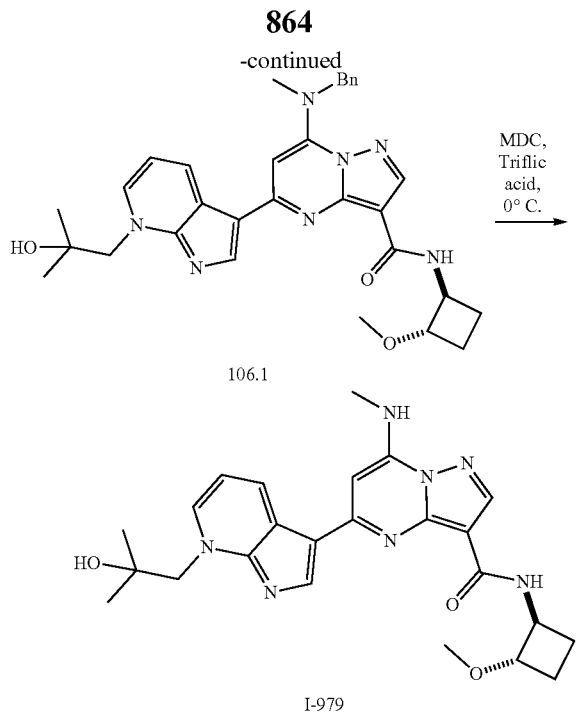

Synthesis of compound 106. Compound 106 was synthesized as per experimental protocol I-920 to obtain 106. (Yield: 60.33%). MS (ES): m/z 482.23 [M+H]$^+$ Synthesis of compound 106.1. To a solution of 106 (0.3 g, 0.62 mmol, 1.0 eq) in Toluene (5 mL) was added 2,2-dimethyloxirane (0.223 g, 3.1 mmol, 5.0 eq) and P-Toluenesulfonic Acid Monohydrate (0.047 g, 0.24 mmol, 3.0 eq). The reaction mixture was stirred at 95° C. for 7 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.8% methanol in dichloromethane to obtain 106.1. (0.140 g, Yield: 40.59%). MS (ES): m/z 554.28 [M+H]$^+$ Synthesis of compound I-979: A solution of 106.1 (0.040 g, 0.054 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-979 (0.013 g, Yield: 51.76%). MS (ES): m/z 464.63 [M+H]$^+$ LCMS purity: 95.0%, HPLC purity: 100%, CHIRAL HPLC: 47.51%, 48.64%, $^1$H NMR (DMSO-d$_6$, 400 MHZ): 8.97-8.95 (d, J=7.6 Hz, 1H), 8.64 (s, 1H), 8.58-8.56 (d, J=8.8 Hz, 1H), 8.32 (s, 1H), 8.26-8.25 (d, J=6 Hz, 1H), 8.11-8.10 (d, J=4.8 Hz, 1H), 7.30-7.27 (t, J=6.8 Hz, 1H), 6.67 (s, 1H), 4.80 (s, 2H), 4.45-4.39 (m, 1H), 3.82 (bs, 1H), 3.25 (s, 3H), 3.10-3.08 (d, J=4.8 Hz, 3H), 2.26-2.15 (m, 2H), 1.56 (bs, 1H), 1.23 (bs, 2H), 1.14 (s, 6H).

Example 107: N-(2-hydroxycyclobutyl)-5-(7-((3S,4R)-4-methoxytetrahydrofuran-3-yl)-7H-pyrrolo[2,3-b]pyridin-3-yl)-7-(methylamino)pyrazolo[1,5-a]pyrimidine-3-carboxamide (I-980)
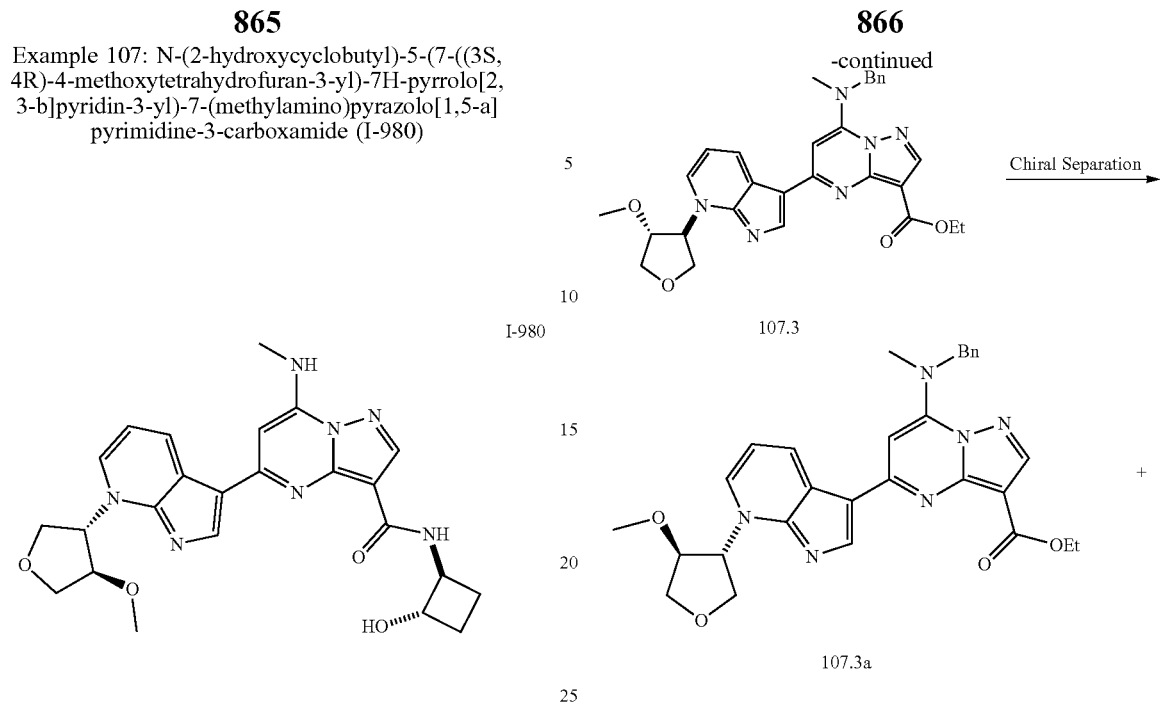
Scheme 107
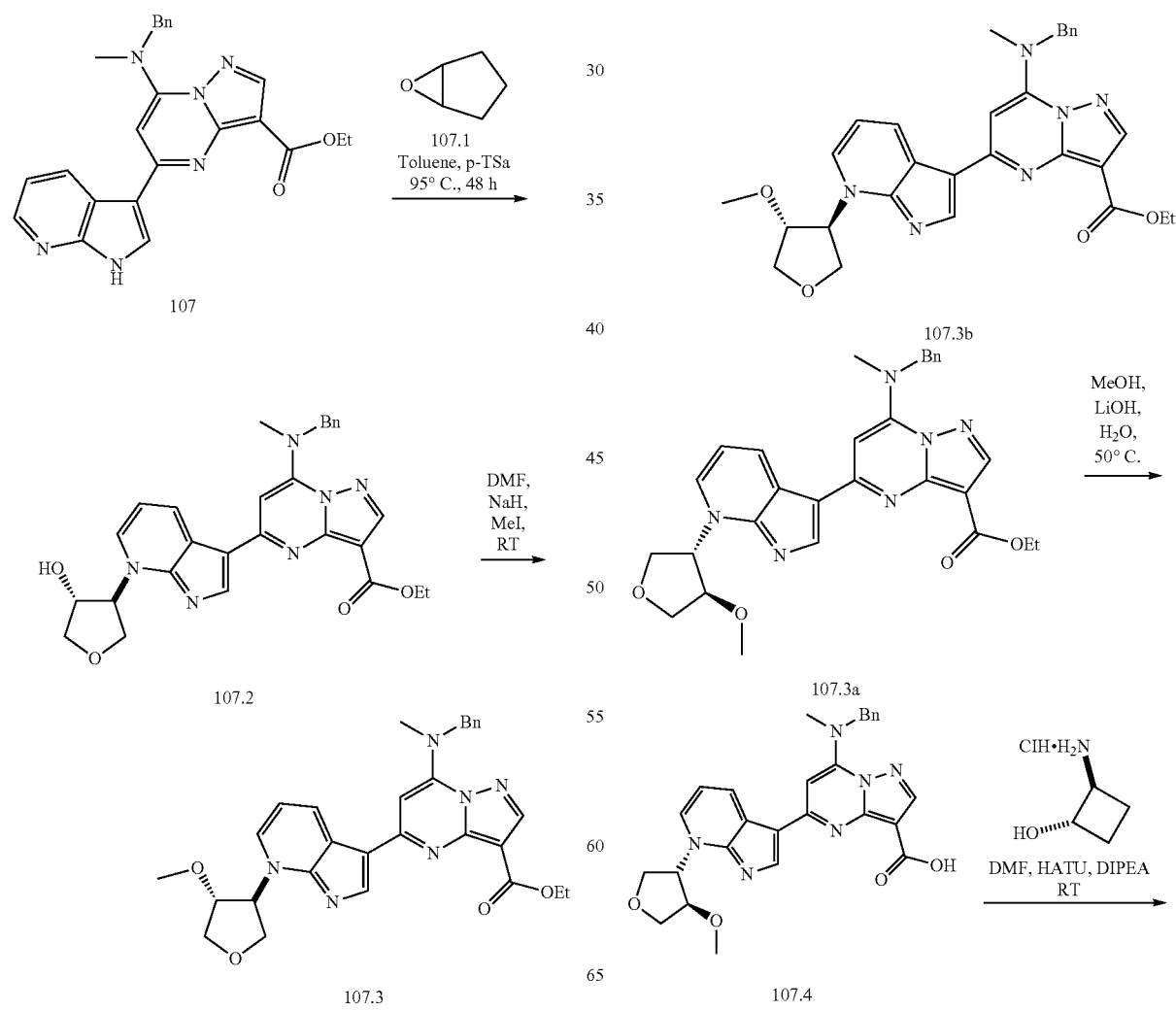

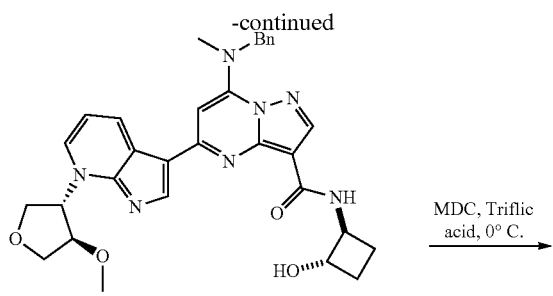

107.5

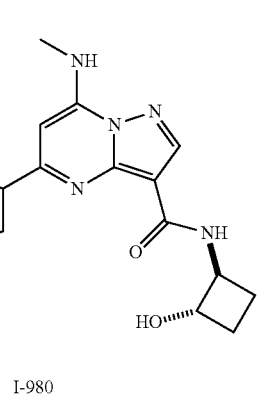

I-980

Synthesis of compound 107. Compound 107 was synthesized as per experimental protocol of Core D to obtain 107. (Yield: 83.54%), MS (ES): m/z 427.18[M+H]$^+$ Synthesis of compound 107.2. To a solution of 107.1 (2.2 g, 5.16 mmol, 1.0 eq) in toluene (25 mL) was added 107.1. (0.650 g, 7.74 mmol, 1.5 eq) and p-Toluene sulfonic acid (0.088 g, 0.51 mmol, 0.1 eq). The reaction mixture was stirred at 95° C. for 48 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.5% methanol in dichloromethane to obtain 107.2. (1.37 g, Yield: 51.81%). MS (ES): m/z 513.22 [M+H]$^+$ Synthesis of compound 107.3. To a solution of compound 107.2 (1.37 g, 2.67 mmol, 1.0 eq) in dimethylformamide (15 mL), was added sodium hydride (0.128 g, 5.34 mmol, 2.0 eq) at 0° C. and stirred for 20 min. Methyl iodide (0.417 g, 2.93 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulphate and concentrated under reduced pressure to obtain crude material. This was further purified by column chromatography and the compound was eluted in 2.0% methanol in dichloromethane to obtain 107.3. (1.1 g, Yield: 78.72%). MS (ES): m/z 527.24 [M+H]$^+$ Synthesis of compound 107.3a and 107.3b.: Isomers of 107.3 (1.1 g) were separated out using column CHIRAL-CEL OJ-H (250 mm*4.6 mm, 5 u) and 0.1% DEA in IPA:ACN (50:50) as co-solvent with flow rate of 4 mL/min. to obtain pure fraction-1 (FR-a) and fraction-2 (FR-b). FR-a was concentrated under reduced pressure at 30° C. to afford pure 107.3a. (0.400 g). MS (ES): m/z 527.24 [M+H]$^+$. FR-b was concentrated under reduced pressure at 30° C. to afford pure 107.3b. (0.404 g). MS (ES): m/z 527.24 [M+H]$^+$ Synthesis of compound 107.4. To a solution of 107.3a (0.5 g, 0.95 mmol, 1.0 eq), in tetrahydrofuran:methanol:water (8 mL, 2:2:1) was added lithium hydroxide (0.4 g, 9.5 mmol, 5.0 eq). The reaction was stirred at 50° C. for 16 h. After completion of reaction, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 107.4. (0.370 g, Yield: 78.16%). MS (ES): m/z 499.2 [M+H]$^+$ Synthesis of compound 107.5. Compound 107.5 was synthesized using general procedure A to obtain 107.5. (0.160 g, Yield: 70.26%). MS (ES): m/z 568.2 [M+H]$^+$ Synthesis of compound I-980: A solution of 107.5 (0.040 g, 0.070 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-980 (0.025 g, Yield: 74.30%). MS (ES): m/z 478.63 [M+H]$^+$ LCMS purity: 100%, HPLC purity: 98.52%, CHIRAL HPLC: 46.01%, 53.10%, $^1$H NMR (DMSO-d$_6$, 400 MHZ): 8.98-8.97 (d, J=7.2 Hz, 1H), 8.72 (s, 1H), 8.55-8.53 (d, J=8.4 Hz, 1H), 8.32 (s, 1H), 8.26-8.24 (d, J=6.4 Hz, 1H), 8.14-8.13 (d, J=4.8 Hz, 1H), 7.35-7.31 (t, J=6.8 Hz, 1H), 6.70 (s, 1H), 5.53-5.52 (d, J=7.2 Hz, 1H), 4.42-4.26 (m, 3H), 4.02-3.96 (m, 1H), 3.80 (bs, 1H), 3.45 (s, 3H), 3.10-3.09 (d, J=4.8 Hz, 3H), 2.13-2.06 (m, 2H), 1.57-1.52 (m, 2H), 1.35-1.30 (d, J=9.6 Hz, 2H), 1.24 (bs, 1H).

Example 108: N-(2-methoxycyclobutyl)-7-(methylamino)-5-(7-(3-morpholinopropyl)-7H-pyrrolo[2,3-b]pyridin-3-yl)pyrazolo[1,5-a]pyrimidine-3-carboxamide (I-981)

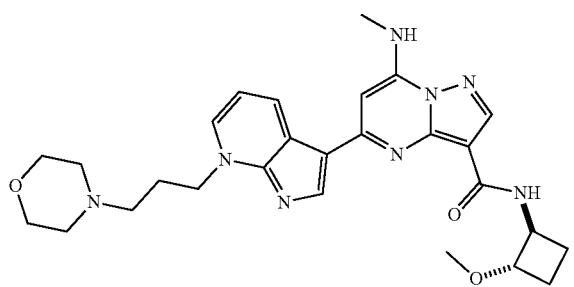

Scheme 108

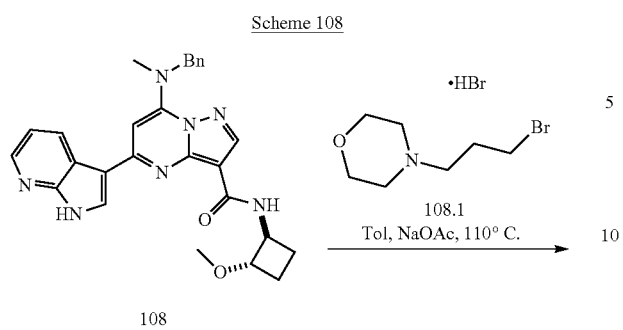

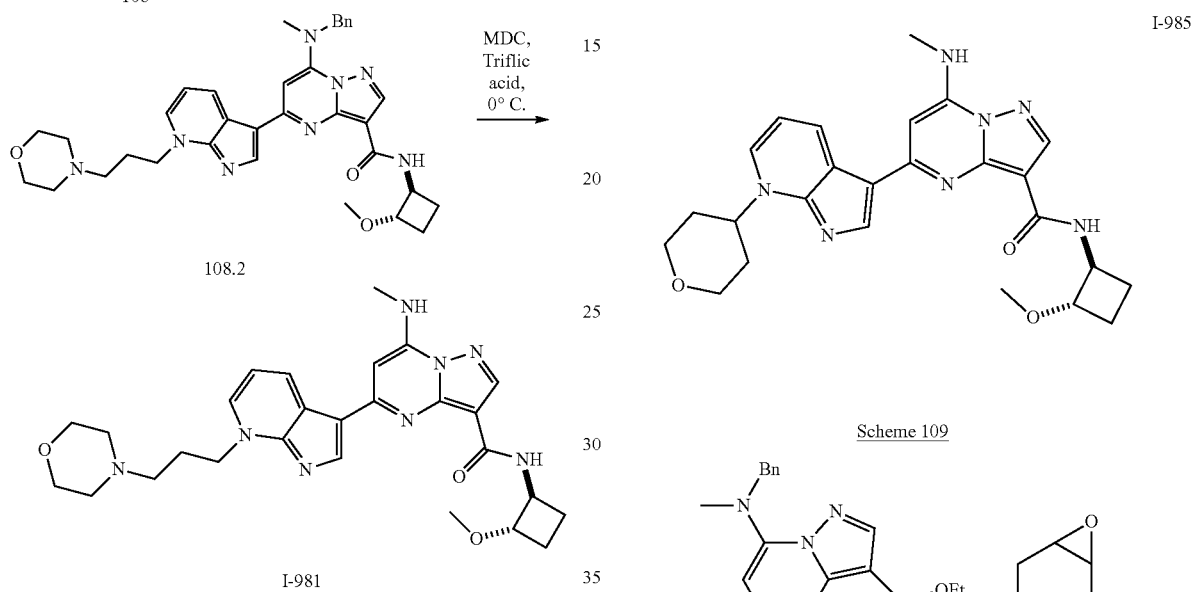

Synthesis of compound 108. Compound 108 was synthesized as per experimental protocol of Core D to obtain 108. (Yield: 60.33%). MS (ES): m/z 482.23 [M+H]+

Synthesis of compound 108.2. To a solution of 108 (0.2 g, 0.41 mmol, 1.0 eq) in toluene (3 mL) was added 108.1 (0.236 g, 0.82 mmol, 2.0 eq) and Sodium acetate (0.1 g, 1.23 mmol, 3.0 eq). The reaction mixture was stirred at 110° C. for 16 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.8% methanol in dichloromethane to obtain 108.2. (0.160 g, Yield: 63.29%). MS (ES): m/z 609.3 [M+H]+

Synthesis of compound I-981: A solution of 108.2 (0.040 g, 0.065 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-981 (0.025 g, Yield: 73.36%). MS (ES): m/z 519.44 [M+H]+ LCMS purity: 100%, HPLC purity: 100%, CHIRAL HPLC: 49.72%, 50.06%, ¹H NMR (DMSO-d₆, 400 MHZ): 8.94-8.92 (d, J=7.2 Hz, 1H), 8.67 (s, 1H), 8.59-8.57 (d, J=9.2 Hz, 1H), 8.36-8.35 (d, J=5.6 Hz, 1H), 8.32 (s, 1H), 8.11-8.10 (d, J=4.8 Hz, 1H), 7.28-7.25 (t, J=6.8 Hz, 1H), 6.68 (s, 1H), 4.83-4.80 (t, J=6.4 Hz, 2H), 4.42-4.38 (m, 1H), 3.85-3.81 (m, 1H), 3.52 (bs, 4H), 3.24 (s, 3H), 3.10-3.09 (d, J=4.4 Hz, 3H), 2.36-2.31 (m, 2H), 2.21-2.14 (m, 4H), 1.60-1.50 (m, 3H), 1.24 (bs, 3H).

Example 109: N-(2-methoxycyclobutyl)-7-(methylamino)-5-(7-(tetrahydro-2H-pyran-4-yl)-7H-pyrrolo[2,3-b]pyridin-3-yl)pyrazolo[1,5-a]pyrimidine-3-carboxamide (I-985)

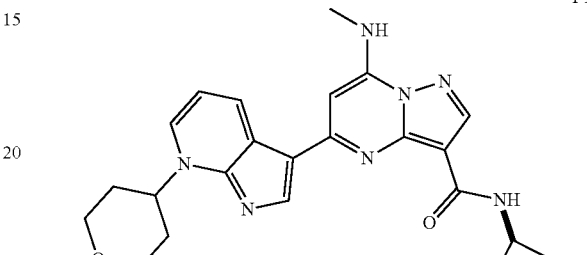

Scheme 109

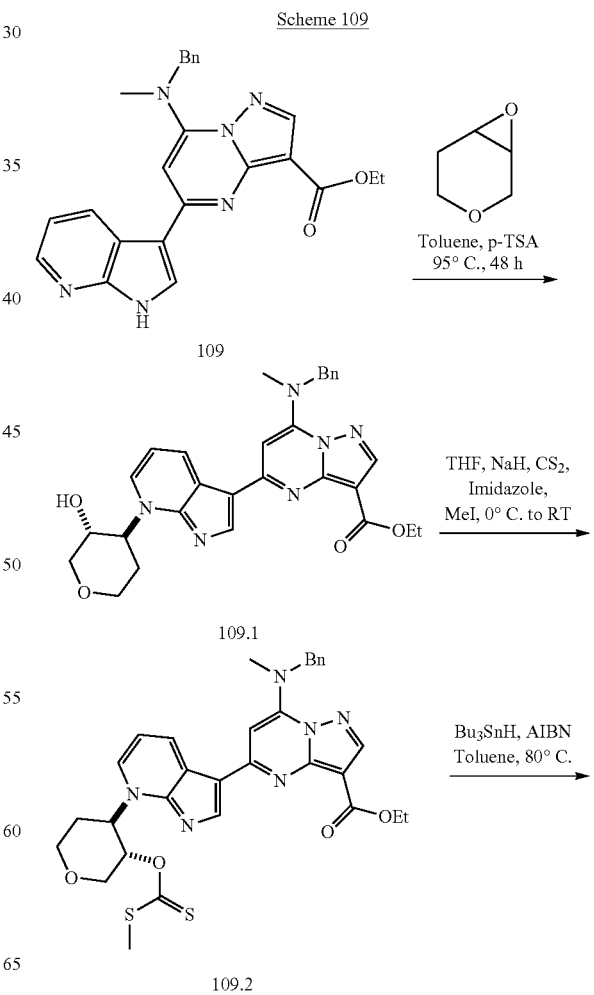

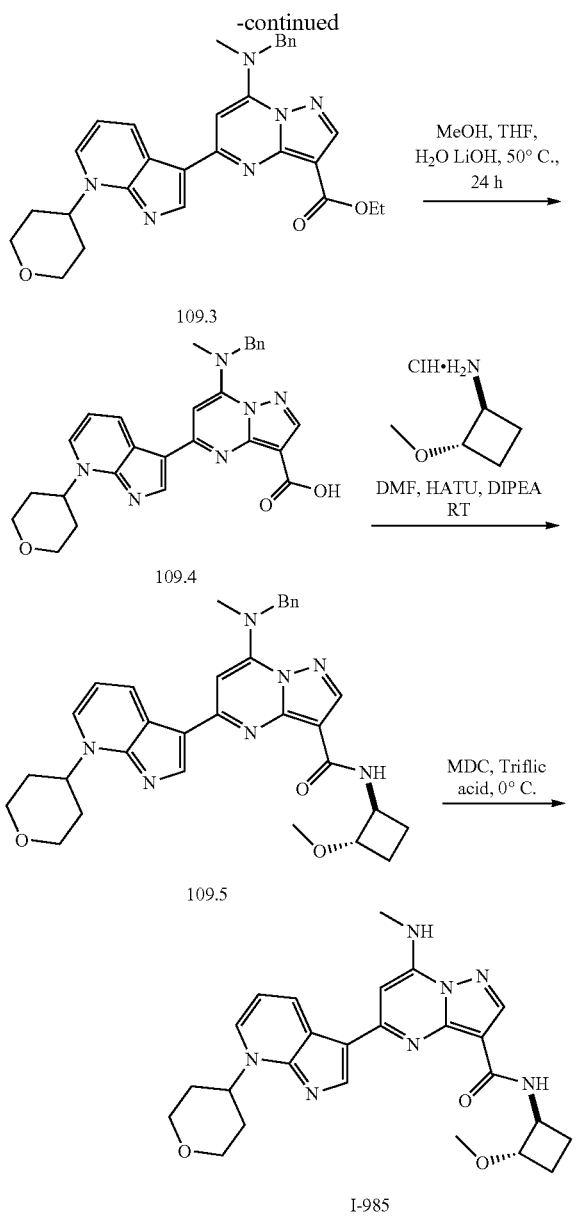

Synthesis of compound 109. Compound 109 was synthesized as per experimental protocol of Core D to obtain 109. (Yield: 83.54%), MS (ES): m/z 427.18 [M+H]$^+$ Synthesis of compound 109.1. To a solution of 109 (2.0 g, 4.69 mmol, 1.0 eq) in toluene (25 mL) was added 3,7-dioxabicyclo[4.1.0]heptane (0.703 g, 7.03 mmol, 1.5 eq) and p-Toluene sulfonic acid (0.080 g, 0.46 mmol, 0.1 eq). The reaction mixture was stirred at 95° C. for 48 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.5% methanol in dichloromethane to obtain 109.1. (1.4 g, Yield: 56.69%). MS (ES): m/z 527.2[M+H]$^+$ Synthesis of compound 109.2. A solution of 109.1 (1.4 g, 2.66 mmol, 1.0 eq) in tetrahydrofuran (28 mL) was cooled to 0° C. for 15 min. Sodium hydride (60%) (0.076 g, 3.19 mmol, 1.2 eq) was added portionwise to the reaction mixture and stirred for 20-25 min. Imidazole (0.025 g, 0.37 mmol, 0.14 eq) was added into the reaction mixture and stirred for 15 min. Carbon disulfide (0.323 g, 4.25 mmol, 1.6 eq) was added to the reaction mixture and stirred for 15-20 min. Methyl iodide (0.491 g, 3.45 mmol, 1.3 eq) was added to the reaction mixture and stirred for 1 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 109.2. (1.43 g, Yield: 87.21%). MS (ES): m/z 617.20 [M+H]$^+$ Synthesis of compound 109.3. To a solution of 109.2 (1.43 g, 2.32 mmol, 1.0 eq) in toluene (20 mL) was added dropwise Tributyltin hydride (2.5 mL, 9.28 mmol, 4.0 eq) and stirred for 15-20 min. Azobisisobutyronitrile (0.1 mL, 0.69 mmol, 0.3 eq) was added and stirred at 80° C. for 1 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 2.5% methanol in dichloromethane to obtain 109.3. (0.590 g, Yield: 49.84%). MS (ES): m/z 511.2 [M+H]$^+$ Synthesis of compound 109.4. To a solution of 109.3 (0.590 g, 1.15 mmol, 1.0 eq), in tetrahydrofuran:methanol:water (25 mL, 2:2:1) was added lithium hydroxide (0.241 g, 5.75 mmol, 5.0 eq). The reaction was stirred at 50° C. for 16 h. After completion of reaction, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 109.4. (0.480 g, Yield: 86.09%). MS (ES): m/z 483.2 [M+H]$^+$ Synthesis of compound 109.5. Compound 109.5 was synthesized using general procedure A to obtain 109.5. (0.160 g, Yield: 62.04%). MS (ES): m/z 566.2 [M+H]$^+$ Synthesis of compound I-985: A solution of 109.5 (0.040 g, 0.070 mmol, 1.0 eq) in dichloromethane (1 mL) was cooled to 0° C. and triflic acid (1 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-985 (0.031 g, Yield: 92.19%). MS (ES): m/z 476.71 [M+H]$^+$ LCMS purity: 100%, HPLC purity: 98.82%, CHIRAL HPLC: 48.77%, 49.66%, $^1$H NMR (DMSO-d$_6$, 400 MHZ): 8.96-8.94 (d, J=7.2 Hz, 1H), 8.67 (s, 1H), 8.57-8.51 (m, 2H), 8.32 (s, 1H), 8.12-8.11 (d, J=5.2 Hz, 1H), 7.32-7.28 (d, J=6.8 Hz, 1H), 6.68 (s, 1H), 5.16 (bs, 1H), 4.42-4.38 (t, J=8.4 Hz, 1H), 4.11 (s, 1H), 3.84-3.81 (m, 2H), 3.66-3.61 (t, J=9.6 Hz, 1H), 3.25 (s, 3H), 3.11-3.09 (d, J=4.8 Hz, 3H), 2.22-2.13 (m, 3H), 1.86 (bs, 2H), 1.62-1.51 (m, 2H), 1.24 (bs, 2H).

Example 110: N-(2-hydroxycyclobutyl)-5-(7-isopropyl-7H-pyrrolo[2,3-c]pyridazin-5-yl)-7-(methylamino)pyrazolo[1,5-a]pyrimidine-3-carboxamide (I-992)
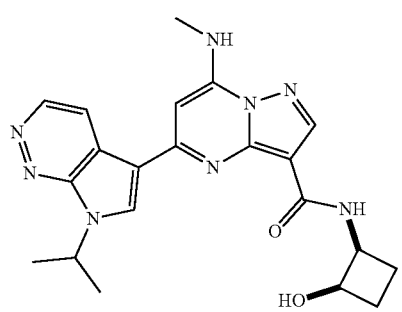
I-992
Scheme 110
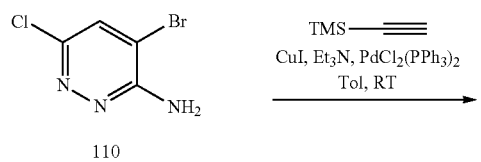
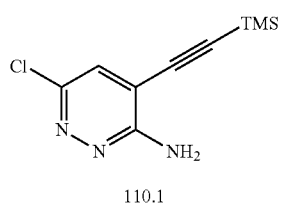
110.1
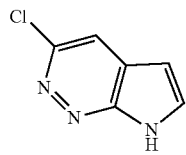
110.2
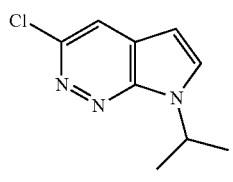
110.3
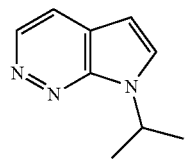
110.4
-continued
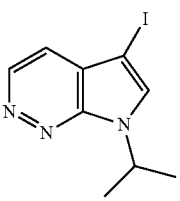
110.5
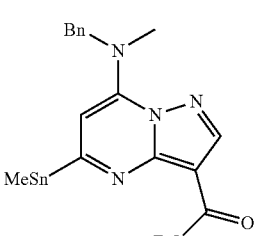
110.6
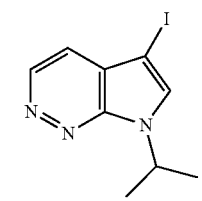
110.5
Dioxane, tetrakis, Copper(1)-2-thiophene carboxylate, 80° C.
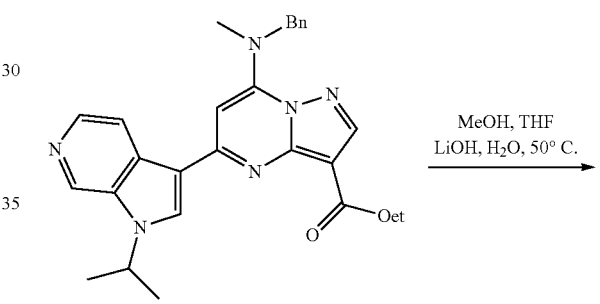
110.7
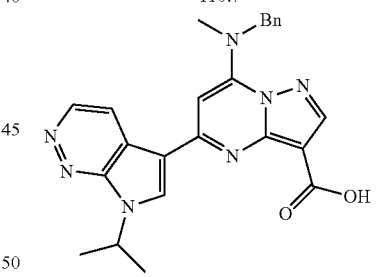
110.8
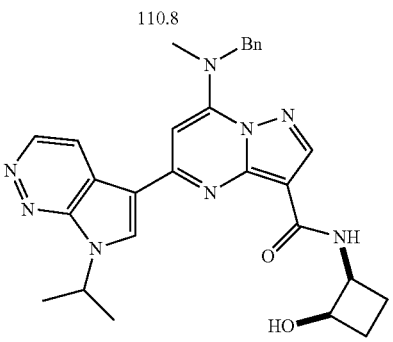
110.9

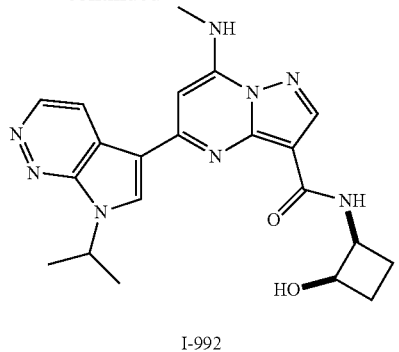

I-992

Synthesis of compound 110.1. To a solution of 110 (14.2 g, 68.26 mmol, 1.0 eq) in Toluene (200 mL) was added Triethylamine (17.2 g, 170.65 mmol, 2.5 eq) and ethynyltrimethylsilane (7.3 g, 75.08 mmol, 1.1 eq). The reaction mixture was degassed for 15 min. Then Bis(triphenylphosphine)palladium(II) dichloride (4.79 g, 6.82 mmol, 0.1 eq) and Copper(I) iodide (1.3 g, 6.82 mmol, 0.1 eq) were added. Reaction mixture was stirred at room temperature for 3 h under nitrogen atmosphere. After completion of reaction, reaction mixture was diluted by ethyl acetate, filtered through celite-bed and washed with water. Organic layer was combined, dried over sodium sulphate and concentrated under reduced pressure to obtain 110.1. (7.2 g Yield: 46.82%). MS (ES): m/z 225.05 [M+H]$^+$ Synthesis of compound 110.2. To a solution of 110.1 (7.2 g, 32.0 mmol, 1.0 eq) in N,N-Dimethylformamide (200 mL) was added Potassium tert-butoxide (5.3 g, 48.0 mmol, 1.5 eq). Methylamine (2M in tetrahydrofuran) (3.2 mL, 6.4 mmol, 0.2 eq) was added and reaction mixture was stirred at 120° C. for 2 h. After completion of reaction, reaction mixture was diluted with water and filtered through celite-bed and extracted with ethyl acetate. Organic layer was combined, dried over sodium sulphate and concentrated under reduced pressure to obtain crude material. This was further purified by column chromatography and compound was eluted in 20% ethyl acetate in hexane to obtain pure 110.2. (2.5 g Yield: 51.04%). MS (ES): m/z 153.01 [M+H]$^+$ Synthesis of compound 110.3. To a cooled solution of 110.2 (2.5 g, 16.33 mmol, 1.0 eq) in N,N-Dimethylformamide (50 mL), cesium carbonate (15.9 g, 48.99 mmol, 3.0 eq) was added. Isopropyl iodide (3.26 mL, 32.66 mmol, 2.0 eq) was added and stirred at room temperature for 1 h. After completion of reaction, reaction mixture was transferred into ice cold water and product was extracted with ethylacetate. Organic layer was combined, washed with brine solution, dried over sodium sulphate and concentrated under reduced pressure to obtain crude material. This was further purified by 1.5% methanol in dichloromethane to obtain 110.3. (0.540 g, Yield: 16.95%). MS (ES): m/z 195.06 [M+H]$^+$ Synthesis of compound 110.4. To a solution of 110.3 (0.440 g, 2.25 mmol, 1.0 eq) in methanol (6 ml), was added (10%) palladium on charcoal (0.229 g). Hydrogen was purged through reaction mixture for 4 h at room temperature. After completion, reaction mixture was filtered through celite-bed and washed with methanol. Filtrate was concentrated under reduced pressure to obtain crude material. This was further purified by trituration with n-pentane to obtain pure 110.4. (0.360 g, Yield: 99.30%). MS (ES): m/z 161.10 [M+H]$^+$ Synthesis of compound 110.5. To a cooled solution of 110.4 (0.360 g, 2.23 mmol, 1.0 eq) in N,N-Dimethylformamide (5 mL), N-Iodosuccinimide (0.551 g, 2.45 mmol, 1.1 eq) was added. Reaction mixture was stirred at room temperature for 4 h. After completion of reaction, reaction mixture was transferred to water and product was extracted with ethylacetate. Organic layer was combined, washed with brine solution, dried over sodium sulphate and concentrated under reduced pressure to obtain crude material. This was further purified by 36% ethyl acetate in hexane to obtain 110.5. (0.334 g, Yield: 52.09%). MS (ES): m/z 286.9 [M+H]$^+$ Synthesis of compound 110.6. Compound 110.6 was synthesized as per experimental protocol of I-792 to obtain 110.6 (Yield: 21.86%). MS (ES): m/z 474.11 [M+H]$^+$ Synthesis of compound 110.7. To a solution of 110.6 (0.334 g, 0.70 mmol, 1.0 eq) in 1,4-dioxane (15 mL) was added 110.5 (0.2 g, 0.70 mmol, 1.0 eq). The reaction mixture was degassed for 10 min. under argon atmosphere, then Tetrakis(triphenylphosphine)palladium(0) (0.040 g, 0.035 mmol, 0.05 eq) and Copper(I) thiophene-2-carboxylate (0.020 g, 0.0 7 mmol, 0.1 eq) were added under argon atmosphere and stirred at 80° C. for 4 h. After completion of reaction, reaction mixture was transferred into ice cold water and product was extracted with ethyl acetate. Organic layer was combined, dried over sodium sulphate and concentrated under reduced pressure to obtain crude material. This was further purified by column chromatography and compound was eluted in 20% ethyl acetate in hexane to obtain pure 110.7. (0.250 g, Yield: 75.43%). MS (ES): m/z 469.2 [M+H]$^+$ Synthesis of compound 110.8. To a solution of 110.7 (0.380 g, 0.81 mmol, 1.0 eq), in tetrahydrofuran:methanol:water (8 mL, 2:1:1) was added lithium hydroxide (0.170 g, 4.05 mmol, 5.0 eq). The reaction was stirred at 50° C. for 24 h. After completion, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 110.8. (0.310 g, Yield: 86.76%). MS (ES): m/z 441.1 [M+H]$^+$ Synthesis of compound 110.9. Compound 110.9 was synthesized using general procedure A to obtain 110.9. (0.140 g, Yield: 78.10%). MS (ES): m/z 510.25 [M+H]$^+$ Synthesis of compound I-992: A solution of 110.9 (0.030 g, 0.078 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-992 (0.028 g, Yield: 85.00%). MS (ES): m/z 421.15 [M+H]$^+$ LCMS purity: 100%, HPLC purity: 97.35%, CHIRAL HPLC: 49.24%, 50.02%, $^1$H NMR (DMSO-d$_6$, 400 MHZ): 9.15 (s, 1H), 9.07-9.05 (d, J=5.6 Hz, 1H), 8.83-8.82 (d, J=5.6 Hz, 1H), 8.67-8.65 (d, J=7.6 Hz, 1H), 8.39 (s, 1H), 8.35-8.33 (d, J=5.2 Hz, 1H), 6.80 (s, 1H), 5.68-5.67 (d, J=3.6 Hz, 1H), 5.42-5.39 (m, 1H), 4.57 (bs, 1H), 4.48 (bs, 1H), 3.16-3.15 (d, J=4.4 Hz, 3H), 2.19-2.14 (m, 1H), 2.05-2.00 (m, 1H), 1.89 (bs, 1H), 1.67-1.65 (d, J=6.4 Hz, 6H), 1.24 (bs, 1H).
Example 111: N-(2-methoxycyclobutyl)-7-(methylamino)-5-(7-((S)-tetrahydrofuran-3-yl)-7H-pyrrolo[2,3-b]pyridin-3-yl)pyrazolo[1,5-a]pyrimidine-3-carboxamide (I-994)
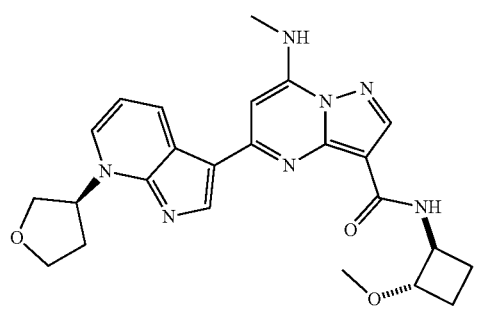
I-994
Scheme 111
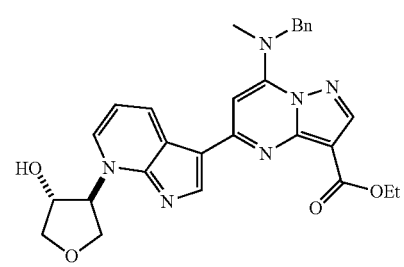
111.1
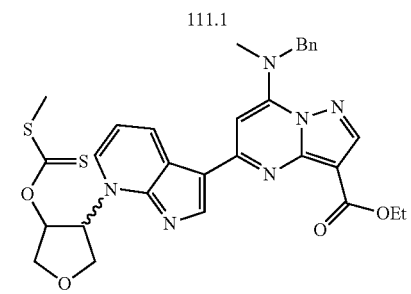
111.2
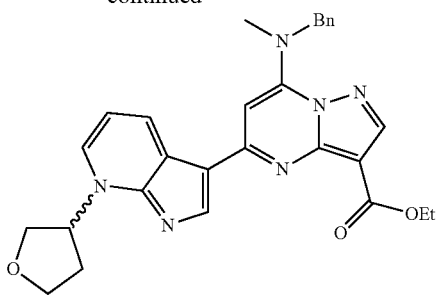
111.3
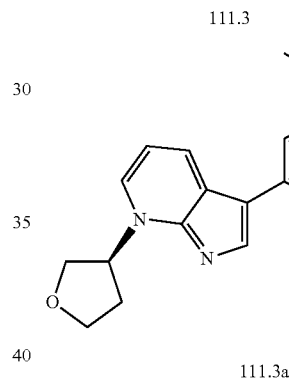
111.3
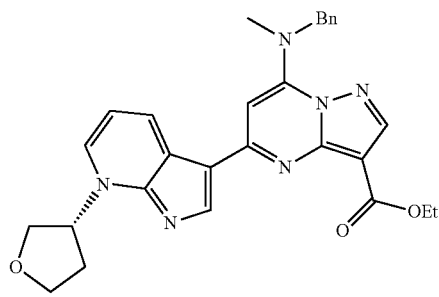
111.3a
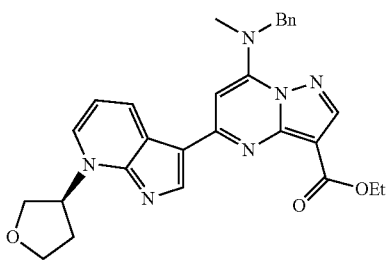
111.3a

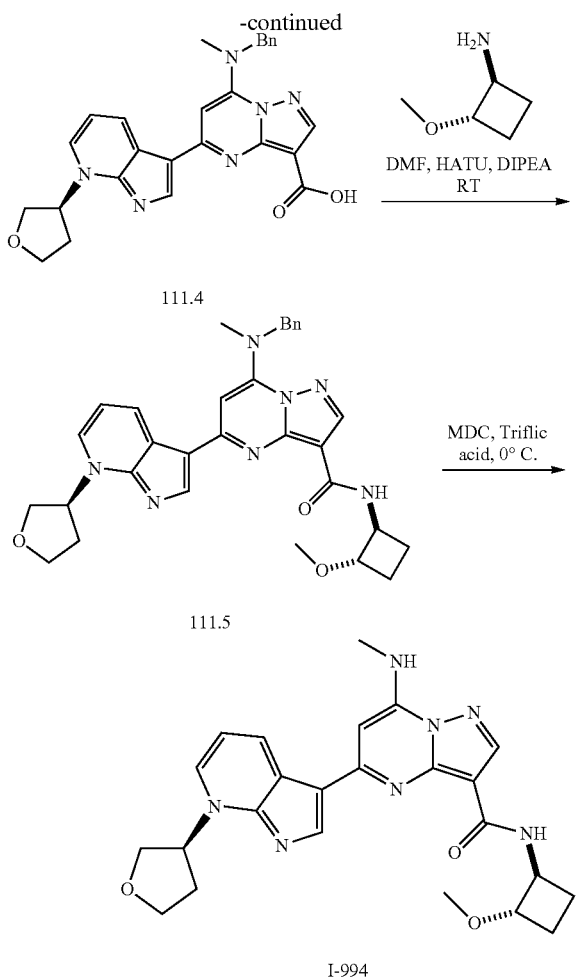

Synthesis of compound 111. Compound 111 was synthesized as per experimental protocol of Core D to obtain 111. (Yield: 83.64%). MS (ES): m/z 427.18 [M+H]$^+$ Synthesis of compound 111.1. To a solution of 111 (1.5 g, 3.52 mmol, 1.0 eq) in Toluene (20 mL) was added 3,6-dioxabicyclo[3.1.0]hexane (1.5 g, 17.6 mmol, 5.0 eq) and P-Toluenesulfonic Acid Monohydrate (0.267 g, 1.40 mmol, 0.4 eq). The reaction mixture was stirred at 95° C. for 48 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 111.1. (1.5 g, Yield: 83.20%). MS (ES): m/z 512.2 [M+H]$^+$ Synthesis of compound 111.2. To a solution of compound 111.1 (1.5 g, 2.92 mmol, 1.0 eq) in dry tetrahydrofuran (30 mL), was added Sodium hydride (60%) (0.084 g, 3.50 mmol, 1.2 eq) at 0° C. After 15 min Imidazole (0.027 g, 0.40 mmol, 0.14 eq) was added and stirred at room temperature for 2 h. Carbon disulfide (0.355 g, 4.67 mmol, 1.6 eq) was added and after 15 min Methyl iodide (0.539 g, 3.79 mmol, 1.3 eq) was added and stirred at room temperature for 20 min. After completion of reaction, reaction mixture was transferred into water and product was extracted with ethylacetate. Organic layer was combined, washed with brine solution, dried over sodium sulphate and concentrated under reduced pressure to obtain crude material. This was further purified by 1.9% methanol in dichloromethane to obtain 111.2. (1.5 g Yield: 85.04%). MS (ES): m/z 602.18 [M+H]$^+$ Synthesis of compound 111.3. Compound 111.2 (1.5 g, 2.49 mmol, 1.0 eq) in dry Toluene (25 mL) was stirred at 80° C. under argon atmosphere. Tributyltin hydride (2.6 mL, 9.96 mmol, 4.0 eq) was added dropwise to reaction mixture. After 30 min Azobisisobutyronitrile (0.11 mL, 0.74 mmol, 0.3 eq) was added to the reaction mixture and was stirred at 80° C. for 1 h. After completion of reaction, reaction mixture was transferred to water and product was extracted with ethylacetate. Organic layer was combined, washed with brine solution, dried over sodium sulphate and concentrated under reduced pressure to obtain crude material. This was further purified by 2.2% methanol in dichloromethane to obtain 111.3. (0.480 g Yield: 38.34%). MS (ES): m/z 496.2 [M+H]$^+$ Synthesis of compound 111.3a and 111.3b.: Isomers of 111.3 (0.480 g) were separated out using column CHIRAL-CEL OJ-H (250 mm*4.6 mm, 5 u) and 0.1% DEA in methanol as co-solvent with flow rate of 4 mL/min. to obtain pure fraction-1 (FR-a) and fraction-2 (FR-b). FR-a was concentrated under reduced pressure at 30° C. to afford pure 111.3a. (0.180 g). MS (ES): m/z 496.2 [M+H]$^+$. FR-b was concentrated under reduced pressure at 30° C. to afford pure 111.3b. (0.185 g). MS (ES): m/z 496.2 [M+H]$^+$ Synthesis of compound 111.4. To a solution of 111.3a (0.180 g, 0.36 mmol, 1.0 eq), in tetrahydrofuran:methanol:water (4 mL, 2:1:1) was added lithium hydroxide (0.075 g, 1.8 mmol, 5.0 eq). The reaction was stirred at 50° C. for 24 h. After completion of reaction, reaction mixture was concentrated under reduced pressure to obtain a residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 111.4. (0.155 g, Yield: 91.27%). MS (ES): m/z 468.1 [M+H]$^+$ Synthesis of compound 111.5. Compound 111.5 was synthesized using general procedure A to obtain 111.5. (0.140 g, Yield: 76.71%). MS (ES): m/z 552.27 [M+H]$^+$ Synthesis of compound I-994: A solution of 111.5 (0.040 g, 0.072 mmol, 1.0 eq) in dichloromethane (1 mL) was cooled to 0° C. and triflic acid (0.5 mL) was added. Reaction mixture was stirred at same temperature for 10 min. After completion, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-994 (0.016 g, Yield: 47.81%). MS (ES): m/z 462.71 [M+H]$^+$ LCMS purity: 98.84%, HPLC purity: 95.0%, CHIRAL HPLC: 47.22%, 48.43%, $^1$H NMR (DMSO-d$_6$, 400 MHZ): 9.00 (s, 1H), 8.71 (s, 1H), 8.56-8.8.54 (d, J=8.4 Hz, 1H), 8.34 (bs, 1H), 8.29 (s, 1H), 8.15 (bs, 1H), 7.35 (s, 1H), 6.71 (s, 1H), 4.42-4.38 (t, J=8.8 Hz, 1H), 4.26-4.21 (m, 2H), 3.93-3.83 (m, 2H), 3.25 (s, 3H), 3.11-3.10 (d, J=4.4 Hz, 3H), 2.22-2.12 (m, 2H), 1.61-1.49 (m, 2H), 1.25 (bs, 2H), 0.87 (bs, 2H).

Example 112: 7-amino-N-(2-methoxycyclobutyl)-5-(7-((3R,4S)-4-methoxytetrahydrofuran-3-yl)-7H-pyrrolo[2,3-b]pyridin-3-yl)pyrazolo[1,5-a]pyrimidine-3-carboxamide (I-998)
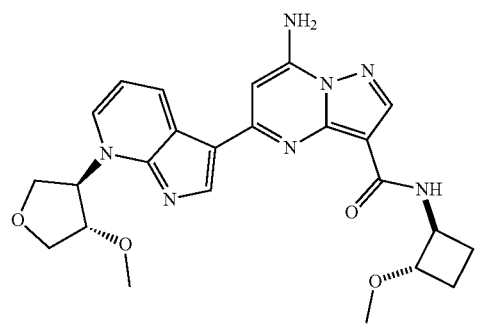
I-998
Scheme 112
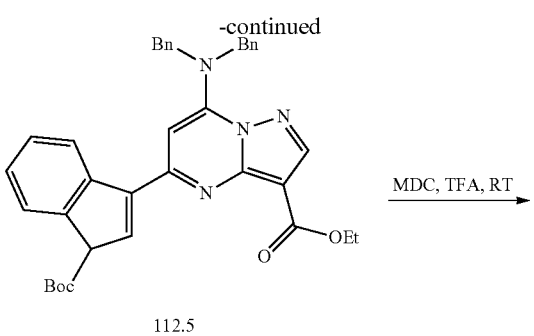
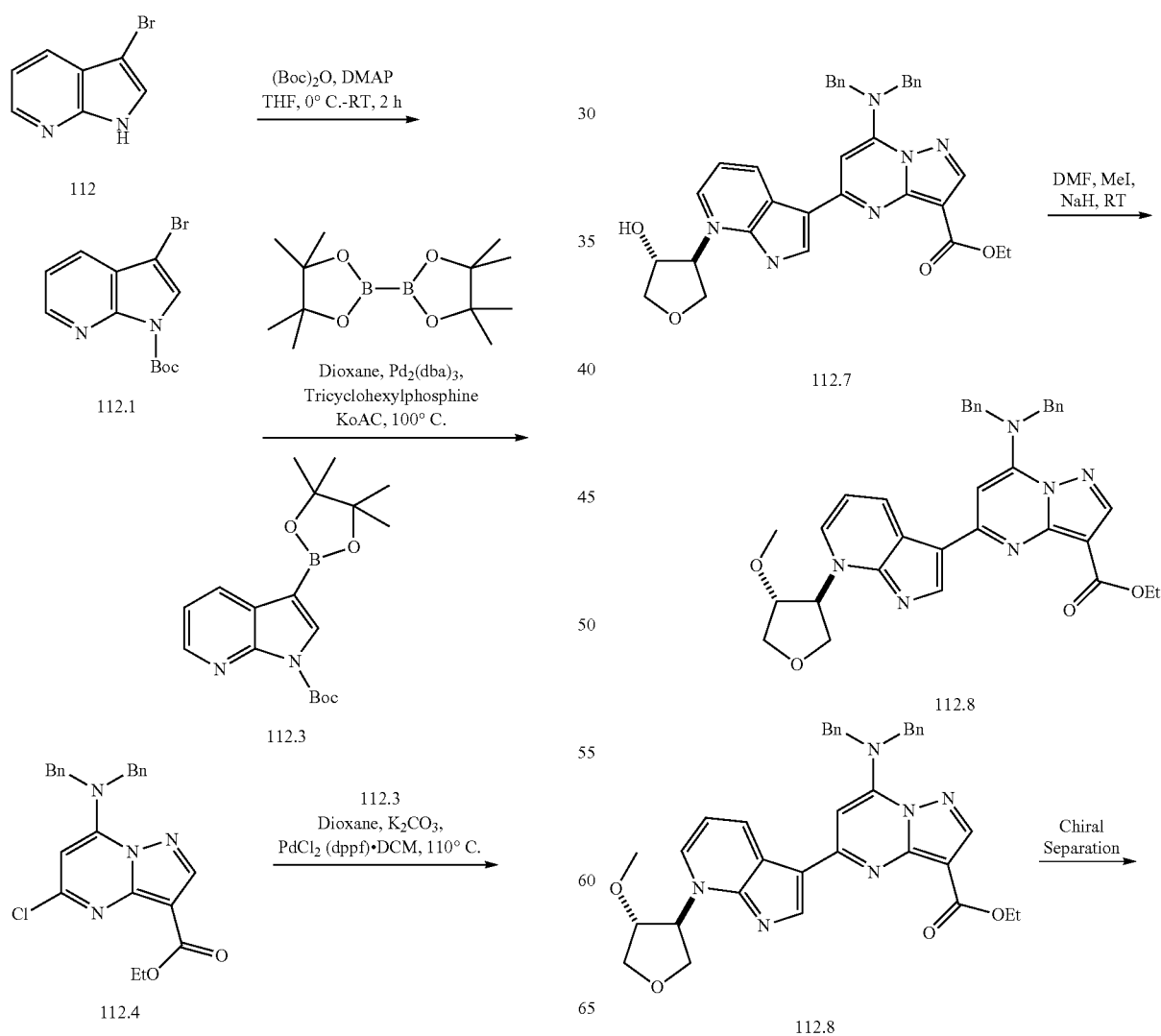

-continued

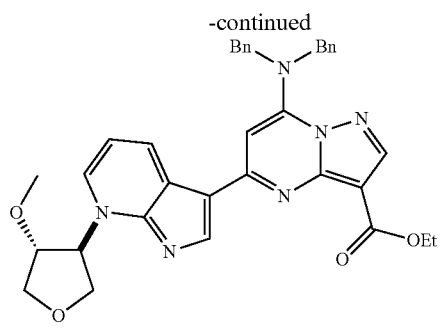

112.8a

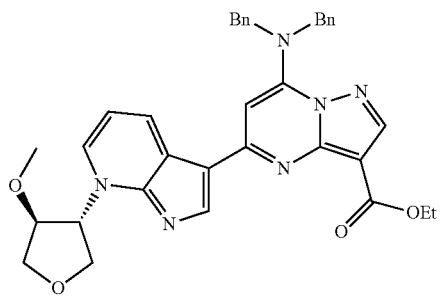

112.8b

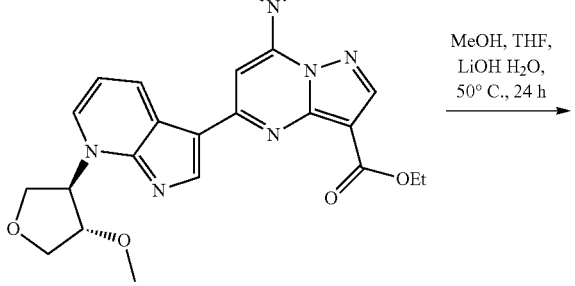

112.8a

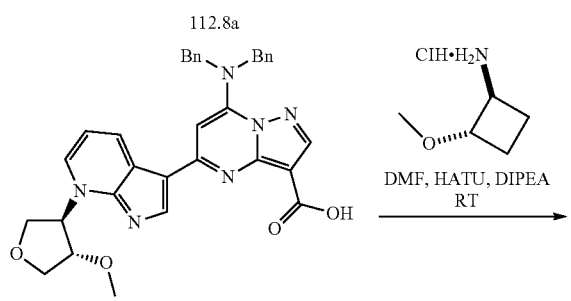

112.9

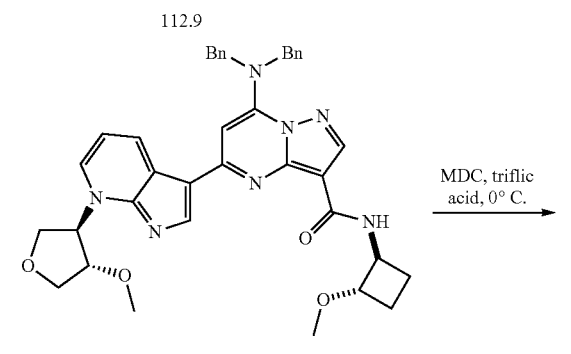

112.10

-continued

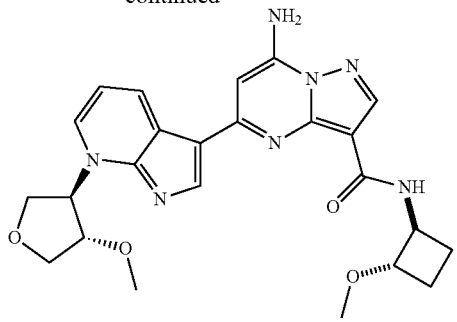

I-998

Synthesis of compound 112.1. To a solution of 112 (100 g, 507.61 mmol, 1.0 eq) in tetrahydrofuran (1000 mL) was added N,N-dimethylaminopyridine (6.1 g, 50.76 mmol, 0.1 eq) at 0° C. followed by Di-tert-butyl dicarbonate (165.9 g, 761.41 mmol, 1.5 eq) and reaction mixture was stirred at room temperature for 2 h. After completion of reaction, reaction mixture was transferred in water and product was extracted with ethyl acetate. Organic layer was combined and dried over sodium sulphate and concentrated under reduced pressure to obtain crude material. This was further purified by column chromatography and the compound was eluted in 0-10% ethyl acetate in hexane to obtain 112.1. (120 g, Yield: 79.57%). MS (ES): m/z 298.01 [M+H]$^+$.

Synthesis of compound 112.3. To a solution of 112.1 (10 g, 33.67 mmol, 1.0 eq) in 1,4-dioxane (100 mL) was added 112.2 (9.3 g, 37.03 mmol, 1.1 eq), and Potassium acetate (5.0 g, 51.51 mmol, 1.53 eq). The reaction mixture was degassed for 10 min. under argon atmosphere, then tris (dibenzylideneacetone)dipalladium(0) (1.54 g, 1.68 mmol, 0.05 eq) and Tricyclohexylphosphine (1.13 g, 4.04 mmol, 0.12 eq) were added, again degassed for 5 min. The reaction was stirred at 110° C. for 7 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 15% ethyl acetate in hexane as eluant to obtain pure 112.3. (10.0 g, Yield: 86.33%). MS (ES): m/z 344.1 [M+H]$^+$ Synthesis of compound 112.4. Compound 112.4 was synthesized using general procedure of core synthesis to obtain 112.4. (Yield: 62.00%). MS (ES): m/z 421.9 [M+H]$^+$ Synthesis of compound 112.5. Argon was purged for 15 min through a stirred solution of 112.4 (2.0 g, 4.76 mmol, 1.0 eq), 112.3 (2.12 g, 6.18 mmol, 1.3 eq). Potassium carbonate (1.6 g, 11.9 mmol, 2.5 eq) in 1,4 dioxane (10 mL) [1,1'-Bis(diphenylphosphino)ferrocene]dichloropalladium (II), complex with dichloromethane (0.388 g, 0.47 mmol, 0.1 eq) were added and further purging done for 10 min. Reaction was allowed to stir at 110° C. for 5 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and compound was eluted in 0.5% methanol in dichloromethane to obtain pure 112.5. (1.2 g, Yield: 41.90%). MS (ES): m/z 602.26 [M+H]$^+$ Synthesis of compound 112.6. The compound 112.5 (1.2 g, 1.99 mmol, 1.0 eq) was dissolved in dichloromethane (20 mL) and trifluoroacetic acid (1.7 mL) was added to the reaction mixture. The reaction was stirred at room temperature for 1 h. After completion of reaction, reaction mixture was transferred into saturated bicarbonate solution and product was extracted with dichloromethane. Organic layer was combined and dried over sodium sulphate and concentrated under reduced pressure to obtain crude material. This was further purified by trituration with diethyl ether to obtain pure 112.6. (0.9 g, 89.94%). MS (ES): m/z 502.21 [M+H]$^+$ Synthesis of compound 112.7. To a solution of 112.6 (0.9 g, 1.79 mmol, 1.0 eq) in Toluene (15 mL) was added 3,6-dioxabicyclo[3.1.0]hexane (0.769 g, 8.95 mmol, 5.0 eq) and P-Toluenesulfonic Acid Monohydrate (0.136 g, 0.71 mmol, 0.4 eq). The reaction mixture was stirred at 95° C. for 48 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 112.7. (0.730 g, Yield: 69.25%). MS (ES): m/z 588.25 [M+H]$^+$ Synthesis of compound 112.8. To a solution of 112.7 (0.730 g, 1.24 mmol, 1.0 eq) in Dimethylformamide (10 mL), was added sodium hydride (0.059 g, 2.48 mmol, 2 eq) at 0° C. and stirred for 20 min. Methyl iodide (0.193 g, 1.36 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulphate and concentrated under reduced pressure to obtain crude material. This was further purified by column chromatography and the compound was eluted in 2.4% methanol in dichloromethane to obtain 112.8. (0.640 g, Yield: 85.63%). MS (ES): m/z 602.26 [M+H]$^+$ Synthesis of compound 112.8a and 112.8b.: Isomers of 112.8 (0.640 g) were separated out using column CHIRALCEL OJ-H (250 mm*4.6 mm, 5 u) and 0.1% DEA in methanol as co-solvent with flow rate of 4 mL/min. to afford pure fraction-1 (FR-a) and fraction-2 (FR-b). FR-a was concentrated under reduced pressure at 30° C. to afford pure 112.8a. (0.255 g). MS (ES): m/z 602.26 [M+H]$^+$. FR-b was concentrated under reduced pressure at 30° C. to afford pure 112.8b. (0.260 g). MS (ES): m/z 602.26 [M+H]$^+$ Synthesis of compound 112.9. To a solution of 112.8a (0.255 g, 0.42 mmol, 1.0 eq), in tetrahydrofuran:methanol:water (4 mL, 2:1:1) was added lithium hydroxide (0.088 g, 2.1 mmol, 5.0 eq). The reaction was stirred at 50° C. for 24 h. After completion, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 112.9. (0.180 g, Yield: 74.03%). MS (ES): m/z 574.23 [M+H]$^+$ Synthesis of compound 112.10. Compound 112.10 was synthesized using general procedure A to obtain 2.0. (0.140 g, Yield: 67.95%). MS (ES): m/z 657.3 [M+H]$^+$ Synthesis of compound I-998: A solution of 112.10 (0.140 g, 0.21 mmol, 1.0 eq) in dichloromethane (3 mL) was cooled to 0° C. and triflic acid (1 mL) was added. Reaction mixture was stirred at same temperature for 10 min. After completion, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-998 (0.021 g, Yield: 20.66%). MS (ES): m/z 478.49 [M+H]$^+$ LCMS purity: 96.50%, HPLC purity: 97.60%, CHIRAL HPLC: 49.82%, 49.14%, $^1$H NMR (DMSO-d$_6$, 400 MHZ): 8.94-8.93 (d, J=7.2 Hz, 1H), 8.58-8.55 (d, J=8.4 Hz, 1H), 8.47 (bs, 1H), 8.34 (bs, 1H), 8.28-8.26 (d, J=6 Hz 1H), 7.92 (bs, 1H), 7.35 (s, 1H), 6.68 (s, 1H), 6.06 (s, 1H), 4.39-4.28 (m, 4H), 3.83 (bs, 3H), 3.44 (m, 3H), 3.25 (s, 3H), 2.23-2.09 (m, 2H), 1.60-1.50 (m, 2H), 1.24 (bs, 1H).

Example 113: N-(2-methoxycyclobutyl)-5-(1-((R)-1-methyl-5-oxopyrrolidin-3-yl)-1H-pyrrolo[2,3-b]pyridin-3-yl)-7-(methylamino)pyrazolo[1,5-a]pyrimidine-3-carboxamide (I-1016)

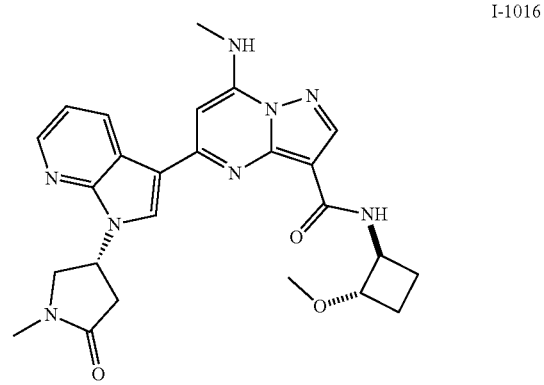

I-1016

Scheme 113

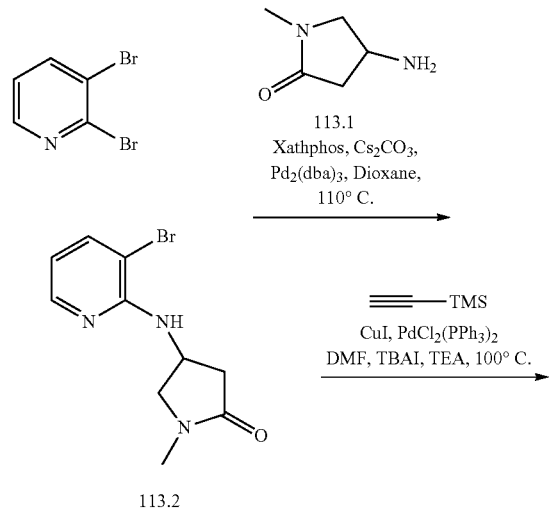

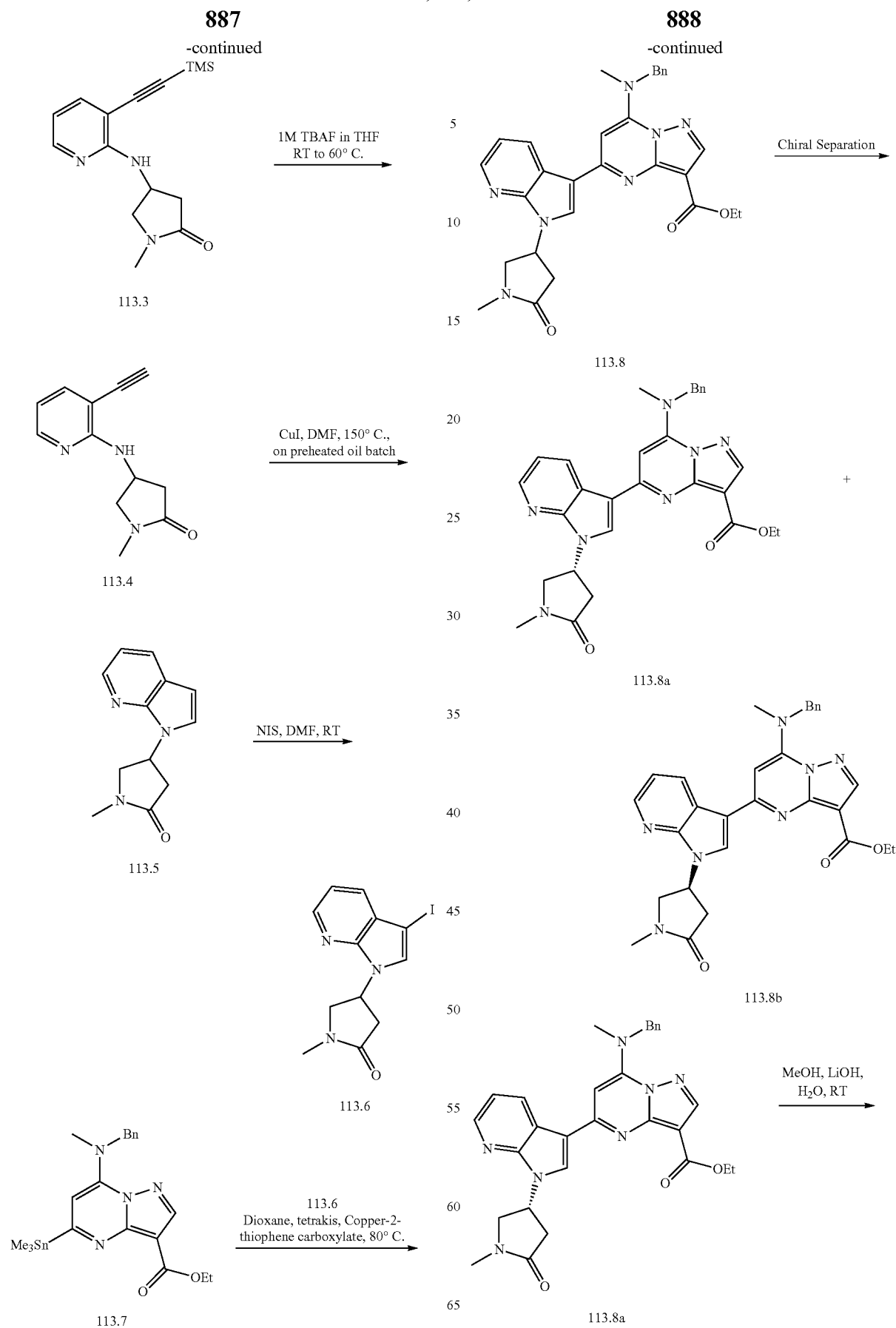

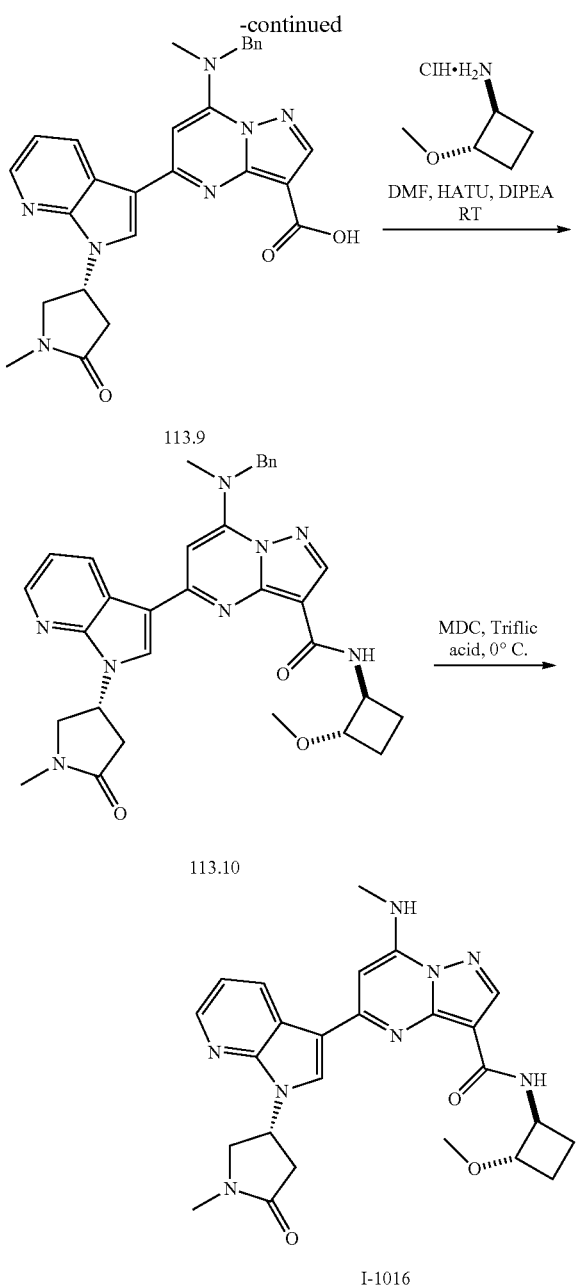

Synthesis of compound 113.2. To a solution of 113 (6.0 g, 25.42 mmol, 1.0 eq) in 1,4-dioxane (200 mL) was added 113.1 (2.8 g, 25.42 mmol, 1.0 eq), cesium carbonate (20.6 g, 63.55 mmol, 2.5 eq). The reaction mixture was degassed for 10 min. under argon atmosphere, then tris(dibenzylideneacetone)dipalladium(0) (1.1 g, 1.27 mmol, 0.05 eq) and 4,5-Bis(diphenylphosphino)-9,9-dimethylxanthene (1.4 g, 2.54 mmol, 0.1 eq) were added, and again degassed for 5 min. The reaction mixture was stirred at 110° C. for 4 h. After completion, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 2.2% methanol in dichloromethane as eluant to obtain pure 113.2. (4.2 g, Yield: 61.39%). MS (ES): m/z 270.1 [M+H]$^+$ Synthesis of compound 113.3. To a solution of 113.2 (4.2 g, 15.55 mmol, 1.0 eq) in N,N-Dimethylformamide (60 mL) was added Triethylamine (5.6 g, 38.87 mmol, 2.5 eq) and ethynyltrimethylsilane (3.0 g, 31.1 mmol, 2.0 eq). The reaction mixture was degassed for 15 min. Then Tetrabutylammonium iodide (11.4 g, 31.1 mmol, 2.0 eq), Bis(triphenylphosphine)palladium(II) dichloride (0.545 g, 0.77 mmol, 0.05 eq) and Copper(I) iodide (0.074 g, 0.38 mmol, 0.025 eq) were added. Reaction mixture was stirred at room temperature for 3 h under nitrogen atmosphere. After completion of reaction, reaction mixture was diluted with ethyl acetate, filtered through celite-bed and washed with water. Organic layer was combined, dried over sodium sulphate and concentrated under reduced pressure to obtain crude material. This was further purified by combi flash using 2.5% methanol in dichloromethane as eluant to obtain pure 113.3. (1.7 g, Yield: 38.04%). MS (ES): m/z 288.1 [M+H]$^+$ Synthesis of compound 113.4. To a solution of 113.3 (1.7 g, 5.92 mmol, 1.0 eq) in tetrahydrofuran (20 mL) was added tetrabutylammonium fluoride solution in tetrahydrofuran (7.2 mL). The reaction mixture was stirred at 60° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 1.2% methanol in dichloromethane as eluant to obtain pure 113.4. (0.763 g, Yield: 59.93%). MS (ES): m/z 215.1 [M+H]$^+$ Synthesis of compound 113.5. To a solution of 113.4 (0.763 g, 3.54 mmol, 1.0 eq) in N,N-Dimethylformamide (20 mL) was added Copper(I) iodide (0.674 g, 3.54 mmol, 1.0 eq). The reaction mixture was heated up to 150° C. for 48 h. After completion, reaction mixture was cooled to room temperature, transferred into water and filtered to remove Copper(I) iodide, and was extracted with dichloromethane. Organic layer was combined, washed with brine solution, dried over sodium sulphate and concentrated under reduced pressure to obtain crude material. This was further purified by combi flash using 1.4% methanol in dichloromethane as eluant to obtain pure 113.5. (0.327 g, Yield: 42.86%). MS (ES): m/z 216.1 [M+H]$^+$ Synthesis of compound 113.6. To a cooled solution of 113.5 (0.310 g, 1.43 mmol, 1.0 eq) in N,N-Dimethylformamide (10 mL) was added portionwise N-Iodosuccinimide (0.353 g, 1.57 mmol, 1.1 eq). The reaction mixture was stirred at room temperature for 30 min. After completion of reaction, reaction mixture was transferred into water and product was extracted with ethyl acatate. Organic layer was combined, washed with brine solution and sodium thiosulphate solution, dried over sodium sulphate and concentrated under reduced pressure to obtain crude material. This was further purified by combi flash using 2.0% methanol in dichloromethane as eluant to obtain pure 113.6. (0.310 g, Yield: 63.10%). MS (ES): m/z 342.01 [M+H]$^+$ Synthesis of compound 113.7. Compound 113.7 was synthesized as per experimental protocol of I-792 to obtain 113.7. (Yield: 21.86%). MS (ES): m/z 474.11 [M+H]$^+$ Synthesis of compound 113.8. To a solution of 113.7 (0.310 g, 0.65 mmol, 1.0 eq) in 1,4-dioxane (10 mL) was added 113.6 (0.221 g, 0.65 mmol, 1.0 eq). The reaction mixture was degassed for 10 min. under argon atmosphere, then Tetrakis(triphenylphosphine)palladium(0) (0.037 g, 0.032 mmol, 0.05 eq) and Copper(I) thiophene-2-carboxylate (0.012 g, 0.065 mmol, 0.1 eq) were added under argon atmosphere and stirred at 80° C. for 5 h. After completion, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 1.3% methanol in dichloromethane to obtain pure 113.8. (0.270 g, Yield: 78.71%). MS (ES): m/z 524.2 [M+H]$^+$ Synthesis of compound 113.8a and 113.8b.: Isomers of 113.8 (0.270 g) were separated out using column CHIRAL-CEL OJ-H (250 mm*4.6 mm, 5 u) and 0.1% DEA in IPA:ACN (50:50) as co-solvent with flow rate of 4 mL/min. to obtain pure fraction-1 (FR-a) and fraction-2 (FR-b). FR-a was concentrated under reduced pressure at 30° C. to afford pure 113.8a. (0.120 g). MS (ES): m/z 524.2 [M+H]$^+$. FR-b was concentrated under reduced pressure at 30° C. to afford pure 113.8b. (0.120 g). MS (ES): m/z 524.2 [M+H]$^+$ Synthesis of compound 113.9. To a solution of 113.8a (0.120 g, 0.22 mmol, 1.0 eq), in tetrahydrofuran:methanol:water (10 mL, 2:2:1) was added lithium hydroxide (0.046 g, 1.1 mmol, 5.0 eq). The reaction was stirred at 50° C. for 16 h. After completion of reaction, reaction mixture was concentrated under reduced pressure to obtain residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 113.9. (0.092 g, Yield: 81.01%). MS (ES): m/z 496.2 [M+H]$^+$ Synthesis of compound 113.10. Compound 113.10 was synthesized using general procedure A to obtain 113.10. (0.052 g, Yield: 48.40%). MS (ES): m/z 579.2 [M+H]$^+$ Synthesis of compound I-1016: A solution of 113.10 (0.052 g, 0.089 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1016 (0.033 g, Yield: 75.17%). MS (ES): m/z 489.73 [M+H]$^+$ LCMS purity: 100%, HPLC purity: 97.47%, CHIRAL HPLC: 48.84%, 47.60%, $^1$H NMR (DMSO-d$_6$, 400 MHZ): 8.79-8.77 (d, J=8 Hz, 1H), 8.75 (s, 1H), 8.49-8.47 (d, J=8.4 Hz, 1H), 8.43-8.42 (d, J=4 Hz, 1H), 8.37 (d, J=6 Hz, 1H), 8.31-8.29 (d, J=5.2 Hz, 1H), 7.36-7.33 (m, 1H), 6.77 (s, 1H), 5.71 (bs, 1H), 4.39 (bs, 1H), 3.83-3.79 (t, J=7.2 Hz, 1H), 3.69-3.65 (m, 1H), 3.23 (s, 3H), 3.11-3.09 (d, J=4.8 Hz, 3H), 2.85 (s, 3H), 2.13-2.11 (m, 2H), 1.55 (bs, 2H), 1.22 (bs, 3H).

Example 114: N-((1S,2S)-2-methoxycyclobutyl)-5-(1-(5-(methoxymethyl)tetrahydrofuran-3-yl)-1H-pyrrolo[2,3-b]pyridin-3-yl)-7-(methylamino)pyrazolo[1,5-a]pyrimidine-3-carboxamide (I-1018)

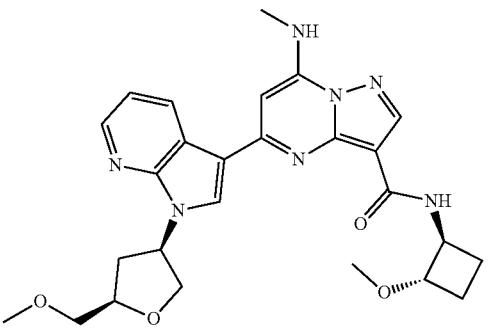

I-1018

Scheme 114

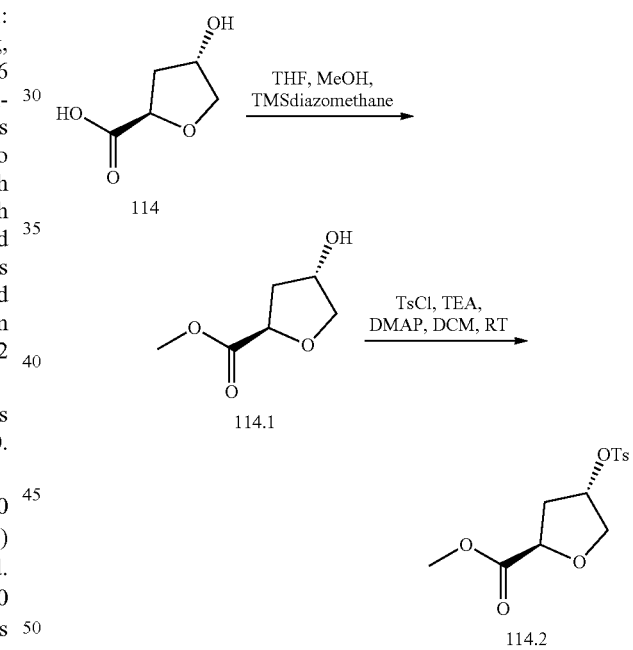

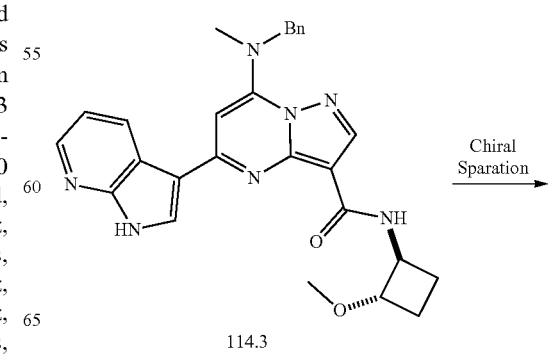

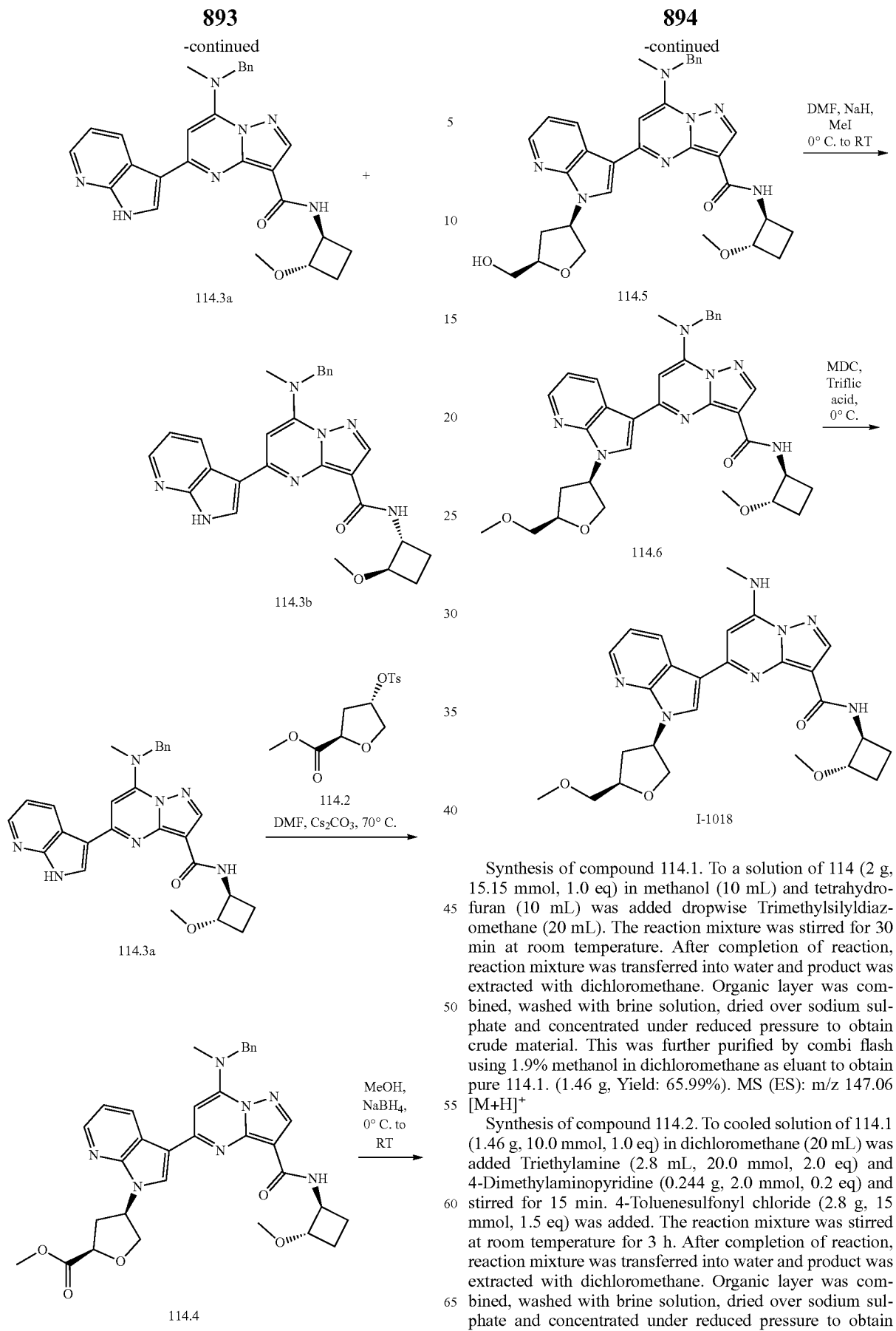

Synthesis of compound 114.1. To a solution of 114 (2 g, 15.15 mmol, 1.0 eq) in methanol (10 mL) and tetrahydrofuran (10 mL) was added dropwise Trimethylsilyldiazomethane (20 mL). The reaction mixture was stirred for 30 min at room temperature. After completion of reaction, reaction mixture was transferred into water and product was extracted with dichloromethane. Organic layer was combined, washed with brine solution, dried over sodium sulphate and concentrated under reduced pressure to obtain crude material. This was further purified by combi flash using 1.9% methanol in dichloromethane as eluant to obtain pure 114.1. (1.46 g, Yield: 65.99%). MS (ES): m/z 147.06 [M+H]$^+$ Synthesis of compound 114.2. To cooled solution of 114.1 (1.46 g, 10.0 mmol, 1.0 eq) in dichloromethane (20 mL) was added Triethylamine (2.8 mL, 20.0 mmol, 2.0 eq) and 4-Dimethylaminopyridine (0.244 g, 2.0 mmol, 0.2 eq) and stirred for 15 min. 4-Toluenesulfonyl chloride (2.8 g, 15 mmol, 1.5 eq) was added. The reaction mixture was stirred at room temperature for 3 h. After completion of reaction, reaction mixture was transferred into water and product was extracted with dichloromethane. Organic layer was combined, washed with brine solution, dried over sodium sulphate and concentrated under reduced pressure to obtain crude material. This was further purified by combi flash using 22% ethyl acetate in hexane as eluant to obtain pure 114.2. (1.2 g, Yield: 40.00%). MS (ES): m/z 301.07 [M+H]⁺

Synthesis of compound 114.3. Compound 114.3 was synthesized as per experimental protocol of I-920 to obtain 114.3 (Yield: 60.33%). MS (ES): m/z 482.23 [M+H]⁺

Synthesis of compound 114.3a and 114.3b.: Isomers of 114.3 (0.990 g) were separated out using column CHIRAL-CEL OJ-H (250 mm*4.6 mm, 5 u) and 0.1% DEA in IPA:ACN (50:50) as co-solvent with flow rate of 4 mL/min. to obtain pure fraction-1 (FR-a) and fraction-2 (FR-b). FR-a was concentrated under reduced pressure at 30° C. to afford pure 114.3a. (0.380 g). MS (ES): m/z 482.23 [M+H]⁺. FR-b was concentrated under reduced pressure at 30° C. to afford pure 114.3b. (0.390 g). MS (ES): m/z 482.23 [M+H]⁺

Synthesis of compound 114.4. To a solution of 114.3a (0.381 g, 0.79 mmol, 1.0 eq) in N,N-Dimethylformamide (8 mL) was added 114.2 (0.474 g, 1.58 mmol, 2.0 eq) and Cesium carbonate (0.770 g, 2.37 mmol, 3.0 eq). The reaction mixture was stirred at 70° C. for 3 h. After completion, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 114.4. (0.220 g, Yield: 45.73%). MS (ES): m/z 610.2 [M+H]⁺

Synthesis of compound 114.5. A solution of 114.4 (0.220 g, 0.36 mmol, 1.0 eq) in methanol (5 mL) was cooled to 0° C. and Sodium borohydride (0.016 g, 0.43 mmol, 1.2 eq) was added portionwise. The reaction mixture was stirred at room temperature for 30 min. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 2.7% methanol in dichloromethane to obtain 114.5. (0.160 g, Yield: 76.23%). MS (ES): m/z 582.2 [M+H]⁺

Synthesis of compound 114.6. To a solution of 114.5 (0.160 g, 0.27 mmol, 1.0 eq) in N,N-Dimethylformamide (3 mL) was added sodium hydride (50%) (0.013 g, 0.54 mmol, 2.0 eq) at 0° C. and stirred for 20 min. Methyl iodide (0.026 mL, 0.40 mmol, 1.5 eq) was added dropwise and reaction mixture was stirred at room temperature for 2 h. After completion of reaction, reaction mixture was transferred into ice, stirred and extracted with diethyl ether. Organic layer was combined, dried over sodium sulphate and concentrated under reduced pressure to obtain crude material. This was further purified by column chromatography and the compound was eluted in 1.9% methanol in dichloromethane to obtain 114.6. (0.130 g, Yield: 79.34%). MS (ES): m/z 596.2 [M+H]⁺

Synthesis of compound I-1018: A solution of 114.6 (0.040 g, 0.067 mmol, 1.0 eq) in dichloromethane (1 mL) was cooled to 0° C. and triflic acid (0.5 mL) was added. Reaction mixture was stirred at the same temperature for 10 min. After completion, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1018 (0.027 g, Yield: 79.53%). MS (ES): m/z 506.47 [M+H]⁺ LCMS purity: 100%, HPLC purity: 99.74%, CHIRAL HPLC: 98.23%, ¹H NMR (DMSO-d₆, 400 MHZ): 8.77-8.76 (d, J=7.2 Hz, 1H), 8.70 (s, 1H), 8.52-8.50 (d, J=9.2 Hz, 1H), 8.42-8.41 (d, J=4 Hz, 1H), 8.37 (d, 1H), 8.31-8.30 (d, J=4.8 Hz, 1H), 7.34-7.31 (m, 1H), 6.72 (s, 1H), 5.62 (bs, 1H), 4.40-4.36 (m, 1H), 4.16-4.11 (m, 2H), 3.82 (bs, 1H), 3.58-3.57 (d, J=4.4 Hz, 2H), 3.22 (bs, 3H), 3.12-3.11 (d, J=4.4 Hz, 3H), 2.19-2.06 (m, 4H), 1.55-1.47 (m, 3H), 1.22 (bs, 2H), 0.83 (bs, 1H).

Example 115: N-((1R,2R)-2-methoxycyclobutyl)-5-(1-(5-(methoxymethyl)tetrahydrofuran-3-yl)-1H-pyrrolo[2,3-b]pyridin-3-yl)-7-(methylamino)pyrazolo[1,5-a]pyrimidine-3-carboxamide (I-1019)

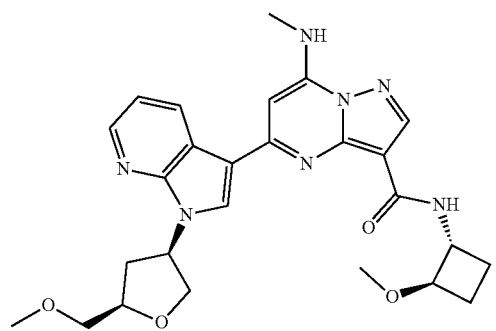

I-1019

Scheme 115

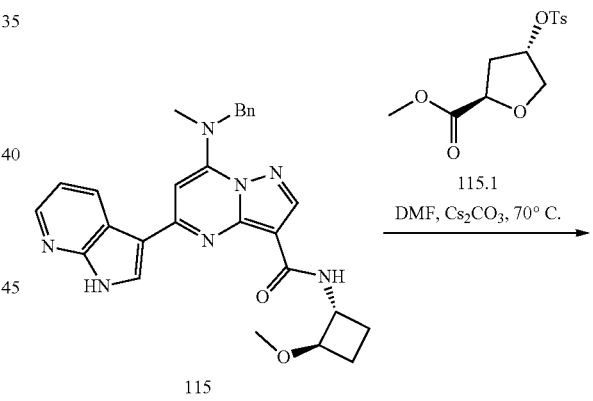

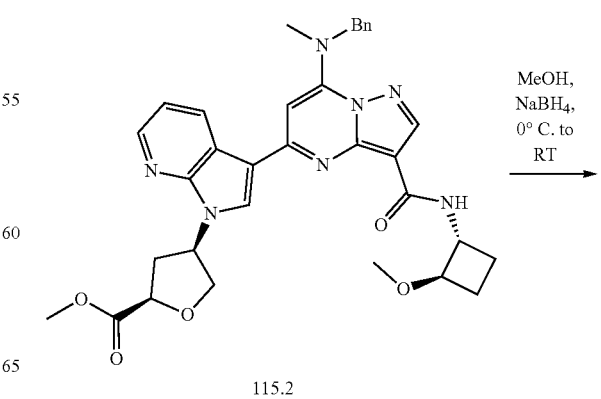

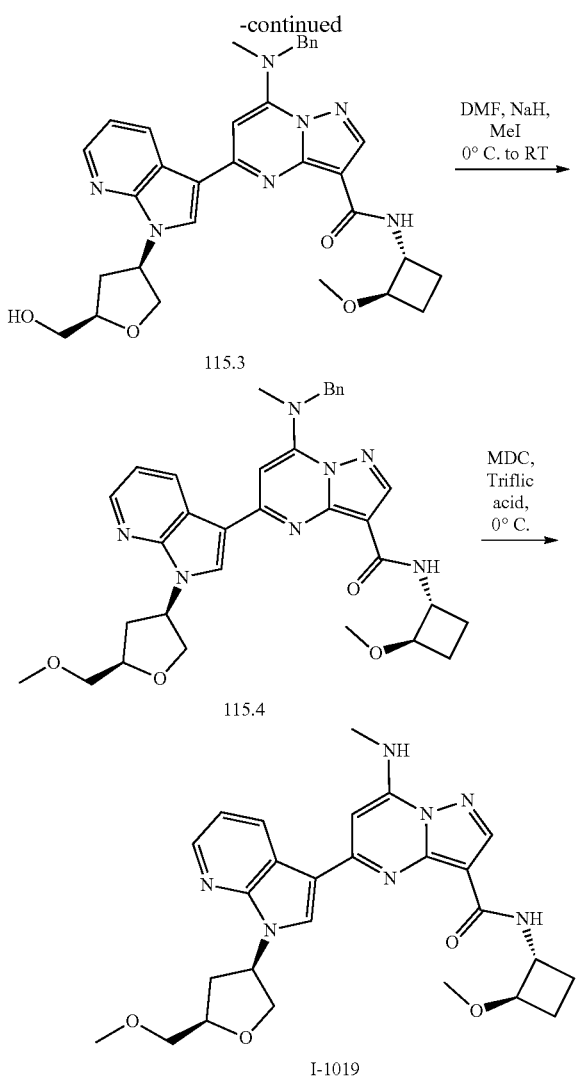

product was extracted with ethyl acetate. Organic layer was combined, washed with brine solution, dried over sodium sulphate and concentrated under reduced pressure to obtain crude material. This was further purified by column chromatography and the compound was eluted in 2.7% methanol in dichloromethane to obtain 115.3. (0.150 g, Yield: 78.61%). MS (ES): m/z 582.2 [M+H]$^+$ Synthesis of compound 115.4. To a solution of 115.3 (0.150 g, 0.25 mmol, 1.0 eq) in N,N-Dimethylformamide (3 mL) was added sodium hydride (50%) (0.012 g, 0.5 mmol, 2.0 eq) at 0° C. and stirred for 20 min. Methyl iodide (0.024 mL, 0.37 mmol, 1.5 eq) was added dropwise and reaction mixture was stirred at room temperature for 2 h. After completion of reaction, reaction mixture was transferred into ice, stirred and extracted with diethyl ether. Organic layer was combined, dried over sodium sulphate and concentrated under reduced pressure to obtain crude material. This was further purified by column chromatography and the compound was eluted in 1.9% methanol in dichloromethane to obtain 115.4. (0.128 g, Yield: 83.32%). MS (ES): m/z 596.2 [M+H]$^+$ Synthesis of compound I-1019: A solution of 115.4 (0.040 g, 0.067 mmol, 1.0 eq) in dichloromethane (1 mL) was cooled to 0° C. and triflic acid (0.5 mL) was added. Reaction mixture was stirred at same temperature for 10 min. After completion, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1019 (0.028 g, Yield: 82.48%). MS (ES): m/z 506.47 [M+H]$^+$ LCMS purity: 98.92%, HPLC purity: 99.26%, CHIRAL HPLC: 99.77%, $^1$H NMR (DMSO-d$_6$, 400 MHZ): 8.78-8.76 (d, J=7.6 Hz, 1H), 8.69 (s, 1H), 8.52-8.50 (d, J=9.2 Hz, 1H), 8.42-8.41 (d, J=4 Hz, 1H), 8.37 (d, 1H), 8.31-8.30 (d, J=4.8 Hz, 1H), 7.33-7.31 (m, 1H), 6.72 (s, 1H), 5.63 (bs, 1H), 4.41-4.37 (m, 1H), 4.16-4.11 (m, 2H), 3.82 (bs, 1H), 3.58-3.57 (d, J=4.4 Hz, 2H), 3.23 (bs, 3H), 3.12-3.11 (d, J=4.4 Hz, 3H), 2.18-2.09 (m, 4H), 1.55-1.47 (m, 3H), 1.22 (bs, 2H), 0.84 (bs, 1H).

Synthesis of compound 115. Compound 115 was synthesized as per experimental protocol of I-920 to obtain 115. MS (ES): m/z 482.23 [M+H]$^+$ Synthesis of compound 115.1. Compound 115.1 was synthesized as per experimental protocol of I-1018 to obtain 115.1 (Yield: 40%) MS (ES): m/z 301.07 [M+H]$^+$ Synthesis of compound 115.2. To a solution of 115 (0.390 g, 0.81 mmol, 1.0 eq) in N,N-Dimethylformamide (8 mL) was added 115.1 (0.486 g, 1.62 mmol, 2.0 eq) and Cesium carbonate (0.790 g, 2.43 mmol, 3.0 eq). The reaction mixture was stirred at 70° C. for 3 h. After completion, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 115.2. (0.2 g, Yield: 40.51%). MS (ES): m/z 610.2 [M+H]$^+$ Synthesis of compound 115.3. A solution of 115.2 (0.2 g, 0.32 mmol, 1.0 eq) in methanol (5 mL) was cooled to 0° C. and Sodium borohydride (0.014 g, 0.38 mmol, 1.2 eq) was added portionwise to the reaction mixture. The reaction mixture was stirred at room temperature for 30 min. After completion, reaction mixture was transferred into water and Example 116: N-((1S,2S)-2-methoxycyclobutyl)-5-(7-(1-(2-methoxyethyl)piperidin-4-yl)-7H-pyrrolo[2,3-b]pyridin-3-yl)-7-(methylamino)pyrazolo[1,5-a]pyrimidine-3-carboxamide (I-1020) and N-((1R,2R)-2-methoxycyclobutyl)-5-(7-(1-(2-methoxyethyl)piperidin-4-yl)-7H-pyrrolo[2,3-b]pyridin-3-yl)-7-(methylamino)pyrazolo[1,5-a]pyrimidine-3-carboxamide (I-1021)

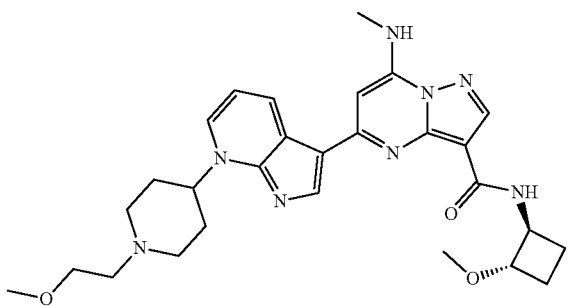

-continued
I-1021
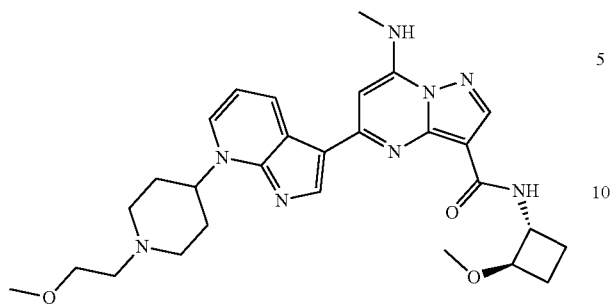
Scheme 116
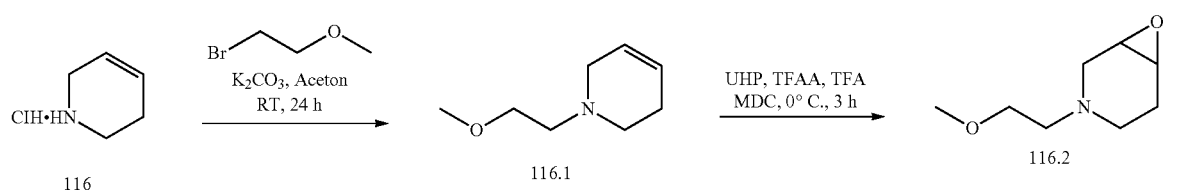
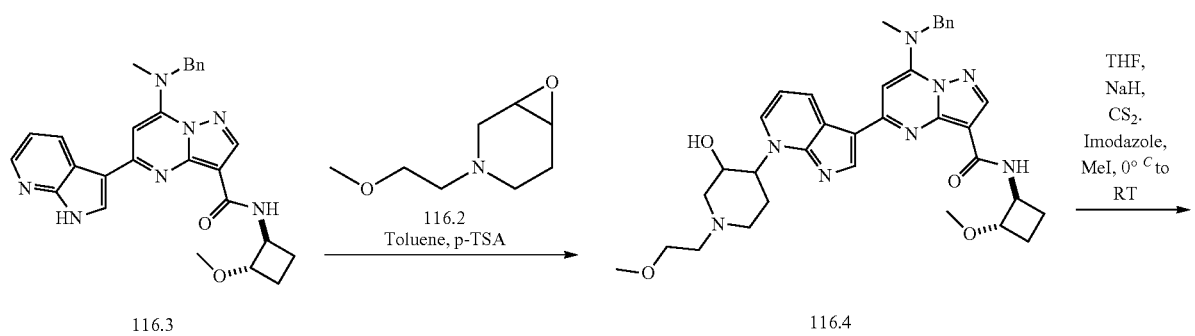
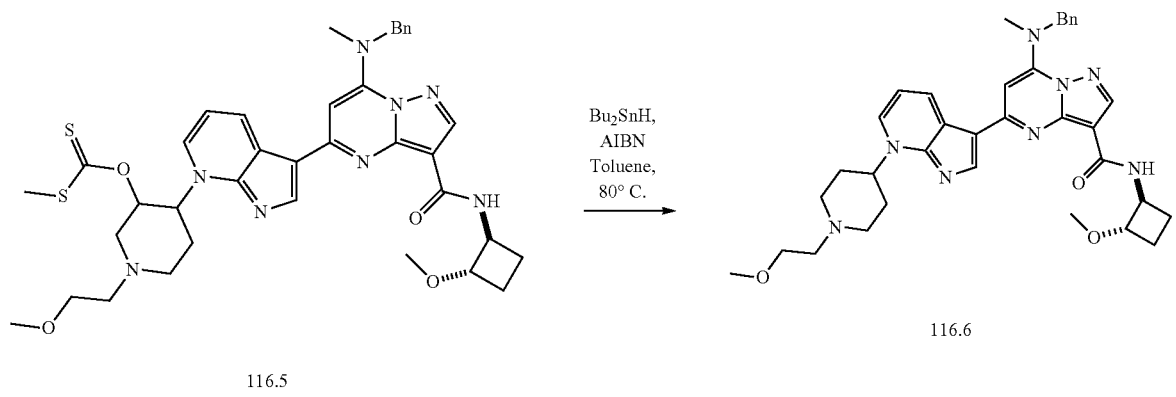

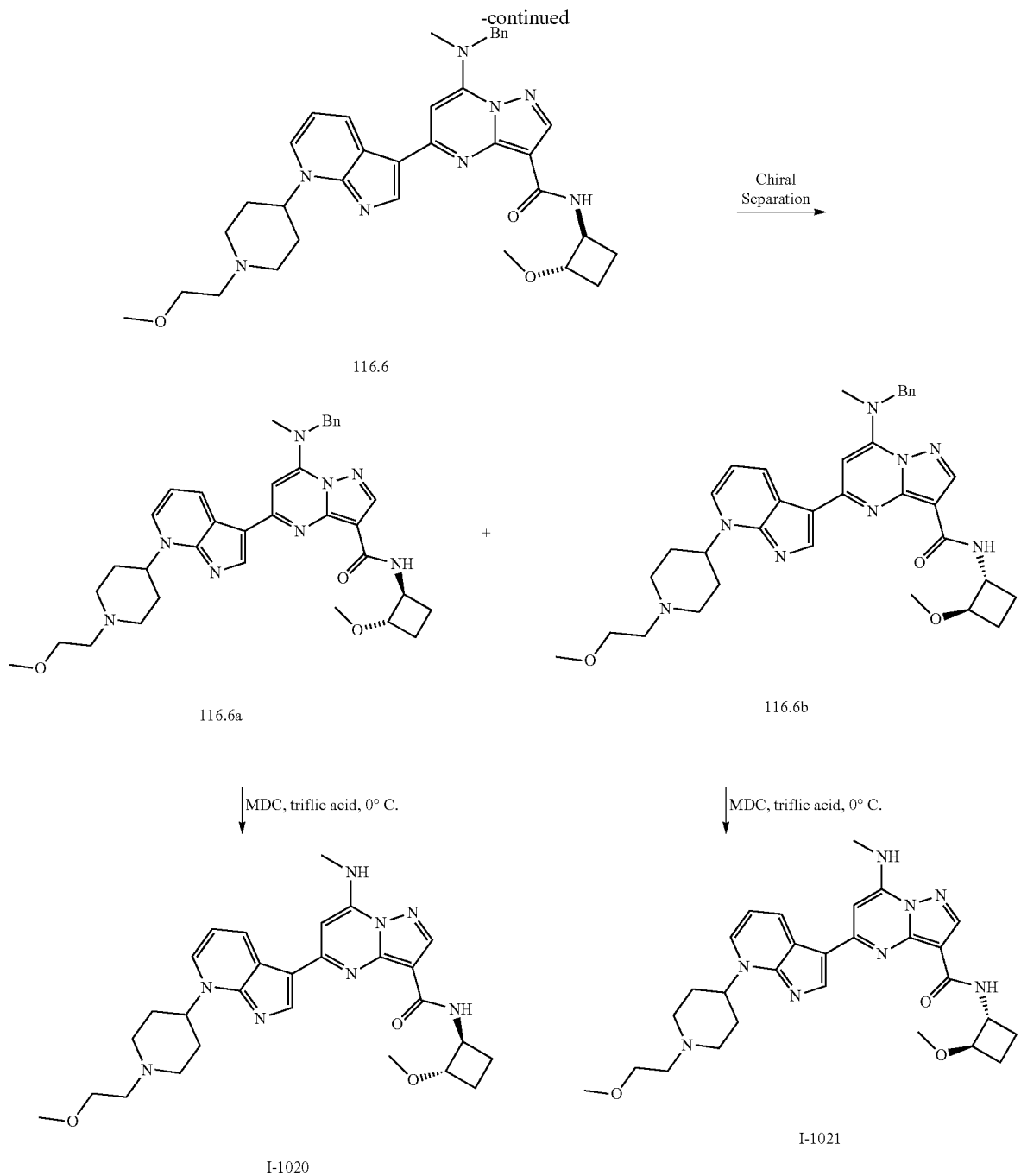

Synthesis of compound 116.1. To a solution of 116 (4.0 g, 33.61 mmol, 1.0 eq) in Acetone (50 mL) was added Potassium carbonate (1.9 g, 134.44 mmol, 4.0 eq) and 1-bromo-2-methoxyethane (7.0 g, 50.41 mmol, 1.5 eq). The reaction mixture was stirred at room temperature for 24 h. After completion of reaction, reaction mixture was filtered and washed with Acetone. Filtrate was concentrated under reduced pressure to obtain crude material. This was further purified by column chromatography and the compound was eluted in 7.0% methanol in dichloromethane to obtain 116.1. (1.9 g, Yield: 27.96%). MS (ES): m/z 141.1 [M+H]+

Synthesis of compound 116.2. A solution of Urea Hydrogen peroxide (3.7 g, 40.41 mmol, 3.0 eq) in dichloromethane (20 mL) was cooled to 0° C. Trifluoroacetic anhydride dissolved in dichloromethane (10 mL) (5.6 g, 26.94 mmol, 2.0 eq) was added to the reaction mixture and the reaction mixture was stirred at 0° C. for 1 h. A cooled solution of 116.1 (1.9 g, 13.47 mmol, 1.0 eq) and Trifluoroacetic acid (2.3 g, 20.20 mmol, 1.5 eq) in dichloromethane (10 mL) was added dropwise in to the reaction mixture and stirred at 0° C. for 20 min. After completion, reaction mixture was transferred into aqueous solution of mixture of potassium carbonate and sodium carbonate and product was extracted with ethyl aceate. Organic layer was combined, washed with brine solution, dried over sodium sulphate and concentrated under reduced pressure to obtain 116.2. (0.880 g, Yield: 41.60%). MS (ES): m/z 157.1 [M+H]⁺

Synthesis of compound 116.3. Compound 116.3 was synthesized as per experimental protocol of I-920 to obtain 116.3. (Yield: 60.33%). MS (ES): m/z 482.23 [M+H]⁺

Synthesis of compound 116.4. To a solution of 116.3 (0.880 g, 1.82 mmol, 1.0 eq) in toluene (15 mL) was added 116.2 (0.857 g, 5.46 mmol, 3.0 eq) and p-Toluene sulfonic acid (0.138 g, 0.72 mmol, 0.4 eq). The reaction mixture was stirred at 110° C. for 24 h. After completion, reaction mixture was transferred into water and product was extracted with dichloromethane. Organic layer was combined, washed with brine solution, dried over sodium sulphate and concentrated under reduced pressure to obtain crude material. This was further purified by column chromatography and the compound was eluted in 2.5% methanol in dichloromethane to obtain 116.4. (0.419 g, Yield: 35.90%). MS (ES): m/z 638.3 [M+H]⁺

Synthesis of compound 116.5. A solution of 116.4 (0.419 g, 0.65 mmol, 1.0 eq) in tetrahydrofuran (15 mL) was cooled to 0° C. for 15 min. Sodium hydride (60%) (0.018 g, 0.78 mmol, 1.2 eq) was added portionwise under argon atmosphere to the reaction mixture and stirred for 20-25 min. Imidazole (0.006 g, 0.091 mmol, 0.14 eq) was added into the reaction mixture and stirred for 1 h. Carbon disulfide (0.079 g, 1.04 mmol, 1.6 eq) was added to the reaction mixture and stirred for 15-20 min. Methyl iodide (0.119 g, 0.84 mmol, 1.3 eq) was added to the reaction mixture and stirred for 1 h. After completion of reaction, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 116.5. (0.440 g, Yield: 92.02%). MS (ES): m/z 728.2 [M+H]⁺

Synthesis of compound 116.6. A solution of 116.5 (0.440 g, 0.60 mmol, 1.0 eq) in toluene (10 mL) was stirred at 80° C. under argon atmosphere. Tributyltin hydride (0.64 mL, 2.4 mmol, 4.0 eq) was added dropwise to the reaction mixture and stirred for 15-20 min. Azobisisobutyronitrile (0.029 g, 0.18 mmol, 0.3 eq) was added to the reaction mixture and stirred at 80° C. for 1 h. After completion, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 2.9% methanol in dichloromethane to obtain 116.6. (0.170 g, Yield: 45.22%). MS (ES): m/z 623.3 [M+H]⁺

Synthesis of compound 116.6a and 116.6b.: Isomers of 116.6 (0.170 g) were separated out using column CHIRALCEL OJ-H (250 mm*4.6 mm, 5 u) and 0.1% DEA in methanol as co-solvent with flow rate of 4 mL/min. to get obtain fraction-1 (FR-a) and fraction-2 (FR-b). FR-a was concentrated under reduced pressure at 30° C. to afford pure 116.6a. (0.080 g). MS (ES): m/z 623.3 [M+H]⁺. FR-b was concentrated under reduced pressure at 30° C. to afford pure 116.6b. (0.080 g). MS (ES): m/z 623.3 [M+H]⁺

Synthesis of compound I-1020: A solution of 116.6a (0.080 g, 0.12 mmol, 1.0 eq) in dichloromethane (2 mL) was cooled to 0° C. and triflic acid (0.5 mL) was added. Reaction mixture was stirred at same temperature for 10 min. After completion, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1020 (0.046 g, Yield: 67.23%). MS (ES): m/z 533.30 [M+H]⁺ LCMS purity: 99.55%, HPLC purity: 99.20%, CHIRAL HPLC: 99.33%, ¹H NMR (DMSO-d₆, 400 MHZ): 8.93-8.92 (d, J=6.8 Hz, 1H), 8.65 (bs, 2H), 8.56-8.54 (d, J=8.4 Hz, 1H), 8.31 (s, 1H), 8.12-8.10 (d, J=4.8 Hz, 1H), 7.26 (bs, 1H), 6.67 (s, 1H), 5.64 (bs, 1H), 4.40-4.36 (m, 1H), 3.81 (bs, 1H), 3.48 (bs, 2H), 3.23 (s, 3H), 3.09-3.07 (d, J=4.8 Hz, 3H), 2.76 (bs, 2H), 2.20-2.09 (m, 4H), 1.80 (bs, 2H), 1.72 (bs, 2H), 1.58-1.47 (m, 3H), 1.23 (bs, 4H).

Synthesis of compound I-1021: A solution of 116.6b (0.080 g, 0.12 mmol, 1.0 eq) in dichloromethane (2 mL) was cooled to 0° C. and triflic acid (0.5 mL) was added. Reaction mixture was stirred at same temperature for 10 min. After completion, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1021 (0.047 g, Yield: 68.69%). MS (ES): m/z 533.30 [M+H]⁺ LCMS purity: 100%, HPLC purity: 99.52%, CHIRAL HPLC: 98.09%, ¹H NMR (DMSO-d₆, 400 MHZ): 8.93-8.92 (d, J=6.8 Hz, 1H), 8.65 (bs, 2H), 8.56-8.54 (d, J=8.4 Hz, 1H), 8.31 (s, 1H), 8.12-8.10 (d, J=4.8 Hz, 1H), 7.26 (bs, 1H), 6.67 (s, 1H), 5.65 (bs, 1H), 4.40-4.36 (m, 1H), 3.83 (bs, 1H), 3.49 (bs, 2H), 3.23 (s, 3H), 3.09-3.07 (d, J=4.8 Hz, 3H), 2.76 (bs, 2H), 2.20-2.11 (m, 4H), 1.80 (bs, 2H), 1.72 (bs, 2H), 1.58-1.47 (m, 3H), 1.23 (bs, 4H).

Example 117: N-(2-methoxycyclobutyl)-7-(methylamino)-5-(1-((R)-5-oxo-1-(tetrahydro-2H-pyran-4-yl)pyrrolidin-3-yl)-1H-pyrrolo[2,3-b]pyridin-3-yl)pyrazolo[1,5-a]pyrimidine-3-carboxamide (I-1026)

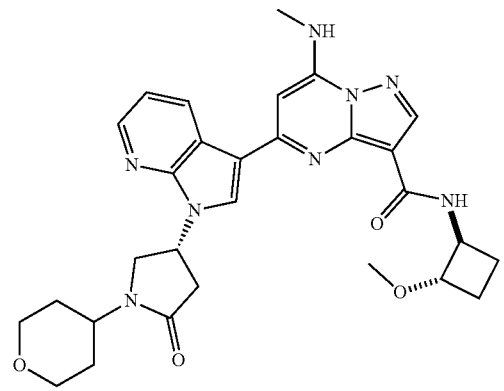

I-1026

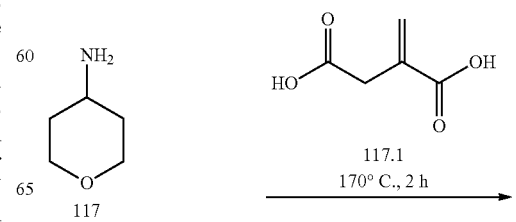

Scheme 117

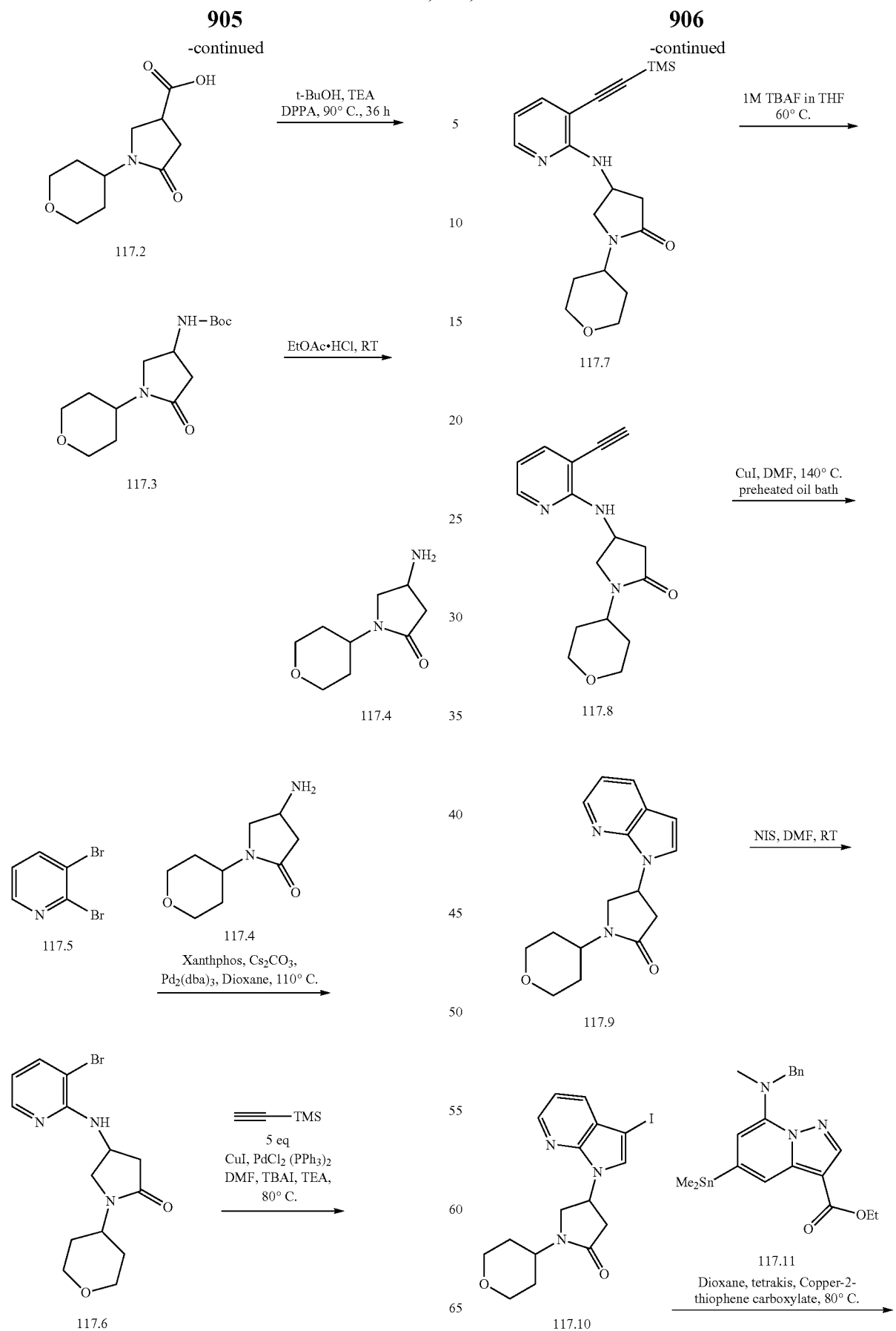

-continued
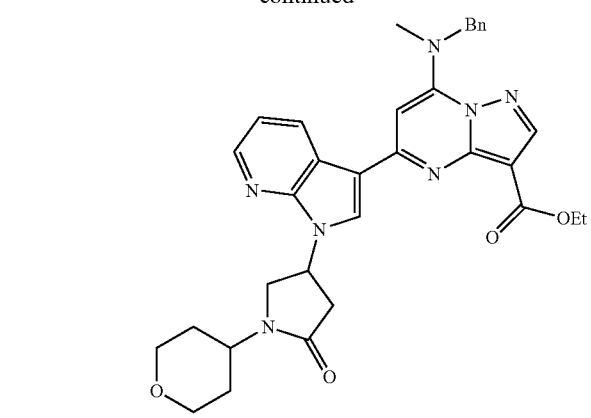
117.12
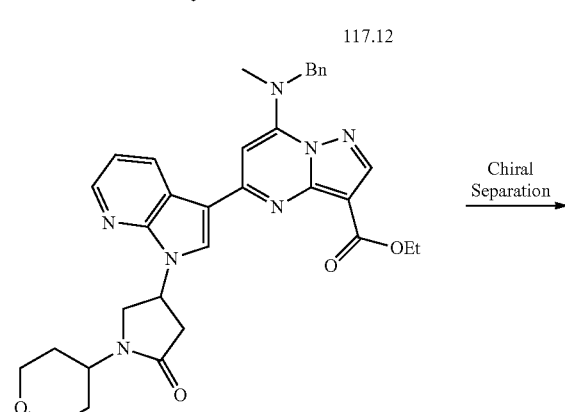
117.12a
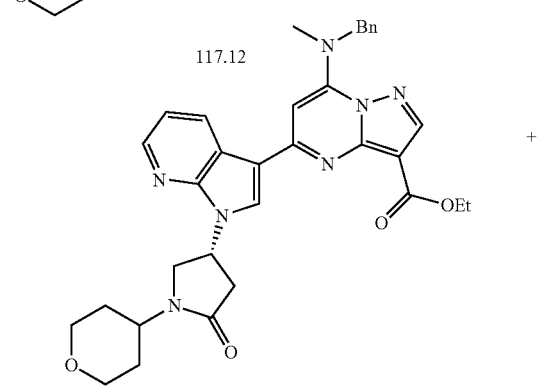
117.12b
-continued
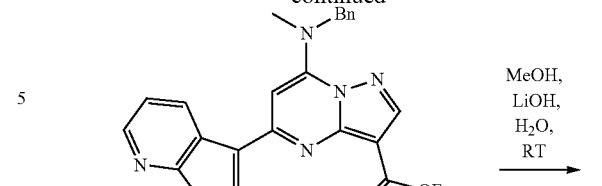
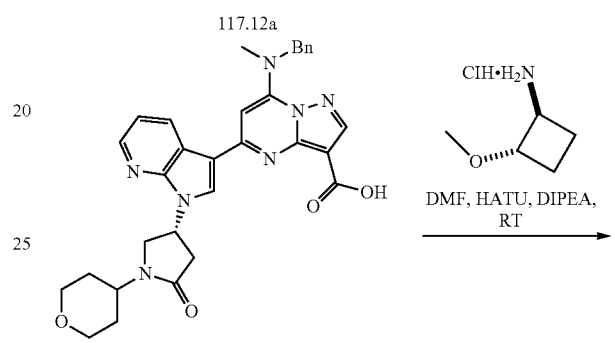
117.13
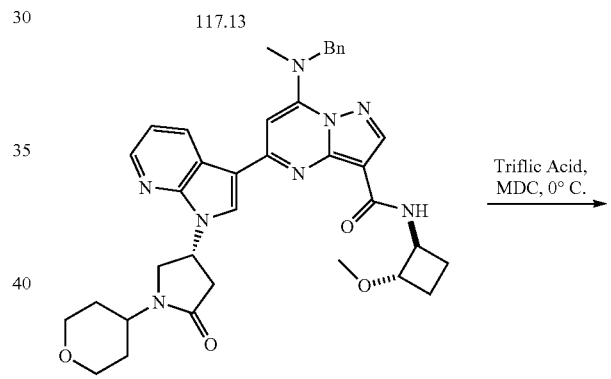
117.14
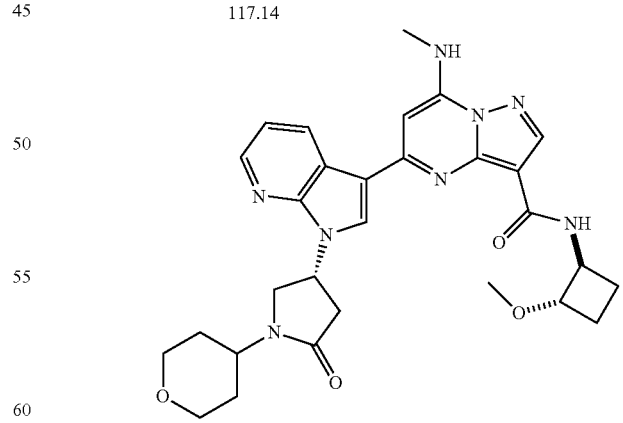
I-1026
Synthesis of compound 117.2. A suspension of 117 (15.0 g, 148.51 mmol, 1.0 eq) and 117.1 (12 mL, 148.51 mmol, 1.0 eq) was stirred at 170° C. for 2 h. The reaction mixture was stirred at room temperature for 5 min. After completion, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by trituration with ethanol to obtain 117.2. (18.3 g, Yield: 57.87%). MS (ES): m/z 213.10 $[M+H]^+$ Synthesis of compound 117.3. To a solution of 117.2 (18.3 g, 85.91 mmol, 1.0 eq) in tert-Butyl alcohol (30 mL) was added Triethylamine (18.5 mL, 128.86 mmol, 1.5 eq) at room temperature. To this was added dropwise Diphenylphosphoryl azide (20.3 mL, 94.50 mmol, 1.1 eq) at 0° C. The reaction mixture was stirred at 90° C. for 36 h. After completion, reaction mixture was transferred into water and product was extracted with ethyl acetate. Organic layer was combined, washed with brine solution, dried over sodium sulphate and concentrated under reduced pressure to obtain crude material. This was further purified by column chromatography and the compound was eluted in 1.5% methanol in dichloromethane to obtain 117.3. (8.1 g, Yield: 33.19%). MS (ES): m/z 284.17 $[M+H]^+$ Synthesis of compound 117.4. To 117.3 (8.1 g, 28.52 mmol, 1.0 eq) was added 4M hydrochloric acid in 1,4 Dioxane (30 mL) and stirred at room temperature for 30 min. After completion, reaction mixture was concentrated under reduced pressure to obtained residue which was triturated with diethyl ether to obtain 117.4. (4.7 g, Yield: 89.56%). MS (ES): m/z 184.1 $[M+H]^+$ Synthesis of compound 117.6. To a solution of 117.5 (10.0 g, 42.37 mmol, 1.0 eq) in 1,4-dioxane (300 mL) was added 117.4 (7.7 g, 42.37 mmol, 1.0 eq), cesium carbonate (34.4 g, 105.92 mmol, 2.5 eq). The reaction mixture was degassed for 10 min. under argon atmosphere, then tris(dibenzylideneacetone)dipalladium(0) (1.9 g, 2.11 mmol, 0.05 eq) and 4,5-Bis(diphenylphosphino)-9,9-dimethylxanthene (2.4 g, 4.23 mmol, 0.1 eq) were added, and degassed for 5 min. The reaction was stirred at 11 0° C. for 4 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 2.8% methanol in dichloromethane as eluant to obtain pure 117.6. (5.2 g, Yield: 36.21%). MS (ES): m/z 341.2 $[M+H]^+$ Synthesis of compound 117.7. To a solution of 117.6 (5.2 g, 15.29 mmol, 1.0 eq) in N,N-Dimethylformamide (60 mL) was added Triethylamine (3.8 g, 38.22 mmol, 2.5 eq) and ethynyltrimethylsilane (3.0 g, 30.58 mmol, 2.0 eq). The reaction mixture was degassed for 15 min. Then Tetrabutylammonium iodide (11.2 g, 30.5 8 mmol, 2.0 eq), Bis (triphenylphosphine)palladium(II) dichloride (0.536 g, 0.76 mmol, 0.05 eq) and Copper(I) iodide (0.072 g, 0.38 mmol, 0.025 eq) were added. Reaction mixture was stirred at 80° C. for 3 h under nitrogen atmosphere. After completion of reaction, reaction mixture was diluted with ethyl acetate, filtered through celite-bed and washed with water. Organic layer was combined, dried over sodium sulphate and concentrated under reduced pressure to obtain crude material. This was further purified by combi flash using 2.5% methanol in dichloromethane as eluant to obtain pure 117.7. (3.1 g, Yield: 56.73%). MS (ES): m/z 357.1 $[M+H]^+$ Synthesis of compound 117.8. To a solution of 117.7 (3.1 g, 8.68 mmol, 1.0 eq) in tetrahydrofuran (30 mL) was added tetrabutylammonium fluoride solution in tetrahydrofuran (13 mL). The reaction mixture was stirred at 60° C. for 1 h. After completion of reaction, reaction mixture was cooled to room temperature, transferred into water and product was extracted with ethyl acetate. Organic layer was combined, washed with brine solution, dried over sodium sulphate and concentrated under reduced pressure to obtain crude material. This was further purified by combi flash using 1.2% methanol in dichloromethane as eluant to obtain pure 117.8. (1.4 g, Yield: 56.59%). MS (ES): m/z 286.1 $[M+H]^+$ Synthesis of compound 117.9. To a solution of 117.8 (1.4 g, 4.91 mmol, 1.0 eq) in N,N-Dimethylformamide (15 mL) was added Copper(I) iodide (0.935 g, 4.91 mmol, 1.0 eq). The reaction mixture was heated up to 140° C. for 48 h. After completion of reaction, reaction mixture was cooled to room temperature, transferred into water and filtered to remove Copper(I) iodide and was extracted with dichloromethane. Organic layer was combined, washed with brine solution, dried over sodium sulphate and concentrated under reduced pressure to obtain crude material. This was further purified by combi flash using 1.4% methanol in dichloromethane as eluant to obtain pure 117.9. (1.0 g, Yield: 71.43%). MS (ES): m/z 285.1 $[M+H]^+$ Synthesis of compound 117.10. To a cooled solution of 117.9 (1.0 g, 3.50 mmol, 1.0 eq) in N,N-Dimethylformamide (10 mL) was added portionwise N-Iodosuccinimide (0.866 g, 3.85 mmol, 1.1 eq). The reaction mixture was stirred at room temperature for 30 min. After completion, reaction mixture was transferred into water and product was extracted with ethyl acatate. Organic layer was combined, washed with brine solution and sodium thiosulphate solution, dried over sodium sulphate and concentrated under reduced pressure to obtain crude material. This was further purified by combi flash using 2.0% methanol in dichloromethane as eluant to obtain pure 117.10. (1.1 g, Yield: 76.33%). MS (ES): m/z 411.04 $[M+H]^+$ Synthesis of compound 117.11. Compound 117.11 was synthesized as per experimental protocol of I-792 to obtain 117.11. (Yield: 21.86%). MS (ES): m/z 474.11 $[M+H]^+$ Synthesis of compound 117.12. To a solution of 117.10 (1.1 g, 2.67 mmol, 1.0 eq) in 1,4-dioxane (10 mL) was added 117.11 (1.2 g, 2.67 mmol, 1.0 eq). The reaction mixture was degassed for 10 min. under argon atmosphere, then Tetrakis (triphenylphosphine)palladium(0) (0.154 g, 0.13 mmol, 0.05 eq) and Copper(I) thiophene-2-carboxylate (0.050 g, 0.26 mmol, 0.1 eq) were added under argon atmosphere and stirred reaction mixture at 80° C. for 5 h. After completion of reaction, reaction mixture was transferred into ice cold water and product was extracted with ethyl acetate. Organic layer was combined and dried over sodium sulphate and concentrated under reduced pressure to obtain crude material. This was further purified by column chromatography and compound was eluted in 1.3% methanol in dichloromethane to obtain pure 117.12. (0.520 g, Yield: 32.75%). MS (ES): m/z 594.2 $[M+H]^+$ Synthesis of compound 117.12a and 117.12b.: Isomers of 117.12 (0.520 g) were separated out using column CHIRALCEL OJ-H (250 mm*4.6 mm, 5 u) and 0.1% DEA in IPA:ACN (50:50) as co-solvent with flow rate of 4 mL/min. to obtain pure fraction-1 (FR-a) and fraction-2 (FR-b). FR-a was concentrated under reduced pressure at 30° C. to afford pure 117.12a. (0.230 g). MS (ES): m/z 594.2 $[M+H]^+$. FR-b was concentrated under reduced pressure at 30° C. to afford pure 117.12b. (0.235 g). MS (ES): m/z 594.2 $[M+H]^+$ Synthesis of compound 117.13. To a solution of 117.12a (0.110 g, 0.18 mmol, 1.0 eq), in tetrahydrofuran:methanol: water (10 mL, 2:2:1) was added lithium hydroxide (0.075 g, 1.8 mmol, 10 eq). The reaction was stirred at 50° C. for 16 h. After completion, reaction mixture was concentrated under reduced pressure to obtain a residue. To this was added water and acidified with 1N hydrochloric acid to adjust pH~6-6.5 at 10° C. Product was extracted with dichloromethane. Organic layer was combined, washed with brine solution, dried over sodium sulphate and concentrated under reduced pressure to obtain crude material. This was further purified by column chromatography and compound was eluted in 2.1% methanol in dichloromethane to obtain pure 117.13. (0.055 g, Yield: 52.48%). MS (ES): m/z 566.2 [M+H]$^+$ Synthesis of compound 117.14. Compound 117.14 was synthesized using general procedure A to obtain 117.14. (0.045 g, Yield: 71.33%). MS (ES): m/z 648.2 [M+H]$^+$ Synthesis of compound I-1026: A solution of 117.14 (0.045 g, 0.069 mmol, 1.0 eq) in dichloromethane (1 mL) was cooled to 0° C. and triflic acid (0.5 mL) was added. Reaction mixture was stirred at same temperature for 10 min. After completion of reaction, reaction mixture was transferred into 1N sodium hydroxide solution and product was extracted with dichloromethane. Organic layer was combined, dried over sodium sulphate and concentrated under reduced pressure to obtain crude material. This was further purified by trituration with diethyl ether to a obtain I-1026 (0.015 g, Yield: 38.71%). MS (ES): m/z 559.90 [M+H]$^+$ LCMS purity: 96.42%, HPLC purity: 96.98%, CHIRAL HPLC: 47.18%, 47.00%, $^1$H NMR (DMSO-d$_6$, 400 MHZ): 8.79-8.77 (d, J=8 Hz, 1H), 8.54 (bs, 1H), 8.41 (bs, 1H), 8.34 (bs, 1H), 7.94 (bs, 2H), 7.36-7.33 (m, 1H), 6.67 (s, 1H), 5.68 (bs, 1H), 4.40 (bs, 1H), 3.88 (bs, 2H), 3.69-3.65 (m, 2H), 3.26 (s, 3H), 3.14 (bs, 3H), 3.11-3.09 (d, J=4.8 Hz, 3H), 2.13-2.11 (m, 2H), 1.77 (bs, 2H), 1.65 (bs, 2H), 1.56 (bs, 2H), 1.27 (bs, 3H).

Example 118: $^1$H NMR, Mass Spectral, and Chromatographic Data for Exemplary Compounds $^1$H NMR, MS, and chromatographic data for additional exemplary compounds which were prepared using similar synthetic methodology and routes are provided in Table 2, below.

Lengthy table referenced here

US12221453-20250211-T00001

Please refer to the end of the specification for access instructions.

Example 119: TYK2 JH12 Domain Binding Assay

Binding constants for compounds of the present invention against the JH2 domain were determined by the following protocol for a KINOMVEscan® assay (DiscoveRx). A fusion protein of a partial length construct of human TYK2 (JH12domain-pseudokinase) (amino acids G556 to D888 based on reference sequence NP_003322.3) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The TYK2 (JH2domain-pseudokinase) fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a $\geq$10,000-fold overall stock dilution (final DNA-tagged enzyme concentration <0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$s were determined using a compound top concentration of 30,000 nM. $K_d$ measurements were performed in duplicate.

Binding constants ($K_d$s) were calculated with a standard dose-response curve using the Hill equation:

$$\text{Response} = \text{Background} + \frac{(\text{Signal} - \text{Background})}{\left(1 + \left(\frac{Kd^{Hill\,Slope}}{Dose^{Hill\,Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, Q. Appl. Math. 2, 164-168 (1944)).

Results of the Tyk2 JH2 Domain Binding Assay are presented in Table 3. Compounds denoted as "A" had a $K_d$ lower than 200 pM; compounds denoted as "B" had a $K_d$ between 200 pM and 1 nM; compounds denoted as "C" had a $K_d$ between 1 nM and 10 nM; and compounds denoted as "D" had a $K_d$ greater than 10 nM.

TABLE 3

Results of TYK2 JH2 Domain Binding Assay

| Compound Number | hTYK2_JH2_Binding (Kd; nM) |
|---|---|
| I-1 | A |
| I-2 | B |
| I-3 | A |
| I-4 | A |
| I-5 | A |
| I-6 | A |
| I-7 | A |
| I-8 | A |
| I-9 | A |
| I-10 | A |
| I-11 | A |
| I-12 | A |
| I-13 | B |
| I-14 | A |
| I-15 | B |
| I-16 | A |
| I-17 | C |
| I-18 | A |
| I-19 | B |
| I-20 | A |
| I-21 | C |
| I-22 | B |
| I-23 | A |
| I-24 | A |
| I-25 | A |
| I-26 | B |
| I-27 | A |
| I-28 | A |
| I-29 | B |
| I-30 | B |
| I-31 | A |
| I-32 | A |
| I-33 | A |
| I-34 | A |
| I-35 | A |
| I-36 | B |
| I-37 | B |
| I-38 | B |
| I-39 | B |
| I-40 | B |
| I-41 | B |
| I-42 | B |
| I-43 | B |
| I-44 | B |
| I-45 | B |
| I-46 | A |
| I-47 | D |
| I-48 | A |
| I-49 | A |
| I-50 | C |
| I-51 | A |
| I-52 | B |
| I-53 | A |
| I-54 | A |
| I-55 | B |
| I-56 | C |
| I-57 | A |
| I-58 | B |
| I-59 | C |
| I-60 | A |
| I-61 | C |
| I-62 | A |
| I-63 | B |
| I-64 | B |
| I-65 | A |
| I-66 | C |
| I-67 | C |
| I-68 | C |
| I-69 | B |
| I-70 | C |
| I-71 | B |
| I-72 | C |
| I-73 | C |
| I-74 | B |
| I-75 | C |
| I-76 | B |
| I-77 | C |
| I-78 | B |
| I-79 | B |
| I-80 | C |
| I-81 | C |
| I-82 | D |
| I-83 | B |
| I-84 | B |
| I-85 | C |
| I-86 | C |
| I-87 | D |
| I-88 | D |
| I-89 | B |
| I-90 | D |
| I-91 | A |
| I-92 | D |
| I-93 | B |
| I-94 | C |
| I-95 | C |
| I-96 | C |
| I-97 | C |
| I-98 | A |
| I-99 | B |
| I-100 | B |
| I-101 | B |
| I-102 | A |
| I-103 | C |
| I-104 | C |
| I-105 | C |
| I-106 | A |
| I-107 | B |
| I-108 | A |
| I-109 | A |
| I-110 | B |
| I-111 | A |
| I-112 | C |
| I-113 | A |
| I-114 | A |
| I-115 | A |
| I-116 | C |
| I-117 | D |
| I-118 | C |
| I-119 | A |
| I-120 | B |
| I-121 | D |
| I-122 | A |
| I-123 | B |
| I-124 | A |
| I-125 | A |
| I-126 | D |
| I-127 | A |
| I-128 | B |
| I-129 | A |
| I-130 | A |
| I-131 | A |
| I-132 | B |
| I-133 | A |
| I-134 | B |
| I-135 | A |
| I-136 | B |
| I-137 | A |
| I-138 | A |
| I-139 | A |

TABLE 3-continued

Results of TYK2 JH2 Domain Binding Assay

| Compound Number | hTYK2_JH2_Binding (Kd; nM) |
|---|---|
| I-140 | B |
| I-141 | A |
| I-142 | A |
| I-143 | A |
| I-144 | A |
| I-145 | A |
| I-146 | B |
| I-147 | A |
| I-148 | A |
| I-149 | A |
| I-150 | B |
| I-151 | A |
| I-152 | A |
| I-153 | B |
| I-154 | A |
| I-155 | A |
| I-156 | B |
| I-157 | A |
| I-158 | A |
| I-159 | C |
| I-160 | A |
| I-161 | A |
| I-162 | A |
| I-163 | A |
| I-164 | A |
| I-165 | A |
| I-166 | B |
| I-167 | A |
| I-168 | B |
| I-169 | A |
| I-170 | A |
| I-171 | C |
| I-172 | A |
| I-173 | A |
| I-174 | A |
| I-175 | B |
| I-176 | A |
| I-177 | B |
| I-178 | A |
| I-179 | A |
| I-180 | A |
| I-181 | A |
| I-182 | B |
| I-183 | B |
| I-184 | B |
| I-185 | A |
| I-186 | A |
| I-187 | A |
| I-188 | A |
| I-189 | B |
| I-190 | A |
| I-191 | A |
| I-192 | A |
| I-193 | A |
| I-194 | A |
| I-195 | C |
| I-196 | A |
| I-197 | A |
| I-198 | A |
| I-199 | A |
| I-200 | A |
| I-201 | A |
| I-202 | B |
| I-203 | A |
| I-204 | A |
| I-205 | A |
| I-206 | A |
| I-207 | B |
| I-208 | A |
| I-209 | A |
| I-210 | A |
| I-211 | A |
| I-212 | A |
| I-213 | B |
| I-214 | A |
| I-215 | A |
| I-216 | C |
| I-217 | A |
| I-218 | C |
| I-219 | C |
| I-220 | B |
| I-221 | C |
| I-222 | C |
| I-223 | C |
| I-224 | A |
| I-225 | A |
| I-226 | B |
| I-227 | A |
| I-228 | A |
| I-229 | A |
| I-230 | A |
| I-231 | A |
| I-232 | B |
| I-233 | A |
| I-234 | B |
| I-235 | A |
| I-236 | A |
| I-237 | A |
| I-238 | B |
| I-239 | A |
| I-240 | A |
| I-241 | B |
| I-242 | B |
| I-243 | A |
| I-244 | C |
| I-245 | A |
| I-246 | A |
| I-247 | D |
| I-250 | A |
| I-251 | C |
| I-252 | A |
| I-253 | A |
| I-254 | B |
| I-255 | A |
| I-256 | B |
| I-257 | B |
| I-258 | A |
| I-259 | B |
| I-260 | A |
| I-261 | C |
| I-262 | A |
| I-263 | B |
| I-264 | A |
| I-265 | A |
| I-266 | A |
| I-267 | C |
| I-268 | A |
| I-269 | A |
| I-270 | C |
| I-271 | A |
| I-272 | A |
| I-273 | B |
| I-274 | A |
| I-275 | B |
| I-276 | A |
| I-277 | A |
| I-278 | C |
| I-279 | A |
| I-280 | A |
| I-281 | B |
| I-282 | A |
| I-283 | A |
| I-284 | B |
| I-285 | A |
| I-286 | A |
| I-287 | A |
| I-288 | B |
| I-289 | B |

TABLE 3-continued

Results of TYK2 JH2 Domain Binding Assay

| Compound Number | hTYK2_JH2_Binding (Kd; nM) |
|---|---|
| I-290 | A |
| I-291 | C |
| I-292 | A |
| I-293 | A |
| I-294 | B |
| I-295 | A |
| I-296 | A |
| I-297 | A |
| I-298 | B |
| I-299 | C |
| I-300 | B |
| I-301 | C |
| I-302 | B |
| I-303 | A |
| I-304 | B |
| I-305 | A |
| I-306 | A |
| I-307 | A |
| I-308 | A |
| I-309 | A |
| I-310 | B |
| I-311 | A |
| I-312 | A |
| I-313 | B |
| I-314 | A |
| I-315 | A |
| I-316 | B |
| I-317 | A |
| I-318 | A |
| I-319 | B |
| I-320 | A |
| I-321 | A |
| I-322 | A |
| I-323 | B |
| I-324 | A |
| I-325 | A |
| I-326 | B |
| I-327 | A |
| I-328 | A |
| I-329 | A |
| I-330 | A |
| I-331 | A |
| I-332 | B |
| I-333 | B |
| I-334 | C |
| I-335 | B |
| I-336 | A |
| I-337 | C |
| I-338 | A |
| I-339 | A |
| I-340 | A |
| I-341 | A |
| I-342 | A |
| I-343 | B |
| I-344 | B |
| I-345 | B |
| I-346 | B |
| I-347 | B |
| I-348 | A |
| I-349 | A |
| I-350 | B |
| I-351 | B |
| I-352 | B |
| I-353 | C |
| I-354 | C |
| I-355 | C |
| I-356 | B |
| I-357 | B |
| I-358 | D |
| I-359 | B |
| I-360 | B |
| I-361 | C |
| I-362 | B |
| I-363 | B |
| I-364 | D |
| I-365 | B |
| I-366 | B |
| I-367 | B |
| I-368 | C |
| I-369 | B |
| I-370 | D |
| I-371 | B |
| I-372 | C |
| I-373 | D |
| I-374 | C |
| I-375 | B |
| I-376 | C |
| I-377 | A |
| I-378 | B |
| I-379 | C |
| I-380 | B |
| I-381 | B |
| I-382 | D |
| I-383 | B |
| I-384 | C |
| I-385 | B |
| I-386 | D |
| I-387 | B |
| I-388 | C |
| I-389 | B |
| I-390 | A |
| I-391 | A |
| I-392 | C |
| I-393 | C |
| I-394 | D |
| I-395 | C |
| I-396 | B |
| I-397 | C |
| I-398 | B |
| I-399 | B |
| I-400 | C |
| I-401 | A |
| I-402 | B |
| I-403 | C |
| I-404 | B |
| I-405 | A |
| I-406 | C |
| I-407 | A |
| I-408 | B |
| I-409 | C |
| I-410 | A |
| I-411 | C |
| I-412 | B |
| I-413 | C |
| I-414 | A |
| I-415 | A |
| I-416 | C |
| I-417 | B |
| I-418 | C |
| I-419 | B |
| I-420 | C |
| I-421 | C |
| I-422 | D |
| I-423 | A |
| I-424 | A |
| I-425 | C |
| I-426 | B |
| I-427 | C |
| I-428 | A |
| I-429 | B |
| I-430 | C |
| I-431 | A |
| I-432 | C |
| I-433 | B |
| I-434 | B |
| I-435 | A |
| I-436 | A |
| I-437 | B |

TABLE 3-continued

Results of TYK2 JH2 Domain Binding Assay

| Compound Number | hTYK2_JH2_Binding (Kd; nM) |
|---|---|
| I-438 | A |
| I-439 | C |
| I-440 | C |
| I-441 | C |
| I-442 | B |
| I-443 | C |
| I-444 | B |
| I-445 | C |
| I-446 | C |
| I-447 | C |
| I-448 | B |
| I-449 | C |
| I-450 | B |
| I-451 | B |
| I-452 | C |
| I-453 | B |
| I-454 | C |
| I-455 | B |
| I-456 | B |
| I-457 | C |
| I-458 | A |
| I-459 | C |
| I-460 | B |
| I-461 | C |
| I-462 | C |
| I-463 | C |
| I-464 | C |
| I-465 | C |
| I-466 | B |
| I-467 | B |
| I-468 | B |
| I-469 | B |
| I-470 | B |
| I-471 | B |
| I-472 | B |
| I-473 | D |
| I-474 | C |
| I-475 | C |
| I-476 | B |
| I-477 | D |
| I-478 | B |
| I-479 | A |
| I-480 | A |
| I-481 | A |
| I-482 | B |
| I-483 | A |
| I-484 | A |
| I-485 | A |
| I-486 | C |
| I-487 | B |
| I-488 | A |
| I-489 | D |
| I-490 | A |
| I-491 | A |
| I-492 | C |
| I-493 | B |
| I-494 | D |
| I-495 | A |
| I-496 | A |
| I-497 | A |
| I-498 | A |
| I-499 | A |
| I-500 | A |
| I-501 | A |
| I-502 | A |
| I-503 | A |
| I-504 | A |
| I-505 | A |
| I-506 | A |
| I-507 | A |
| I-508 | A |
| I-509 | A |
| I-510 | A |
| I-511 | A |
| I-512 | B |
| I-513 | A |
| I-514 | A |
| I-515 | B |
| I-516 | A |
| I-517 | A |
| I-518 | B |
| I-519 | A |
| I-520 | A |
| I-521 | B |
| I-522 | A |
| I-523 | A |
| I-524 | B |
| I-525 | A |
| I-526 | A |
| I-527 | C |
| I-528 | A |
| I-529 | A |
| I-530 | A |
| I-531 | A |
| I-532 | A |
| I-533 | A |
| I-534 | A |
| I-535 | A |
| I-536 | B |
| I-537 | A |
| I-538 | A |
| I-539 | B |
| I-540 | B |
| I-541 | B |
| I-542 | B |
| I-543 | B |
| I-544 | B |
| I-545 | B |
| I-546 | A |
| I-547 | B |
| I-548 | A |
| I-549 | A |
| I-550 | C |
| I-551 | A |
| I-552 | A |
| I-553 | A |
| I-554 | A |
| I-555 | A |
| I-556 | B |
| I-557 | A |
| I-558 | A |
| I-559 | B |
| I-560 | A |
| I-561 | B |
| I-562 | A |
| I-563 | A |
| I-564 | A |
| I-565 | A |
| I-566 | B |
| I-567 | A |
| I-568 | A |
| I-569 | B |
| I-570 | A |
| I-571 | A |
| I-572 | B |
| I-573 | A |
| I-574 | A |
| I-575 | A |
| I-576 | A |
| I-577 | A |
| I-578 | C |
| I-579 | A |
| I-580 | A |
| I-581 | C |
| I-582 | C |
| I-583 | A |
| I-584 | A |
| I-585 | A |

TABLE 3-continued

Results of TYK2 JH2 Domain Binding Assay

| Compound Number | hTYK2_JH2_Binding (Kd; nM) |
|---|---|
| I-586 | C |
| I-587 | A |
| I-588 | A |
| I-589 | A |
| I-590 | B |
| I-591 | A |
| I-592 | A |
| I-593 | A |
| I-594 | C |
| I-595 | C |
| I-596 | D |
| I-597 | A |
| I-598 | A |
| I-599 | C |
| I-600 | B |
| I-601 | A |
| I-602 | C |
| I-603 | B |
| I-604 | B |
| I-605 | D |
| I-606 | A |
| I-607 | B |
| I-608 | A |
| I-609 | A |
| I-610 | A |
| I-611 | B |
| I-612 | A |
| I-613 | A |
| I-614 | C |
| I-615 | A |
| I-616 | A |
| I-617 | B |
| I-618 | A |
| I-619 | A |
| I-620 | B |
| I-621 | A |
| I-622 | A |
| I-623 | A |
| I-624 | A |
| I-625 | A |
| I-626 | B |
| I-627 | A |
| I-628 | C |
| I-629 | A |
| I-630 | A |
| I-631 | A |
| I-632 | B |
| I-633 | A |
| I-634 | A |
| I-635 | B |
| I-636 | A |
| I-637 | A |
| I-638 | B |
| I-639 | A |
| I-640 | A |
| I-641 | C |
| I-642 | A |
| I-643 | A |
| I-644 | B |
| I-645 | A |
| I-646 | A |
| I-647 | C |
| I-648 | A |
| I-649 | A |
| I-650 | B |
| I-651 | A |
| I-652 | A |
| I-653 | A |
| I-654 | A |
| I-655 | A |
| I-656 | A |
| I-657 | A |
| I-658 | B |
| I-659 | A |
| I-660 | A |
| I-661 | C |
| I-662 | A |
| I-663 | A |
| I-664 | C |
| I-665 | A |
| I-666 | A |
| I-667 | B |
| I-668 | A |
| I-669 | A |
| I-670 | C |
| I-671 | A |
| I-672 | A |
| I-673 | A |
| I-674 | C |
| I-675 | A |
| I-676 | A |
| I-677 | A |
| I-678 | A |
| I-679 | B |
| I-680 | A |
| I-681 | A |
| I-682 | B |
| I-683 | A |
| I-684 | C |
| I-685 | A |
| I-686 | A |
| I-687 | A |
| I-688 | A |
| I-689 | A |
| I-690 | A |
| I-691 | B |
| I-692 | A |
| I-693 | A |
| I-694 | B |
| I-695 | A |
| I-696 | A |
| I-697 | B |
| I-698 | A |
| I-699 | A |
| I-700 | B |
| I-701 | A |
| I-702 | A |
| I-703 | A |
| I-704 | C |
| I-705 | A |
| I-706 | A |
| I-707 | B |
| I-708 | A |
| I-709 | A |
| I-710 | C |
| I-711 | A |
| I-712 | D |
| I-713 | A |
| I-714 | D |
| I-715 | A |
| I-716 | A |
| I-717 | C |
| I-718 | A |
| I-719 | A |
| I-720 | D |
| I-721 | A |
| I-722 | A |
| I-723 | C |
| I-724 | B |
| I-725 | A |
| I-726 | A |
| I-727 | C |
| I-728 | D |
| I-729 | C |
| I-730 | A |
| I-731 | A |
| I-732 | C |
| I-733 | A |

TABLE 3-continued

Results of TYK2 JH2 Domain Binding Assay

| Compound Number | hTYK2_JH2_Binding (Kd; nM) |
|---|---|
| I-734 | B |
| I-735 | C |
| I-736 | A |
| I-737 | C |
| I-738 | D |
| I-739 | C |
| I-740 | A |
| I-741 | A |
| I-742 | A |
| I-743 | C |
| I-744 | A |
| I-745 | C |
| I-746 | A |
| I-747 | C |
| I-748 | A |
| I-749 | A |
| I-750 | B |
| I-751 | A |
| I-752 | A |
| I-753 | A |
| I-754 | A |
| I-755 | A |
| I-756 | A |
| I-757 | A |
| I-758 | A |
| I-759 | A |
| I-760 | A |
| I-761 | B |
| I-762 | A |
| I-763 | D |
| I-764 | A |
| I-765 | A |
| I-766 | A |
| I-767 | A |
| I-768 | A |
| I-769 | A |
| I-770 | D |
| I-771 | A |
| I-772 | A |
| I-773 | A |
| I-774 | A |
| I-775 | A |
| I-776 | A |
| I-777 | B |
| I-780 | A |
| I-781 | B |
| I-782 | C |
| I-783 | C |
| I-784 | A |
| I-785 | A |
| I-786 | B |
| I-787 | A |
| I-788 | B |
| I-789 | A |
| I-790 | A |
| I-791 | B |
| I-792 | A |
| I-793 | A |
| I-794 | B |
| I-795 | A |
| I-796 | A |
| I-797 | C |
| I-798 | A |
| I-799 | C |
| I-800 | A |
| I-801 | C |
| I-802 | A |
| I-803 | C |
| I-804 | A |
| I-805 | D |
| I-806 | A |
| I-807 | C |
| I-808 | A |
| I-809 | C |
| I-810 | C |
| I-811 | A |
| I-812 | D |
| I-813 | A |
| I-814 | A |
| I-815 | B |
| I-816 | A |
| I-817 | A |
| I-818 | A |
| I-819 | A |
| I-820 | A |
| I-821 | A |
| I-822 | A |
| I-823 | A |
| I-824 | A |
| I-825 | A |
| I-826 | A |
| I-827 | A |
| I-828 | A |
| I-829 | B |
| I-830 | A |
| I-831 | B |
| I-832 | A |
| I-833 | A |
| I-834 | B |
| I-835 | A |
| I-836 | A |
| I-837 | C |
| I-838 | A |
| I-839 | A |
| I-840 | A |
| I-841 | A |
| I-842 | A |
| I-843 | A |
| I-844 | A |
| I-845 | A |
| I-846 | B |
| I-847 | A |
| I-848 | A |
| I-849 | B |
| I-850 | B |
| I-851 | B |
| I-852 | B |
| I-853 | B |
| I-854 | B |
| I-855 | B |
| I-856 | A |
| I-857 | A |
| I-858 | C |
| I-859 | A |
| I-860 | A |
| I-861 | C |
| I-862 | A |
| I-863 | A |
| I-864 | C |
| I-865 | A |
| I-866 | C |
| I-867 | A |
| I-868 | C |
| I-869 | C |
| I-870 | D |
| I-871 | B |
| I-872 | B |
| I-873 | D |
| I-874 | A |
| I-875 | C |
| I-876 | A |
| I-877 | A |
| I-878 | A |
| I-879 | B |
| I-880 | A |
| I-881 | A |
| I-882 | B |
| I-883 | A |

TABLE 3-continued

Results of TYK2 JH2 Domain Binding Assay

| Compound Number | hTYK2_JH2_Binding (Kd; nM) |
|---|---|
| I-884 | A |
| I-885 | B |
| I-886 | A |
| I-887 | A |
| I-888 | A |
| I-889 | A |
| I-890 | A |
| I-891 | B |
| I-892 | A |
| I-893 | A |
| I-894 | C |
| I-895 | A |
| I-896 | A |
| I-897 | C |
| I-898 | A |
| I-899 | A |
| I-900 | B |
| I-901 | A |
| I-902 | A |
| I-903 | B |
| I-904 | B |
| I-905 | B |
| I-906 | C |
| I-907 | A |
| I-908 | C |
| I-909 | B |
| I-910 | C |
| I-911 | C |
| I-912 | A |
| I-913 | C |
| I-914 | A |
| I-915 | A |
| I-916 | A |
| I-917 | C |
| I-918 | A |
| I-919 | B |
| I-920 | A |
| I-921 | A |
| I-922 | C |
| I-923 | A |
| I-924 | C |
| I-925 | A |
| I-926 | A |
| I-927 | B |
| I-928 | A |
| I-929 | A |
| I-930 | C |
| I-931 | A |
| I-932 | A |
| I-933 | A |
| I-934 | A |
| I-935 | D |
| I-936 | B |
| I-937 | A |
| I-938 | B |
| I-939 | A |
| I-940 | A |
| I-941 | B |
| I-942 | A |
| I-943 | A |
| I-944 | A |
| I-945 | C |
| I-946 | A |
| I-947 | A |
| I-948 | B |
| I-949 | A |
| I-950 | C |
| I-951 | A |
| I-952 | B |
| I-953 | C |
| I-954 | A |
| I-955 | C |
| I-956 | D |
| I-957 | D |
| I-958 | B |
| I-959 | A |
| I-960 | A |
| I-961 | A |
| I-962 | A |
| I-963 | A |
| I-964 | B |
| I-965 | A |
| I-966 | C |
| I-967 | A |
| I-968 | B |
| I-969 | B |
| I-970 | A |
| I-971 | D |
| I-972 | B |
| I-973 | C |
| I-974 | D |
| I-975 | C |
| I-976 | A |
| I-977 | A |
| I-978 | B |
| I-979 | A |
| I-980 | A |
| I-981 | A |
| I-982 | A |
| I-983 | A |
| I-984 | B |
| I-985 | A |
| I-986 | C |
| I-987 | D |
| I-988 | B |
| I-989 | B |
| I-990 | A |
| I-991 | B |
| I-992 | A |
| I-993 | A |
| I-994 | A |
| I-995 | A |
| I-996 | A |
| I-997 | B |
| I-998 | A |
| I-999 | A |
| I-1000 | A |
| I-1001 | B |
| I-1002 | A |
| I-1003 | B |
| I-1004 | A |
| I-1005 | A |
| I-1006 | A |
| I-1007 | D |
| I-1008 | C |
| I-1009 | A |
| I-1010 | A |
| I-1011 | C |
| I-1012 | A |
| I-1013 | A |
| I-1014 | A |
| I-1015 | A |
| I-1016 | A |
| I-1017 | A |
| I-1018 | A |
| I-1019 | C |
| I-1020 | A |
| I-1021 | B |
| I-1022 | A |
| I-1023 | B |
| I-1024 | A |
| I-1025 | C |
| I-1026 | A |
| I-1027 | A |
| I-1028 | A |
| I-1029 | B |

TABLE 3-continued

Results of TYK2
JH2 Domain Binding Assay

| Compound Number | hTYK2_JH2_Binding (Kd; nM) |
|---|---|
| I-1030 | A |
| I-1031 | B |

Example 120: TYK2 & JAK2 Radioactive Kinase Assay

Peptide substrate, [KKSRGDYMTMQIG], (20 μM) was prepared in reaction buffer (20 mM Hepes pH 7.5, 10 mM $MgCl_2$, 1 mM EGTA, 0.02% Brij35, 0.02 mg/mL BSA, 0.1 mM $Na_3PO_4$, 2 mM DTT, 1% DMSO. TYK2 (Invitrogen) kinase was added, followed by compounds in DMSO. 33PATP was added to initiate the reaction in ATP at 10 μM. Kinase reaction was incubated for 120 min at room temp and reactions were spotted onto $P^{81}$ ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr] (4:1), 0.2 mg/mL was used, in the reaction carried out the same as for TYK2.

Results of the TYK2 and JAK2 radioactive kinase assay are presented in Table 4. Compounds denoted as "A" had a percent inhibition at 10 μM lower than 50; compounds denoted as "B" had a percent inhibition at 10 μM between 50 and 70; compounds denoted "C" had a percent inhibition at 10 μM between 70 and 90; and compounds denoted as "D had a percent inhibition at 10 μM greater than 90.

TABLE 4

Results of TYK2 & JAK2 Radioactive Kinase Assays

| Number | TYK2 (% Inhibition at 10 μM) | JAK2 (% Inhibition at 10 μM) |
|---|---|---|
| I-1 | A | A |
| I-6 | A | A |
| I-7 | A | A |
| I-18 | A | A |
| I-19 | A | A |
| I-24 | A | A |
| I-33 | A | A |
| I-36 | A | A |
| I-37 | A | A |
| I-46 | A | A |
| I-47 | A | A |
| I-48 | A | A |
| I-58 | A | A |
| I-59 | A | A |
| I-62 | A | A |
| I-63 | A | A |
| I-66 | A | A |
| I-67 | A | A |
| I-68 | A | A |
| I-69 | A | A |
| I-70 | A | A |
| I-94 | A | A |
| I-95 | A | A |
| I-116 | A | A |
| I-117 | A | A |

Example 121: Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 μL of diluted compound was added into wells first, then 10 ul of enzyme mix was added into wells, followed by 10 μL of substrate mix (peptide and ATP in 10 mM $MgCl_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 μM, respectively. JAK2 assay uses peptide 22 and TYK2 uses peptide 30 (Caliper), each at 3 μM.

Example 122: IL-12 Induced pSTAT4 in Human PBMC

Human PBMC were isolated from buffy coat and are stored frozen for assays as needed. Cells for assay were thawed and resuspended in complete media containing serum, then cells were diluted to $1.67 \times 10^6$ cells/mL so that 120 μL per well is 200,000 cells. 15 μL of compound or DMSO was added to the well at the desired concentrations and incubated at 1 hr at 37° C. 15 μL of stimulus (final concentration of 1.7 ng/mL IL-12) was added for 30 minutes prior to pSTAT4 and total STAT4 analysis using cell lysates prepared and analyzed by MSD reagents as per manufacturer protocol. The final DMSO concentration of compound in the assay was 0.1%.

The IL-12 induced pSTAT4 assay evaluates the inhibition of IL-12 induced STAT4 phosphorlyation mediated by TYK2/JAK2 (heterpdimeric complex).

Results of the IL-12 induced pSTAT4 assay in human PBMC are presented in Table 5. Compounds denoted as "A" had an $IC_{50}$ lower than 0.1 μM; compounds denoted as "B" had an $IC_{50}$ between 0.1 and 0.5 μM; compounds denoted "C" had an $IC_{50}$ between 0.5 and 1.0 μM; all compounds denoted as "D" had an $IC_{50}$ greater than 1.0 μM.

TABLE 5

Results IL-12 Induced pSTAT4 Inhibition in Human PBMC

| Compound Number | PBMC Il-12-pSTAT4 ($IC_{50}$; μM) |
|---|---|
| I-1 | D |
| I-3 | A |
| I-4 | A |
| I-7 | A |
| I-8 | A |
| I-10 | A |
| I-11 | B |
| I-12 | A |
| I-14 | A |
| I-16 | A |
| I-18 | A |
| I-20 | A |
| I-24 | A |
| I-25 | A |
| I-31 | A |
| I-32 | A |
| I-33 | A |
| I-34 | A |
| I-41 | A |
| I-46 | A |
| I-48 | A |
| I-49 | A |

TABLE 5-continued

Results IL-12 Induced pSTAT4 Inhibition in Human PBMC

| Compound Number | PBMC Il-12-pSTAT4 (IC$_{50}$; μM) |
|---|---|
| I-51 | A |
| I-53 | A |
| I-54 | A |
| I-57 | A |
| I-102 | A |
| I-108 | B |
| I-109 | B |
| I-111 | B |
| I-114 | A |
| I-115 | A |
| I-119 | B |
| I-124 | A |
| I-125 | A |
| I-129 | A |
| I-130 | A |
| I-131 | A |
| I-133 | A |
| I-135 | A |
| I-138 | A |
| I-139 | A |
| I-141 | A |
| I-142 | A |
| I-143 | A |
| I-144 | A |
| I-145 | A |
| I-147 | A |
| I-148 | A |
| I-149 | A |
| I-151 | A |
| I-155 | A |
| I-158 | A |
| I-160 | A |
| I-162 | A |
| I-163 | A |
| I-164 | A |
| I-165 | A |
| I-167 | A |
| I-169 | A |
| I-173 | A |
| I-174 | A |
| I-176 | A |
| I-178 | A |
| I-179 | A |
| I-181 | A |
| I-185 | A |
| I-186 | A |
| I-188 | A |
| I-190 | A |
| I-191 | A |
| I-192 | A |
| I-193 | A |
| I-194 | A |
| I-196 | A |
| I-197 | A |
| I-198 | A |
| I-200 | A |
| I-201 | A |
| I-203 | A |
| I-204 | A |
| I-205 | A |
| I-206 | A |
| I-208 | A |
| I-209 | A |
| I-211 | A |
| I-212 | B |
| I-214 | A |
| I-217 | A |
| I-224 | A |
| I-225 | A |
| I-227 | A |
| I-228 | A |
| I-230 | A |
| I-231 | A |
| I-235 | A |
| I-236 | A |
| I-237 | A |
| I-239 | A |
| I-240 | A |
| I-243 | A |
| I-246 | B |
| I-247 | B |
| I-250 | A |
| I-252 | A |
| I-253 | A |
| I-255 | A |
| I-258 | A |
| I-260 | A |
| I-262 | A |
| I-264 | A |
| I-265 | A |
| I-266 | A |
| I-268 | A |
| I-269 | A |
| I-271 | A |
| I-272 | A |
| I-274 | A |
| I-276 | A |
| I-277 | A |
| I-279 | A |
| I-280 | A |
| I-282 | A |
| I-283 | A |
| I-285 | A |
| I-286 | A |
| I-287 | A |
| I-290 | A |
| I-292 | A |
| I-293 | A |
| I-295 | A |
| I-296 | A |
| I-303 | A |
| I-305 | A |
| I-306 | A |
| I-307 | A |
| I-309 | A |
| I-311 | A |
| I-312 | A |
| I-314 | A |
| I-315 | A |
| I-317 | A |
| I-318 | A |
| I-320 | A |
| I-321 | A |
| I-322 | A |
| I-324 | A |
| I-325 | A |
| I-327 | A |
| I-328 | A |
| I-330 | A |
| I-331 | A |
| I-336 | A |
| I-338 | A |
| I-339 | A |
| I-341 | A |
| I-348 | A |
| I-349 | A |
| I-377 | A |
| I-390 | A |
| I-391 | A |
| I-405 | A |
| I-407 | A |
| I-410 | A |
| I-414 | A |
| I-415 | A |
| I-423 | A |
| I-424 | A |

TABLE 5-continued

Results IL-12 Induced pSTAT4 Inhibition in Human PBMC

| Compound Number | PBMC Il-12-pSTAT4 (IC$_{50}$; μM) |
|---|---|
| I-428 | A |
| I-431 | A |
| I-436 | A |
| I-479 | A |
| I-481 | A |
| I-483 | A |
| I-484 | A |
| I-485 | A |
| I-488 | A |
| I-490 | A |
| I-495 | A |
| I-500 | B |
| I-502 | B |
| I-507 | A |
| I-508 | A |
| I-510 | A |
| I-511 | A |
| I-513 | A |
| I-514 | A |
| I-523 | A |
| I-528 | A |
| I-529 | A |
| I-530 | A |
| I-531 | A |
| I-538 | A |
| I-546 | A |
| I-548 | A |
| I-549 | A |
| I-552 | A |
| I-555 | A |
| I-558 | A |
| I-571 | A |
| I-573 | A |
| I-574 | A |
| I-583 | B |
| I-587 | C |
| I-588 | B |
| I-591 | C |
| I-592 | A |
| I-606 | A |
| I-608 | A |
| I-609 | A |
| I-610 | A |
| I-612 | A |
| I-613 | A |
| I-615 | A |
| I-616 | A |
| I-618 | A |
| I-619 | A |
| I-621 | A |
| I-622 | A |
| I-624 | A |
| I-625 | A |
| I-629 | A |
| I-630 | B |
| I-631 | A |
| I-633 | A |
| I-634 | A |
| I-636 | A |
| I-637 | A |
| I-639 | A |
| I-640 | A |
| I-642 | A |
| I-643 | A |
| I-645 | A |
| I-646 | A |
| I-649 | A |
| I-651 | A |
| I-652 | A |
| I-663 | A |
| I-665 | A |
| I-666 | A |
| I-668 | A |
| I-669 | A |
| I-671 | A |
| I-672 | A |
| I-673 | A |
| I-675 | A |
| I-676 | A |
| I-677 | A |
| I-680 | A |
| I-681 | A |
| I-683 | A |
| I-685 | A |
| I-686 | A |
| I-692 | A |
| I-693 | A |
| I-695 | A |
| I-699 | A |
| I-702 | A |
| I-703 | A |
| I-709 | B |
| I-711 | A |
| I-713 | B |
| I-721 | A |
| I-722 | A |
| I-726 | A |
| I-730 | B |
| I-741 | A |
| I-742 | A |
| I-744 | A |
| I-746 | A |
| I-752 | A |
| I-753 | A |
| I-754 | A |
| I-756 | A |
| I-757 | A |
| I-759 | A |
| I-760 | A |
| I-762 | A |
| I-765 | A |
| I-766 | A |
| I-768 | A |
| I-769 | A |
| I-771 | A |
| I-772 | A |
| I-774 | A |
| I-775 | A |
| I-776 | A |
| I-780 | A |
| I-784 | A |
| I-787 | A |
| I-790 | A |
| I-792 | A |
| I-793 | A |
| I-795 | A |
| I-796 | A |
| I-798 | A |
| I-802 | A |
| I-804 | A |
| I-806 | A |
| I-808 | A |
| I-811 | A |
| I-816 | A |
| I-817 | A |
| I-818 | A |
| I-819 | A |
| I-820 | A |
| I-821 | B |
| I-824 | A |
| I-825 | A |
| I-826 | A |
| I-827 | A |
| I-828 | A |
| I-830 | A |
| I-833 | A |

TABLE 5-continued

Results IL-12 Induced pSTAT4 Inhibition in Human PBMC

| Compound Number | PBMC Il-12-pSTAT4 (IC$_{50}$; µM) |
|---|---|
| I-835 | A |
| I-838 | A |
| I-839 | A |
| I-840 | A |
| I-841 | A |
| I-848 | A |
| I-865 | C |
| I-867 | B |
| I-876 | A |
| I-877 | B |
| I-878 | A |
| I-880 | A |
| I-881 | A |
| I-883 | A |
| I-884 | A |
| I-896 | A |
| I-898 | A |
| I-901 | A |
| I-902 | A |
| I-912 | A |
| I-914 | A |
| I-915 | A |
| I-916 | B |
| I-918 | A |
| I-920 | B |
| I-921 | A |
| I-923 | A |
| I-925 | A |
| I-928 | B |
| I-929 | B |
| I-931 | B |
| I-932 | A |
| I-933 | A |
| I-937 | B |
| I-939 | B |
| I-942 | C |
| I-943 | A |
| I-944 | A |
| I-947 | A |
| I-959 | A |
| I-960 | B |
| I-962 | C |
| I-963 | B |
| I-965 | A |
| I-976 | B |
| I-977 | D |
| I-979 | B |
| I-981 | B |
| I-983 | A |
| I-985 | A |
| I-990 | A |
| I-993 | A |
| I-994 | A |
| I-995 | A |
| I-999 | B |
| I-1000 | C |
| I-1002 | A |
| I-1004 | A |
| I-1005 | B |
| I-1006 | A |
| I-1009 | A |
| I-1010 | B |
| I-1012 | D |
| I-1014 | A |
| I-1015 | C |
| I-1016 | B |
| I-1017 | B |
| I-1018 | A |
| I-1020 | A |
| I-1022 | B |
| I-1024 | A |
| I-1026 | B |
| I-1027 | B |
| I-1028 | B |
| I-1030 | B |

Example 123: GM-CSF Induced pSTAT5 in Human PBMC

Cells are prepared for analysis as in the above procedure and 15 µl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

Example 124: Ex Vivo Mouse IL-12 Induced IFNγ Studies

C57/BL6 mice are given a single oral dose of either vehicle or different doses of compound at a volume of 10 mL/kg. 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Example 125: T-ALL Cell Proliferation Assay

T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1 \times 10^4$ cells per well in 96-well plates. T-ALL cell lines DU.528, LOUCY, and SUP-T13 are cultured in the same medium and plated at a density of $1.5 \times 10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. IC$_{50}$ value is calculated by nonlinear regression using GraphPad Prism software.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

LENGTHY TABLES

The patent contains a lengthy table section. A copy of the table is available in electronic form from the USPTO web site (https://seqdata.uspto.gov/?pageRequest=docDetail&DocID=US12221453B2). An electronic copy of the table will also be available from the USPTO upon request and payment of the fee set forth in 37 CFR 1.19(b)(3).

We claim:

1. A compound of Formula I':

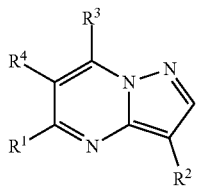

or a pharmaceutically acceptable salt or stereoisomer thereof, wherein:

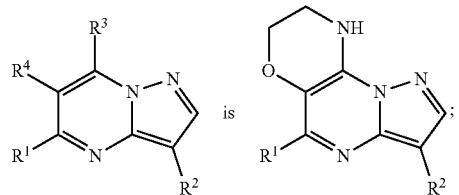

$R^1$ is -$L^1$-$R^{1A}$;
$L^1$ is a covalent bond;
$R^{1A}$ is an 8- to 10-membered heteroaryl ring;
  wherein the heteroaryl ring is bicyclic;
  wherein the heteroaryl ring has 1, 2, 3, or 4 heteroatoms independently selected from the group consisting of nitrogen, oxygen, and sulfur;
  wherein the heteroaryl ring is optionally substituted with one or more substituents independently selected from the group consisting of halogen, CN, $C_{1-6}$ aliphatic, C(O)NRR, OR, a 3- to 7-membered carbocyclic ring, and a 4- to 7-membered heterocyclic ring;
  wherein each 3- to 7-membered carbocyclic ring and 4- to 7-membered heterocyclic ring substituent is independently saturated or partially unsaturated;
  wherein each 4- to 7-membered heterocyclic ring substituent has 1 or 2 heteroatoms independently selected from the group consisting of nitrogen, oxygen, and sulfur; and
  wherein each 3- to 7-membered carbocyclic ring and 4- to 7-membered heterocyclic ring substituent is optionally and independently substituted with one or more OH substituents;
  each R is independently H, $C_{1-6}$ aliphatic, a 3- to 7-membered heterocyclic ring, phenyl, or a 5- or 6-membered heteroaryl ring;
  wherein each heterocyclic ring is independently saturated or partially unsaturated;
  wherein each heterocyclic ring independently has 1 or 2 heteroatoms independently selected from the group consisting of nitrogen, oxygen, and sulfur; and
  wherein each heteroaryl ring independently has 1, 2, 3, or 4 heteroatoms independently selected from the group consisting of nitrogen, oxygen, and sulfur; or
  any two geminal R substituents, taken together with the nitrogen atom to which they are attached, independently form a 4- to 7-membered heterocyclic ring or a 5- or 6-membered heteroaryl ring;
  wherein each heterocyclic ring is independently saturated or partially unsaturated; and
  wherein each heterocyclic ring and heteroaryl ring independently has 0, 1, 2, or 3 additional heteroatoms independently selected from the group consisting of nitrogen, oxygen, and sulfur;
$R^2$ is C(O)NHR$^{2A}$;
$R^{2A}$ is a 3- to 7-membered saturated carbocyclic ring;
  wherein the carbocyclic ring is saturated; and
  wherein the carbocyclic ring is substituted with n independently selected $R^{2C}$ substituents;
  each $R^{2C}$ is independently halogen or OH; and
  n is 0, 1, or 2.

2. The compound of claim 1, or a stereoisomer thereof, wherein the compound, or stereoisomer thereof, is selected from the group consisting of:

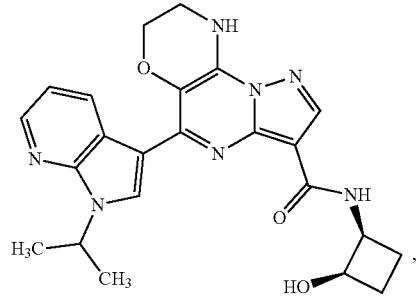

I-753

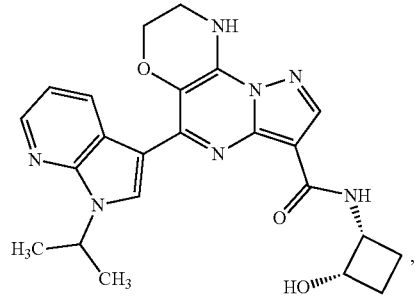

I-755

I-756
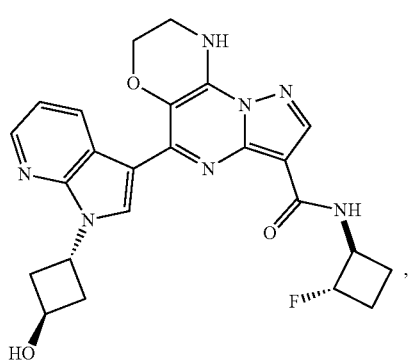
I-758
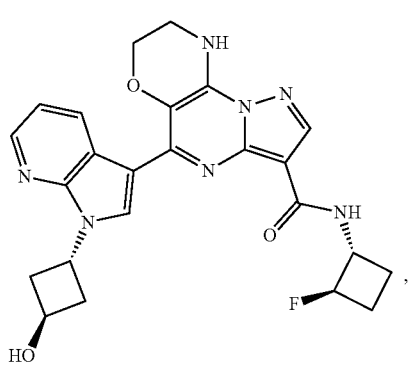
I-771
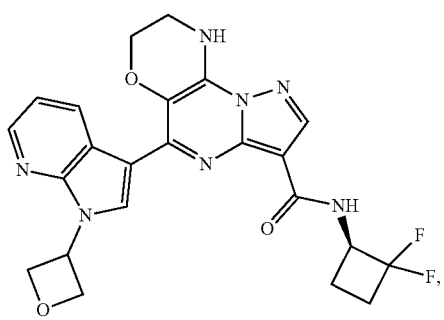
I-773
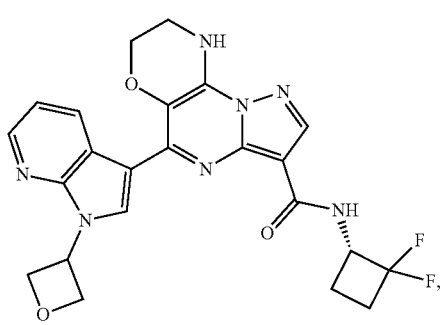
I-774
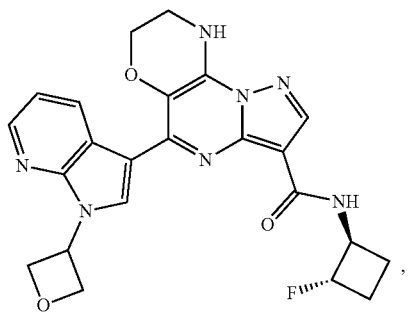
I-775
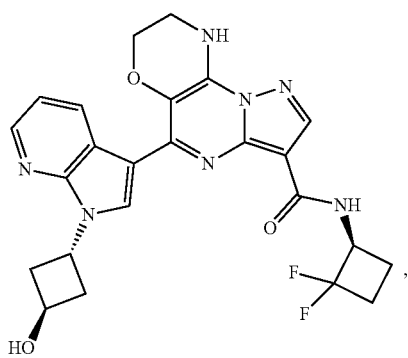
I-777
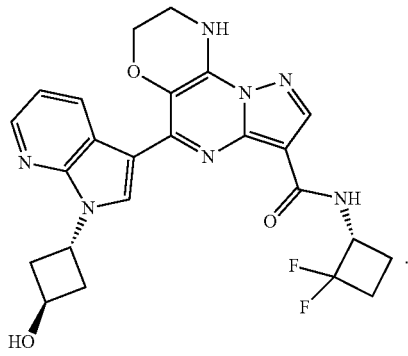
or a pharmaceutically acceptable salt thereof.
3. A pharmaceutical composition comprising a pharmaceutically acceptable carrier, adjuvant, or vehicle and a compound of claim 1, or a pharmaceutically acceptable salt or stereoisomer thereof.
* * * * *